United States Patent
Choi et al.

(10) Patent No.: US 11,833,208 B2
(45) Date of Patent: Dec. 5, 2023

(54) PLK1 SELECTIVE DEGRADATION INDUCING COMPOUND

(71) Applicant: Uppthera, Incheon (KR)

(72) Inventors: Si Woo Choi, Incheon (KR); Soo Hee Ryu, Incheon (KR); Ji Hoon Ryu, Seoul (KR); San Ha Son, Incheon (KR); Hwa Jin Lee, Incheon (KR); Seong Hoon Kim, Incheon (KR); Boas Nam, Incheon (KR); Im Suk Min, Gyeonggi-do (KR); Hye Guk Ryu, Incheon (KR); Keum Young Kang, Incheon (KR)

(73) Assignee: UPPTHERA, INC., Incheon (KR)

( * ) Notice: Subject to any disclaimer, the term of this patent is extended or adjusted under 35 U.S.C. 154(b) by 63 days.

(21) Appl. No.: 17/428,467

(22) PCT Filed: Mar. 27, 2021

(86) PCT No.: PCT/KR2021/003807
§ 371 (c)(1),
(2) Date: Aug. 4, 2021

(87) PCT Pub. No.: WO2021/194318
PCT Pub. Date: Sep. 30, 2021

(65) Prior Publication Data
US 2023/0104076 A1    Apr. 6, 2023

(30) Foreign Application Priority Data

Mar. 27, 2020 (KR) .......................... 10-2020-0037875

(51) Int. Cl.
| | | |
|---|---|---|
| A61K 47/55 | (2017.01) | |
| A61K 47/54 | (2017.01) | |
| C07D 409/14 | (2006.01) | |
| C07D 417/14 | (2006.01) | |

(52) U.S. Cl.
CPC ............ *A61K 47/55* (2017.08); *A61K 47/545* (2017.08); *C07D 409/14* (2013.01); *C07D 417/14* (2013.01)

(58) Field of Classification Search
CPC .................................................. A61K 47/55
See application file for complete search history.

(56) References Cited

U.S. PATENT DOCUMENTS

2017/0281784 A1    10/2017 Wang et al.

FOREIGN PATENT DOCUMENTS

| CN | 106543185 A | 3/2017 | | |
|---|---|---|---|---|
| CN | 106977584 | * | 4/2017 | ........... C07D 471/18 |
| CN | 106977584 A | 7/2017 | | |
| CN | 109879877 | * | 3/2019 | ........... C07D 471/18 |
| CN | 109879877 A | 6/2019 | | |
| JP | 2010540463 A | 12/2010 | | |
| JP | 2010540464 A | 12/2010 | | |
| JP | 2015508414 A | 3/2015 | | |
| KR | 10-2010-0087292 | 8/2010 | | |
| WO | WO2008113711 | * | 9/2008 | ........... C07D 471/18 |
| WO | WO 2009/042711 | 4/2009 | | |
| WO | WO 2009/042711 A1 | 4/2009 | | |
| WO | WO 2009/153197 A1 | 12/2009 | | |
| WO | WO 2020/073930 A1 | 4/2020 | | |
| WO | WO2023017446 | * | 2/2023 | ........... C07D 487/04 |

OTHER PUBLICATIONS

Tinworth, Med. Chem. Commun., 2016, 7, 2206-2216.*
International Search Report for corresponding PCT Application No. PCT/KR2021/003807, dated Jul. 6, 2021.
Written Opinion of the International Searching Authority for corresponding PCT Application No. PCT/KR2021/003807, dated Jul. 6, 2021.
Akuffo, Afua A., et al. "Ligand-mediated protein degradation reveals functional conservation among sequence variants of the CUL4-type E3 ligase substrate receptor cereblon." Journal of Biological Chemistry 293.16 (2018): 6187-6200.
Bolden, Jessica E., et al. "Inducible in vivo silencing of Brd4 identifies potential toxicities of sustained BET protein inhibition." Cell Reports 8.6 (2014): 1919-1929.
Buckley, Dennis L., et al. "Targeting the von Hippel-Lindau E3 ubiquitin ligase using small molecules to disrupt the VHL/HIF-1α interaction." Journal of the American Chemical Society 134.10 (2012): 4465-4468.
Buckley, Dennis L., and Craig M. Crews. "Small-Molecule Control of Intracellular Protein Levels through Modulation of the Ubiquitin Proteasome System." Angewandte Chemie International Edition 53.9 (2014): 2312-2330.
Burslem, George M., et al. "The advantages of targeted protein degradation over inhibition: an RTK case study." Cell chemical biology 25.1 (2018): 67-77.
Burslem, George M., and Craig M. Crews. "Small-molecule modulation of protein homeostasis." Chemical reviews 117.17 (2017): 11269-11301.
Chamberlain, Philip P., and Brian E. Cathers. "Cereblon modulators: Low molecular weight inducers of protein degradation." Drug Discovery Today: Technologies 31 (2019): 29-34.

(Continued)

*Primary Examiner* — Nizal S Chandrakumar
(74) *Attorney, Agent, or Firm* — Klarquist Sparkman, LLP

(57) ABSTRACT

The present invention provides novel compounds that induce selective polo-like kinase 1 (PLK1) degradation. Specifically, the present invention provides a bifunctional compound in which a PLK1 binding moiety and an E3 ubiquitin ligase-binding moiety are linked by a chemical linker. The present invention provides the compound, a method for preparing the same, and the use thereof. The compounds may be effectively utilized for preventing or treating PLK1 related diseases.

8 Claims, 1 Drawing Sheet

(56) References Cited

OTHER PUBLICATIONS

Galdeano, Carles, et al. "Structure-guided design and optimization of small molecules targeting the protein-protein interaction between the von Hippel-Lindau (VHL) E3 ubiquitin ligase and the hypoxia inducible factor (HIF) alpha subunit with in vitro nanomolar affinities." Journal of Medicinal Chemistry 57.20 (2014): 8657-8663.
Gheghiani et al., "PLK1 Activation in Late G2 Sets Up Commitment to Mitosis." Cell Reports 19 (2017): 2060-2073.
Hansen, J. D. et al., "Discovery of CRBN E3 ligase modulator CC-92480 for the treatment of relapsed and refractory multiple myeloma", Journal of Medicinal Chemistry, Mar. 4, 2020 (E-pub.), vol. 63, No. 13, pp. 6648-6676.
Ito, Takumi, et al. "Identification of a primary target of thalidomide teratogenicity." science 327.5971 (2010): 1345-1350.
Mu, Xupeng, et al. "Protein targeting chimeric molecules specific for dual bromodomain 4 (BRD4) and Polo-like kinase 1 (PLK1) proteins in acute myeloid leukemia cells." Biochemical and biophysical research communications 521.4 (2020): 833-839.
Nie, Zhe, et al. Bioorganic & medicinal chemistry letters 23.12 (2013): 3662-3666.
Rodriguez-Gonzalez, A., et al. "Targeting steroid hormone receptors for ubiquitination and degradation in breast and prostate cancer." Oncogene 27.57 (2008): 7201-7211.
Schneekloth, John S., et al. "Chemical genetic control of protein levels: selective in vivo targeted degradation." Journal of the American Chemical Society 126.12 (2004): 3748-3754.
Soares, Michael J., Khursheed Iqbal, and Keisuke Kozai. "Hypoxia and placental development." Birth Defects Research 109.17 (2017): 1309-1329.
European Search Report of European application 21749059.8 dated Apr. 8, 2022, 7 pages.
Chen Shaoqing et al, "Identification of novel, potent and selective inhibitors of Polo-like Kinase 1", Bioorganic & Medicinal Chemistry Letters, vol. 22, No. 2, 2012 pp. 1247-1250.
First Office Action for Chinese patent application No. 202180002576. X, dated May 20, 2022, with English translation, 19 pgs.
Japanese Office Action with English Translation, dated Dec. 20, 2022, pp. 1-16, issued in Japanese Patent Application No. 2021-578216, Japan Patent Office, Chiyoda Tokyo, Japan.
Zengerle, M. et al, Selective Small Molecule Induced Degradation of the BET Bromodomain Protein BRD4, dated 2015, pp. 1770-1777, ACS Chemical Biology, vol. 10.

\* cited by examiner

[Fig. 1]
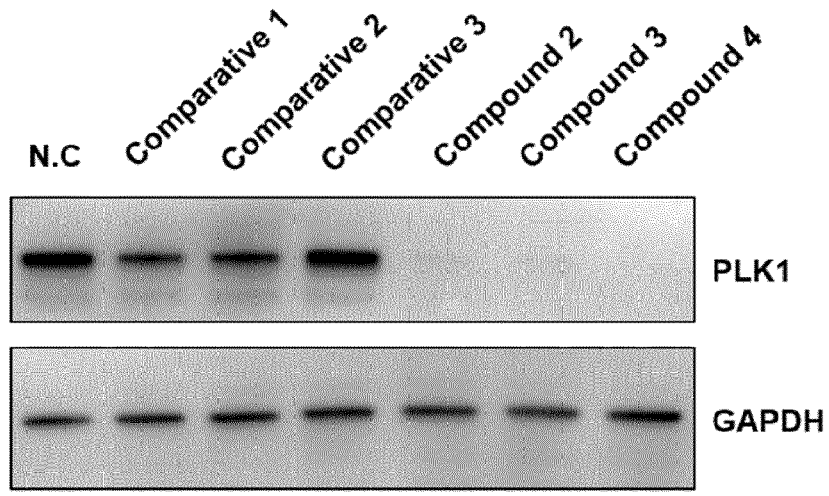
[Fig. 2]
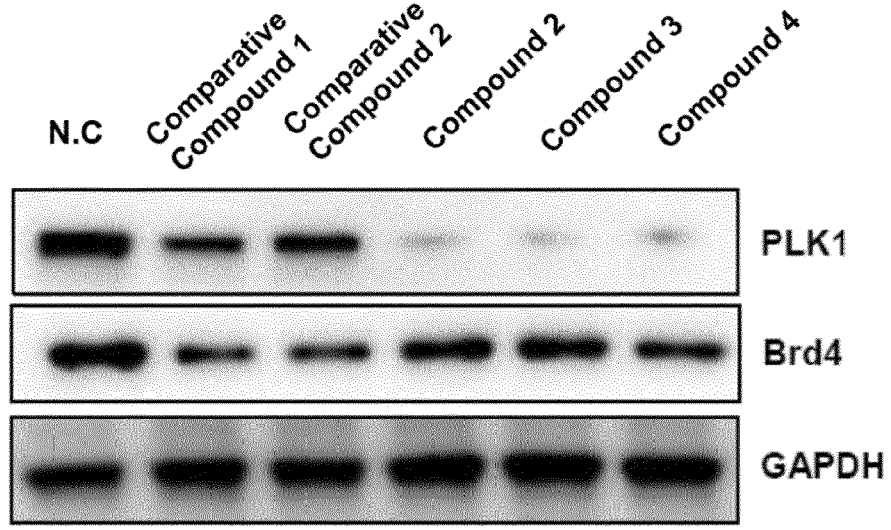

PLK1 SELECTIVE DEGRADATION INDUCING COMPOUND

CROSS-REFERENCE TO RELATED APPLICATIONS

This application is the U.S. National Stage application of PCT application no. PCT/KR2021/003807, filed on Mar. 27, 2021, titled PLK1 SELECTIVE DEGRADATION INDUCING COMPOUND, designating the United States, which claims priority to Korean application no. 10-2020-0037875, filed on Mar. 27, 2020, the contents of each of which each incorporated herein by reference in their entireties.

TECHNICAL FIELD

The present invention relates to a selective PLK1 degradation inducing compound, a method for preparing the same, and the use thereof.

BACKGROUND ART

Polo-like kinase 1 (PLK1) is a serine/threonine kinase involved in the conversion of G2/M phase during cell growth and division. PLK1 is expressed and activated in a pulse form from the S phase to the G2/M phase, and rapidly degrades as mitosis ends.

PLK1 is overexpressed in various carcinomas such as colon cancer, lung cancer, bladder cancer, and melanoma, etc., and cancer cells overexpressing PLK1 tend to show resistance to various types of anticancer drugs. As the PLK1 dependence in various carcinomas was revealed as described above, there have been attempts to develop PLK1 inhibitor compounds such as volasertib (also known as BI6727), etc.

However, the conventional PLK1 inhibitors do not sufficiently inhibit PLK1 activity at concentrations that are clinically safe. Thus, there is a problem that even if the cell cycle of cancer cells is temporarily delayed, some cancer cells eventually restart the cell cycle, which may not obtain sufficient clinical effects (see Gheghiani et al., Cell Reports, 2017, etc.). In fact, many pharmaceutical companies such as Boehringer Ingelheim, GlaxoSmithKline, etc., have attempted to develop small-molecular compound-based PLK1 inhibitors, but most of them have failed or stopped in the clinical trial stage, and thus there are no commercially available PLK1 inhibitors to date. It shows that pharmacological mechanism that follows the method of inhibiting enzyme activity by binding to the active site of PLK1 like the small molecule compound inhibitors is not sufficiently effective in the development of new drugs intended to derive anticancer effects by inhibiting PLK1 activity of cancer cells.

Recently, a proteolysis targeting chimera (PROTAC) has been proposed as a small molecule-based platform technology capable of inducing proteolysis of a target protein in the body. The PROTAC is a bifunctional compound in which a ligand molecule that binds to disease-related target protein and an E3 ubiquitin ligase binding moiety are linked by a chemical linker. Theoretically, the PROTAC compound is capable of inducing degradation of the target protein by placing the disease-related target protein near the E3 ubiquitin ligase.

In the case of the PROTAC compound using PLK1 as a target protein, Chinese Patent Laid-Open No. 106543185 A discloses some bifunctional compounds in which a volasertib derivative compound and a binding moiety for the E3 ubiquitin ligase CRBN are linked by a chemical linker.

However, the related art document merely describes some limited forms of synthesis examples of PROTAC compounds, wherein in general, the target degradation activity and selectivity of PROTAC may vary significantly depending on selection of the target protein moiety, the E3 ubiquitin ligase binding moiety, and the like (see Burslem and Crews, 2017, etc.).

Further, the PROTAC compound described in the above-described document is characterized by a compound that simultaneously degrades PLK1 and BRD4, and degrade various proteins such as other PLK family proteins and BRD4, etc.), which may cause side effects due to off-target effects at the time of drug development. In particular, it is known that strong inhibition of BRD4 activity inevitably accompanies on-target toxicity such as blood toxicity and gastrointestinal toxicity along with pharmacological effects. Therefore, the PROTAC compound described in the above document would expect to face greater clinical side effects as more BRD4 protein gets degraded (see Bolden et al. Cell Reports, 2014).

Moreover, according to the document published by the inventors of the above document (see Mu et al. BBRC, 2019), it can be confirmed that the PROTAC compound, which simultaneously degrades PLK1 and BRD4, has much stronger BRD4 degradation ability than PLK1 degradation ability at the cellular level, and the cell cycle thereof almost stops in the G1 phase, etc., that is, the PROTAC compound actually acts only as a BRD4 inhibitor regardless of the way that the conventional PLK1 inhibitors exert pharmacological effects.

Therefore, there is an unsatisfied demand for effective and selective PLK1 degradation inducing compound, with no or minimal side effects.

DISCLOSURE OF INVENTION

Technical Problem

An object of the present invention is to provide selective PLK1 degradation inducing compounds.

Another object of the present invention is to provide a method for preparing the compounds.

Still another object of the present invention is to provide a use of the compounds.

Solution to Problem

Selective PLK1 Degradation Inducing Compounds

The present invention provides novel compounds that induce selective polo-like kinase 1 (PLK1) degradation. Specifically, the present invention provides a bifunctional compound in which a PLK1 binding moiety and an E3 ubiquitin ligase-binding moiety are linked by a chemical linker.

In one general aspect, there is provided a compound represented by the following Formula I, a stereoisomer thereof or a pharmaceutically acceptable salt thereof:

$$\text{ULM-Linker-PTM} \qquad \text{[Formula I]}$$

in the Formula I above,

ULM is CRBN or VHL E3 ubiquitin ligase binding moiety;-

PTM is PLK1 binding moiety represented by the following Formula II:

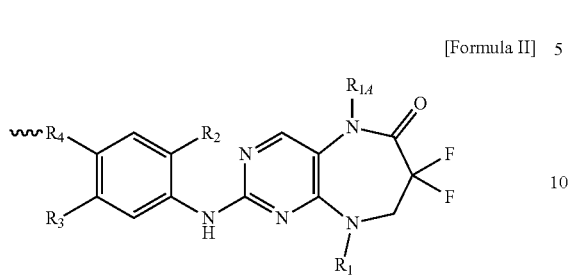

[Formula II]

{in the Formula II above,
$R_1$ is hydrogen, $C_{1-5}$ alkyl, or $C_{3-6}$ cycloalkyl;
$R_{1A}$ is hydrogen or $C_{1-3}$ alkyl;
$R_2$ is hydrogen, halogen, $C_{1-6}$ alkyl or $-OR_{2A}$;
$R_{2A}$ is $C_{1-4}$ alkyl or $C_{3-6}$ cycloalkyl, optionally substituted by one or more halogen or hydroxy;
$R_3$ is hydrogen, halogen, $-NO_2$, $-CN$, $-OH$, $C_{1-4}$ alkyl or $-OC_{1-4}$ alkyl;
$R_4$ is selected from the group consisting of a single bond,

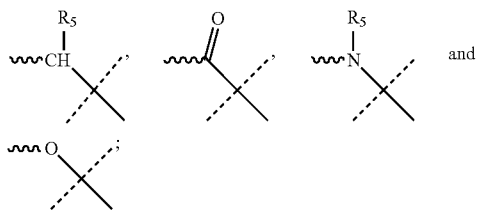

and $R_5$ is hydrogen or $C_{1-4}$ alkyl}; and
Linker is a chemical group that links ULM and PTM.
In the Formula II, ∿∿ indicates a covalent bond that links PTM into Linker.

(1) E3 Ubiquitin Ligase Binding Moiety (ULM)

In one embodiment of the present invention, ULM is a CRBN E3 ubiquitin ligase binding moiety.

In the present invention, CRBN means Cereblon E3 ubiquitin ligase. CRBN constitutes an E3 ubiquitin ligase complex together with DDB1, Cul4A and ROC1, wherein the CRBN is a substrate recognition subunit of the complex. Some compounds capable of binding to the CRBN E3 ubiquitin ligase are known in the art. For example, after it was known that thalidomide binds to the CRBN E3 ubiquitin ligase (see Ito et al. 2010), it has been reported that a number of immunomodulatory imide drugs (IMiD) including lenalidomide and pomalidomide have CRBN binding ability (see Chamberlain and Brian. 2019; Akuffo et al. 2018; and Burslem et al. 2018, etc.).

In one embodiment, the CRBN E3 ubiquitin ligase binding moiety in Formula I is represented by the following Formula A-1:

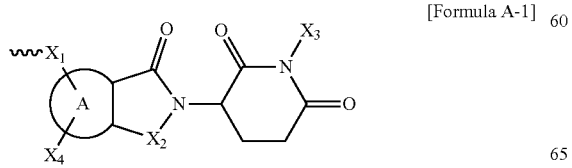

[Formula A-1]

wherein:

is a ring selected from the group consisting of

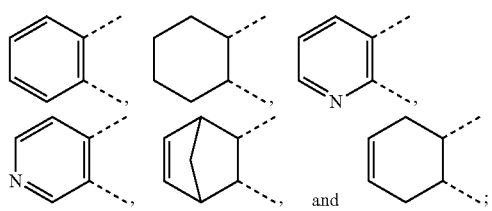

and $X_1$ is a single bond, $-CH_2-$, $-NH-$, $-O-$, $-CH_2CH_2-$, $-CC-$, $-CO-$, $-COO-$, $-NHCO-$ or $-CONH-$;
$X_2$ is $-CH_2-$, $-CH(C_{1-4}$ alkyl)-, $-NH-$, $-N(C_{1-4}$ alkyl)-, $-O-$, $-CO-$, $-CH_2-CH_2-$, $-NH-CH_2-$, $-NH-CH(C_{1-4}$ alkyl)-, $-N=CH-$, $-N=C(C_{1-4}$ alkyl)- or $-N=N-$;
$X_3$ is hydrogen or $C_{1-4}$alkyl; and
$X_4$ is hydrogen, halogen, $C_{1-6}$ alkyl, CN, $NH_2$, $NO_2$, OH, COH, COOH or $CF_3$.

In one embodiment, Formula A-1 is represented by the following Formula A-2:

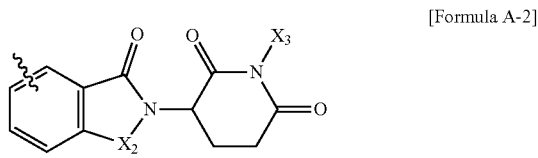

[Formula A-2]

wherein:
$X_2$ is $-CH_2-$, $-CH(C_{1-4}$ alkyl)-, $-CO-$ or $-N=N-$; and
$X_3$ is hydrogen or $C_{1-3}$ alkyl.

In certain embodiment, Formula A-2 is selected from the group consisting of:

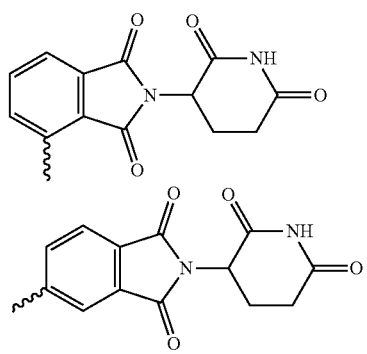

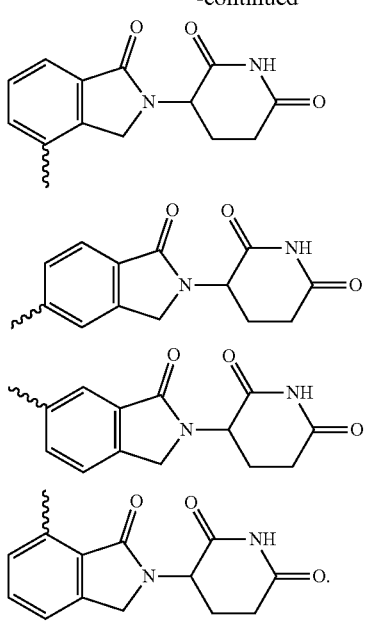
One example of CRBN E3 ubiquitin ligase binding moieties of Formula A-1 or A-2 may be derived from the compounds having the following structures (Chamberlain and Brian. 2019; Akuffo et al. 2018; etc.):
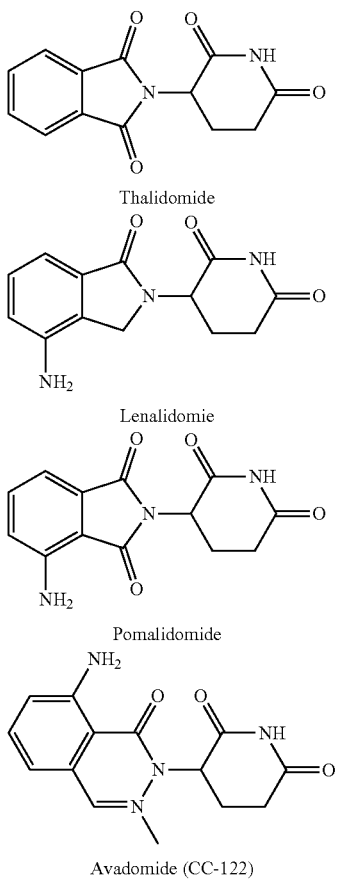
Another example of CRBN E3 ubiquitin ligase binding moieties of Formula A-1 or A-2 may be derived from the compounds having the following structures (Burslem et al. 2018; etc.):
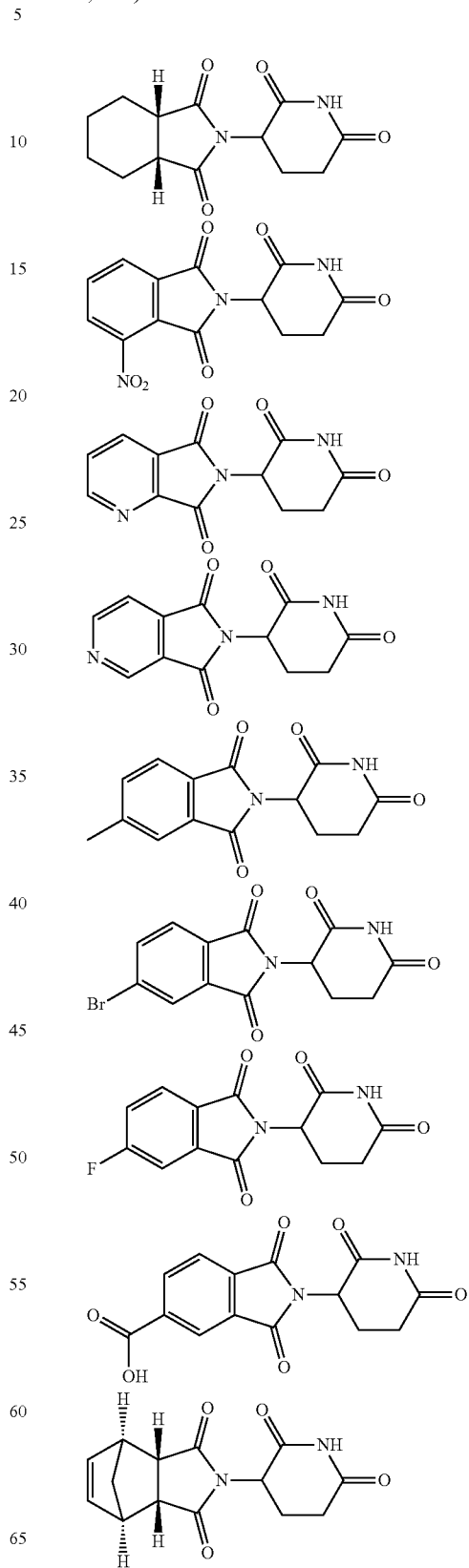

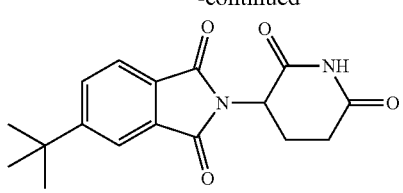
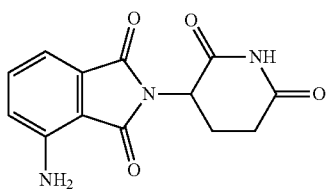
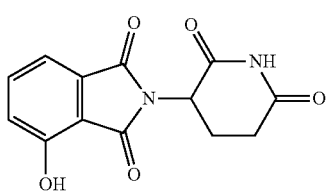
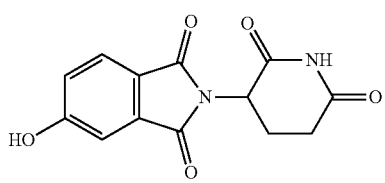
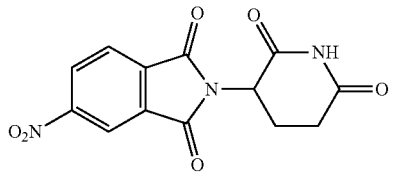
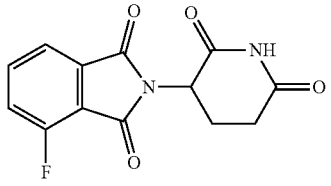
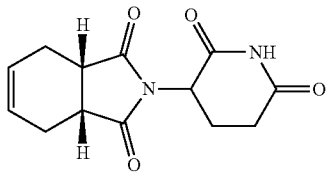
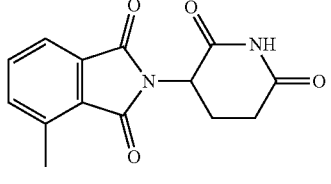
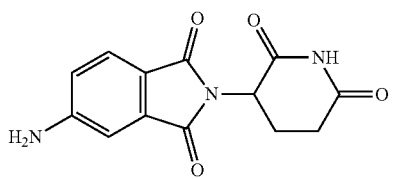

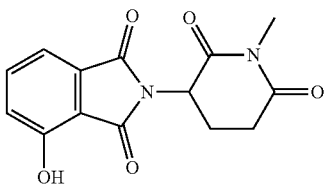 [SMILES: CN1C(=O)CCC(N2C(=O)c3cccc(O)c3C2=O)C1=O]

In specific example, the CRBN E3 ubiquitin ligase binding moieties of the present invention have one of the following structures:

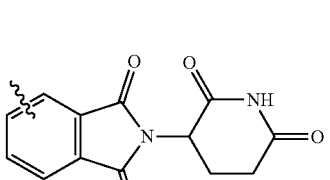
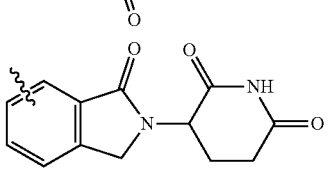
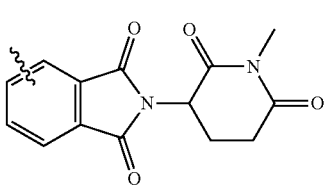
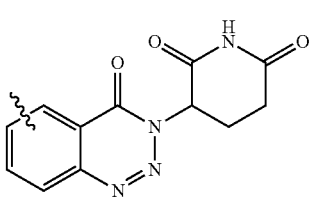

In another embodiment of the present invention, ULM is a VHL E3 ubiquitin ligase ligand binding moiety.

In the present invention, VHL means a von Hippel-Lindau tumor suppressor. VHL constitutes a VCB E3 ligation complex together with Elongin B, Elongin C, CUL2 and Rbx1, wherein VHL is a substrate recognition subunit of the complex. Some compounds capable of binding to the VHL E3 ubiquitin ligase are known in the art. For example, after it was known that peptide such as Ala-Leu-Ala-(Hy)Pro-Tyr-Ile-Pro heptapeptide (see Schneekloth et al. 2004) and Leu-Ala-(Hy)Pro-Tyr-Ile pentapeptide (see Rodriguez-Gonzalez et al. 2008), an improved low-molecular VHL E3 ubiquitin ligase binding compound has been reported (see Buckley et al. J. Am. Chem. Soc. 2012; Buckley et al. Ang. Chem. Int. Ed. 2012; Galdeano et al. 2014; Soares et al. 2017, etc.).

In one embodiment, the VHL E3 ubiquitin ligase binding moiety in Formula I is represented by the following Formula B-1:

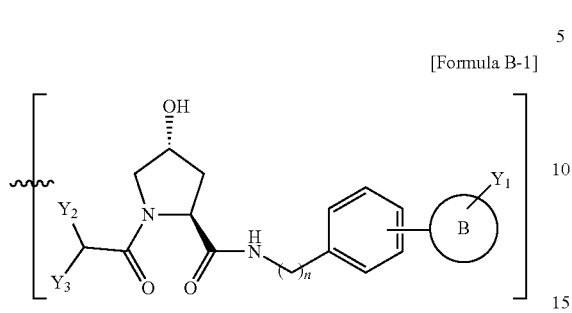

[Formula B-1]

wherein:

n is an integer from 1 to 3;

is 5- to 6-membered cycloalkyl, phenyl, 5- to 6-membered heterocycloalkyl, or 5- to 6-membered heteroaryl, wherein the heterocycloalkyl or the heteroaryl contains one to three N, O or S atoms;

$Y_1$ is hydrogen or $C_{1-4}$ alkyl;

$Y_2$ is $C_{1-4}$alkyl, hydroxy($C_{1-4}$alkyl), —($C_{0-2}$alkyl)-COH, $C_{3-8}$cycloalkyl, or phenyl;

$Y_3$ is hydrogen, or

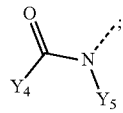

$Y_4$ is hydrogen, halogen, $C_{1-4}$alkyl, —O($C_{1-4}$alkyl), $C_{3-6}$cycloalkyl or 4- to 6-membered heterocycloalkyl, optionally substituted by halogen, —OH, —CN, —NHCOH, —NHCOCH$_3$, —COH or —COCH$_3$; and $Y_5$ is hydrogen or $C_{1-4}$ alkyl.

In one embodiment, the VHL E3 ubiquitin ligase binding moiety in Formula B-1 is selected from the group consisting of the following Formula B-2-1 and B-2-2:

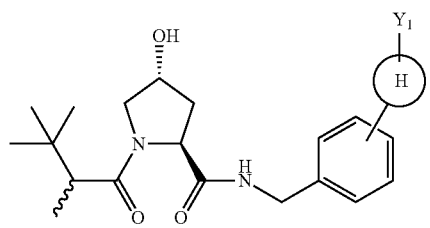

[Formula B-2-1]

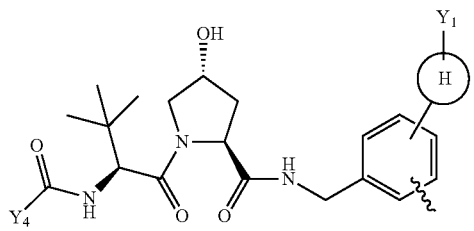

[Formula B-2-2]

wherein:

is 5-membered heteroaryl ring selected from the group consisting of oxazole, isoxazole, thiazole, isothiazole, imidazole, pyrazole, triazole, oxadiazole, pyrrole, pyrrolidine, furan, dihydrofuran and tetrahydrofuran;

$Y_1$ is hydrogen or $C_{1-3}$ alkyl; and $Y_4$ is $C_{1-4}$ alkyl or $C_{3-5}$cycloalkyl, optionally substituted by hydrogen or halogen.

In certain example, Formula B-2-1 is represented by the moiety selected from the group consisting of:

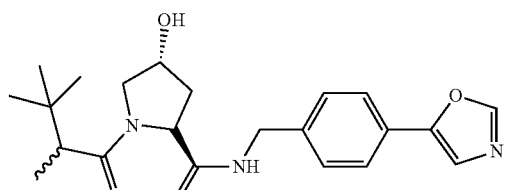

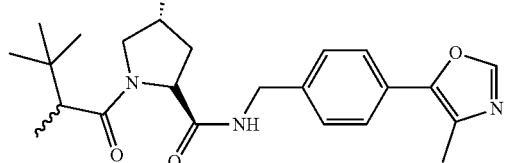

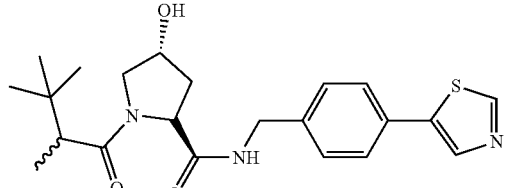

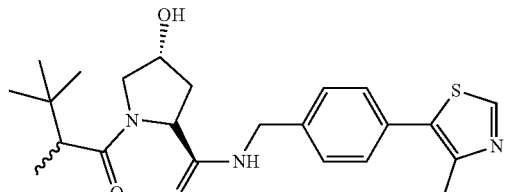

In certain example, Formula B-2-2 is represented by the moiety selected from the group consisting of:
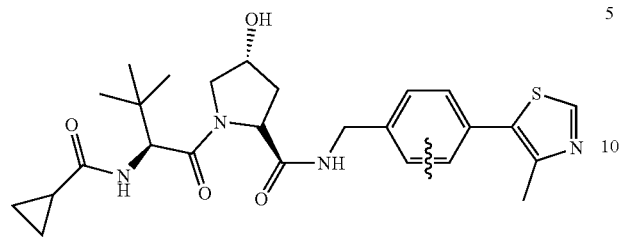
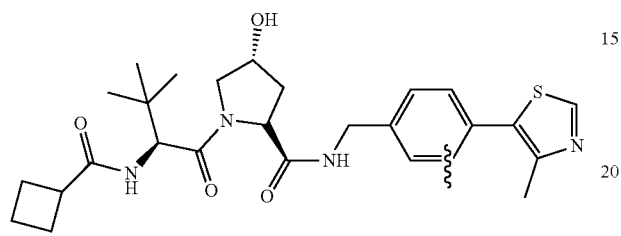
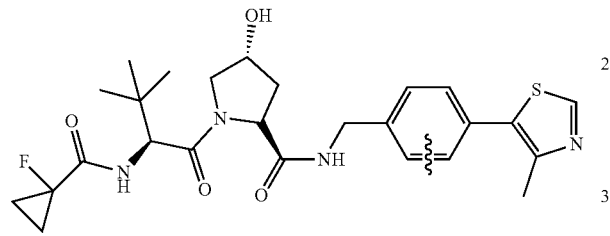
One example of CRBN E3 ubiquitin ligase binding moieties of Formula B-1, B-2-1 or B-2-2 may be derived from the compounds having the following structures (Galdeano et al. (2014); etc.):
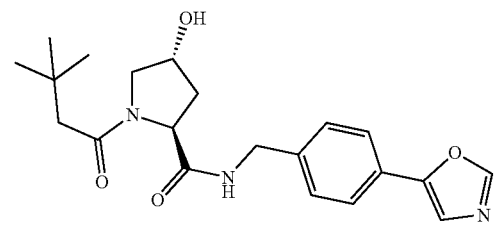
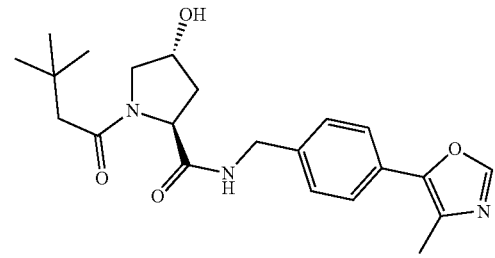
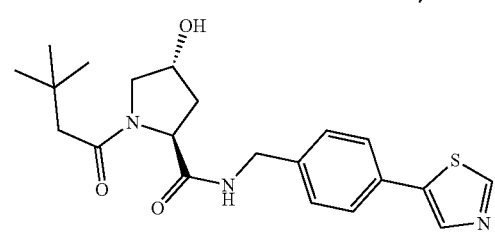
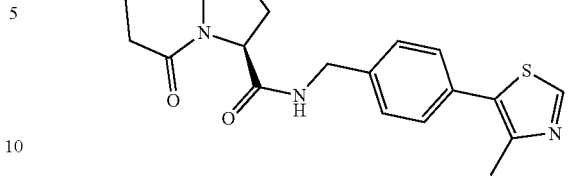
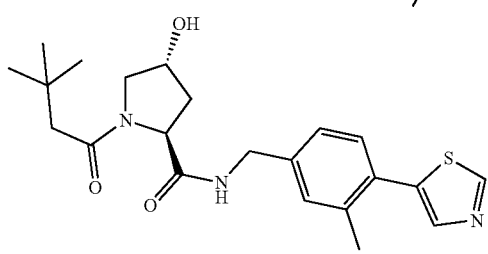
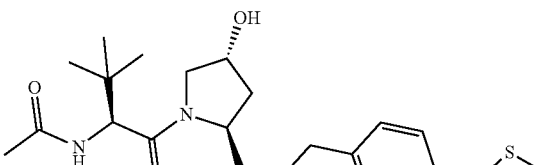
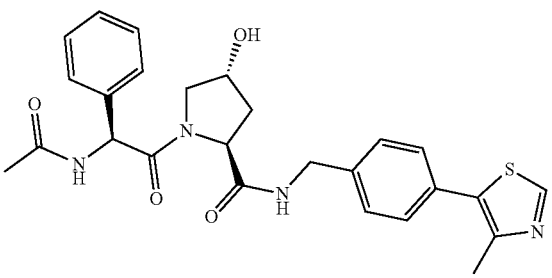
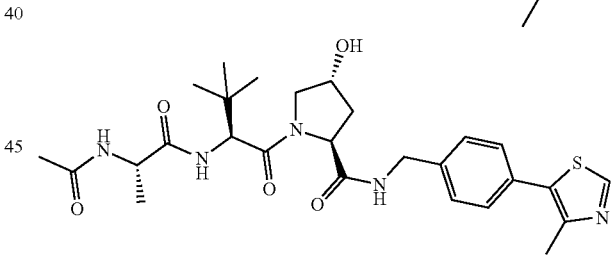
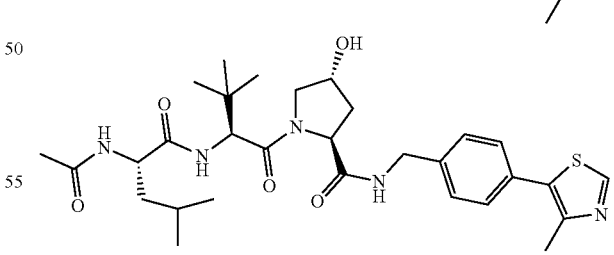
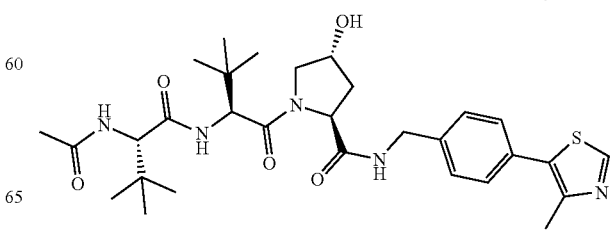

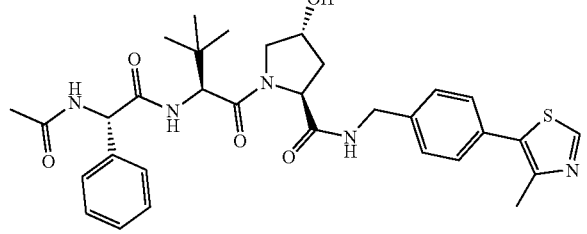
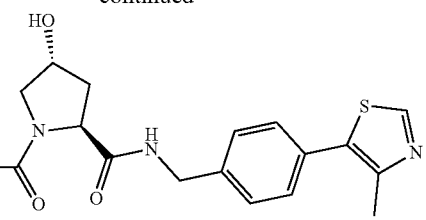
Another example of CRBN E3 ubiquitin ligase binding moieties of Formula B-1, B2-1 or B-2-2 may be derived from the compounds having the following structures (Soares et al. 2017; etc.):
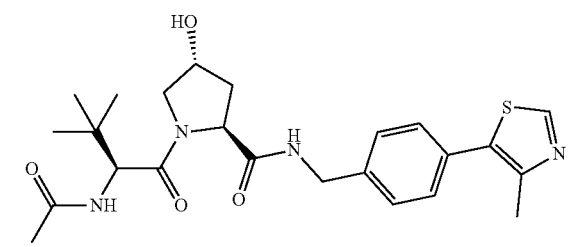
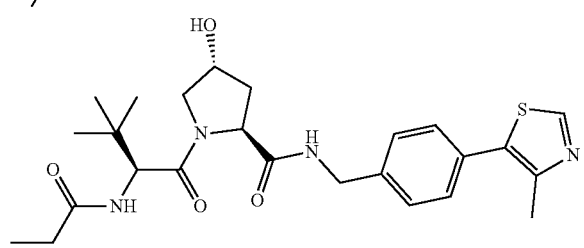
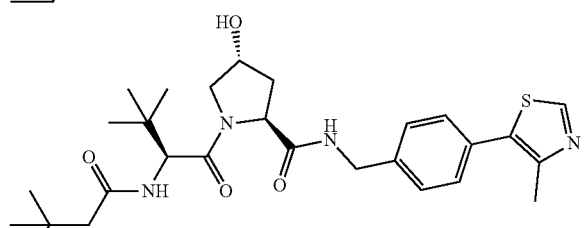
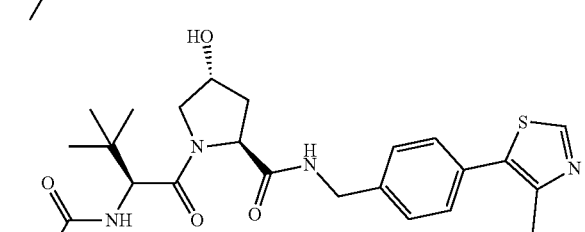
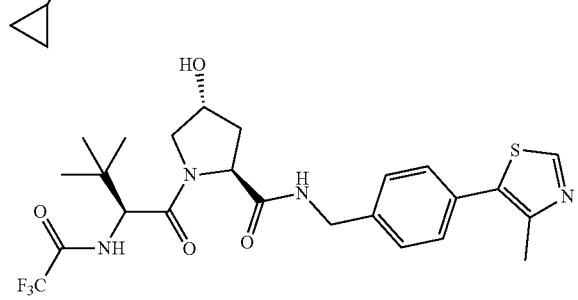
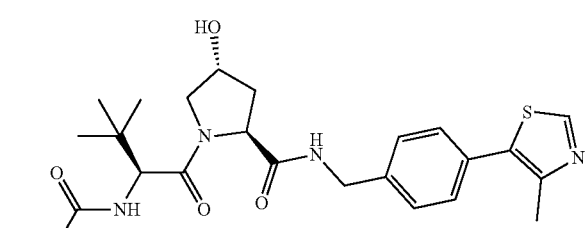
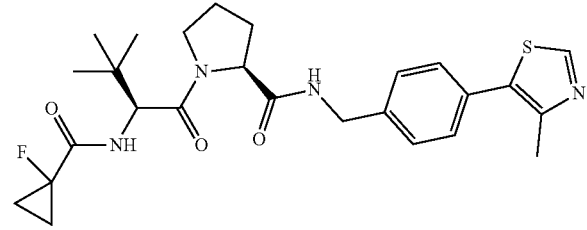
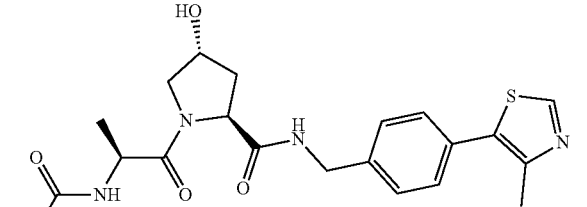
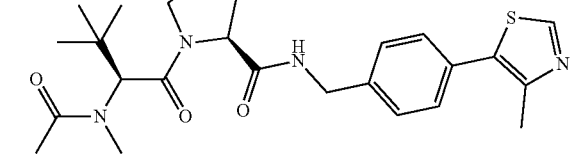
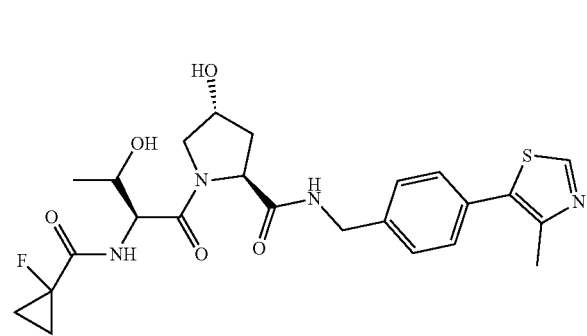

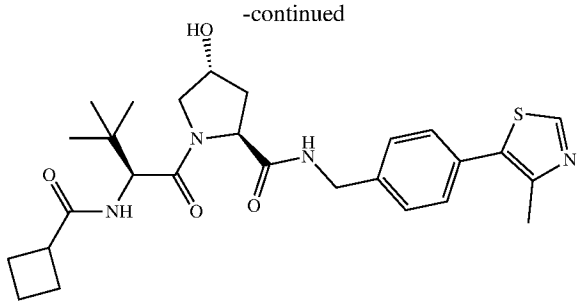

In the present invention, ULM have a linker attached at a position necessary to exhibit the biofunctionality of PROTAC. In the present invention, the Linker may be covalently linked through represented in Formulas A-1, A-2, B-1, B-2-1, and B-2-2. If there is not indicated, one hydrogen in the moiety of E3 ubiquitin ligase binding compound may be substituted into a single bond to be connected to the Linker.

(2) Protein Target Moiety (PTM)

In the compound represented by Formula I, the PTM, a moiety that performs a target protein ligand function, is a polo-like kinase 1 (PLK1) binding moiety represented by Formula II above.

The compound represented by Formula II alone is a pyrimidodiazepinone derivative that may bind to the active site of PLK1 (see Nie, Zhe, et al. Bioorganic & medicinal). chemistry letters 23.12 (2013): 3662-3666.] and International Patent Publication No. WO2009/042711, etc.)

In one embodiment, Formula II is represented by the following Formula III:

[Formula III]

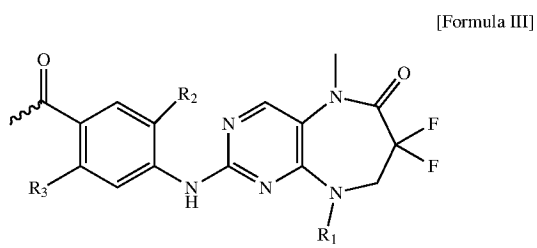

wherein:

$R_1$ is $C_{1-5}$ alkyl or $C_{3-7}$ cycloalkyl;

$R_2$ is hydrogen or $-OR_{2A}$;

$R_{2A}$ is $C_{1-6}$ alkyl, $C_{3-7}$ cycloalkyl, $CF_3$ or $-(C_{1-3}$alkylene$)$-OH;

$R_3$ is hydrogen or halogen.

In one embodiment, the PTM moiety is PTM moiety that is included in the compound selected from the group consisting of Compound 1 to 175.

(3) Linker

In one embodiment of the present invention, the Linker as defined in Formula I is represented by the following Formula L:

[Formula L]

wherein:

⌇⌇⌇ and − − − − − are each independently bond;

$L_{ULM}$ is covalently bonded to ULM moiety through ⌇⌇⌇ that is linked thereto, $L_{PTM}$ is covalently bonded to PTM moiety through ⌇⌇⌇ that is linked thereto, $L_{ULM}$, $L_{PTM}$ and $L_{INT}$ are independently selected from the group consisting of null, a single bond, $-CH_2-$, $-NH-$, $-O-$, $-S-$, $-SO-$, $-SO_2-$, $-CO-$, $-CH_2CH_2-$, $-CHCH-$, $-CC-$, $-CH_2CH_2O-$, $-OCH_2CH_2-$, $-CH_2CH_2S-$, $-SCH_2CH_2-$, $-COO-$, $-CONH-$, $-NHCO-$ and

, optionally subsisted by one or more $C_{1-6}$ alkyl, $C_{3-8}$cycloalkyl, halogen, hydroxy, amino, nitro, cyano or haloalkyl {wherein

is cycloalkyl, heterocycloalkyl, aryl, or heteroaryl}; and p is an integer from 1 to 30.

In one embodiment, p is 1 or more; 5 or more; 10 or more; 15 or more; 20 or more; or 25 or more. In another embodiment, p is 25 or less; 20 or less; 15 or less; 10 or less; 5 or less.

In Formula L above, $L_{ULM}$ may be

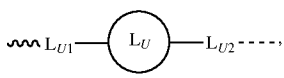, wherein:

$L_{U1}$ is selected from the group consisting of a single bond, $-CH_2-$, $-CH_2CH_2-$, $-CH=CH-$, $-CC-$, $-NH-$, $-NCH_3-$, $-CO-$, $-NHCO-$ and $-O-$;

$L_{U2}$ is selected from the group consisting of a single bond, $-CH_2-$, $-NH-$, $-O-$, $-CO-$ and $-CONH-$; and

is null or a ring selected from the group consisting of 3- to 10-membered cycloalkyl, 4- to 10-membered heterocycloalkyl, 6- to 10-membered aryl and 5- to 10-membered heteroaryl.

In certain embodiment,

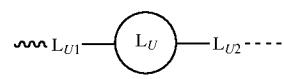

is selected from the group consisting of $-CH_2-$, $-CC-$, $-NH-$, $-NHCO-$, $-NHCO-CH_2-O-$, $-NH-CH_2-CONH-$, $-O-$, $-OCH_2-CONH-$,

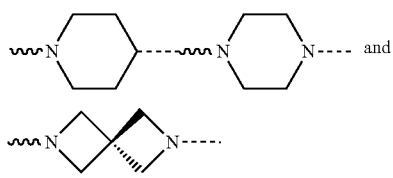

In Formula L above, $L_{ULM}$ may be

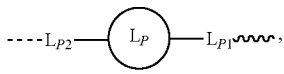

wherein:
$L_{P1}$ is selected from the group consisting of a single bond, —O—, —S—, —NH—, —N(C$_{1-4}$ alkyl)-, —CH$_2$—, —CH(C$_{1-4}$ alkyl)-, —CH$_2$NH—, and —CH$_2$CH$_2$—;
$L_{P2}$ selected from the group consisting of a single bond, —CO—, —COCH$_2$—, —NHCO—, —NHCOCH$_2$—, -HET- and -HET-CH$_2$— {wherein HET is 5- to 6-membered heterocyclyl or heteroaryl containing one ore more N, S or O atoms}; and

is null, amino substituted C$_{1-8}$ alkyl, or a ring selected from the group consisting of 3- to 10-membered cycloalkyl, 4- to 10-membered heterocycloalkyl, 6- to 10-membered aryl and 5- to 10-membered heteroaryl.

In certain embodiment,

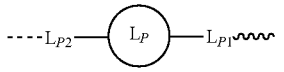

is selected from the group consisting of

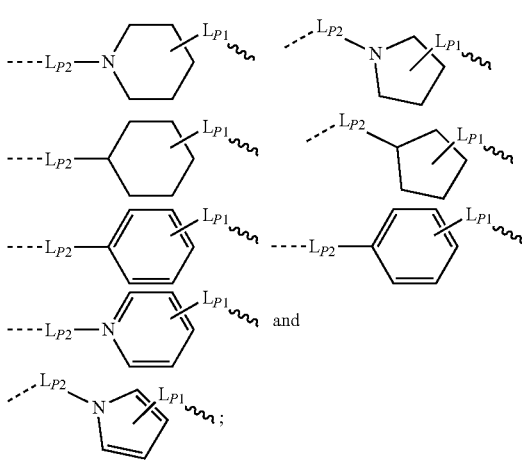

and for example, selected from the group consisting of

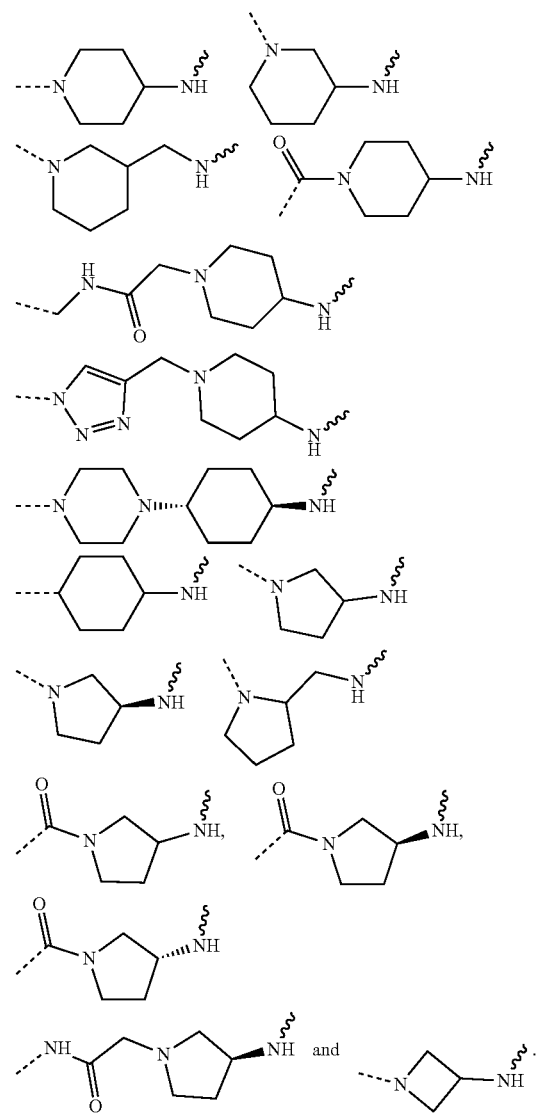

In certain embodiment,

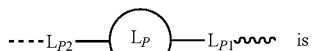

is

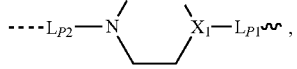

wherein $X_1$ is CH or N; $X_2$ and $X_3$ are each independently hydrogen, CH$_3$ or CH$_2$CH$_3$.

In certain embodiment,

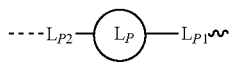

is selected from the group consisting of

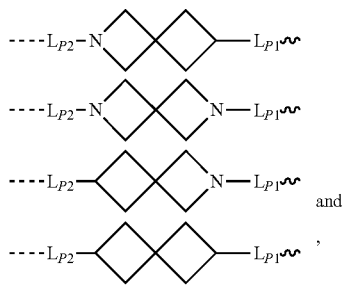

and for example,

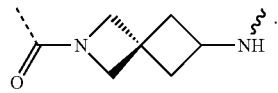

In Formula L above,

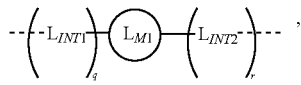

may be

, wherein:

$L_{M1}$ is null or a ring selected from the group consisting of 3- to 10-membered cycloalkyl, 4- to 10-membered heterocycloalkyl, 6- to 10-membered aryl and 5- to 10-membered heteroaryl.

$L_{INT1}$ and $L_{INT2}$ are each independently selected from the group consisting of $CH_2$—, —NH—, —NCH$_3$—, —O—, —S—, —SO—, —SO$_2$—, —CO—, —CH$_2$CH$_2$O—, —OCH$_2$CH$_2$—, —CH$_2$CH$_2$S—, —SCH$_2$CH$_2$—, —COO—, —CONH— and —NHCO—; and q and r are each independently an integer from 1 to 10.

In one embodiment, Linker is a linker that is included in the compound selected from the group consisting of Compound 1 to 175.

In a certain embodiment of the present invention, the compound represented by Formula I is a compound that is selected from the group consisting of Compound 1 to 175.

In the present invention, a pharmaceutically acceptable salt refers to any organic or inorganic acid addition salt with a concentration that is relatively non-toxic, is harmless, and has effective action to patients, wherein side effects caused by this salt does not deteriorate beneficial efficacy of the compound represented by Formula I. For example, the pharmaceutically acceptable salt may be an inorganic acid such as hydrochloric acid, phosphoric acid, sulfuric acid, nitric acid, or the like, or an organic acid such as methanesulfonic acid, p-toluenesulfonic acid, acetic acid, trifluoroacetic acid, maleic acid, succinic acid, oxalic acid, benzoic acid, tartaric acid, fumaric acid, manderic acid, propionic acid, citric acid, lactic acid, glycolic acid, gluconic acid, galacturonic acid, glutamic acid, glutaric acid, glucuronic acid, aspartic acid, ascorbic acid, carbonic acid, vanillic acid or hydroiodic acid, but is not limited thereto.

Method for the Preparing the Selective PLK1 Degradation Inducing Compounds

In the present invention, the compound represented by Formula I above, a stereoisomer thereof, or a pharmaceutically acceptable salt thereof may be prepared through reactions such as the following Reaction Schemes 1 to 3 by a synthetic method known in the field of organic chemistry or a modification technique apparent to those skilled in the art.

[Reaction Scheme 1]

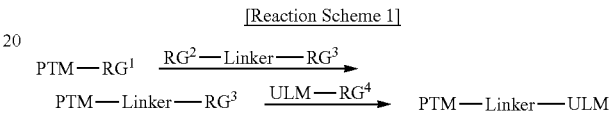

[Reaction Scheme 2]

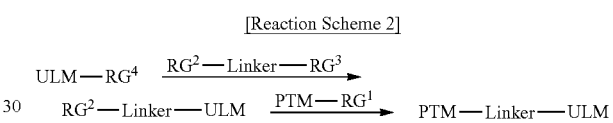

[Reaction Scheme 3]

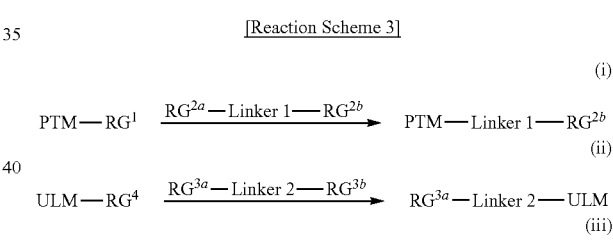

In the Reaction Schemes 1 to 3 above, PTM, Linker and ULM are a group defined in the above, or a suitable derivative thereof. $RG^1$, $RG^2$, $RG^{2a}$, $RG^{2b}$, $RG^3$, $RG^{3a}$, $RG^{3b}$ and $RG^4$ are moieties including a suitable reactive group capable of linking together with an intermediate of the PROTAC compound represented by Formula I through formation of the covalent bond in the field of organic synthesis. The formation of the covalent bond may be achieved by synthetic reactions such as amide formation, ester formation, carbamate formation, urea formation, ether formation, amine formation, and single bonds, double bond formation between various carbons, click chemistry and the like, depending on specific reaction groups, but is not limited thereto.

Variations of each step in the above Reaction Scheme may include one or multiple synthesis steps. Isolation and purification of the product may be accomplished by standard procedures known to those skilled in the art of organic chemistry.

In one embodiment, the compounds of the present invention can be prepared through Reaction Scheme 1 by one or multiple synthetic steps.

In one example of Reaction Scheme 1, when ULM is Formula A-1, the compound of the present invention may be prepared through the following Reaction Scheme 1-A (see Example 40).

[Reaction Scheme 1-A]

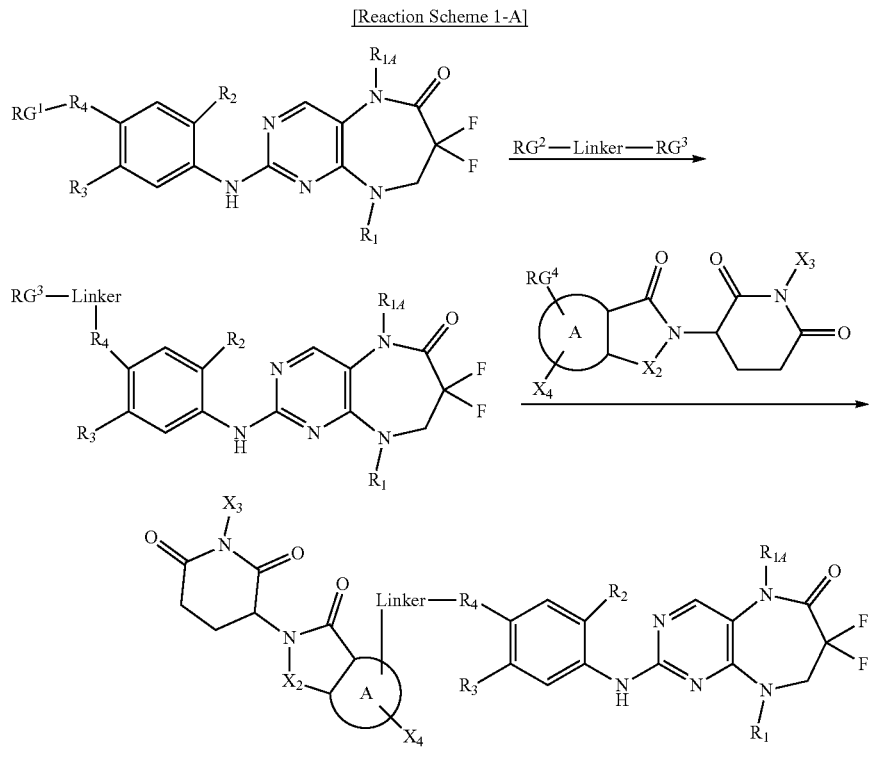

Formula 1A

In one example of Reaction Scheme 1, when ULM is Formula B-1, the compound of the present invention may be prepared through the following Reaction Scheme 1-B.

[Reaction Scheme 1-B]

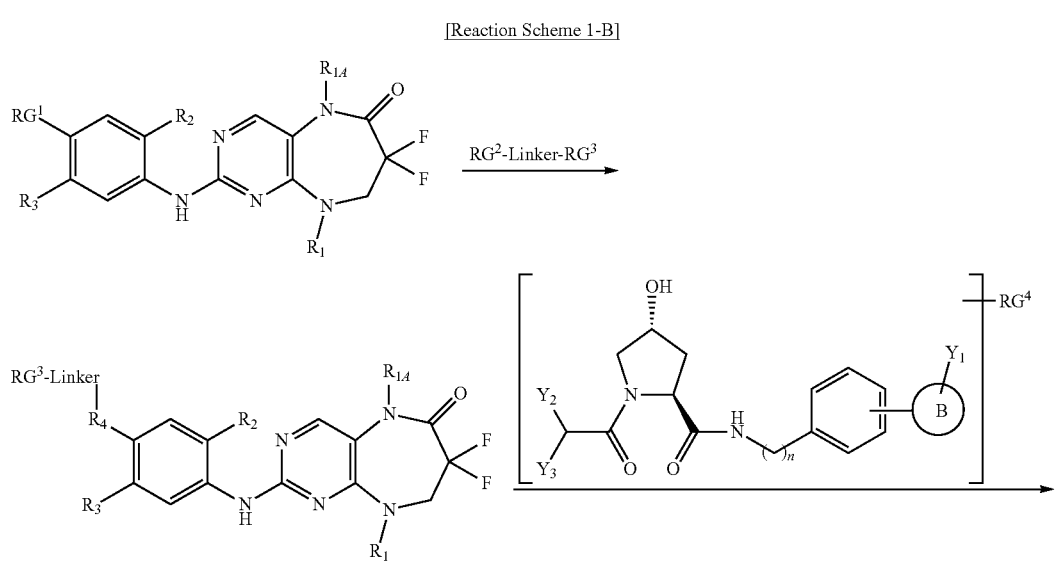

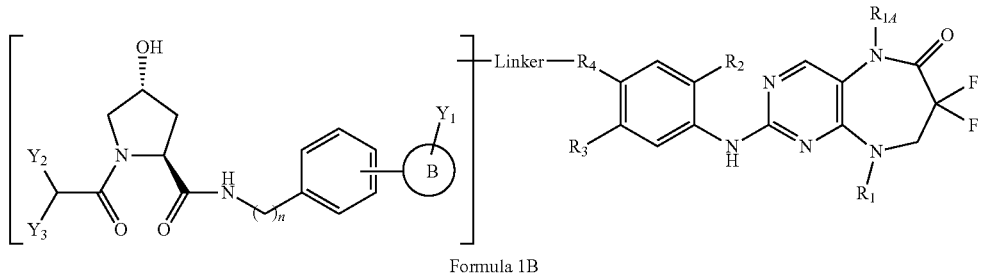
Formula 1B
In one example of Reaction Scheme 2, when ULM is Formula A-1, the compound of the present invention may be prepared through the following Reaction Scheme 2-A (see Example 1-39, 41-60, 63-79, 90-122, 124-158, 162-175).
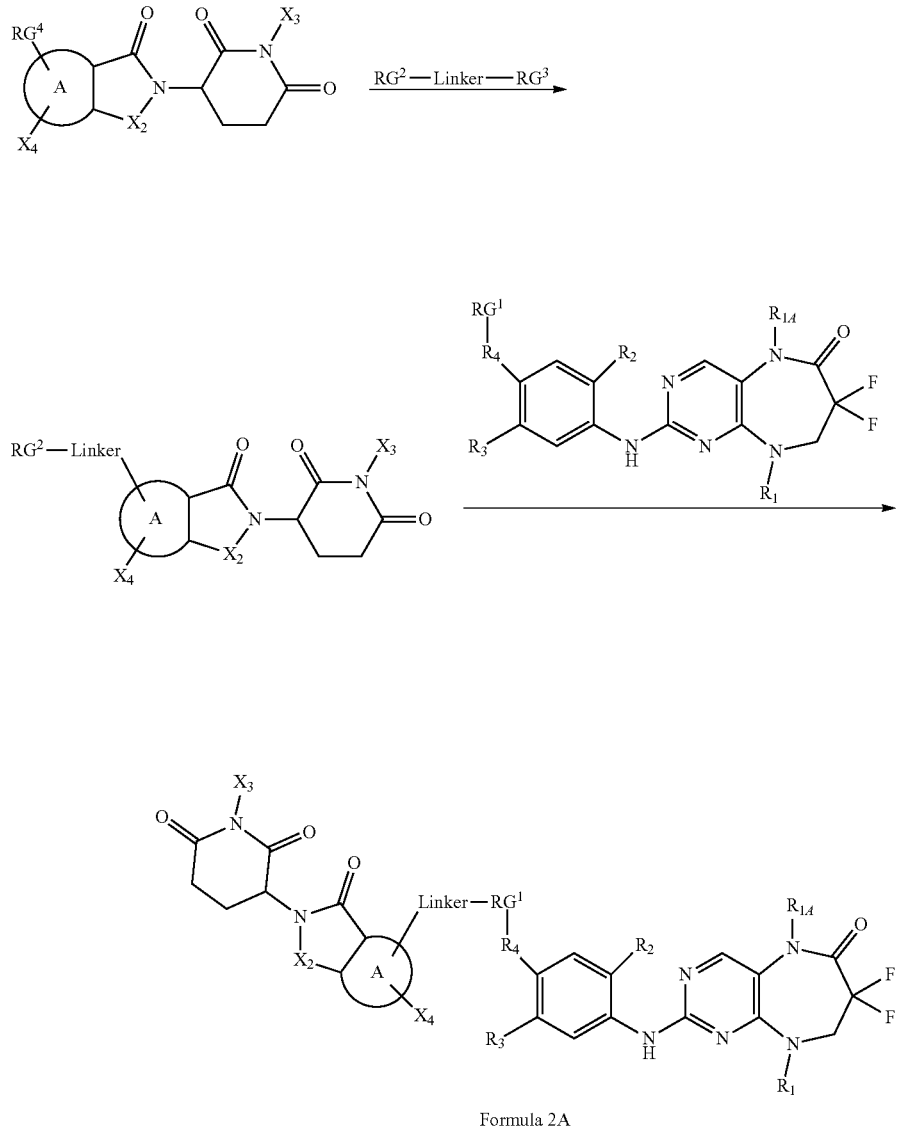
Formula 2A In one example of Reaction Scheme 2, when ULM is Formula B-1, the compound of the present invention may be prepared through the following Reaction Scheme 2-B (see Example 80-89)

[Reaction Scheme 2-B]

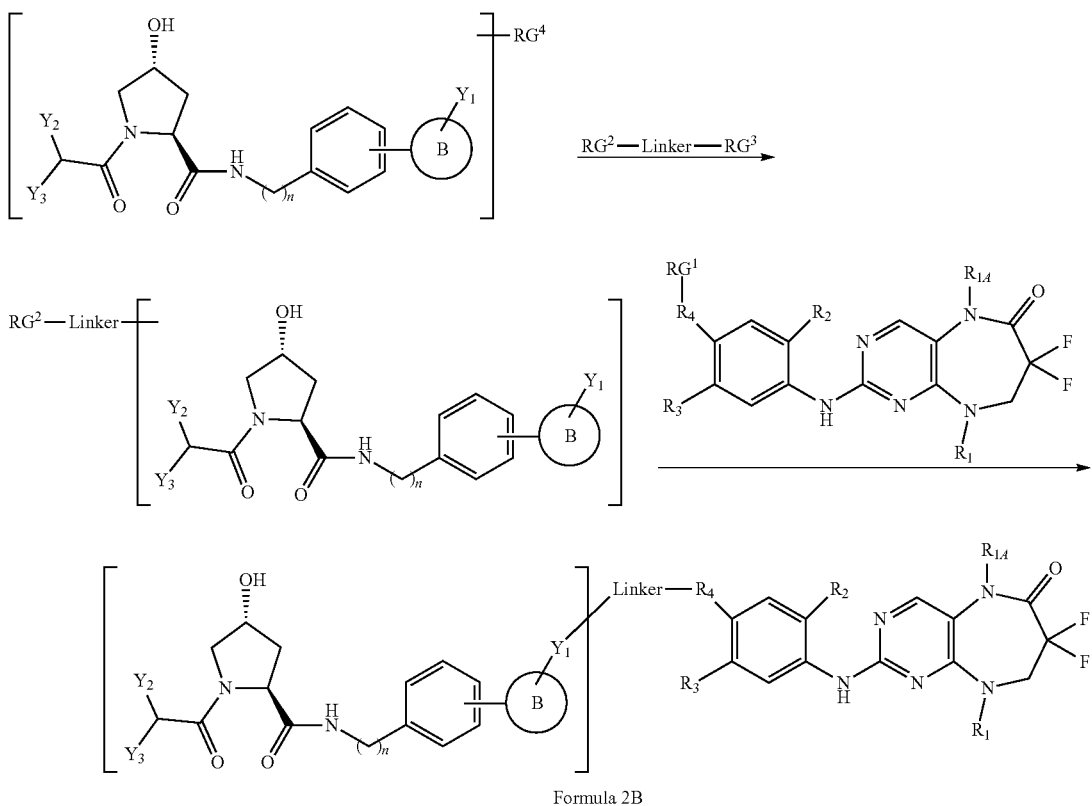

Formula 2B

In one example of Reaction Scheme 3, when ULM is Formula A-1, the compound of the present invention may be prepared through the following Reaction Scheme 3-A (see Example 61, 62, 123, 159, 160, 161).

[Reaction Scheme 3-A]

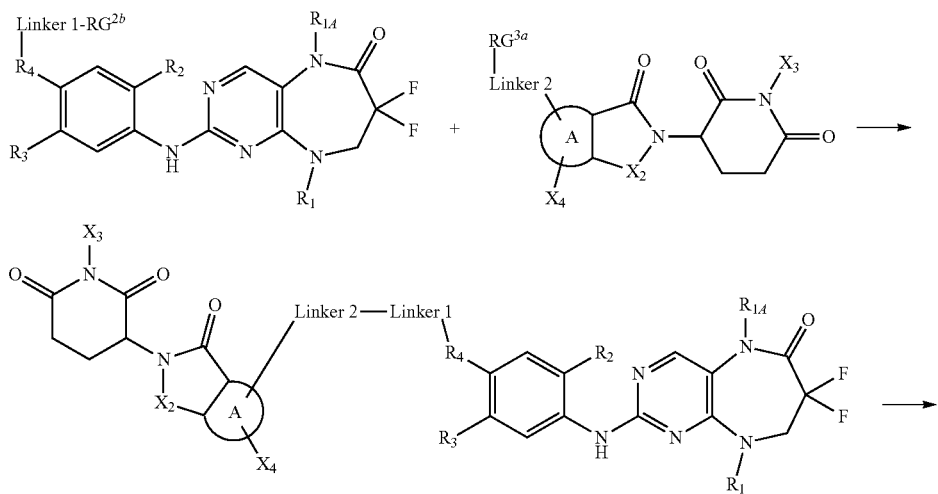

-continued

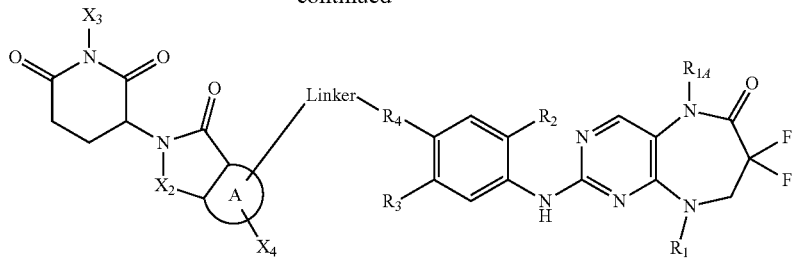

Formula 3A

In one example of Reaction Scheme 3, when ULM is Formula B-1, the compound of the present invention may be prepared through the following Reaction Scheme 3-B.

skilled in the art with reference to documents known in the field of organic chemistry, descriptions of Examples of the present invention, and the like.

[Reaction Scheme 3-B]

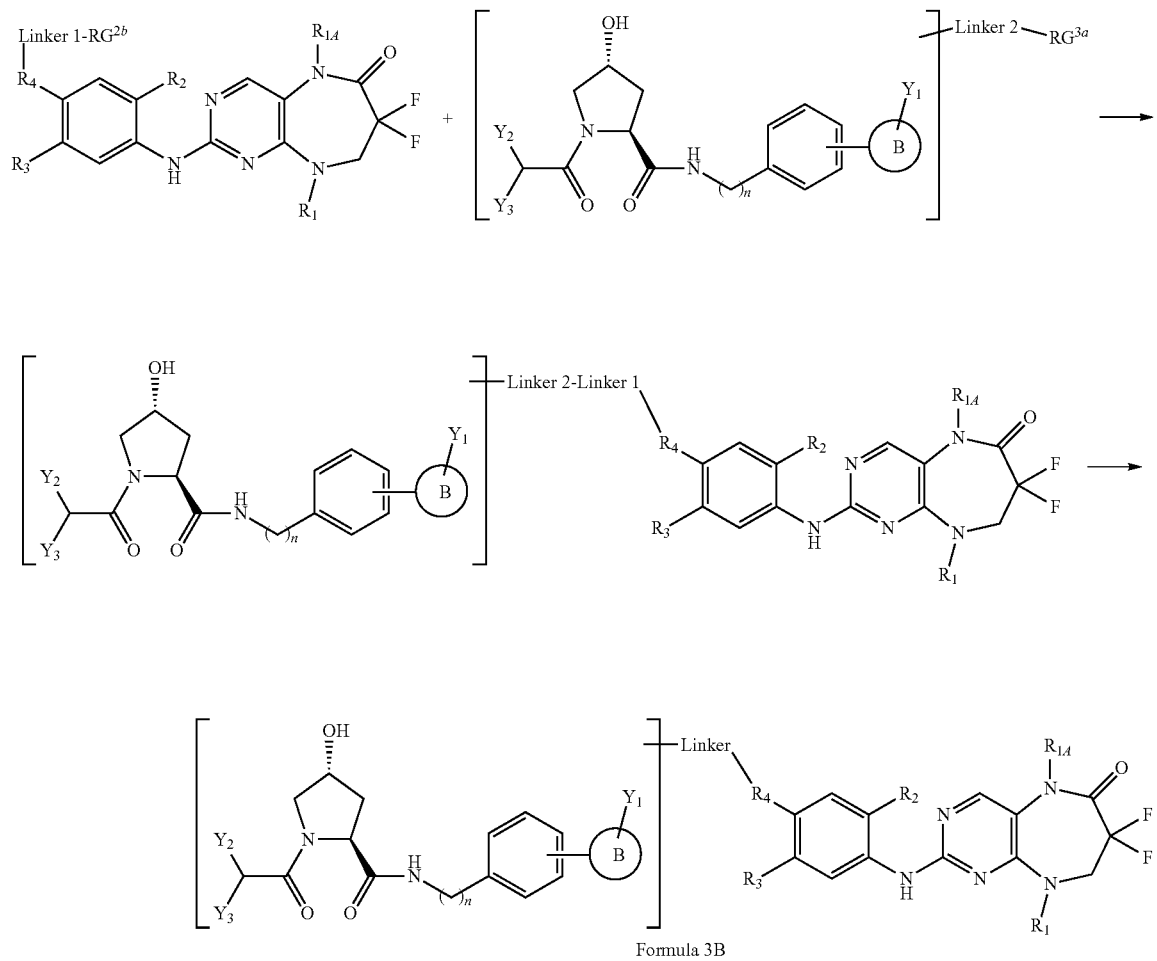

Formula 3B

In the above schemes, $RG^1$, $RG^2$, and $RG^{2a}$ are each independently $L_{PTM}$ or any reaction precursor thereof, $RG^3$, $RG^4$ and $RG^{3a}$ are each independently $L_{ULM}$ or any reaction precursor thereof, and $RG^1$, $RG^2$, $RG^{2a}$, $RG^3$, $RG^{3a}$ and $RG^4$ may be appropriately selected according to the structure and linker position of the target compound.

In the above Reaction Scheme, each compound represented by PTM and ULM may be synthesized by a person The present invention also provides the compounds represented by PTM-Linker-$RG^3$ or PTM-Linker 1-$RG^{2b}$ that are the reaction intermediates of the compounds represented by Formula I.

Use of the Selective PLK1 Degradation Inducing Compounds

An embodiment of the present invention is a composition for inducing PLK1 degradation including a compound represented by Formula I or a pharmaceutically acceptable salt thereof. The Formula I is the same as defined above.

In the experimental examples of the present invention, it was confirmed that the compounds of the present invention effectively induce the protein degradation of PLK1 (Table 2). Specifically, the compounds of the present invention have significantly superior protein degradability of PLK1 compared to the compounds disclosed in CN 106543185 A, which is a prior art document (FIGS. 1 & 2). Further, the compounds of the present invention have little or no degradability to BRD4, a target protein other than PLK1. Therefore, there is an advantage of minimizing side effects due to off-target degradation occurring in the compounds disclosed in the prior art documents (FIG. 2).

The PLK1 degradation-inducing PROTAC compound of the present invention is capable of fundamentally degrading the target protein, PLK1 in view of the mechanism of action, thereby achieving an excellent PLK1 inhibitory effect as compared to the conventional PLK1 small molecule inhibitor that inhibits the simple activity of PLK1.

Accordingly, the composition including the compound represented by Formula I of the present invention or a pharmaceutically acceptable salt thereof may be effectively employed for selective degradation of PLK1.

An embodiment of the present invention is a composition for preventing or treating PLK1-related diseases including the compound represented by Formula I or the pharmaceutically acceptable salt thereof. An another embodiment of the present invention is a method for the prevention or treatment of PLK-related diseases comprising administering the composition to a subject in need thereof. The Formula I is the same as defined above.

In the present invention, the PLK1-related disease refers to any disease or condition capable of being treated, alleviated, delayed, inhibited or prevented from induction of degradation or inhibition of activity of PLK1. In an embodiment, the PLK1-related disease may be a cancer (malignant tumor), a benign tumor, a neurological disease, or other genetic or non-genetic diseases caused by excessive cell division.

The cancer includes all cancers capable of exhibiting prophylactic or therapeutic efficacy due to inhibition of PLK1 activity, and may be solid cancer or blood cancer. For example, the cancer may be one or more selected from the group consisting of squamous cell carcinoma, small cell lung cancer, non-small cell lung cancer, lung adenocarcinoma, lung squamous cell carcinoma, peritoneal cancer, skin cancer, skin or intraocular melanoma, rectal cancer, anal muscle cancer, esophageal cancer, small intestine cancer, endocrine cancer, parathyroid cancer, adrenal cancer, soft tissue sarcoma, urethral cancer, chronic or acute leukemia, lymphocytic lymphoma, hepatocellular carcinoma, gastrointestinal cancer, gastric cancer, pancreatic cancer, glioblastoma, cervical cancer, ovarian cancer, liver cancer, bladder cancer, liver tumor, breast cancer, colon cancer, colorectal cancer, endometrial or uterine cancer, salivary gland cancer, kidney cancer, prostate cancer, vulvar cancer, thyroid cancer, head and neck cancer, brain cancer, osteosarcoma, and the like, but is not limited thereto. The cancer includes not only primary cancer but also metastatic cancer.

The benign tumors include all benign tumors capable of exhibiting prophylactic or therapeutic efficacy due to the inhibition of PLK1 activity, such as benign tumors in pre-cancer stages, and may be solid tumors or blood tumors.

For example, the tumor may be one or more selected from the group consisting of Barrett's esophagus, colon adenoma and polyp, breast fibroadenoma and cyst, monoclonal gammopathy of undetermined significance (MGUS), monoclonal lymphocytosis, and the like, but is not limited thereto.

The neurological diseases include all neurological diseases capable of exhibiting prophylactic or therapeutic efficacy due to the inhibition of PLK1 activity, and specifically, may be one or more selected from the group consisting of central nervous system disease, neurodegenerative disease, Alzheimer's disease, Parkinson's disease, multiple sclerosis, Huntington's disease, senile dementia, epilepsy, Lou Gehrig, stroke, and nerve damage and axonal degeneration-related disorders following brain or spinal cord injury, but is not limited thereto.

The pharmaceutical composition of the present invention may further include one or more active ingredients exhibiting the same or similar medicinal effects in addition to the compound represented by Formula I above, or the pharmaceutically acceptable salt thereof.

An embodiment of the present invention is a method of degrading PLK1 by administering a compound represented by Formula I or a pharmaceutically acceptable salt thereof to mammals including humans.

Another embodiment of the present invention is a method of degrading PLK1 by administering the compound represented by Formula I or the pharmaceutically acceptable salt thereof to a sample in vitro. The sample may be a cell, a cell culture, a body fluid or tissue of a mammal including a human, but is not limited thereto.

Advantageous Effects of Invention

The compound of the present invention exhibits an effect of inducing PLK1 degradation. Therefore, the pharmaceutical compound of the present invention may be effectively utilized for preventing or treating PLK1-related diseases.

BRIEF DESCRIPTION OF DRAWINGS

FIG. 1 shows the western blotting results from the measurement of the protein degradability of PLK1 according to the bifunctional compound of the present invention; and FIG. 2 shows the results of western blotting results from the measurement of selective PLK1 protein degradability and off-target degradability other than PLK1.

BEST MODE FOR CARRYING OUT THE INVENTION

Unless otherwise defined, all technical and scientific terms used herein have the same meaning as commonly understood by one of ordinary skill in the art to which this disclosure belongs. The terminology used in the description is for describing particular embodiments only and is not intended to be limiting of the disclosure.

The present invention provides synthetic methods for Compound 1 to 175 shown in the table below.

TABLE 1
| Compound | Structure |
|---|---|
| 1 | 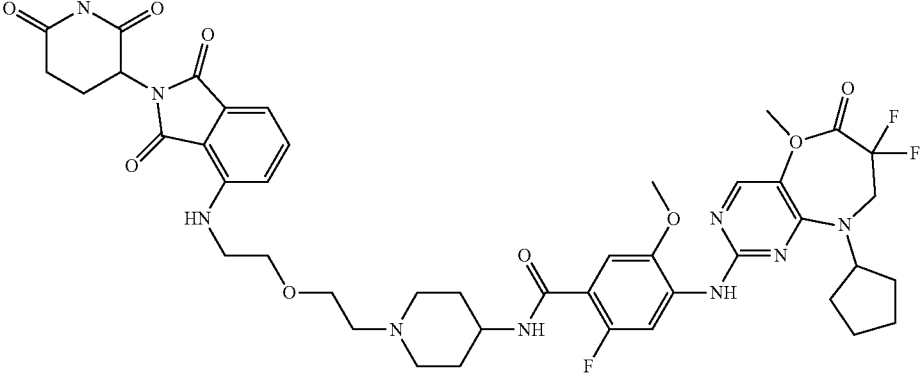 |
| 2 | 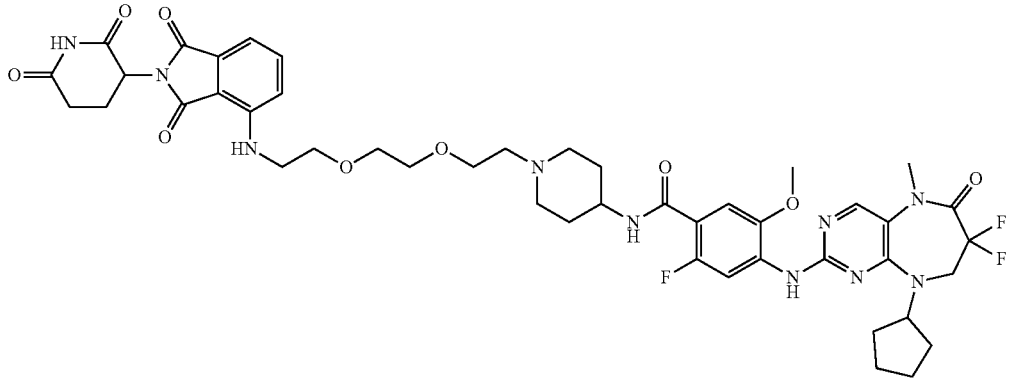 [SMILES: COc1cc(C(=O)NC2CCN(CCOCCOCCNc3cccc4c3C(=O)N(C3CCC(=O)NC3=O)C4=O)CC2)c(F)cc1Nc1ncc2c(n1)N(C1CCCC1)CC(F)(F)C(=O)N2C] |
| 3 | 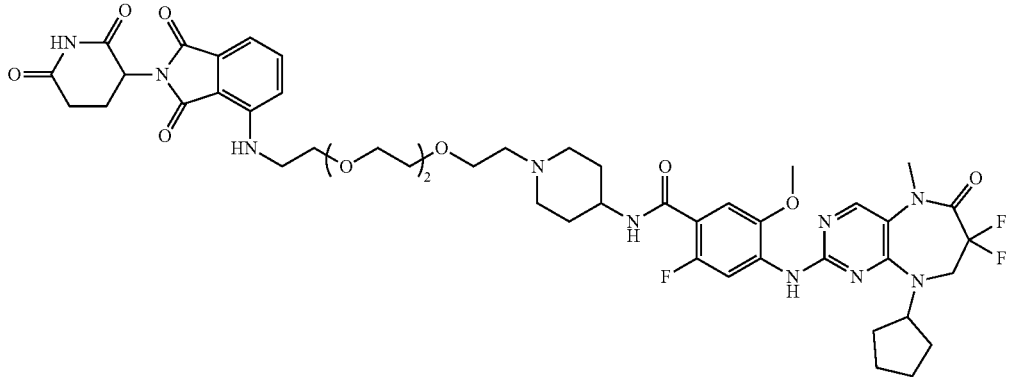 |
| 4 | 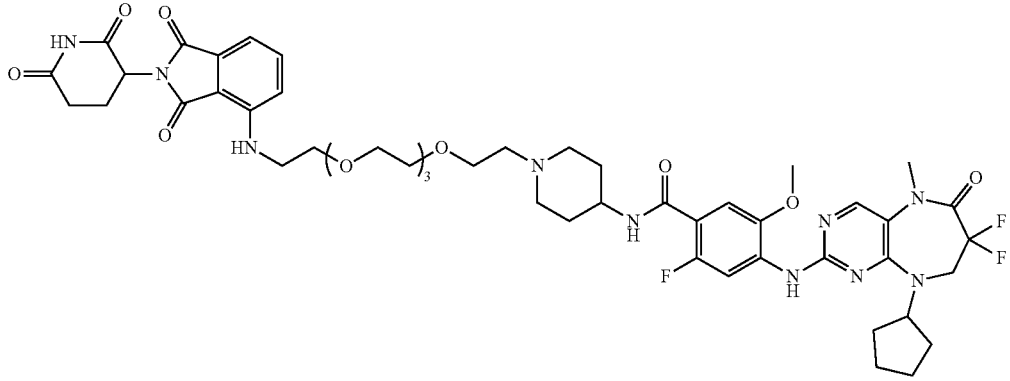 |

TABLE 1-continued

| Compound | Structure |
| --- | --- |
| 5 | 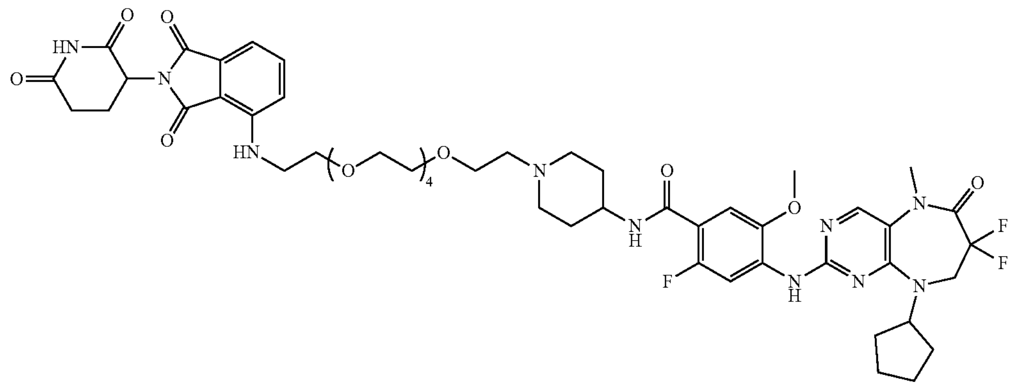 |
| 6 | 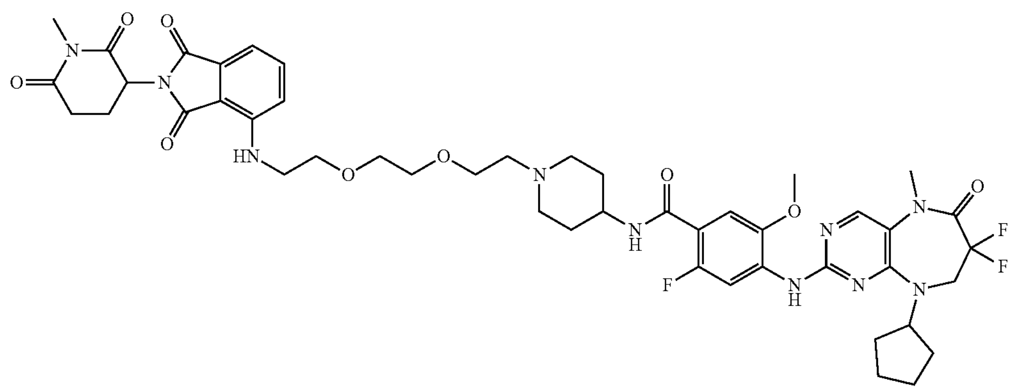 [SMILES: COc1cc(C(=O)NC2CCN(CCOCCOCCNc3cccc4c3C(=O)N(C3CCC(=O)N(C)C3=O)C4=O)CC2)c(F)cc1Nc1ncc2c(n1)N(C1CCCC1)CC(F)(F)C(=O)N2C] |
| 7 | 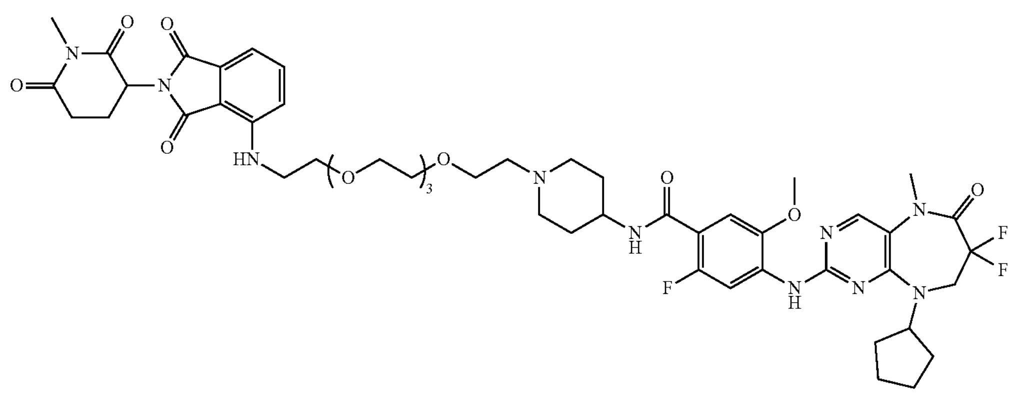 |
| 8 | 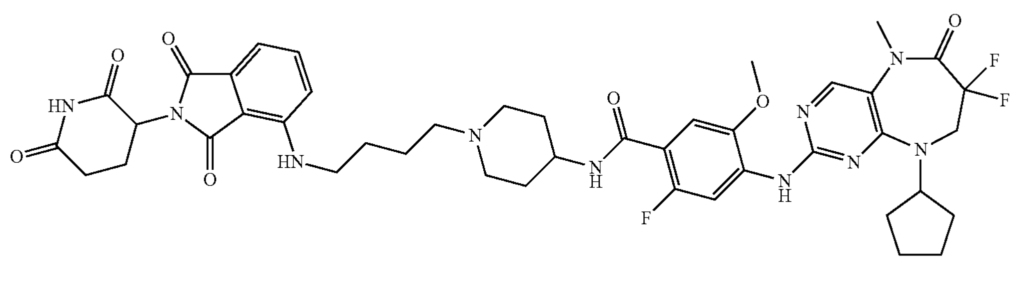 [SMILES: COc1cc(C(=O)NC2CCN(CCCCNc3cccc4c3C(=O)N(C3CCC(=O)NC3=O)C4=O)CC2)c(F)cc1Nc1ncc2c(n1)N(C1CCCC1)CC(F)(F)C(=O)N2C] |

TABLE 1-continued
| Compound | Structure |
|---|---|
| 9 | 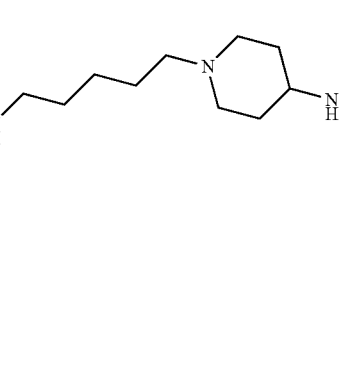 |
| 10 | 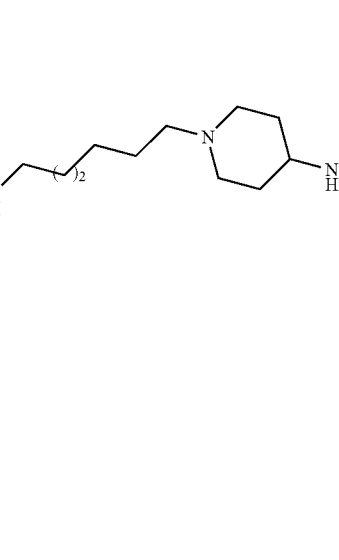 |
| 11 | 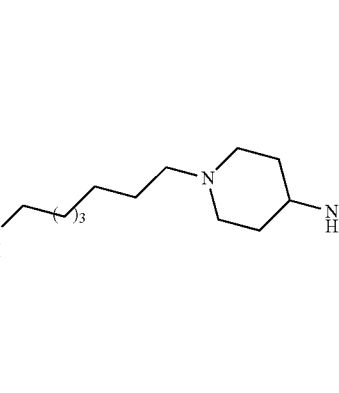 |

TABLE 1-continued

| Compound | Structure |
|---|---|
| 12 | 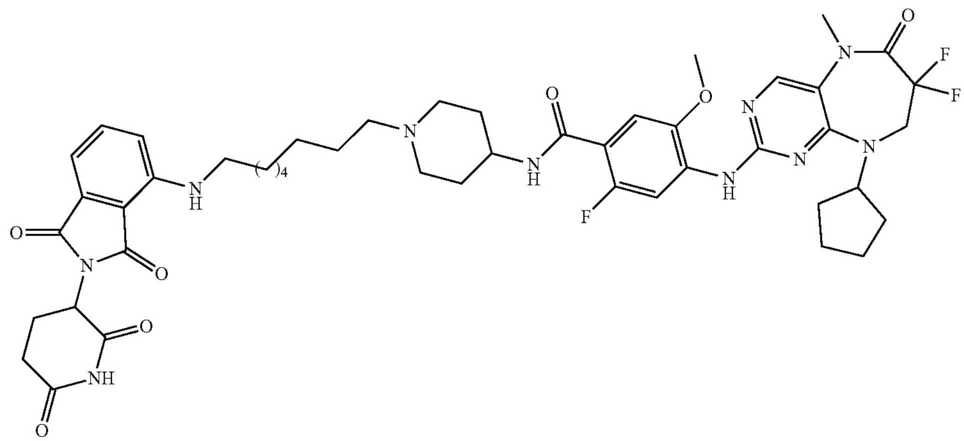 |
| 13 | 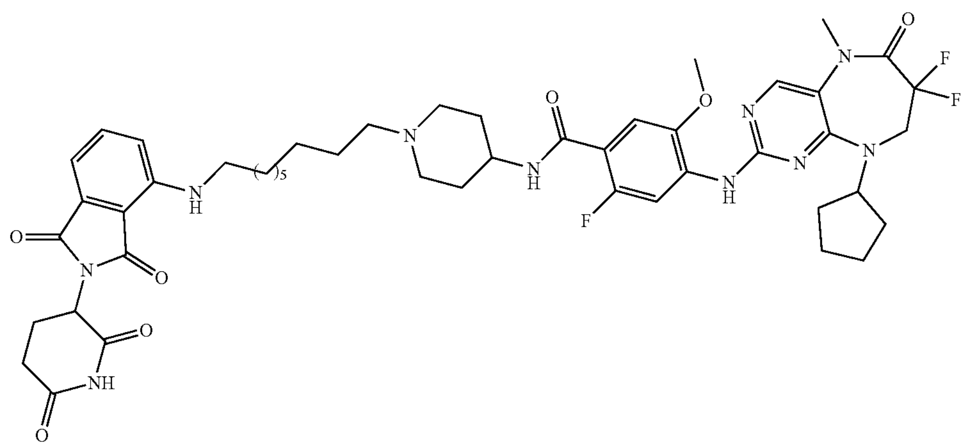 |
| 14 | 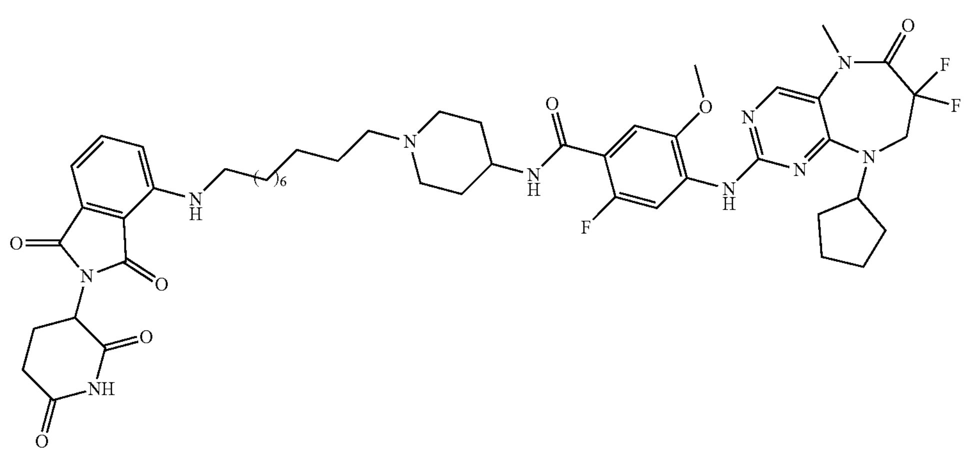 |

TABLE 1-continued

| Compound | Structure |
|---|---|
| 15 | 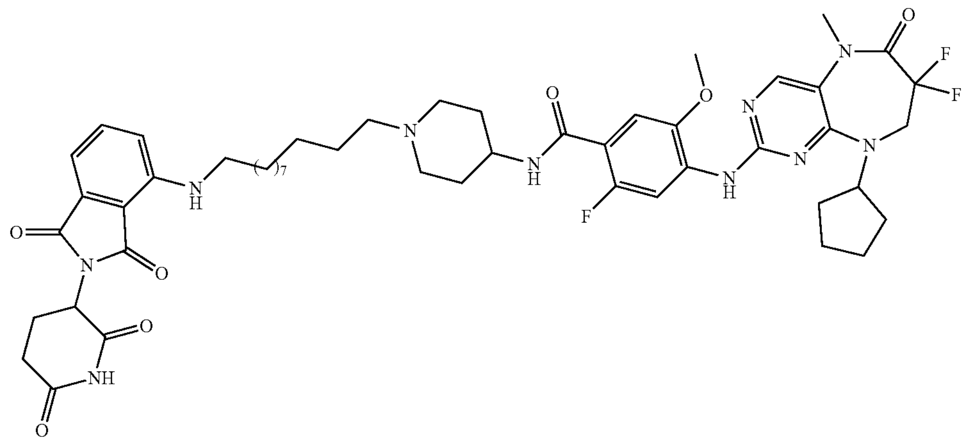 |
| 16 | 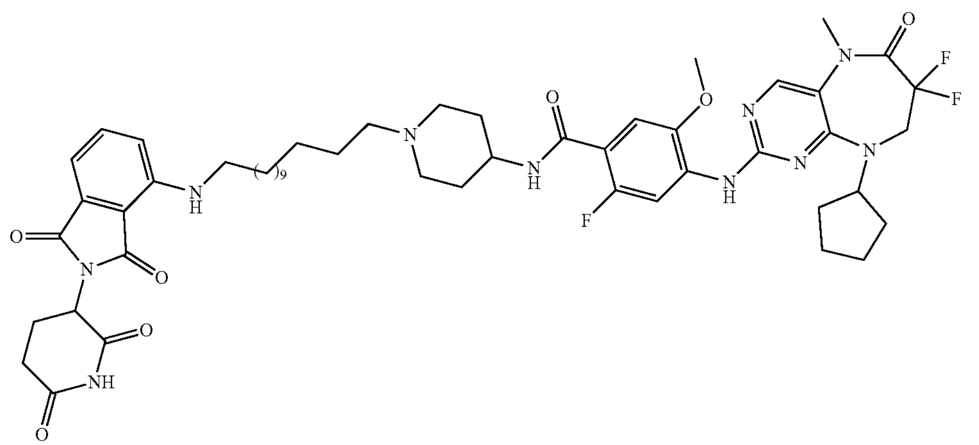 |
| 17 | 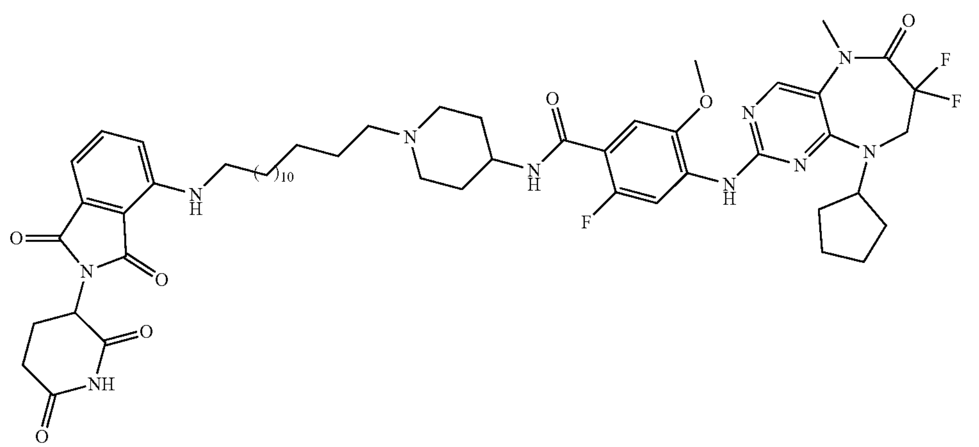 |
| 18 | 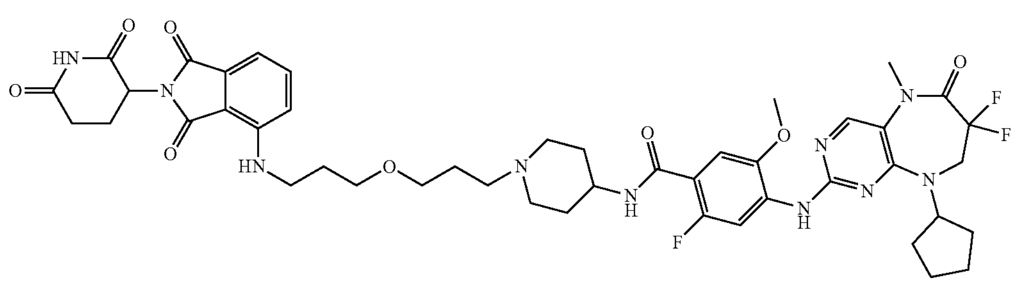 [SMILES: COc1cc(C(=O)NC2CCN(CCCOCCCNc3cccc4c3C(=O)N(C3CCC(=O)NC3=O)C4=O)CC2)c(F)cc1Nc1ncc2c(n1)N(C1CCCC1)CC(F)(F)C(=O)N2C] |

TABLE 1-continued

| Compound | Structure |
|---|---|
| 19 | 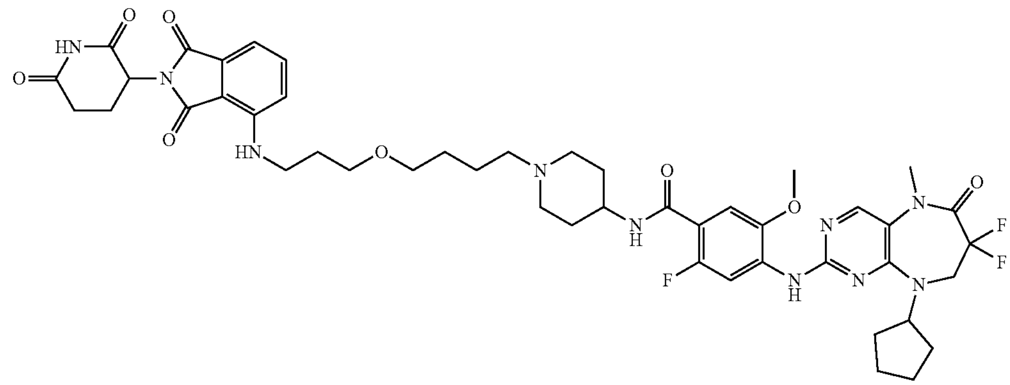 [SMILES: COc1cc(C(=O)NC2CCN(CCCCOCCCNc3cccc4c3C(=O)N(C3CCC(=O)NC3=O)C4=O)CC2)c(F)cc1Nc1ncc2c(n1)N(C1CCCC1)CC(F)(F)C(=O)N2C] |
| 20 | 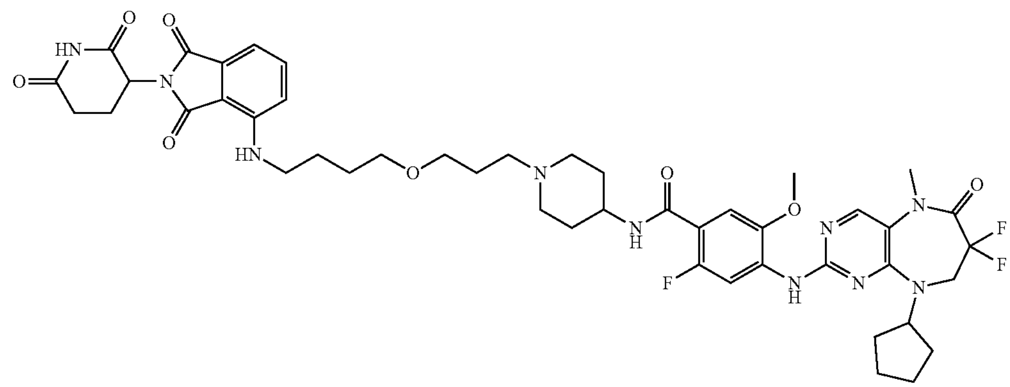 |
| 21 | 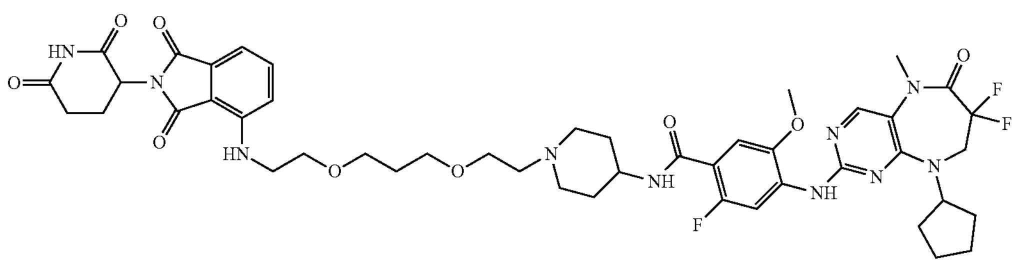 [SMILES: COc1cc(C(=O)NC2CCN(CCOCCCOCCNc3cccc4c3C(=O)N(C3CCC(=O)NC3=O)C4=O)CC2)c(F)cc1Nc1ncc2c(n1)N(C1CCCC1)CC(F)(F)C(=O)N2C] |
| 22 | 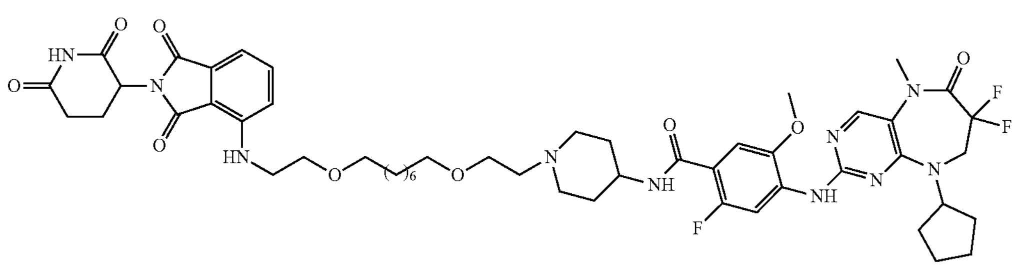 |
| 23 | 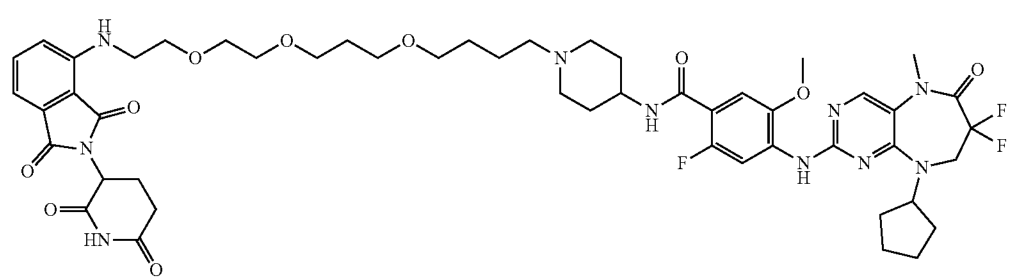 [SMILES: COc1cc(C(=O)NC2CCN(CCCCOCCCOCCOCCNc3cccc4c3C(=O)N(C3CCC(=O)NC3=O)C4=O)CC2)c(F)cc1Nc1ncc2c(n1)N(C1CCCC1)CC(F)(F)C(=O)N2C] |

TABLE 1-continued

| Compound | Structure |
|---|---|
| 24 | 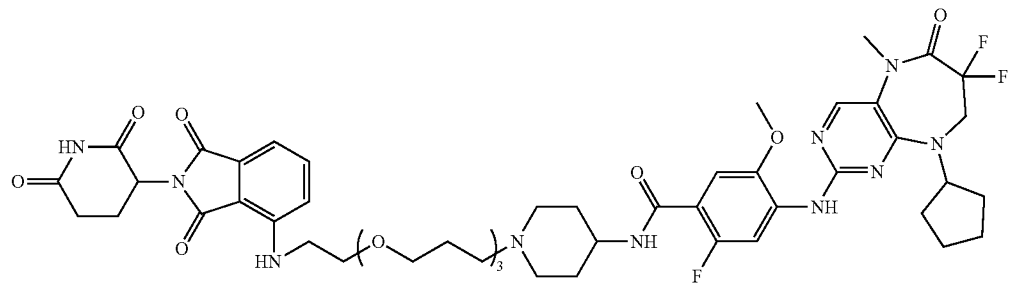 |
| 25 | 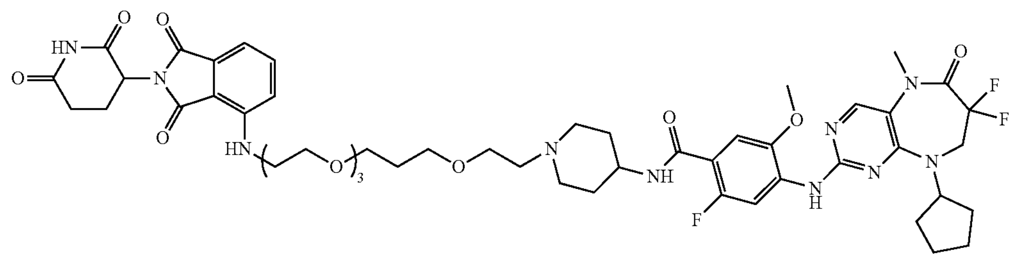 |
| 26 | 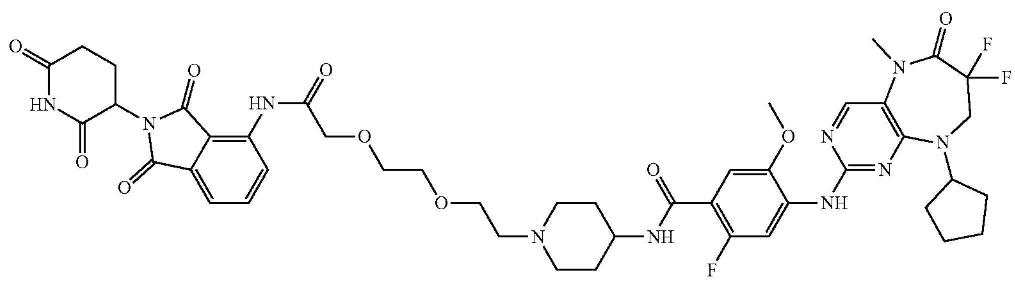 |
| 27 | 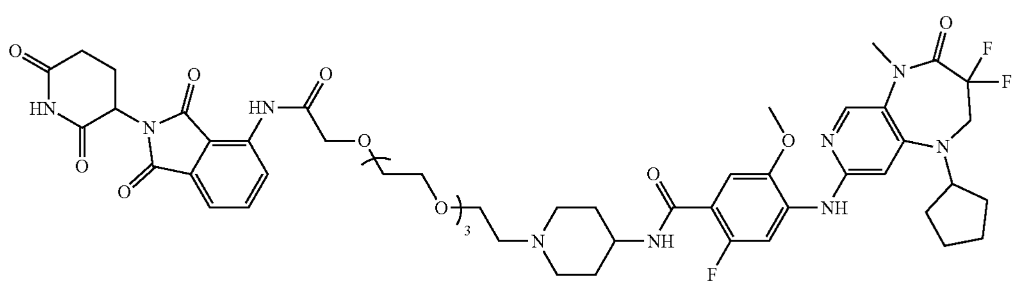 |
| 28 | 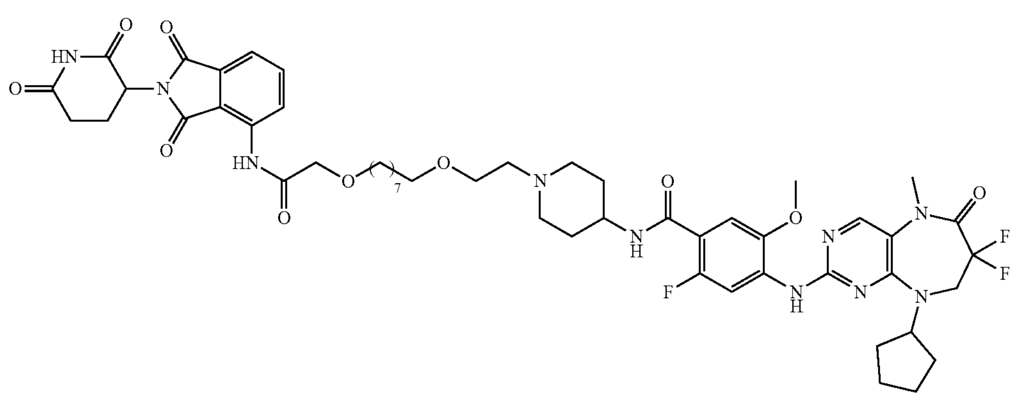 |

TABLE 1-continued

| Compound | Structure |
|---|---|
| 29 | 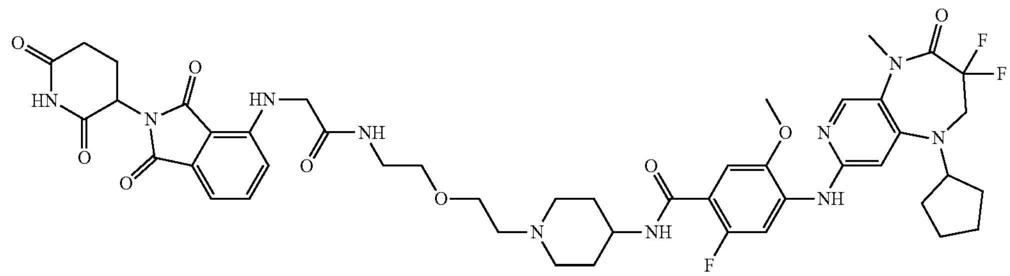 [SMILES: COc1cc(C(=O)NC2CCN(CCOCCNC(=O)CNc3cccc4c3C(=O)N(C3CCC(=O)NC3=O)C4=O)CC2)c(F)cc1Nc1cc2c(cn1)N(C)C(=O)C(F)(F)CN2C1CCCC1] |
| 30 | 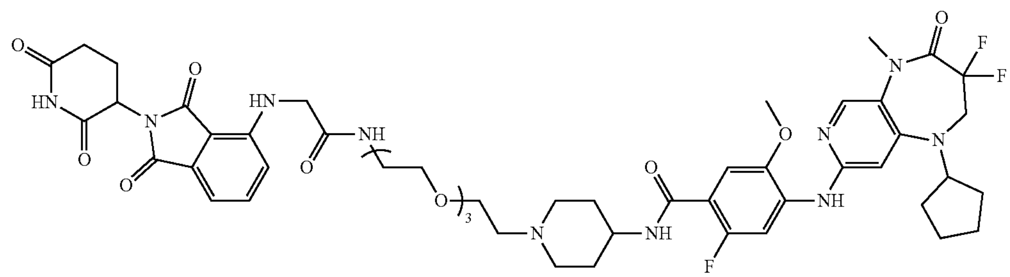 |
| 31 | 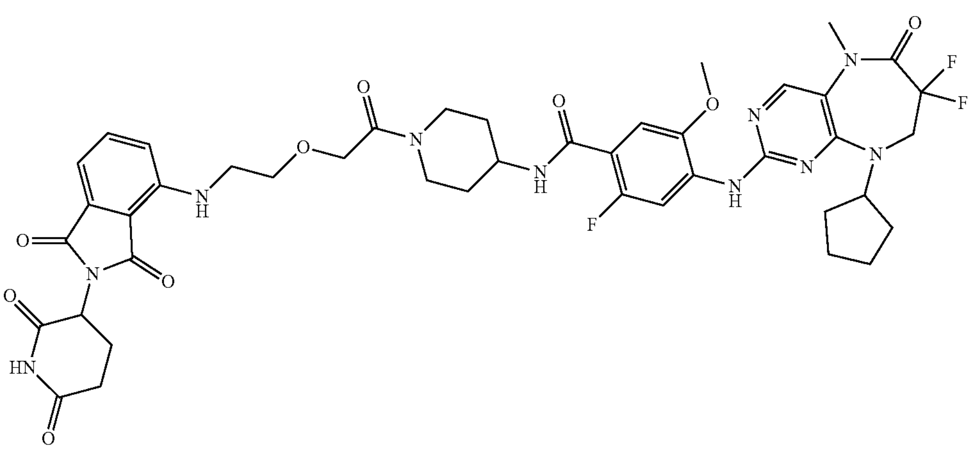 [SMILES: COc1cc(C(=O)NC2CCN(C(=O)COCCNc3cccc4c3C(=O)N(C3CCC(=O)NC3=O)C4=O)CC2)c(F)cc1Nc1ncc2c(n1)N(C1CCCC1)CC(F)(F)C(=O)N2C] |
| 32 | 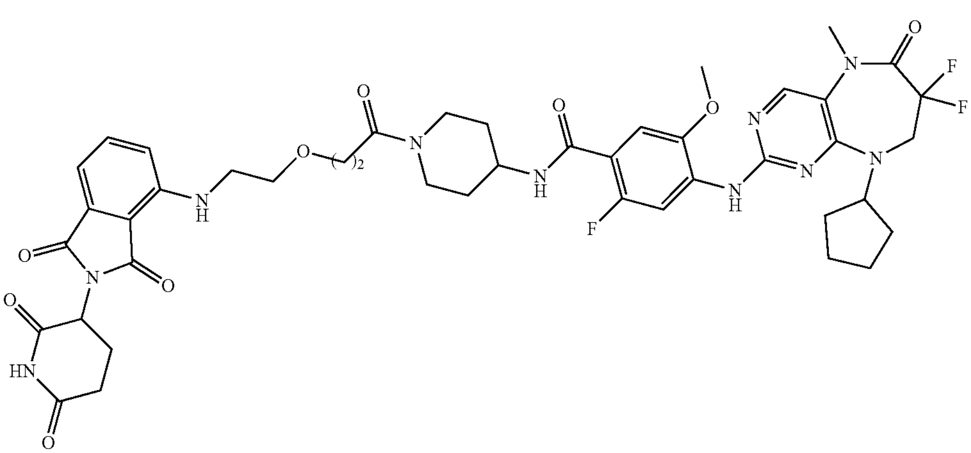 |

TABLE 1-continued

| Compound | Structure |
|---|---|
| 33 | 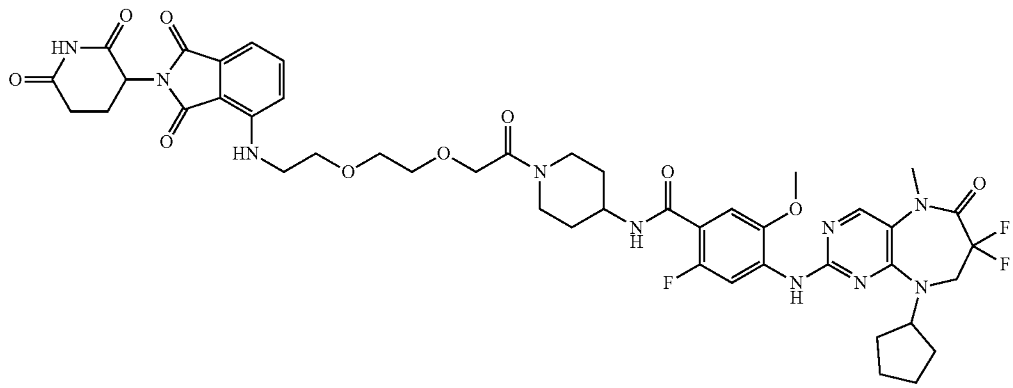 [SMILES: COc1cc(C(=O)NC2CCN(C(=O)COCCOCCNc3cccc4c3C(=O)N(C3CCC(=O)NC3=O)C4=O)CC2)c(F)cc1Nc1ncc2c(n1)N(C1CCCC1)CC(F)(F)C(=O)N2C] |
| 34 | 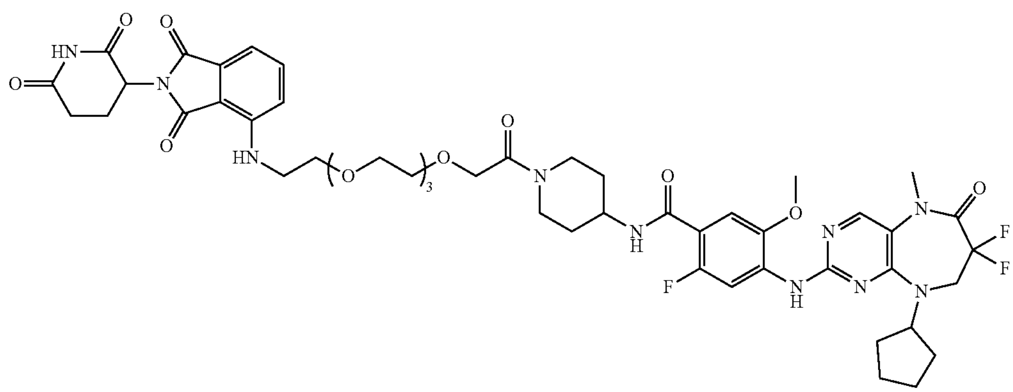 |
| 35 | 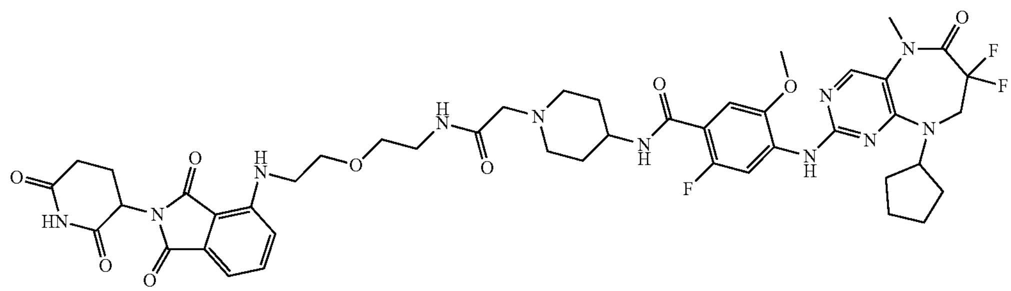 [SMILES: COc1cc(C(=O)NC2CCN(CC(=O)NCCOCCNc3cccc4c3C(=O)N(C3CCC(=O)NC3=O)C4=O)CC2)c(F)cc1Nc1ncc2c(n1)N(C1CCCC1)CC(F)(F)C(=O)N2C] |
| 36 | 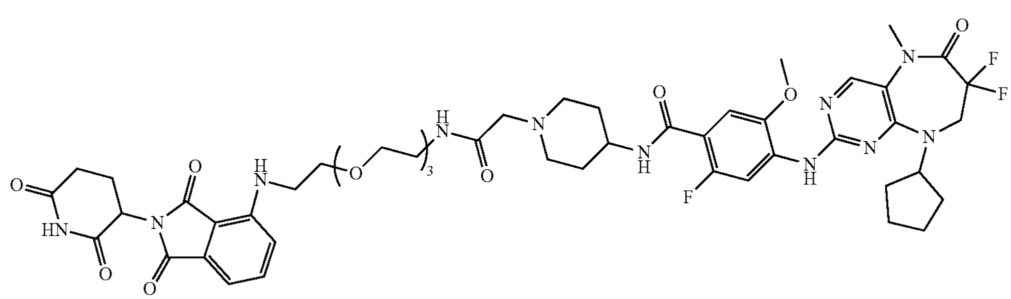 |

TABLE 1-continued

| Compound | Structure |
|---|---|
| 37 | 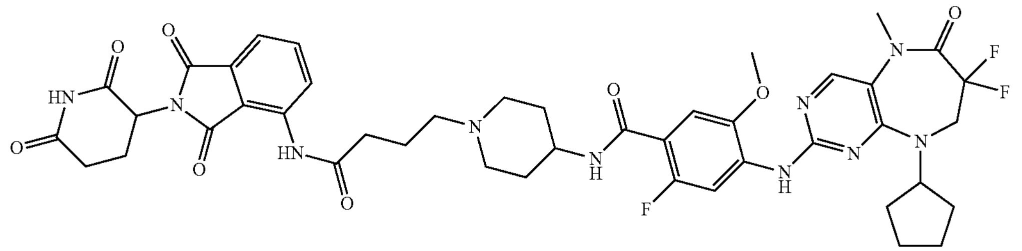 [SMILES: COc1cc(C(=O)NC2CCN(CCCC(=O)Nc3cccc4c3C(=O)N(C3CCC(=O)NC3=O)C4=O)CC2)c(F)cc1Nc1ncc2c(n1)N(C1CCCC1)CC(F)(F)C(=O)N2C] |
| 38 | 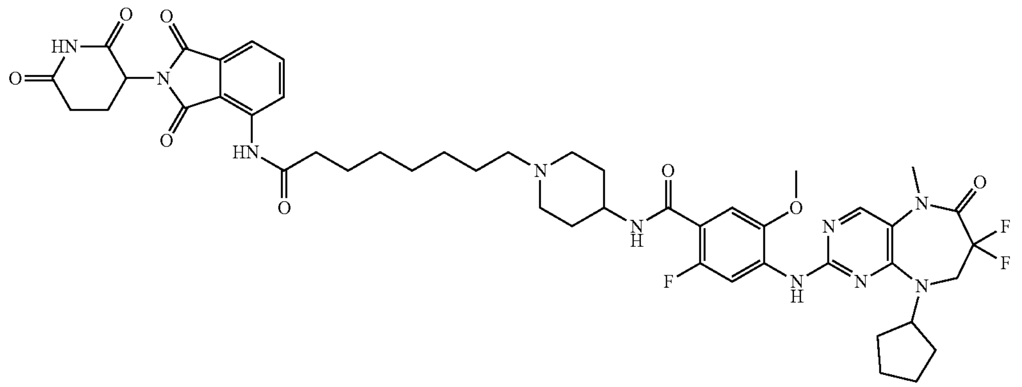 [SMILES: COc1cc(C(=O)NC2CCN(CCCCCCCC(=O)Nc3cccc4c3C(=O)N(C3CCC(=O)NC3=O)C4=O)CC2)c(F)cc1Nc1ncc2c(n1)N(C1CCCC1)CC(F)(F)C(=O)N2C] |
| 39 | 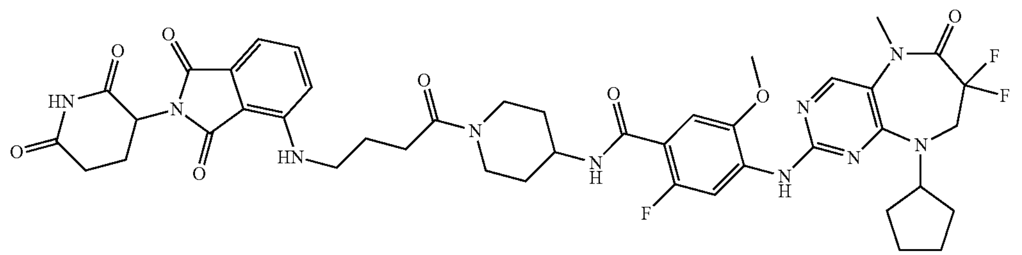 [SMILES: COc1cc(C(=O)NC2CCN(C(=O)CCCNc3cccc4c3C(=O)N(C3CCC(=O)NC3=O)C4=O)CC2)c(F)cc1Nc1ncc2c(n1)N(C1CCCC1)CC(F)(F)C(=O)N2C] |
| 40 | 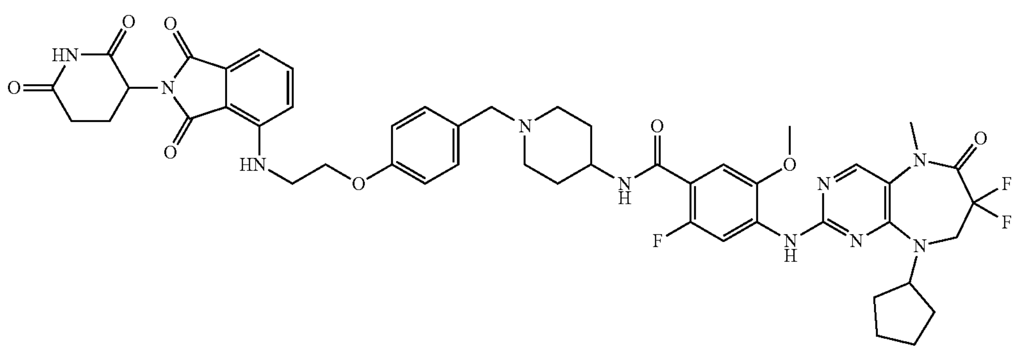 [SMILES: COc1cc(C(=O)NC2CCN(Cc3ccc(OCCNc4cccc5c4C(=O)N(C4CCC(=O)NC4=O)C5=O)cc3)CC2)c(F)cc1Nc1ncc2c(n1)N(C1CCCC1)CC(F)(F)C(=O)N2C] |
| 41 | 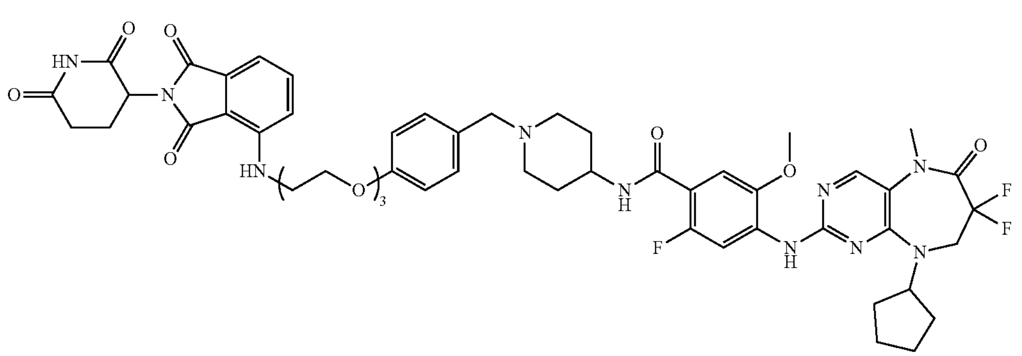 |

TABLE 1-continued

| Compound | Structure |
|---|---|
| 42 | 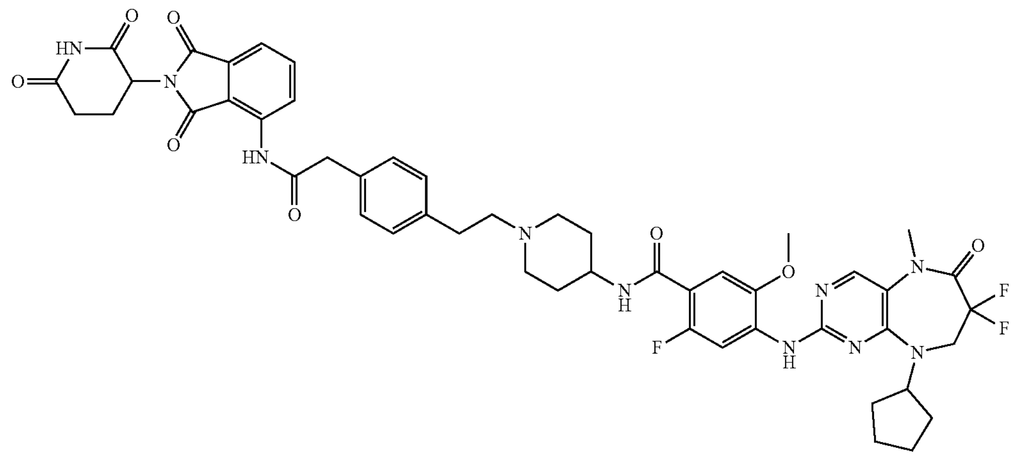 [SMILES: COc1cc(C(=O)NC2CCN(CCc3ccc(CC(=O)Nc4cccc5c4C(=O)N(C4CCC(=O)NC4=O)C5=O)cc3)CC2)c(F)cc1Nc1ncc2c(n1)N(C1CCCC1)CC(F)(F)C(=O)N2C] |
| 43 | 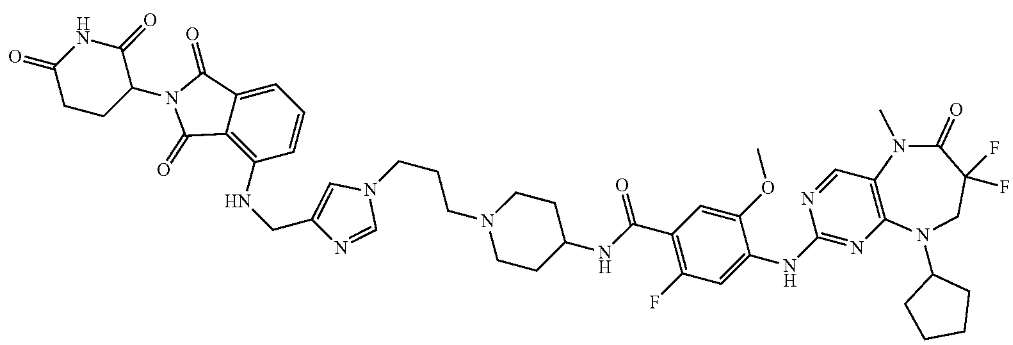 [SMILES: COc1cc(C(=O)NC2CCN(CCCn3cnc(CNc4cccc5c4C(=O)N(C4CCC(=O)NC4=O)C5=O)c3)CC2)c(F)cc1Nc1ncc2c(n1)N(C1CCCC1)CC(F)(F)C(=O)N2C] |
| 44 | 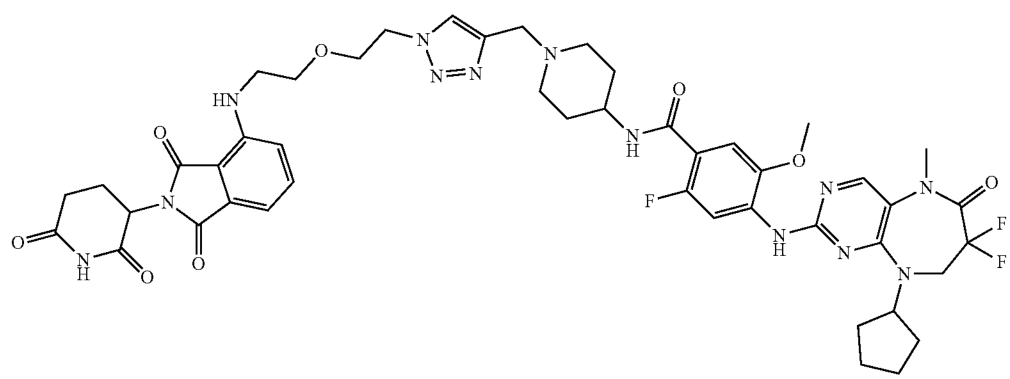 [SMILES: COc1cc(C(=O)NC2CCN(Cc3cn(CCOCCNc4cccc5c4C(=O)N(C4CCC(=O)NC4=O)C5=O)nn3)CC2)c(F)cc1Nc1ncc2c(n1)N(C1CCCC1)CC(F)(F)C(=O)N2C] |
| 45 | 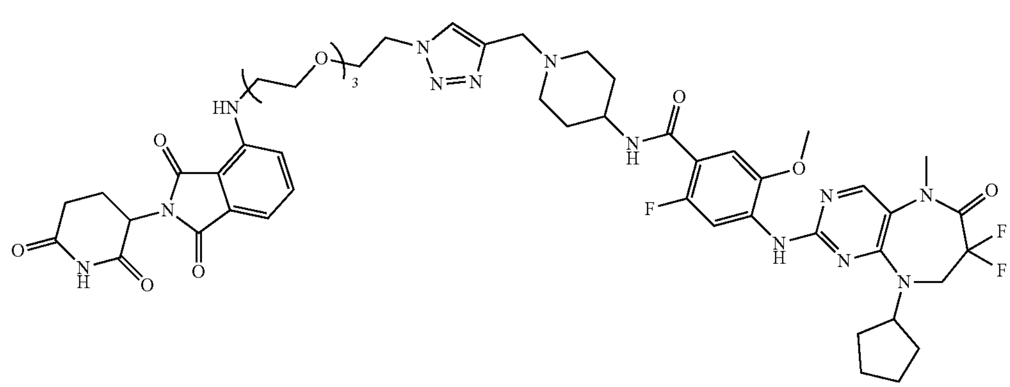 |

TABLE 1-continued
| Compound | Structure |
|---|---|
| 46 | 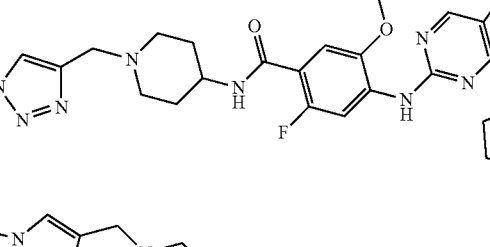 |
| 47 | 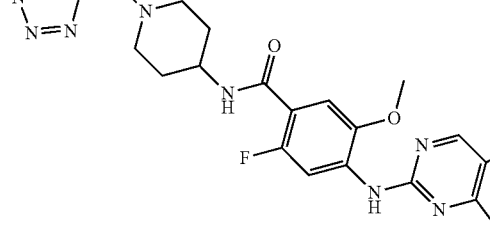 |
| 48 | 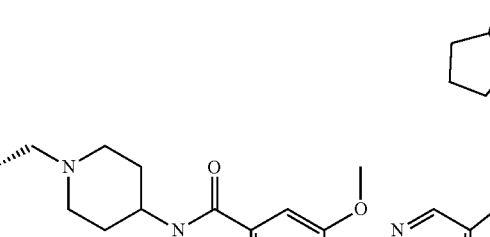 |
| 49 | 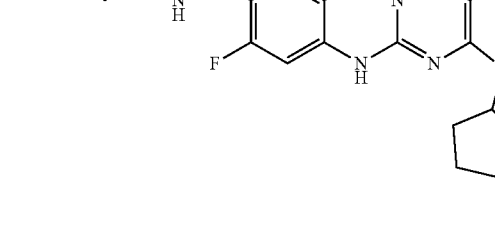 |
| 50 | 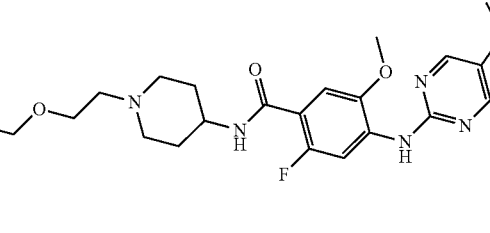 |

TABLE 1-continued

| Compound | Structure |
| --- | --- |
| 51 | 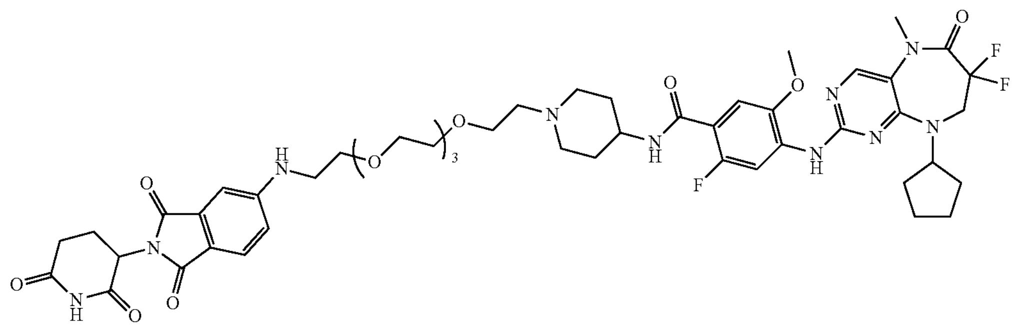 |
| 52 | 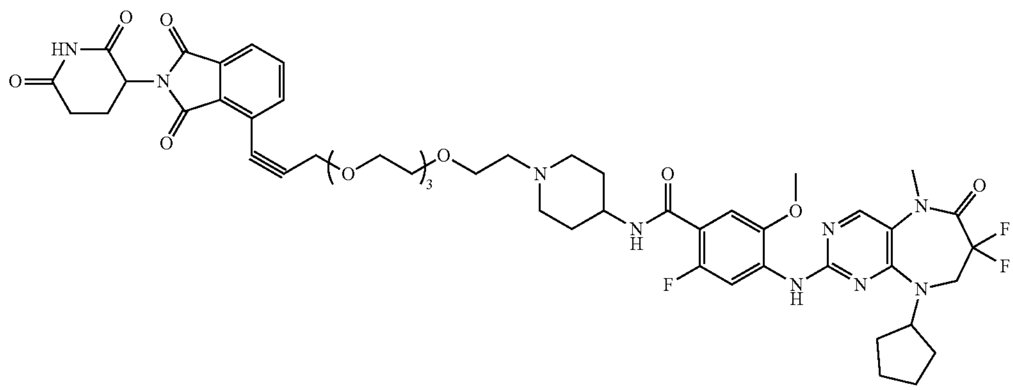 |
| 53 | 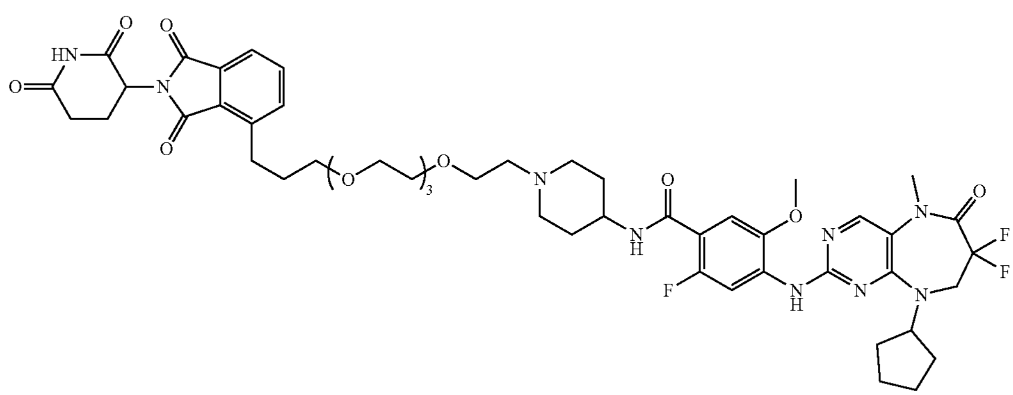 |
| 54 | 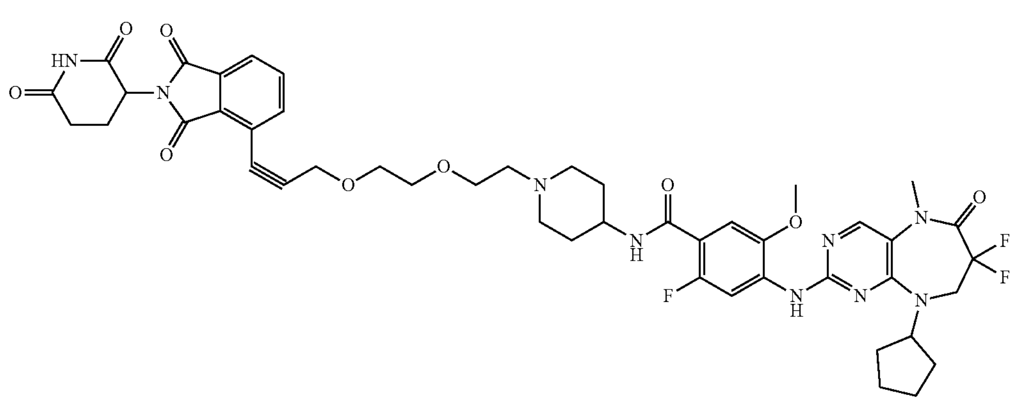 [SMILES: COc1cc(C(=O)NC2CCN(CCOCCOCC#Cc3cccc4c3C(=O)N(C3CCC(=O)NC3=O)C4=O)CC2)c(F)cc1Nc1ncc2c(n1)N(C1CCCC1)CC(F)(F)C(=O)N2C] |

TABLE 1-continued

| Compound | Structure |
|---|---|
| 55 | 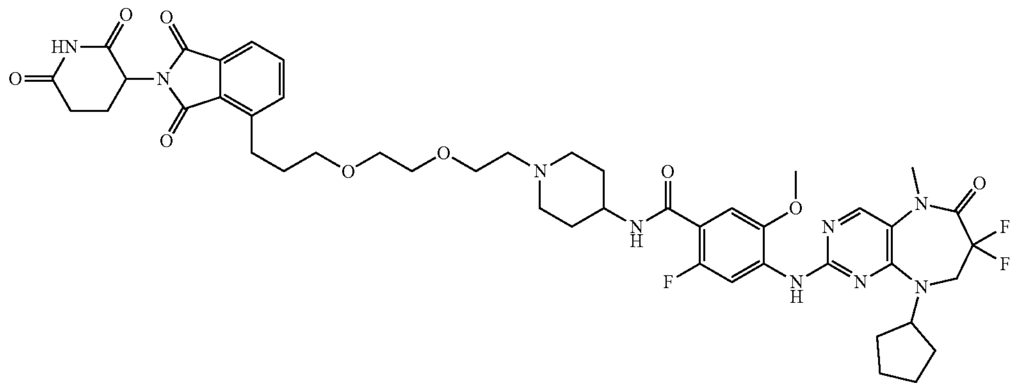 [SMILES: COc1cc(C(=O)NC2CCN(CCOCCOCCCc3cccc4c3C(=O)N(C3CCC(=O)NC3=O)C4=O)CC2)c(F)cc1Nc1ncc2c(n1)N(C1CCCC1)CC(F)(F)C(=O)N2C] |
| 56 | 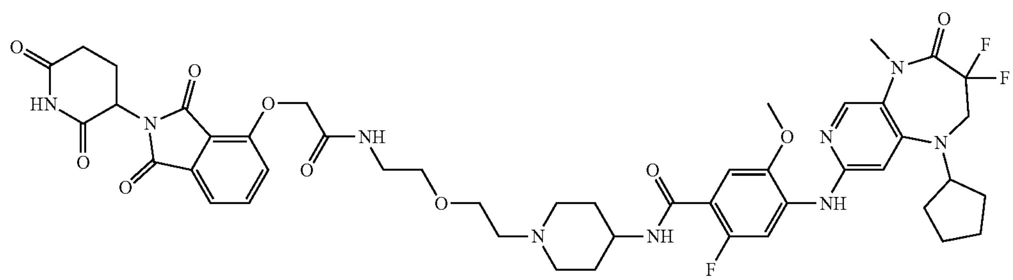 [SMILES: COc1cc(C(=O)NC2CCN(CCOCCNC(=O)COc3cccc4c3C(=O)N(C3CCC(=O)NC3=O)C4=O)CC2)c(F)cc1Nc1cc2c(cn1)N(C)C(=O)C(F)(F)CN2C1CCCC1] |
| 57 | 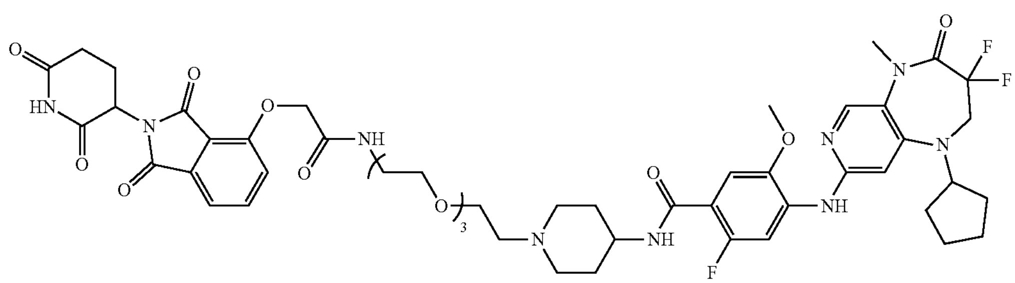 |
| 58 | 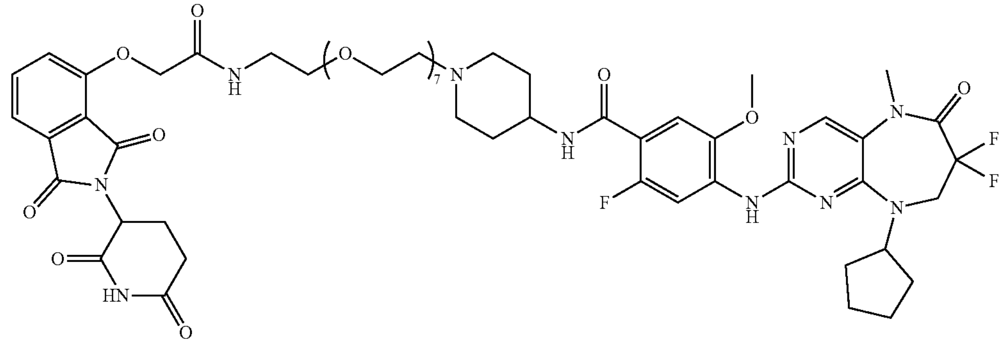 |

TABLE 1-continued

| Compound | Structure |
|---|---|
| 59 | (structure) |
| 60 | (structure) |
| 61 | (structure) |
| 62 | (structure) |

TABLE 1-continued
| Compound | Structure |
| --- | --- |
| 63 | 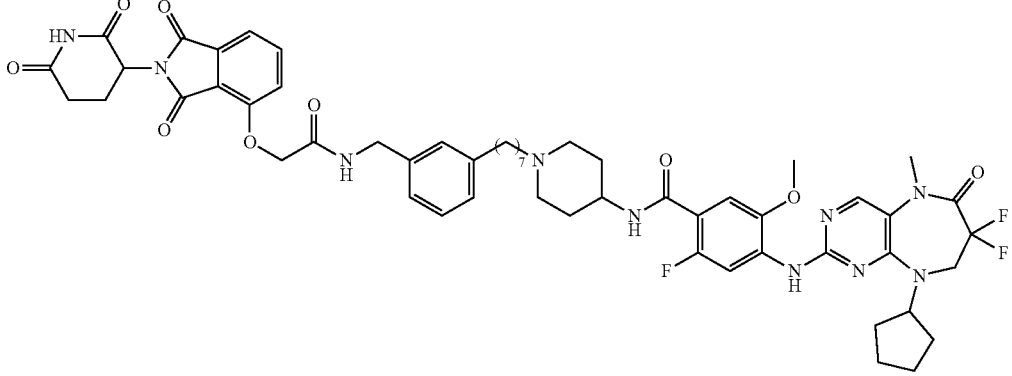 |
| 64 | 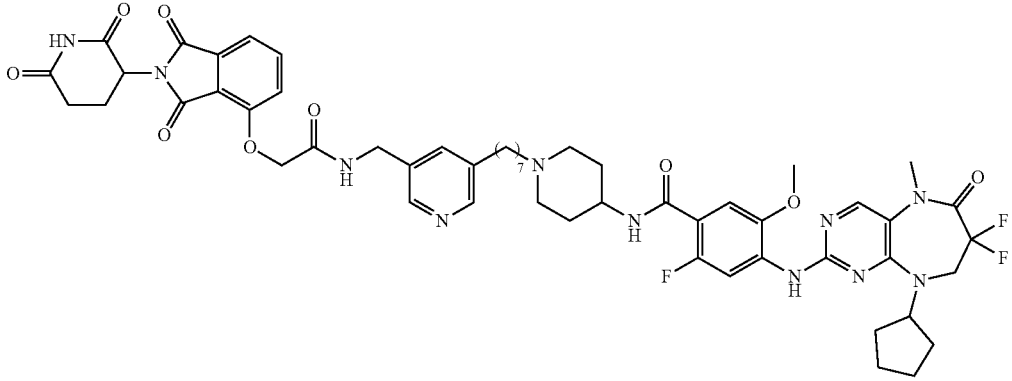 [SMILES: COc1cc(C(=O)NC2CCN(Cc3cccc(CNC(=O)COc4cccc5c4C(=O)N(C4CCC(=O)NC4=O)C5=O)c3)CC2)c(F)cc1Nc1ncc2c(n1)N(C1CCCC1)CC(F)(F)C(=O)N2C] |
| 65 | 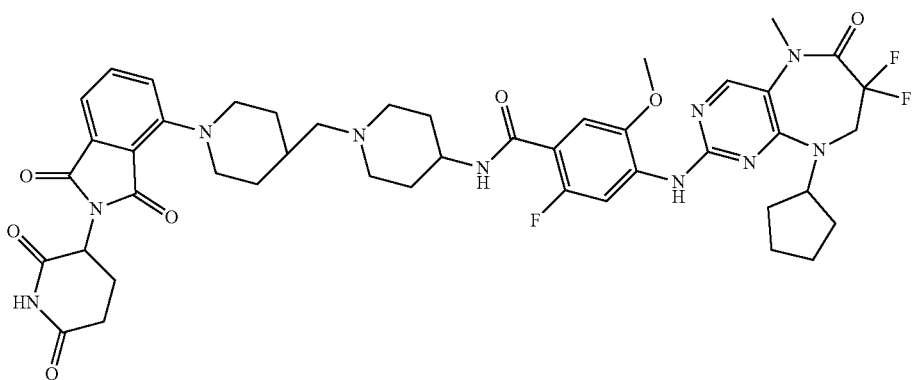 [SMILES: COc1cc(C(=O)NC2CCN(CC3CCN(c4cccc5c4C(=O)N(C4CCC(=O)NC4=O)C5=O)CC3)CC2)c(F)cc1Nc1ncc2c(n1)N(C1CCCC1)CC(F)(F)C(=O)N2C] |
| 66 | 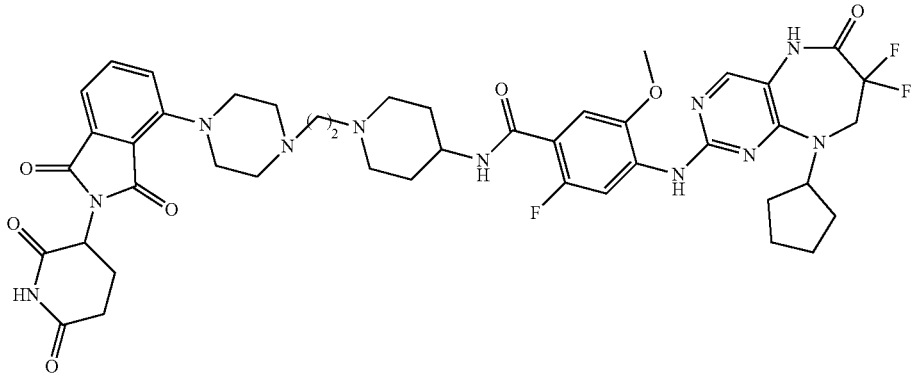 |

TABLE 1-continued

| Compound | Structure |
|---|---|
| 67 | 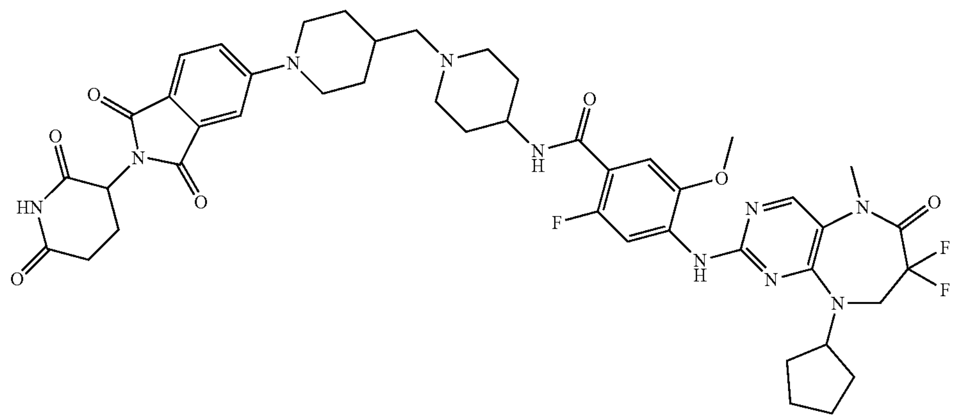 [SMILES: COc1cc(C(=O)NC2CCN(CC3CCN(c4ccc5c(c4)C(=O)N(C4CCC(=O)NC4=O)C5=O)CC3)CC2)c(F)cc1Nc1ncc2c(n1)N(C1CCCC1)CC(F)(F)C(=O)N2C] |
| 68 | 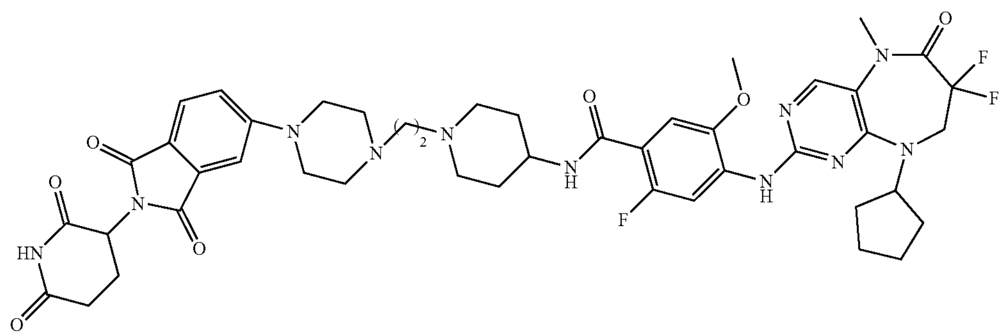 |
| 69 | 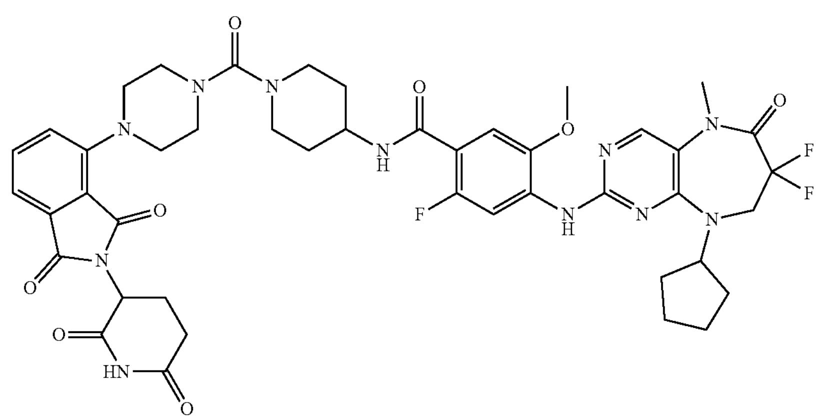 [SMILES: COc1cc(C(=O)NC2CCN(C(=O)N3CCN(c4cccc5c4C(=O)N(C4CCC(=O)NC4=O)C5=O)CC3)CC2)c(F)cc1Nc1ncc2c(n1)N(C1CCCC1)CC(F)(F)C(=O)N2C] |
| 70 | 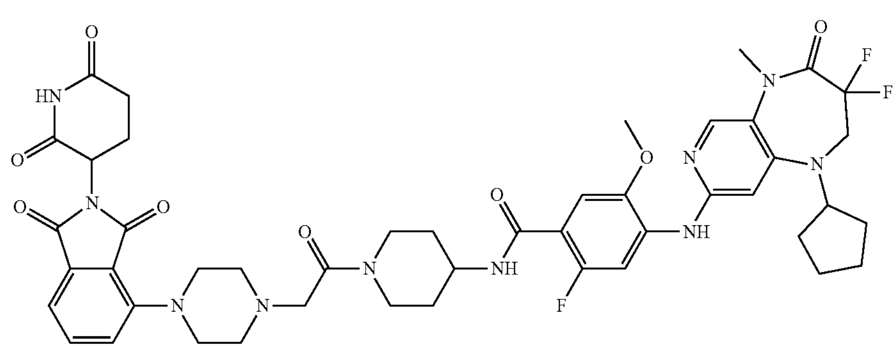 [SMILES: COc1cc(C(=O)NC2CCN(C(=O)CN3CCN(c4cccc5c4C(=O)N(C4CCC(=O)NC4=O)C5=O)CC3)CC2)c(F)cc1Nc1cc2c(cn1)N(C)C(=O)C(F)(F)CN2C1CCCC1] |

TABLE 1-continued

| Compound | Structure |
|---|---|
| 71 | 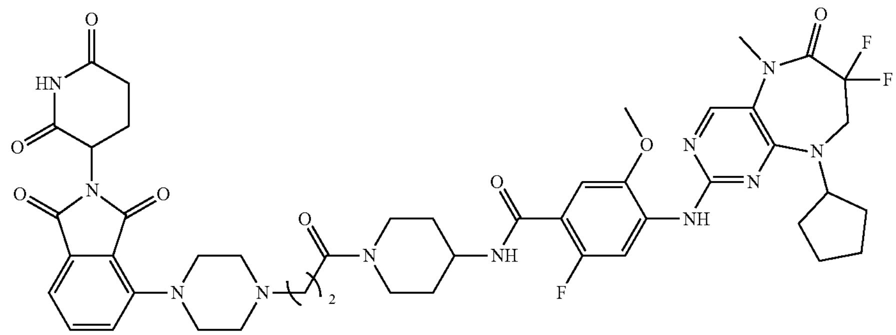 |
| 72 | 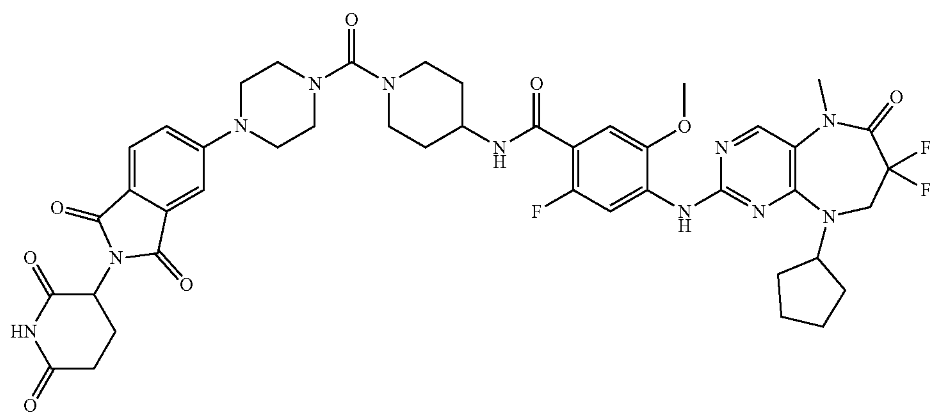 [SMILES: COc1cc(C(=O)NC2CCN(C(=O)N3CCN(c4ccc5c(c4)C(=O)N(C4CCC(=O)NC4=O)C5=O)CC3)CC2)c(F)cc1Nc1ncc2c(n1)N(C1CCCC1)CC(F)(F)C(=O)N2C] |
| 73 | 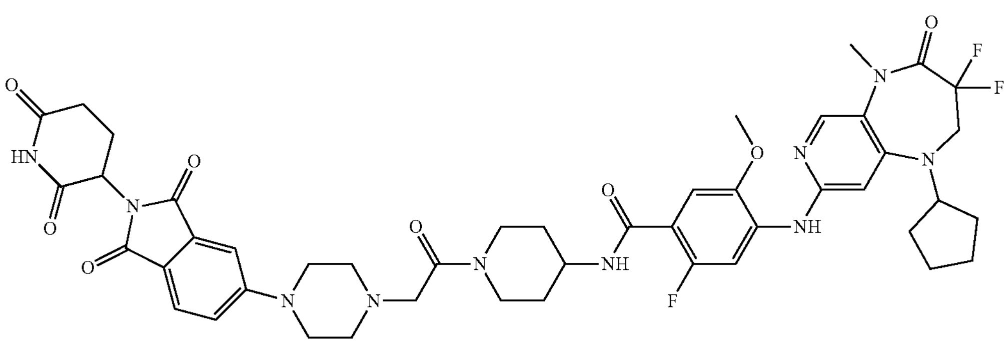 [SMILES: COc1cc(C(=O)NC2CCN(C(=O)CN3CCN(c4ccc5c(c4)C(=O)N(C4CCC(=O)NC4=O)C5=O)CC3)CC2)c(F)cc1Nc1cc2c(cn1)N(C)C(=O)C(F)(F)CN2C1CCCC1] |
| 74 | 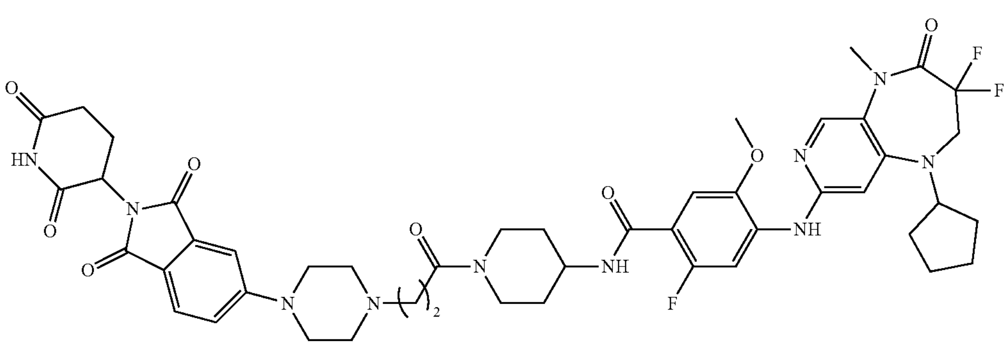 |

TABLE 1-continued

| Compound | Structure |
|---|---|
| 75 | (chemical structure) |
| 76 | (chemical structure) |
| 77 | (chemical structure) |
| 78 | (chemical structure) |

| Compound | Structure |
|---|---|
| 79 | 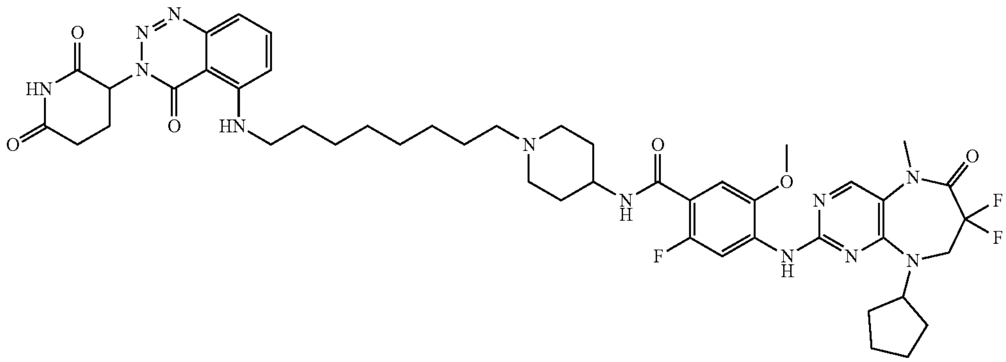 [SMILES: COc1cc(C(=O)NC2CCN(CCCCCCCCNc3cccc4nnn(C5CCC(=O)NC5=O)c(=O)c34)CC2)c(F)cc1Nc1ncc2c(n1)N(C1CCCC1)CC(F)(F)C(=O)N2C] |
| 80 | 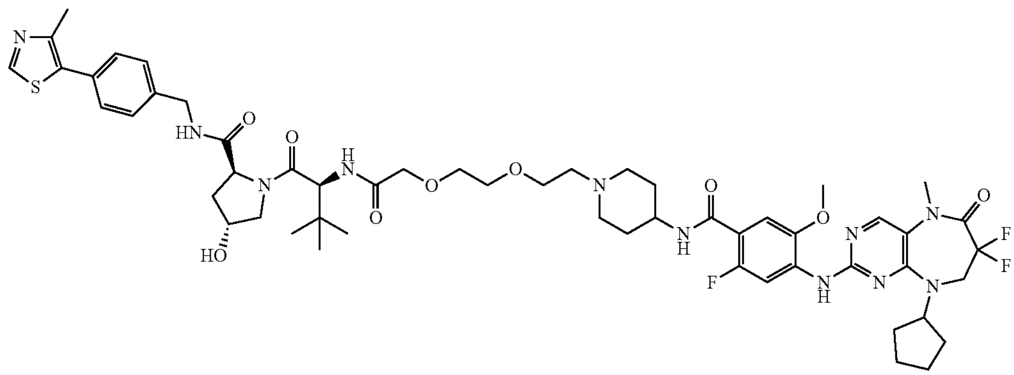 [SMILES: COc1cc(C(=O)NC2CCN(CCOCCOCC(=O)N[C@H](C(=O)N3C[C@H](O)C[C@H]3C(=O)NCc3ccc(-c4scnc4C)cc3)C(C)(C)C)CC2)c(F)cc1Nc1ncc2c(n1)N(C1CCCC1)CC(F)(F)C(=O)N2C] |
| 81 | 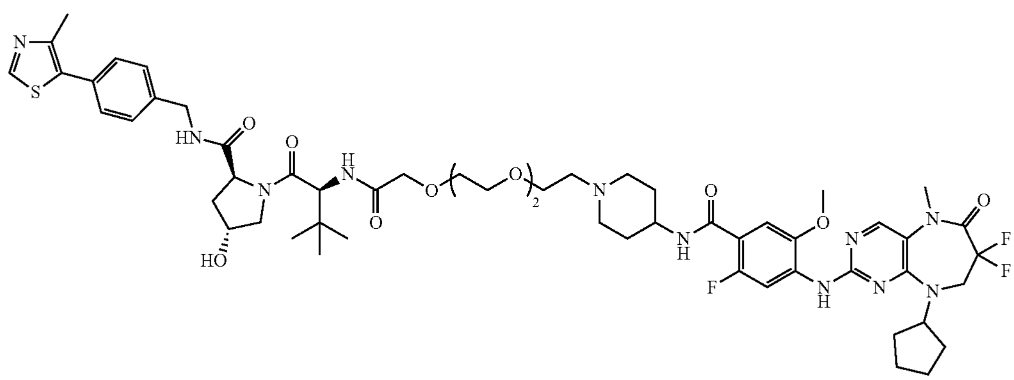 |
| 82 | 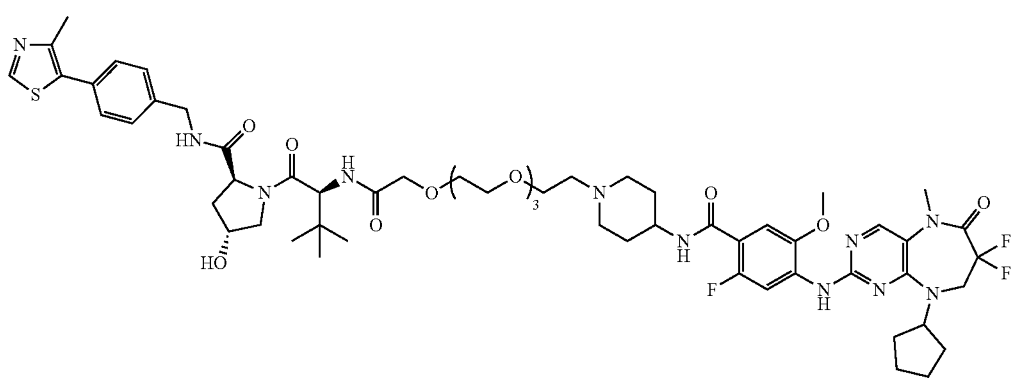 |

TABLE 1-continued
| Compound | Structure |
|---|---|
| 83 | 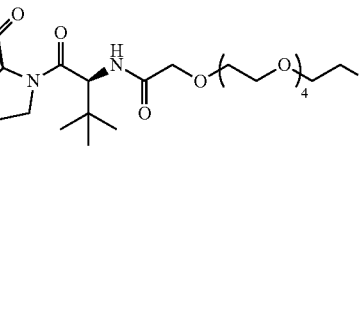 |
| 84 | 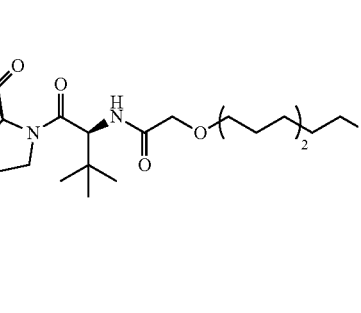 |
| 85 | 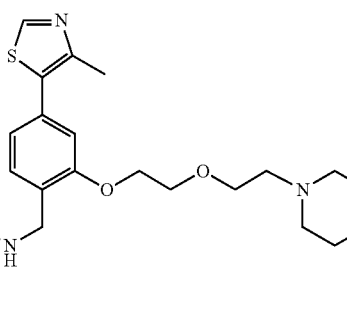 |
| 86 | 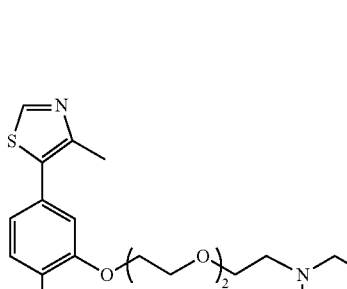 |

TABLE 1-continued

| Compound | Structure |
|---|---|
| 87 | 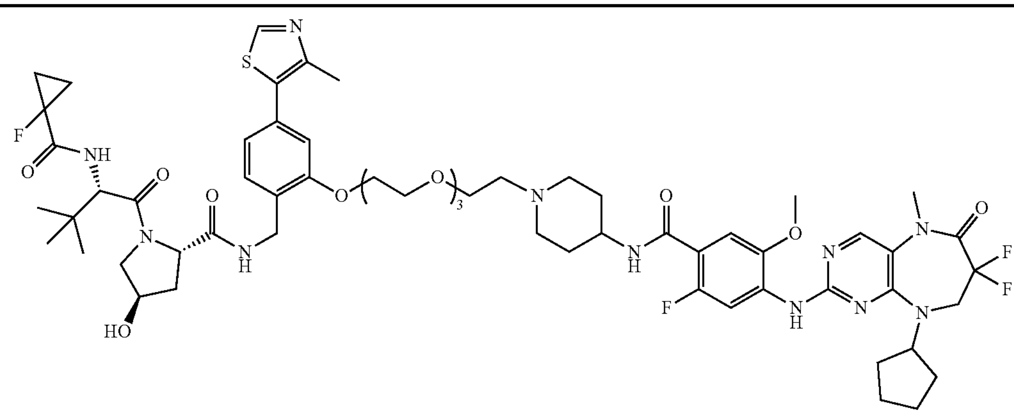 |
| 88 | 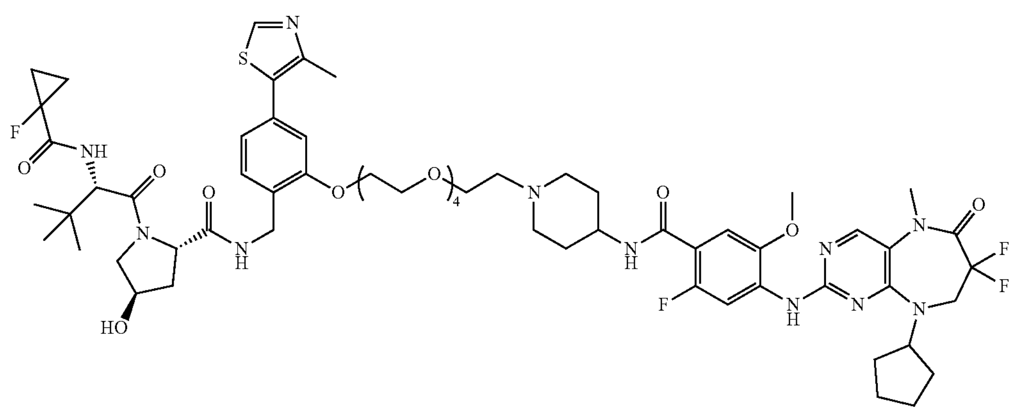 |
| 89 | 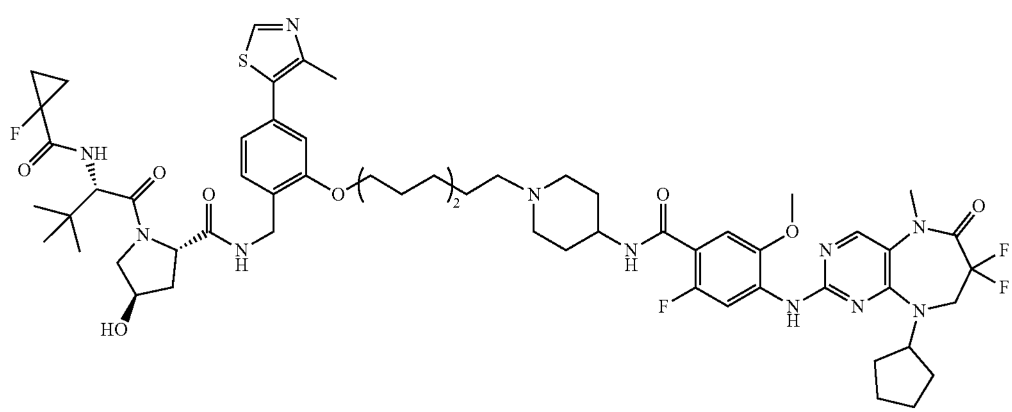 |
| 90 | 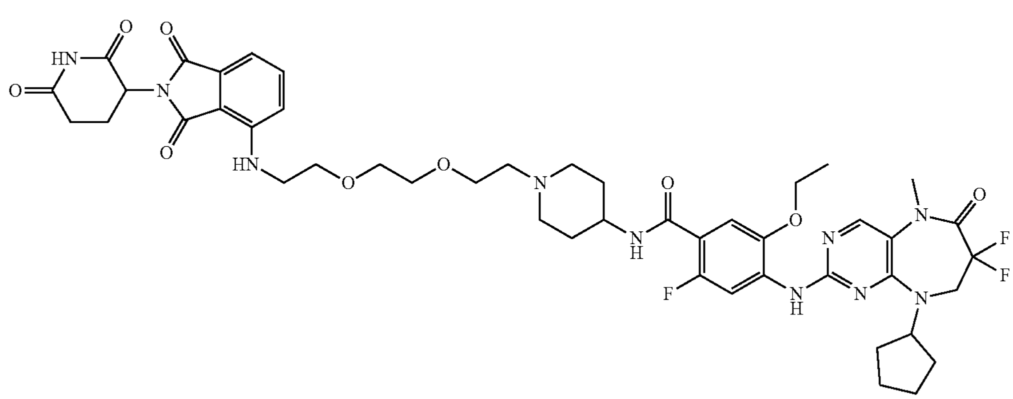 |

TABLE 1-continued

| Compound | Structure |
|---|---|
| 91 | 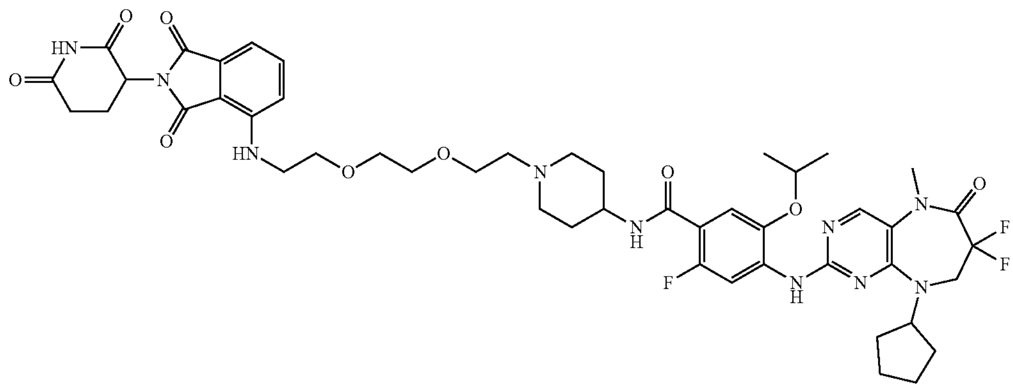 [SMILES: CC(C)Oc1cc(C(=O)NC2CCN(CCOCCOCCNc3cccc4c3C(=O)N(C3CCC(=O)NC3=O)C4=O)CC2)c(F)cc1Nc1ncc2c(n1)N(C1CCCC1)CC(F)(F)C(=O)N2C] |
| 92 | 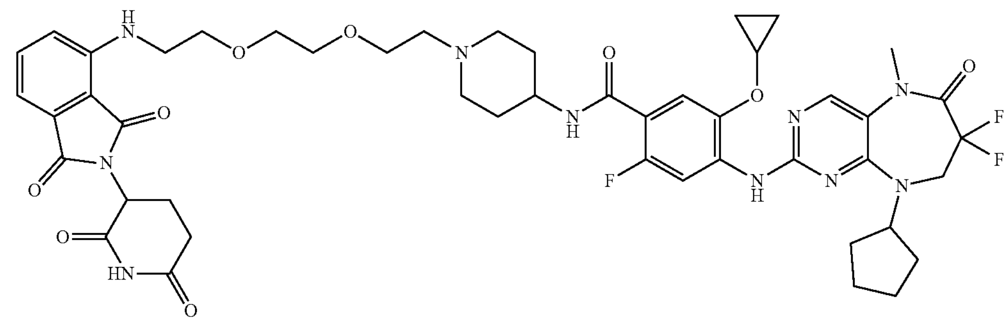 [SMILES: CN1C(=O)C(F)(F)CN(C2CCCC2)c2nc(Nc3cc(F)c(C(=O)NC4CCN(CCOCCOCCNc5cccc6c5C(=O)N(C5CCC(=O)NC5=O)C6=O)CC4)cc3OC3CC3)ncc21] |
| 93 | 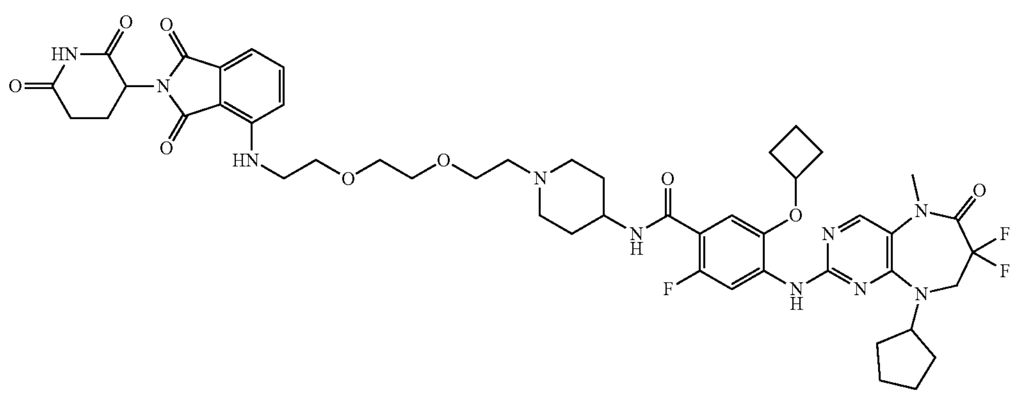 [SMILES: CN1C(=O)C(F)(F)CN(C2CCCC2)c2nc(Nc3cc(F)c(C(=O)NC4CCN(CCOCCOCCNc5cccc6c5C(=O)N(C5CCC(=O)NC5=O)C6=O)CC4)cc3OC3CCC3)ncc21] |
| 94 | 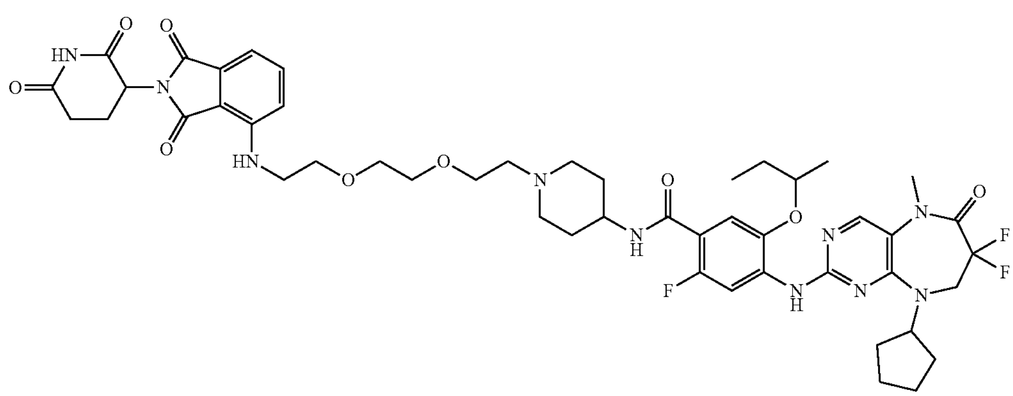 [SMILES: CCC(C)Oc1cc(C(=O)NC2CCN(CCOCCOCCNc3cccc4c3C(=O)N(C3CCC(=O)NC3=O)C4=O)CC2)c(F)cc1Nc1ncc2c(n1)N(C1CCCC1)CC(F)(F)C(=O)N2C] |

TABLE 1-continued
| Compound | Structure |
|---|---|
| 95 | 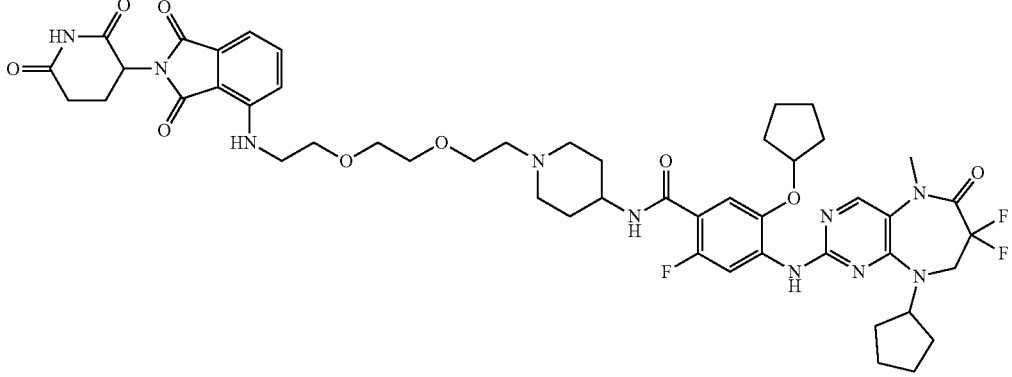 |
| 96 | 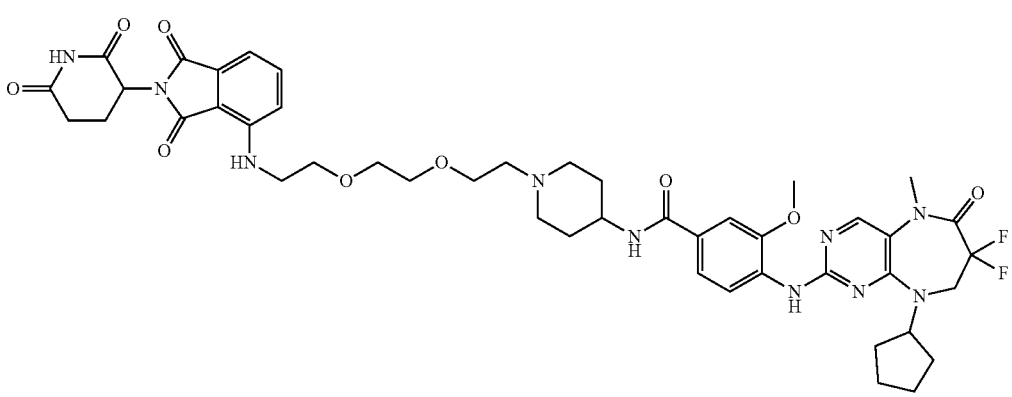 [SMILES: COc1cc(C(=O)NC2CCN(CCOCCOCCNc3cccc4c3C(=O)N(C3CCC(=O)NC3=O)C4=O)CC2)ccc1Nc1ncc2c(n1)N(C1CCCC1)CC(F)(F)C(=O)N2C] |
| 97 | 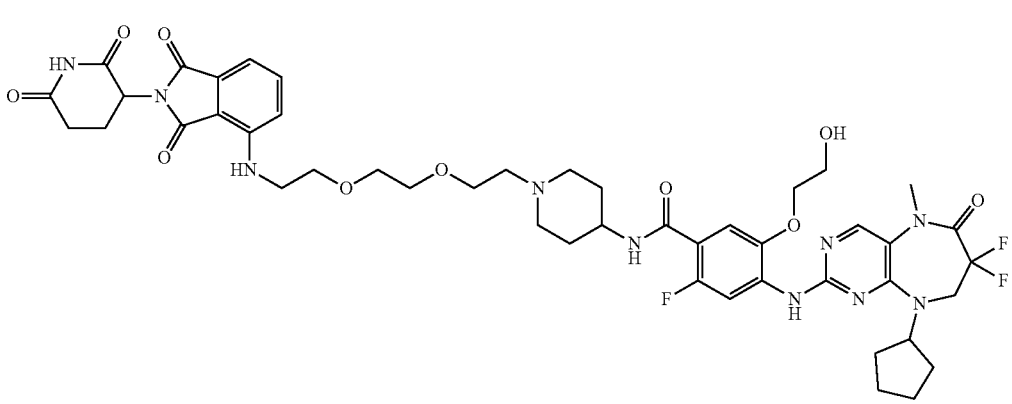 [SMILES: CN1C(=O)C(F)(F)CN(C2CCCC2)c2nc(Nc3cc(F)c(C(=O)NC4CCN(CCOCCOCCNc5cccc6c5C(=O)N(C5CCC(=O)NC5=O)C6=O)CC4)cc3OCCO)ncc21] |
| 98 | 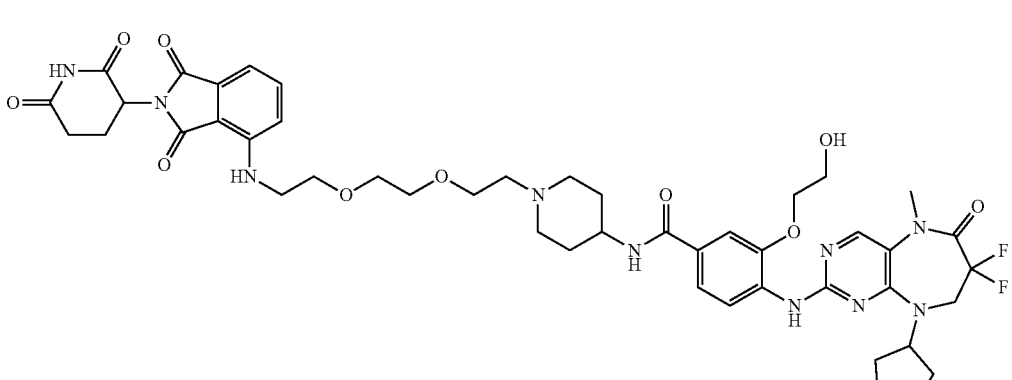 |

TABLE 1-continued

| Compound | Structure |
|---|---|
| 99 | 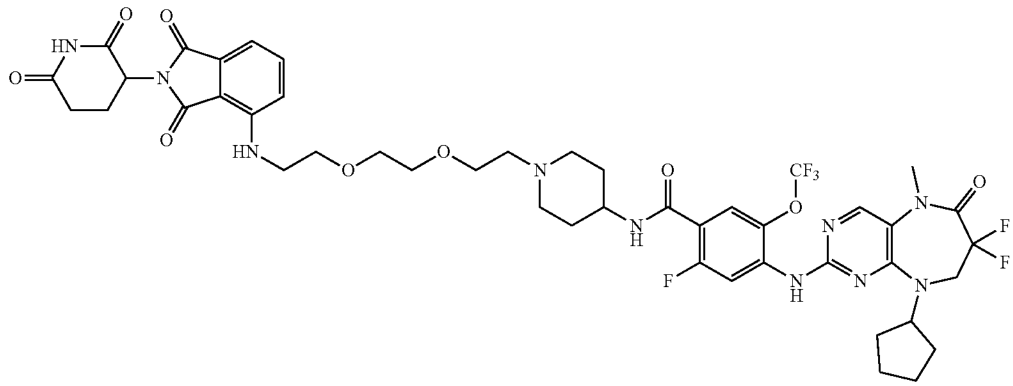 |
| 100 | 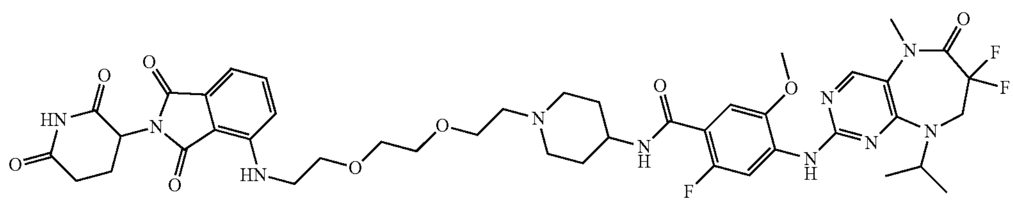 [SMILES: COc1cc(C(=O)NC2CCN(CCOCCOCCNc3cccc4c3C(=O)N(C3CCC(=O)NC3=O)C4=O)CC2)c(F)cc1Nc1ncc2c(n1)N(C(C)C)CC(F)(F)C(=O)N2C] |
| 101 | 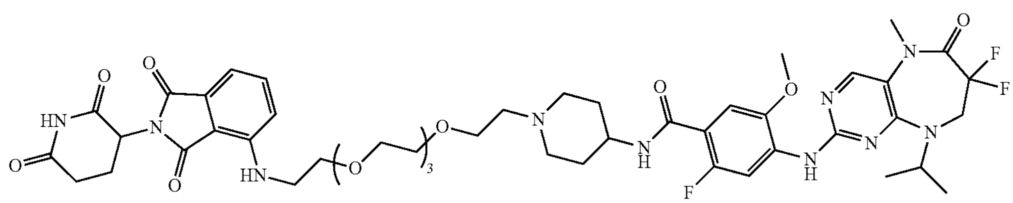 |
| 102 | 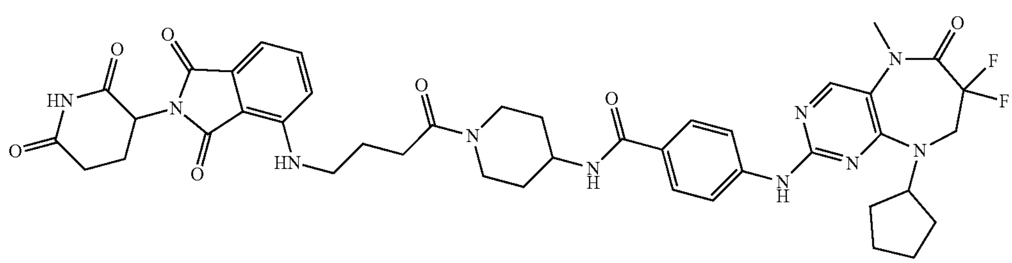 [SMILES: CN1C(=O)C(F)(F)CN(C2CCCC2)c2nc(Nc3ccc(C(=O)NC4CCN(C(=O)CCCNc5cccc6c5C(=O)N(C5CCC(=O)NC5=O)C6=O)CC4)cc3)ncc21] |
| 103 | 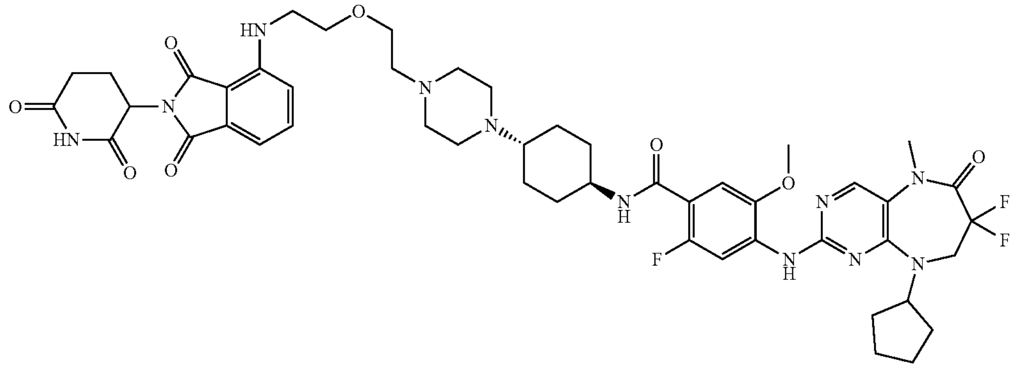 [SMILES: COc1cc(C(=O)N[C@H]2CC[C@H](N3CCN(CCOCCNc4cccc5c4C(=O)N(C4CCC(=O)NC4=O)C5=O)CC3)CC2)c(F)cc1Nc1ncc2c(n1)N(C1CCCC1)CC(F)(F)C(=O)N2C] |

TABLE 1-continued
| Compound | Structure |
|---|---|
| 104 | 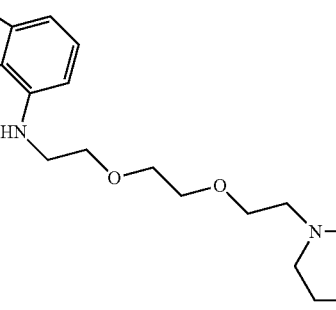 |
| 105 | 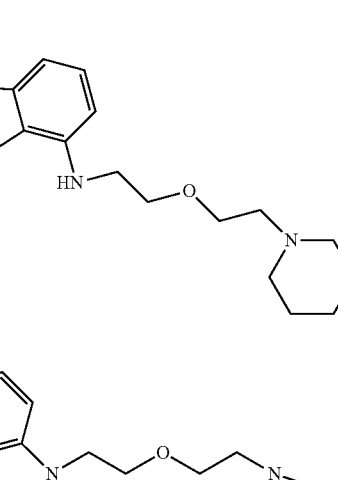 |
| 106 | 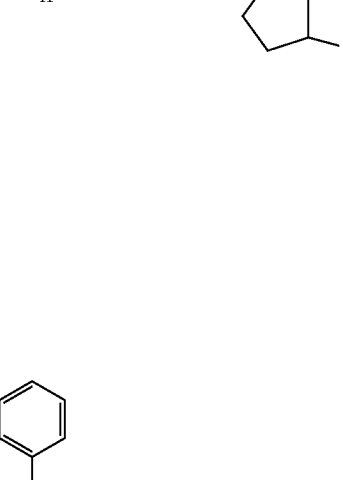 |
| 107 | 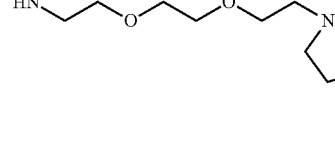 |

TABLE 1-continued

| Compound | Structure |
|---|---|
| 108 | 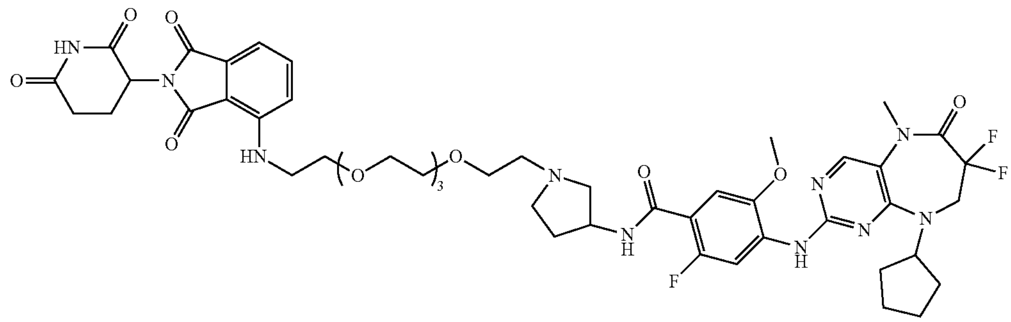 |
| 109 | 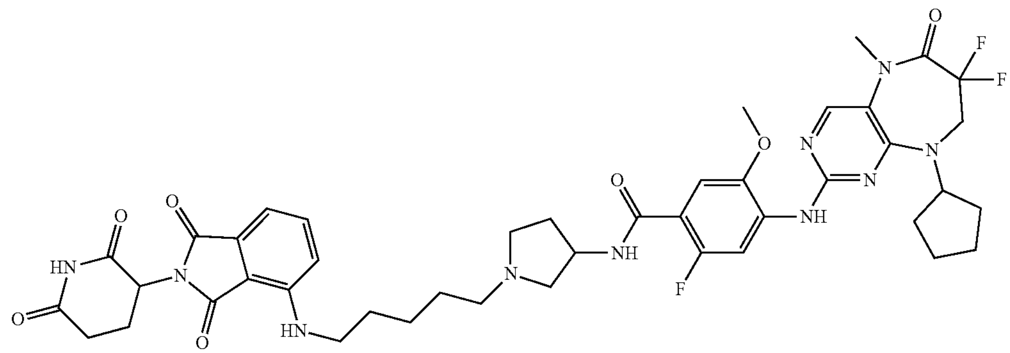 [SMILES: COc1cc(C(=O)NC2CCN(CCCCCNc3cccc4c3C(=O)N(C3CCC(=O)NC3=O)C4=O)C2)c(F)cc1Nc1ncc2c(n1)N(C1CCCC1)CC(F)(F)C(=O)N2C] |
| 110 | 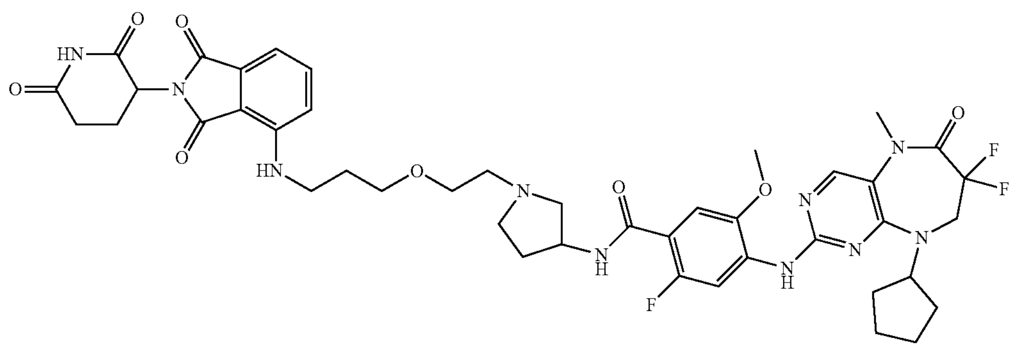 [SMILES: COc1cc(C(=O)NC2CCN(CCOCCCNc3cccc4c3C(=O)N(C3CCC(=O)NC3=O)C4=O)C2)c(F)cc1Nc1ncc2c(n1)N(C1CCCC1)CC(F)(F)C(=O)N2C] |
| 111 | 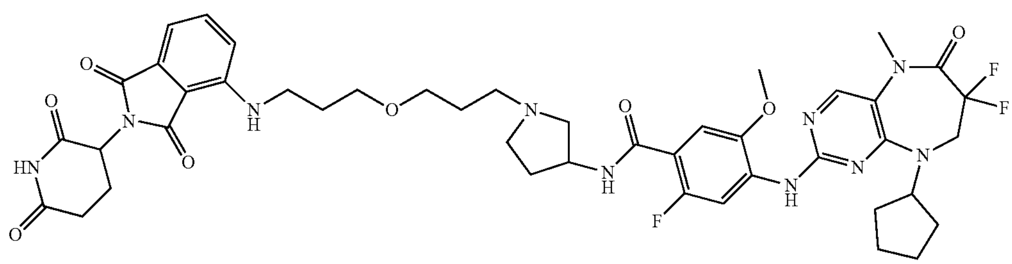 [SMILES: COc1cc(C(=O)NC2CCN(CCCOCCCNc3cccc4c3C(=O)N(C3CCC(=O)NC3=O)C4=O)C2)c(F)cc1Nc1ncc2c(n1)N(C1CCCC1)CC(F)(F)C(=O)N2C] |
| 112 | 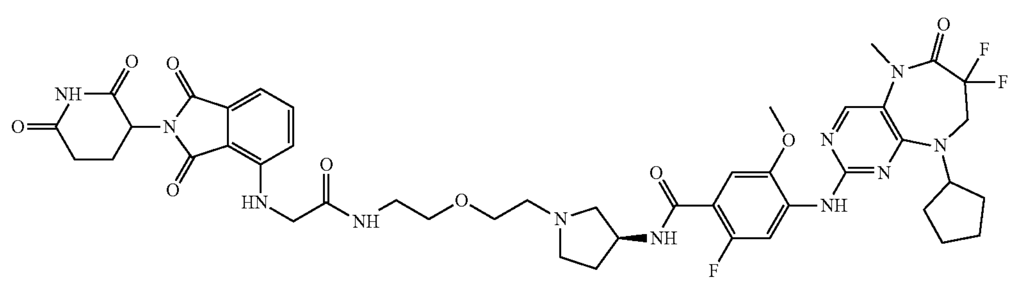 [SMILES: COc1cc(C(=O)N[C@H]2CCN(CCOCCNC(=O)CNc3cccc4c3C(=O)N(C3CCC(=O)NC3=O)C4=O)C2)c(F)cc1Nc1ncc2c(n1)N(C1CCCC1)CC(F)(F)C(=O)N2C] |

TABLE 1-continued
| Compound | Structure |
|---|---|
| 113 | 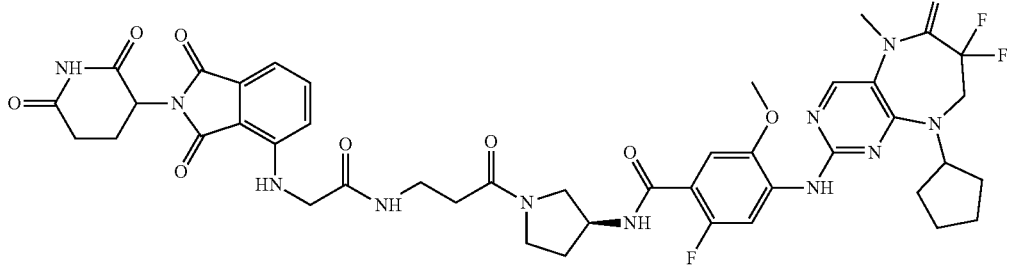 |
| 114 | 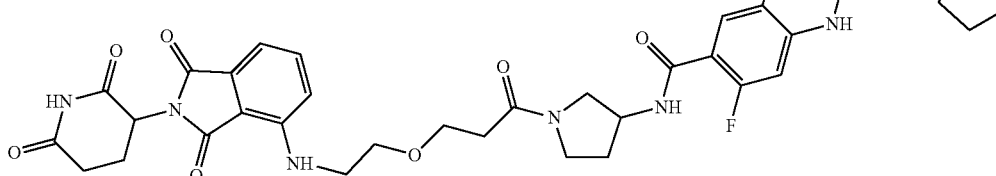 |
| 115 | 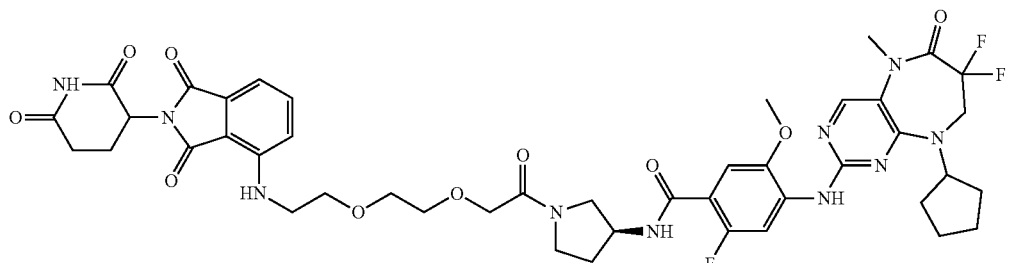 |
| 116 | 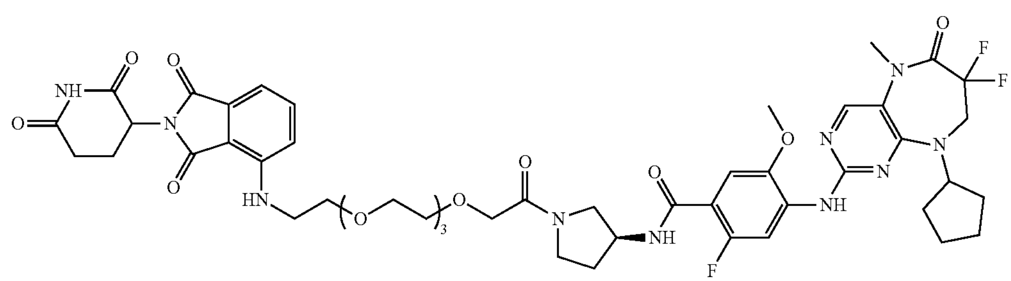 |
| 117 | 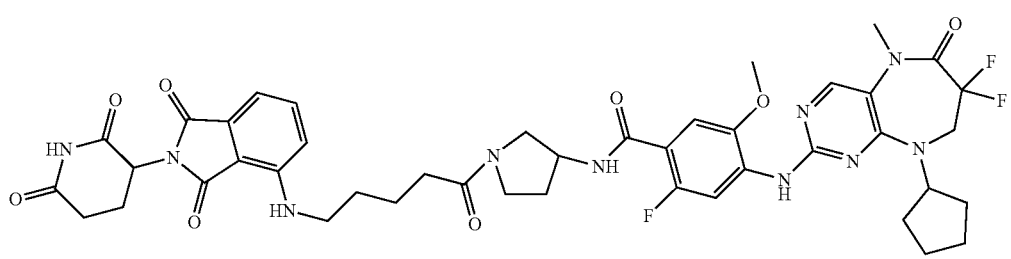 [SMILES: COc1cc(C(=O)NC2CCN(C(=O)CCCCNc3cccc4c3C(=O)N(C3CCC(=O)NC3=O)C4=O)C2)c(F)cc1Nc1ncc2c(n1)N(C1CCCC1)CC(F)(F)C(=O)N2C] |

TABLE 1-continued
| Compound | Structure |
|---|---|
| 118 | 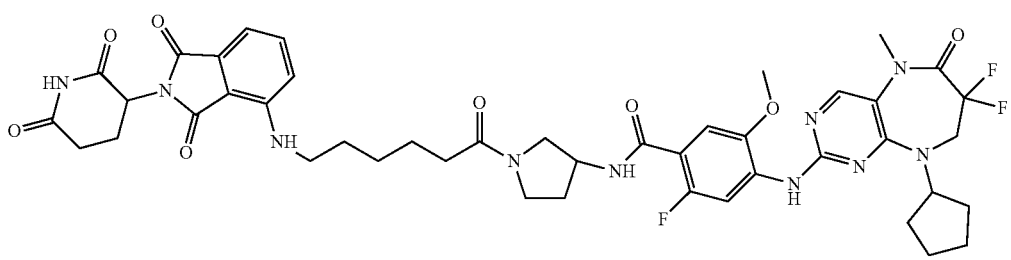 [SMILES: COc1cc(C(=O)NC2CCN(C(=O)CCCCCNc3cccc4c3C(=O)N(C3CCC(=O)NC3=O)C4=O)C2)c(F)cc1Nc1ncc2c(n1)N(C1CCCC1)CC(F)(F)C(=O)N2C] |
| 119 | 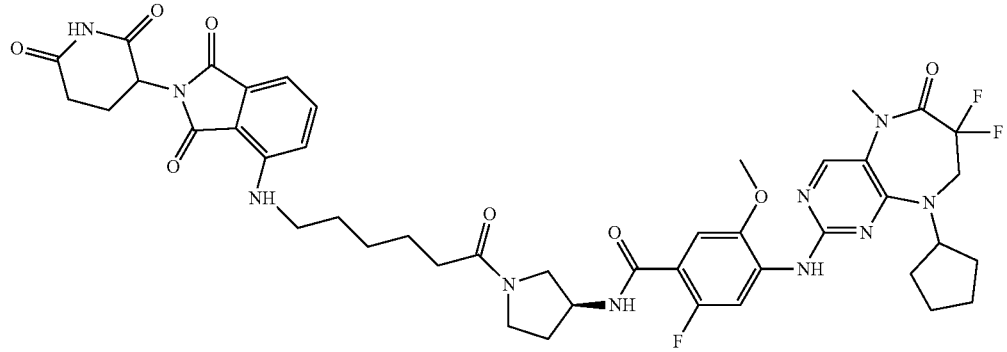 [SMILES: COc1cc(C(=O)N[C@H]2CCN(C(=O)CCCCCNc3cccc4c3C(=O)N(C3CCC(=O)NC3=O)C4=O)C2)c(F)cc1Nc1ncc2c(n1)N(C1CCCC1)CC(F)(F)C(=O)N2C] |
| 120 | 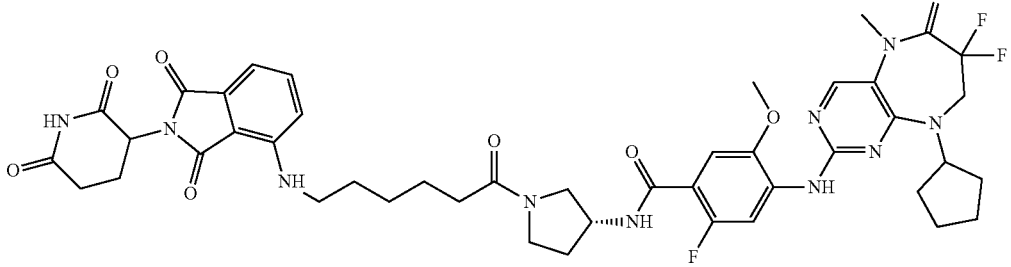 |
| 121 | 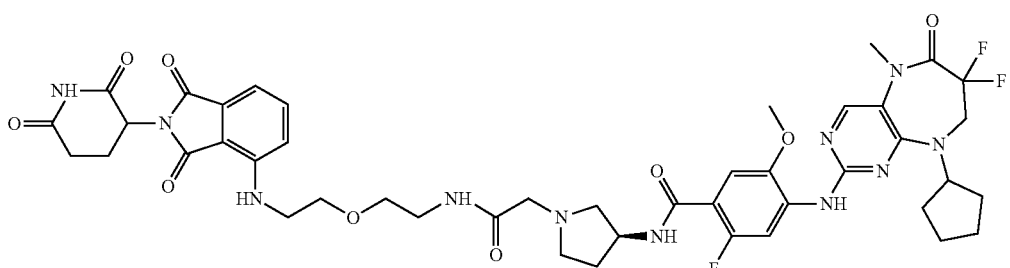 |
| 122 | 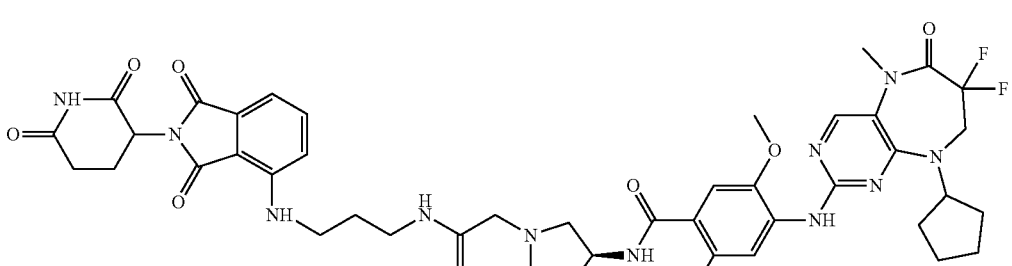 |

TABLE 1-continued
| Compound | Structure |
|---|---|
| 123 | 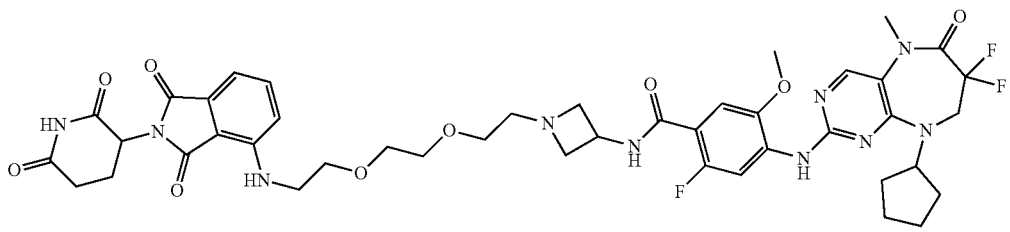 [SMILES: COc1cc(C(=O)NC2CN(CCOCCOCCNc3cccc4c3C(=O)N(C3CCC(=O)NC3=O)C4=O)C2)c(F)cc1Nc1ncc2c(n1)N(C1CCCC1)CC(F)(F)C(=O)N2C] |
| 124 | 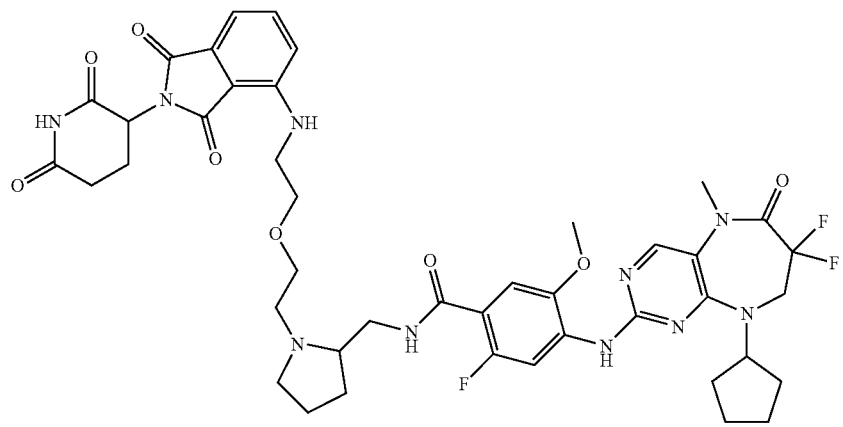 [SMILES: COc1cc(C(=O)NCC2CCCN2CCOCCNc2cccc3c2C(=O)N(C2CCC(=O)NC2=O)C3=O)c(F)cc1Nc1ncc2c(n1)N(C1CCCC1)CC(F)(F)C(=O)N2C] |
| 125 | 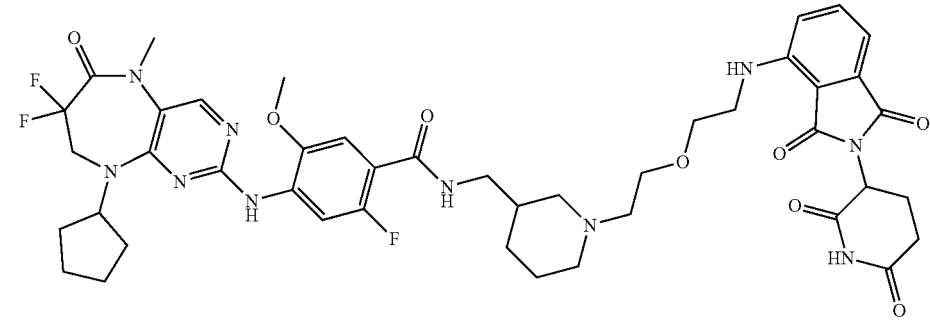 [SMILES: COc1cc(C(=O)NCC2CCCN(CCOCCNc3cccc4c3C(=O)N(C3CCC(=O)NC3=O)C4=O)C2)c(F)cc1Nc1ncc2c(n1)N(C1CCCC1)CC(F)(F)C(=O)N2C] |
| 126 | 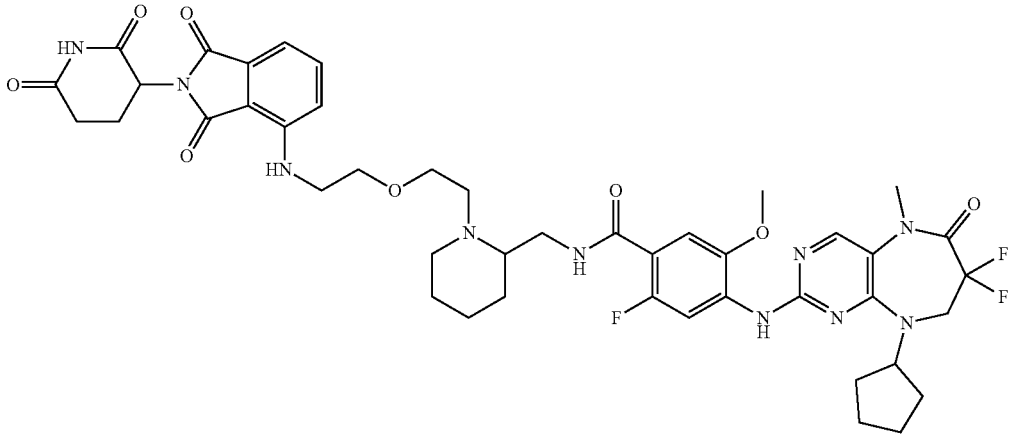 [SMILES: COc1cc(C(=O)NCC2CCCCN2CCOCCNc2cccc3c2C(=O)N(C2CCC(=O)NC2=O)C3=O)c(F)cc1Nc1ncc2c(n1)N(C1CCCC1)CC(F)(F)C(=O)N2C] |

TABLE 1-continued

| Compound | Structure |
| --- | --- |
| 127 | 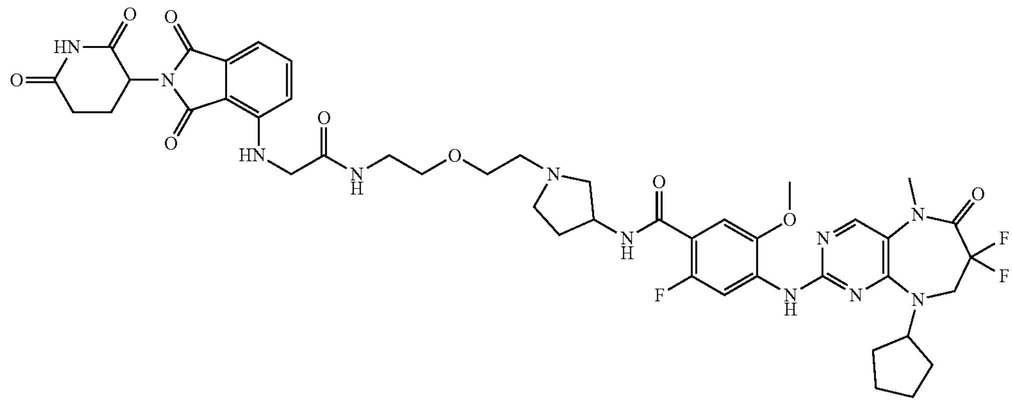 [SMILES: COc1cc(C(=O)NC2CCN(CCOCCNC(=O)CNc3cccc4c3C(=O)N(C3CCC(=O)NC3=O)C4=O)C2)c(F)cc1Nc1ncc2c(n1)N(C1CCCC1)CC(F)(F)C(=O)N2C] |
| 128 | 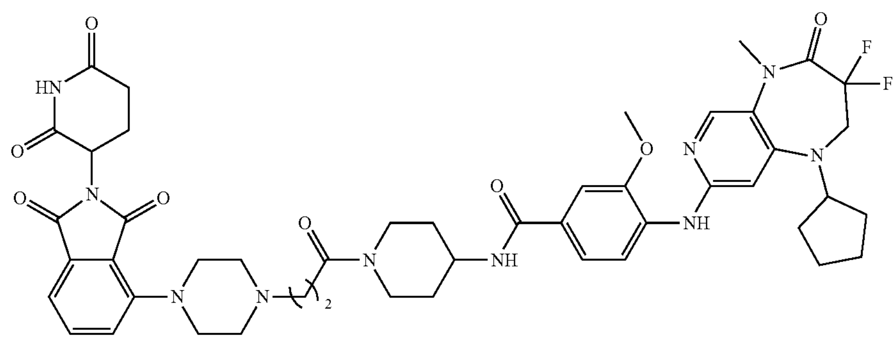 |
| 129 | 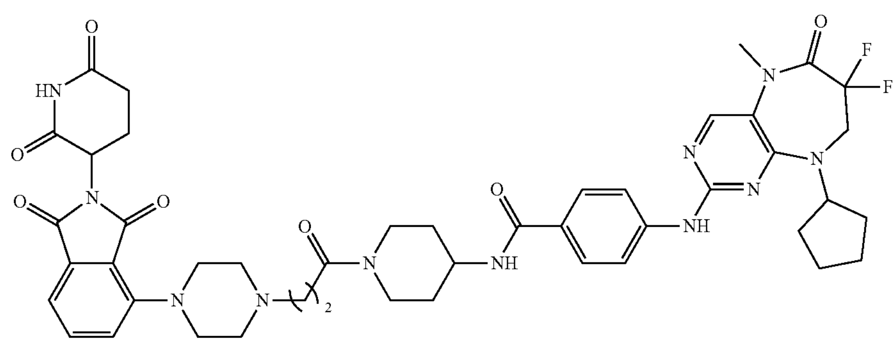 |
| 130 | 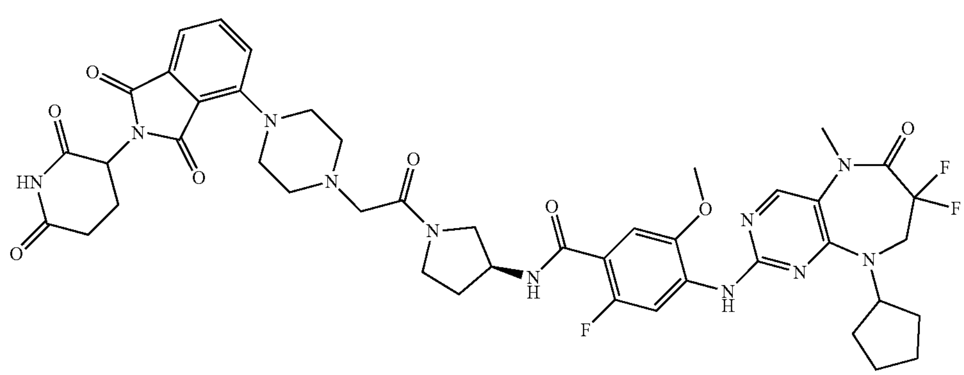 [SMILES: COc1cc(C(=O)N[C@H]2CCN(C(=O)CN3CCN(c4cccc5c4C(=O)N(C4CCC(=O)NC4=O)C5=O)CC3)C2)c(F)cc1Nc1ncc2c(n1)N(C1CCCC1)CC(F)(F)C(=O)N2C] |

TABLE 1-continued
| Compound | Structure |
|---|---|
| 131 | 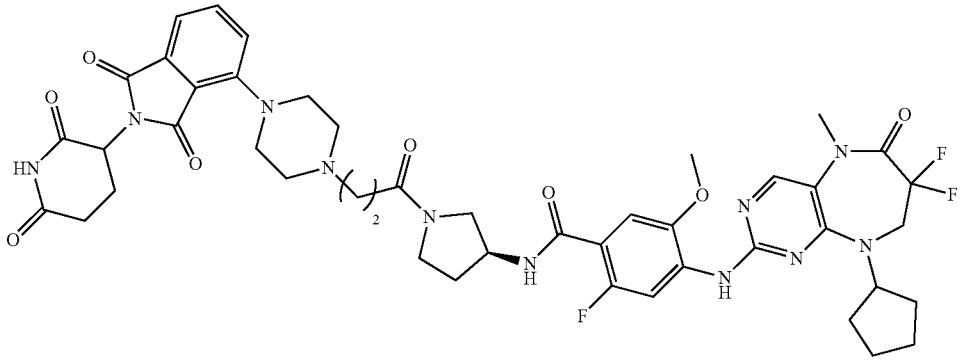 |
| 132 | 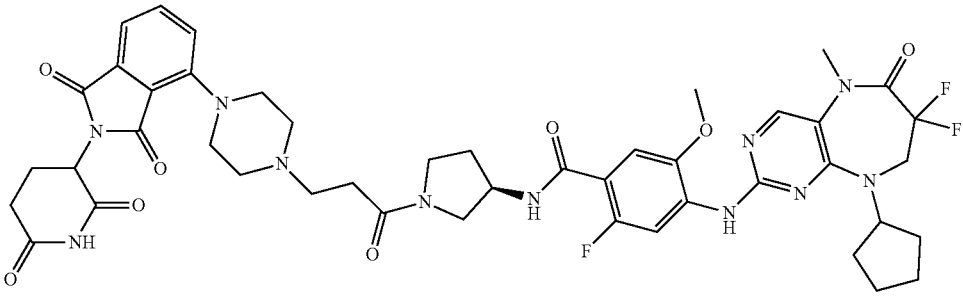 [SMILES: COc1cc(C(=O)N[C@@H]2CCN(C(=O)CCN3CCN(c4cccc5c4C(=O)N(C4CCC(=O)NC4=O)C5=O)CC3)C2)c(F)cc1Nc1ncc2c(n1)N(C1CCCC1)CC(F)(F)C(=O)N2C] |
| 133 | 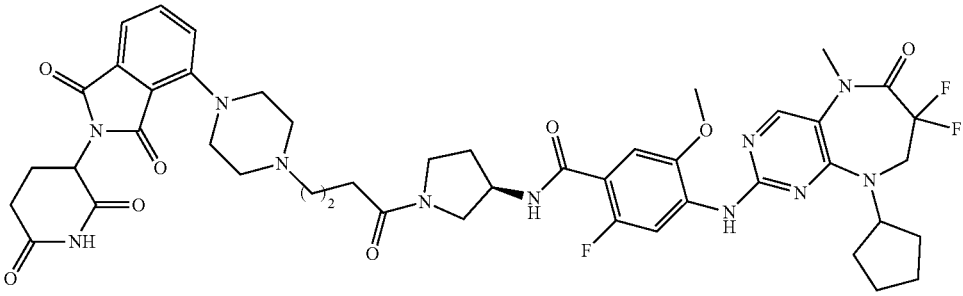 |
| 134 | 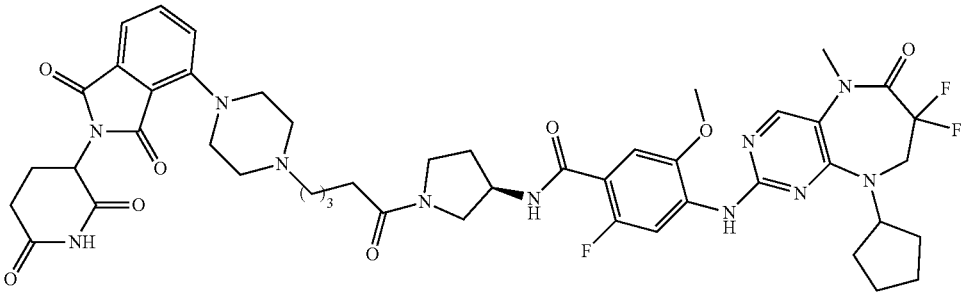 |
| 135 | 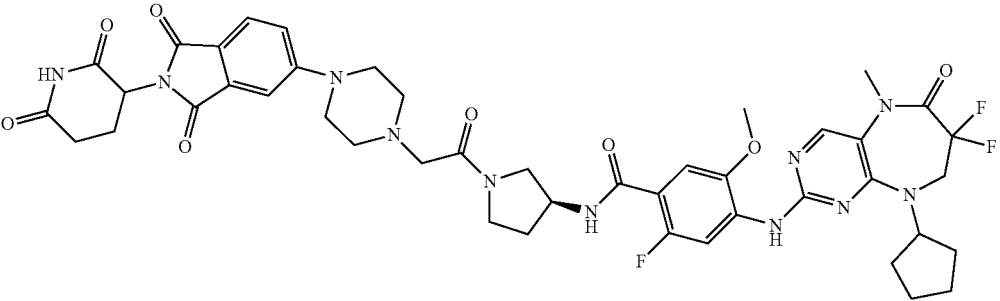 [SMILES: COc1cc(C(=O)N[C@H]2CCN(C(=O)CN3CCN(c4ccc5c(c4)C(=O)N(C4CCC(=O)NC4=O)C5=O)CC3)C2)c(F)cc1Nc1ncc2c(n1)N(C1CCCC1)CC(F)(F)C(=O)N2C] |

TABLE 1-continued

| Compound | Structure |
|---|---|
| 136 | 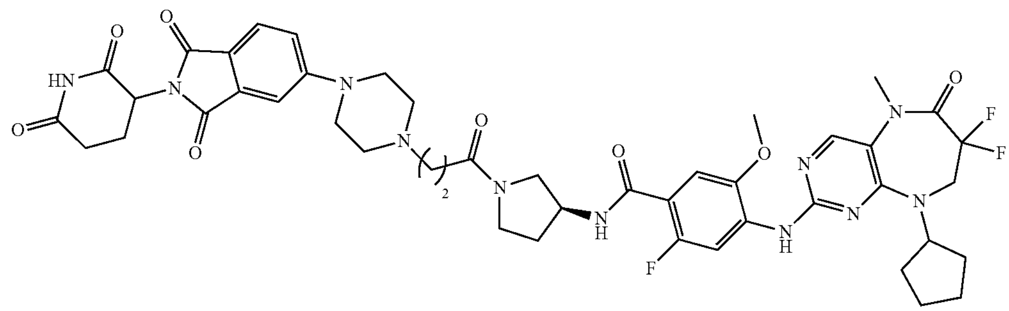 |
| 137 | 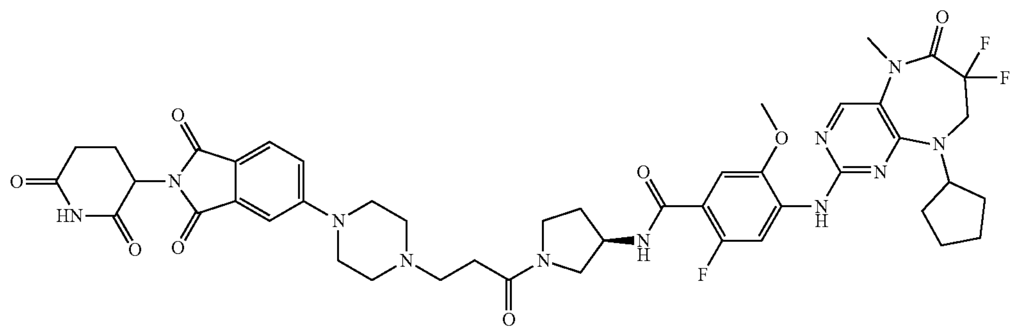 [SMILES: COc1cc(C(=O)N[C@@H]2CCN(C(=O)CCN3CCN(c4ccc5c(c4)C(=O)N(C4CCC(=O)NC4=O)C5=O)CC3)C2)c(F)cc1Nc1ncc2c(n1)N(C1CCCC1)CC(F)(F)C(=O)N2C] |
| 138 | 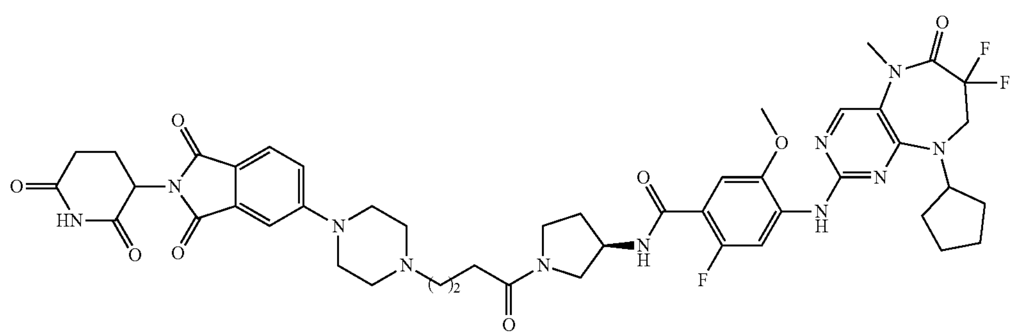 |
| 139 | 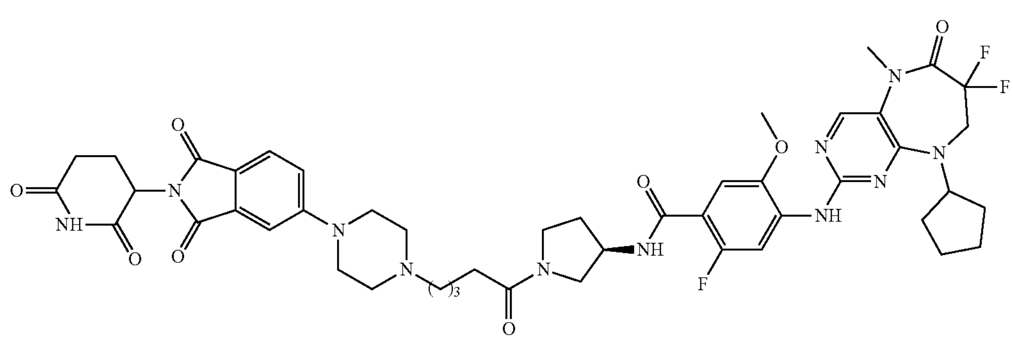 |

TABLE 1-continued
| Compound | Structure |
|---|---|
| 140 | 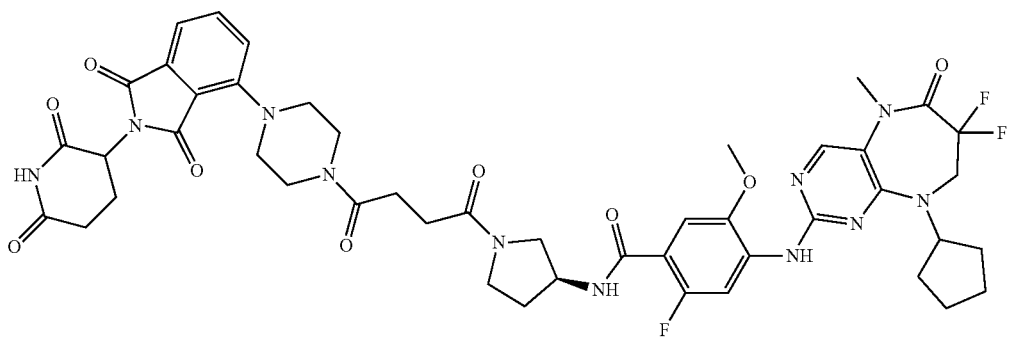 [SMILES: COc1cc(C(=O)N[C@H]2CCN(C(=O)CCC(=O)N3CCN(c4cccc5c4C(=O)N(C4CCC(=O)NC4=O)C5=O)CC3)C2)c(F)cc1Nc1ncc2c(n1)N(C1CCCC1)CC(F)(F)C(=O)N2C] |
| 141 | 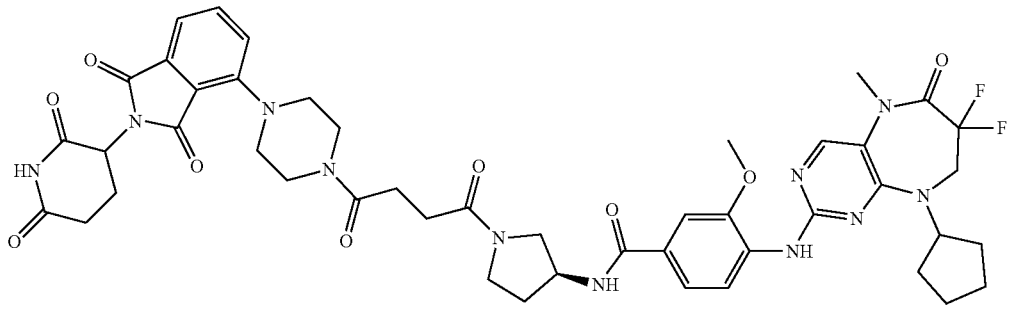 [SMILES: COc1cc(C(=O)N[C@H]2CCN(C(=O)CCC(=O)N3CCN(c4cccc5c4C(=O)N(C4CCC(=O)NC4=O)C5=O)CC3)C2)ccc1Nc1ncc2c(n1)N(C1CCCC1)CC(F)(F)C(=O)N2C] |
| 142 | 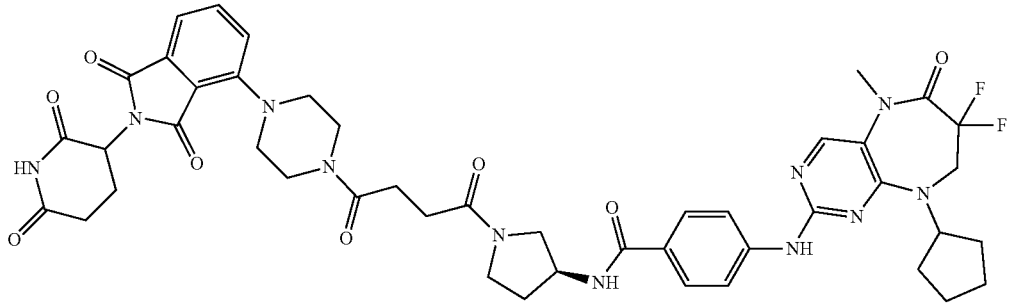 [SMILES: CN1C(=O)C(F)(F)CN(C2CCCC2)c2nc(Nc3ccc(C(=O)N[C@H]4CCN(C(=O)CCC(=O)N5CCN(c6cccc7c6C(=O)N(C6CCC(=O)NC6=O)C7=O)CC5)C4)cc3)ncc21] |
| 143 | 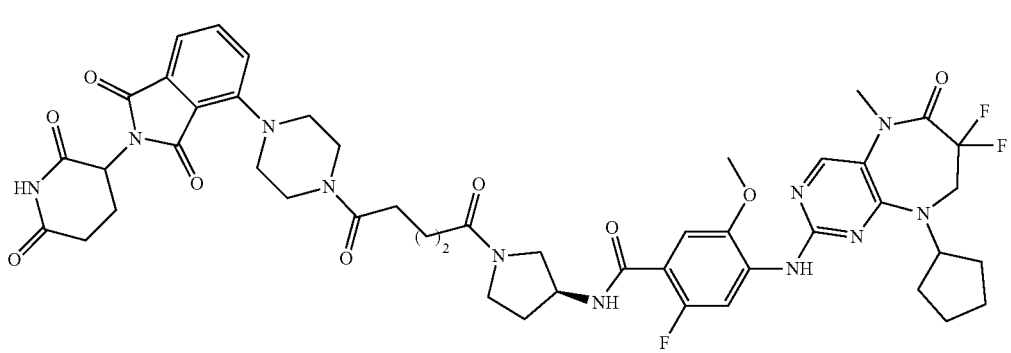 |

TABLE 1-continued

| Compound | Structure |
|---|---|
| 144 | 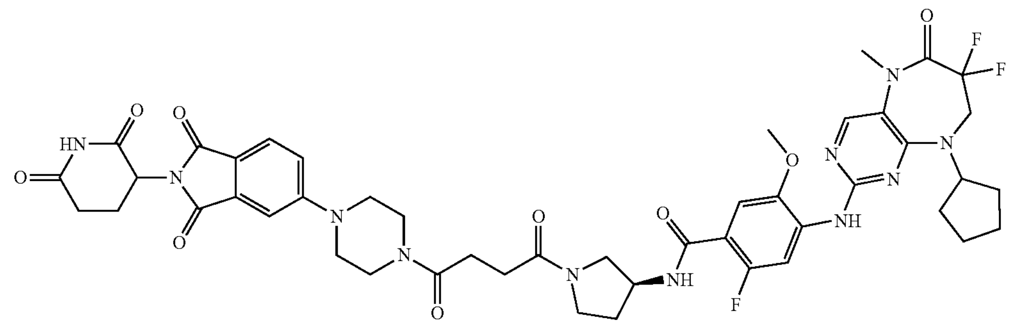 [SMILES: COc1cc(C(=O)N[C@H]2CCN(C(=O)CCC(=O)N3CCN(c4ccc5c(c4)C(=O)N(C4CCC(=O)NC4=O)C5=O)CC3)C2)c(F)cc1Nc1ncc2c(n1)N(C1CCCC1)CC(F)(F)C(=O)N2C] |
| 145 | 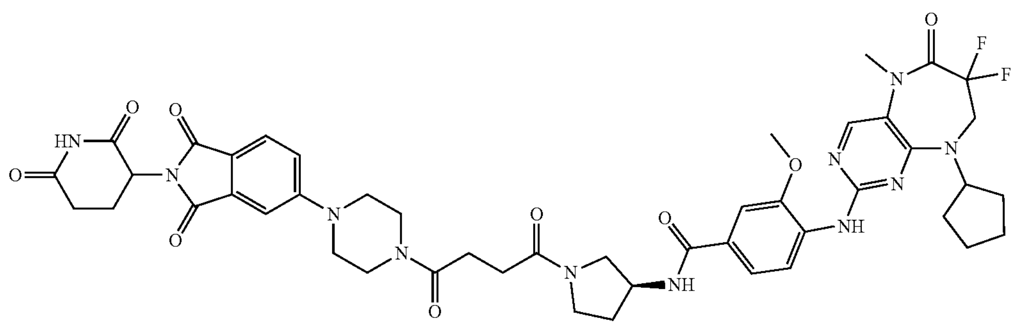 [SMILES: COc1cc(C(=O)N[C@H]2CCN(C(=O)CCC(=O)N3CCN(c4ccc5c(c4)C(=O)N(C4CCC(=O)NC4=O)C5=O)CC3)C2)ccc1Nc1ncc2c(n1)N(C1CCCC1)CC(F)(F)C(=O)N2C] |
| 146 | 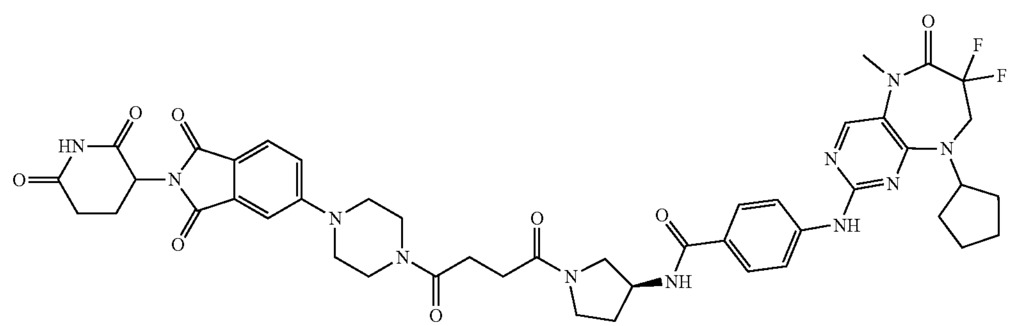 [SMILES: CN1C(=O)C(F)(F)CN(C2CCCC2)c2nc(Nc3ccc(C(=O)N[C@H]4CCN(C(=O)CCC(=O)N5CCN(c6ccc7c(c6)C(=O)N(C6CCC(=O)NC6=O)C7=O)CC5)C4)cc3)ncc21] |
| 147 | 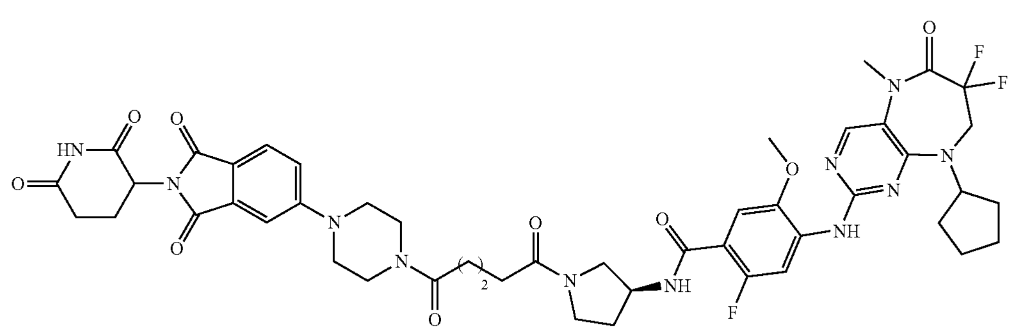 |

TABLE 1-continued

| Compound | Structure |
|---|---|
| 148 | 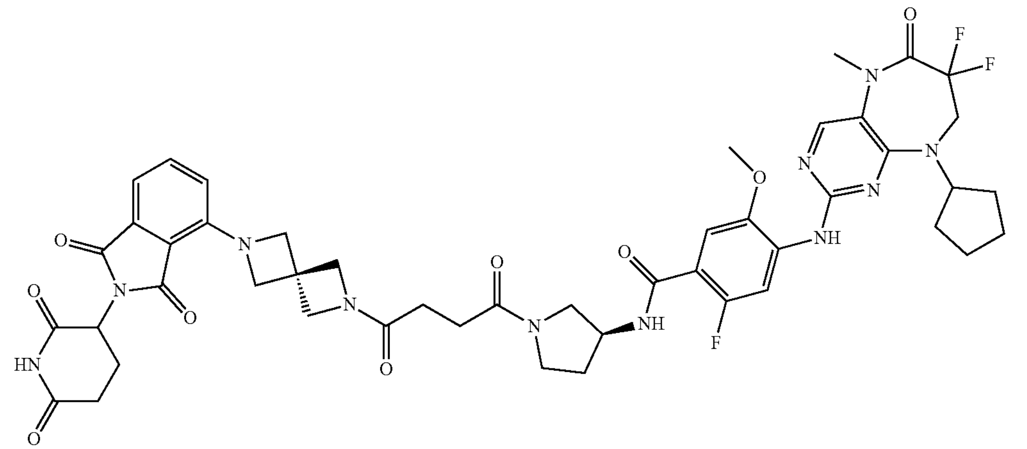 |
| 149 | 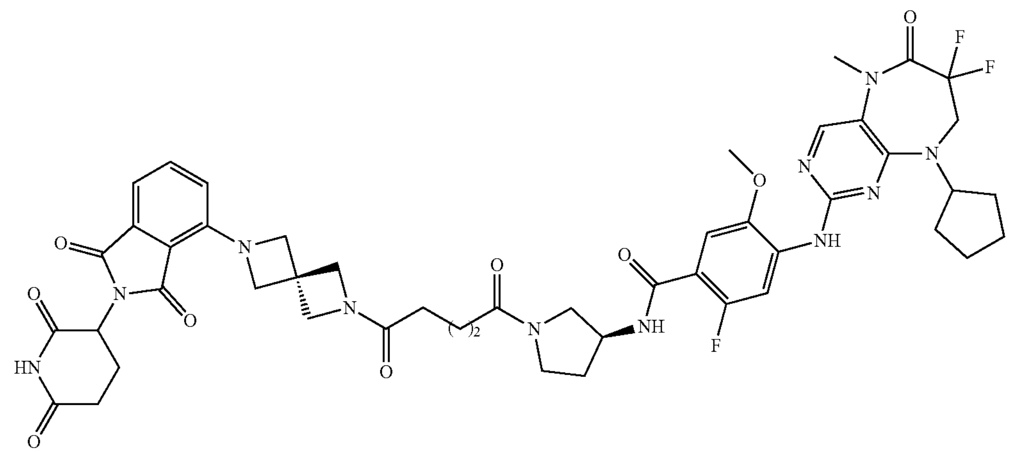 |
| 150 | 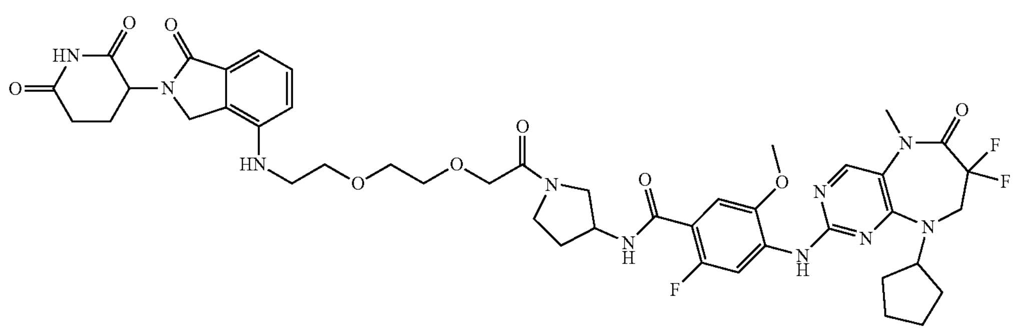 [SMILES: COc1cc(C(=O)NC2CCN(C(=O)COCCOCCNc3cccc4c3CN(C3CCC(=O)NC3=O)C4=O)C2)c(F)cc1Nc1ncc2c(n1)N(C1CCCC1)CC(F)(F)C(=O)N2C] |
| 151 | 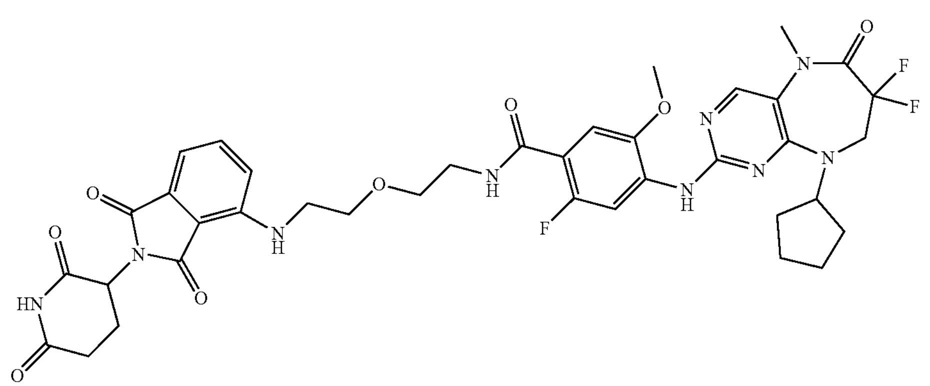 [SMILES: COc1cc(C(=O)NCCOCCNc2cccc3c2C(=O)N(C2CCC(=O)NC2=O)C3=O)c(F)cc1Nc1ncc2c(n1)N(C1CCCC1)CC(F)(F)C(=O)N2C] |

TABLE 1-continued

| Compound | Structure |
|---|---|
| 152 | 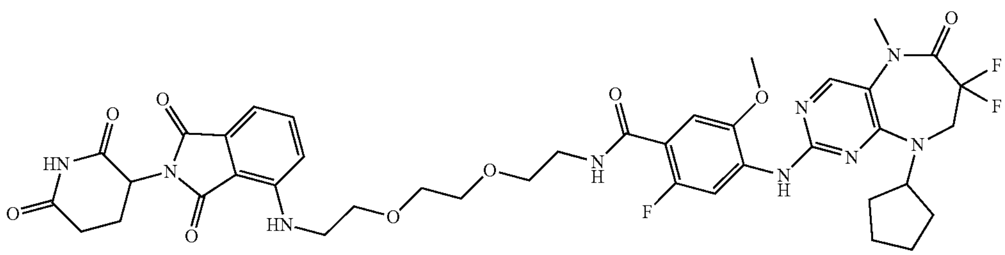 |
| 153 | 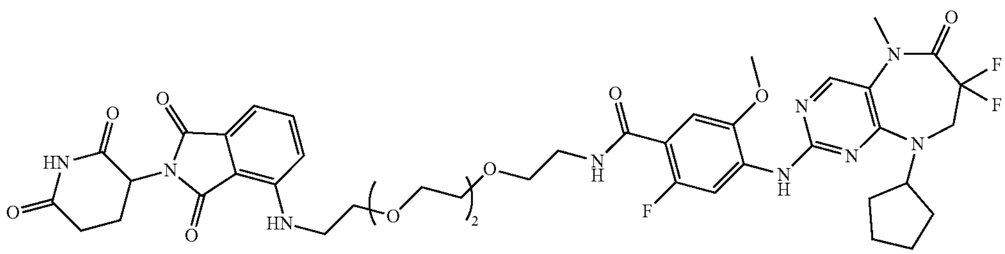 |
| 154 | 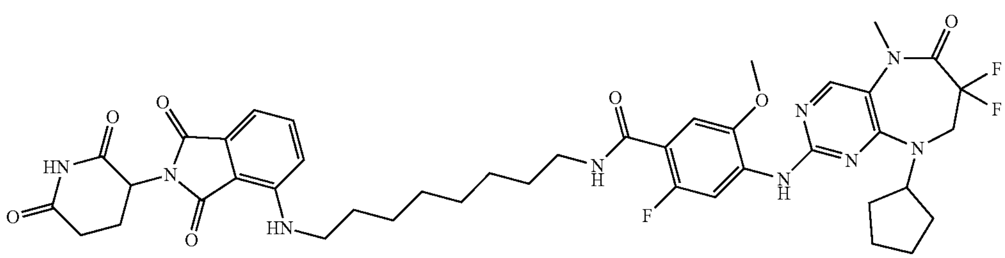 [SMILES: COc1cc(C(=O)NCCCCCCCCNc2cccc3c2C(=O)N(C2CCC(=O)NC2=O)C3=O)c(F)cc1Nc1ncc2c(n1)N(C1CCCC1)CC(F)(F)C(=O)N2C] |
| 155 | 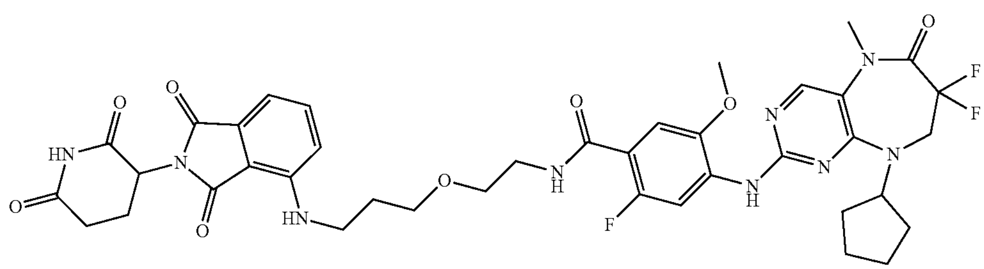 [SMILES: COc1cc(C(=O)NCCOCCCNc2cccc3c2C(=O)N(C2CCC(=O)NC2=O)C3=O)c(F)cc1Nc1ncc2c(n1)N(C1CCCC1)CC(F)(F)C(=O)N2C] |
| 156 | 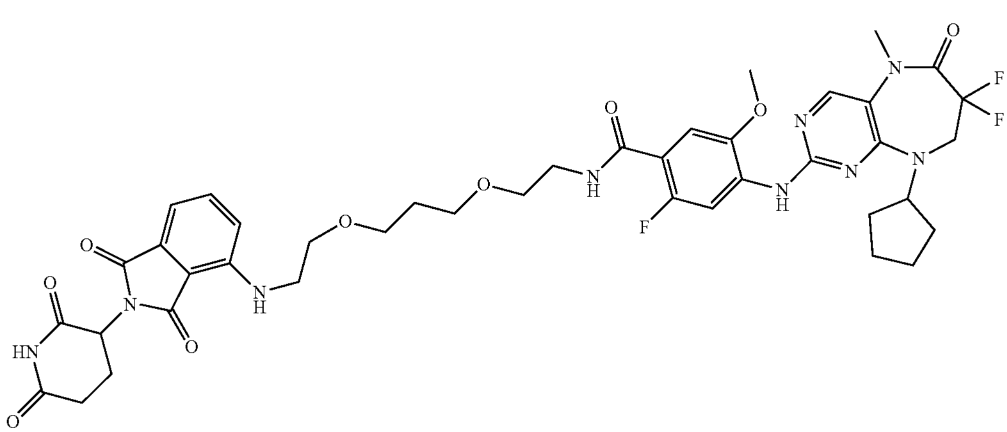 [SMILES: COc1cc(C(=O)NCCOCCCOCCNc2cccc3c2C(=O)N(C2CCC(=O)NC2=O)C3=O)c(F)cc1Nc1ncc2c(n1)N(C1CCCC1)CC(F)(F)C(=O)N2C] |

TABLE 1-continued
| Compound | Structure |
|---|---|
| 157 | 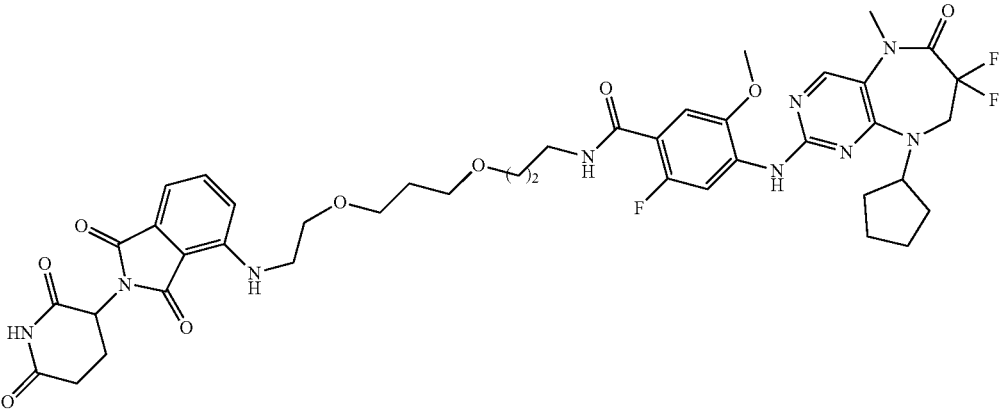 |
| 158 | 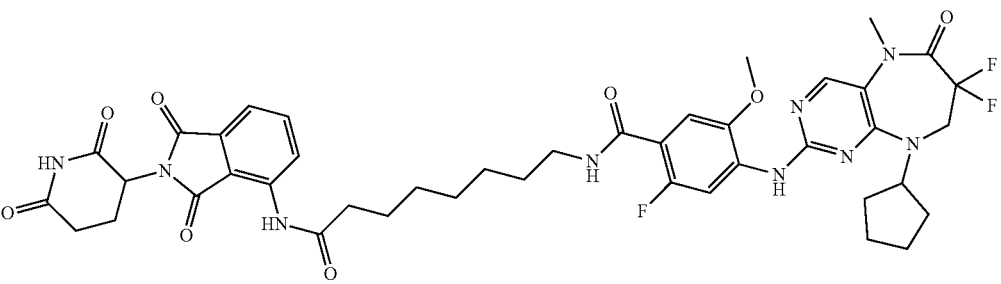 [SMILES: COc1cc(C(=O)NCCCCCCCC(=O)Nc2cccc3c2C(=O)N(C2CCC(=O)NC2=O)C3=O)c(F)cc1Nc1ncc2c(n1)N(C1CCCC1)CC(F)(F)C(=O)N2C] |
| 159 | 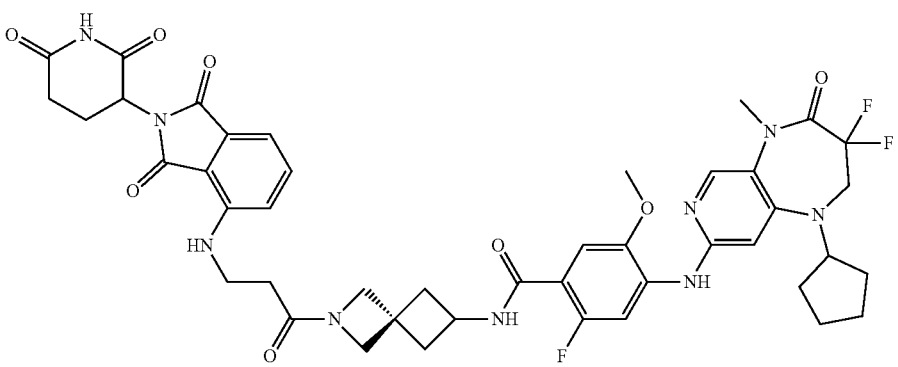 |
| 160 | 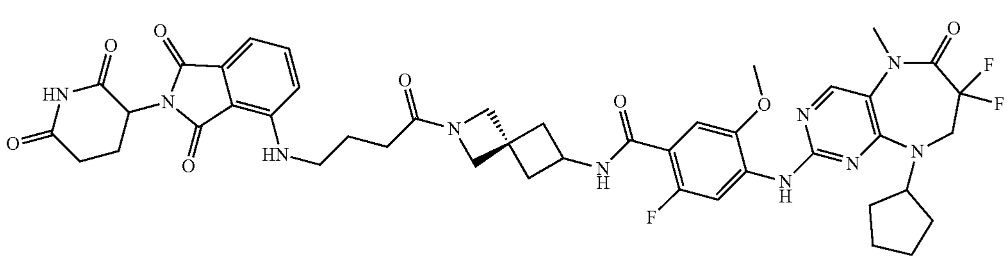 |
| 161 | 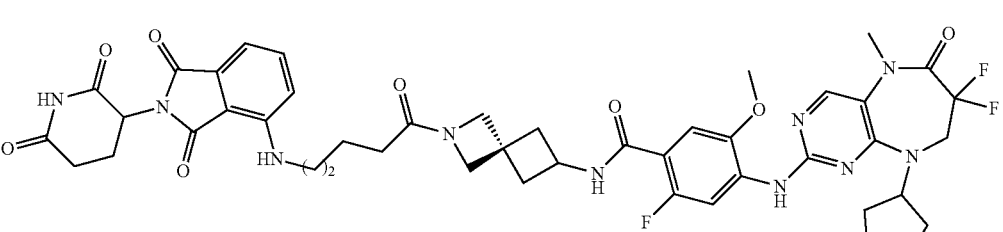 |

TABLE 1-continued
| Compound | Structure |
|---|---|
| 162 | 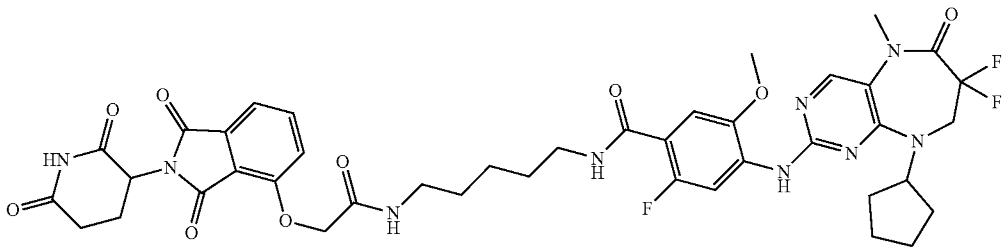 [SMILES: COc1cc(C(=O)NCCCCCNC(=O)COc2cccc3c2C(=O)N(C2CCC(=O)NC2=O)C3=O)c(F)cc1Nc1ncc2c(n1)N(C1CCCC1)CC(F)(F)C(=O)N2C] |
| 163 | 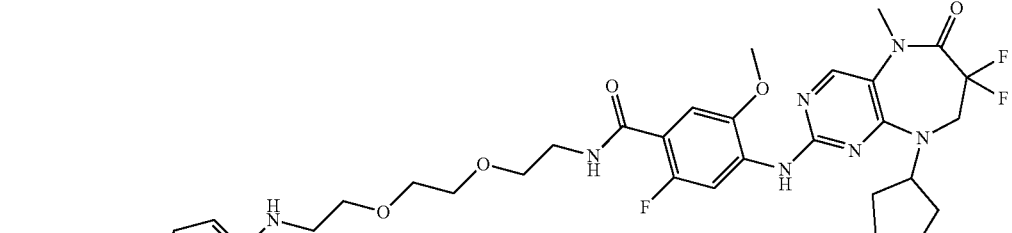 |
| 164 | 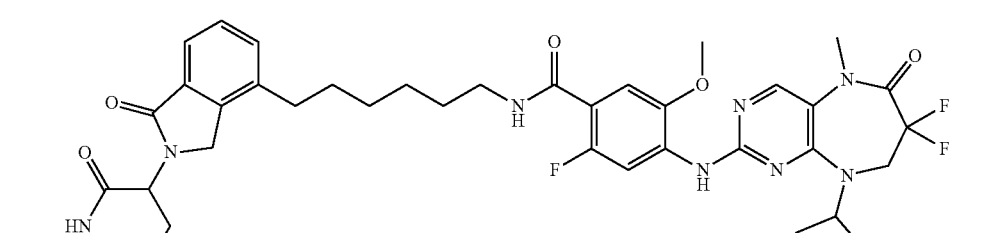 |
| 165 | 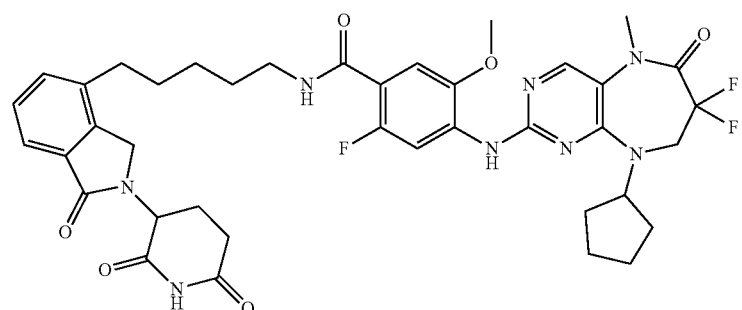 [SMILES: COc1cc(C(=O)NCCCCCc2cccc3c2CN(C2CCC(=O)NC2=O)C3=O)c(F)cc1Nc1ncc2c(n1)N(C1CCCC1)CC(F)(F)C(=O)N2C] |

TABLE 1-continued

| Compound | Structure |
|---|---|
| 166 | 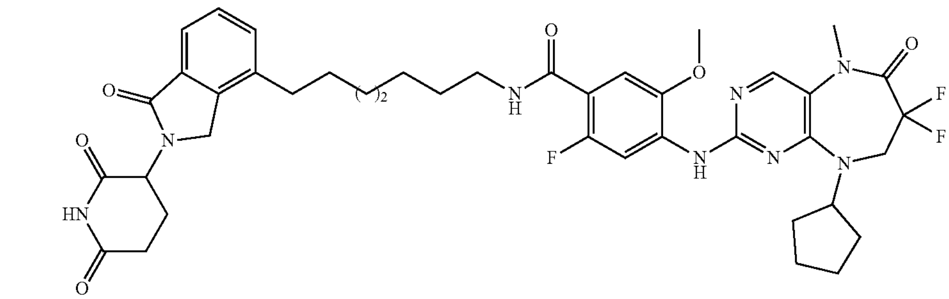 |
| 167 | 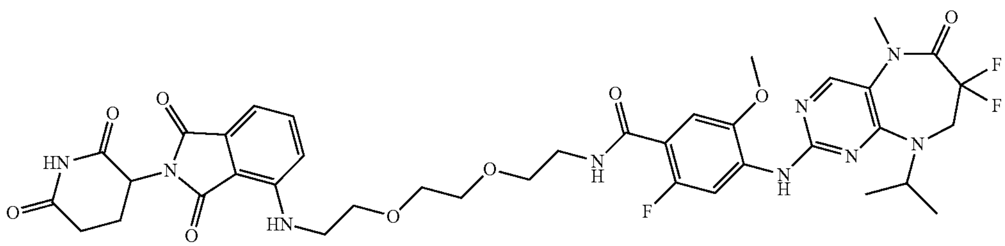 [SMILES: COc1cc(C(=O)NCCOCCOCCNc2cccc3c2C(=O)N(C2CCC(=O)NC2=O)C3=O)c(F)cc1Nc1ncc2c(n1)N(C(C)C)CC(F)(F)C(=O)N2C] |
| 168 | 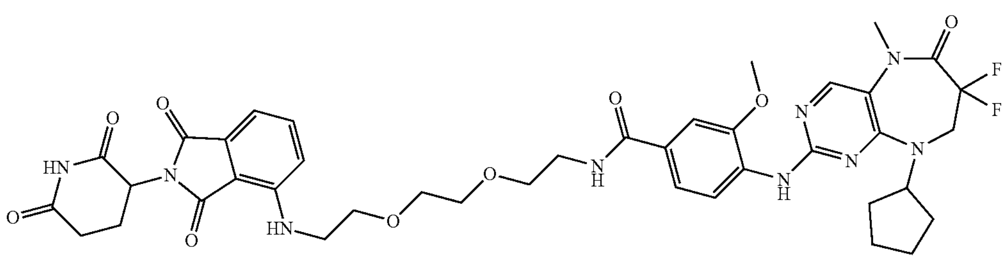 [SMILES: COc1cc(C(=O)NCCOCCOCCNc2cccc3c2C(=O)N(C2CCC(=O)NC2=O)C3=O)ccc1Nc1ncc2c(n1)N(C1CCCC1)CC(F)(F)C(=O)N2C] |
| 169 | 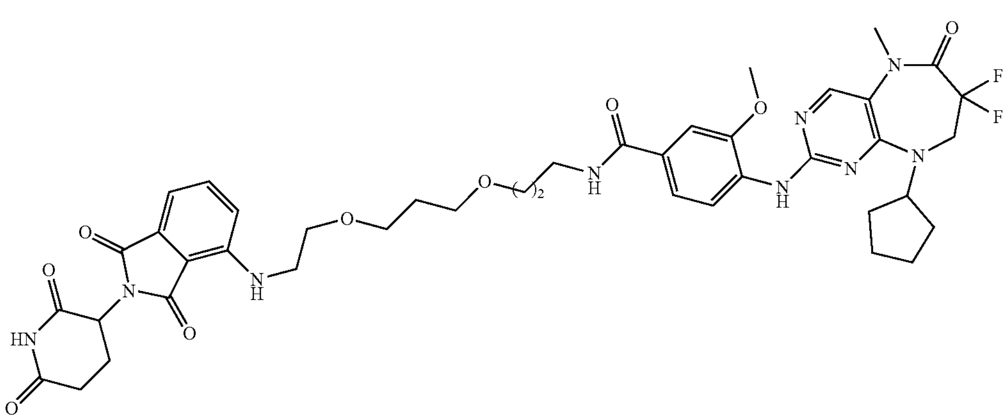 |

TABLE 1-continued
| Compound | Structure |
|---|---|
| 170 | 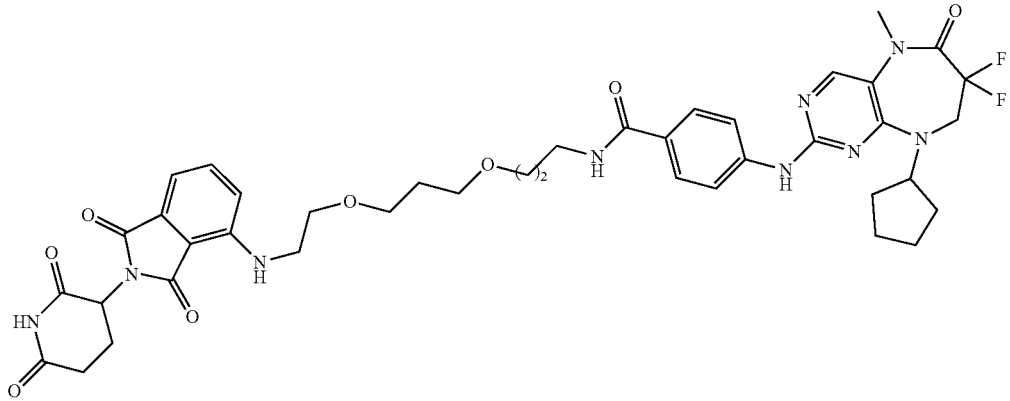 |
| 171 | 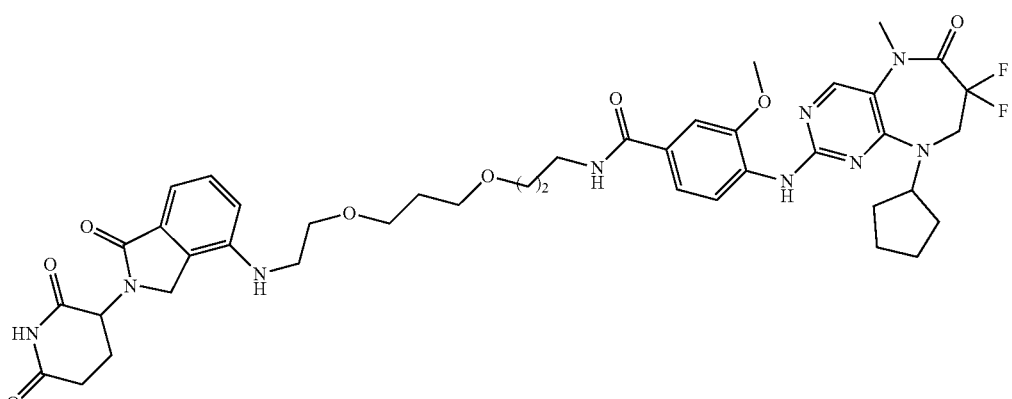 |
| 172 | 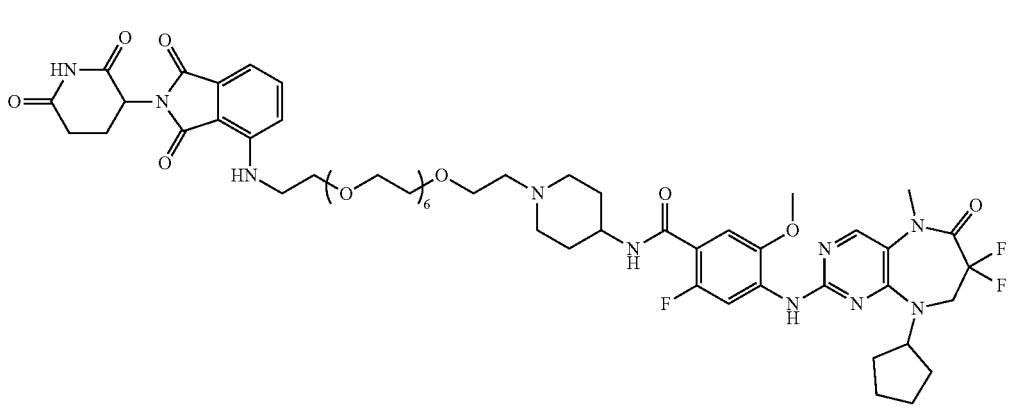 |
| 173 | 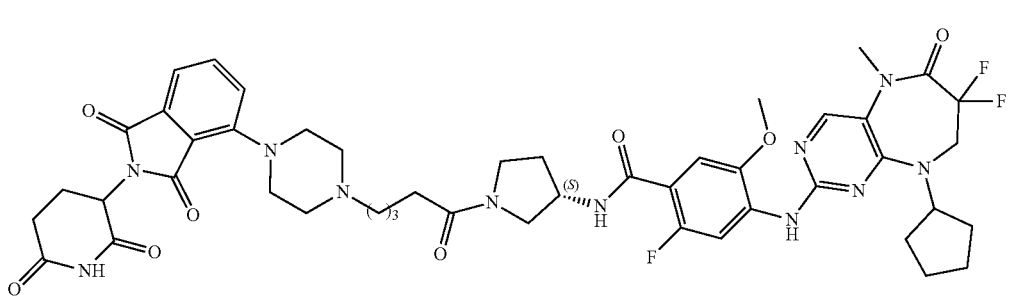 |

TABLE 1-continued

| Compound | Structure |
|---|---|
| 174 | 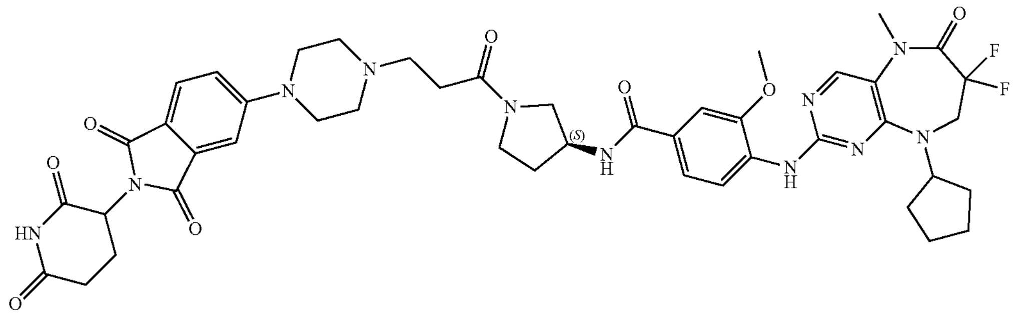 |
| 175 | 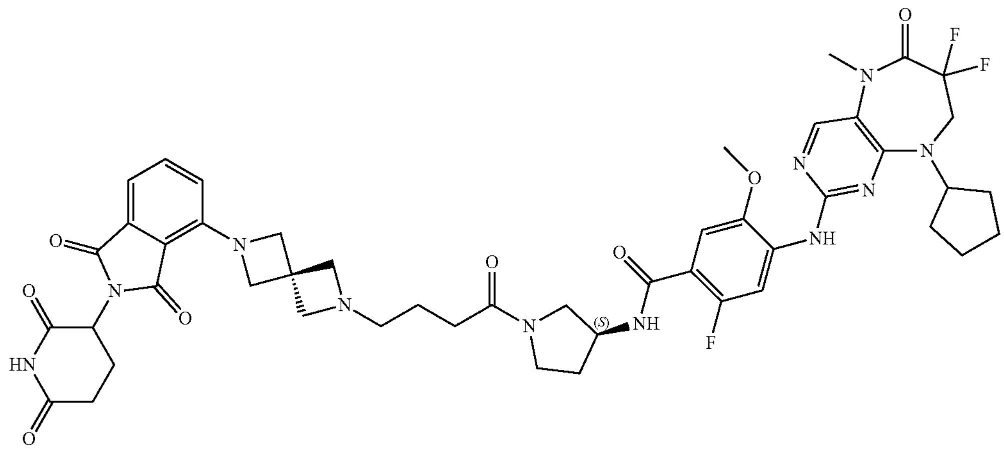 |

The compounds of the present invention were purified according to the following method and the structure was analyzed.

Instruments
LCMS: Shimadzu LCMS-2020
NMR: BRUKER AVANCE III 400 MHz
HPLC: Shimadzu LC-20AB, Shimadzu LC-20AD, Agilent 1100 LC, Agilent 1200 LC, Agilent 1290 LC LCSM Analysis LCMS data were recorded with Shimadzu LCMS-2020 equipped with an electron spray ionization device. 0.0375% TFA in water (solvent A) and 0.01875% TFA in acetonitrile (solvent B) were used as mobile phases. As a column, Kinetex EVO C18 (2.1*30) mm, 5 um was used.

HPLC Analysis

In HPLC analysis, Shimadzu LC-20AB, Shimadzu LC-20AD, Agilent 1100 LC, Agilent 1200 LC or Agilent 1290 LC was used. 0.0375% TFA in water (solvent A) and 0.01875% TFA in acetonitrile (solvent B) or 0.025% $NH_3 \cdot H_2O$ in water (solvent A) and acetonitrile (Solvent B) was used as the mobile phase. As a column, XBridge C18 (2.1*50) mm, 5 um or Kinetex C18 LC column (4.6*50) mm, 5 um or Eclipse plus C18 (4.6*150) mm, 3.5 um or Waters XBridge® C18 (4.6*150) mm, 3.5 μm was used.

NMR Analysis $^1$H NMR spectrum was recorded with Bruker AVANCE III 400 MHz/5 mm Probe (BBO).

Example 1. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(2-(2-((2-(2,6-dioxopiperidin-3-yl)-1,3-dioxoisoindolin-4-yl)amino)ethoxy)ethyl)piperidin-4-yl)-2-fluoro-5-methoxybenzamide

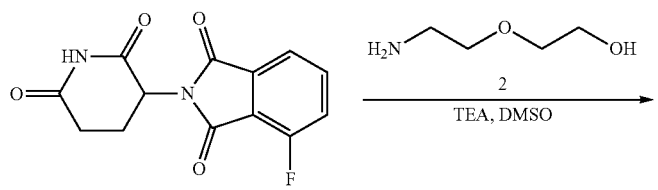

-continued
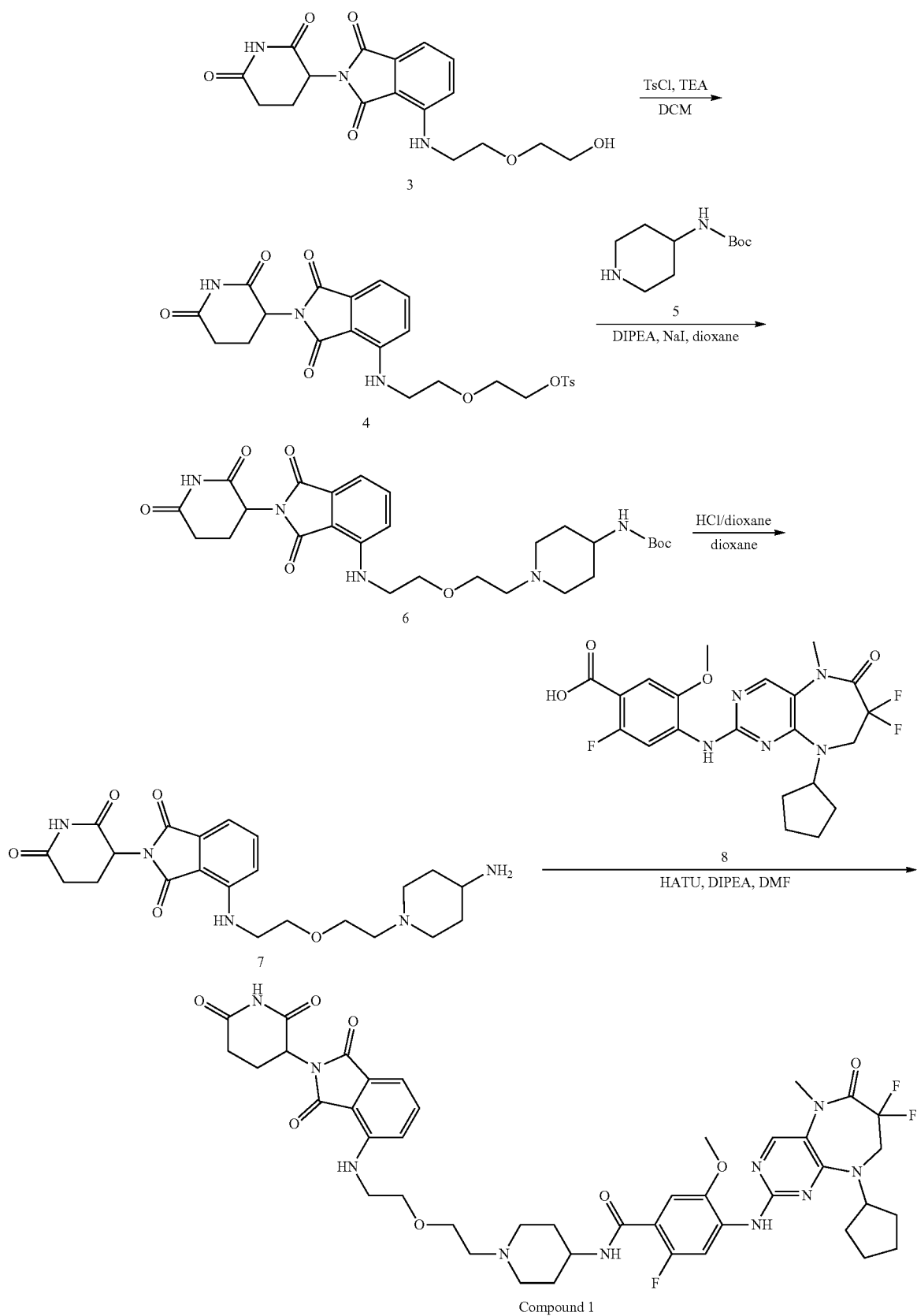
Compound 1

Step 1: Synthesis of 2-(2,6-dioxopiperidin-3-yl)-4-((2-(2-hydroxyethoxy)ethyl)amino)isoindoline-1,3-dione To a solution of 2-(2,6-dioxopiperidin-3-yl)-4-fluoroisoindoline-1,3-dione (4 g, 14.48 mmol) and 2-(2-aminoethoxy)ethanol (2.10 g, 19.97 mmol, 2 mL) in DMSO (60 mL) was added TEA (4.40 g, 43.44 mmol, 6.05 mL). The reaction mixture was stirred at 90° C. for 16 hr. LCMS showed one main peak with desired mass. The reaction mixture was diluted with $H_2O$ (200 mL) and extracted with EtOAc (150 mL×3). The combined organic layer was dried over $Na_2SO_4$, filtered. The filtrate was concentrated in vacuo to afford the titled compound (3.5 g, 9.69 mmol, 66.89% yield) as a green oil, which was used for the next step directly. $MS(M+H)^+=362.1$.

Step 2: Synthesis of 2-(2-((2-(2,6-dioxopiperidin-3-yl)-1,3-dioxoisoindolin-4-yl)amino)ethoxy)ethyl 4-methylbenzenesulfonate (4)

To a solution of 2-(2,6-dioxopiperidin-3-yl)-4-((2-(2-hydroxyethoxy)ethyl)amino) isoindoline-1,3-dione (3.5 g, 9.69 mmol) and TosCl (2.22 g, 11.62 mmol) in DCM (100 mL) was added TEA (2.94 g, 29.06 mmol, 4.04 mL). The mixture was stirred at 20° C. for 16 hr. LCMS showed a peak (55%) with desired mass. The reaction was concentrated in vacuo. The residue was purified by reverse MPLC (FA, MeCN/$H_2O$), the eluent was freeze-dried to afford the titled compound (1 g, 1.94 mmol, 20.03% yield) as a yellow solid. $MS(M+H)^+=516.1$.

Step 3: Synthesis of tert-butyl (1-(2-(2-((2-(2,6-dioxopiperidin-3-yl)-1,3-dioxoisoindolin-4-yl)amino) ethoxy)ethyl)piperidin-4-yl)carbamate (6)

To a solution of 2-(2-((2-(2,6-dioxopiperidin-3-yl)-1,3-dioxoisoindolin-4-yl)amino)ethoxy)ethyl 4-methylbenzenesulfonate (1 g, 1.94 mmol) and tert-butyl piperidin-4-ylcarbamate (582.73 mg, 2.91 mmol) in dioxane (15 mL) were added DIPEA (752.09 mg, 5.82 mmol, 1.01 mL) and NaI (29.08 mg, 193.97 µmol), the reaction mixture was stirred at 65° C. for 3 hr. LCMS showed 50% of material remained, the reaction mixture was stirred at 65° C. for another 16 hr. LCMS showed one main peak with desired mass. The reaction mixture was diluted with $H_2O$ (50 mL) and extracted with EtOAc (60 mL×2). The combined organic layer was dried over $Na_2SO_4$, filtered and concentrated in vacuo. The residue was purified by column chromatography ($SiO_2$, EA/MeOH=100%-8%), the eluent was concentrated in vacuo to afford the titled compound (600 mg, 1.09 mmol, 56.33% yield, 99% purity) as a yellow solid. $MS(M+H)^+=544.2$.

Step 4: Synthesis of 4-((2-(2-(4-aminopiperidin-1-yl)ethoxy)ethyl)amino)-2-(2,6-dioxopiperidin-3-yl) isoindoline-1,3-dione (7)

To a solution of tert-butyl (1-(2-(2-((2-(2,6-dioxopiperidin-3-yl)-1,3-dioxoisoindolin-4-yl)amino) ethoxy)ethyl)piperidin-4-yl)carbamate (600 mg, 1.10 mmol) in dioxane (5 mL) was added HCl/dioxane (4 M, 16.22 mL), the mixture was stirred at 20° C. for 3 hours. LCMS showed the starting material was consumed completely and one main peak (74%) with desired mass. The reaction mixture was concentrated in vacuo afford 4-((2-(2-(4-aminopiperidin-1-yl)ethoxy)ethyl)amino)-2-(2,6-dioxopiperidin-3-yl)isoindoline-1,3-dione (810 mg, crude, HCl salt) as a yellow solid. $MS(M+H)^+=444.2$.

Step 5: Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(2-(2-((2-(2,6-dioxopiperidin-3-yl)-1,3-dioxoisoindolin-4-yl)amino)ethoxy)ethyl)piperidin-4-yl)-2-fluoro-5-methoxybenzamide (Compound 1)

To a solution of 4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzoic acid (174.55 mg, 375.03 mol) in DMF (7 mL) were added HATU (356.50 mg, 937.59 µmol) and DIEA (403.92 mg, 3.13 mmol, 544.37 µL), the mixture was stirred at 20° C. for 2 hours. Then to this mixture was added 4-((2-(2-(4-aminopiperidin-1-yl)ethoxy)ethyl)amino)-2-(2,6-dioxopiperidin-3-yl)isoindoline-1,3-dione (300 mg, crude, HCl salt), the resulting mixture was stirred at 20° C. for 12 hours. LCMS showed the reactant was consumed completely and one main peak (85%) with desired mass. The reaction mixture was filtered and the filtrate was purified by prep-HPLC (column: Phenomenex luna $C_{18}$ 150*40 mm*15 um; mobile phase: [water (0.1% TFA)-ACN]; B %: 22%-52%, 10 min), the eluent was freeze-dried to afford the titled compound (237.5 mg, 224.52 µmol, 35.92% yield, 95% purity, TFA salt) as a yellow solid. $MS(M+H)^+=891.6$.

$^1H$ NMR (400 MHz, DMSO-$d_6$) δ=11.09-11.08 (m, 1H), 9.53-9.36 (m, 1H), 8.34-8.22 (m, 2H), 8.22-8.08 (m, 2H), 7.61 (dd, $J_1$=8.4 Hz, $J_2$=7.2 Hz, 1H), 7.25-7.13 (m, 2H), 7.10-7.01 (m, 1H), 6.63 (s, 1H), 5.08 (dd, $J_1$=12.8 Hz, $J_2$=5.4 Hz, 1H), 4.84 (t, J=8.1 Hz, 1H), 4.15-4.05 (m, 3H), 3.95-3.92 (m, 3H), 3.80 (s, 2H), 3.71-3.66 (m, 2H), 3.57-3.48 (m, 4H), 3.33 (s, 3H), 3.32-3.27 (m, 2H), 3.20-3.08 (m, 1H), 2.94-2.80 (m, 1H), 2.58-2.51 (m, 1H), 2.16-1.83 (m, 6H), 1.82-1.47 (m, 8H).

Example 2. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(2-(2-(2-((2-(2,6-dioxopiperidin-3-yl)-1,3-dioxoisoindolin-4-yl)amino)ethoxy)ethoxy)ethyl)piperidin-4-yl)-2-fluoro-5-methoxybenzamide

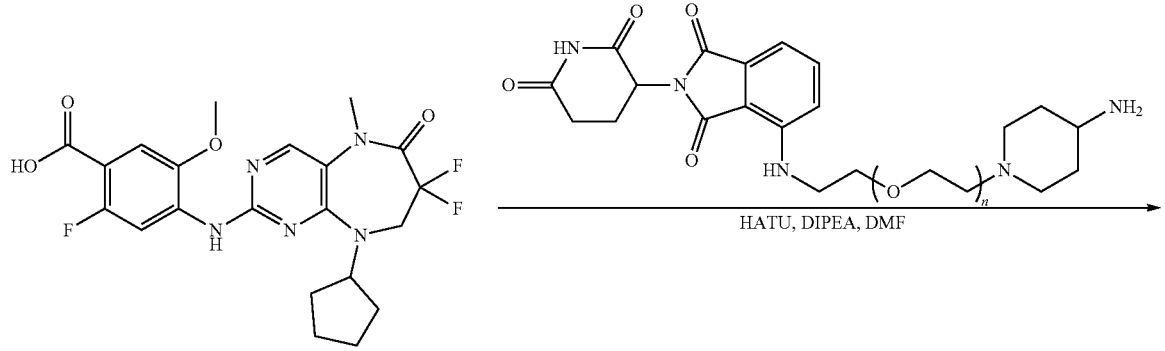

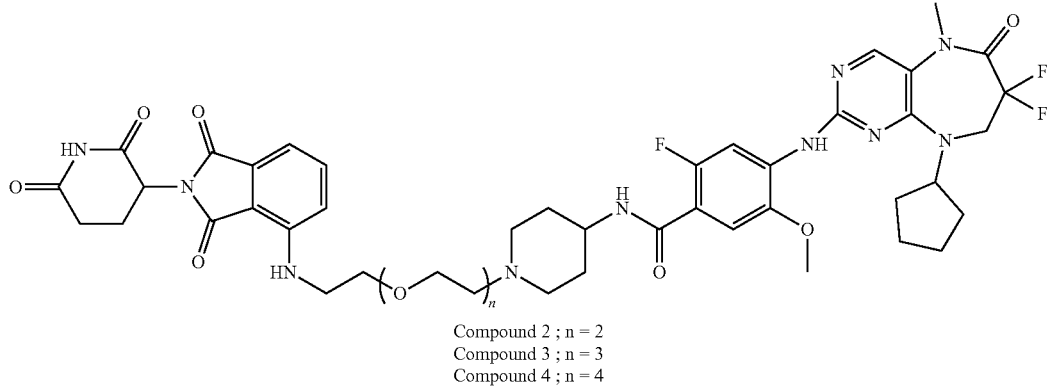

Compound 2 ; n = 2
Compound 3 ; n = 3
Compound 4 ; n = 4

According to the reaction scheme, in a manner similar to the above-described example, the titled compound (126.5 mg, 133.95 umol, 31.17% yield, 99% purity) as was obtained as a yellow solid.

MS (M+H)$^+$=935.5

$^1$H NMR (400 MHz, CDCl3) δ=9.15 (br s, 1H), 8.38 (d, J=14.6 Hz, 1H), 8.07 (s, 1H), 7.86 (s, 1H), 7.56-7.43 (m, 2H), 7.09 (d, J=7.0 Hz, 1H), 6.94 (d, J=8.8 Hz, 1H), 6.88-6.79 (m, 1H), 6.48-6.45 (m, 1H), 5.01-4.98 (m, 1H), 4.87 (t, J=8.6 Hz, 1H), 4.25 (br s, 1H), 4.04-3.87 (m, 7H), 3.77-3.69 (m, 6H), 3.49-3.46 (m, 2H), 3.42 (s, 3H), 3.40-325 (m, 2H), 3.09-3.06 (m, 2H), 2.93-2.71 (m, 3H), 2.30-2.02 (m, 6H), 1.85-1.77 (m, 3H), 1.70-1.56 (m, 6H).

Example 3. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(2-(2-(2-(2-((2-(2,6-dioxopiperidin-3-yl)-1,3-dioxoisoindolin-4-yl)amino)ethoxy)ethoxy)ethoxy)ethyl)piperidin-4-yl)-2-fluoro-5-methoxybenzamide In a manner similar to the other examples, the titled compound (112.5 mg, 113.76 umol, 26.47% yield, 99% purity) was obtained as a yellow solid.

MS (M+H)$^+$=979.4

$^1$H NMR (400 MHz, DMSO-d6) δ 11.11 (s, 1H), 8.30 (s, 1H), 8.24 (d, J=13.3 Hz, 1H), 8.03 (s, 1H), 7.87 (dd, J=7.6, 3.2 Hz, 1H), 7.61-7.55 (m, 1H), 7.17 (dd, J=21.8, 7.6 Hz, 2H), 7.04 (d, J=7.0 Hz, 1H), 6.61 (t, J=5.8 Hz, 1H), 5.06 (dd, J=12.9, 5.5 Hz, 1H), 4.81 (q, J=8.5 Hz, 1H), 4.08 (t, J=13.8 Hz, 2H), 3.91 (s, 3H), 3.75-3.68 (m, 1H), 3.63 (t, J=5.5 Hz, 2H), 3.59-3.56 (m, 2H), 3.55-3.53 (m, 2H), 3.52-3.50 (m, 2H), 3.49-3.46 (m, 6H), 3.31-3.26 (m, 2H), 2.94-2.79 (m, 3H), 2.66-2.51 (m, 3H), 2.43 (t, J=6.1 Hz, 2H), 2.07-2.00 (m, 3H), 2.00-1.93 (m, 2H), 1.81-1.69 (m, 4H), 1.67-1.57 (m, 4H), 1.56-1.46 (m, 2H).

Example 4. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(14-((2-(2,6-dioxopiperidin-3-yl)-1,3-dioxoisoindolin-4-yl)amino)-3,6,9,12-tetraoxatetradecyl)piperidin-4-yl)-2-fluoro-5-methoxybenzamide In a manner similar to the other examples, the titled compound (97.2 mg, 95.01 umol, 27.64% yield, 100% purity) was obtained as a yellow solid.

MS (M+H)$^+$=1023.5

$^1$H NMR (400 MHz, Chloroform-d) δ 9.08 (s, 1H), 8.33 (d, J=14.9 Hz, 1H), 8.05 (s, 1H), 7.84 (s, 1H), 7.55-7.37 (m, 2H), 7.06 (d, J=7.1 Hz, 1H), 6.96-6.77 (m, 2H), 6.51-6.40 (m, 1H), 5.02-4.78 (m, 2H), 4.34-4.09 (m, 1H), 3.98-3.85 (m, 5H), 3.82 (t, J=4.9 Hz, 2H), 3.78-3.59 (m, 17H), 3.53-3.42 (m, 3H), 3.40 (s, 3H), 3.37-3.17 (m, 2H), 3.12-3.01 (m, 1H), 2.90-2.65 (m, 3H), 2.26 (d, J=13.7 Hz, 1H), 2.18-2.01 (m, 5H), 1.79-1.69 (m, 4H), 1.65-1.50 (m, 2H).

Example 5. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(17-((2-(2,6-dioxopiperidin-3-yl)-1,3-dioxoisoindolin-4-yl)amino)-3,6,9,12,15-pentaoxaheptadecyl)piperidin-4-yl)-2-fluoro-5-methoxybenzamide

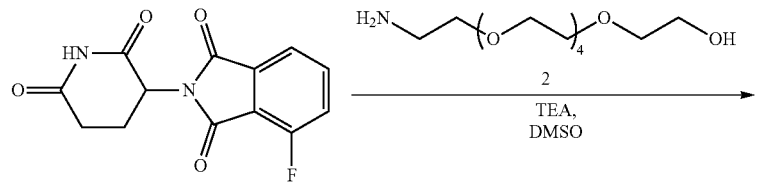

-continued
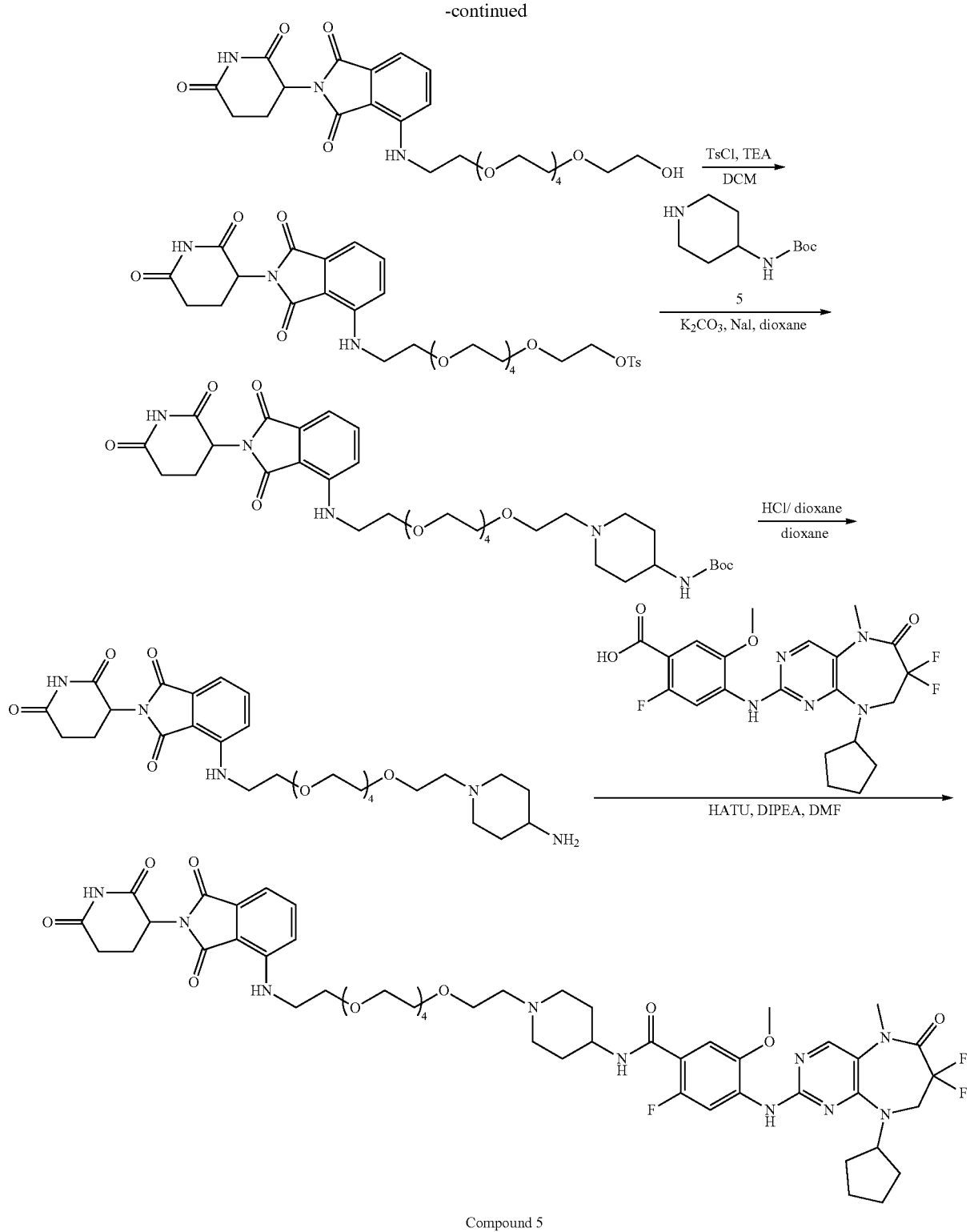
Compound 5
According to the above reaction scheme, in a manner similar to the other examples, obtained the titled compound (36.5 mg, 31.81 μmol, 13.77% yield, 93% purity) as yellow solid. MS(M+H)$^+$=1067.9
$^1$H NMR (400 MHz, DMSO-d$_6$) δ=11.07 (br s, 1H), 8.30 (s, 1H), 8.24 (d, J=13.3 Hz, 1H), 8.02 (s, 1H), 7.90-7.81 (m, 1H), 7.62-7.54 (m, 1H), 7.23-7.11 (m, 2H), 7.03 (d, J=7.1 Hz, 1H), 6.60 (br t, J=5.5 Hz, 1H), 5.10-4.99 (m, 1H), 4.88-4.75 (m, 1H), 4.07 (br t, J=13.8 Hz, 2H), 3.91 (s, 3H), 3.75-3.69 (m, 1H), 3.65-3.59 (m, 2H), 3.56-3.48 (m, 18H), 3.47-3.44 (m, 2H), 3.33-3.21 (m, 3H), 2.88-2.79 (m, 2H), 2.62-2.54 (m, 2H), 2.48-2.42 (m, 2H), 2.10-1.92 (m, 6H), 1.81-1.68 (m, 5H), 1.67-1.47 (m, 5H).

Example 6. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxy-N-(1-(2-(2-(2-((2-(1-methyl-2,6-dioxopiperidin-3-yl)-1,3-dioxoisoindolin-4-yl)amino)ethoxy)ethoxy)ethyl)piperidin-4-yl)benzamide
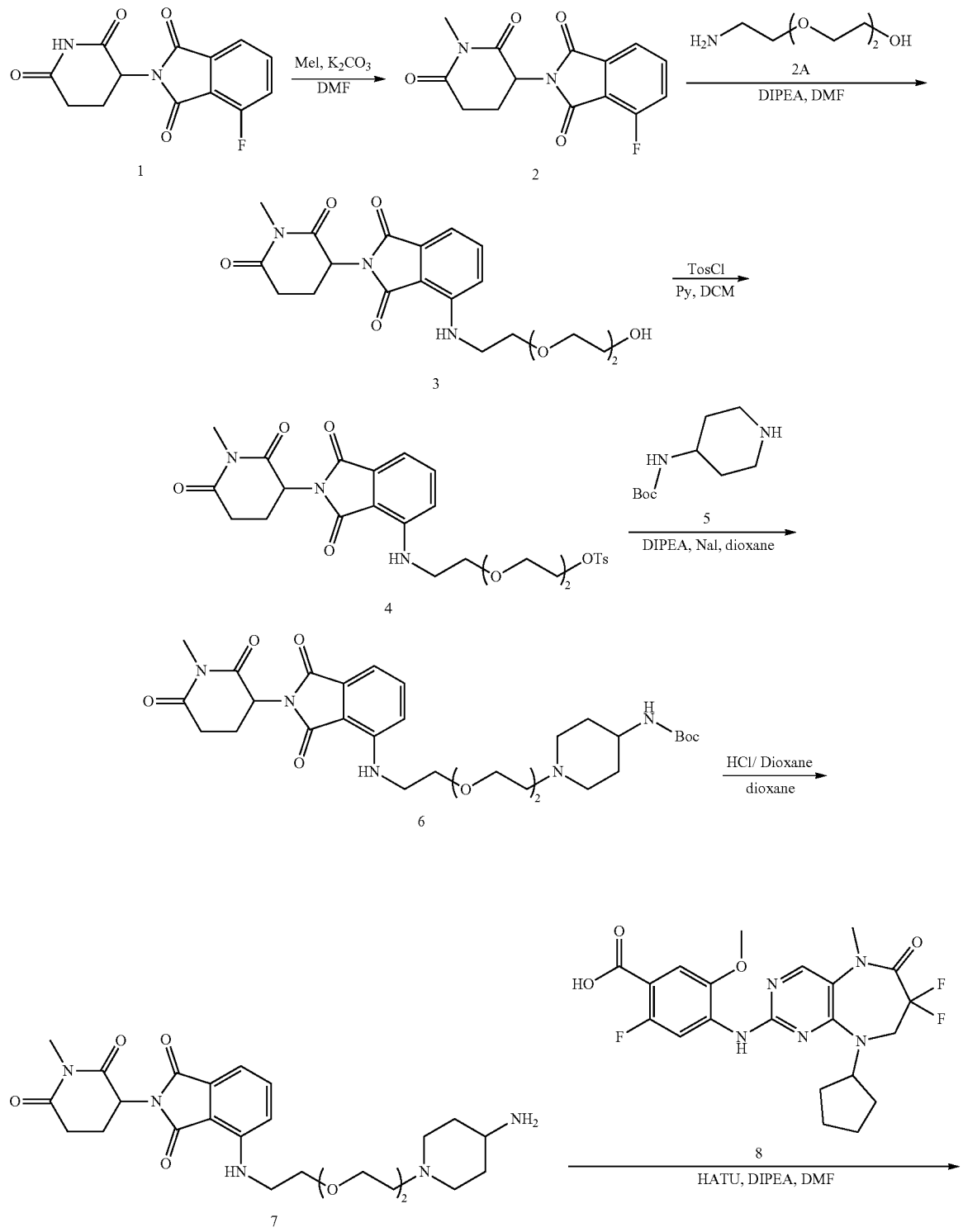

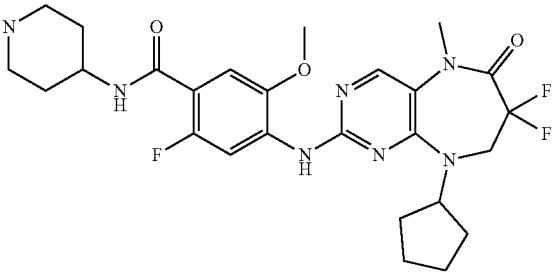

Compound 6

Step 1: Synthesis of 4-fluoro-2-(1-methyl-2,6-dioxopiperidin-3-yl)isoindoline-1,3-dione (2)

To a mixture of 2-(2,6-dioxopiperidin-3-yl)-4-fluoroisoindoline-1,3-dione (5 g, 18.10 mmol) and MeI (3.08 g, 21.72 mmol, 1.35 mL) in DMF (50 mL) was added $K_2CO_3$ (2.75 g, 19.91 mmol) and the resulting mixture was stirred at 25° C. for 14 h. LCMS showed the starting material was consumed and one main peak (89%) with desired mass. EtOAc (100 mL) and water (100 mL) were added and layers were separated. The aqueous phase was extracted with EtOAc (100 mL×2). Combined extracts were washed with brine (100 mL), dried over $Na_2SO_4$, filtered. The filtrate was concentrated under vacuum. The residue was purified by silica gel chromatography (Petroleum ether/Ethyl acetate=2/1 to 1/1) to afford the titled compound (2.5 g, 8.53 mmol, 47.11% yield, 99% purity) as a white solid. $MS(M+H)^+$=291.1

Step 2: Synthesis of 4-((2-(2-(2-hydroxyethoxy)ethoxy)ethyl)amino)-2-(1-methyl-2,6-dioxopiperidin-3-yl)isoindoline-1,3-dione (3)

To a solution of 4-fluoro-2-(1-methyl-2,6-dioxopiperidin-3-yl)isoindoline-1,3-dione (1 g, 3.42 mmol) in DMF (25 mL) were added 2-(2-(2-aminoethoxy)ethoxy)ethanol (510.46 mg, 3.42 mmol) and DIPEA (884.43 mg, 6.84 mmol, 1.19 mL) and the resulting mixture was heated to 90° C. for 16 hr. LCMS showed reactant was consumed completely and 37% of desired mass was detected. The mixture was combined with another batch (1 g scale). The combined mixture was diluted with $H_2O$ (80 mL) and extracted with EtOAc (80 mL×2). The combined organic layer was dried over $Na_2SO_4$, filtered and concentrated in vacuo. The residue was purified by column chromatography ($SiO_2$, PE/EtOAc~50%~100%) to afford the titled compound (1.45 g, 3.34 mmol, 97.54% yield, 97% purity) as a yellow oil. $MS(M+H)^+$=420.1

Step 3: Synthesis of 2-(2-(2-((2-(1-methyl-2,6-dioxopiperidin-3-yl)-1,3-dioxoisoindolin-4-yl)amino)ethoxy)ethoxy)ethyl 4-methylbenzenesulfonate (4)

To a solution of 4-((2-(2-(2-hydroxyethoxy)ethoxy)ethyl)amino)-2-(1-methyl-2,6-dioxopiperidin-3-yl)isoindoline-1,3-dione (1.45 g, 3.46 mmol, and TosCl (3.30 g, 17.29 mmol) in DCM (20 mL) was added Py (2.19 g, 27.66 mmol, 2.23 mL) and the resulting mixture was stirred at 15° C. for 16 hr. LCMS showed one peak (30%) with desired mass. The mixture was diluted with $H_2O$ (60 mL) and extracted with DCM (80 mL×2). The combined organic layer was dried over $Na_2SO_4$, filtered. The filtrate was concentrated in vacuo. The residue was purified by column chromatography ($SiO_2$, PE/EtOAc, 50%~100%) to afford the titled compound (1.64 g, 2.77 mmol, 80.22% yield, 97% purity) as a green oil.
$MS(M+H)^+$=574.1

Step 4: Synthesis of tert-butyl (1-(2-(2-(2-((2-(1-methyl-2,6-dioxopiperidin-3-yl)-1,3-dioxoisoindolin-4-yl)amino)ethoxy)ethoxy)ethyl)piperidin-4-yl)carbamate (6)

To a solution of 2-(2-(2-((2-(1-methyl-2,6-dioxopiperidin-3-yl)-1,3-dioxoisoindolin-4-yl)amino)ethoxy)ethoxy)ethyl 4-methylbenzenesulfonate (1.64 g, 2.86 mmol) and tert-butyl piperidin-4-ylcarbamate (1.15 g, 5.72 mmol) in dioxane (20 mL) were added DIPEA (1.11 g, 8.58 mmol, 1.49 mL) and NaI (42.86 mg, 285.91 umol) and the resulting mixture was heated to 80° C. for 16 hr. LCMS showed one main peak with desired mass. The mixture was diluted with $H_2O$ (50 mL) and extracted with EtOAc (50 mL×2). The combined organic layer was dried over $Na_2SO_4$ and filtered. The filtrate was concentrated in vacuo. The residue was purified by column chromatography ($SiO_2$, EtOAc (100%)~DCM/MeOH (10%)) to afford the titled compound (1.46 g, 2.38 mmol, 83.17% yield, 98% purity) as a green oil. $MS(M+H)^+$=602.3

Step 5: Synthesis of 4-((2-(2-(2-(4-aminopiperidin-1-yl)ethoxy)ethoxy)ethyl)amino)-2-(1-methyl-2,6-dioxopiperidin-3-yl)isoindoline-1,3-dione (7)

tert-butyl (1-(2-(2-(2-((2-(1-methyl-2,6-dioxopiperidin-3-yl)-1,3-dioxoisoindolin-4-yl)amino) ethoxy)ethoxy)ethyl) piperidin-4-yl)carbamate (1.46 g, 2.43 mmol, was dissolved in dioxane (10 mL), and HCl/dioxane (4 M, 10 mL) was added. The mixture was stirred at 15° C. for 16 hr. LCMS showed one main peak with desired mass. The mixture was concentrated in vacuo to afford the titled compound (1.4 g, crude, HCl salt) as a brown oil. $Ms(M+H)^+$=502.1

Step 6: Synthesis of 4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxy-N-(1-(2-(2-(2-((2-(1-methyl-2,6-dioxopiperidin-3-yl)-1,3-dioxoisoindolin-4-yl)amino)ethoxy)ethoxy)ethyl)piperidin-4-yl)benzamide (Compound 6)

To a solution of 4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzoic acid (300 mg, 644.57 umol, in DMF (6 mL) was added HATU (367.63 mg, 966.86 umol) and DIPEA (249.92 mg, 1.93 mmol, 336.82 uL), after stirring for 10 min, 4-((2-(2-(2-(4-aminopiperidin-1-yl)ethoxy)ethoxy)ethyl)amino)-2-(1-methyl-2,6-dioxopiperidin-3-yl)isoindoline-1,3-dione (416.16 mg, 773.49 umol, HCl salt) was added and the resulting mixture was stirred at 15° C. for 2 hr. LCMS showed one main peak with desired mass. The mixture was diluted with H₂O (30 mL) and extracted with EtOAc (30 mL×2). The combined organic layer was dried over Na₂SO₄, filtered. The filtrate was concentrated in vacuo. The residue was diluted with MeCN and purified by prep-HPLC (column: Phenomenex Luna C$_{18}$ 150*25 mm*10 um; mobile phase: [water (0.225% FA)-ACN]; B %: 25%-55%, 10 min) to afford two batches and the eluent was lyophilized to afford the titled compound (1st batch: 108 mg, 110.16 umol, 17.09% yield, 96.8% purity) as a yellow solid and the titled compound (2nd batch: 72 mg, 75.87 umol, 11.77% yield, FA salt, 100% purity) as a yellow solid. MS(M+H)⁺=949.2

¹H NMR (400 MHz, CDCl₃) δ=8.51 (s, 1H), 8.39 (d, J=15.1 Hz, 1H), 8.09 (s, 1H), 7.84 (s, 1H), 7.58-7.47 (m, 2H), 7.12 (d, J=6.9 Hz, 1H), 6.95 (d, J=8.5 Hz, 1H), 6.73 (br dd, J=7.7, 14.9 Hz, 1H), 6.50 (t, J=5.5 Hz, 1H), 5.01-4.82 (m, 2H), 4.15-4.05 (m, 1H), 4.02-3.88 (m, 5H), 3.78-3.73 (m, 4H), 3.71-3.65 (m, 4H), 3.50 (q, J=5.4 Hz, 2H), 3.44 (s, 3H), 3.25-3.15 (m, 5H), 3.02-2.96 (m, 1H), 2.88-2.76 (m, 4H), 2.55-2.47 (m, 2H), 2.19-2.05 (m, 5H), 1.87-1.72 (m, 6H), 1.69-1.56 (m, 2H).

Example 7. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxy-N-(1-(14-((2-(1-methyl-2,6-dioxopiperidin-3-yl)-1,3-dioxoisoindolin-4-yl)amino)-3,6,9,12-tetraoxatetradecyl)piperidin-4-yl)benzamide

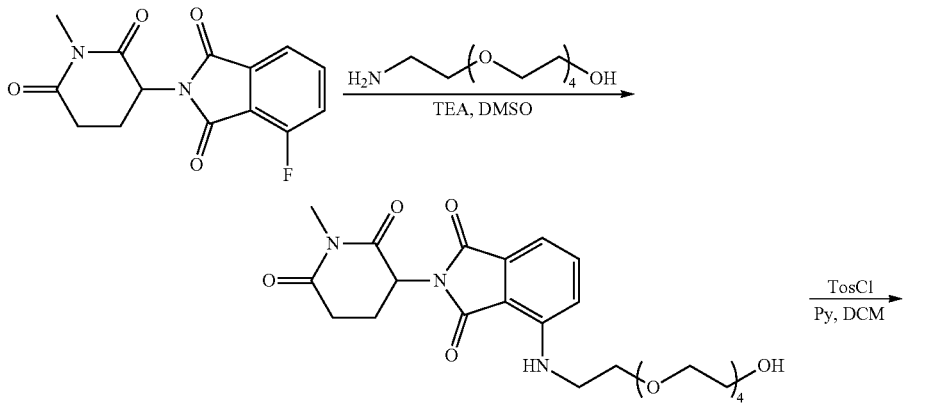

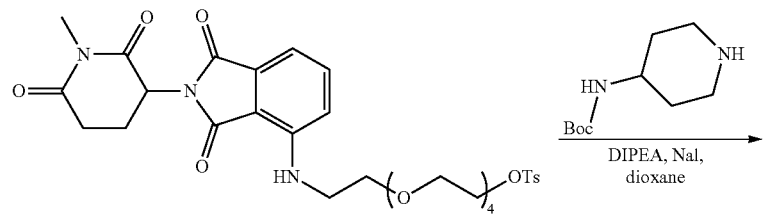

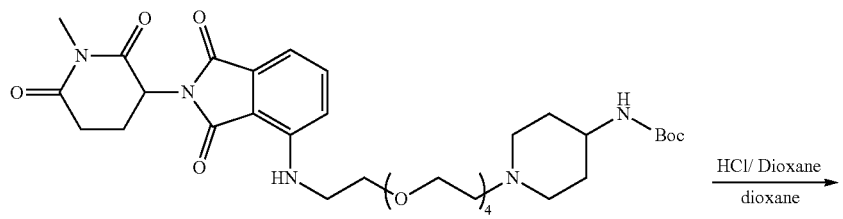

-continued

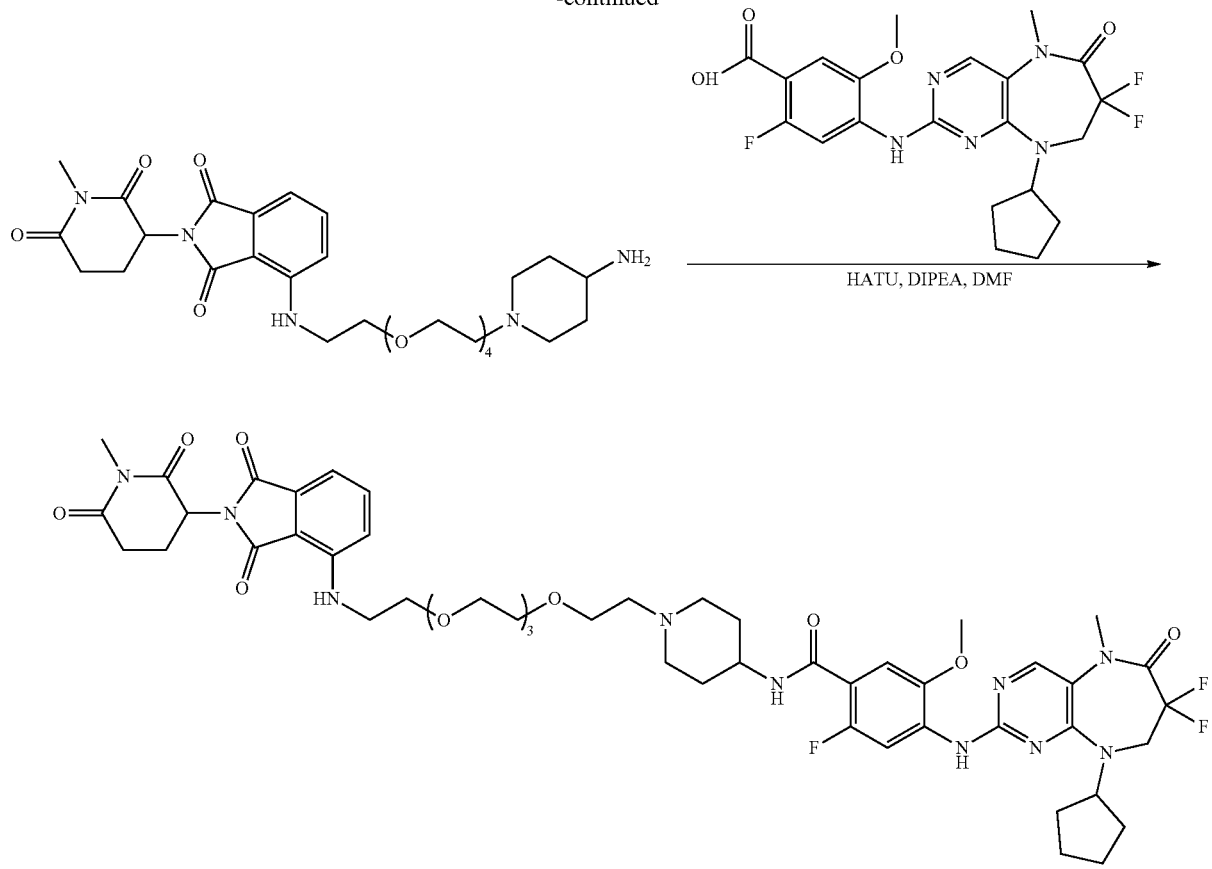

Compound 7

According to the above reaction scheme, in a manner similar to the other examples afforded two batches and lyophilized. As the first batch, the titled compound (103 mg, 92.36 umol, 14.33% yield, 93% purity) was obtained as a yellow solid. As the second batch, the titled compound (99 mg, 95.46 umol, 14.81% yield, 100% purity) was obtained as a yellow solid.

Ms (M+H)$^+$=1037.4

$^1$H NMR (400 MHz, Chloroform-d) δ 8.37 (d, J=15.0 Hz, 1H), 8.05 (s, 1H), 7.87-7.80 (m, 1H), 7.51-7.44 (m, 2H), 7.08 (d, J=7.0 Hz, 1H), 6.91 (d, J=8.5 Hz, 1H), 6.79 (dd, J=14.7, 7.7 Hz, 1H), 6.46 (t, J=5.7 Hz, 1H), 5.00-4.80 (m, 2H), 4.29-4.16 (m, 1H), 4.00-3.87 (m, 7H), 3.71 (t, J=5.4 Hz, 2H), 3.67-3.53 (m, 14H), 3.46 (q, J=5.5 Hz, 2H), 3.41 (s, 3H), 3.19 (s, 3H), 3.18-3.12 (m, 2H), 3.00-2.88 (m, 3H), 2.82-2.70 (m, 2H), 2.28-2.16 (m, 4H), 2.16-2.04 (m, 3H), 1.84-1.71 (m, 4H), 1.67-1.51 (m, 2H).

Example 8. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(4-((2-(2,6-dioxopiperidin-3-yl)-1,3-dioxoisoindolin-4-yl)amino)butyl)piperidin-4-yl)-2-fluoro-5-methoxybenzamide

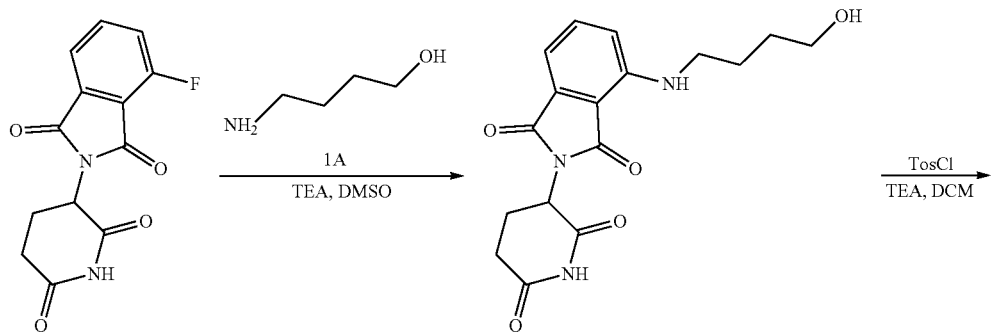

-continued
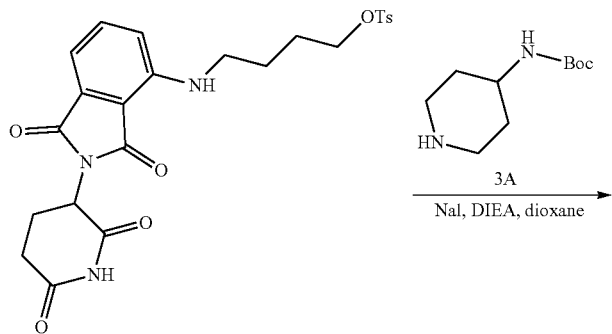
3
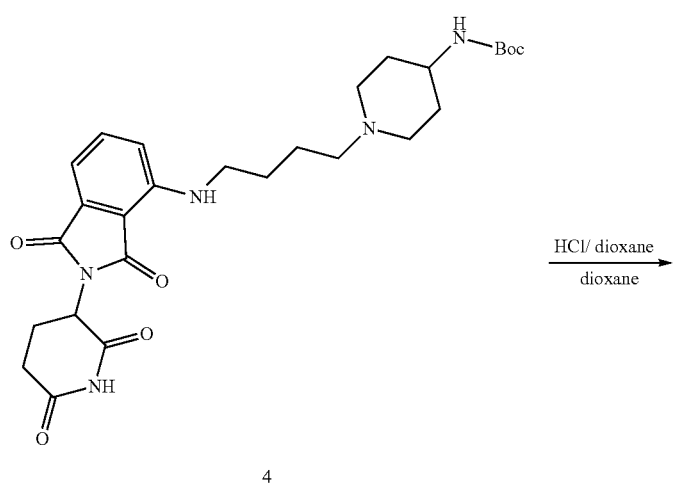
4
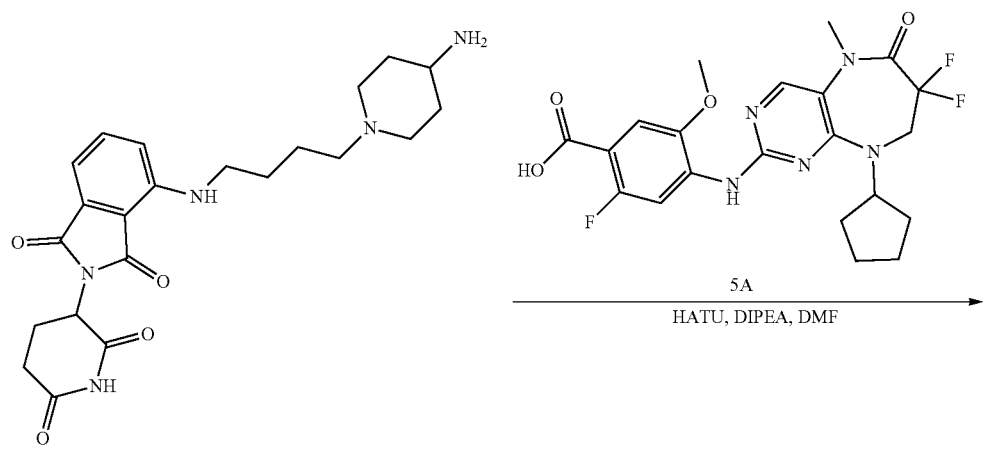
5
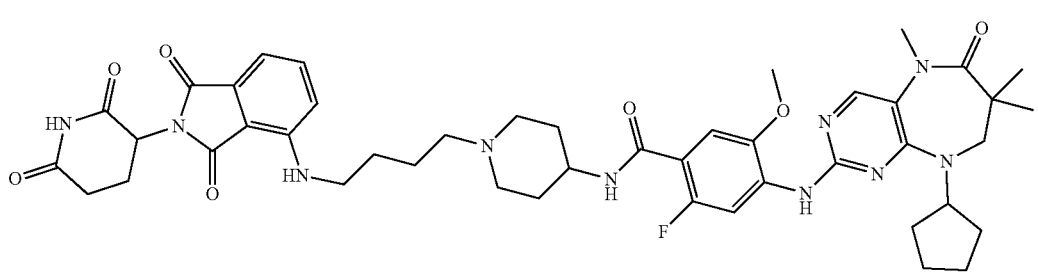
Compound 8

According to the above reaction scheme, in a manner similar to the other examples, obtained the titled compound (234.1 mg, 244.03 μmol, 37.74% yield, 96% purity, FA salt) as a yellow solid. MS(M+H)$^+$=875.7.

$^1$H NMR (400 MHz, DMSO-d$_6$) δ=11.10 (s, 1H), 8.36-8.20 (m, 2H), 8.14 (s, 1H), 8.10-7.97 (m, 2H), 7.60 (dd, J$_1$=8.3 Hz, J$_2$=7.4 Hz, 1H), 7.23-7.08 (m, 2H), 7.04 (d, J=7.0 Hz, 1H), 6.61 (t, J=5.8 Hz, 1H), 5.05 (dd, J$_1$=12.8 Hz, J$_2$=5.3 Hz, 1H), 4.86-4.82 (m, 1H), 4.08 (t, J=13.9 Hz, 2H), 3.96-3.87 (m, 4H), 3.23-3.02 (m, 6H), 2.90-2.83 (m, 1H), 2.78-2.70 (m, 2H), 2.69-2.41 (m, 4H), 2.06-1.88 (m, 5H), 1.86-1.39 (m, 13H).

Example 9. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(5-((2-(2,6-dioxopiperidin-3-yl)-1,3-dioxoisoindolin-4-yl)amino)pentyl)piperidin-4-yl)-2-fluoro-5-methoxybenzamide

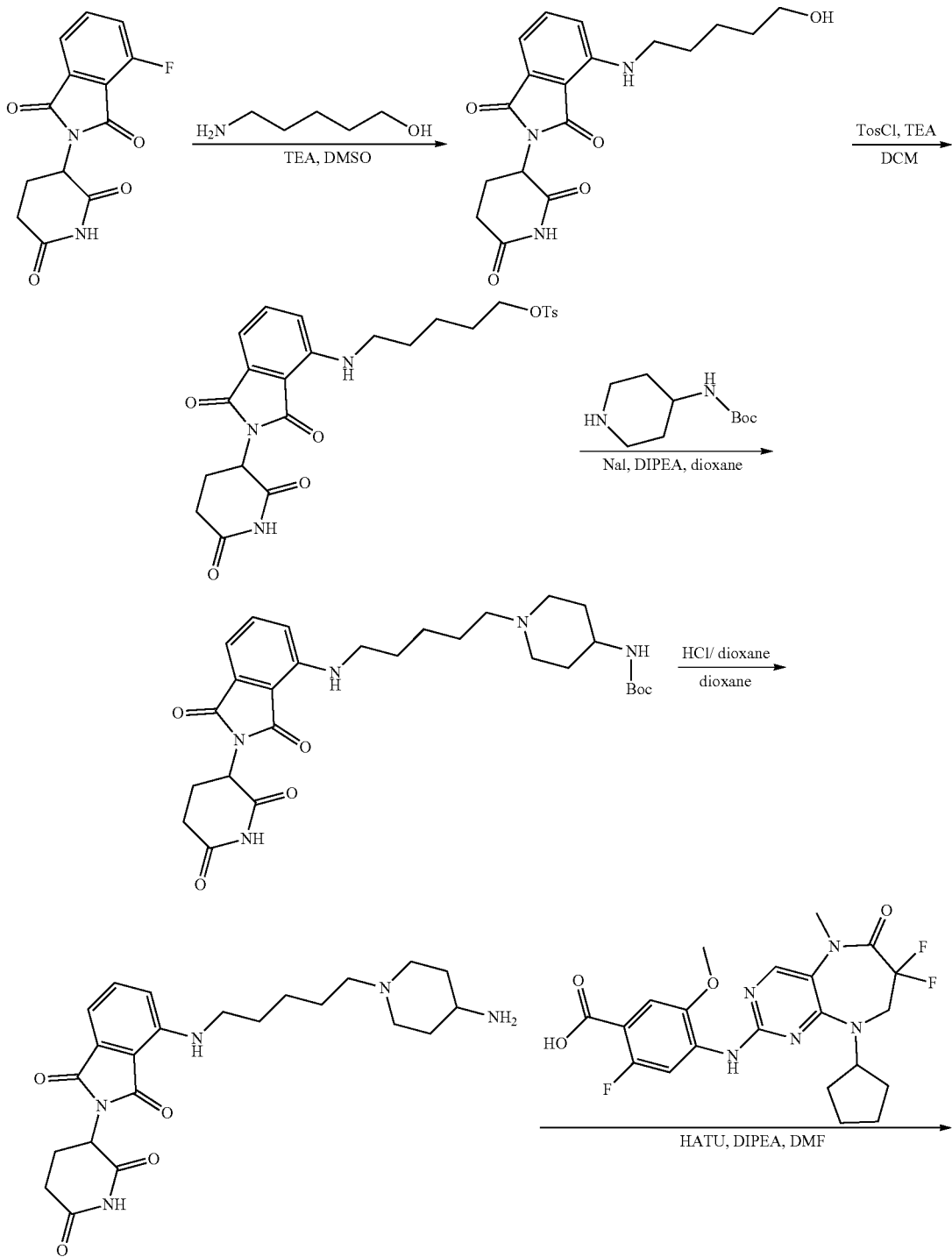

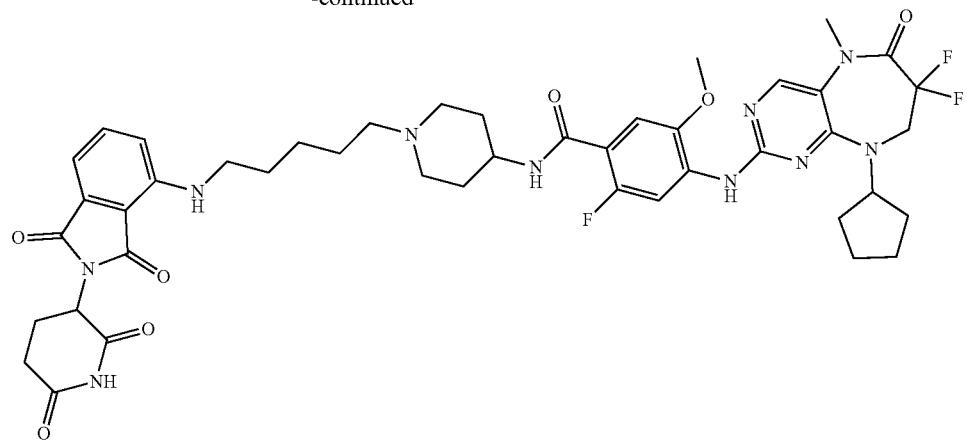

Compound 9

According to the above reaction scheme, in a manner similar to the other examples, obtained the titled compound (224.8 mg, 230.13 mol, 42.84% yield, 91% purity, FA salt) as a yellow solid. MS(M+H)$^+$=889.3

$^1$H NMR (400 MHz, DMSO-d$_6$) δ=11.09 (s, 1H), 8.29 (s, 1H), 8.26 (s, 1H), 8.21 (d, J=10.4 Hz, 1H), 8.03 (s, 1H), 7.88 (dd, J=3.2, 7.2 Hz, 1H), 7.58 (dd, J=7.2, 8.4 Hz, 1H), 7.19 (d, J=6.6 Hz, 1H), 7.10 (d, J=8.8 Hz, 1H), 7.02 (d, J=7.0 Hz, 1H), 6.53 (t, J=5.8 Hz, 1H), 5.04 (dd, J=5.4, 12.8 Hz, 1H), 4.86-4.76 (m, 1H), 4.12-4.02 (m, 2H), 3.91 (s, 3H), 3.81-3.67 (m, 2H), 3.33 (s, 3H), 2.93-2.82 (m, 3H), 2.63-2.52 (m, 3H), 2.34-2.27 (m, 2H), 2.07-1.91 (m, 5H), 1.83-1.68 (m, 4H), 1.66-1.43 (m, 10H), 1.40-1.29 (m, 2H).

Example 10. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(6-((2-(2,6-dioxopiperidin-3-yl)-1,3-dioxoisoindolin-4-yl)amino)hexyl)piperidin-4-yl)-2-fluoro-5-methoxybenzamide

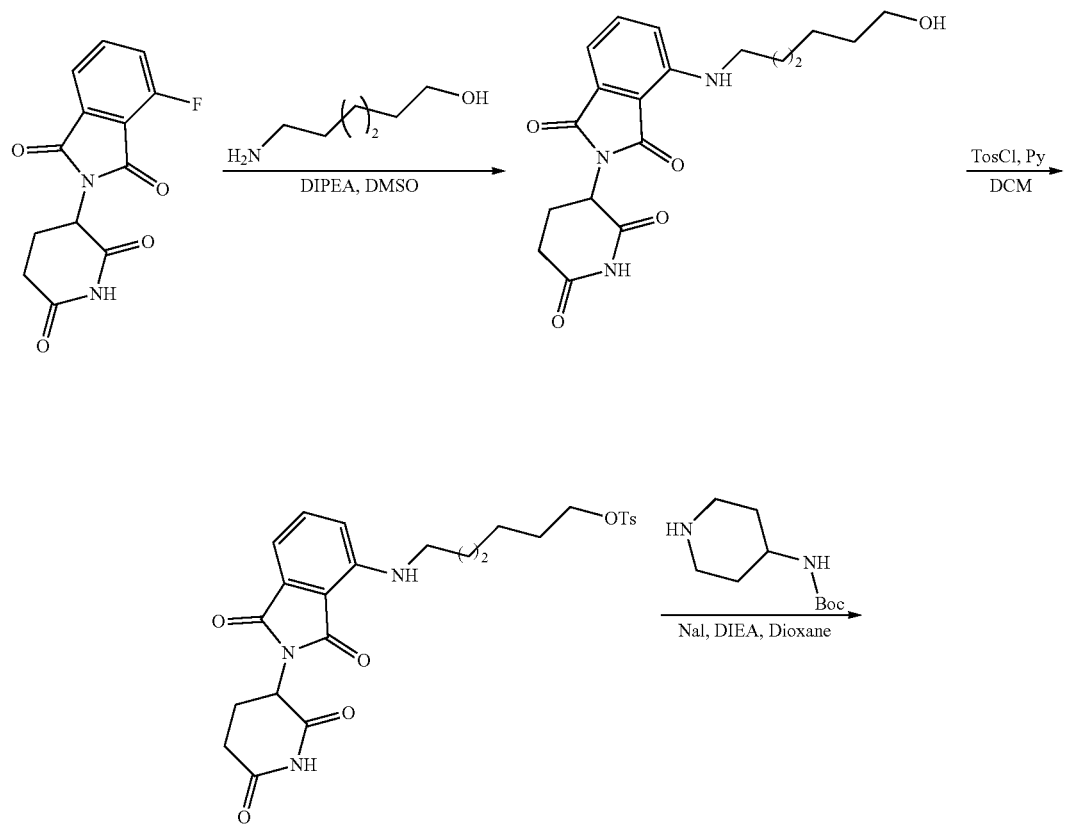

-continued
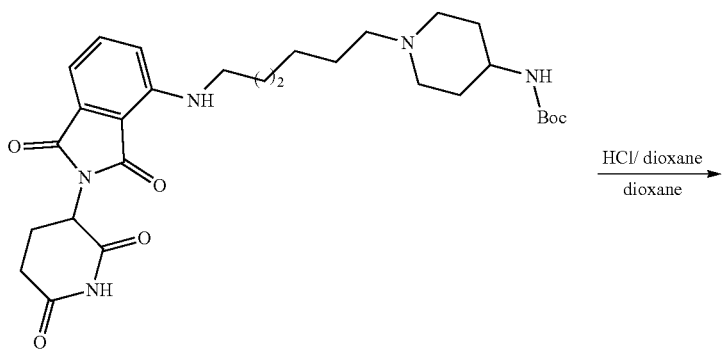
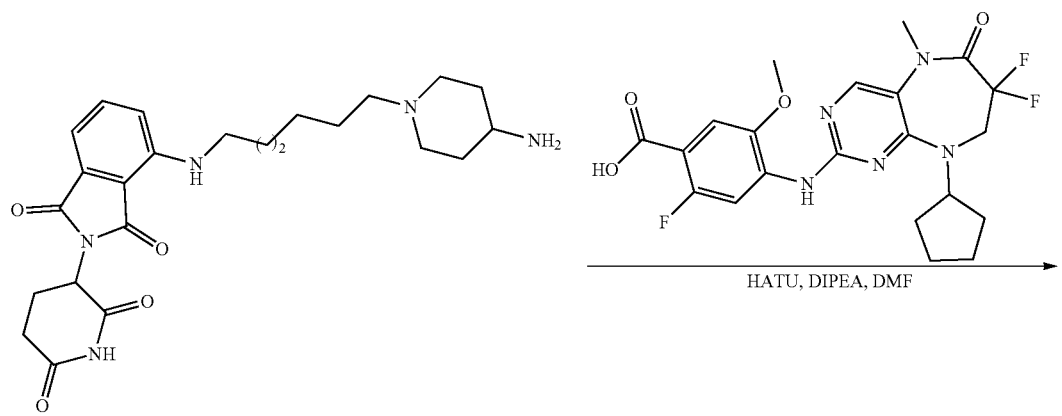
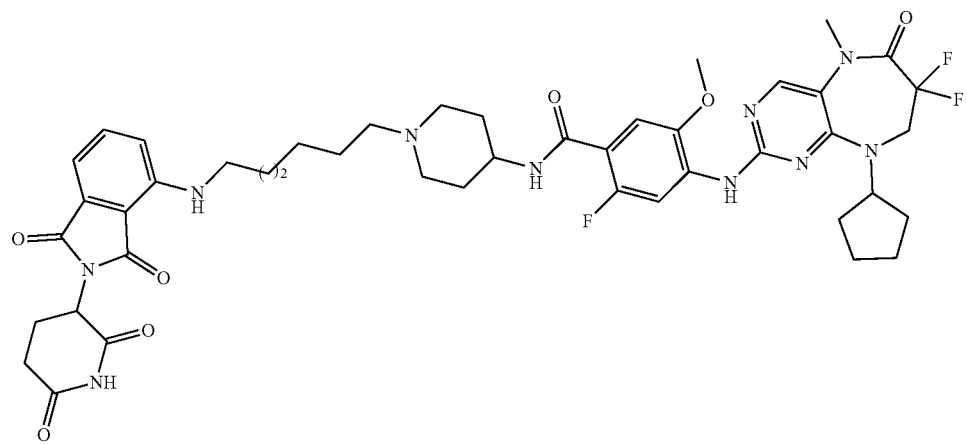
Compound 10
According to the above reaction scheme, in a manner similar to the other examples, obtained the titled compound (23.2 mg, 23.89 umol, 28.13% yield, 93% purity) as a yellow solid. MS(M+H)$^+$=903.7
$^1$H NMR (400 MHz, CDCl$_3$) δ=9.21-8.79 (m, 1H), 8.38 (d, J=15.2 Hz, 1H), 8.07 (s, 1H), 7.86 (s, 1H), 7.55-7.47 (m, 2H), 7.11 (d, J=7.1 Hz, 1H), 6.94-6.81 (m, 2H), 6.20 (br t, J=5.5 Hz, 1H), 4.97-4.90 (m, 1H), 4.89-4.82 (m, 1H), 4.40-4.18 (m, 1H), 3.97 (s, 3H), 3.92 (m, 2H), 3.63-3.49 (m, 2H), 3.42 (s, 3H), 3.30 (q, J=5.6 Hz, 2H), 3.04-2.68 (m, 8H), 2.16-2.11 (m, 5H), 1.88-1.72 (m, 7H), 1.71-1.64 (m, 2H), 1.60 (m, 2H), 1.51-1.40 (m, 4H).

Example 11. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(7-((2-(2,6-dioxopiperidin-3-yl)-1,3-dioxoisoindolin-4-yl)amino)heptyl)piperidin-4-yl)-2-fluoro-5-methoxybenzamide
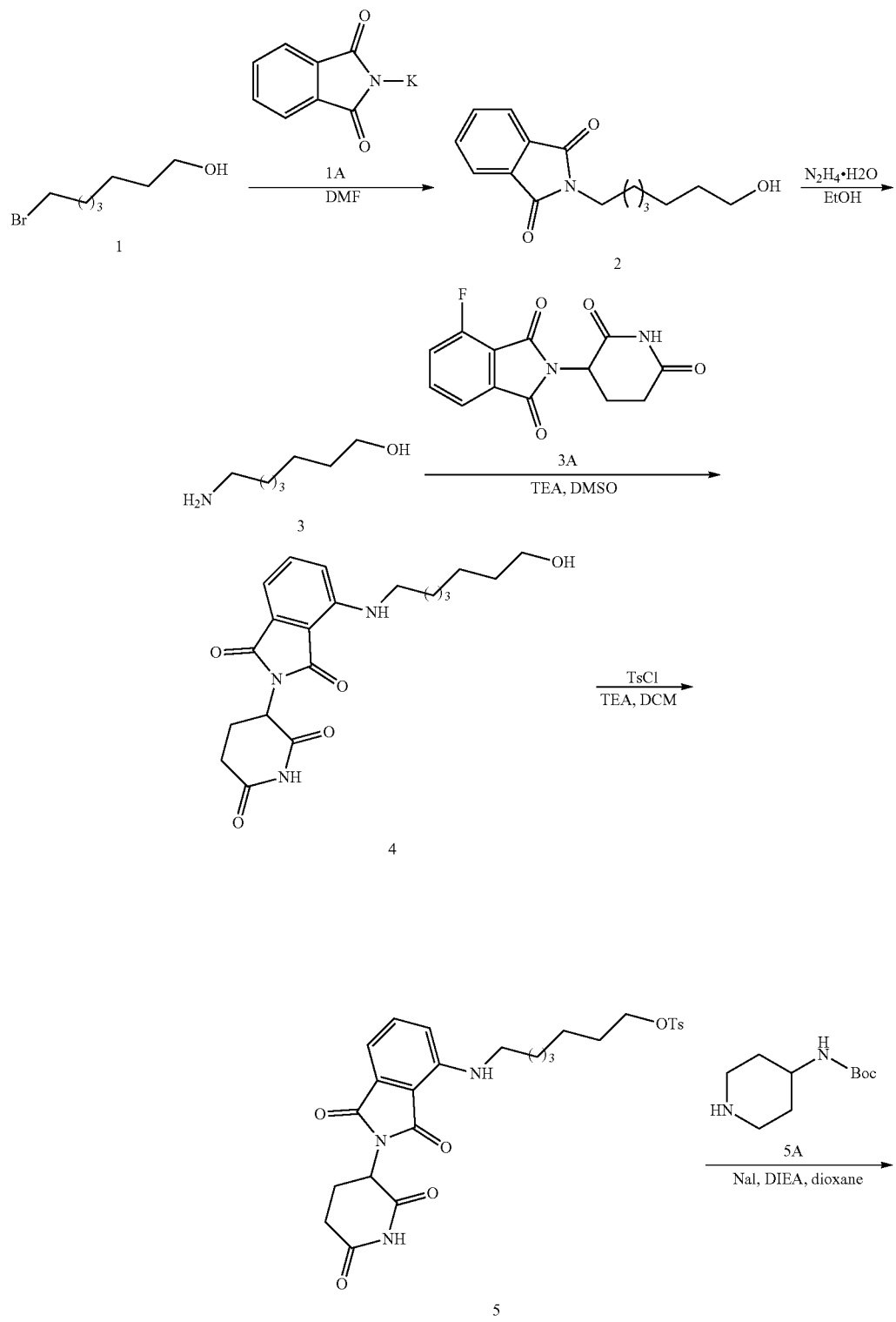

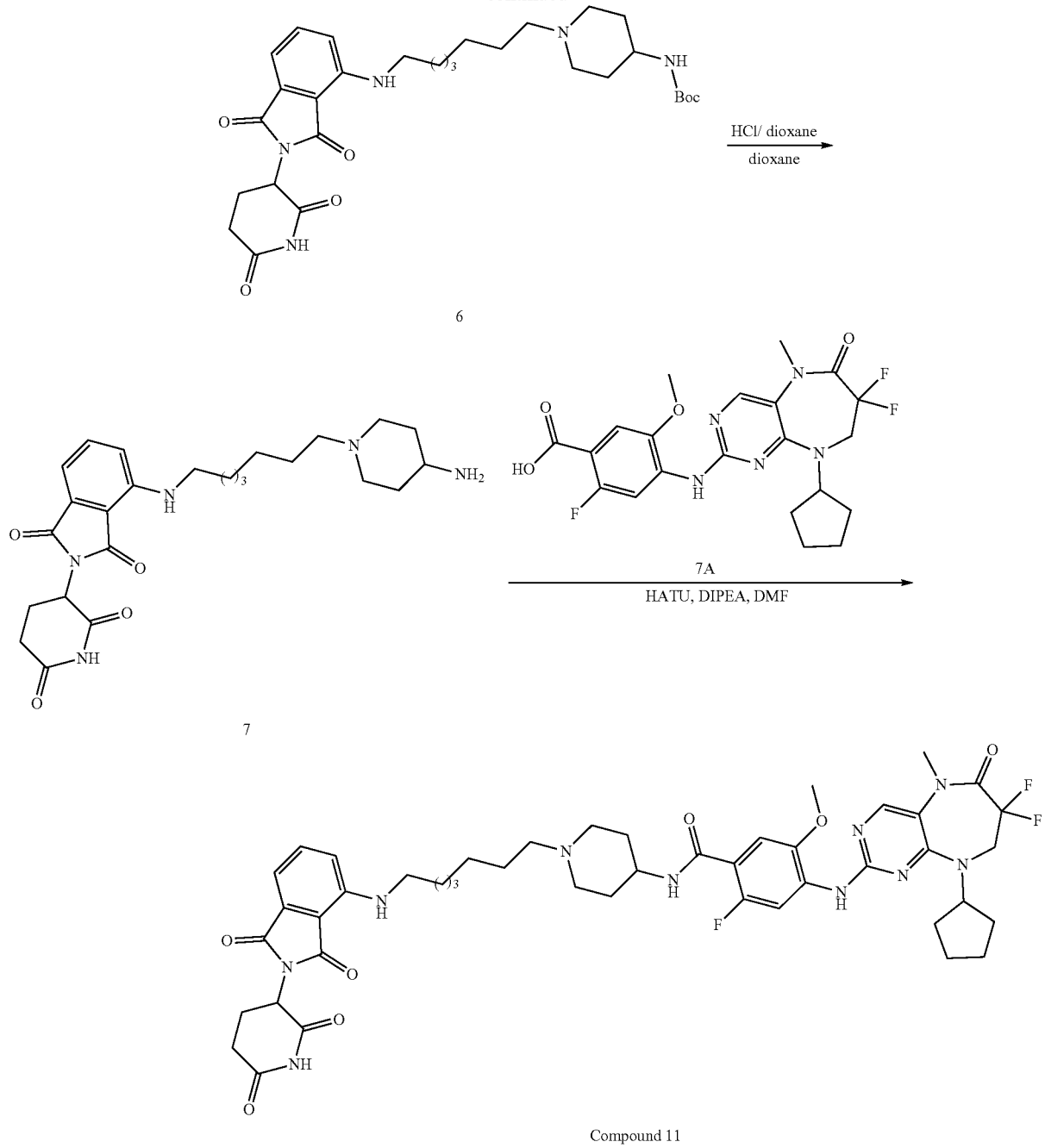

Compound 11

Step 1: Synthesis of 2-(7-hydroxyheptyl)isoindoline-1,3-dione (2)

A mixture of 7-bromoheptan-1-ol (5 g, 25.63 mmol) and potassium 1,3-dioxoisoindolin-2-ide (7.12 g, 38.44 mmol) in DMF (20 mL) was stirred at 85° C. for 16 hours. LCMS showed no reactant and 64% of desired mass was detected. The reaction mixture was diluted with H₂O (150 mL) and extracted with EtOAc (100 mL×3). The combined organic layers were washed with brine (200 mL×5), dried over Na₂SO₄, filtered and concentrated in vacuo. The residue was purified by silica gel chromatography (SiO₂, Petroleum ether/Ethyl acetate=10/1 to 5/1) to afford 2-(7-hydroxyheptyl)isoindoline-1,3-dione (6.4 g, 24.49 mmol, 95.56% yield) as a white solid. MS(M+H)⁺=262.0.

Step 2: Synthesis of 7-aminoheptan-1-ol (3)

To a solution of 2-(7-hydroxyheptyl)isoindoline-1,3-dione (6.4 g, 24.49 mmol) in EtOH (120 mL) was added N₂H₄·H₂O (14.42 g, 244.91 mmol, 14.00 mL, 85% purity in H₂O), the mixture was stirred at 80° C. for 4 hours. TLC (EtOAc:MeOH=10:1) indicated the starting material was consumed completely, and one major new spot with larger polarity was detected. The reaction mixture was concentrated in vacuo to remove most of the solvent, the residue was diluted with DCM (50 mL) and filtered, the filtrate was concentrated in vacuo. The residue was purified by flash silica gel chromatography (20 g SepaFlash® Silica Flash Column, Eluent of 0~14% MeOH/Ethyl acetate gradient @ 100 mL/min) to afford 7-aminoheptan-1-ol (1.3 g, 9.91 mmol, 40.45% yield) as a light yellow oil.

$^1$H NMR (400 MHz, DMSO-$d_6$) δ=3.43-3.30 (m, 4H), 1.54-1.37 (m, 2H), 1.37-1.30 (m, 2H), 1.30-1.18 (m, 6H).

Step 3: Synthesis of 2-(2,6-dioxopiperidin-3-yl)-4-((7-hydroxyheptyl)amino)isoindoline-1,3-dione (4)

A mixture of 2-(2,6-dioxopiperidin-3-yl)-4-fluoroisoindoline-1,3-dione (2.3 g, 8.33 mmol), 7-aminoheptan-1-ol (1.20 g, 9.16 mmol) and TEA (2.53 g, 24.98 mmol, 3.48 mL) in DMSO (20 mL) was stirred at 85° C. for 16 hours under $N_2$ atmosphere. LCMS showed reactant was consumed completely and 61% of desired mass was detected. The reaction mixture was diluted with $H_2O$ (200 mL) and extracted with EtOAc (200 mL×3). The combined organic layers were washed with brine (400 mL×5), dried over $Na_2SO_4$, filtered and concentrated in vacuo. The residue was purified by flash silica gel chromatography (40 g SepaFlash® Silica Flash Column, Eluent of 50~65% Ethyl acetate/Petroleum ether gradient @ 80 mL/min) to afford 2-(2,6-dioxopiperidin-3-yl)-4-((7-hydroxyheptyl)amino)isoindoline-1,3-dione (1.74 g, 4.49 mmol, 53.94% yield) as a green oil. MS(M+H)$^+$=388.2.

Step 4: Synthesis of 7-((2-(2,6-dioxopiperidin-3-yl)-1,3-dioxoisoindolin-4-yl)amino)heptyl 4-methylbenzenesulfonate (5)

To a solution of 2-(2,6-dioxopiperidin-3-yl)-4-((7-hydroxyheptyl)amino)isoindoline-1,3-dione (1.74 g, 4.49 mmol) in DCM (25 mL) were added TEA (1.82 g, 17.96 mmol, 2.50 mL) and TosCl (1.71 g, 8.98 mmol), the mixture was stirred at 20° C. for 16 hours. LCMS showed trace of the starting material remained and 69% of desired mass was detected. The reaction mixture was concentrated in vacuo. The residue was purified by flash silica gel chromatography (40 g SepaFlash® Silica Flash Column, Eluent of 50~70% Ethyl acetate/Petroleum ether gradient @ 100 mL/min) to afford 7-((2-(2,6-dioxopiperidin-3-yl)-1,3-dioxoisoindolin-4-yl)amino)heptyl 4-methylbenzenesulfonate (1.64 g, 3.03 mmol, 67.42% yield) as a yellow oil. MS(M+H)$^+$=542.2.

$^1$H NMR (400 MHz, DMSO-$d_6$) δ=11.09 (s, 1H), 7.77 (d, J=8.3 Hz, 2H), 7.58 (dd, J=7.2 Hz, J=8.5 Hz, 1H), 7.47 (d, J=8.1 Hz, 2H), 7.07 (d, J=8.6 Hz, 1H), 7.02 (d, J=7.0 Hz, 1H), 6.51 (t, J=5.9 Hz, 1H), 5.05 (dd, J=5.4 Hz, J=12.8 Hz, 1H), 4.02-3.96 (m, 2H), 3.25 (q, J=6.7 Hz, 2H), 2.94-2.82 (m, 1H), 2.68-2.51 (m, 2H), 2.40 (s, 3H), 2.07-1.99 (m, 1H), 1.60-1.44 (m, 4H), 1.32-1.19 (m, 6H).

Step 5: Synthesis of tert-butyl (1-(7-((2-(2,6-dioxopiperidin-3-yl)-1,3-dioxoisoindolin-4-yl)amino)heptyl)piperidin-4-yl)carbamate (6)

To a solution of 7-((2-(2,6-dioxopiperidin-3-yl)-1,3-dioxoisoindolin-4-yl)amino)heptyl 4-methylbenzenesulfonate (1.64 g, 3.03 mmol), tert-butyl piperidin-4-ylcarbamate (909.66 mg, 4.54 mmol) and DIEA (978.36 mg, 7.57 mmol, 1.32 mL) in dioxane (20 mL) was added NaI (45.39 mg, 302.80 μmol), the mixture was stirred at 60° C. for 16 hours. LCMS showed the starting material was consumed completely and 96% of desired mass was detected. The reaction mixture was concentrated in vacuo. The residue was purified by flash silica gel chromatography (40 g SepaFlash® Silica Flash Column, Eluent of 60~100% Ethyl acetate/Petroleum ether gradient @ 100 mL/min) to afford tert-butyl (1-(7-((2-(2,6-dioxopiperidin-3-yl)-1,3-dioxoisoindolin-4-yl)amino)heptyl)piperidin-4-yl)carbamate (1.21 g, 2.12 mmol, 70.14% yield) as a yellow solid. MS(M+H)$^+$=570.6.

Step 6: Synthesis of 4-((7-(4-aminopiperidin-1-yl)heptyl)amino)-2-(2,6-dioxopiperidin-3-yl)isoindoline-1,3-dione (7)

To solution of tert-butyl (1-(7-((2-(2,6-dioxopiperidin-3-yl)-1,3-dioxoisoindolin-4-yl)amino)heptyl)piperidin-4-yl)carbamate (1.21 g, 2.12 mmol) in dioxane (10 mL) was added HCl/dioxane (4 M, 20 mL), the mixture was stirred at 20° C. for 3 hours. LCMS showed the starting material was consumed completely. The reaction mixture was concentrated in vacuo to afford 4-((7-(4-aminopiperidin-1-yl)heptyl)amino)-2-(2,6-dioxopiperidin-3-yl)isoindoline-1,3-dione (1.52 g, HCl salt, crude) as a yellow solid, which was used for the next step directly. MS(M+H)$^+$=470.4.

Step 7: Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(7-((2-(2,6-dioxopiperidin-3-yl)-1,3-dioxoisoindolin-4-yl)amino)heptyl)piperidin-4-yl)-2-fluoro-5-methoxybenzamide (Compound 11)

To a solution of 4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzoic acid (252.93 mg, 543.44 μmol) in DMF (8 mL) were added HATU (563.54 mg, 1.48 mmol) and DIEA (766.21 mg, 5.93 mmol, 1.03 mL), the mixture was stirred at 20° C. for 15 minutes, to this mixture was added 4-((7-(4-aminopiperidin-1-yl)heptyl)amino)-2-(2,6-dioxopiperidin-3-yl)isoindoline-1,3-dione (500 mg, 988.07 μmol, HCl salt), the resulting mixture was stirred at 20° C. for 2 hours. LCMS showed trace of reactant remained and 68% of desired mass was detected. The reaction mixture was filtered and the filtrate was purified by prep-HPLC (column: Phenomenex luna $C_{18}$ 150*40 mm*15 um; mobile phase: [water(0.1% TFA)-ACN]; B %: 26%-56%, 10 min) followed by prep-HPLC (column: Phenomenex luna $C_{18}$ 150*40 mm*15 um; mobile phase: [water (0.1% TFA)-ACN]; B %: 27%-57%, 10 min), the eluent was freeze-dried to afford the titled compound (181.6 mg, 169.09 μmol, 17.11% yield, 96% purity, TFA salt) as a yellow solid. MS(M+H)$^+$=917.2.

$^1$H NMR (400 MHz, DMSO-$d_6$) δ=11.11 (s, 1H), 9.47-9.34 (m, 1H), 8.43-8.08 (m, 4H), 7.59 (t, J=7.7 Hz, 1H), 7.19-7.17 (m, 1H), 7.09 (d, J=8.5 Hz, 1H), 7.03 (d, J=6.9 Hz, 1H), 6.54 (s, 1H), 5.05 (dd, J=5.1 Hz, J=12.6 Hz, 1H), 4.86-4.79 (m, 1H), 4.10 (t, J=13.7 Hz, 2H), 3.91 (s, 3H), 3.52 (d, J=10.3 Hz, 2H), 3.40-3.27 (m, 5H), 3.12-2.97 (m, 4H), 2.93-2.83 (m, 1H), 2.62-2.56 (m, 1H), 2.23-1.84 (m, 6H), 1.84-1.48 (m, 12H), 1.46-1.21 (m, 6H).

Example 12. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(8-((2-(2,6-dioxopiperidin-3-yl)-1,3-dioxoisoindolin-4-yl)amino)octyl)piperidin-4-yl)-2-fluoro-5-methoxybenzamide
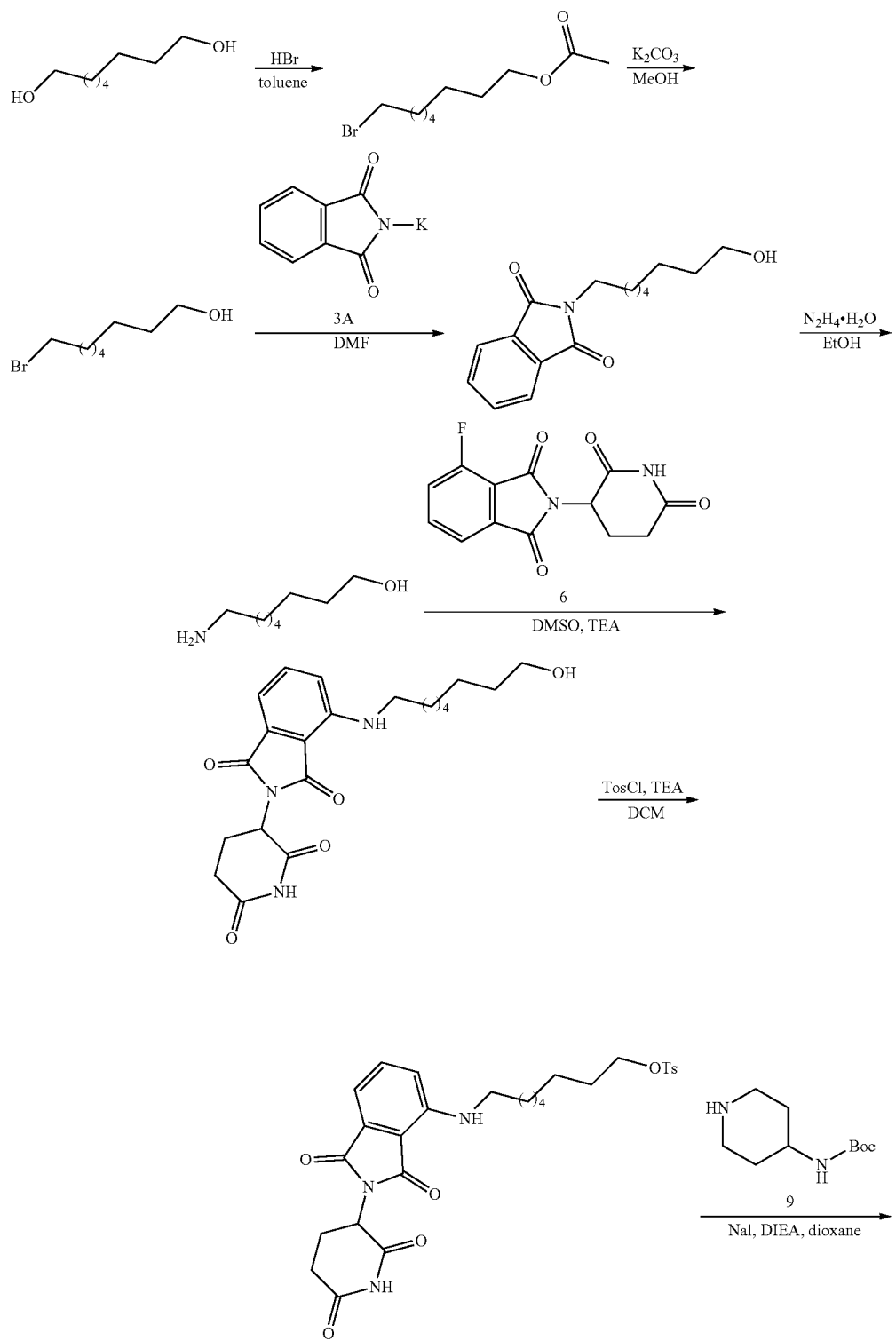

-continued
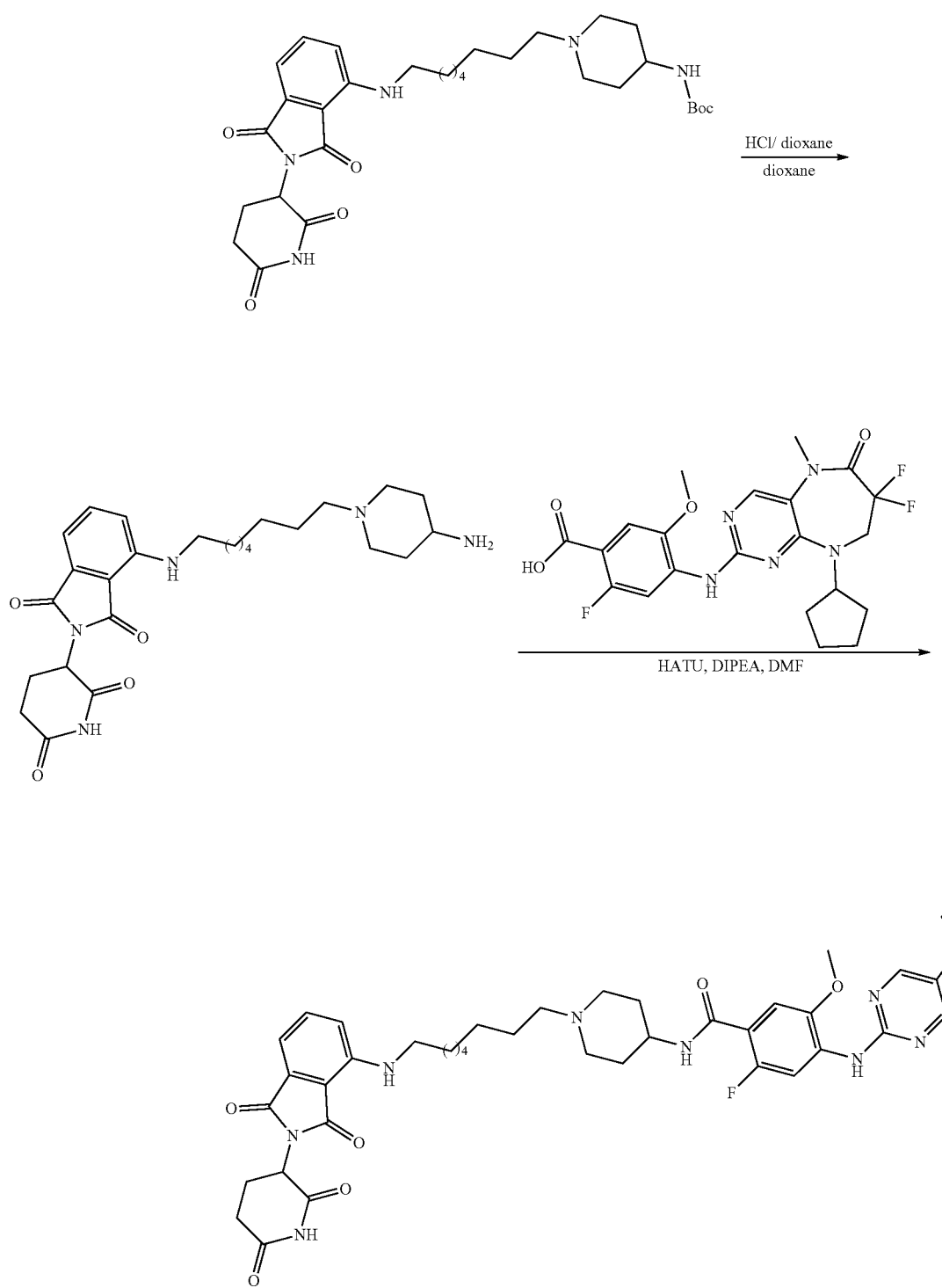
Compound 12
According to the above reaction scheme, in a manner similar to the other examples, obtained the titled compound (191.9 mg, 176.77 μmol, 22.98% yield, 90% purity, FA salt) as a yellow solid. MS(M+H)$^+$=931.8.
$^1$H NMR (400 MHz, DMSO-d$_6$) δ=11.09 (br s, 1H), 8.28 (s, 1H), 8.25 (d, J=13.4 Hz, 1H), 8.05 (s, 1H), 8.09-8.01 (m, 2H), 7.58 (dd, J=7.2, 8.4 Hz, 1H), 7.21-7.15 (m, 1H), 7.09 (d, J=8.5 Hz, 1H), 7.02 (d, J=6.9 Hz, 1H), 6.51 (t, J=5.8 Hz, 1H), 5.04 (dd, J=5.4, 12.7 Hz, 1H), 4.86-4.77 (m, 1H), 4.06 (br t, J=13.9 Hz, 3H), 3.96-3.83 (m, 5H), 3.32 (s, 3H), 3.15 (br d, J=11.0 Hz, 2H), 2.91-2.84 (m, 1H), 2.71-2.55 (m, 5H), 2.04-1.87 (m, 5H), 1.80-1.45 (m, 13H), 1.30 (br d, J=12.1 Hz, 8H).

Example 13. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(9-((2-(2,6-dioxopiperidin-3-yl)-1,3-dioxoisoindolin-4-yl)amino)nonyl)piperidin-4-yl)-2-fluoro-5-methoxybenzamide
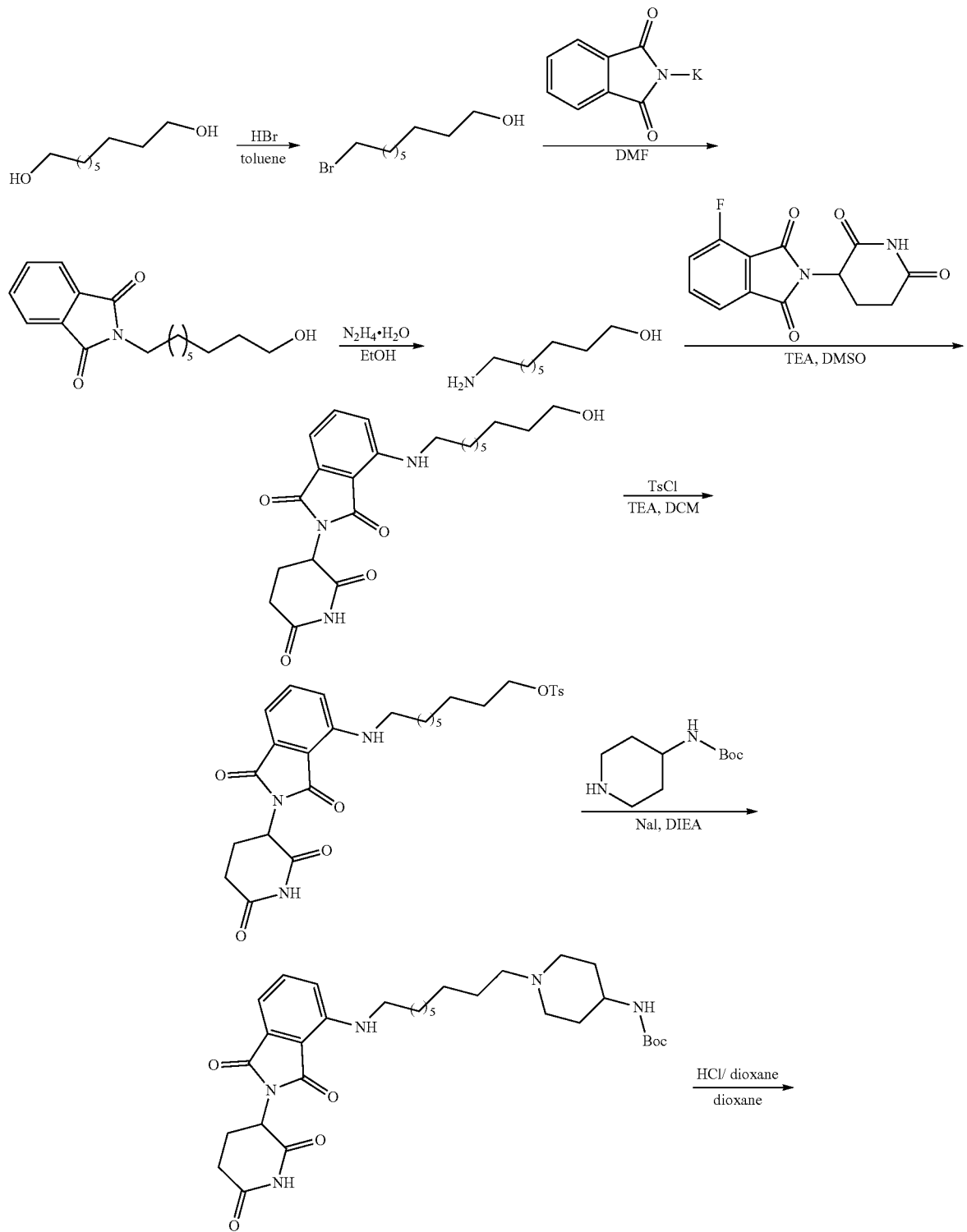

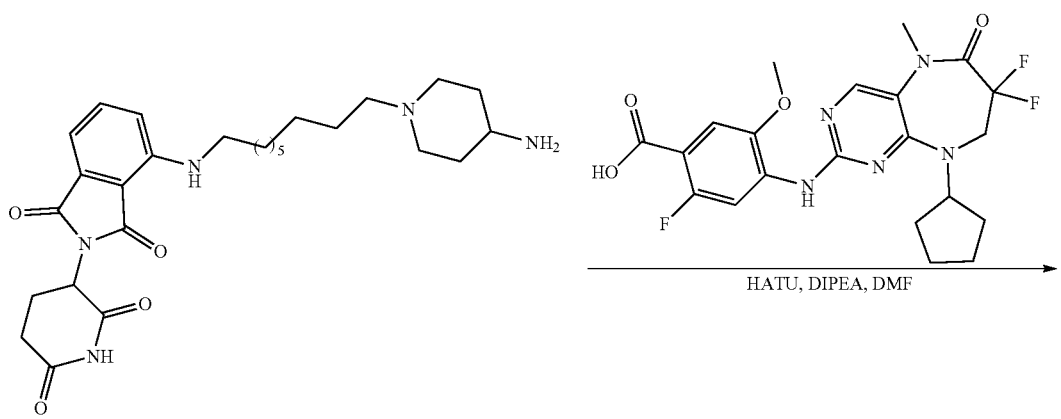

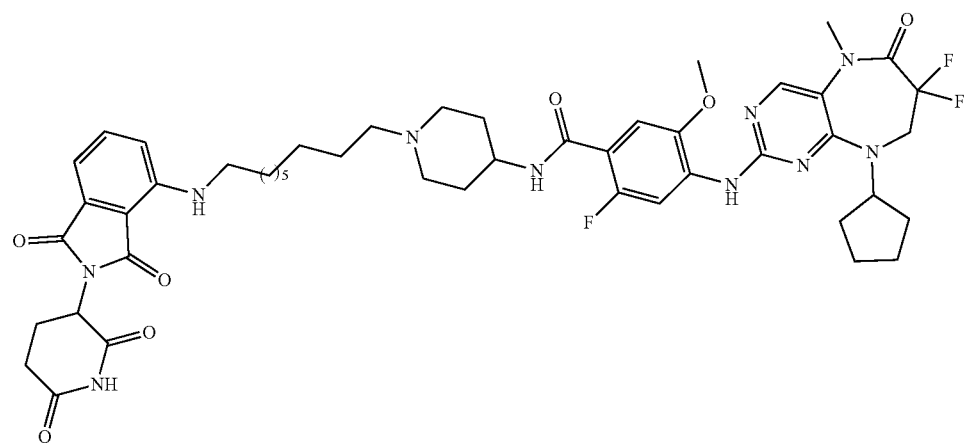

Compound 13

According to the above reaction scheme, in a manner similar to the other examples, obtained the titled compound (312.6 mg, 283.36 μmol, 30.27% yield, 96% purity, TFA salt) as a yellow solid. MS(M+H)$^+$=945.6.

$^1$H NMR (400 MHz, DMSO-d$_6$) δ=11.10 (s, 1H), 9.56-9.24 (m, 1H), 8.31 (s, 1H), 8.19-8.27 (m, 2H), 8.17 (s, 1H), 7.66-7.55 (m, 1H), 7.26-7.16 (m, 1H), 7.13-7.07 (m, 1H), 7.06-7.00 (m, 1H), 6.53 (s, 1H), 5.06 (dd, J$_1$=12.8 Hz, J$_2$=5.3 Hz, 1H), 4.82-4.86 (m, 1H), 4.21-4.02 (m, 3H), 3.92 (s, 3H), 3.52 (d, J=10.8 Hz, 2H), 3.37-3.27 (m, 5H), 3.09-2.99 (m, 3H), 2.94-2.84 (m, 1H), 2.63-2.57 (m, 1H), 2.29-1.87 (m, 6H), 1.86-1.50 (m, 12H), 1.39-1.22 (m, 10H).

Example 14. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(10-((2-(2,6-dioxopiperidin-3-yl)-1,3-dioxoisoindolin-4-yl)amino)decyl)piperidin-4-yl)-2-fluoro-5-methoxybenzamide

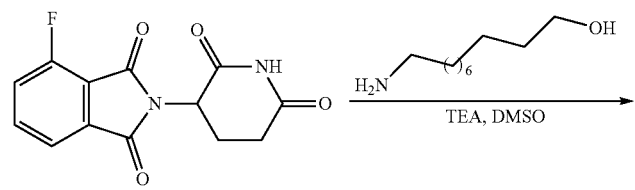

153
154
-continued
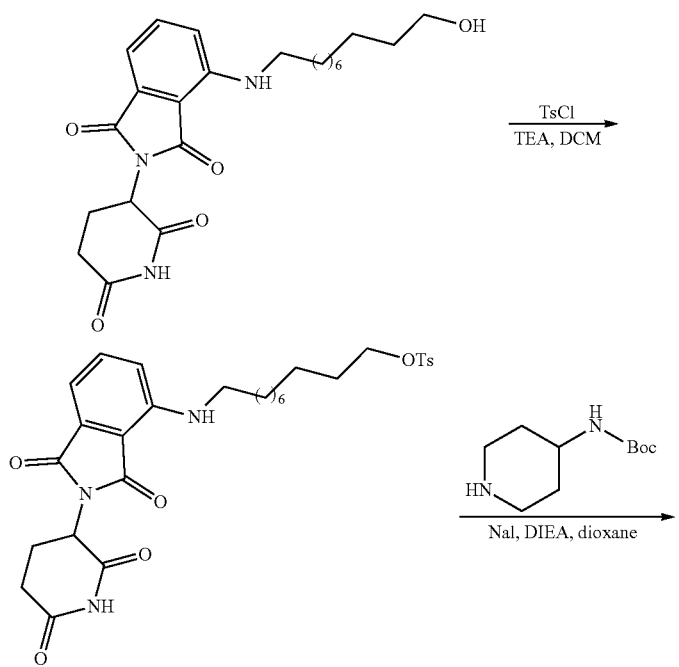
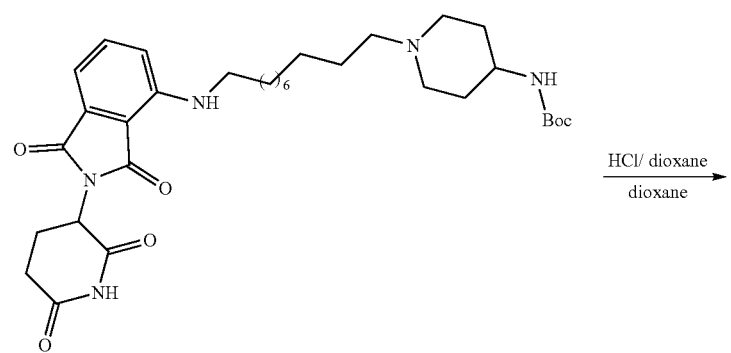
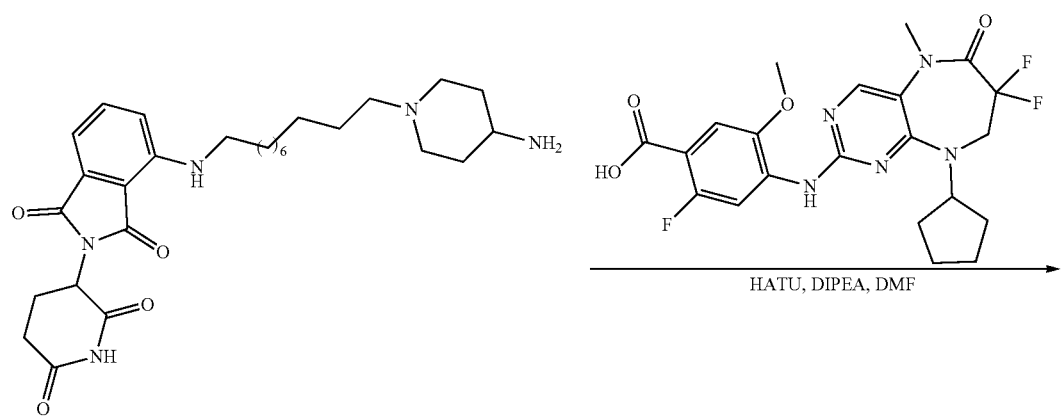

-continued

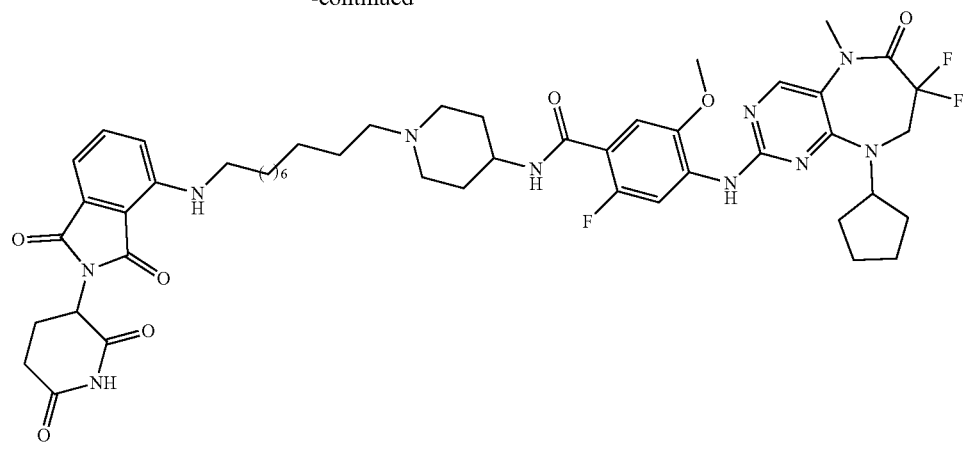

Compound 14

According to the above reaction scheme, in a manner similar to the other examples, obtained the titled compound (144.2 mg, 124.97 μmol, 19.57% yield, 93% purity, TFA salt) as a yellow solid. MS(M+H)$^+$=959.7.

$^1$H NMR (400 MHz, DMSO-d$_6$) δ=11.09 (s, 1H), 9.39-9.08 (m, 1H), 8.30 (s, 1H), 8.29-8.17 (m, 2H), 8.13 (s, 1H), 7.62-7.54 (m, 1H), 7.25-7.15 (m, 1H), 7.12-7.06 (m, 1H), 7.05-7.00 (m, 1H), 6.52 (s, 1H), 5.05 (dd, J$_1$=12.7 Hz, J$_2$=5.4 Hz, 1H), 4.83 (t, J=8.3 Hz, 1H), 4.13-4.06 (m, 2H), 3.91 (s, 3H), 3.52 (d, J=10.9 Hz, 2H), 3.33 (s, 3H), 3.31-2.26 (m, 2H), 3.13-2.95 (m, 4H), 2.93-2.84 (m, 1H), 2.62-2.56 (m, 1H), 2.17-1.85 (m, 6H), 1.84-1.68 (m, 4H), 1.66-1.54 (m, 8H), 1.36-1.25 (m, 12H).

Example 15. Synthesis of 4-((9-cyclopentyl-7,7-difluoro-5-methyl-6-oxo-5H,6H,7H,8H,9H-pyrimido[4,5-b][1,4]diazepin-2-yl)amino)-N-(1-(11-((2-(2,6-dioxopiperidin-3-yl)-1,3-dioxo-2,3-dihydro-1H-isoindol-4-yl)amino)undecyl)piperidin-4-yl)-2-fluoro-5-methoxybenzamide

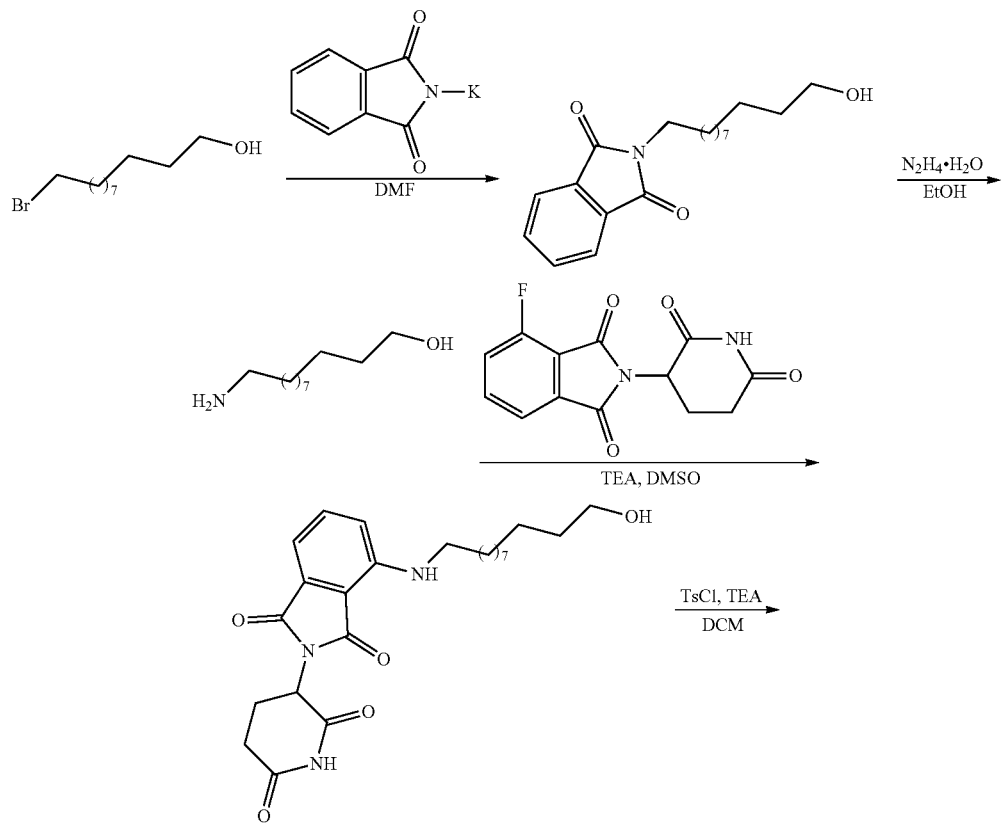

-continued
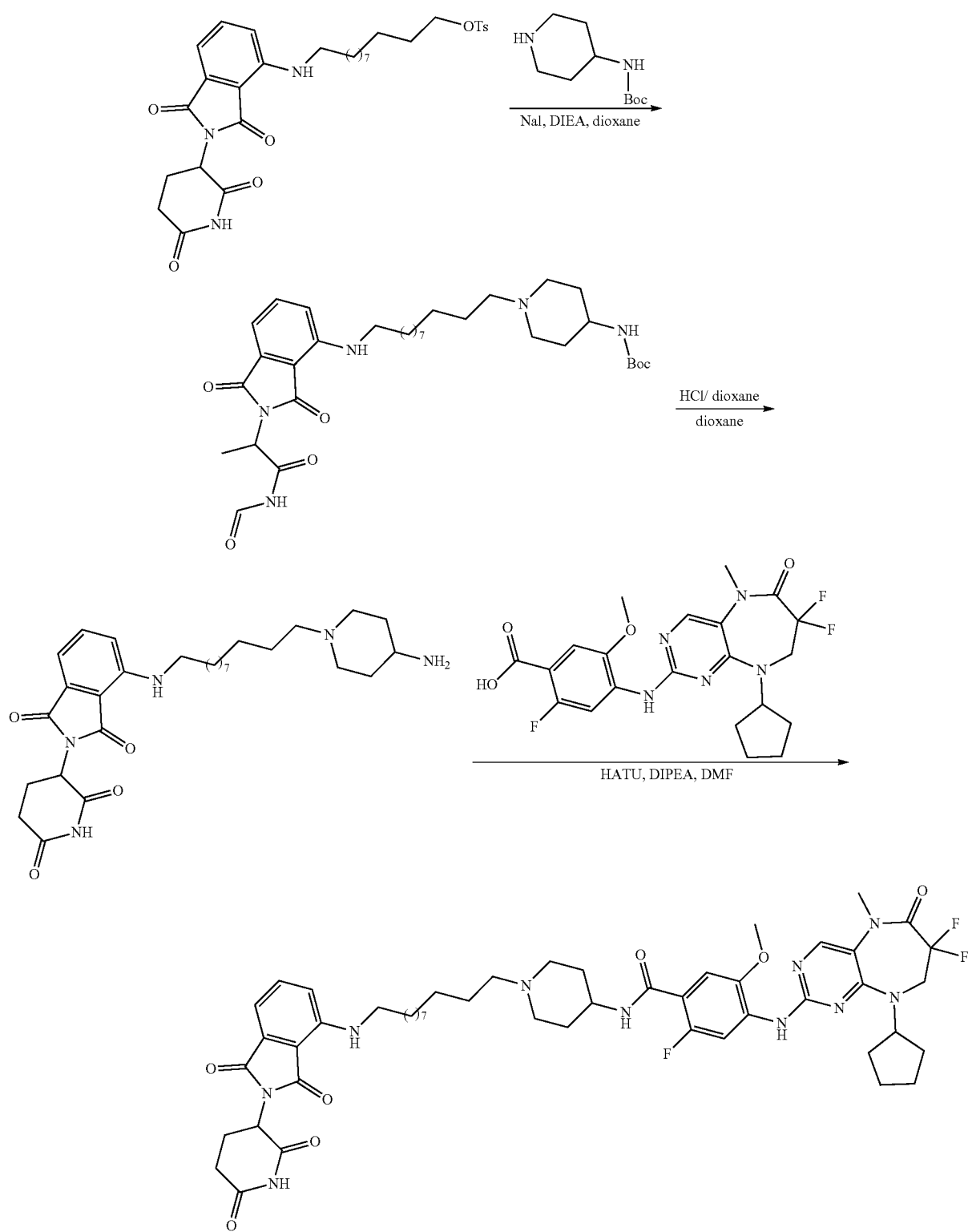
Compound 15
According to the above reaction scheme, in a manner similar to the other examples, obtained the titled compound (215.1 mg, 210.00 μmol, 39.35% yield, 95% purity) as a yellow solid. MS(M+H)⁺=973.3.
$^1$H NMR (400 MHz, DMSO-d$_6$) δ=11.09 (s, 1H), 8.29 (s, 1H), 8.24 (d, J=13.3 Hz, 1H), 8.03 (s, 1H), 7.86 (dd, J$_1$=7.4 Hz, J$_2$=3.4 Hz, 1H), 7.57 (dd, J$_1$=8.4 Hz, J$_2$=7.3 Hz, 1H), 7.19 (d, J=6.6 Hz, 1H), 7.08 (d, J=8.6 Hz, 1H), 7.01 (d, J=7.0

Hz, 1H), 6.52 (t, J=5.6 Hz, 1H), 5.04 (dd, J₁=12.5 Hz, J₂=5.4 Hz, 1H), 4.88-4.76 (m, 1H), 4.07 (t, J=13.9 Hz, 2H), 3.91 (s, 3H), 3.78-3.65 (m, 1H), 3.30-3.24 (m, 3H), 2.94-2.85 (m, 1H), 2.80 (d, J=11.4 Hz, 2H), 2.64-2.55 (m, 2H), 2.22 (t, J=7.3 Hz, 2H), 2.04-1.90 (m, 5H), 1.82-1.69 (m, 4H), 1.66-1.50 (m, 8H), 1.49-1.13 (m, 18H).
Example 16. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(13-((2-(2,6-dioxopiperidin-3-yl)-1,3-dioxoisoindolin-4-yl)amino)tridecyl)piperidin-4-yl)-2-fluoro-5-methoxybenzamide
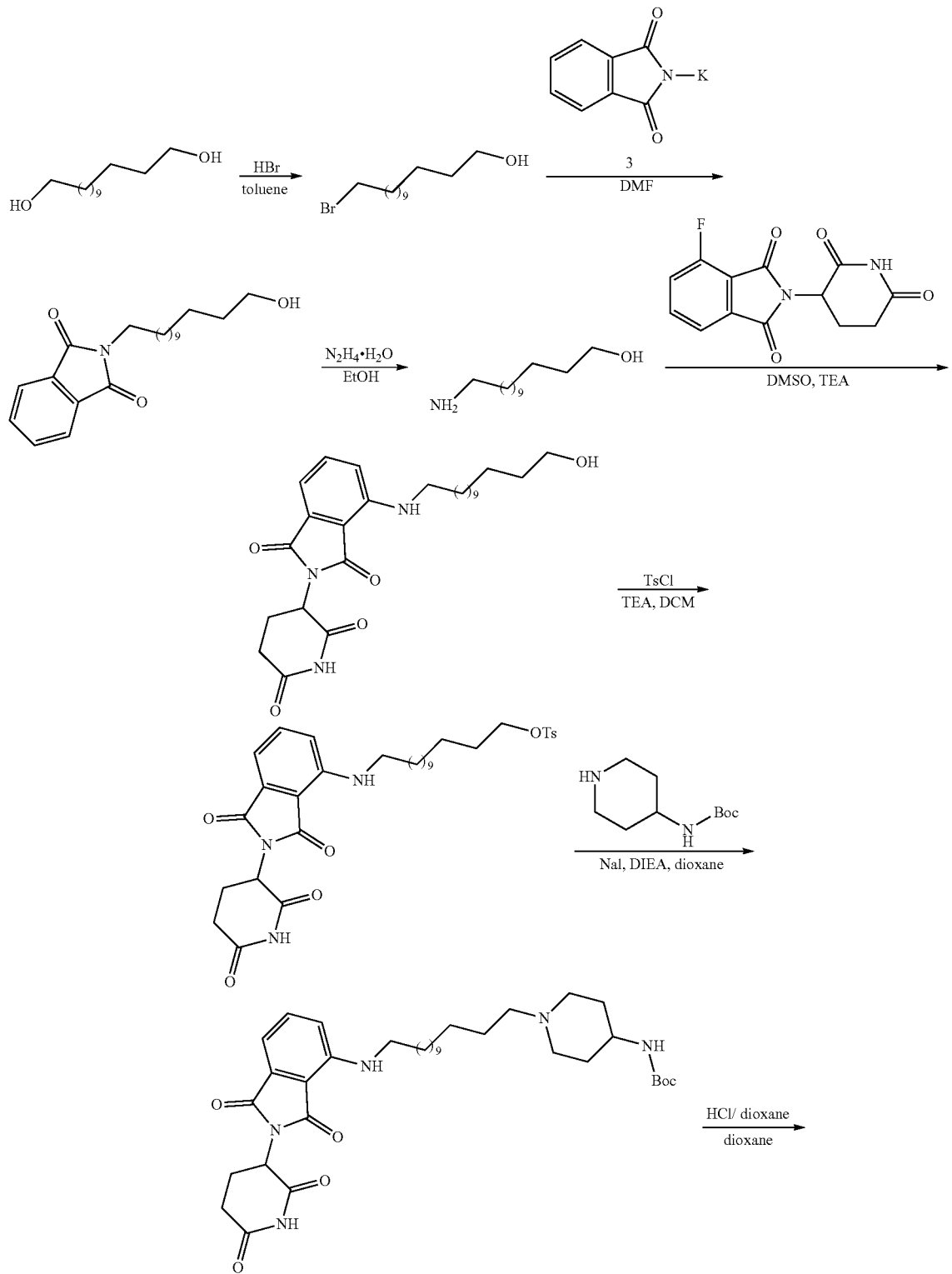

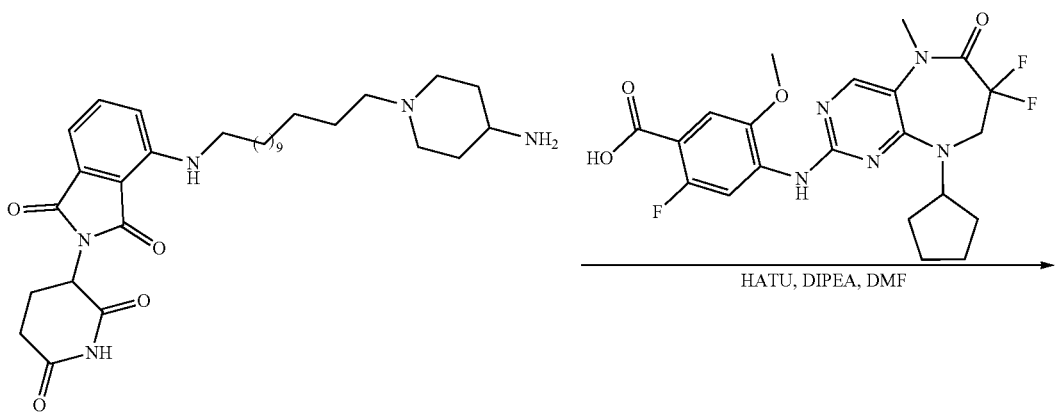

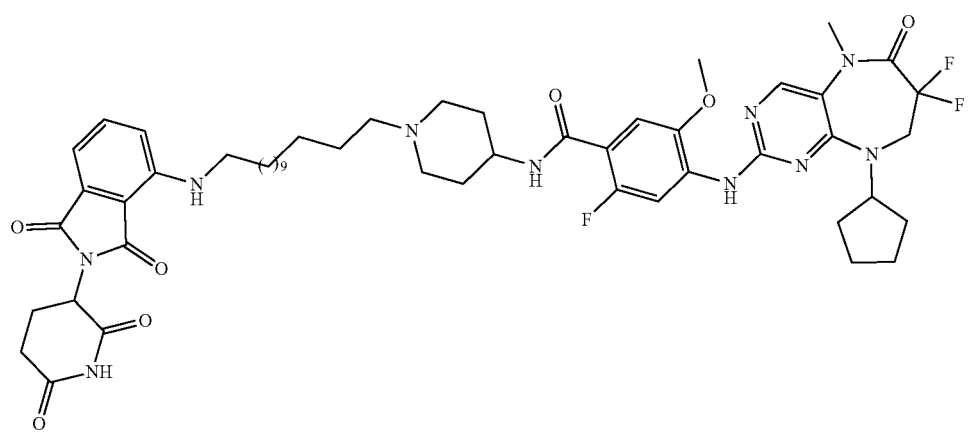

Compound 16

According to the above reaction scheme, in a manner similar to the other examples, obtained the titled compound (142.5 mg, 142.34 μmol, 17.87% yield) as a yellow solid. MS(M+H)$^+$=1001.4.

$^1$H NMR (400 MHz, DMSO-d$_6$) δ=11.09 (s, 1H), 8.34-8.20 (m, 2H), 8.03 (s, 1H), 7.87 (dd, J$_1$=7.7 Hz, J$_2$=3.5 Hz, 1H), 7.57 (dd, J$_1$=8.4 Hz, J$_2$=7.2 Hz, 1H), 7.18 (d, J=6.7 Hz, 1H), 7.08 (d, J=8.5 Hz, 1H), 7.01 (d, J=6.9 Hz, 1H), 6.52 (t, J=5.8 Hz, 1H), 5.04 (dd, J$_1$=12.9 Hz, J$_2$=5.4 Hz, 1H), 4.89-4.73 (m, 1H), 4.07 (t, J=13.9 Hz, 2H), 3.91 (s, 3H), 3.76-3.67 (m, 1H), 3.31-3.26 (m, 3H), 2.94-2.85 (m, 1H), 2.84-2.76 (m, 2H), 2.85-2.75 (m, 2H), 2.23 (t, J=7.3 Hz, 2H), 2.05-1.90 (m, 5H), 1.81-1.68 (m, 4H), 1.66-1.49 (m, 8H), 1.43-1.17 (m, 22H).

Example 17. Synthesis of 4-((9-cyclopentyl-7,7-difluoro-5-methyl-6-oxo-5H,6H,7H,8H,9H-pyrimido[4,5-b][1,4]diazepin-2-yl)amino)-N-(1-(14-((2-(2,6-dioxopiperidin-3-yl)-1,3-dioxo-2,3-dihydro-1H-isoindol-4-yl)amino)tetradecyl)piperidin-4-yl)-2-fluoro-5-methoxybenzamide

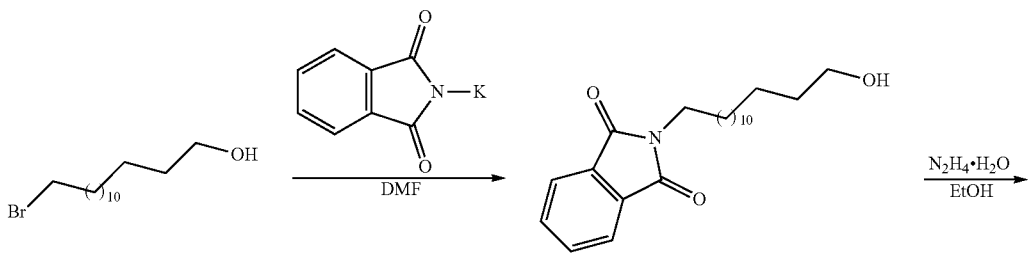

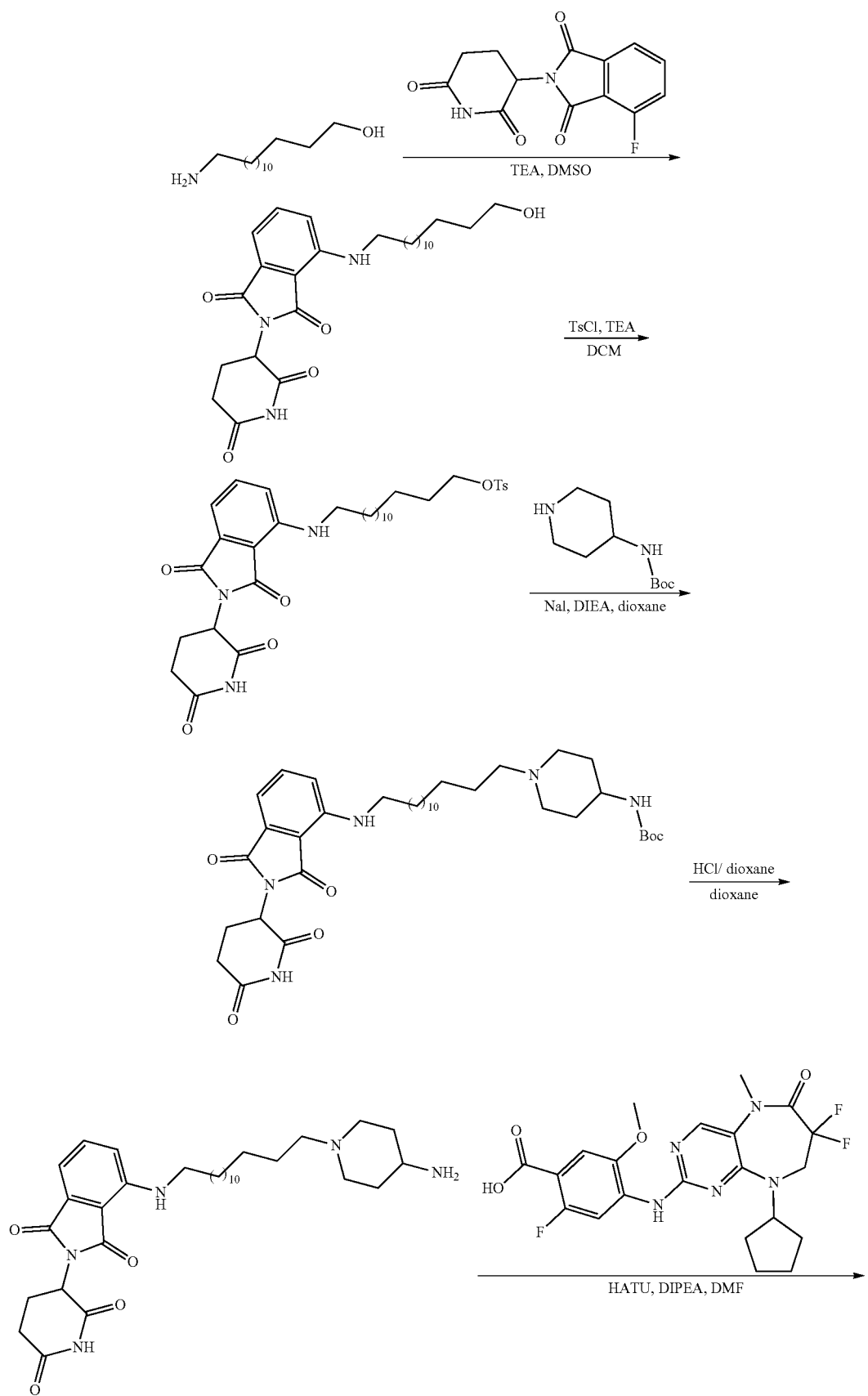

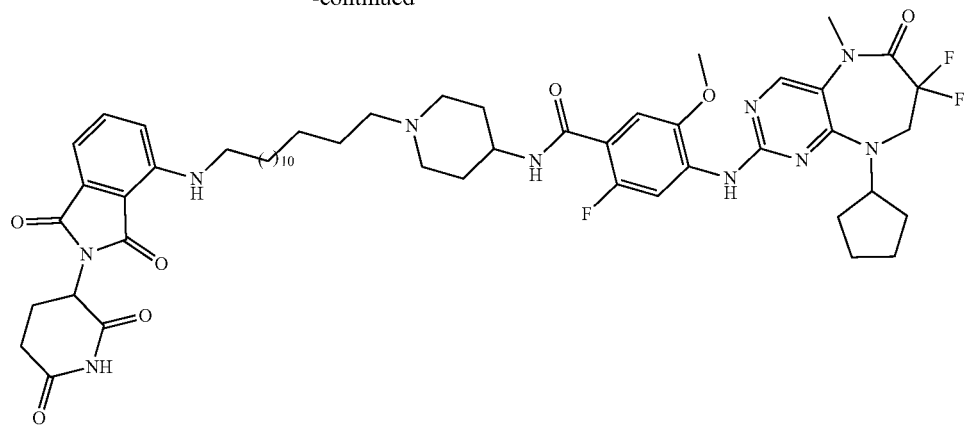

Compound 17

According to the above reaction scheme, in a manner similar to the other examples, obtained the titled compound (80.7 mg, 75.52 μmol, 22.82% yield, 95% purity) as a yellow solid. MS(M+H)⁺=1015.5.

¹H NMR (400 MHz, CDCl₃) δ=8.37 (d, J=15.2 Hz, 1H), 8.07 (s, 1H), 7.83 (s, 1H), 7.57 (d, J=7.1 Hz, 1H), 7.49 (dd, J=7.3, 8.4 Hz, 1H), 7.09 (d, J=7.1 Hz, 1H), 6.89 (d, J=8.6 Hz, 1H), 6.70 (dd, J=7.5, 15.2 Hz, 1H), 6.23 (t, J=5.4 Hz, 1H), 4.97-4.80 (m, 2H), 4.13-4.00 (m, 1H), 3.99-3.87 (m, 5H), 3.42 (s, 3H), 3.31-3.23 (m, 2H), 3.00-2.68 (m, 5H), 2.48-2.31 (m, 2H), 2.26-2.04 (m, 7H), 1.86-1.69 (m, 6H), 1.53-1.49 (m, 2H), 1.45-1.39 (m, 2H), 1.36-1.22 (m, 22H).

Example 18. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(3-(3-((2-(2,6-dioxopiperidin-3-yl)-1,3-dioxoisoindolin-4-yl)amino)propoxy)propyl)piperidin-4-yl)-2-fluoro-5-methoxybenzamide

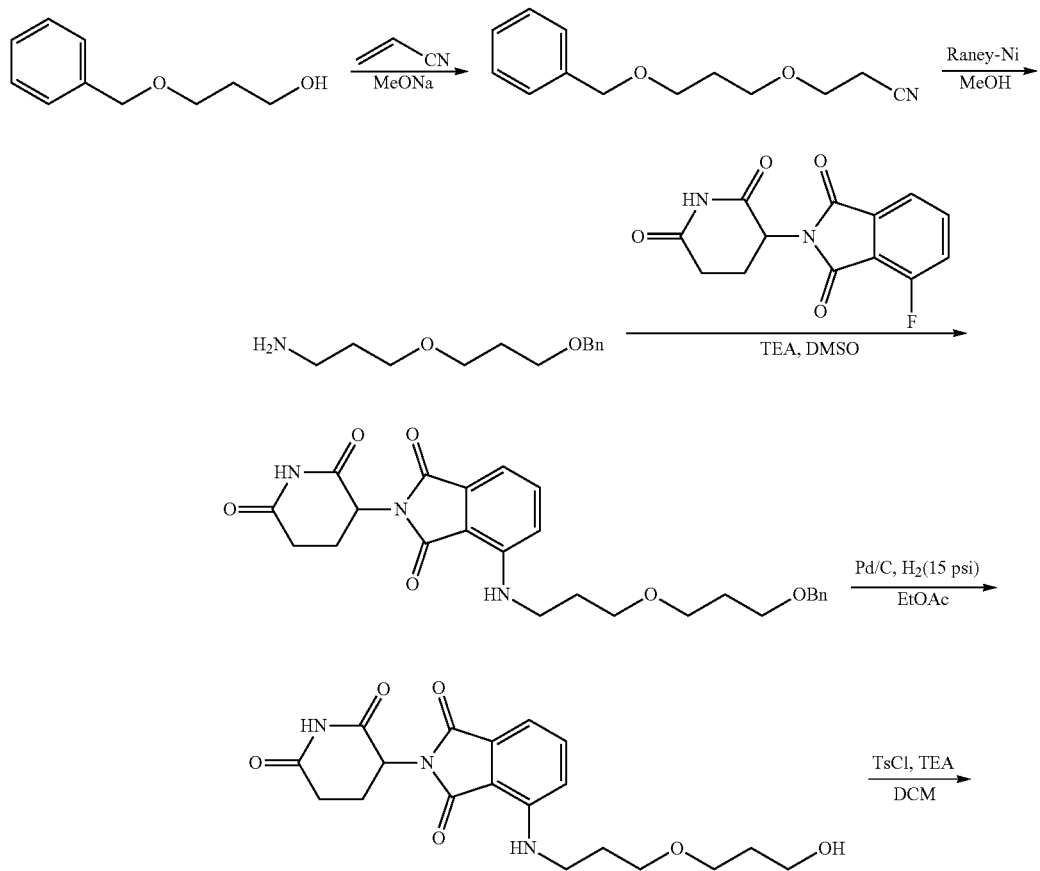

167

-continued

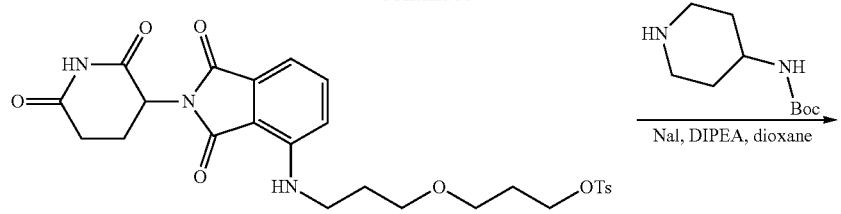

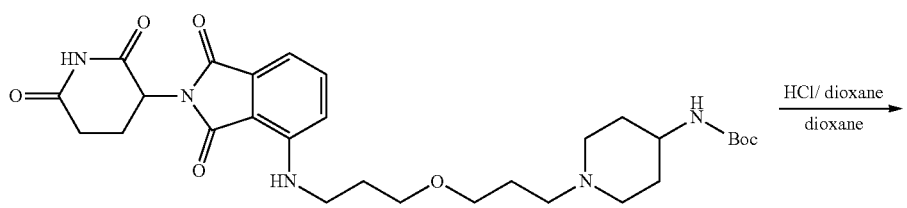

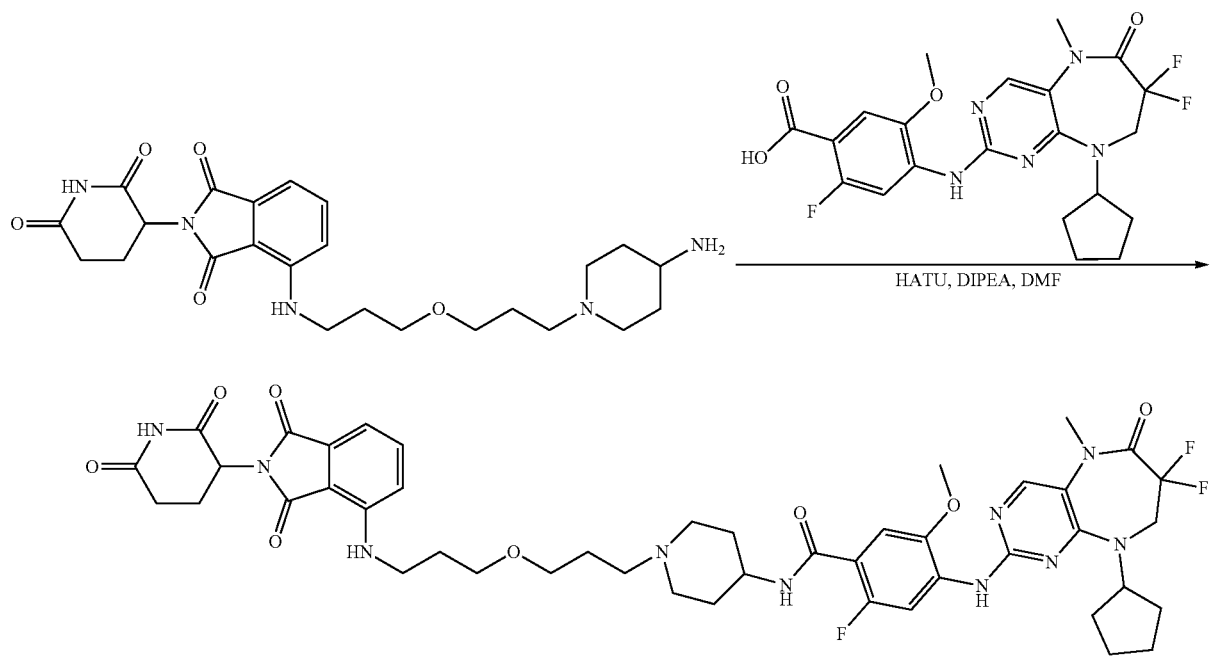

Compound 18

According to the above reaction scheme, in a manner similar to the other examples, obtained the titled compound (58.7 mg, 58.13 umol, 85.97% yield, 91% purity) as a yellow solid. MS(M+H)$^+$=919.7

$^1$H NMR (400 MHz, CDCl$_3$) δ=8.39 (d, J=15.2 Hz, 1H), 8.07 (s, 1H), 7.85 (s, 1H), 7.57-7.48 (m, 2H), 7.11 (d, J=6.8 Hz, 1H), 6.94-6.82 (m, 2H), 6.59 (t, J=5.2 Hz, 1H), 5.00-4.93 (m, 1H), 4.90-4.82 (m, 1H), 4.45-4.25 (m, 1H), 3.97 (s, 3H), 3.92 (t, J=13.4 Hz, 2H), 3.64-3.46 (m, 6H), 3.42 (s, 3H), 3.09-3.02 (m, 2H), 2.92-2.72 (m, 6H), 2.19-2.12 (m, 8H), 2.01-1.92 (m, 3H), 1.84-1.75 (m, 5H), 1.67-1.54 (m, 3H)

Example 19. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(4-(3-((2-(2,6-dioxopiperidin-3-yl)-1,3-dioxoisoindolin-4-yl)amino)propoxy)butyl)piperidin-4-yl)-2-fluoro-5-methoxybenzamide

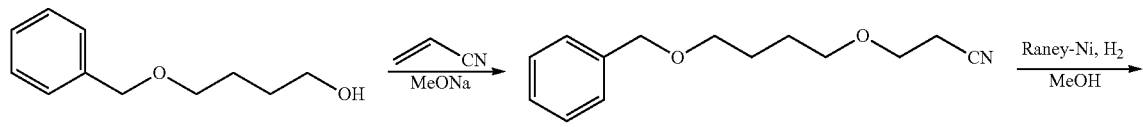

-continued
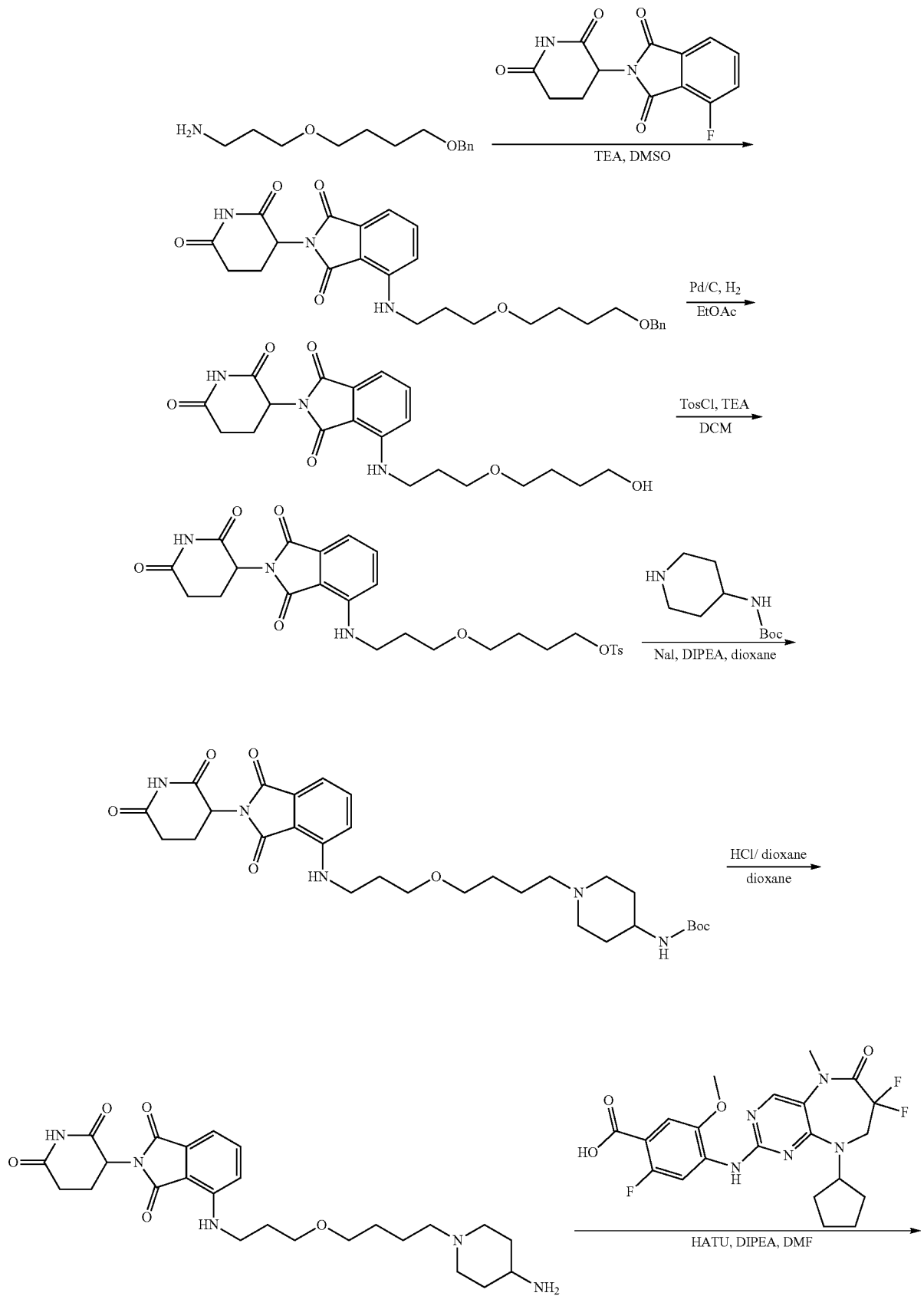

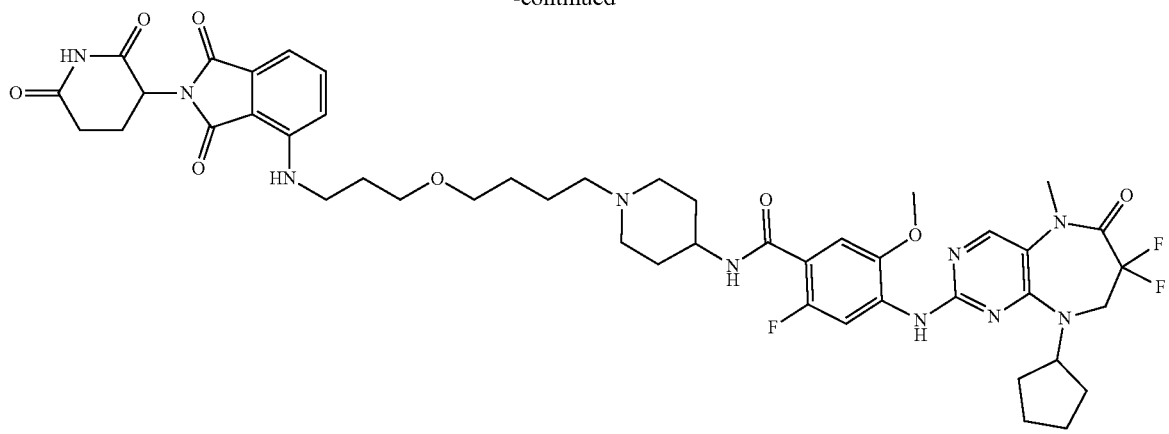

Compound 19

According to the above reaction scheme, in a manner similar to the other examples, obtained the titled compound (37.2 mg, 35.88 μmol, 6.68% yield, 90% purity) as a yellow solid. MS(M+H)$^+$=933.4

$^1$H NMR (400 MHz, CDCl$_3$) δ=8.39 (d, J=15.2 Hz, 1H), 8.07 (s, 1H), 7.84 (s, 1H), 7.55-7.47 (m, 2H), 7.10 (d, J=7.1 Hz, 1H), 6.91 (d, J=8.6 Hz, 1H), 6.82 (dd, J=7.9, 14.7 Hz, 1H), 6.72-6.65 (m, 1H), 4.98-4.90 (m, 1H), 4.90-4.82 (m, 1H), 4.33-4.12 (m, 1H), 3.97 (s, 3H), 3.96-3.88 (m, 2H), 3.63-3.43 (m, 6H), 3.42 (s, 3H), 3.03-2.56 (m, 8H), 2.17-2.07 (m, 6H), 1.97-1.86 (m, 6H), 1.75-1.52 (m, 8H)

Example 20. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(3-(4-((2-(2,6-dioxopiperidin-3-yl)-1,3-dioxoisoindolin-4-yl)amino)butoxy)propyl)piperidin-4-yl)-2-fluoro-5-methoxybenzamide

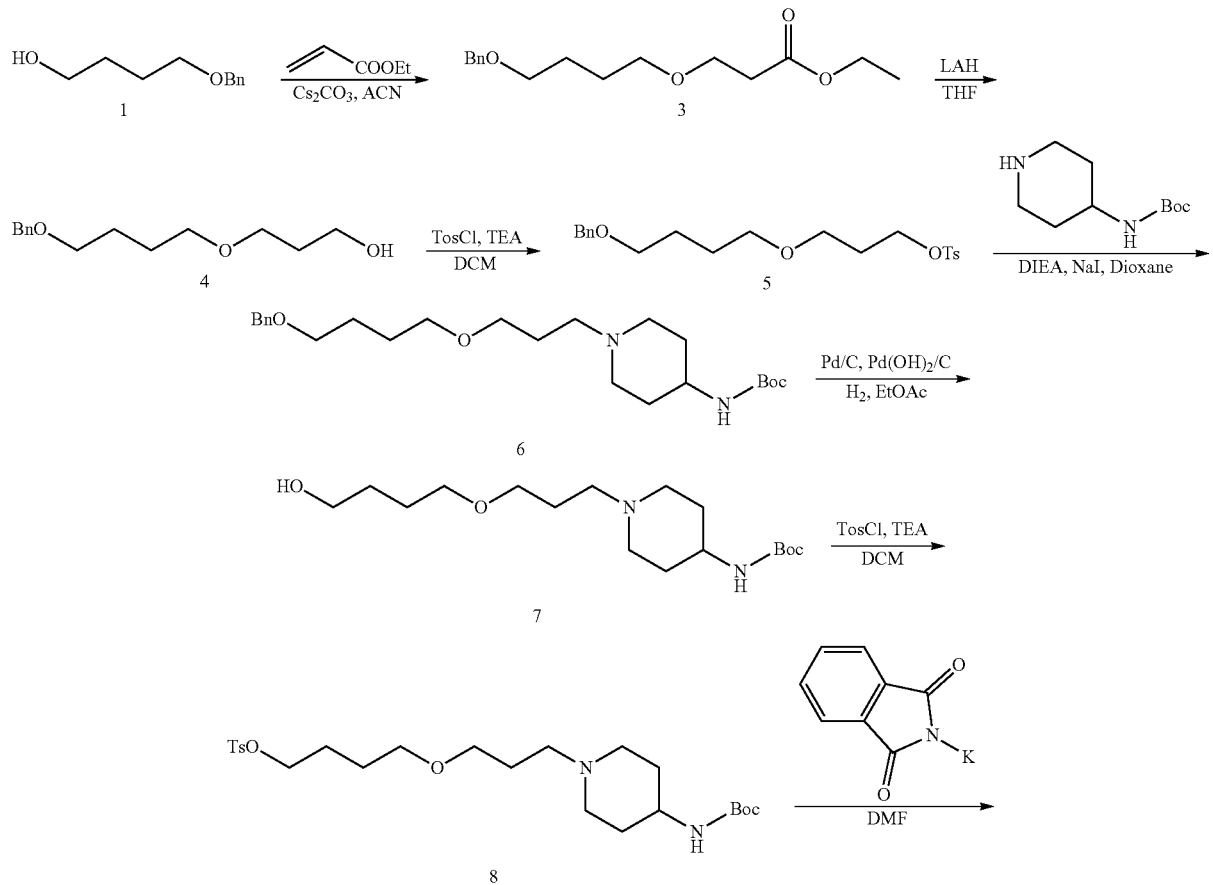

-continued
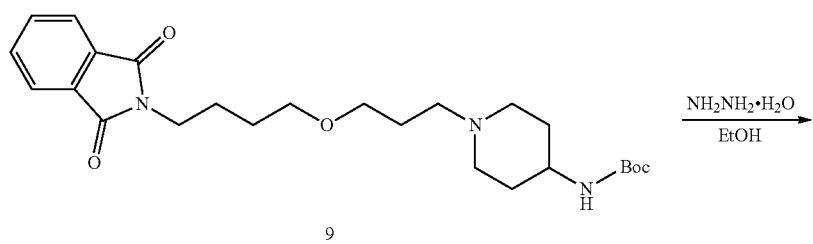
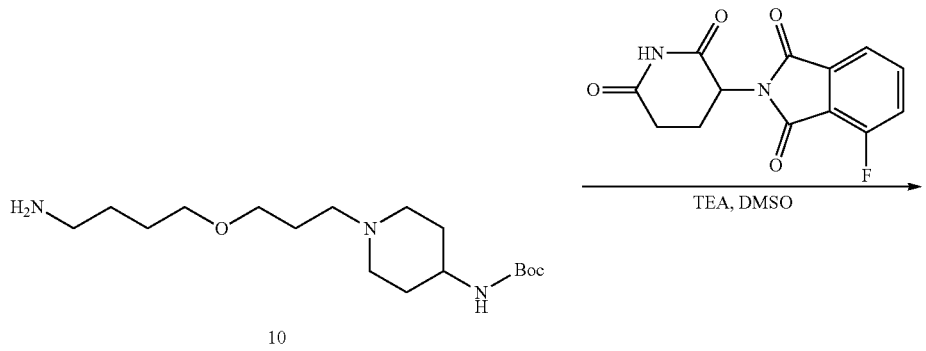
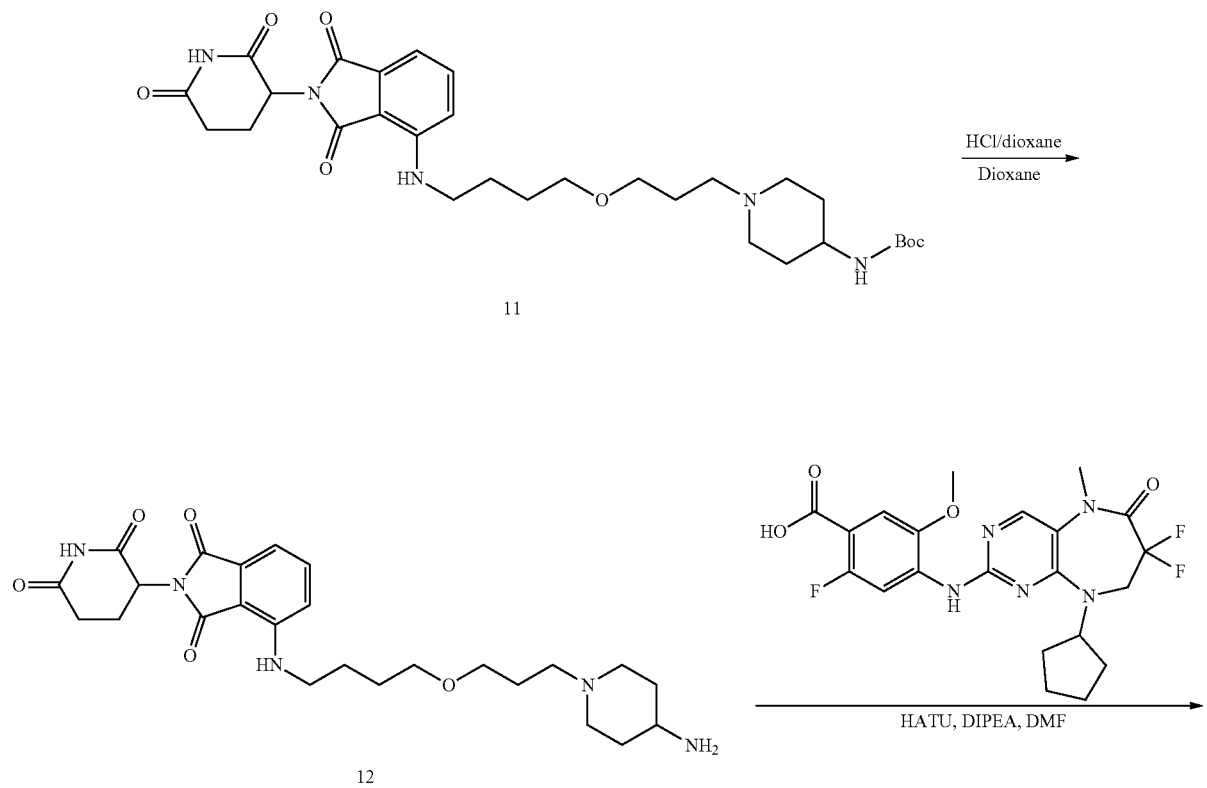

-continued

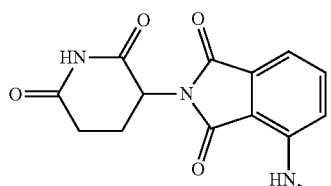
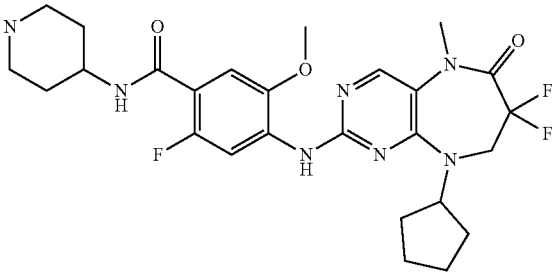

Compound 20

Step 1: Synthesis of ethyl 3-(4-(benzyloxy)butoxy)propanoate (3)

A solution of 4-benzyloxybutan-1-ol (8.0 g, 44.38 mmol, 7.77 mL), $Cs_2CO_3$ (28.92 g, 88.77 mmol), ethyl prop-2-enoate (44.44 g, 443.85 mmol, 48.25 mL) in $CH_3CN$ (100 mL) was stirred at 25° C. for 12 h. LCMS showed that the reaction was completed. The mixture was filtered; the filter liquor was concentrated in vacuo. The crude product was purified by reversed-phase HPLC (0.1% FA condition, MeCN/water) to afford the titled compound (9.04 g, crude) as colorless oil. $MS(M+H)^+=281.0$

Step 2: Synthesis of 3-(4-(benzyloxy)butoxy)propan-1-ol (4)

To a solution of ethyl 3-(4-benzyloxybutoxy) propanoate (9.04 g, 32.24 mmol) in THF (100 mL) was added LAH (1.47 g, 38.69 mmol) at 0° C., the mixture was stirred at 25° C. for 2 h. TLC (Petroleum ether/EtOAc=3/1) showed that the reaction was completed. The mixture was quenched with water (1.5 mL), 1.5 mL 15% NaOH (aq) and water (4.5 mL) sequently. The mixture was stirred at 25° C. for 30 min, the mixture was filtered and the filtrate was concentrated under vacuum to afford the titled compound (8.41 g, crude) as colorless oil.

Step 3: Synthesis of 3-(4-(benzyloxy)butoxy)propyl 4-methylbenzenesulfonate (5)

To a solution of 3-(4-benzyloxybutoxy) propan-1-ol (8.41 g, 35.29 mmol) in DCM (100 mL) were added TEA (4.28 g, 42.35 mmol, 5.89 mL) followed by TosCl (8.07 g, 42.35 mmol). The reaction mixture was stirred at 20° C. for 3 h. LCMS showed the desired mass was detected. The reaction mixture was diluted with $H_2O$ (250 mL) and extracted with DCM (200 mL×3), the combined organic layers were washed with brine (50 mL×1), dried over $Na_2SO_4$, filtered and concentrated under reduced pressure. The residue was purified by flash silica gel chromatography (20 g SepaFlash® Silica Flash Column, Eluent of 10~30% Ethyl acetate/Petroleum ether gradient @ 60 mL/min) to afford the titled compound (6.8 g, 17.32 mmol, 49.09% yield) as colorless oil. $MS(M+H)^+=393.0$

Step 4: Synthesis of tert-butyl (1-(3-(4-(benzyloxy)butoxy)propyl)piperidin-4-yl)carbamate (6)

To a solution of 3-(4-benzyloxybutoxy) propyl 4-methylbenzenesulfonate (3.4 g, 8.66 mmol) and tert-butyl piperidin-4-ylcarbamate (2.60 g, 12.99 mmol) in dioxane (20 mL) were added NaI (129.84 mg, 866.22 µmol) and DIEA (2.24 g, 17.32 mmol, 3.02 mL), the mixture was heated at 60° C. for 12 h. LCMS showed the desired mass was detected. The mixture was concentrated in vacuo. The residue was purified by column chromatography ($SiO_2$, Petroleum ether/Ethyl acetate=2/1 to EtOAc/MeOH=10/1) to afford the titled compound (3.05 g, 7.25 mmol, 83.72% yield) as yellow oil. $MS(M+H)^+=421.2$

Step 5: Synthesis of tert-butyl (1-(3-(4-hydroxybutoxy)propyl)piperidin-4-yl)carbamate (7)

To a solution of tert-butyl (1-(3-(4-(benzyloxy)butoxy) propyl)piperidin-4-yl)carbamate (2.4 g, 5.71 mmol) in EtOAc (20 mL) was added Pd/C (400 mg, 10% purity) and $Pd(OH)_2/C$ (400 mg, 10% purity) under $N_2$. The suspension was degassed under vacuum and purged with $H_2$ several times. The mixture was stirred under $H_2$ (50 psi) at 60° C. for 24 h. TLC (EtOAc/MeOH=10/1) showed the reactant was remained and the desired product was detected. The mixture was filtered, the filtrate was concentrated in vacuo to afford the titled compound (1.9 g, 4.52 mmol, 79.17% yield) as colorless oil.

Step 6: Synthesis of 4-(3-(4-((tert-butoxycarbonyl)amino)piperidin-1-yl)propoxy)butyl 4-methylbenzenesulfonate (8)

To a solution of tert-butyl (1-(3-(4-hydroxybutoxy)propyl)piperidin-4-yl)carbamate (1.69 g, 5.11 mmol) in DCM (20 mL) were added TEA (1.55 g, 15.34 mmol, 2.14 mL) and TosCl (1.46 g, 7.67 mmol), the mixture was stirred at 25° C. for 12 h. LCMS showed the desired mass was detected. The mixture was concentrated in vacuo. The residue was purified by flash silica gel chromatography (Biotage, 25 g SepaFlash® Silica Flash Column, Eluent of 30~100% Ethyl acetate/Petroleum ether gradient @ 80 mL/min) to afford the titled compound (1.23 g, 2.09 mmol, 40.84% yield, 82.3% purity) as yellow oil. $MS(M+H)^+=485.3$.

Step 7: Synthesis of tert-butyl (1-(3-(4-(1,3-dioxoisoindolin-2-yl)butoxy)propyl)piperidin-4-yl)carbamate (9)

A solution of 4-(3-(4-((tert-butoxycarbonyl)amino)piperidin-1-yl)propoxy)butyl 4-methylbenzenesulfonate (1.23 g, 2.54 mmol) and (1,3-dioxoisoindolin-2-yl) potassium (940.15 mg, 5.08 mmol) in DMF (15 mL), the mixture was heated at 80° C. for 12 h. LCMS showed the desired mass was detected. The reaction mixture was diluted with brine (10 mL) and extracted with EtOAc (30 mL×2). The combined organic layers were dried over $Na_2SO_4$, filtered and concentrated under reduced pressure. The residue was purified by flash silica gel chromatography (Biotage, 25 g SepaFlash® Silica Flash Column, Eluent of 30~100% Ethyl acetate/Petroleum ether gradient @ 80 mL/min) to afford the titled compound (600 mg, 1.30 mmol, 51.34% yield, 99.8% purity) as colorless oil. MS $(M+H)^+$=460.2.

Step 8: Synthesis of tert-butyl (1-(3-(4-aminobutoxy))propyl)piperidin-4-yl)carbamate tert-butyl (1-(3-(4-(1,3-dioxoisoindolin-2-yl)butoxy)propyl)piperidin-4-yl)carbamate (0.78 g, 1.70 mmol) and $NH_2NH_2 \cdot H_2O$ (999.56 mg, 16.97 mmol, 970.45 µL, 85% purity) were placed in a 50 mL round bottom flask, and EtOH (10 mL) was added. The mixture was stirred at 75° C. for 2 h. TLC (Ethyl acetate/Methanol=10/1) showed that the reaction was completed. Stop heating, remove insoluble solids by filtration, the filtrate was concentrated to the titled compound (0.5 g, 1.52 mmol, 89.41% yield) as yellow oil.
$^1$H NMR (400 MHz, MeOD) δ=3.51-3.41 (m, 4H), 3.40-3.35 (m, 1H), 2.92 (d, J=11.6 Hz, 2H), 2.73 (t, J=7.0 Hz, 2H), 2.51-2.38 (m, 2H), 2.17-2.06 (m, 2H), 1.90-1.81 (m, 2H), 1.82-1.73 (m, 2H), 1.65-1.55 (m, 4H), 1.48-1.40 (m, 11H).

Step 9: Synthesis of tert-butyl (1-(3-(4-((2-(2,6-dioxopiperidin-3-yl)-1,3-dioxoisoindolin-4-yl)amino)butoxy)propyl)piperidin-4-yl)carbamate (11)

To the solution of tert-butyl (1-(3-(4-aminobutoxy)propyl)piperidin-4-yl)carbamate (440 mg, 1.34 mmol) and 2-(2,6-dioxo-3-piperidyl)-4-fluoro-isoindoline-1,3-dione (400 mg, 1.45 mmol) in DMSO (5 mL) was added TEA (439.60 mg, 4.34 mmol, 604.68 µL) and the mixture was stirred at 60° C. for 12 h. TLC (Ethyl acetate/Methanol=10/1) showed that the reaction was completed, the mixture was poured into water (30 mL) and extracted with EtOAc (20 mL×3), the combined organic layer was dried over $Na_2SO_4$, filtered and concentrated. The residue was purified by silica gel column (Ethyl acetate/Methanol=10/1) to the titled compound (160 mg, 264.99 µmol, 18.30% yield, 97% purity) as yellow oil. MS$(M+H)^+$=586.2

Step 10: Synthesis of 4-((4-(3-(4-aminopiperidin-1-yl)propoxy)butyl)amino)-2-(2,6-dioxopiperidin-3-yl)isoindoline-1,3-dione (12)

to the solution of tert-butyl (1-(3-(4-((2-(2,6-dioxopiperidin-3-yl)-1,3-dioxoisoindolin-4-yl)amino)butoxy)propyl)piperidin-4-yl)carbamate (160 mg, 273.18 µmol) in dioxane (5 mL) was added HCV/dioxane (4 M, 5 mL) and the mixture was stirred at 20° C. for 1 h. LCMS showed that the reaction was completed. The mixture was concentrated to afford the titled compound (140 mg, 268.18 µmol, 98.17% yield, HCl) as yellow oil. MS$(M+H)^+$=486.5.

Step 11: Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(3-(4-((2-(2,6-dioxopiperidin-3-yl)-1,3-dioxoisoindolin-4-yl)amino)butoxy)propyl)piperidin-4-yl)-2-fluoro-5-methoxybenzamide (Compound 20)

To the solution of 4-((4-(3-(4-aminopiperidin-1-yl)propoxy)butyl)amino)-2-(2,6-dioxopiperidin-3-yl)isoindoline-1,3-dione (140 mg, 268.18 µmol, HCl) and 4-[(9-cyclopentyl-7,7-difluoro-5-methyl-6-oxo-8H-pyrimido[4,5-b][1,4]diazepin-2-yl) amino]-2-fluoro-5-methoxy-benzoic acid (124.82 mg, 268.18 umol) in DMF (3 mL) were added HATU (203.94 mg, 536.36 µmol) and DIPEA (103.98 mg, 804.54 µmol, 140.14 µL) and the resulting mixture was stirred at 20° C. for 1 h. LCMS showed that the reaction was completed, the mixture was poured into water (20 mL) and extracted with EtOAc (20 mL×3), the combined organic layers were washed with brine (50 mL), dried over $Na_2SO_4$, filtered and concentrated. The residue was purified by prep-HPLC (column: Unisil 3-100 $C_{18}$ µLtra 150*50 mm*3 um; mobile phase: [water (0.225% FA)-ACN]; B %: 33%-53%, 10 min) and the eluant was lyophilized to afford the titled compound (14.8 mg, 15.55 µmol, 5.80% yield, 98% purity, FA) as yellow solid. MS$(M+H)^+$=933.3
$^1$H NMR (400 MHz, DMSO-d$_6$) δ=11.10 (s, 1H), 8.30 (s, 1H), 8.26 (d, J=13.2 Hz, 1H), 8.14 (s, 1H), 8.08-7.99 (m, 2H), 7.65-7.54 (m, 1H), 7.19 (d, J=6.8 Hz, 1H), 7.11 (d, J=8.6 Hz, 1H), 7.04 (d, J=6.8 Hz, 1H), 6.61-6.54 (m, 1H), 5.12-5.00 (m, 1H), 4.89-4.77 (m, 1H), 4.08 (t, J=13.6 Hz, 2H), 3.95-4.83 (m, 5H), 3.42-3.41 (m, 8H), 3.18-3.07 (m, 1H), 2.95-2.82 (m, 2H), 2.70-2.56 (m, 5H), 1.97-1.95 (m, 2H), 1.89-1.88 (m, 2H), 1.76-1.72 (m, 4H), 1.71-1.55 (m, 12H).

Example 21. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(2-(3-(2-((2-(2,6-dioxopiperidin-3-yl)-1,3-dioxoisoindolin-4-yl)amino)ethoxy)propoxy)ethyl)piperidin-4-yl)-2-fluoro-5-methoxybenzamide

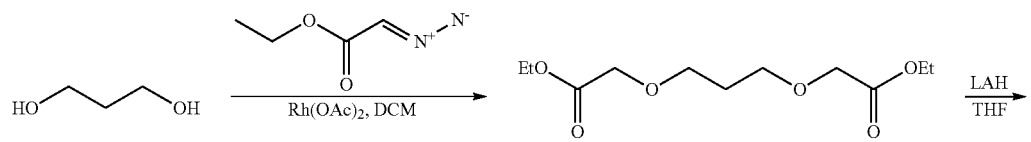

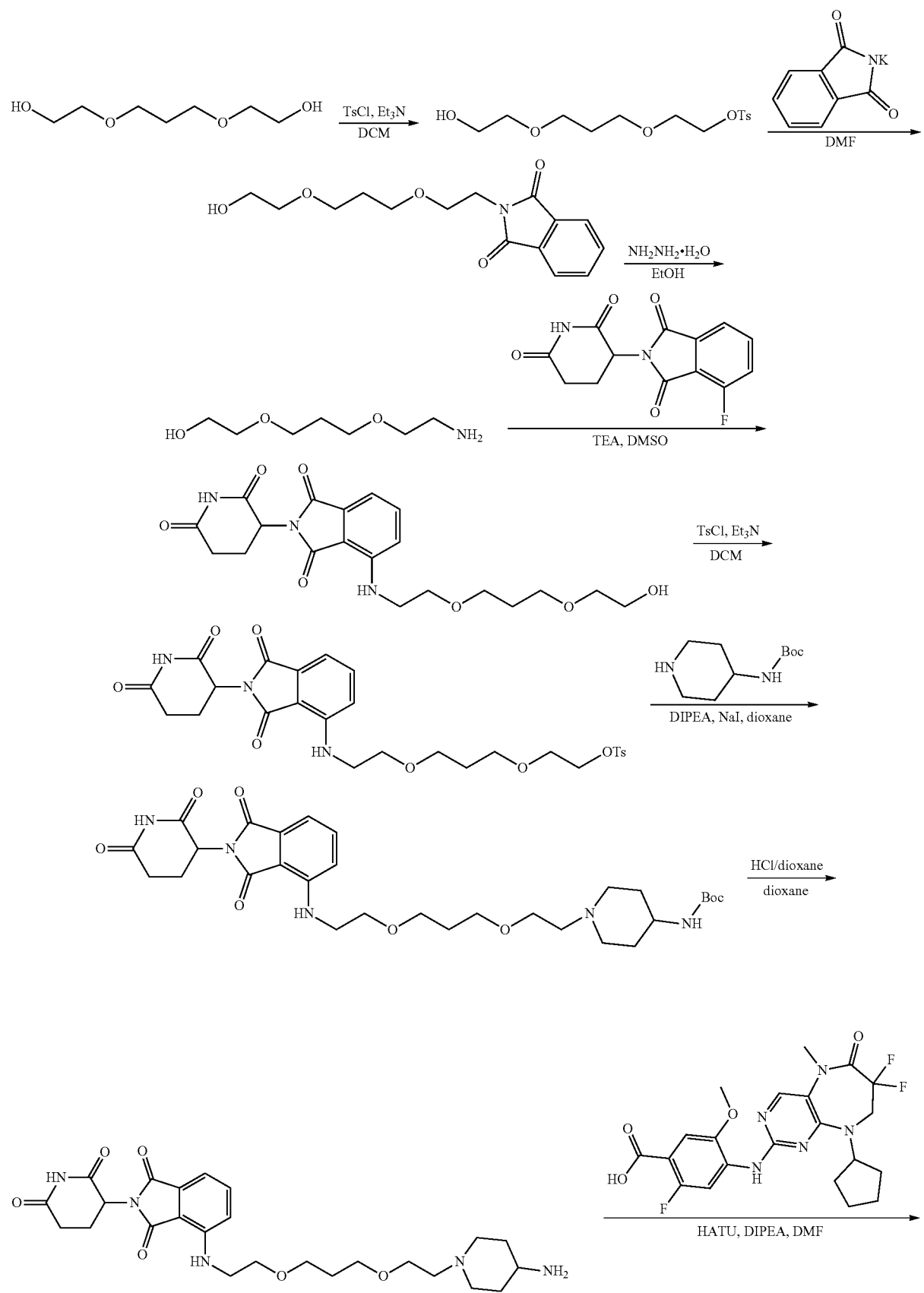

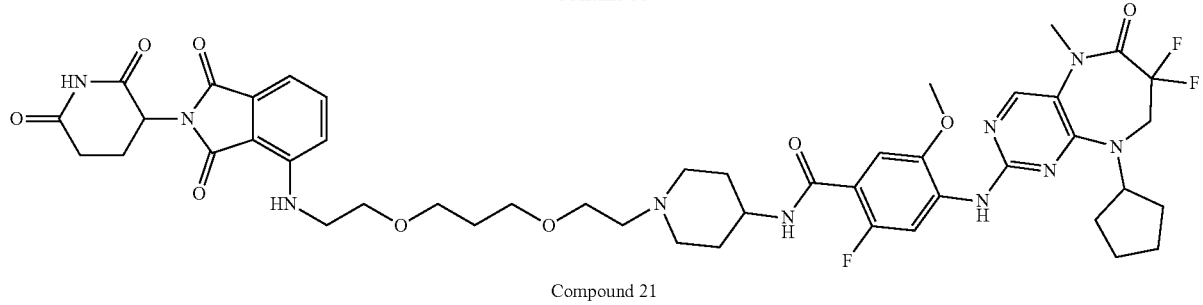

Compound 21

According to the above reaction scheme, in a manner similar to the other examples, obtained the titled compound (199.8 mg, 200.01 μmol, 46.55% yield, 95% purity) as yellow solid. MS(M+H)$^+$=949.2.

$^1$H NMR (400 MHz, DMSO-d$_6$) δ=11.10 (s, 1H), 8.30 (s, 1H), 8.26 (d, J=13.2 Hz, 1H), 8.16-8.15 (m, 1H), 8.06 (s, 1H), 7.61-7.57 (m, 1H), 7.25-7.14 (m, 2H), 7.05 (d, J=6.8 Hz, 1H), 6.66-6.65 (m, 1H), 5.13-5.05 (m, 1H), 4.81-4.73 (m, 1H), 4.13-4.06 (m, 2H), 4.12-3.95 (m, 4H), 3.69-3.64 (m, 2H), 3.60-3.56 (m, 2H), 3.53-3.46 (m, 8H), 3.33 (s, 3H), 3.27-3.18 (m, 2H), 3.15-3.05 (m, 2H), 2.78-2.69 (m, 1H), 2.58-2.50 (m, 2H), 2.05-1.94 (m, 5H), 1.87-1.73 (m, 6H), 1.67-1.56 (m, 4H).

Example 22. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(2-((8-(2-((2-(2,6-dioxopiperidin-3-yl)-1,3-dioxoisoindolin-4-yl)amino)ethoxy)octyl)oxy)ethyl)piperidin-4-yl)-2-fluoro-5-methoxybenzamide

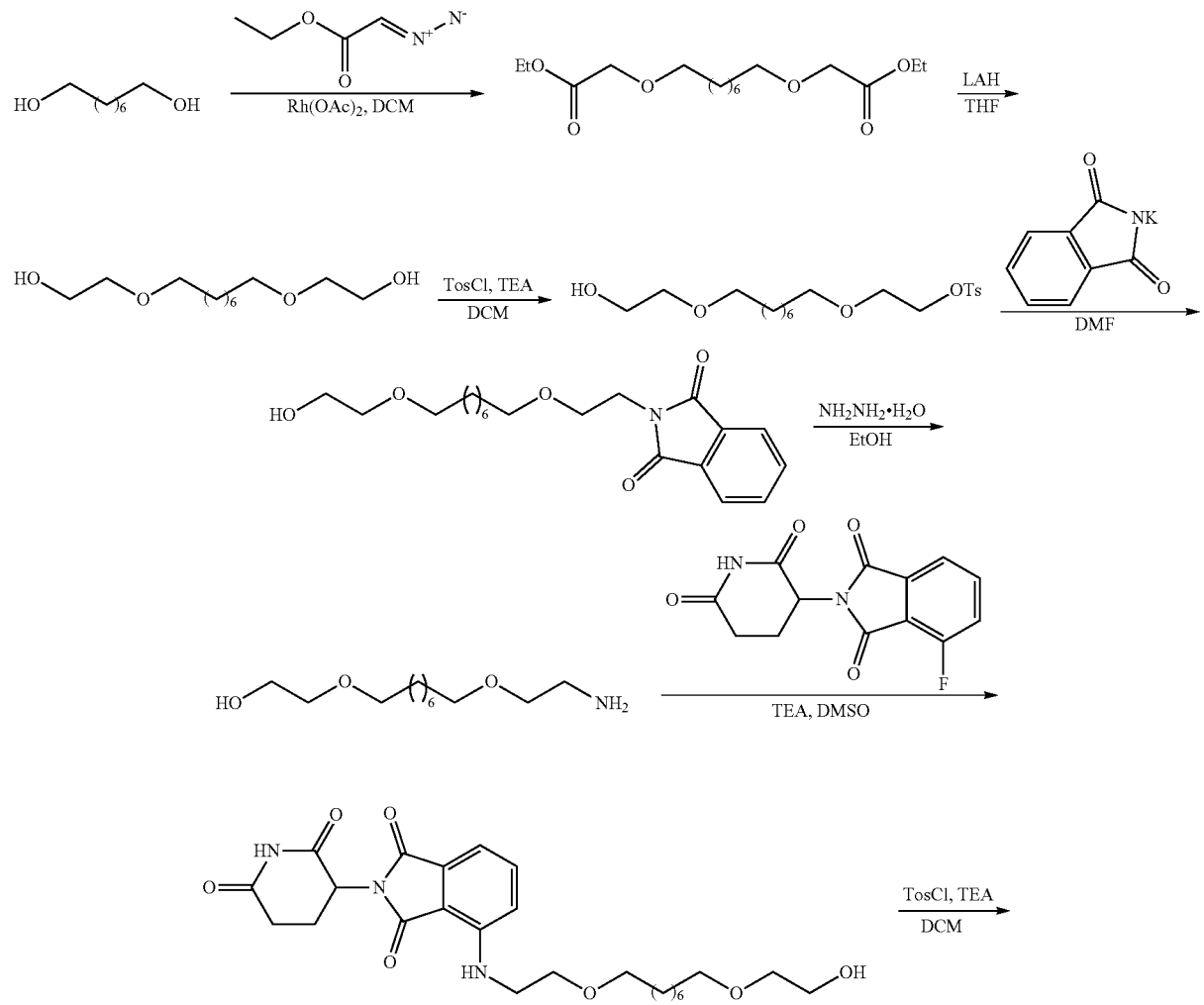

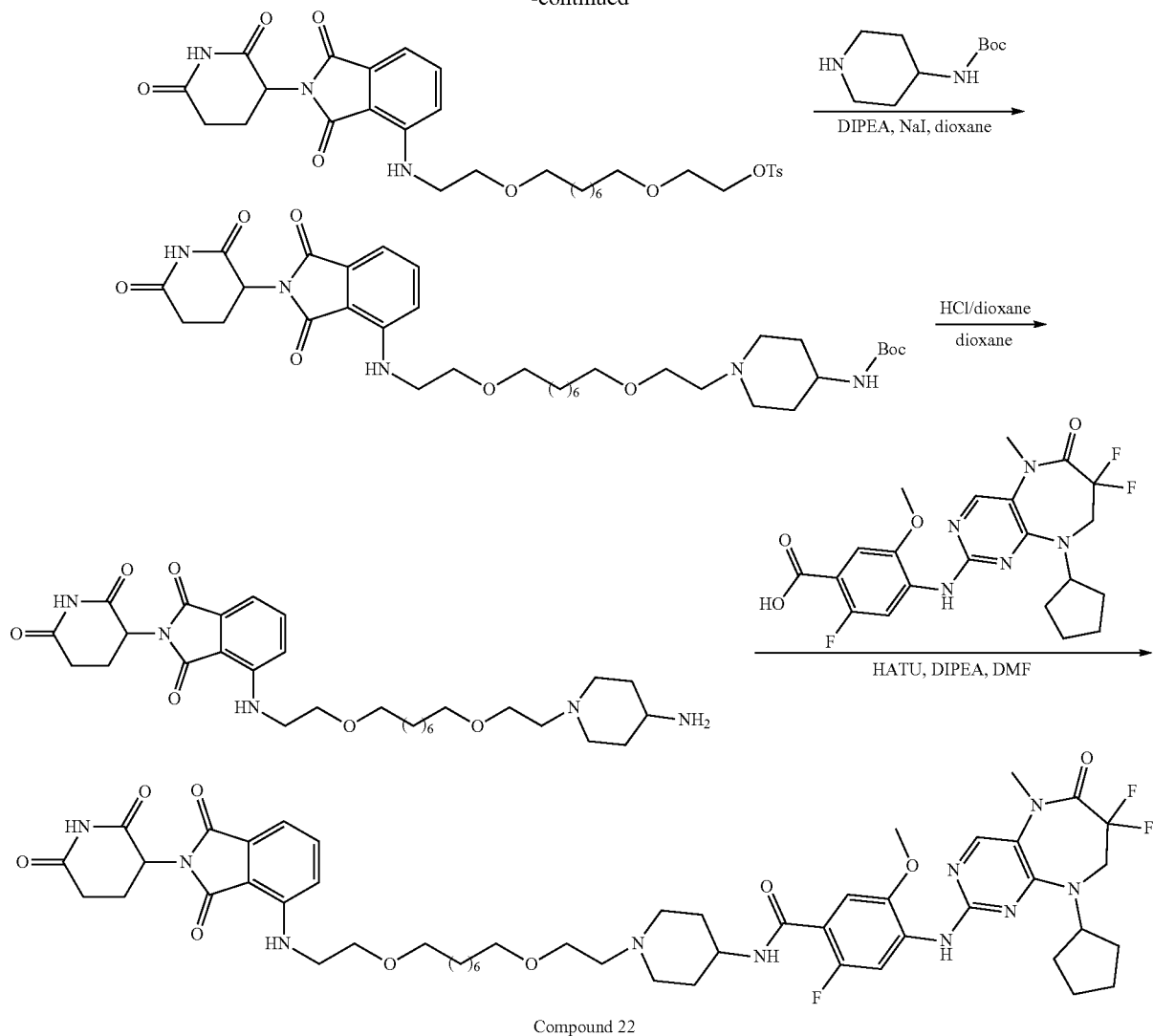

According to the above reaction scheme, in a manner similar to the other examples, obtained the titled compound (172.4 mg, 164.09 μmol, 55.14% yield, 97% purity) as yellow solid. MS(M+H)$^+$=1019.3.

$^1$H NMR (400 MHz, CDCl$_3$) δ=9.09 (s, 1H), 8.36 (d, J=15.2 Hz, 1H), 8.06 (s, 1H), 7.87 (s, 1H), 7.49-7.45 (m, 2H), 7.07 (d, J=6.8 Hz, 1H), 6.92-6.87 (m, 2H), 6.54-6.51 (m, 1H), 4.97-4.94 (m, 1H), 4.89-4.83 (m, 1H), 4.34-4.16 (m, 1H), 3.94-3.91 (m, 5H), 3.78-3.77 (m, 3H), 3.70-3.65 (m, 2H), 3.49-3.41 (m, 11H), 3.19-3.11 (m, 2H), 2.81-2.78 (m, 3H), 2.31-2.25 (m, 2H), 2.19-2.07 (m, 5H), 1.78-1.71 (m, 6H), 1.62-1.49 (m, 6H), 1.42-4.33 (m, 2H), 1.32-1.21 (m, 6H).

Example 23. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(4-(3-(2-(2-((2-(2,6-dioxopiperidin-3-yl)-1,3-dioxoisoindolin-4-yl)amino)ethoxy)ethoxy)propoxy)butyl)piperidin-4-yl)-2-fluoro-5-methoxybenzamide

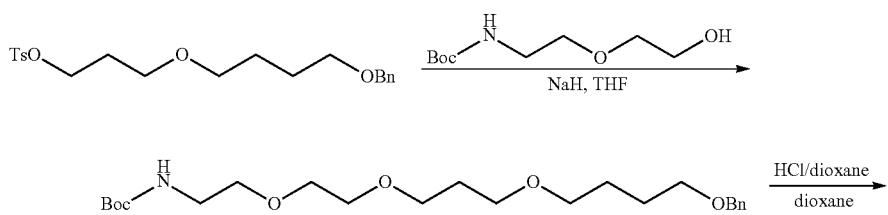

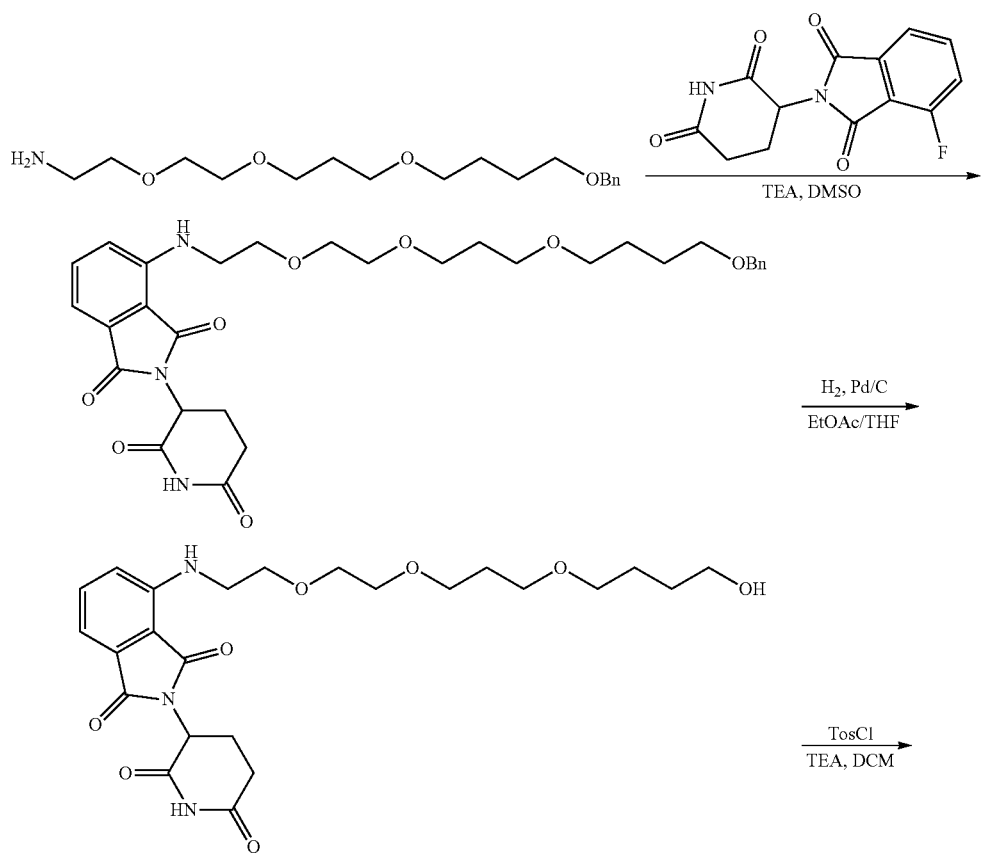
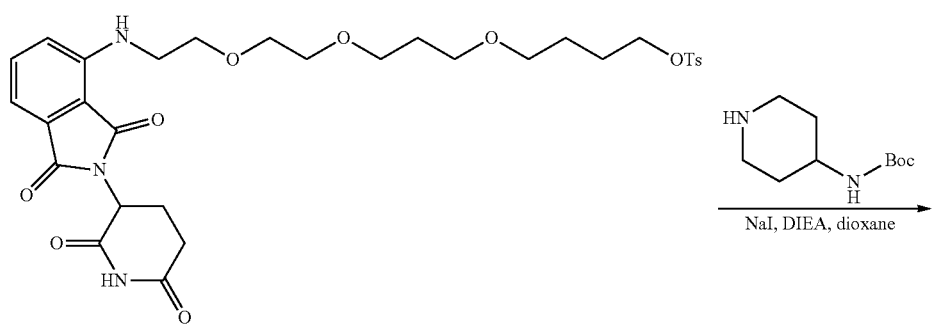
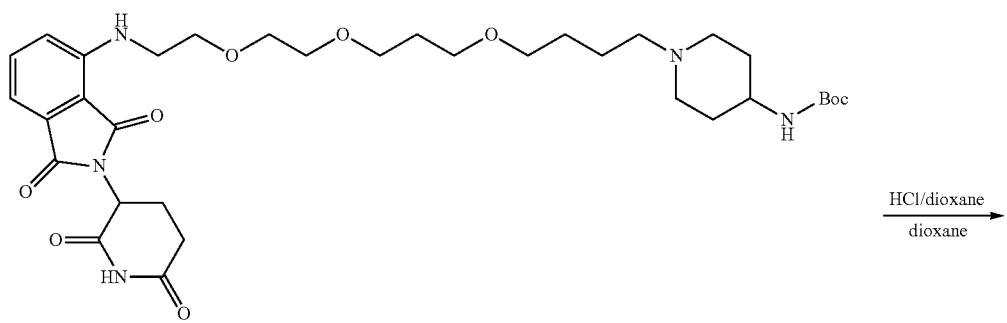

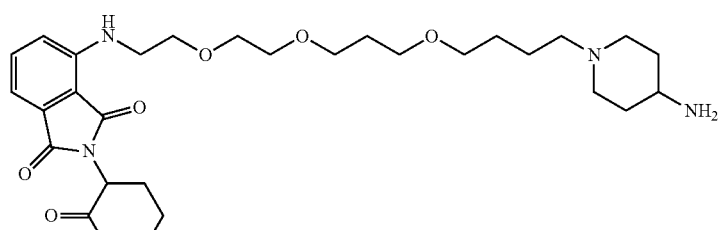
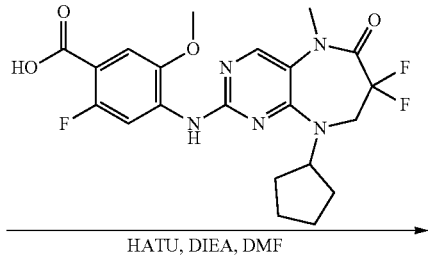

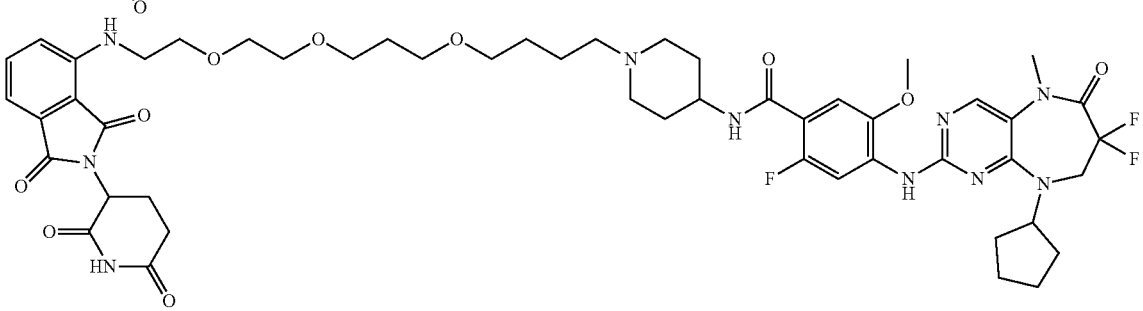

Compound 23

According to the above reaction scheme, in a manner similar to the other examples, obtained the titled compound (6.3 mg, 5.80 μmol, 8.85% yield, 94% purity, FA salt) as yellow solid. MS(M+H)$^+$=1021.8.

$^1$H NMR (400 MHz, DMSO-d$_6$) δ=11.10 (br s, 1H), 8.31 (s, 1H), 8.25 (d, J=13.2 Hz, 1H), 8.18 (s, 1H), 8.04 (s, 1H), 7.94-7.86 (m, 1H), 7.62-7.55 (m, 1H), 7.19 (d, J=6.6 Hz, 1H), 7.15 (d, J=8.6 Hz, 1H), 7.05 (d, J=7.0 Hz, 1H), 6.61 (t, J=5.6 Hz, 1H), 5.11-5.02 (m, 1H), 4.87-4.79 (m, 1H), 4.08 (t, J=14.0 Hz, 2H), 3.92 (s, 3H), 3.83-3.72 (m, 2H), 3.63 (t, J=5.3 Hz, 2H), 3.59-3.55 (m, 2H), 3.51-3.40 (m, 13H), 2.95-2.82 (m, 2H), 2.63-2.56 (m, 4H), 2.53 (s, 3H), 2.37-2.31 (m, 2H), 2.12-1.96 (m, 4H), 1.87-1.78 (m, 2H), 1.75-1.68 (m, 4H), 1.64-1.55 (m, 4H), 1.50-1.42 (m, 2H).

Example 24. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(3-(3-(2-((2-(2,6-dioxopiperidin-3-yl)-1,3-dioxoisoindolin-4-yl)amino)ethoxy)propoxy)propoxy)propyl)piperidin-4-yl)-2-fluoro-5-methoxybenzamide

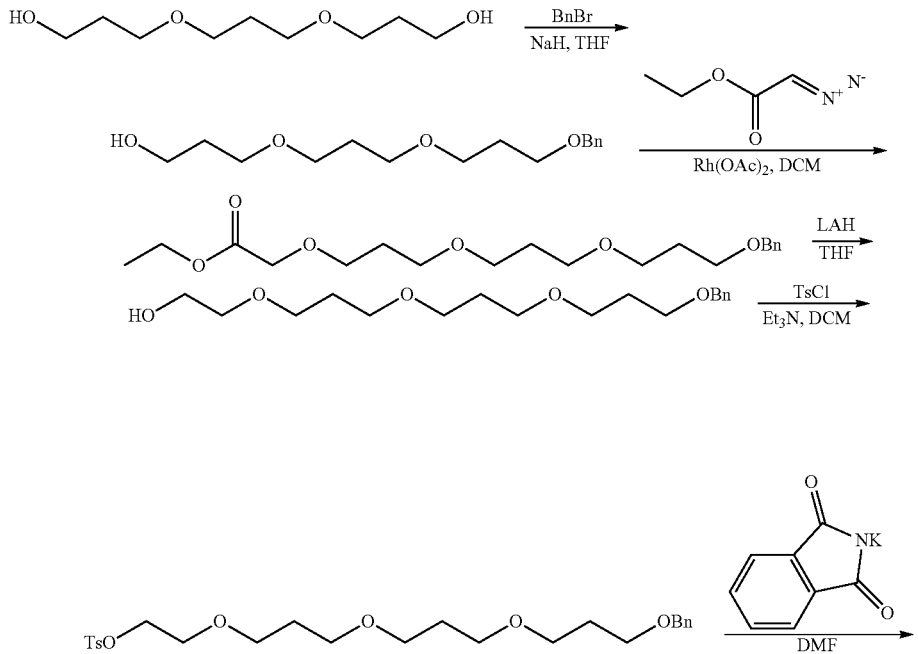

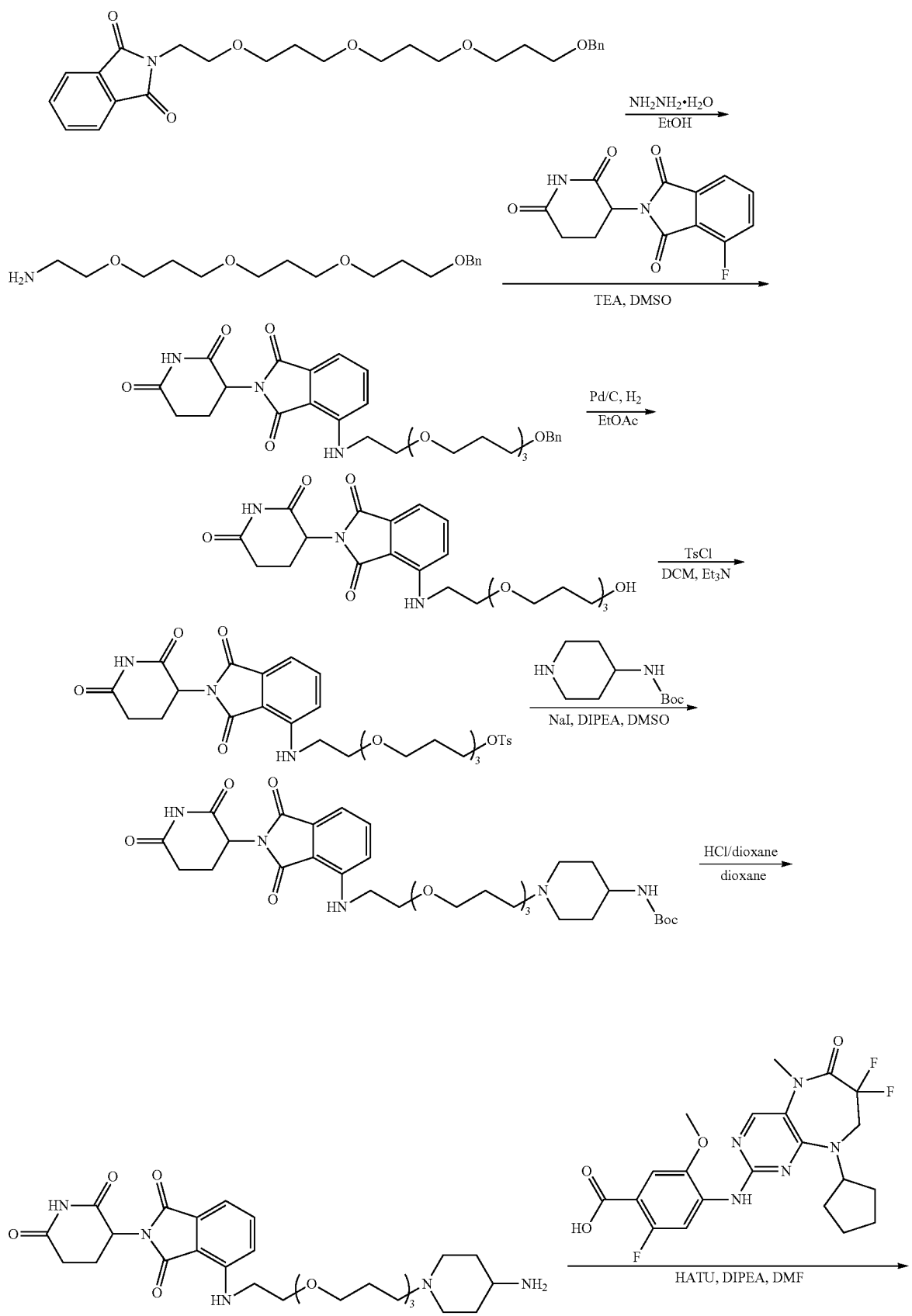

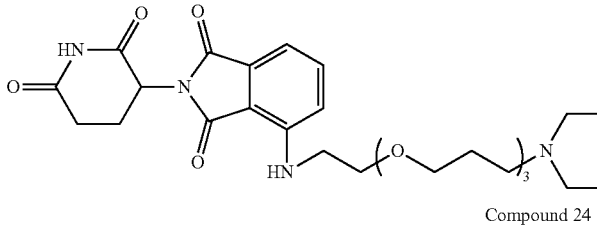

Compound 24

According to the above reaction scheme, in a manner similar to the other examples, obtained the titled compound (134.7 mg, 120.05 μmol, 35.21% yield, 91% purity) as yellow solid. MS(M+H)+=1021.7.

$^1$H NMR (400 MHz, CD$_3$OD) δ=8.41 (d, J=14.8 Hz, 1H), 8.21 (s, 1H), 7.56-7.52 (m, 1H), 7.33 (d, J=6.4 Hz, 1H), 7.09-7.04 (m, 2H), 5.08-5.06 (m, 1H), 4.94-4.92 (m, 1H), 4.62-4.55 (m, 2H), 4.24-4.12 (m, 1H), 4.07-3.98 (m, 5H), 3.70-3.66 (m, 2H), 3.57-3.48 (m, 14H), 3.04 (s, 3H), 3.26-3.25 (m, 2H), 3.15-3.10 (m, 1H), 2.76-2.72 (m, 1H), 2.70-2.65 (m, 2H), 2.21-2.28 (m, 2H), 2.11-2.18 (m, 3H), 2.03-1.97 (m, 2H), 1.80-1.75 (m, 4H), 1.69-1.62 (m, 4H).

Example 25. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(1-((2-(2,6-dioxopiperidin-3-yl)-1,3-dioxoisoindolin-4-yl)amino)-3,6,9,13-tetraoxapentadecan-15-yl)piperidin-4-yl)-2-fluoro-5-methoxybenzamide

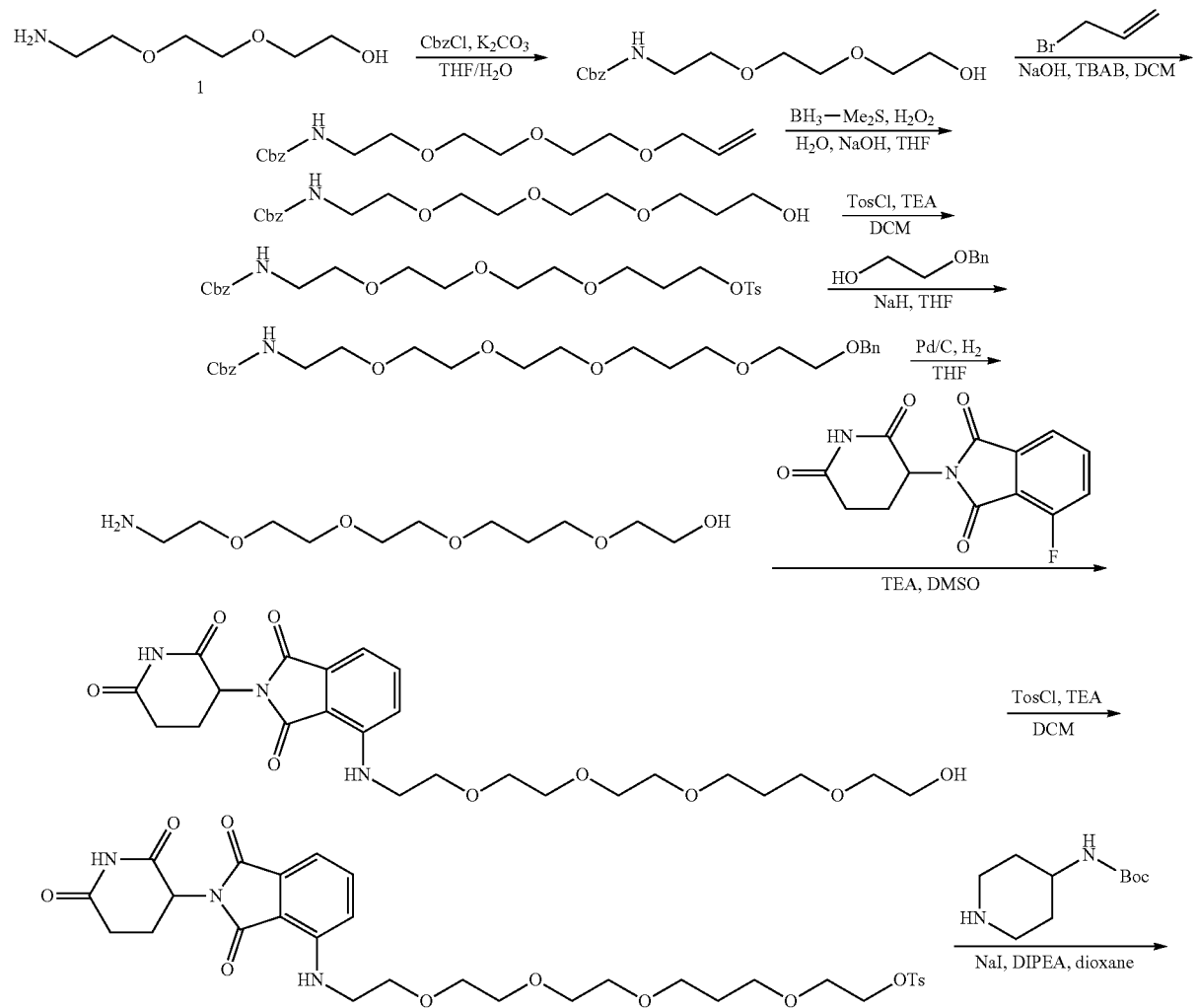

-continued

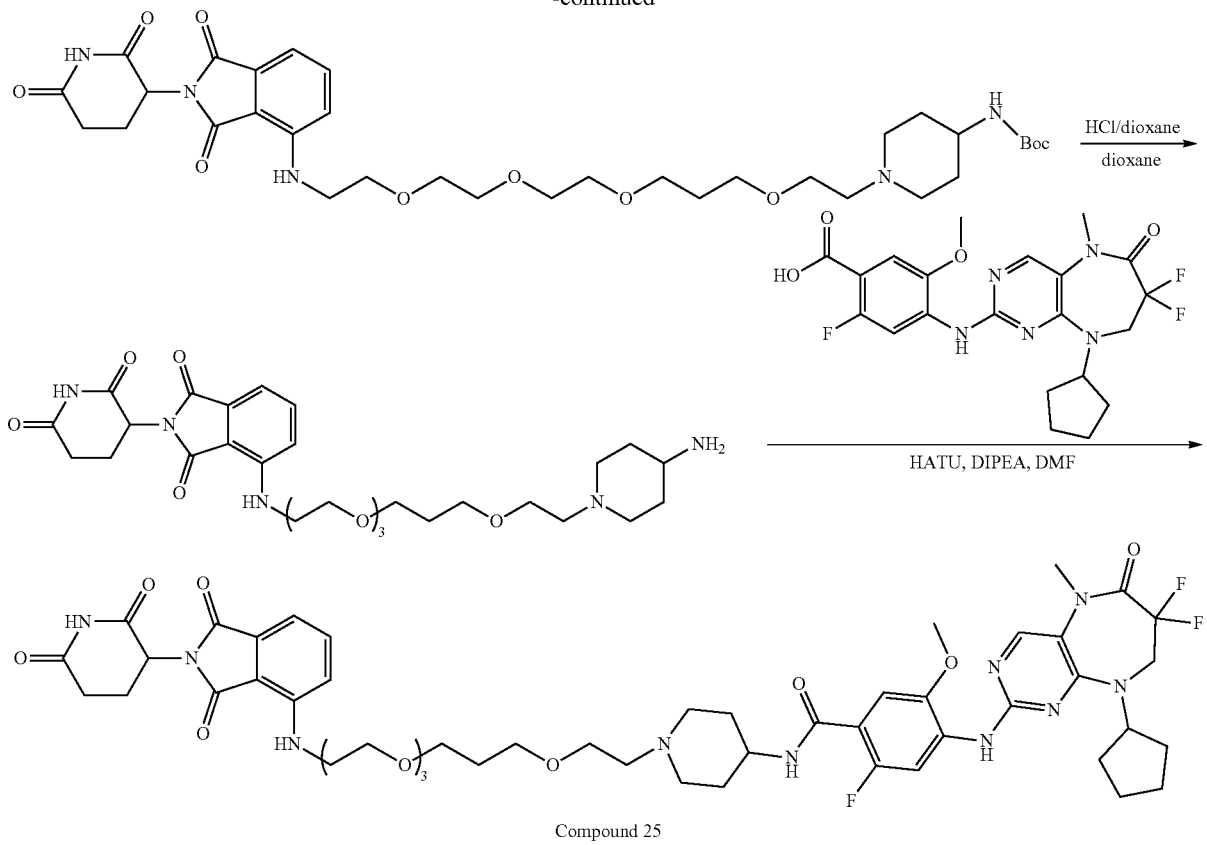

Compound 25

According to the above reaction scheme, in a manner similar to the other examples, obtained the titled compound (21.3 mg, 17.21 μmol, 11.44% yield, 93% purity, TFA) as a yellow solid. MS(M+H)$^+$=1037.5

$^1$H NMR (400 MHz, CD$_3$OD) δ=8.36-8.29 (m, 1H), 8.21 (s, 1H), 7.53 (dd, J=7.2, 8.6 Hz, 1H), 7.37-7.32 (m, 1H), 7.08-7.03 (m, 2H), 5.06 (dd, J=5.6, 12.6 Hz, 1H), 4.99-4.94 (m, 1H), 4.08 (t, J=13.0 Hz, 2H), 3.98 (s, 3H), 3.77-3.70 (m, 6H), 3.67-3.63 (m, 6H), 3.60-3.56 (m, 6H), 3.49 (t, J=5.4 Hz, 3H), 3.41 (s, 3H), 3.37-3.30 (m, 2H), 3.21-3.13 (m, 2H), 2.93-2.80 (m, 1H), 2.78-2.67 (m, 2H), 2.32-2.26 (m, 2H), 2.15-2.07 (m, 4H), 1.93-1.83 (m, 5H), 1.77-1.70 (m, 4H).

Example 26. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(2-(2-(2-((2-(2,6-dioxopiperidin-3-yl)-1,3-dioxoisoindolin-4-yl)amino)-2-oxoethoxy)ethoxy)ethyl)piperidin-4-yl)-2-fluoro-5-methoxybenzamide

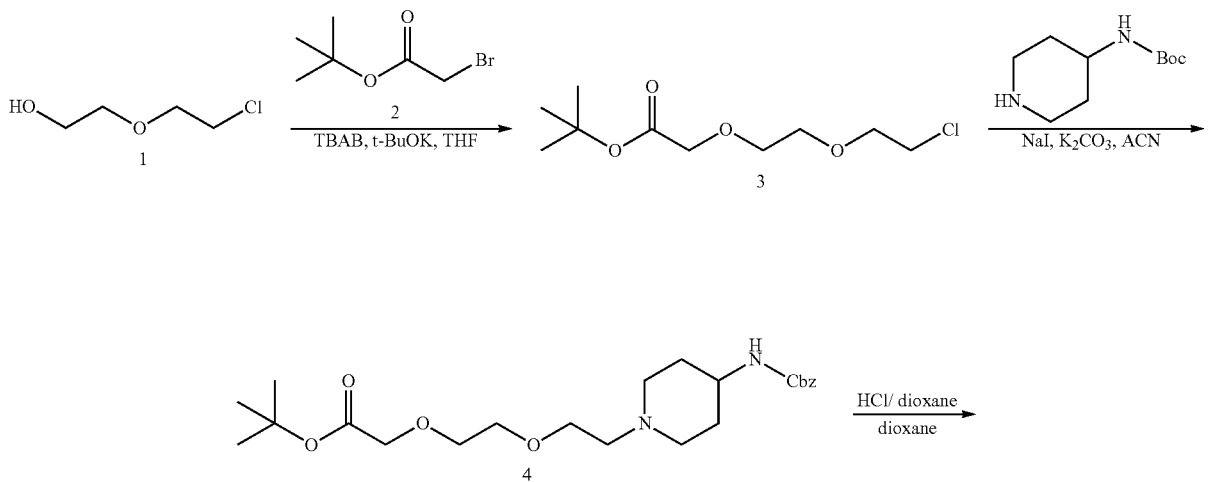

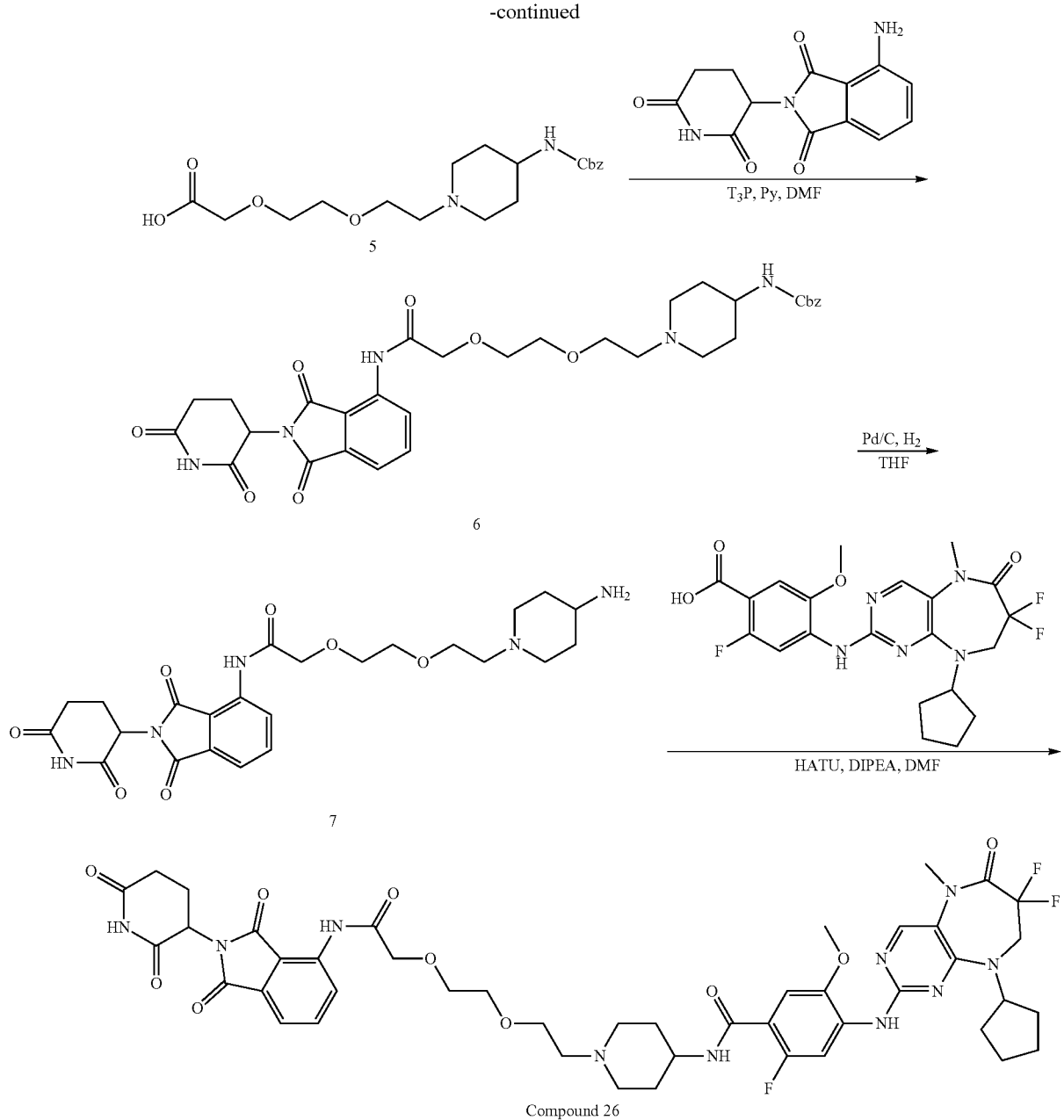

Compound 26

Step 1: Synthesis of tert-butyl 2-(2-(2-chloroethoxy)ethoxy)acetate (3)

To a mixture of 2-(2-chloroethoxy)ethanol (10 g, 80.28 mmol, 8.47 mL) and tert-butyl 2-bromoacetate (31.32 g, 160.56 mmol, 23.73 mL) in THF (100 mL) were added TBAB (25.88 g, 80.28 mmol) and t-BuOK (9.01 g, 80.28 mmol) in one portion at 20° C. and the resulting mixture was stirred at 20° C. for 16 h. TLC (SiO$_2$, Petroleum ether:Ethyl acetate=5:1) indicated 2-(2-chloroethoxy)ethanol remained and three new spots were detected. The reaction mixture was concentrated in vacuum. The residue was purified by column chromatography (SiO$_2$, Petroleum ether/Ethyl acetate=10/1 to 5/1) to afford the titled compound (3 g, 12.57 mmol, 15.66% yield) as a yellow oil.

Step 2: Synthesis of tert-butyl 2-(2-(2-(4-(((benzyloxy)carbonyl)amino)piperidin-1-yl)ethoxy)ethoxy)acetate (4)

To a mixture of tert-butyl 2-(2-(2-chloroethoxy)ethoxy)acetate (1.5 g, 6.28 mmol) and benzyl piperidin-4-ylcarbamate (1.77 g, 7.54 mmol) in ACN (20 mL) was added K$_2$CO$_3$ (2.61 g, 18.85 mmol) in one portion at 20° C. and the resulting mixture was stirred at 60° C. for 16 h. LCMS showed 64% of tert-butyl 2-(2-(2-chloroethoxy)ethoxy)acetate remained and 14% peak with desired mass was detected. NaI (188.38 mg, 1.26 mmol) was added to this reaction mixture at 20° C. and the resulting mixture was stirred at 80° C. for 12 h. LCMS showed 51% of tert-butyl 2-(2-(2-chloroethoxy)ethoxy)acetate remained and 36% desired mass was detected and the reaction mixture was concentrated in vacuum. The residue was diluted with dioxane (20 mL) at 20° C. and the resulting mixture was stirred at 90° C. for 16 h. LCMS showed 46% of tert-butyl 2-(2-(2-chloroethoxy)ethoxy)acetate remained and 38% desired mass was detected. The reaction mixture was concentrated in vacuum. The residue was purified by column chromatography (SiO$_2$, Petroleum ether/Ethyl acetate=3/1 to 0/1) to afford the titled compound (860 mg, 1.77 mmol, 28.22% yield, 90% purity) as a yellow oil. MS(M+H)$^+$=437.2

Step 3: Synthesis of 2-(2-(2-(4-(((benzyloxy)carbonyl)amino)piperidin-1-yl)ethoxy)ethoxy)acetic acid (5)

To a mixture of tert-butyl 2-(2-(2-(4-(((benzyloxy)carbonyl)amino)piperidin-1-yl)ethoxy)ethoxy)acetate (750 mg, 1.72 mmol) in dioxane (5 mL) was added HCl/dioxane (4 M, 10 mL) in one portion at 20° C. and the resulting mixture was stirred at 20° C. for 2 h. LCMS showed starting material was consumed completely and one peak with desired mass was detected. The reaction mixture was concentrated in vacuum to afford the titled compound (680 mg, crude) as a yellow oil. MS(M+H)$^+$=381.2

Step 4: Synthesis of benzyl (1-(2-(2-(2-((2-(2,6-dioxopiperidin-3-yl)-1,3-dioxoisoindolin-4-yl)amino)-2-oxoethoxy)ethoxy)ethyl)piperidin-4-yl)carbamate (6)

To a mixture of 2-(2-(2-(4-(((benzyloxy)carbonyl)amino)piperidin-1-yl)ethoxy)ethoxy)acetic acid (650 mg, 1.71 mmol) and 4-amino-2-(2,6-dioxopiperidin-3-yl)isoindoline-1,3-dione (560.23 mg, 2.05 mmol) in DMF (4 mL) were added T$_3$P (6.52 g, 10.25 mmol, 6.10 mL, 50% purity in EtOAc solution) and Py (1.35 g, 17.09 mmol, 1.38 mL) in one portion at 20° C. and the resulting mixture was stirred at 80° C. for 16 h. LCMS showed all starting material was consumed completely and one peak with desired mass was detected. The reaction mixture was diluted with H$_2$O (15 mL) and extracted with EtOAc (15 mL×3). The organic layer was washed with brine (15 mL×3), dried over Na$_2$SO$_4$, filtered and concentrated. The crude product was purified by prep-HPLC (column: Phenomenex luna C$_{18}$ 150*40 mm*15 um; mobile phase: [water (0.1% TFA)-ACN]; B %: 17%-47%, 10 min) and then lyophilized to afford the titled compound (910 mg, 1.40 mmol, 82.11% yield, 98% purity) as a yellow solid. MS(M+H)$^+$=636.1

$^1$H NMR (400 MHz, CD$_3$OD) δ=8.79 (d, J=8.6 Hz, 1H), 7.84-7.76 (m, 1H), 7.61 (d, J=7.4 Hz, 1H), 7.34-7.26 (m, 5H), 5.15 (dd, J=5.6, 12.8 Hz, 1H), 5.04 (s, 2H), 4.22 (s, 2H), 3.90 (t, J=5.0 Hz, 2H), 3.85-3.83 (m, 3H), 3.75-3.54 (m, 3H), 3.50-3.33 (m, 2H), 3.29-3.05 (m, 2H), 2.94-2.65 (m, 3H), 2.24-1.91 (m, 4H), 1.86-1.56 (m, 2H)

Step 5: Synthesis of 2-(2-(2-(4-aminopiperidin-1-yl)ethoxy)ethoxy)-N-(2-(2,6-dioxopiperidin-3-yl)-1,3-dioxoisoindolin-4-yl)acetamide (7)

To a solution of benzyl (1-(2-(2-(2-((2-(2,6-dioxopiperidin-3-yl)-1,3-dioxoisoindolin-4-yl)amino)-2-oxoethoxy)ethoxy)ethyl)piperidin-4-yl)carbamate (810 mg, 1.27 mmol) in THF (10 mL) was added Pd/C (0.1 g, 10% purity) under N$_2$. The suspension was degassed under vacuum and purged with H$_2$ several times. The mixture was stirred under H$_2$ (15 psi) at 20° C. for 16 h. LCMS showed 72% of starting material remained and 18% peak with desired mass was detected. Pd/C (0.4 g, 127.43 μmol, 10% purity) was added to this reaction mixture under N$_2$. The reaction mixture was stirred under H$_2$ (15 psi) at 20° C. for 16 h. LCMS showed starting material was consumed completely and one peak with desired mass was detected. The reaction mixture was diluted with THF (20 mL) and filtered. The filtrate was concentrated in vacuum to afford the titled compound (563 mg, 1.04 mmol, 81.93% yield, 93% purity) as a yellow solid. MS(M+H)$^+$=502.1

Step 6: Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(2-(2-(2-((2-(2,6-dioxopiperidin-3-yl)-1,3-dioxoisoindolin-4-yl)amino)-2-oxoethoxy)ethoxy)ethyl)piperidin-4-yl)-2-fluoro-5-methoxybenzamide (Compound 26)

To a solution of 4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzoic acid (120 mg, 257.83 μmol) in DMF (2 mL) were added HATU (98.03 mg, 257.83 μmol) and DIPEA (99.97 mg, 773.49 μmol, 134.73 μL). The mixture was stirred at 20° C. for 10 min and a solution of 2-(2-(2-(4-aminopiperidin-1-yl)ethoxy)ethoxy)-N-(2-(2,6-dioxopiperidin-3-yl)-1,3-dioxoisoindolin-4-yl)acetamide (168.10 mg, crude) in DMF (2 mL) were added drop-wise at 20° C. and the resulting mixture was stirred at 20° C. for 1 h. LCMS showed all starting material was consumed completely and one peak with desired mass was detected. The reaction mixture was diluted with H$_2$O (10 mL×3) and extracted with EtOAc (10 mL×3). The organic layer was dried over Na$_2$SO$_4$, filtered and concentrated. The residue was purified by prep-HPLC (column: 3_Phenomenex Luna C$_{18}$ 75*30 mm*3 um; mobile phase: [water (0.1% TFA)-ACN]; B %: 34%-54%, 7 min) and then lyophilized to afford the titled compound (105.3 mg, 95.10 μmol, 36.88% yield, 96% purity, TFA) as a white solid. MS(M+H)$^+$=949.0

$^1$H NMR (400 MHz, CD$_3$OD) δ=8.85-8.74 (m, 1H), 8.38-8.29 (m, 1H), 8.23-8.20 (m, 1H), 7.83-7.76 (m, 1H), 7.62-7.53 (m, 1H), 7.31 (d, J=6.8 Hz, 1H), 5.17 (dd, J=5.4, 12.8 Hz, 1H), 4.99-4.94 (m, 1H), 4.26-4.21 (m, 2H), 4.08 (t, J=13.2 Hz, 2H), 3.99 (s, 3H), 3.93 (t, J=4.8 Hz, 2H), 3.90-3.84 (m, 4H), 3.73-3.69 (m, 1H), 3.50-3.44 (m, 1H), 3.40 (s, 3H), 3.39-3.35 (m, 2H), 3.25-3.11 (m, 2H), 2.96-2.69 (m, 3H), 2.26-2.03 (m, 6H), 1.93-1.78 (m, 4H), 1.76-1.66 (m, 4H)

Example 27. Synthesis of 14-(4-(4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzamido)piperidin-1-yl)-N-(2-(2,6-dioxopiperidin-3-yl)-1,3-dioxoisoindolin-4-yl)-3,6,9,12-tetraoxatetradecanamide

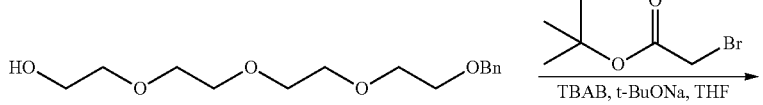
TBAB, t-BuONa, THF

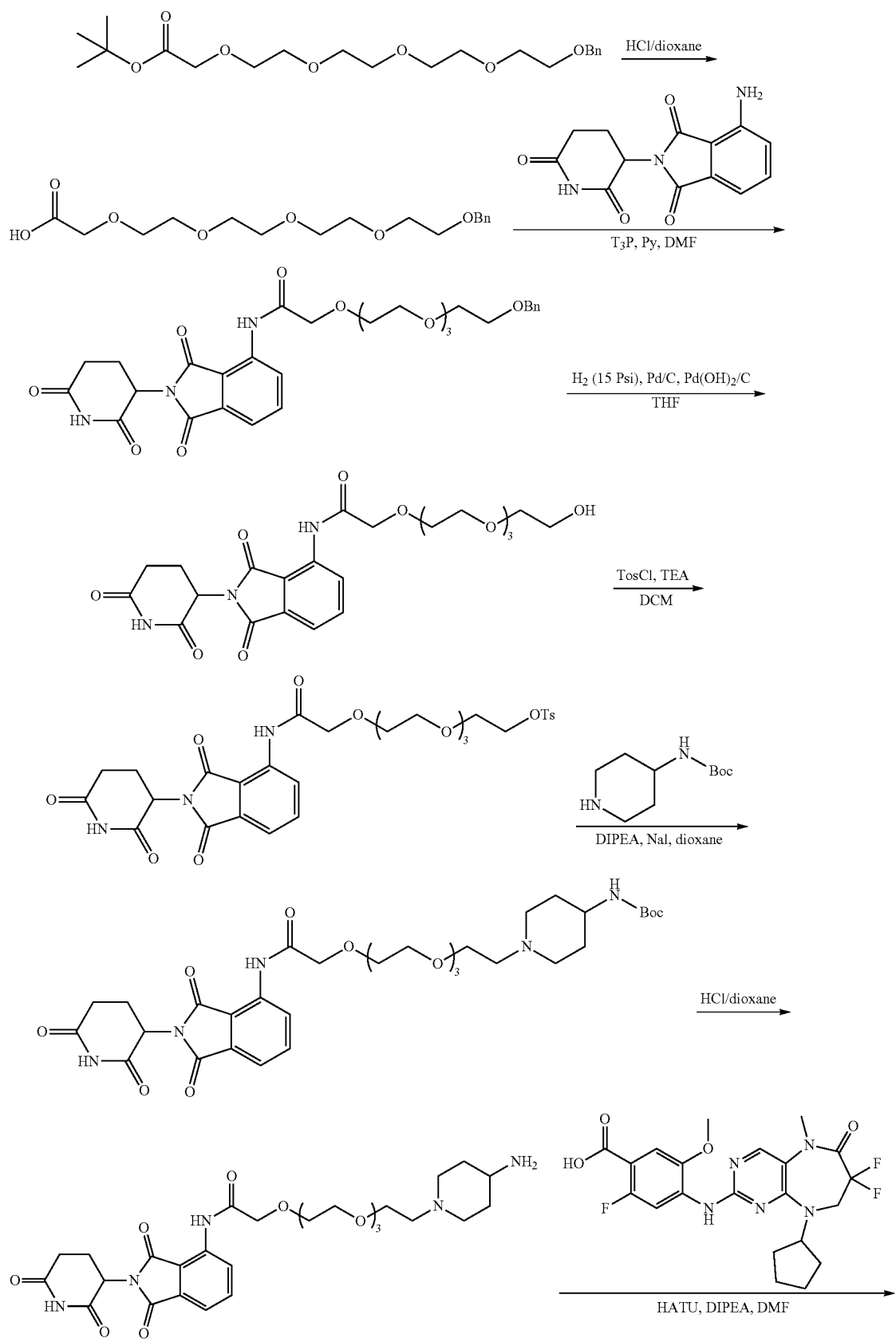

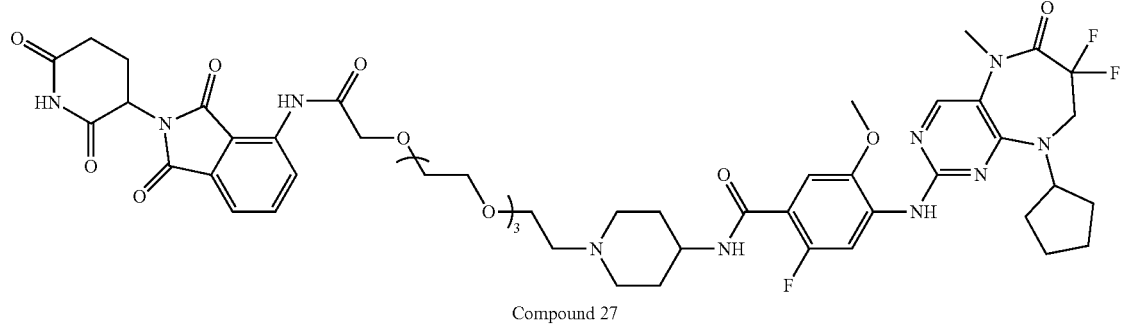

Compound 27

According to the above reaction scheme, in a manner similar to the other examples, obtained the titled compound (22.6 mg, 20.70 μmol, 9.64% yield, 95% purity) as white solid. MS(M+H)+=1037.3

¹H NMR (400 MHz, DMSO-d₆) δ=11.20 (br s, 1H), 10.36 (s, 1H), 8.72 (d, J=8.4 Hz, 1H), 8.29 (s, 1H), 8.23 (d, J=13.4 Hz, 1H), 8.04 (s, 1H), 7.94-7.81 (m, 2H), 7.62 (d, J=7.6 Hz, 1H), 7.17 (d, J=6.8 Hz, 1H), 5.16 (dd, J=5.6, 12.8 Hz, 1H), 4.88-4.73 (m, 1H), 4.20 (s, 2H), 4.08 (t, J=13.6 Hz, 2H), 3.90 (s, 3H), 3.80-3.73 (m, 2H), 3.72-3.63 (m, 3H), 3.58-3.35 (m, 12H), 2.95-2.79 (m, 3H), 2.69-2.53 (m, 2H), 2.43 (t, J=5.9 Hz, 2H), 2.14-1.99 (m, 3H), 1.97-1.87 (m, 2H), 1.79-1.69 (m, 4H), 1.69-1.44 (m, 7H).

Example 28. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(2-((8-(2-((2-(2,6-dioxopiperidin-3-yl)-1,3-dioxoisoindolin-4-yl)amino)-2-oxoethoxy)octyl)oxy)ethyl)piperidin-4-yl)-2-fluoro-5-methoxybenzamide

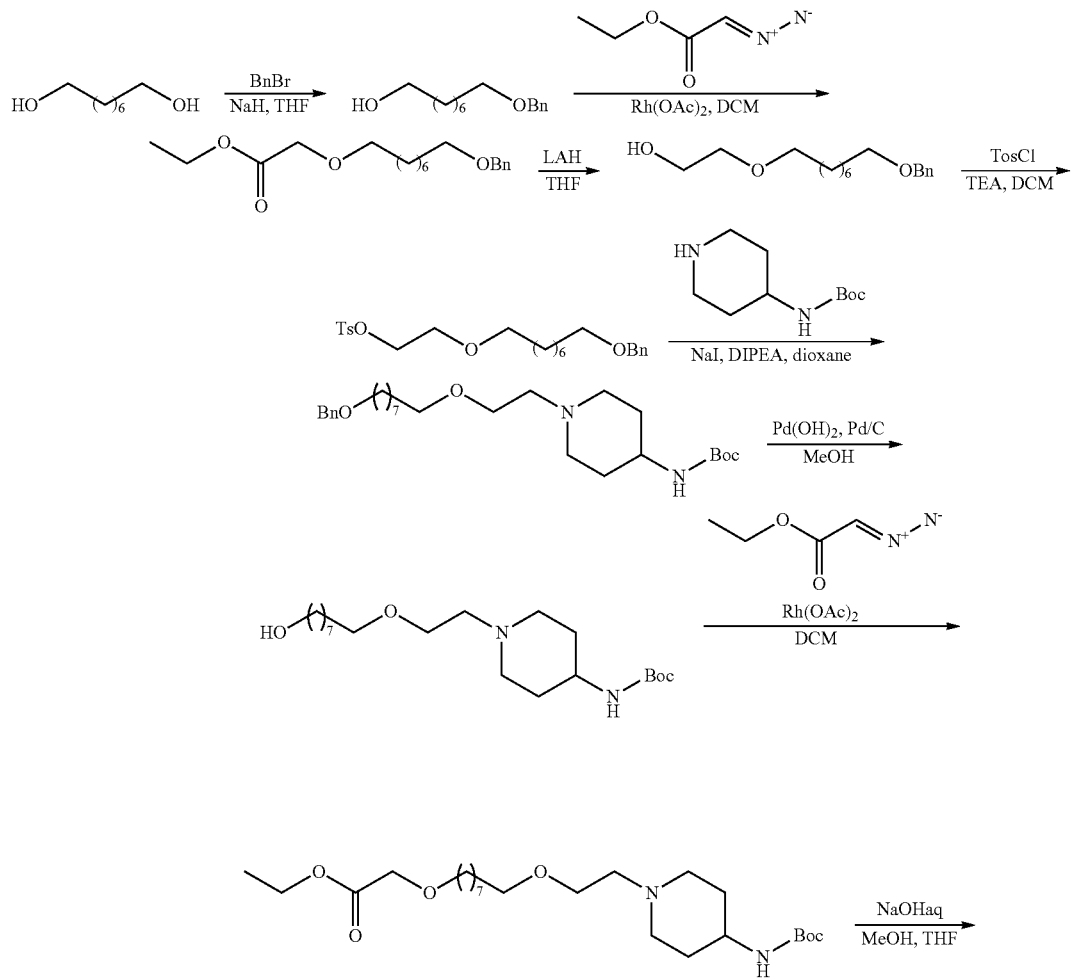

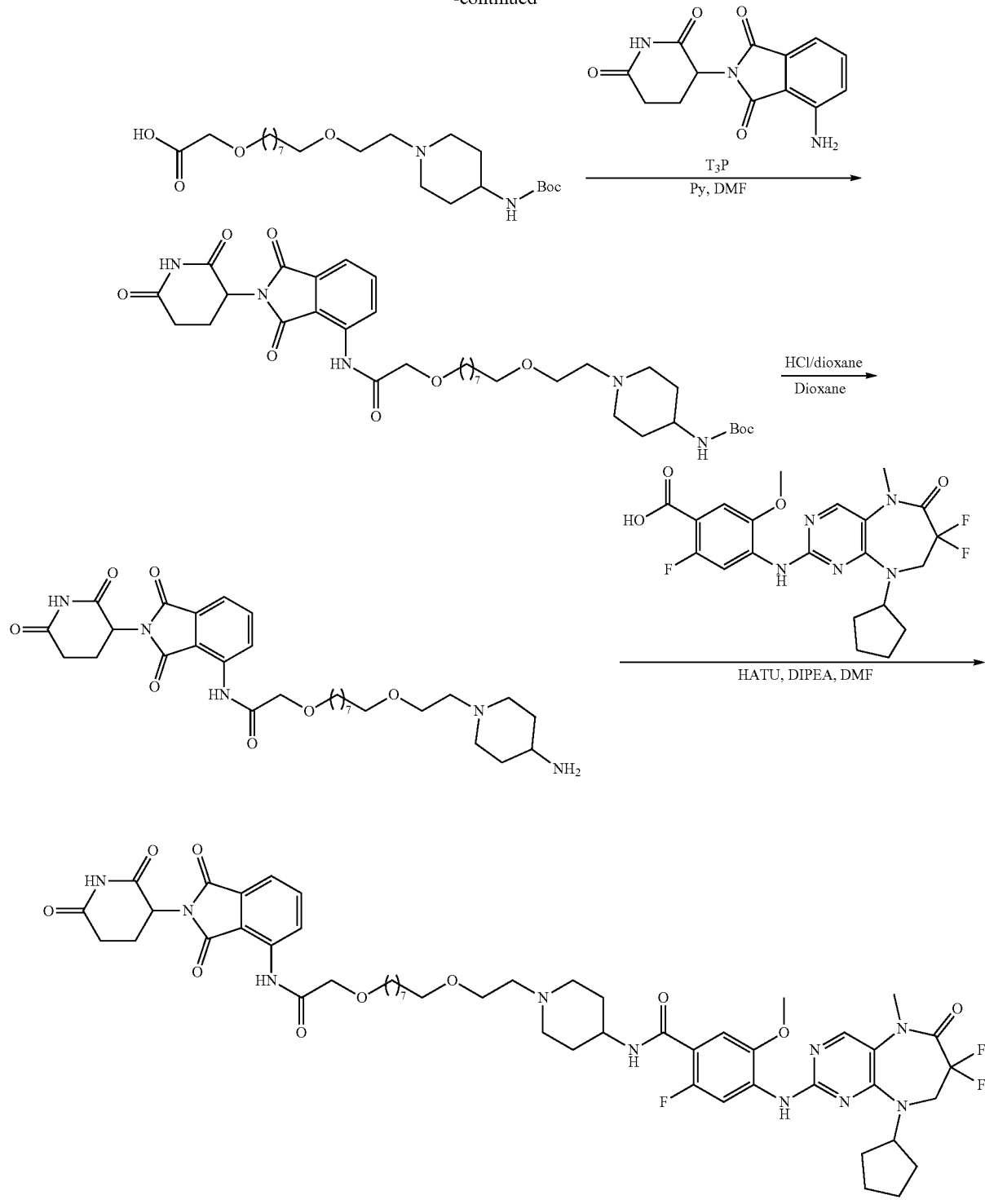
Compound 28
According to the above reaction scheme, in a manner similar to the other examples, obtained the titled compound (14.1 mg, 12.15 μmol, 6.30% yield, 89% purity) as white solid. MS (M+H)$^+$=1033.4
$^1$H NMR (400 MHz, DMSO-d$_6$) δ=11.17 (s, 1H), 10.35 (s, 1H), 8.74 (d, J=8.4 Hz, 1H), 8.30 (s, 1H), 8.24 (d, J=13.6 Hz, 1H), 8.03 (s, 1H), 7.89-7.84 (m, 2H), 7.63 (d, J=7.2 Hz, 1H), 7.18 (d, J=6.4 Hz, 1H), 5.18-5.14 (m, 1H), 4.86-4.77 (m, 1H), 4.14-4.08 (m, 5H), 3.91 (s, 4H), 3.76-3.69 (m, 1H), 3.61-3.57 (m, 3H), 3.46-3.43 (m, 1H), 2.88-2.86 (m, 2H), 2.63-2.54 (m, 2H), 2.15-2.10 (m, 2H), 2.05-1.95 (m, 2H), 1.76-1.73 (m, 5H), 1.65-1.61 (m, 10H), 1.47-1.39 (m, 5H), 1.28-1.19 (m, 9H).

Example 29. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(2-(2-(2-((2-(2,6-dioxopiperidin-3-yl)-1,3-dioxoisoindolin-4-yl)amino)acetamido)ethoxy)ethyl)piperidin-4-yl)-2-fluoro-5-methoxybenzamide
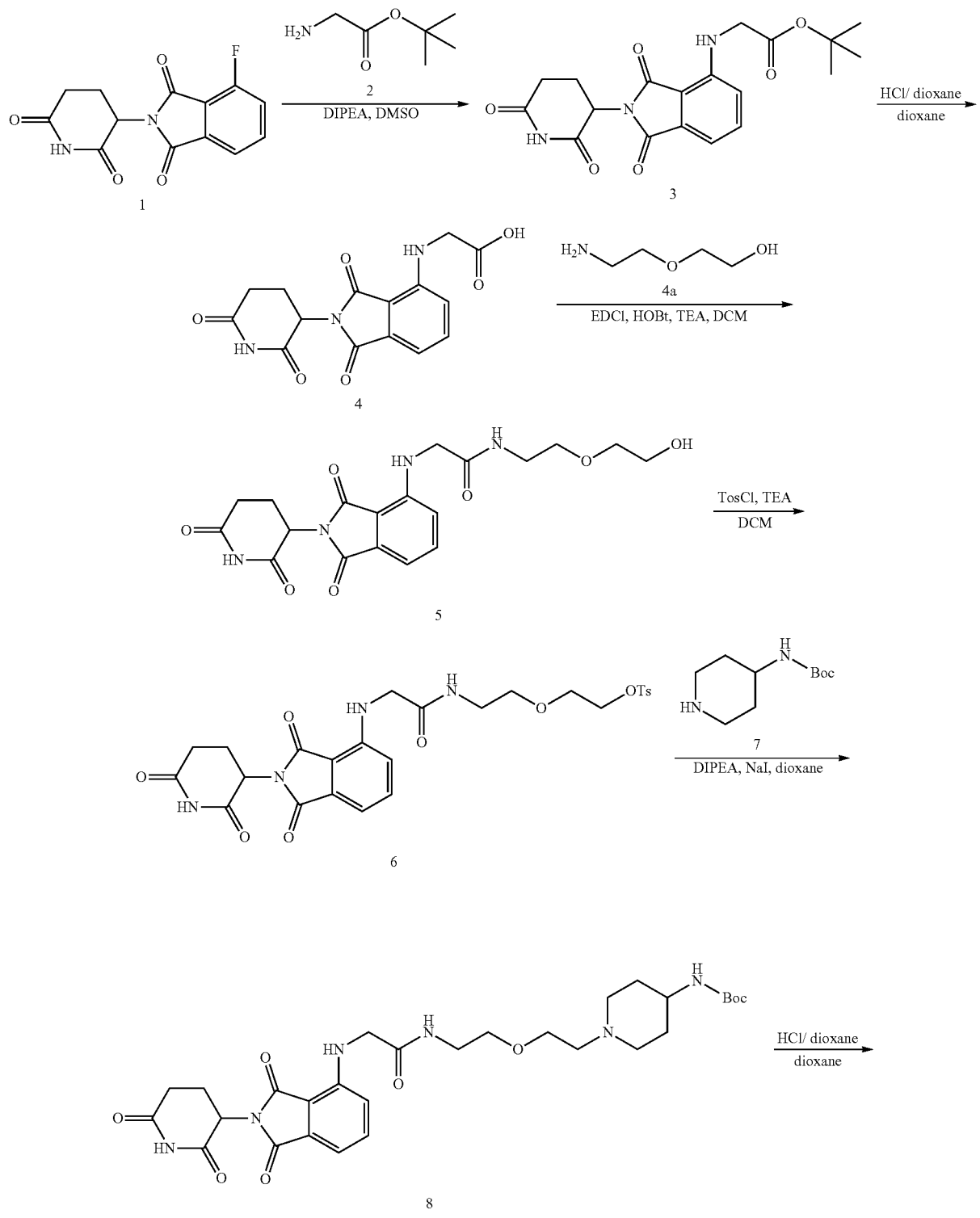

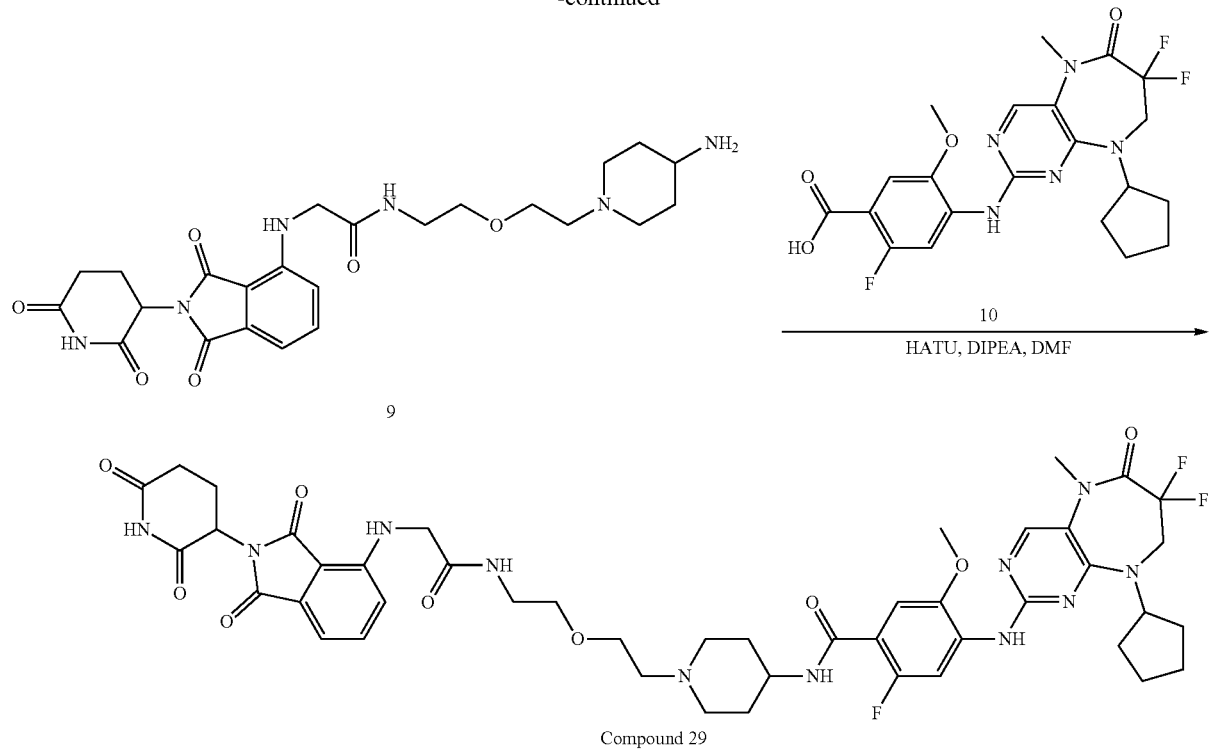

Compound 29

Step 1: Synthesis of tert-butyl 2-((2-(2,6-dioxopiperidin-3-yl)-1,3-dioxoisoindolin-4-yl)amino)acetate (3)

To a solution of 2-(2,6-dioxopiperidin-3-yl)-4-fluoroisoindoline-1,3-dione (5 g, 18.10 mmol) and tert-butyl 2-aminoacetate (2.37 g, 18.10 mmol) in DMSO (50 mL) was added DIPEA (4.68 g, 36.20 mmol, 6.31 mL). The reaction mixture was stirred at 90° C. for 24 h. LCMS showed 51% of desired mass was detected. The mixture was poured into H$_2$O (100 mL) and extracted with ethyl acetate (50 mL×3). The combined organic phase was washed with brine (30 mL×3), dried over Na$_2$SO$_4$, filtered. The filtrate was concentrated under reduced pressure. The residue was purified by silica gel column chromatography (1000 mesh silica gel, eluted with petroleum ether:ethyl acetate=10:1 to 1:1) to afford the titled compound (4.4 g, crude) as green solid. MS(M−56+H)$^+$=332.0

Step 2: Synthesis of 2-((2-(2,6-dioxopiperidin-3-yl)-1,3-dioxoisoindolin-4-yl)amino)acetic acid (4)

To a solution of tert-butyl 2-((2-(2,6-dioxopiperidin-3-yl)-1,3-dioxoisoindolin-4-yl)amino)acetate (4 g, 10.33 mmol) in dioxane (5 mL) was added HCl/dioxane (4 M, 40 mL) and the resulting mixture was stirred at 25° C. for 2 h. LCMS showed one peak (72%) with desired mass. The mixture was concentrated under reduced pressure. The residue was triturated with petroleum ether:ethyl acetate (10:1, 40 mL) and stirred for 20 min. Then the suspension was filtrated. The filter cake was collected and dried in vacuo to the titled compound (3.3 g, crude) as yellow solid. MS(M+H)$^+$=332.0

Step 3: Synthesis of 2-((2-(2,6-dioxopiperidin-3-yl)-1,3-dioxoisoindolin-4-yl)amino)-N-(2-(2-hydroxyethoxy)ethyl)acetamide (5)

To a mixture of 2-((2-(2,6-dioxopiperidin-3-yl)-1,3-dioxoisoindolin-4-yl)amino)acetic acid (3.15 g, 9.51 mmol) and 2-(2-aminoethoxy)ethanol (1.40 g, 13.31 mmol, 1.33 mL) in DCM (40 mL) were added HOBt (1.54 g, 11.41 mmol), EDCI (2.19 g, 11.41 mmol) and TEA (2.89 g, 28.53 mmol, 3.97 mL) and the resulting mixture was stirred at 25° C. for 12 h. LCMS showed one peak (83%) with desired mass. The mixture was concentrated under reduced pressure. The residue was purified by reversed-phase HPLC (0.1% FA condition) to the titled compound (1.79 g, 4.28 mmol, 44.99% yield, 100% purity) as green solid. MS(M+H)$^+$=419.2

Step 4: Synthesis of 2-(2-(2-((2-(2,6-dioxopiperidin-3-yl)-1,3-dioxoisoindolin-4-yl)amino)acetamido)ethoxy)ethyl 4-methylbenzenesulfonate (6)

To a solution of 2-((2-(2,6-dioxopiperidin-3-yl)-1,3-dioxoisoindolin-4-yl)amino)-N-(2-(2-hydroxyethoxy)ethyl)acetamide (1.69 g, 4.04 mmol) and TEA (1.63 g, 16.16 mmol, 2.25 mL) in DCM (20 mL) was added TosCl (3.08 g, 16.16 mmol) at 25° C. The solution was stirred at 25° C. for 12 h. LCMS showed the starting material was consumed completely, and a peak (15%) with desired mass. The mixture was concentrated under reduced pressure. The residue was purified by silica gel column chromatography (1000 mesh silica gel, eluted with petroleum ether:ethyl acetate=3:1 to 0:1) to afford the titled compound (1.7 g, 2.67 mmol, 66.15% yield, 90% purity) as brown oil. MS(M+H)$^+$=573.1

Step 5: Synthesis of tert-butyl (1-(2-(2-(2-((2-(2,6-dioxopiperidin-3-yl)-1,3-dioxoisoindolin-4-yl)amino)acetamido)ethoxy)ethyl)piperidin-4-yl)carbamate (8)

To a solution of 2-(2-(2-((2-(2,6-dioxopiperidin-3-yl)-1,3-dioxoisoindolin-4-yl)amino)acetamido)ethoxy)ethyl 4-methylbenzenesulfonate (787.00 mg, 3.93 mmol) tert-butyl N-(4-piperidyl)carbamate (787.00 mg, 3.93 mmol) in dioxane (20 mL) were added DIPEA (1.02 g, 7.86 mmol, 1.37 mL) and NaI (196.34 mg, 1.31 mmol). The reaction mixture was stirred at 100° C. for 16 h. LCMS showed one peak (72%) with desired mass. The mixture was concentrated under reduced pressure. The residue was purified by silica gel column chromatography (1000 mesh silica gel, eluted with petroleum ether:ethyl acetate=5:1 to 0:1; ethyl acetate:methanol=10:1) to afford the titled compound (0.8 g, 1.31 mmol, 49.82% yield, 98% purity) as green solid. MS(M+H)$^+$=601.2

Step 6: Synthesis of N-(2-(2-(4-aminopiperidin-1-yl)ethoxy)ethyl)-2-((2-(2,6-dioxopiperidin-3-yl)-1,3-dioxoisoindolin-4-yl)amino)acetamide (9)

A solution of tert-butyl (1-(2-(2-(2-((2-(2,6-dioxopiperidin-3-yl)-1,3-dioxoisoindolin-4-yl)amino)acetamido)ethoxy)ethyl)piperidin-4-yl)carbamate (1.2 g, 2.00 mmol) in HCl/dioxane (4 M, 40 mL) was stirred at 25° C. for 2 h. LCMS showed one peak (41%) with desired mass. The mixture was concentrated under reduced pressure. The residue was purified by reversed-phase HPLC (0.1% HCl condition) to afford the titled compound (500 mg, crude, HCl salt) as yellow solid. MS (M+H)$^+$=501.3

Step 7: Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(2-(2-(2-((2-(2,6-dioxopiperidin-3-yl)-1,3-dioxoisoindolin-4-yl)amino)acetamido)ethoxy)ethyl)piperidin-4-yl)-2-fluoro-5-methoxybenzamide (Compound 29)

To a solution of 4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzoic acid (150 mg, 322.29 mol) in DMF (2 mL) were added HATU (134.80 mg, 354.51 μmol) and DIPEA (83.31 mg, 644.57 μmol, 112.27 μL). The mixture was stirred at 25° C. for 10 min and a solution of N-(2-(2-(4-aminopiperidin-1-yl)ethoxy)ethyl)-2-((2-(2,6-dioxopiperidin-3-yl)-1,3-dioxoisoindolin-4-yl)amino)acetamide (224.99 mg, 418.97 μmol, HCl salt), DIPEA (83.31 mg, 644.57 mol, 112.27 μL) in DMF (2 mL) was added and the resulting mixture was stirred at 25° C. for 1 h. LCMS showed the starting material remained. Additional HATU (110.29 mg, 290.06 μmol) was added and the resulting mixture was stirred at 25° C. for another 12 hrs. LCMS showed the starting material was consumed completely, and a main peak with desired mass. The mixture was concentrated under reduced pressure. The crude product was purified prep-HPLC (column: Phenomenex luna $C_{18}$ 150*40 mm*15 um; mobile phase: [water (0.1% TFA)-ACN]; B %: 19%-49%, 10 min) and the eluent was lyophilized to afford the titled compound (94.1 mg, 82.41 μmol, 25.57% yield, 95% purity, TFA salt) as yellow solid. MS (M+H)$^+$=948.2.

$^1$H NMR (400 MHz, CD$_3$OD) δ=8.36 (d, J=13.9 Hz, 1H), 8.21 (s, 1H), 7.64-7.55 (m, 1H), 7.40-7.31 (m, 1H), 7.17-7.10 (m, 1H), 6.97-6.90 (m, 1H), 4.97 (br dd, J=7.0, 11.6 Hz, 2H), 4.11-4.03 (m, 4H), 4.00 (s, 3H), 3.84-3.75 (m, 2H), 3.69-3.56 (m, 4H), 3.54-3.42 (m, 3H), 3.41 (s, 3H), 3.31-3.41 (m, 1H), 3.22-3.06 (m, 2H), 2.65-2.83 (m, 3H), 2.29-1.84 (m, 8H), 1.84-1.64 (m, 6H).

Example 30. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(1-((2-(2,6-dioxopiperidin-3-yl)-1,3-dioxoisoindolin-4-yl)amino)-2-oxo-6,9,12-trioxa-3-azatetradecan-14-yl)piperidin-4-yl)-2-fluoro-5-methoxybenzamide

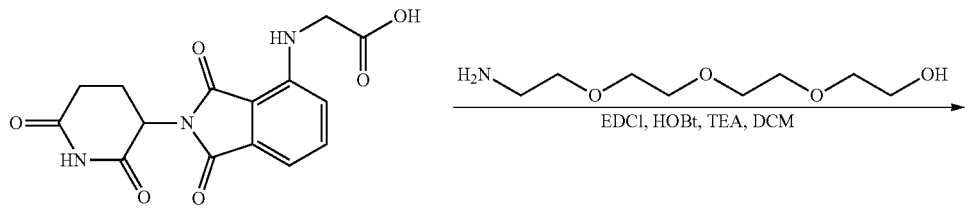

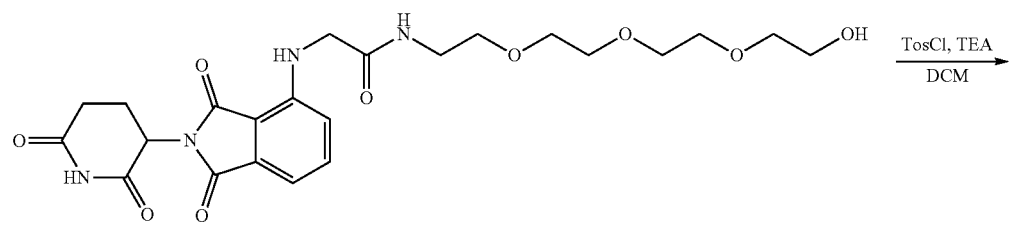

211
212
-continued
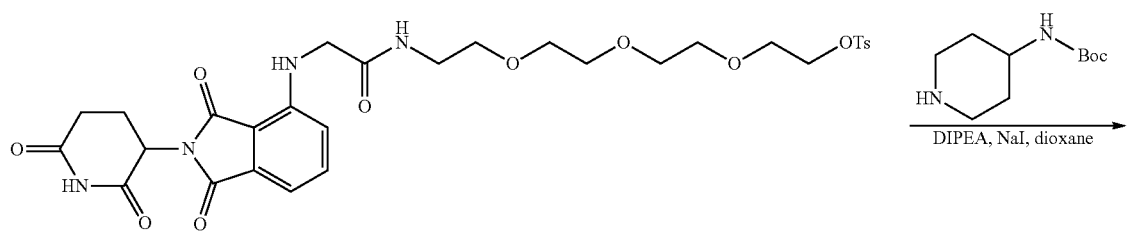
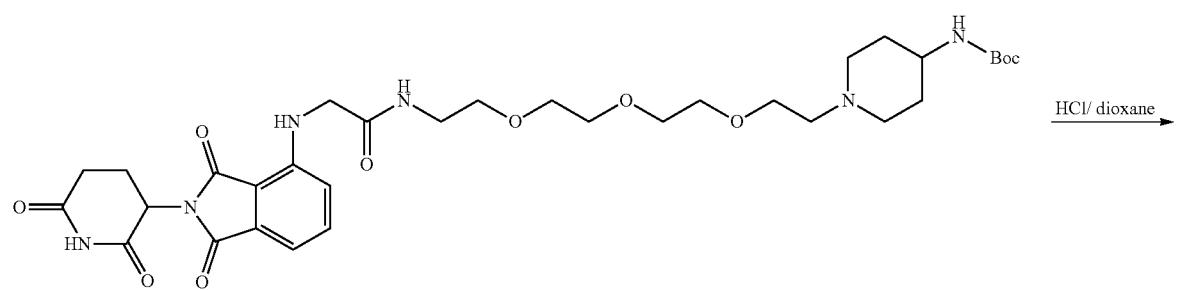
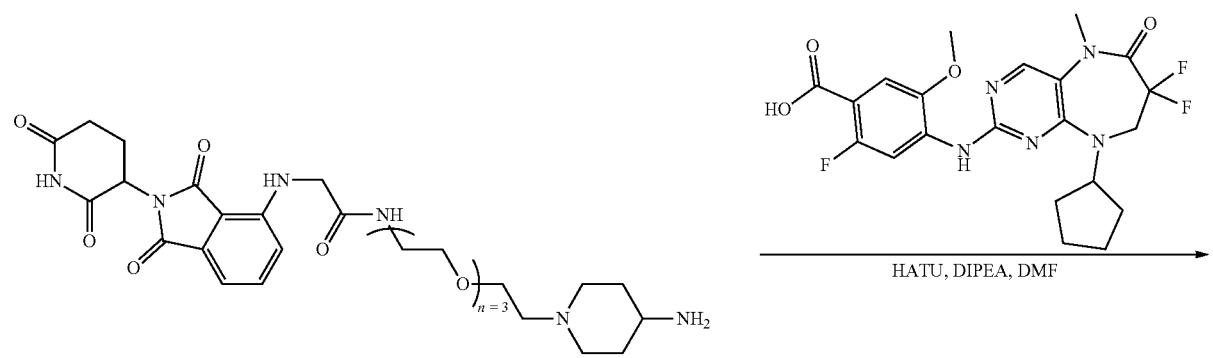
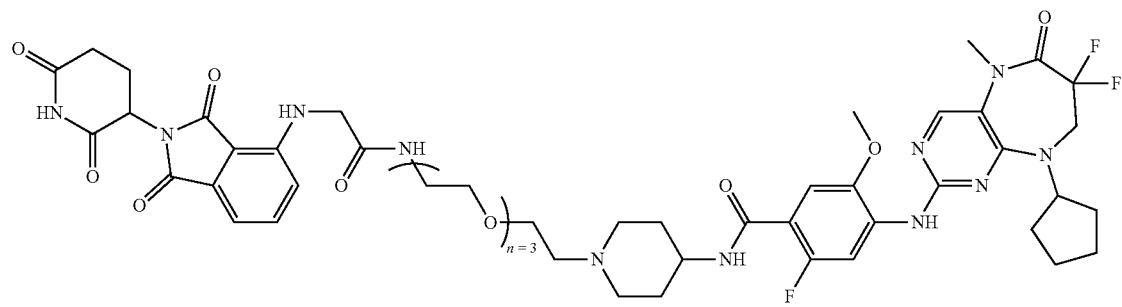
Compound 30

According to the above reaction scheme, in a manner similar to the other examples, obtained the titled compound (99.4 mg, 83.84 μmol, 26.01% yield, 97% purity, TFA salt) as yellow solid. MS(M+H)+=1036.8

¹H NMR (400 MHz, CD₃OD) δ=8.30 (d, J=13.8 Hz, 1H), 8.19 (s, 1H), 7.51 (dd, J=7.2, 8.4 Hz, 1H), 7.32 (d, J=6.8 Hz, 1H), 7.07 (d, J=7.0 Hz, 1H), 6.83 (d, J=8.4 Hz, 1H), 5.06 (dd, J=5.4, 12.4 Hz, 2H), 4.07 (m, 2H), 3.99-3.95 (m, 5H), 3.85-3.79 (m, 2H), 3.72 (m, 2H), 3.68-3.63 (m, 4H), 3.60 (s, 3H), 3.55 (m, 2H), 3.50-3.42 (m, 3H), 3.41 (s, 3H), 3.36 (m, 2H), 3.25-3.10 (m, 2H), 2.93-2.81 (m, 1H), 2.79-2.67 (m, 2H), 2.35-1.86 (m, 8H), 1.84-1.63 (m, 6H).

Example 31. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(2-(2-((2-(2,6-dioxopiperidin-3-yl)-1,3-dioxoisoindolin-4-yl)amino)ethoxy)acetyl)piperidin-4-yl)-2-fluoro-5-methoxybenzamide

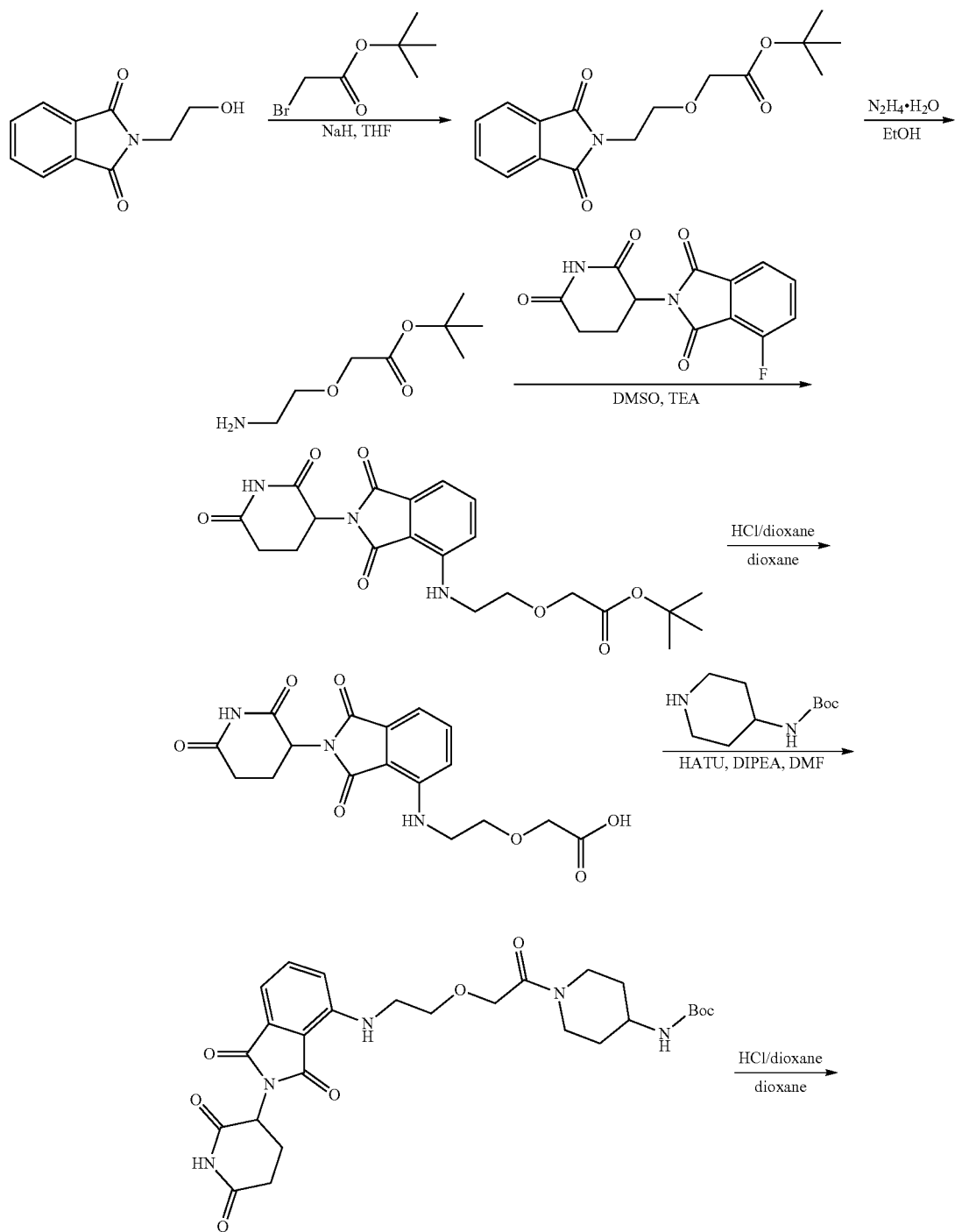

-continued

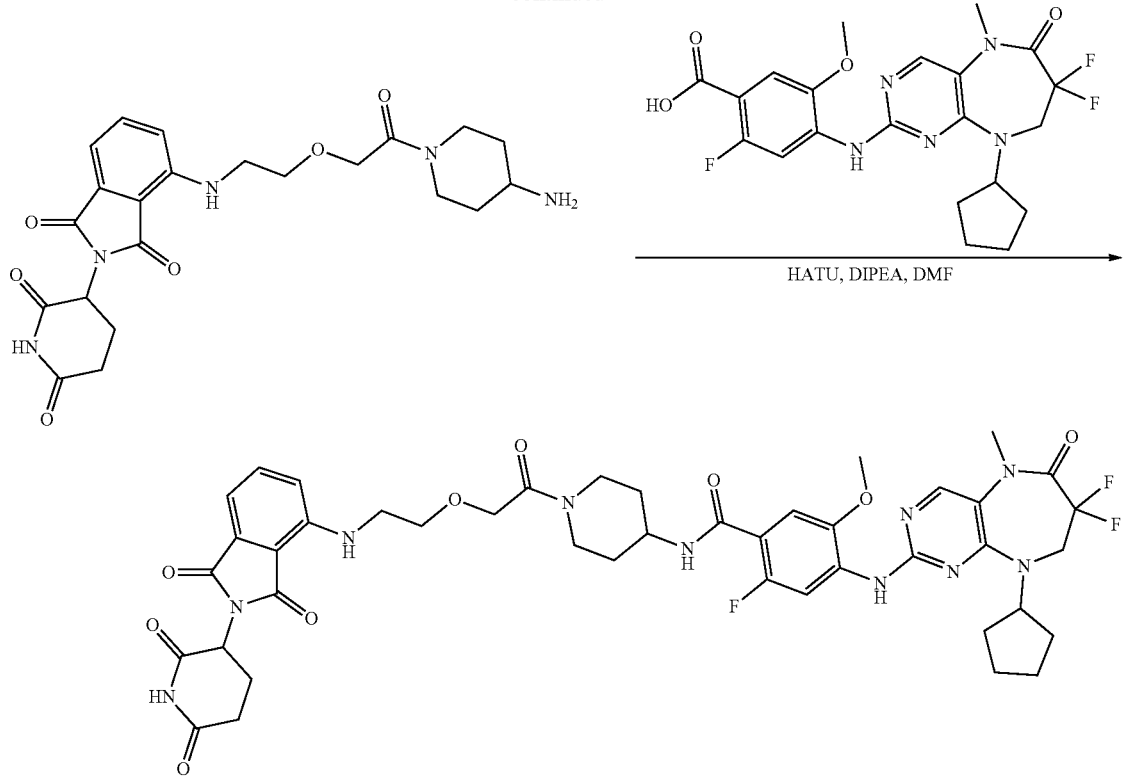

Compound 31

According to the above reaction scheme, in a manner similar to the other examples, obtained the titled compound (35.3 mg, 36.80 μmol, 83.25% yield, 94.330% purity) as a yellow solid. MS(M+H)+=905.4

$^1$H NMR (400 MHz, CDCl$_3$) δ=9.91-9.22 (m, 1H), 8.44-8.31 (m, 1H), 8.08 (s, 1H), 7.84 (br d, J=7.5 Hz, 1H), 7.72-7.48 (m, 2H), 7.13 (t, J=6.7 Hz, 1H), 6.95-6.85 (m, 1H), 6.81-6.66 (m, 1H), 6.58-6.48 (m, 1H), 4.98-4.78 (m, 2H), 4.60-4.47 (m, 1H), 4.45-4.21 (m, 2H), 4.19-4.08 (m, 1H), 4.06-3.87 (m, 6H), 3.82-3.70 (m, 2H), 3.60-3.46 (m, 2H), 3.42 (s, 3H), 3.36-3.22 (m, 1H), 2.99-2.66 (m, 4H), 2.26-2.03 (m, 5H), 1.85-1.70 (m, 4H), 1.61-1.55 (m, 2H), 1.53-1.34 (m, 2H).

Example 32. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(3-(2-((2-(2,6-dioxopiperidin-3-yl)-1,3-dioxoisoindolin-4-yl)amino)ethoxy)propanoyl)piperidin-4-yl)-2-fluoro-5-methoxybenzamide

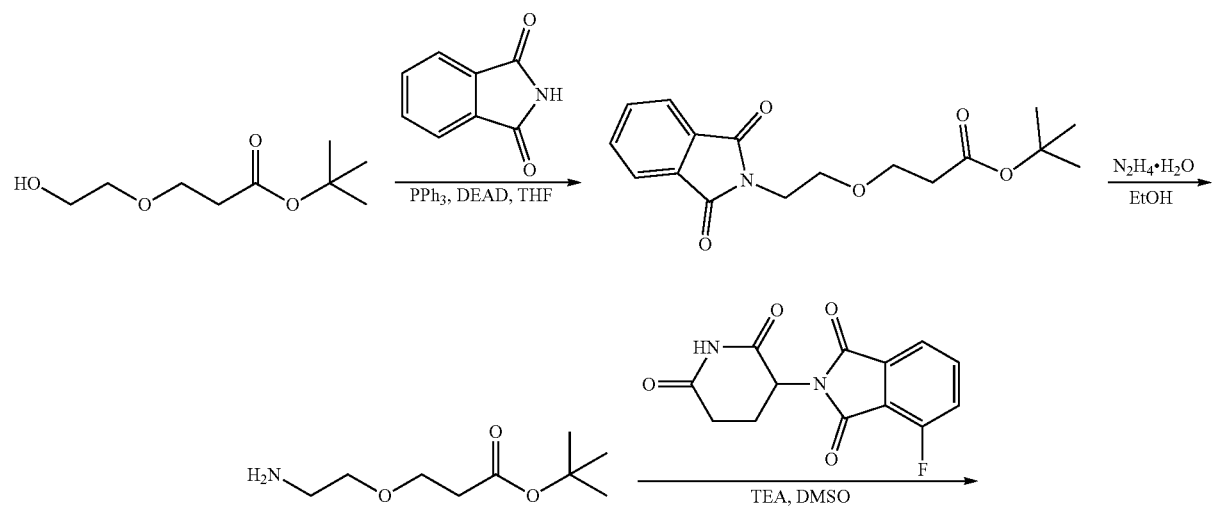

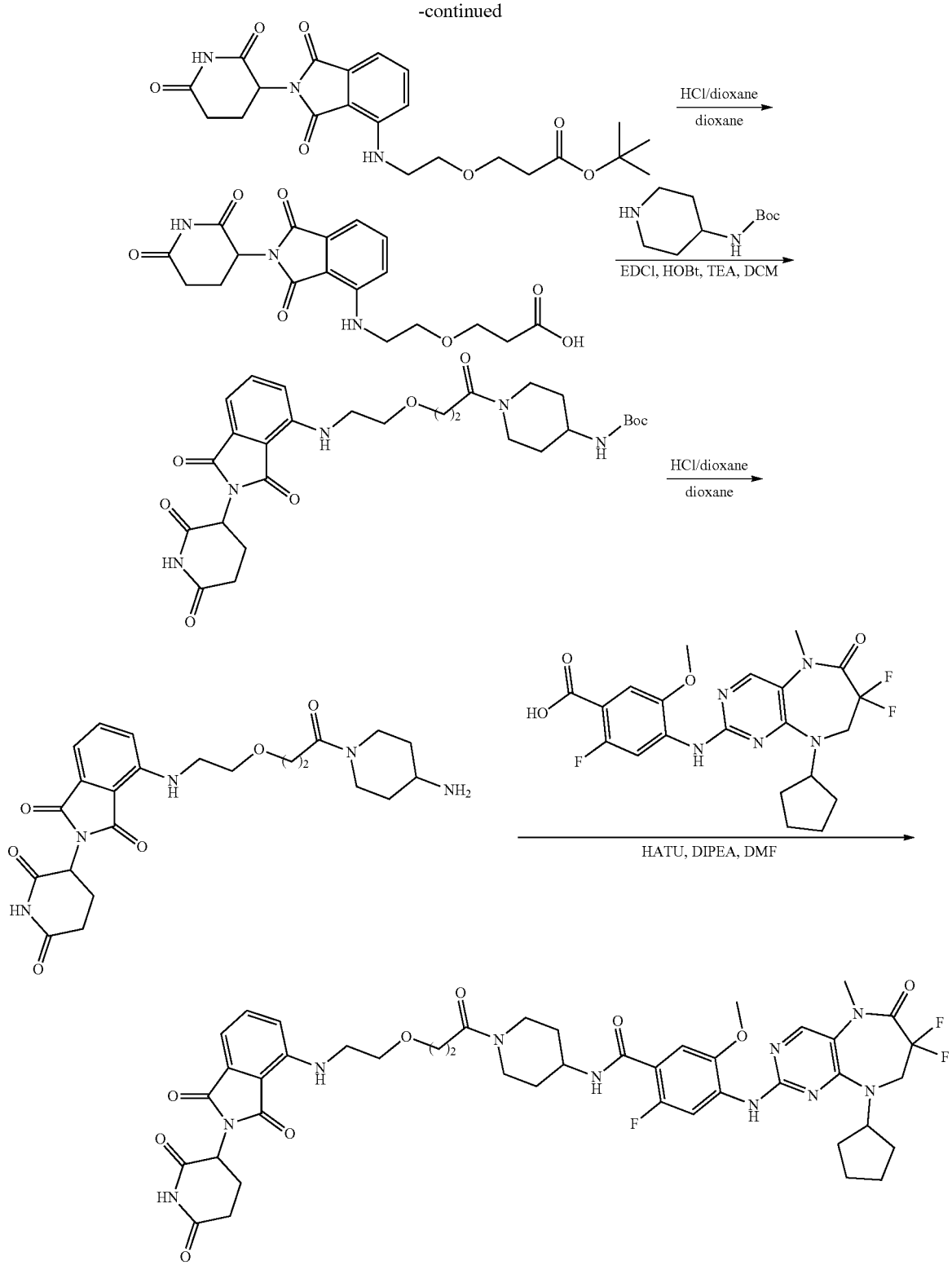
Compound 32
According to the above reaction scheme, in a manner similar to the other examples, obtained the titled compound (82.1 mg, 86.66 μmol, 33.61% yield, 97% purity) as a yellow solid. Ms (M+H)$^+$=918.8
$^1$H NMR (400 MHz, DMSO-d$_6$) δ=11.29-10.79 (m, 1H), 8.32-8.22 (m, 2H), 8.03 (s, 1H), 7.94 (dd, J=3.1, 7.6 Hz, 1H), 7.62-7.55 (m, 1H), 7.20 (d, J=6.7 Hz, 1H), 7.14 (d, J=8.7 Hz, 1H), 7.04 (d, J=7.1 Hz, 1H), 6.59 (t, J=5.6 Hz, 1H), 5.06 (dd, J=5.3, 13.2 Hz, 1H), 4.84-4.80 (m, 1H), 4.29 (d, J=12.1 Hz, 1H), 4.07 (t, J=13.9 Hz, 2H), 4.03-3.96 (m, 1H), 3.91 (s, 3H), 3.89-3.86 (m, 1H), 3.68 (t, J=6.5 Hz, 2H), 3.63-3.58 (m, 2H), 3.47 (q, J=5.2 Hz, 2H), 3.33 (s, 3H), 3.12 (t, J=12.3 Hz, 1H), 2.93-2.83 (m, 1H), 2.77-2.69 (m, 1H), 2.63-2.55 (m, 4H), 2.06-1.94 (m, 3H), 1.87-1.78 (m, 2H), 1.71-1.67 (m, 2H), 1.67-1.57 (m, 4H), 1.49-1.34 (m, 2H)
Example 33. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(2-(2-(2-((2-(2,6-dioxopiperidin-3-yl)-1,3-dioxoisoindolin-4-yl)amino)ethoxy)ethoxy)acetyl)piperidin-4-yl)-2-fluoro-5-methoxybenzamide
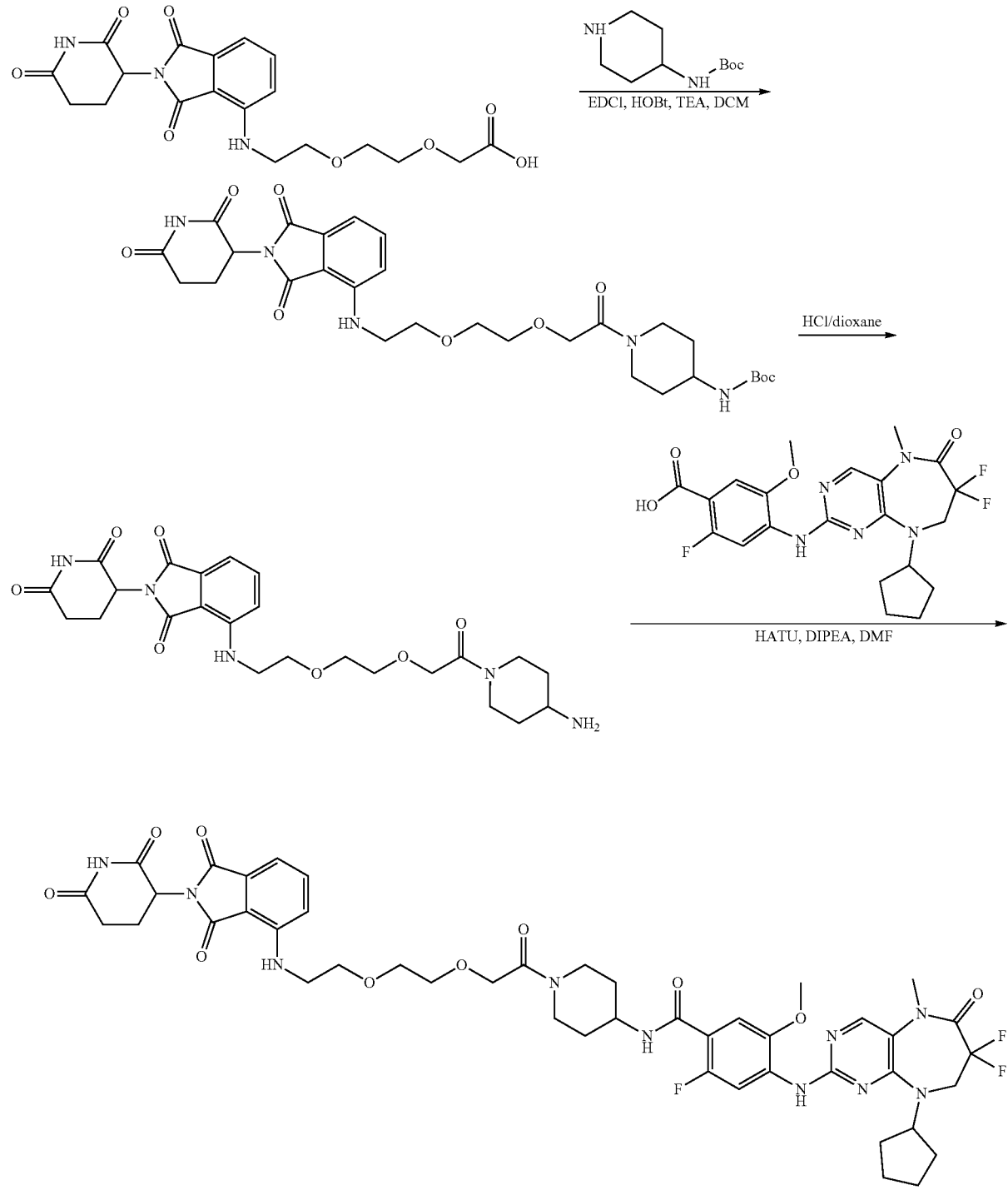
Compound 33

221

According to the above reaction scheme, in a manner similar to the other examples, obtained the titled compound (20.5 mg, 21.39 μmol, 11.06% yield, 99% purity) as yellow solid. MS(M+H)⁺=949.4

¹H NMR (400 MHz, DMSO-d$_6$) δ=11.20-10.96 (m, 1H), 8.30 (s, 1H), 8.24 (d, J=13.3 Hz, 1H), 8.03 (s, 1H), 7.95 (dd, J=3.2, 7.7 Hz, 1H), 7.62-7.53 (m, 1H), 7.23-7.11 (m, 2H), 7.03 (d, J=7.0 Hz, 1H), 6.61 (t, J=5.8 Hz, 1H), 5.04 (dd, J=5.2, 12.9 Hz, 1H), 4.82 (br t, J=7.8 Hz, 1H), 4.30-4.20 (m, 1H), 4.19-4.14 (m, 2H), 4.12-3.98 (m, 3H), 3.91 (s, 3H), 3.83-3.72 (m, 1H), 3.66-3.55 (m, 6H), 3.51-3.44 (m, 2H), 3.17-3.00 (m, 1H), 2.93-2.81 (m, 1H), 2.80-2.69 (m, 1H), 2.64-2.51 (m, 5H), 2.09-1.89 (m, 3H), 1.88-1.77 (m, 2H), 1.76-1.54 (m, 6H), 1.54-1.29 (m, 2H).

Example 34. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(14-((2-(2,6-dioxopiperidin-3-yl)-1,3-dioxoisoindolin-4-yl)amino)-3,6,9,12-tetraoxatetradecanoyl)piperidin-4-yl)-2-fluoro-5-methoxybenzamide

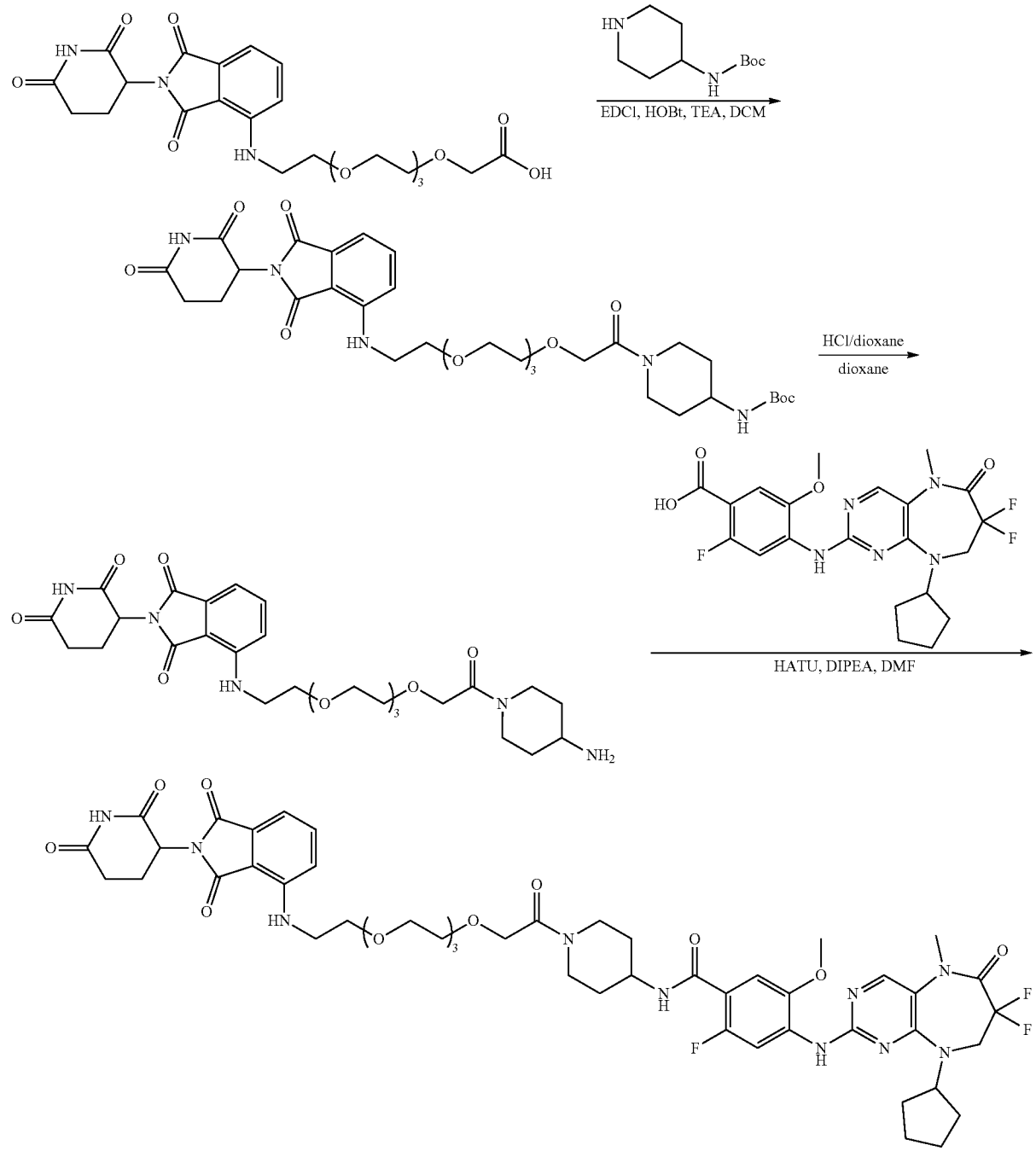

Compound 34

According to the above reaction scheme, in a manner similar to the other examples, obtained the titled compound (75.6 mg, 69.98 μmol, 32.57% yield, 96% purity) as a yellow solid. MS(M+H)⁺=1037.4.

¹H NMR (400 MHz, DMSO-d₆) δ=11.09 (s, 1H), 8.30 (s, 1H), 8.24 (d, J=13.3 Hz, 1H), 8.06 (s, 1H), 7.96 (dd, J₁=3.0, J₂=7.5 Hz, 1H), 7.57 (dd, J₁=7.2, J₂=8.5 Hz, 1H), 7.20 (d, J=6.7 Hz, 1H), 7.13 (d, J=8.5 Hz, 1H), 7.03 (d, J=7.0 Hz, 1H), 6.64-6.54 (m, 1H), 5.05 (dd, J₁=5.3, J₂=12.9 Hz, 1H), 4.82 (br t, J=7.5 Hz, 1H), 4.24 (br d, J=11.9 Hz, 1H), 4.13 (br d, J=12.5 Hz, 2H), 4.10-3.95 (m, 3H), 3.91 (s, 3H), 3.79 (br d, J=12.8 Hz, 1H), 3.63-3.59 (m, 2H), 3.58-3.50 (m, 12H), 3.46 (br d, J=6.0 Hz, 2H), 3.33 (s, 3H), 3.09 (br t, J=11.9 Hz, 1H), 2.93-2.83 (m, 1H), 2.80-2.71 (m, 1H), 2.62-2.55 (m, 2H), 2.06-1.91 (m, 3H), 1.89-1.78 (m, 2H), 1.77-1.65 (m, 2H), 1.68-1.56 (m, 4H), 1.55-1.45 (m, 1H), 1.44-1.33 (m, 1H).

Example 35. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(2-((2-(2-((2-(2,6-dioxopiperidin-3-yl)-1,3-dioxoisoindolin-4-yl)amino)ethoxy)ethyl)amino)-2-oxoethyl)piperidin-4-yl)-2-fluoro-5-methoxybenzamide

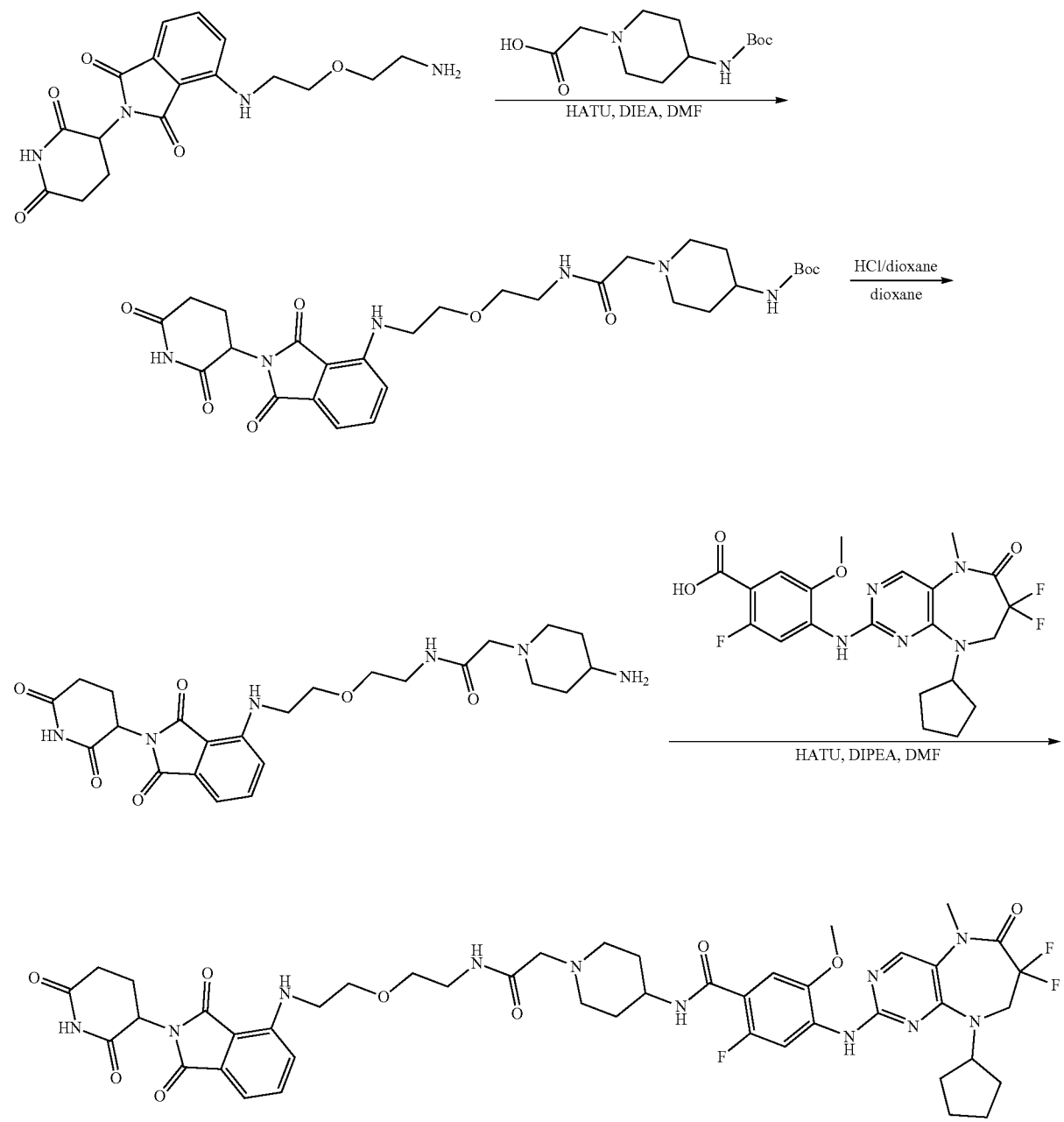

Compound 35

According to the above reaction scheme, in a manner similar to the other examples, obtained the titled compound (170.2 mg, 163.19 μmol, 49.11% yield, 91% purity) as a light yellow solid. MS(M+H)⁺=948.3

¹H NMR (400 MHz, DMSO-d₆) δ 11.10 (s, 1H), 8.31 (s, 1H), 8.25 (d, J=13.4 Hz, 1H), 8.04 (s, 1H), 7.87 (dd, J=3.4, 7.5 Hz, 1H), 7.69 (br t, J=5.9 Hz, 1H), 7.62-7.54 (m, 1H), 7.21-7.11 (m, 2H), 7.04 (d, J=7.0 Hz, 1H), 6.61 (t, J=5.6 Hz, 1H), 5.09-5.03 (m, 1H), 4.87-4.77 (m, 1H), 4.08 (br t, J=13.7 Hz, 2H), 3.92 (s, 3H), 3.80-3.68 (m, 1H), 3.64-3.58 (m, 2H), 3.53-3.46 (m, 4H), 3.31-3.28 (m, 2H), 2.96-2.85 (m, 3H), 2.81-2.75 (m, 2H), 2.61-2.53 (m, 4H), 2.17 (t, J=10.6 Hz, 2H), 2.06-1.92 (m, 3H), 1.83-1.50 (m, 11H).

Example 36. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(14-((2-(2,6-dioxopiperidin-3-yl)-1,3-dioxoisoindolin-4-yl)amino)-2-oxo-6,9,12-trioxa-3-azatetradecyl)piperidin-4-yl)-2-fluoro-5-methoxybenzamide

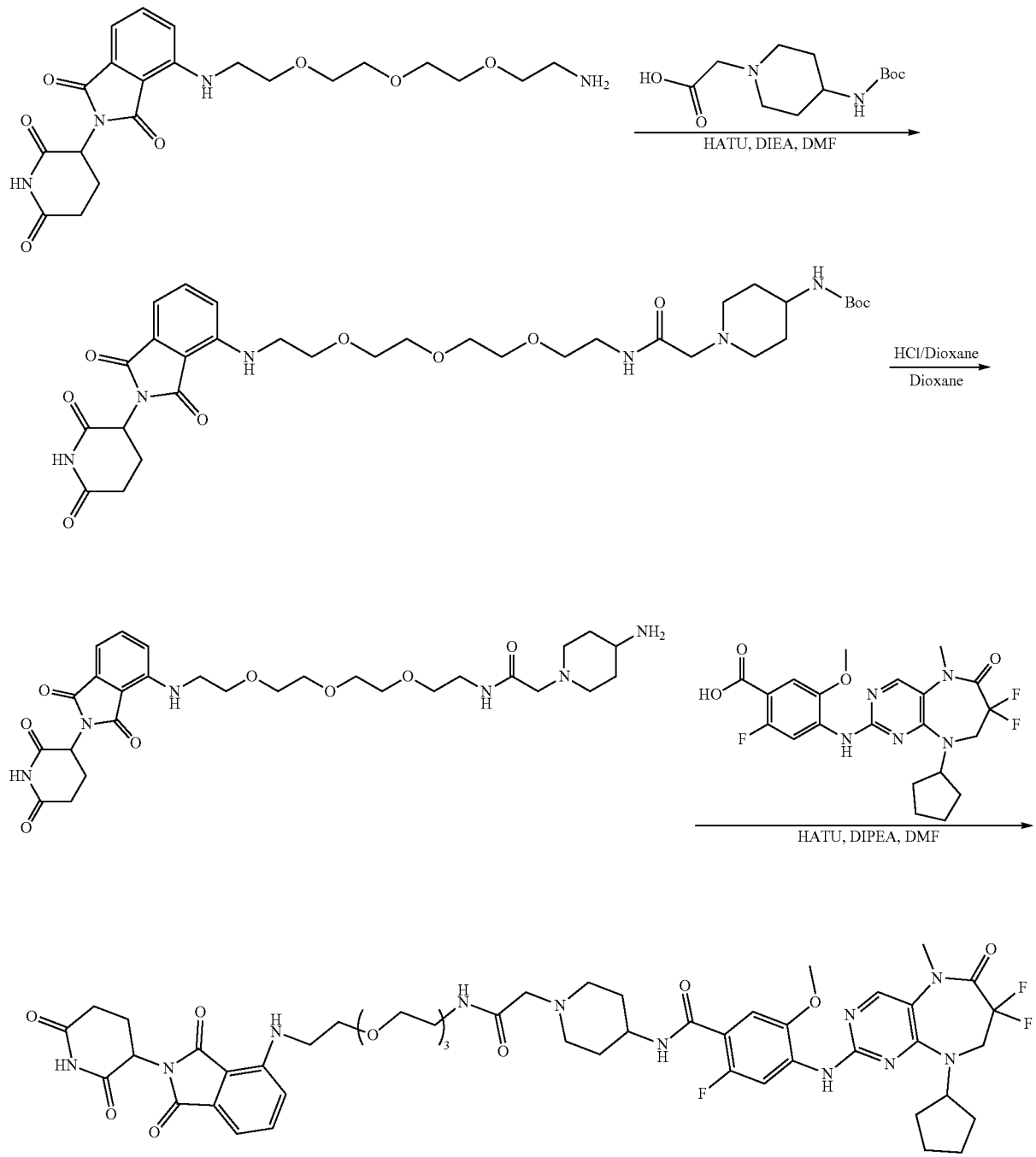

Compound 36

According to the above reaction scheme, in a manner similar to the other examples, obtained the titled compound (53.8 mg, 50.89 μmol, 15.79% yield, 98% purity) as a light yellow solid. MS(M+H)$^+$=1036.6

$^1$H NMR (400 MHz, DMSO-d$_6$) δ 11.08 (br s, 1H), 8.30 (s, 1H), 8.25 (d, J=13.3 Hz, 1H), 8.03 (s, 1H), 7.88 (dd, J=3.5, 7.5 Hz, 1H), 7.65 (t, J=5.7 Hz, 1H), 7.60-7.54 (m, 1H), 7.19 (d, J=6.7 Hz, 1H), 7.13 (d, J=8.7 Hz, 1H), 7.03 (d, J=7.0 Hz, 1H), 6.59 (t, J=5.6 Hz, 1H), 5.10-5.02 (m, 1H), 4.87-4.77 (m, 1H), 4.08 (t, J=13.9 Hz, 2H), 3.91 (s, 3H), 3.80-3.69 (m, 1H), 3.65-3.59 (m, 2H), 3.58-3.53 (m, 4H), 3.53-3.48 (m, 4H), 3.47-3.40 (m, 4H), 3.34 (s, 3H), 3.28-3.22 (m, 2H), 2.93-2.84 (m, 3H), 2.82-2.75 (m, 2H), 2.62-2.55 (m, 2H), 2.17 (t, J=10.9 Hz, 2H), 2.06-1.93 (m, 3H), 1.85-1.58 (m, 10H).

Example 37. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(4-((2-(2,6-dioxopiperidin-3-yl)-1,3-dioxoisoindolin-4-yl)amino)-4-oxobutyl)piperidin-4-yl)-2-fluoro-5-methoxybenzamide

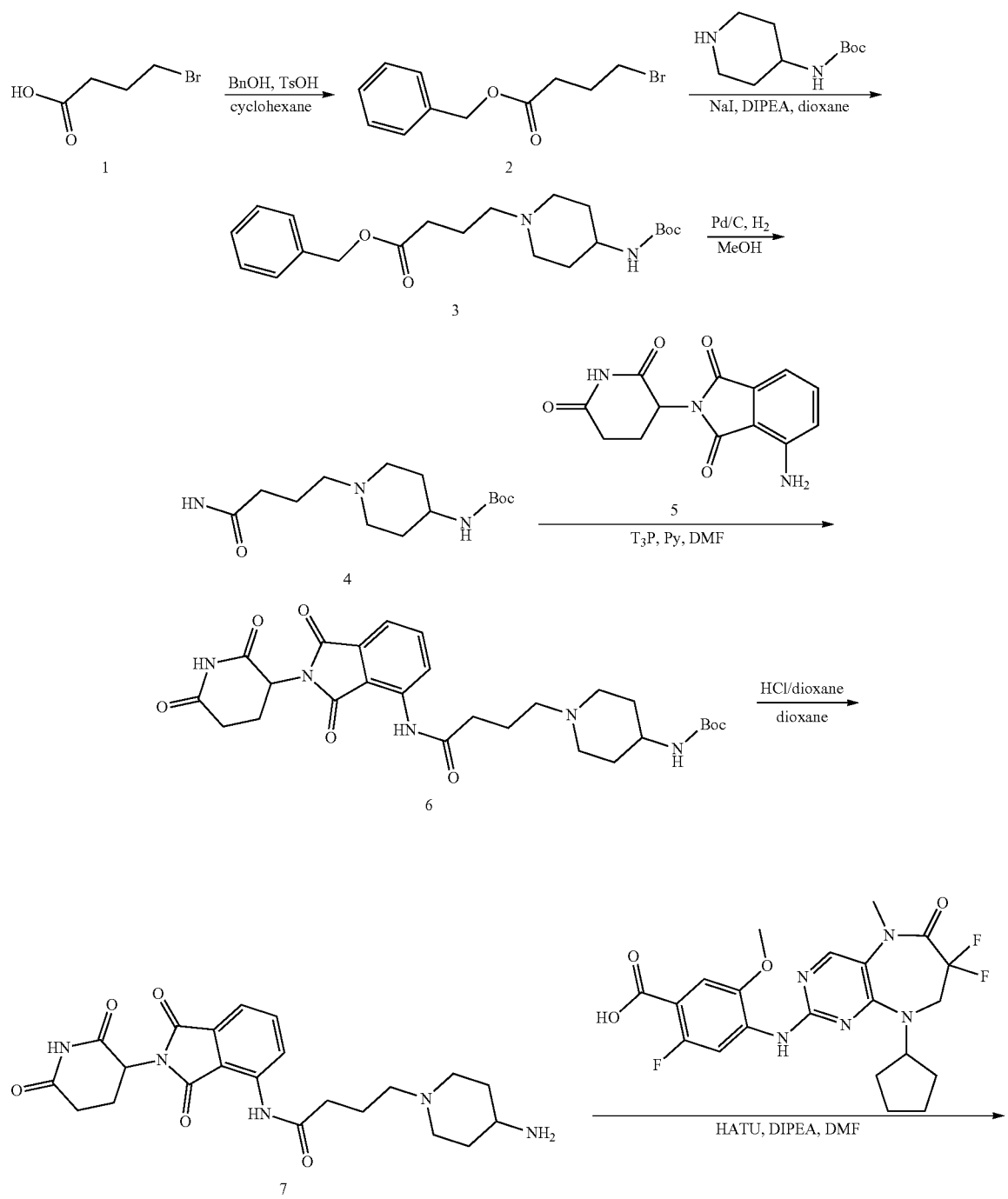

-continued

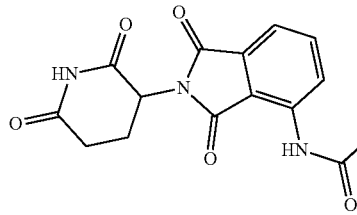 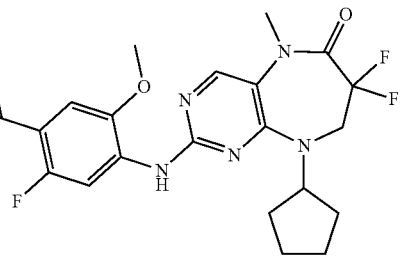

Compound 37

Step 1: Synthesis of benzyl 4-bromobutanoate (2)

To a mixture of 4-bromobutanoic acid (5 g, 29.94 mmol) and phenylmethanol (4.21 g, 38.92 mmol, 4.05 mL) in cyclohexane (50 mL) was added TsOH (257.79 mg, 1.50 mmol) in one portion at 20° C. and the resulting mixture was stirred at 90° C. for 16 h. LCMS showed starting material was consumed completely and no peak with desired mass was detected. TLC (SiO$_2$, Petroleum ether:Ethyl acetate=5:1) indicated starting material was consumed completely and two new spots were detected. The reaction mixture was concentrated in vacuum. The residue was purified by column chromatography (SiO$_2$, Petroleum ether/Ethyl acetate=1/0 to 10/1) to afford the titled compound (6.5 g, 25.28 mmol, 84.43% yield) as a yellow oil.

$^1$H NMR (400 MHz, CDCl$_3$) δ=7.46-7.32 (m, 5H), 5.17 (s, 2H), 3.49 (t, J=6.5 Hz, 2H), 2.59 (t, J=7.2 Hz, 2H), 2.18-2.25 (m, 2H).

Step 2: Synthesis of benzyl 4-(4-((tert-butoxycarbonyl)amino)piperidin-1-yl)butanoate (3)

To a mixture of benzyl 4-bromobutanoate (6.5 g, 25.28 mmol) and tert-butyl piperidin-4-ylcarbamate (7.59 g, 37.92 mmol) in dioxane (60 mL) were added NaI (378.93 mg, 2.53 mmol) and DIPEA (9.80 g, 75.84 mmol, 13.21 mL) in one portion at 20° C. and the resulting mixture was stirred at 80° C. for 16 h. LCMS showed all starting material was consumed completely and one peak with desired mass was detected. The reaction mixture was concentrated in vacuum. The residue was purified by column chromatography (SiO$_2$, Petroleum ether/Ethyl acetate=1/1 to 0/1 to Dichloromethane:Methanol=1/0 to 10/1) to afford the titled compound (6.8 g, 16.26 mmol, 64.30% yield, 90% purity) as a yellow solid. MS(M+H)$^+$=377.4

Step 3: Synthesis of 4-(4-((tert-butoxycarbonyl)amino)piperidin-1-yl)butanoic acid (4)

To a solution of benzyl 4-(4-((tert-butoxycarbonyl)amino)piperidin-1-yl)butanoate (3.4 g, 9.03 mmol) in MeOH (40 mL) was added Pd/C (340 mg, 10% purity) under N$_2$. The suspension was degassed under vacuum and purged with H$_2$ several times. The mixture was stirred under H$_2$ (15 psi) at 20° C. for 16 h. LCMS showed starting material was consumed completely and one peak with desired mass was detected. The reaction mixture was diluted with MeOH (40 mL) and filtered. The filtrate was concentrated in vacuum to afford the titled compound (2.7 g, crude) as a white oil. MS(M+H)$^+$=287.2

Step 4: Synthesis of tert-butyl (1-(4-((2-(2,6-dioxopiperidin-3-yl)-1,3-dioxoisoindolin-4-yl)amino)-4-oxobutyl)piperidin-4-yl)carbamate (6)

To a mixture of 4-amino-2-(2,6-dioxo-3-piperidyl) isoindoline-1,3-dione (1.5 g, 5.49 mmol) and 4-(4-((tert-butoxycarbonyl)amino)piperidin-1-yl)butanoic acid (2.04 g, 7.14 mmol) in DMF (15 mL) were added T$_3$P (20.96 g, 32.94 mmol, 19.59 mL, 50% purity in EtOAc solution) and Py (4.34 g, 54.90 mmol, 4.43 mL) in one portion at 20° C. and the resulting mixture was stirred at 80° C. for 16 h. LCMS showed 4-amino-2-(2, 6-dioxo-3-piperidyl) isoindoline-1,3-dione was consumed completely and one peak with desired mass was detected. The reaction mixture was diluted with H$_2$O (30 mL) and extracted with EtOAc (30 mL×3). The organic layer was washed with brine (30 mL×3), dried over Na$_2$SO$_4$, filtered and concentrated. The residue was purified by column chromatography (SiO$_2$, Petroleum ether/Ethyl acetate=1/1 to 0/1 to Dichloromethane/Methanol=1/0 to 10/1) to afford the titled compound (825 mg, 1.49 mmol, 27.19% yield, 98% purity) as a yellow solid. MS(M+H)$^+$=542.2

Step 5: Synthesis of 4-(4-aminopiperidin-1-yl)-N-(2-(2,6-dioxopiperidin-3-yl)-1,3-dioxoisoindolin-4-yl)butanamide (7)

To a mixture of t tert-butyl (1-(4-((2-(2,6-dioxopiperidin-3-yl)-1,3-dioxoisoindolin-4-yl)amino)-4-oxobutyl)piperidin-4-yl)carbamate (825 mg, 1.52 mmol) in dioxane (5 mL) was added HCl/dioxane (4 M, 10 mL) in one portion at 20° C. and the resulting mixture was stirred at 20° C. for 1 h. TLC (SiO$_2$, Dichloromethane:Methanol=10:1) indicated starting material was consumed completely and one new spot was detected. The reaction mixture was concentrated in vacuum to afford the titled compound (730 mg, crude, HCl) as an off-white solid.

Step 6: Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(4-((2-(2,6-dioxopiperidin-3-yl)-1,3-dioxoisoindolin-4-yl)amino)-4-oxobutyl)piperidin-4-yl)-2-fluoro-5-methoxybenzamide (Compound 37)

To a solution of 4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzoic acid (200 mg, 429.71 μmol) in DMF (3 mL) were added HATU (179.73 mg, 472.69 μmol) and DIPEA (111.08 mg, 859.43 μmol, 149.70 μL). The mixture was stirred at 20° C. for 10 min and a solution of 4-(4-aminopiperidin-1-yl)-N-(2-(2,6-dioxopiperidin-3-yl)-1,3-dioxoisoindolin-4-yl)butanamide (246.62 mg, crude, HCl) in DMF (3 mL) and DIPEA (111.08 mg, 859.43 mol, 149.70 μL) were added and the resulting mixture was stirred at 20° C. for 1 h. LCMS showed all starting material was consumed completely and one peak with desired mass was detected. The reaction mixture was diluted with $H_2O$ (10 mL) and extracted with EtOAc (10 mL×3). The organic layer was dried over $Na_2SO_4$, filtered and concentrated. The residue was purified by prep-HPLC (column: Phenomenex luna $C_{18}$ 150*40 mm*15 um; mobile phase: [water (0.225% FA)-ACN]; B %: 17%-47%, 10 min) and then lyophilized to afford the titled compound (116.9 mg, 124.94 μmol, 29.07% yield, 95% purity) as a white solid. MS(M+H)$^+$=888.7

$^1$H NMR (400 MHz, DMSO-d$_6$) δ=11.16 (s, 1H), 9.71 (s, 1H), 8.48 (d, J=8.3 Hz, 1H), 8.30-8.25 (m, 1H), 8.22 (d, J=5.5 Hz, 1H), 8.04 (s, 1H), 7.91-7.77 (m, 2H), 7.61 (d, J=7.2 Hz, 1H), 7.18 (d, J=6.7 Hz, 1H), 5.19-5.10 (m, 1H), 4.89-4.75 (m, 1H), 4.13-4.02 (m, 2H), 3.91 (s, 3H), 3.81-3.63 (m, 2H), 3.33 (s, 3H), 2.94-2.81 (m, 3H), 2.69-2.54 (m, 3H), 2.38-2.32 (m, 2H), 2.09-1.93 (m, 5H), 1.81-1.46 (m, 12H)

Example 38. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(8-((2-(2,6-dioxopiperidin-3-yl)-1,3-dioxoisoindolin-4-yl)amino)-8-oxooctyl)piperidin-4-yl)-2-fluoro-5-methoxybenzamide

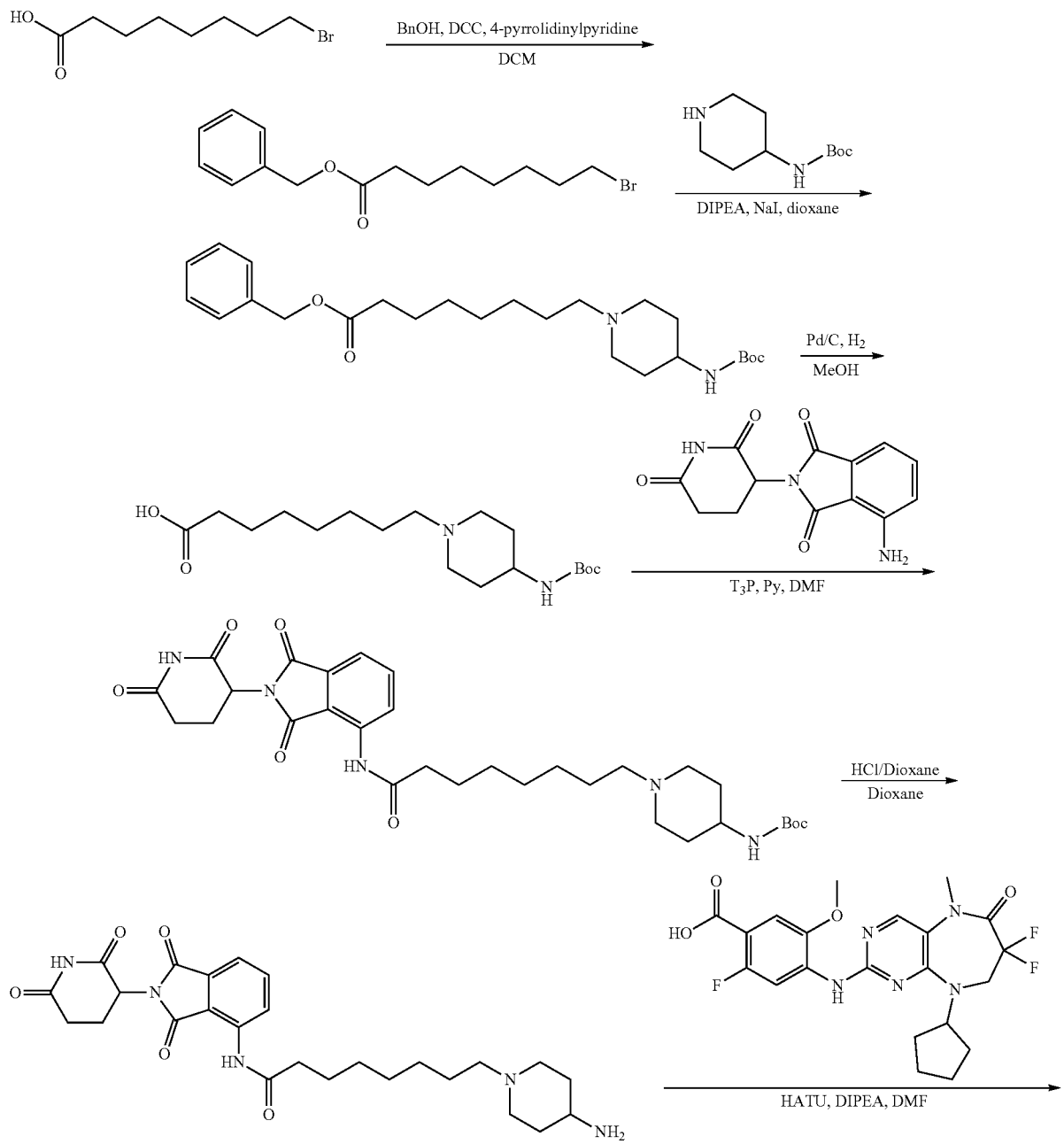

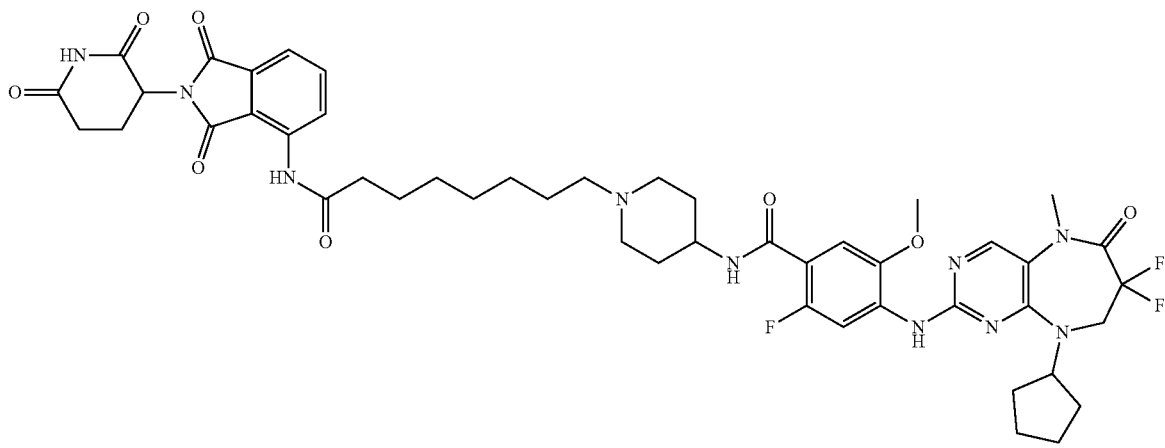

Compound 38

According to the above reaction scheme, in a manner similar to the other examples, obtained the titled compound (230.9 mg, 239.45 umol, 46.44% yield, 98% purity) as a light yellow solid. MS (M+H)$^+$=945.6

$^1$H NMR (400 MHz, CD$_3$OD) b 8.69-8.63 (m, 1H), 8.35-8.28 (m, 1H), 8.23 (s, 1H), 7.81 (dd, J=7.4, 8.4 Hz, 1H), 7.63-7.58 (m, 1H), 7.37 (d, J=6.5 Hz, 1H), 5.20-5.12 (m, 1H), 5.07-5.00 (m, 1H), 4.13 (t, J=12.9 Hz, 2H), 4.01 (s, 3H), 3.72-3.63 (m, 2H), 3.42 (s, 3H), 3.23-3.08 (m, 4H), 2.96-2.85 (m, 1H), 2.83-2.71 (m, 2H), 2.55 (t, J=7.3 Hz, 2H), 2.30 (d, J=14.6 Hz, 2H), 2.22-2.05 (m, 4H), 1.94-1.71 (m, 12H), 1.55-1.42 (m, 6H)

Example 39. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(4-((2-(2,6-dioxopiperidin-3-yl)-1,3-dioxoisoindolin-4-yl)amino)butanoyl)piperidin-4-yl)-2-fluoro-5-methoxybenzamide

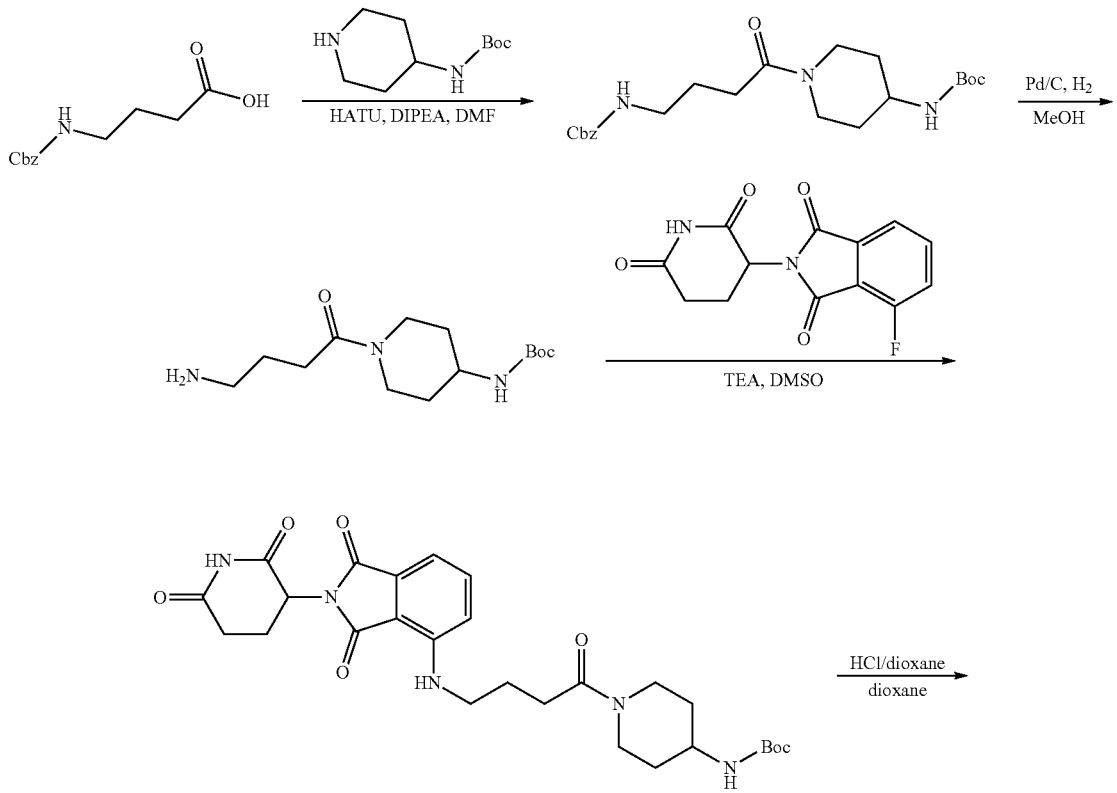

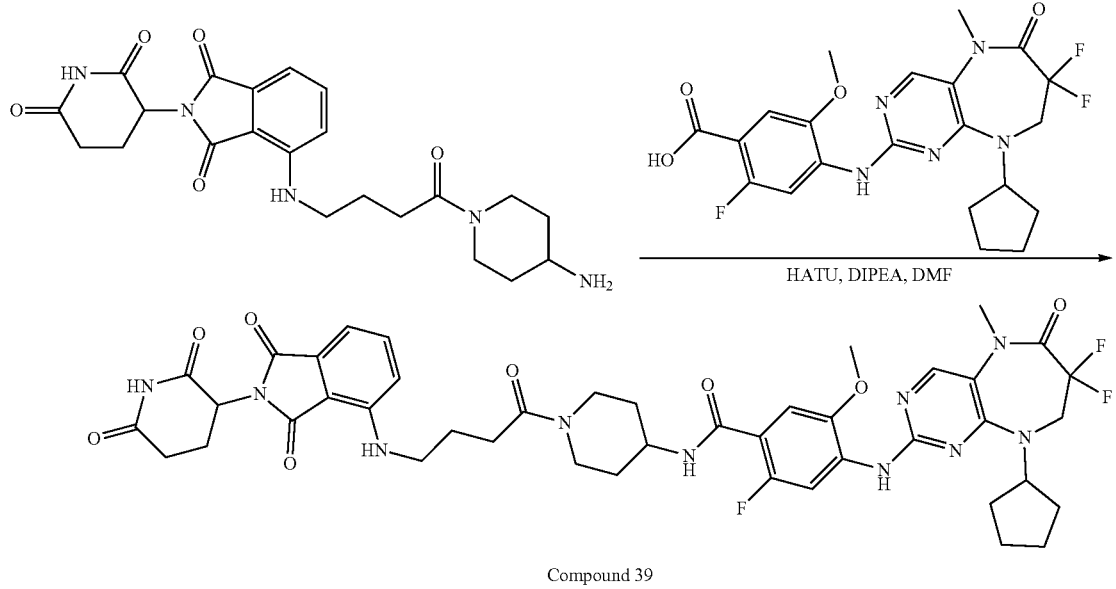

According to the above reaction scheme, in a manner similar to the other examples, obtained the titled compound (202.8 mg, 221.31 μmol, 51.50% yield, 97% purity) as a yellow solid. MS(M+H)$^+$=889.0

$^1$H NMR (400 MHz, CD$_3$OD) δ=8.39 (d, J=14.0 Hz, 1H), 8.20 (s, 1H), 7.56 (dd, J=7.2, 8.6 Hz, 1H), 7.32 (d, J=6.6 Hz, 1H), 7.12 (d, J=8.4 Hz, 1H), 7.04 (d, J=7.0 Hz, 1H), 5.04 (dd, J=5.0, 12.2 Hz, 1H), 4.49 (d, J=11.8 Hz, 1H), 4.18-4.10 (m, 1H), 4.07-4.00 (m, 2H), 3.98 (s, 3H), 3.52-3.41 (m, 2H), 3.40 (s, 3H), 3.25-3.17 (m, 1H), 2.89-2.79 (m, 2H), 2.78-2.68 (m, 2H), 2.54 (t, J=6.7 Hz, 2H), 2.15-1.92 (m, 8H), 1.87-1.62 (m, 7H), 1.58-1.44 (m, 2H)

Example 40. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(4-(2-((2-(2,6-dioxopiperidin-3-yl)-1,3-dioxoisoindolin-4-yl)amino)ethoxy)benzyl)piperidin-4-yl)-2-fluoro-5-methoxybenzamide

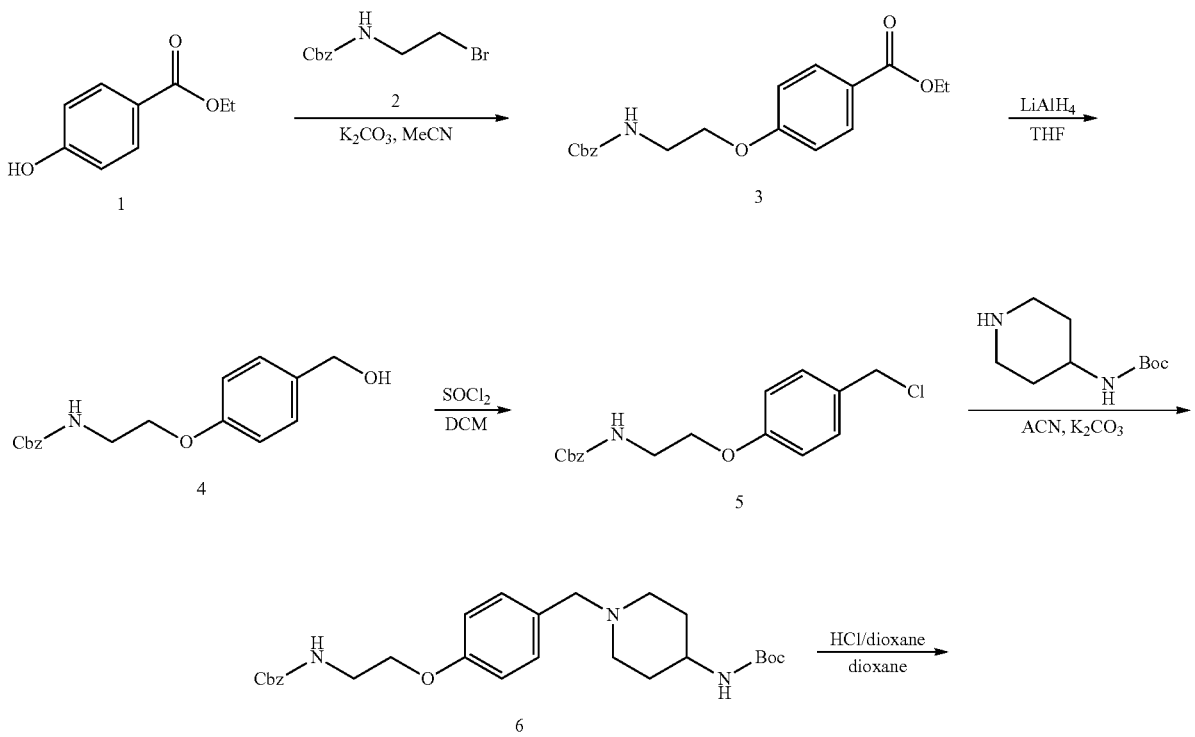

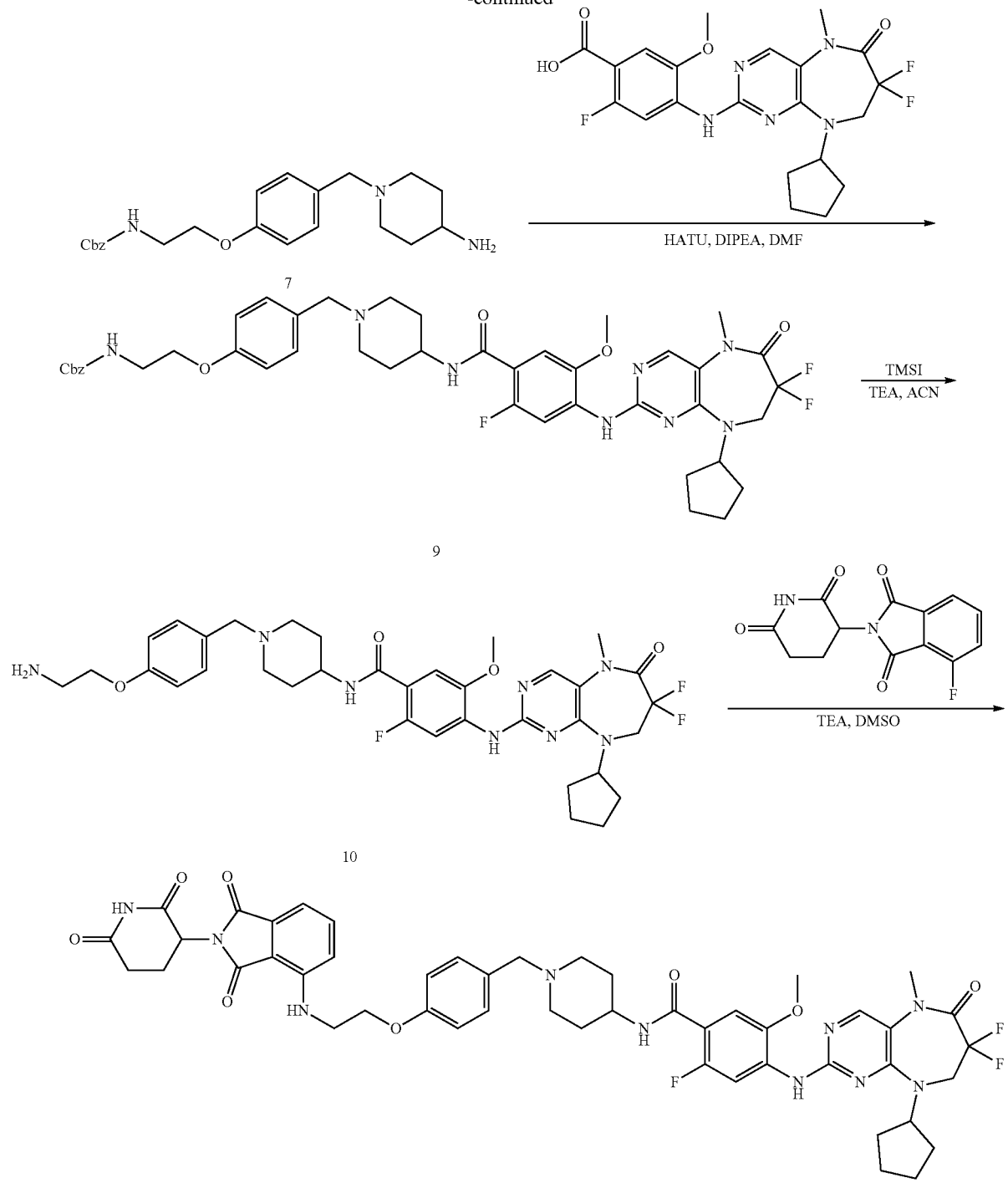

Compound 40

Step 1: Synthesis of ethyl 4-(2-(((benzyloxy)carbonyl)amino)ethoxy)benzoate (3)

To a solution of ethyl 4-hydroxybenzoate (3 g, 18.05 mmol) and benzyl (2-bromoethyl)carbamate (4.19 g, 16.25 mmol) in MeCN (70 mL) was added K$_2$CO$_3$ (4.99 g, 36.11 mmol). The reaction mixture was heated to 85° C. for 4 hr. LCMS showed one peak (69%) with desired mass. The reaction mixture was diluted with H$_2$O (150 mL) and extracted with EtOAc (150 Ml×2). The combined organic layer was washed with NaOH (100 mL, 3M), dried over Na$_2$SO$_4$, filtered. The filtrate was concentrated in vacuo to afford the titled compound (5 g, 14.56 mmol, 80.66% yield) as a white solid. MS(M+H)$^+$=344.1

Step 2: Synthesis of benzyl (2-(4-(hydroxymethyl)phenoxy)ethyl)carbamate (4)

To a solution of ethyl 4-(2-(((benzyloxy)carbonyl)amino) ethoxy)benzoate (5 g, 14.56 mmol) in THF (80 mL) was added LiAlH$_4$ (718.47 mg, 18.93 mmol) at 0° C. portionwise. The reaction mixture was stirred at 20° C. for 2 hr. One main peak showed on LCMS. The reaction mixture was quenched with H$_2$O (0.8 mL), NaOH (0.8 mL, 15% solution) and H$_2$O (2.4 mL). The suspension was diluted with THF (120 mL), dried over Na$_2$SO$_4$, filtered. The filtrate was concentrated in vacuo. The residue was purified by column chromatography (SiO$_2$, PE/EtOAc=30%~50%) to afford the titled compound (2.2 g, 7.15 mmol, 49.14% yield, 98% purity) as a white solid. MS(M–OH+H)$^+$=284.1

Step 3: Synthesis of benzyl (2-(4-(chloromethyl)phenoxy)ethyl)carbamate (5)

To a mixture of benzyl (2-(4-(hydroxymethyl)phenoxy) ethyl)carbamate (1.5 g, 4.98 mmol) in DCM (15 mL) was added SOCl$_2$ (710.65 mg, 5.97 mmol, 433.33 µL) in one portion at 20° C. and the resulting mixture was stirred at 20° C. for 2 h. LCMS showed 75% of starting material remained and a peak (21%) with desired mass. Additional SOCl$_2$ (710.65 mg, 5.97 mmol, 433.33 µL) was added and the resulting mixture was stirred at 20° C. for another 2 h. LCMS showed 70% of starting material remained. Additional SOCl$_2$ (710.65 mg, 5.97 mmol, 433.33 µL) was added and the resulting mixture was continue to stir at 20° C. for 16 h. TLC (SiO$_2$, Petroleum ether:Ethyl acetate=1:1) indicated starting material was consumed completely and one new spot was detected. The reaction mixture was concentrated in vacuum to afford the titled compound (1.6 g, crude) as a white solid. MS(M+Na)$^+$=342.3

Step 4: Synthesis of tert-butyl N-[1-[[4-[2-(benzyloxycarbonylamino) ethoxy]phenyl]methyl]-4-piperidyl]carbamate (6)

To a mixture of benzyl (2-(4-(chloromethyl)phenoxy) ethyl)carbamate (1.6 g, 5.00 mmol) and tert-butyl piperidin-4-ylcarbamate (1.20 g, 6.00 mmol) in ACN (20 mL) was added K$_2$CO$_3$ (2.07 g, 15.01 mmol) in one portion at 20° C. and the resulting mixture was stirred at 60° C. for 2 h. LCMS showed all starting material was consumed completely and one peak with desired mass was detected. The reaction mixture was concentrated in vacuum. The residue was purified by column chromatography (SiO$_2$, Petroleum ether/ Ethyl acetate=5/1 to 0/1) to afford the titled compound (2.3 g, 4.71 mmol, 94.10% yield, 99% purity) as a white solid. MS(M+H)$^+$=484.4

Step 5: Synthesis of benzyl (2-(4-((4-aminopiperidin-1-yl)methyl)phenoxy)ethyl)carbamate (7)

To a mixture of tert-butyl N-[1-[[4-[2-(benzyloxycarbonylamino) ethoxy]phenyl]methyl]-4-piperidyl]carbamate (1 g, 2.07 mmol) in dioxane (5 mL) was added HCl/dioxane (4 M, 10 mL) in one portion at 20° C. and the resulting mixture was stirred at 20° C. for 2 h. LCMS showed starting material was consumed completely and one peak with desired mass was detected. The reaction mixture was concentrated in vacuo to afford the titled compound (890 mg, crude, HCl salt) as a white solid. MS(M+H)$^+$=384.2

Step 6: Synthesis of benzyl (2-(4-((4-(4-((9-cyclopentyl-7,7-difluoro-5-methyl-6-oxo-6,7,8,9-tetrahydro-5H-pyrimido[4,5-b][1,4]diazepin-2-yl) amino)-2-fluoro-5-methoxybenzamido)piperidin-1-yl)methyl)phenoxy)ethyl)carbamate (9)

To a solution of 4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzoic acid (0.5 g, 1.07 mmol) in DMF (5 mL) were added HATU (449.32 mg, 1.18 mmol) and DIPEA (277.69 mg, 2.15 mmol, 374.24 µL), the mixture was stirred at 20° C. for 10 min and a solution of benzyl (2-(4-((4-aminopiperidin-1-yl)methyl)phenoxy) ethyl)carbamate (541.37 mg, 1.29 mmol, HCl salt) in DMF (5 mL) with DIPEA (277.69 mg, 2.15 mmol, 374.24 µL) were added and the resulting mixture was stirred at 20° C. for 1 h. LCMS showed all starting material was consumed completely and one peak with desired mass was detected. The reaction mixture was diluted with H$_2$O (20 mL) and extracted with EtOAc (20 mL×3). The organic layer was washed with brine (20 mL×3), dried over Na$_2$SO$_4$, filtered and concentrated. The residue was purified by column chromatography (SiO$_2$, Petroleum ether/Ethyl acetate=1/1 to 0/1 to Dichloromethane/Methanol=1/0 to 10/1) to afford the titled compound (612 mg, 714.46 µmol, 66.51% yield, 97% purity) as a white oil. MS(M+H)$^+$=831.1

Step 7: Synthesis of N-(1-(4-(2-aminoethoxy)benzyl)piperidin-4-yl)-4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzamide (10)

To a mixture of benzyl (2-(4-((4-(4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzamido)piperidin-1-yl)methyl)phenoxy)ethyl)carbamate (612 mg, 736.56 µmol) in ACN (10 mL) was added TMSI (221.07 mg, 1.10 mmol, 150.39 µL) in one portion at 20° C. and the resulting mixture was stirred at 20° C. for 2 h. LCMS showed starting material was consumed completely and one peak with desired mass. To the reaction mixture was added TEA (223.59 mg, 2.21 mmol, 307.56 µL) and stirred at 20° C. for 1 h. The reaction mixture was concentrated in vacuo. The residue was purified by prep-HPLC (column: Phenomenex luna C$_{18}$ 150*40 mm*15 um; mobile phase: [water (0.225% FA)-ACN]; B %: 10%-40%, 10 min) and the eluent was lyophilized to afford the titled compound (393 mg, 547.12 µmol, 74.28% yield, 97% purity) as a white solid. MS(M+H)$^+$=697.2

Step 8: Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(4-(2-((2-(2,6-dioxopiperidin-3-yl)-1,3-dioxoisoindolin-4-yl) amino)ethoxy)benzyl)piperidin-4-yl)-2-fluoro-5-methoxybenzamide (Compound 40)

To a mixture of 2-(2,6-dioxopiperidin-3-yl)-4-fluoroisoindoline-1,3-dione (150 mg, 543.05 µmol) and N-(1-(4-(2-aminoethoxy)benzyl)piperidin-4-yl)-4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzamide (378.37 mg, 543.05 mol) in DMSO (5 mL) was added TEA (164.85 mg, 1.63 mmol, 226.75 µL) in one portion and the resulting mixture was stirred at 80° C. for 16 h. LCMS showed all starting material was consumed completely and one peak with desired mass was detected. The reaction mixture was diluted with H$_2$O (12 mL) and extracted with EtOAc (12 mL×3). The organic layer was washed with brine (12 mL×3), dried over Na$_2$SO$_4$, filtered and concentrated. The residue was purified by prep-HPLC (column: Phenomenex luna C$_{18}$ 150*40 mm*15 um; mobile phase: [water (0.225% FA)-ACN]; B %: 18%-48%, 10 min) and the eluent was lyophilized to afford the titled compound (30 mg, 29.59 μmol, 5.45% yield, 94% purity) as a yellow solid. MS(M+H)$^+$=953.3

$^1$H NMR (400 MHz, CD$_3$OD) δ=8.41 (d, J=14.1 Hz, 1H), 8.22 (s, 1H), 7.59 (dd, J=7.2, 8.5 Hz, 1H), 7.35-7.28 (m, 3H), 7.20 (d, J=8.6 Hz, 1H), 7.09 (d, J=7.1 Hz, 1H), 6.97 (d, J=8.7 Hz, 2H), 5.07 (br dd, J=5.5, 12.5 Hz, 1H), 4.97-4.93 (m, 1H), 4.24 (t, J=5.1 Hz, 2H), 4.05 (br t, J=13.5 Hz, 2H), 4.00 (s, 3H), 3.79-3.64 (m, 4H), 3.42 (s, 3H), 3.12-3.01 (m, 2H), 2.89-2.70 (m, 2H), 2.54-2.29 (m, 2H), 2.22-1.96 (m, 6H), 1.90-1.64 (m, 9H).

Example 41. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(4-(2-(2-(2-((2-(2,6-dioxopiperidin-3-yl)-1,3-dioxoisoindolin-4-yl)amino)ethoxy)ethoxy)ethoxy)benzyl)piperidin-4-yl)-2-fluoro-5-methoxybenzamide

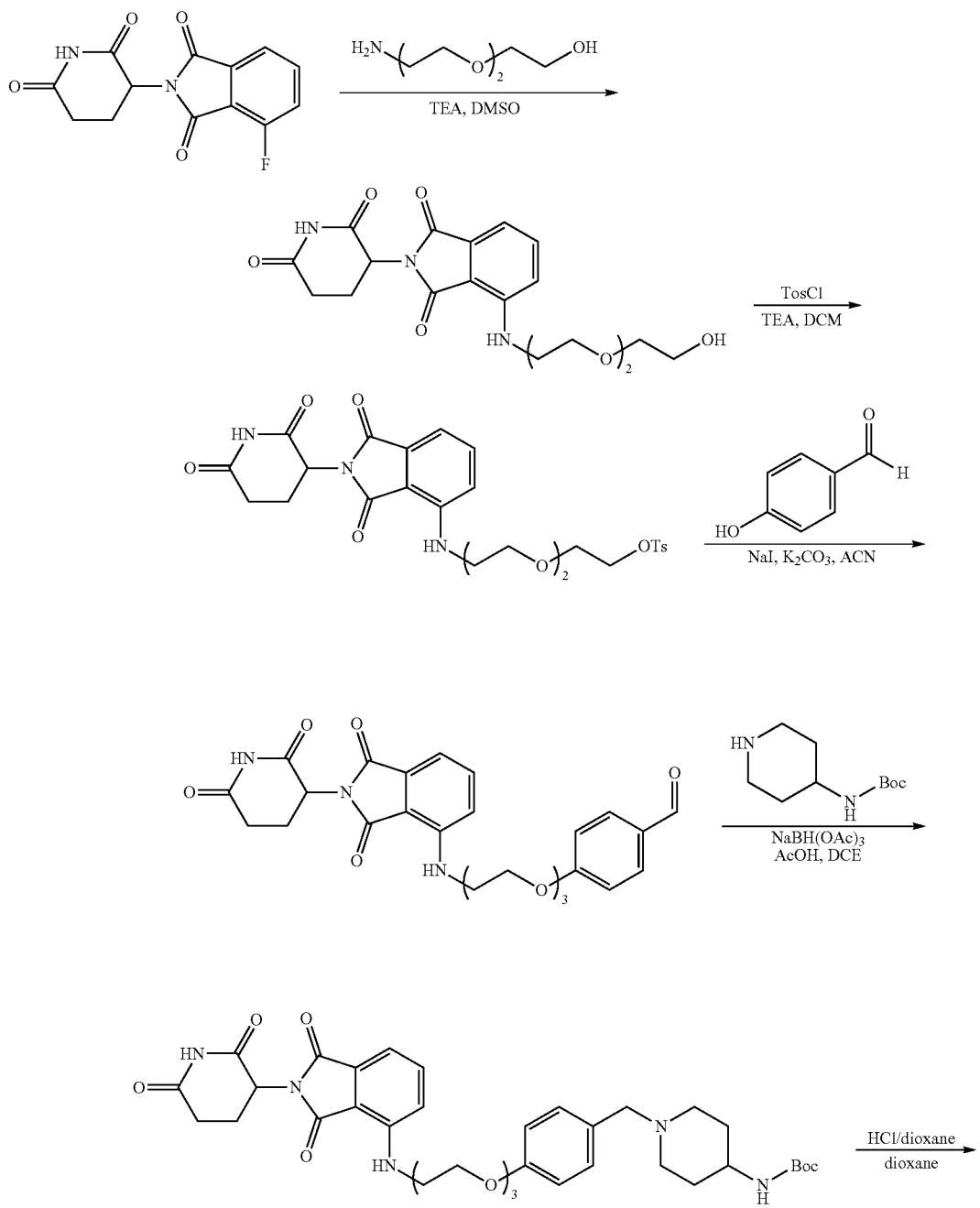

243 244

-continued

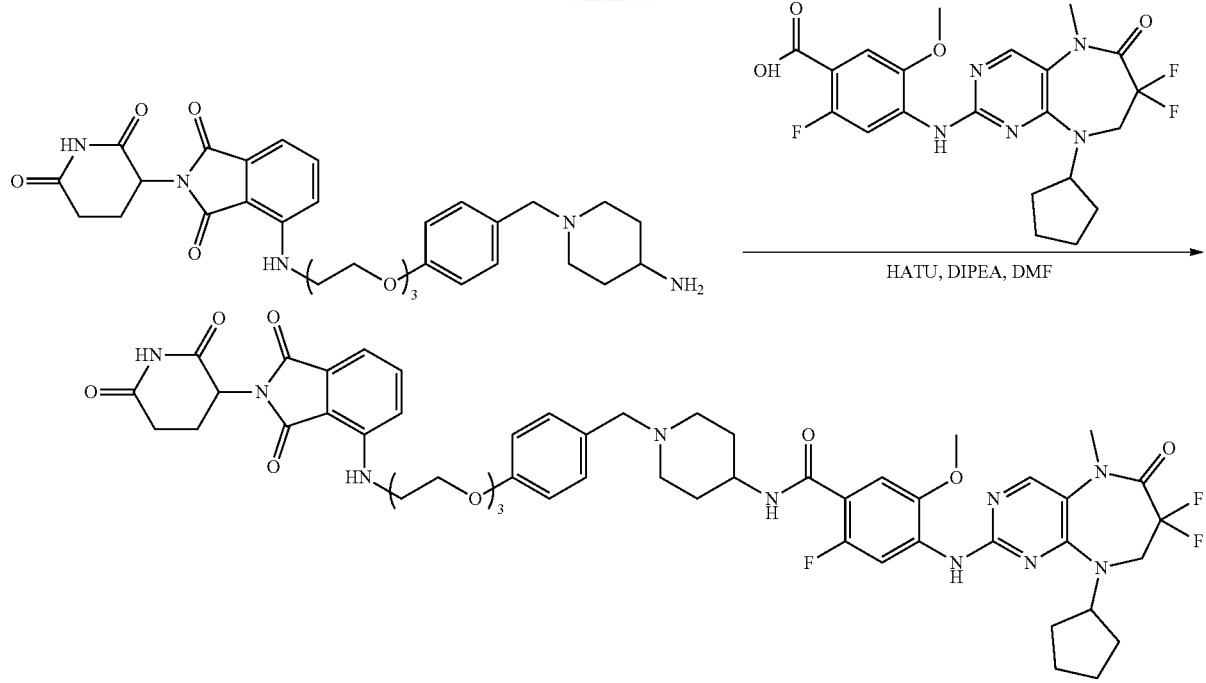

Compound 41

According to the above reaction scheme, in a manner similar to the other examples, obtained the titled compound (112.4 mg, 92.44 μmol, 20.80% yield, 95% purity, TFA salt) as a yellow solid. MS(M+H)$^+$=1042.1.

$^1$H NMR (400 MHz, CD$_3$OD) δ=8.32 (d, J=13.7 Hz, 1H), 8.24-8.22 (m, 1H), 7.55 (dd, J$_1$=8.5 Hz, J2=7.2 Hz, 1H), 7.43-7.31 (m, 3H), 7.14-7.07 (m, 1H), 7.07-6.97 (m, 3H), 5.07-4.99 (m, 2H), 4.33-4.23 (m, 2H), 4.22-4.05 (m, 5H), 4.03-3.97 (m, 3H), 3.93-3.85 (m, 2H), 3.78-3.68 (m, 6H), 3.62-3.46 (m, 4H), 3.42 (s, 3H), 3.20-3.03 (m, 2H), 2.91-2.78 (m, 1H), 2.75-2.70 (m, 1H), 2.34-2.20 (m, 2H), 2.19-2.00 (m, 4H), 1.92-1.67 (m, 8H).

Example 42. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(4-(2-((2-(2,6-dioxopiperidin-3-yl)-1,3-dioxoisoindolin-4-yl)amino)-2-oxoethyl)phenethyl)piperidin-4-yl)-2-fluoro-5-methoxybenzamide

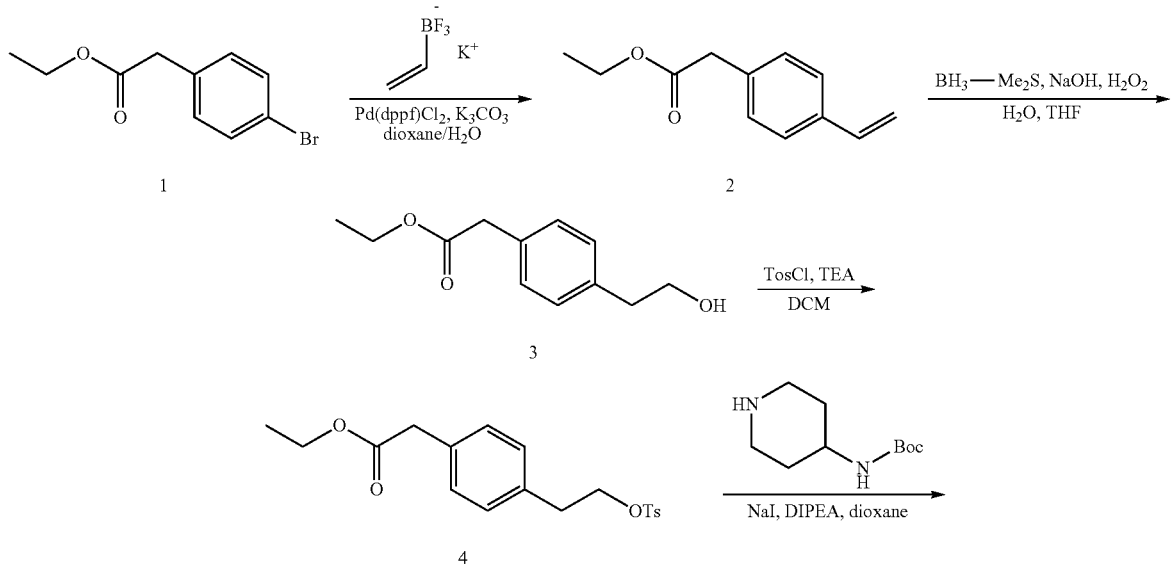

-continued
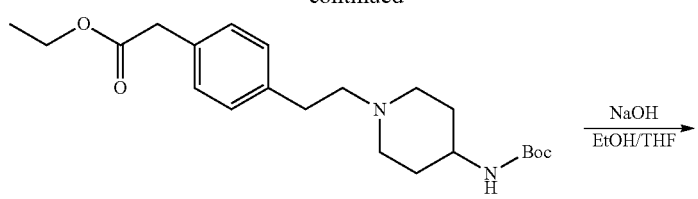
5
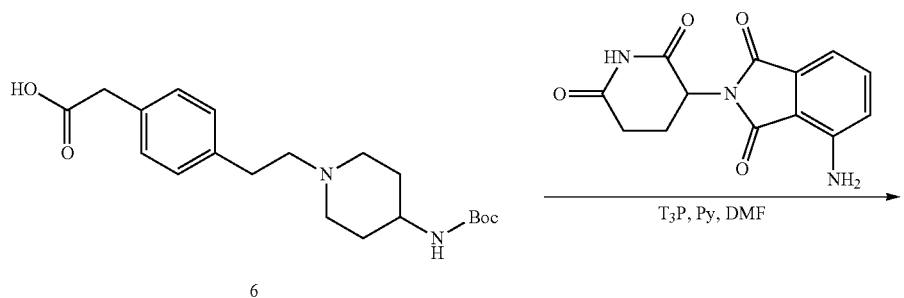
6
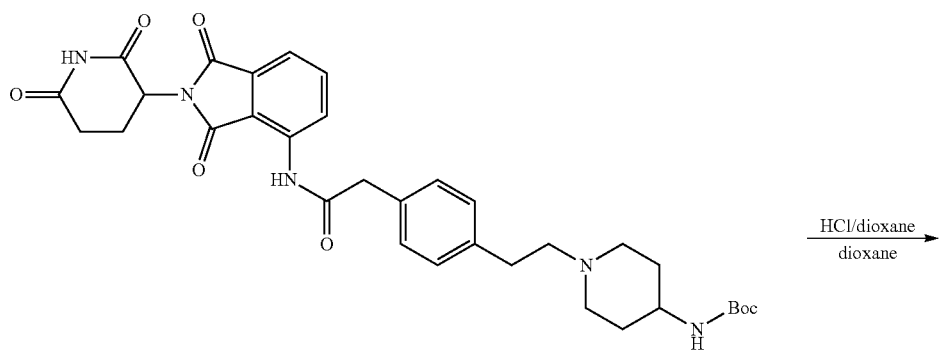
7
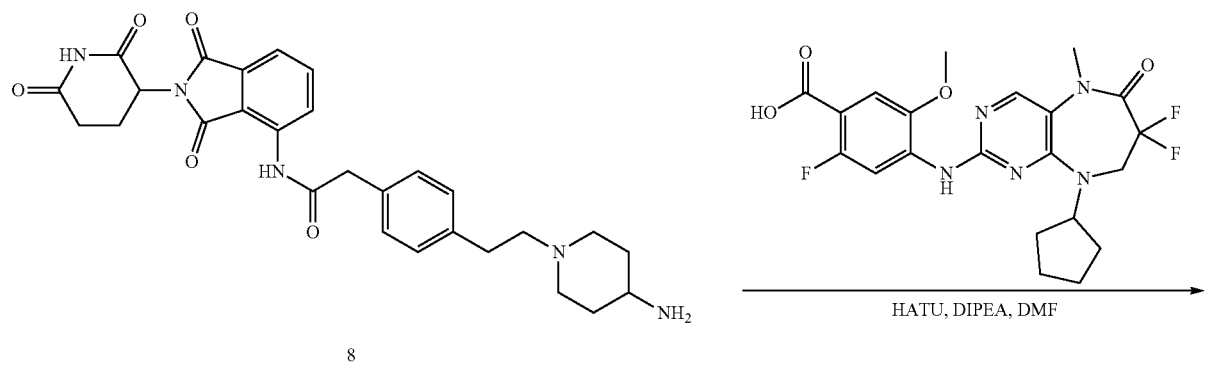
8

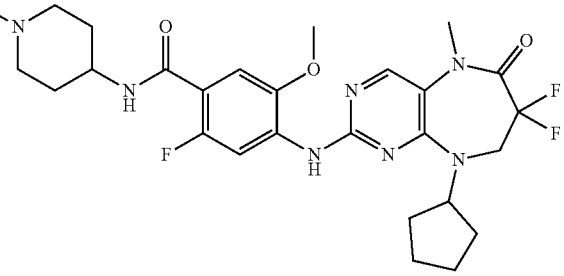

Compound 42

Step 1: Synthesis of ethyl 2-(4-vinylphenyl)acetate (2)

To a mixture of ethyl 2-(4-bromophenyl)acetate (10 g, 41.14 mmol) and potassium; trifluoro (vinyl) boranuide (6.61 g, 49.36 mmol) in H₂O (20 mL) and dioxane (100 mL) were added K₂CO₃ (17.06 g, 123.41 mmol) and Pd(dppf)Cl₂ (1.50 g, 2.06 mmol) in one portion at 20° C. under N₂. The suspension was degassed under vacuum and purged with N₂ several times and the resulting mixture was stirred at 100° C. for 16 h. LCMS showed all starting material was consumed completely and one peak with desired mass was detected. TLC (SiO₂, Petroleum ether:Ethyl acetate=10:1) indicated ethyl 2-(4-bromophenyl)acetate was consumed completely and two new spots were detected. The reaction mixture was diluted with H₂O (100 mL) and extracted with EtOAc (100 mL×3). The organic layer dried over Na₂SO₄, filtered and concentrated. The residue was purified by column chromatography (SiO₂, Petroleum ether/Ethyl acetate=1/0 to 100/1) to afford the titled compound (5.3 g, 25.91 mmol, 62.99% yield, 93% purity) as a yellow oil. MS(M+H)⁺=191.5

Step 2: Synthesis of ethyl 2-(4-(2-hydroxyethyl)phenyl)acetate (3)

To a mixture of ethyl 2-(4-vinylphenyl)acetate (2.3 g, 12.09 mmol) in THF (20 mL) was added BH₃·Me₂S (10 M, 1.81 mL) drop-wise at 0° C. under N₂ and the resulting mixture was stirred at 20° C. for 2 h. TLC (SiO₂, Petroleum ether:Ethyl acetate=5:1) indicated starting material was consumed completely and one major new spot was detected. Then H₂O (8.28 g, 459.61 mmol, 8.28 mL), NaOH (3 M, 4.60 mL) and H₂O₂ (9.77 g, 86.17 mmol, 8.28 mL, 30% purity) were added sequentially to this reaction at 0° C. and the resulting mixture was allowed to stir another 2 h at 20° C. TLC (SiO₂, Petroleum ether:Ethyl acetate=5:1) indicated starting material was consumed completely and four new spots were detected. The reaction mixture was quenched with saturated Na₂SO₃ (50 mL) and extracted with EtOAc (50 mL×3). The organic layer was dried over Na₂SO₄, filtered and concentrated. The residue was purified by column chromatography (SiO₂, Petroleum ether/Ethyl acetate=10/1 to 5/1) to afford the titled compound (1.2 g, 4.84 mmol, 40.03% yield, 84% purity) as a white oil. MS(M+H)⁺=209.2

Step 3: Synthesis of ethyl 2-(4-(2-(tosyloxy)ethyl)phenyl)acetate (4)

To a mixture of ethyl 2-(4-(2-hydroxyethyl)phenyl)acetate (1.2 g, 4.84 mmol, 84% purity) in DCM (12 mL) were added TEA (1.47 g, 14.52 mmol, 2.02 mL) and TosCl (1.38 g, 7.26 mmol) in one portion at 20° C. and the resulting mixture was stirred at 20° C. for 16 h. LCMS showed ethyl 2-(4-(2-hydroxyethyl)phenyl)acetate was consumed completely and one peak with desired mass was detected. TLC (SiO₂, Petroleum ether:Ethyl acetate=5:1) indicated ethyl 2-(4-(2-hydroxyethyl)phenyl)acetate was consumed completely and three new spots were detected. The reaction mixture was concentrated in vacuum. The residue was purified by column chromatography (SiO₂, Petroleum ether/Ethyl acetate=10/1 to 5/1) to afford ethyl 2-(4-(2-(tosyloxy)ethyl)phenyl)acetate (1.7 g, 4.60 mmol, 94.97% yield, 98% purity) as a white solid. MS(M+NH 4)⁺=380.2

Step 4: Synthesis of ethyl 2-(4-(2-(4-((tert-butoxycarbonyl)amino)piperidin-1-yl)ethyl)phenyl)acetate (5)

To a mixture of ethyl 2-(4-(2-(tosyloxy)ethyl)phenyl) acetate (1.7 g, 4.69 mmol) and tert-butyl N-(4-piperidyl) carbamate (1.88 g, 9.38 mmol) in dioxane (10 mL) were added NaI (140.61 mg, 938.09 µmol) and DIPEA (1.82 g, 14.07 mmol, 2.45 mL) in one portion at 20° C. and the resulting mixture was stirred at 60° C. for 16 h. LCMS showed ethyl 2-(4-(2-(tosyloxy)ethyl)phenyl) acetate remained and one peak with desired mass was detected. TLC (SiO₂, Petroleum ether:Ethyl acetate=1:3) indicated ethyl 2-(4-(2-(tosyloxy)ethyl)phenyl) acetate remained and four new spots were detected. The reaction mixture was concentrated in vacuum. The residue was purified by column chromatography (SiO₂, Petroleum ether/Ethyl acetate=2/1 to 1/3) to afford the titled compound (1.36 g, 3.27 mmol, 69.79% yield, 94% purity) as a white solid. MS(M+H)$^+$=391.4

Step 5: Synthesis of 2-(4-(2-(4-((tert-butoxycarbonyl)amino)piperidin-1-yl)ethyl)phenyl)acetic acid (6)

To a mixture of ethyl 2-(4-(2-(4-((tert-butoxycarbonyl)amino)piperidin-1-yl)ethyl)phenyl)acetate (600 mg, 1.54 mmol) in EtOH (6 mL) and THF (6 mL) was added NaOH (2 M, 1.54 mL) in one portion at 20° C. and the resulting mixture was stirred at 20° C. for 1 h. LCMS showed starting material was consumed completely and one peak with desired mass was detected. HCl (12 N) was added to this reaction mixture to adjust the pH=7 at 0° C. The reaction mixture was concentrated in vacuum to afford the titled compound (710 mg, crude) as a white solid. MS(M−H)$^+$=361.0

Step 6: Synthesis of tert-butyl (1-(4-(2-((2-(2,6-dioxopiperidin-3-yl)-1,3-dioxoisoindolin-4-yl)amino)-2-oxoethyl)phenethyl)piperidin-4-yl)carbamate (7)

To a mixture of 4-amino-2-(2,6-dioxopiperidin-3-yl)isoindoline-1,3-dione (400 mg, 1.46 mmol) and 2-(4-(2-(4-((tert-butoxycarbonyl)amino)piperidin-1-yl)ethyl)phenyl)acetic acid (689.79 mg, 1.90 mmol) in DMF (5 mL) were added T$_3$P (2.79 g, 8.78 mmol, 50% purity EtOAc in solution, 2.61 mL) and Py (1.16 g, 14.64 mmol, 1.18 mL) in one portion at 20° C. and the resulting mixture was stirred at 80° C. for 16 h. LCMS showed all starting material was consumed completely and one peak with desired mass was detected. TLC (SiO$_2$, Dichloromethane:Methanol=10:1) indicated all starting material was consumed completely and one major new spot was detected. The reaction mixture was diluted with H$_2$O (15 mL) and extracted with EtOAc (15 mL×3). The organic layer was washed with brine (15 mL×3), dried over Na$_2$SO$_4$, filtered and concentrated. The residue was purified by column chromatography (SiO$_2$, Petroleum ether/Ethyl acetate=1/1 to 0/1 to Dichloromethane/Methanol=1/0 to 10/1) to afford the titled compound (618 mg, 930.47 μmol, 63.56% yield, 93% purity) as a yellow solid. MS(M+H)$^+$=618.2

Step 7: Synthesis of 2-(4-(2-(4-aminopiperidin-1-yl)ethyl)phenyl)-N-(2-(2,6-dioxopiperidin-3-yl)-1,3-dioxo isoindolin-4-yl)acetamide (8)

To a mixture of tert-butyl (1-(4-(2-((2-(2,6-dioxopiperidin-3-yl)-1,3-dioxoisoindolin-4-yl)amino)-2-oxoethyl)phenethyl)piperidin-4-yl)carbamate (615 mg, 995.64 μmol) in dioxane (3 mL) was added HCl/dioxane (4 M, 9 mL) in one portion at 20° C. and the resulting mixture was stirred at 20° C. for 16 h. LCMS showed starting material was consumed completely and one peak with desired mass was detected. The reaction mixture was concentrated in vacuum to afford the titled compound (556 mg, crude, HCl) as a white solid. MS(M+H)$^+$=518.2

Step 8: Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(4-(2-((2-(2,6-dioxopiperidin-3-yl)-1,3-dioxoisoindolin-4-yl)amino)-2-oxoethyl)phenethyl)piperidin-4-yl)-2-fluoro-5-methoxybenzamide (Compound 42)

To a solution of 4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzoic acid (250 mg, 537.14 μmol) in DMF (3 mL) were added HATU (224.66 mg, 590.86 μmol) and DIPEA (138.84 mg, 1.07 mmol, 187.12 μL). The mixture was stirred at 20° C. for 10 min and a solution of 2-(4-(2-(4-aminopiperidin-1-yl)ethyl)phenyl)-N-(2-(2,6-dioxopiperidin-3-yl)-1,3-dioxo isoindolin-4-yl)acetamide (357.12 mg, crude, HCl) in DMF (3 mL) and DIPEA (138.84 mg, 1.07 mmol, 187.12 μL, 2 eq) were added and the resulting mixture was stirred at 20° C. for 1 h. LCMS showed all starting material was consumed completely and one peak with desired mass was detected. The reaction mixture was diluted with H$_2$O (15 mL) and extracted with EtOAc (15 mL×3). The organic layer was washed with brine (15 mL×3), dried over Na$_2$SO$_4$, filtered and concentrated. The residue was purified by prep-HPLC (column: Phenomenex luna C$_{18}$ 150*40 mm*15 um; mobile phase: [water (0.225% FA)-ACN]; B %: 20%-50%, 10 min) and then lyophilized to the titled compound (132.9 mg, 130.84 μmol, 24.36% yield, 95% purity) as a off-white solid. MS(M+H)$^+$=965.2

$^1$H NMR (400 MHz, DMSO-d$_6$) δ=11.33-10.96 (m, 1H), 9.79 (s, 1H), 8.49 (d, J=8.4 Hz, 1H), 8.30 (s, 1H), 8.24 (d, J=13.6 Hz, 1H), 8.03 (s, 1H), 7.88 (dd, J=3.2, 7.2 Hz, 1H), 7.82 (t, J=7.9 Hz, 1H), 7.60 (d, J=7.2 Hz, 1H), 7.31-7.25 (m, 2H), 7.23-7.16 (m, 3H), 5.12 (dd, J=5.4, 12.8 Hz, 1H), 4.85-4.77 (m, 1H), 4.07 (t, J=13.9 Hz, 2H), 3.91 (s, 3H), 3.85-3.68 (m, 4H), 3.33 (s, 3H), 2.94-2.84 (m, 3H), 2.76-2.56 (m, 4H), 2.11-1.93 (m, 5H), 1.85-1.48 (m, 11H)

Example 43. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(3-(4-(((2-(2,6-dioxopiperidin-3-yl)-1,3-dioxoisoindolin-4-yl)amino)methyl)-1H-imidazol-1-yl)propyl)piperidin-4-yl)-2-fluoro-5-methoxybenzamide

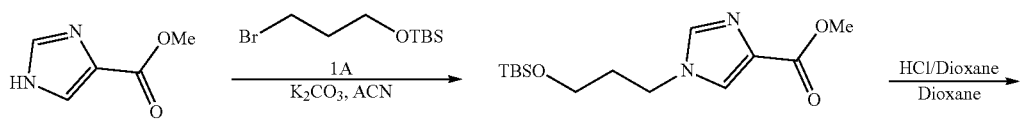

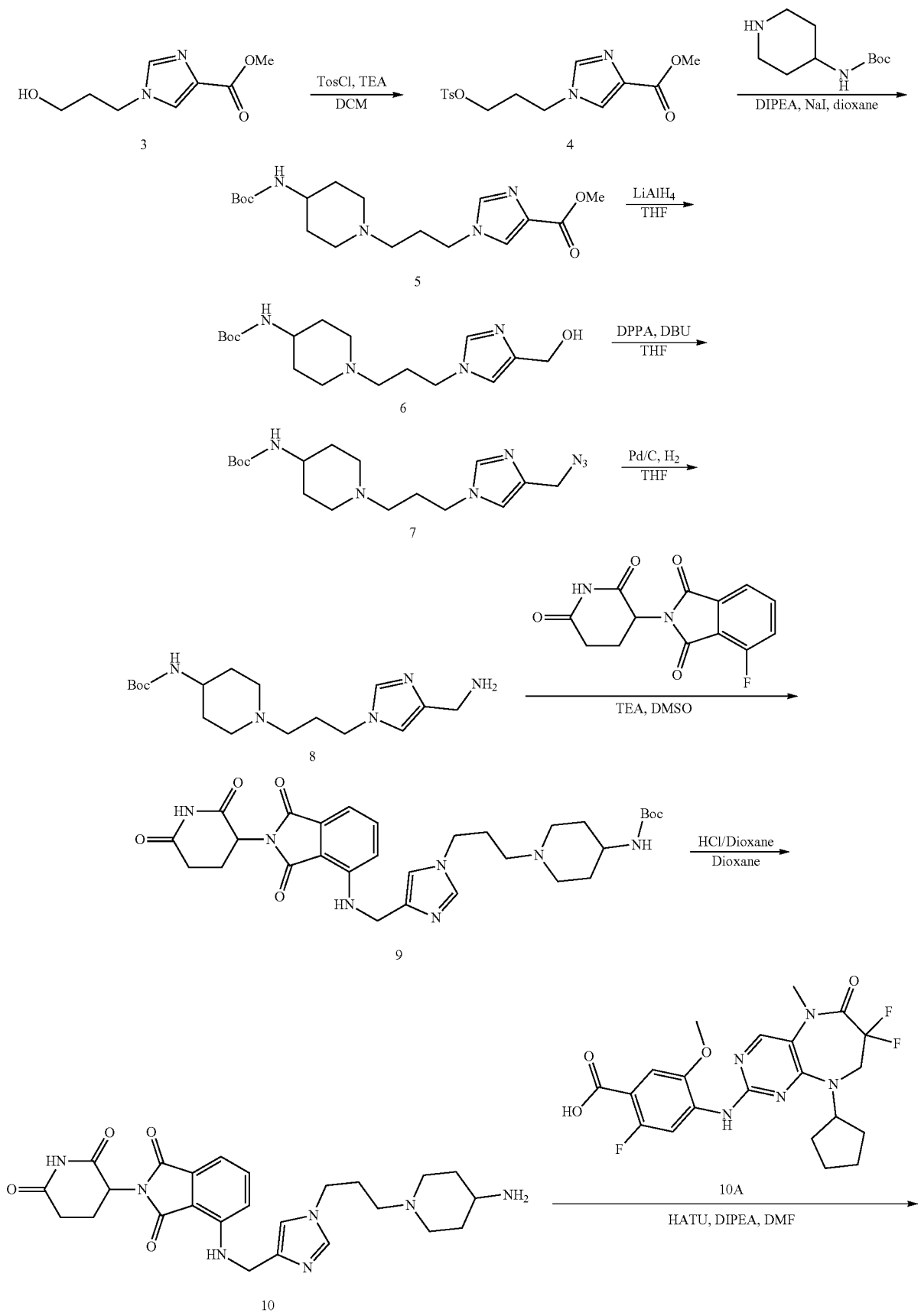
-continued

-continued

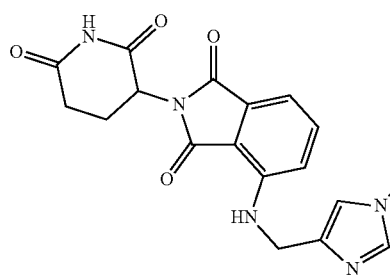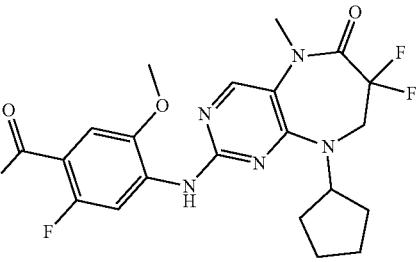

Compound 43

Step 1: Synthesis of methyl 1-(3-((tert-butyldimethylsilyl)oxy)propyl)-1H-imidazole-4-carboxylate (2)

To a solution of methyl 1H-imidazole-4-carboxylate (10 g, 79.29 mmol) in $CH_3CN$ (200 mL) were added $K_2CO_3$ (35 g, 253.25 mmol) and 3-bromopropoxy-tert-butyl-dimethylsilane (25.78 g, 101.80 mmol). The mixture was stirred at 25° C. for 16 h. LCMS showed a main peak with desired mass. The reaction mixture was filtered, and the filtrate was concentrated under reduced pressure. The residue was purified by column chromatography ($SiO_2$, Petroleum ether/Ethyl acetate=10:1-0:1) to afford the titled compound (8.2 g, 27.20 mmol, 34.30% yield, 99% purity) as a light yellow oil. MS $(M+H)^+=299.1$ Step 2: Synthesis of methyl 1-(3-hydroxypropyl)-1H-imidazole-4-carboxylate (3)

To a solution of methyl 1-(3-((tert-butyldimethylsilyl)oxy)propyl)-1H-imidazole-4-carboxylate (6.5 g, 21.78 mmol) in dioxane (20 mL) was added HCl/dioxane (4 M, 86.67 mL) at 25° C. The mixture was stirred at 25° C. for 16 h. LCMS showed a main peak with the desired mass. The reaction mixture was concentrated under reduced pressure to afford the titled compound (4.0 g, crude) as a light yellow oil. MS $(M+H)^+=185.2$ Step 3: Synthesis of methyl 1-(3-(tosyloxy)propyl)-1H-imidazole-4-carboxylate (4)

To a solution of methyl 1-(3-hydroxypropyl)-1H-imidazole-4-carboxylate (4 g, 21.72 mmol) in DCM (50 mL) was added TEA (18.18 g, 179.61 mmol, 25 mL) and TosCl (13.33 g, 69.94 mmol) at 25° C. The mixture was stirred at 25° C. for 16 h. LCMS showed 26% peak with the desired mass. The reaction mixture was concentrated under reduced pressure to give a residue. Then $H_2O$ (40 mL) was added, the mixture was extracted with EtOAc (80 mL×3), the combined organic layers were washed with brine 180 ml (60 mL×3), dried over $Na_2SO_4$, filtered and the filtrate was concentrated under reduced pressure. The residue was purified by column chromatography ($SiO_2$, Petroleum ether:Ethyl acetate=5:1–0:1) to afford the titled compound (4.5 g, 13.30 mmol, 61.24% yield) as a light yellow oil. MS $(M+H)^+=339.2$ Step 4: Synthesis of methyl 1-(3-(4-((tert-butoxycarbonyl)amino)piperidin-1-yl)propyl)-1H-imidazole-4-carboxylate (5)

To a solution of methyl 1-(3-(tosyloxy)propyl)-1H-imidazole-4-carboxylate (2 g, 5.91 mmol) in dioxane (40 mL) were added NaI (400.00 mg, 2.67 mmol), DIPEA (2.97 g, 22.96 mmol, 4.00 mL) and tert-butyl piperidin-4-ylcarbamate (2.00 g, 9.99 mmol) at 25° C. The mixture was stirred at 80° C. for 16 h. LCMS showed 56% peak with the desired mass. The reaction mixture was concentrated under reduced pressure to give a residue. The residue was purified by prep-HPLC (column: Waters Xbridge BEH $C_{18}$ 250*50 mm*10 um; mobile phase: [water (10 mM $NH_4HCO_3$)-ACN]; B %: 10%-40%, 25 min, Column Temp: 30° C.) followed by lyophilization to afford the titled compound (1.5 g, 4.09 mmol, 69.25% yield) as a light yellow oil. MS $(M+H)^+=367.1$.

Step 5: Synthesis of tert-butyl (1-(3-(4-(hydroxymethyl)-1H-imidazol-1-yl)propyl)piperidin-4-yl)carbamate (6)

To a solution of methyl 1-(3-(4-((tert-butoxycarbonyl)amino)piperidin-1-yl)propyl)-1H-imidazole-4-carboxylate (1.5 g, 4.09 mmol) in THF (20 mL) was added $LiAlH_4$ (300 mg, 7.90 mmol) at −20° C. The mixture was stirred at 20° C. for 3 hr. LCMS showed main peak with the mass [M+Li] was detected. The reaction mixture was quenched with $H_2O$ (2 mL) and NaOH solution (15%, 3 mL) at 0° C., then $Na_2SO_4$ (25 g) was added, the mixture was filtered and the filtrate was concentrated under reduced pressured to afford the titled compound (1.3 g, crude) as a light yellow oil. MS $(M+Li)^+=345.1$.

Step 6: Synthesis of tert-butyl (1-(3-(4-(azidomethyl)-1H-imidazol-1-yl)propyl)piperidin-4-yl)carbamate (7)

To a solution of tert-butyl (1-(3-(4-(hydroxymethyl)-1H-imidazol-1-yl)propyl)piperidin-4-yl)carbamate (1.3 g, 3.84 mmol) in THF (30 mL) were added DPPA (2.54 g, 9.23 mmol, 2 mL) and DBU (2.02 g, 13.27 mmol, 2 mL) at 0° C. The mixture was stirred at 25° C. for 16 h under $N_2$ atmosphere. LCMS showed 32% peak with the desired mass. To the reaction mixture was added $H_2O$ (20 mL), the mixture was extracted with EtOAc (50 mL×2), the combined organic layers were washed with brine (30 mL×3), dried over $Na_2SO_4$, filtered and the filtrate was concentrated under reduced pressure. The residue was purified by column chromatography ($SiO_2$, Ethyl acetate:Methanol=1:0-3:1) to afford the titled compound (850 mg, 2.34 mmol, 60.88% yield) as a light yellow oil. MS $(M+H)^+=364.1$ Step 7: Synthesis of tert-butyl (1-(3-(4-(aminomethyl)-1H-imidazol-1-yl)propyl)piperidin-4-yl)carbamate (8)

To a solution of tert-butyl (1-(3-(4-(azidomethyl)-1H-imidazol-1-yl)propyl)piperidin-4-yl)carbamate (680 mg, 1.87 mmol, 1 eq) in THF (30 mL) was added Pd/C (200 mg, 10% purity) at 25° C. The mixture was stirred at 25° C. for 16 h under $H_2$ atmosphere (15 Psi). LCMS showed 40% peak with the desired mass. The reaction mixture was filtered and the filtrate was concentrated under reduced pressure to afford the titled compound (600 mg, crude) as a light yellow oil. MS (M+H)$^+$=338.3

Step 8: Synthesis of tert-butyl (1-(3-(4-(((2-(2,6-dioxopiperidin-3-yl)-1,3-dioxoisoindolin-4-yl)amino)methyl)-1H-imidazol-1-yl)propyl)piperidin-4-yl)carbamate (9)

To a solution of tert-butyl (1-(3-(4-(aminomethyl)-1H-imidazol-1-yl)propyl)piperidin-4-yl)carbamate (600 mg, 1.78 mmol) in DMSO (15 mL) were added TEA (727.00 mg, 7.18 mmol, 1 mL) and 2-(2,6-dioxopiperidin-3-yl)-4-fluoroisoindoline-1,3-dione (400 mg, 1.45 mmol) at 25° C. The mixture was stirred at 100° C. for 16 h under $N_2$ atmosphere. LCMS showed 33% peak with the desired mass. To the reaction mixture was added $H_2O$ (20 mL), the mixture was extracted with EtOAc (30 mL×2), the combined organic layers were washed with brine (30 mL×3), dried over $Na_2SO_4$, filtered and the filtrate was concentrated under reduced pressure. The residue was purified by column chromatography ($SiO_2$, DCM/MeOH=30/1~10/1) to afford the titled compound (400 mg, 673.77 mol, 37.90% yield) as a light yellow oil. MS (M+H)$^+$=594.5

Step 9: Synthesis 4-(((1-(3-(4-aminopiperidin-1-yl)propyl)-1H-imidazol-4-yl)methyl)amino)-2-(2,6-dioxopiperidin-3-yl)isoindoline-1,3-dione (10)

To a solution of tert-butyl (1-(3-(4-(((2-(2,6-dioxopiperidin-3-yl)-1,3-dioxoisoindolin-4-yl)amino)methyl)-1H-imidazol-1-yl)propyl)piperidin-4-yl)carbamate (400 mg, 673.77 μmol) in dioxane (10 mL) was added HCl/dioxane (4 M, 10 mL) at 25° C. The mixture was stirred at 25° C. for 16 h under $N_2$ atmosphere. LCMS showed 62% peak with the desired mass. The reaction mixture was concentrated under reduced pressure to afford the titled compound (350 mg, crude, 2HCl) as a light yellow solid. MS (M+H)$^+$=494.4

Step 10: Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(3-(4-(((2-(2,6-dioxopiperidin-3-yl)-1,3-dioxoisoindolin-4-yl)amino)methyl)-1H-imidazol-1-yl)propyl)piperidin-4-yl)-2-fluoro-5-methoxybenzamide (Compound 43)

To a solution of 4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzoic acid (200 mg, 429.71 μmol) in DMF (4 mL) were added HATU (400 mg, 1.05 mmol), DIPEA (445.20 mg, 3.44 mmol, 600 μL) and 4-(((1-(3-(4-aminopiperidin-1-yl)propyl)-1H-imidazol-4-yl)methyl)amino)-2-(2,6-dioxopiperidin-3-yl)isoindoline-1,3-dione (300 mg, 529.59 μmol, 2HCl) at 25° C. The mixture was stirred at 25° C. for 16 h under $N_2$ atmosphere. LCMS showed 39% peak with the desired mass. To the reaction mixture was added $H_2O$ (10 mL), the mixture was extracted with EtOAc (30 mL×2), the combined organic layers were washed with brine (30 mL×3), dried over $Na_2SO_4$, filtered and the filtrate was concentrated under reduced pressure. The residue was purified by prep-HPLC (column: Waters Xbridge 150*25 mm*5 um; mobile phase: [water (10 mM $NH_4HCO_3$)-ACN]; B %: 42%-62%, 9 min, Column Temp: 30° C.) followed by lyophilization to afford the titled compound (84.7 mg, 83.71 μmol, 19.48% yield, 93% purity) as a light yellow solid. MS (M+H)$^+$=941.7

$^1$H NMR (400 MHz, DMSO-d$_6$) δ 11.08 (br s, 1H), 8.31 (s, 1H), 8.25 (d, J=13.3 Hz, 1H), 8.04 (s, 1H), 7.87 (dd, J=3.1, 7.7 Hz, 1H), 7.61-7.50 (m, 2H), 7.23-7.14 (m, 2H), 7.09 (s, 1H), 7.04 (d, J=7.0 Hz, 1H), 6.89 (t, J=5.8 Hz, 1H), 5.05 (dd, J=5.5, 12.7 Hz, 1H), 4.86-4.77 (m, 1H), 4.40-4.33 (m, 2H), 4.08 (t, J=13.9 Hz, 2H), 3.97-3.93 (m, 2H), 3.92 (s, 3H), 3.80-3.59 (m, 1H), 3.34 (s, 3H), 2.95-2.83 (m, 1H), 2.81-2.73 (m, 2H), 2.62-2.54 (m, 2H), 2.22-2.14 (m, 2H), 2.06-1.87 (m, 6H), 1.83-1.72 (m, 5H), 1.64-1.47 (m, 6H)

Example 44. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-((1-(2-(2-((2-(2,6-dioxopiperidin-3-yl)-1,3-dioxoisoindolin-4-yl)amino)ethoxy)ethyl)-1H-1,2,3-triazol-4-yl)methyl)piperidin-4-yl)-2-fluoro-5-methoxybenzamide

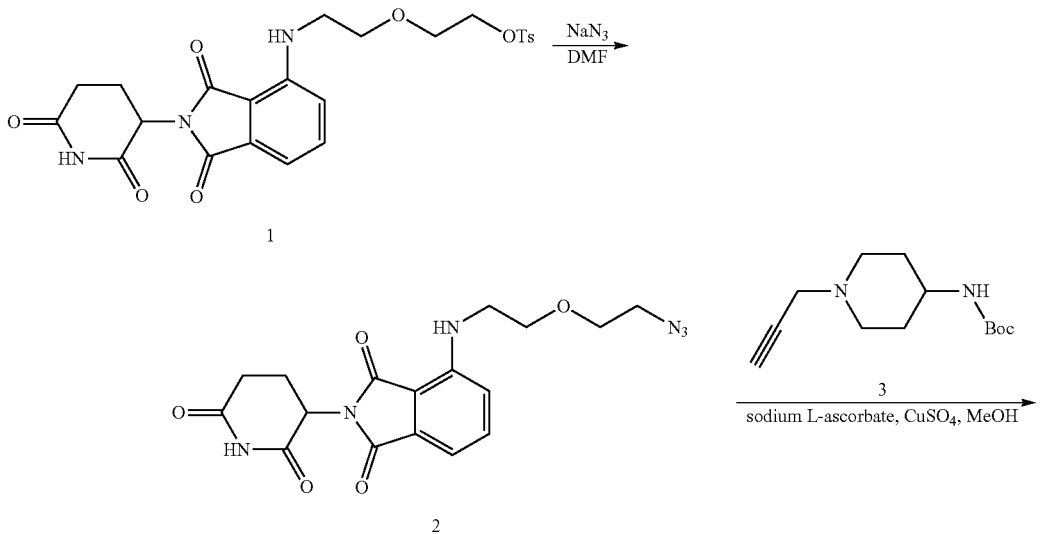

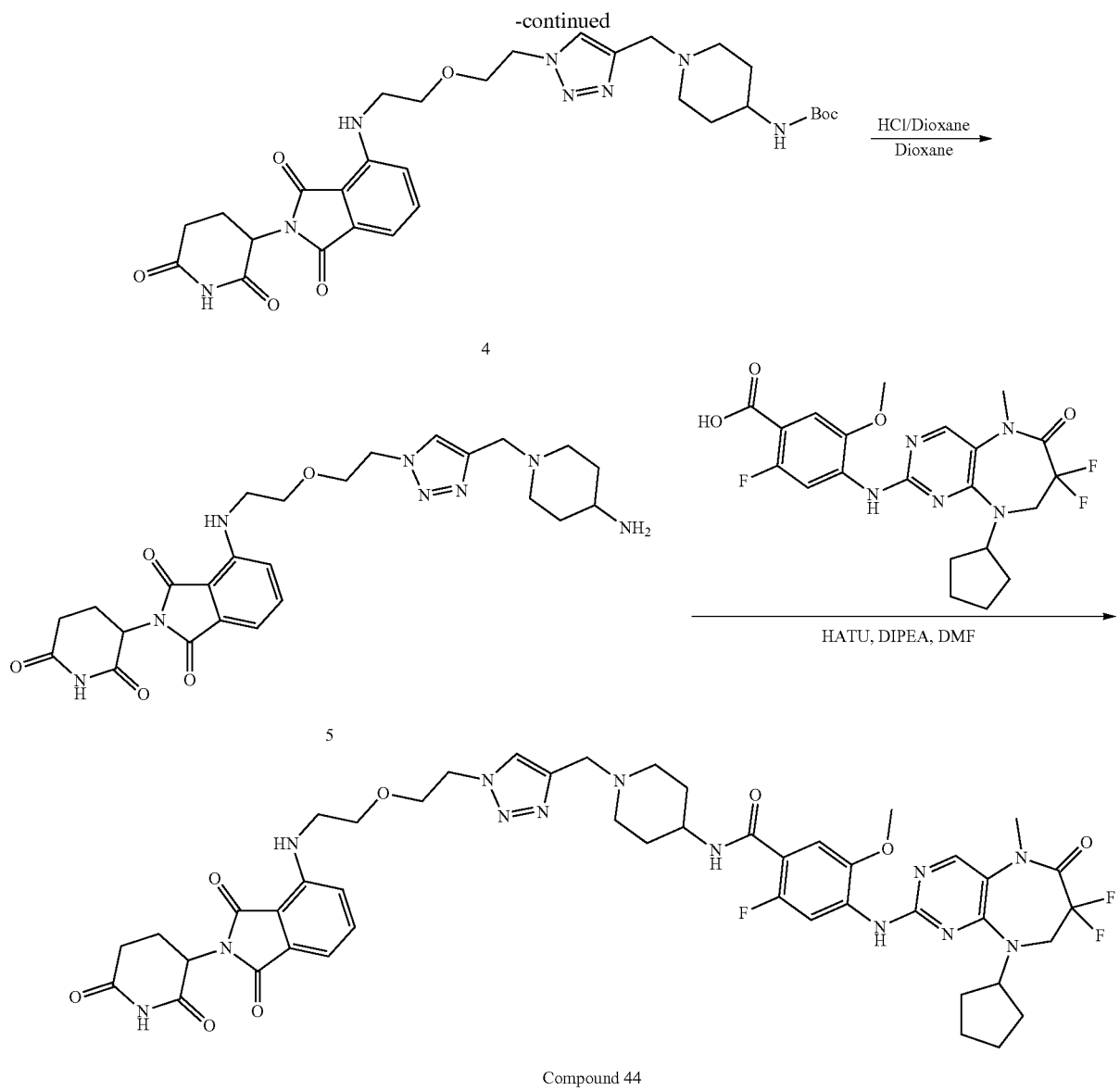

Compound 44

Step 1: Synthesis of 4-((2-(2-azidoethoxy)ethyl)amino)-2-(2,6-dioxopiperidin-3-yl)isoindoline-1,3-dione To a solution of 2-(2-((2-(2,6-dioxopiperidin-3-yl)-1,3-dioxoisoindolin-4-yl)amino)ethoxy)ethyl 4-methylbenzenesulfonate (2 g, 3.88 mmol) in DMF (20 mL) was added NaN$_3$ (450 mg, 6.92 mmol). The mixture was stirred at 70° C. for 16 h. LCMS showed main peak with the desired mass. The reaction mixture was poured into H$_2$O (20 mL) and extracted with EA (30 mL×3). The combined organic layer was washed with brine (30 mL×3). The organic layer was dried over Na$_2$SO$_4$, filtrated and concentrated to afford the titled compound (1.40 g, crude) as a light yellow solid. MS(M+H)$^+$=387.1

$^1$H NMR (400 MHz, DMSO-d$_6$) δ 11.15 (s, 1H), 7.64 (dd, J=7.2, 8.4 Hz, 1H), 7.21 (d, J=8.6 Hz, 1H), 7.10 (d, J=7.0 Hz, 1H), 6.68 (t, J=5.9 Hz, 1H), 5.15-5.05 (m, 1H), 3.74-3.66 (m, 4H), 3.55 (q, J=5.5 Hz, 2H), 3.49-3.43 (m, 2H), 2.99-2.89 (m, 1H), 2.69-2.57 (m, 2H), 2.12-2.04 (m, 1H).

Step 2: Synthesis of tert-butyl (1-((1-(2-(2-((2-(2,6-dioxopiperidin-3-yl)-1,3-dioxoisoindolin-4-yl)amino)ethoxy)ethyl)-1H-1,2,3-triazol-4-yl)methyl)piperidin-4-yl)carbamate (4)

To a solution of tert-butyl (1-(prop-2-yn-1-yl)piperidin-4-yl)carbamate (900 mg, 3.78 mmol) in MeOH (20 mL) was added CuSO$_4$ (750 mg, 4.70 mmol, 721.15 μL), sodium L-ascorbate (1 g, 5.05 mmol) and 4-((2-(2-azidoethoxy)ethyl)amino)-2-(2,6-dioxopiperidin-3-yl)isoindoline-1,3-dione (1.2 g, 3.11 mmol) at 25° C. The mixture was stirred at 25° C. for 16 h. LCMS showed 90% peak with the desired mass. The reaction mixture was filtered and the filtrate was concentrated under reduced pressure. The residue was purified by prep-HPLC (column: Phenomenex Synergi Max-RP 250*50 mm*10 um; mobile phase: [water (10 mM NH$_4$HCO$_3$)-ACN]; B %: 32%-62%, 14 min, Column Temp: 30° C.) followed by lyophilization to afford the titled compound (1.5 g, 2.40 mmol, 63.59% yield) as a light yellow solid. MS(M+H)$^+$=625.5

Step 3: Synthesis of 4-((2-(2-(4-((4-aminopiperidin-1-yl)methyl)-1H-1,2,3-triazol-1-yl)ethoxy)ethyl)amino)-2-(2,6-dioxopiperidin-3-yl)isoindoline-1,3-dione (5)

To a solution of tert-butyl (1-((1-(2-(2-((2-(2,6-dioxopiperidin-3-yl)-1,3-dioxoisoindolin-4-yl)amino)ethoxy)ethyl)-1H-1,2,3-triazol-4-yl)methyl)piperidin-4-yl)carbamate (500 mg, 800.40 µmol) in dioxane (10 mL) was added HCl/dioxane (4 M, 10 mL). The mixture was stirred at 25° C. for 16 h. LCMS showed 82% peak with the desired mass. The reaction mixture was concentrated to give a residue to afford the titled compound (450 mg, crude, 2HCl) as a light yellow solid.

MS(M+H)$^+$=525.4

Step 4: Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-((1-(2-(2-((2-(2,6-dioxopiperidin-3-yl)-1,3-dioxoisoindolin-4-yl)amino)ethoxy)ethyl)-1H-1,2,3-triazol-4-yl)methyl)piperidin-4-yl)-2-fluoro-5-methoxybenzamide (Compound 44)

To a solution of 4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzoic acid (200 mg, 429.71 µmol) in DMF (4 mL) were added HATU (400 mg, 1.05 mmol), DIPEA (445.20 mg, 3.44 mmol, 600 µL) and 4-((2-(2-(4-((4-aminopiperidin-1-yl)methyl)-1H-1,2,3-triazol-1-yl)ethoxy)ethyl)amino)-2-(2,6-dioxopiperidin-3-yl)isoindoline-1,3-dione (350 mg, 585.78 µmol, 2HCl). The mixture was stirred at 25° C. for 16 h. LCMS showed 46% peak with the desired mass. To the reaction mixture was added H$_2$O (10 mL), the mixture was extracted with EtOAc (30 mL×2), the combined organic layers were washed with brine 90 mL (30 mL×3), dried over anhydrous Na$_2$SO$_4$, filtered and the filtrate was concentrated under reduced pressure. The residue was purified by prep-HPLC (column: 3_Phenomenex Luna C$_{18}$ 75*30 mm*3 um; mobile phase: [water (0.1% TFA)-ACN]; B %: 32%-52%, 7 min, Column Temp: 30° C.) followed by lyophilization to the titled compound (101.3 mg, 0.0886 mmol, 20.62% yield, 95% purity, TFA) as a light yellow solid. MS(M+H)$^+$=972.7

$^1$H NMR (400 MHz, DMSO-d$_6$) δ 11.12 (s, 1H), 9.95-9.72 (m, 1H), 8.35-8.08 (m, 5H), 7.58 (t, J=7.8 Hz, 1H), 7.17-7.05 (m, 2H), 6.56 (s, 1H), 5.11-5.06 (m, 1H), 4.88-4.79 (m, 1H), 4.62 (t, J=4.9 Hz, 2H), 4.44-4.36 (m, 2H), 4.13-4.06 (m, 1H), 3.94-3.92 (m, 2H), 3.91 (s, 3H), 3.89-3.88 (m, 2H), 3.68-3.60 (m, 2H), 3.51-3.43 (m, 4H), 3.33 (s, 3H), 3.12-2.91 (m, 2H), 2.68-2.55 (m, 2H), 2.16-1.83 (m, 6H), 1.78-1.53 (m, 8H).

Example 45. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-((1-(2-(2-(2-((2-(2,6-dioxopiperidin-3-yl)-1,3-dioxoisoindolin-4-yl)amino)ethoxy)ethoxy)ethoxy)ethyl)-1H-1,2,3-triazol-4-yl)methyl)piperidin-4-yl)-2-fluoro-5-methoxybenzamide

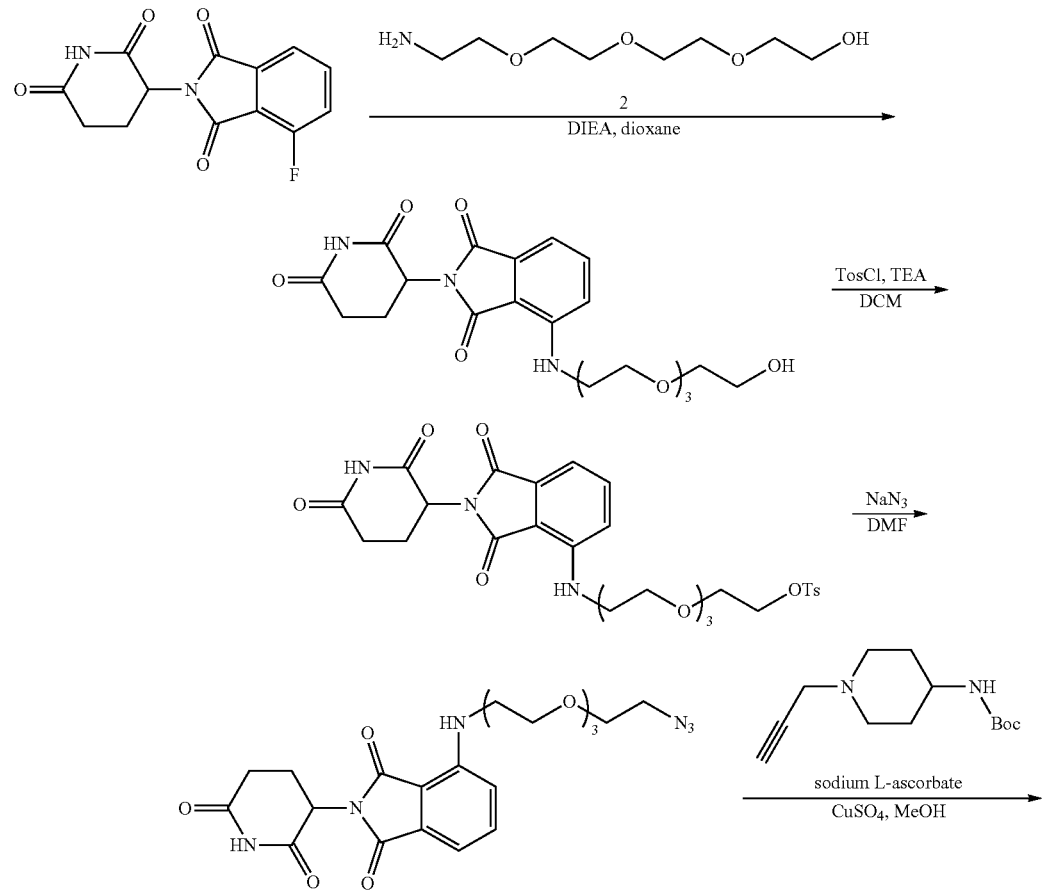

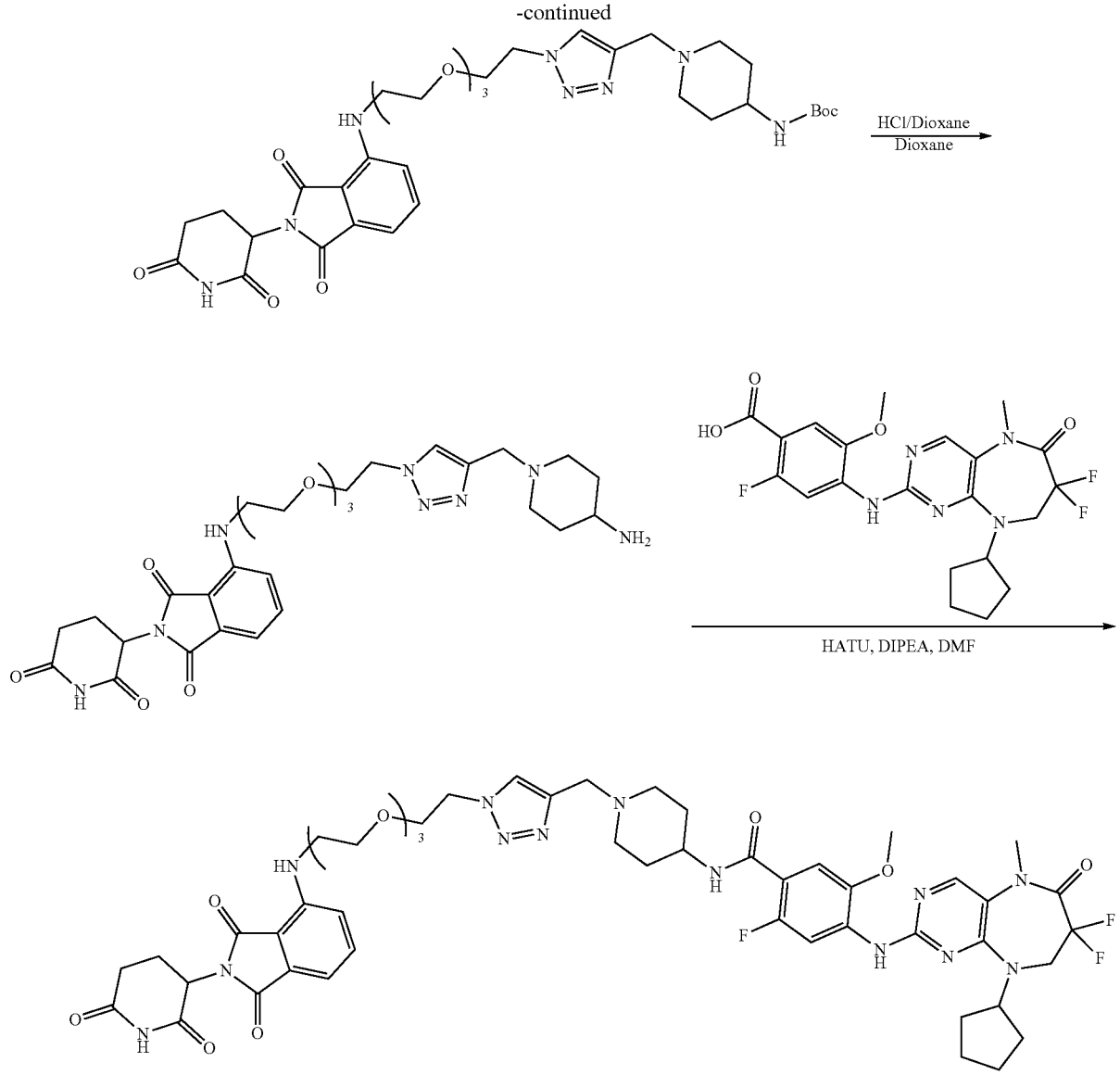

Compound 45

According to the above reaction scheme, in a manner similar to the other examples, obtained the titled compound (75.3 mg, 66.77 μmol, 15.54% yield, 94% purity, TFA) as a light yellow solid.

MS(M+H)$^+$=1060.8

$^1$H NMR (400 MHz, DMSO-d$_6$) δ 11.10 (s, 1H), 9.91-9.71 (m, 1H), 8.32-8.09 (m, 5H), 7.62-7.53 (m, 1H), 7.16-7.04 (m, 2H), 6.60 (s, 1H), 5.06 (dd, J=5.2, 13.0 Hz, 1H), 4.89-4.79 (m, 1H), 4.62-4.55 (m, 2H), 4.48-4.39 (m, 2H), 4.09 (t, J=13.9 Hz, 1H), 3.94-3.92 (m, 2H), 3.91-3.89 (m, 3H), 3.86-3.82 (m, 2H), 3.64-3.61 (m, 2H), 3.56-3.44 (m, 12H), 3.34 (s, 3H), 3.14-2.90 (m, 2H), 2.67-2.53 (m, 2H), 2.11-1.91 (m, 6H), 1.78-1.55 (m, 8H).

Example 46. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-((1-(4-((2-(2,6-dioxopiperidin-3-yl)-1,3-dioxoisoindolin-4-yl)amino)-4-oxobutyl)-1H-1,2,3-triazol-4-yl)methyl)piperidin-4-yl)-2-fluoro-5-methoxybenzamide

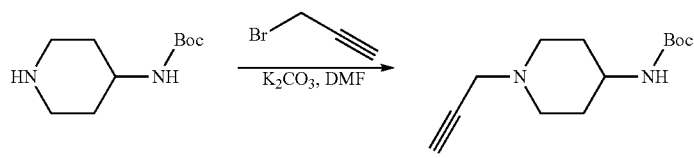

-continued
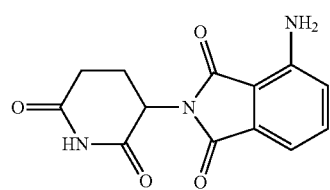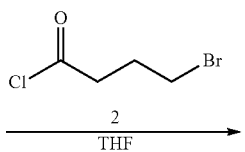
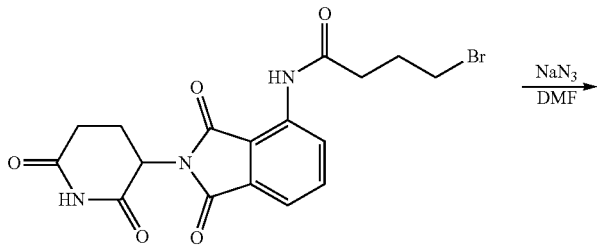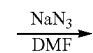
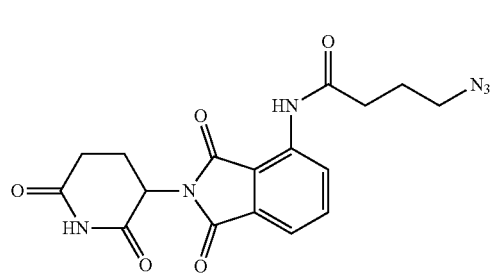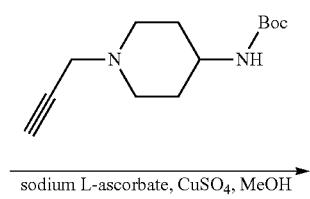
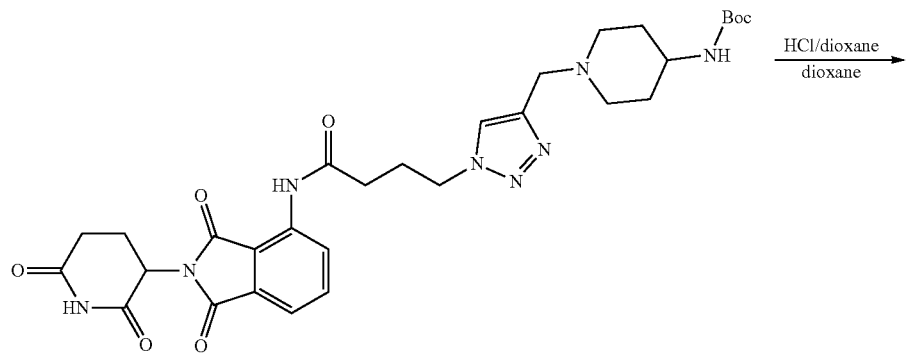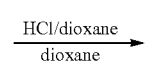
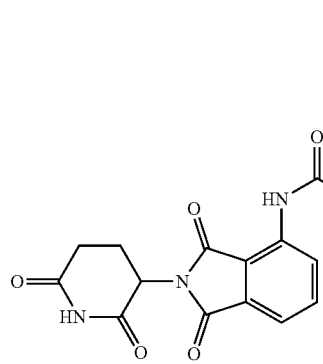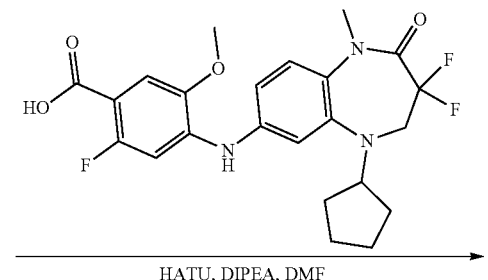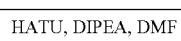

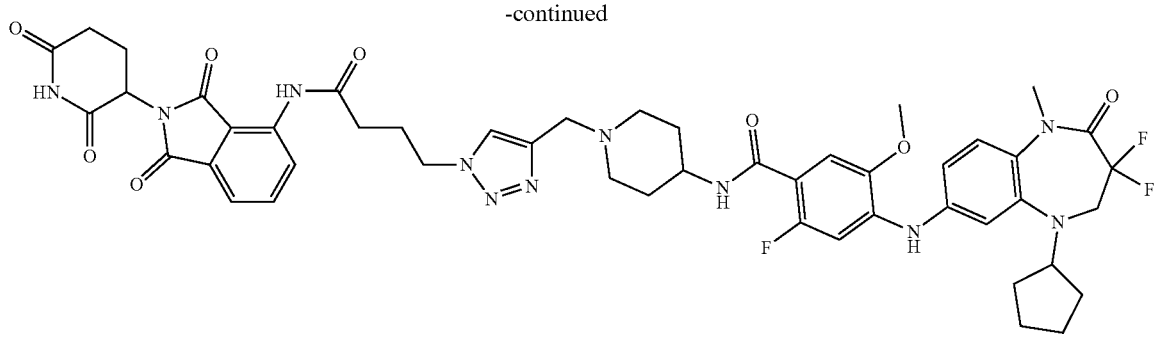

Compound 46

According to the above reaction scheme, in a manner similar to the other examples, obtained the titled compound (42.5 mg, 36.85 μmol, 8.58% yield, 94% purity, TFA) as a white solid. MS(M+H)$^+$=970.2

$^1$H NMR (400 MHz, DMSO-d$_6$) δ=11.15 (s, 1H), 9.93-9.67 (m, 2H), 8.39 (d, J=8.2 Hz, 1H), 8.30 (d, J=5.8 Hz, 1H), 8.28-8.17 (m, 2H), 8.11 (s, 1H), 7.84 (t, J=7.8 Hz, 1H), 7.64 (d, J=7.4 Hz, 1H), 7.23-7.15 (m, 1H), 5.13 (dd, J=5.2, 12.8 Hz, 1H), 4.85-4.79 (m, 1H), 4.52 (t, J=7.0 Hz, 2H), 4.46-4.39 (m, 2H), 4.13-4.09 (m, 1H), 4.08 (t, J=13.8 Hz, 2H), 4.02-3.93 (m, 2H), 3.91 (s, 3H), 3.33 (s, 3H), 3.30-3.03 (m, 4H), 2.65-2.53 (m, 4H), 2.22-2.12 (m, 2H), 2.10-2.00 (m, 2H), 2.00-1.90 (m, 2H), 1.80-1.68 (m, 4H), 1.66-1.56 (m, 4H)

Example 47. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-((1-(2-(2-((2-(2,6-dioxopiperidin-3-yl)-1,3-dioxoisoindolin-4-yl)amino)acetamido)ethyl)-1H-1,2,3-triazol-4-yl)methyl)piperidin-4-yl)-2-fluoro-5-methoxybenzamide

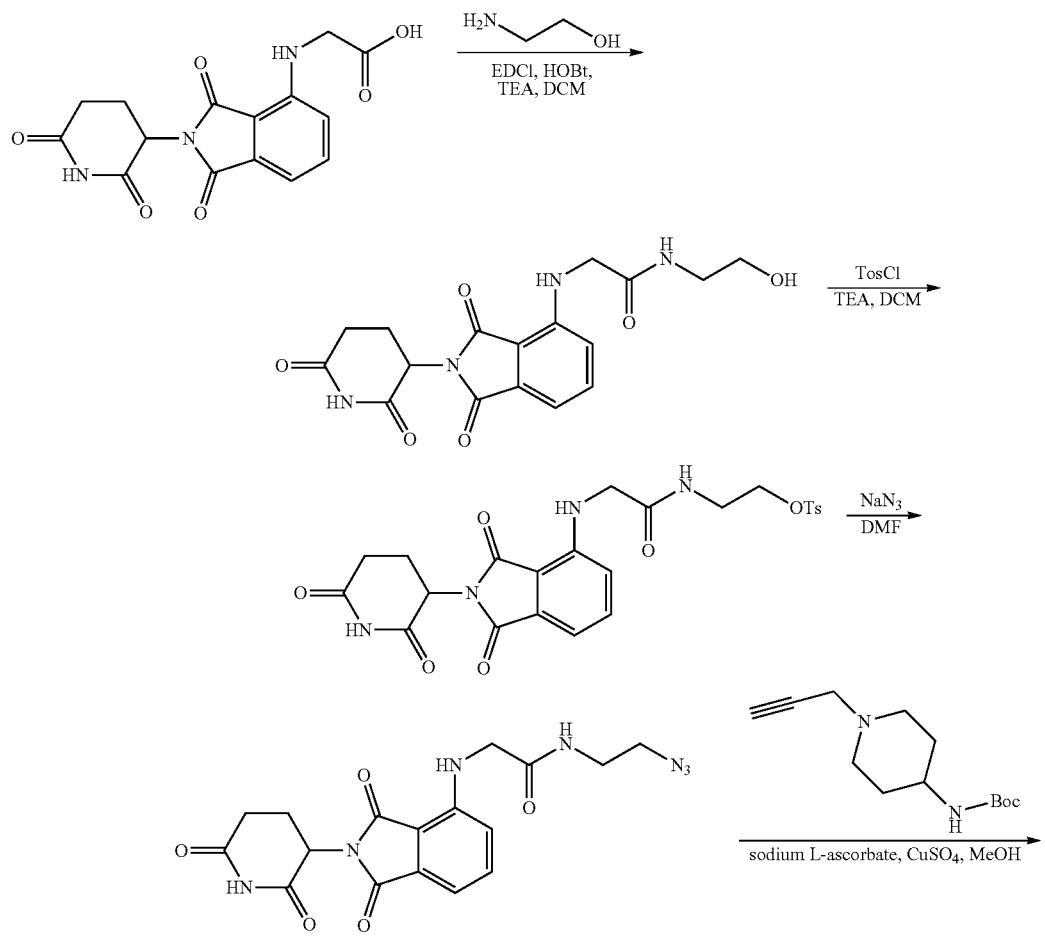

-continued
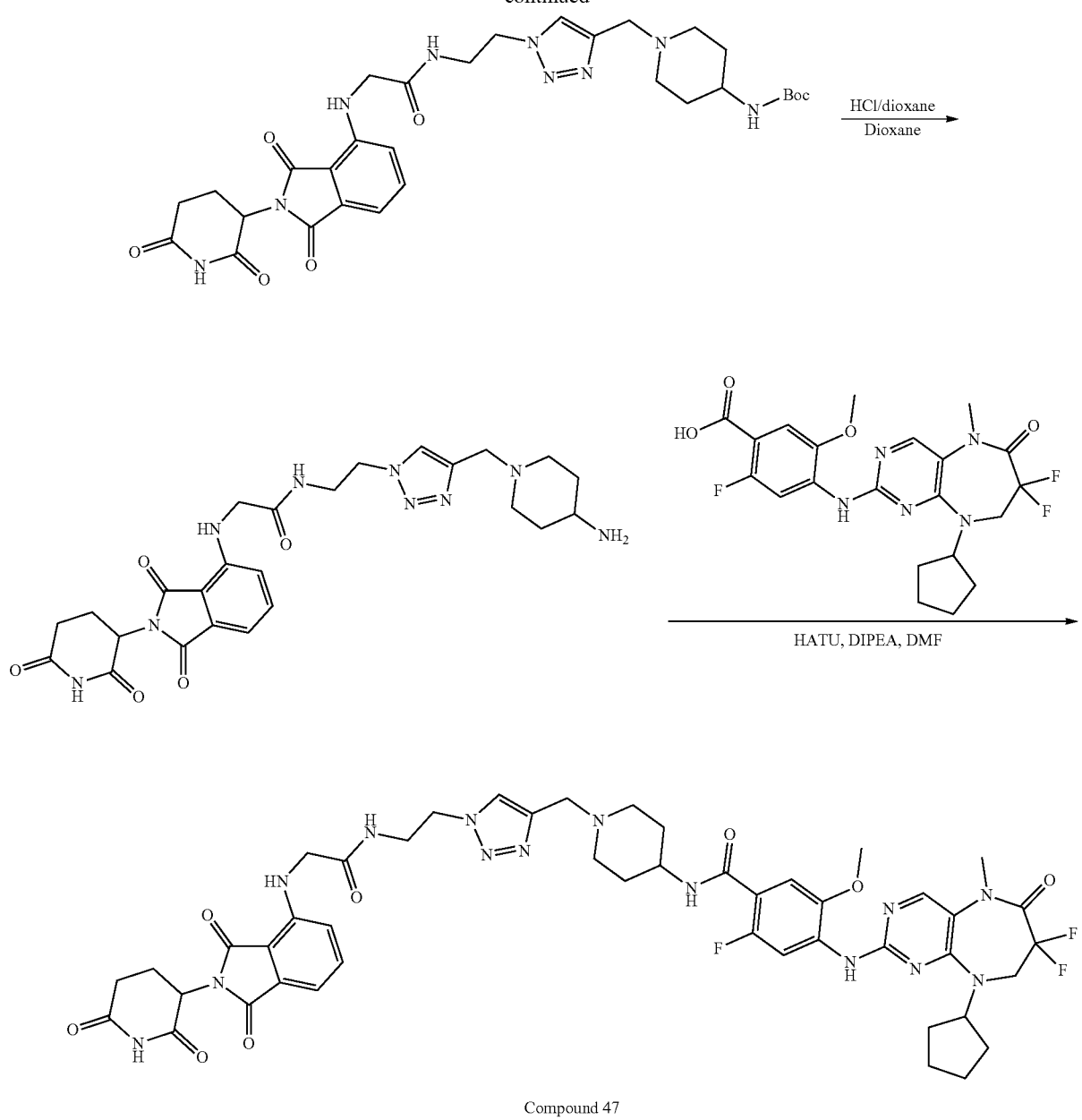
Compound 47
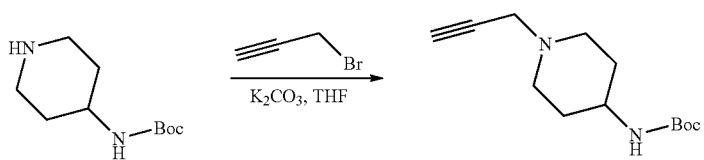
According to the above reaction scheme, in a manner similar to the other examples, obtained the titled compound (7.5 mg, 7.46 μmol, 3.19% yield, 98% purity) as yellow solid. MS(M+H)+=985.3
$^1$H NMR (400 MHz, CDCl3) δ=8.45-8.28 (m, 1H), 8.13-7.97 (m, 2H), 7.58-7.48 (m, 2H), 7.26-7.22 (m, 1H), 7.18 (d, J=7.3 Hz, 1H), 7.15-7.10 (m, 1H), 7.07 (d, J=7.3 Hz, 1H), 6.87-6.74 (m, 1H), 5.02-4.81 (m, 2H), 4.63-4.45 (m, 2H), 4.41-5.36 (m, 1H), 4.34-4.21 (m, 2H), 4.13-4.02 (m, 1H), 4.00-3.86 (m, 6H), 3.85-3.71 (m, 3H), 3.44-3.41 (m, 3H), 2.91-2.71 (m, 3H), 2.28-2.22 (m, 2H), 2.24-2.07 (m, 3H), 1.80-1.78 (m, 4H), 1.68-1.59 (m, 7H).

Example 48. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(((1R,2S)-2-(((2-(2,6-dioxopiperidin-3-yl)-1,3-dioxoisoindolin-4-yl)amino)methyl)cyclopropyl)methyl)piperidin-4-yl)- 2-fluoro-5-methoxybenzamide
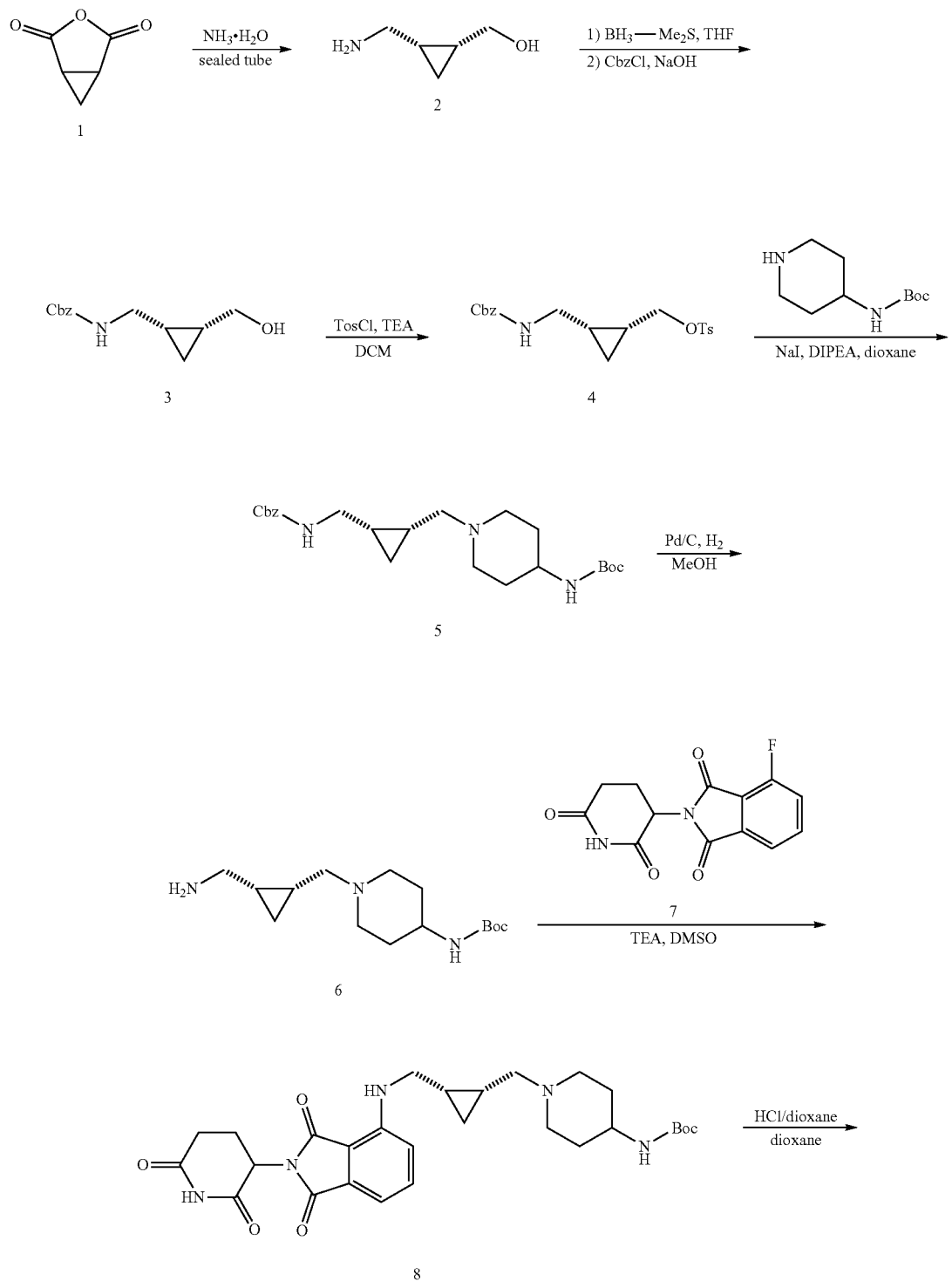

-continued

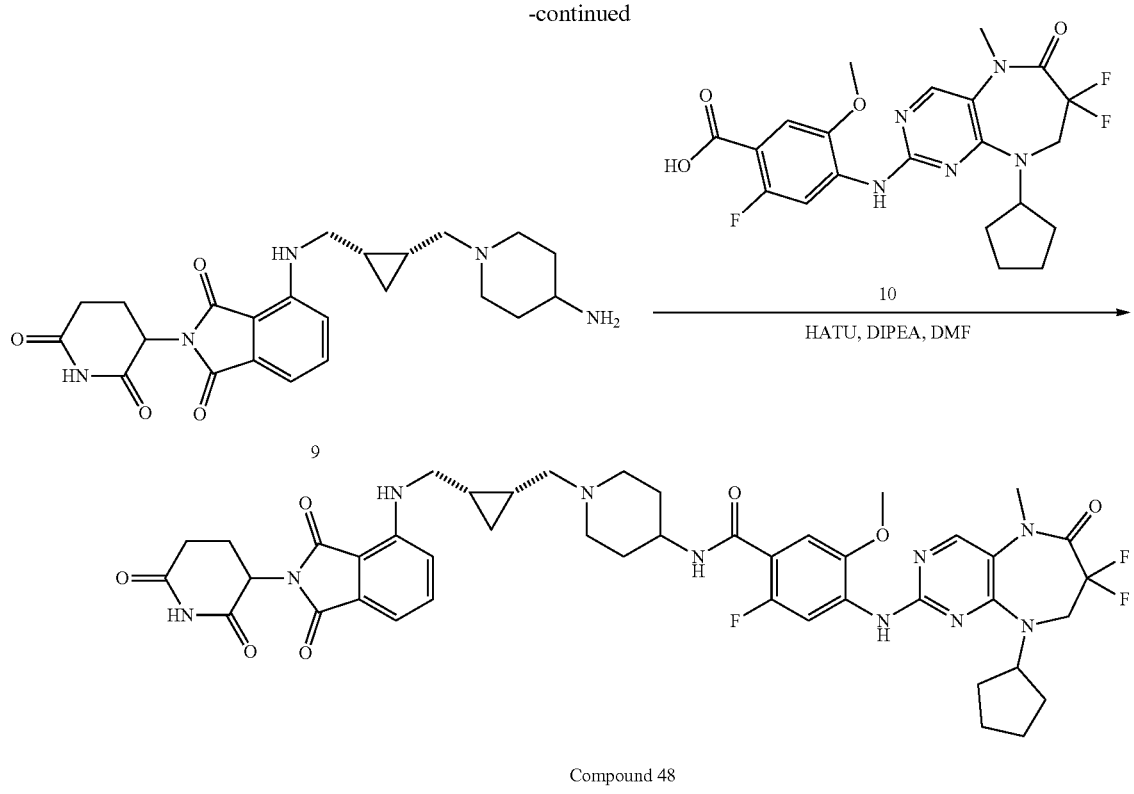

Compound 48

Step 1: Synthesis of (1R,2S)-2-carbamoylcyclopropanecarboxylic acid (2)

A solution of 3-oxabicyclo[3.1.0]hexane-2,4-dione (5 g, 44.61 mmol) in NH$_3$·H$_2$O (50 mL) was stirred at 20° C. for 16 h in a 100 mL of sealed tube. TLC (SiO$_2$, Petroleum ether:Ethyl acetate=1:2) indicated starting material was consumed completely and one new spot was detected. The reaction mixture was concentrated in vacuum to afford (1R,2S)-2-carbamoylcyclopropanecarboxylic acid (6.2 g, crude) as an off-white solid.

$^1$H NMR (400 MHz, DMSO-d$_6$) δ=8.37 (br s, 1H), 6.82-6.38 (m, 2H), 1.71-1.63 (m, 1H), 1.59-1.50 (m, 1H), 1.20-1.10 (m, 1H), 1.10-1.00 (m, 1H)

Step 2: Synthesis of benzyl (((1S,2R)-2-(hydroxymethyl)cyclopropyl)methyl)carbamate (3)

To a mixture of (1R,2S)-2-carbamoylcyclopropanecarboxylic acid (6.2 g, 48.02 mmol) in THF (100 mL) was added BH$_3$-Me$_2$S (10 M, 48.02 mL) drop-wise at 20° C. under N$_2$ and the resulting mixture was stirred at 60° C. for 16 h. The reaction mixture was quenched with HCl (1 N) and the reaction mixture was stirred at 60° C. for 4 h. NaOH (2 M, 72.03 mL) and CbzCl (12.29 g, 72.03 mmol, 10.24 mL) were added to this reaction mixture at 20° C. and the reaction mixture was stirred at 60° C. for 12 h. LCMS showed all starting material was consumed completely and peak with desired mass was detected. The reaction mixture was diluted with H$_2$O (100 mL) and extracted with EtOAc (100 mL×3). The organic layer was dried over Na$_2$SO$_4$, filtered and concentrated. The crude product was purified by reversed-phase HPLC (method: FA) and then lyophilized to afford to the titled compound (5.4 g, 22.49 mmol, 46.84% yield, 98% purity) as a white oil. MS(M+Na)$^+$=258.4

Step 3: Synthesis of ((1R,2S)-2-((((benzyloxy)carbonyl)amino)methyl)cyclopropyl)methyl 4-methylbenzenesulfonate (4)

To a mixture of benzyl (((1S,2R)-2-(hydroxymethyl)cyclopropyl)methyl)carbamate (2.7 g, 11.48 mmol) in DCM (30 mL) were added TEA (3.48 g, 34.43 mmol, 4.79 mL) and TosCl (3.28 g, 17.21 mmol) in one portion at 20° C. and the resulting mixture was stirred at 20° C. for 16 h. LCMS showed all starting material was consumed completely and one peak with desired mass was detected. The reaction mixture was concentrated in vacuum. The residue was purified by column chromatography (SiO$_2$, Petroleum ether/Ethyl acetate=5/1 to 0/1) to afford to the titled compound (2.4 g, 6.16 mmol, 53.70% yield) as a yellow oil. MS(M+Na)$^+$=412.1

Step 4: Synthesis of tert-butyl N-[1-[[2-(benzyloxycarbonylaminomethyl) cyclopropyl]methyl]-4-piperidyl]carbamate (5)

To a mixture of ((1R,2S)-2-((((benzyloxy)carbonyl)amino)methyl)cyclopropyl)methyl 4-methylbenzenesulfonate and tert-butyl N-(4-piperidyl)carbamate (1.60 g, 8.01 mmol) in dioxane (30 mL) were added DIPEA (2.39 g, 18.49 mmol, 3.22 mL) and NaI (184.74 mg, 1.23 mmol) in one portion at 20° C. and the resulting mixture was stirred at 80° C. for 16 h. LCMS showed ((1R,2S)-2-((((benzyloxy)carbonyl)amino)methyl)cyclopropyl)methyl 4-methylbenzenesulfonate was consumed completely and one peak with desired mass was detected. The reaction mixture was concentrated in vacuum. The residue was purified by column chromatography (SiO$_2$, Petroleum ether/Ethyl acetate=1/1 to 0/1) to afford to the titled compound (1.4 g, 3.15 mmol, 51.15% yield, 94% purity) as a white oil. MS(M+H)$^+$=418.3

Step 5: Synthesis of tert-butyl (1-(((1R,2S)-2-(aminomethyl)cyclopropyl)methyl)piperidin-4-yl)carbamate (6)

To a solution of tert-butyl N-[1-[[2-(benzyloxycarbonylaminomethyl)cyclopropyl]methyl]-4-piperidyl]carbamate (1.40 g, 3.35 mmol) in MeOH (15 mL) was added Pd/C (0.2 g, 10% purity) under N$_2$. The suspension was degassed under vacuum and purged with H$_2$ several times. The mixture was stirred under H$_2$ (15 psi) at 20° C. for 16 h. LCMS showed starting material was consumed completely and one peak with desired mass was detected. The reaction mixture was diluted with MeOH (60 mL) and filtrated. The filtrate was concentrated in vacuum to afford to the titled compound (920 mg, crude) as a white oil. MS(M+H)$^+$=284.3

Step 6: Synthesis of tert-butyl (1-(((1R,2S)-2-(((2-(2,6-dioxopiperidin-3-yl)-1,3-dioxoisoindolin-4-yl)amino)methyl)cyclopropyl)methyl)piperidin-4-yl)carbamate (8)

To a mixture of 2-(2,6-dioxopiperidin-3-yl)-4-fluoroisoindoline-1,3-dione (0.8 g, 2.90 mmol) and tert-butyl (1-(((1R,2S)-2-(aminomethyl)cyclopropyl)methyl) piperidin-4-yl)carbamate (902.90 mg, 3.19 mmol) in DMSO (5 mL) was added TEA (879.20 mg, 8.69 mmol, 1.21 mL) in one portion at 20° C. and the resulting mixture was stirred at 80° C. for 16 h. LCMS showed 2-(2,6-dioxopiperidin-3-yl)-4-fluoroisoindoline-1,3-dione was consumed completely and one peak with desired mass was detected. The reaction mixture was diluted with H$_2$O (15 mL) and extracted with EtOAc (15 mL×3). The organic layer was washed with brine (15 mL×3), dried over Na$_2$SO$_4$, filtered and concentrated. The residue was purified by column chromatography (SiO$_2$, Petroleum ether/Ethyl acetate=10/1 to 1/4) to afford to the titled compound (850 mg, 1.56 mmol, 53.84% yield, 99% purity) as a green solid. MS(M+H)$^+$=540.2

Step 7: Synthesis of 4-((((1S,2R)-2-((4-aminopiperidin-1-yl)methyl)cyclopropyl)methyl)amino)-2-(2,6-dioxopiperidin-3-yl)isoindoline-1,3-dione (9)

To a mixture of tert-butyl (1-(((1R,2S)-2-(((2-(2,6-dioxopiperidin-3-yl)-1,3-dioxoisoindolin-4-yl)amino)methyl)cyclopropyl)methyl)piperidin-4-yl)carbamate (850 mg, 1.58 mmol) in dioxane (4 mL) was added HCl/dioxane (4 M, 8 mL, 20.32 eq) in one portion at 20° C. and the resulting mixture was stirred at 20° C. for 1 h. LCMS showed starting material was consumed completely and one peak with desired mass was detected. The reaction mixture was concentrated in vacuum to afford to the titled compound (760 mg, crude, HCl) as a green solid. MS(M+H)$^+$=440.3

Step 8: Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(((1R,2S)-2-(((2-(2,6-dioxopiperidin-3-yl)-1,3-dioxoisoindolin-4-yl)amino)methyl)cyclopropyl)methyl)piperidin-4-yl)-2-fluoro-5-methoxybenzamide (Compound 48)

To a solution of 4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzoic acid (200 mg, 429.71 μmol) in DMF (4 mL) were added HATU (163.39 mg, 429.71 μmol) and DIPEA (111.08 mg, 859.43 μmol, 149.70 μL). The mixture was stirred at 20° C. for 10 min and a solution of 4-((((1 S,2R)-2-((4-aminopiperidin-1-yl)methyl)cyclopropyl)methyl)amino)-2-(2,6-dioxopiperidin-3-yl)isoindoline-1,3-dione (226.63 mg, crude, HCl) in DMF (4 mL) and DIPEA (111.08 mg, 859.43 μmol, 149.70 μL) was added drop-wise at 20° C. and the resulting mixture was stirred at 20° C. for 1 h. LCMS showed all starting material was consumed completely and one peak with desired mass was detected. The reaction mixture was diluted with H$_2$O (12 mL) and extracted with EtOAc (12 mL×3). The organic layer was dried over Na$_2$SO$_4$, filtered and concentrated. The residue was purified by prep-HPLC (column: Phenomenex luna C$_{18}$ 150*40 mm*15 um; mobile phase: [water (0.1% TFA)-ACN]; B %: 30%-40%, 10 min) and re-purified by prep-HPLC (column: 3_Phenomenex Luna C$_{18}$ 75*30 mm*3 um; mobile phase: [water (0.1% TFA)-ACN]; B %: 34%-54%, 7 min) and then lyophilized to afford to the titled compound (104 mg, 100.79 μmol, 23.45% yield, 97% purity, TFA) as a yellow solid. MS(M+H)$^+$=887.2

$^1$H NMR (400 MHz, CD$_3$OD) δ=8.33 (d, J=13.6 Hz, 1H), 8.21 (s, 1H), 7.64-7.57 (m, 1H), 7.38-7.34 (m, 1H), 7.16-7.08 (m, 2H), 5.12-5.06 (m, 1H), 5.04-4.91 (m, 2H), 4.25-4.14 (m, 1H), 4.09 (t, J=13.0 Hz, 2H), 4.00 (s, 3H), 3.79 (d, J=12.4 Hz, 1H), 3.60-3.45 (m, 2H), 3.40 (s, 3H), 3.29-3.12 (m, 4H), 2.94-2.82 (m, 1H), 2.79-2.66 (m, 2H), 2.38-2.19 (m, 2H), 2.17-2.05 (m, 3H), 1.99-1.67 (m, 8H), 1.64-1.53 (m, 1H), 1.36-1.26 (m, 1H), 1.17-1.11 (m, 1H), 0.59-0.51 (m, 1H)

Example 49. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(2-(2-((2-((2-(2,6-dioxopiperidin-3-yl)-1,3-dioxoisoindolin-4-yl)amino)ethyl)(methyl)amino)ethoxy)ethyl)piperidin-4-yl)-2-fluoro-5-methoxybenzamide

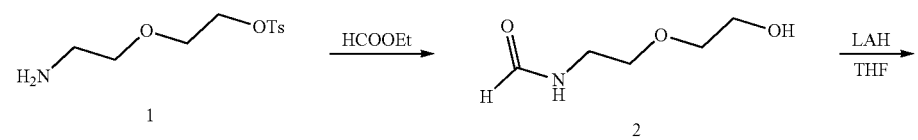

-continued
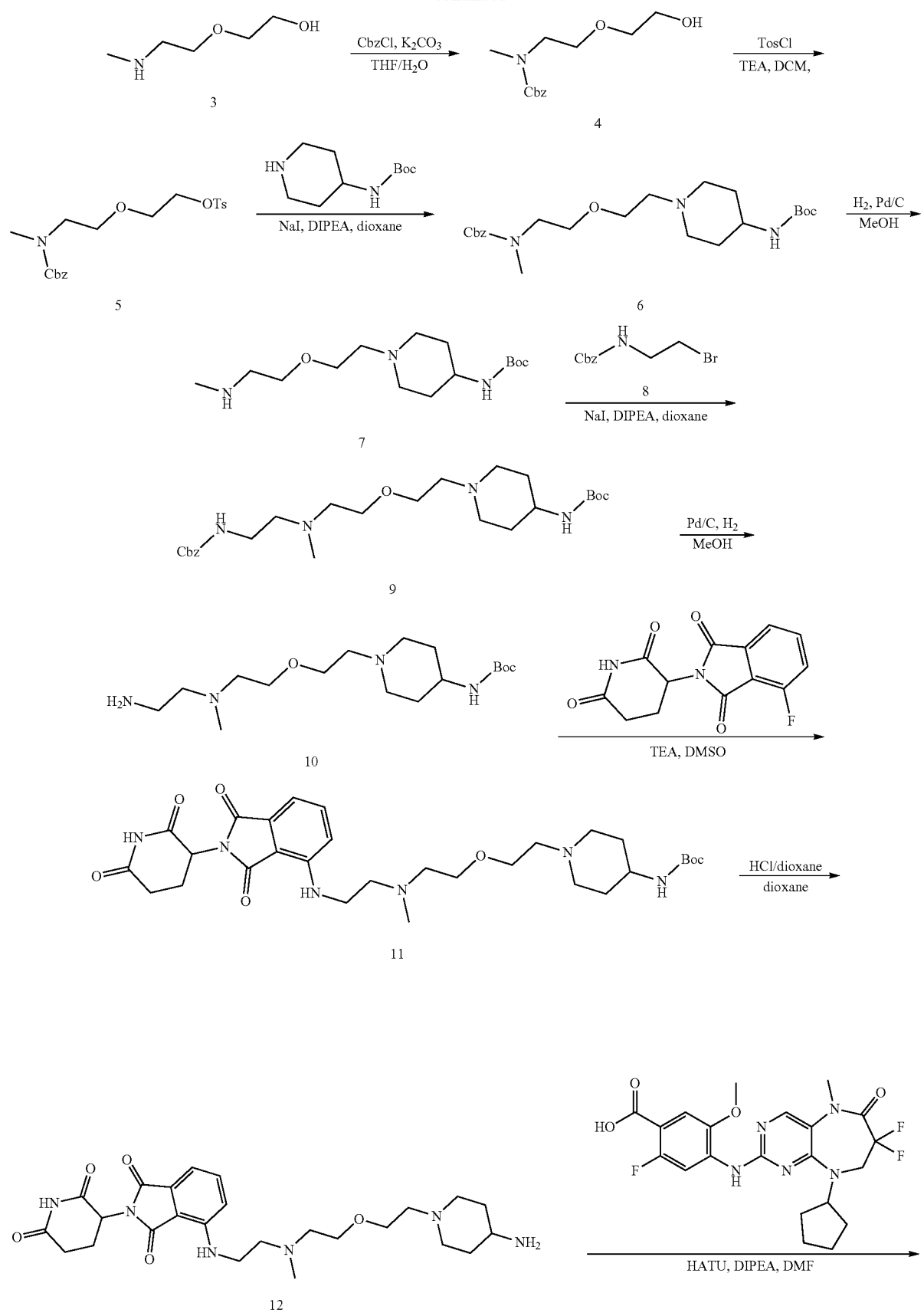

-continued

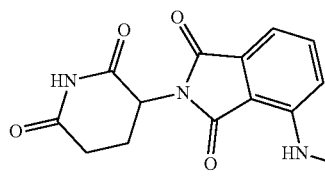 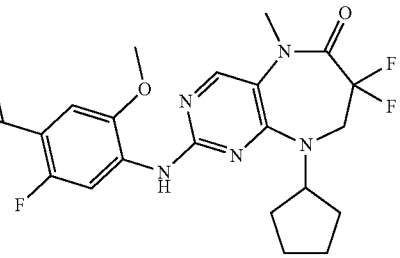

Compound 49

Step 1: Synthesis of N-(2-(2-hydroxyethoxy)ethyl)formamide (2)

A solution of 2-(2-aminoethoxy) ethanol (7 g, 66.58 mmol, 6.67 mL) in ethyl formate (32.24 g, 435.15 mmol, 35.00 mL) was stirred at 90° C. for 12 h. LCMS showed that the reaction was completed. The mixture was combined with the pilot (0.5 g scale) and concentrated to afford to the titled compound (8 g, 60.08 mmol, 90.24% yield) as yellow oil. MS(M+H)$^+$=134.1

Step 2: Synthesis of 2-(2-(methylamino) ethoxy) ethanol (3)

To the mixture of LAH (2.57 g, 67.60 mmol) in THF (100 mL) was added a solution of N-(2-(2-hydroxyethoxy) ethyl) formamide (6 g, 45.06 mmol) in THF (10 mL) and the resulting mixture was stirred at 20° C. for 3 h. TLC (Ethyl acetate/Methanol=10/1) showed that the reaction was completed. The mixture was quenched with water (2.5 mL), 2.5 mL 15% NaOH in water and water (7.5 mL) sequently. The mixture was stirred at 25° C. for 30 min, the mixture was filtered and the filtrate was concentrated under vacuum to afford to the titled compound (9.7 g, crude) as yellow oil.

Step 3: Synthesis of benzyl (2-(2-hydroxyethoxy)ethyl)(methyl)carbamate (4)

To the mixture of 2-(2-(methylamino) ethoxy) ethanol (9.7 g, 81.40 mmol) and K$_2$CO$_3$ (22.50 g, 162.80 mmol) in THF (40 mL) and H$_2$O (20 mL) was added CbzCl (20.83 g, 122.10 mmol, 17.36 mL) and the resulting mixture was stirred at 20° C. for 12 h. LCMS showed that the reaction was completed. The mixture was combined with the pilot (1.3 g scale) and poured into water (100 mL) and extracted with EtOAc (50 mL×3), the combined organic layer was washed with brine (50 mL), dried over Na$_2$SO$_4$, filtered and concentrated. The residue was purified by silica gel column (Petroleum ether/Ethyl acetate=1/1) to the titled compound (7.6 g, 30.00 mmol, 36.86% yield) as yellow oil.

Step 4: Synthesis of 2-(2-(((benzyloxy)carbonyl) (methyl)amino)ethoxy)ethyl 4-methylbenzenesulfonate (5)

To the mixture of benzyl (2-(2-hydroxyethoxy)ethyl) (methyl)carbamate (7.6 g, 30.00 mmol) and TEA (9.11 g, 90.01 mmol, 12.53 mL) in DCM (50 mL) was added TosCl (8.58 g, 45.01 mmol) and the resulting mixture was stirred at 20° C. for 12 h. LCMS showed that the reaction was completed. The mixture was concentrated under vacuum. The residue was purified by silica gel chromatography (Petroleum ether/Ethyl acetate=2/1) to the titled compound (7.6 g, 14.92 mmol, 49.73% yield, 80% purity) as yellow oil. MS(M+H)$^+$=408.1

Step 5: Synthesis of benzyl (2-(2-(4-((tert-butoxycarbonyl)amino)piperidin-1-yl)ethoxy)ethyl) (methyl)carbamate To the mixture of 2-(2-(((benzyloxy)carbonyl)(methyl) amino)ethoxy)ethyl 4-methylbenzenesulfonate (4 g, 7.85 mmol, 80% purity) and tert-butyl piperidin-4-ylcarbamate (2.36 g, 11.78 mmol) in Dioxane (20 mL) were added NaI (117.71 mg, 785.31 µmol) and DIPEA (2.03 g, 15.71 mmol, 2.74 mL) and the resulting mixture was stirred at 80° C. for 12 h. LCMS showed that the reaction was completed. The mixture was concentrated under vacuum. The residue was purified by silica gel chromatography (Ethyl acetate) to afford the titled compound (1.8 g, 4.05 mmol, 51.57% yield, 98% purity) as yellow oil. MS(M+H)$^+$=436.1

Step 6: Synthesis of tert-butyl (1-(2-(2-(methylamino)ethoxy)ethyl)piperidin-4-yl)carbamate (7)

To the solution of benzyl (2-(2-(4-((tert-butoxycarbonyl) amino)piperidin-1-yl)ethoxy)ethyl)(methyl)carbamate (1.8 g, 4.13 mmol) in MeOH (20 mL) was added Pd/C (0.2 g, 4.13 mmol, 10% purity) and the resulting mixture was stirred at 20° C. for 12 h under H$_2$ (15 psi). LCMS showed that the reaction was completed. The mixture was filtered and concentrated to afford the titled compound (1.2 g, 3.98 mmol, 96.33% yield) as brown oil. MS(M+H)$^+$=302.2

Step 7: Synthesis of tert-butyl N-[1-[2-[2-[2-(benzyloxycarbonylamino)ethyl-methyl-amino]ethoxy] ethyl]-4-piperidyl]carbamate (9)

To the solution of tert-butyl (1-(2-(2-(methylamino) ethoxy)ethyl)piperidin-4-yl)carbamate (1 g, 3.32 mmol) and benzyl (2-bromoethyl) carbamate (1.03 g, 3.98 mmol) in dioxane (4 mL) were added NaI (49.73 mg, 331.76 µmol) and DIPEA (857.55 mg, 6.64 mmol, 1.16 mL) and the resulting mixture was stirred at 80° C. for 12 h. LCMS showed that the reaction was completed. The mixture was combined with the pilot (0.2 g scale) and concentrated. The residue was purified by reserved phase column (method: FA, MeCN/water) to afford the titled compound (0.9 g, 1.77 mmol, 53.28% yield, 94% purity) as red oil. MS(M+H)$^+$=479.4

Step 8: Synthesis of tert-butyl (1-(2-(2-((2-aminoethyl)(methyl)amino)ethoxy)ethyl)piperidin-4-yl) carbamate (10)

To the solution of tert-butyl N-[1-[2-[2-[2-(benzyloxycarbonylamino)ethyl-methyl-amino]ethoxy]ethyl]-4-piperidyl]carbamate (0.9 g, 1.88 mmol) in MeOH (10 mL) was added Pd/C (0.1 g, 10% purity) and the resulting mixture was stirred at 20° C. for 12 h under $H_2$ (15 psi). LCMS showed that the reaction was completed. The mixture was filtered and concentrated to afford the titled compound (0.5 g, 1.45 mmol, 77.19% yield) as yellow oil. $MS(M+H)^+=345.2$ Step 9: Synthesis of tert-butyl (1-(2-(2-((2-((2-(2,6-dioxopiperidin-3-yl)-1,3-dioxoisoindolin-4-yl)amino)ethyl)(methyl)amino)ethoxy)ethyl)piperidin-4-yl)carbamate (11)

To the solution of 2-(2,6-dioxo-3-piperidyl)-4-fluoro-isoindoline-1,3-dione (0.3 g, 1.09 mmol) and tert-butyl (1-(2-(2-((2-aminoethyl)(methyl)amino)ethoxy)ethyl)piperidin-4-yl)carbamate (340 mg, 986.96 μmol) in DMSO (5 mL) was added TEA (329.70 mg, 3.26 mmol, 453.51 μL) and the resulting mixture was stirred at 60° C. for 12 h. TLC (Ethyl acetate/Methanol=10/1) showed that the reaction was completed. The mixture was combined with the pilot (50 mg scale) and poured into water (30 mL) and extracted with EtOAc (20 mL×3), the combined organic layer was dried over $Na_2SO_4$, filtered and concentrated. The residue was purified by silica gel column (Ethyl acetate/Methanol=10/1) to afford the titled compound (0.12 g, 193.77 μmol, 17.84% yield, 97% purity) as yellow oil. $MS(M+H)^+=601.3$ Step 10: Synthesis of 4-((2-((2-(2-(4-aminopiperidin-1-yl)ethoxy)ethyl)(methyl)amino)ethyl)amino)-2-(2,6-dioxopiperidin-3-yl)isoindoline-1,3-dione (12)

To the mixture of tert-butyl (1-(2-(2-((2-((2-(2,6-dioxopiperidin-3-yl)-1,3-dioxoisoindolin-4-yl)amino)ethyl)(methyl)amino)ethoxy)ethyl)piperidin-4-yl)carbamate (120 mg, 199.77 μmol) in dioxane (5 mL) was added HCl/dioxane (4 M, 5 mL) and the resulting mixture was stirred at 20° C. for 1 h. LCMS showed that the reaction was completed. The mixture was concentrated to afford the titled compound (110 mg, crude, HCl) as yellow oil.

Step 11: Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(2-(2-((2-((2-(2,6-dioxopiperidin-3-yl)-1,3-dioxoisoindolin-4-yl)amino)ethyl)(methyl)amino)ethoxy)ethyl)piperidin-4-yl)-2-fluoro-5-methoxybenzamide (Compound 49)

To the solution of 4-((2-((2-(2-(4-aminopiperidin-1-yl)ethoxy)ethyl)(methyl)amino)ethyl)amino)-2-(2,6-dioxopiperidin-3-yl)isoindoline-1,3-dione (110 mg, 204.82 μmol, HCl) and 4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzoic acid (95.33 mg, 204.82 μmol) in DMF (3 mL) were HATU (155.76 mg, 409.65 μmol) and DIPEA (105.89 mg, 819.29 mol, 142.71 μL) and the mixture was stirred at 20° C. for 1 h. LCMS showed that the reaction was completed, the mixture was poured into water (20 mL) and extracted with EtOAc (20 mL×3), the combined organic layer was washed with brine (50 mL), dried over $Na_2SO_4$, filtered and concentrated, the residue was purified by prep-HPLC (column: Unisil 3-100 $C_{18}$ μLtra 150*50 mm*3 um; mobile phase: [water (0.225% FA)-ACN]; B %: 30%-50%, 10 min) and the eluant was lyophilized. The solid was dissolved in DMF, the mixture was adjusted pH=8 by DIPEA and the resulting mixture was re-purified by prep-HPLC (column: Waters Xbridge 150*25 mm*5 um; mobile phase: [water (10 mM $NH_4HCO_3$)-ACN]; B %: 43%-76%, 8 min) followed by prep-TLC (Ethyl acetate/Methanol=6/1) to afford the titled compound (10.7 mg, 10.61 μmol, 15.03% yield, 94% purity) as yellow solid. $MS(M+H)^+=948.3$ $^1$H NMR (400 MHz, DMSO-$d_6$) δ=11.09 (s, 1H), 8.30 (s, 1H), 8.24 (d, J=13.2 Hz, 1H), 8.03 (s, 1H), 7.86-7.84 (m, 1H), 7.58-7.56 (m, 1H), 7.18 (d, J=7.2 Hz, 1H), 7.08 (d, J=8.8 Hz, 1H), 7.02 (d, J=6.8 Hz, 1H), 6.75-6.71 (m, 1H), 5.07-5.04 (m, 1H), 4.84-4.79 (m, 1H), 4.11-4.03 (m, 3H), 3.91 (s, 3H), 3.73-3.65 (m, 2H), 3.52-3.45 (m, 4H), 2.91-2.80 (m, 3H), 2.65-2.58 (m, 2H), 2.58-2.55 (m, 4H), 2.45-2.42 (m, 2H), 2.26 (s, 3H), 2.01-1.98 (m, 6H), 1.77-1.72 (m, 5H), 1.70-1.60 (m, 4H), 1.49-1.41 (m, 3H).

Example 50. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(2-(2-(2-((2-(2,6-dioxopiperidin-3-yl)-1,3-dioxoisoindolin-5-yl)amino)ethoxy)ethoxy)ethyl)piperidin-4-yl)-2-fluoro-5-methoxybenzamide

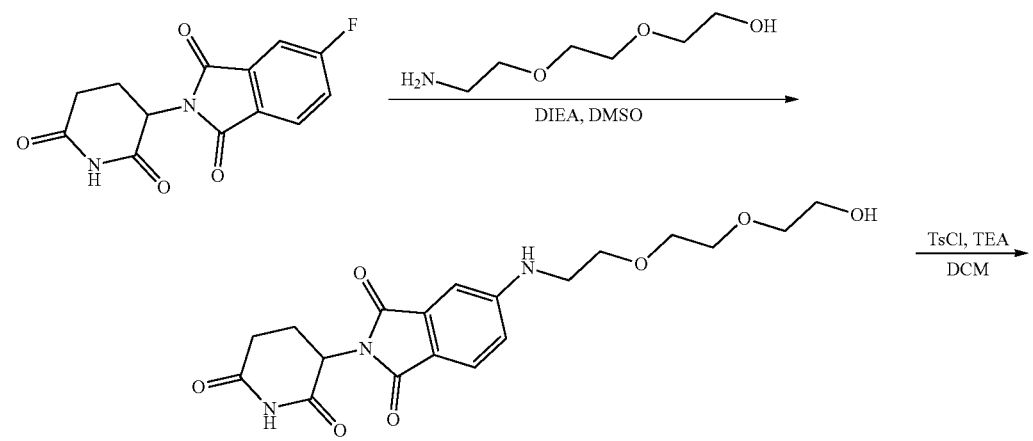

-continued
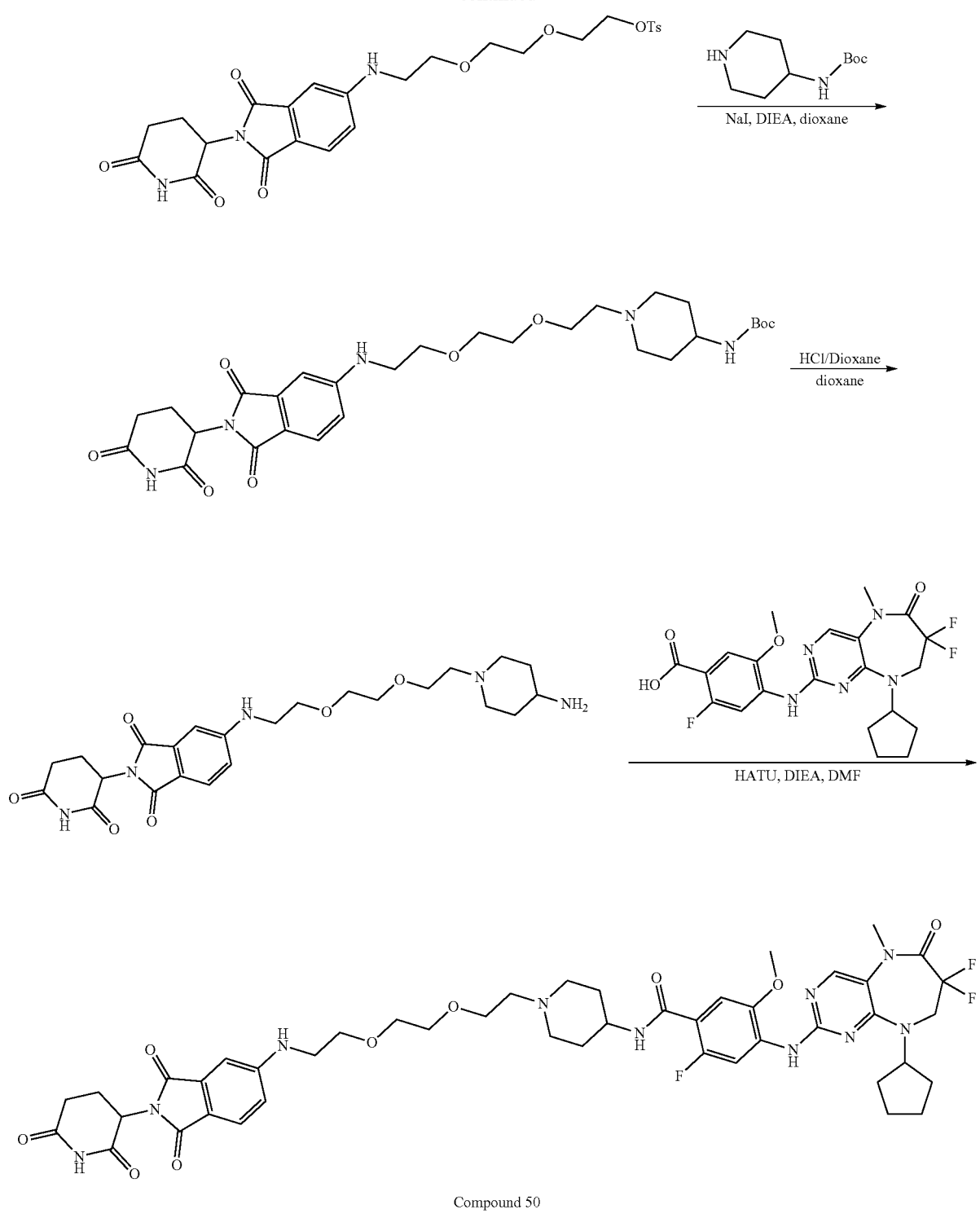
Compound 50
According to the above reaction scheme, in a manner similar to the other examples, obtained the titled compound (69 mg, 69.37 μmol, 18.18% yield, 94% purity) as a yellow solid. MS(M+H)$^+$=935.4.
$^1$H NMR (400 MHz, CDCl$_3$) δ=8.29 (d, J=14.9 Hz, 1H), 8.00 (s, 1H), 7.74 (s, 1H), 7.54 (d, J=8.3 Hz, 1H), 7.48 (d, J=7.2 Hz, 1H), 6.97-6.91 (m, 1H), 6.71 (dd, J=2.1, 8.3 Hz, 1H), 6.68-6.60 (m, 1H), 5.33-5.24 (m, 1H), 4.88-4.72 (m, 2H), 4.04-3.92 (m, 1H), 3.90 (s, 3H), 3.87-3.80 (m, 2H), 3.67 (t, J=5.0 Hz, 2H), 3.62-3.53 (m, 6H), 3.37-3.30 (m, 5H), 2.91-2.61 (m, 5H), 2.56 (t, J=5.4 Hz, 2H), 2.27-2.11 (m, 2H), 2.08-1.95 (m, 5H), 1.77-1.63 (m, 5H), 1.55-1.47 (m, 3H).

Example 51. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(14-((2-(2,6-dioxopiperidin-3-yl)-1,3-dioxoisoindolin-5-yl)amino)-3,6,9,12-tetraoxatetradecyl)piperidin-4-yl)-2-fluoro-5-methoxybenzamide
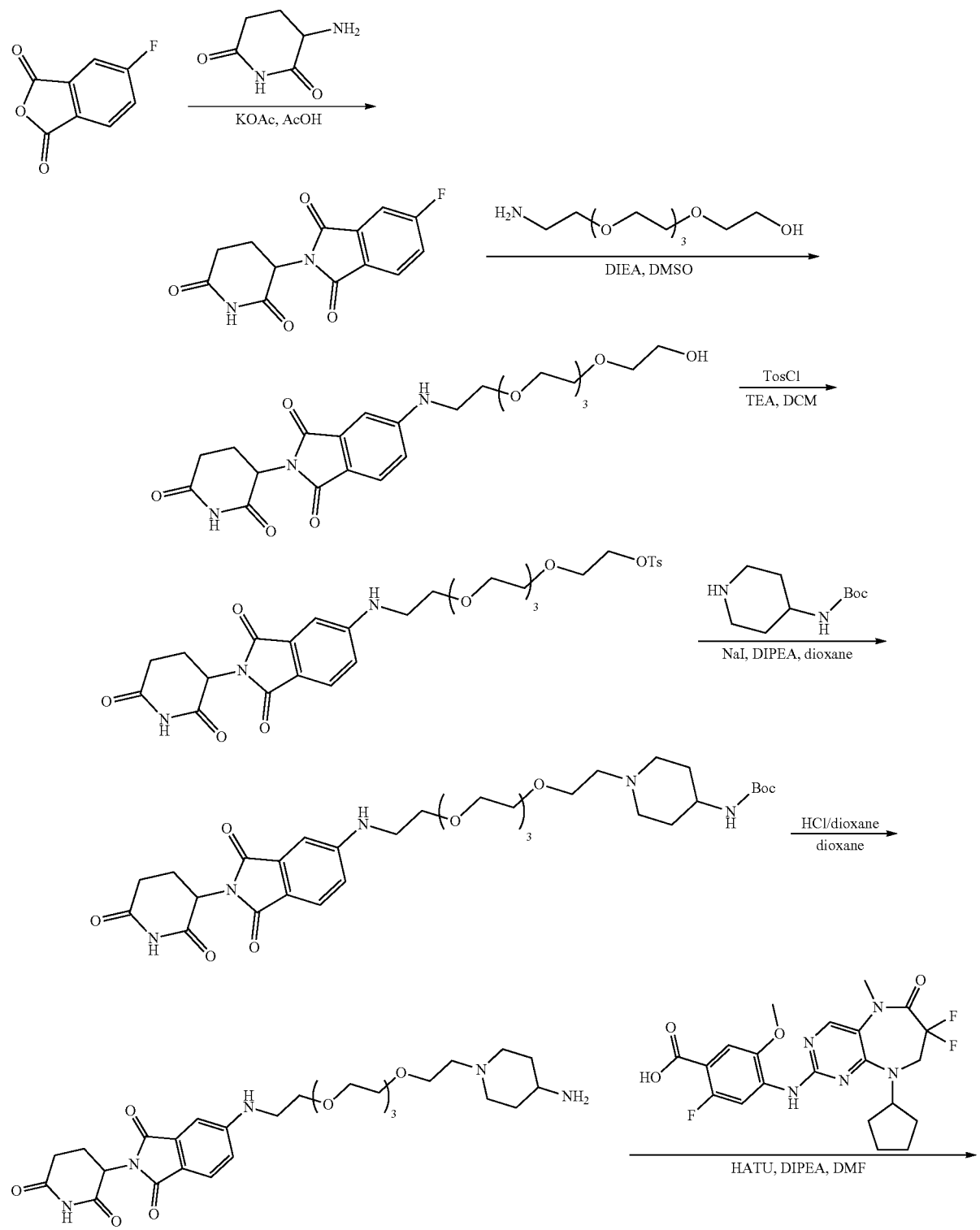

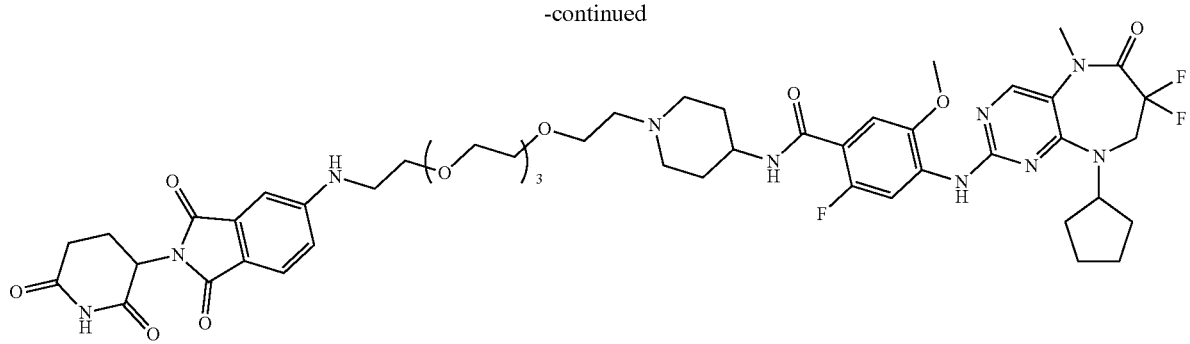

Compound 51

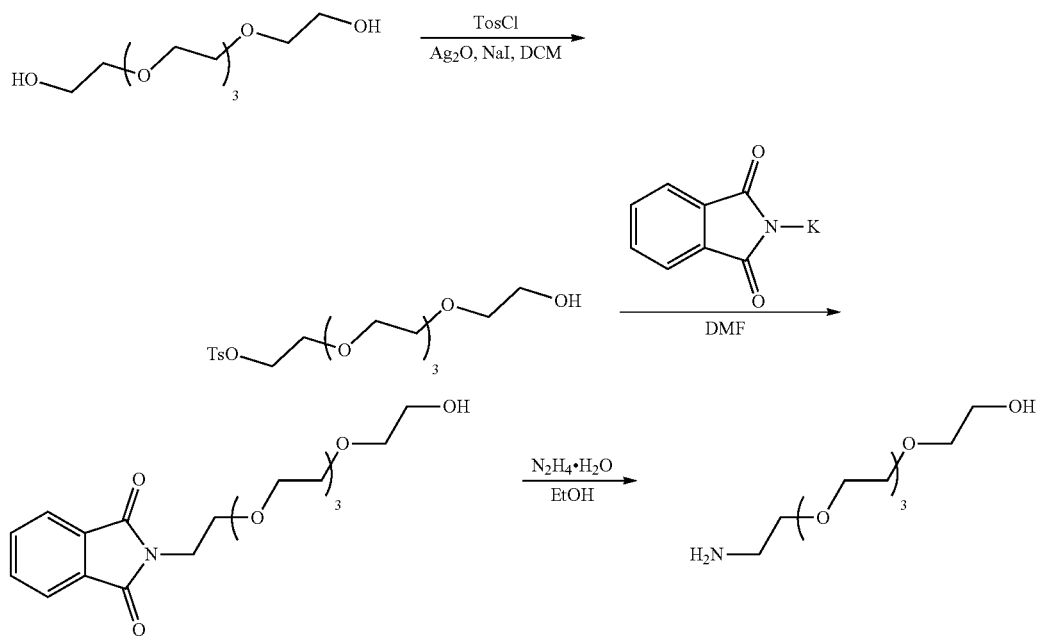

According to the above reaction scheme, in a manner similar to the other examples, obtained the titled compound (45.6 mg, 36.89 μmol, 9.03% yield, 92% purity, TFA salt) as a brown solid. MS(M+H)⁺=1023.3.

¹H NMR (400 MHz, CD₃OD) δ=8.29 (d, J=13.8 Hz, 1H), 8.23-8.15 (m, 1H), 7.55-7.53 (m, 1H), 7.36 (d, J=6.7 Hz, 1H), 7.01 (d, J=1.9 Hz, 1H), 6.83 (dd, J₁=8.4 Hz, J₂=2.1 Hz, 1H), 5.05-5.00 (m, 2H), 4.09 (t, J=13.1 Hz, 3H), 4.01-3.95 (m, 3H), 3.83-3.79 (m, 2H), 3.74-3.62 (m, 16H), 3.53-3.46 (m, 1H), 3.44-3.35 (m, 7H), 3.19-3.13 (m, 1H), 2.92-2.81 (m, 1H), 2.75-2.70 (m, 1H), 2.35-2.21 (m, 2H), 2.18-2.02 (m, 4H), 1.98-1.77 (m, 4H), 1.78-1.67 (m, 4H).

Examples 52 & 53. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(15-(2-(2,6-dioxopiperidin-3-yl)-1,3-dioxoisoindolin-4-yl)-3,6,9,12-tetraoxapentadec-14-yn-1-yl)piperidin-4-yl)-2-fluoro-5-methoxybenzamide and 4-((9-cyclopentyl-7,7-difluoro-5-methyl-6-oxo-6,7,8,9-tetrahydro-5H-pyrimido[4,5-b][1,4]diazepin-2-yl)amino)-N-(1-(15-(2-(2,6-dioxopiperidin-3-yl)-1,3-dioxoisoindolin-4-yl)-3,6,9,12-tetraoxapentadecyl)piperidin-4-yl)-2-fluoro-5-methoxybenzamide

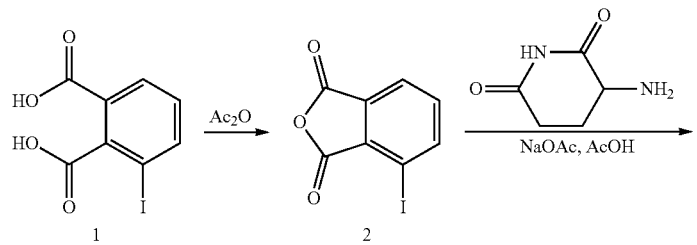

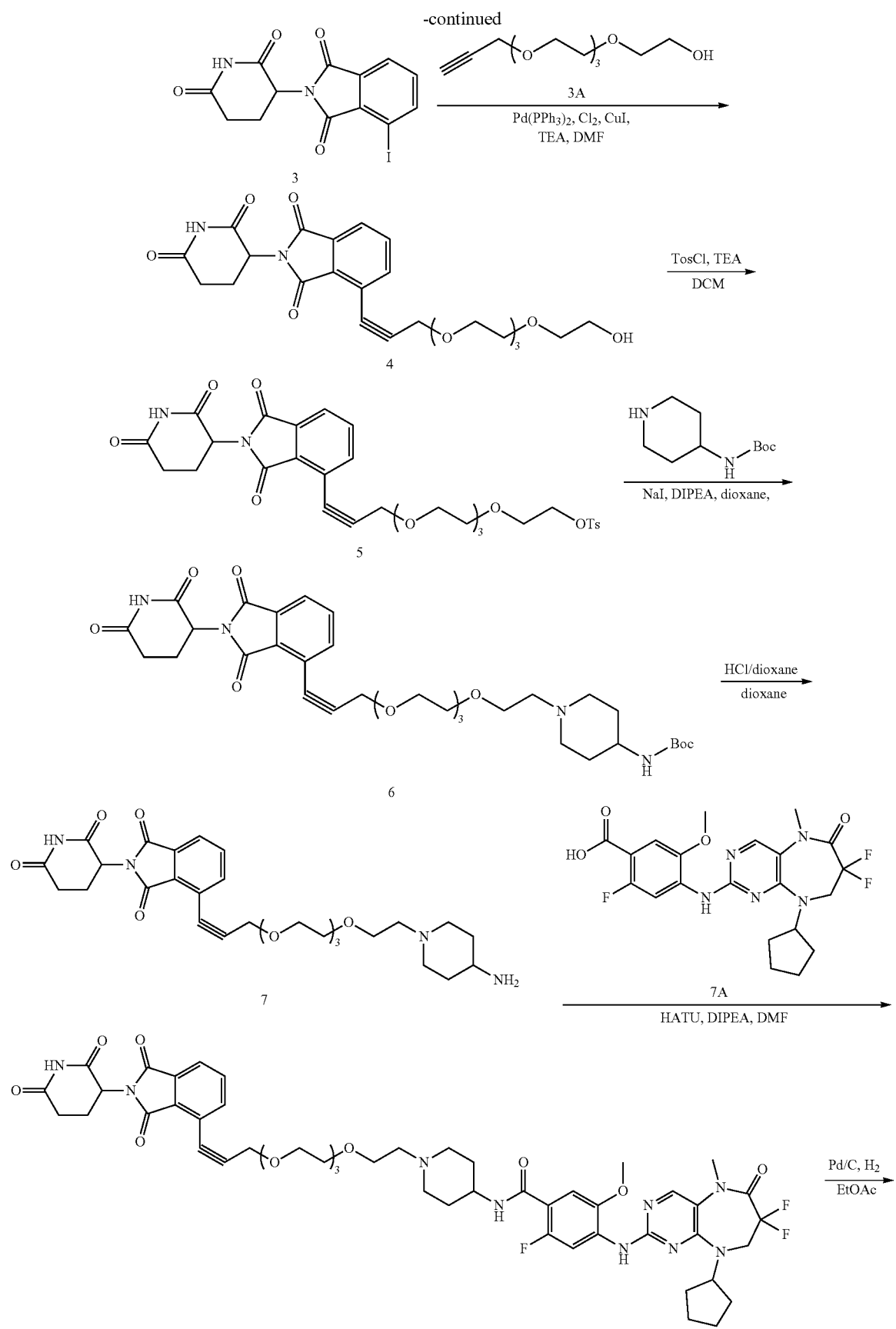

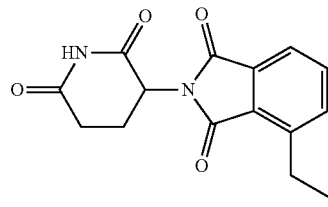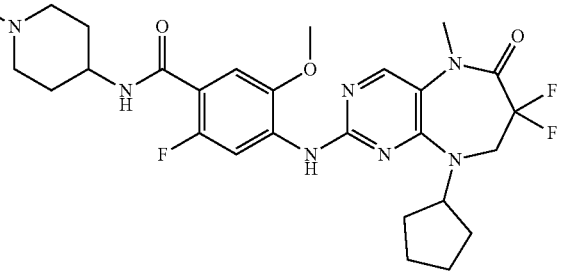

Compound 53

Step 1: Synthesis of 4-iodoisobenzofuran-1,3-dione (2)

The mixture of 3-iodophthalic acid (25 g, 85.61 mmol) in Ac$_2$O (100 mL) was stirred at 80° C. for 16 hours. LCMS showed the reaction was completed. The reaction mixture was concentrated in vacuum. The crude product was washed with petrol ether (40 mL×5) and dried in vacuum to afford the titled compound (22.4 g, crude) as white solid. MS(M+Na)$^+$=296.2

Step 2: Synthesis of 2-(2,6-dioxopiperidin-3-yl)-4-iodoisoindoline-1,3-dione (3)

To a solution of 4-iodoisobenzofuran-1,3-dione (10 g, 36.49 mmol) in AcOH (100 mL) was added 3-aminopiperidine-2,6-dione (6.61 g, 40.14 mmol, HCl), NaOAc (3.59 g, 43.79 mmol) in one portion and the mixture was stirred at 140° C. for 16 hours. TLC (EtOAc) indicated that the reaction was completed. The reaction mixture was filtered and the cake was washed with H$_2$O (100 mL×3), the cake was dried in vacuum to afford the titled compound (13 g, crude) as black solid.

$^1$H NMR (400 MHz, DMSO-d$_6$) δ=11.2 (s, 1H), 8.27 (d, J=7.6, 1H), 7.92 (d, J=7.2, 1H), 7.58 (d, J=7.6, 1H), 5.18-5.14 (m, 1H), 2.96-2.83 (m, 1H), 2.63-2.53 (m, 2H), 2.09-2.05 (m, 1H).

Step 3: Synthesis of 2-(2,6-dioxopiperidin-3-yl)-4-(1-hydroxy-3,6,9,12-tetraoxapentadec-14-yn-15-yl)isoindoline-1,3-dione (4)

To a mixture of 2-(2,6-dioxopiperidin-3-yl)-4-iodoisoindoline-1,3-dione (2 g, 5.21 mmol) and 2-[2-[2-(2-prop-2-ynoxyethoxy) ethoxy]ethoxy]ethanol (1.81 g, 7.81 mmol) in DMF (20 mL) were added Pd(PPh$_3$)$_2$Cl$_2$ (380.97 mg, 520.67 umol), CuI (198.32 mg, 1.04 mmol) and TEA (5.27 g, 52.07 mmol, 7.25 mL) and the mixture was stirred at 60° C. for 0.5 h under microwave under N$_2$. LCMS indicated that the reaction was completed. The reaction mixture was concentrated. The residue was purified by silica gel column (EtOAc) to afford the titled compound (2 g, 4.09 mmol, 78.64% yield) as yellow oil. MS(M+H)$^+$=489.1

Step 4: Synthesis of 15-(2-(2,6-dioxopiperidin-3-yl)-1,3-dioxoisoindolin-4-yl-3,6,9,12-tetraoxapentadec-14-yn-1-yl 4-methylbenzenesulfonate (5)

To a mixture of 2-(2,6-dioxopiperidin-3-yl)-4-(1-hydroxy-3,6,9,12-tetraoxapentadec-14-yn-15-yl)isoindoline-1,3-dione (2 g, 4.09 mmol) and TEA (1.24 g, 12.28 mmol, 1.71 mL) in DCM (10 mL) was added TosCl (1.17 g, 6.14 mmol) and the mixture was stirred at 20° C. for 16 hours. LCMS indicated the reaction was completed. The reaction mixture was concentrated. The residue was purified by silica gel column (EtOAc) to afford the titled compound (1.8 g, 2.49 mmol, 60.88% yield, 89% purity) as yellow oil. MS (M+H)$^+$=643.1

Step 5: Synthesis of tert-butyl (1-(15-(2-(2,6-dioxopiperidin-3-yl)-1,3-dioxoisoindolin-4-yl)-3,6,9,12-tetraoxapentadec-14-yn-1-yl)piperidin-4-yl)carbamate (6)

To the solution of 15-(2-(2,6-dioxopiperidin-3-yl)-1,3-dioxoisoindolin-4-yl)-3,6,9,12-tetraoxapentadec-1 4-yn-1-yl 4-methylbenzenesulfonate (1 g, 1.56 mmol) and tert-butyl piperidin-4-ylcarbamate (467.45 mg, 2.33 mmol) in dioxane (10 mL) were added NaI (23.32 mg, 155.60 μmol) and DIPEA (402.21 mg, 3.11 mmol, 542.06 μL) and the resulting mixture was stirred at 80° C. for 12 hours. TLC (Ethyl acetate/Methanol=10/1) showed that the reaction was completed. The mixture was concentrated and the residue was purified by silica gel column (Ethyl acetate/Methanol=10/1) to afford the titled compound (0.9 g, 1.29 mmol, 82.78% yield, 96% purity) as yellow oil.
MS(M+H)$^+$=671.2

Step 6: Synthesis of 4-(1-(4-aminopiperidin-1-yl)-3,6,9,12-tetraoxapentadec-14-yn-15-yl)-2-(2,6-dioxopiperidin-3-yl)isoindoline-1,3-dione (7)

To the solution of tert-butyl (1-(15-(2-(2,6-dioxopiperidin-3-yl)-1,3-dioxoisoindolin-4-yl)-3,6,9,12-tetraoxapentadec-14-yn-1-yl)piperidin-4-yl)carbamate (0.9 g, 1.34 mmol) in dioxane (10 mL) was added HCl/dioxane (4 M, 10 mL) and the resulting mixture was stirred at 25° C. for 2 h. LCMS showed that the reaction was completed. The mixture was concentrated under vacuum to afford 4-(1-(4-aminopiperidin-1-yl)-3,6,9,12-tetraoxapentadec-14-yn-15-yl)-2-(2,6-dioxopiperidin-3-yl)isoindoline-1,3-dione (0.8 g, 1.32 mmol, 98.21% yield, HCl) as yellow oil. MS(M+H)$^+$=571.2

Step 7: Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(15-(2-(2,6-dioxopiperidin-3-yl)-1,3-dioxoisoindolin-4-yl)-3,6,9,12-tetraoxapentadec-14-yn-1-yl)piperidin-4-yl)-2-fluoro-5-methoxybenzamide (Compound 52)

To the solution of 4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzoic acid (300 mg, 644.57 μmol), 4-(1-(4-aminopiperidin-1-yl)-3,6,9,12-tetraoxapentadec-14-yn-15-yl)-2-(2,6-dioxopiperidin-3-yl)isoindoline-1,3-dione (391.32 mg, 644.57 μmol, HCl) and HATU (490.17 mg, 1.29 mmol) in DMF (4 mL) was added DIPEA (249.91 mg, 1.93 mmol, 336.81 μL) and the resulting mixture was stirred at 25° C. for 12 hours. LCMS showed that the reaction was completed. The mixture was poured into water (20 mL) and extracted with EtOAc (20 mL×3), the combined organic layer was washed with brine (50 mL), dried over Na$_2$SO$_4$, filtered and concentrated. The residue was purified by prep-HPLC (column: Phenomenex luna C$_{18}$ 150*40 mm*15 um; mobile phase: [water (0.225% FA)-ACN]; B %: 27%-57%, 10 min) and the eluant was lyophilized to afford the titled compound (229.4 mg, 218.57 μmol, 33.91% yield, 97% purity) as yellow solid. MS(M+H)$^+$=1018.6

$^1$H NMR (400 MHz, DMSO-d$_6$) δ=11.15 (s, 1H), 9.38-9.09 (m, 1H), 8.30 (s, 1H), 8.28-8.08 (m, 3H), 7.94-7.83 (m, 3H), 7.26-7.14 (m, 1H), 5.16 (dd, J=5.3, 12.8 Hz, 1H), 4.83 (t, J=7.9 Hz, 1H), 4.55-4.47 (m, 2H), 4.10 (t, J=13.8 Hz, 2H), 4.04-3.96 (m, 1H), 3.94-3.89 (m, 3H), 3.80-3.70 (m, 4H), 3.64-3.53 (m, 12H), 3.34 (s, 3H), 3.27 (d, J=4.6 Hz, 2H), 3.12 (d, J=12.0 Hz, 1H), 2.95-2.85 (m, 1H), 2.65-2.54 (m, 2H), 2.10-2.04 (m, 2H), 1.98 (d, J=5.4 Hz, 3H), 1.87-1.70 (m, 4H), 1.57-1.47 (m, 4H).

Step 8: Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(15-(2-(2,6-dioxopiperidin-3-yl)-1,3-dioxoisoindolin-4-yl)-3,6,9,12-tetraoxapentadecyl)piperidin-4-yl)-2-fluoro-5-methoxybenzamide (Compound 53)

To the solution of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(15-(2-(2,6-dioxopiperidin-3-yl)-1,3-dioxoisoindolin-4-yl)-3,6,9,12-tetraoxapentadec-14-yn-1-yl)piperidin-4-yl)-2-fluoro-5-methoxybenzamide (70 mg, 68.76 μmol) in EtOAc (5 mL) was added Pd/C (20 mg, 10% purity) and the resulting mixture was stirred at 25° C. for 12 hours under H$_2$ (15 psi). LCMS showed that the reaction was completed. The mixture was combined with the pilot (50 mg scale) and filtered and the filtrate was concentrated, the residue was purified by prep-HPLC (column: Phenomenex Synergi C$_{18}$ 150*25 mm*10 um; mobile phase: [water (0.225% FA)-ACN]; B %: 19%-49%, min) and the eluant was lyophilized to afford the titled compound (23 mg, 21.60 μmol, 31.42% yield, 96% purity, FA salt) as white solid. MS(M+H)$^+$=1022.7

$^1$H NMR (400 MHz, DMSO-d$_6$) δ=11.12 (s, 1H), 8.30 (s, 1H), 8.24 (t, J=6.6 Hz, 2H), 8.03 (s, 1H), 7.87 (dd, J=3.3, 7.6 Hz, 1H), 7.80-7.73 (m, 2H), 7.72-7.69 (m, 1H), 7.19 (d, J=6.8 Hz, 1H), 5.18-5.04 (m, 1H), 4.87-4.76 (m, 1H), 4.08 (t, J=13.9 Hz, 2H), 3.91 (s, 3H), 3.79-3.67 (m, 1H), 3.53-3.48 (m, 18H), 3.34 (s, 3H), 3.10-3.03 (m, 2H), 2.95-2.80 (m, 4H), 2.65-2.53 (m, 2H), 2.48-2.45 (m, 2H), 2.11-2.03 (m, 2H), 1.99-1.93 (m, 2H), 1.89-1.82 (m, 2H), 1.80-1.71 (m, 4H), 1.61-1.52 (m, 4H).

Example 54. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(2-(2-((3-(2-(2,6-dioxopiperidin-3-yl)-1,3-dioxoisoindolin-4-yl)prop-2-yn-1-yl)oxy)ethoxy)ethyl)piperidin-4-yl)-2-fluoro-5-methoxybenzamide

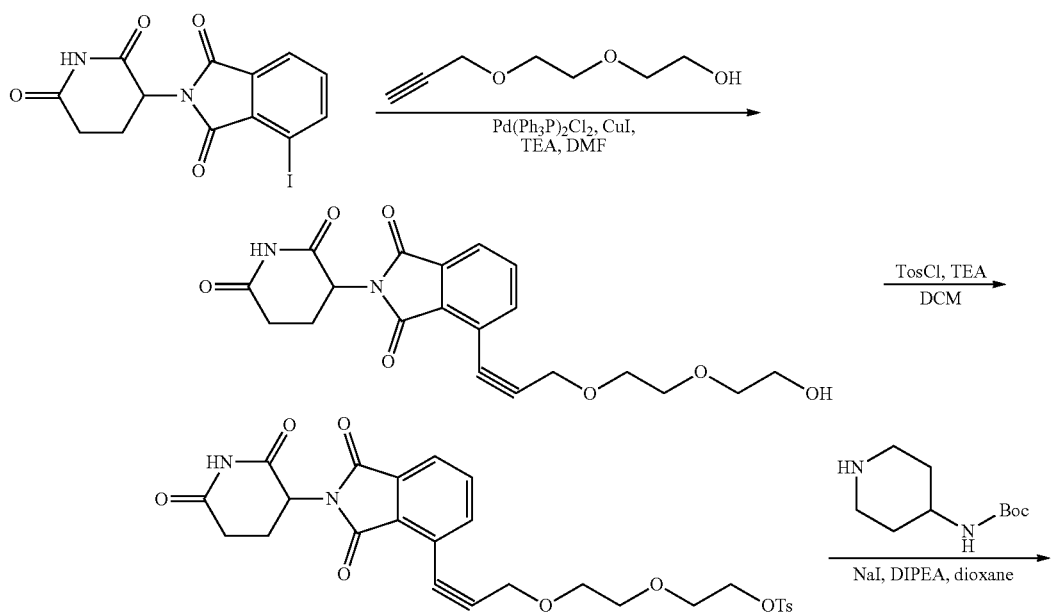

-continued

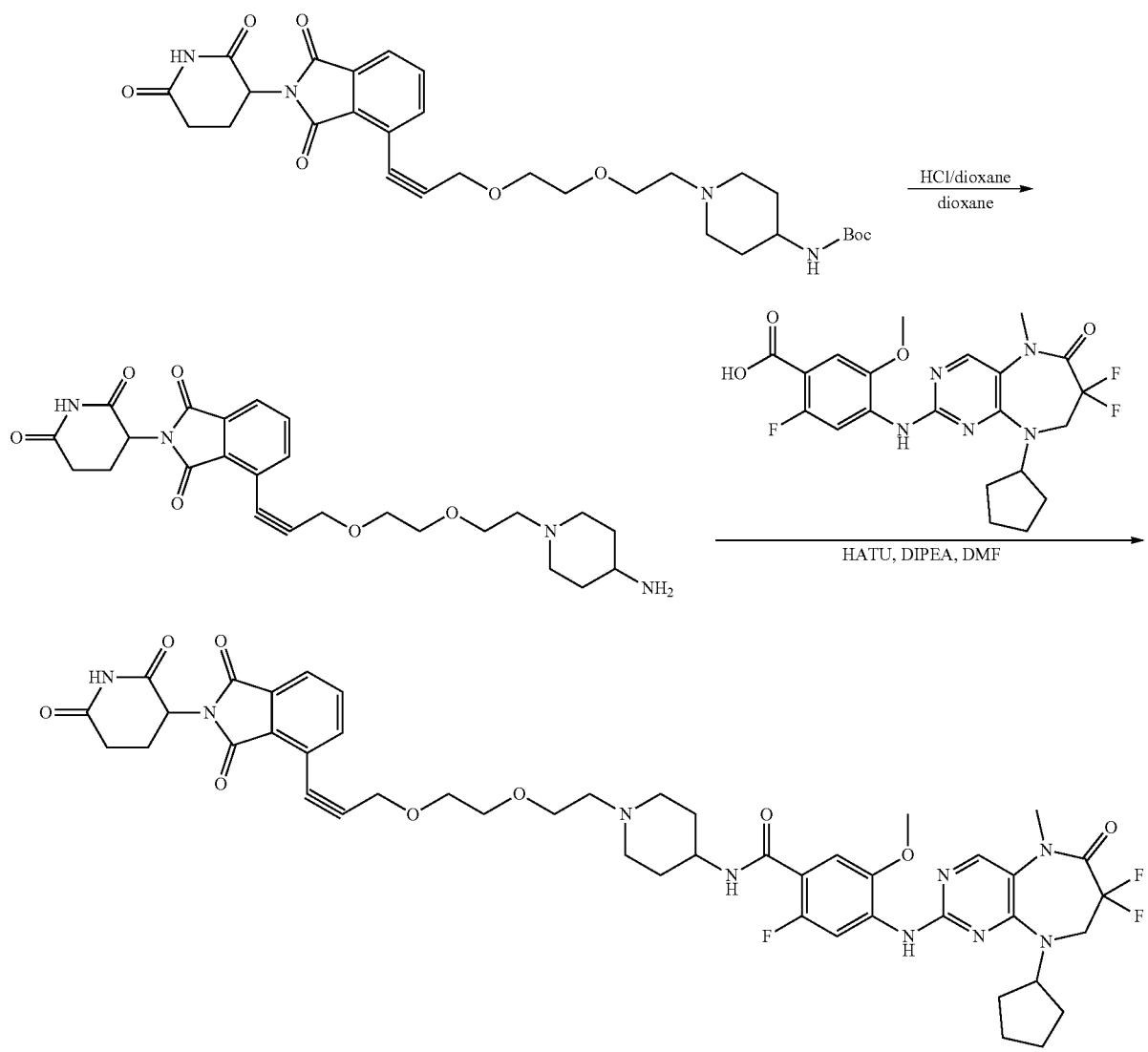

Compound 54

According to the above reaction scheme, in a manner similar to the other examples, obtained the titled compound (36.2 mg, 36.35 μmol, 6.29% yield, 98% purity, FA salt) as white solid. MS(M+H)⁺=930.3.

$^1$H NMR (400 MHz, CD$_3$OD) δ=8.49 (br s, 1H), 8.40 (d, J=14.2 Hz, 1H), 8.21 (s, 1H), 7.86-7.74 (m, 3H), 7.30 (d, J=6.8 Hz, 1H), 5.15-5.11 (m, 1H), 4.98-4.96 (m, 1H), 4.66-5.47 (m, 2H), 4.55 (s, 2H), 4.08-3.99 (m, 5H), 3.97-3.92 (m, 1H), 3.91-3.74 (m, 5H), 3.51 (d, J=11.8 Hz, 2H), 3.41 (s, 3H), 3.25-3.16 (m, 2H), 3.07-2.94 (m, 2H), 2.94-2.83 (m, 1H), 2.81-2.64 (m, 2H), 2.18-2.09 (m, 4H), 1.90-1.77 (m, 4H), 1.76-1.65 (m, 4H).

Example 55. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(2-(2-(3-(2-(2,6-dioxopiperidin-3-yl)-1,3-dioxoisoindolin-4-yl)propoxy)ethoxy)ethyl)piperidin-4-yl)-2-fluoro-5-methoxybenzamide

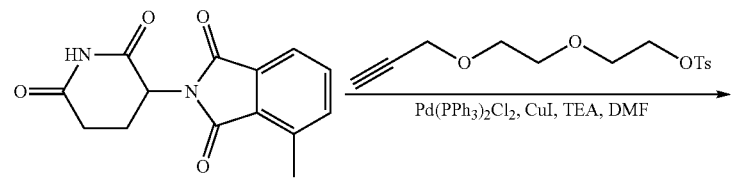

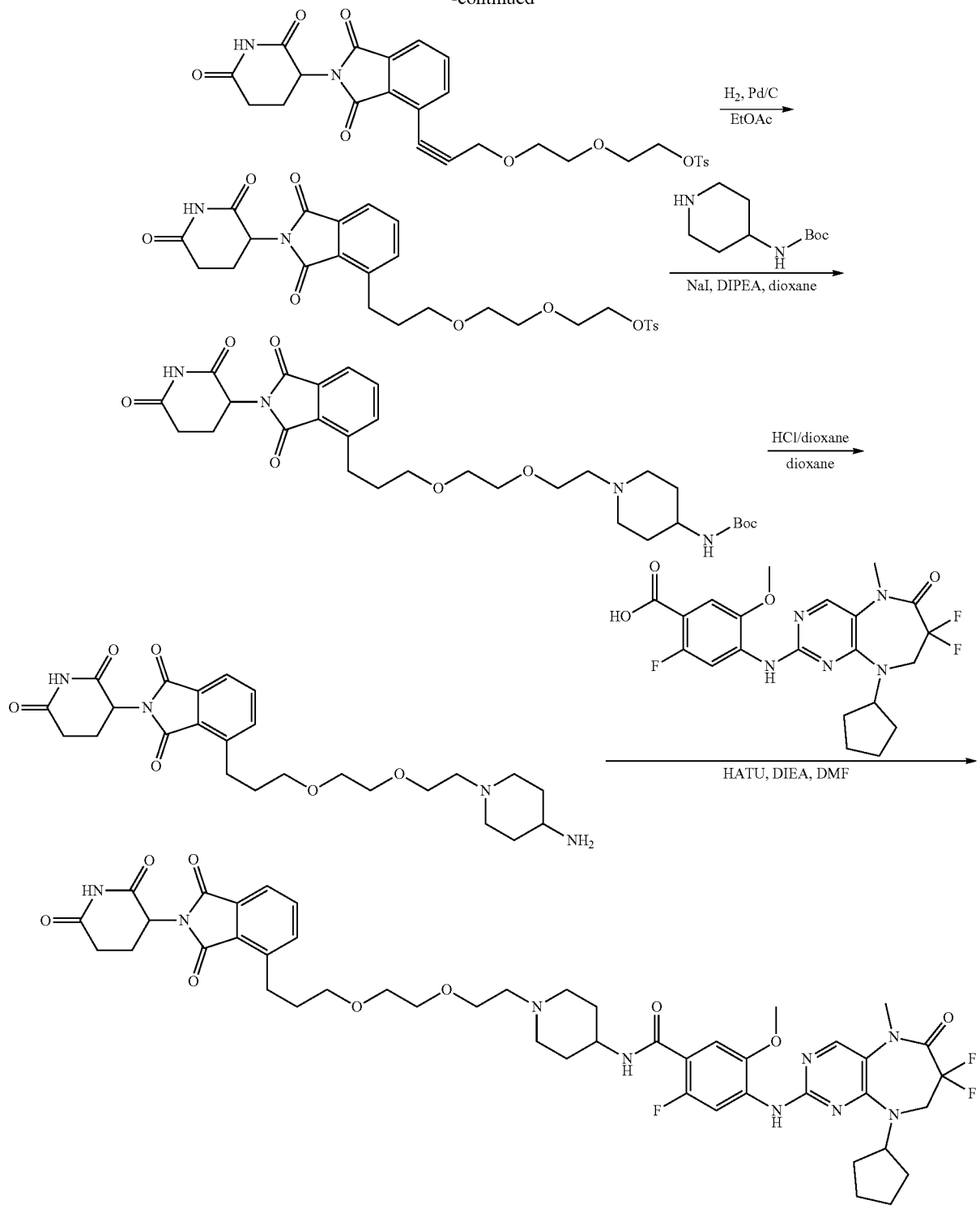
Compound 55
According to the above reaction scheme, in a manner similar to the other examples, obtained the titled compound (118.1 mg, 121.39 μmol, 42.33% yield, 96% purity) as white solid. MS(M+H)⁺=934.7.
¹H NMR (400 MHz, DMSO-d₆) δ=11.13 (s, 1H), 8.30 (s, 1H), 8.24 (d, J=13.2 Hz, 1H), 8.03 (s, 1H), 7.90-7.84 (m, 1H), 7.81-7.72 (m, 2H), 7.72-7.65 (m, 1H), 7.18 (d, J=6.8 Hz, 1H), 5.16-5.08 (m, 1H), 4.87-4.77 (m, 1H), 4.07 (t, J=13.8 Hz, 2H), 3.91 (s, 3H), 3.76-3.66 (m, 1H), 3.54-3.45 (m, 6H), 3.42 (t, J=6.4 Hz, 2H), 3.33 (s, 3H), 3.07 (t, J=7.6 Hz, 2H), 2.97-2.77 (m, 3H), 2.67-2.51 (m, 3H), 2.45 (t, J=5.8 Hz, 2H), 2.06-1.93 (m, 4H), 1.89-1.80 (m, 2H), 1.79-1.68 (m, 4H), 1.67-1.50 (m, 6H).

Example 56. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(2-(2-(2-((2-(2,6-dioxopiperidin-3-yl)-1,3-dioxoisoindolin-4-yl)oxy)acetamido)ethoxy)ethyl)piperidin-4-yl)-2-fluoro-5-methoxybenzamide
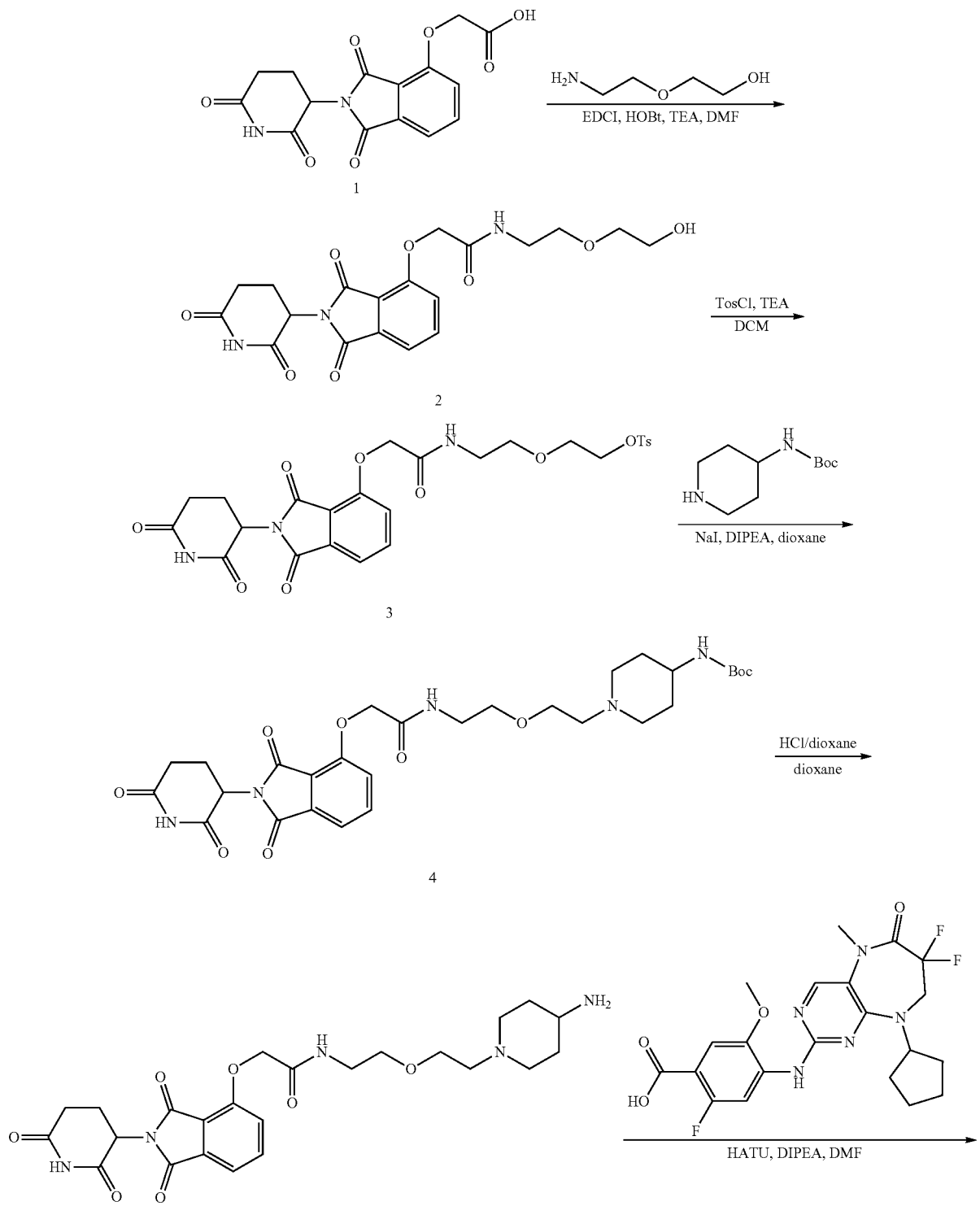

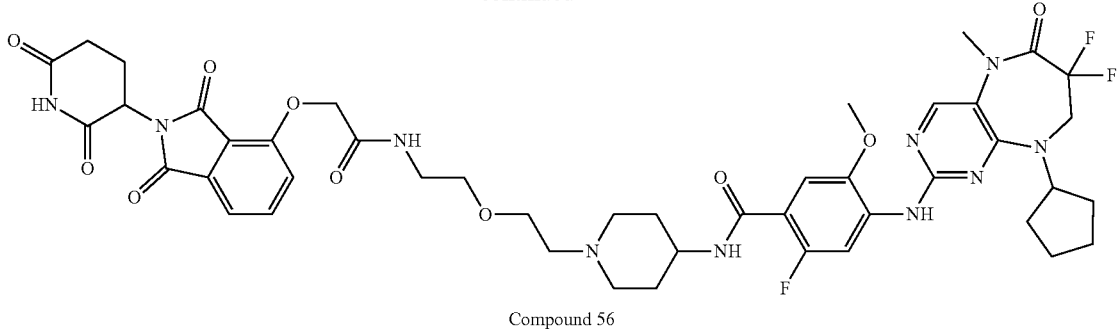

Compound 56

Step 1: Synthesis of 2-((2-(2,6-dioxopiperidin-3-yl)-1,3-dioxoisoindolin-4-yl)oxy)-N-(2-(2-hydroxyethoxy)ethyl)acetamide (2)

To a solution of 2-((2-(2,6-dioxopiperidin-3-yl)-1,3-dioxoisoindolin-4-yl)oxy)acetic acid (6.95 g, 20.93 mmol) and 2-(2-aminoethoxy) ethanol (2.0 g, 19.02 mmol, 1.90 mL) in DMF (20 mL) were added EDCI (5.47 g, 28.53 mmol), HOBt (3.86 g, 28.53 mmol) and TEA (11.55 g, 114.14 mmol, 15.89 mL) and the mixture was stirred at 25° C. for 12 h. LCMS showed that the reaction was completed. The mixture was concentrated in vacuo. The residue was purified by reversed-phase HPLC (0.1% FA condition, MeCN, water) to afford 2-((2-(2,6-dioxopiperidin-3-yl)-1,3-dioxoisoindolin-4-yl)oxy)-N-(2-(2-hydroxyethoxy) ethyl)acetamide (5.6 g, 13.35 mmol, 70.19% yield) as gray solid. MS(M+H)$^+$=420.0

Step 2: Synthesis of 2-(2-(2-((2-(2,6-dioxopiperidin-3-yl)-1,3-dioxoisoindolin-4-yl)oxy)acetamido)ethoxy)ethyl 4-methylbenzenesulfonate (3)

To a solution of 2-((2-(2,6-dioxopiperidin-3-yl)-1,3-dioxoisoindolin-4-yl)oxy)-N-(2-(2-hydroxyethoxy) ethyl)acetamide (2.5 g, 5.96 mmol) in DCM (20 mL) were added TEA (723.84 mg, 7.15 mmol, 995.65 µL) and TosCl (1.36 g, 7.15 mmol) and the mixture was stirred at 25° C. for 12 h. LCMS showed that the reaction was completed. The mixture was filtered and the filtrate was diluted with H$_2$O (20 mL) and extracted with DCM (50 mL×3). The combined organic layers were washed with brine (15 mL), dried over Na$_2$SO$_4$, filtered and concentrated under reduced pressure. The residue was purified by flash silica gel chromatography (25 g SepaFlash® Silica Flash Column, Eluent of 20-60% Ethyl acetate/Petroleum ether gradient @ 60 mL/min) to afford the titled compound (2.0 g, 4.77 mmol, 80.00% yield) as gray solid. MS(M+H)$^+$=574.0

Step 3: Synthesis of tert-butyl (1-(2-(2-(2-((2-(2,6-dioxopiperidin-3-yl)-1,3-dioxoisoindolin-4-yl)oxy)acetamido)ethoxy)ethyl)piperidin-4-yl)carbamate (4)

To a solution of 2-(2-(2-((2-(2,6-dioxopiperidin-3-yl)-1,3-dioxoisoindolin-4-yl)oxy)acetamido)ethoxy)ethyl 4-methylbenzenesulfonate (350 mg, 610.21 µmol) and tert-butyl piperidin-4-ylcarbamate (183.32 mg, 915.32 µmol) in dioxane (5 mL) were added NaI (9.15 mg, 61.02 µmol) and DIPEA (78.87 mg, 610.21 µmol, 106.29 µL) and the resulting mixture was stirred at 60° C. for 24 h. LCMS showed that the reaction was completed. The reaction mixture was diluted with H$_2$O (20 mL) and extracted with EtOAc (20 mL×3), the combined organic layers were dried over Na$_2$SO$_4$, filtered and concentrated under reduced pressure. The residue was purified by flash silica gel chromatography (12 g SepaFlash® Silica Flash Column, Eluent of 30~100% Ethyl acetate/Petroleum ether gradient @ 60 mL/min) to afford the titled compound (166 mg, 275.91 µmol, 45.22% yield) as white solid.
MS(M+H)$^+$=602.2

Step 4: Synthesis of N-(2-(2-(4-aminopiperidin-1-yl)ethoxy)ethyl)-2-((2-(2,6-dioxopiperidin-3-yl)-1,3-dioxoisoindolin-4-yl)oxy)acetamide (5)

To a solution of tert-butyl (1-(2-(2-(2-((2-(2,6-dioxopiperidin-3-yl)-1,3-dioxoisoindolin-4-yl)oxy)acetamido)ethoxy)ethyl)piperidin-4-yl)carbamate (166 mg, 275.91 µmol) in dioxane (2 mL) was added HCl/dioxane (4 M, 3 mL) and the resulting mixture was stirred at 25° C. for 2 h. TLC (EA/MeOH=10:1) showed that the reaction was completed. The mixture was concentrated to afford the titled compound (150 mg, crude, HCl) as white solid. MS(M+H)$^+$=502.2

Step 5: Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(2-(2-(2-((2-(2,6-dioxopiperidin-3-yl)-1,3-dioxo isoindolin-4-yl)oxy)acetamido)ethoxy)ethyl)piperidin-4-yl)-2-fluoro-5-methoxybenzamide (Compound 56)

To the solution of N-(2-(2-(4-aminopiperidin-1-yl)ethoxy)ethyl)-2-((2-(2,6-dioxopiperidin-3-yl)-1,3-dioxoisoindolin-4-yl)oxy)acetamide (150 mg, 278.81 µmol, HCl) and 4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzoic acid (129.77 mg, 278.81 µmol) in DMF (3 mL) were added HATU (212.03 mg, 557.63 µmol) and DIPEA (108.10 mg, 836.44 µmol, 145.69 µL) and the resulting mixture was stirred at 20° C. for 1 h. LCMS showed that the reaction was completed. The mixture was poured into water (20 mL) and extracted with EtOAc (20 mL×3), the combined organic layer was washed with brine (50 mL), dried over Na$_2$SO$_4$, filtered and concentrated. The residue was purified by prep-HPLC (column: Unisil 3-100 C$_{18}$ µLtra 150*50 mm*3 um; mobile phase: [water (0.225% FA)-ACN]; B %: 28%-48%, 10 min) and the eluant was lyophilized to afford the titled compound (114 mg, 118.93 umol, 42.66% yield, 99% purity, FA) as yellow solid. MS(M+H)$^+$=949.2.
$^1$H NMR (400 MHz, DMSO-d$_6$) δ=11.13 (s, 1H), 9.19 (br s, 1H), 8.31 (s, 1H), 8.27 (d, J=13.2 Hz, 1H), 8.14 (s, 1H), 8.06 (s, 1H), 8.01 (t, J=5.5 Hz, 1H), 7.83 (dd, J=7.5, 8.4 Hz, 1H), 7.52 (d, J=7.2 Hz, 1H), 7.43 (d, J=8.6 Hz, 1H), 7.18 (s, 1H), 5.18-5.06 (m, 1H), 4.89-4.77 (m, 3H), 4.09 (t, J=13.9 Hz, 2H), 3.92 (s, 4H), 3.75 (s, 2H), 3.55 (t, J=5.4 Hz, 2H), 3.43-3.37 (m, 3H), 3.34 (s, 3H), 3.29-3.05 (m, 3H), 2.96-2.84 (m, 1H), 2.65-2.52 (m, 5H), 2.13-1.93 (m, 5H), 1.82-1.55 (m, 7H).
Example 57. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(1-((2-(2,6-dioxopiperidin-3-yl)-1,3-dioxoisoindolin-4-yl)oxy)-2-oxo-6,9,12-trioxa-3-azatetradecan-14-yl)piperidin-4-yl)-2-fluoro-5-methoxybenzamide
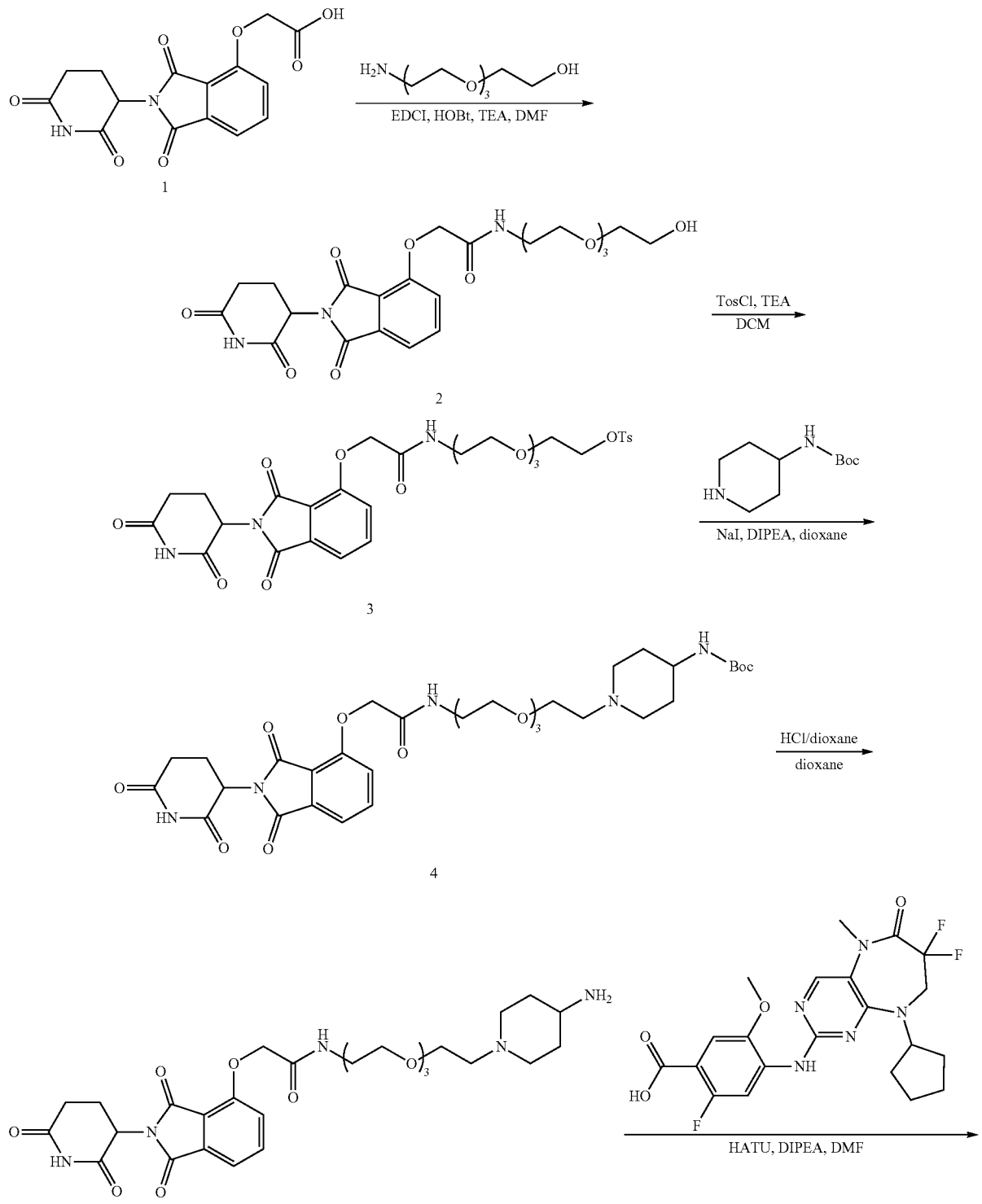

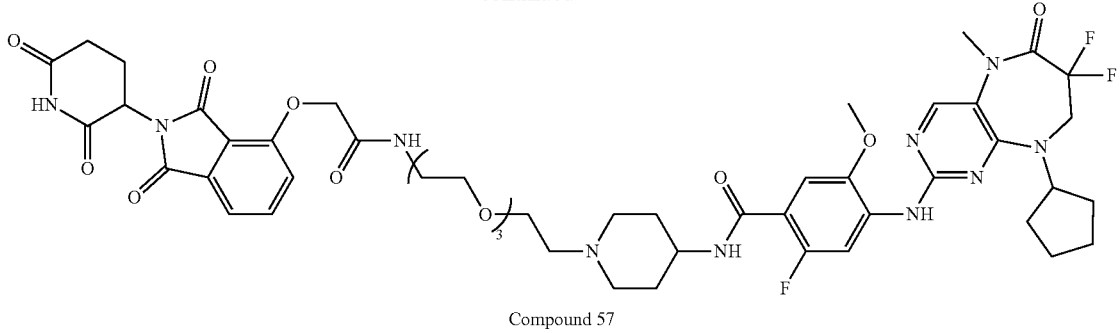

Compound 57

Step 1: Synthesis of 2-((2-(2,6-dioxopiperidin-3-yl)-1,3-dioxoisoindolin-4-yl)oxy)-N-(2-(2-(2-(2-hydroxyethyl)ethoxy)ethoxy)ethyl)acetamide (2)

To a solution of 2-((2-(2,6-dioxopiperidin-3-yl)-1,3-dioxoisoindolin-4-yl)oxy)acetic acid (1.89 g, 5.69 mmol) and 2-(2-(2-(2-aminoethoxy)ethoxy)ethoxy)ethanol (1 g, 5.17 mmol) in DMF (10 mL) were added EDCI (1.49 g, 7.76 mmol), HOBt (1.05 g, 7.76 mmol) and TEA (3.14 g, 31.05 mmol, 4.32 mL) and the resulting mixture was stirred at 25° C. for 16 h. LCMS showed that the reaction was completed. The mixture was purified by reversed-phase column (0.1% FA condition, MeCN/water) to afford the titled compound (1.63 g, 3.18 mmol, 61.45% yield, 99% purity) as white solid. MS(M+H)$^+$=508.1

Step 2: Synthesis of 1-((2-(2,6-dioxopiperidin-3-yl)-1,3-dioxoisoindolin-4-yl)oxy)-2-oxo-6,9,12-trioxa-3-azatetradecan-14-yl 4-methylbenzenesulfonate (3)

To a solution of 2-((2-(2,6-dioxopiperidin-3-yl)-1,3-dioxoisoindolin-4-yl)oxy)-N-(2-(2-(2-(2-hydroxyethoxy)ethoxy)ethoxy)ethyl)acetamide (1.63 g, 3.21 mmol) in DCM (20 mL) were added TosCl (1.22 g, 6.42 mmol) and TEA (975.02 mg, 9.64 mmol, 1.34 mL) and the mixture was stirred at 25° C. for 40 h. LCMS showed that some of the starting material remained. To the reaction were added TosCl (1.22 g, 6.42 mmol) and TEA (975.02 mg, 9.64 mmol, 1.34 mL) and the resulting mixture was stirred at 25° C. for another 40 h. LCMS showed that the reaction was completed. The reaction mixture was concentrated under reduced pressure. The residue was purified by column chromatography (SiO$_2$, Ethyl acetate/MeOH=1/0 to 10/1) to afford the titled compound (1.56 g, 2.05 mmol, 63.86% yield, 87% purity) as white solid. MS(M+H)$^+$=662.1

Step 3: Synthesis of tert-butyl (1-(1-((2-(2,6-dioxopiperidin-3-yl)-1,3-dioxoisoindolin-4-yl)oxy)-2-oxo-6,9,12-trioxa-3-azatetradecan-14-yl)piperidin-4-yl)carbamate (4)

To a solution of 1-((2-(2,6-dioxopiperidin-3-yl)-1,3-dioxoisoindolin-4-yl)oxy)-2-oxo-6,9,12-trioxa-3-azatetradecan-14-yl 4-methylbenzenesulfonate (1.56 g, 2.36 mmol) and tert-butyl piperidin-4-ylcarbamate (708.28 mg, 3.54 mmol) in dioxane (15 mL) were added NaI (35.34 mg, 235.77 μmol) and DIPEA (304.71 mg, 2.36 mmol, 410.66 μL) and the mixture was stirred at 80° C. for 16 h. LCMS showed that the reaction was completed. The reaction mixture was poured into H$_2$O (50 mL) and extracted with EtOAc (100 mL×3), the combined organic layer was washed with brine (100 mL×3), dried over Na$_2$SO$_4$, filtered and concentrated under reduced pressure. The residue was purified by column chromatography (SiO$_2$, Ethyl acetate/MeOH=1/0 to 10/1) to afford the titled compound (1.15 g, 1.57 mmol, 66.47% yield, 94% purity) as red solid. MS(M+H)$^+$=690.3

Step 4: Synthesis of N-(2-(2-(2-(2-(4-aminopiperidin-1-yl)ethoxy)ethoxy)ethoxy)ethyl)-2-((2-(2,6-dioxopiperidin-3-yl)-1,3-dioxoisoindolin-4-yl)oxy)acetamide (5)

To a solution of tert-butyl (1-(1-((2-(2,6-dioxopiperidin-3-yl)-1,3-dioxoisoindolin-4-yl)oxy)-2-oxo-6,9,12-trioxa-3-azatetradecan-14-yl)piperidin-4-yl)carbamate (1.15 g, 1.67 mmol) in dioxane (10 mL) was added HCl/dioxane (4 M, 20.03 mL) and the mixture was stirred at 25° C. for 16 h. LCMS showed that the reaction was completed. The mixture was concentrated in vacuum to afford the titled compound (1.1 g, crude, HCl) as white solid. MS(M+H)$^+$=590.2

Step 5: Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(1-((2-(2,6-dioxopiperidin-3-yl)-1,3-dioxoisoindolin-4-yl)oxy)-2-oxo-6,9,12-trioxa-3-azatetradecan-14-yl)piperidin-4-yl)-2-fluoro-5-methoxybenzamide (Compound 57)

To the solution of N-(2-(2-(2-(2-(4-aminopiperidin-1-yl)ethoxy)ethoxy)ethoxy)ethyl)-2-((2-(2,6-dioxopiperidin-3-yl)-1,3-dioxoisoindolin-4-yl)oxy)acetamide (250 mg, 399.30 μmol, HCl) and 4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzoic acid (185.84 mg, 399.30 μmol) in DMF (4 mL) were added HATU (303.65 mg, 798.60 μmol) and DIPEA (154.82 mg, 1.20 mmol, 208.65 μL) and the resulting mixture was stirred at 20° C. for 1 h. LCMS showed that the reaction was completed. The mixture was poured into water (20 mL) and extracted with EtOAc (20 mL×3), the combined organic layer was washed with brine (50 mL), dried over Na$_2$SO$_4$, filtered and concentrated. The residue was purified by prep-HPLC (column: Unisil 3-100 C$_{18}$ μLtra 150*50 mm*3 um; mobile phase: [water (0.225% FA)-ACN]; B %: 28%-48%, 10 min) and the eluant was lyophilized to afford the titled compound (170.3 mg, 162.57 μmol, 40.71% yield, 99% purity, FA) as yellow solid. MS(M+H)$^+$=1037.2.

$^1$H NMR (400 MHz, DMSO-d$_6$) δ=11.13 (s, 1H), 9.53-9.03 (m, 1H), 8.31 (s, 1H), 8.26 (d, J=13.3 Hz, 1H), 8.14 (s, 1H), 8.05 (s, 1H), 7.99 (t, J=5.0 Hz, 1H), 7.81 (t, J=8.0 Hz, 1H), 7.51 (d, J=7.1 Hz, 1H), 7.40 (d, J=8.4 Hz, 1H), 7.19 (br d, J=6.1 Hz, 1H), 5.17-5.06 (m, 1H), 4.88-4.76 (m, 3H), 4.09 (t, J=13.8 Hz, 2H), 4.02-3.90 (m, 4H), 3.73 (s, 2H), 3.61-3.52 (m, 9H), 3.50-3.46 (m, 3H), 3.34 (s, 3H), 3.21-3.00 (m, 4H), 2.97-2.85 (m, 1H), 2.71-2.53 (m, 5H), 2.13-1.90 (m, 5H), 1.78-1.57 (m, 7H).

Example 58. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(1-((2-(2,6-dioxopiperidin-3-yl)-1,3-dioxoisoindolin-4-yl)oxy)-2-oxo-6,9,12,15,18,21,24-heptaoxa-3-azahexacosan-26-yl)piperidin-4-yl)-2-fluoro-5-methoxybenzamide
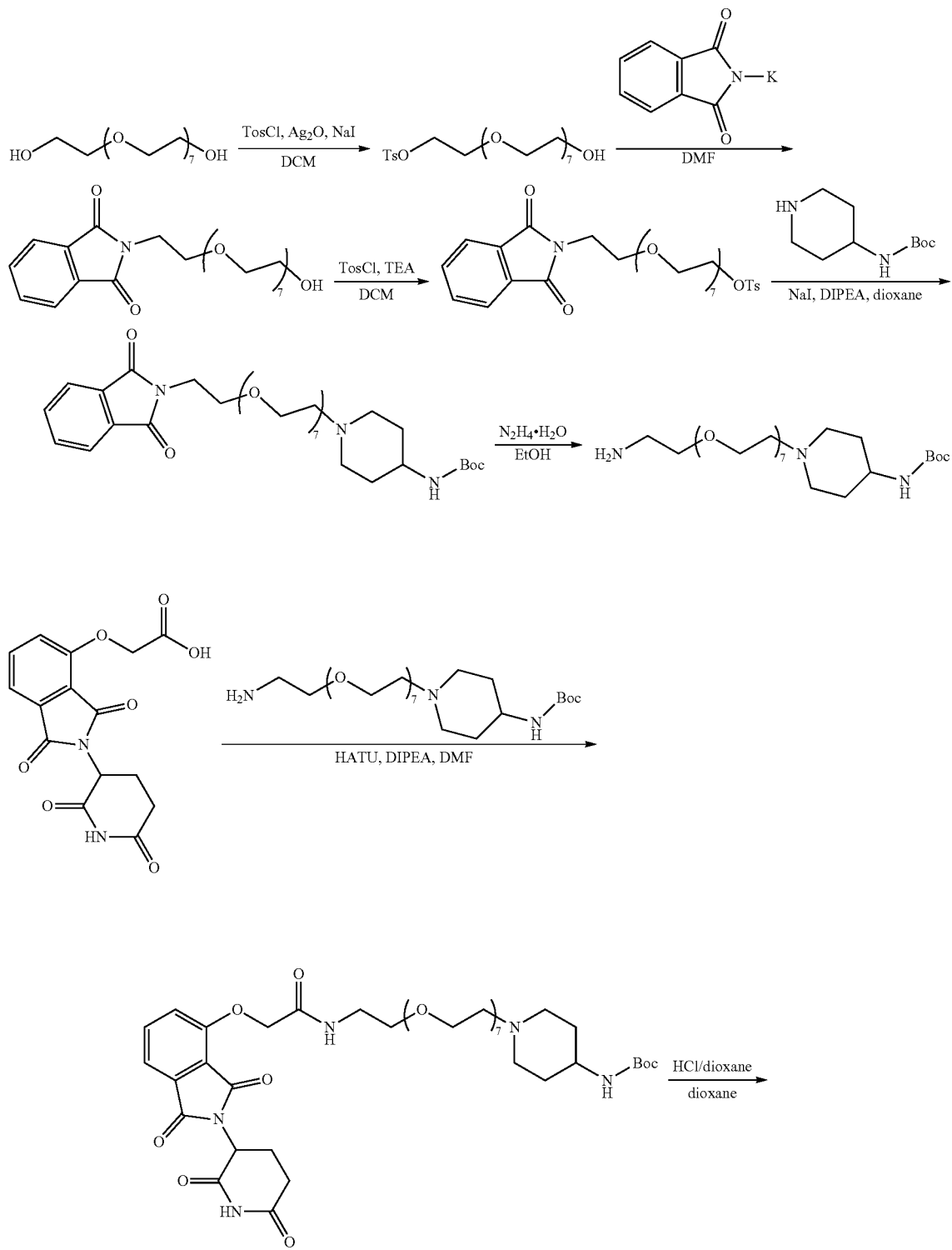

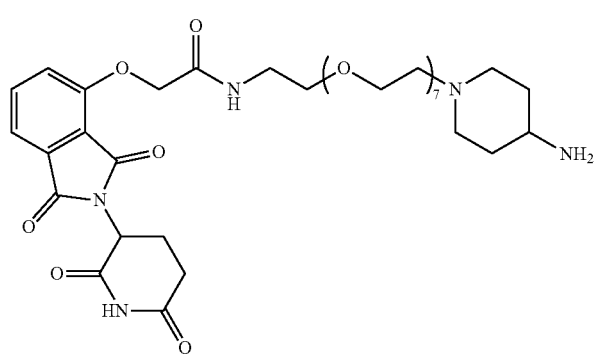
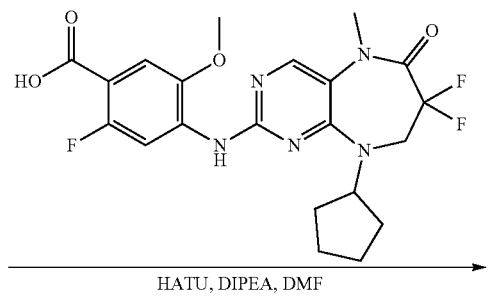

HATU, DIPEA, DMF

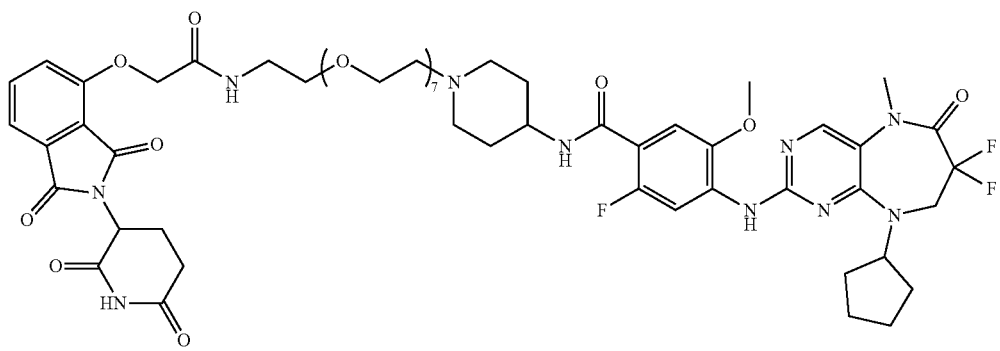

Compound 58

According to the above reaction scheme, in a manner similar to the other examples, obtained the titled compound (43.2 mg, 31.25 μmol, 9.70% yield, 96% purity, TFA) as a white solid. MS(M+H)$^+$=1213.7

$^1$H NMR (400 MHz, DMSO-d$_6$) δ=11.11 (s, 1H), 9.52-9.29 (m, 1H), 8.30 (s, 1H), 8.28-8.24 (m, 1H), 8.23-8.19 (m, 1H), 8.15 (s, 1H), 8.00 (t, J=5.6 Hz, 1H), 7.81 (dd, J=7.3, 8.4 Hz, 1H), 7.50 (d, J=7.2 Hz, 1H), 7.40 (d, J=8.4 Hz, 1H), 7.25-7.16 (m, 1H), 5.11 (dd, J=5.4, 12.8 Hz, 1H), 4.86-4.78 (m, 3H), 4.13-4.05 (m, 4H), 3.91 (s, 3H), 3.77-3.74 (m, 2H), 3.61-3.58 (m, 2H), 3.57 (br d, J=1.7 Hz, 2H), 3.53-3.47 (m, 22H), 3.47-3.43 (m, 2H), 3.33 (s, 3H), 3.31 (br d, J=5.7 Hz, 2H), 3.29-3.25 (m, 2H), 3.21-3.03 (m, 2H), 2.94-2.85 (m, 1H), 2.64-2.54 (m, 2H), 2.07-2.03 (m, 2H), 1.99-1.95 (m, 2H), 1.86-1.69 (m, 4H), 1.68-1.57 (m, 4H)

Example 59. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(5-(2-((2-(2,6-dioxopiperidin-3-yl)-1,3-dioxoisoindolin-4-yl)oxy)acetamido)pentyl)piperidin-4-yl)-2-fluoro-5-methoxybenzamide

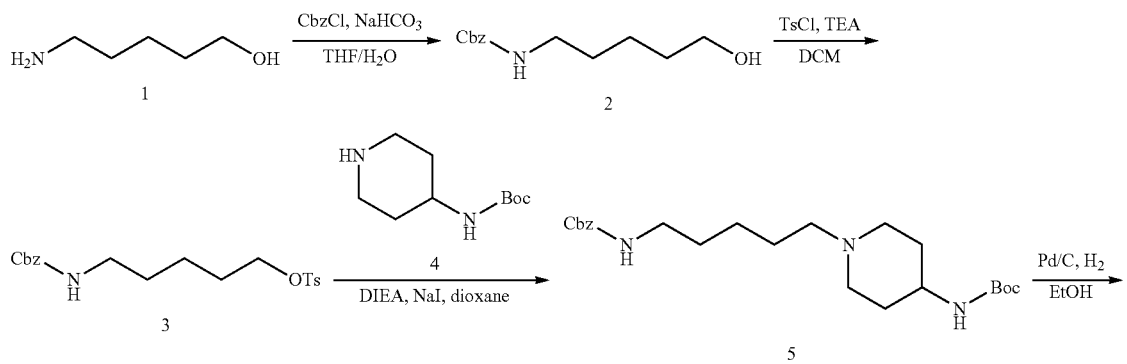

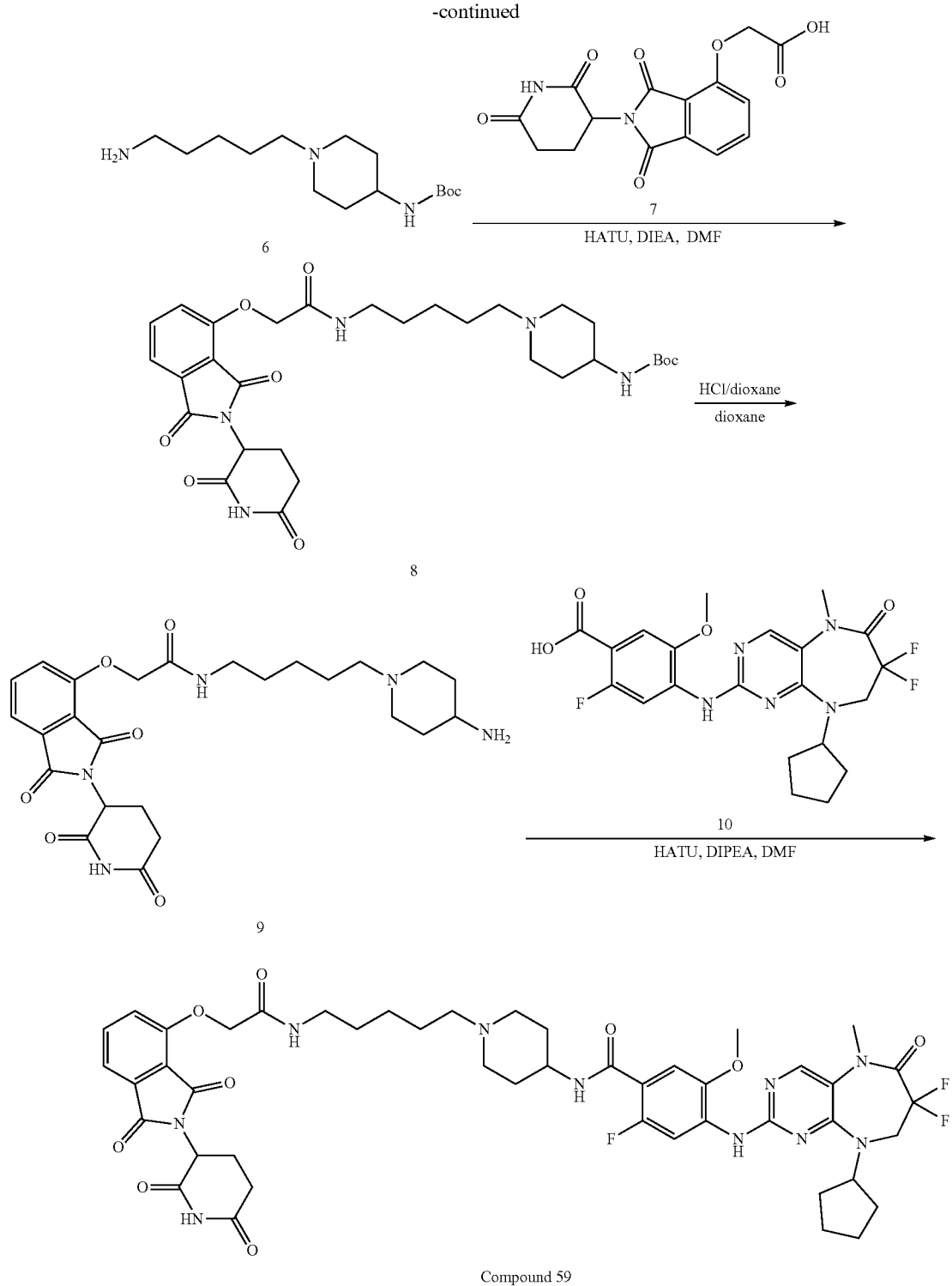

Compound 59

Step 1: Synthesis of benzyl (5-hydroxypentyl)carbamate (2)

To a solution of 5-aminopentan-1-ol (10 g, 96.93 mmol) and NaHCO$_3$ (24.43 g, 290.80 mmol, 11.31 mL) in THF (100 mL) and H$_2$O (20 mL) was added CbzCl (21.50 g, 126.02 mmol, 17.91 mL) at 0° C. and the reaction mixture was stirred at 20° C. for 16 hr. LCMS showed one peak (60%) with desired mass. The reaction mixture was diluted with H$_2$O (100 mL) and extracted with EtOAc (100 mL×2). The combined organic layer was dried over Na$_2$SO$_4$, filtered. The filtrate was concentrated in vacuo to afford the titled compound (22 g, crude) as a colorless oil.

Step 2: Synthesis of 5-(((benzyloxy)carbonyl)amino)pentyl 4-methylbenzenesulfonate (3)

To a solution of benzyl (5-hydroxypentyl)carbamate (10 g, 42.14 mmol) in DCM (120 mL) were added TEA (8.53 g, 84.28 mmol, 11.73 mL) and TosCl (10.44 g, 54.78 mmol). The mixture was stirred at 20° C. for 16 hr. LCMS showed one peak (72%) with desired mass. The reaction mixture was diluted with H$_2$O (60 mL) and separated the DCM layer. The organic layer was dried over Na$_2$SO$_4$, filtered. The filtrate was concentrated in vacuo. The residue was purified by column chromatography (SiO$_2$, PE/EtOAc=10/1~3/1) to afford the titled compound (7.8 g, 17.53 mmol, 41.61% yield, 88% purity) as a colorless oil. MS(M+H)$^+$=392.1

Step 3: Synthesis of tert-butyl N-[1-[5-(benzyloxycarbonylamino)pentyl]-4-piperidyl]carbamate (5)

To a solution of 5-(((benzyloxy)carbonyl)amino)pentyl 4-methylbenzenesulfonate (5 g, 12.77 mmol) in dioxane (60 mL) were added tert-butyl piperidin-4-ylcarbamate (3.33 g, 16.60 mmol), DIPEA (4.95 g, 38.32 mmol, 6.67 mL) and NaI (191.45 mg, 1.28 mmol). The reaction mixture was heated to 60° C. for 16 hr. LCMS showed the starting material remained. Additional 3 g of reactant was added and the reaction mixture was stirred at 60° C. for another 16 hr. The reaction mixture was diluted with H$_2$O (100 mL) and extracted with EtOAc (100 mL×2). The combined organic layer was dried over Na$_2$SO$_4$, filtered and concentrated in vacuo. The residue was purified by reverse HPLC (FA) to afford the titled compound (5 g, 11.92 mmol, 93.31% yield) as a white solid. MS(M+H)$^+$=420.2

Step 4: Synthesis of tert-butyl (1-(5-aminopentyl)piperidin-4-yl)carbamate (6)

To a solution of tert-butyl N-[1-[5-(benzyloxycarbonylamino)pentyl]-4-piperidyl]carbamate (5 g, 11.92 mmol) in EtOH (60 mL) was added Pd/C (500 mg, 10% purity) under N$_2$ atmosphere. The reaction mixture was stirred at 20° C. for 16 hr under H$_2$ (15 psi). TLC (DCM/MeOH=10/1) showed the starting material was consumed. The reaction mixture was filtered and the filtrate was concentrated in vacuo to afford the titled compound (3.4 g, crude) as a colorless oil.

Step 5: Synthesis of tert-butyl (1-(5-(2-((2-(2,6-dioxopiperidin-3-yl)-1,3-dioxoisoindolin-4-yl)oxy)acetamido)pentyl) piperidin-4-yl)carbamate (8)

To a solution of 2-((2-(2,6-dioxopiperidin-3-yl)-1,3-dioxoisoindolin-4-yl)oxy)acetic acid (500 mg, 1.50 mmol) and tert-butyl (1-(5-aminopentyl)piperidin-4-yl)carbamate (515.42 mg, 1.81 mmol) in DMF (8 mL) were added HATU (686.61 mg, 1.81 mmol) and DIPEA (583.46 mg, 4.51 mmol, 786.34 uL). The reaction mixture was stirred at 20° C. for 16 hr. LCMS showed one main peak with desired mass. The reaction mixture was diluted with H$_2$O (50 mL) and extracted with EtOAc (50 mL×2). The combined organic layer was dried over Na$_2$SO$_4$, filtered and concentrated in vacuo to afford the titled compound (1 g, crude) as a brown oil. MS(M+H)$^+$=600.2

Step 6: Synthesis of N-(5-(4-aminopiperidin-1-yl)pentyl)-2-((2-(2,6-dioxopiperidin-3-yl)-1,3-dioxoisoindolin-4-yl)oxy)acetamide (9)

tert-butyl (1-(5-(2-((2-(2,6-dioxopiperidin-3-yl)-1,3-dioxoisoindolin-4-yl)oxy)acetamido) pentyl)piperidin-4-yl)carbamate (1 g, 1.67 mmol) was dissolved in HCl/dioxane (4 M, 416.89 uL) and the reaction mixture was stirred at 15° C. for 1 hr. LCMS showed one main peak with desired mass. The reaction mixture was concentrated in vacuo to afford the titled compound (1 g, crude, HCl salt) as a brown oil. MS(M+H)$^+$=500.4

Step 7: Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(5-(2-((2-(2,6-dioxopiperidin-3-yl)-1,3-dioxoisoindolin-4-yl)oxy)acetamido)pentyl)piperidin-4-yl)-2-fluoro-5-methoxybenzamide (Compound 59)

To a solution of 4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzoic acid (250 mg, 537.14 μmol) in DMF (4 mL) were added HATU (204.24 mg, 537.14 μmol) and DIPEA (138.84 mg, 1.07 mmol, 187.12 μL). The mixture was stirred at 20° C. for 10 min and a solution of N-(5-(4-aminopiperidin-1-yl)pentyl)-2-((2-(2,6-dioxopiperidin-3-yl)-1,3-dioxoisoindol in-4-yl)oxy)acetamide (575.84 mg, 1.07 mmol, HCl salt) in DMF (4 mL) with DIPEA (138.84 mg, 1.07 mmol, 187.12 μL) was added and the resulting mixture was stirred at 20° C. for 1 h. LCMS showed all starting material was consumed completely and one peak with desired mass was detected. The reaction mixture was diluted with H$_2$O (15 mL) and extracted with EtOAc (15 mL×3). The organic layer was washed with brine (15 mL×3), dried over Na$_2$SO$_4$, filtered and concentrated. The residue was purified by prep-HPLC (column: Phenomenex luna C$_{18}$ 150*40 mm*15 um; mobile phase: [water (0.225% FA)-ACN]; B %: 18%-48%, 10 min) and the eluent was lyophilized to afford 4 the titled compound (82.2 mg, 78.12 μmol, 14.54% yield, 90% purity, FA salt) as a white solid. MS(M+H)$^+$=946.7

$^1$H NMR (400 MHz, CD$_3$OD) δ=8.41 (d, J=14.0 Hz, 1H), 8.21 (s, 1H), 7.83 (dd, J=7.4, 8.4 Hz, 1H), 7.56 (d, J=7.0 Hz, 1H), 7.46 (d, J=8.5 Hz, 1H), 7.33 (d, J=6.6 Hz, 1H), 5.14 (dd, J=5.6, 12.4 Hz, 1H), 4.93 (br d, J=8.4 Hz, 1H), 4.78 (s, 2H), 4.18-4.00 (m, 3H), 3.99 (s, 3H), 3.52-3.43 (m, 2H), 3.40 (s, 3H), 3.39-3.35 (m, 2H), 3.03-2.67 (m, 7H), 2.23-2.06 (m, 5H), 1.91-1.63 (m, 12H), 1.49-1.39 (m, 2H).

Example 60. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(3-((7-(2-((2-(2,6-dioxopiperidin-3-yl)-1,3-dioxoisoindolin-4-yl)oxy)acetamido)heptyl)amino)-3-oxopropyl)piperidin-4-yl)-2-fluoro-5-methoxybenzamide

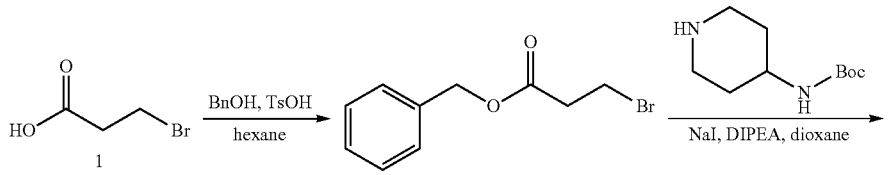

-continued
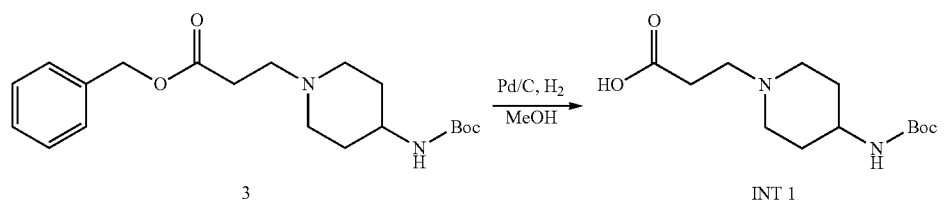
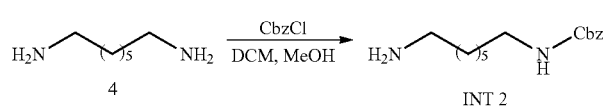
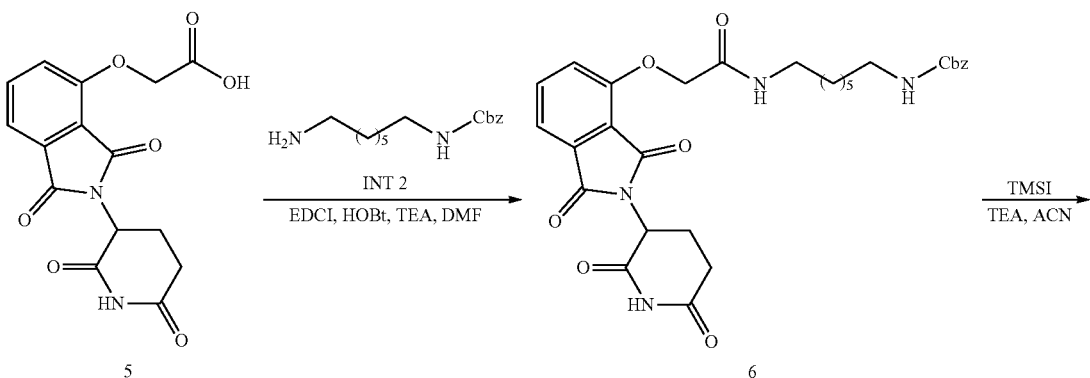
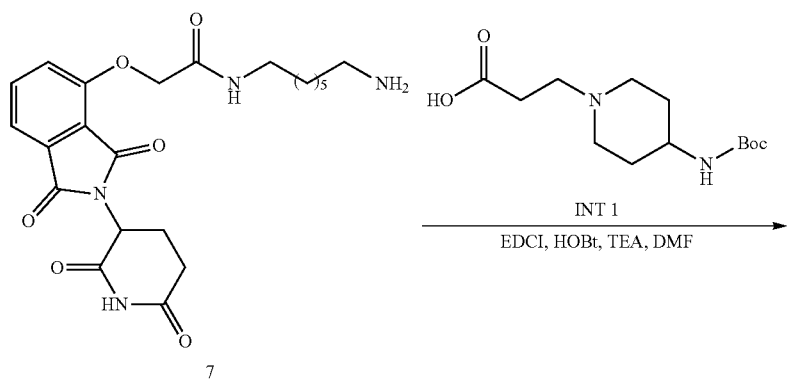
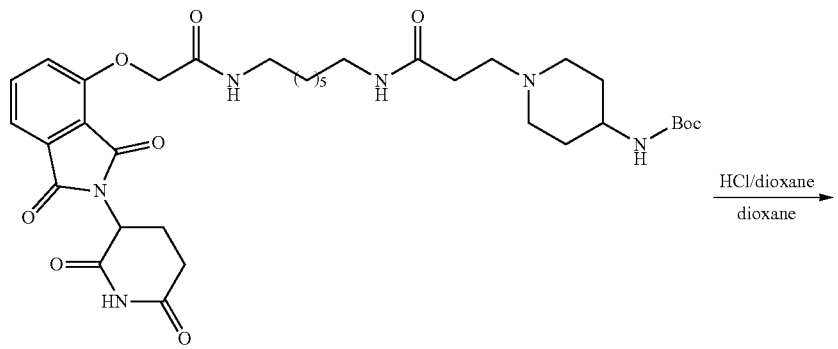

315

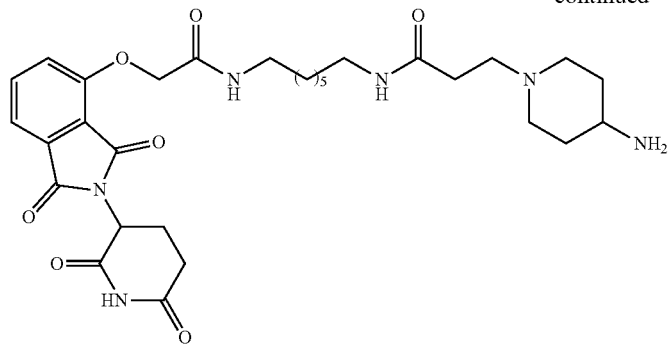

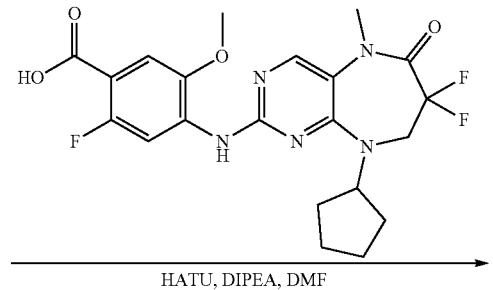

HATU, DIPEA, DMF

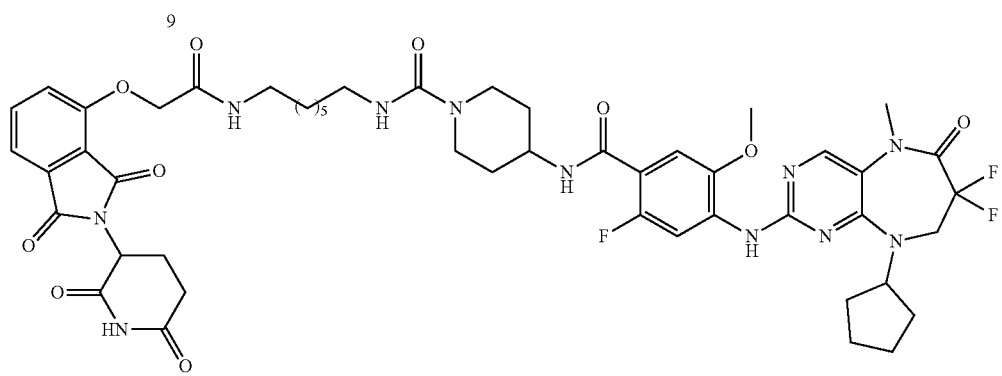

Compound 60

Step 1: Synthesis of benzyl 3-bromopropanoate (2)

To a mixture of 3-bromopropanoic acid (5 g, 32.69 mmol, 3.38 mL) and phenylmethanol (4.59 g, 42.49 mmol, 4.42 mL) in hexane (100 mL) was added TsOH (281.42 mg, 1.63 mmol) in one portion at 20° C. and the resulting mixture was stirred at 90° C. for 16 h. TLC (SiO$_2$, Petroleum ether:Ethyl acetate=5:1) indicated starting material was consumed completely and two new spots were detected. The reaction mixture was concentrated in vacuum. The residue was purified by column chromatography (SiO$_2$, Petroleum ether/Ethyl acetate=100/1 to 10/1) to afford the titled compound (7.8 g, 32.09 mmol, 98.17% yield) as a white oil.

$^1$H NMR (400 MHz, CDCl$_3$) δ=7.44-7.35 (m, 5H), 5.21 (s, 2H), 3.62 (t, J=6.8 Hz, 2H), 2.99 (t, J=6.8 Hz, 2H)

Step 2: Synthesis of benzyl 3-(4-((tert-butoxycarbonyl)amino)piperidin-1-yl)propanoate (3)

To a mixture of benzyl 3-bromopropanoate (7.8 g, 32.09 mmol) and tert-butyl N-(4-piperidyl) carbamate (7.71 g, 38.50 mmol) in dioxane (80 mL) were added DIPEA (12.44 g, 96.26 mmol, 16.77 mL), NaI (961.90 mg, 6.42 mmol) in one portion at 20° C. and the resulting mixture was stirred at 80° C. for 16 h. LCMS showed starting material was consumed completely and desired mass was detected. The reaction mixture was concentrated in vacuum. The residue was purified by column chromatography (SiO$_2$, Petroleum ether/Ethyl acetate=10/1 to 1/2) to afford the titled compound (9.3 g, 25.66 mmol, 79.97% yield) as an orange solid. MS(M+H)$^+$=363.4

Step 3: Synthesis of 3-(4-((tert-butoxycarbonyl)amino)piperidin-1-yl)propanoic acid (INT1)

To a solution of benzyl 3-(4-((tert-butoxycarbonyl)amino) piperidin-1-yl)propanoate (9.3 g, 25.66 mmol) in MeOH (100 mL) was added Pd/C (1 g, 10% purity) under N$_2$. The suspension was degassed under vacuum and purged with H$_2$ several times. The mixture was stirred under H$_2$ (15 psi) at 20° C. for 16 h. LCMS showed starting material was consumed completely and desired mass was detected. The reaction mixture was filtered and the filtrate was concentrated in vacuum to afford the titled compound (6.7 g, 24.60 mmol, 95.88% yield) as a white solid. MS(M+H)$^+$=273.2

Step 4: Synthesis of benzyl (7-aminoheptyl)carbamate (INT2)

To a mixture of heptane-1,7-diamine (9 g, 69.11 mmol) in DCM (396 mL) was added MeOH (396 mL) at 5° C., then a solution of CbzCl (10.61 g, 62.20 mmol, 8.84 mL) in MeOH (396 mL) was added drop-wise at 5° C. and the resulting mixture was stirred at 20° C. for 16 h. LCMS showed all starting material was consumed completely and one peak with desired mass was detected. The reaction mixture was concentrated in vacuum. The crude product was purified by reversed-phase HPLC (method: 0.1% FA, MeCN/water) to afford the titled compound (4.1 g, 15.04 mmol, 21.77% yield, 97% purity) as a white solid. MS(M+H)$^+$=265.4

Step 5: Synthesis of benzyl (7-(2-((2-(2,6-dioxopiperidin-3-yl)-1,3-dioxoisoindolin-4-yl)oxy) acetamido)heptyl)carbamate (6)

A mixture of 2-((2-(2,6-dioxopiperidin-3-yl)-1,3-dioxoisoindolin-4-yl)oxy)acetic acid (1 g, 3.01 mmol), benzyl(7-aminoheptyl)carbamate (1.03 g, 3.91 mmol), EDCI (865.43 mg, 4.51 mmol), HOBt (610.01 mg, 4.51 mmol) and TEA (913.63 mg, 9.03 mmol, 1.26 mL) in DMF (10 mL) a was stirred at 20° C. for 16 h. LCMS showed all starting material was consumed completely and one peak with desired mass was detected. The reaction mixture was diluted with H$_2$O (20 mL) and extracted with EtOAc (20 mL×3). The organic layer was washed with brine (20 mL×3), dried over Na$_2$SO$_4$, filtered and concentrated. The residue was purified by column chromatography (SiO$_2$, Petroleum ether/Ethyl acetate=3/1 to 0/1) to afford the titled compound (1.7 g, 2.67 mmol, 88.84% yield, 91% purity) as a yellow oil. MS(M+H)$^+$=579.2

Step 6: Synthesis of N-(7-aminoheptyl)-2-((2-(2,6-dioxopiperidin-3-yl)-1,3-dioxoisoindolin-4-yl) oxy) acetamide (7)

To a solution of benzyl (7-(2-((2-(2,6-dioxopiperidin-3-yl)-1,3-dioxoisoindolin-4-yl)oxy)acetamido)heptyl)carbamate (1.7 g, 2.94 mmol) in ACN (10 mL) was added TMSI (1.76 g, 8.81 mmol, 1.20 mL) at 20° C. and the resulting mixture was stirred at 20° C. for 2 h. LCMS showed starting material was consumed completely and one peak with desired mass was detected. TEA (891.90 mg, 8.81 mmol, 1.23 mL) was added to this reaction mixture at 20° C. and the resulting mixture was stirred at 20° C. for 2 h. The reaction mixture was concentrated in vacuum. The residue was purified by prep-HPLC (column: Phenomenex luna C$_{18}$ 150*40 mm*15 um; mobile phase: [water (0.1% TFA)-ACN]; B %: 6%-36%, 10 min) and then lyophilized to afford the titled compound (920 mg, 2.07 mmol, 70.45% yield) as a yellow solid. MS(M+H)$^+$=445.2

Step 7: Synthesis of tert-butyl (1-(3-((7-(2-((2-(2,6-dioxopiperidin-3-yl)-1,3-dioxoisoindolin-4-yl) oxy) acetamido)heptyl)amino)-3-oxopropyl)piperidin-4-yl)carbamate (8)

To a solution of 3-(4-((tert-butoxycarbonyl)amino)piperidin-1-yl)propanoic acid (500 mg, 1.84 mmol) and N-(7-aminoheptyl)-2-((2-(2,6-dioxopiperidin-3-yl)-1,3-dioxoisoindolin-4-yl)oxy) acetamide (816.04 mg, 1.84 mmol) in DMF (5 mL) were added EDCI (527.93 mg, 2.75 mmol), HOBt (372.12 mg, 2.75 mmol) and TEA (557.33 mg, 5.51 mmol, 766.62 μL) at 20° C. and The resulting mixture was stirred at 20° C. for 16 h. LCMS showed all starting material was consumed completely and one peak with desired mass was detected. The reaction mixture was diluted with H$_2$O (15 m) and extracted with EtOAc (15 mL×3). The organic layer was washed with brine (15 mL×3), dried over Na$_2$SO$_4$, filtrated and concentrated. The residue was purified by column chromatography (SiO$_2$, Petroleum ether/Ethyl acetate=1/1 to 0/1 to Dichloromethane/Methanol=1/0 to 10/1) to afford the titled compound (1.1 g, 1.43 mmol, 78.02% yield, 91% purity) as a yellow oil. MS(M+H)$^+$=699.2

Step 8: Synthesis of 3-(4-aminopiperidin-1-yl)-N-(7-(2-((2-(2,6-dioxopiperidin-3-yl)-1,3-dioxoisoindolin-4-yl)oxy)acetamido)heptyl)propanamide (9)

To a mixture of tert-butyl (1-(3-((7-(2-((2-(2,6-dioxopiperidin-3-yl)-1,3-dioxoisoindolin-4-yl)oxy)acetamido)heptyl)amino)-3-oxopropyl)piperidin-4-yl)carbamate (1.1 g, 1.57 mmol) in dioxane (10 mL) was added HCl/dioxane (4 M, 10 mL) in one portion at 20° C. and the resulting mixture was stirred at 20° C. for 1 h. LCMS showed starting material was consumed completely and one peak with desired mass was detected. The reaction mixture was concentrated in vacuum to afford the titled compound (1 g, crude, HCl) as a yellow solid. MS(M+H)$^+$=599.2

Step 9: Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(3-((7-(2-((2-(2,6-dioxopiperidin-3-yl)-1,3-dioxoisoindolin-4-yl)oxy) acetamido)heptyl)amino)-3-oxopropyl)piperidin-4-yl)-2-fluoro-5-methoxybenzamide (Compound 60)

To a solution of 4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzoic acid (200 mg, 429.71 mol) in DMF (4 mL) were added HATU (179.73 mg, 472.69 μmol) and DIPEA (111.08 mg, 859.43 μmol, 149.70 μL). The mixture was stirred at 20° C. for 10 min and a solution of 3-(4-aminopiperidin-1-yl)-N-(7-(2-((2-(2,6-dioxopiperidin-3-yl)-1,3-dioxoisoindolin-4-yl)oxy)acetamido)heptyl)propanamide (327.52 mg, crude, HCl) in DMF (4 mL) and DIPEA (111.08 mg, 859.43 μmol, 149.70 μL) was added and the resulting mixture was stirred at 20° C. for 1 h. LCMS showed all starting material was consumed completely and one peak with desired mass was detected. The reaction mixture was diluted with H$_2$O (12 mL) and extracted with EtOAc (12 mL×3). The organic layer was dried over Na$_2$SO$_4$, filtered and concentrated. The residue was purified by prep-HPLC (column: 3_Phenomenex Luna C$_{18}$ 75*30 mm*3 um; mobile phase: [water (0.1% TFA)-ACN]; B %: 34%-54%, 7 min) and then lyophilized to afford the titled compound (48.5 mg, 40.97 μmol, 9.53% yield, 98% purity, TFA) as a white solid. MS(M+H)$^+$=1046.7

$^1$H NMR (400 MHz, CD$_3$OD) δ=8.34 (d, J=13.8 Hz, 1H), 8.21 (s, 1H), 7.85-7.77 (m, 1H), 7.54 (d, J=7.4 Hz, 1H), 7.43 (d, J=8.4 Hz, 1H), 7.35 (d, J=6.7 Hz, 1H), 5.14 (dd, J=5.6, 12.6 Hz, 1H), 5.02-4.94 (m, 1H), 4.75 (s, 2H), 4.25-4.14 (m, 1H), 4.08 (t, J=13.2 Hz, 2H), 3.99 (s, 3H), 3.79-3.62 (m, 2H), 3.56-3.47 (m, 1H), 3.46-3.41 (m, 2H), 3.40 (s, 3H), 3.24-3.12 (m, 4H), 2.96-2.84 (m, 1H), 2.80 (s, 1H), 2.76-2.70 (m, 3H), 2.38-2.21 (m, 2H), 2.19-2.04 (m, 4H), 1.99-1.86 (m, 2H), 1.85-1.78 (m, 2H), 1.76-1.65 (m, 4H), 1.62-1.48 (m, 4H), 1.44-1.28 (m, 6H)

Example 61. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(3-((2-((2-(2,6-dioxopiperidin-3-yl)-1,3-dioxoisoindolin-4-yl)oxy)acetamido)methyl)benzyl)piperidin-4-yl)-2-fluoro-5-methoxybenzamide

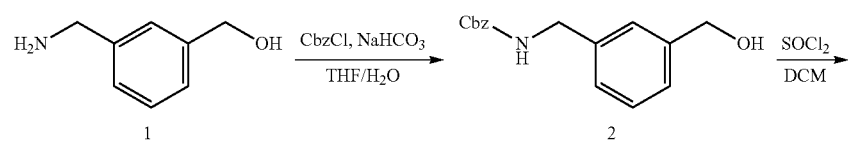

-continued
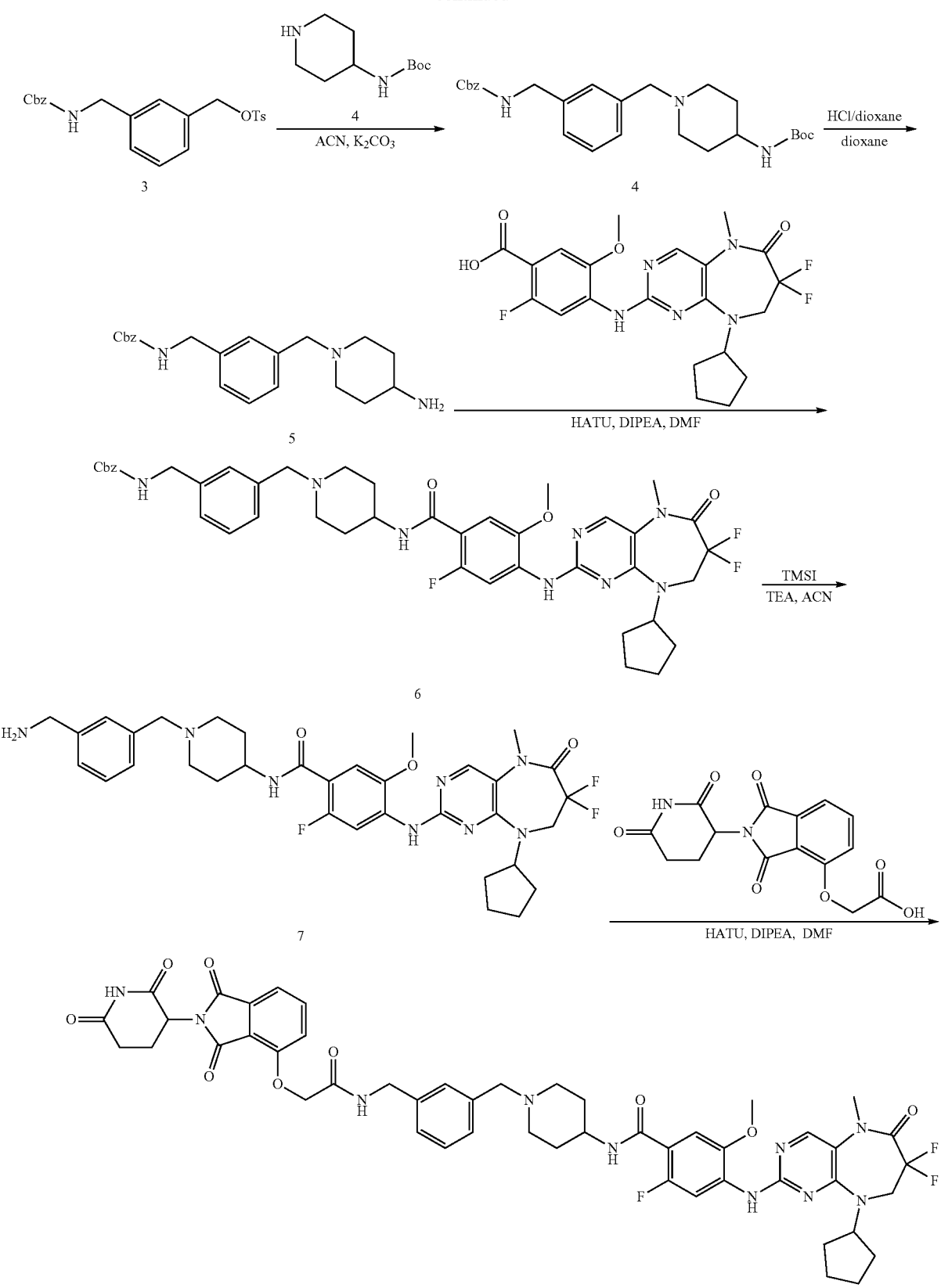
Compound 61

Step 1: Synthesis of benzyl 3-(hydroxymethyl)benzylcarbamate (2)

To a mixture of (3-(aminomethyl)phenyl)methanol (1 g, 7.29 mmol) in THF (10 mL) and H$_2$O (5 mL) was added Na$_2$CO$_3$ (1.55 g, 14.58 mmol) at 20° C. Then CbzCl (1.37 g, 8.02 mmol, 1.14 mL) was added drop-wise at 20° C. and the resulting mixture was stirred at 20° C. for 16 h. LCMS showed (3-(aminomethyl)phenyl)methanol was consumed completely and one peak with desired mass was detected. The reaction mixture was diluted with H$_2$O (20 mL) and extracted with EtOAc (20 mL×3). The organic layer was dried over Na$_2$SO$_4$, filtered and concentrated. The residue was purified by column chromatography (SiO$_2$, Petroleum ether/Ethyl acetate=10/1 to 2/1) to afford the titled compound (1.7 g, 5.89 mmol, 80.80% yield, 94% purity) as a white solid. MS(M+Na)$^+$=294.3

Step 2: Synthesis of benzyl 3-(chloromethyl)benzylcarbamate (3)

To a mixture of benzyl 3-(hydroxymethyl)benzylcarbamate (1.7 g, 6.27 mmol) in DCM (15 mL) was added SOCl$_2$ (1.12 g, 9.40 mmol, 681.81 µL) in one portion at 20° C. and the resulting mixture was stirred at 20° C. for 2 h. TLC (SiO$_2$, Petroleum ether:Ethyl acetate=2:1) indicated starting material was consumed completely and one new spot was detected. The reaction mixture was concentrated in vacuum to afford the titled compound (1.6 g, 5.52 mmol, 88.13% yield) as a white solid.

Step 3: Synthesis of tert-butyl N-[1-[[3-(benzyloxycarbonylaminomethyl)phenyl]methyl]-4-piperidyl]carbamate (4)

To a mixture of benzyl 3-(chloromethyl)benzylcarbamate (1.6 g, 5.52 mmol) and tert-butyl piperidin-4-ylcarbamate (1.44 g, 7.18 mmol) in ACN (20 mL) was added K$_2$CO$_3$ (2.29 g, 16.57 mmol) in one portion at 20° C. and the resulting mixture was stirred at 20° C. for 4 h. LCMS showed all starting material was consumed completely and one peak with desired mass was detected. The reaction mixture was concentrated in vacuum. The residue was purified by column chromatography (SiO$_2$, Petroleum ether/Ethyl acetate=5/1 to 1/4) to afford the titled compound (2.4 g, 5.29 mmol, 95.82% yield) as a white solid. MS(M+H)$^+$=454.3

Step 4: Synthesis of benzyl 3-((4-aminopiperidin-1-yl)methyl)benzylcarbamate (5)

To a mixture of tert-butyl N-[1-[[3-(benzyloxycarbonylaminomethyl)phenyl]methyl]-4-piperidyl]carbamate (2.4 g, 5.29 mmol) in dioxane (10 mL) was added HCl/dioxane (4 M, 20 mL) in one portion at 20° C. and the resulting mixture was stirred at 20° C. for 1 h. LCMS showed starting material was consumed completely and one peak with desired mass was detected. The reaction mixture was concentrated in vacuum to afford the titled compound (2.1 g, crude, HCl) as a white solid. MS(M+H)$^+$=354.4

Step 5: Synthesis of benzyl 3-((4-(4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzamido)piperidin-1-yl)methyl)benzylcarbamate (6)

To a solution of 4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzoic acid (0.7 g, 1.50 mmol) in DMF (5 mL) were added HATU (629.05 mg, 1.65 mmol) and DIPEA (388.76 mg, 3.01 mmol, 523.94 µL). The reaction mixture was stirred at 20° C. for 10 min and a solution of benzyl 3-((4-aminopiperidin-1-yl) methyl)benzylcarbamate (821.01 mg, 2.11 mmol, HCl) in DMF (5 mL) and DIPEA (388.76 mg, 3.01 mmol, 523.94 µL) was added and the resulting mixture was stirred at 20° C. for 1 h. LCMS showed all starting material was consumed completely and one peak with desired mass was detected. The reaction mixture was diluted with H$_2$O (20 mL) and extracted with EtOAc (20 mL×3). The organic layer was washed with brine (20 mL×3), dried over Na$_2$SO$_4$, filtered and concentrated. The residue was purified by column chromatography (SiO$_2$, Petroleum ether/Ethyl acetate=3/1 to 1/2) to afford the titled compound (362 mg, 424.89 µmol, 28.25% yield, 94% purity) as a white oil. MS(M+H)$^+$=801.4

Step 6: Synthesis of N-(1-(3-(aminomethyl)benzyl) piperidin-4-yl)-4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzamide (7)

To a mixture of benzyl 3-((4-(4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzamido)piperidin-1-yl)methyl) benzylcarbamate (360 mg, 449.51 µmol) in ACN (2 mL) was added TMSI (179.89 mg, 899.03 µmol, 122.37 µL) in one portion at 20° C. and the resulting mixture was stirred at 20° C. for 1 h. LCMS showed starting material remained and one peak with desired mass was detected. TMSI (89.94 mg, 449.51 µmol, 61.19 µL) was added to this reaction mixture at 20° C. and the resulting mixture was stirred at 20° C. for 12 h. LCMS showed starting material was consumed completely and desired mass was detected. TEA (136.46 mg, 1.35 mmol, 187.70 µL) was added to this reaction mixture at 20° C. The reaction mixture was stirred at 20° C. for 2 h. The reaction mixture was concentrated in vacuum to afford the titled compound (330 mg, crude) as a orange solid. MS(M+H)$^+$=667.3

Step 7: Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(3-((2-((2-(2,6-dioxopiperidin-3-yl)-1,3-dioxoisoindolin-4-yl)oxy) acetamido)methyl)benzyl)piperidin-4-yl)-2-fluoro-5-methoxybenzamide (Compound 61)

To a solution of 2-((2-(2,6-dioxopiperidin-3-yl)-1,3-dioxoisoindolin-4-yl)oxy)acetic acid (150 mg, 451.45 µmol) in DMF (2 mL) were added HATU (188.82 mg, 496.59 mol) and DIPEA (175.04 mg, 1.35 mmol, 235.90 µL). The mixture was stirred at 20° C. for 10 min and a solution of N-(1-(3-(aminomethyl)benzyl)piperidin-4-yl)-4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzamide (316.05 mg, 474.02 µmol) in DMF (2 mL) was added and the resulting mixture was stirred at 20° C. for 1 h. LCMS showed all starting material was consumed completely and one peak with desired mass was detected. The reaction mixture was diluted with H$_2$O (12 mL) and extracted with EtOAc (12 mL×3). The organic layer was dried over Na$_2$SO$_4$, filtered and concentrated. The residue was purified by prep-HPLC (column: 3_Phenomenex Luna C$_{18}$ 75*30 mm*3 um; mobile phase: [water (0.1% TFA)-

ACN]; B %: 32%-52%, 7 min) and then lyophilized to afford two batches of products with 59% and 42% purity. They were re-purified by prep-HPLC (column: Waters Xbridge 150*25 mm*5 um; mobile phase: [water (10 mM NH$_4$HCO$_3$)-ACN]; B %: 46%-76%, 10 min) and combined the eluents to lyophilize to afford product with 75% purity by LCMS and HPLC. It was re-purified by prep-HPLC (column: 3_Phenomenex Luna C$_{18}$ 75*30 mm*3 um; mobile phase: [water (0.1% TFA)-ACN]; B %: 32%-52%, 7 min) and then lyophilized to afford 4-((9-cyclopentyl-7,7-difluoro-5-methyl-6-oxo-6,7,8,9-tetrahydro-5H-pyrimido[4,5-b][1,4]diazepin-2-yl)amino)-N-(1-(3-((2-((2-(2,6-dioxopiperidin-3-yl)-1,3-dioxoisoindolin-4-yl)oxy)acetamido)methyl)benzyl)piperidin-4-yl)-2-fluoro-5-methoxybenzamide (9.5 mg, 9.59 μmol, 2.12% yield, 99% purity, TFA) as a white solid. MS(M+H)$^+$=981.2

$^1$H NMR (400 MHz, CD$_3$OD) δ=8.33 (br d, J=13.7 Hz, 1H), 8.20 (s, 1H), 7.85-7.78 (m, 1H), 7.56 (d, J=7.3 Hz, 1H), 7.51-7.40 (m, 5H), 7.33 (d, J=6.6 Hz, 1H), 5.12 (dd, J=5.4, 12.8 Hz, 1H), 4.98-4.93 (m, 2H), 4.57 (s, 2H), 4.44-4.32 (s, 2H), 4.28-4.13 (m, 1H), 4.07 (t, J=13.1 Hz, 2H), 3.98 (s, 3H), 3.55 (d, J=12.5 Hz, 2H), 3.40 (s, 3H), 3.16 (t, J=12.4 Hz, 2H), 2.93-2.82 (m, 1H), 2.78-2.62 (m, 2H), 2.24 (d, J=13.3 Hz, 2H), 2.17-2.03 (m, 4H), 1.91-1.79 (m, 4H), 1.77-1.64 (m, 4H)

Example 62. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-((5-((2-((2-(2,6-dioxopiperidin-3-yl)-1,3-dioxoisoindolin-4-yl)oxy)acetamido)methyl)pyridin-3-yl)methyl)piperidin-4-yl)-2-fluoro-5-methoxybenzamide

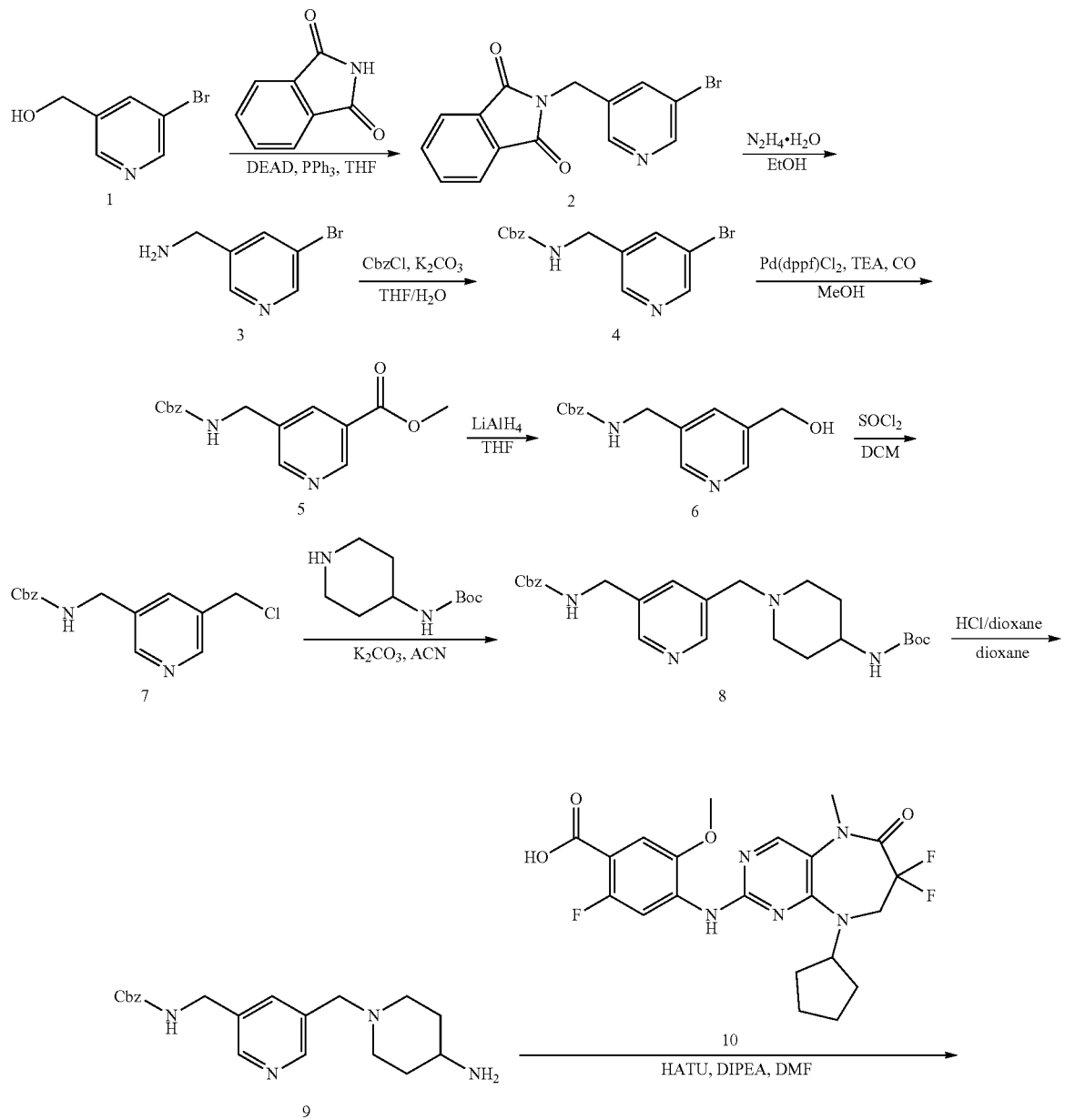

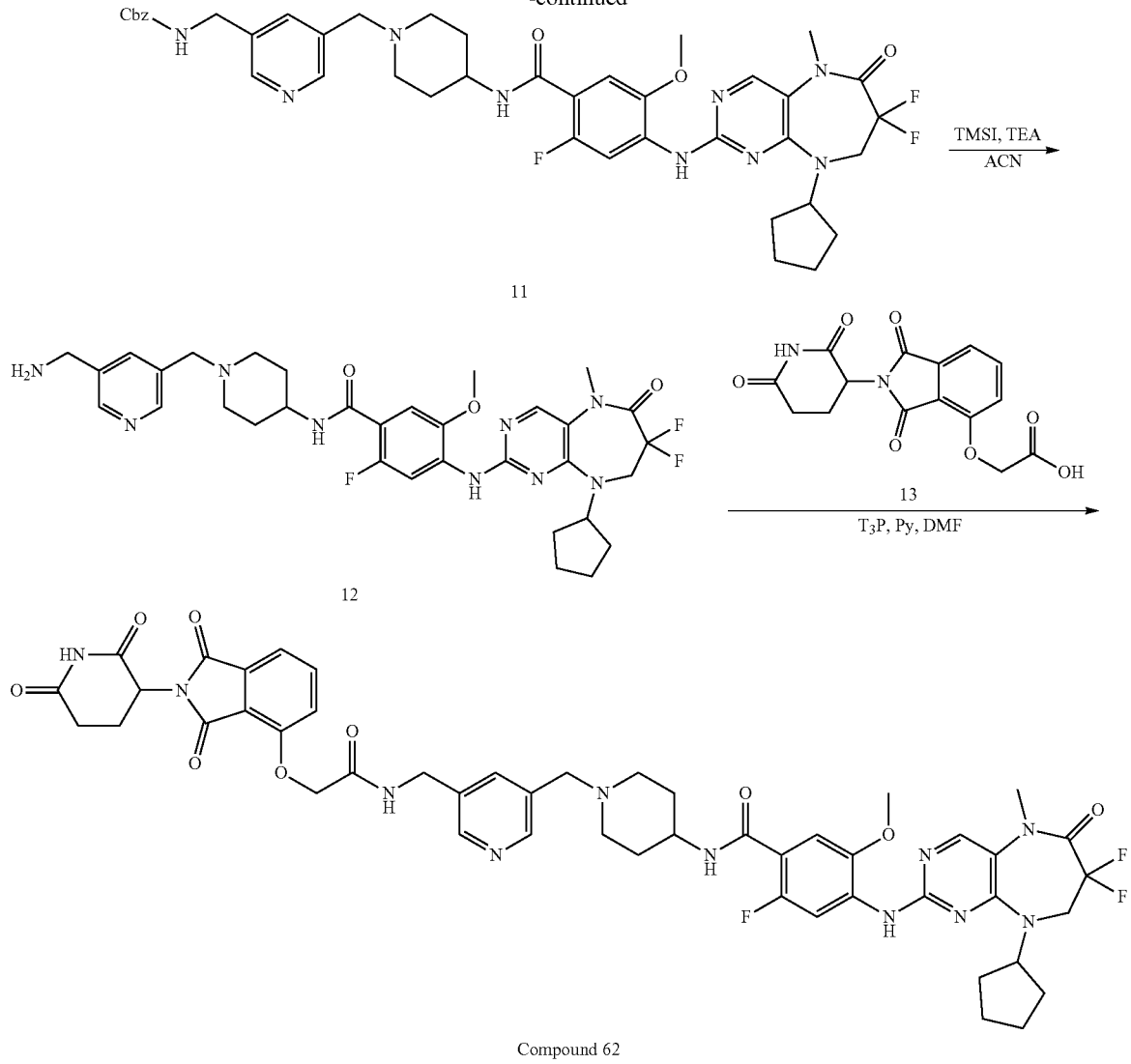

Compound 62

Step 1: Synthesis of 2-((5-bromopyridin-3-yl)methyl)isoindoline-1,3-dione (2)

To a mixture of (5-bromo-3-pyridyl) methanol (7 g, 37.23 mmol) and phthalimide (5.48 g, 37.23 mmol), PPh$_3$ (14.65 g, 55.84 mmol) in THF (50 mL) was added DEAD (9.73 g, 55.84 mmol, 10.15 mL) drop-wise at 0° C. under N$_2$ and the resulting mixture was stirred at 20° C. for 12 h. LCMS showed all starting material was consumed completely and one peak with desired mass was detected. The reaction mixture was diluted with brine (150 mL) and extracted with EtOAc (150 mL×3). The organic layer was dried over Na$_2$SO$_4$, filtered and concentrated. The residue was purified by column chromatography (SiO$_2$, Petroleum ether/Ethyl acetate=10/1 to 4/1) to afford the titled compound (8.2 g, 25.86 mmol, 69.46% yield) as a white solid. MS(M+H)$^+$=317.0

Step 2: Synthesis of (5-bromopyridin-3-yl)methanamine (3)

To a mixture of 2-((5-bromopyridin-3-yl)methyl)isoindoline-1,3-dione (8.2 g, 25.86 mmol) in EtOH (80 mL) was added N$_2$H$_4$·H$_2$O (15.23 g, 258.56 mmol, 14.78 mL, 85% purity) in one portion at 20° C. and the resulting mixture was stirred at 80° C. for 4 h. TLC (SiO$_2$, Petroleum ether:Ethyl acetate=3:1) indicated starting material was consumed completely and one new spot was detected. The reaction mixture was diluted with EtOH (160 mL) and filtered. The filtrate was concentrated in vacuum. The residue was diluted with DCM (160 mL) and filtered. The filtrate was concentrated in vacuum to afford the titled compound (7.2 g, crude) as a yellow oil.

Step 3: Synthesis of benzyl ((5-bromopyridin-3-yl)methyl)carbamate (4)

To a mixture of (5-bromopyridin-3-yl)methanamine (7.2 g, 38.50 mmol) in THF (70 mL) and H$_2$O (35 mL) was added K$_2$CO$_3$ (10.64 g, 76.99 mmol) at 20° C. Then CbzCl (7.22 g, 42.34 mmol, 6.02 mL) was added drop-wise at 20° C. and The resulting mixture was stirred at 20° C. for 16 h. LCMS showed all starting material was consumed completely and one peak with desired mass was detected. The reaction mixture was diluted with H$_2$O (30 mL) and extracted with EtOAc (70 mL×3). The organic was dried over Na₂SO₄, filtrated and concentrated. The residue was purified by column chromatography (SiO₂, Petroleum ether/Ethyl acetate=10/1 to 3/1) to afford the titled compound (4.4 g, 12.33 mmol, 32.03% yield, 90% purity) as a yellow oil. MS(M+H)$^+$=321.0

Step 4: Synthesis of methyl 5-((((benzyloxy)carbonyl)amino)methyl)nicotinate (5)

To a solution of benzyl ((5-bromopyridin-3-yl)methyl)carbamate (4.4 g, 13.70 mmol) in MeOH (50 mL) were added Pd(dppf)Cl₂ (501.22 mg, 685.00 µmol), TEA (4.16 g, 41.10 mmol, 5.72 mL, 3 eq). The suspension was degassed under vacuum and purged with CO several times. The mixture was stirred under CO (50 psi) at 80° C. for 16 h. LCMS showed starting material was consumed completely and one peak with desired mass was detected. The reaction mixture was diluted with MeOH (200 mL) and filtered. The filtrate was concentrated in vacuum. The residue was purified by column chromatography (SiO₂, Petroleum ether/Ethyl acetate=5/1 to 1/1) to afford the titled compound (3.42 g, 9.79 mmol, 71.49% yield, 86% purity) as a yellow oil. MS(M+H)$^+$=301.1

Step 5: Synthesis of benzyl ((5-(hydroxymethyl)pyridin-3-yl)methyl)carbamate (6)

To a suspension of LiAlH₄ (554.32 mg, 14.60 mmol) in THF (30 mL) was added a solution of methyl 5-((((benzyloxy)carbonyl)amino)methyl)nicotinate (3.4 g, 9.74 mmol, 86% purity) in THF (15 mL) drop-wise at 0° C. and the resulting mixture was stirred at 20° C. for 2 h. TLC (SiO₂, Petroleum ether:Ethyl acetate=1:2) indicated starting material was consumed completely and one new spot was detected. The reaction mixture was quenched with H₂O (1 mL), NaOH (15% aq, 1 mL) and H₂O (3 mL). The reaction mixture was filtered. The filtrate was concentrated in vacuum to afford the titled compound (3 g, crude) as a yellow oil. MS(M+H)$^+$=273.3

Step 6: Synthesis of benzyl ((5-(chloromethyl)pyridin-3-yl)methyl)carbamate (7)

To a mixture of benzyl ((5-(hydroxymethyl)pyridin-3-yl)methyl)carbamate (2.8 g, 10.28 mmol) in DCM (20 mL) was added SOCl₂ (1.47 g, 12.34 mmol, 895.13 µL) in one portion at 20° C. and the resulting mixture was stirred at 20° C. for 2 h. LCMS showed starting material was consumed completely and one peak with desired mass was detected. The reaction mixture was concentrated in vacuum to afford the titled compound (3 g, crude) as a yellow solid. MS(M+H)$^+$=291.3

Step 7: Synthesis of tert-butyl N-[1-[[5-(benzyloxycarbonylaminomethyl)-3-pyridyl]methyl]-4-piperidyl]carbamate (8)

To a mixture of benzyl ((5-(chloromethyl)pyridin-3-yl)methyl)carbamate (2.7 g, 9.29 mmol) and tert-butyl N-(4-piperidyl) carbamate (2.23 g, 11.14 mmol) in ACN (30 mL) was added K₂CO₃ (3.85 g, 27.86 mmol) in one portion at 20° C. and the resulting mixture was stirred at 60° C. for 4 h. LCMS showed all starting material was consumed completely and one peak with desired mass was detected. The reaction mixture was filtered and the filtrate was concentrated in vacuum. The residue was purified by column chromatography (SiO₂, Petroleum ether/Ethyl acetate=1/1 to 0/1) to afford the titled compound (3.7 g, 7.49 mmol, 80.64% yield, 92% purity) as a off-white solid. MS(M+H)$^+$=455.4

Step 8: Synthesis of benzyl ((5-((4-aminopiperidin-1-yl)methyl)pyridin-3-yl)methyl)carbamate (9)

To a solution of tert-butyl N-[1-[[5-(benzyloxycarbonylaminomethyl)-3-pyridyl]methyl]-4-piperidyl]carbamate (1 g, 2.20 mmol) in dioxane (5 mL) was added HCl/dioxane (4 M, 10 mL) at 20° C. and the resulting mixture was stirred at 20° C. for 1 h. LCMS showed starting material was consumed completely and one peak with desired mass was detected. The reaction mixture was concentrated in vacuum to afford the titled compound (910 mg, crude, HCl) as a orange solid. MS(M+H)$^+$=355.3

Step 9: Synthesis of benzyl ((5-((4-(4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzamido)piperidin-1-yl)methyl)pyridin-3-yl)methyl)carbamate (11)

To a solution of 4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzoic acid (525.24 mg, 1.13 mmol) in DMF (4 mL) were added HATU (472.01 mg, 1.24 mmol) and DIPEA (291.71 mg, 2.26 mmol, 393.14 µL). The mixture was stirred at 20° C. for 10 min and a solution of benzyl ((5-((4-aminopiperidin-1-yl)methyl)pyridin-3-yl)methyl)carbamate (400.00 mg, crude, HCl) in DMF (4 mL) and DIPEA (291.71 mg, 2.26 mmol, 393.14 µL) was added and the resulting mixture was stirred at 20° C. for 1 h. LCMS showed all starting material was consumed completely and one peak with desired mass was detected. The reaction mixture was diluted with H₂O (12 mL) and extracted with EtOAc (12 mL×3). The organic layer was washed with brine (12 mL×3), dried over Na₂SO₄, filtered and concentrated. The residue was purified by column chromatography (SiO₂, Petroleum ether/Ethyl acetate=1/1 to 0/1 to Dichloromethane/Methanol=1/0 to 10/1) to afford the titled compound (426 mg, 531.27 µmol, 47.08% yield) as a off-white solid. MS(M+H)$^+$=802.1

Step 10: Synthesis of N-(1-((5-(aminomethyl)pyridin-3-yl)methyl)piperidin-4-yl)-4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzamide (12)

To a mixture of benzyl ((5-((4-(4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzamido)piperidin-1-yl)methyl)pyridin-3-yl)methyl)carbamate (426 mg, 531.27 µmol) in ACN (10 mL) was added TMSI (159.45 mg, 796.90 µmol, 108.47 µL) in one portion at 20° C. and the resulting mixture was stirred at 20° C. for 2 h. LCMS showed starting material was consumed completely and one peak with desired mass was detected. TEA (161.28 mg, 1.59 mmol, 221.84 µL) was added to this reaction mixture at 20° C. and the resulting mixture was stirred at 20° C. for 1 h. The reaction mixture was concentrated in vacuum. The residue was purified by prep-HPLC (column: Phenomenex luna C₁₈ 150*40 mm*15 um; mobile phase: [water (0.225% FA)-ACN]; B %: 7%-37%, 10 min)

and then lyophilized to afford the titled compound (212 mg, 307.97 μmol, 57.97% yield, 97% purity) as a white solid. MS(M+H)+=668.2

Step 11: Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-((5-((2-((2-(2,6-dioxopiperidin-3-yl)-1,3-dioxoisoindolin-4-yl)oxy)acetamido)methyl)pyridin-3-yl)methyl)piperidin-4-yl)-2-fluoro-5-methoxybenzamide (Compound 62)

To a mixture of 2-((2-(2,6-dioxopiperidin-3-yl)-1,3-dioxoisoindolin-4-yl)oxy)acetic acid (100 mg, 300.97 μmol) and N-(1-((5-(aminomethyl)pyridin-3-yl)methyl)piperidin-4-yl)-4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzamide (211.01 mg, 316.01 μmol) in DMF (4 mL) were added T3P (1.15 g, 1.81 mmol, 1.07 mL, 50% purity in EtOAc solution) and Py (238.06 mg, 3.01 mmol, 242.92 μL) in one portion at 20° C. and the resulting mixture was stirred at 80° C. for 16 h. LCMS showed all starting material was consumed completely and one peak with desired mass was detected. The reaction mixture was diluted with H2O (12 mL) and extracted with EtOAc (12 mL×3). The organic layer was washed with brine (12 mL×3), dried over Na2SO4, filtered and concentrated. The residue was purified by prep-HPLC (column: Phenomenex luna C18 150*40 mm*15 um; mobile phase: [water (0.225% FA)-ACN]; B %: 18%-48%, 10 min) and then lyophilized to afford product A (24 mg) with 89% purity by LCMS and HPLC and product B (72 mg). The product A was re-purified by prep-HPLC (column: 3_Phenomenex Luna C18 75*30 mm*3 um; mobile phase: [water (0.1% TFA)-ACN]; B %: 28%-48%, 7 min). The product B was re-purified by prep-HPLC (column: 3_Phenomenex Luna C18 75*30 mm*3 um; mobile phase: [water (0.1% TFA)-ACN]; B %: 30%~50%, 7 min), two batches of eluents were combined and lyophilized to afford the titled compound (64.4 mg, 64.27 μmol, 21.35% yield, 98% purity, TFA salt) as a white solid. MS(M+H)+=981.7

1H NMR (400 MHz, CD3OD) δ=8.71 (d, J=1.7 Hz, 1H), 8.64 (d, J=1.8 Hz, 1H), 8.27 (d, J=13.4 Hz, 1H), 8.21 (s, 1H), 8.03 (s, 1H), 7.86-7.78 (m, 1H), 7.56 (d, J=7.2 Hz, 1H), 7.46 (d, J=8.6 Hz, 1H), 7.34 (d, J=6.6 Hz, 1H), 5.13 (dd, J=5.4, 12.8 Hz, 1H), 5.05-4.90 (m, 2H), 4.81-4.74 (m, 1H), 4.63 (s, 2H), 4.44 (s, 2H), 4.25-4.04 (m, 3H), 3.98 (s, 3H), 3.69-3.45 (m, 2H), 3.40 (s, 3H), 3.26-3.11 (m, 2H), 2.93-2.83 (m, 1H), 2.80-2.67 (m, 2H), 2.31-2.18 (m, 2H), 2.17-2.06 (m, 3H), 1.98-1.66 (m, 8H)

Example 63. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(7-(3-((2-((2-(2,6-dioxopiperidin-3-yl)-1,3-dioxoisoindolin-4-yl)oxy)acetamido)methyl)phenyl)heptyl)piperidin-4-yl)-2-fluoro-5-methoxybenzamide

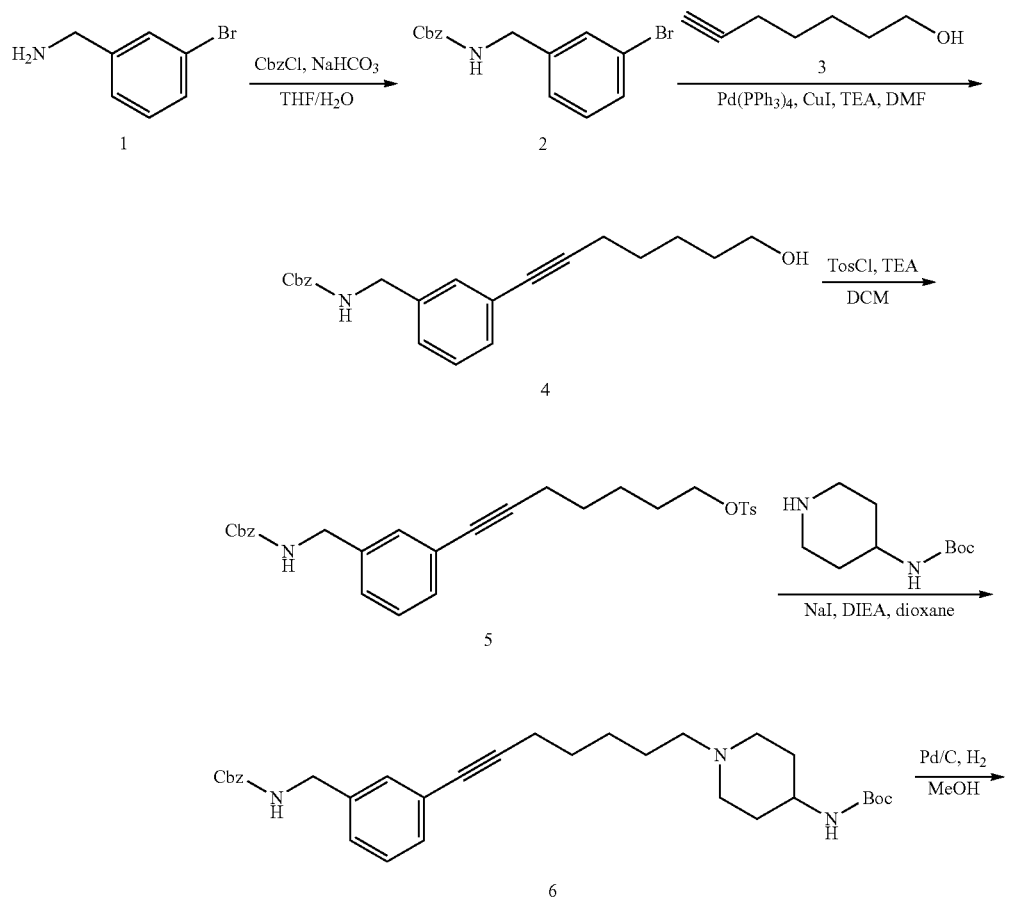

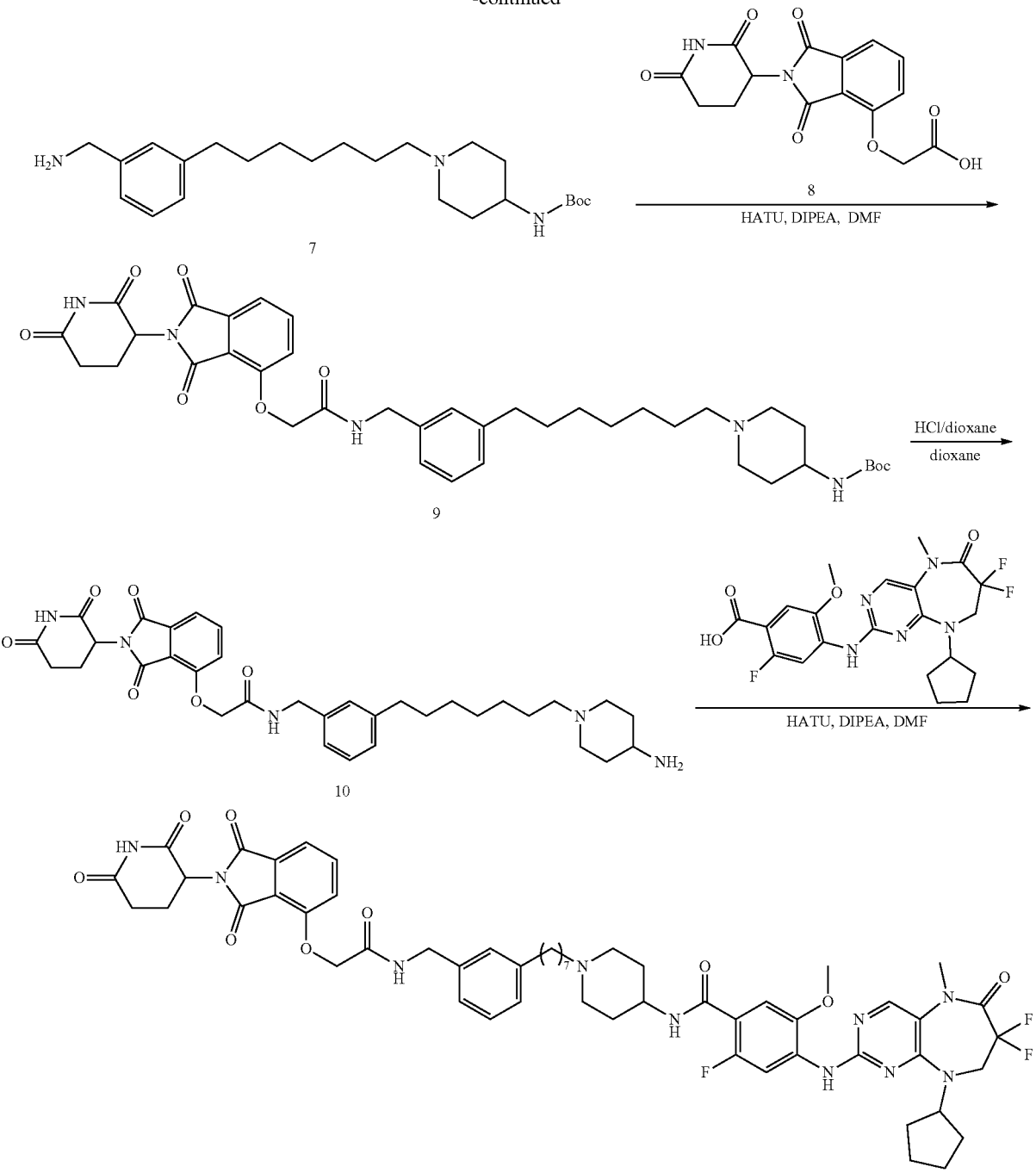

Compound 63

Step 1: Synthesis of benzyl 3-bromobenzylcarbamate (2)

To a solution of (3-bromophenyl)methanamine (5 g, 26.87 mmol) in THF (50 mL) was added a solution of $K_2CO_3$ (7.43 g, 53.75 mmol) in $H_2O$ (25 mL) followed by CbzCl (5.50 g, 32.25 mmol, 4.58 mL) drop-wise at 25° C. and the resulting mixture was stirred at 25° C. for 12 h. LCMS showed starting material was consumed completely and one peak with desired mass was detected. TLC ($SiO_2$, Petroleum ether:Ethyl acetate=5:1) indicated starting material was consumed completely and two new spots were detected. The reaction mixture was diluted with $H_2O$ (50 mL) and extracted with EtOAc (50 mL×3). The organic layer was dried over $Na_2SO_4$, filtered and concentrated. The residue was purified by column chromatography ($SiO_2$, Petroleum ether/Ethyl acetate=1/0 to 5/1) to afford the titled compound (6.8 g, 20.60 mmol, 76.66% yield, 97% purity) as a white solid. MS(M+H)$^+$=320.0

Step 2: Synthesis of benzyl 3-(7-hydroxyhept-1-yn-1-yl)benzylcarbamate (4)

To a mixture of benzyl 3-bromobenzylcarbamate (6 g, 18.74 mmol) and hept-6-yn-1-ol (3.15 g, 28.11 mmol) in DMF (60 mL) were added CuI (713.78 mg, 3.75 mmol), TEA (5.69 g, 56.22 mmol, 7.82 mL) and Pd(PPh$_3$)$_4$ (1.08 g, 936.97 μmol) in one portion at 20° C. under N$_2$ and the resulting mixture was stirred at 80° C. for 16 h. LCMS showed all starting material was consumed completely and one peak with desired mass was detected. TLC (SiO$_2$, Petroleum ether:Ethyl acetate=1:1) indicated starting material was consumed completely and three new spots was detected. The reaction mixture was diluted with H$_2$O (120 mL) and extracted with EtOAc (120 mL×3). The organic layer was washed with brine (120 mL×3), dried over Na$_2$SO$_4$, filtered and concentrated. The residue was purified by column chromatography (SiO$_2$, Petroleum ether/Ethyl acetate=10/1 to 1/1) to afford the titled compound (6.8 g, 16.06 mmol, 85.70% yield, 83% purity) as a yellow oil. MS(M+Na)$^+$=374.4

Step 3: Synthesis of 7-(3-((((benzyloxy)carbonyl)amino)methyl)phenyl)hept-6-yn-1-yl 4-methylbenzenesulfonate (5)

To a mixture of benzyl 3-(7-hydroxyhept-1-yn-1-yl)benzylcarbamate (6.8 g, 16.06 mmol, 83% purity) in DCM (70 mL) were added TEA (4.88 g, 48.18 mmol, 6.71 mL) and TosCl (4.59 g, 24.09 mmol) in one portion at 20° C. and the resulting mixture was stirred at 20° C. for 16 h. LCMS showed all starting material was consumed completely and desired mass was detected. TLC (SiO$_2$, Petroleum ether:Ethyl acetate=2:1) indicated starting material was consumed completely and one major new spot was detected. The reaction mixture was concentrated in vacuum. The residue was purified by column chromatography (SiO$_2$, Petroleum ether/Ethyl acetate=10/1 to 2/1) to afford the titled compound (6.2 g, 12.02 mmol, 74.83% yield, 98% purity) as a yellow oil. MS(M+H)$^+$=506.4

Step 4: Synthesis of tert-butyl N-[1-[7-[3-(benzyloxycarbonylaminomethyl) phenyl]hept-6-ynyl]-4-piperidyl]carbamate (6)

To a mixture of 7-(3-((((benzyloxy)carbonyl)amino)methyl)phenyl)hept-6-yn-1-yl 4-methylbenzenesulfonate (3.1 g, 6.13 mmol) and tert-butyl piperidin-4-ylcarbamate (2.46 g, 12.26 mmol) in dioxane (40 mL) were added NaI (91.90 mg, 613.10 μmol) and DIPEA (2.38 g, 18.39 mmol, 3.20 mL) in one portion at 20° C. under N$_2$ and the resulting mixture was stirred at 60° C. for 16 h. LCMS showed all starting material was consumed completely and one peak with desired mass was detected. TLC (SiO$_2$, Petroleum ether:Ethyl acetate=1:2) indicated starting material was consumed completely and three new spots were detected. The reaction mixture was concentrated in vacuum. The residue was purified by column chromatography (SiO$_2$, Petroleum ether/Ethyl acetate=10/1 to 1/2) to afford the titled compound (2.4 g, 4.50 mmol, 73.35% yield) as a yellow oil. MS(M+H)$^+$=534.3

Step 5: Synthesis of tert-butyl (1-(7-(3-(aminomethyl)phenyl)heptyl)piperidin-4-yl)carbamate (7)

To a solution of tert-butyl N-[1-[7-[3-(benzyloxycarbonylaminomethyl) phenyl]hept-6-ynyl]-4-piperidyl]carbamate (2.4 g, 4.50 mmol) in MeOH (24 mL) was added Pd/C (1 g, 10% purity) under N$_2$. The suspension was degassed under vacuum and purged with H$_2$ several times. The mixture was stirred under H$_2$ (15 psi) at 20° C. for 16 h. LCMS showed starting material was consumed completely and one peak with desired mass was detected. The reaction mixture was diluted with MeOH (80 mL) and filtered. The filtrate was concentrated in vacuum to afford the titled compound (1.3 g, crude) as a white oil. MS(M+H)$^+$=404.5

Step 6: Synthesis of tert-butyl (1-(7-(3-((2-((2-(2,6-dioxopiperidin-3-yl)-1,3-dioxoisoindolin-4-yl)oxy)acetamido)methyl)phenyl)heptyl)piperidin-4-yl)carbamate (9)

To a mixture of 2-((2-(2,6-dioxopiperidin-3-yl)-1,3-dioxoisoindolin-4-yl)oxy)acetic acid (800 mg, 2.41 mmol) and tert-butyl (1-(7-(3-(aminomethyl)phenyl)heptyl)piperidin-4-yl)carbamate (1.17 g, 2.89 mmol) in DMF (10 mL) were added HATU (915.49 mg, 2.41 mmol) and DIPEA (933.54 mg, 7.22 mmol, 1.26 mL) in one portion at 20° C. and the resulting mixture was stirred at 20° C. for 2 h. LCMS showed all starting material was consumed completely and one peak with desired mass was detected. TLC (SiO$_2$, Petroleum ether:Ethyl acetate=1:3) indicated starting material was consumed completely and four new spots were detected. The reaction mixture was diluted with H$_2$O (30 mL) and extracted with EtOAc (30 mL×3). The organic layer was washed with brine (30 mL×3), dried over Na$_2$SO$_4$, filtered and concentrated. The residue was purified by column chromatography (SiO$_2$, Petroleum ether/Ethyl acetate=5/1 to 0/1) to afford the titled compound (1.17 g, 1.63 mmol, 67.69% yield) as a yellow oil. MS(M+H)$^+$=718.2

Step 7: Synthesis of N-(3-(7-(4-aminopiperidin-1-yl)heptyl)benzyl)-2-((2-(2,6-dioxopiperidin-3-yl)-1,3-dioxoisoindolin-4-yl)oxy)acetamide (10)

To a mixture of tert-butyl (1-(7-(3-((2-((2-(2,6-dioxopiperidin-3-yl)-1,3-dioxoisoindolin-4-yl)oxy) acetamido) methyl)phenyl)heptyl)piperidin-4-yl)carbamate (1.17 g, 1.63 mmol) in dioxane (5 mL) was added HCl/dioxane (4 M, 10 mL) in one portion at 20° C. and the resulting mixture was stirred at 20° C. for 1 h. LCMS showed starting material was consumed completely and one peak with desired mass was detected. The reaction mixture was concentrated in vacuum to afford the titled compound (1.5 g, crude, HCl) as a yellow solid. MS(M+H)$^+$=618.2

Step 8: Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(7-(3-((2-((2-(2,6-dioxopiperidin-3-yl)-1,3-dioxoisoindolin-4-yl)oxy)acetamido)methyl)phenyl)heptyl)piperidin-4-yl)-2-fluoro-5-methoxybenzamide (Compound 63)

To a mixture of 4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzoic acid (250 mg, 537.14 μmol) and N-(3-(7-(4-aminopiperidin-1-yl)heptyl)benzyl)-2-((2-(2,6-dioxopiperidin-3-yl)-1,3-dioxoisoindolin-4-yl)oxy)acetamide (421.68 mg, crude, HCl) in DMF (3 mL) were added HATU (224.66 mg, 590.86 μmol) and DIPEA (208.27 mg, 1.61 mmol, 280.68 μL) in one portion at 20° C. and the resulting mixture was stirred at 20° C. for 2 h. LCMS showed starting material was consumed completely and desired mass was detected. The reaction mixture was diluted with toluene (15 mL) and the reaction mixture was concentrated in vacuum. The residue was purified by prep-HPLC (column: Phenomenex luna $C_{18}$ 150*40 mm*15 um; mobile phase: [water (0.225% FA)-ACN]; B %: 30%-60%, 10 min) and then lyophilized to afford product (192 mg) with 59% purity. The product was re-purified by prep-HPLC (column: Shim-pack $C_{18}$ 150*25*10 um; mobile phase: [water (0.225% FA)-ACN]; B %: 31%-57%, 13 min) and then lyophilized to afford the titled compound (81.2 mg, 72.42 μmol, 69.25% yield, 95% purity) as a white solid. MS(M+H)$^+$=1065.4

$^1$H NMR (400 MHz, DMSO-d$_6$) δ=11.11 (s, 1H), 8.50 (t, J=6.0 Hz, 1H), 8.30 (s, 1H), 8.26 (d, J=13.4 Hz, 1H), 8.13 (s, 1H), 8.06 (s, 1H), 7.81 (dd, J=7.4, 8.4 Hz, 1H), 7.51 (d, J=7.2 Hz, 1H), 7.41 (d, J=8.6 Hz, 1H), 7.27-7.14 (m, 2H), 7.12-7.01 (m, 3H), 5.11 (dd, J=5.4, 12.8 Hz, 1H), 4.87 (s, 2H), 4.85-4.76 (m, 1H), 4.34 (d, J=6.0 Hz, 2H), 4.14-4.03 (m, 2H), 4.02-3.95 (m, 1H), 3.92 (s, 3H), 3.33 (s, 3H), 3.00-2.81 (m, 4H), 2.69-2.51 (m, 7H), 2.09-1.88 (m, 5H), 1.84-1.67 (m, 4H), 1.67-1.48 (m, 8H), 1.35-1.21 (m, 6H)

Example 64. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(7-(5-((2-((2-(2,6-dioxopiperidin-3-yl)-1,3-dioxoisoindolin-4-yl)oxy)acetamido)methyl)pyridin-3-yl)heptyl)piperidin-4-yl)-2-fluoro-5-methoxybenzamide

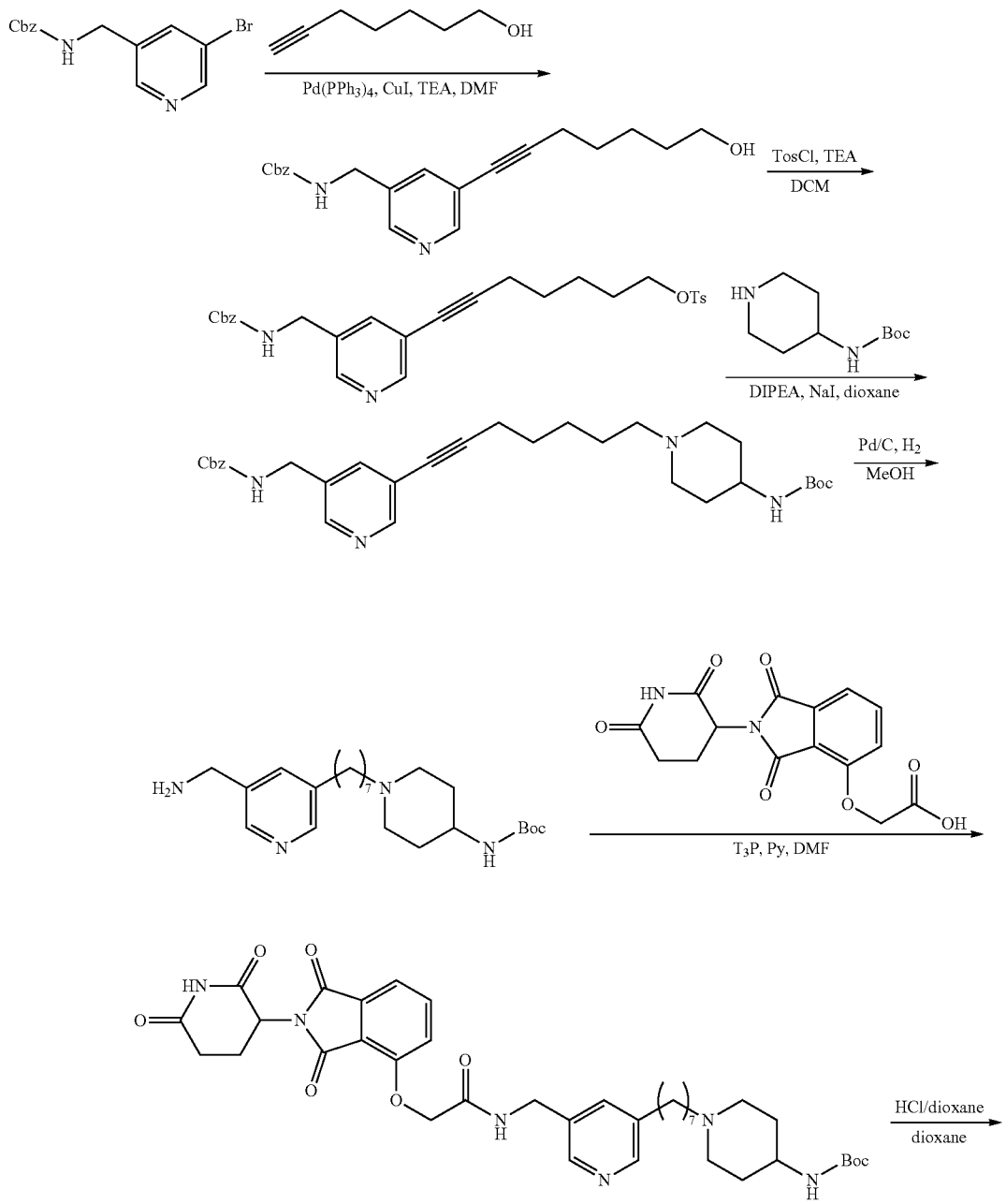

337                                                                                       338

-continued

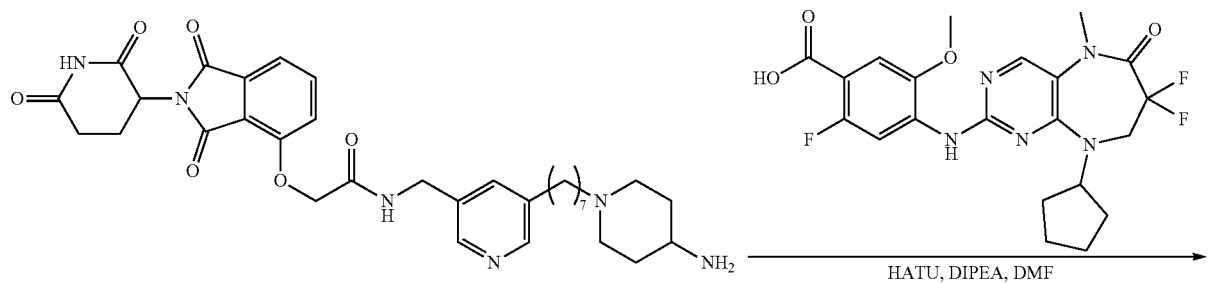

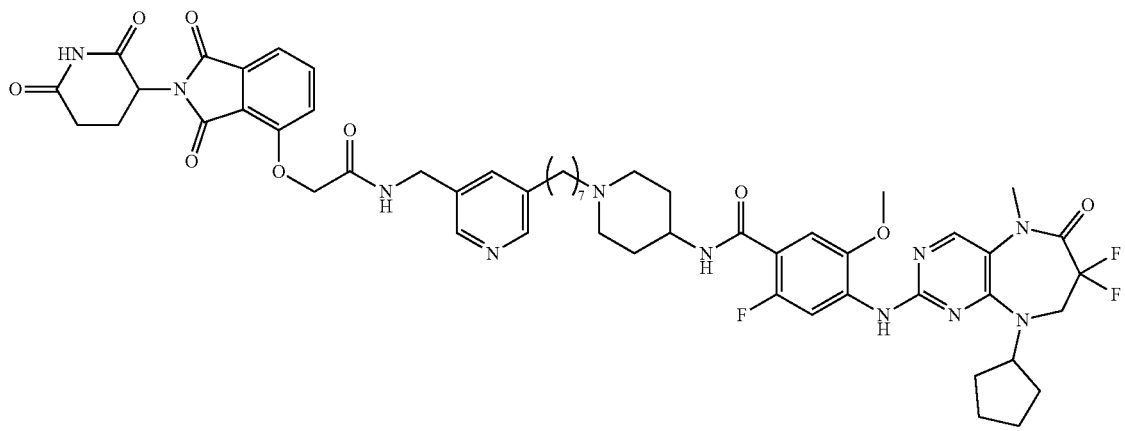

Compound 64

According to the above reaction scheme, in a manner similar to the other examples obtained the titled compound (161.2 mg, 137.59 μmol, 32.02% yield, 91% purity) as a white solid. MS(M+H)⁺=1065.6

¹H NMR (400 MHz, DMSO-d$_6$) δ=11.12 (br s, 1H), 8.58 (t, J=5.9 Hz, 1H), 8.34-8.28 (m, 3H), 8.25 (d, J=13.3 Hz, 1H), 8.20 (s, 1H), 8.03 (s, 1H), 7.88 (dd, J=3.5, 7.5 Hz, 1H), 7.80 (dd, J=7.4, 8.4 Hz, 1H), 7.53-7.46 (m, 2H), 7.40 (d, J=8.4 Hz, 1H), 7.20 (d, J=6.8 Hz, 1H), 5.11 (dd, J=5.4, 12.9 Hz, 1H), 4.88 (s, 2H), 4.86-4.77 (m, 1H), 4.37 (d, J=6.0 Hz, 2H), 4.08 (t, J=13.9 Hz, 2H), 3.92 (s, 3H), 3.34 (s, 3H), 2.97-2.79 (m, 4H), 2.58-2.54 (m, 3H), 2.28 (t, J=7.3 Hz, 2H), 2.06-1.94 (m, 5H), 1.83-1.70 (m, 4H), 1.66-1.50 (m, 8H), 1.46-1.37 (m, 2H), 1.32-1.20 (m, 6H)

Example 65. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-((1-(2-(2,6-dioxopiperidin-3-yl)-1,3-dioxoisoindolin-4-yl)piperidin-4-yl)methyl)piperidin-4-yl)-2-fluoro-5-methoxybenzamide

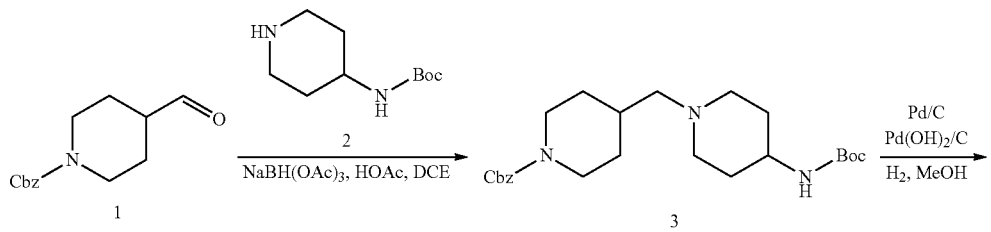

-continued
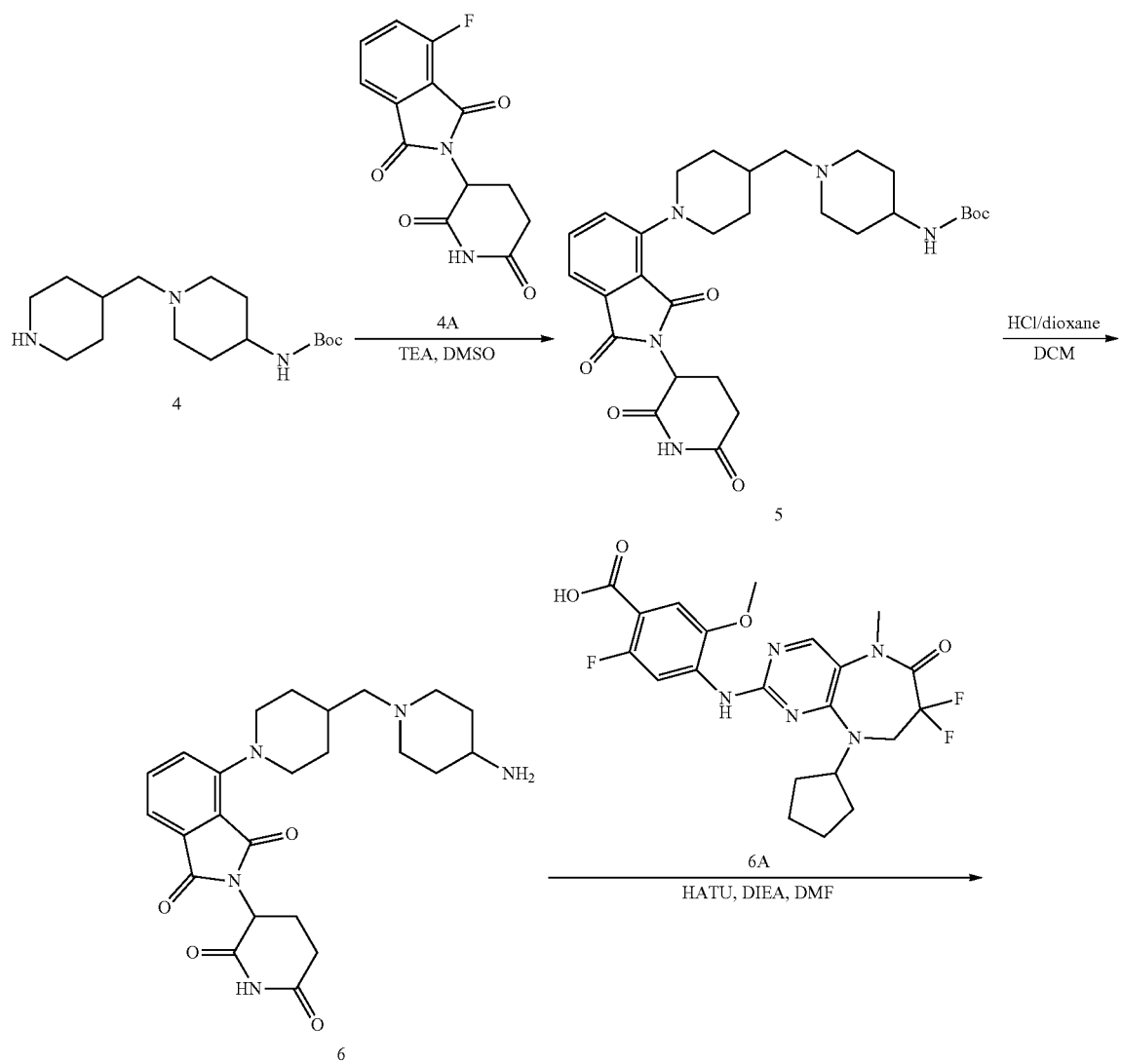
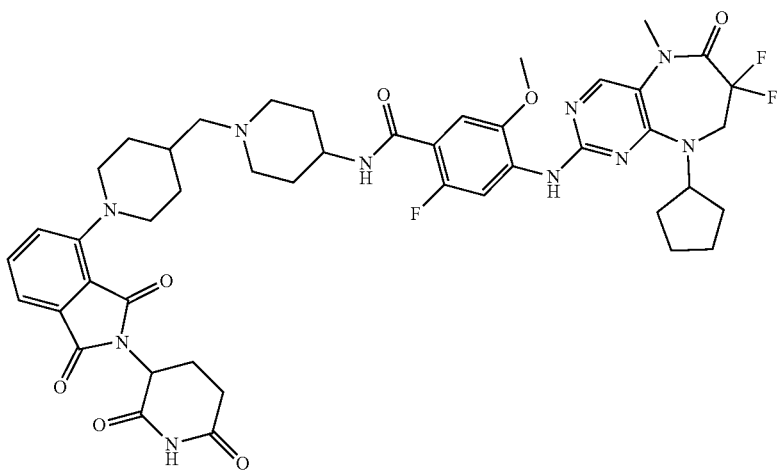
Compound 65

Step 1: Synthesis of benzyl 4-((4-((tert-butoxycarbonyl)amino)piperidin-1-yl)methyl)piperidine-1-carboxylate (3)

To a solution of benzyl 4-formylpiperidine-1-carboxylate (5 g, 20.22 mmol) in DCE (80 mL) were added tert-butyl piperidin-4-ylcarbamate (4.50 g, 22.47 mmol) and HOAc (1.21 g, 20.22 mmol, 1.16 mL). The mixture was stirred at 20° C. for 2 h. Then NaBH(OAc) 3 (16.00 g, 75.49 mmol) was added to the mixture at 20° C., the mixture was stirred at 20° C. for 14 hr. LCMS showed the starting material was consumed and main peak with the desired mass. To the reaction mixture was added H$_2$O (100 mL) at 0° C. and adjusted to pH=9 at 0° C. by saturated Na$_2$CO$_3$ solution, the aqueous phase was extracted with Ethyl acetate (200 mL×3), then the combined organic layers were washed with brine (250 mL×2), dried over Na$_2$SO$_4$, filtered and the filtrate was concentrated under reduced pressure to give a residue. The crude product was triturated with Petroleum ether:Ethyl acetate=5:1 (120 mL) at 20° C. for 30 min, then it was filtered and the cake was dried under reduced pressure to afford the titled compound (8 g, 18.54 mmol, 91.68% yield) as a white solid. MS (M+H)$^+$=432.3

Step 2: Synthesis of tert-butyl (1-(piperidin-4-ylmethyl)piperidin-4-yl)carbamate (4)

To a solution of benzyl 4-((4-((tert-butoxycarbonyl)amino)piperidin-1-yl)methyl)piperidine-1-carboxylate (4 g, 9.27 mmol) in MeOH (100 mL) was added Pd/C (0.4 g, 10% purity) and Pd(OH)$_2$/C (0.4 g, 20% purity), the mixture was stirred at 20° C. for 16 h under H$_2$ atmosphere (15 Psi). LCMS showed the starting material was consumed and desired mass was detected. The reaction mixture was filtered and the filtrate was concentrated under reduced pressure to afford the titled compound (2.6 g, crude) as a light yellow oil. MS (M+H)$^+$=298.3

Step 3: Synthesis of tert-butyl (1-((1-(2-(2,6-dioxopiperidin-3-yl)-1,3-dioxoisoindolin-4-yl) piperidin-4-yl)methyl)piperidin-4-yl)carbamate (5)

To a solution of 2-(2,6-dioxopiperidin-3-yl)-4-fluoroisoindoline-1,3-dione (800 mg, 2.90 mmol) in DMSO (3 mL) was added TEA (1.16 g, 11.50 mmol, 1.60 mL) and tert-butyl (1-(piperidin-4-ylmethyl)piperidin-4-yl)carbamate (1.0 g, 3.36 mmol). The mixture was stirred at 100° C. for 16 h under N$_2$ atmosphere. LCMS showed the starting material was consumed and a main peak with desired mass. To the reaction mixture was added H$_2$O (20 mL), the mixture was extracted with EtOAc (50 mL×2), the combined organic layers were washed with brine (40 mL×3), dried over Na$_2$SO$_4$, filtered and the filtrate was concentrated under reduced pressure. The residue was purified by flash silica gel chromatography (Biotage; 10 g SepaFlash® Silica Flash Column, Eluent of 0~10% Methanol:Ethyl acetate gradient, 50 mL/min) to the titled compound (1.5 g, 2.71 mmol, 93.55% yield) as a yellow oil. MS (M+H)$^+$=554.5

Step 4: Synthesis of 4-(4-((4-aminopiperidin-1-yl)methyl)piperidin-1-yl)-2-(2,6-dioxopiperidin-3-yl)isoindoline-1,3-dione (6)

To a solution of tert-butyl (1-((1-(2-(2,6-dioxopiperidin-3-yl)-1,3-dioxoisoindolin-4-yl)piperidin-4-yl)methyl)piperidin-4-yl)carbamate (1.5 g, 2.71 mmol) in DCM (10 mL) was added HCl/dioxane (4 M, 10 mL) at 20° C. The mixture was stirred at 20° C. for 16 h under N$_2$ atmosphere. LCMS showed the starting material was consumed and a main peak with the desired mass. The reaction mixture was concentrated under reduced pressure to afford the titled compound (1.4 g, crude, 2HCl) as a light yellow solid. MS (M+H)$^+$=454.5

Step 5: Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-((1-(2-(2,6-dioxopiperidin-3-yl)-1,3-dioxoisoindolin-4-yl)piperidin-4-yl)methyl)piperidin-4-yl)-2-fluoro-5-methoxybenzamide (Compound 65)

To a solution of 4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzoic acid (150 mg, 322.29 μmol) in DMF (4 mL) were added HATU (245.09 mg, 644.58 μmol), DIPEA (222.60 mg, 1.72 mmol, 300 μL) and 4-(4-((4-aminopiperidin-1-yl)methyl)piperidin-1-yl)-2-(2,6-dioxopiperidin-3-yl)isoindoline-1,3-dione (200 mg, 379.90 μmol, 2HCl) at 25° C. The mixture was stirred at 25° C. for 2 h under N$_2$ atmosphere. LCMS showed the starting material was consumed and a main peak with the desired mass. To the reaction mixture was added H$_2$O (10 mL), the mixture was extracted with EtOAc (30 mL×2), the combined organic layers were washed with brine 90 mL (30 mL×3), dried over Na$_2$SO$_4$, filtered and the filtrate was concentrated under reduced pressure. The residue was purified by prep-HPLC (column: Waters Xbridge 150*25 mm*5 um; mobile phase: [water (10 mM NH$_4$HCO$_3$)-ACN]; B %: 48%-81%, 9 min; Column Temp: 30° C.) followed by lyophilization to afford the titled compound (123.3 mg, 127.28 μmol, 39.49% yield, 93% purity) as a light yellow solid. MS (M+H)$^+$=901.6

$^1$H NMR (400 MHz, DMSO-d$_6$) δ 11.10 (s, 1H), 8.35-8.22 (m, 2H), 8.04 (s, 1H), 7.95-7.83 (m, 1H), 7.68 (t, J=7.8 Hz, 1H), 7.33 (t, J=7.3 Hz, 2H), 7.20 (d, J=6.6 Hz, 1H), 5.09 (dd, J=5.3, 12.9 Hz, 1H), 4.88-4.78 (m, 1H), 4.09 (t, J=13.9 Hz, 2H), 3.92 (s, 3H), 3.83-3.67 (m, 3H), 3.32 (s, 3H), 2.93-2.75 (m, 5H), 2.63-2.57 (m, 2H), 2.25-2.14 (m, 2H), 2.08-1.95 (m, 5H), 1.84-1.56 (m, 13H), 1.37-1.25 (m, 2H)

Example 66. Synthesis of 4-((9-cyclopentyl-7,7-difluoro-5-methyl-6-oxo-6,7,8,9-tetrahydro-5H-pyrimido[4,5-b][1, 4]diazepin-2-yl)amino)-N-(1-(2-(4-(2-(2,6-dioxopiperidin-3-yl)-1,3-dioxoisoindolin-4-yl)piperazin-1-yl)ethyl)piperidin-4-yl)-2-fluoro-5-methoxybenzamide
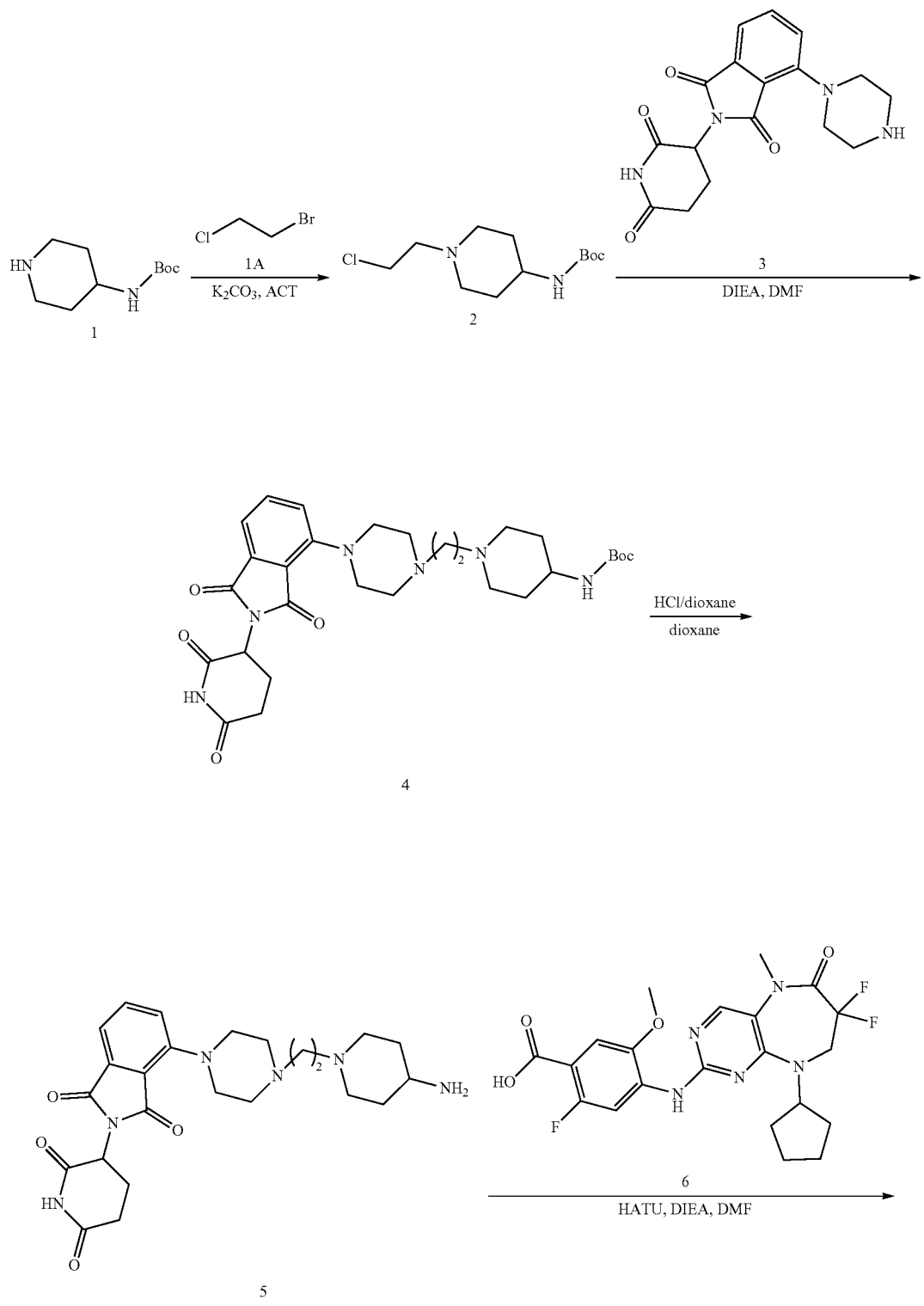

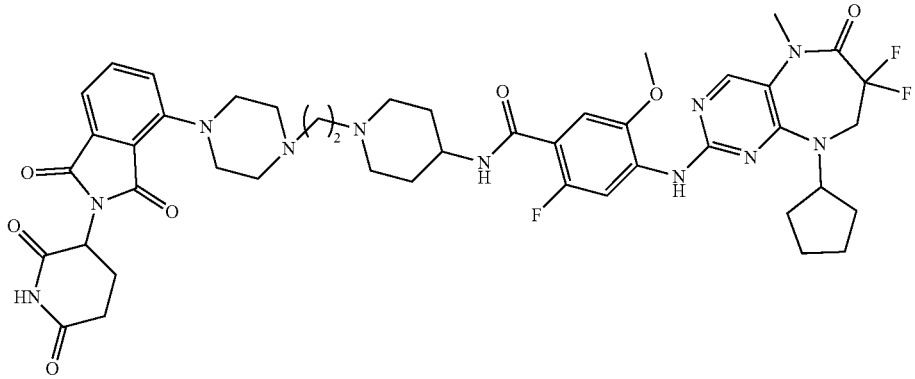

Compound 66

Step 1: Synthesis of tert-butyl (1-(2-chloroethyl) piperidin-4-yl)carbamate (2)

A mixture of tert-butyl piperidin-4-ylcarbamate (10 g, 49.93 mmol), 1-bromo-2-chloroethane (10.74 g, 74.90 mmol, 6.21 mL) and $K_2CO_3$ (20.70 g, 149.79 mmol) in acetone (100 mL) was stirred at 15° C. for 16 h. LCMS showed reactant was consumed completely and 100% of the desired mass was detected. The reaction mixture was filtered and the filtrate was concentrated in vacuo. The residue was purified by flash silica gel chromatography (25 g Sepa-Flash® Silica Flash Column, Eluent of 20~51% Ethyl acetate/Petroleum ether gradient @ 100 mL/min) to afford the titled compound (2 g, 7.61 mmol, 15.24% yield) as a white solid.

$^1$H NMR (400 MHz, DMSO-$d_6$) δ=6.75 (br d, J=7.5 Hz, 1H), 3.64 (t, J=6.8 Hz, 2H), 3.26-3.12 (m, 1H), 2.80 (br d, J=11.5 Hz, 2H), 2.59 (br t, J=6.8 Hz, 2H), 2.05-1.95 (m, 2H), 1.65 (br d, J=11.0 Hz, 2H), 1.41-1.29 (m, 11H).

Step 2: Synthesis of tert-butyl (1-(2-(4-(2-(2,6-dioxopiperidin-3-yl)-1,3-dioxoisoindolin-4-yl) piperazin-1-yl)ethyl)piperidin-4-yl)carbamate (4)

To a solution of 2-(2,6-dioxopiperidin-3-yl)-4-(piperazin-1-yl)isoindoline-1,3-dione (200 mg, 527.97 umol, HCl salt) in DMF (3 mL) were added DIEA (204.71 mg, 1.58 mmol, 275.89 μL) and tert-butyl (1-(2-chloroethyl)piperidin-4-yl) carbamate (194.23 mg, 739.16 μmol), the mixture was stirred at 15° C. for 16 hours. LCMS showed 15% of reactant remained and 66% of desired mass was detected. The reaction mixture was diluted with $H_2O$ (50 mL) and extracted with EtOAc (50 mL×3). The combined organic layers were washed with brine (80 mL×5), dried over $Na_2SO_4$, filtered and concentrated in vacuo. The residue was purified by flash silica gel chromatography (12 g Sepa-Flash® Silica Flash Column, Eluent of 0~18% MeOH/Ethyl acetate gradient @60 mL/min) to afford the titled compound (110 mg, 193.44 μmol, 36.64% yield) as a yellow solid. MS(M+H)$^+$=569.6.

Step 3: Synthesis of 4-(4-(2-(4-aminopiperidin-1-yl) ethyl)piperazin-1-yl)-2-(2,6-dioxopiperidin-3-yl) isoindoline-1,3-dione (5)

To a solution of tert-butyl (1-(2-(4-(2-(2,6-dioxopiperidin-3-yl)-1,3-dioxoisoindolin-4-yl)piperazin-1-yl)ethyl)piperidin-4-yl)carbamate (110 mg, 193.44 μmol) in dioxane (5 mL) was added HCl/dioxane (4 M in dioxane, 10 mL), the mixture was stirred at 15° C. for 16 hours. LCMS showed reactant was consumed completely and desired mass was detected. The reaction mixture was concentrated in vacuo to afford the titled compound (160 mg, crude, HCl salt) as a yellow solid. MS(M+H)$^+$=469.2.

Step 4: Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(2-(4-(2-(2,6-dioxopiperidin-3-yl)-1,3-dioxoisoindolin-4-yl) piperazin-1-yl)ethyl)piperidin-4-yl)-2-fluoro-5-methoxybenzamide (Compound 66)

To a solution of 4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzoic acid (90 mg, 193.37 mol) in DMF (2 mL) were added HATU (110.29 mg, 290.06 μmol) and DIEA (99.97 mg, 773.49 μmol, 134.73 μL), the mixture was stirred at 15° C. for 15 minutes, then 4-(4-(2-(4-aminopiperidin-1-yl)ethyl)piperazin-1-yl)-2-(2,6-dioxopiperidin-3-yl)isoindoline-1,3-dione (156.25 mg, 309.39 μmol, HCl salt) was added and the resulting mixture was stirred at 15° C. for 1 hour. LCMS showed reactant was consumed completely and 91% of desired mass was detected. The mixture was added $CH_3COOH$ to adjust pH<7. The resulting mixture was purified by prep-HPLC (column: Waters Xbridge 150*25 mm*5 um; mobile phase: [water(10 mM $NH_4HCO_3$)-ACN]; B %: 40%-70%, 8 min) followed by prep-HPLC (column: Phenomenex luna $C_{18}$ 150*25 mm*10 um; mobile phase: [water(0.225% FA)-ACN]; B %: 18%-38%, 10 min) to afford the titled compound (32.4 mg, 32.54 μmol, 16.83% yield, 92% purity) as a yellow solid. MS(M+H)$^+$=916.3.

347
$^1$H NMR (400 MHz, DMSO-d$_6$) δ=11.09 (s, 1H), 8.30 (s, 1H), 8.24 (d, J=13.4 Hz, 1H), 8.03 (s, 1H), 7.89 (br dd, J$_1$=3.3, J$_2$=7.5 Hz, 1H), 7.70 (dd, J$_1$=7.3, J$_2$=8.3 Hz, 1H), 7.40-7.28 (m, 2H), 7.19 (d, J=6.6 Hz, 1H), 5.09 (dd, J$_1$=5.5, J$_2$=12.8 Hz, 1H), 4.90-4.76 (m, 1H), 4.08 (br t, J=13.9 Hz, 2H), 3.91 (s, 3H), 3.80-3.67 (m, 1H), 3.31-3.23 (m, 4H), 2.96-2.78 (m, 3H), 2.65-2.57 (m, 4H), 2.57-2.51 (m, 9H), 2.09-1.91 (m, 5H), 1.85-1.68 (m, 4H), 1.68-1.48 (m, 6H).
348
Example 67. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-((1-(2-(2,6-dioxopiperidin-3-yl)-1,3-dioxoisoindolin-5-yl)piperidin-4-yl)methyl)piperidin-4-yl)-2-fluoro-5-methoxybenzamide
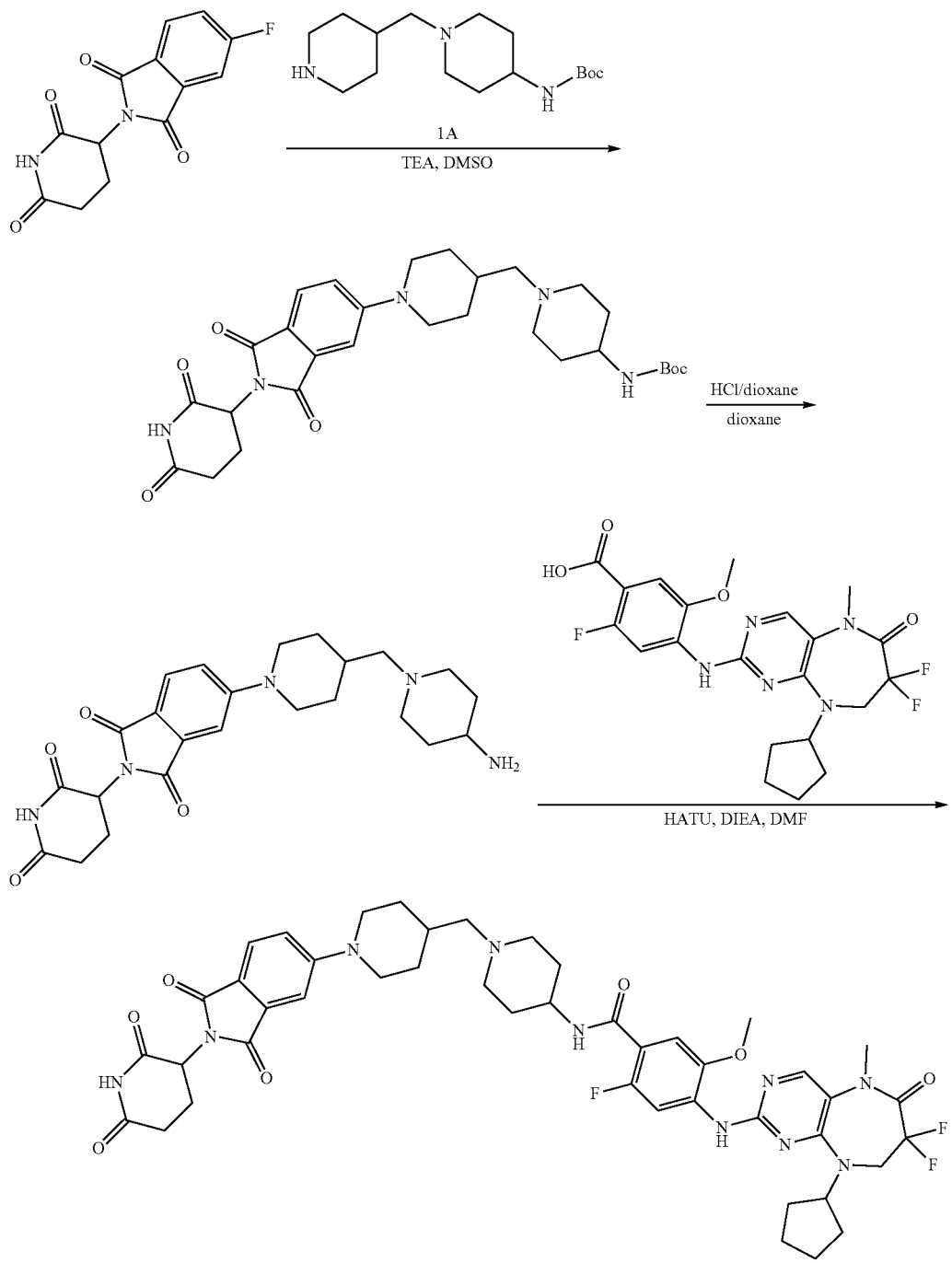
Compound 67

According to the above reaction scheme, in a manner similar to the other examples, obtained the titled compound (129.2 mg, 130.50 μmol, 40.49% yield, 91% purity) as a light yellow solid. MS (M+H)$^+$=901.5

$^1$H NMR (400 MHz, DMSO-d$_6$) δ 11.07 (br s, 1H), 8.31-8.22 (m, 2H), 8.03 (s, 1H), 7.87 (dd, J=3.4, 7.5 Hz, 1H), 7.64 (d, J=8.5 Hz, 1H), 7.29 (d, J=1.6 Hz, 1H), 7.24-7.18 (m, 2H), 5.06 (dd, J=5.4, 12.9 Hz, 1H), 4.87-4.78 (m, 1H), 4.12-3.98 (m, 4H), 3.91 (s, 3H), 3.78-3.70 (m, 1H), 3.33 (s, 3H), 2.99-2.79 (m, 5H), 2.63-2.54 (m, 2H), 2.15-2.08 (m, 2H), 2.03-1.93 (m, 5H), 1.81-1.55 (m, 13H), 1.18-1.09 (m, 2H)

Example 68. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(2-(4-(2-(2,6-dioxopiperidin-3-yl)-1,3-dioxoisoindolin-5-yl)piperazin-1-yl)ethyl)piperidin-4-yl)-2-fluoro-5-methoxybenzamide

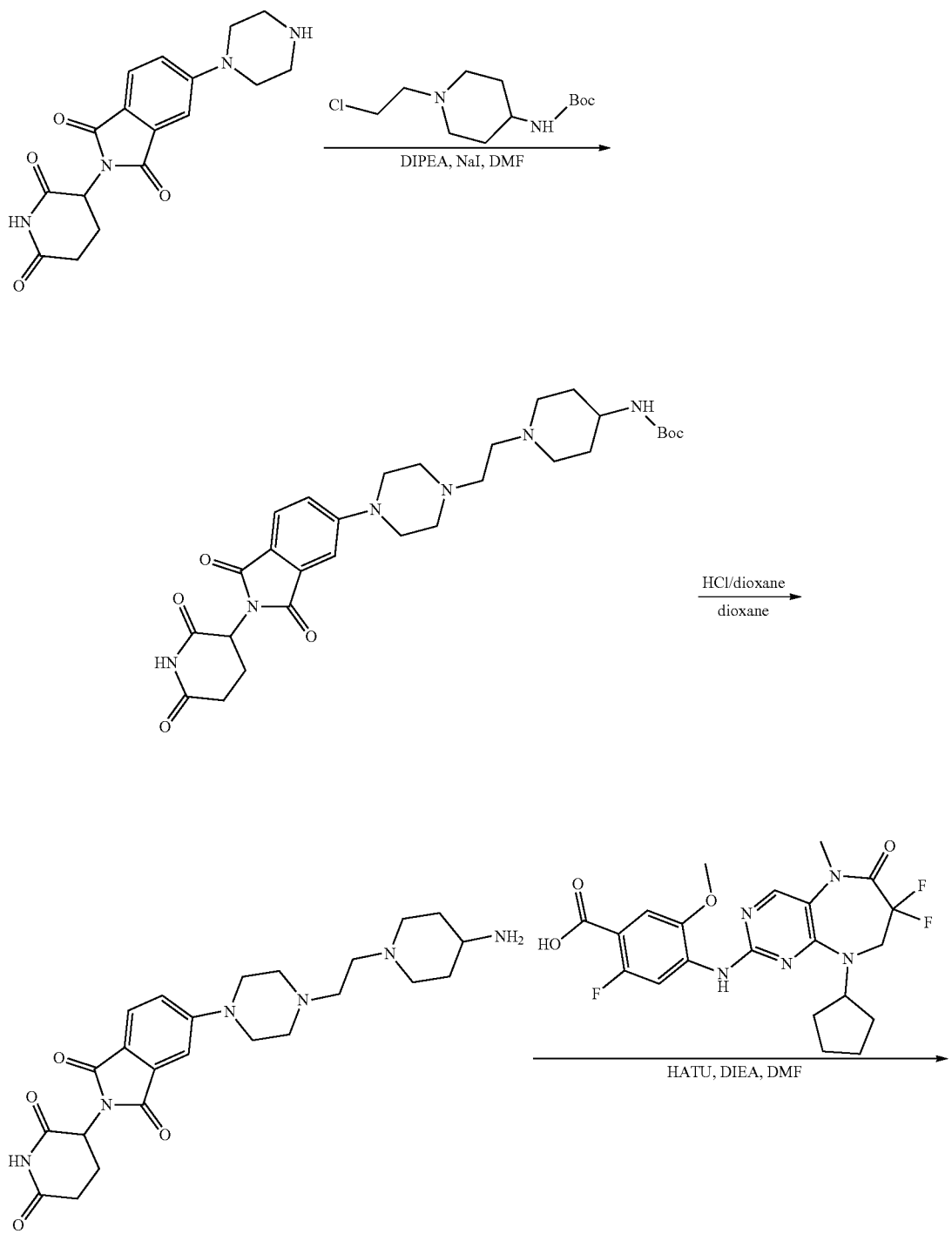

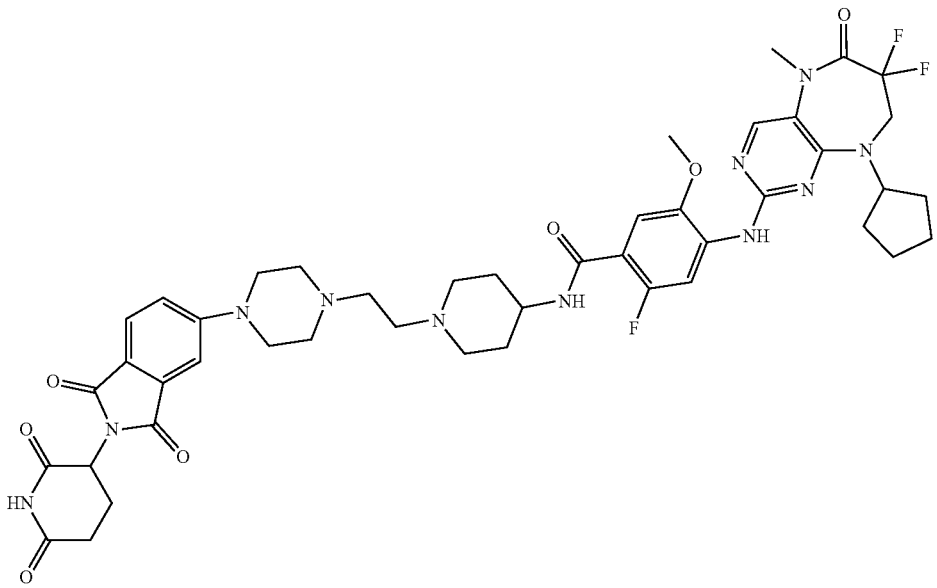

Compound 68

According to the above reaction scheme, in a manner similar to the other examples, obtained the titled compound (79.1 mg, 84.63 μmol, 39.39% yield, 98% purity) as yellow solid. MS(M+H)⁺=917.0

1H NMR (400 MHz, DMSO-d6) δ 11.09 (s, 1H), 8.30 (s, 1H), 8.24 (d, J=13.3 Hz, 1H), 8.04 (d, J=1.3 Hz, 1H), 7.90 (dd, J=7.8, 3.4 Hz, 1H), 7.68 (d, J=8.5 Hz, 1H), 7.34 (d, J=2.2 Hz, 1H), 7.25 (dd, J=8.7, 2.3 Hz, 1H), 7.19 (d, J=6.7 Hz, 1H), 5.07 (dd, J=12.9, 5.3 Hz, 1H), 4.91-4.74 (m, 1H), 4.08 (t, J=13.9 Hz, 2H), 3.91 (s, 3H), 3.80-3.67 (m, 1H), 3.50-3.37 (m, 4H), 3.31 (s, 3H), 2.97-2.78 (m, 3H), 2.65-2.51 (m, 6H), 2.47-2.44 (m, 4H), 2.08-1.92 (m, 5H), 1.83-1.68 (m, 4H), 1.66-1.49 (m, 6H).

Example 69. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(4-(2-(2,6-dioxopiperidin-3-yl)-1,3-dioxoisoindolin-4-yl)piperazine-1-carbonyl)piperidin-4-yl)-2-fluoro-5-methoxybenzamide

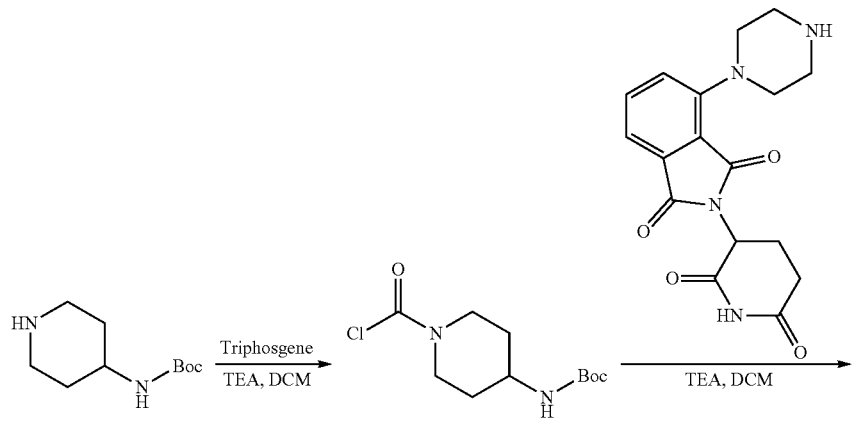

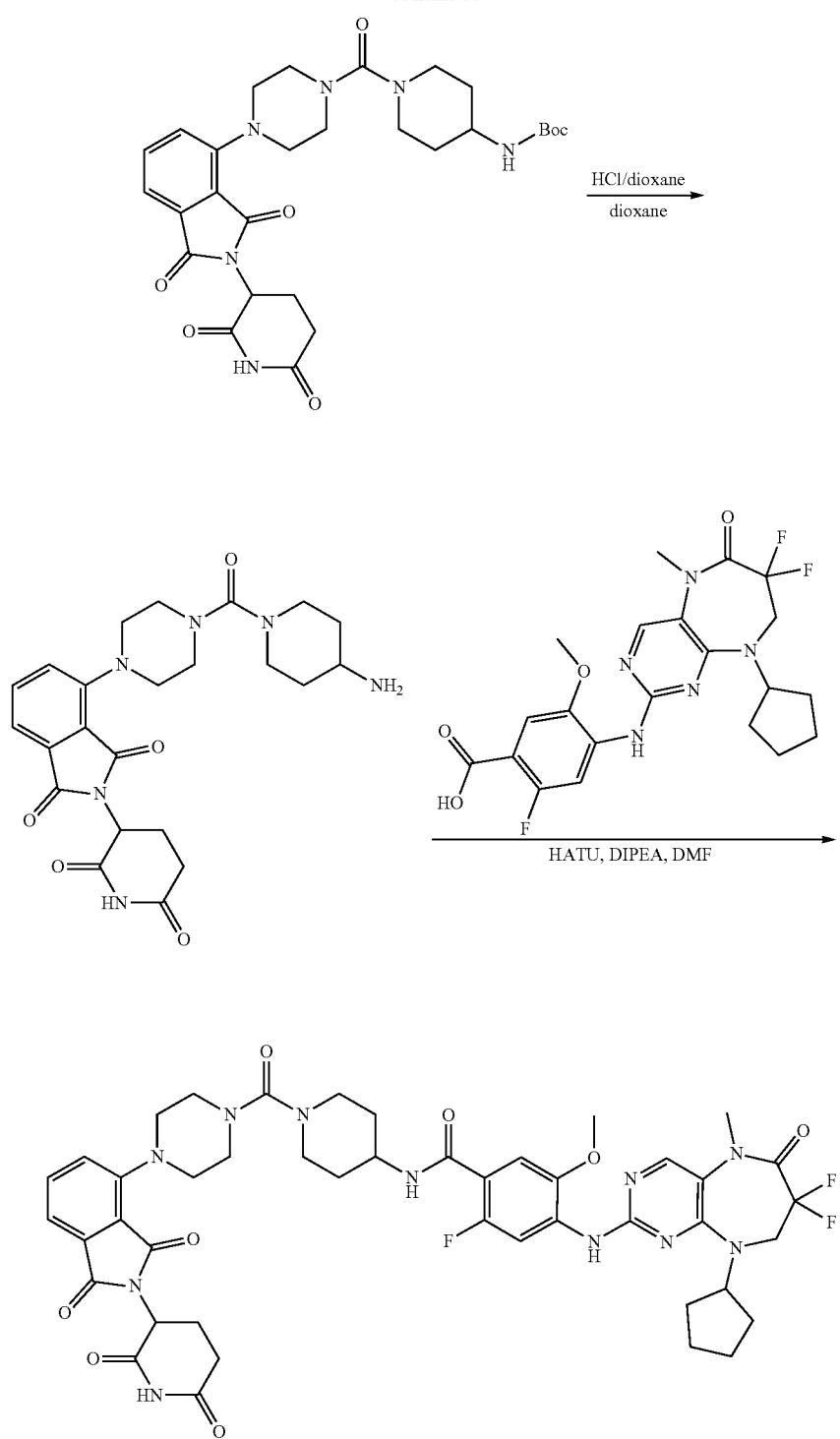
Compound 69
According to the above reaction scheme, in a manner similar to the other examples, obtained the titled compound (78.3 mg, 83.78 μmol, 25.99% yield, 98% purity) as a light yellow solid. MS(M+H)$^+$=916.6
$^1$H NMR (400 MHz, DMSO-d$_6$) δ 11.07 (br s, 1H), 8.34-8.23 (m, 2H), 8.04 (s, 1H), 7.96 (dd, J=3.0, 7.7 Hz, 1H), 7.73 (dd, J=7.3, 8.2 Hz, 1H), 7.38 (dd, J=7.8, 12.0 Hz, 2H), 7.21 (d, J=6.7 Hz, 1H), 5.11 (dd, J=5.4, 12.9 Hz, 1H), 4.87-4.75 (m, 1H), 4.08 (t, J=13.9 Hz, 2H), 4.02-3.97 (m, 1H), 3.92 (s, 3H), 3.65 (d, J=12.7 Hz, 2H), 3.40-3.37 (m, 2H), 3.32-3.30 (m, 5H), 2.96-2.84 (m, 3H), 2.64-2.52 (m, 6H), 2.06-1.90 (m, 3H), 1.86-1.79 (m, 2H), 1.75-1.50 (m, 8H).

Example 70. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(2-(4-(2-(2,6-dioxopiperidin-3-yl)-1,3-dioxoisoindolin-4-yl)piperazin-1-yl)acetyl)piperidin-4-yl)-2-fluoro-5-methoxybenzamide

According to the above reaction scheme, in a manner similar to the other examples, obtained the titled compound (81.8 mg, 86.20 µmol, 33.43% yield, 98% purity) as a yellow solid. MS (M+H)$^+$=930.1

$^1$H NMR (400 MHz, DMSO-d δ=11.08 (s, 1H), 8.31-8.22 (m, 2H), 8.07-7.93 (m, 2H), 7.70 (dd, J=7.2, 8.2 Hz, 1H), 7.39-7.31 (m, 2H), 7.19 (d, J=6.8 Hz, 1H), 5.14-5.04 (m,

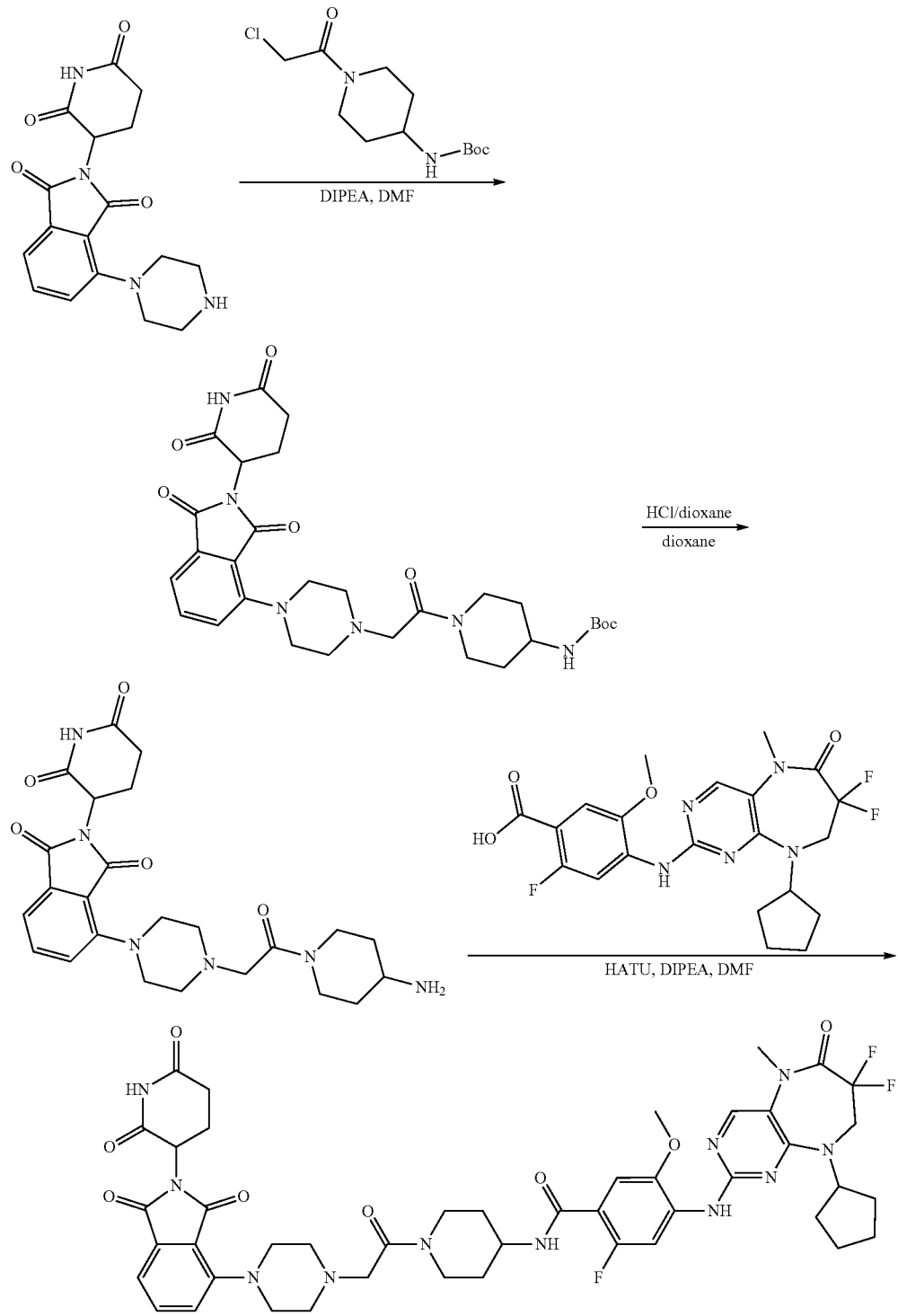

Compound 70

1H), 4.87-4.76 (m, 1H), 4.35-4.24 (m, 1H), 4.12-4.01 (m, 4H), 3.91 (s, 3H), 3.33 (s, 3H), 3.19-3.10 (m, 2H), 2.95-2.68 (m, 3H), 2.65-2.53 (m, 10H), 2.04-1.81 (m, 5H), 1.72-1.50 (m, 7H), 1.46-1.32 (m, 1H)
Example 71. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(3-(4-(2-(2,6-dioxopiperidin-3-yl)-1,3-dioxoisoindolin-4-yl)piperazin-1-yl)propanoyl)piperidin-4-yl)-2-fluoro-5-methoxybenzamide
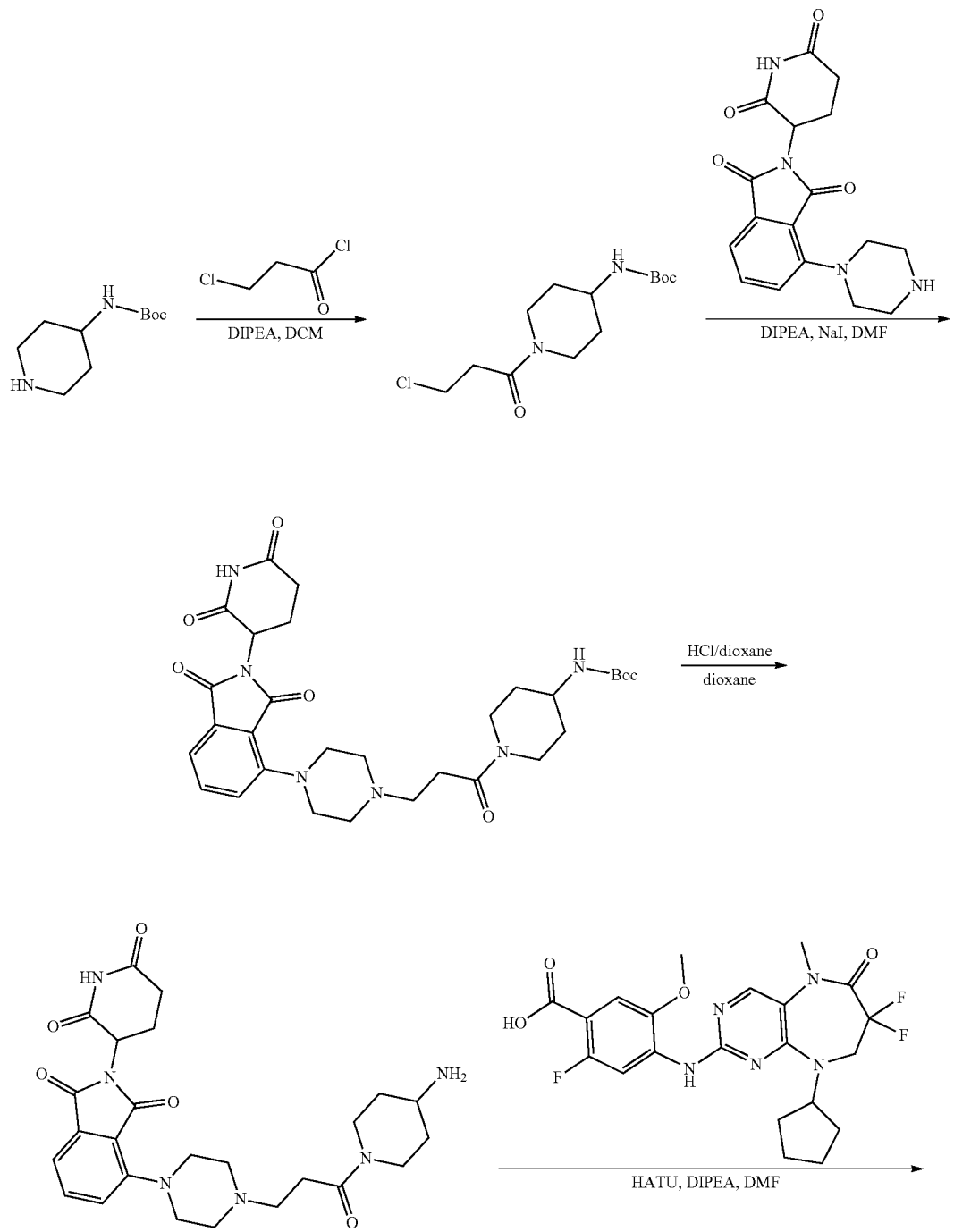

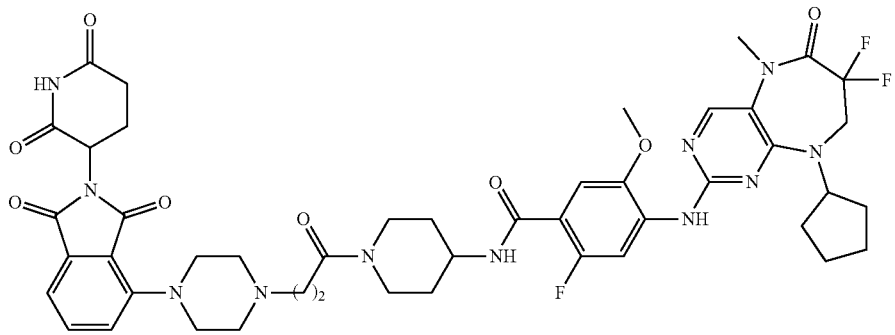

Compound 71

According to the above reaction scheme, in a manner similar to the other examples, obtained the titled compound (62.2 mg, 64.57 μmol, 25.05% yield, 98% purity) as a yellow solid. MS (M+H)$^+$=943.9

$^1$H NMR (400 MHz, DMSO-d$_6$) δ=11.08 (s, 1H), 8.34-8.23 (m, 2H), 8.06-7.93 (m, 2H), 7.73-7.67 (m, 1H), 7.35 (t, J=7.0 Hz, 2H), 7.20 (d, J=6.6 Hz, 1H), 5.09 (dd, J=5.4, 12.6 Hz, 1H), 4.88-4.76 (m, 1H), 4.36-4.26 (m, 1H), 4.11-4.04 (m, 2H), 3.91 (s, 3H), 3.33 (s, 3H), 3.27-3.06 (m, 5H), 2.89-2.82 (m, 1H), 2.78-2.70 (m, 1H), 2.69-2.65 (m, 1H), 2.65-2.51 (m, 10H), 2.07-1.78 (m, 6H), 1.76-1.68 (m, 2H), 1.68-1.56 (m, 4H), 1.53-1.45 (m, 1H), 1.42-1.32 (m, 1H)

Example 72. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(4-(2-(2,6-dioxopiperidin-3-yl)-1,3-dioxoisoindolin-5-yl)piperazine-1-carbonyl)piperidin-4-yl)-2-fluoro-5-methoxybenzamide

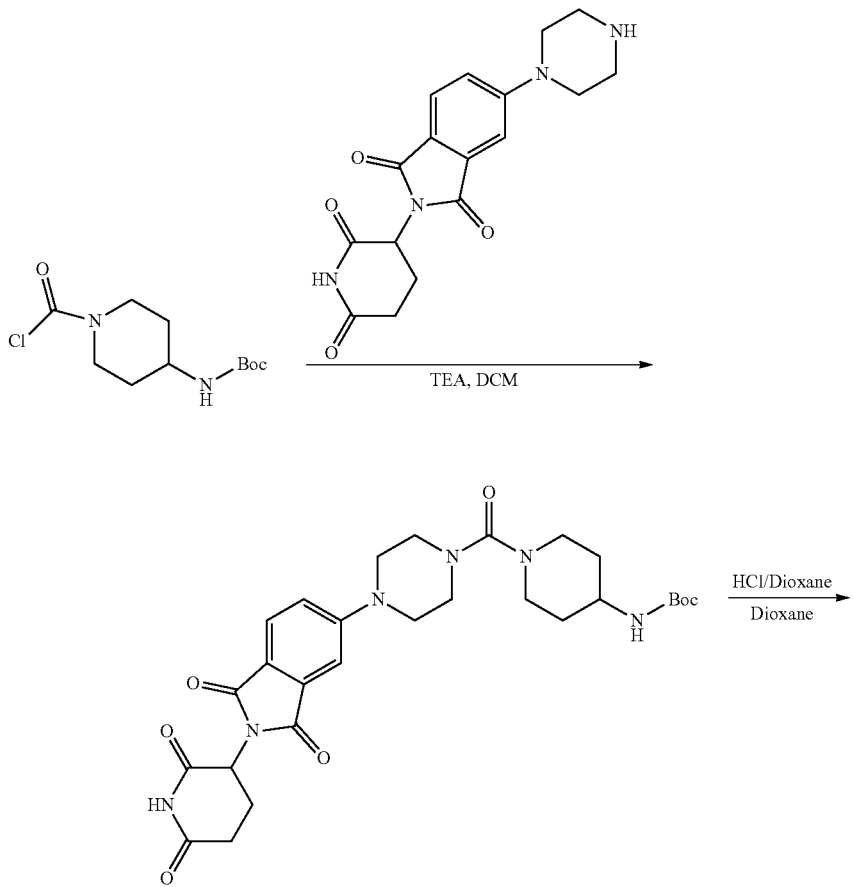

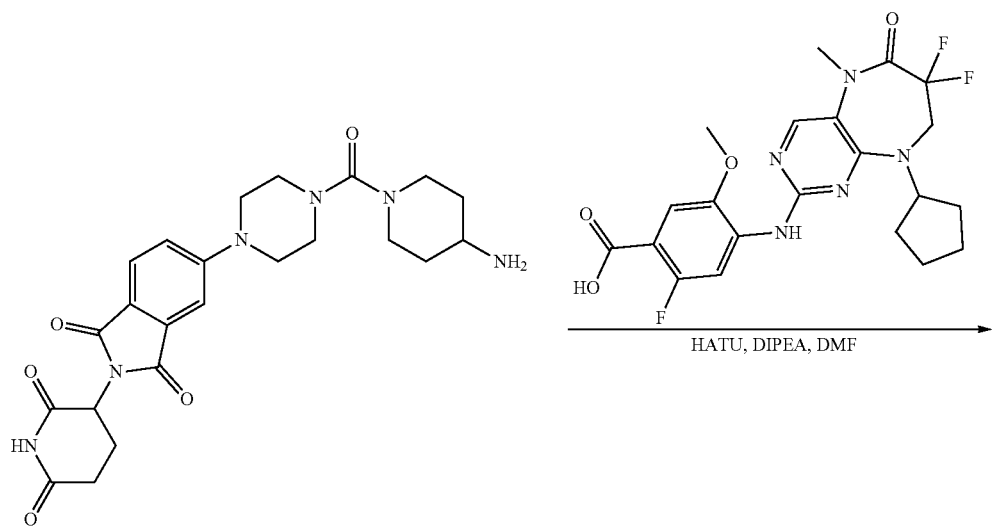
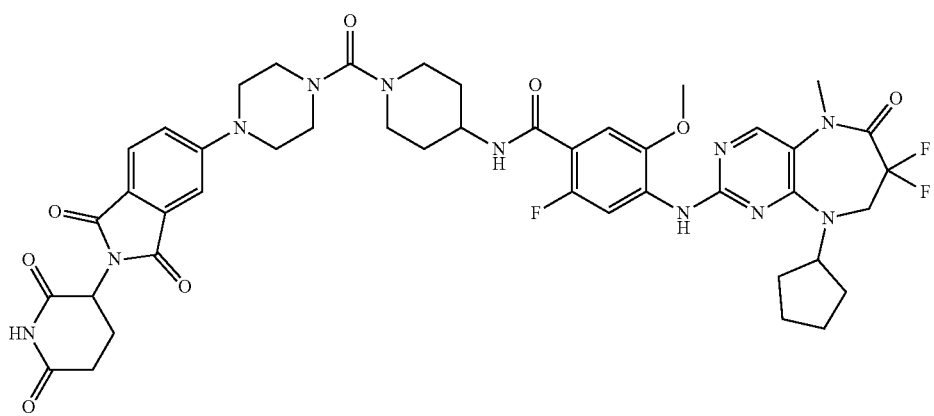
Compound 72
According to the above reaction scheme, in a manner similar to the other examples, obtained the titled compound (39.9 mg, 42.69 μmol, 13.25% yield, 98% purity) as a light yellow solid. MS(M+H)$^+$=916.6
$^1$H NMR (400 MHz, DMSO-d$_6$) δ 11.06 (br s, 1H), 8.32-8.24 (m, 2H), 8.04 (s, 1H), 7.98 (dd, J=3.0, 7.5 Hz, 1H), 7.71 (d, J=8.5 Hz, 1H), 7.36 (d, J=1.8 Hz, 1H), 7.26 (dd, J=2.0, 8.7 Hz, 1H), 7.21 (d, J=6.8 Hz, 1H), 5.08 (dd, J=5.3, 12.9 Hz, 1H), 4.83 (t, J=8.0 Hz, 1H), 4.08 (t, J=13.9 Hz, 2H), 4.02-3.97 (m, 1H), 3.92 (s, 3H), 3.65 (d, J=13.1 Hz, 2H), 3.53-3.45 (m, 4H), 3.32-3.29 (m, 3H), 2.97-2.85 (m, 3H), 2.65-2.51 (m, 6H), 2.04-1.91 (m, 3H), 1.83 (d, J=10.4 Hz, 2H), 1.76-1.52 (m, 8H).

Example 73. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(2-(4-(2-(2,6-dioxopiperidin-3-yl)-1,3-dioxoisoindolin-5-yl)piperazin-1-yl)acetyl)piperidin-4-yl)-2-fluoro-5-methoxybenzamide
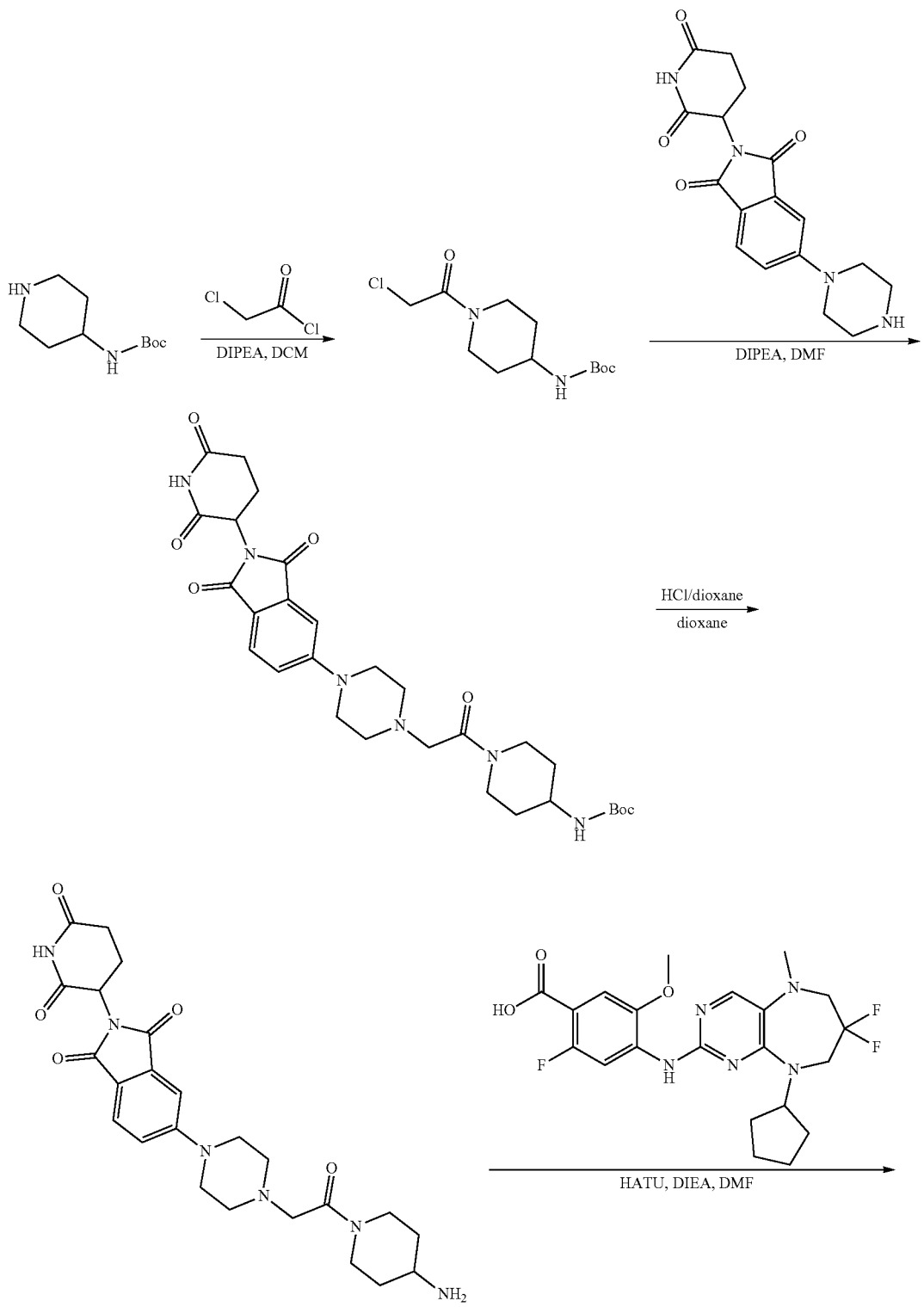

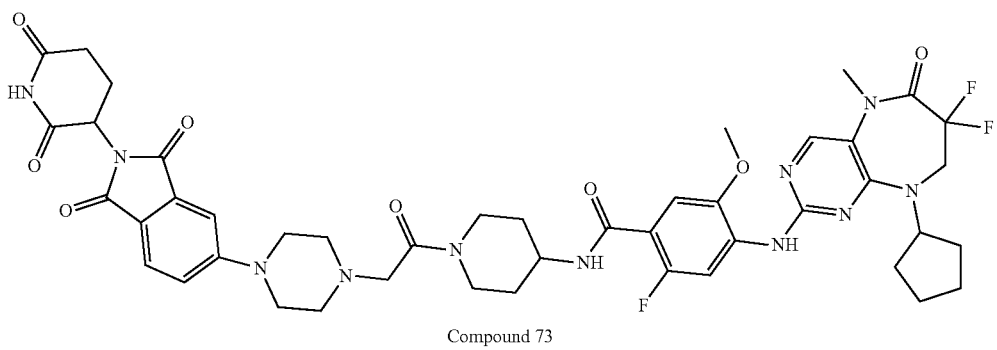

Compound 73

According to the above reaction scheme, in a manner similar to the other examples, obtained the titled compound (51.8 mg, 54.59 μmol, 25.41% yield, 98% purity) as a yellow solid. MS(M+H)$^+$=930.7.

$^1$H NMR (400 MHz, DMSO-d$_6$) δ=11.06 (br s, 1H), 8.45-8.16 (m, 2H), 8.13-7.91 (m, 2H), 7.68 (d, J=8.6 Hz, 1H), 7.35 (d, J=1.7 Hz, 1H), 7.25 (dd, J$_1$=1.9, J$_2$=8.7 Hz, 1H), 7.19 (d, J=6.7 Hz, 1H), 5.07 (dd, J$_1$=5.4, J$_2$=12.8 Hz, 1H), 4.81 (br t, J=7.9 Hz, 1H), 4.29 (br d, J=11.7 Hz, 1H), 4.16-3.97 (m, 4H), 3.91 (s, 3H), 3.52-3.35 (m, 8H), 3.20-3.06 (m, 2H), 2.94-2.82 (m, 1H), 2.81-2.71 (m, 1H), 2.63-2.53 (m, 6H), 2.10-1.91 (m, 3H), 1.91-1.75 (m, 2H), 1.71-1.60 (m, 2H), 1.67-1.47 (m, 5H), 1.46-1.30 (m, 1H).

Example 74. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(3-(4-(2-(2,6-dioxopiperidin-3-yl)-1,3-dioxoisoindolin-5-yl)piperazin-1-yl)propanoyl)piperidin-4-yl)-2-fluoro-5-methoxybenzamide

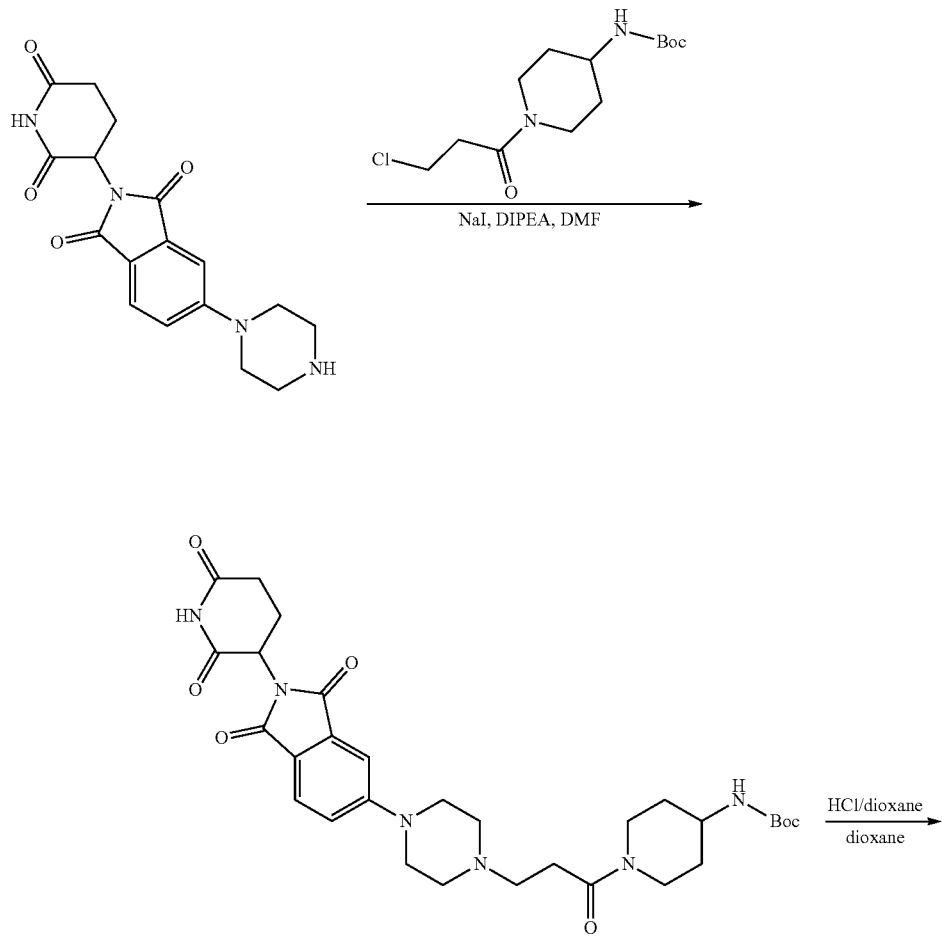

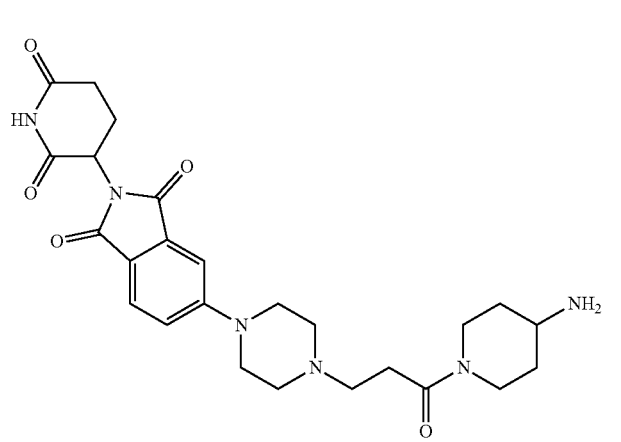
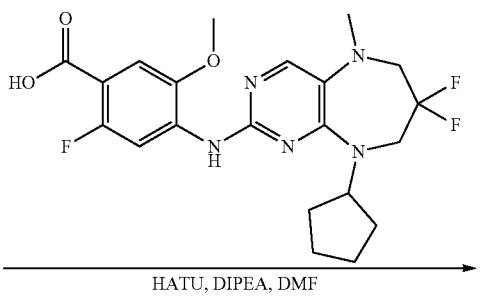

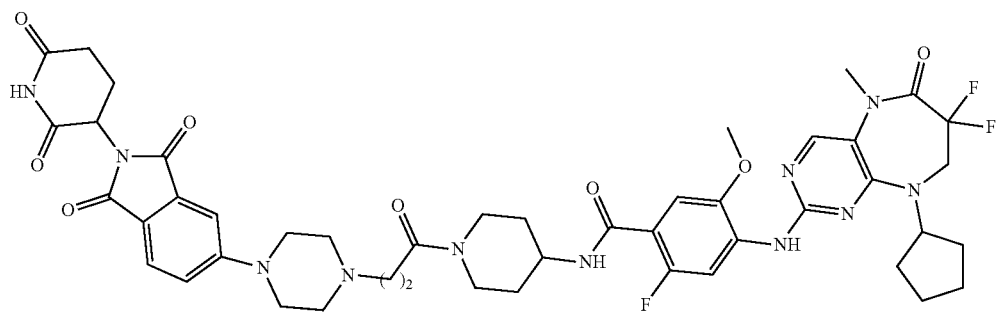

Compound 74

According to the above reaction scheme, in a manner similar to the other examples, obtained the titled compound (29.8 mg, 30.94 μmol, 28.80% yield, 98% purity) as a yellow solid. MS(M+H)$^+$=944.8.

$^1$H NMR (400 MHz, DMSO-d$_6$) δ=11.07 (s, 1H), 8.30 (s, 1H), 8.24 (d, J=13.3 Hz, 1H), 8.04 (s, 1H), 7.97 (br dd, J$_1$=2.7, J$_2$=7.2 Hz, 1H), 7.67 (d, J=8.4 Hz, 1H), 7.34 (s, 1H), 7.31-7.23 (m, 1H), 7.20 (d, J=6.7 Hz, 1H), 5.07 (dd, J$_1$=5.4, J$_2$=12.8 Hz, 1H), 4.82 (br t, J=8.1 Hz, 1H), 4.31 (br d, J=12.6 Hz, 1H), 4.14-3.99 (m, 3H), 3.98-3.84 (m, 4H), 3.48-3.38 (m, 7H), 3.15 (br t, J=12.5 Hz, 1H), 2.94-2.81 (m, 1H), 2.74 (br t, J=11.4 Hz, 1H), 2.63-2.54 (m, 10H), 2.09-1.92 (m, 3H), 1.91-1.78 (m, 2H), 1.72 (br d, J=1.2 Hz, 2H), 1.68-1.54 (m, 4H), 1.53-1.43 (m, 1H), 1.43-1.29 (m, 1H).

Example 75. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(2-(2-(2-((2-(2,6-dioxopiperidin-3-yl)-1-oxoisoindolin-4-yl)amino)ethoxy)ethoxy)ethyl)piperidin-4-yl)-2-fluoro-5-methoxybenzamide

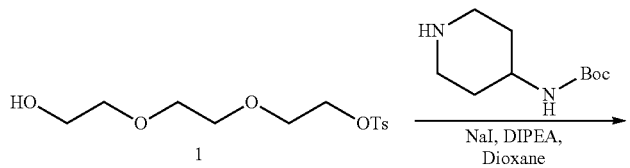

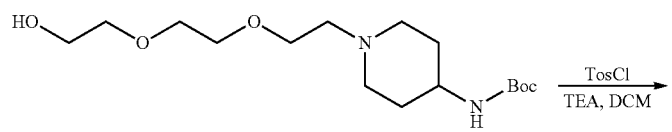

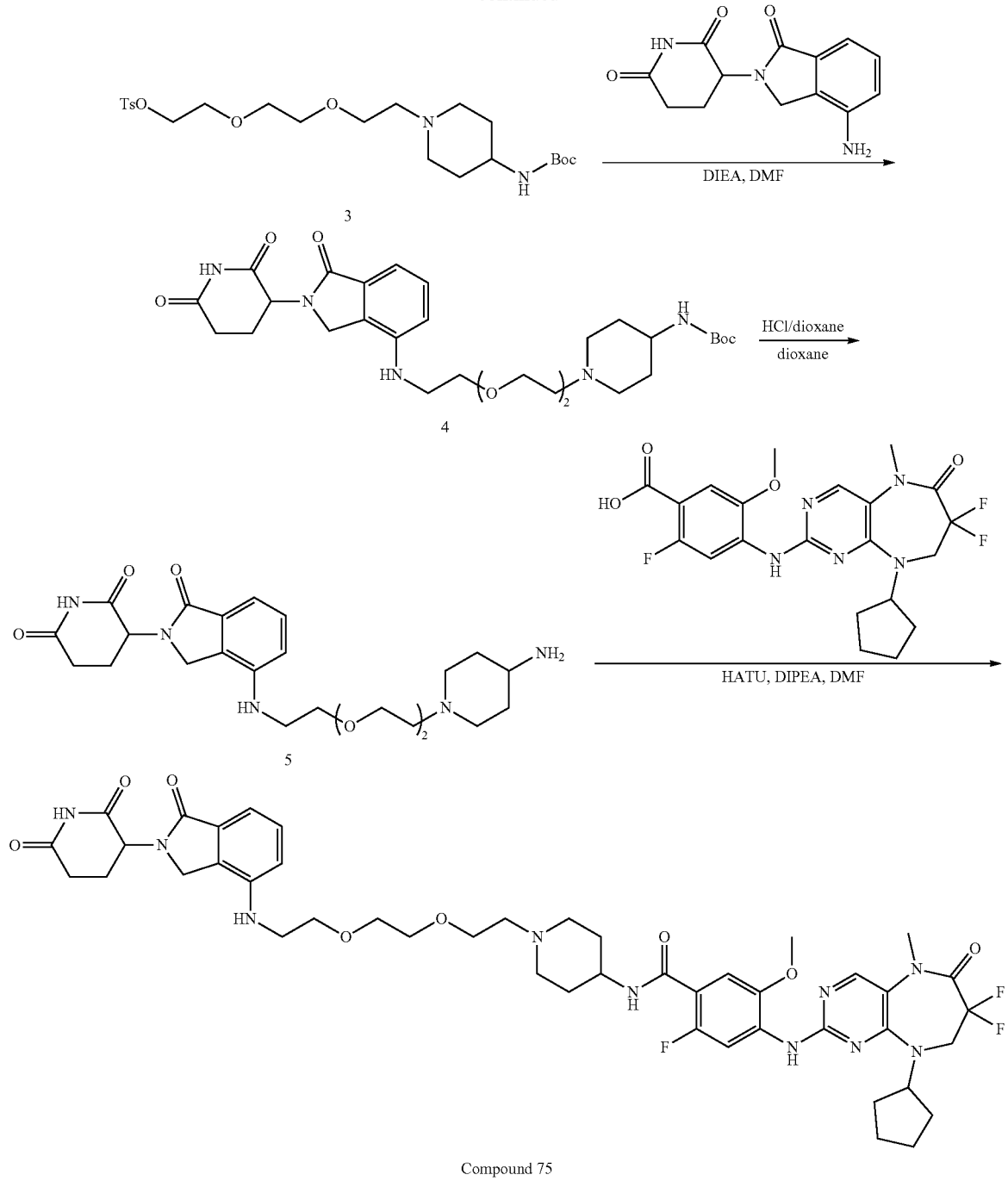

Compound 75

Step 1: Synthesis of tert-butyl (1-(2-(2-(2-hydroxyethoxy)ethoxy)ethyl)piperidin-4-yl)carbamate (2)

To a solution of 2-(2-(2-hydroxyethoxy)ethoxy)ethyl 4-methylbenzenesulfonate (4.0 g, 13.14 mmol) and tert-butyl N-(4-piperidyl)carbamate (3.95 g, 19.71 mmol) in dioxane (20 mL) were added NaI (197.00 mg, 1.31 mmol) and DIPEA (1.70 g, 13.14 mmol, 2.29 mL) and the resulting mixture was stirred at 60° C. for 12 h. LCMS showed that the reaction was completed. The mixture was diluted with H₂O (100 mL) and extracted with EtOAc (300 mL×3), the combined organic layers were washed with Brine (100 mL×1), dried over Na₂SO₄, filtered and concentrated under reduced pressure to afford the titled compound (5.55 g, crude) as yellow solid. MS(M+H)⁺=333.4

Step 2: Synthesis of 2-(2-(2-(4-((tert-butoxycarbonyl)amino)piperidin-1-yl)ethoxy)ethoxy)ethyl 4-methylbenzenesulfonate (3)

To a solution of tert-butyl (1-(2-(2-(2-hydroxyethoxy)ethoxy)ethyl)piperidin-4-yl)carbamate (5.55 g, 16.70 mmol) in DCM (30 mL) were added TEA (5.07 g, 50.09 mmol, 6.97 mL) followed by TosCl (6.37 g, 33.39 mmol) and the mixture was stirred at 15° C. for 16 h. LCMS showed that the reaction was completed. The mixture was concentrated in vacuo. The residue was purified by column chromatography (SiO$_2$, EtOAc/MeOH=10/1) to afford the titled compound (4.27 g, 8.77 mmol, 52.56% yield) as brown oil. MS (M+H)$^+$=487.2

Step 3: Synthesis of tert-butyl (1-(2-(2-(2-((2-(2,6-dioxopiperidin-3-yl)-1-oxoisoindolin-4-yl)amino) ethoxy)ethoxy)ethyl)piperidin-4-yl)carbamate (4)

To a solution of 2-(2-(2-(4-((tert-butoxycarbonyl)amino)piperidin-1-yl)ethoxy)ethoxy)ethyl 4-methylbenzenesulfonate (4.27 g, 8.77 mmol) and 3-(4-amino-1-oxo-isoindolin-2-yl) piperidine-2,6-dione (2.73 g, 10.53 mmol) in DMF (30 mL) was added DIEA (1.13 g, 8.77 mmol, 1.53 mL) and the mixture was stirred at 110° C. for 16 h. LCMS showed that the reaction was completed. The reaction mixture was diluted with H$_2$O (30 mL) and extracted with EtOAc (500 mL×3), the combined organic layers were dried over Na$_2$SO$_4$, filtered and concentrated under reduced pressure. The residue was purified by reversed-phase HPLC (0.1% FA condition, MeCN/water) to afford the titled compound (200 mg, 0.322 mmol, 3.68% yield, FA) as brown solid. MS(M+H)$^+$=574.3

Step 4: Synthesis of 3-(4-((2-(2-(2-(4-aminopiperidin-1-yl)ethoxy)ethoxy)ethyl)amino)-1-oxoisoindolin-2-yl)piperidine-2,6-dione (5)

To the mixture of tert-butyl (1-(2-(2-(2-((2-(2,6-dioxopiperidin-3-yl)-1-oxoisoindolin-4-yl)amino)ethoxy)ethoxy)ethyl)piperidin-4-yl)carbamate (200 mg, 348.63 μmol) in dioxane (2 mL) was added HCl/dioxane (4 M, 2 mL) and the resulting mixture was stirred at 25° C. for 0.5 h. LCMS showed that the reaction was completed. The mixture was concentrated to afford the titled compound (178 mg, crude, HCl salt) as yellow oil. MS(M+H)$^+$=474.2

Step 5: Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(2-(2-(2-((2-(2,6-dioxopiperidin-3-yl)-1-oxoisoindolin-4-yl)amino)ethoxy)ethoxy)ethyl)piperidin-4-yl)-2-fluoro-5-methoxybenzamide (Compound 75)

To the mixture of 4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzoic acid (160 mg, 343.77 μmol), 3-(4-((2-(2-(2-(4-aminopiperidin-1-yl)ethoxy)ethoxy)ethyl)amino)-1-oxoisoindolin-2-yl)piperidine-2,6-dione (175.33 mg, 343.77 μmol, HCl salt) and HATU (261.42 mg, 687.54 μmol) in DMF (4 mL) was added DIPEA (133.29 mg, 1.03 mmol, 179.64 μL) and the resulting mixture was stirred at 20° C. for 12 h. LCMS showed that the reaction was completed. The mixture was poured into water (50 mL) and extracted with EtOAc (50 mL×3), the combined organic layer was washed with brine (100 mL), dried over Na$_2$SO$_4$, filtered and concentrated. The residue was purified by prep-HPLC (column: Phenomenex luna C$_{18}$ 150*40 mm*15 um; mobile phase: [water (0.225% FA)-ACN]; B %: 18%-48%, 10 min) and the eluant was lyophilized to afford the titled compound (44.3 mg, 44.73 μmol, 13.01% yield, 93% purity) as black brown solid. MS (M+H)$^+$=921.7.

$^1$H NMR (400 MHz, DMSO-d6) δ 11.02 (s, 1H), 8.30 (s, 1H), 8.25 (d, J=13.3 Hz, 1H), 8.16 (s, 1H), 8.05 (s, 1H), 7.94 (dd, J=7.8, 3.3 Hz, 1H), 7.29 (t, J=7.8 Hz, 1H), 7.19 (d, J=6.7 Hz, 1H), 6.95 (d, J=7.4 Hz, 1H), 6.81 (d, J=8.1 Hz, 1H), 5.61 (t, J=5.7 Hz, 1H), 5.12 (dd, J=13.3, 5.1 Hz, 1H), 4.91-4.74 (m, 1H), 4.23 (d, J=17.2 Hz, 1H), 4.17-4.02 (m, 3H), 3.91 (s, 3H), 3.82-3.73 (m, 1H), 3.62-3.58 (m, 2H), 3.58-3.51 (m, 7H), 3.32 (s, 3H), 3.00-2.85 (m, 3H), 2.66-2.54 (m, 3H), 2.38-2.16 (m, 3H), 2.08-1.90 (m, 3H), 1.87-1.77 (m, 2H), 1.76-1.69 (m, 2H), 1.68-1.53 (m, 6H).

Example 76. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(14-((2-(2,6-dioxopiperidin-3-yl)-1-oxoisoindolin-4-yl)amino)-3,6,9,12-tetraoxatetradecyl)piperidin-4-yl)-2-fluoro-5-methoxybenzamide

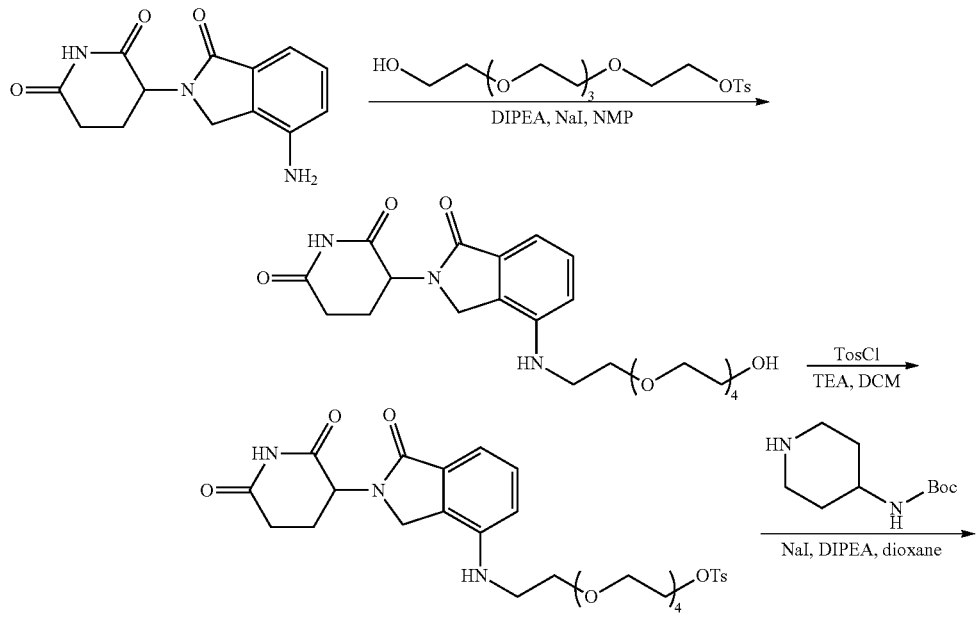

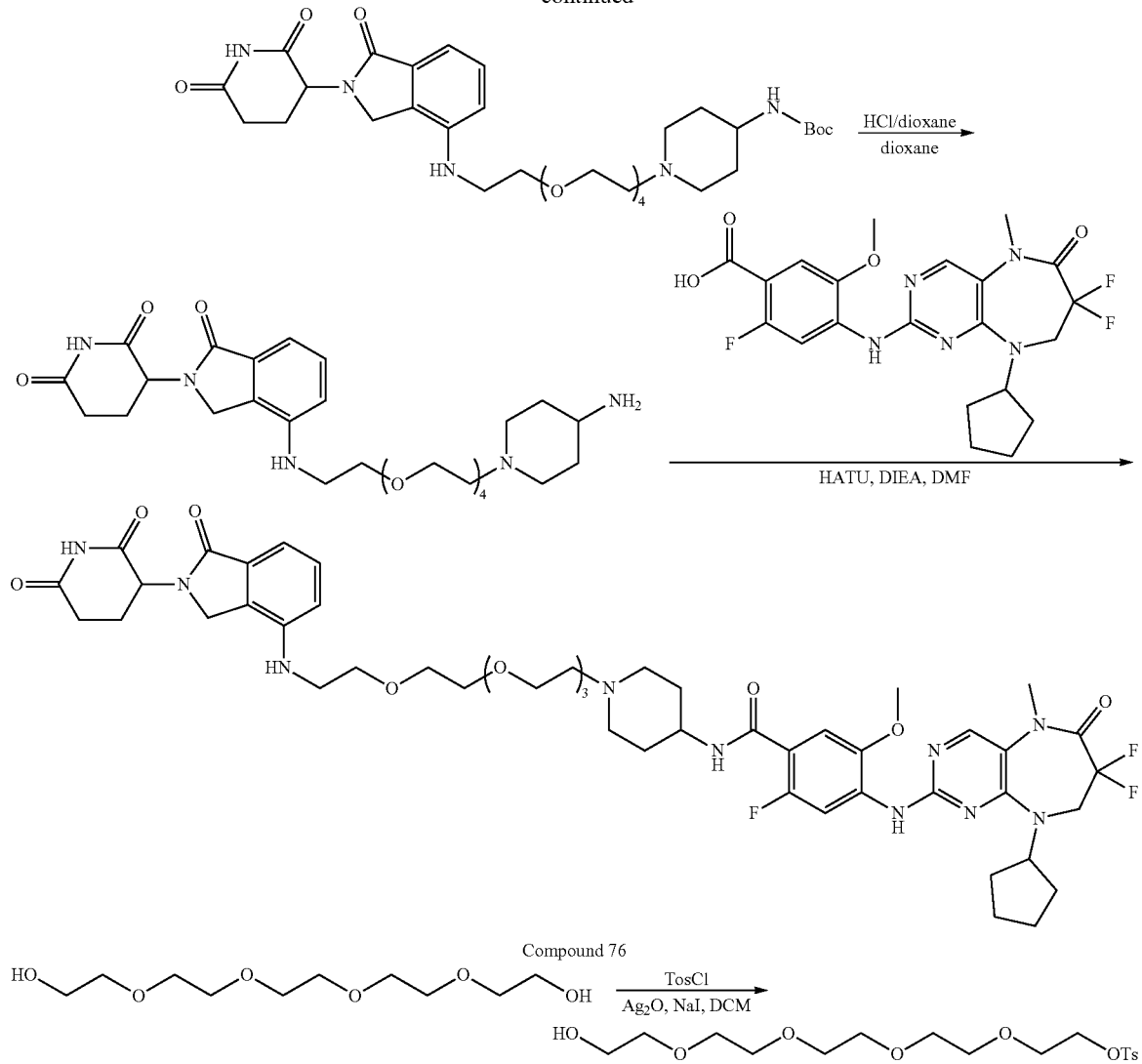

According to the above reaction scheme, in a manner similar to the other examples, obtained the titled compound (41.3 mg, 34.20 μmol, 6.20% yield, 93% purity, TFA salt) as a light brown solid. MS(M+H)⁺=1009.1

¹H NMR (400 MHz, CD₃OD) δ=8.30-8.13 (m, 2H), 7.42-7.23 (m, 2H), 7.13-7.00 (m, 1H), 6.86 (d, J=8.0 Hz, 1H), 5.21-5.10 (m, 1H), 5.05-4.97 (m, 1H), 4.38-4.22 (m, 2H), 4.21-4.05 (m, 3H), 4.01-3.94 (m, 3H), 3.85-3.54 (m, 18H), 3.48-3.35 (m, 6H), 3.28-3.25 (m, 1H), 3.12-3.06 (m, 1H), 2.98-2.85 (m, 1H), 2.83-2.74 (m, 1H), 2.5-2.38 (m, 1H), 2.33-2.14 (m, 3H), 2.13-2.00 (m, 3H), 1.98-1.65 (m, 8H).

Example 77. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(8-((2-(2,6-dioxopiperidin-3-yl)-1-oxoisoindolin-4-yl)amino)octyl)piperidin-4-yl)-2-fluoro-5-methoxybenzamide

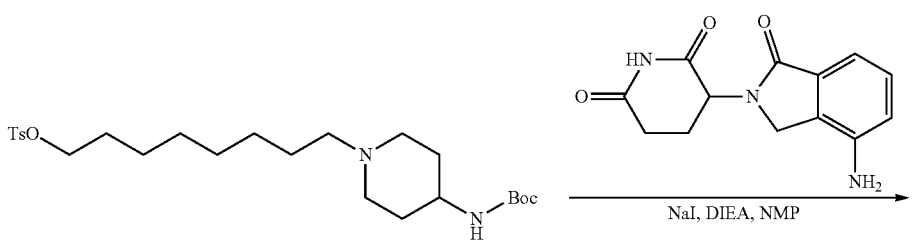

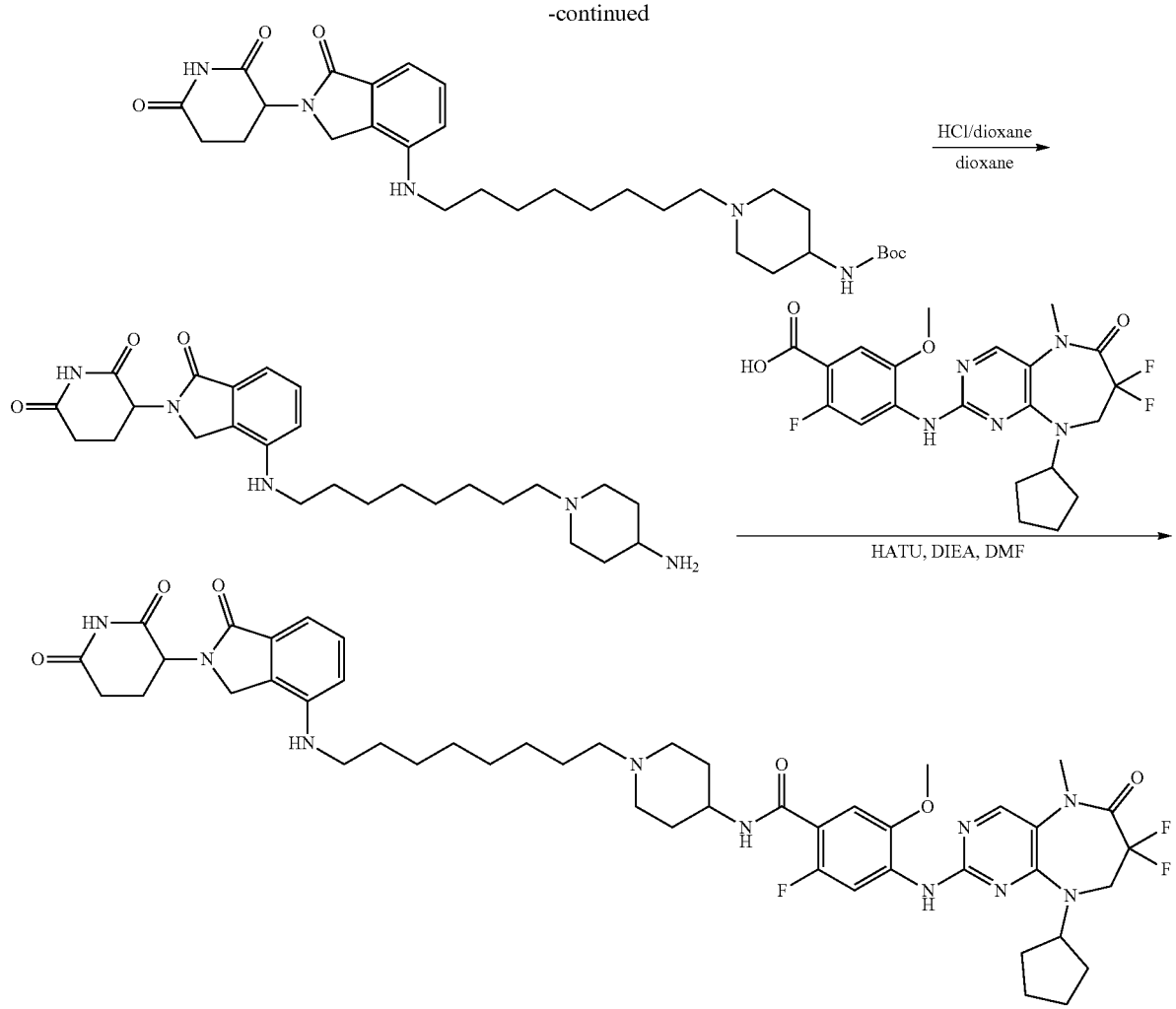

Compound 77

According to the above reaction scheme, in a manner similar to the other examples, obtained the titled compound (17.7 mg, 18.14 μmol, 8.44% yield, 94% purity). MS(M+H)+=917.8.

1H NMR (400 MHz, DMSO-d$_6$) δ=11.01 (br s, 1H), 8.30 (s, 1H), 8.25 (d, J=13.3 Hz, 1H), 8.04 (s, 1H), 7.88 (br dd, J=3.3, 7.6 Hz, 1H), 7.28 (t, J=7.7 Hz, 1H), 7.19 (d, J=6.6 Hz, 1H), 6.93 (d, J=7.4 Hz, 1H), 6.74 (d, J=7.9 Hz, 1H), 5.56 (br t, J=5.2 Hz, 1H), 5.12 (dd, J=5.0, 13.3 Hz, 1H), 4.89-4.75 (m, 1H), 4.27-4.11 (m, 2H), 4.11-4.02 (m, 2H), 3.92 (s, 3H), 3.79-3.67 (m, 1H), 3.33-3.29 (m, 3H), 3.15-3.08 (m, 2H), 2.98-2.88 (m, 1H), 2.81 (br d, J=11.4 Hz, 2H), 2.65-2.59 (m, 1H), 2.35-2.28 (m, 1H), 2.24 (br t, J=7.4 Hz, 2H), 2.08-1.89 (m, 5H), 1.90-1.65 (m, 4H), 1.68-1.48 (m, 8H), 1.45-1.22 (m, 10H).

Example 78. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(14-((3-(2,6-dioxopiperidin-3-yl)-4-oxo-3,4-dihydrobenzo[d][1,2,3]triazin-5-yl)amino)-3,6,9,12-tetraoxatetradecyl)piperidin-4-yl)-2-fluoro-5-methoxybenzamide

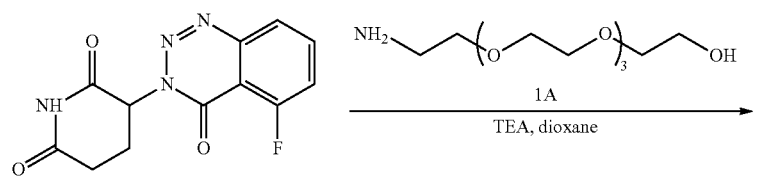

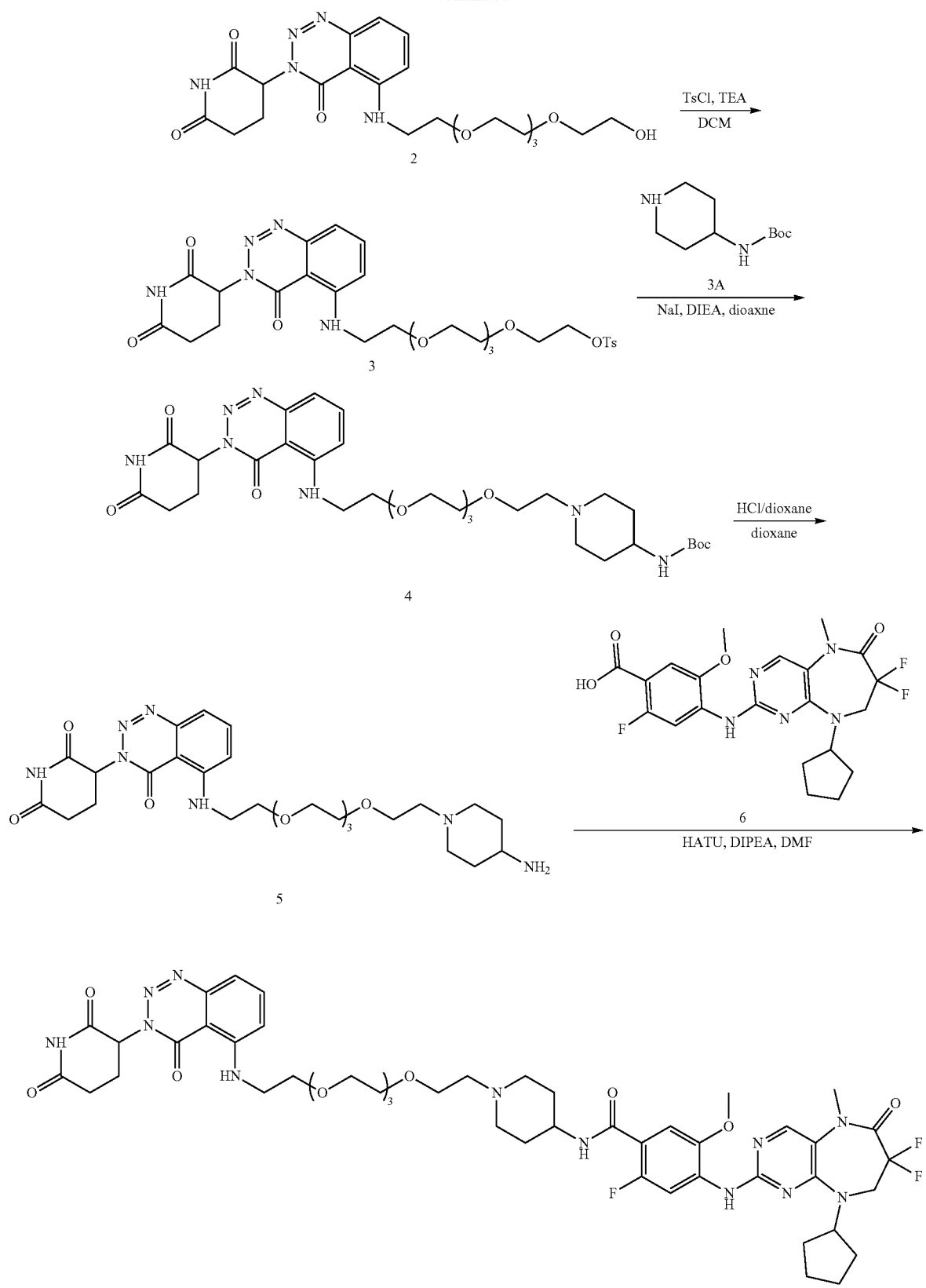
Compound 78

Step 1: Synthesis of 3-(5-((14-hydroxy-3,6,9,12-tetraoxatetradecyl)amino)-4-oxobenzo[d][1,2,3]triazin-3(4H)-yl)piperidine-2,6-dione (2)

To a solution of 3-(5-fluoro-4-oxobenzo[d][1,2,3]triazin-3(4H)-yl)piperidine-2,6-dione (1 g, 3.62 mmol) and TEA (1.10 g, 10.86 mmol, 1.51 mL) in dioxane (10 mL) was added 2-[2-[2-[2-(2-aminoethoxy) ethoxy]ethoxy]ethoxy]ethanol (944.97 mg, 3.98 mmol) at 25° C. and the resulting mixture was stirred at 110° C. for 14 h. LCMS showed main peak with the desired mass. The mixture was concentrated under reduced pressure. The residue was purified by flash silica gel chromatography (Silica Flash Column, Eluent of 0~15% Ethyl acetate/Methanol @ 30 mL/min) to afford the titled compound (1.6 g, 3.05 mmol, 84.18% yield, 94% purity) as a yellow oil. MS(M+H)$^+$=494.2

According to the above reaction scheme, in a manner similar to the other examples, obtained the titled compound (25.8 mg, 24.21 μmol, 11.27% yield, 96% purity) as a yellow solid. MS(M+H)$^+$=1023.3

$^1$H NMR (400 MHz, DMSO-d$_6$) δ=11.20 (br s, 1H), 8.32 (t, J=5.4 Hz, 1H), 8.29 (s, 1H), 8.23 (d, J=13.6 Hz, 1H), 8.05 (s, 1H), 7.96-7.86 (m, 1H), 7.79 (t, J=8.0 Hz, 1H), 7.19 (dd, J=7.2, 18.8 Hz, 2H), 7.00 (d, J=8.8 Hz, 1H), 5.86 (dd, J=4.8, 11.6 Hz, 1H), 4.97-4.69 (m, 1H), 4.08 (br t, J=14.0 Hz, 2H), 3.90 (s, 3H), 3.66 (br t, J=5.2 Hz, 3H), 3.59-3.53 (m, 4H), 3.50-3.46 (m, 7H), 3.46-3.44 (m, 3H), 3.34-3.31 (m, 4H), 3.01-2.88 (m, 1H), 2.83 (br d, J=11.6 Hz, 2H), 2.71-2.61 (m, 2H), 2.43 (t, J=5.8 Hz, 2H), 2.29-2.17 (m, 1H), 2.05-1.90 (m, 4H), 1.82-1.42 (m, 11H).

Example 79. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(8-((3-(2,6-dioxopiperidin-3-yl)-4-oxo-3,4-dihydrobenzo[d][1,2,3]triazin-5-yl)amino)octyl)piperidin-4-yl)-2-fluoro-5-methoxybenzamide

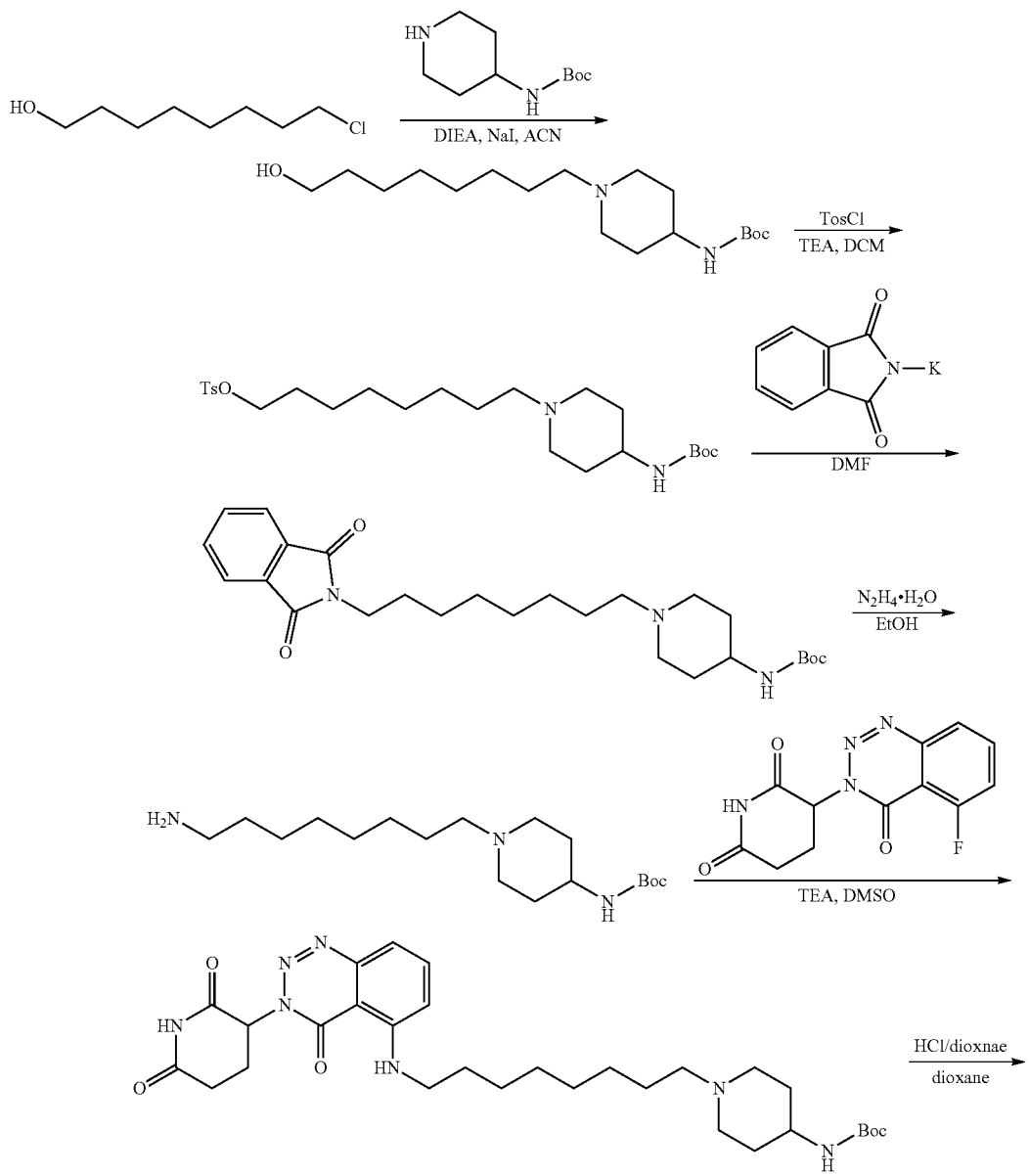

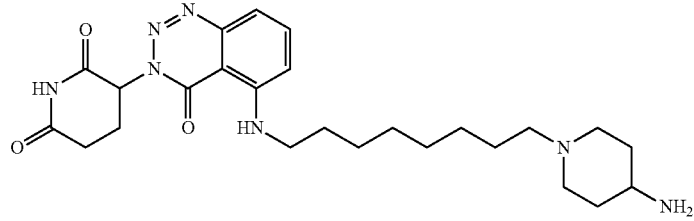
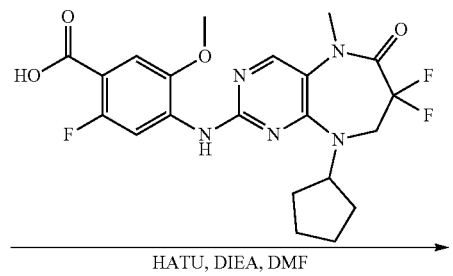

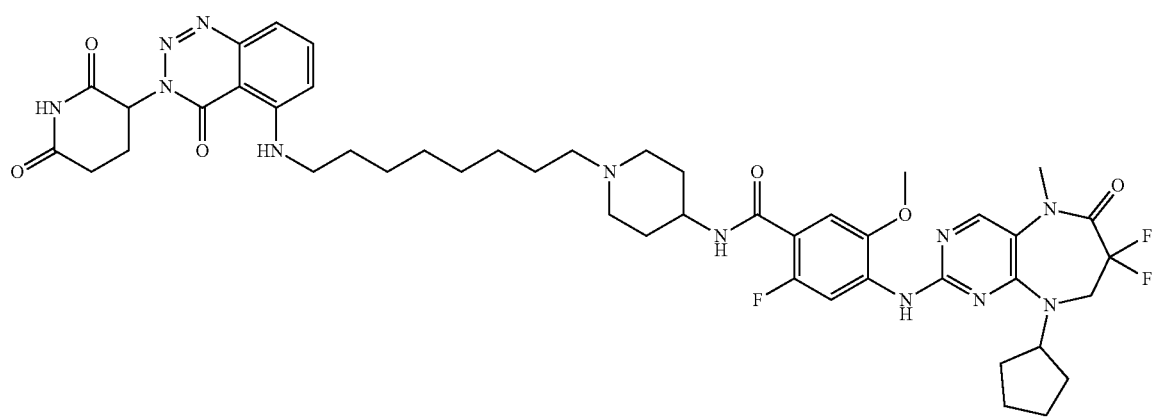

Compound 79

According to the above reaction scheme, in a manner similar to the other examples, obtained the titled compound (49.1 mg, 51.68 μmol, 24.05% yield, 98% purity) as a yellow solid. MS(M+H)$^+$=931.8.

$^1$H NMR (400 MHz, DMSO-d$_6$) δ=11.18 (s, 1H), 8.30 (s, 1H), 8.27-8.16 (m, 2H), 8.03 (s, 1H), 7.86 (dd, J$_1$=7.8 Hz, J$_2$=3.4 Hz, 1H), 7.79 (t, J=8.2 Hz, 1H), 7.19 (dd, J$_1$=8.3 Hz, J$_2$=7.4 Hz, 2H), 6.96 (d, J=8.5 Hz, 1H), 5.86 (dd, J$_1$=11.9 Hz, J$_2$=5.2 Hz, 1H), 4.90-4.73 (m, 1H), 4.07 (t, J=13.9 Hz, 2H), 3.91 (s, 3H), 3.78-3.65 (m, 1H), 3.33 (s, 3H), 3.25-3.20 (m, 2H), 2.99-2.88 (m, 1H), 2.80 (d, J=11.1 Hz, 2H), 2.70-2.61 (m, 2H), 2.28-2.18 (m, 3H), 2.01-1.88 (m, 4H), 1.82-1.68 (m, 4H), 1.66-1.44 (m, 8H), 1.43-1.23 (m, 10H).

Example 80. Synthesis of (2S,4R)-1-((S)-2-(2-(2-(2-(4-(4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenz amido)piperidin-1-yl)ethoxy)ethoxy)acetamido)-3,3-dimethylbutanoyl)-4-hydroxy-N-(4-(4-methylthiazol-5-yl)benzyl)pyrrolidine-2-carboxamide

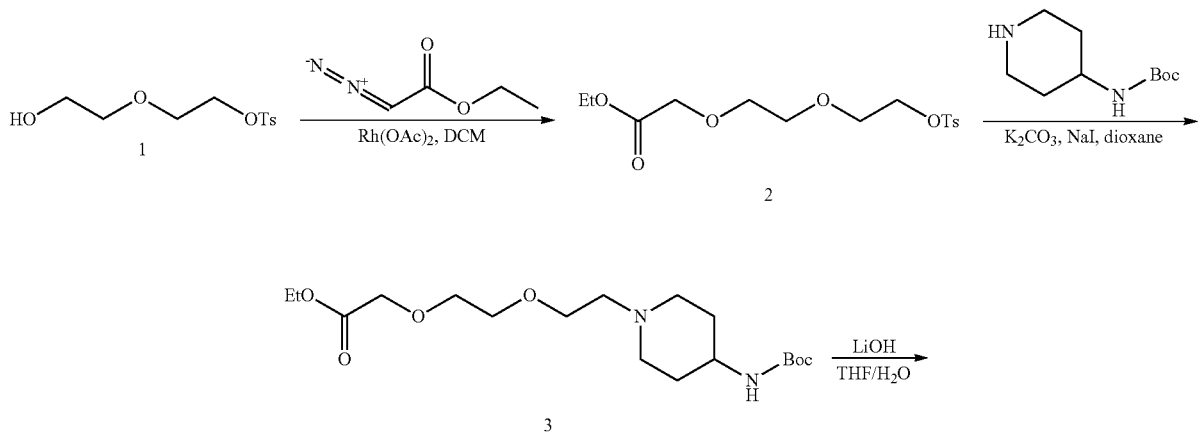

-continued
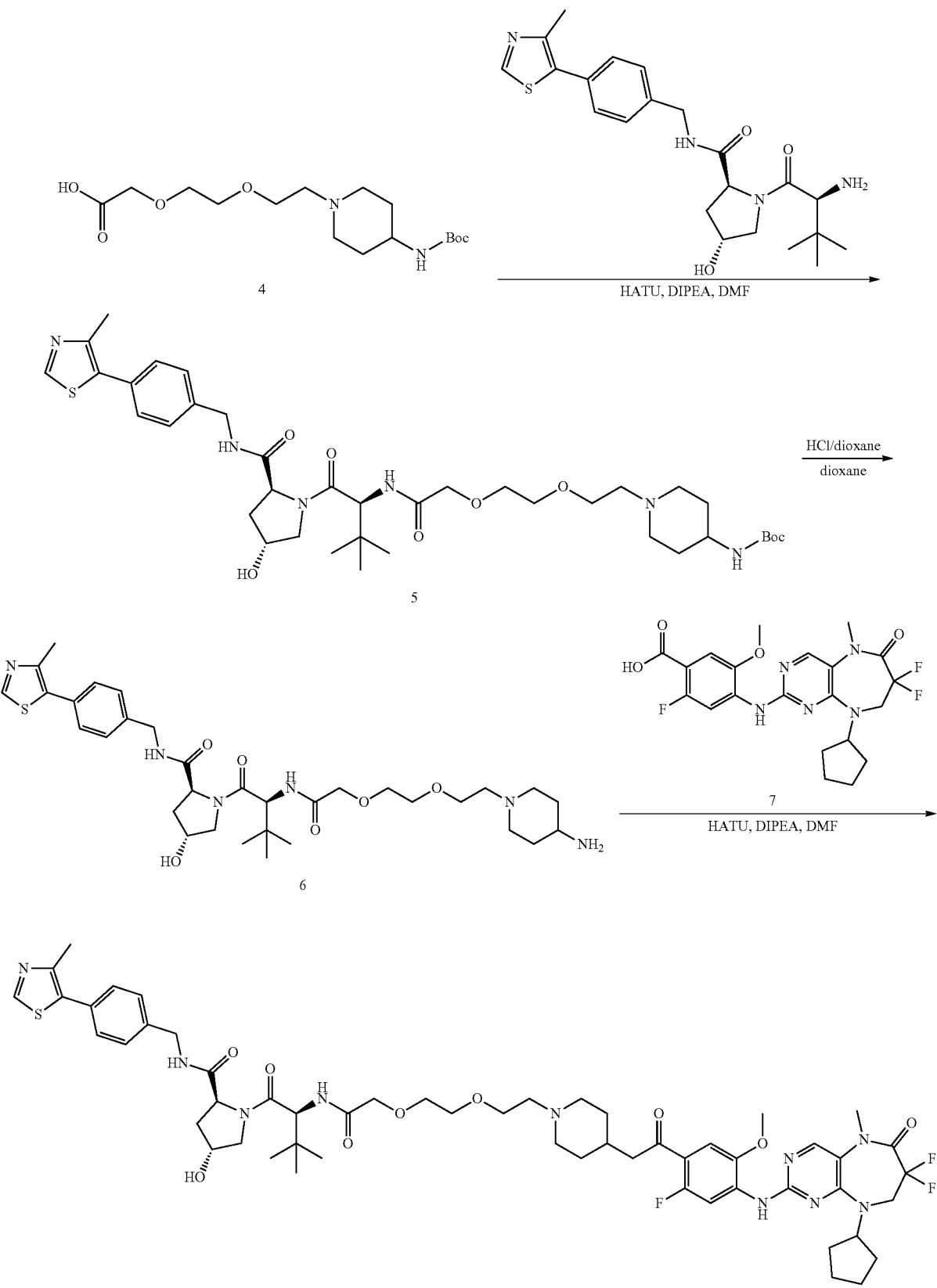
Compound 80

Step 1: Synthesis of ethyl 2-(2-(2-(tosyloxy)ethoxy)ethoxy)acetate (2)

To a solution of 2-(2-hydroxyethoxy)ethyl 4-methylbenzenesulfonate (500 mg, 1.92 mmol) and Rh(OAc)$_2$ (42 mg, 190.05 μmol) in DCM (10 mL) was added ethyl 2-diazoacetate (327.00 mg, 2.87 mmol, 300 μL) and the mixture was stirred at 20° C. for 14 h. LCMS showed the desired mass was detected and the starting material remained. Additional ethyl 2-diazoacetate (218.00 mg, 1.91 mmol, 200 μL) was added and the mixture was stirred at 30° C. for another 3 h. TLC (Petroleum ether:Ethyl acetate=1:1) showed the starting material was consumed and the new spot was detected. The mixture was concentrated under reduce pressure. The residue was purified by flash silica gel chromatography (5 g SepaFlash® Silica Flash Column, Eluent of 10~30% Ethyl acetate/Petroleum ether gradient @ 50 mL/min) to afford the titled compound (460 mg, 1.33 mmol, 69.14% yield) as a yellow oil. MS(M+H)$^+$=347.3

Step 2: Synthesis of ethyl 2-(2-(2-(4-((tert-butoxycarbonyl)amino)piperidin-1-yl) ethoxy)ethoxy)acetate (3)

To a solution of ethyl 2-(2-(2-(tosyloxy)ethoxy)ethoxy)acetate (460 mg, 1.33 mmol) and tert-butyl piperidin-4-ylcarbamate (240 mg, 1.20 mmol) in dioxane (10 mL) were added NaI (39.87 mg, 266.00 μmol) and K$_2$CO$_3$ (551.44 mg, 3.99 mmol) and the mixture was stirred at 80° C. for 14 h. LCMS showed the desired mass was detected. The mixture was filtered and the filter cake was washed with EtOAc (30 mL). The filtrate was concentrated under reduce pressure. The residue was purified by flash silica gel chromatography (5 g SepaFlash® Silica Flash Column, Eluent of 20-90% MeOH/Ethyl acetate gradient @ 50 mL/min) to afford the titled compound (370 mg, 938.66 μmol, 70.58% yield, 95% purity) as yellow oil. MS(M+H)$^+$=375.5.

Step 3: Synthesis of 2-(2-(2-(4-((tert-butoxycarbonyl)amino)piperidin-1-yl)ethoxy)ethoxy)acetic acid (4)

To a solution of ethyl 2-(2-(2-(4-((tert-butoxycarbonyl)amino)piperidin-1-yl)ethoxy)ethoxy)acetate (370 mg, 988.06 μmol) in THF (3 mL) was added a solution of LiOH.H$_2$O (49.76 mg, 1.19 mmol) in H$_2$O (1.5 mL) and the mixture was stirred at 40° C. for 14 h. LCMS showed the desired mass was detected. The mixture was concentrated under reduce pressure to afford the titled compound (350 mg, crude) as yellow solid.

Step 4: Synthesis of tert-butyl (1-(2-(2-(2-(((S)-1-((2S,4R)-4-hydroxy-2-((4-(4-methylthiazol-5-yl)benzyl)carbamoyl) pyrrolidin-1-yl)-3,3-dimethyl-1-oxobutan-2-yl)amino)-2-oxoethoxy)ethoxy)ethyl) piperidin-4-yl)carbamate (5)

To a solution of 2-(2-(2-(4-((tert-butoxycarbonyl)amino)piperidin-1-yl)ethoxy)ethoxy)acetic acid (300 mg, 851.42 μmol) in DMF (3 mL) were added HATU (647.47 mg, 1.70 mmol) and DIPEA (222.60 mg, 1.72 mmol, 300.00 μL) and the mixture was stirred at 20° C. for 15 min. Then a solution of (2S,4R)-1-((S)-2-amino-3,3-dimethylbutanoyl)-4-hydroxy-N-(4-(4-methylthiazol-5-yl)benzyl)pyrrolidine-2-carboxamide (360 mg, 770.84 μmol, HCl salt) and DIPEA (222.60 mg, 1.72 mmol, 300.00 μL) in DMF (3 mL) was added and the mixture was stirred at 20° C. for 14 h. LCMS showed the starting material remained and trace of the desired mass was detected. Additional HATU (647.47 mg, 1.70 mmol) was added and the mixture was stirred at 40° C. for another 14 h. LCMS showed desired mass was detected. The mixture was diluted with H$_2$O (10 mL) and extracted with EtOAc (10 mL×3). The combined organic layer was washed with H$_2$O (10 mL) and brine (10 mL×2), dried over Na$_2$SO$_4$ and filtered. The filtrate was concentrated under reduce pressure. The residue was purified by flash silica gel chromatography (5 g SepaFlash® Silica Flash Column, Eluent of 50~100% Ethyl acetate/Petroleum ether to 0~50% MeOH/EtOAc gradient @ 50 mL/min) and then re-purified by prep-HPLC (column: Waters Xbridge C$_{18}$ 150*50 mm*10 um; mobile phase: [water (10 mM NH$_4$HCO$_3$)-ACN]; B %: 26%-56%, min) the titled compound (80 mg, 100.14 μmol, 11.76% yield, 95% purity) as a yellow solid. MS(M+H)$^+$=759.8.

Step 5: Synthesis of (2S,4R)-1-((S)-2-(2-(2-(2-(4-aminopiperidin-1-yl)ethoxy)ethoxy)acetamido)-3,3-dimethylbutanoyl)-4-hydroxy-N-(4-(4-methylthiazol-5-yl)benzyl)pyrrolidine-2-carboxamide To a solution of tert-butyl (1-(2-(2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)ethoxy)ethyl)piperidin-4-yl)carbamate (80 mg, 105.41 μmol) in dioxane (2 mL) was added HCl/dioxane (4 M, 2 mL) and the mixture was stirred at 20° C. for 1 h. LCMS showed the desired mass was detected after work-up. The reaction was concentrated under reduce pressure to afford the titled compound (70 mg, HCl salt) as a yellow solid. MS(M+H)$^+$=659.7.

Step 6: Synthesis of (2S,4R)-1-((S)-2-(2-(2-(2-(4-(4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzamido)piperidin-1-yl)ethoxy)ethoxy)acetamido)-3,3-dimethylbutanoyl)-4-hydroxy-N-(4-(4-methylthiazol-5-yl)benzyl)pyrrolidine-2-carboxamide (Compound 80)

To a solution of 4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzoic acid (45 mg, 96.69 umol) in DMF (1 mL) were added HATU (55 mg, 144.65 umol) and DIPEA (22.26 mg, 172.23 μmol, 30 μL), after stirring at 20° C. for 15 min. Then a solution of (2S,4R)-1-((S)-2-(2-(2-(2-(4-aminopiperidin-1-yl)ethoxy)ethoxy)acetamido)-3,3-dimethylbutanoyl)-4-hydroxy-N-(4-(4-methylthiazol-5-yl)benzyl)pyrrolidine-2-carboxamide (70 mg, 95.66 μmol, HCl salt) in DMF (1 mL) was added and the mixture was stirred at 20° C. for 1 h. LCMS showed the desired mass was detected. The mixture was diluted with H$_2$O (10 mL) and extracted with EtOAc (10 mL×3). The combined organic layer was washed with H$_2$O (10 mL) and brine (10 mL×2), dried over Na$_2$SO$_4$ and filtered. The filtrate was concentrated under reduced pressure. The crude was purified by prep-HPLC (column: Waters Xbridge 150*25 mm*5 um; mobile phase: [water (10 mM NH$_4$HCO$_3$)-ACN]; B %: 43%-73%, 10 min) and the eluent was lyophilized to afford the titled compound (23.8 mg, 20.44 μmol, 21.37% yield, 95% purity) as a white solid. MS(M+H)$^+$=1106.6.

387
$^1$H NMR (400 MHz, DMSO-d$_6$) δ=8.98 (s, 1H), 8.62-8.57 (m, 1H), 8.30 (s, 1H), 8.24 (d, J=13.3 Hz, 1H), 8.03 (s, 1H), 7.88-7.82 (m, 1H), 7.45-7.38 (m, 5H), 7.19 (d, J=6.6 Hz, 1H), 5.17-5.14 (m, 1H), 4.86-4.79 (m, 1H), 4.57 (br d, J=9.7 Hz, 1H), 4.47-4.41 (m, 1H), 4.39-4.34 (m, 1H), 4.29-4.23 (m, 1H), 4.08 (br t, J=13.9 Hz, 3H), 3.98 (s, 2H), 3.94-3.89 (s, 4H), 3.71-3.65 (m, 2H), 3.64-3.59 (m, 4H), 3.58-3.54 (m, 2H), 3.30 (br s, 3H), 2.86-2.80 (m, 2H), 2.53-2.52 (m, 2H), 2.44 (s, 3H), 2.09-1.90 (m, 6H), 1.79-1.69 (m, 4H), 1.65-1.49 (m, 6H), 0.95 (s, 9H).
388
Example 81. Synthesis of (2S,4R)-1-((S)-2-(tert-butyl)-14-(4-(4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzamido)piperidin-1-yl)-4-oxo-6,9,12-trioxa-3-azatetradecanoyl)-4-hydroxy-N-(4-(4-methylthiazol-5-yl)benzyl)pyrrolidine-2-carboxamide
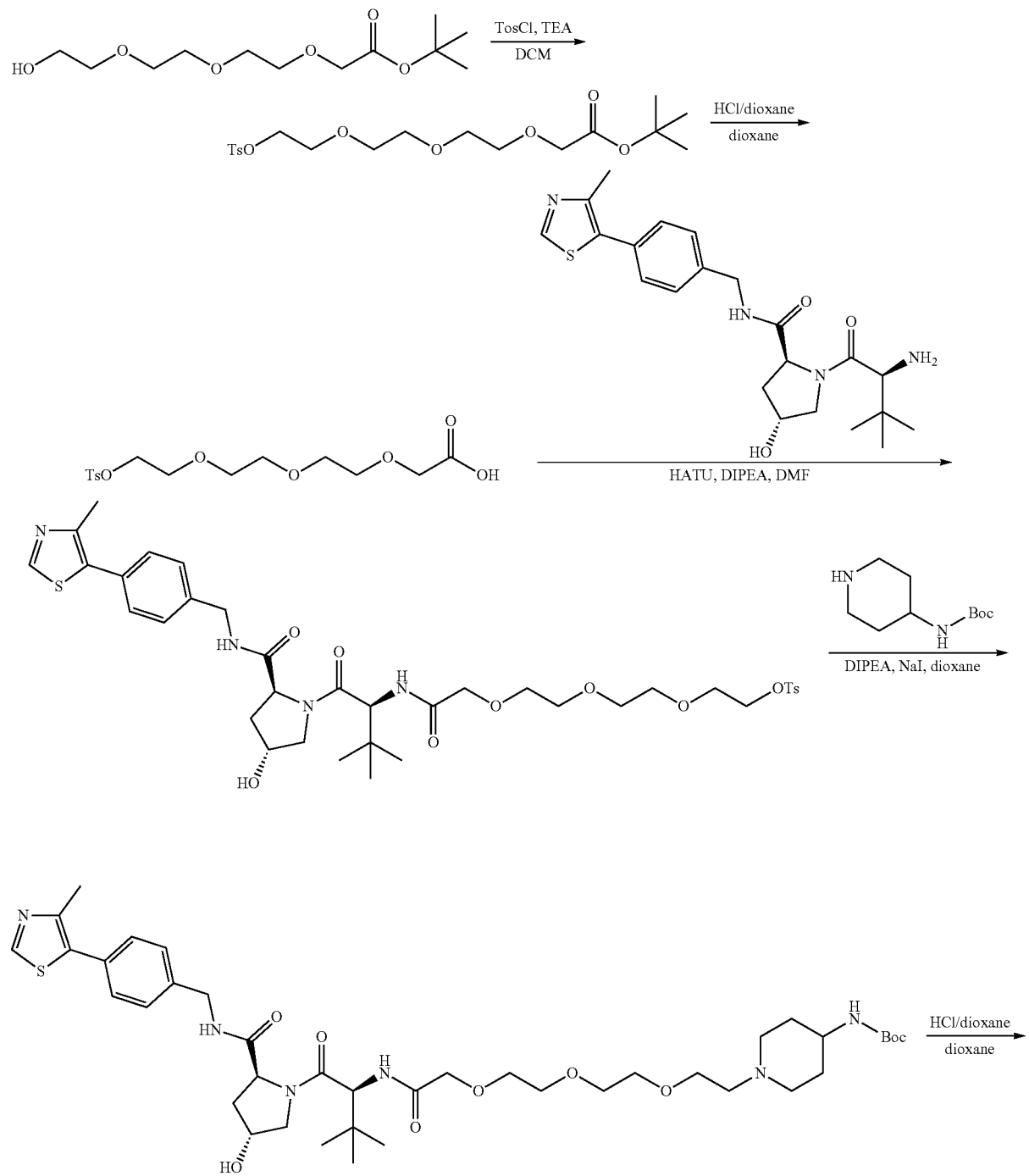

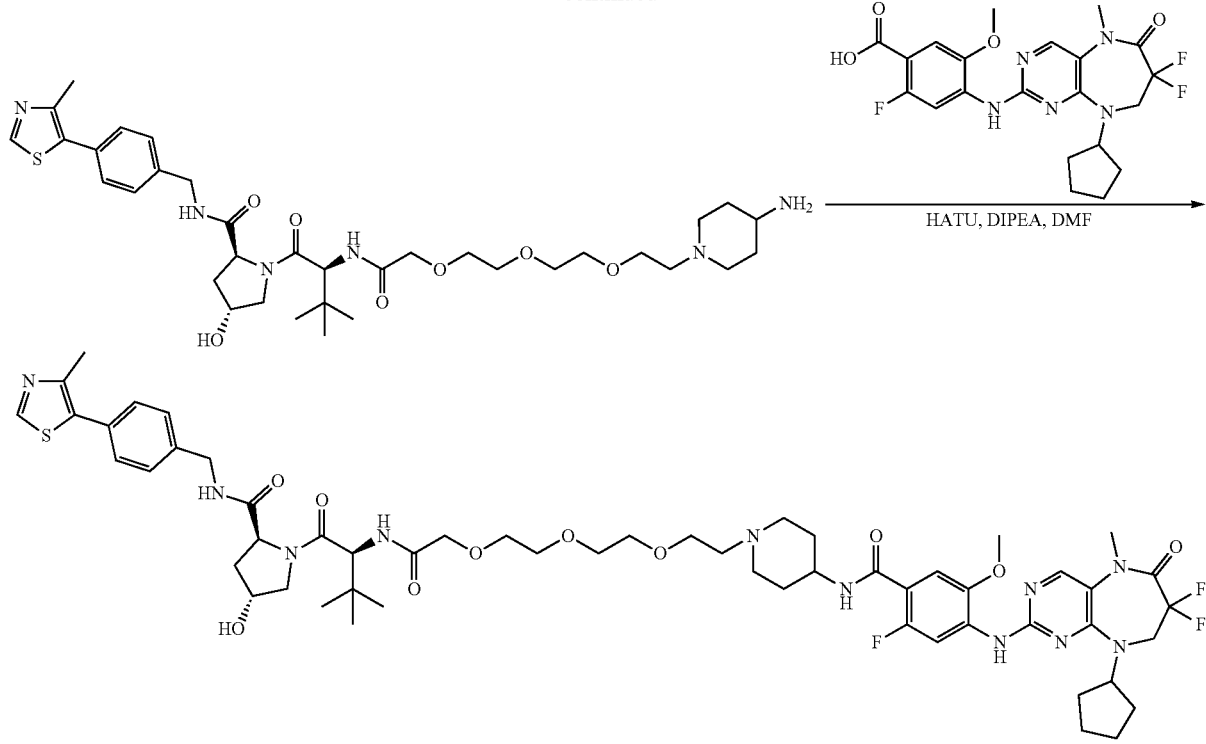

Compound 81

According to the above reaction scheme, in a manner similar to the other examples, obtained the titled compound (51.9 mg, 41.06 μmol, 27.41% yield, 91% purity) as white solid. MS(M+H)⁺=1150.7

¹H NMR (400 MHz, DMSO-d₆) δ=8.97 (s, 1H), 8.59 (t, J=6.0 Hz, 1H), 8.29 (s, 1H), 8.23 (d, J=13.3 Hz, 1H), 8.02 (s, 1H), 7.86 (br s, 1H), 7.44-7.35 (m, 5H), 7.18 (d, J=6.8 Hz, 1H), 5.15 (d, J=3.4 Hz, 1H), 4.85-4.77 (m, 1H), 4.56 (d, J=9.7 Hz, 1H), 4.47-4.32 (m, 3H), 4.28-4.19 (m, 1H), 4.07 (br t, J=13.8 Hz, 2H), 3.96 (s, 2H), 3.90 (s, 3H), 3.69-3.43 (m, 15H), 2.82 (br s, 2H), 2.43 (s, 3H), 2.10-1.85 (m, 7H), 1.82-1.44 (m, 12H), 0.96-0.91 (m, 9H).

Example 82. Synthesis of (2S,4R)-1-((S)-2-(tert-butyl)-17-(4-(4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzamido)piperidin-1-yl)-4-oxo-6,9,12,15-tetraoxa-3-azaheptadecanoyl)-4-hydroxy-N-(4-(4-methylthiazol-5-yl)benzyl)pyrrolidine-2-carboxamide

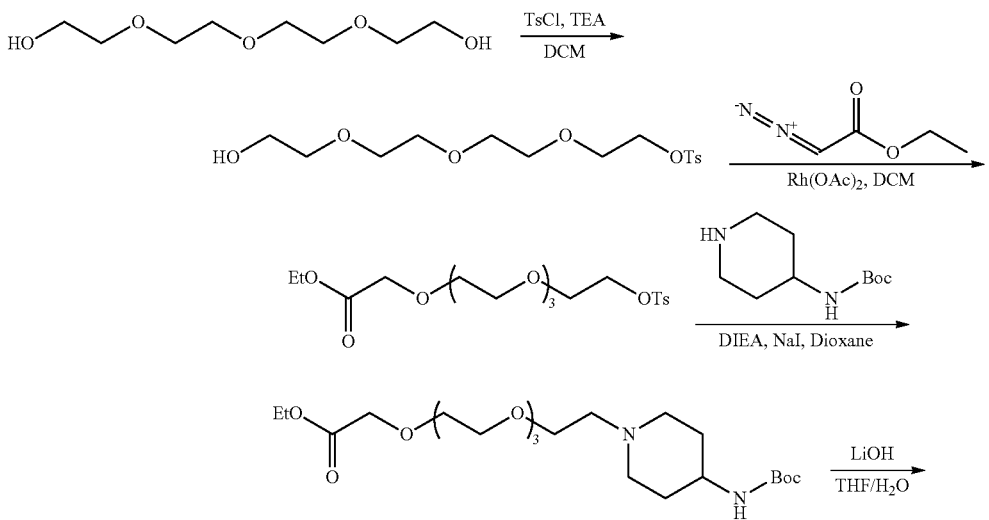

-continued
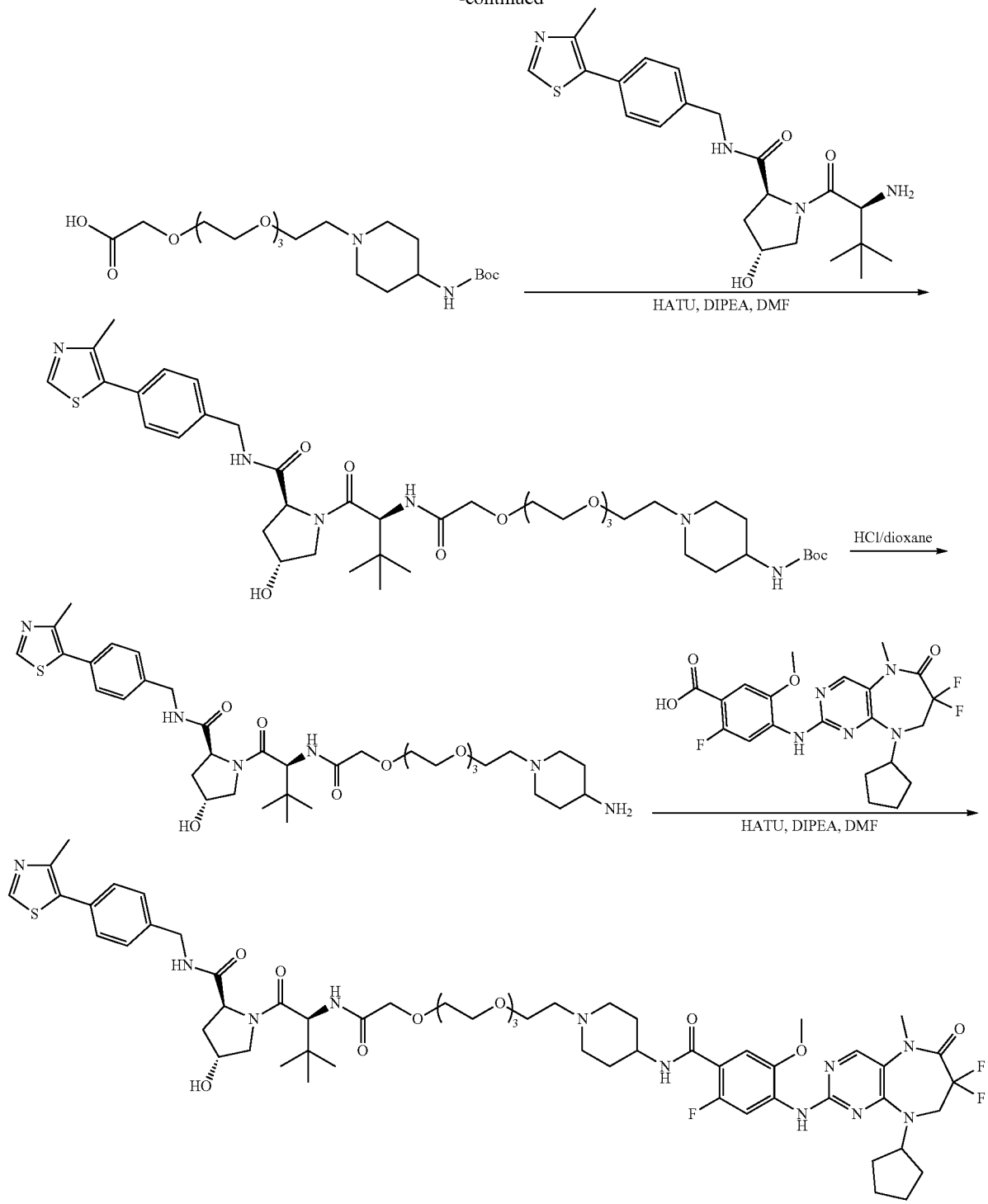
Compound 82
According to the above reaction scheme, in a manner similar to the other examples, obtained the titled compound (14.1 mg, 11.33 μmol, 4.40% yield, 96% purity) as a white solid.
MS(M+H)$^+$=1194.6
$^1$H NMR (400 MHz, DMSO-d$_6$) δ=8.98 (s, 1H), 8.59 (br t, J=6.0 Hz, 1H), 8.30 (s, 1H), 8.24 (d, J=13.3 Hz, 1H), 8.02 (s, 1H), 7.86 (br dd, J=3.4, 7.6 Hz, 1H), 7.46-7.36 (m, 5H), 7.19 (d, J=6.7 Hz, 1H), 5.17 (br s, 1H), 4.82 (br t, J=8.2 Hz, 1H), 4.56 (d, J=9.7 Hz, 1H), 4.47-4.32 (m, 3H), 4.26 (m, 1H), 4.07 (br t, J=13.9 Hz, 2H), 3.97 (s, 2H), 3.91 (s, 3H), 3.66-3.57 (m, 6H), 3.56-3.52 (m, 4H), 3.50-3.45 (m, 6H), 3.33 (br s, 3H), 2.83 (br d, J=11.4 Hz, 2H), 2.44 (s, 3H), 2.11-1.99 (m, 4H), 1.98-1.86 (m, 3H), 1.82-1.67 (m, 5H), 1.67-1.48 (m, 7H), 0.97-0.91 (s, 9H).

Example 83. Synthesis of (2S,4R)-1-((S)-2-(tert-butyl)-20-(4-(4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzamido)piperidin-1-yl)-4-oxo-6,9,12,15,18-pentaoxa-3-azaicosanoyl)-4-hydroxy-N-(4-(4-methylthiazol-5-yl)benzyl)pyrrolidine-2-carboxamide
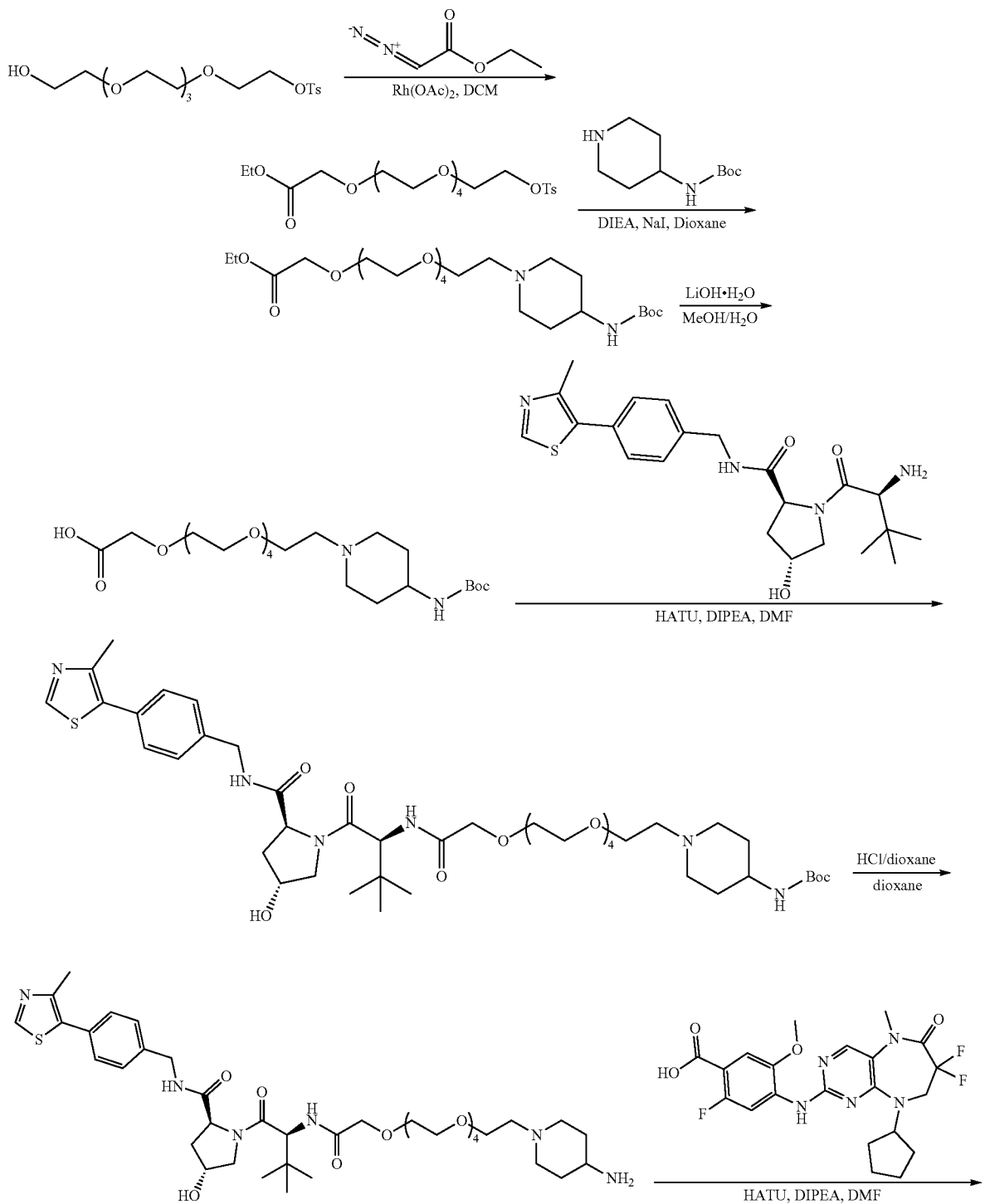

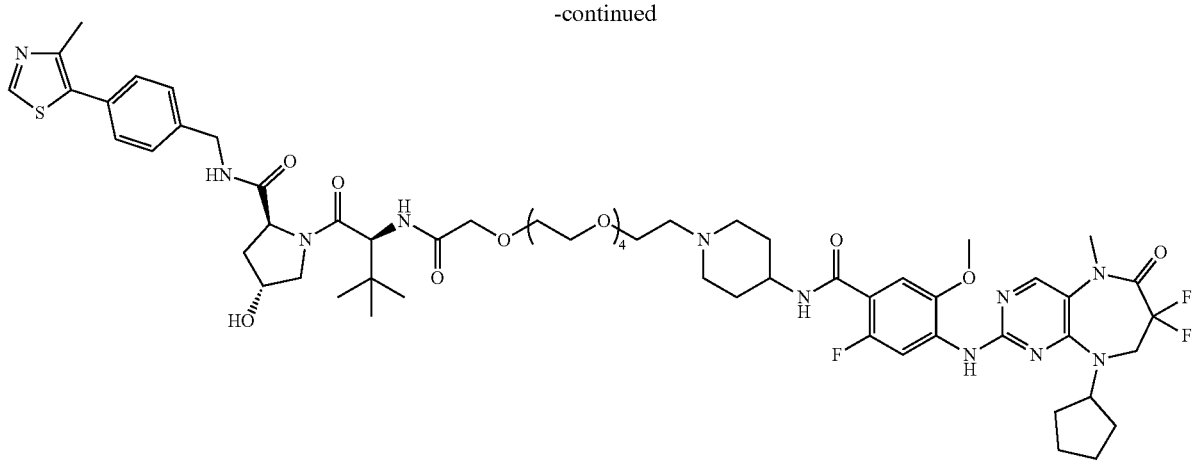

Compound 83

According to the above reaction scheme, in a manner similar to the other examples, obtained the titled compound (31.7 mg, 25.34 μmol, 9.83% yield, 99% purity) as a white solid.

MS(M+H)⁺=1238.9

¹H NMR (400 MHz, DMSO-d$_6$) δ 8.98 (s, 1H), 8.59 (t, J=6.1 Hz, 1H), 8.30 (s, 1H), 8.24 (d, J=13.3 Hz, 1H), 8.02 (s, 1H), 7.87 (dd, J=3.3, 7.8 Hz, 1H), 7.43-7.37 (m, 5H), 7.19 (d, J=6.6 Hz, 1H), 5.16-5.14 (m, 1H), 4.84-4.76 (m, 1H), 4.57-4.55 (m, 1H), 4.47-4.33 (m, 3H), 4.28-4.21 (m, 1H), 4.07 (t, J=13.9 Hz, 2H), 3.96 (s, 2H), 3.91 (s, 3H), 3.71-3.51 (m, 13H), 3.50-3.46 (m, 10H), 3.33 (s, 3H), 2.85-2.82 (m, 2H), 2.44 (s, 3H), 2.08-1.91 (m, 6H), 1.76-1.52 (m, 10H), 0.94 (s, 9H)

Example 84. Synthesis of (2S,4R)-1-((S)-2-(2-((8-(4-(4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzamido)piperidin-1-yl)octyl)oxy)acetamido)-3,3-dimethylbutanoyl)-4-hydroxy-N-(4-(4-methylthiazol-5-yl)benzyl)pyrrolidine-2-carboxamide

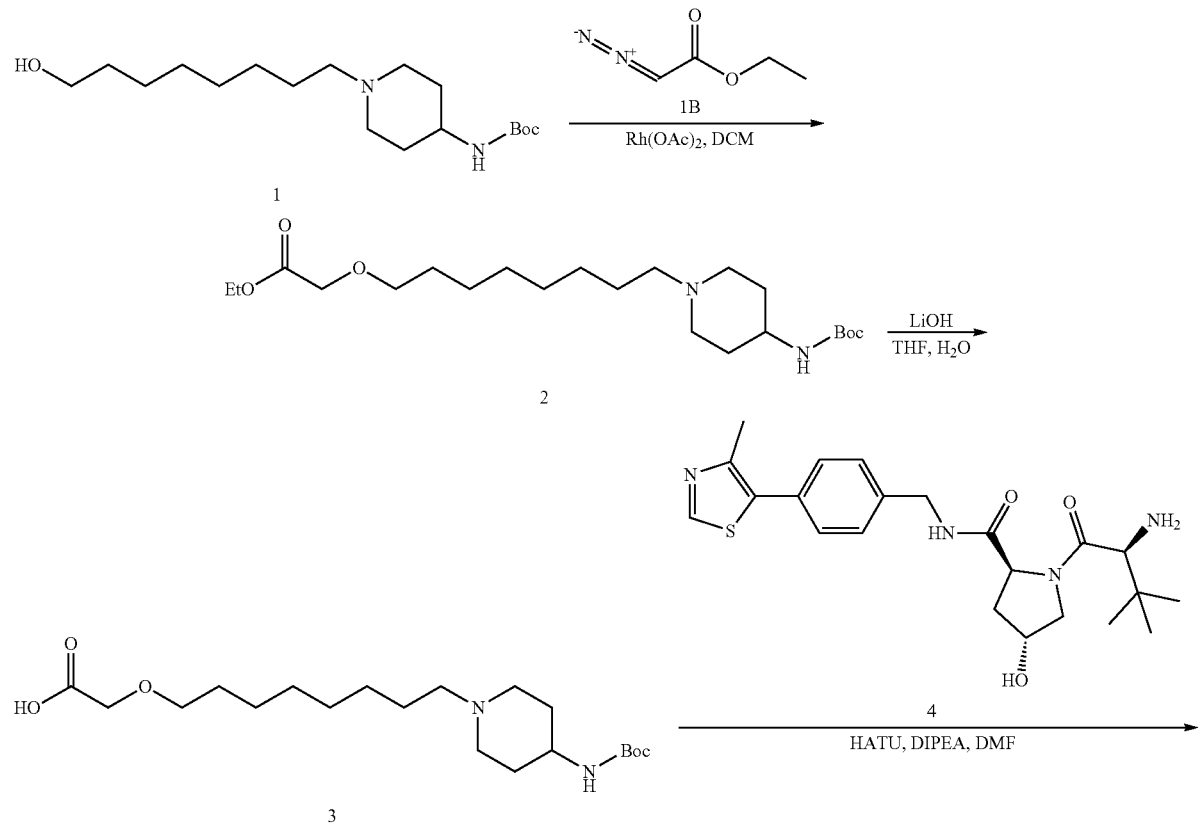

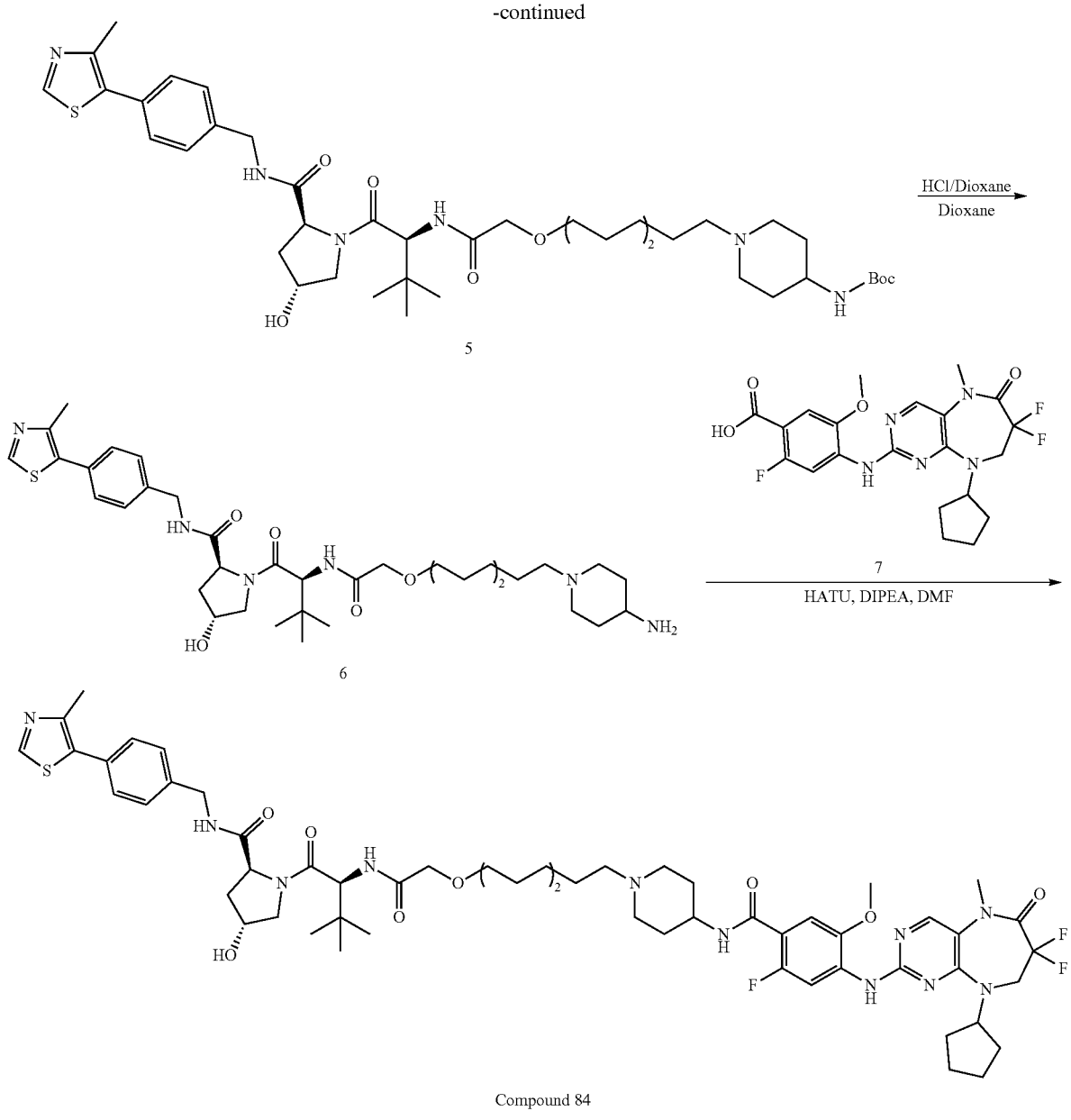

Compound 84

Step 1: Synthesis of ethyl 2-((8-(4-((tert-butoxycarbonyl)amino)piperidin-1-yl)octyl)oxy)acetate (2)

To a solution of tert-butyl (1-(8-hydroxyoctyl)piperidin-4-yl)carbamate (5.5 g, 16.74 mmol) and Rh(OAc)$_2$ (37.00 mg, 167.43 μmol) in DCM (50 mL) was added solution of ethyl 2-diazoacetate (2.48 g, 21.77 mmol, 2.28 mL) in DCM (10 mL) drop-wise at 0° C. The mixture was stirred at 25° C. for 12 hr. LCMS showed most of the starting material remained. Another portion of Rh(OAc)$_2$ (185.01 mg, 837.17 μmol) was added to the reaction mixture at 25° C. The resulting mixture was stirred at 40° C. for another 6 hrs. LCMS showed 76% of desired mass. The mixture solution was concentrated under reduced pressure. The crude product was purified by silica gel column chromatography (1000 mesh silica gel, eluted with petroleum ether:ethyl acetate=10/1 to 0/1) to give ethyl 2-((8-(4-((tert-butoxycarbonyl)amino)piperidin-1-yl)octyl)oxy)acetate (4.5 g, crude) as yellow oil, which was used for the next step directly. MS(M+H)$^+$=415.2

Step 2: Synthesis of 2-((8-(4-((tert-butoxycarbonyl)amino)piperidin-1-yl)octyl)oxy)acetic acid (3)

A mixture of ethyl 2-((8-(4-((tert-butoxycarbonyl)amino)piperidin-1-yl)octyl)oxy)acetate (4.5 g, 10.85 mmol), LiOH (519.89 mg, 21.71 mmol) in THF (30 mL) and H$_2$O (30 mL) was stirred at 45° C. for 12 hr. LCMS showed the starting material was consumed completely. The reaction solution was concentrated to remove the organic phase. The residual aqueous solution was washed with EtOAc (50 mL×3). The 1M HCl aqueous solution was added to the suspension to adjust pH to 6. The aqueous layer was extracted with EtOAc (50 mL×4). The combined organic layers were dried over Na$_2$SO$_4$ and concentrated. The crude product was purified by reversed-phase HPLC (0.1% NH$_3$·H$_2$O condition, MeCN/H$_2$O) afford 2-((8-(4-(((tert-butoxycarbonyl)amino)piperidin-1-yl)octyl)oxy)acetic acid (1.8 g, 4.66 mmol, 42.90% yield, 100% purity) as white solid which was used for the next step directly. MS (M–H)$^+$=385.4

Step 3: Synthesis of tert-butyl (1-(8-(2-(((S)-1-((2S,4R)-4-hydroxy-2-((4-(4-methylthiazol-5-yl) benzyl) carbamoyl)pyrrolidin-1-yl-3,3-dimethyl-1-oxobutan-2-yl)amino)-2-oxoethoxy)octyl)piperidin-4-yl) carbamate (5)

To a solution of 2-((8-(4-(((tert-butoxycarbonyl)amino)piperidin-1-yl)octyl)oxy)acetic acid (300 mg, 776.15 μmol) in DMF (5 mL) was added HATU (442.67 mg, 1.16 mmol) and DIPEA (300.93 mg, 2.33 mmol, 405.56 μL). The mixture was stirred at 25° C. for 10 min. To mixture was added (2S,4R)-1-((S)-2-amino-3,3-dimethylbutanoyl)-4-hydroxy-N-(4-(4-methylthiazol-5-yl) benzyl)pyrrolidine-2-carboxamide (289.98 mg, 620.92 μmol, 0.8 eq, HCl). The mixture was stirred at 25° C. for 12 h. LCMS showed 63% peak with desired mass. The solution was diluted with ethyl acetate (30 mL) and concentrated under reduced pressure. The residue was purified by flash silica gel chromatography (20 g SepaFlash® Silica Flash Column, Eluent of 0~100% Ethyl acetate/Petroleum ether gradient @ 100 mL/min; Eluent of 0~50% Ethyl acetate/Methanol gradient @ 100 mL/min) to afford the titled compound (0.5 g, crude) was obtained as brown oil which was used for the next step directly. MS(M+H)$^+$=799.4

Step 4: Synthesis of (2S,4R)-1-((S)-2-(2-((8-(4-aminopiperidin-1-yl)octyl)oxy)acetamido)-3,3-dimethylbutanoyl)-4-hydroxy-N-(4-(4-methylthiazol-5-yl)benzyl)pyrrolidine-2-carboxamide (6)

To a solution of tert-butyl (1-(8-(2-(((S)-1-((2S,4R)-4-hydroxy-2-((4-(4-methylthiazol-5-yl)benzyl) carbamoyl) pyrrolidin-1-yl)-3,3-dimethyl-1-oxobutan-2-yl)amino)-2-oxoethoxy)octyl)piperidin-4-yl)carbamate (0.5 g, 625.73 μmol) in dioxane (2 mL) was added HCl/dioxane (4 M, 10 mL, 63.93 eq) at 25° C. The resulting mixture was stirred at 25° C. for 0.5 hr. LCMS showed the starting material was consumed completely and a main peak with desired mass. The mixture solution was concentrated under reduced pressure to afford the titled compound (380 mg, crude, HCl) as brown solid, which was used for the next step directly. MS(M+H)$^+$=699.4

Step 5: Synthesis of (2S,4R)-1-((S)-2-(2-((8-(4-(4-((9-cyclopentyl-7,7-difluoro-5-methyl-6-oxo-6,7,8,9-tetrahydro-5H-pyrimido[4,5-b][1,4]diazepin-2-yl) amino)-2-fluoro-5-methoxybenzamido)piperidin-1-yl)octyl)oxy)acetamido)-3,3-dimethylbutanoyl)-4-hydroxy-N-(4-(4-methylthiazol-5-yl)benzyl) pyrrolidine-2-carboxamide (Compound 84)

To a solution of 4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzoic acid (70 mg, 150.40 mol) in DMF (5 mL) were added HATU (85.78 mg, 225.60 μmol) and DIPEA (58.31 mg, 451.20 μmol, 78.59 μL). The mixture was stirred at 25° C. for 10 min. To mixture was added (2S,4R)-1-((S)-2-(2-((8-(4-aminopiperidin-1-yl) octyl)oxy)acetamido)-3,3-dimethylbutanoyl)-4-hydroxy-N-(4-(4-methylthiazol-5-yl)benzyl)pyrrolidine-2-carboxamide (110.61 mg, 150.40 μmol, HCl). The mixture was stirred at 25° C. for 12 h. LCMS showed a main peak with desired mass. The mixture solution was concentrated under reduced pressure. The crude product was purified prep-HPLC (column: Waters Xbridge 150*25 mm*5 um; mobile phase: [water (10 mM NH$_4$HCO$_3$)-ACN]; B %: 58%-88%, 10 min) and lyophilized to afford the titled compound (22.9 mg, 19.18 mol, 12.75% yield, 96% purity) as white solid. MS(M+H)$^+$=1146.4

$^1$H NMR (400 MHz, DMSO-d$_6$) δ=8.98 (s, 1H), 8.62 (t, J=5.9 Hz, 1H), 8.34-8.17 (m, 2H), 8.03 (s, 1H), 7.86 (dd, J=3.4, 7.7 Hz, 1H), 7.44-7.36 (m, 4H), 7.34 (d, J=9.6 Hz, 1H), 7.19 (d, J=6.8 Hz, 1H), 5.29-5.07 (m, 1H), 4.88-4.70 (m, 1H), 4.55 (d, J=9.6 Hz, 1H), 4.48-4.32 (m, 3H), 4.30-4.18 (m, 1H), 4.07 (t, J=13.9 Hz, 2H), 3.94-3.87 (m, 5H), 3.77-3.55 (m, 3H), 3.50-3.45 (m, 2H), 2.77 (d, J=11.0 Hz, 2H), 2.46-2.42 (m, 4H), 2.19 (t, J=7.3 Hz, 2H), 2.11-2.02 (m, 1H), 2.00-1.80 (m, 5H), 1.82-1.69 (m, 4H), 1.66-1.43 (m, 9H), 1.40-1.31 (m, 4H), 1.30-1.15 (m, 7H), 0.94 (s, 9H).

Example 85. Synthesis of (2S,4R)—N-(2-(2-(2-(4-(4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzamido)piperidin-1-yl)ethoxy)ethoxy)-4-(4-methylthiazol-5-yl) benzyl)-1-((S)-2-(1-fluorocyclopropane-1-carboxamido)-3,3-dimethylbutanoyl)-4-hydroxypyrrolidine-2-carboxamide

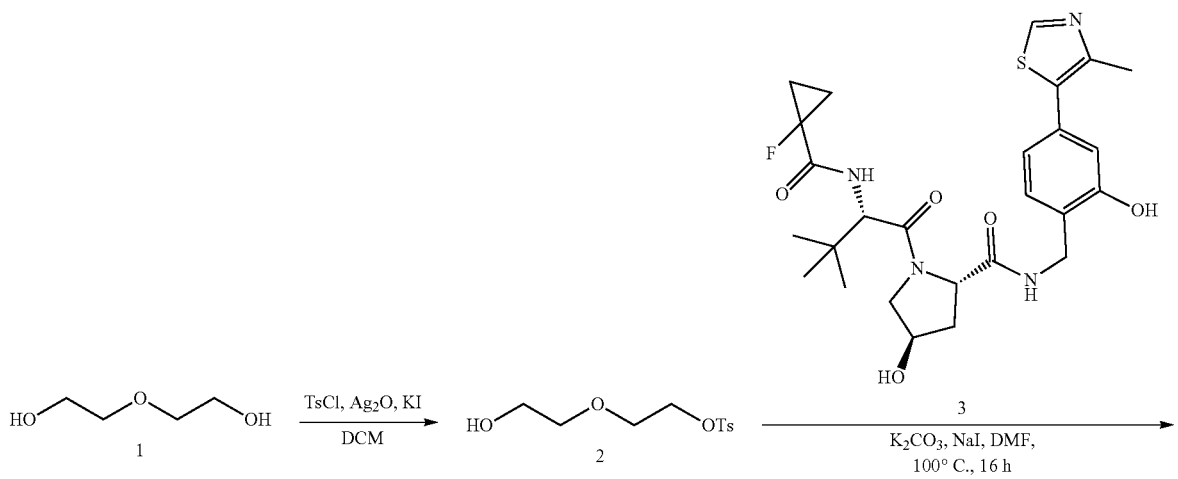

-continued
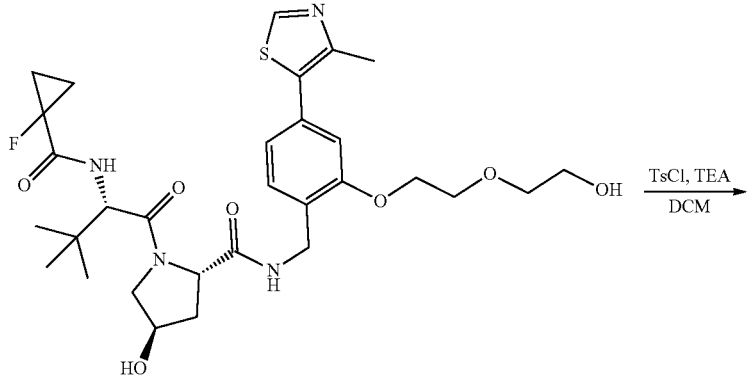
4
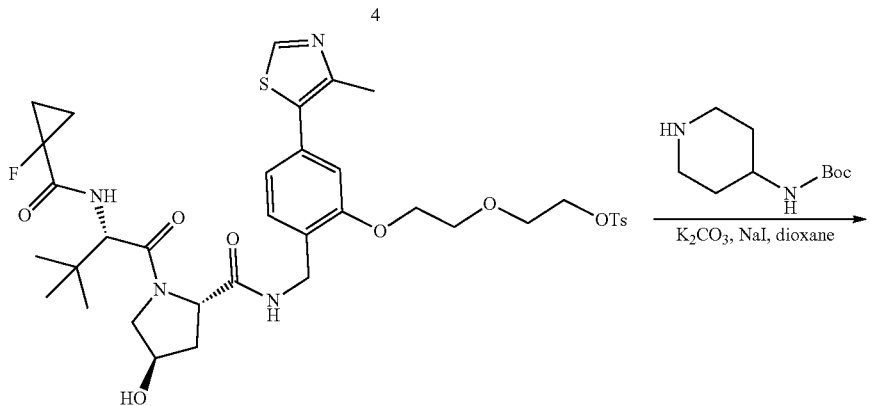
5
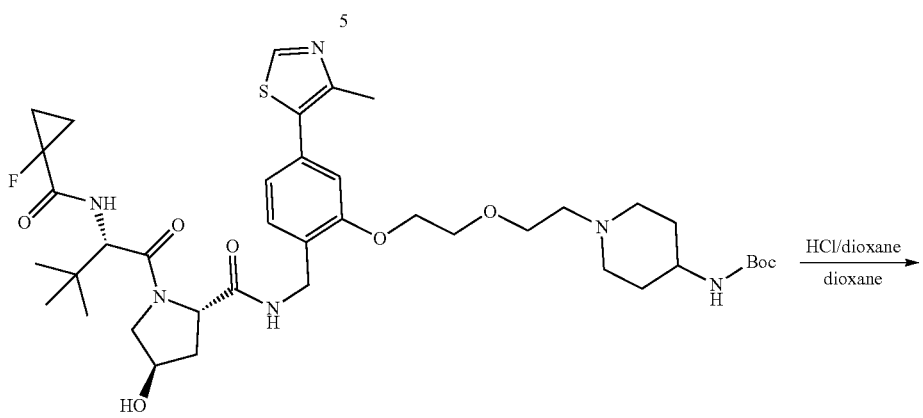
6
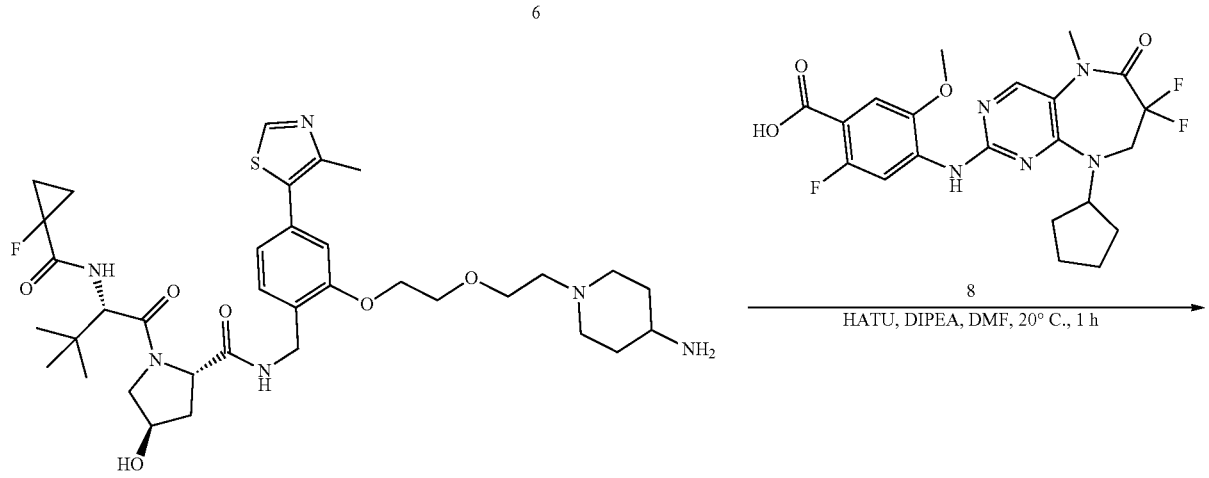
7

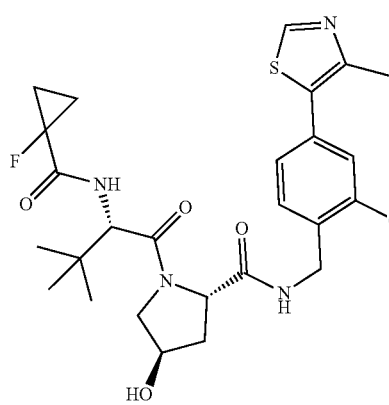

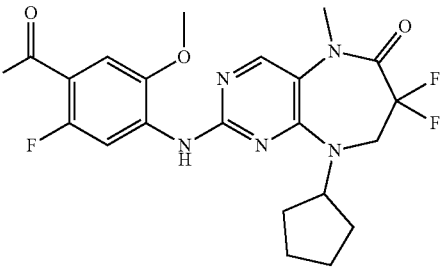

Compound 85

Step 1: Synthesis of 2-(2-hydroxyethoxy)ethyl 4-methylbenzenesulfonate (3)

To a solution of 2,2'-oxydiethanol (20 g, 188.47 mmol, 17.86 mL) in DCM (200 mL) were added TosCl (35.93 g, 188.47 mmol), KI (6.26 g, 37.69 mmol) and silver oxide (65.51 g, 282.71 mmol). The mixture was stirred at 20° C. for 14 h. LCMS showed the desired mass was detected. The mixture was filtered and the filter cake was washed with EtOAc (100 mL). The filtrate was concentrated under reduced pressure. The residue was purified by flash silica gel chromatography (120 g SepaFlash® Silica Flash Column, Eluent of 0~100% Ethyl acetate/Petroleum ether to 0~50% MeOH/EtOAc gradient @ 80 mL/min) to afford (27.1 g, 104.11 mmol, 55.24% yield) as a yellow oil. MS(M+H)$^+$=261.1.

Step 2: Synthesis of (2S,4R)-1-((S)-2-(1-fluorocyclopropanecarboxamido)-3,3-dimethylbutanoyl)-4-hydroxy-N-(2-(2-(2-hydroxyethoxy)ethoxy)-4-(4-methylthiazol-5-yl)benzyl)pyrrolidine-2-carboxamide (4)

To a solution of (2S,4R)-1-((S)-2-(1-fluorocyclopropanecarboxamido)-3,3-dimethylbutanoyl)-4-hydroxy-N-(2-hydroxy-4-(4-methylthiazol-5-yl)benzyl)pyrrolidine-2-carboxamide (500 mg, 938.74 μmol) and 2-(2-hydroxyethoxy)ethyl 4-methylbenzenesulfonate (293 mg, 1.13 mmol) in DMF (10 mL) were added NaI (70.35 mg, 469.37 μmol) and K$_2$CO$_3$ (389.23 mg, 2.82 mmol). The reaction mixture was stirred at 100° C. for 14 h. LCMS showed the desired mass was detected. The mixture was diluted with H$_2$O (10 mL) and extracted with EtOAc (10 mL×3). The combined organic layer was washed with H$_2$O (10 mL) and brine (10 mL×2), dried over Na$_2$SO$_4$ and filtered. The filtrate was concentrated under reduced pressure. The residue was purified by flash silica gel chromatography (5 g SepaFlash® Silica Flash Column, Eluent of 50~100% Ethyl acetate/Petroleum ether to 0~20% MeOH/EtOAc gradient @ 50 mL/min) to afford the titled compound (460 mg, 741.06 μmol, 78.94% yield) as a yellow oil. MS(M+H)$^+$=621.4.

Step 3: Synthesis of 2-(2-(2-(((2S,4R)-1-((S)-2-(1-fluorocyclopropanecarboxamido)-3,3-dimethylbutanoyl)-4-hydroxypyrrolidine-2-carboxamido)methyl)-5-(4-methylthiazol-5-yl)phenoxy)ethoxy)ethyl 4-methylbenzenesulfonate (5)

To a solution of (2S,4R)-1-((S)-2-(1-fluorocyclopropanecarboxamido)-3,3-dimethylbutanoyl)-4-hydroxy-N-(2-(2-(2-hydroxyethoxy)ethoxy)-4-(4-methylthiazol-5-yl)benzyl)pyrrolidine-2-carboxamide (510 mg, 821.61 μmol) in DCM (8 mL) were added TEA (501.63 mg, 4.96 mmol, 690 μL) and a solution of TosCl (469.91 mg, 2.46 mmol) in DCM (2 mL). The mixture was stirred at 20° C. for 14 h. TLC (Ethyl acetate:Methanol=10:1) showed the desired spot was detected. The mixture was concentrated under reduced pressure. The residue was purified by flash silica gel chromatography (5 g SepaFlash® Silica Flash Column, Eluent of 20~100% Ethyl acetate/Petroleum ether gradient @ 50 mL/min) to afford (0.3 g, 387.14 μmol, 47.12% yield) as a white solid. MS(M+H)$^+$=775.6.

Step 4: Synthesis of tert-butyl (1-(2-(2-(2-(((2S,4R)-1-((S)-2-(1-fluorocyclopropanecarboxamido)-3,3-dimethylbutanoyl)-4-hydroxypyrrolidine-2-carboxamido)methyl)-5-(4-methylthiazol-5-yl)phenoxy)ethoxy)ethyl)piperidin-4-yl)carbamate (6)

To a solution of 2-(2-(2-(((2S,4R)-1-((S)-2-(1-fluorocyclopropanecarboxamido)-3,3-dimethylbutanoyl)-4-hydroxypyrrolidine-2-carboxamido)methyl)-5-(4-methylthiazol-5-yl)phenoxy)ethoxy)ethyl 4-methylbenzenesulfonate (300 mg, 387.14 μmol) and tert-butyl piperidin-4-ylcarbamate (74 mg, 369.49 μmol) in dioxane (6 mL) were added NaI (5.80 mg, 38.71 μmol) and K$_2$CO$_3$ (160.51 mg, 1.16 mmol) and the mixture was stirred at 80° C. for 14 h. LCMS showed the desired mass was detected. The mixture was concentrated under reduced pressure. The residue was purified by flash silica gel chromatography (5 g SepaFlash® Silica Flash Column, Eluent of 0~100% MeOH/Ethyl acetate gradient @ 50 mL/min) to afford the titled compound (280 mg, 348.70 μmol, 90.07% yield) as a yellow solid. MS(M+H)$^+$=803.8.

Step 5: Synthesis of (2S,4R)—N-(2-(2-(2-(4-aminopiperidin-1-yl)ethoxy)ethoxy)-4-(4-methylthiazol-5-yl))benzyl)-1-((S)-2-(1-fluorocyclopropanecarboxamido)-3,3-dimethylbutanoyl)-4-hydroxypyrrolidine-2-carboxamide (7)

To a solution of tert-butyl (1-(2-(2-(2-(((2S,4R)-1-((S)-2-(1-fluorocyclopropanecarboxamido)-3,3-dimethylbutanoyl)-4-hydroxypyrrolidine-2-carboxamido)methyl)-5-(4-methylthiazol-5-yl)phenoxy)ethoxy)ethyl)piperidin-4-yl)carbamate (280 mg, 348.70 μmol) in dioxane (4 mL) was added HCl/dioxane (4 M, 4 mL) and the mixture was stirred at 20° C. for 1 h. LCMS showed the desired mass was detected after work-up. The reaction mixture was concentrated under reduced pressure to afford the titled compound (260 mg, crude, HCl salt) as a yellow solid. MS(M+H)$^+$=703.7.

Step 6: Synthesis of (2S,4R)—N-(2-(2-(2-(4-(4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzamido)piperidin-1-yl)ethoxy)ethoxy)-4-(4-methylthiazol-5-yl)benzyl)-1-((S)-2-(1-fluorocyclopropanecarboxamido)-3,3-dimethylbutanoyl)-4-hydroxypyrrolidine-2-carboxamide (8)

To a solution of 4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzoic acid (60 mg, 128.91 mol) in DMF (1 mL) were added HATU (74 mg, 194.62 μmol) and DIPEA (37.10 mg, 287.06 umol, 50 μL) and the mixture was stirred at 20° C. for 15 min. Then a solution of (2S,4R)—N-(2-(2-(2-(4-aminopiperidin-1-yl)ethoxy)ethoxy)-4-(4-methylthiazol-5-yl)benzyl)-1-((S)-2-(1-fluorocyclopropanecarboxamido)-3,3-dimethylbutanoyl)-4-hydroxypyrrolidine-2-carboxamide (120 mg, 137.00 μmol, HCl salt) and DIPEA (44.52 mg, 344.47 μmol, 60 μL) in DMF (1 mL) was added and the mixture was stirred at 20° C. for 1 h. LCMS showed the desired mass was detected. The mixture was diluted with H$_2$O (10 mL) and extracted with EtOAc (10 mL×3). The combined organic layer was washed with H$_2$O (10 mL) and brine (10 mL×2), dried over Na$_2$SO$_4$ and filtered. The filtrate was concentrated under reduced pressure. The crude was purified by prep-HPLC (column: Waters Xbridge 150*25 mm*5 um; mobile phase: [water (10 mM NH$_4$HCO$_3$)-ACN]; B %: 49%-79%, 10 min) and the eluent was lyophilized to afford the titled compound (32.0 mg, 26.43 μmol, 20.50% yield, 95% purity) as a white solid. MS(M+H)$^+$=1150.5

$^1$H NMR (400 MHz, DMSO-d$_6$) δ=8.98 (s, 1H), 8.49 (br t, J=5.9 Hz, 1H), 8.30 (s, 1H), 8.24 (d, J=13.3 Hz, 1H), 8.03 (s, 1H), 7.85-7.80 (m, 1H), 7.41 (d, J=7.7 Hz, 1H), 7.31-7.26 (m, 1H), 7.19 (d, J=6.6 Hz, 1H), 7.05 (s, 1H), 6.96 (br d, J=8.1 Hz, 1H), 5.17-5.14 (m, 1H), 4.85-4.78 (m, 1H), 4.59 (br d, J=9.2 Hz, 1H), 4.51 (br t, J=8.2 Hz, 1H), 4.36-4.28 (m, 2H), 4.23-4.16 (m, 3H), 4.07 (br t, J=13.9 Hz, 2H), 3.91 (s, 3H), 3.77 (br d, J=3.3 Hz, 2H), 3.73-3.69 (m, 1H), 3.63-3.58 (m, 4H), 3.33-3.33 (m, 3H), 2.89-2.82 (m, 2H), 2.53-2.52 (m, 2H), 2.46 (s, 3H), 2.11-2.02 (m, 4H), 2.00-1.89 (m, 4H), 1.76-1.71 (m, 2H), 1.64-1.57 (m, 4H), 1.55-1.49 (m, 2H), 1.40-1.32 (m, 2H), 1.24-1.19 (m, 2H), 0.95 (s, 9H).

Example 86. Synthesis of (2S,4R)—N-(2-(2-(2-(2-(4-(4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzamido)piperidin-1-yl)ethoxy)ethoxy)ethoxy)-4-(4-methylthiazol-5-yl)benzyl)-1-((S)-2-(1-fluorocyclopropane-1-carboxamido)-3,3-dimethylbutanoyl)-4-hydroxypyrrolidine-2-carboxamide

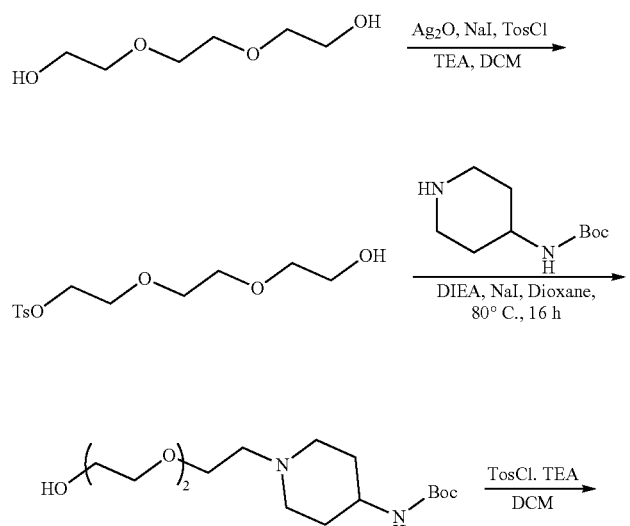

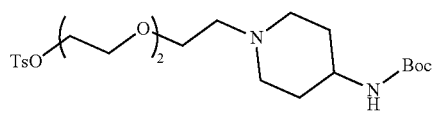

407 -continued 408
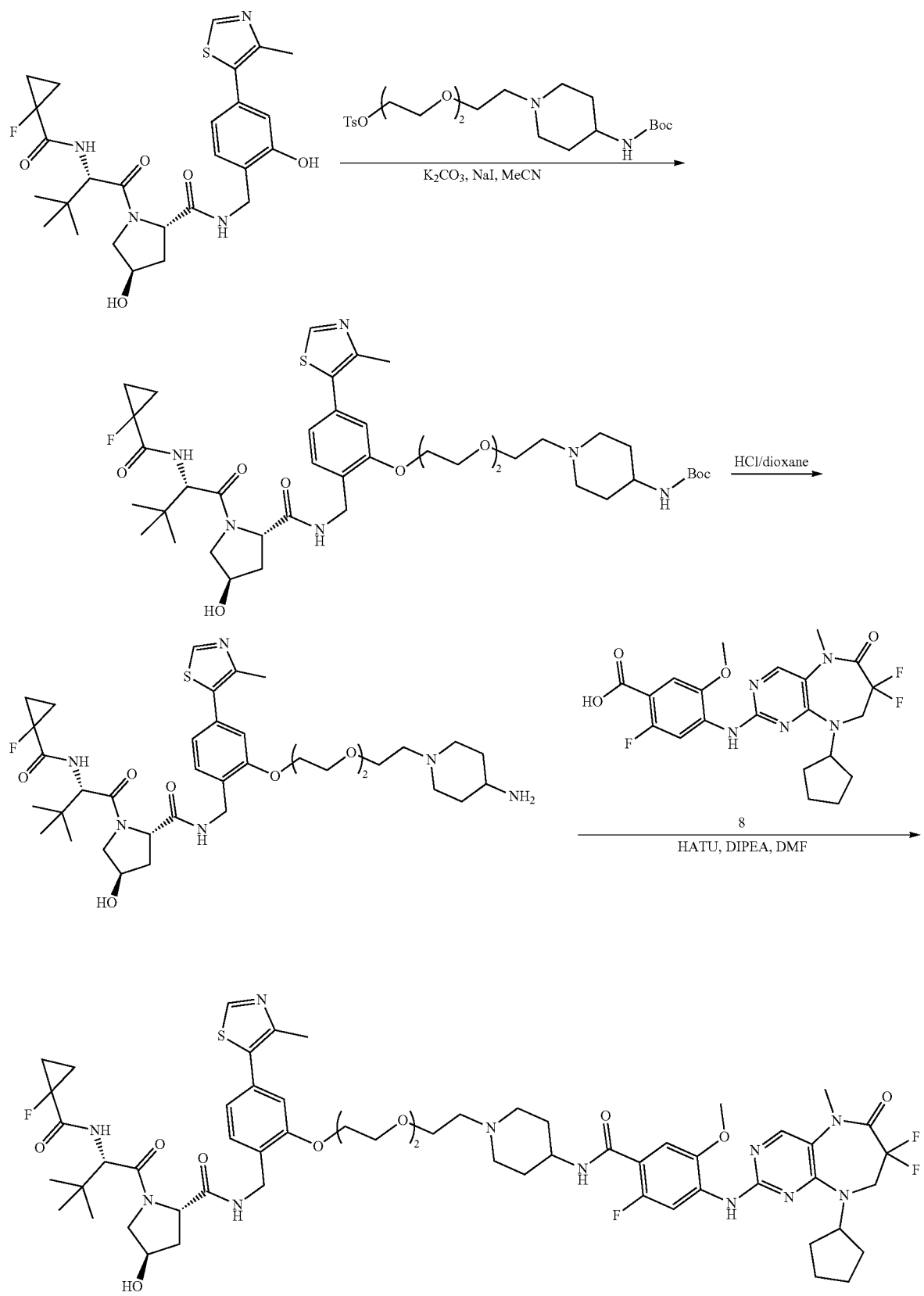
Compound 86

According to the above reaction scheme, in a manner similar to the other examples, obtained the titled compound (49.5 mg, 37.72 µmol, 29.26% yield, 91% purity) as white solid. MS(M+H)⁺=1193.6

$^1$H NMR (400 MHz, DMSO-d$_6$) δ=8.97 (s, 1H), 8.49 (br t, J=6.0 Hz, 1H), 8.30 (s, 1H), 8.24 (d, J=13.4 Hz, 1H), 8.03 (s, 1H), 7.85 (dd, J=3.2, 7.6 Hz, 1H), 7.41 (d, J=7.6 Hz, 1H), 7.29 (dd, J=2.8, 9.0 Hz, 1H), 7.18 (d, J=6.8 Hz, 1H), 7.04 (d, J=1.4 Hz, 1H), 6.97 (s, 1H), 5.17 (d, J=3.6 Hz, 1H), 4.91-4.77 (m, 1H), 4.59 (d, J=8.8 Hz, 1H), 4.51 (t, J=8.2 Hz, 1H), 4.39-4.27 (m, 2H), 4.25-4.15 (m, 3H), 4.07 (br t, J=14.0 Hz, 2H), 3.91 (s, 3H), 3.84-3.77 (m, 2H), 3.77-3.56 (m, 6H), 3.56-3.41 (m, 6H), 2.92-2.78 (m, 2H), 2.42-2.51 (m, 4H), 2.07 (br d, J=8.8 Hz, 3H), 1.95 (br d, J=4.0 Hz, 3H), 1.81-1.69 (m, 4H), 1.67-1.45 (m, 7H), 1.43-1.30 (m, 2H), 1.21 (br dd, J=3.6, 8.8 Hz, 2H), 0.95 (s, 9H).

Example 87. Synthesis of (2S,4R)—N-(2-(2-(2-(2-(2-(4-(4-(4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzamido)piperidin-1-yl)ethoxy)ethoxy)ethoxy)ethoxy)-4-(4-methylthiazol-5-yl)benzyl)-1-((S)-2-(1-fluorocyclopropane-1-carboxamido)-3,3-dimethylbutanoyl)-4-hydroxypyrrolidine-2-carboxamide

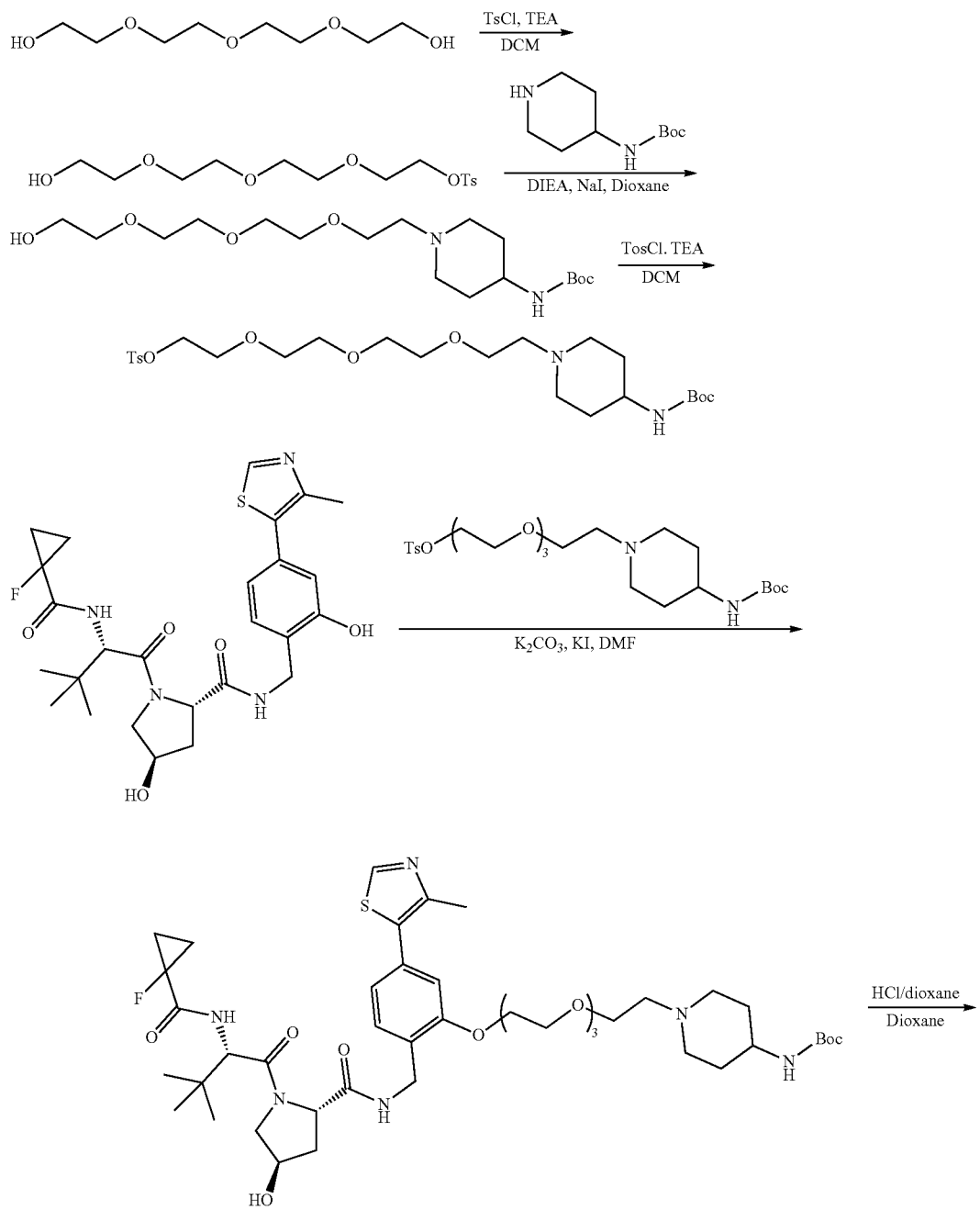

-continued

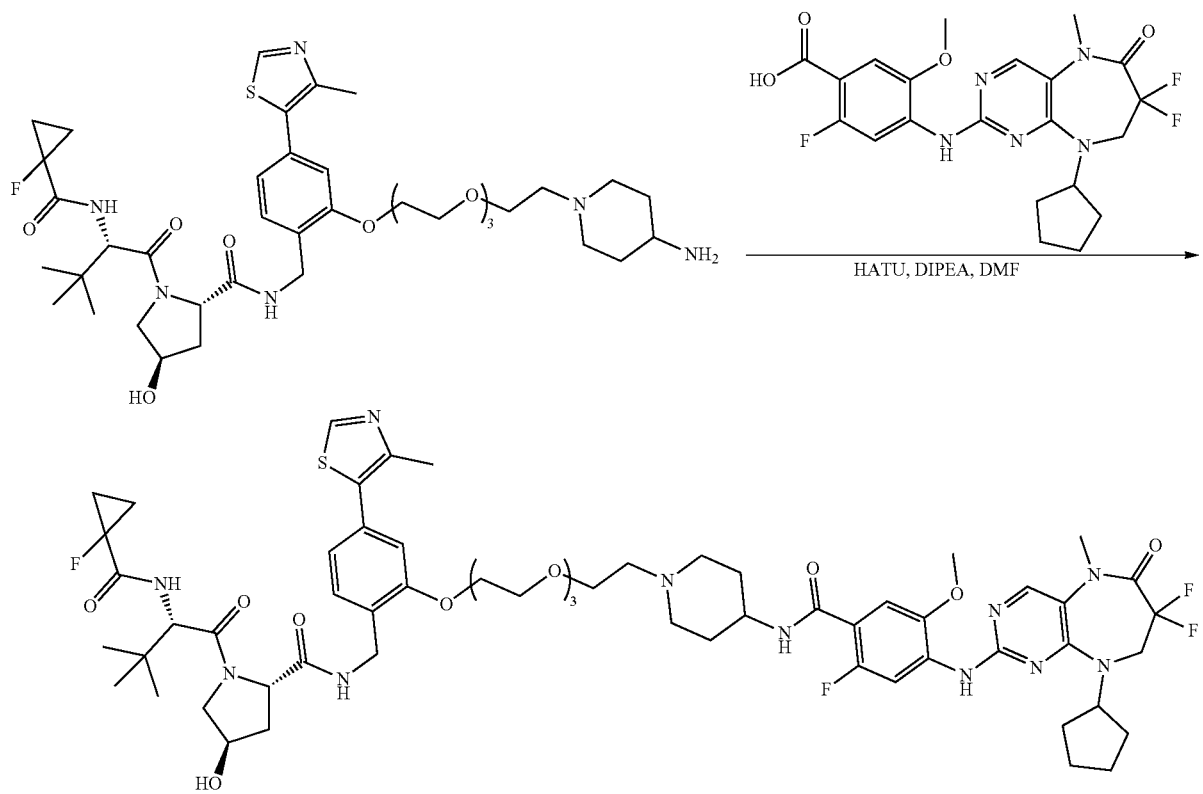

Compound 87

According to the above reaction scheme, in a manner similar to the other examples, obtained the titled compound (15.5 mg, 11.26 μmol, 6.55% yield, 90% purity) as white solid. MS(M+H)$^+$=1238.7

$^1$H NMR (400 MHz, DMSO-d6) δ 8.98 (s, 1H), 8.51 (t, J=5.9 Hz, 1H), 8.30 (s, 1H), 8.24 (d, J=13.3 Hz, 1H), 8.04 (s, 1H), 7.93-7.83 (m, 1H), 7.41 (d, J=7.8 Hz, 1H), 7.34-7.23 (m, 1H), 7.18 (d, J=6.7 Hz, 1H), 7.04 (d, J=1.7 Hz, 1H), 6.99-6.92 (m, 1H), 5.19 (s, 1H), 4.90-4.75 (m, 1H), 4.65-4.43 (m, 2H), 4.42-4.25 (m, 2H), 4.25-4.12 (m, 3H), 4.08 (t, J=13.9 Hz, 2H), 3.94-3.87 (m, 4H), 3.79 (t, J=4.6 Hz, 2H), 3.75-3.65 (m, 2H), 3.65-3.60 (m, 3H), 3.59-3.53 (m, 3H), 3.53-3.45 (m, 7H), 2.82 (d, J=10.9 Hz, 2H), 2.47-2.41 (m, 5H), 2.12-1.99 (m, 3H), 1.98-1.88 (m, 3H), 1.80-1.69 (m, 4H), 1.66-1.57 (m, 4H), 1.56-1.46 (m, 2H), 1.42-1.31 (m, 2H), 1.25-1.22 (m, 1H), 1.22-1.19 (m, 1H), 0.95 (s, 9H).

Example 88. Synthesis of (2S,4R)—N-(2-((14-(4-(4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzamido)piperidin-1-yl)-3,6,9,12-tetraoxatetradecyl)oxy)-4-(4-methylthiazol-5-yl)benzyl)-1-((S)-2-(1-fluorocyclopropane-1-carboxamido)-3,3-dimethylbutanoyl)-4-hydroxypyrrolidine-2-carboxamide

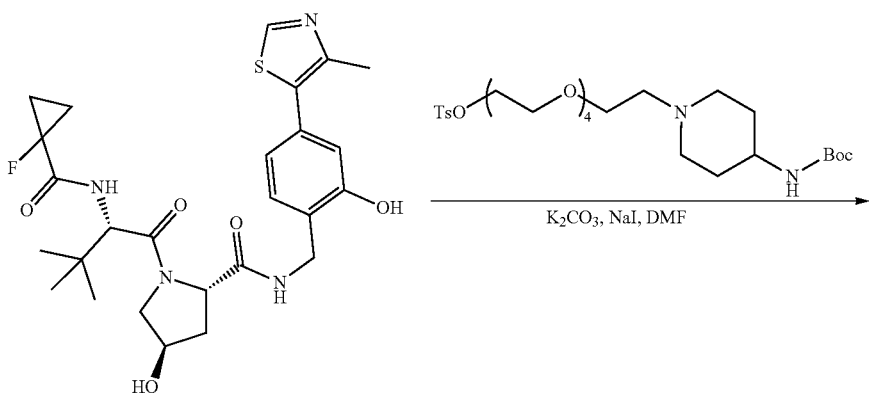

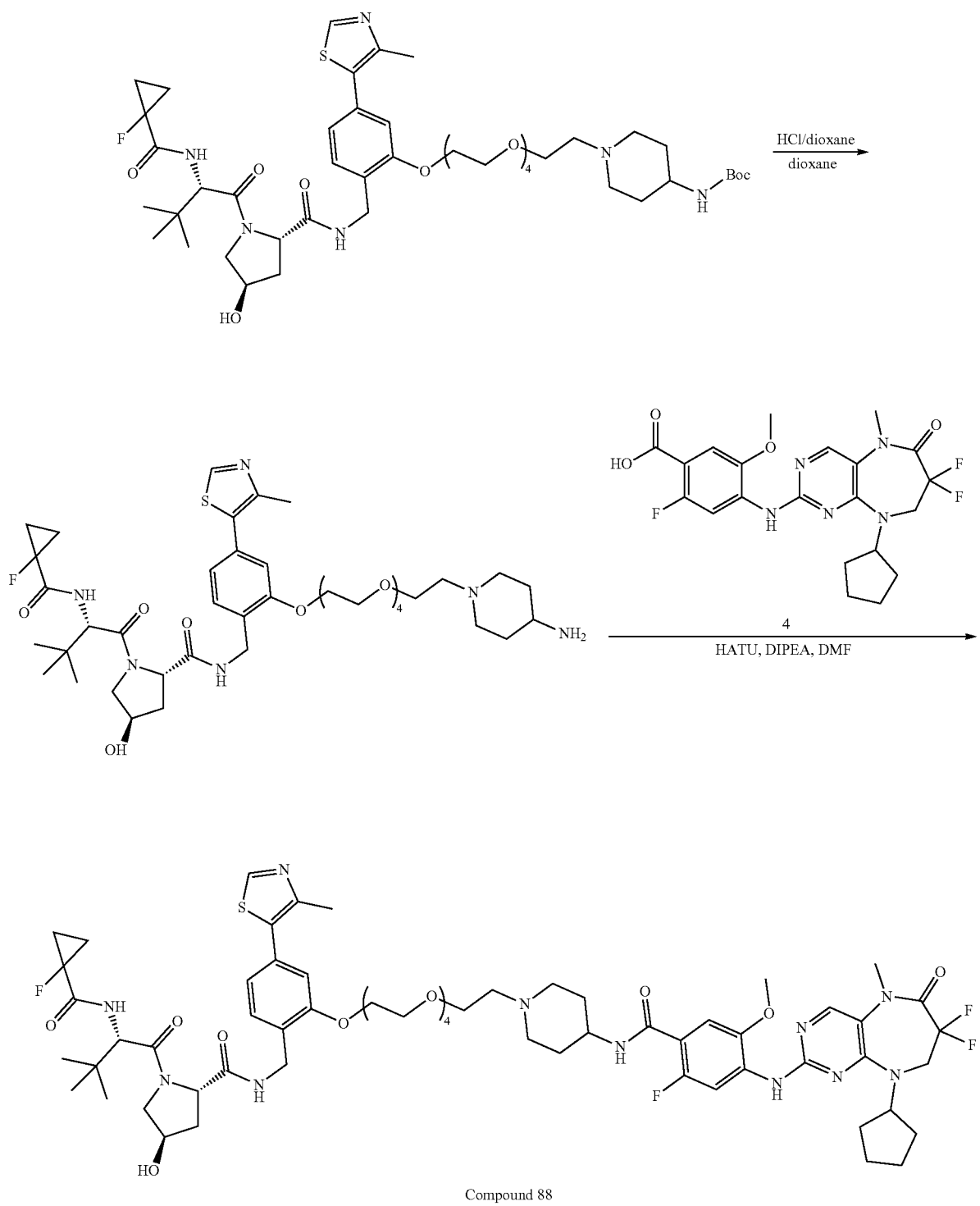
Compound 88
According to the above reaction scheme, in a manner similar to the other examples, obtained the titled compound (16 mg, 11.73 μmol, 10.65% yield, 94% purity) as yellow solid. MS(M+H)$^+$=1283.2
$^1$H NMR (400 MHz, DMSO-d$_6$) δ=8.97 (s, 1H), 8.50-8.45 (m, 1H), 8.30 (s, 1H), 8.24 (d, J=13.3 Hz, 1H), 8.02 (s, 1H), 7.88-7.83 (m, 1H), 7.40 (d, J=7.7 Hz, 1H), 7.31-7.25 (m, 1H), 7.18 (d, J=6.7 Hz, 1H), 7.05-7.02 (m, 1H), 6.98-6.94 (m, 1H), 5.16 (d, J=3.5 Hz, 1H), 4.86-4.76 (m, 1H), 4.59 (br d, J=9.0 Hz, 1H), 4.51 (t, J=8.3 Hz, 1H), 4.39-4.27 (m, 2H), 4.24-4.15 (m, 3H), 4.07 (br t, J=13.9 Hz, 2H), 3.91 (s, 3H), 3.82-3.76 (m, 2H), 3.75-3.68 (m, 1H), 3.65-3.59 (m, 3H), 3.57-3.53 (m, 2H), 3.52-3.46 (m, 11H), 3.30 (s, 3H), 2.86-2.80 (m, 2H), 2.47-2.44 (m, 5H), 2.11-1.89 (m, 8H), 1.81-1.69 (m, 3H), 1.67-1.47 (m, 5H), 1.42-1.31 (m, 2H), 1.26-1.18 (m, 2H), 0.95 (s, 9H).

Example 89. Synthesis of (2S,4R)—N-(2-((8-(4-(4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzamido) piperidin-1-yl)octyl)oxy)-4-(4-methylthiazol-5-yl)benzyl)-1-((S)-2-(1-fluorocyclopropane-1-carboxamido)-3,3-dimethylbutanoyl)-4-hydroxypyrrolidine-2-carboxamide
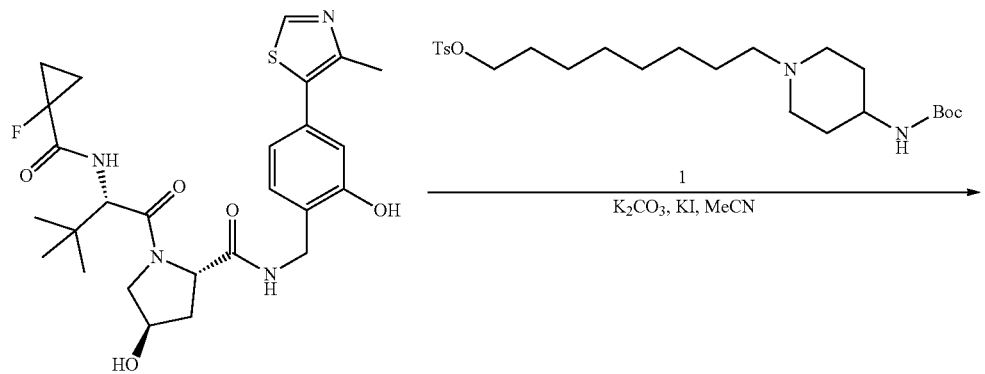
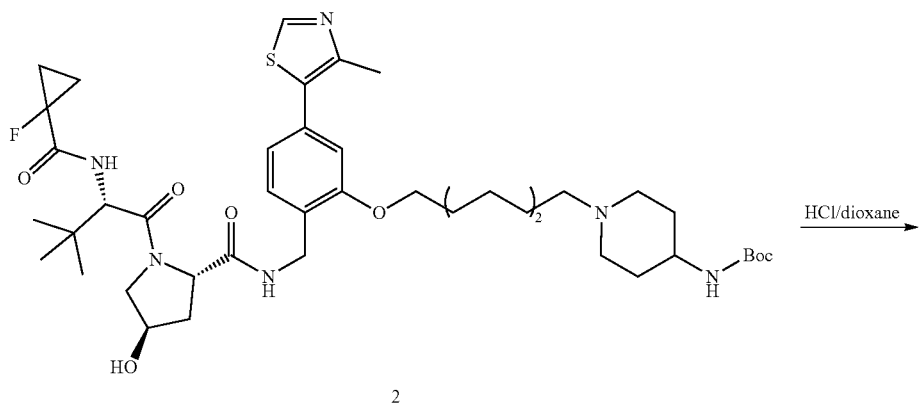
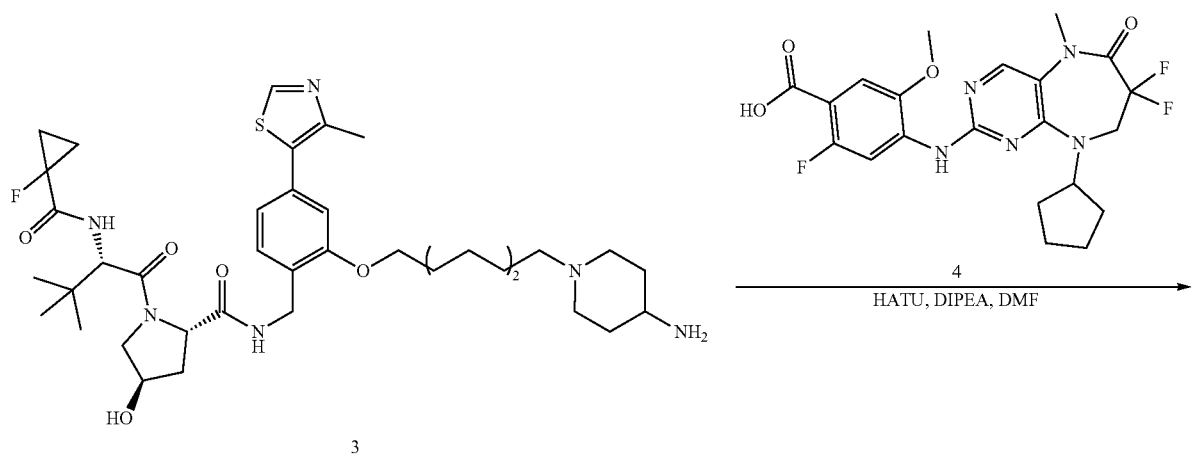

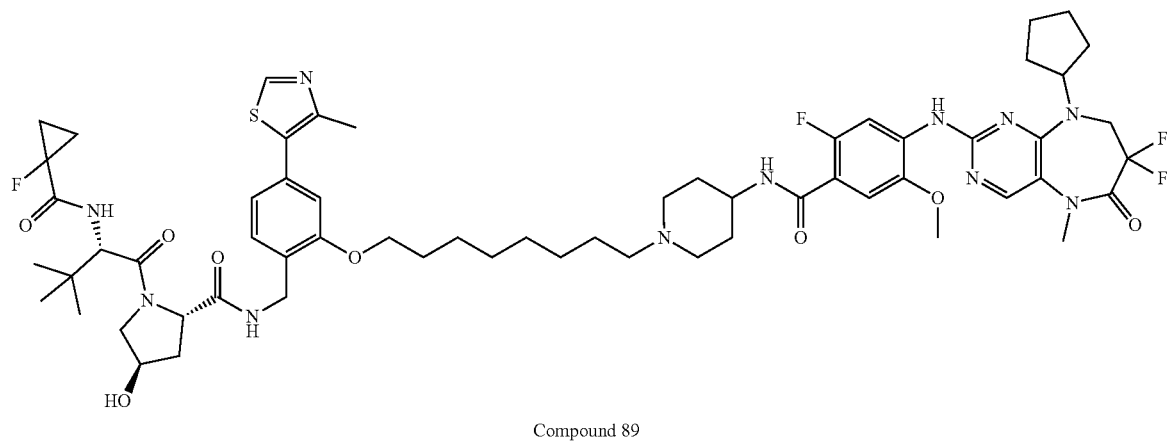

Compound 89

Step 1: Synthesis of tert-butyl (1-(8-(2-(((2S,4R)-1-((S)-2-(1-fluorocyclopropanecarboxamido)-3,3-dimethylbutanoyl)-4-hydroxypyrrolidine-2-carboxamido)methyl)-5-(4-methylthiazol-5-yl)phenoxy)octyl)piperidin-4-yl)carbamate (2)

To a solution of (2S,4R)-1-((S)-2-(1-fluorocyclopropanecarboxamido)-3,3-dimethylbutanoyl)-4-hydroxy-N-(2-hydroxy-4-(4-methylthiazol-5-yl)benzyl)pyrrolidine-2-carboxamide (0.5 g, 938.74 μmol) and 8-(4-((tert-butoxycarbonyl)amino)piperidin-1-yl)octyl 4-methylbenzenesulfonate (589.04 mg, 1.22 mmol) in MeCN (2 mL) were added $K_2CO_3$ (259.48 mg, 1.88 mmol) and NaI (70.36 mg, 469.37 μmol) and the resulting mixture was heated to 60° C. for 16 hours. LCMS showed 33% of reactant remained. Additional 8-(4-((tert-butoxycarbonyl)amino)piperidin-1-yl)octyl 4-methylbenzenesulfonate (543.74 mg, 1.12 mmol) was added and the resulting mixture was stirred at 60° C. for another 24 hrs. LCMS showed the starting material was consumed completely and a main peak with desired mass. The mixture was diluted with ethyl acetate (30 mL) and filtered. The filtrate was concentrated. The residue was purified by flash silica gel chromatography (25 g SepaFlash® Silica Flash Column, Eluent of 0~100% Ethyl acetate/Petroleum ether gradient @ 50 mL/min; Eluent of 0~20% Methanol/Ethyl acetate @ 100 mL/min) to afford the titled compound (0.6 g, crude) as a yellow oil, which was used for the next step directly. $MS(M+H)^+$=843.7

Step 2: Synthesis of (2S,4R)—N-(2-((8-(4-aminopiperidin-1-yl)octyl)oxy)-4 (4-methylthiazol-5-yl))benzyl)-1-((S)-2-(1-fluorocyclopropanecarboxamido)-3,3-dimethylbutanoyl)-4-hydroxypyrrolidine-2-carboxamide (3)

To a solution of tert-butyl (1-(8-(2-(((2S,4R)-1-((S)-2-(1-fluorocyclopropanecarboxamido)-3,3-dimethylbutanoyl)-4-hydroxypyrrolidine-2-carboxamido)methyl)-5-(4-methylthiazol-5-yl)phenoxy)octyl)piperidin-4-yl)carbamate (0.6 g, 711.66 μmol) in dioxane (5 mL) was added HCl/dioxane (4 M, 15 mL) at 0° C. The mixture was stirred at 25° C. for 0.5 hr. TLC (Ethyl acetate:Methanol=10:1; Rf=0) showed the starting material was consumed completely and new spot was formed. The reaction mixture was concentrated under reduced pressure to afford the titled compound (0.9 g, crude, HCl salt) as a yellow solid, which was used for the next step directly. $MS(M+H)^+$=743.7

Step 3: Synthesis of (2S,4R)—N-(2-((8-(4-(4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzamido)piperidin-1-yl)octyl)oxy)-4-(4-methylthiazol-5-yl)benzyl)-1-((S)-2-(1-fluorocyclopropanecarboxamido)-3,3-dimethylbutanoyl)-4-hydroxypyrrolidine-2-carboxamide (Compound 89)

To a solution of 4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzoic acid (60 mg, 128.91 mol) in DMF (2 mL) were added HATU (122.54 mg, 322.27 μmol) and DIPEA (33.32 mg, 257.82 μmol, 44.91 μL), the mixture was stirred at 20° C. for 10 min. Then a solution of (2S,4R)—N-(2-((8-(4-aminopiperidin-1-yl)octyl)oxy)-4-(4-methylthiazol-5-yl)benzyl)-1-((S)-2-(1-fluorocyclopropanecarboxamido)-3,3-dimethylbutanoyl)-4-hydroxypyrrolidine-2-carboxamide (120.57 mg, 154.69 mol, HCl salt) in DMF (2 mL) and DIPEA (33.32 mg, 257.82 μmol, 44.91 μL) were added and the resulting mixture was stirred at 25° C. for 12 h. LCMS showed the starting material was consumed completely and a main peak with desired mass. The mixture solution was concentrated under reduced pressure. The crude product was purified prep-HPLC (column: Waters Xbridge 150*25 mm*5 um; mobile phase: [water (10 mM $NH_4HCO_3$)-ACN]; B %: 62%-92%, 10 min) and the eluent was lyophilized to afford the titled compound (58.4 mg, 47.10 mol, 36.53% yield, 96% purity) as a white solid. $MS(M+H)^+$=1190.9

$^1$H NMR (400 MHz, DMSO-$d_6$) δ=8.97 (s, 1H), 8.48 (t, J=5.8 Hz, 1H), 8.33-8.18 (m, 2H), 8.03 (s, 1H), 7.85 (dd, J=3.4, 7.6 Hz, 1H), 7.40 (d, J=7.6 Hz, 1H), 7.29 (dd, J=2.8, 9.2 Hz, 1H), 7.19 (d, J=6.8 Hz, 1H), 7.03-6.90 (m, 2H), 5.17 (br s, 1H), 4.89-4.74 (m, 1H), 4.59 (d, J=8.8 Hz, 1H), 4.51 (t, J=8.2 Hz, 1H), 4.40-4.14 (m, 3H), 4.13-3.99 (m, 4H), 3.91 (s, 3H), 3.79-3.68 (m, 1H), 3.68-3.42 (m, 2H), 2.80 (br d, J=11.0 Hz, 2H), 2.53-2.51 (m, 1H), 2.45 (s, 3H), 2.23 (br t, J=7.2 Hz, 2H), 2.14-2.04 (m, 1H), 2.01-1.88 (m, 5H), 1.84-1.49 (m, 13H), 1.48-1.18 (m, 15H), 0.95 (s, 9H).

Example 90. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(2-(2-(2-((2-(2,6-dioxopiperidin-3-yl)-1,3-dioxoisoindolin-4-yl)amino)ethoxy)ethoxy)ethyl)piperidin-4-yl)-5-ethoxy-2-fluorobenzamide
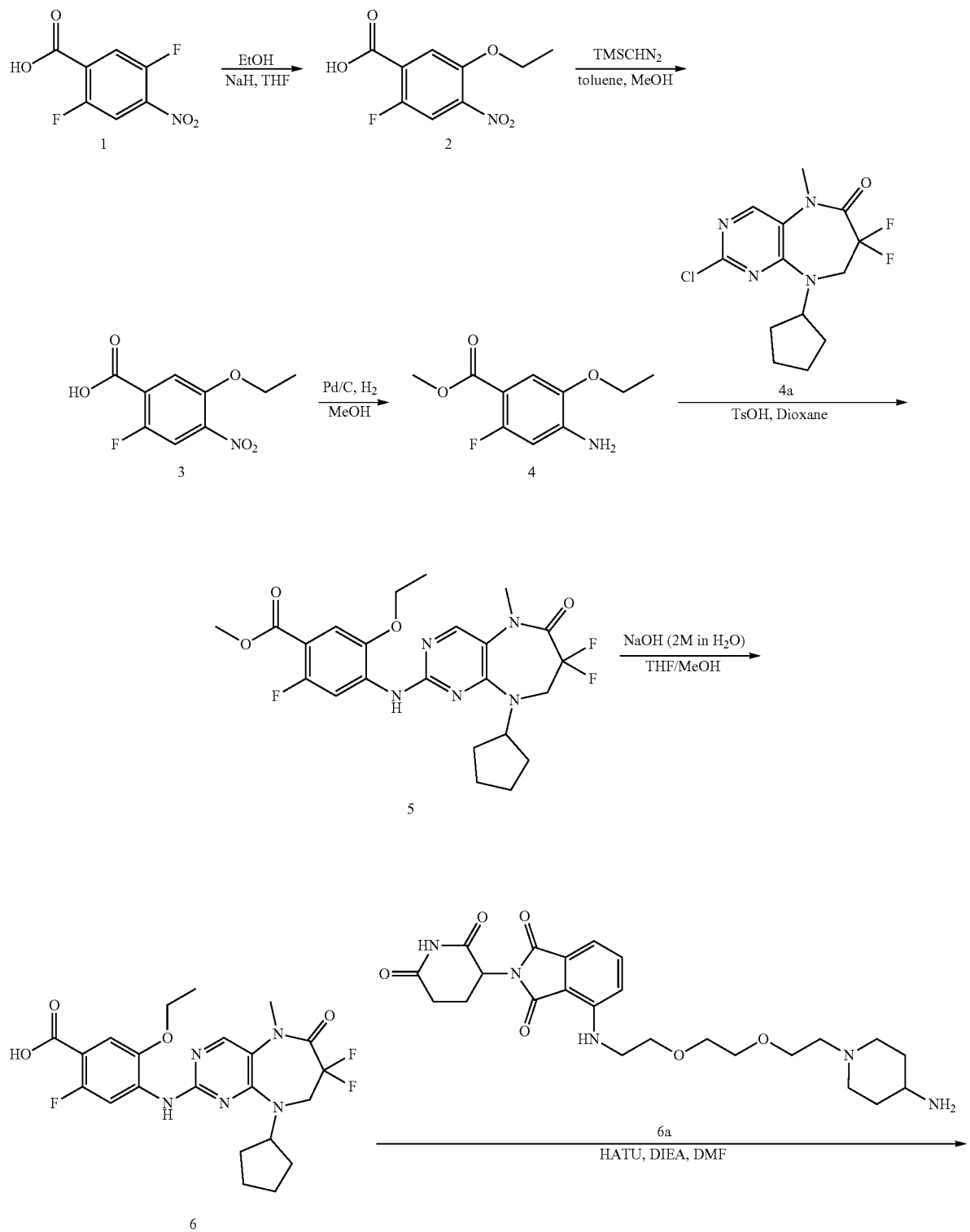

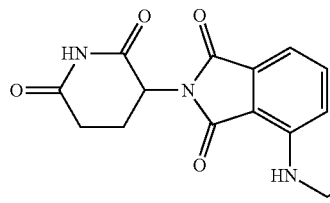
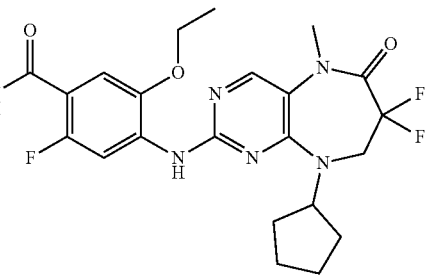

Compound 90

Step 1: Synthesis of 5-ethoxy-2-fluoro-4-nitrobenzoic acid (2)

To a solution of ethanol (499.02 mg, 10.83 mmol, 633.27 μL) in THF (10 mL) was added NaH (787.71 mg, 19.69 mmol, 60% purity in mineral oil) at 0° C., the mixture was stirred at 0° C. for 15 minutes. To this mixture was added a solution of 2,5-difluoro-4-nitrobenzoic acid (2 g, 9.85 mmol) in THF (10 mL) slowly at 0° C., the resulting mixture was stirred at 15° C. for 3 hours. TLC (SiO$_2$, Petroleum ether/Ethyl acetate=1/1) indicated the starting material was consumed completely, and one major new spot with lower polarity was detected. The reaction mixture was quenched by addition H$_2$O (50 mL), and adjusted to pH=5 HCl by a solution (1M) of HCl. The resulting mixture was extracted with EtOAc (80 mL×3). The combined organic layers were washed with brine (100 mL×2), dried over Na$_2$SO$_4$, filtered and concentrated in vacuo to afford the titled compound (2.4 g, 9.74 mmol, 98.91% yield, 93% purity) as a gray solid, which was used for the next step directly.

Step 2: Synthesis of methyl 5-ethoxy-2-fluoro-4-nitrobenzoate (3)

A solution of 5-ethoxy-2-fluoro-4-nitrobenzoic acid (2.4 g, 9.74 mmol, 93% purity) in toluene (30 mL) was added a solution of TMSCHN$_2$ (2 M, 7.30 mL) in toluene (6 mL) and MeOH (6 mL) slowly, the mixture was stirred at 15° C. for 2 hours. TLC (SiO$_2$, Petroleum ether/Ethyl acetate=2/1) indicated trace of the starting material remained and one major new spot with lower polarity was detected. The reaction mixture was quenched by addition H$_2$O (80 mL), then extracted with EtOAc (100 mL×3). The combined organic layers were washed with brine (150 mL×2), dried over Na$_2$SO$_4$, filtered and concentrated in vacuo. The residue was purified by flash silica gel chromatography (25 g SepaFlash® Silica Flash Column, Eluent of 12~50% Ethyl acetate/Petroleum ether gradient @ 65 mL/min) to afford the titled compound (1.1 g, 4.52 mmol, 46.44% yield) as a brown solid.

Step 3: Synthesis of methyl 4-amino-5-ethoxy-2-fluorobenzoate (4)

To a solution of methyl 5-ethoxy-2-fluoro-4-nitrobenzoate (1.1 g, 4.52 mmol) in MeOH (20 mL) was added Pd/C (600 mg, 10% purity) under N$_2$ atmosphere, the mixture was degassed and purged with H$_2$ for 3 times, the mixture was stirred at 15° C. for 16 hours under H$_2$ atmosphere (15 psi). LCMS showed reactant was consumed completely and 80% of desired mass was detected. The reaction mixture was filtered and the filtrate was concentrated in vacuo to afford the titled compound (940 mg, 3.53 mmol, 77.98% yield, 80% purity) as a brown solid, which was used for the next step directly. MS(M+H)$^+$=214.2.

Step 4: Synthesis of methyl 4-((9-cyclopentyl-7,7-difluoro-5-methyl-6-oxo-6,7,8,9-tetrahydro-5H-pyrimido[4,5-b][1,4]diazepin-2-yl)amino)-5-ethoxy-2-fluorobenzoate (5)

A mixture of 2-chloro-9-cyclopentyl-7,7-difluoro-5-methyl-8,9-dihydro-5H-pyrimido[4,5-b][1,4]diazepin-6(7H)-one (300 mg, 947.17 μmol), methyl 4-amino-5-ethoxy-2-fluorobenzoate (378.64 mg, 1.42 mmol, 80% purity) and TsOH (326.21 mg, 1.89 mmol) in 1,4-dioxane (8 mL) was stirred at 100° C. for 12 hours. LCMS showed 13% of reactant remained and 39% of desired mass was detected. To this mixture was added methyl 4-amino-5-ethoxy-2-fluorobenzoate (126.21 mg, 473.59 μmol, 80% purity) followed by TsOH (163.10 mg, 947.17 μmol), the resulting mixture was stirred at 100° C. for 12 hours. LCMS showed reactant was consumed completely and 37% of desired mass was detected. The reaction mixture was concentrated in vacuo. The residue was purified by prep-HPLC (column: Waters Xbridge 150*25 mm*5 um; mobile phase: [water(10 mM NH$_4$HCO$_3$)-ACN]; B %: 60%-90%, 10 min), the eluent was freeze-dried to afford the titled compound (80 mg, 162.11 umol, 17.12% yield) as a brown solid. MS(M+H)$^+$=494.3.

Step 5: Synthesis of 4-((9-cyclopentyl-7,7-difluoro-5-methyl-6-oxo-6,7,8,9-tetrahydro-5H-pyrimido[4,5-b][1,4]diazepin-2-yl)amino)-5-ethoxy-2-fluorobenzoic acid (6)

To a solution of methyl 4-((9-cyclopentyl-7,7-difluoro-5-methyl-6-oxo-6,7,8,9-tetrahydro-5H-pyrimido[4,5-b][1,4]diazepin-2-yl)amino)-5-ethoxy-2-fluorobenzoate (80 mg, 162.11 μmol) in THF (2 mL) and MeOH (2 mL) was added NaOH (2 M in H$_2$O, 2 mL), the mixture was stirred at 25° C. for 16 hours. LCMS showed reactant was consumed completely and 90% of desired mass was detected. The reaction mixture was quenched by addition with HCl solution (1 M) to adjust pH=5. The resulting mixture was concentrated in vacuo to afford the titled compound (310 mg, 646.57 µmol, 398.84% yield) as a brown solid, which was used for the next step directly. MS(M+H)$^+$=480.1.

Step 6: Synthesis of 4-((9-cyclopentyl-7,7-difluoro-5-methyl-6-oxo-6,7,8,9-tetrahydro-5H-pyrimido[4,5-b][1, 4]diazepin-2-yl)amino)-N-(1-(2-(2-(2-((2-(2,6-dioxopiperidin-3-yl)-1,3-dioxoisoindolin-4-yl) amino)ethoxy)ethoxy)ethyl)piperidin-4-yl)-5-ethoxy-2-fluorobenzamide (Compound 90)

To a solution of 4-((2-(2-(2-(4-aminopiperidin-1-yl) ethoxy)ethoxy)ethyl)amino)-2-(2,6-dioxopiperidin-3-yl) isoindoline-1,3-dione (65 mg, 115.97 µmol, 2HCl salt), 4-((9-cyclopentyl-7,7-difluoro-5-methyl-6-oxo-6,7,8,9-tetrahydro-5H-pyrimido[4,5-b][1, 4]diazepin-2-yl)amino)-5-ethoxy-2-fluorobenzoic acid (233.54 mg, 487.09 mol) and HATU (66.15 mg, 173.96 µmol) in DMF (2 mL) was added DIEA (89.93 mg, 695.85 µmol, 121.20 µL), the mixture was stirred at 15° C. for 2 hours. LCMS showed 17% of reactant remained and 33% of desired mass was detected. To this mixture was added 4-[2-[2-[2-(4-amino-1-piperidyl)ethoxy] ethoxy]ethylamino]-2-(2,6-dioxo-3-piperidyl)isoindoline-1, 3-dione (13.00 mg, 23.19 µmol, 2HCl salt), the resulting mixture was stirred at 15° C. for 2 hours. The reaction mixture was combined with another batch (20 mg). The reaction mixture was filtered and the filtrate was purified by prep-HPLC (column: Waters Xbridge 150*25 mm*5 um; mobile phase: [water(10 mM NH$_4$HCO$_3$)-ACN]; B %: 36%-69%, 10 min) followed by prep-HPLC (column: Phenomenex luna C$_{18}$ 150*40 mm*15 um; mobile phase: [water (0.225% FA)-ACN]; B %: 18%-48%, 10 min), the eluent was freeze-dried to afford the titled compound (29.2 mg, 29.54 µmol, 25.47% yield, 96% purity) as a yellow solid. MS(M+H)$^+$=949.6.

$^1$H NMR (400 MHz, CDCl$_3$) δ=8.35 (d, J=15.0 Hz, 1H), 8.07 (s, 1H), 7.85 (s, 1H), 7.64-7.41 (m, 2H), 7.11 (d, J=7.1 Hz, 1H), 6.92 (d, J=8.6 Hz, 1H), 6.76-6.60 (m, 1H), 6.53 (s, 1H), 5.03-4.69 (m, 2H), 4.20 (q, J=6.8 Hz, 2H), 4.03 (m, 1H), 3.92 (t, J=13.3 Hz, 2H), 3.75-3.71 (m, 2H), 3.70-3.59 (m, 6H), 3.47 (m, 2H), 3.42 (s, 3H), 3.06-2.84 (m, 3H), 2.83-2.69 (m, 2H), 2.66-2.61 (m, 2H), 2.30-2.23 (m, 2H), 2.20-2.07 (m, 3H), 2.07-2.00 (m, 2H), 1.92-1.74 (m, 5H), 1.69-1.55 (m, 4H), 1.54-1.45 (m, 3H).

Example 91. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(2-(2-(2-((2-(2,6-dioxopiperidin-3-yl)-1,3-dioxoisoindolin-4-yl)amino)ethoxy)ethoxy)ethyl)piperidin-4-yl)-2-fluoro-5-isopropoxybenzamide

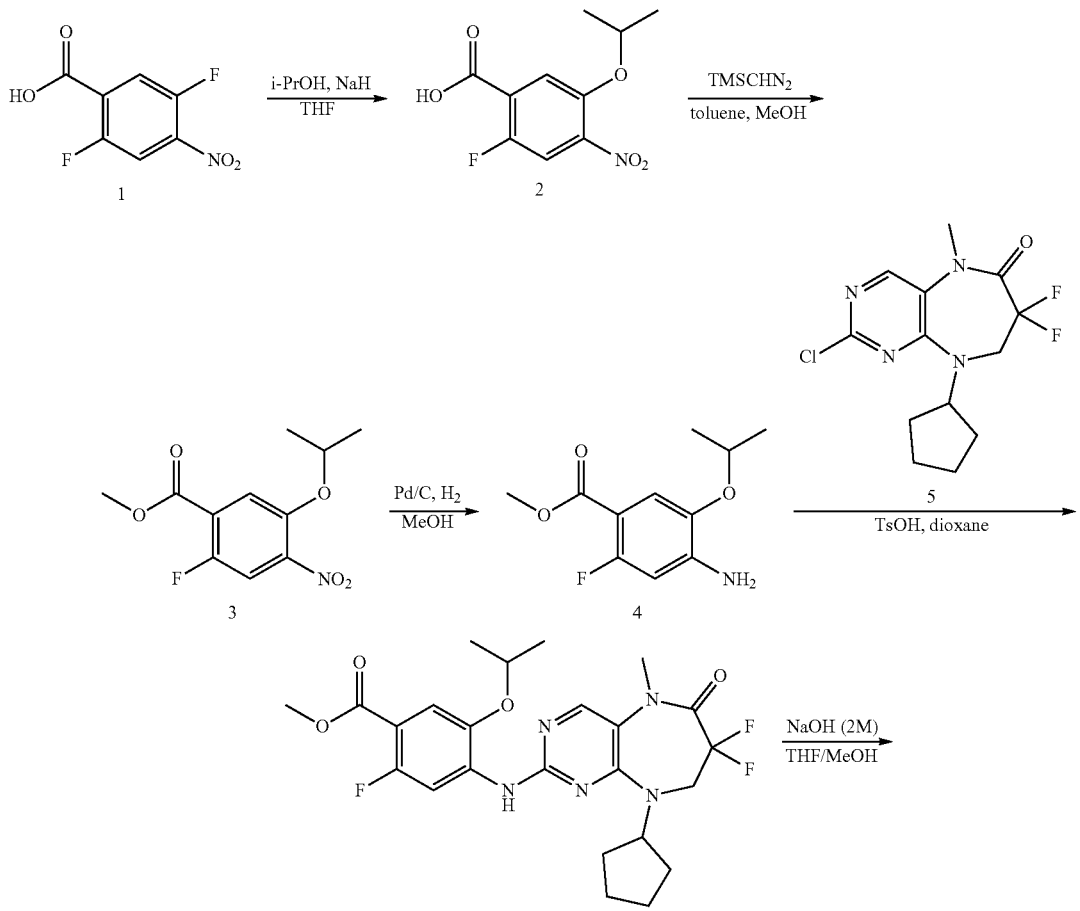

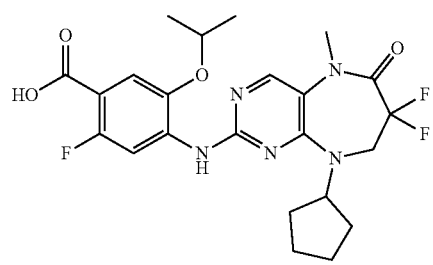

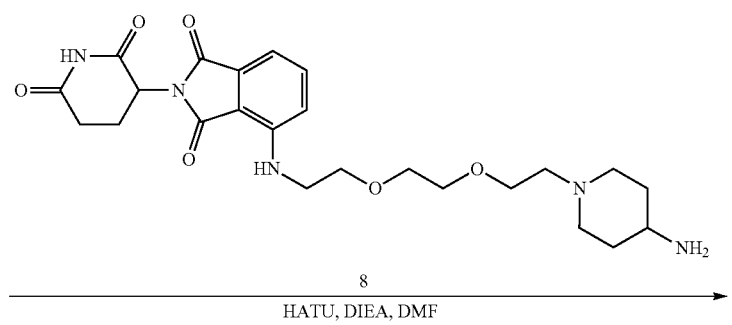

7 → 8, HATU, DIEA, DMF

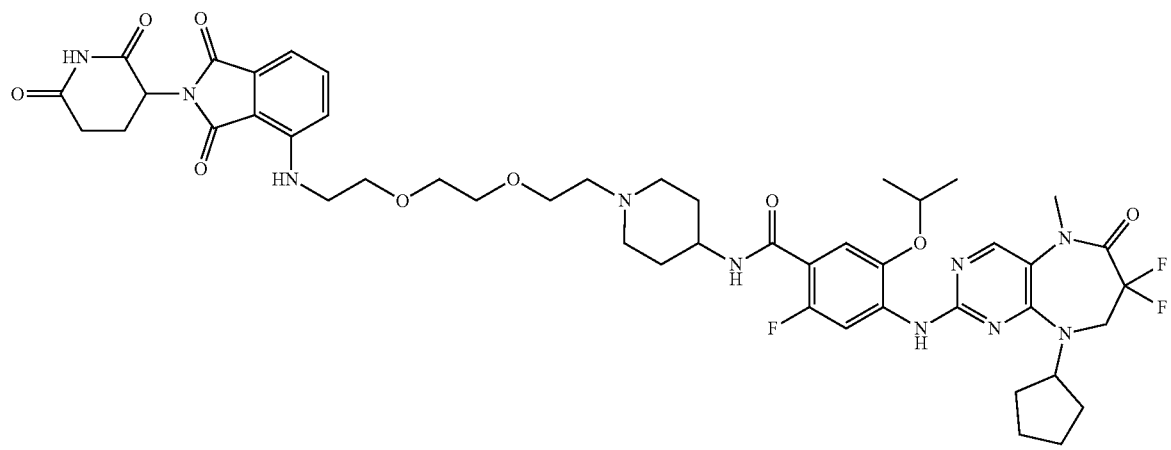

Compound 91

Step 1-5 are Described in the Above Reaction Scheme

Step 6: Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(2-(2-(2-((2-(2,6-dioxopiperidin-3-yl)-1,3-dioxo isoindolin-4-yl)amino)ethoxy)ethoxy)ethyl)piperidin-4-yl)-2-fluoro-5-isopropoxybenzamide (Compound 91)

To a solution of 4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-isopropoxybenzoic acid (306.93 mg, 621.98 μmol), 4-((2-(2-(2-(4-aminopiperidin-1-yl)ethoxy)ethoxy)ethyl)amino)-2-(2,6-dioxopiperidin-3-yl)isoindoline-1,3-dione (83 mg, 148.09 μmol, 2HCl salt) and HATU (84.46 mg, 222.14 μmol) in DMF (3 mL) was added DIEA (95.70 mg, 740.45 μmol, 128.97 μL), the mixture was stirred at 15° C. for 2 hours. LCMS showed reactant was consumed completely and 82% of desired mass was detected. The reaction mixture was filtered and the filtrate was purified by prep-HPLC (column: Waters Xbridge BEH $C_{18}$ 150*25 mm*5 um; mobile phase: [water (10 mM $NH_4HCO_3$)-ACN]; B %: 53%-83%, 10 min) to afford the titled compound (38.4 mg, 38.28 μmol, 25.85% yield, 96% purity) as a yellow solid. MS(M+H)$^+$=963.6.

$^1$H NMR (400 MHz, CDCl$_3$) δ=8.35 (d, J=15.3 Hz, 1H), 8.07 (s, 1H), 7.86 (s, 1H), 7.58 (d, J=7.3 Hz, 1H), 7.50 (dd, J1=8.3 Hz, J2=7.3 Hz, 1H), 7.11 (d, J=7.0 Hz, 1H), 6.92 (d, J=8.6 Hz, 1H), 6.69 (dd, J=7.6, 14.9 Hz, 1H), 6.53 (t, J=5.4 Hz, 1H), 4.98-4.79 (m, 2H), 4.73-4.71 (m, 1H), 4.11-3.99 (m, 1H), 3.92 (t, J=13.4 Hz, 2H), 3.78-3.61 (m, 8H), 3.48-3.47 (m, 2H), 3.42 (s, 3H), 3.04-2.91 (m, 2H), 2.90-2.83 (m, 1H), 2.84-2.77 (m, 1H), 2.77-2.71 (m, 1H), 2.69-2.56 (m, 2H), 2.27 (t, J=10.8 Hz, 2H), 2.19-2.09 (m, 3H), 2.06-2.03 (m, 2H), 1.88-1.69 (m, 9H), 1.40 (d, J=6.1 Hz, 6H).

Example 92. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-5-cyclopropoxy-N-(1-(2-(2-(2-((2-(2,6-dioxopiperidin-3-yl)-1,3-dioxoisoindolin-4-yl)amino)ethoxy)ethoxy)ethyl)piperidin-4-yl)-2-fluorobenzamide
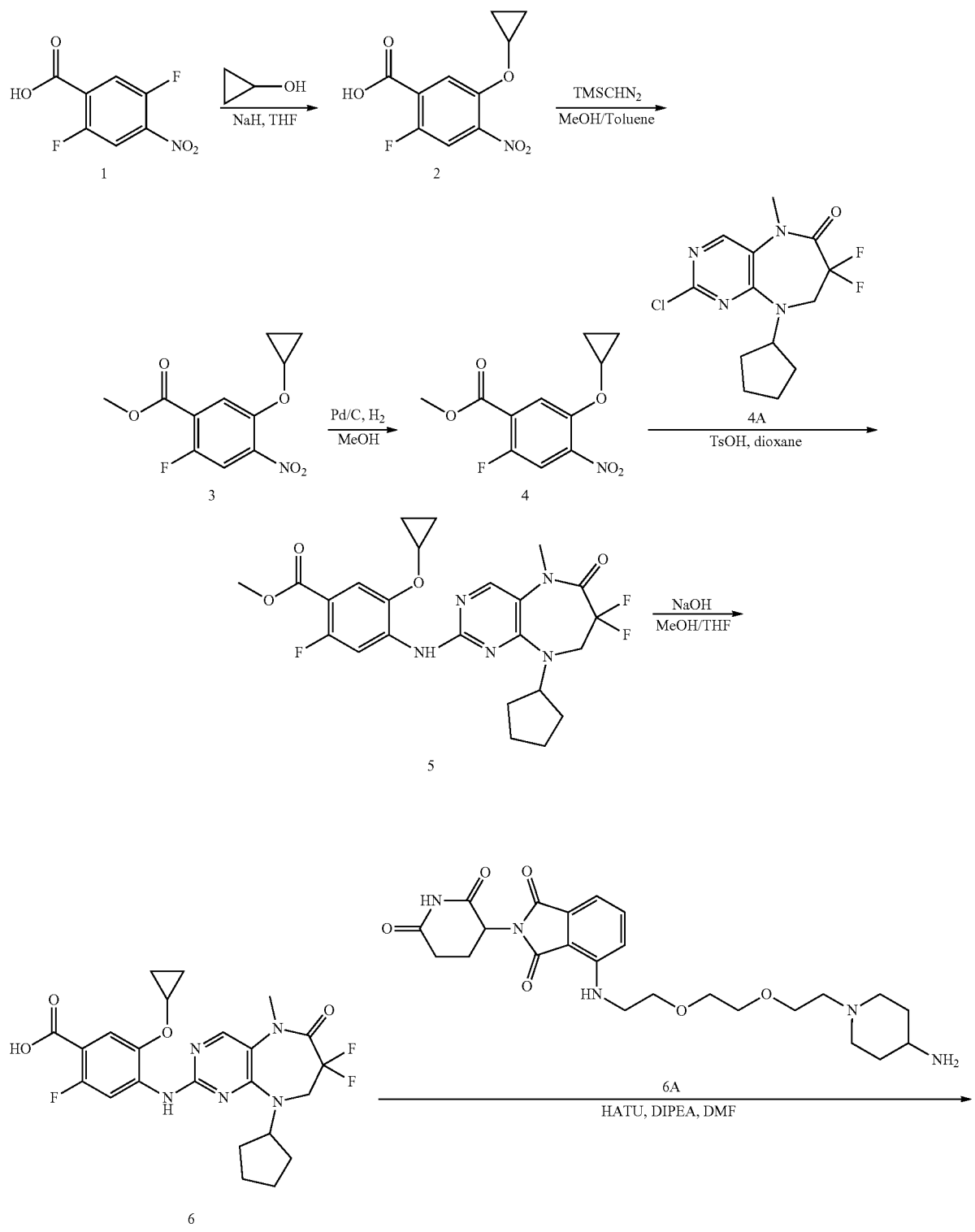

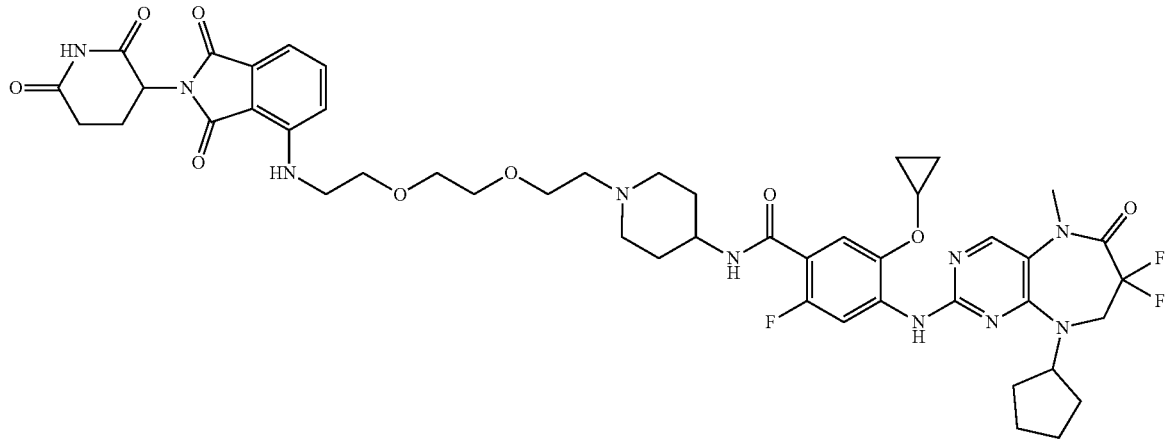

Compound 92

Step 1-5 are Described in the Above Reaction Scheme

Step 6: Synthesis of 4-((9-cyclopentyl-7,7-difluoro-5-methyl-6-oxo-6,7,8,9-tetrahydro-5H-pyrimido[4,5-b][1,4]diazepin-2-yl)amino)-5-cyclopropoxy-N-(1-(2-(2-(2-((2-(2,6-dioxopiperidin-3-yl))-1,3-dioxoisoindolin-4-yl)amino)ethoxy)ethoxy)ethyl)piperidin-4-yl)-2-fluorobenzamide (Compound 92)

To a solution of 4-((9-cyclopentyl-7,7-difluoro-5-methyl-6-oxo-6,7,8,9-tetrahydro-5H-pyrimido[4,5-b][1,4]diazepin-2-yl)amino)-5-cyclopropoxy-2-fluorobenzoic acid (180 mg, 366.25 umol) in DMF (4 mL) were added HATU (181.04 mg, 476.13 umol) and DIPEA (236.68 mg, 1.83 mmol, 318.97 uL), after stirring for 20 min, 4-((2-(2-(2-(4-aminopiperidin-1-yl)ethoxy)ethoxy)ethyl)amino)-2-(2,6-dioxopiperidin-3-yl)isoindoline-1,3-dione (211.11 mg, 402.88 umol, HCl salt) was added and the resulting mixture was stirred at 15° C. for 3 hr. LCMS showed one peak (78%) with desired mass. The reaction mixture was diluted with H₂O (50 mL) and extracted with EtOAc (40 mL×2). The combined organic layer was dried over Na₂SO₄, filtered. The filtrate was concentrated in vacuo. The residue was purified by prep-HPLC (column: Phenomenex luna C18 150*40 mm*15 um; mobile phase: [water (0.225% FA)-ACN]; B %: 18%-48%, 10 min) followed by prep-HPLC (column: Phenomenex Gemini-NX C18 75*30 mm*3 um; mobile phase: [water (10 mM NH₄HCO₃)-ACN]; B %: 38%-68%, 8 min) to afford the titled compound (60 mg, 60.56 umol, 16.54% yield, 95% purity) as a yellow solid. MS(M+H)⁺=961.6

¹H NMR (400 MHz, MeOD) δ=8.41-8.33 (m, 1H), 8.19 (s, 1H), 7.66 (d, J=7.0 Hz, 1H), 7.55 (dd, J=7.2, 8.5 Hz, 1H), 7.10 (d, J=8.6 Hz, 1H), 7.05 (d, J=7.1 Hz, 1H), 5.05 (dd, J=5.5, 12.5 Hz, 1H), 4.95-4.92 (m, 1H), 4.08-3.87 (m, 4H), 3.76-3.63 (m, 8H), 3.53-3.47 (m, 2H), 3.40 (s, 3H), 3.02 (br d, J=10.0 Hz, 2H), 2.91-2.81 (m, 1H), 2.78-2.69 (m, 2H), 2.68-2.60 (m, 2H), 2.37-2.22 (m, 2H), 2.15-2.05 (m, 3H), 1.94 (br d, J=12.2 Hz, 2H), 1.85-1.63 (m, 8H), 0.94-0.88 (m, 2H), 0.87-0.79 (m, 2H).

Example 93. Synthesis of 5-cyclobutoxy-4-((9-cyclopentyl-7,7-difluoro-5-methyl-6-oxo-6,7,8,9-tetrahydro-5H-pyrimido[4,5-b][1,4]diazepin-2-yl)amino)-N-(1-(2-(2-(2-((2-(2,6-dioxopiperidin-3-yl)-1,3-dioxoisoindolin-4-yl)amino)ethoxy)ethoxy)ethyl)piperidin-4-yl)-2-fluorobenzamide

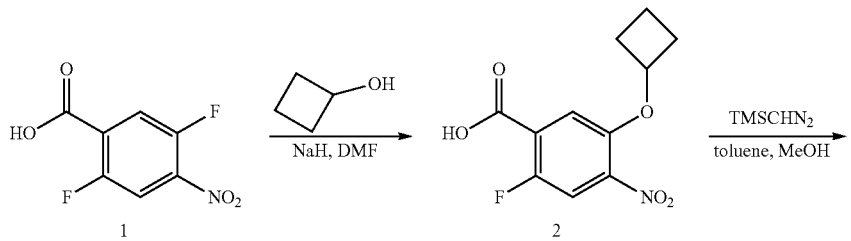

-continued
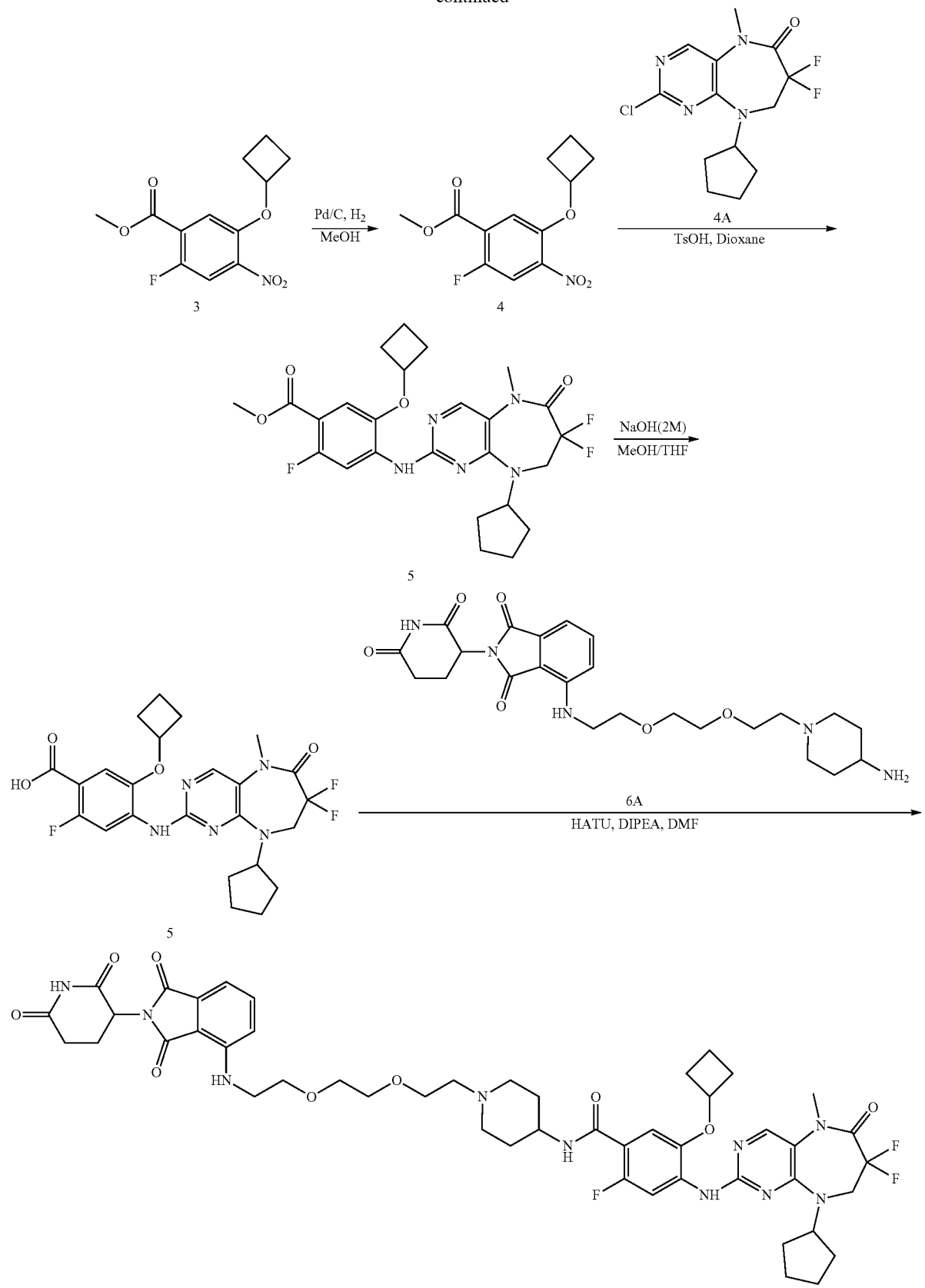
Compound 93

Step 1-5 are Described in the Above Reaction Scheme

Step 6: Synthesis of 5-cyclobutoxy-4-((9-cyclopentyl-7,7-difluoro-5-methyl-6-oxo-6,7,8,9-tetrahydro-5H-pyrimido[4,5-b][1,4]diazepin-2-yl)amino)-N-(1-(2-(2-(2-((2-(2,6-dioxopiperidin-3-yl)-1,3-dioxoisoindolin-4-yl)amino)ethoxy)ethoxy)ethyl)piperidin-4-yl)-2-fluorobenzamide (Compound 93)

To a solution of 5-cyclobutoxy-4-((9-cyclopentyl-7,7-difluoro-5-methyl-6-oxo-6,7,8,9-tetrahydro-5H-pyrimido[4,5-b][1,4]diazepin-2-yl)amino)-2-fluorobenzoic acid (268.00 mg, 530.18 umol) in DMF (4 mL) were added HATU (262.07 mg, 689.23 umol) and DIPEA (342.60 mg, 2.65 mmol, 461.73 uL), after stirring for 20 min, 4-((2-(2-(2-(4-aminopiperidin-1-yl)ethoxy)ethoxy)ethyl)amino)-2-(2,6-dioxopiperidin-3-yl)isoindoline-1,3-dione (305.60 mg, 583.20 umol, HCl salt) was added and the resulting mixture was stirred at 15° C. for 3 hr. LCMS showed one peak (87%) with desired mass. The reaction mixture was diluted with H$_2$O (50 mL) and extracted with EtOAc (40 mL×2). The combined organic layer was dried over Na$_2$SO$_4$, filtered. The filtrate was concentrated in vacuo. The residue was purified by prep-HPLC (column: Phenomenex luna C18 150*40 mm*15 um; mobile phase: [water (0.225% FA)-ACN]; B %: 25%-55%, 10 min) followed by prep-HPLC (column: Phenomenex Gemini-NX C18 75*30 mm*3 um; mobile phase: [water (10 mM NH$_4$HCO$_3$)-ACN]; B %: 42%-72%, 8 min) to afford the titled compound (69.1 mg, 69.45 umol, 13.10% yield, 98% purity) as a yellow solid.

MS(M+H)$^+$=975.5

$^1$H NMR (400 MHz, CD$_3$OD) δ=8.40 (d, J=14.1 Hz, 1H), 8.22 (s, 1H), 7.57 (dd, J=7.1, 8.6 Hz, 1H), 7.21 (d, J=6.8 Hz, 1H), 7.12 (d, J=8.6 Hz, 1H), 7.06 (d, J=7.1 Hz, 1H), 5.06 (dd, J=5.5, 12.5 Hz, 1H), 4.99-4.82 (m, 1H), 4.07 (t, J=13.4 Hz, 2H), 3.96-3.85 (m, 1H), 3.75 (t, J=5.2 Hz, 2H), 3.72-3.61 (m, 6H), 3.57-3.49 (m, 2H), 3.43 (s, 3H), 3.00 (br d, J=12.6 Hz, 2H), 2.93-2.82 (m, 1H), 2.80-2.70 (m, 2H), 2.66-2.52 (m, 4H), 2.33-2.20 (m, 4H), 2.18-2.07 (m, 3H), 2.00-1.52 (m, 13H).

Example 94. Synthesis of 5-(sec-butoxy)-4-((9-cyclopentyl-7,7-difluoro-5-methyl-6-oxo-6,7,8,9-tetrahydro-5H-pyrimido[4,5-b][1,4]diazepin-2-yl)amino)-N-(1-(2-(2-(2-((2-(2,6-dioxopiperidin-3-yl)-1,3-dioxoisoindolin-4-yl)amino)ethoxy)ethoxy)ethyl)piperidin-4-yl)-2-fluorobenzamide

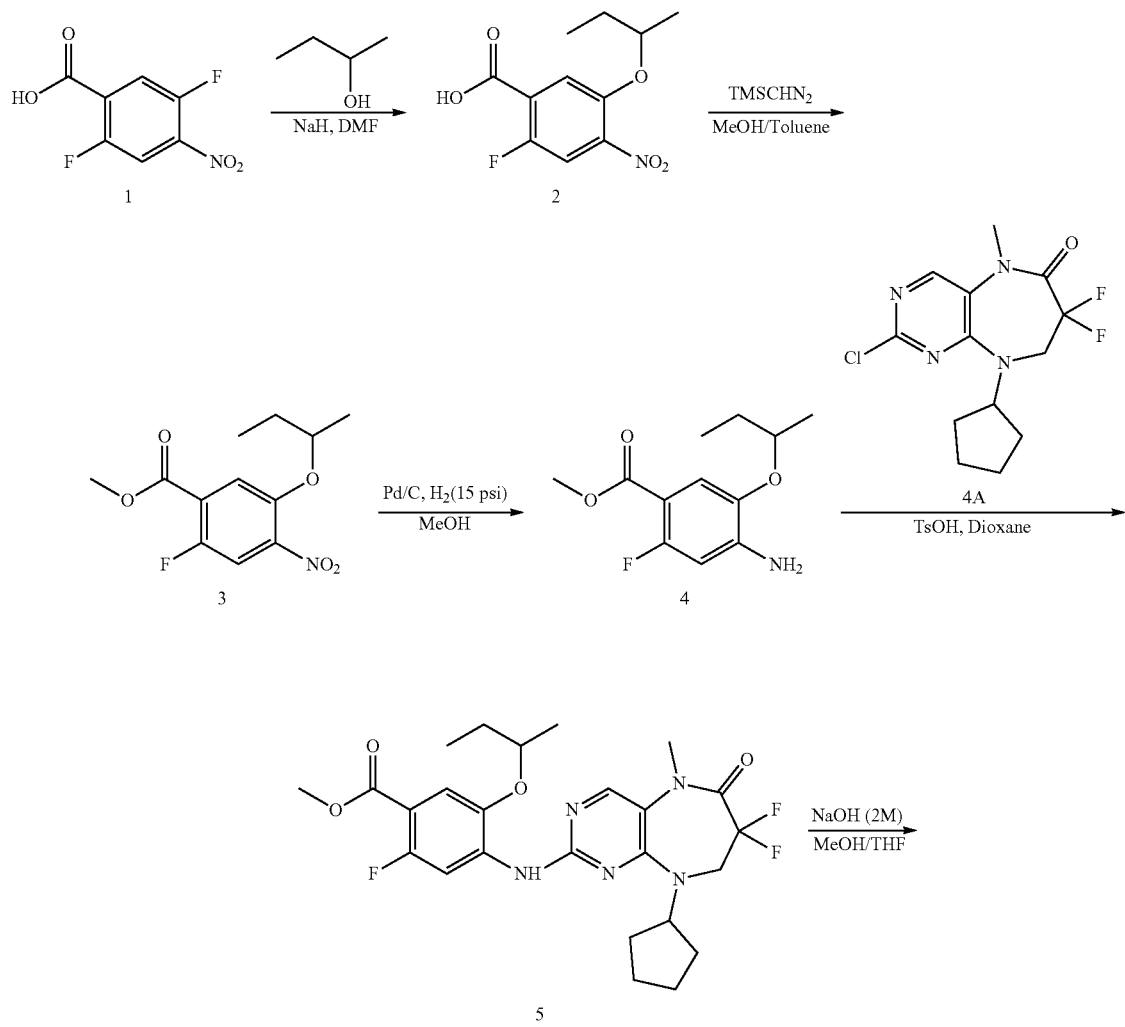

-continued

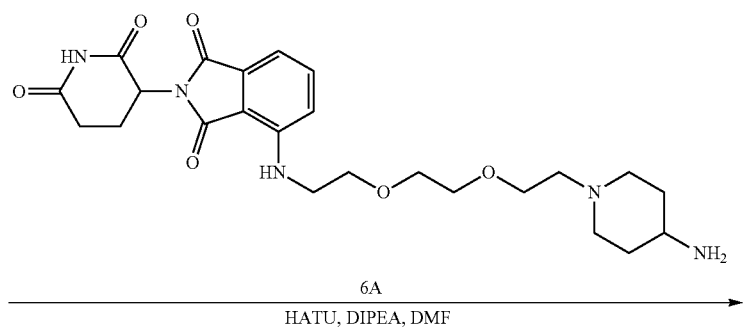
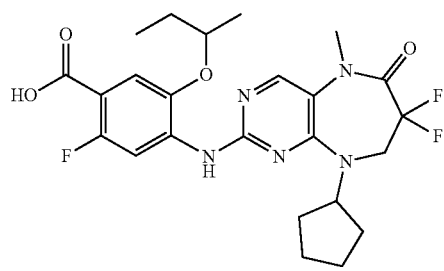

6
→ 6A
HATU, DIPEA, DMF

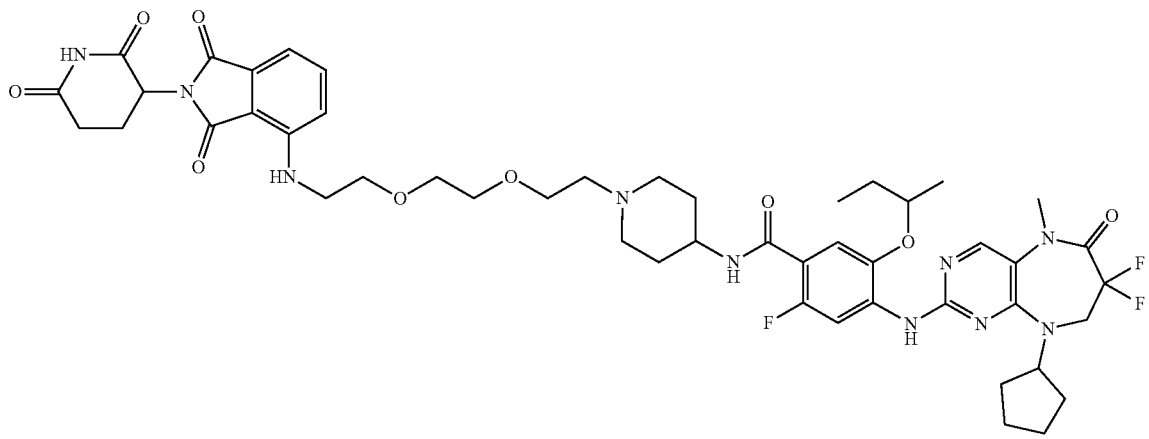

Compound 94

Step 1-5 are Described in the Above Reaction Scheme

Step 6: Synthesis of 5-(sec-butoxy)-4-((9-cyclopentyl-7,7-difluoro-5-methyl-6-oxo-6,7,8,9-tetrahydro-5H-pyrimido[4,5-b][1,4]diazepin-2-yl)amino)-N-(1-(2-(2-(2-((2-(2,6-dioxopiperidin-3-yl)-1,3-dioxoisoindolin-4-yl)amino)ethoxy)ethoxy)ethyl)piperidin-4-yl)-2-fluorobenzamide (Compound 94)

To a solution of 5-(sec-butoxy)-4-((9-cyclopentyl-7,7-difluoro-5-methyl-6-oxo-6,7,8,9-tetrahydro-5H-pyrimido[4,5-b][1,4]diazepin-2-yl)amino)-2-fluorobenzoic acid (180 mg, 354.68 umol) in DMF (8 mL) were added HATU (175.32 mg, 461.08 umol) and DIPEA (229.19 mg, 1.77 mmol, 308.88 uL), after stirring for 20 min, 4-((2-(2-(2-(4-aminopiperidin-1-yl)ethoxy)ethoxy)ethyl)amino)-2-(2,6-dioxopiperidin-3-yl)isoindoline-1,3-dione (204.44 mg, 390.14 umol, HCl salt) was added and the resulting mixture was stirred at 15° C. for 3 hr. LCMS showed one peak (67%) with desired mass. The reaction mixture was diluted with H$_2$O (50 mL) and extracted with EtOAc (40 mL×2). The combined organic layer was dried over Na$_2$SO$_4$, filtered. The filtrate was concentrated in vacuo. The residue was purified by prep-HPLC (column: Phenomenex luna C18 150*40 mm*15 um; mobile phase: [water (0.225% FA)-ACN]; B %: 25%-55%, 10 min) to obtain 172.5 mg of product with 92% purity, which was treated with basic ion exchange resin and lyophilized to afford 5-(sec-butoxy)-4-((9-cyclopentyl-7,7-difluoro-5-methyl-6-oxo-6,7,8,9-tetrahydro-5H-pyrimido[4,5-b][1,4]diazepin-2-yl)amino)-N-(1-(2-(2-(2-((2-(2,6-dioxopiperidin-3-yl)-1,3-dioxoisoindolin-4-yl)amino)ethoxy)ethoxy)ethyl)piperidin-4-yl)-2-fluorobenzamide (134.9 mg, 125.64 umol, 35.42% yield, 91% purity) as a yellow solid. MS(M+H)$^+$=977.6

$^1$H NMR (400 MHz, CD$_3$OD) δ=8.41 (d, J=14.1 Hz, 1H), 8.22 (s, 1H), 7.57 (dd, J=7.1, 8.6 Hz, 1H), 7.36 (d, J=6.8 Hz, 1H), 7.12 (d, J=8.7 Hz, 1H), 7.09-7.04 (m, 1H), 5.07 (dd, J=5.5, 12.5 Hz, 1H), 4.99-4.92 (m, 1H), 4.57-4.48 (m, 1H), 4.07 (t, J=13.4 Hz, 2H), 3.99-3.89 (m, 1H), 3.76 (t, J=5.2 Hz, 2H), 3.73-3.63 (m, 6H), 3.58-3.50 (m, 2H), 3.42 (s, 3H), 3.07 (br d, J=11.1 Hz, 2H), 2.94-2.82 (m, 1H), 2.80-2.65 (m, 4H), 2.43-2.30 (m, 2H), 2.18-2.07 (m, 3H), 1.97 (br d, J=11.1 Hz, 2H), 1.91-1.62 (m, 10H), 1.39 (d, J=6.0 Hz, 3H), 1.06 (t, J=7.5 Hz, 3H).

Example 95. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-5-(cyclopentyloxy)-N-(1-(2-(2-(2-((2-(2,6-dioxopiperidin-3-yl)-1,3-dioxoisoindolin-4-yl)amino)ethoxy)ethoxy)ethyl)piperidin-4-yl)-2-fluorobenzamide
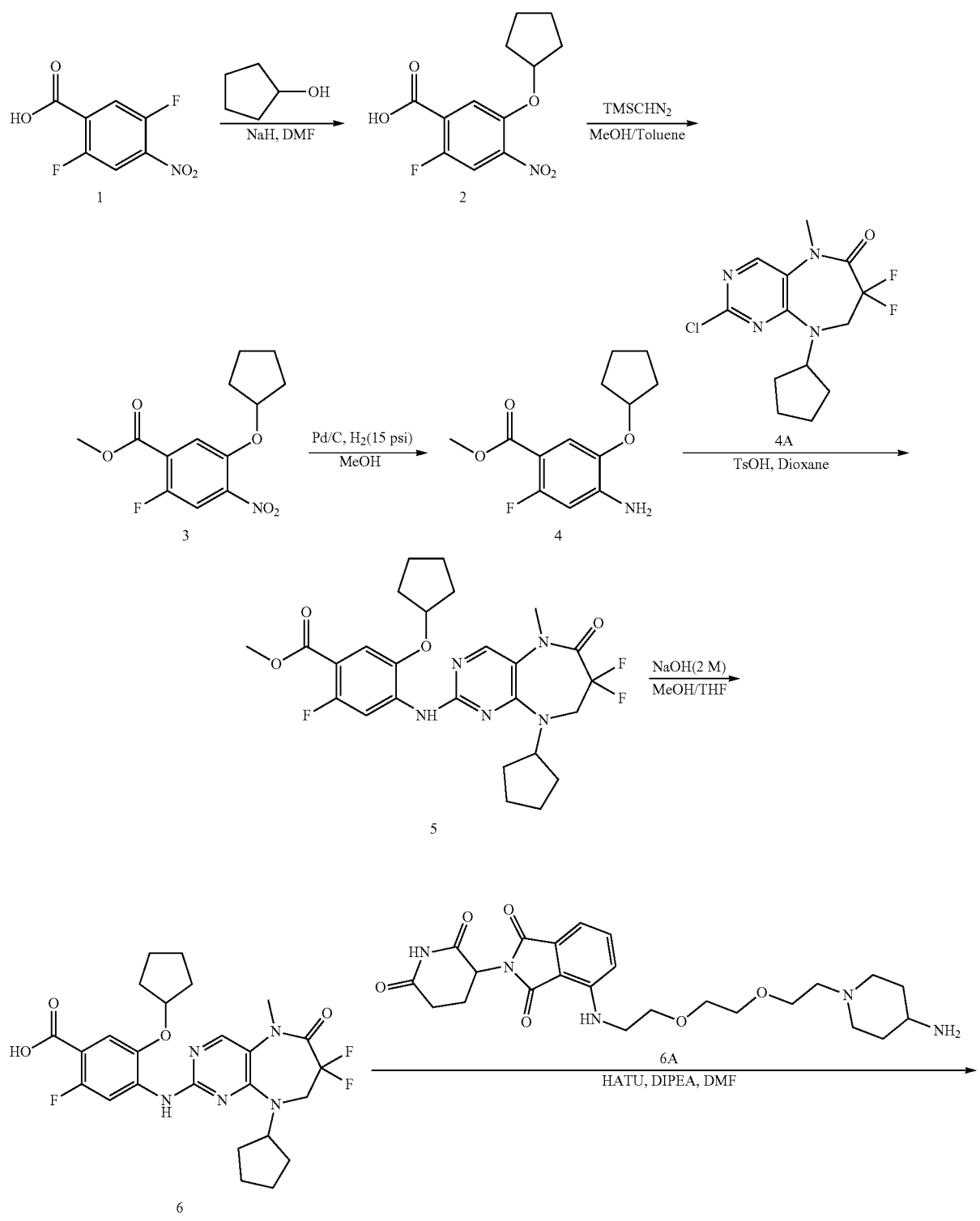

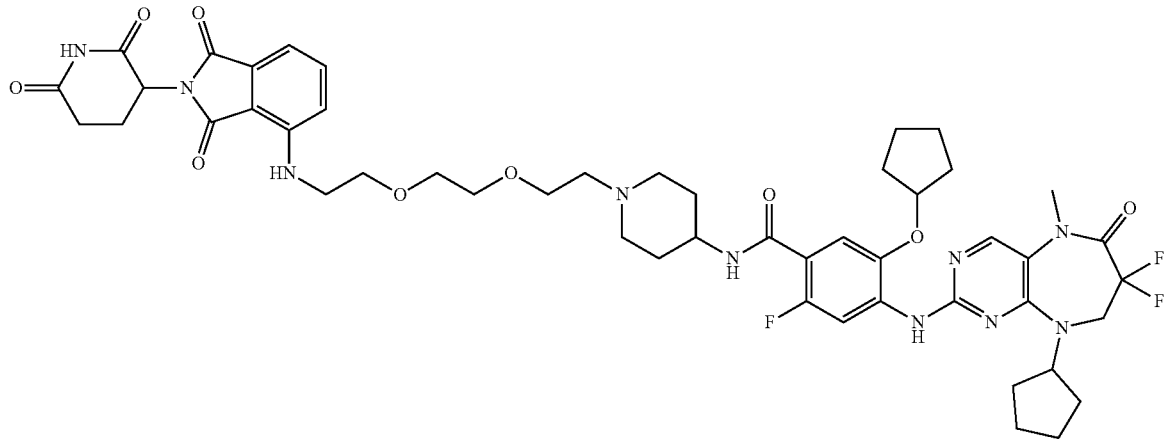

Compound 95

Step 1-5 are Described in the Above Reaction Scheme

Step 6: Synthesis of 4-((9-cyclopentyl-7,7-difluoro-5-methyl-6-oxo-6,7,8,9-tetrahydro-5H-pyrimido[4,5-b][1,4]diazepin-2-yl)amino)-5-(cyclopentyloxy)-N-(1-(2-(2-(2-((2-(2,6-dioxopiperidin-3-yl)-1,3-dioxoisoindolin-4-yl)amino)ethoxy)ethoxy)ethyl)piperidin-4-yl)-2-fluorobenzamide (Compound 95)

To a solution of 4-((9-cyclopentyl-7,7-difluoro-5-methyl-6-oxo-6,7,8,9-tetrahydro-5H-pyrimido[4,5-b][1,4]diazepin-2-yl)amino)-5-(cyclopentyloxy)-2-fluorobenzoic acid (108.00 mg, 207.89 umol) in DMF (8 mL) were added HATU (102.76 mg, 270.25 umol) and DIPEA (134.34 mg, 1.04 mmol, 181.05 uL), after stirring for 20 min, 4-((2-(2-(2-(4-aminopiperidin-1-yl)ethoxy)ethoxy)ethyl)amino)-2-(2,6-dioxopiperidin-3-yl)isoindoline-1,3-dione (119.83 mg, 228.67 umol, HCl salt) was added and the resulting mixture was stirred at 15° C. for 3 hr. LCMS showed one peak (84%) with desired mass. The reaction mixture was diluted with H$_2$O (50 mL) and extracted with EtOAc (40 mL×2). The combined organic layer was dried over Na$_2$SO$_4$, filtered. The filtrate was concentrated in vacuo. The residue was purified by prep-HPLC (column: Phenomenex luna C18 150*40 mm*15 um; mobile phase: [water (0.225% FA)-ACN]; B %: 22%-52%, 10 min). The product was treated with basic ion exchange resin and lyophilized to afford (64.7 mg, 59.53 umol, 28.64% yield, 91% purity) as a yellow solid. MS(M+H)$^+$=990.4

$^1$H NMR (400 MHz, CD$_3$OD) δ=8.40 (d, J=14.1 Hz, 1H), 8.22 (s, 1H), 7.57 (dd, J=7.2, 8.5 Hz, 1H), 7.35 (d, J=6.8 Hz, 1H), 7.12 (d, J=8.6 Hz, 1H), 7.07 (d, J=7.1 Hz, 1H), 5.07 (dd, J=5.4, 12.5 Hz, 1H), 5.02-4.93 (m, 2H), 4.07 (t, J=13.4 Hz, 2H), 4.01-3.90 (m, 1H), 3.79-3.64 (m, 8H), 3.59-3.48 (m, 3H), 3.42 (s, 3H), 3.18-3.06 (m, 2H), 2.94-2.82 (m, 1H), 2.81-2.67 (m, 3H), 2.55-2.34 (m, 2H), 2.17-1.64 (m, 21H).

Example 96. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(2-(2-(2-((2-(2,6-dioxopiperidin-3-yl)-1,3-dioxoisoindolin-4-yl)amino)ethoxy)ethoxy)ethyl)piperidin-4-yl)-3-methoxybenzamide

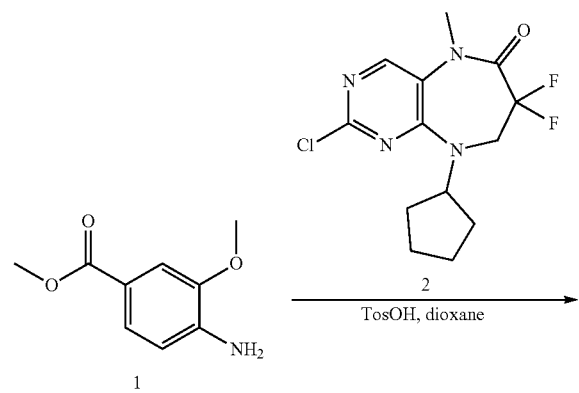

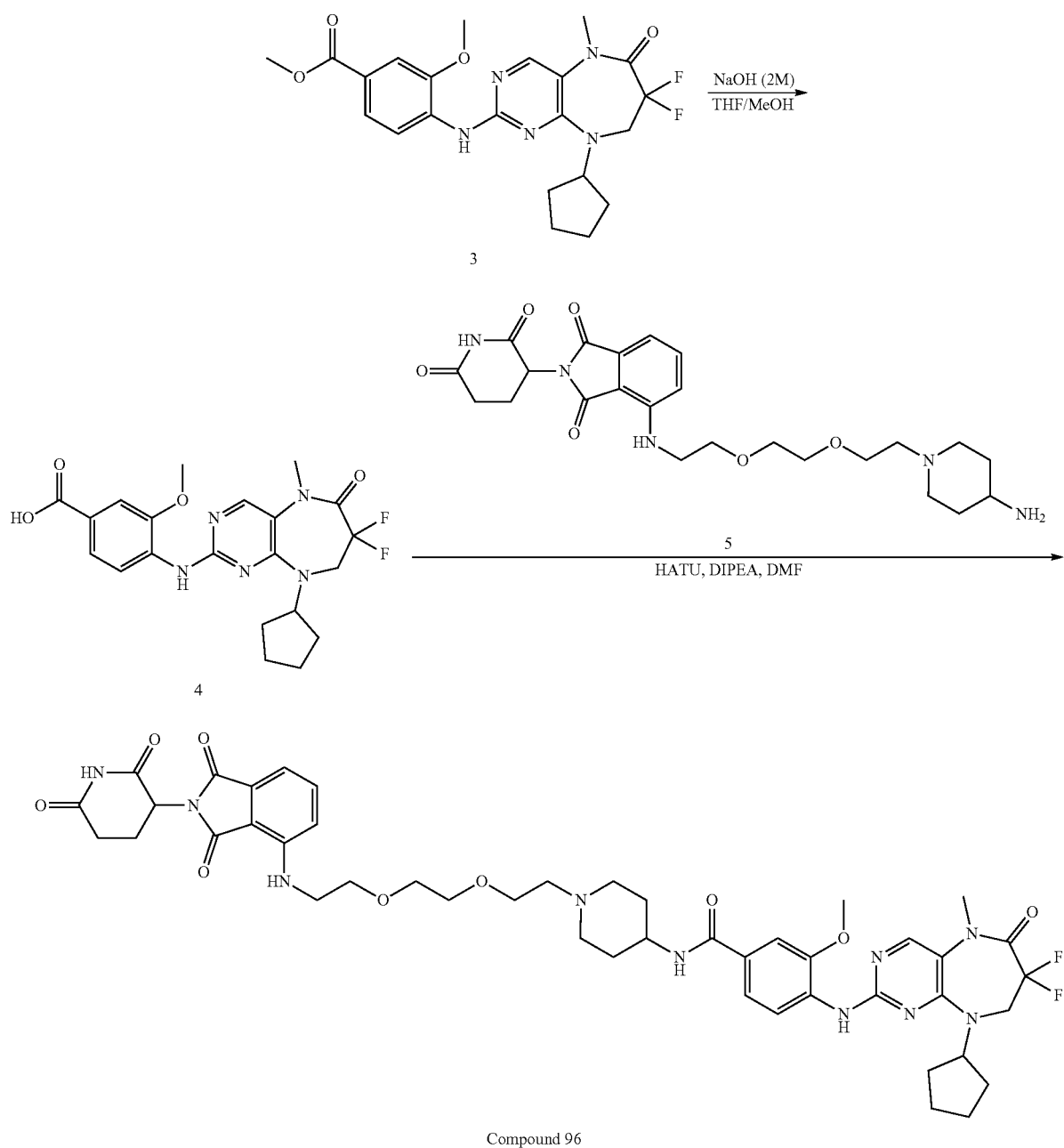

Compound 96

Step 1: Synthesis of methyl 4-((9-cyclopentyl-7,7-difluoro-5-methyl-6-oxo-6,7,8,9-tetrahydro-5H-pyrimido[4,5-b][1,4]diazepin-2-yl)amino)-3-methoxybenzoate (3)

A mixture of methyl 4-amino-3-methoxybenzoate (514.85 mg, 2.84 mmol), 2-chloro-9-cyclopentyl-7,7-difluoro-5-methyl-8,9-dihydro-5H-pyrimido[4,5-b][1,4]diazepin-6(7H)-one (300 mg, 947.17 μmol) and TosOH (148.01 mg, 2.84 mmol) in 1,4-dioxane (10 mL) was stirred at 100° C. for 16 hours. LCMS showed 39% of methyl 4-amino-3-methoxybenzoate remained and 55% of desired mass was detected. The reaction mixture was diluted with H₂O (30 mL) and the resulting mixture was added NaHCO₃ solution to adjust pH=8, and extracted with EtOAc (50 mL×3). The combined organic layers were washed with brine (50 mL×3), dried over Na₂SO₄, filtered and concentrated in vacuo. The residue was purified by flash silica gel chromatography (12 g SepaFlash® Silica Flash Column, Eluent of 0~20% Ethyl acetate/Petroleum ether gradient @ 65 mL/min) to afford the titled compound (1 g, 1.76 mmol, 185.32% yield, 81% purity) as a yellow solid. MS(M+H)⁺=462.3.

Step 2: Synthesis of 4-((9-cyclopentyl-7,7-difluoro-5-methyl-6-oxo-6,7,8,9-tetrahydro-5H-pyrimido[4,5-b][1,4]diazepin-2-yl)amino)-3-methoxybenzoic acid (4)

To a solution of methyl 4-((9-cyclopentyl-7,7-difluoro-5-methyl-6-oxo-6,7,8,9-tetrahydro-5H-pyrimido[4,5-b][1,4]

diazepin-2-yl)amino)-3-methoxybenzoate (900 mg, 1.54 mmol, 79% purity) in THF (8 mL) and MeOH (8 mL) was added NaOH (2 M in H$_2$O, 8 mL), the mixture was stirred at 25° C. for 12 hours. LCMS showed the starting material was consumed completely and 63% of desired mass was detected. The reaction mixture was acidified with HCl solution (1 M) to adjust pH=5, and then diluted with H$_2$O (30 mL) and extracted with EtOAc (40 mL×3). The combined organic layers were washed with brine (50 mL×2), dried over Na$_2$SO$_4$, filtered and concentrated in vacuo to afford the titled compound (160 mg, 318.26 μmol, 20.66% yield, 89% purity) as a white solid.

Step 3: Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(2-(2-(2-((2-(2,6-dioxopiperidin-3-yl)-1,3-dioxo isoindolin-4-yl)amino)ethoxy)ethoxy)ethyl)piperidin-4-yl)-3-methoxybenzamide (Compound 96)

To a solution of 4-((9-cyclopentyl-7,7-difluoro-5-methyl-6-oxo-6,7,8,9-tetrahydro-5H-pyrimido[4,5-b][1,4]diazepin-2-yl)amino)-3-methoxybenzoic acid (383.19 mg, 856.42 μmol) in DMF (6 mL) were added HATU (305.29 mg, 802.90 μmol) and DIEA (276.72 mg, 2.14 mmol, 372.93 μL), the mixture was stirred at 15° C. for 15 minutes, then 4-((2-(2-(2-(4-aminopiperidin-1-yl)ethoxy)ethoxy)ethyl)amino)-2-(2,6-dioxopiperidin-3-yl)isoindoline-1,3-dione (300 mg, 535.27 μmol, 2HCl) was added and the resulting mixture was stirred at 15° C. for 2 hours. LCMS showed reactant was consumed completely and 68% of desired mass was detected. The reaction mixture was purified by prep-HPLP (column: Waters Xbridge 150*25 mm*5 um; mobile phase: [water (10 mM NH$_4$HCO$_3$)-ACN]; B %: 33%-63%, 9 min) followed by prep-HPLC (column: Phenomenex luna C$_{18}$ 150*40 mm*15 um; mobile phase: [water(0.225% FA)-ACN]; B %: 15%-45%, 10 min) twice and freeze dried to afford the titled compound (71 mg, 75.88 μmol, 14.18% yield, 98% purity) as a yellow solid. MS(M+H)$^+$=917.5.

$^1$H NMR (400 MHz, CDCl$_3$) δ=8.46 (d, J=8.4 Hz, 1H), 8.06 (s, 1H), 7.75 (s, 1H), 7.50 (dd, J=8.3 Hz, 7.3 Hz, 1H), 7.44 (d, J=1.6 Hz, 1H), 7.24 (d, J=1.6 Hz, 1H), 7.11 (d, J=7.0 Hz, 1H), 6.92 (d, J=8.7 Hz, 1H), 6.55 (t, J=5.7 Hz, 1H), 6.06 (d, J=8.3 Hz, 1H), 4.98-4.76 (m, 2H), 4.05-3.96 (m, 4H), 3.90 (t, J=13.5 Hz, 2H), 3.74 (t, J=5.3 Hz, 2H), 3.70-3.63 (m, 6H), 3.50-3.45 (m, 2H), 3.41 (s, 3H), 3.09-2.93 (m, 2H), 2.90-2.75 (m, 2H), 2.74-2.60 (m, 3H), 2.31-2.21 (m, 2H), 2.16-2.07 (m, 3H), 2.06-2.00 (m, 2H), 1.88-1.50 (m, 9H).

Example 97. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(2-(2-(2-((2-(2,6-dioxopiperidin-3-yl)-1,3-dioxoisoindolin-4-yl)amino)ethoxy)ethoxy)ethyl)piperidin-4-yl)-2-fluoro-5-(2-hydroxyethoxy)benzamide

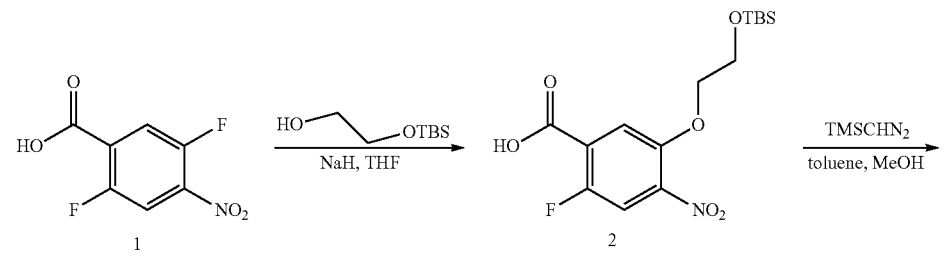

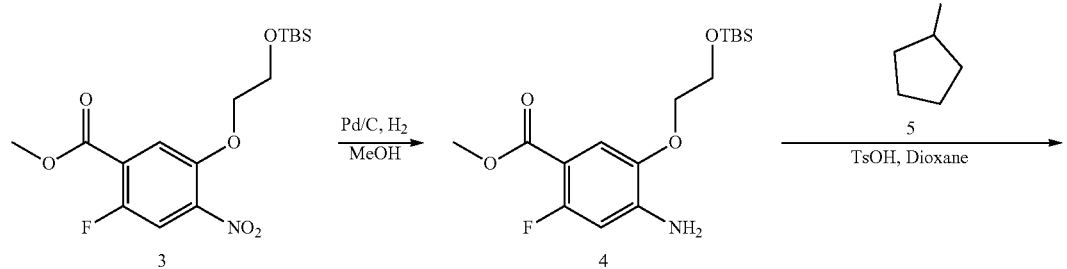

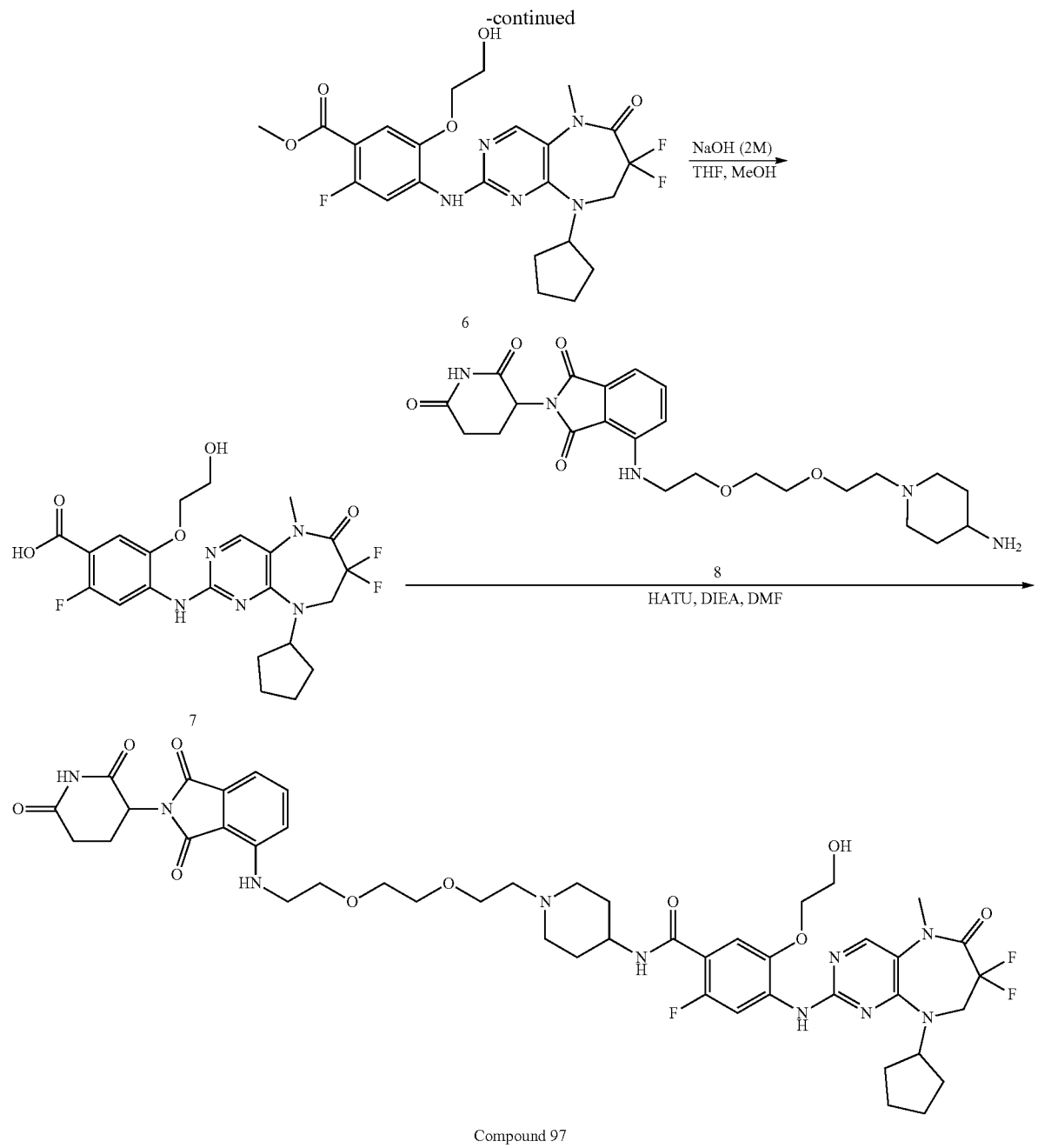

Compound 97

Step 1-5 are Described in the Above Reaction Scheme

Step 6: Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(2-(2-(2-((2-(2,6-dioxopiperidin-3-yl)-1,3-dioxo isoindolin-4-yl)amino)ethoxy)ethoxy)ethyl)piperidin-4-yl)-2-fluoro-5-(2-hydroxyethoxy)benzamide (Compound 97)

To a solution of 4-((2-(2-(2-(4-aminopiperidin-1-yl)ethoxy)ethoxy)ethyl)amino)-2-(2,6-dioxopiperidin-3-yl)isoindoline-1,3-dione (200 mg, 356.84 μmol, 2HCl salt), 4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-(2-hydroxyethoxy)benzoic acid (210.47 mg, 356.84 μmol, 84% purity) and HATU (203.52 mg, 535.27 μmol) in DMF (5 mL) was added DIEA (161.42 mg, 1.25 mmol, 217.55 μL), the mixture was stirred at 15° C. for 3 hours. LCMS showed starting material was consumed completely and 68% of desired mass was detected. The reaction mixture was purified by prep-HPLC (column: Phenomenex Gemini-NX $C_{18}$ 75*30 mm*3 um; mobile phase: [water (10 mM NH 4 HCO$_3$)-ACN]; B %: 28%-58%, 8 min) twice followed by prep-HPLC (column: Phenomenex luna $C_{18}$ 150*40 mm*15 um; mobile phase: [water (0.225% FA)-ACN]; B %: 20%-50%, 10 min) and lyophilized to afford the titled compound (40.7 mg, 40.49 μmol, 11.35% yield, 96% purity) as a yellow solid. MS(M+H)$^+$=965.7.

447
¹H NMR (400 MHz, CDCl₃) δ=8.30 (d, J=15.1 Hz, 1H), 8.23 (s, 1H), 8.09 (s, 1H), 7.56 (d, J=7.2 Hz, 1H), 7.52-7.43 (m, 1H), 7.10 (d, J=7.2 Hz, 1H), 6.92 (d, J=8.5 Hz, 1H), 6.67-6.61 (m, 1H), 6.51 (t, J=5.5 Hz, 1H), 5.00-4.81 (m, 2H), 4.20 (t, J=4.1 Hz, 2H), 4.06-3.96 (m, 3H), 3.91 (t, J=13.1 Hz, 2H), 3.73 3.71 (t, J=5.3 Hz, 2H), 3.69-3.60 (m, 6H), 3.50-3.44 (m, 2H), 3.39 (s, 3H), 2.98-2.84 (m, 3H),
448
2.83-2.72 (m, 2H), 2.62 (t, J=5.7 Hz, 2H), 2.31-1.97 (m, 9H), 1.83-1.71 (m, 4H), 1.62-1.59 (m, 4H).
Example 98. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(2-(2-(2-((2-(2,6-dioxopiperidin-3-yl)-1,3-dioxoisoindolin-4-yl)amino)ethoxy)ethoxy)ethyl)piperidin-4-yl)-3-(2-hydroxyethoxy)benzamide
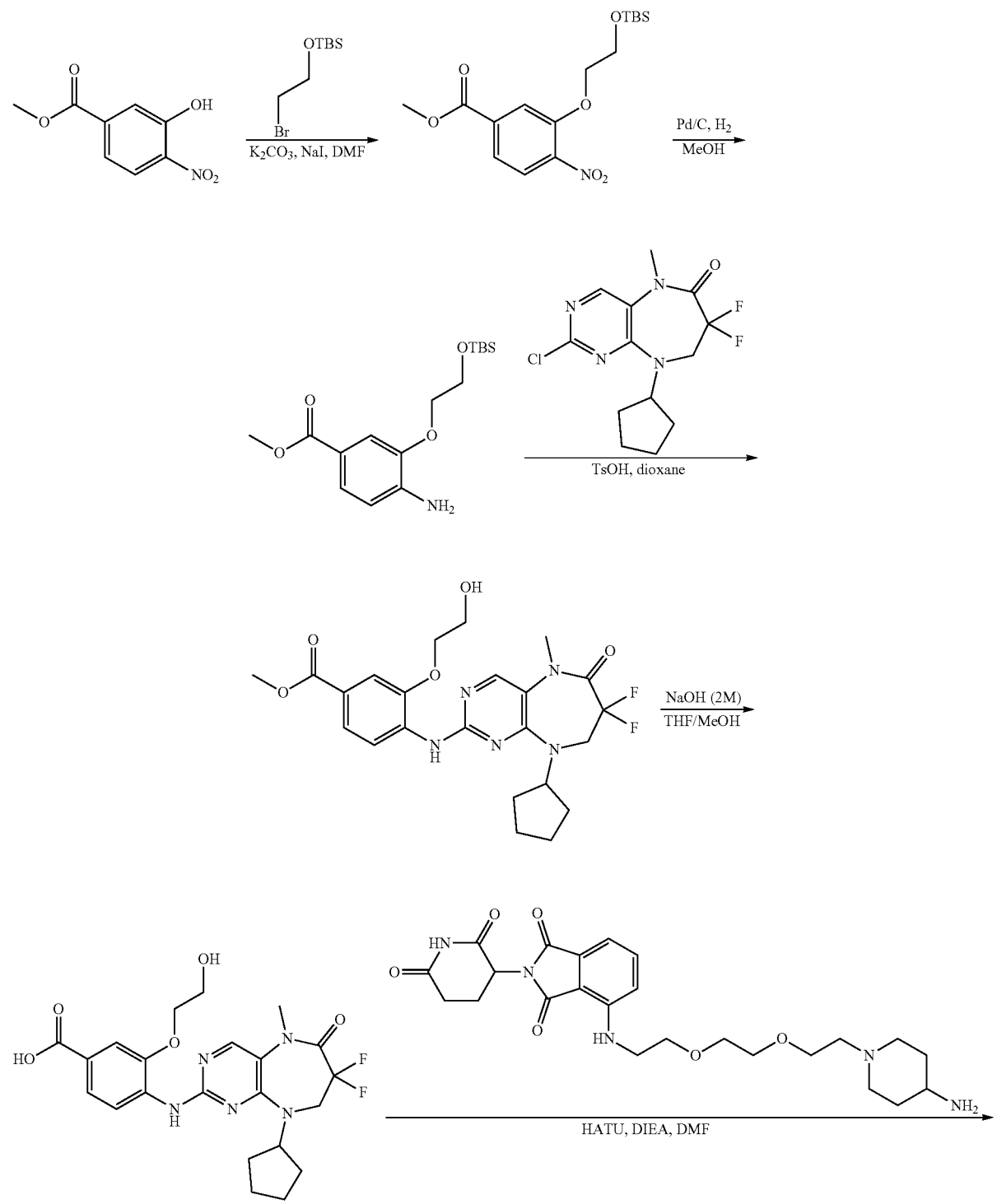

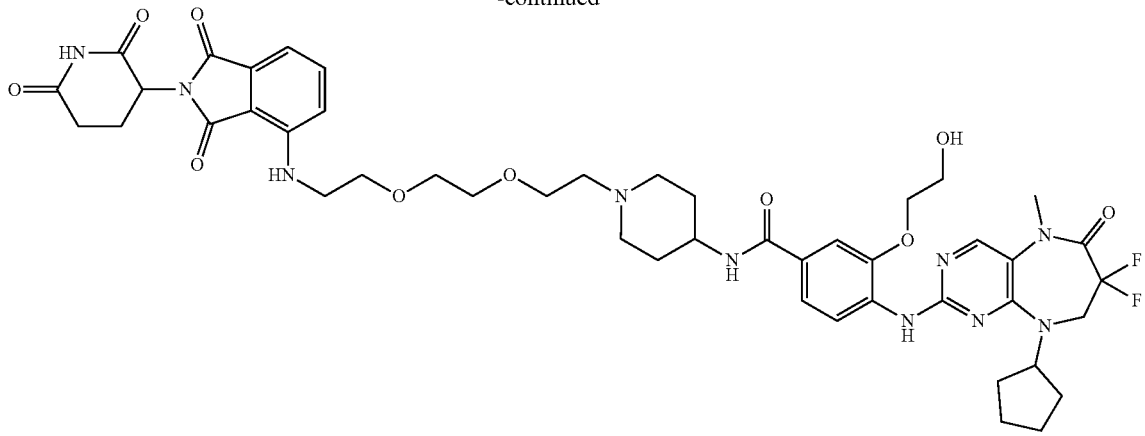

Compound 98

According to the above reaction scheme, in a manner similar to the other examples, obtained the titled compound (57.5 mg, 59.50 μmol, 11.12% yield, 98% purity) as a yellow solid. MS(M+H)$^+$=947.7.

$^1$H NMR (400 MHz, CDCl$_3$) δ=8.35 (d, J=8.4 Hz, 1H), 8.15 (s, 1H), 8.04 (s, 1H), 7.46 (dd, J=8.3 Hz, 7.4 Hz, 1H), 7.40 (d, J=1.5 Hz, 1H), 7.30 (dd, J=8.5 Hz, 1.5 Hz, 1H), 7.07 (d, J=7.0 Hz, 1H), 6.91 (d, J=8.7 Hz, 1H), 6.52 (t, J=5.5 Hz, 1H), 6.43 (d, J=7.9 Hz, 1H), 4.94-4.78 (m, 2H), 4.18 (d, J=3.0 Hz, 2H), 4.01-3.92 (m, 3H), 3.87 (t, J=13.3 Hz, 2H), 3.72 (t, J=5.3 Hz, 2H), 3.63 (dt, J=11.2 Hz, 5.1 Hz, 6H), 3.47 (q, J=5.4 Hz, 2H), 3.36 (s, 3H), 2.95 (d, J=9.3 Hz, 2H), 2.89-2.51 (m, 6H), 2.17 (t, J=11.9 Hz, 2H), 2.11-2.01 (m, 3H), 2.00-1.92 (m, 2H), 1.78-1.52 (m, 8H).

Example 99. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(2-(2-(2-((2-(2,6-dioxopiperidin-3-yl)-1,3-dioxoisoindolin-4-yl)amino)ethoxy)ethoxy)ethyl)piperidin-4-yl)-2-fluoro-5-(trifluoromethoxy)benzamide

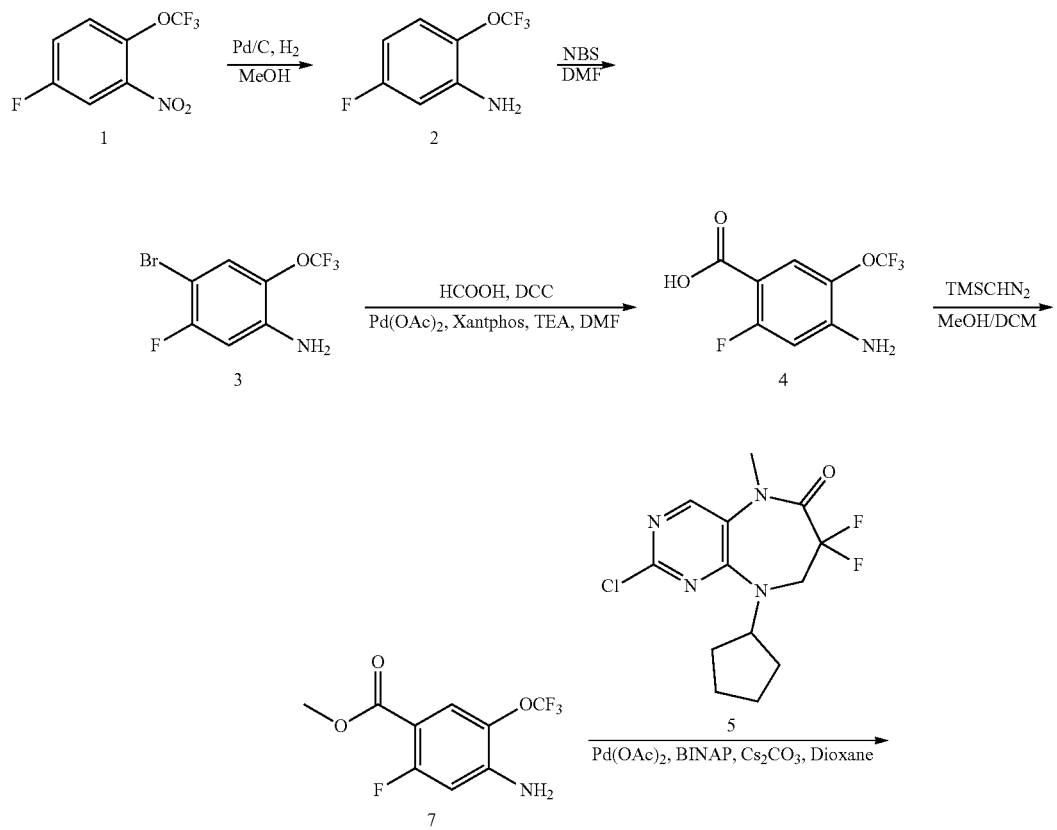

-continued

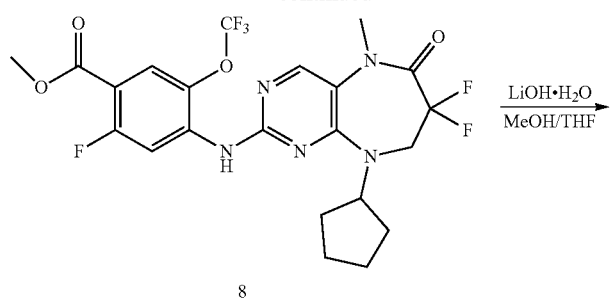

8

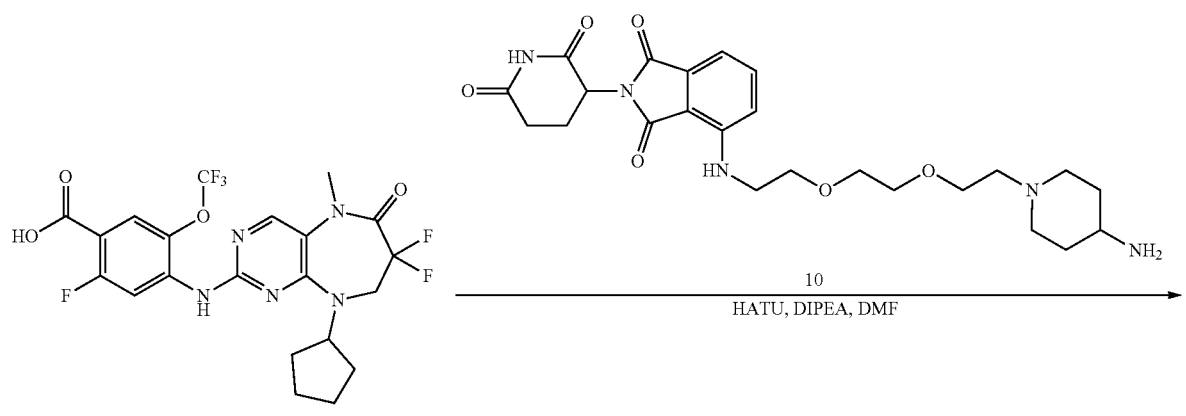

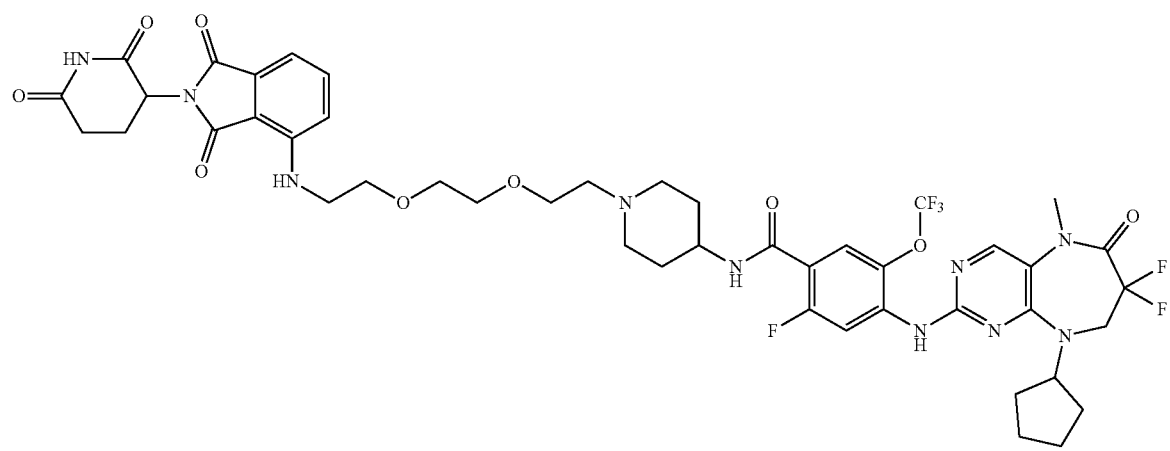

Compound 99

Step 1: Synthesis of 5-fluoro-2-(trifluoromethoxy)aniline (2)

To the suspension of Pd/C (0.2 g, 10% purity) in MeOH (20 mL) was added 4-fluoro-2-nitro-1-(trifluoromethoxy)benzene (2 g, 8.89 mmol) and the resulting mixture was stirred at 20° C. for 12 h under $H_2$ (15 psi). LCMS showed that reactant was consumed and 100% desired mass. The mixture was filtered and concentrated to afford the titled compound (1.4 g, 7.18 mmol, 80.76% yield) as yellow oil. $MS(M+H)^+=195.9$

Step 2: Synthesis of 4-bromo-5-fluoro-2-(trifluoromethoxy)aniline (3)

To the solution of 5-fluoro-2-(trifluoromethoxy)aniline (0.8 g, 4.10 mmol) in DMF (10 mL) was added NBS (875.72 mg, 4.92 mmol) and the resulting mixture was stirred at 25° C. for 12 h. TLC (Petroleum ether:Ethyl acetate=5/1)

showed that most of starting material was consumed and new spot formed. The mixture was poured into water (50 mL) and extracted by EtOAc (50 mL×3), the combined organic layer was washed with brine (50 mL), dried over $Na_2SO_4$, filtered and concentrated. The residue was purified by gel silica column (Petroleum ether:Ethyl acetate=10/1) to afford the titled compound (1.4 g, crude) as yellow oil. MS $(M+H)^+=274.1$ Step 3: Synthesis of 4-amino-2-fluoro-5-(trifluoromethoxy)benzoic acid (4)

To the solution of 4-bromo-5-fluoro-2-(trifluoromethoxy) aniline (1 g, crude) in DMF (10 mL) were added DCC (1.51 g, 7.30 mmol, 1.48 mL), HCOOH (1.23 g, 25.55 mmol), $Pd(OAc)_2$ (81.93 mg, 364.95 μmol), Xantphos (211.17 mg, 364.95 μmol), TEA (738.58 mg, 7.30 mmol, 1.02 mL) and the resulting mixture was stirred at 80° C. for 12 h. LCMS showed that reactant 3 was consumed and desired mass was detected. The mixture was poured into saturated aq. $Na_2CO_3$ (50 mL) and extracted by EtOAc (50 mL×2), the combined organic layer was discarded, the aqueous layer was adjusted pH=4 by con. HCl then extracted by EtOAc (50 mL×3), the combined organic layer was washed by brine (100 mL), dried over $Na_2SO_4$, filtered and concentrated to afford the titled compound (540 mg, 2.26 mmol, 61.88% yield) as yellow solid. $MS(M+H)^+=240.1$ Step 4: Synthesis of methyl 4-amino-2-fluoro-5-(trifluoromethoxy)benzoate (7)

To a solution of 4-amino-2-fluoro-5-(trifluoromethoxy) benzoic acid (200 mg, 836.39 umol) in DCM (3 mL) and MeOH (3 mL) was added $TMSCHN_2$ (2 M, 1.2 mL) at 0° C. The mixture was stirred at 25° C. for 1 h. TLC (Petroleum ether:Ethyl acetate=2:1) showed the starting material was consumed and a new spot was detected. The reaction mixture was concentrated under reduced pressure to afford the titled compound (200 mg, crude) as a light yellow solid. $MS(M+H)^+=253.8$ Step 5: Synthesis of methyl 4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-(trifluoromethoxy)benzoate (8)

To a solution of 2-chloro-9-cyclopentyl-7,7-difluoro-5-methyl-5,7,8,9-tetrahydro-6H-pyrimido[4,5-b][1,4]diazepin-6-one (340 mg, 1.07 mmol) in dioxane (20 mL) were added $Cs_2CO_3$ (1.2 g, 3.68 mmol), BINAP (1.02 g, 1.64 mmol), $Pd(OAc)_2$ (100 mg, 445.41 μmol) and methyl 4-amino-2-fluoro-5-(trifluoromethoxy)benzoate (298.92 mg, 1.18 mmol). The mixture was stirred at 100° C. for 16 h under $N_2$ atmosphere. LCMS showed 17% peak with the desired mass was detected. The reaction mixture was filtered, and the filtrate was concentrated under reduced pressure. The residue was purified by column chromatography ($SiO_2$, Petroleum ether/Ethyl acetate=10:1-2:1) to afford the titled compound (300 mg, 562.41 μmol, 52.39% yield) as a white solid. $MS(M+H)^+=534.0$
$^1H$ NMR (400 MHz, DMSO-$d_6$) δ 9.44 (s, 1H), 8.41-8.30 (m, 2H), 7.80 (dd, J=1.3, 7.0 Hz, 1H), 4.81 (quin, J=8.3 Hz, 1H), 4.08 (t, J=13.8 Hz, 2H), 3.84 (s, 3H), 3.34 (s, 3H), 1.98-1.85 (m, 2H), 1.74-1.68 (m, 2H), 1.66-1.47 (m, 4H).

Step 6: Synthesis of 4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-(trifluoromethoxy)benzoic acid (9)

To a solution of methyl 4-((9-cyclopentyl-7,7-difluoro-5-methyl-6-oxo-6,7,8,9-tetrahydro-5H-pyrimido[4,5-b][1,4] diazepin-2-yl)amino)-2-fluoro-5-(trifluoromethoxy)benzoate (200 mg, 374.94 mol) in THF (5 mL) and MeOH (5 mL) was added $LiOH·H_2O$ (157.34 mg, 3.75 mmol). The mixture was stirred at 20° C. for 2 h. LCMS showed main peak with the desired mass $[M+H+H_2O]$ was detected. The reaction mixture was concentrated under reduced pressure to give a residue. To the residue was added $H_2O$ (10 mL), the mixture was extracted with EtOAc 30 mL (10 mL×3), the aqueous phase was adjust to pH=7 slowly with HCl (1M) at 0° C., then freeze dried to afford the titled compound (190 mg, crude) as a light yellow solid. $MS(M+H+H_2O)^+=538.4$.

Step 7: Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(2-(2-(2-((2-(2,6-dioxopiperidin-3-yl)-1,3-dioxo isoindolin-4-yl) amino)ethoxy)ethoxy)ethyl)piperidin-4-yl)-2-fluoro-5-(trifluoromethoxy)benzamide (Compound 99)

To a solution of 4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-(trifluoromethoxy)benzoic acid (80 mg, 154.03 mol) in DMF (4 mL) were added HATU (151.71 mg, 399.00 μmol), DIPEA (150.09 mg, 1.16 mmol, 202.28 μL) and 4-((2-(2-(2-(4-aminopiperidin-1-yl)ethoxy)ethoxy) ethyl)amino)-2-(2,6-dioxopiperidin-3-yl)isoindoline-1,3-dione (110 mg, 196.26 μmol, 2HCl) at 20° C. The mixture was stirred at 20° C. for 12 h. LCMS showed 60% peak with the desired mass was detected. To the reaction mixture was added $H_2O$ (15 mL), the mixture was extracted with EtOAc (30 mL×2), the combined organic layers were washed with brine (30 mL×3), dried over anhydrous $Na_2SO_4$, filtered and the filtrate was concentrated under reduced pressure to give a residue. The residue was purified by prep-HPLC (column: Unisil 3-100 $C_{18}$ uLtra 150*50 mm*3 um; mobile phase: [water (0.225% FA)-ACN]; B %: 35%-55%, 10 min, Column Temp: 30° C.) followed by prep-HPLC (column: Unisil 3-100 $C_{18}$ uLtra 150*50 mm*3 um; mobile phase: [water (0.225% FA)-ACN]; B %: 35%-55%, 10 min, Column Temp: 30° C.) followed by re-purified by prep-HPLC (column: Unisil 3-100 $C_{18}$ uLtra 150*50 mm*3 um; mobile phase: [water (0.225% FA)-ACN]; B %: 30%-50%, 10 min, Column Temp: 30° C.) and lyophilized to afford the titled compound (29.0 mg, 12.28 μmol, 7.97% yield, 92% purity, FA) as a light yellow solid. MS $(M+H)^+=989.5$.
$^1H$ NMR (400 MHz, DMSO-$d_6$) δ 11.08 (s, 1H), 9.16 (s, 1H), 8.32 (s, 1H), 8.29 (s, 1H), 8.22 (d, J=13.1 Hz, 1H), 8.06 (d, J=6.0 Hz, 1H), 7.61-7.51 (m, 2H), 7.15 (d, J=8.6 Hz, 1H), 7.03 (d, J=6.9 Hz, 1H), 6.60 (t, J=5.6 Hz, 1H), 5.09-5.00 (m, 1H), 4.78 (t, J=8.2 Hz, 1H), 4.09-4.05 (m, 2H), 3.64-3.60 (m, 2H), 3.58-3.55 (m, 2H), 3.53-3.46 (m, 8H), 3.33 (s, 3H), 2.91-2.78 (m, 3H), 2.43-2.39 (m, 2H), 2.09-1.99 (m, 3H), 1.95-1.87 (m, 2H), 1.79-1.63 (m, 5H), 1.62-1.44 (m, 6H).

Example 100. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(1-(2-(2-(2-((2-(2,6-dioxopiperidin-3-yl)-1,3-dioxoisoindolin-4-yl)amino)ethoxy)ethoxy)ethyl)piperidin-4-yl)-2-fluoro-5-methoxybenzamide
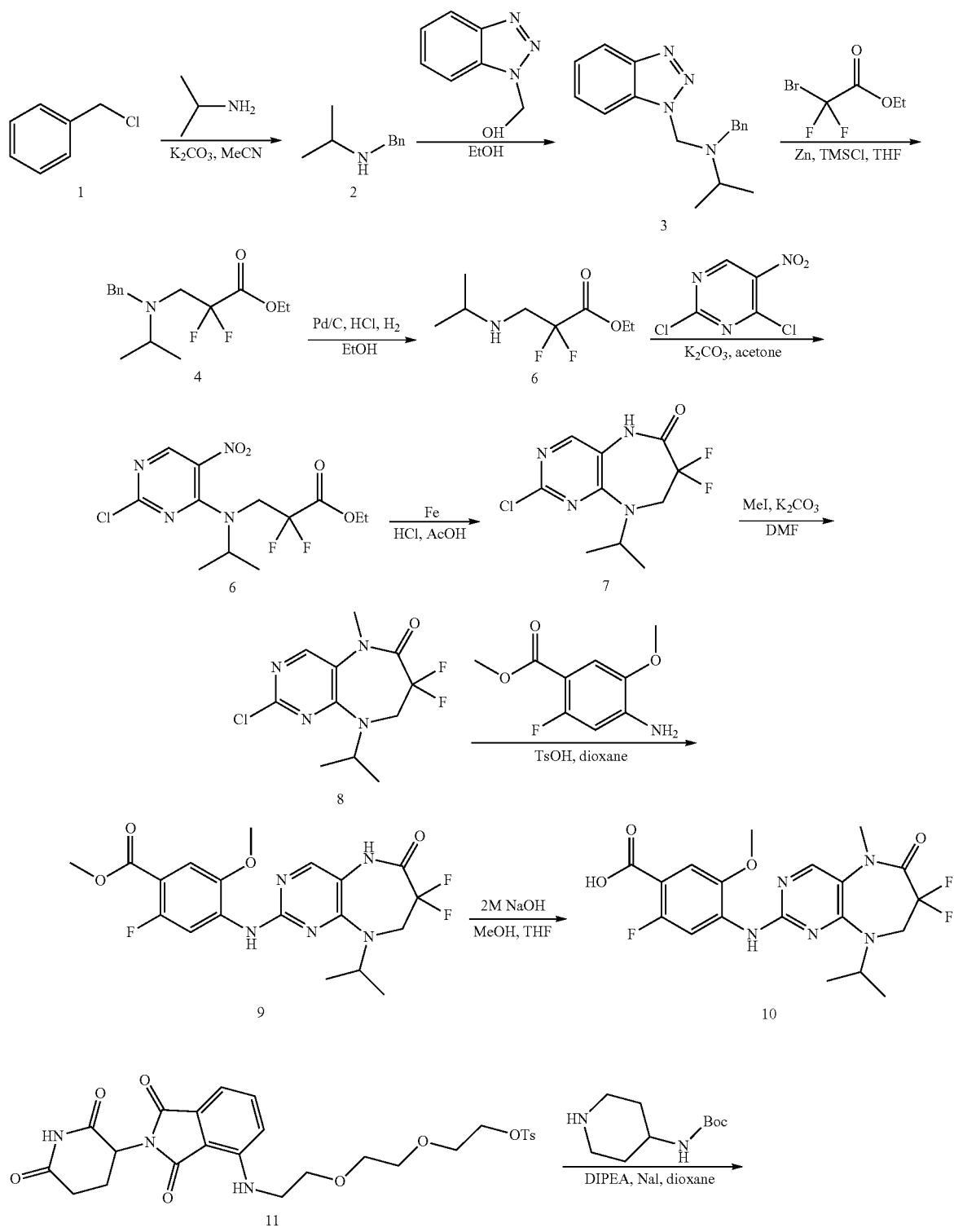

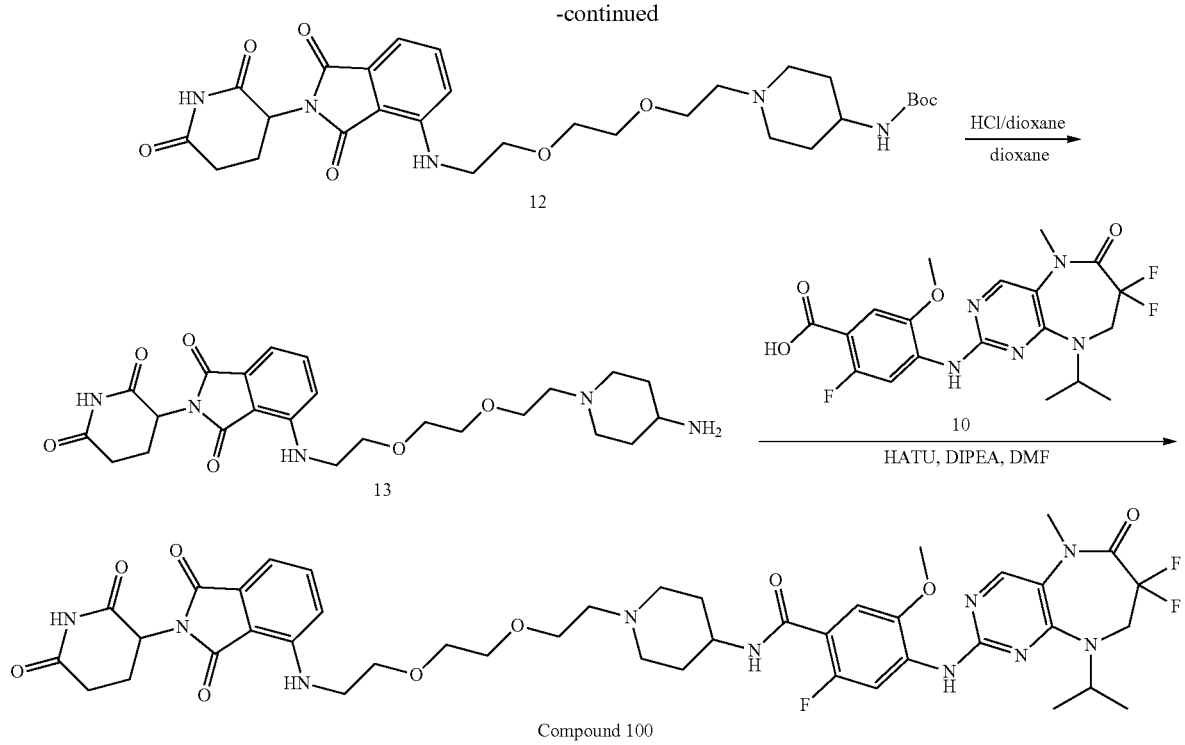

Compound 100

Step 1: Synthesis of N-benzylpropan-2-amine (2)

To a solution of chloromethylbenzene (55.00 g, 434.50 mmol, 50 mL) and propan-2-amine (128.42 g, 2.17 mol, 186.65 mL) in MeCN (1000 mL) was added $K_2CO_3$ (180.16 g, 1.30 mol) and the mixture was stirred at 80° C. for 16 h. TLC indicated the reaction was completed. The reaction mixture was filtered. The filtrate was concentrated in vacuo to afford the titled compound (56.5 g, 378.60 mmol, 87.14% yield) as yellow oil.

$^1$H NMR (400 MHz, $CDCl_3$) δ=7.44-7.19 (m, 5H), 3.68 (s, 2H), 2.80-2.50 (m, 1H), 1.75 (s, 1H), 1.03-0.98 (m, 6H).

Step 2: Synthesis of N-((1H-benzo[d][1,2,3]triazol-1-yl)methyl)-N-benzylpropan-2-amine (3)

To a solution of N-benzylpropan-2-amine (36.72 g, 246.06 mmol, 40.53 mL) in EtOH (150 mL) was added benzotriazol-1-ylmethanol (36.7 g, 246.06 mmol) and the mixture was stirred at 25° C. for 12 h. TLC indicated the reaction was completed. The reaction mixture was concentrated in vacuo. The residue was diluted with $H_2O$ (200 mL) and extracted with EtOAc (300 mL×2), the combined organic layer was dried over $Na_2SO_4$, filtered. The filtrate was concentrated in vacuo to afford the titled compound (77 g, crude) as yellow oil.

Step 3: Synthesis of ethyl 3-(benzyl(isopropyl)amino)-2,2-difluoropropanoate (4)

To a suspension of Zn (23.32 g, 356.68 mmol) in THF (500 mL) was added TMSCl (29.06 g, 267.51 mmol, 33.95 mL) drop wise. After stirring 20 minutes, the ethyl 2-bromo-2,2-difluoro-acetate (54.30 g, 267.51 mmol, 34.37 mL) was added slowly at 0° C. and the mixture was stirred 20 minutes at 0° C. and cooled to −10° C. N-(benzotriazol-1-ylmethyl)-N-benzyl-propan-2-amine (50 g, 178.34 mmol) in THF (250 mL) was added at −10° C. After 20 minutes was warmed to 25° C. and stirred at 25° C. for 12 h. LCMS showed that the reaction was completed. The reaction mixture was filtered and the filtrate was concentrated in vacuo to afford the titled compound (100 g, crude) as yellow oil. MS(M+H)$^+$=286.2

Step 4: Synthesis of ethyl 2,2-difluoro-3-(isopropylamino)propanoate (5)

To a solution of ethyl 3-(benzyl(isopropyl)amino)-2,2-difluoropropanoate (100 g, 350.47 mmol) in EtOH (700 mL) were added Pd/C (10 g, 10% purity) and HCl (12 M, 14.60 mL) and the resulting mixture was stirred at 20° C. for 12 h under $H_2$ (15 psi). LCMS showed that the reaction was completed. The reaction mixture was filtered and the filtrate was concentrated in vacuo to afford the titled compound (68 g, crude) as yellow oil.

Step 5: Synthesis of ethyl 3-((2-chloro-5-nitropyrimidin-4-yl)(isopropyl)amino)-2,2-difluoropropanoate (6)

To a solution of ethyl 2,2-difluoro-3-(isopropylamino) propanoate (68 g, 348.35 mmol) in acetone (500 mL) were added $K_2CO_3$ (57.80 g, 418.22 mmol) and 2,4-dichloro-5-nitro-pyrimidine (33.79 g, 174.17 mmol) and the mixture was stirred at 25° C. for 16 h. TLC indicated that the reaction was completed. The reaction mixture filtered and the filtrate was concentrated under reduced pressure. The residue was purified by column chromatography ($SiO_2$, Petroleum ether/Ethyl acetate=1/0 to 5/1) to afford the titled compound (11 g, 24.33 mmol, 6.98% yield, 78% purity) as yellow solid. MS(M+H)$^+$=353.1

Step 6: Synthesis of 2-chloro-7,7-difluoro-9-isopropyl-8,9-dihydro-5H-pyrimido[4,5-b][1,4]diazepin-6(7H)-one (7)

To a solution of ethyl 3-((2-chloro-5-nitropyrimidin-4-yl)(isopropyl)amino)-2,2-difluoropropanoate (10 g, 28.35 mmol) in AcOH (100 mL) was added Fe (9.50 g, 170.11 mmol) and HCl (12 M, 14.18 mL) and the mixture was stirred at 85° C. for 5 h. LCMS showed that the reaction was completed. The mixture was combined with the pilot (2 g scale) and filtered, concentrated, the residue was diluted with NaHCO$_3$ (sat, aq. 300 mL) and the resulting mixture was extracted with EtOAc (300 mL×3), the combined organic layer was washed with brine (500 mL×2), dried over Na$_2$SO$_4$, filtered and concentrated. The residue was purified by column chromatography (SiO$_2$, Petroleum ether/Ethyl acetate=1/0 to 5/1) to afford the titled compound (5.1 g, 18.06 mmol, 63.72% yield, 98% purity) as gray solid. MS(M+H)$^+$=277.1

$^1$H NMR (400 MHz, DMSO-d$_6$) δ=11.0 (s, 1H), 8.09 (s, 1H), 4.93-4.86 (m, 1H), 4.05-3.95 (m, 2H), 1.19-1.17 (m, 6H).

Step 7: Synthesis of 2-chloro-7,7-difluoro-9-isopropyl-5-methyl-8,9-dihydro-5H-pyrimido[4,5-b][1,4]diazepin-6(7H)-one (8)

To the mixture of 2-chloro-7,7-difluoro-9-isopropyl-8,9-dihydro-5H-pyrimido[4,5-b][1,4]diazepin-6(7H)-one (5.1 g, 18.43 mmol) and K$_2$CO$_3$ (5.10 g, 36.87 mmol) in DMF (50 mL) was added MeI (2.88 g, 20.28 mmol, 1.26 mL) and the resulting mixture was stirred at 20° C. for 12 h. LCMS showed that the reaction was completed. The mixture was poured into water (200 mL) and extracted with EtOAc (100 mL×3), the combined organic layer was washed with brine (300 mL), dried over Na$_2$SO$_4$, filtered and concentrated to afford the titled compound (4.5 g, 15.02 mmol, 81.46% yield, 97% purity) as yellow solid. MS(M+H)$^+$=291.1

Step 8: Synthesis of methyl 4-((7,7-difluoro-9-isopropyl-5-methyl-6-oxo-6,7,8,9-tetrahydro-5H-pyrimido[4,5-b][1,4]diazepin-2-yl)amino)-2-fluoro-5-methoxybenzoate (9)

To a solution of 2-chloro-7,7-difluoro-9-isopropyl-5-methyl-8,9-dihydro-5H-pyrimido[4,5-b][1,4]diazepin-6(7H)-one (1 g, 3.44 mmol) and methyl 4-amino-2-fluoro-5-methoxy-benzoate (1.03 g, 5.16 mmol) in dioxane (20 mL) was added TsOH (1.78 g, 10.32 mmol) and the mixture was stirred at 100° C. for 16 h. LCMS showed that the reaction was completed. The mixture was poured into water (100 mL) and extracted with EtOAc (100 mL×3), the combined organic layer was washed with brine (300 mL), dried over Na$_2$SO$_4$, filtered and concentrated. The residue was purified by column chromatography (SiO$_2$, Petroleum ether/Ethyl acetate=1/0 to 2/1) to afford the titled compound (1.5 g, 3.24 mmol, 94.25% yield, 98% purity) as white solid. MS(M+H)$^+$=454.2

Step 9: Synthesis of 4-((7,7-difluoro-9-isopropyl-5-methyl-6-oxo-6,7,8,9-tetrahydro-5H-pyrimido[4,5-b][1,4]diazepin-2-yl)amino)-2-fluoro-5-methoxybenzoic acid (10)

To a solution of methyl 4-((7,7-difluoro-9-isopropyl-5-methyl-6-oxo-6,7,8,9-tetrahydro-5H-pyrimido[4,5-b][1,4]diazepin-2-yl)amino)-2-fluoro-5-methoxybenzoate (1.5 g, 3.31 mmol) in THF (6 mL) and MeOH (6 mL) was added NaOH (2 M, 6.00 mL, in water) and the mixture was stirred at 25° C. for 12 h. LCMS showed that the reaction was completed. The organic solvent was concentrated and the residue was adjusted pH=6 by 1 M HCl, the suspensions was filtered and collected filter cake to afford the titled compound (590 mg, 1.34 mmol, 40.59% yield, 100% purity) as white solid. MS(M+H)$^+$=440.1

Step 10: Synthesis of tert-butyl (1-(2-(2-(2-((2-(2,6-dioxopiperidin-3-yl)-1,3-dioxoisoindolin-4-yl)amino)ethoxy)ethoxy)ethyl)piperidin-4-yl)carbamate (12)

To a mixture of 2-(2-(2-((2-(2,6-dioxopiperidin-3-yl)-1,3-dioxoisoindolin-4-yl)amino)ethoxy)ethoxy)ethyl 4-methylbenzenesulfonate (600 mg, 1.07 mmol) and tert-butyl piperidin-4-ylcarbamate (429.48 mg, 2.14 mmol) in dioxane (10 mL) were added DIPEA (415.73 mg, 3.22 mmol, 560.28 μL) and NaI (16.07 mg, 107.22 μmol) and the mixture was heated to 80° C. for 16 h. TLC (EtOAc/MeOH=10/1) showed that the reaction was completed. The reaction mixture was diluted with H$_2$O (30 mL) and extracted with EtOAc (30 mL×2), the combined organic layer was dried over Na$_2$SO$_4$, filtered and concentrated in vacuo. The residue was purified by column chromatography (SiO$_2$, EtOAc-~EtOAc/MeOH=10/1) to afford the titled compound (590 mg, 973.86 umol, 90.83% yield, 97% purity) as yellow solid.

MS(M+H)$^+$=588.3

Step 11: Synthesis of 4-((2-(2-(2-(4-aminopiperidin-1-yl)ethoxy)ethoxy)ethyl)amino)-2-(2,6-dioxopiperidin-3-yl)isoindoline-1,3-dione (13)

To a solution of tert-butyl (1-(2-(2-(2-((2-(2,6-dioxopiperidin-3-yl)-1,3-dioxoisoindolin-4-yl)amino)ethoxy)ethoxy)ethyl)piperidin-4-yl)carbamate (590 mg, 1.00 mmol) in dioxane (10 mL) was added HCl/dioxane (4 M, 10 mL) and the reaction mixture was stirred at 25° C. for 3 h. LCMS showed that the reaction was completed. The reaction mixture was concentrated in vacuo to afford the titled compound (0.7 g, 1.44 mmol, 143.01% yield) as yellow solid. MS(M+H)$^+$=488.2

Step 12: Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(1-(2-(2-(2-((2-(2,6-dioxopiperidin-3-yl)-1,3-dioxo isoindolin-4-yl)amino)ethoxy)ethoxy)ethyl)piperidin-4-yl)-2-fluoro-5-methoxybenzamide (Compound 100)

To the solution of 4-((2-(2-(2-(4-aminopiperidin-1-yl)ethoxy)ethoxy)ethyl)amino)-2-(2,6-dioxopiperidin-3-yl)isoindoline-1,3-dione (0.2 g, 381.67 μmol, HCl) and 4-((7,7-difluoro-9-isopropyl-5-methyl-6-oxo-6,7,8,9-tetrahydro-5H-pyrimido[4,5-b][1,4]diazepin-2-yl)amino)-2-fluoro-5-methoxybenzoic acid (167.70 mg, 381.67 μmol) in DMF (3 mL) were added HATU (290.25 mg, 763.35 μmol) and DIPEA (147.99 mg, 1.15 mmol, 199.44 μL) and the resulting mixture was stirred at 20° C. for 1 h. LCMS showed that the reaction was completed. The mixture was poured into water (20 mL) and extracted with EtOAc (20 mL×3), the combined organic layer was washed with brine (50 mL), dried over Na$_2$SO$_4$, filtered and concentrated. The residue was purified by prep-HPLC (column: Phenomenex Gemini-NX C$_{18}$ 75*30 mm*3 um; mobile phase: [water (0.225% FA)-

ACN]; B %: 18%-48%, 7 min) and the eluent was lyophilized. The solid was poured into sat, aq. NaHCO$_3$ (20 mL) and extracted with EtOAc (20 mL×3), the combined organic layer was washed by brine (50 mL), dried over Na$_2$SO$_4$, filtered and concentrated to afford the titled compound (86.4 mg, 90.30 mol, 74.62% yield, 95% purity) as yellow solid. MS(M+H)$^+$=909.5.

$^1$H NMR (400 MHz, DMSO-d$_6$) δ=11.14 (s, 1H), 8.31-8.25 (m, 2H), 8.02 (s, 1H), 7.95-7.86 (m, 1H), 7.63-7.57 (m, 1H), 7.21-7.14 (m, 2H), 7.05 (d, J=8.0 Hz, 1H), 6.61 (t, J=5.7 Hz, 1H), 5.14-5.07 (m, 1H), 5.01-4.92 (m, 1H), 4.07 (t, J=13.4 Hz, 2H), 3.92 (s, 3H), 3.82-3.71 (m, 1H), 3.66-3.62 (m, 2H), 3.60-3.58 (m, 2H), 3.57-3.50 (m, 6H), 3.02-2.85 (m, 3H), 2.70-2.60 (m, 4H), 2.52-2.45 (m, 3H), 2.14-2.05 (m, 3H), 1.84-1.77 (m, 2H), 1.67-1.52 (m, 2H), 1.32 (d, J=6.6 Hz, 6H).

Example 101. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(1-(14-((2-(2,6-dioxopiperidin-3-yl)-1,3-dioxoisoindolin-4-yl)amino)-3,6,9,12-tetraoxatetradecyl)piperidin-4-yl)-2-fluoro-5-methoxybenzamide

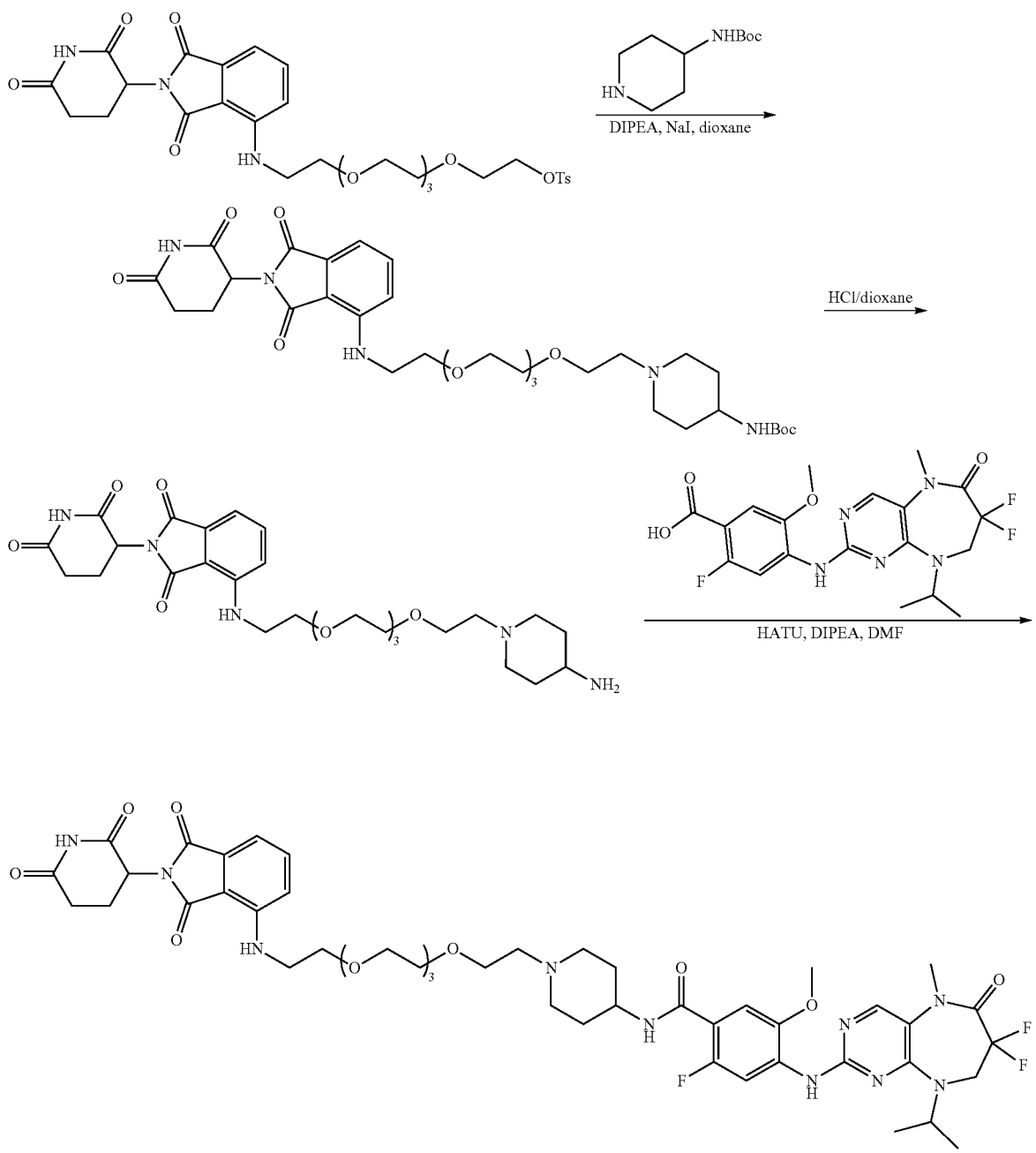

Compound 101

According to the above reaction scheme, in a manner similar to the other examples, obtained the titled compound (16.5 mg, 16.22 μmol, 7.13% yield, 98% purity) as a yellow solid. MS(M+H)⁺=997.7

¹H NMR (400 MHz, DMSO-d₆) δ=11.10 (s, 1H), 8.26 (br t, J=6.0 Hz, 2H), 7.99-7.78 (m, 2H), 7.58 (dd, J=7.2, 8.4 Hz, 1H), 7.22-7.11 (m, 2H), 7.03 (d, J=7.0 Hz, 1H), 6.67-6.55 (m, 1H), 5.05 (dd, J=5.6, 12.8 Hz, 1H), 4.96-4.82 (m, 1H), 4.06 (br t, J=13.6 Hz, 2H), 3.91 (s, 3H), 3.76-3.67 (m, 1H), 3.64-3.59 (m, 2H), 3.59-3.53 (m, 4H), 3.53-3.43 (m, 12H), 3.31-3.28 (m, 2H), 2.97-2.77 (m, 3H), 2.62-2.51 (m, 3H), 2.48-2.39 (m, 2H), 2.14-1.89 (m, 3H), 1.86-1.68 (m, 2H), 1.62-1.45 (m, 2H), 1.26 (s, 3H), 1.25 (s, 3H).

Example 102. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(4-((2-(2,6-dioxopiperidin-3-yl)-1,3-dioxoisoindolin-4-yl)amino)butanoyl)piperidin-4-yl)benzamide

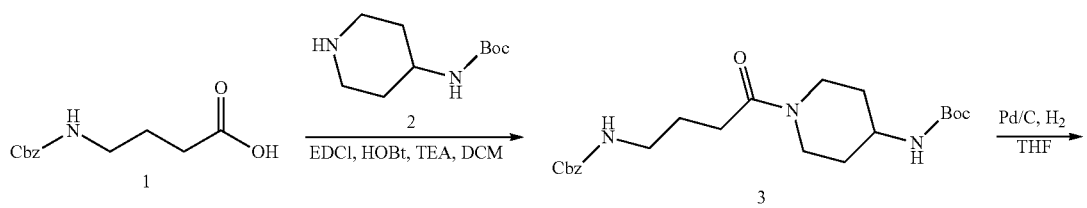

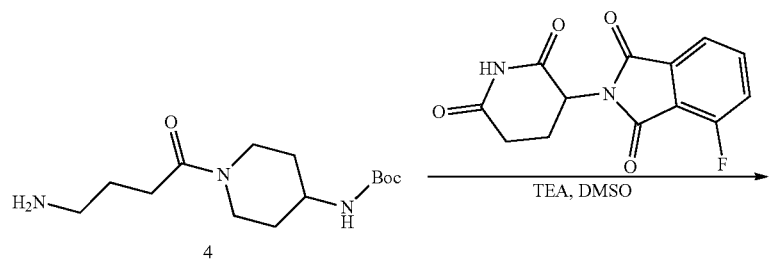

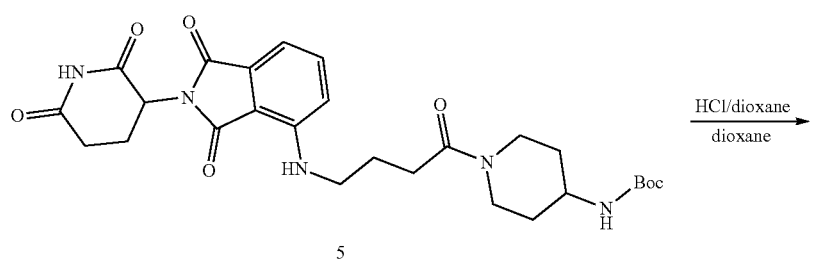

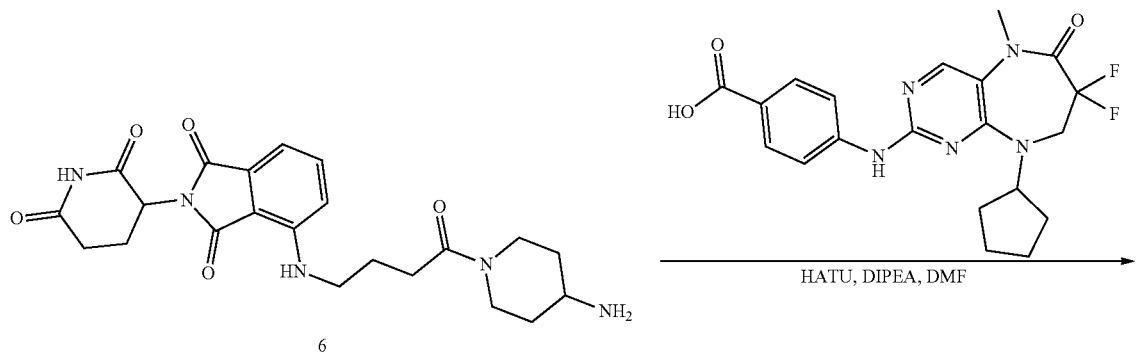

-continued

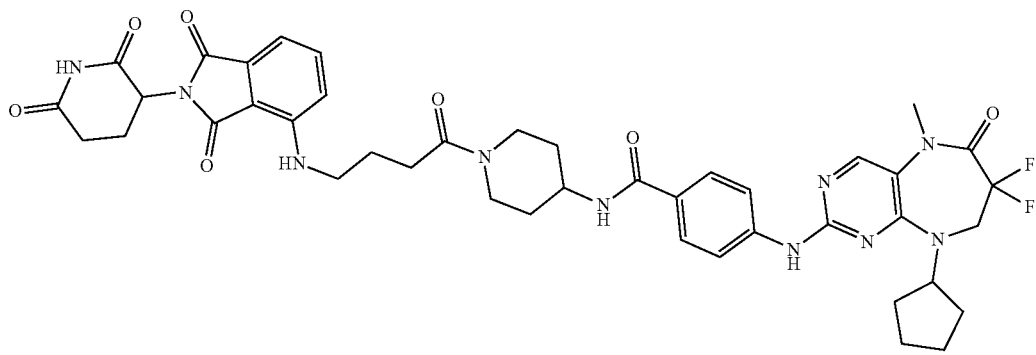

Compound 102

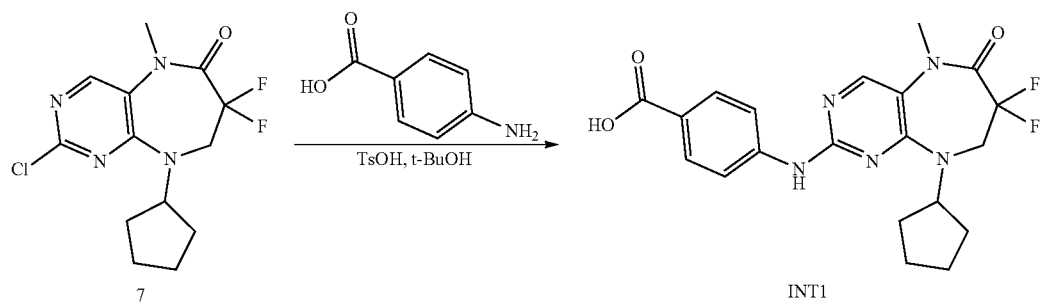

Step 1-5 are Described in the Above Reaction Scheme

Step 6: Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(4-((2-(2,6-dioxopiperidin-3-yl)-1,3-dioxoisoindolin-4-yl)amino)butanoyl)piperidin-4-yl)benzamide (Compound 102)

To a solution of 4-((9-cyclopentyl-7,7-difluoro-5-methyl-6-oxo-6,7,8,9-tetrahydro-5H-pyrimido[4,5-b][1,4]diazepin-2-yl)amino)benzoic acid (130 mg, 311.45 μmol) in DMF (2 mL) was added HATU (130.26 mg, 342.59 μmol) and DIPEA (80.50 mg, 622.89 μmol, 108.50 μL). The mixture was stirred at 20° C. for 10 min and a solution of 4-((4-(4-aminopiperidin-1-yl)-4-oxobutyl)amino)-2-(2,6-dioxopiperidin-3-yl)isoindoline-1,3-dione (163.74 mg, 342.59 μmol, HCl) in DMF (2 mL) and DIPEA (80.50 mg, 622.89 μmol, 108.50 μL) was added drop-wise at the reaction mixture and the resulting mixture was stirred at 20° C. for 1 h. LCMS showed starting material was consumed completely and desired mass was detected. The reaction mixture was diluted with H₂O (12 mL) and extracted with EtOAc (12 mL×3). The organic layer was washed with brine (12 mL×3), dried over Na₂SO₄, filtered and concentrated. The residue was purified by prep-HPLC (column: Unisil 3-100 C₁₈ μLtra 150*50 mm*3 um; mobile phase: [water (0.225% FA)-ACN]; B %: 32%-62%, 10 min) followed by lyophilization to afford the titled compound (185.8 mg, 214.33 μmol, 68.82% yield, 97% purity) as a yellow solid. MS (M+H)⁺ =840.9

¹H NMR (400 MHz, DMSO-d₆) δ=11.09 (s, 1H), 9.67 (s, 1H), 8.27 (s, 1H), 8.06 (d, J=7.7 Hz, 1H), 7.81-7.74 (m, 4H), 7.60 (dd, J=7.3, 8.4 Hz, 1H), 7.19 (d, J=8.7 Hz, 1H), 7.02 (d, J=7.0 Hz, 1H), 6.68 (t, J=6.1 Hz, 1H), 5.05 (dd, J=5.4, 12.8 Hz, 1H), 4.83-4.73 (m, 1H), 4.39 (d, J=12.2 Hz, 1H), 4.08-4.00 (m, 2H), 3.88 (d, J=13.4 Hz, 1H), 3.33 (s, 3H), 3.11 (t, J=11.8 Hz, 1H), 2.94-2.83 (m, 1H), 2.73-2.66 (m, 1H), 2.62-2.51 (m, 4H), 2.45-2.40 (m, 3H), 2.07-1.96 (m, 3H), 1.88-1.78 (m, 4H), 1.75-1.69 (m, 2H), 1.67-1.57 (m, 4H), 1.47-1.35 (m, 2H)

Example 103. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-((1r,4r)-4-(4-(2-(2-((2-(2,6-dioxopiperidin-3-yl)-1,3-dioxoisoindolin-4-yl)amino)ethoxy)ethyl)piperazin-1-yl)cyclohexyl)-2-fluoro-5-methoxybenzamide

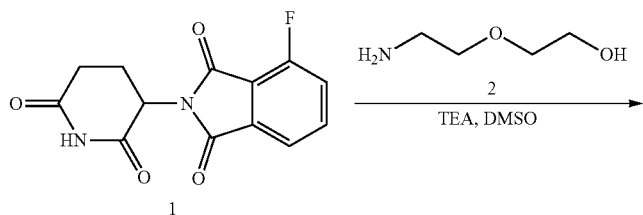

-continued
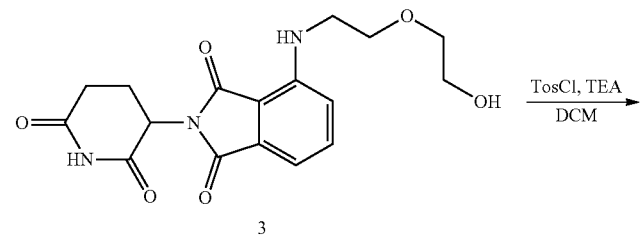
3
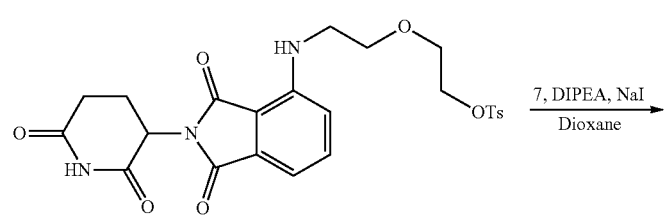
4
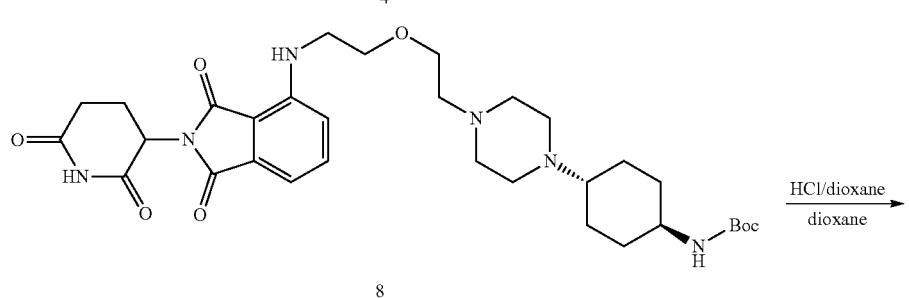
8
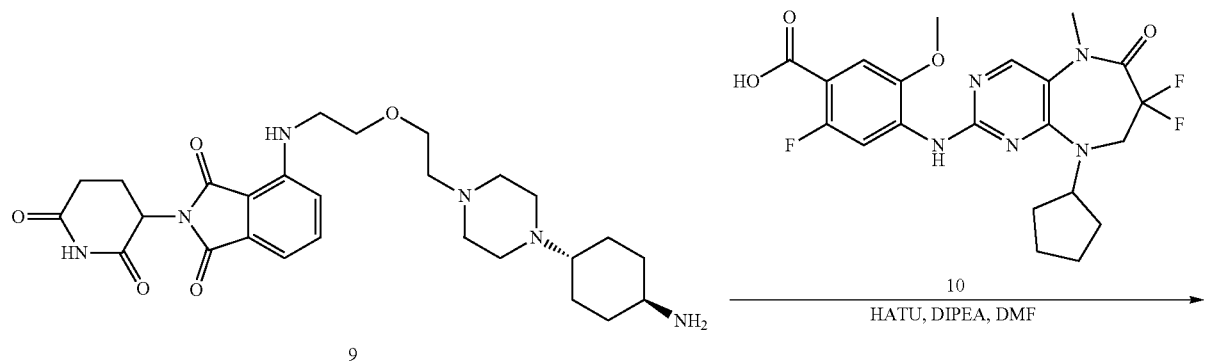
9
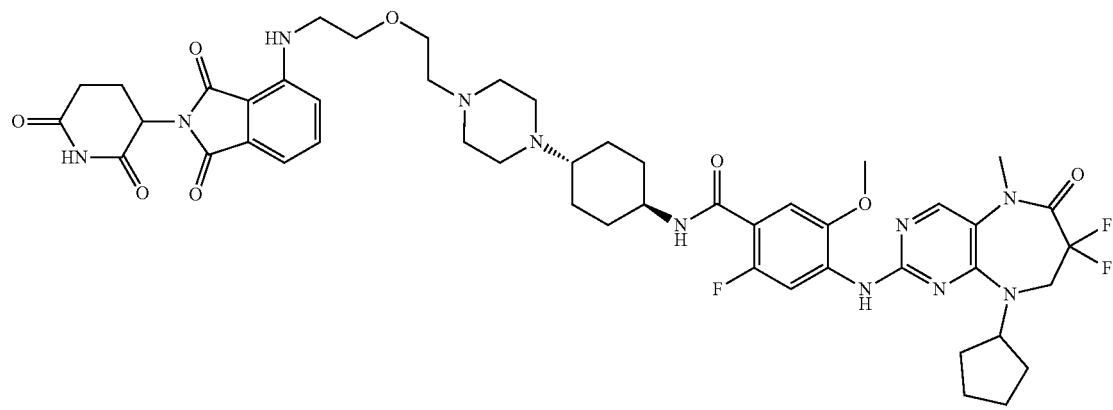
Compound 103

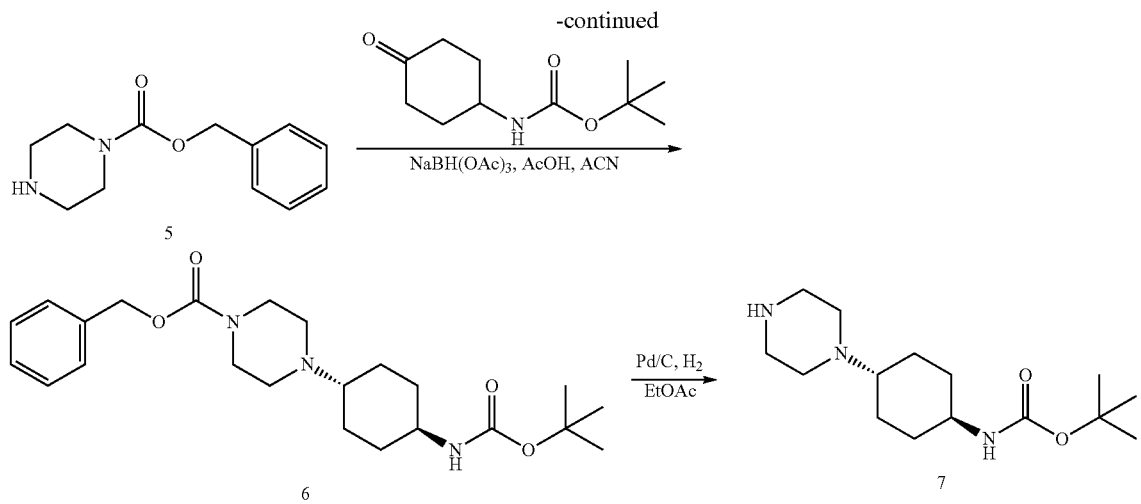

Step 1: Synthesis of 2-(2,6-dioxopiperidin-3-yl)-4-((2-(2-hydroxyethoxy)ethyl)amino)isoindoline-1,3-dione (3)

To a mixture of 2-(2,6-dioxopiperidin-3-yl)-4-fluoroisoindoline-1,3-dione (8 g, 28.96 mmol) in DMSO (50 mL) were added TEA (8.79 g, 86.89 mmol, 12.09 mL) and 2-(2-aminoethoxy) ethanol (3.96 g, 37.65 mmol, 3.77 mL) in one portion at 20° C. and the mixture was stirred at 80° C. for 16 h. LC-MS showed that the reaction was completed. The reaction mixture was partitioned between H$_2$O (300 mL) and EtOAc (600 mL). The organic phase was separated, washed with brine (100 mL×3), dried over Na$_2$SO$_4$, filtered and concentrated under reduced pressure. The residue was purified by column chromatography (SiO$_2$, Petroleum ether/Ethyl acetate=1/0 to 0/1) to afford the titled compound (10.4 g, 27.92 mmol, 96.39% yield, 97% purity) as a green solid. MS(M+H)$^+$=362.1

Step 2: Synthesis of 2-(2-((2-(2,6-dioxopiperidin-3-yl)-1,3-dioxoisoindolin-4-yl)amino)ethoxy)ethyl 4-methylbenzenesulfonate (4)

To a solution of 2-(2,6-dioxopiperidin-3-yl)-4-((2-(2-hydroxyethoxy)ethyl)amino)isoindoline-1,3-dione (10.4 g, 28.78 mmol) in DCM (100 mL) were added TEA (4.37 g, 43.17 mmol, 6.01 mL) and TosCl (6.58 g, 34.54 mmol) and the mixture was stirred at 20° C. for 16 h. LCMS showed that the reaction was completed. The mixture was concentrated under vacuum. The residue was purified by column chromatography (SiO$_2$, Petroleum ether/Ethyl acetate=1/0 to 1/3) to afford the titled compound (4.65 g, 8.57 mmol, 29.77% yield, 95% purity) as a yellow solid. MS (M+H)$^+$=516.1

Step 3: Synthesis of benzyl 4-((1r,4r)-4-((tert-butoxycarbonyl)amino)cyclohexyl)piperazine-1-carboxylate (6)

To a mixture of benzyl piperazine-1-carboxylate (5 g, 22.70 mmol, 4.39 mL) and tert-butyl N-(4-oxocyclohexyl) carbamate (5.81 g, 27.24 mmol, 5.81 mL), AcOH (2.04 g, 34.05 mmol, 1.95 mL) in ACN (200 mL) was added NaBH(OAc)3 (19.24 g, 90.80 mmol) slowly at 20° C. under N$_2$ and the mixture was stirred at 20° C. for 16 h. LCMS showed that the reaction was completed, the reaction mixture was diluted with saturated NaHCO$_3$ (aq.) to adjust the pH>10 and extracted with EtOAc (200 mL×3), the organic layer was dried over Na$_2$SO$_4$, filtrated and concentrated. The residue was purified by column chromatography (SiO$_2$, Petroleum ether/Ethyl acetate=3/1 to 1/1) to afford the titled compound (9.1 g, 18.96 mmol, 83.53% yield, 87% purity) as white solid. 2.0 g of benzyl 4-(4-((tert-butoxycarbonyl) amino)cyclohexyl)piperazine-1-carboxylate was purified by prep-HPLC (column: Waters Xbridge BEH C18 250*50 mm*10 um; mobile phase: [water (0.05% ammonia hydroxide v/v)-ACN]; B %: 40%-65%, 20 min) to afford the titled compound (412 mg, 986.73 umol, 20.60% yield) as white solid. MS(M+H)$^+$=418.4

Step 4: Synthesis of tert-butyl ((1r,4r)-4-(piperazin-1-yl)cyclohexyl)carbamate (7)

To a solution of benzyl 4-((1r,4r)-4-((tert-butoxycarbonyl)amino)cyclohexyl)piperazine-1-carboxylate (200 mg, 479.00 μmol) in EtOAc (30 mL) was added Pd/C (100 mg, 10% purity) under N$_2$ atmosphere and the resulting mixture was stirred under H$_2$ (15 psi) at 20° C. for 16 h. TLC indicated the reaction was completed. The reaction mixture was filtered and the filtrate was concentrated in vacuum to afford the titled compound (120 mg, crude) as white solid.

Step 5: Synthesis of tert-butyl ((1r,4r)-4-(4-(2-(2-((2-(2,6-dioxopiperidin-3-yl)-1,3-dioxoisoindolin-4-yl)amino)ethoxy)ethyl)piperazin-1-yl)cyclohexyl) carbamate (8)

To a solution of 2-(2-((2-(2,6-dioxopiperidin-3-yl)-1,3-dioxoisoindolin-4-yl)amino)ethoxy)ethyl 4-methylbenzenesulfonate (167.91 mg, 325.71 μmol) and tert-butyl ((1r,4r)-4-(piperazin-1-yl)cyclohexyl)carbamate (120 mg, 423.42 μmol) in dioxane (5 mL) were added DIPEA (126.29 mg, 977.12 μmol, 170.20 μL) and NaI (4.88 mg, 32.57 μmol) and the mixture was stirred at 80° C. for 16 h. LCMS showed that the reaction was completed. The reaction mixture was combined with pilot reaction (0.2 g scale) and concentrated under reduced pressure. The residue was purified by column chromatography (SiO$_2$, Petroleum ether/Ethyl acetate=1/0 to 0/1) to afford the titled compound (620 mg, crude) as white solid. MS(M+H)$^+$=627.4

Step 6: Synthesis of 4-((2-(2-(4-((1r,4r)-4-aminocyclohexyl)piperazin-1-yl)ethoxy)ethyl)amino)-2-(2,6-dioxopiperidin-3-yl)isoindoline-1,3-dione (9)

To a solution of tert-butyl ((1r,4r)-4-(4-(2-(2-((2-(2,6-dioxopiperidin-3-yl)-1,3-dioxoisoindolin-4-yl)amino)ethoxy)ethyl)piperazin-1-yl)cyclohexyl)carbamate (620 mg, 989.24 μmol) in dioxane (6 mL) was added HCl/dioxane (4 M, 12 mL, 48.52 eq) and the mixture was stirred at 20° C. for 6 h. LCMS showed that the reaction was completed. The mixture was concentrated in vacuum to afford the titled compound (520 mg, 987.42 μmol, 99.82% yield, 100% purity, HCl) as a white solid. MS(M+H)$^+$=527.2

Step 7: Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-((1r,4r)-4-(4-(2-(2-((2-(2,6-dioxopiperidin-3-yl)-1,3-dioxoisoindolin-4-yl)amino)ethoxy)ethyl)piperazin-1-yl)cyclohexyl)-2-fluoro-5-methoxybenzamide (Compound 103)

To the mixture of 4-((2-(2-(4-((1r,4r)-4-aminocyclohexyl)piperazin-1-yl)ethoxy)ethyl)amino)-2-(2,6-dioxopiperidin-3-yl)isoindoline-1,3-dione (0.2 g, 355.18 μmol HCl) and 4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzoic acid (165.31 mg, 355.18 μmol) in DMF (4 mL) were HATU (270.10 mg, 710.37 μmol) and DIPEA (137.72 mg, 1.07 mmol, 185.60 μL) and the resulting mixture was stirred at 20° C. for 12 h. LCMS showed that the reaction was completed. The mixture was poured into water (20 mL) and extracted with EtOAc (20 mL×3), the combined organic layer was washed with brine (50 mL), dried over Na$_2$SO$_4$, filtered and concentrated, the residue was purified by prep-HPLC (column: Unisil 3-100 C$_{18}$ μLtra 150*50 mm*3 um; mobile phase: [water (0.225% FA)-ACN]; B %: 30%-50%, 10 min) and the eluant was lyophilized to afford the titled compound (151.3 mg, 152.23 μmol, 42.86% yield, 98% purity, FA salt) as yellow solid. MS(M+H)$^+$=974.2.

$^1$H NMR (400 MHz, DMSO-d$_6$) δ=11.12 (s, 1H), 9.34-8.85 (m, 1H), 8.31 (s, 1H), 8.26 (d, J=13.3 Hz, 1H), 8.06 (s, 1H), 7.95 (s, 1H), 7.61 (dd, J=7.3, 8.3 Hz, 1H), 7.22-7.15 (m, 2H), 7.08 (d, J=7.0 Hz, 1H), 6.61 (s, 1H), 5.15-5.03 (m, 1H), 4.91-4.70 (m, 1H), 4.09 (br t, J=13.9 Hz, 2H), 3.92 (s, 3H), 3.79-3.34 (m, 14H), 3.21-2.80 (m, 4H), 2.66-2.52 (m, 5H), 2.44-2.35 (m, 1H), 2.14-1.91 (m, 6H), 1.81-1.49 (m, 8H), 1.47-1.19 (m, 3H).

Example 104. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(2-(2-(2-((2-(2,6-dioxopiperidin-3-yl)-1,3-dioxoisoindolin-4-yl)amino)ethoxy)ethoxy)ethyl)piperidin-3-yl)-2-fluoro-5-methoxybenzamide

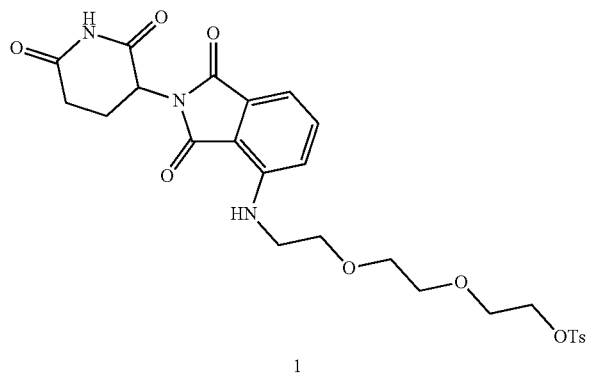

1

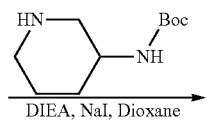

DIEA, NaI, Dioxane

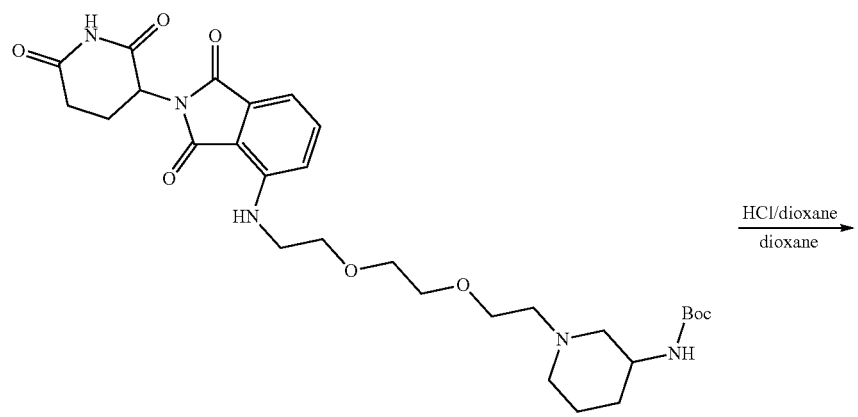

HCl/dioxane
dioxane

2

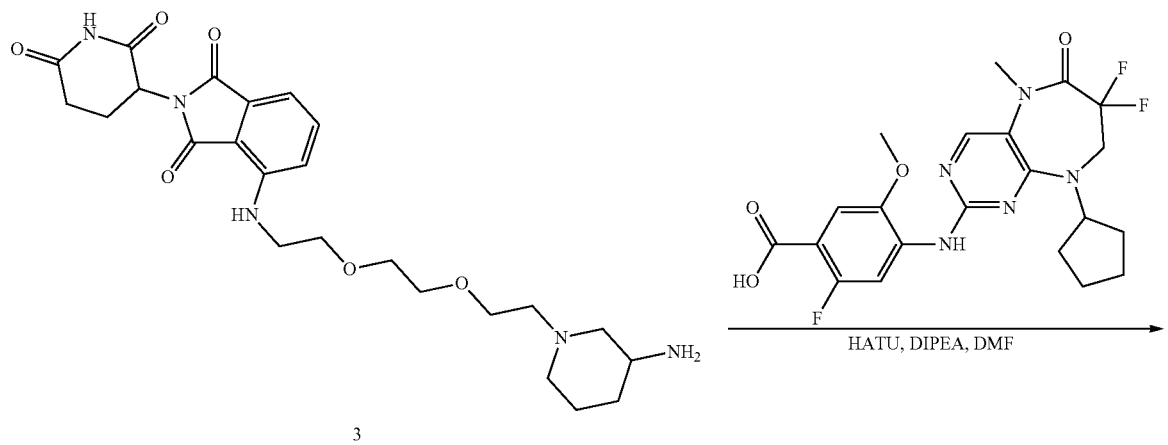

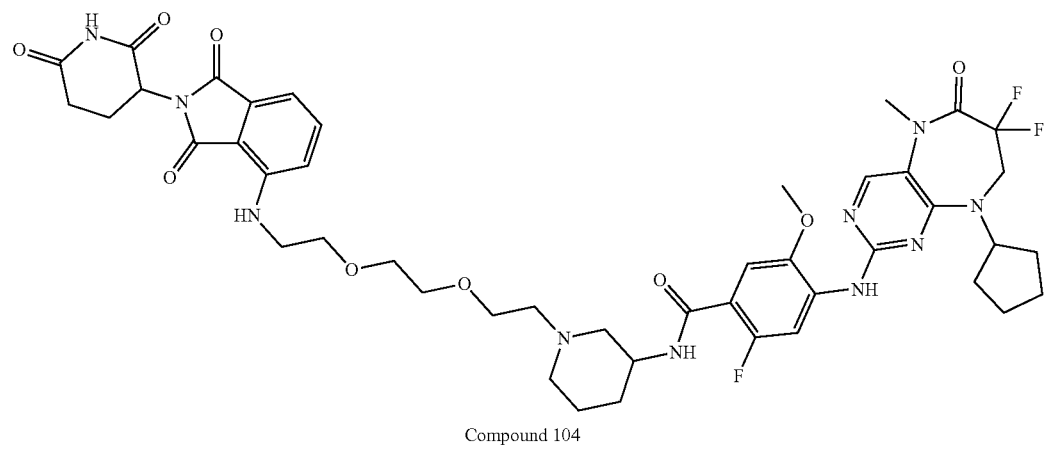

Compound 104

Step 1-2 are Described in the Above Reaction Scheme

Step 3: Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(2-(2-(2-((2-(2,6-dioxopiperidin-3-yl)-1,3-dioxo isoindolin-4-yl)amino)ethoxy)ethoxy)ethyl)piperidin-3-yl)-2-fluoro-5-methoxybenzamide (Compound 104)

To the suspensions of 4-((2-(2-(2-(3-aminopiperidin-1-yl)ethoxy)ethoxy)ethyl)amino)-2-(2,6-dioxopiperidin-3-yl)isoindoline-1,3-dione (230 mg, 471.75 μmol) and 4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzoic acid (219.56 mg, 471.75 μmol) in DMF (4 mL) were added HATU (358.75 mg, 943.50 μmol) and DIPEA (182.91 mg, 1.42 mmol, 246.51 μL) and the resulting mixture was stirred at 20° C. for 1 h. LCMS showed that the reaction was completed, the mixture was poured into water (20 mL) and extracted with EtOAc (20 mL×3), the combined organic layer was washed with brine (50 mL), dried over $Na_2SO_4$, filtered and concentrated. The residue was purified by prep-HPLC (column: Unisil 3-100 $C_{18}$ μLtra 150*50 mm*3 um; mobile phase: [water (0.225% FA)-ACN]; B %: 33%-53%, 10 min) and the eluant was lyophilized to afford the titled compound (156 mg, 161.85 μmol, 34.31% yield, 97% purity, FA) as yellow solid. MS(M+H)$^+$=935.3

$^1$H NMR (400 MHz, $CD_3OD$) δ=8.37-8.27 (m, 1H), 8.22 (d, J=3.2 Hz, 1H), 7.48-7.39 (m, 1H), 7.34 (d, J=6.8 Hz, 1H), 7.02-6.88 (m, 2H), 5.12-5.04 (m, 1H), 4.96-4.92 (m, 1H), 4.41-4.32 (m, 1H), 4.06 (t, J=13.4 Hz, 2H), 3.97 (s, 3H), 3.95-3.84 (m, 2H), 3.81-3.68 (m, 7H), 3.53-3.42 (m, 6H), 3.41-3.34 (m, 2H), 3.09-2.83 (m, 3H), 2.79-2.64 (m, 2H), 2.19-2.01 (m, 5H), 1.98-1.89 (m, 1H), 1.86-1.67 (m, 7H).

Example 105. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(2-(2-((2-(2,6-dioxopiperidin-3-yl)-1,3-dioxoisoindolin-4-yl)amino)ethoxy)ethyl)piperidin-3-yl)-2-fluoro-5-methoxybenzamide
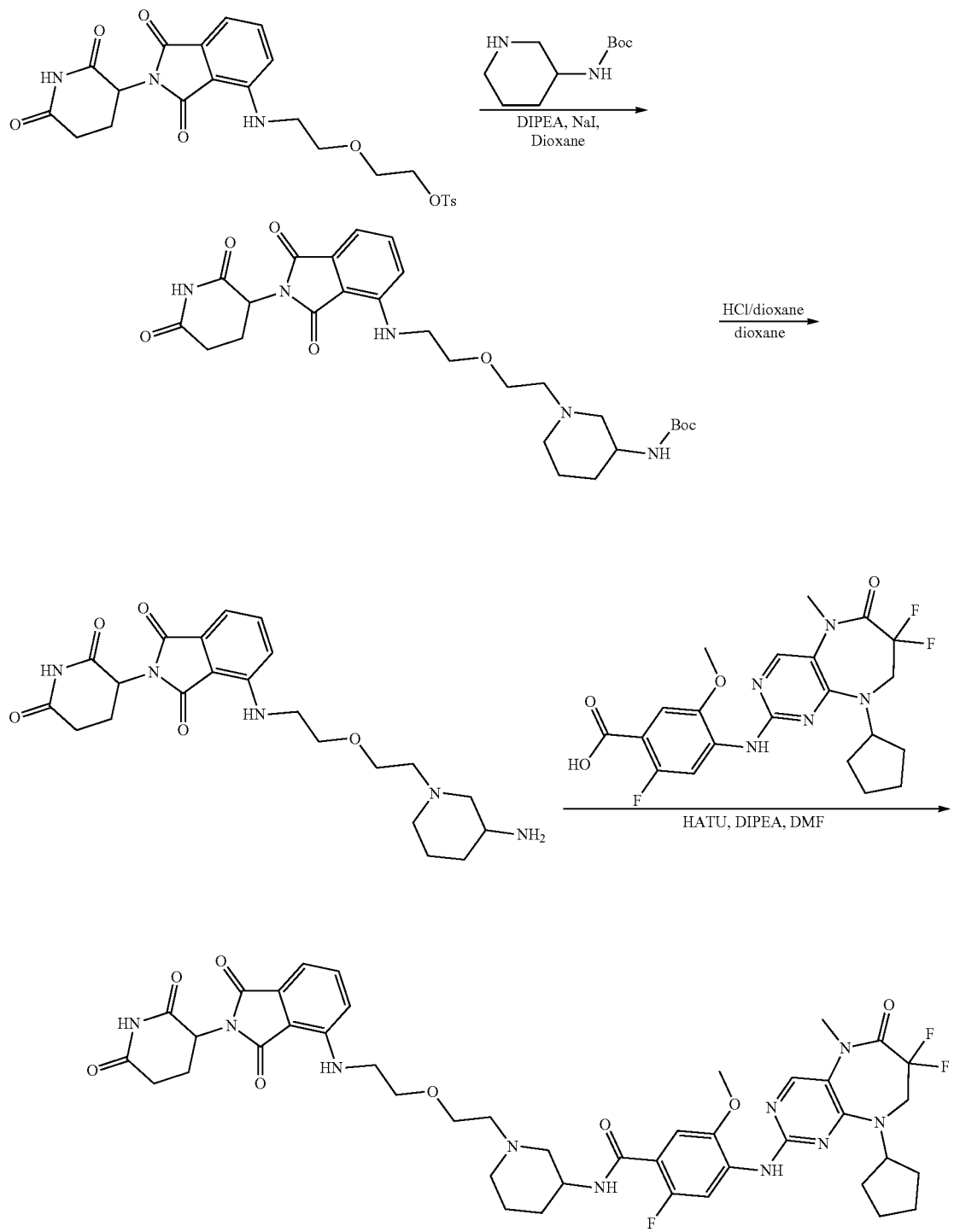
Compound 105

According to the above reaction scheme, in a manner similar to the other examples, obtained the titled compound (56.8 mg, 61.84 μmol, 19.79% yield, 97% purity, FA) as yellow solid. Ms(M+H)+=891.3

¹H NMR (400 MHz, MeOD) δ=8.39 (dd, J=3.6, 14.2 Hz, 1H), 8.23 (s, 1H), 7.57-7.49 (m, 1H), 7.31 (dd, J=6.8, 10.2 Hz, 1H), 7.09 (d, J=6.8 Hz, 1H), 6.99 (t, J=7.8 Hz, 1H), 5.08-5.02 (m, 1H), 4.99-4.93 (m, 1H), 4.37-4.28 (m, 1H), 4.06 (t, J=13.4 Hz, 2H), 3.97 (s, 3H), 3.92-3.82 (m, 2H), 3.84-3.78 (m, 2H), 3.74-3.64 (m, 1H), 3.61-3.55 (m, 2H), 3.51-3.37 (m, 6H), 3.16-2.98 (m, 2H), 2.90-2.80 (m, 1H), 2.78-2.62 (m, 2H), 2.16-2.02 (m, 5H), 1.98-1.64 (m, 8H).

Example 106. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(2-(2-((2-(2,6-dioxopiperidin-3-yl)-1,3-dioxoisoindolin-4-yl)amino)ethoxy)ethyl)pyrrolidin-3-yl)-2-fluoro-5-methoxybenzamide

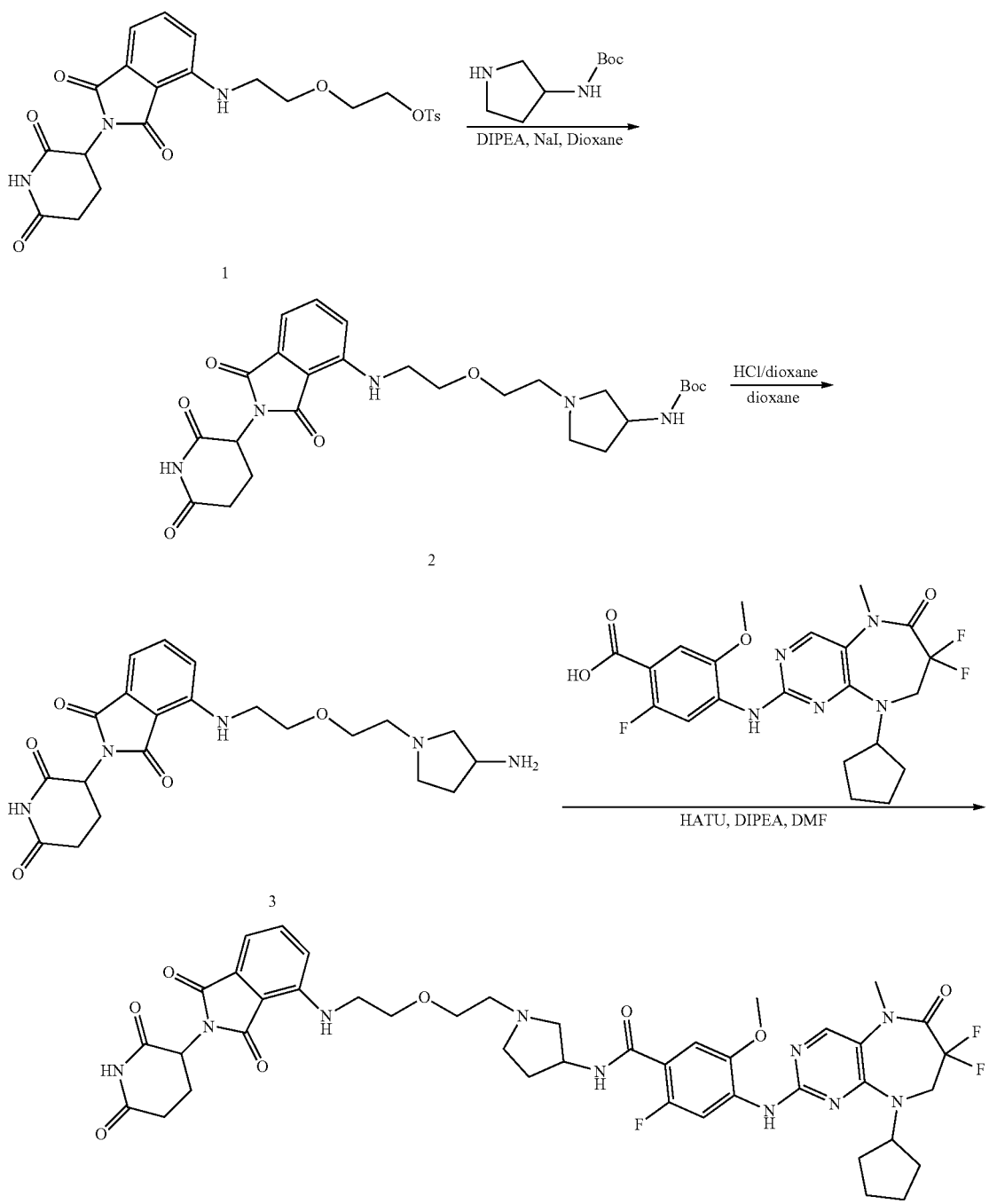

Compound 106

Step 1-2 are Described in the Above Reaction Scheme

Step 3: Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(2-(2-((2-(2,6-dioxopiperidin-3-yl)-1,3-dioxoisoindolin-4-yl)amino)ethoxy)ethyl)pyrrolidin-3-yl)-2-fluoro-5-methoxybenzamide (Compound 106C)

To the suspensions of 4-((2-(2-(3-aminopyrrolidin-1-yl)ethoxy)ethyl)amino)-2-(2,6-dioxopiperidin-3-yl)isoindoline-1,3-dione (166.09 mg, 386.74 μmol, HCl and 4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzoic acid (180 mg, 386.74 mol) in DMF (3 mL) were added HATU (294.10 mg, 773.49 μmol) and DIPEA (149.95 mg, 1.16 mmol, 202.09 μL) and the resulting mixture was stirred at 20° C. for 1 h. LCMS showed that the reaction was completed. The mixture was poured into water (20 mL) and extracted with EtOAc (20 mL×3), the combined organic layer was washed with brine (50 mL), dried over $Na_2SO_4$, filtered and concentrated. The residue was purified by prep-HPLC (column: Unisil 3-100 $C_{18}$ μLtra 150*50 mm*3 um; mobile phase: [water (0.225% FA)-ACN]; B %: 35%-55%. 10 min) and the eluant was lyophilized to afford the titled compound (97.8 mg, 109.30 μmol, 28.26% yield, 98% purity) as yellow solid. MS(M+H)$^+$=877.0.

$^1$H NMR (400 MHz, CD$_3$OD) δ=8.42-8.34 (m, 1H), 8.23 (d, J=1.8 Hz, 1H), 7.61-7.46 (m, 1H), 7.35 (dd, J=3.2, 6.8 Hz, 1H), 7.11 (dd, J=6.8, 8.4 Hz, 1H), 6.98 (t, J=6.8 Hz, 1H), 5.04-4.93 (m, 4H), 4.66-4.60 (m, 2H), 4.06 (t, J=13.4 Hz, 2H), 3.94 (s, 3H), 3.90-3.82 (m, 4H), 3.58-3.52 (m, 2H), 3.43 (s, 3H), 3.13-2.96 (m, 3H), 2.88-2.66 (m, 4H), 2.51-2.37 (m, 1H), 2.15-2.05 (m, 3H), 1.97-1.87 (m, 1H), 1.86-1.67 (m, 5H)

Example 107. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(2-(2-(2-((2-(2,6-dioxopiperidin-3-yl)-1,3-dioxoisoindolin-4-yl)amino)ethoxy)ethoxy)ethyl)pyrrolidin-3-yl)-2-fluoro-5-methoxybenzamide

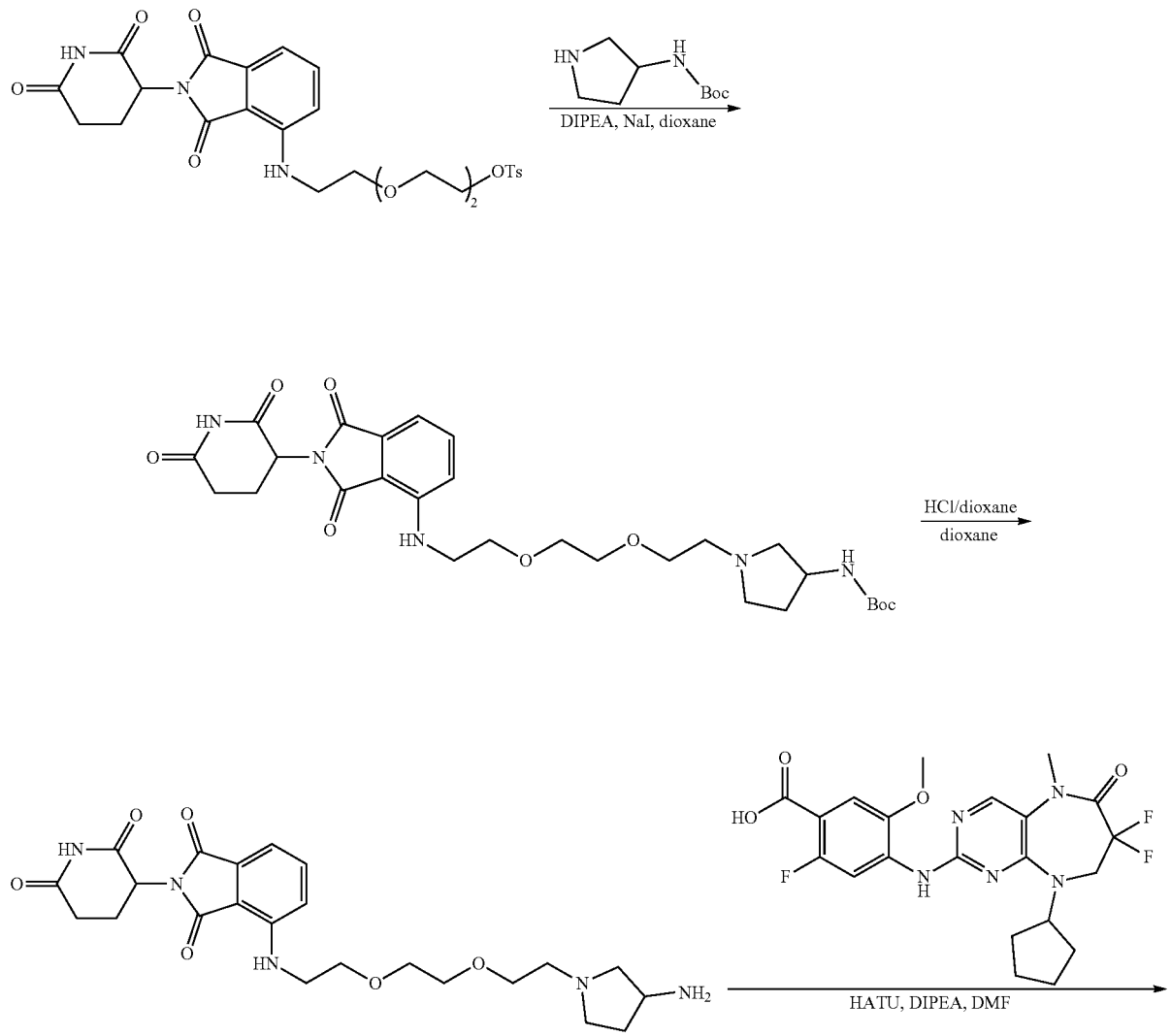

481

-continued

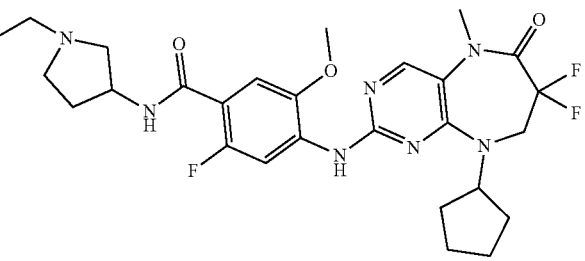

Compound 107

According to the above reaction scheme, in a manner similar to the other examples, obtained the titled compound (40.9 mg, 39.97 μmol, 12.40% yield, 90% purity) as a yellow solid. MS(M+H)⁺=921.6.

¹H NMR (400 MHz, CDCl₃) δ=8.34 (d, J=14.9 Hz, 1H), 8.07 (d, J=1.7 Hz, 1H), 7.82 (d, J=1.7 Hz, 1H), 7.55 (dd, J₁=7.2 Hz, J₂=4.0 Hz, 1H), 7.47 (dd, J₁=8.3 Hz, J₂=7.3 Hz, 1H), 7.09 (d, J=7.0 Hz, 2H), 6.90 (d, J=8.4 Hz, 1H), 6.55-6.46 (m, 1H), 4.92-4.82 (m, 2H), 4.74-4.62 (m, 1H), 3.97-3.92 (m, 4H), 3.93-3.85 (m, 2H), 3.72 (t, J=5.4 Hz, 2H), 3.69-3.62 (m, 6H), 3.48-3.42 (m, 2H), 3.42 (s, 3H), 3.02-2.93 (m, 1H), 2.88-2.79 (m, 3H), 2.77-2.67 (m, 3H), 2.49-2.34 (m, 2H), 2.15-2.08 (m, 3H), 1.71-1.52 (m, 7H).

Example 108. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(14-((2-(2,6-dioxopiperidin-3-yl)-1,3-dioxoisoindolin-4-yl)amino)-3,6,9,12-tetraoxatetradecyl)pyrrolidin-3-yl)-2-fluoro-5-methoxybenzamide

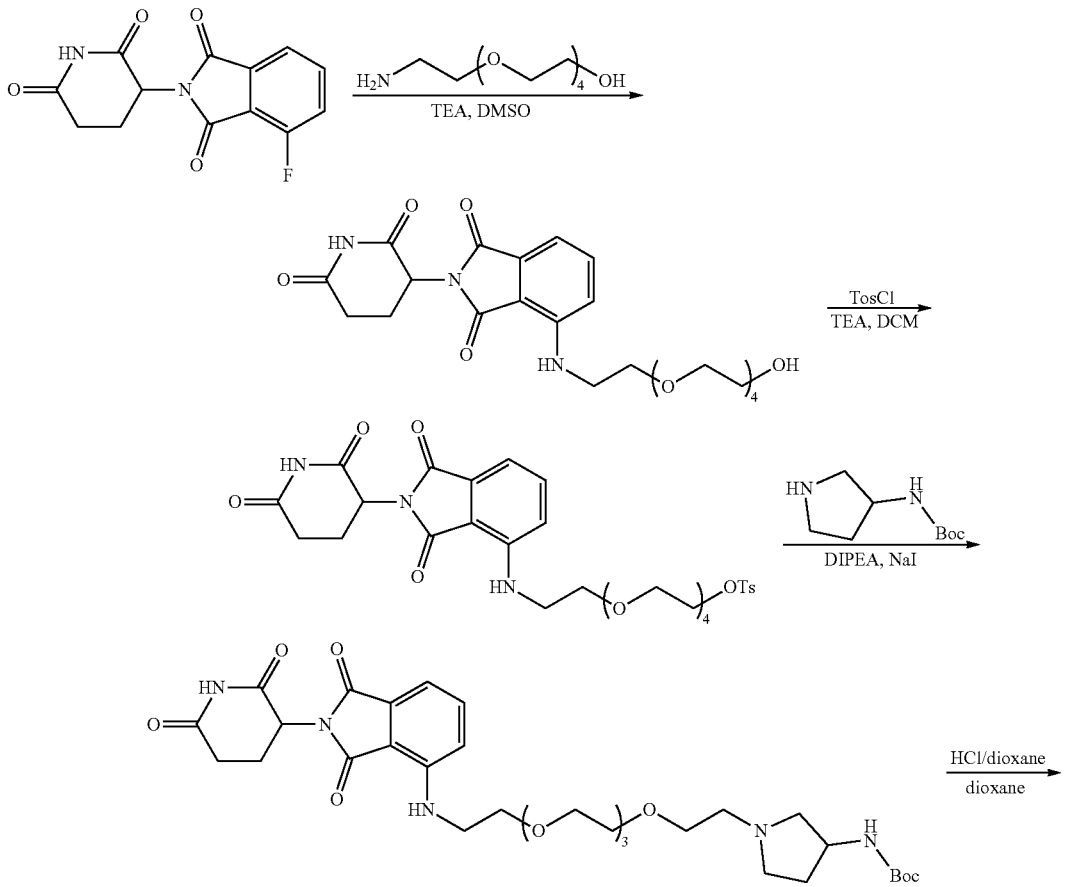

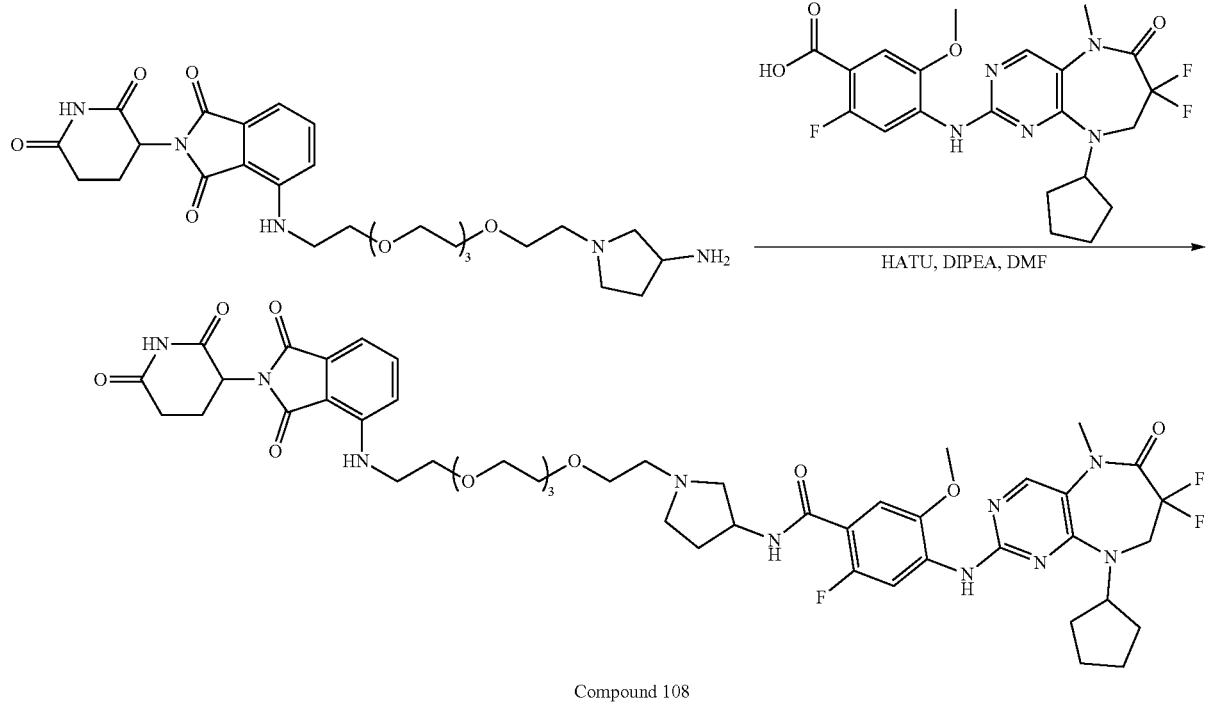

Compound 108

According to the above reaction scheme, in a manner similar to the other examples, obtained the titled compound (61.4 mg, 57.81 μmol, 17.29% yield, 95% purity, FA) as yellow solid. MS(M+H)⁺=1009.3.

¹H NMR (400 MHz, MeOD) δ=8.35-8.24 (m, 1H), 8.20 (s, 1H), 7.50 (dd, J=7.2, 8.5 Hz, 1H), 7.46-7.34 (m, 1H), 7.08-6.94 (m, 2H), 5.08-4.90 (m, 3H), 4.74-4.56 (m, 1H), 4.15-4.05 (m, 2H), 4.07-3.94 (m, 4H), 3.89-3.76 (m, 3H), 3.72-3.59 (m, 13H), 3.55-3.36 (m, 8H), 3.27-3.16 (m, 1H), 2.92-2.79 (m, 1H), 2.78-2.39 (m, 3H), 2.26-2.16 (m, 1H), 2.15-2.01 (m, 3H), 1.88-1.77 (m, 2H), 1.74-1.51 (m, 4H).

Example 109. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(5-((2-(2,6-dioxopiperidin-3-yl)-1,3-dioxoisoindolin-4-yl)amino)pentyl)pyrrolidin-3-yl)-2-fluoro-5-methoxybenzamide

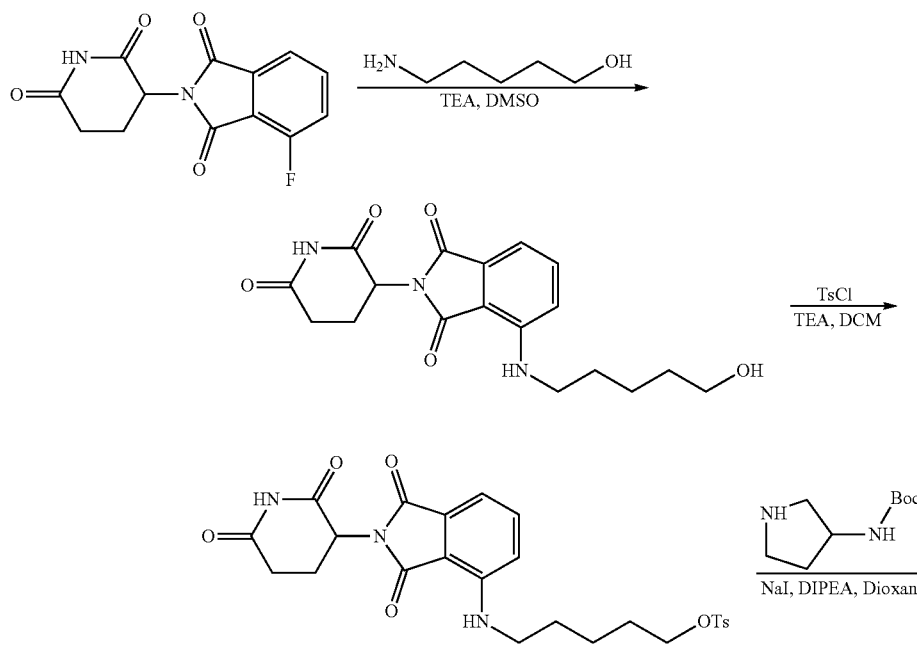

-continued

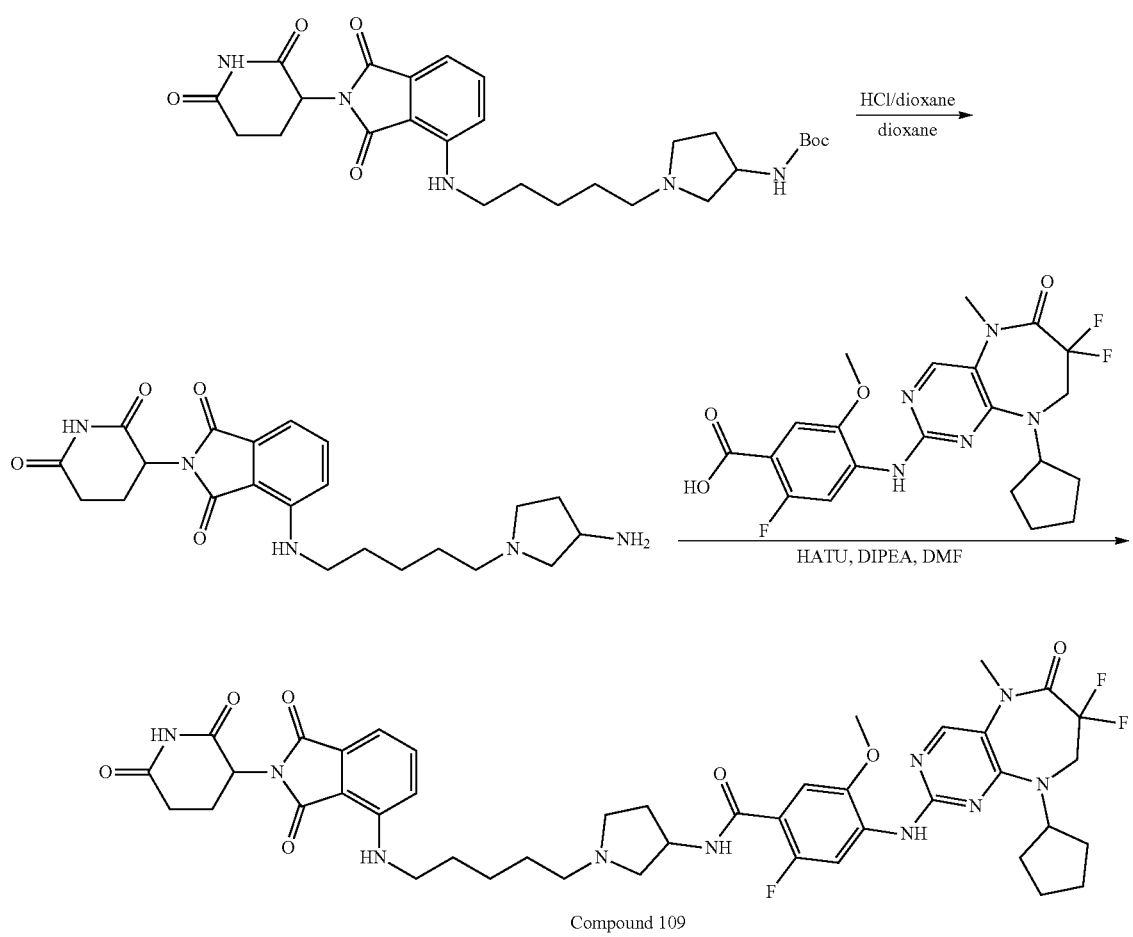

Compound 109

According to the above reaction scheme, in a manner similar to the other examples, obtained the titled compound (41.5 mg, 45.54 μmol, 10.56% yield, 96% purity) as yellow solid. MS (M+H)⁺=875.2.

¹H NMR (400 MHz, CD₃OD) δ=8.42 (d, J=14.4 Hz, 1H), 8.21 (s, 1H), 7.57-7.53 (m, 1H), 7.44-7.33 (m, 1H), 7.08-7.03 (m, 2H), 5.06-5.02 (m, 1H), 4.95-4.92 (m, 2H), 4.70-4.60 (m, 3H), 4.11-3.95 (m, 5H), 3.80-3.71 (m, 1H), 3.40-3.37 (m, 5H), 3.26-3.24 (m, 2H), 2.85-2.75 (m, 1H), 2.71-2.50 (m, 3H), 2.32-2.16 (m, 1H), 2.11-2.08 (m, 3H), 1.78-1.71 (m, 10H) 1.60-1.50 (m, 2H).

Example 110. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(2-(3-((2-(2,6-dioxopiperidin-3-yl)-1,3-dioxoisoindolin-4-yl)amino)propoxy)ethyl)pyrrolidin-3-yl)-2-fluoro-5-methoxybenzamide

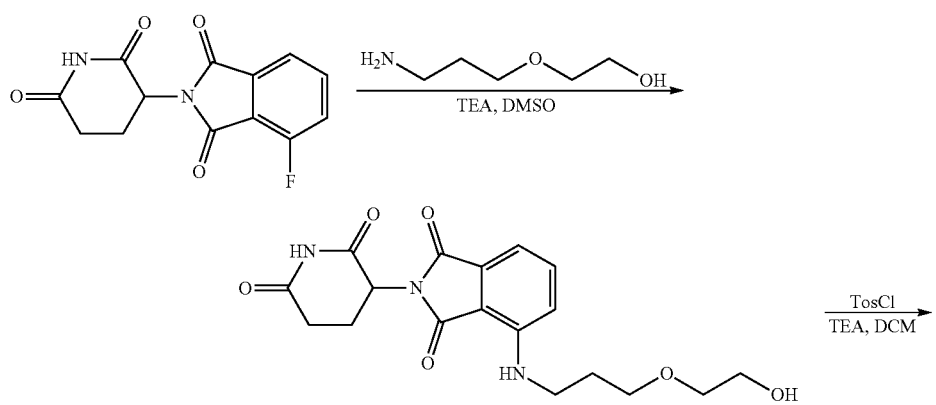

487 488

-continued

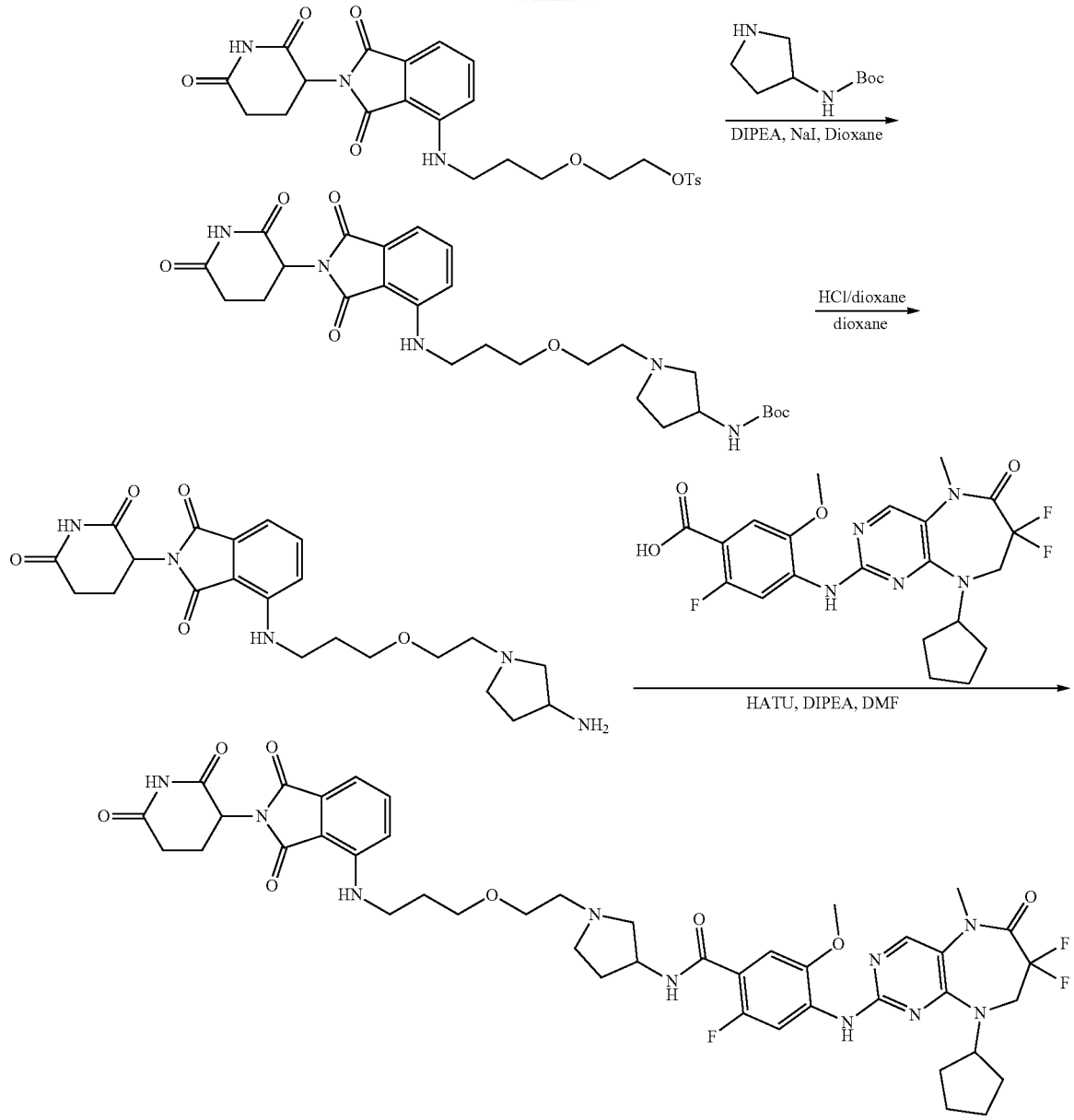

Compound 110

According to the above reaction scheme, in a manner similar to the other examples, obtained the titled compound (67.9 mg, 70.88 μmol, 34.02% yield, 93% purity) as yellow solid. MS(M+H)⁺=891.0

¹H NMR (400 MHz, DMSO-d₆) δ=11.10 (s, 1H), 8.30 (s, 1H), 8.27 (d, J=13.6 Hz, 1H), 8.05-8.02 (m, 2H), 7.57 (t, J=7.8 Hz, 1H), 7.24 (d, J=6.8 Hz, 1H), 7.09 (d, J=8.8 Hz, 1H), 7.01 (d, J=7.0 Hz, 1H), 6.67 (t, J=5.6 Hz, 1H), 5.09-4.98 (m, 1H), 4.89-4.74 (m, 1H), 4.37-4.30 (m, 1H), 4.09 (t, J=13.8 Hz, 2H), 3.91 (s, 3H), 3.57-3.45 (m, 4H), 3.47-3.39 (m, 8H), 2.94-2.76 (m, 2H), 2.71-2.55 (m, 5H), 2.19-2.06 (m, 1H), 2.05-1.90 (m, 3H), 1.85-1.79 (m, 2H), 1.75-1.70 (m, 3H), 1.69-1.52 (m, 3H).

Example 111. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(3-(3-((2-(2,6-dioxopiperidin-3-yl)-1,3-dioxoisoindolin-4-yl)amino)propoxy)propyl)pyrrolidin-3-yl)-2-fluoro-5-methoxybenzamide

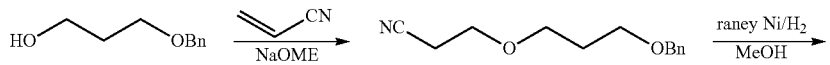

-continued
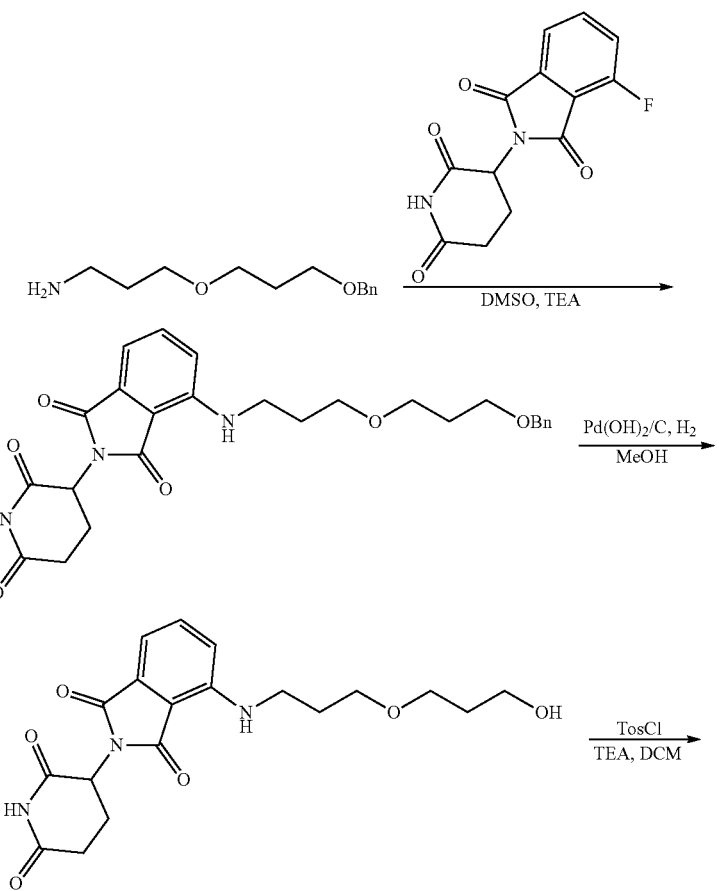
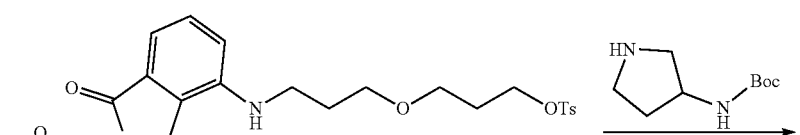
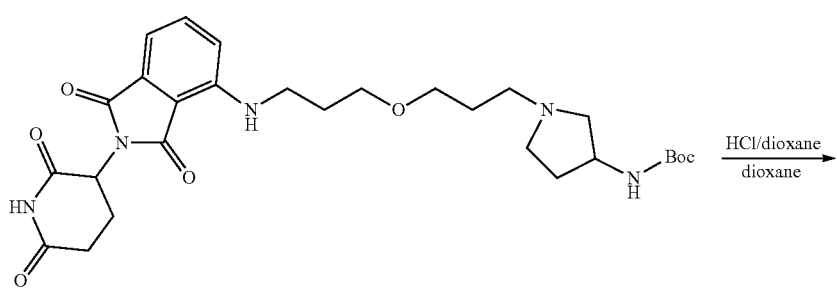

491

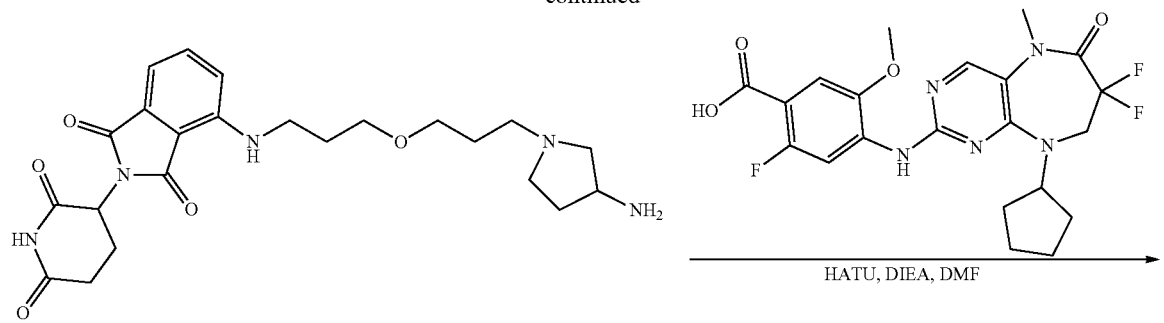

-continued

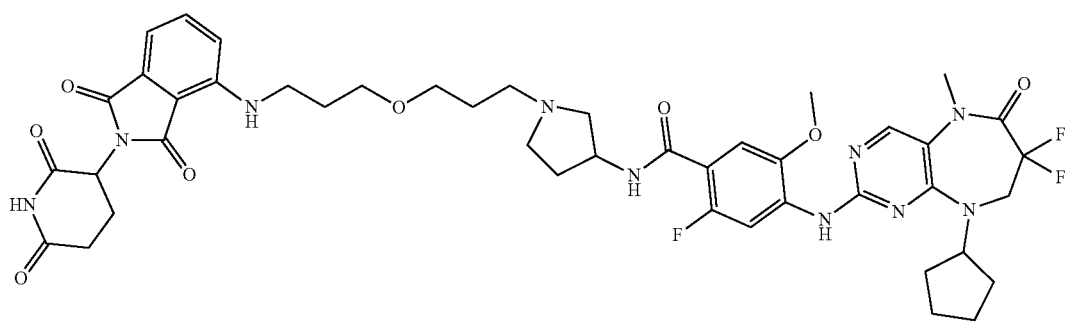

Compound 111

According to the above reaction scheme, in a manner similar to the other examples, obtained the titled compound (98.4 mg, 106.56 μmol, 17.55% yield, 98% purity) as a yellow solid. MS(M+H)$^+$=905.7.

$^1$H NMR (400 MHz, DMSO-d$_6$) δ=11.09 (s, 1H), 8.36-8.16 (m, 2H), 8.11-7.93 (m, 2H), 7.57 (dd, J$_1$=7.3 Hz, J$_2$=8.4 Hz, 1H), 7.20 (d, J=6.7 Hz, 1H), 7.08 (d, J=8.7 Hz, 1H), 7.01 (d, J=7.0 Hz, 1H), 6.66 (t, J=5.6 Hz, 1H), 5.04 (dd, J$_1$=12.9 Hz, J$_2$=5.4 Hz, 1H), 4.90-4.71 (m, 1H), 4.43-4.28 (m, 1H), 4.07 (t, J=13.9 Hz, 2H), 3.91 (s, 3H), 3.51-3.35 (m, 9H), 2.94-2.82 (m, 1H), 2.72 (dd, J$_1$=9.1 Hz, J$_2$=7.3 Hz, 1H), 2.65-2.53 (m, 3H), 2.48-2.37 (m, 5H), 2.18-2.09 (m, 1H), 2.05-1.91 (m, 3H), 1.85-1.77 (m, 2H), 1.73-1.67 (m, 4H), 1.66-1.56 (m, 4H).

Example 112. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-((3S)-1-(2-(2-(2-((2-(2,6-dioxopiperidin-3-yl)-1,3-dioxoisoindolin-4-yl)amino)acetamido)ethoxy)ethyl)pyrrolidin-3-yl)-2-fluoro-5-methoxybenzamide

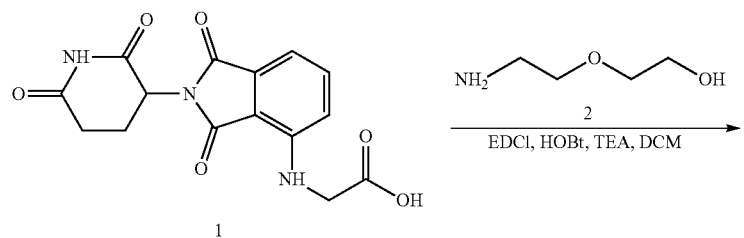

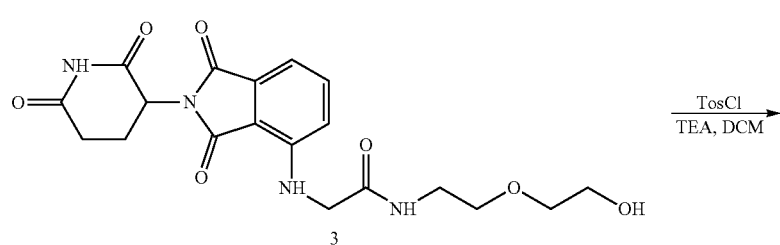

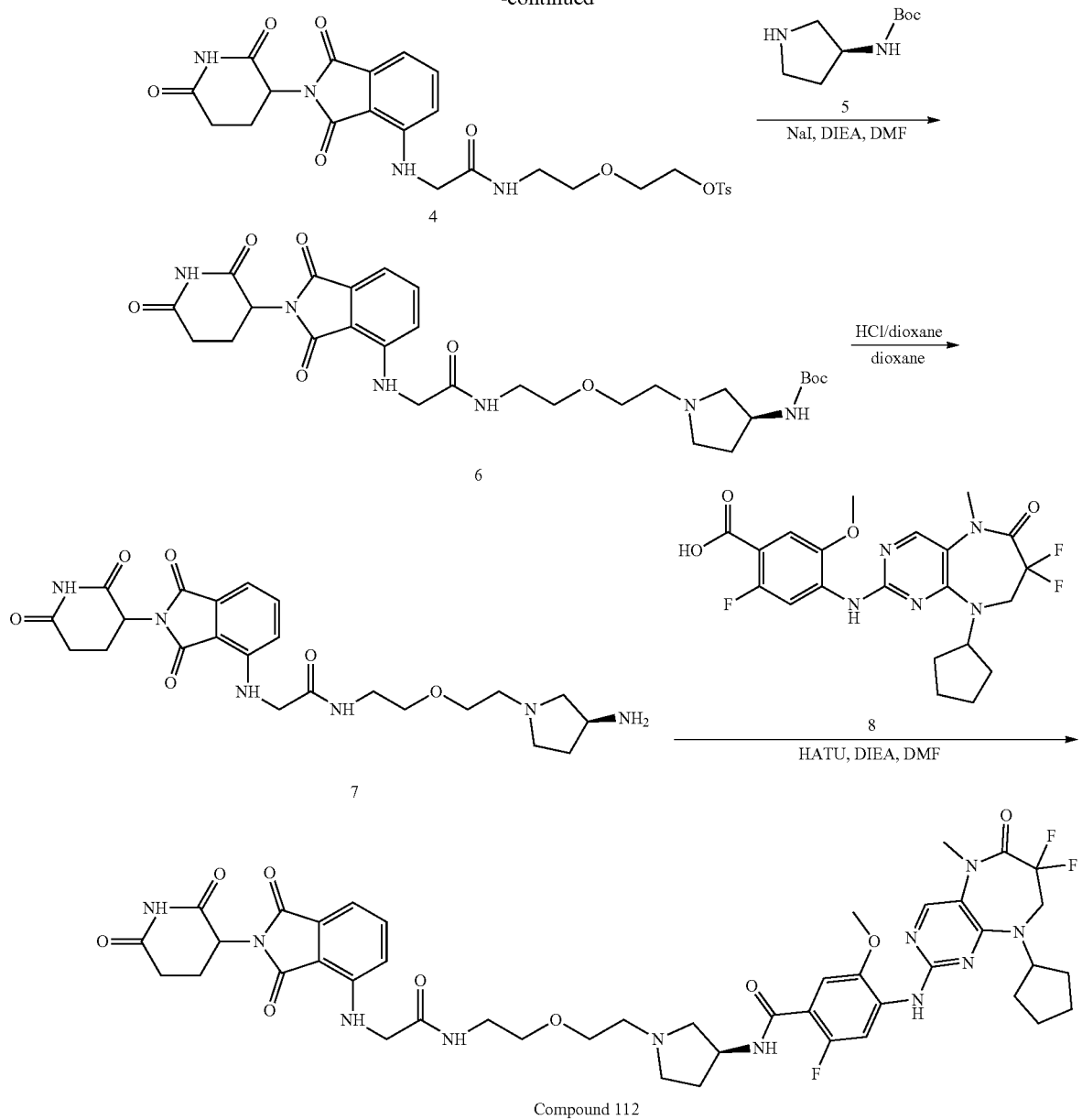

Step 1: Synthesis of 2-((2-(2,6-dioxopiperidin-3-yl)-1,3-dioxoisoindolin-4-yl)amino)-N-(2-(2-hydroxyethoxyethyl)acetamide (3)

A mixture of 2-((2-(2,6-dioxopiperidin-3-yl)-1,3-dioxoisoindolin-4-yl)amino)acetic acid (500 mg, 1.36 mmol, HCl salt), 2-(2-aminoethoxy)ethanol (214.42 mg, 2.04 mmol, 204.21 μL), EDCI (390.97 mg, 2.04 mmol), HOBt (275.58 mg, 2.04 mmol) and TEA (412.75 mg, 4.08 mmol, 567.74 μL) in DCM (5 mL) was stirred at 15° C. for 16 hours. LCMS showed 4% of reactant remained and 79% of desired mass was detected. The reaction mixture was concentrated in vacuo. The residue was purified by flash silica gel chromatography (12 g SepaFlash® Silica Flash Column, Eluent of 0-9% MeOH/Ethyl acetate gradient @ 60 mL/min) to afford the titled compound (400 mg, crude) as a green solid. MS(M+H)$^+$=419.1.

Step 2: Synthesis of 2-(2-(2-((2-(2,6-dioxopiperidin-3-yl)-1,3-dioxoisoindolin-4-yl)amino)acetamido)ethoxy)ethyl 4-methylbenzenesulfonate (4)

To a solution of 2-((2-(2,6-dioxopiperidin-3-yl)-1,3-dioxoisoindolin-4-yl)amino)-N-(2-(2-hydroxyethoxy)ethyl) acetamide (400 mg, 956.02 μmol) in DCM (15 mL) were added TosCl (328.07 mg, 1.72 mmol) and TEA (290.22 mg, 2.87 mmol, 399.20 μL) and the mixture was stirred at 15° C. for 16 hours. LCMS showed 15% of reactant remained and 35% of desired mass was detected. Additional TosCl (273.39 mg, 1.43 mmol) and TEA (193.48 mg, 1.91 mmol, 266.13 μL) were added and the resulting mixture was stirred at 15° C. for further 3 hours. LCMS showed 8% of reactant remained and 38% of desired mass was detected. The reaction mixture was concentrated in vacuo. The residue was purified by flash silica gel chromatography (20 g Sepa- Flash® Silica Flash Column, Eluent of 25~85% Ethyl acetate/Petroleum ether gradient @ 100 mL/min) to afford the titled compound (410 mg, 716.05 µmol, 74.90% yield, N/A purity) as a yellow oil. MS(M+H)$^+$=573.0.

Step 3: Synthesis of tert-butyl ((3S)-1-(2-(2-(2-((2-(2,6-dioxopiperidin-3-yl)-1,3-dioxoisoindolin-4-yl)amino)acetamido)ethoxy)ethyl)pyrrolidin-3-yl)carbamate (6)

A mixture of 2-(2-(2-((2-(2,6-dioxopiperidin-3-yl)-1,3-dioxoisoindolin-4-yl)amino)acetamido) ethoxy)ethyl 4-methylbenzenesulfonate (410 mg, 716.05 µmol), (S)-tert-butyl pyrrolidin-3-ylcarbamate (266.73 mg, 1.43 mmol), NaI (10.73 mg, 71.60 µmol) and DIEA (277.63 mg, 2.15 mmol, 374.17 µL) in DMF (6 mL) was stirred at 60° C. for 16 hours. LCMS showed reactant was consumed completely and 83% of desired mass was detected. The reaction mixture was diluted with H$_2$O (50 mL) and extracted with brine (50 mL×3). The combined organic layers were washed with brine (80 mL×5), dried over Na$_2$SO$_4$, filtered and concentrated under reduced pressure. The residue was purified by flash silica gel chromatography (12 g SepaFlash® Silica Flash Column, Eluent of 0~5% MeOH/Ethyl acetate gradient @ 60 mL/min) to afford the titled compound (160 mg, 272.74 µmol, 38.09% yield) as a yellow solid. MS(M+H)$^+$=587.2.

Step 4: Synthesis of N-(2-(2-((S)-3-aminopyrrolidin-1-yl)ethoxy)ethyl)-2-((2-(2,6-dioxopiperidin-3-yl)-1,3-dioxoisoindolin-4-yl)amino)acetamide (7)

To a solution of tert-butyl ((3S)-1-(2-(2-(2-((2-(2, 6-dioxopiperidin-3-yl)-1,3-dioxoisoindolin-4-yl) amino)acetamido)ethoxy)ethyl)pyrrolidin-3-yl)carbamate (160 mg, 272.74 µmol) in dioxane (5 mL) was added HCl/dioxane (4 M, 10 mL), the mixture was stirred at 15° C. for 2 hours. LCMS showed reactant was consumed completely and 100% of desired mass was detected. The reaction mixture was concentrated in vacuo to afford the titled compound (220 mg, crude, HCl) as a yellow solid, which was used for the next step directly. MS(M+H)$^+$=487.2.

Step 5: Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-((3S)-1-(2-(2-(2-((2-(2,6-dioxopiperidin-3-yl)-1,3-dioxoisoindolin-4-yl)amino)acetamido)ethoxy)ethyl)pyrrolidin-3-yl)-2-fluoro-5-methoxybenzamide (Compound 112)

To a solution of 4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzoic acid (120 mg, 257.83 µmol) in DMF (3 mL) were added HATU (147.05 mg, 386.74 µmol) and DIEA (133.29 mg, 1.03 mmol, 179.64 µL) and the resulting mixture was stirred at 15° C. for 15 minutes, then N-(2-(2-((S)-3-aminopyrrolidin-1-yl)ethoxy)ethyl)-2-((2-(2,6-dioxopiperidin-3-yl)-1,3-dioxoisoindolin-4-yl)amino)acetamide (215.74 mg, 412.53 µmol, HCl salt) and the resulting mixture was stirred at 15° C. for 12 hours. LCMS showed reactant was consumed completely and 79% of desired mass was detected. To the mixture was added CH$_3$COOH to adjust pH<7. The resulting mixture was purified by prep-HPLC (column: Waters Xbridge 150*25 mm*5 um; mobile phase: [water(10 mM NH$_4$HCO$_3$)-ACN]; B %: 37%-67%, 10 min) followed by prep-HPLC (column: Phenomenex luna C$_{18}$ 150*25 mm*10 um; mobile phase: [water(0.225% FA)-ACN]; B %: 15%-55%, 13 min) to afford the titled compound (58.2 mg, 60.45 µmol, 23.44% yield, 97% purity) as a yellow solid. MS(M+H)$^+$=934.2.

$^1$H NMR (400 MHz, DMSO-d$_6$) δ=11.09 (s, 1H), 8.29 (s, 1H), 8.23 (d, J=13.4 Hz, 1H), 8.14 (t, J=5.5 Hz, 1H), 8.09-7.94 (m, 2H), 7.57 (dd, J$_1$=7.5, J$_2$=8.2 Hz, 1H), 7.19 (d, J=6.7 Hz, 1H), 7.05 (d, J=7.0 Hz, 1H), 6.93 (t, J=5.5 Hz, 1H), 6.84 (d, J=8.6 Hz, 1H), 5.07 (dd, J$_1$=5.4, J$_2$=12.9 Hz, 1H), 4.89-4.74 (m, 1H), 4.39-4.27 (m, 1H), 4.07 (t, J=13.9 Hz, 2H), 4.01-3.78 (m, 5H), 3.48 (t, J=5.9 Hz, 2H), 3.45-3.39 (m, 2H), 3.33 (s, 3H), 3.30-3.25 (m, 2H), 2.95-2.83 (m, 1H), 2.79 (dd, J$_1$=7.3, J$_2$=9.3 Hz, 1H), 2.69-2.60 (m, 2H), 2.59-2.52 (m, 4H), 2.45-2.40 (m, 1H), 2.17-2.08 (m, 1H), 2.07-1.90 (m, 3H), 1.78-1.52 (m, 7H).

Example 113. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-((3S)-1-(3-(2-((2-(2,6-dioxopiperidin-3-yl)-1,3-dioxoisoindolin-4-yl)amino)acetamido)propanoyl)pyrrolidin-3-yl)-2-fluoro-5-methoxybenzamide

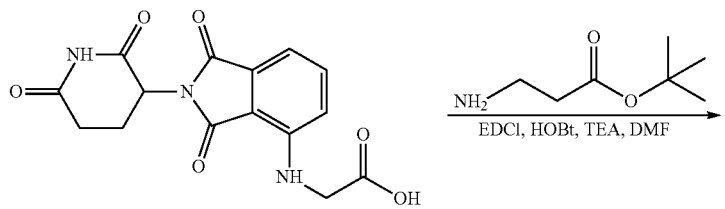

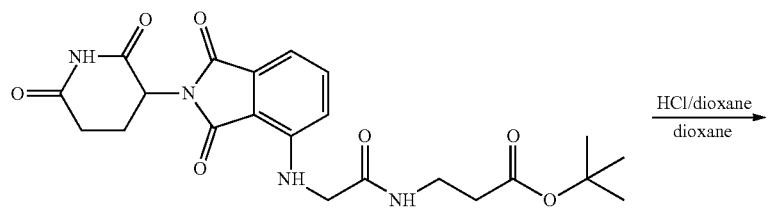

497                                                                                                      498

-continued

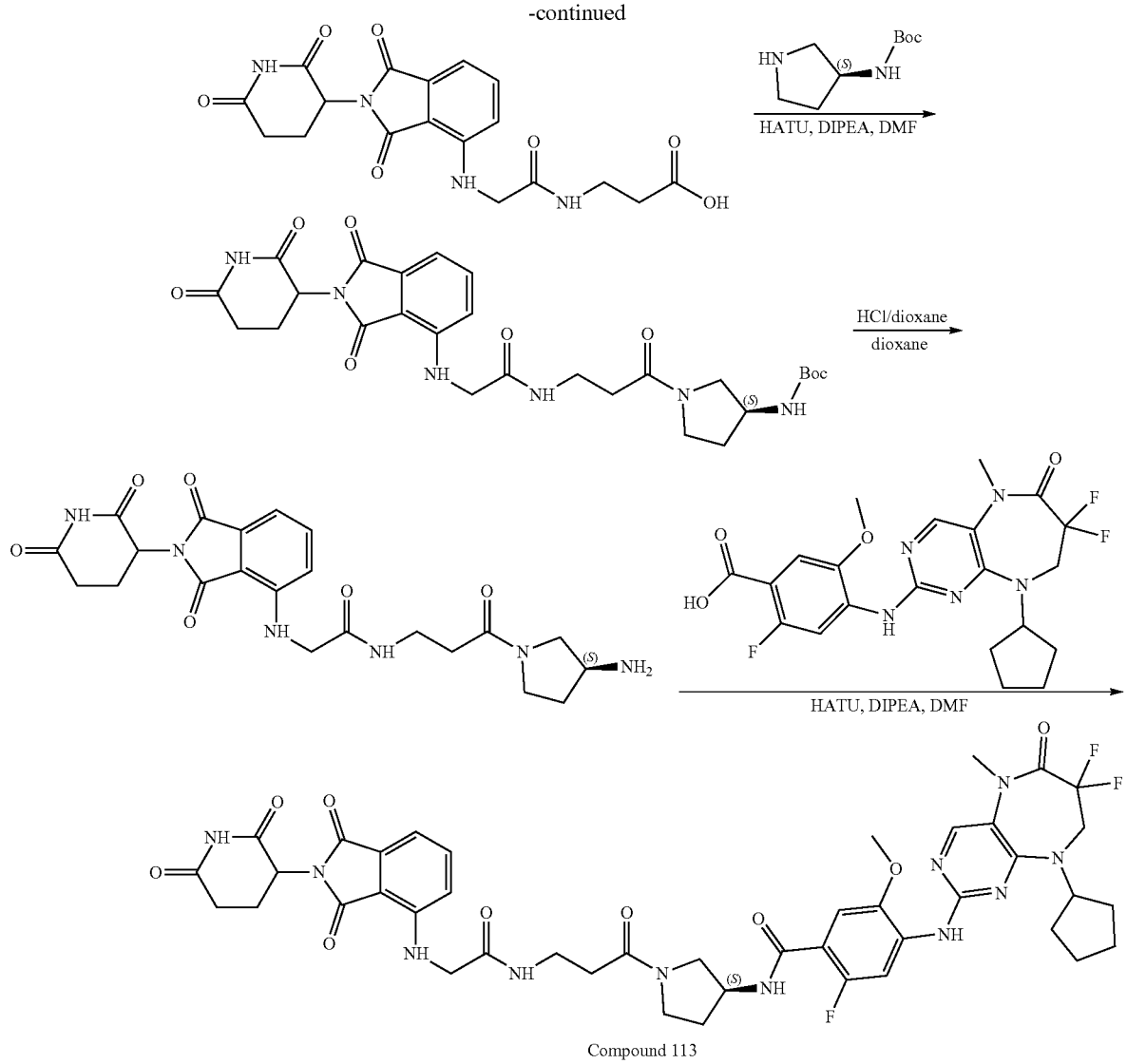

Compound 113

According to the above reaction scheme, in a manner similar to the other examples, obtained the titled compound (40.8 mg, 43.38 μmol, 13.61% yield, 97.6% purity) as a yellow solid. MS(M+H)⁺=918.2

¹H NMR (400 MHz, DMSO-d₆) δ=11.09 (s, 1H), 8.34-8.20 (m, 3H), 8.16-8.07 (m, 1H), 8.04 (s, 1H), 7.63-7.47 (m, 1H), 7.25-7.15 (m, 1H), 7.11-7.03 (m, 1H), 6.94 (t, J=5.5 Hz, 1H), 6.89-6.82 (m, 1H), 5.11-5.03 (m, 1H), 4.87-4.76 (m, 1H), 4.52-4.35 (m, 1H), 4.07 (t, J=13.9 Hz, 2H), 3.91 (d, J=2.0 Hz, 5H), 3.75-3.45 (m, 3H), 3.33-3.21 (m, 5H), 2.94-2.83 (m, 1H), 2.63-2.54 (m, 2H), 2.45-2.37 (m, 2H), 2.26-1.84 (m, 6H), 1.72 (d, J=0.9 Hz, 2H), 1.51-1.68 (m, 4H)

Example 114. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(3-(2-((2-(2,6-dioxopiperidin-3-yl)-1,3-dioxoisoindolin-4-yl)amino)ethoxy)propanoyl)pyrrolidin-3-yl)-2-fluoro-5-methoxybenzamide

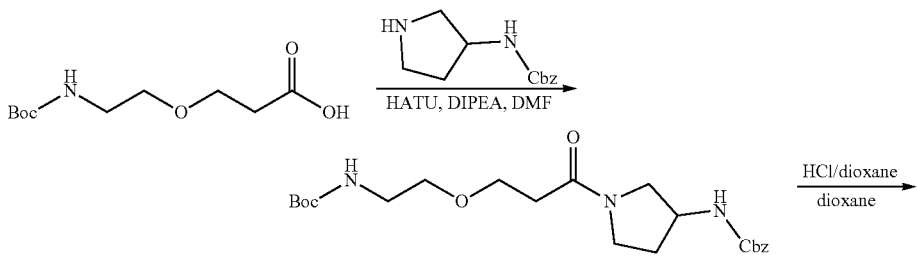

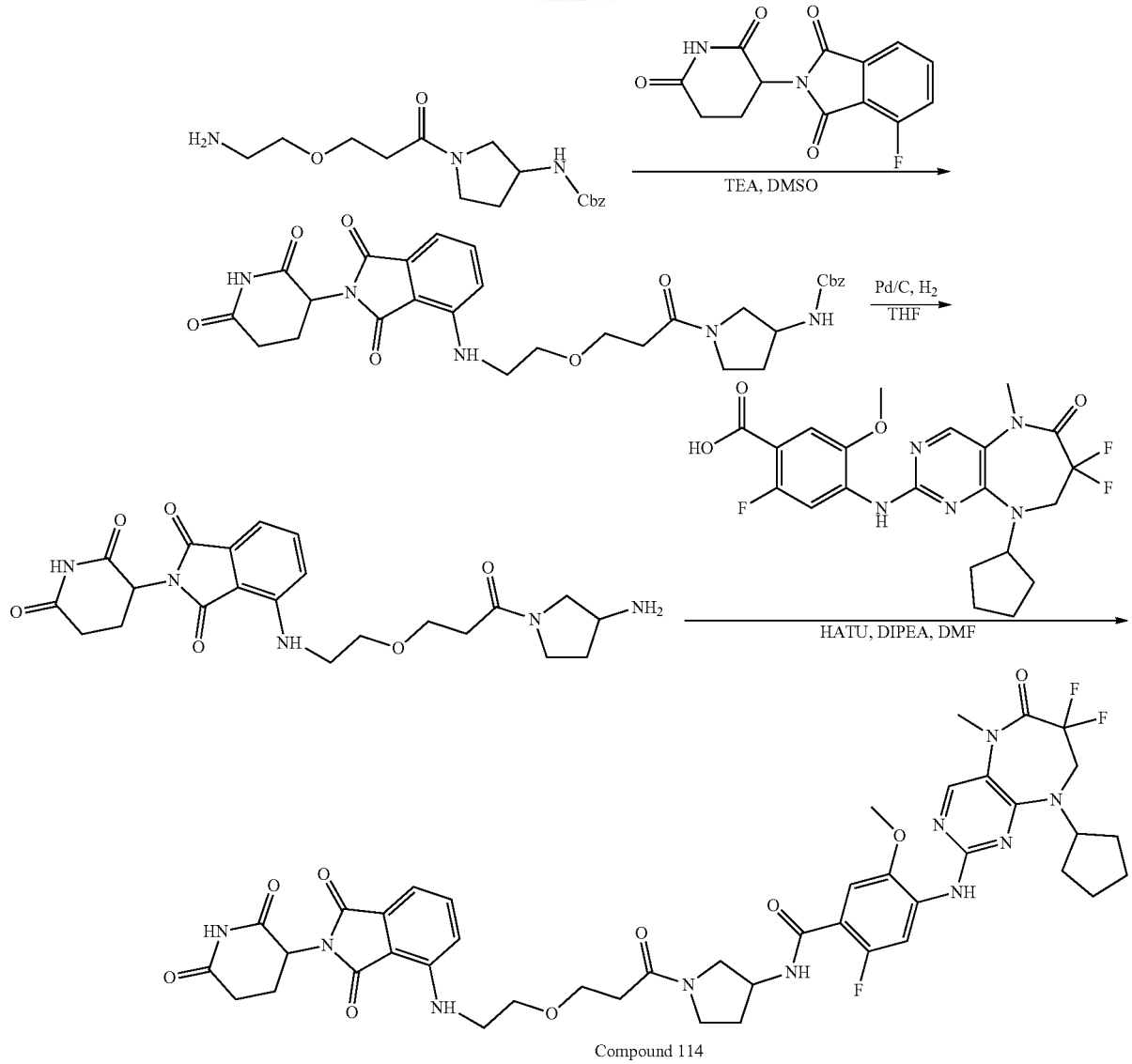

Compound 114

According to the above reaction scheme, in a manner similar to the other examples, obtained the titled compound (71 mg, 76.89 μmol, 22.37% yield, 98% purity) as a yellow solid. MS(M+H)⁺=905.0

¹H NMR (400 MHz, DMSO-d₆) δ=11.08 (br s, 1H), 8.30 (s, 1H), 8.28-8.19 (m, 2H), 8.03 (s, 1H), 7.62-7.53 (m, 1H), 7.22-7.16 (m, 1H), 7.13 (dd, J=6.8, 8.4 Hz, 1H), 7.02 (t, J=6.8 Hz, 1H), 6.62-6.54 (m, 1H), 5.10-5.02 (m, 1H), 4.87-4.77 (m, 1H), 4.53-4.36 (m, 1H), 4.07 (t, J=13.8 Hz, 2H), 3.91 (d, J=2.1 Hz, 3H), 3.72-3.65 (m, 2H), 3.64-3.56 (m, 3H), 3.54-3.36 (m, 6H), 3.34-3.32 (m, 3H), 3.27-3.21 (m, 1H), 2.96-2.80 (m, 1H), 2.62-2.53 (m, 2H), 2.10-1.86 (m, 5H), 1.74-1.57 (m, 6H)

Example 115. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-((3S)-1-(2-(2-(2-((2-(2,6-dioxopiperidin-3-yl)-1,3-dioxoisoindolin-4-yl)amino)ethoxy)ethoxy)acetyl)pyrrolidin-3-yl)-2-fluoro-5-methoxybenzamide

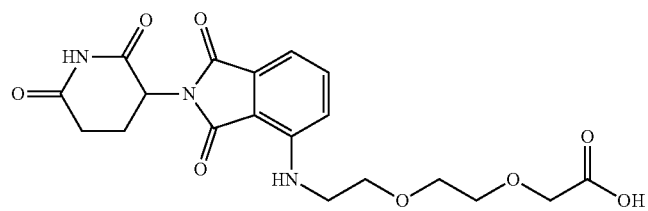 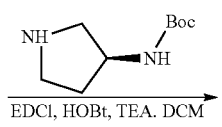

-continued

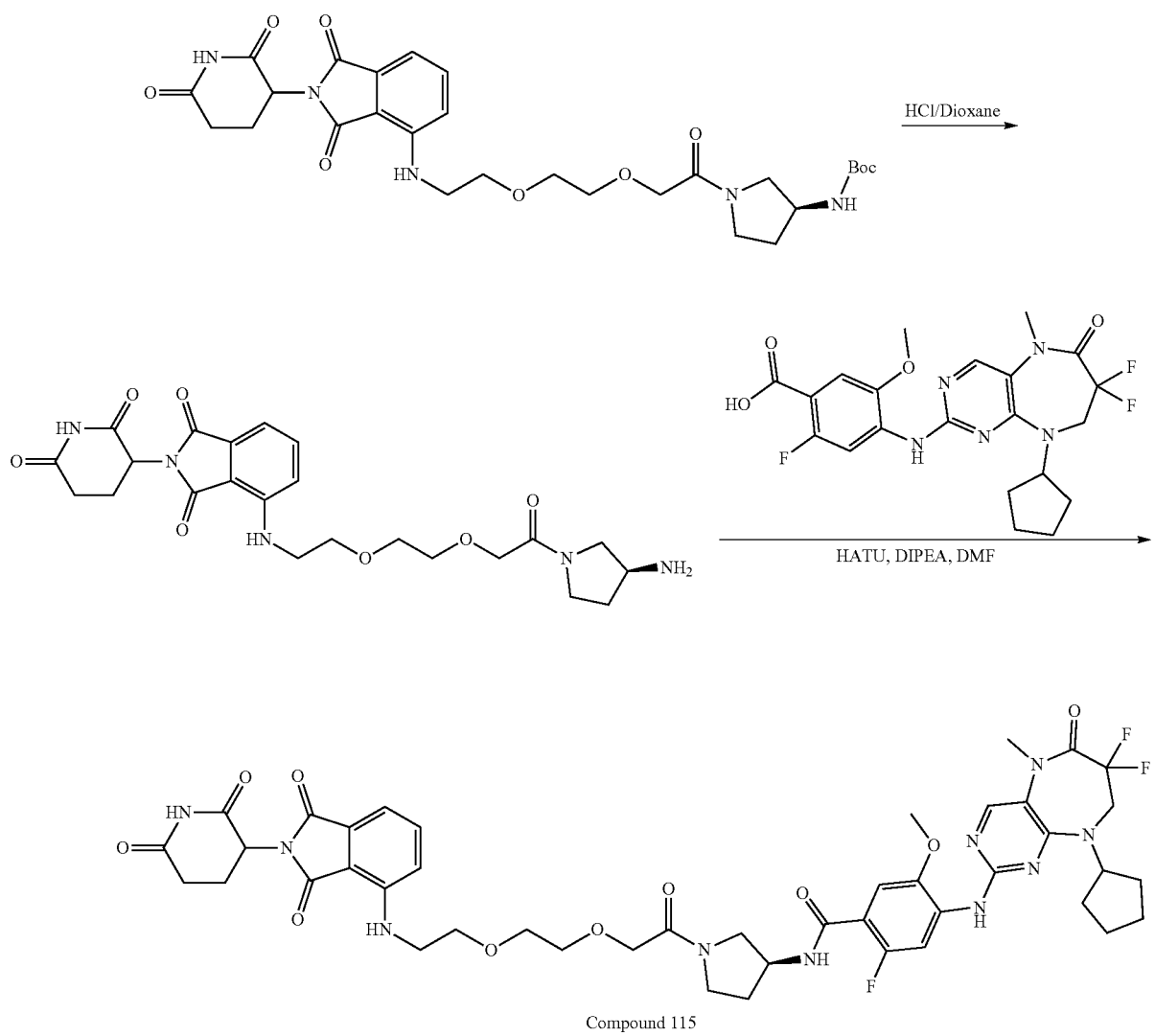

According to the above reaction scheme, in a manner similar to the other examples, obtained the titled compound (53.2 mg, 55.20 μmol, 21.41% yield, 97% purity) as a yellow solid. MS(M+H)+=935.5

$^1$H NMR (400 MHz, DMSO-d$_6$) δ=11.07 (br s, 1H), 8.35-8.17 (m, 3H), 8.03 (br s, 1H), 7.62-7.51 (m, 1H), 7.25-7.08 (m, 2H), 7.06-6.97 (m, 1H), 6.60 (q, J=5.6 Hz, 1H), 5.04 (br dd, J=5.1, 12.5 Hz, 1H), 4.89-4.75 (m, 1H), 4.55-4.31 (m, 1H), 4.16-4.00 (m, 4H), 3.91 (d, J=4.0 Hz, 3H), 3.75-3.56 (m, 7H), 3.55-3.36 (m, 5H), 2.96-2.79 (m, 1H), 2.65-2.51 (m, 5H), 2.19-1.86 (m, 5H), 1.78-1.52 (m, 6H).

Example 116. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-((3S)-1-(14-((2-(2,6-dioxopiperidin-3-yl)-1,3-dioxoisoindolin-4-yl)amino)-3,6,9,12-tetraoxatetradecanoyl)pyrrolidin-3-yl)-2-fluoro-5-methoxybenzamide

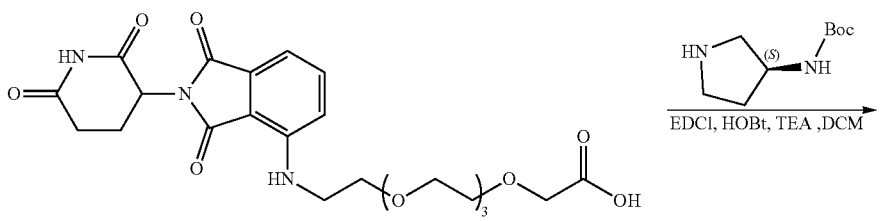

-continued

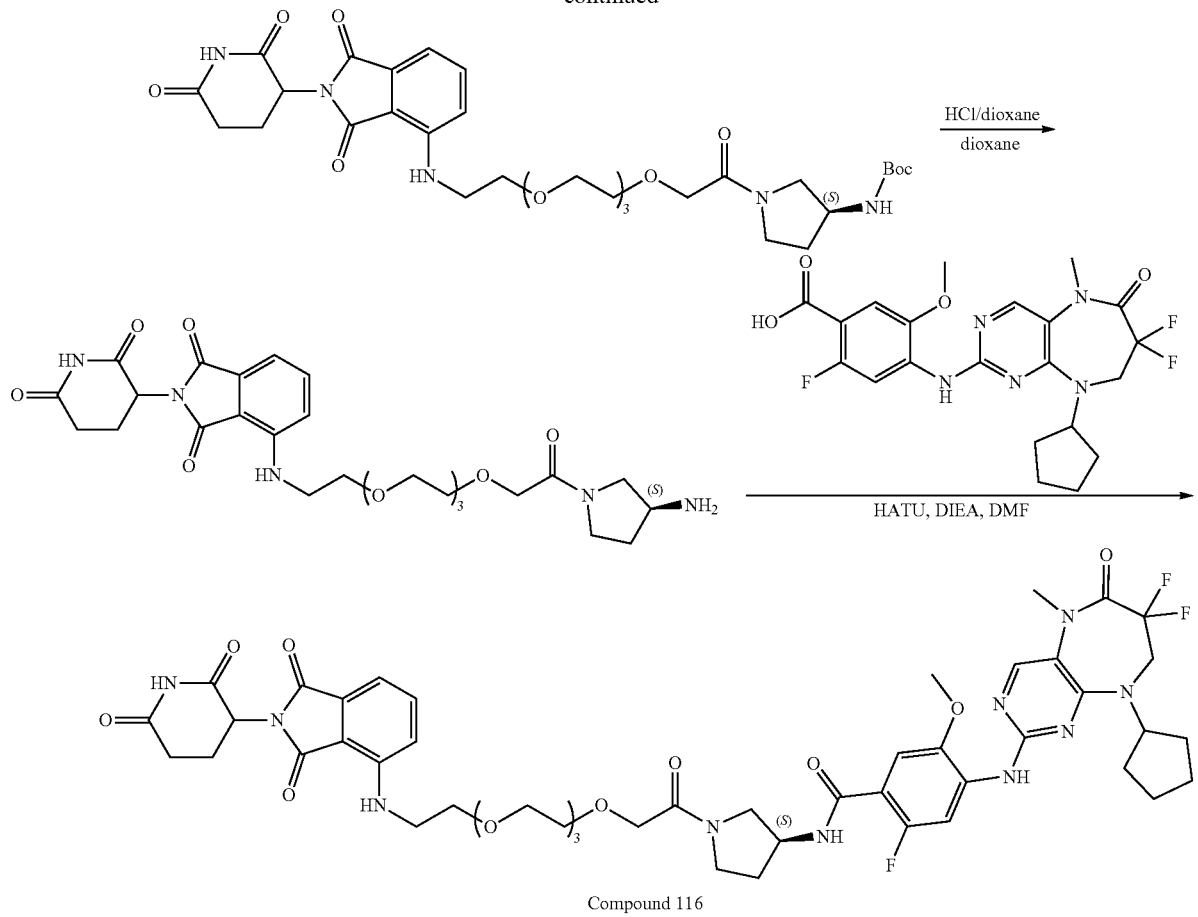

Compound 116 the titled compound (70.7 mg, 67.04 μmol, 31.20% yield, 97% purity) as a yellow solid. MS(M+H)⁺=1023.4.

¹H NMR (400 MHz, DMSO-d₆) δ=11.09 (s, 1H), 8.35-8.18 (m, 3H), 8.09 (s, 1H), 7.62-7.53 (m, 1H), 7.20 (d, J=6.7 Hz, 1H), 7.14 (dd, J₁=3.7, J₂=8.6 Hz, 1H), 7.04 (dd, J₁=1.8, J₂=6.8 Hz, 1H), 6.60 (br s, 1H), 5.06 (br dd, J₁=5.3, J₂=13.0 Hz, 1H), 4.88-4.78 (m, 1H), 4.50-4.39 (m, 1H), 4.13-4.04 (m, 4H), 3.92 (s, 3H), 3.75-3.70 (m, 1H), 3.62 (br d, J=4.8 Hz, 2H), 3.57-3.50 (m, 12H), 3.49-3.44 (m, 4H), 3.34 (br s, 3H), 2.91-2.87 (m, 1H), 2.59-2.51 (m, 2H), 2.21-2.13 (m, 1H), 2.08-1.88 (m, 5H), 1.78-1.69 (m, 2H), 1.68-1.55 (m, 4H).

Example 117. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(5-((2-(2,6-dioxopiperidin-3-yl)-1,3-dioxoisoindolin-4-yl)amino)pentanoyl)pyrrolidin-3-yl)-2-fluoro-5-methoxybenzamide

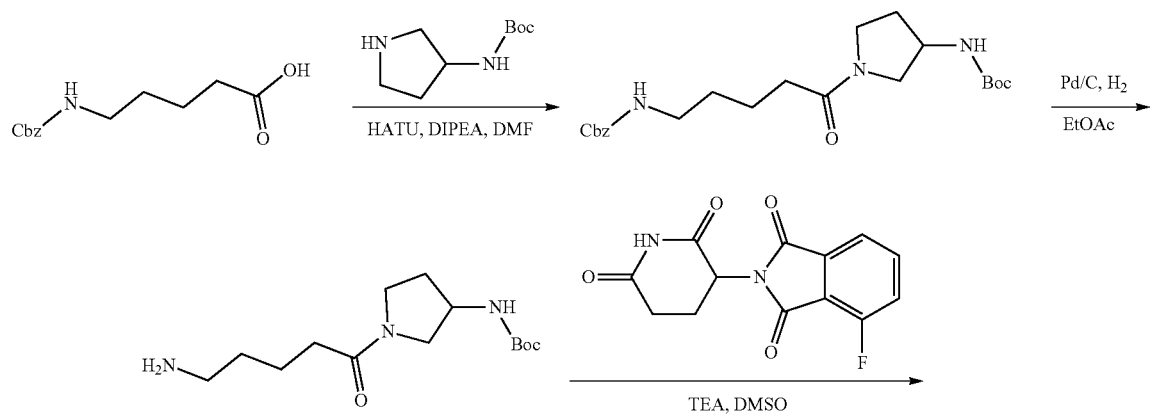

-continued

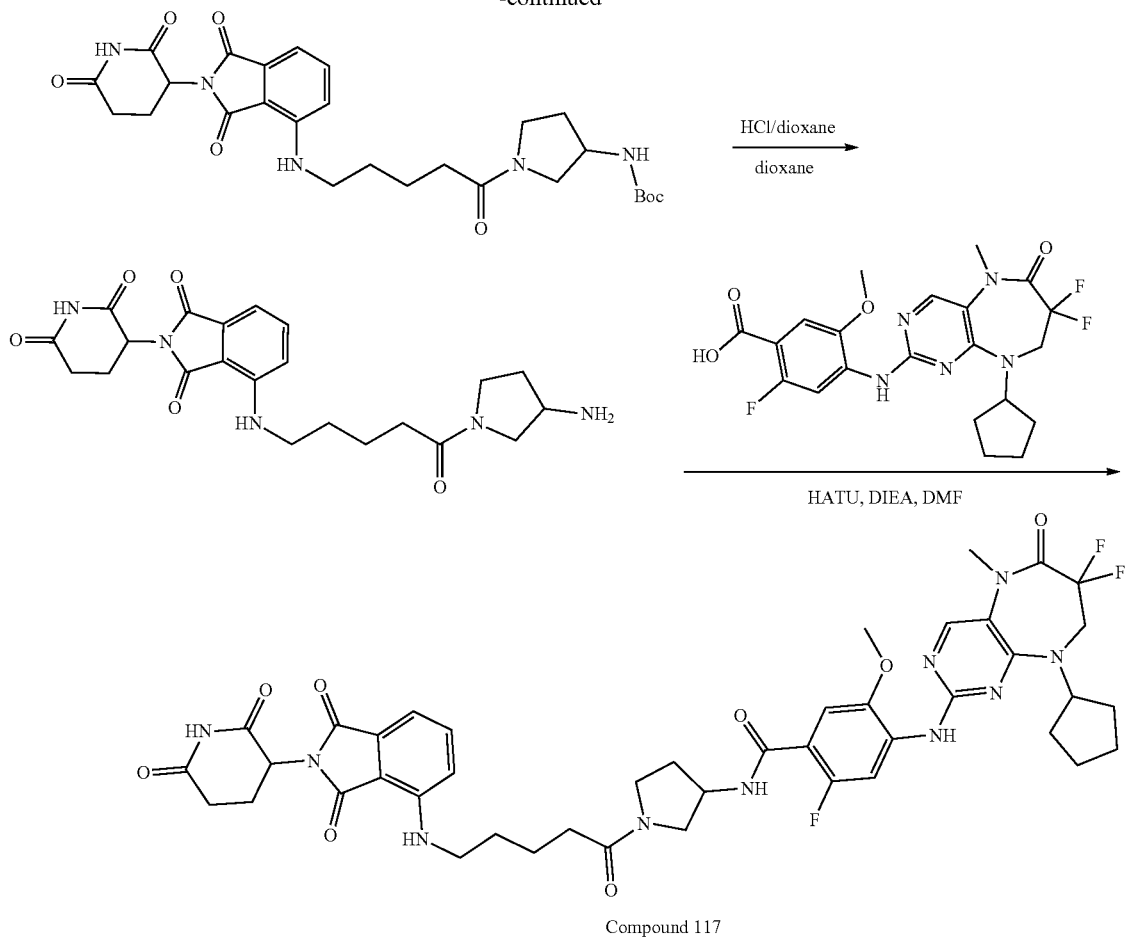

Compound 117

According to the above reaction scheme, in a manner similar to the other examples, obtained the titled compound (76 mg, 79.52 μmol, 19.00% yield, 93% purity) as yellow solid. MS(M+H)$^+$=889.3

$^1$H NMR (400 MHz, DMSO-d$_6$) δ=11.08 (s, 1H), 8.33-8.21 (m, 3H), 8.04 (s, 1H), 7.64-7.51 (m, 1H), 7.19 (d, J=6.6 Hz, 1H), 7.10 (dd, J=3.3, 8.6 Hz, 1H), 7.01 (dd, J=2.6, 7.0 Hz, 1H), 6.62-6.50 (m, 1H), 5.13-4.97 (m, 1H), 4.89-4.73 (m, 1H), 4.56-4.32 (m, 1H), 4.07 (t, J=13.8 Hz, 2H), 3.91 (s, 3H), 3.87-3.73 (m, 1H), 3.64-3.53 (m, 1H), 3.52-3.42 (m, 1H), 3.38-3.36 (m, 1H), 3.29-3.23 (m, 5H), 2.94-2.82 (m, 1H), 2.62-2.51 (m, 2H), 2.35-2.24 (m, 2H), 2.18-1.89 (m, 5H), 1.76-1.56 (m, 10H).

Example 118. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(6-((2-(2,6-dioxopiperidin-3-yl)-1,3-dioxoisoindolin-4-yl)amino)hexanoyl)pyrrolidin-3-yl)-2-fluoro-5-methoxybenzamide

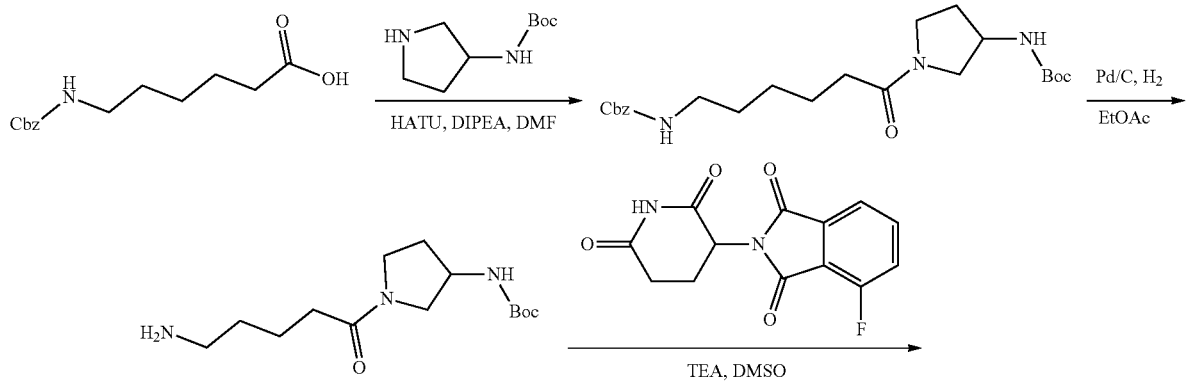

-continued

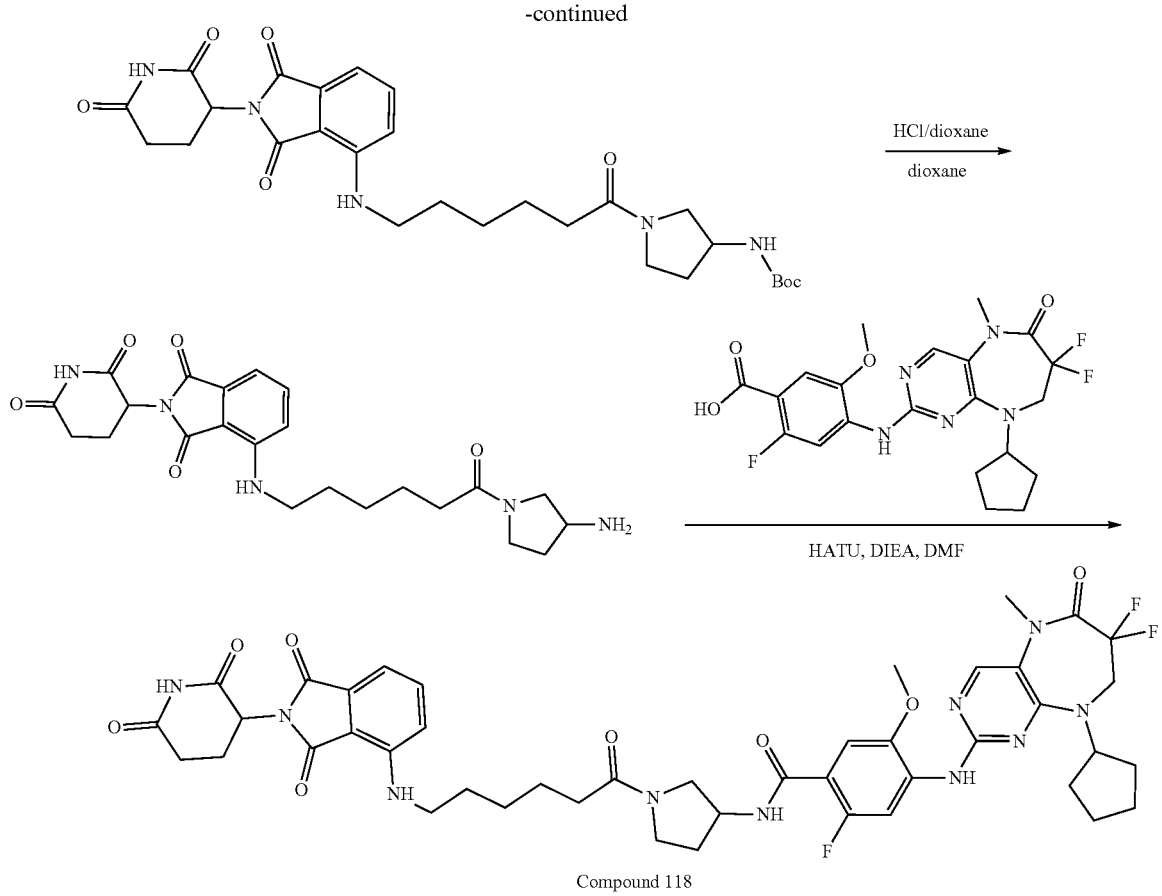

Compound 118

According to the above reaction scheme, in a manner similar to the other examples, obtained the titled compound (143.1 mg, 152.15 μmol, 37.43% yield, 96% purity) as yellow solid. MS(M+H)+=903.6

1H NMR (400 MHz, DMSO-d6) δ 11.10 (s, 1H), 8.35-8.20 (m, 3H), 8.05 (s, 1H), 7.61-7.53 (m, 1H), 7.19 (d, J=6.6 Hz, 1H), 7.08 (dd, J=8.7, 5.9 Hz, 1H), 7.01 (dd, J=7.1, 4.5 Hz, 1H), 6.58-6.50 (m, 1H), 5.10-4.99 (m, 1H), 4.89-4.76 (m, 1H), 4.52-4.32 (m, 0H), 4.07 (t, J=13.8 Hz, 2H), 3.91 (d, J=1.4 Hz, 3H), 3.80-3.53 (m, 1H), 3.53-3.40 (m, 1H), 3.31 (s, 3H), 3.29-3.28 (m, 1H), 2.96-2.82 (m, 0H), 2.71-2.52 (m, 1H), 2.29-2.18 (m, 2H), 2.11-1.85 (m, 4H), 1.78-1.68 (m, 2H), 1.67-1.49 (m, 8H), 1.41-1.30 (m, 2H).

Example 119. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-((3S)-1-(6-((2-(2,6-dioxopiperidin-3-yl)-1,3-dioxoisoindolin-4-yl)amino)hexanoyl)pyrrolidin-3-yl)-2-fluoro-5-methoxybenzamide

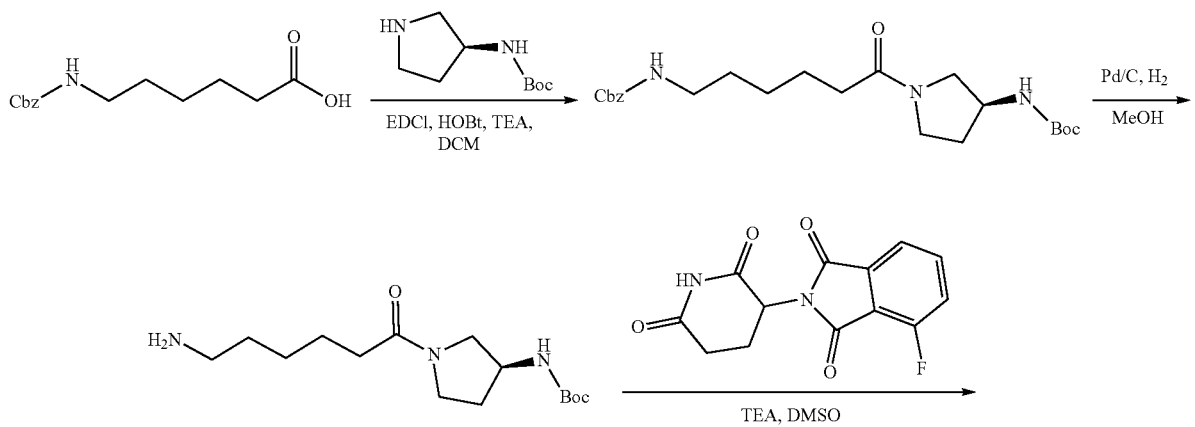

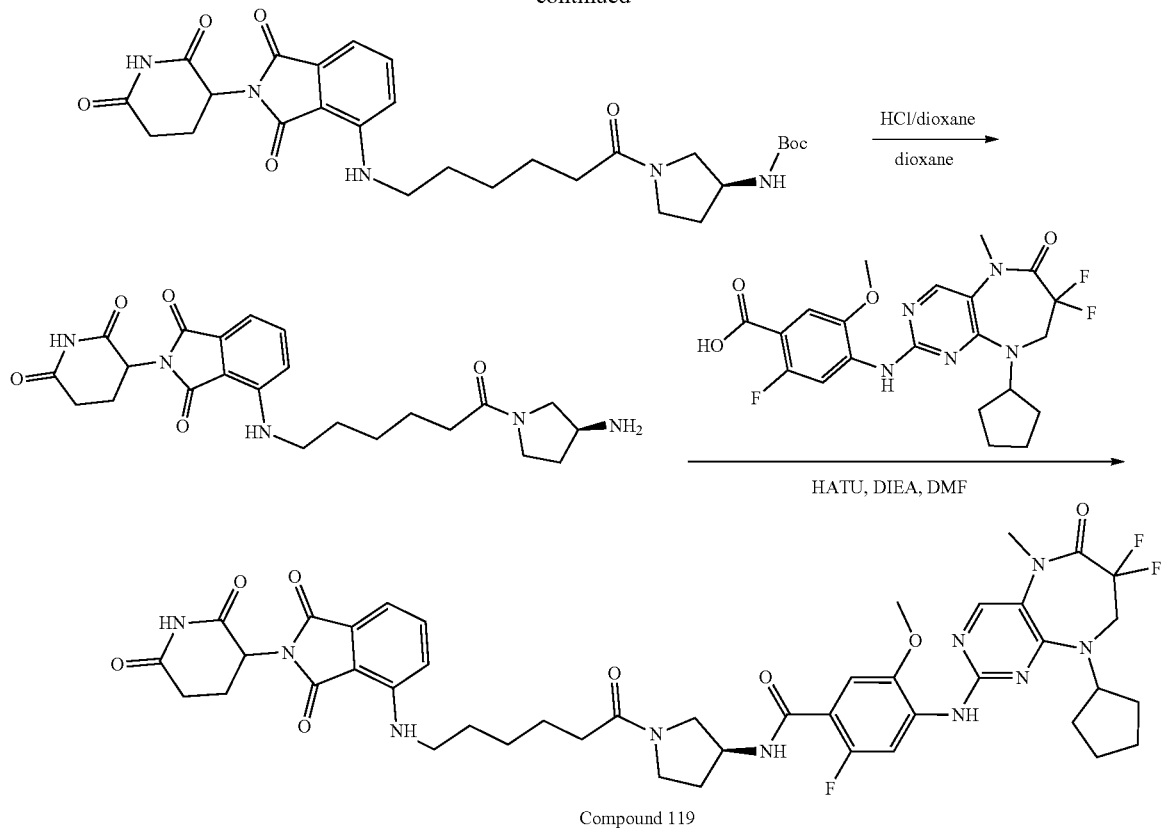

Compound 119

According to the above reaction scheme, in a manner similar to the other examples, obtained the titled compound (64 mg, 68.76 μmol, 26.67% yield, 97% purity) as a yellow solid. MS(M+H)$^+$=903.1

$^1$H NMR (400 MHz, DMSO-d$_6$) δ=11.09 (s, 1H), 8.32-8.20 (m, 3H), 8.04 (s, 1H), 7.63-7.50 (m, 1H), 7.19 (d, J=6.8 Hz, 1H), 7.08 (dd, J=5.8, 8.6 Hz, 1H), 7.01 (dd, J=4.4, 7.0 Hz, 1H), 6.53 (q, J=5.8 Hz, 1H), 5.08-5.01 (m, 1H), 4.86-4.76 (m, 1H), 4.52-4.35 (m, 1H), 4.07 (t, J=13.8 Hz, 2H), 3.91 (s, 3H), 3.79-3.36 (m, 3H), 3.31-3.22 (m, 3H), 2.94-2.82 (m, 1H), 2.63-2.51 (m, 4H), 2.30-1.77 (m, 8H), 1.76-1.68 (m, 2H), 1.65-1.50 (m, 8H), 1.43-1.31 (m, 2H)

Example 120. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-((3R)-1-(6-((2-(2,6-dioxopiperidin-3-yl)-1,3-dioxoisoindolin-4-yl)amino)hexanoyl)pyrrolidin-3-yl)-2-fluoro-5-methoxybenzamide

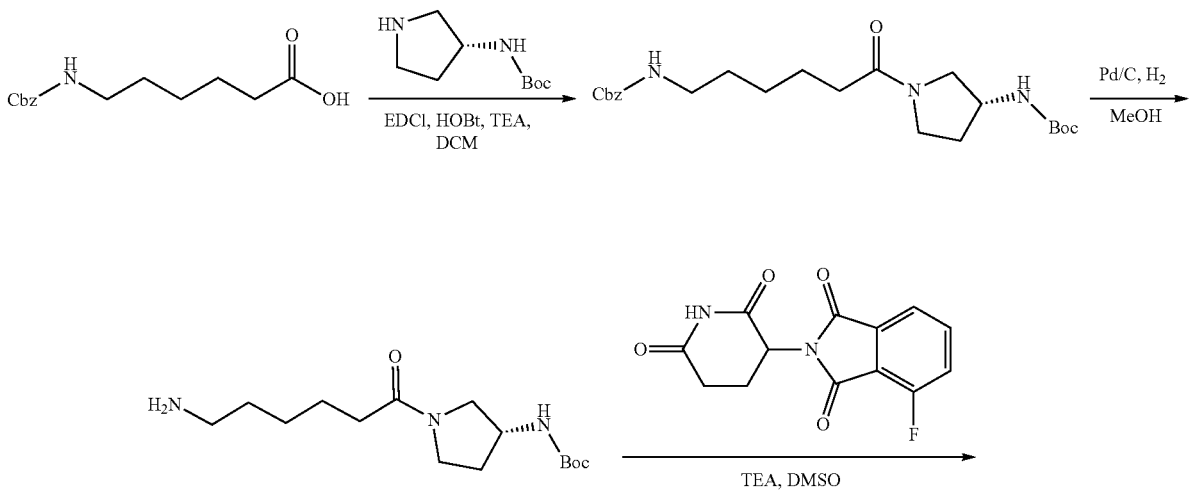

-continued

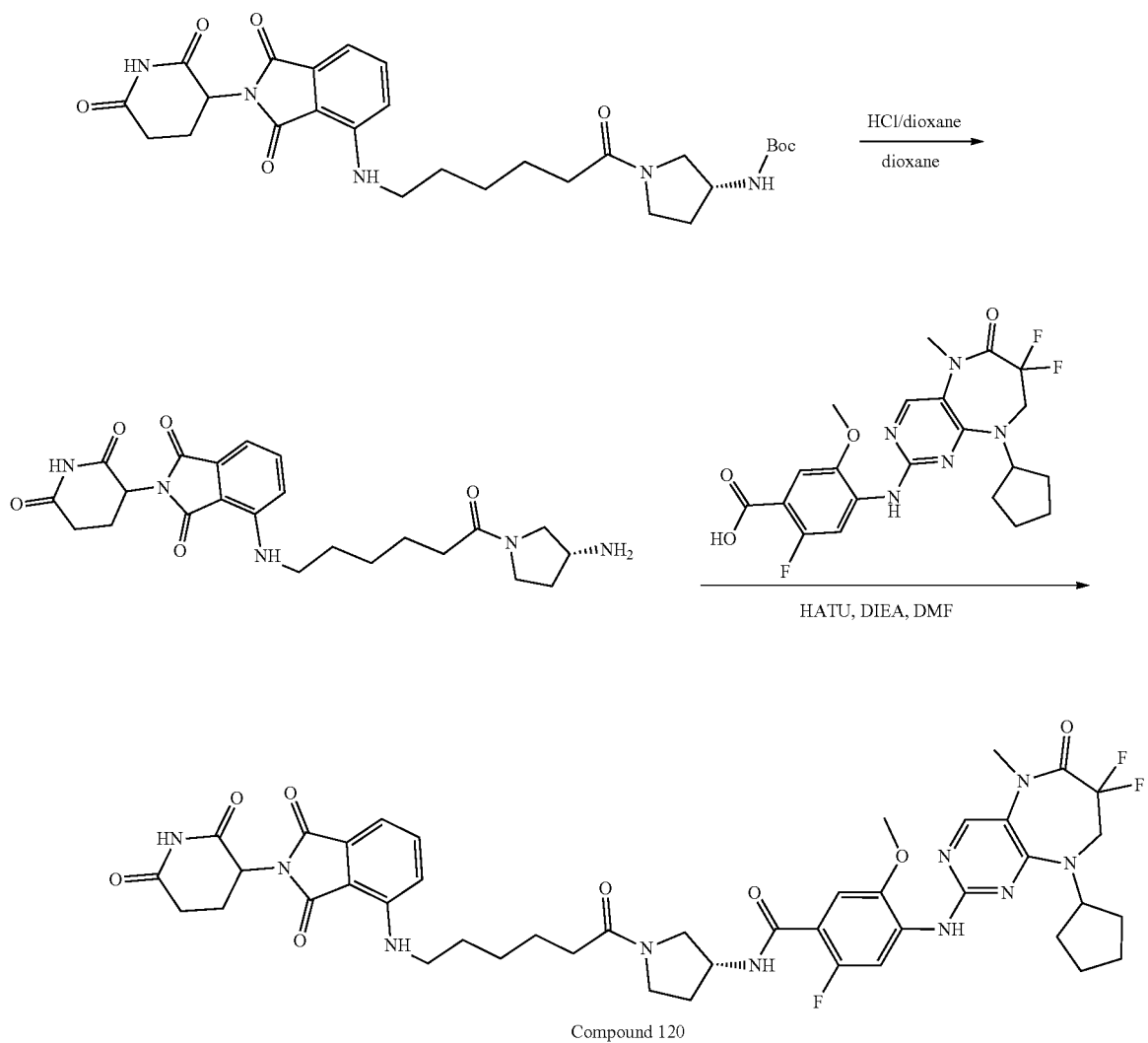

Compound 120

According to the above reaction scheme, in a manner similar to the other examples, obtained the titled compound (39.1 mg, 40.71 μmol, 12.63% yield, 94% purity) as a light yellow solid. MS(M+H)$^+$=903.7

$^1$H NMR (400 MHz, DMSO-d$_6$) δ 11.07 (br s, 1H), 8.31-8.23 (m, 3H), 8.04 (s, 1H), 7.61-7.54 (m, 1H), 7.20 (d, J=6.6 Hz, 1H), 7.09 (dd, J=5.8, 8.6 Hz, 1H), 7.01 (dd, J=4.4, 7.0 Hz, 1H), 6.58-6.50 (m, 1H), 5.03 (dd, J=5.1, 13.0 Hz, 1H), 4.87-4.76 (m, 1H), 4.52-4.36 (m, 1H), 4.08 (t, J=13.9 Hz, 2H), 3.92 (s, 3H), 3.77-3.51 (m, 2H), 3.49-3.41 (m, 1H), 3.34 (s, 3H), 2.93-2.78 (m, 1H), 2.65-2.55 (m, 4H), 2.29-1.91 (m, 8H), 1.80-1.70 (m, 2H), 1.69-1.54 (m, 8H), 1.42-1.33 (m, 2H)

Example 121. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-((3S)-1-(2-((2-(2-((2-(2,6-dioxopiperidin-3-yl)-1,3-dioxoisoindolin-4-yl)amino)ethoxy)ethyl)amino)-2-oxoethyl)pyrrolidin-3-yl)-2-fluoro-5-methoxybenzamide

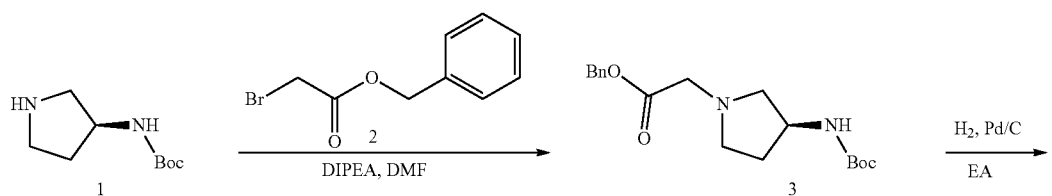

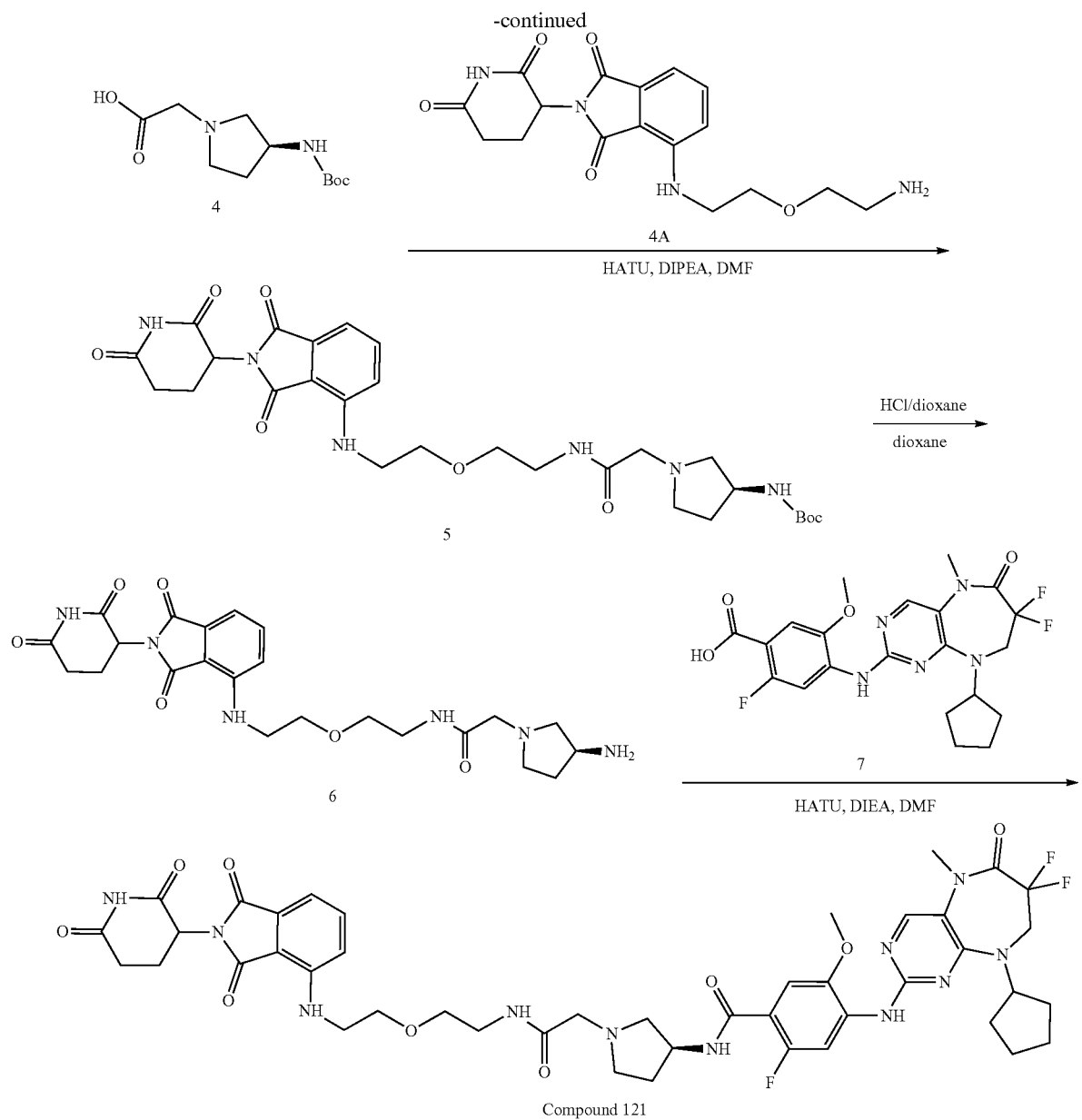

Step 1-4 are Described in the Above Reaction Scheme

Step 5: Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-((3S)-1-(2-((2-(2-((2-(2,6-dioxopiperidin-3-yl)-1,3-dioxoisoindolin-4-yl)amino)ethoxy)ethyl)amino)-2-oxoethyl)pyrrolidin-3-yl)-2-fluoro-5-methoxybenzamide (Compound 121)

To a solution of 4-[(9-cyclopentyl-7,7-difluoro-5-methyl-6-oxo-8H-pyrimido[4,5-b][1, 4]diazepin-2-yl) amino]-2-fluoro-5-methoxy-benzoic acid (177.99 mg, 382.42 mol) in DMF (3 mL) were added HATU (290.82 mg, 764.85 μmol) and DIPEA (197.70 mg, 1.53 mmol, 266.44 μL), the mixture was stirred at 25° C. for 10 min. Then 2-((S)-3-aminopyr-rolidin-1-yl)-N-(2-(2-((2-(2,6-dioxopiperidin-3-yl)-1,3-dioxoisoindolin-4-yl)amino)ethoxy)ethyl)acetamide (200 mg, 382.42 μmol, HCl salt) was added and the resulting mixture was stirred at 25° C. for another 1 h. LCMS showed a peak (55%) with desired mass. The mixture was purified by prep-HPLC (column: Waters Xbridge 150*25 mm*5 um; mobile phase: [water (10 mM $NH_4HCO_3$)-ACN]; B %: 38%-68%, 10 min) and prep-HPLC (column: Waters Xbridge 150*25 mm*5 um; mobile phase: [water (10 mM $NH_4HCO_3$)-ACN]; B %: 40%-70%, 10 min) to afford the titled compound (15.8 mg, 15.72 μmol, 36.70% yield, 92.920% purity) as yellow solid. MS(M+H)$^+$=934.3

$^1$H NMR (400 MHz, DMSO-$d_6$) δ=11.17-10.96 (m, 1H), 8.29 (s, 1H), 8.22 (d, J=13.4 Hz, 1H), 8.14 (br d, J=4.3 Hz, 1H), 8.00 (s, 1H), 7.81 (t, J=5.9 Hz, 1H), 7.58-7.48 (m, 1H), 7.19 (d, J=6.6 Hz, 1H), 7.10 (d, J=8.4 Hz, 1H), 7.00 (d, J=7.1 Hz, 1H), 6.62-6.50 (m, 1H), 5.09-4.96 (m, 1H), 4.85-4.77 (m, 1H), 4.52-4.33 (m, 1H), 4.12-4.03 (m, 2H), 3.90 (s, 3H), 3.61-3.56 (m, 2H), 3.50-3.41 (m, 4H), 3.30 (s, 3H), 3.12-2.99 (m, 2H), 2.94-2.68 (m, 4H), 2.47-2.43 (m, 5H), 2.22-2.11 (m, 1H), 2.04-1.93 (m, 3H), 1.71 (br d, J=6.8 Hz, 3H), 1.65-1.54 (m, 4H).

Example 122. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-((3S)-1-(2-((3-((2-(2,6-dioxopiperidin-3-yl)-1,3-dioxoisoindolin-4-yl)amino)propyl)amino)-2-oxoethyl)pyrrolidin-3-yl)-2-fluoro-5-methoxybenzamide
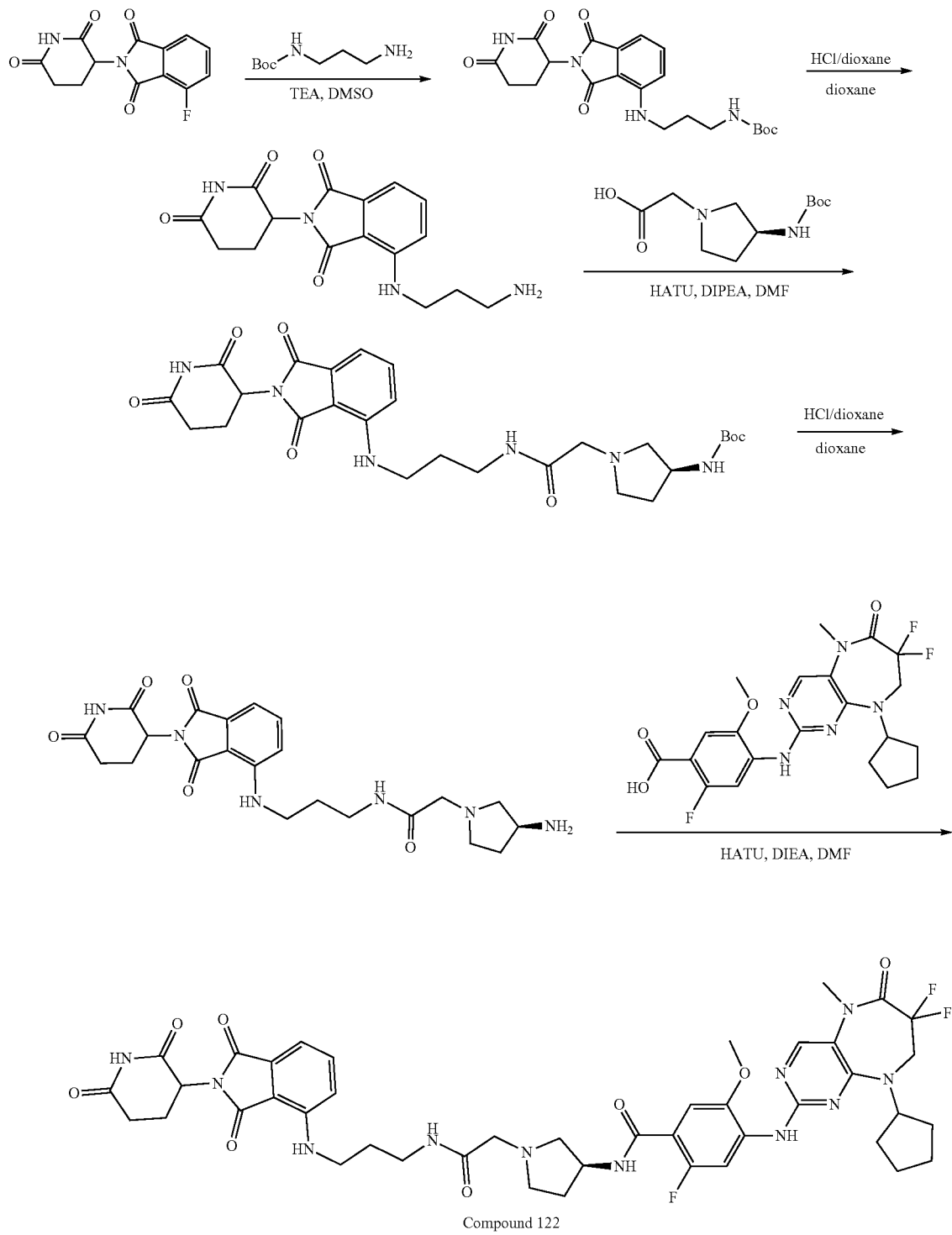
Compound 122

According to the above reaction scheme, in a manner similar to the other examples, obtained the titled compound (48 mg, 52.57 μmol, 27.83% yield, 99% purity) as yellow solid MS(M+H)+=904.9

$^1$H NMR (400 MHz, DMSO-$d_6$) δ=11.14 (br s, 1H), 8.33 (d, J=3.9 Hz, 1H), 8.29-8.22 (m, 2H), 8.13-8.00 (m, 2H), 7.60 (t, J=7.8 Hz, 1H), 7.24 (dd, J=0.9, 6.7 Hz, 1H), 7.10 (dd, J=2.3, 8.6 Hz, 1H), 7.02 (dd, J=3.9, 7.0 Hz, 1H), 6.79-6.71 (m, 1H), 5.15-5.05 (m, 1H), 4.91-4.76 (m, 1H), 4.55-4.44 (m, 1H), 4.13 (t, J=14.0 Hz, 2H), 3.96 (s, 3H), 3.39-3.37 (m, 3H), 3.34-3.26 (m, 3H), 3.25-3.16 (m, 2H), 3.10-3.03 (m, 1H), 3.00-2.90 (m, 1H), 2.88-2.80 (m, 2H), 2.69-2.62 (m, 3H), 2.30-2.21 (m, 1H), 2.10-1.99 (m, 3H), 1.83-1.62 (m, 10H).

Example 123. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(2-(2-(2-((2-(2,6-dioxopiperidin-3-yl)-1,3-dioxoisoindolin-4-yl)amino)ethoxy)ethoxy)ethyl)azetidin-3-yl)-2-fluoro-5-methoxybenzamide

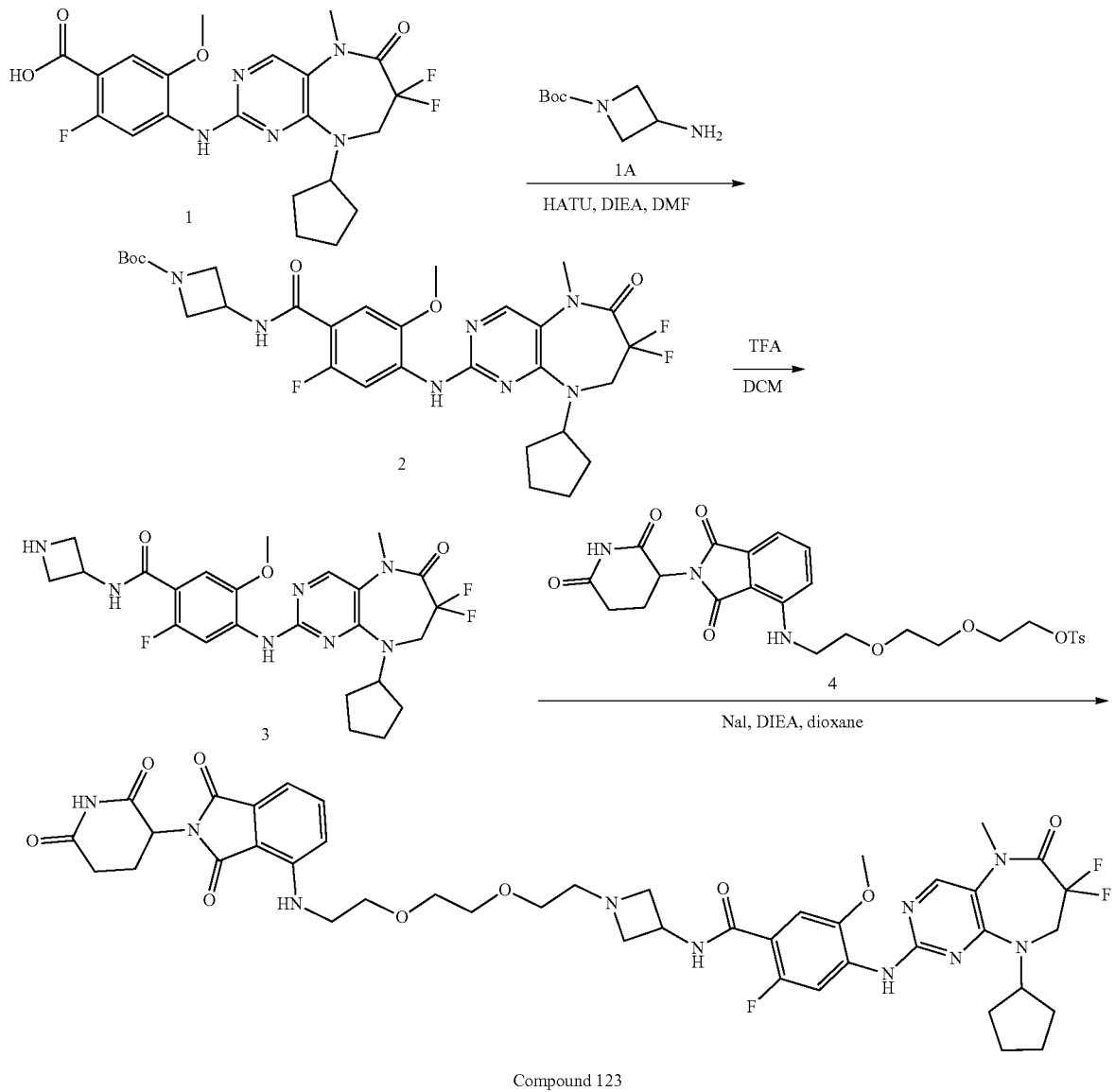

Compound 123

Step 1: Synthesis of tert-butyl 3-(4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzamido) azetidine-1-carboxylate (2)

To a solution of 4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzoic acid (300 mg, 644.57 mol) and tert-butyl 3-aminoazetidine-1-carboxylate (111.01 mg, 644.57 μmol) in DMF (3 mL) were added HATU (490.17 mg, 1.29 mmol) and DIPEA (333.22 mg, 2.58 mmol, 449.08 μL) and the resulting mixture was stirred at 20° C. for 1 h. LCMS showed that 76% desired mass was detected. The reaction mixture was diluted with H$_2$O (20 mL) and extracted with EtOAc (50 mL×3). The combined organic layers were washed with brine (80 mL), dried over Na$_2$SO$_4$, filtered. The filtrate was concentrated under reduced pressure. The residue was purified by flash silica gel chromatography (Biotage, 20 g SepaFlash® Silica Flash Column, Eluent of 30~100% Ethyl acetate/Petroleum ether gradient @ 60 mL/min) to afford the titled compound (360 mg, 580.99 mol, 90.14% yield) as a colorless oil. MS(M+H)$^+$=620.5

Step 2: Synthesis of N-(azetidin-3-yl)-4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzamide (3)

To a solution of tert-butyl 3-(4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzamido)azetidine-1-carboxylate (180 mg, 290.49 μmol) in DCM (2 mL) was added TFA (1.54 g, 13.51 mmol, 1 mL) and the resulting mixture was stirred at 20° C. for 1 h. LCMS showed a peak (97%) with desired mass. The mixture was concentrated. The residue were dissolved in dioxane (2 mL) and basic resin (200 mg) was added, the suspension was stirred for 1 h at 20° C., then filtered. The filtrate was used for next step directly. MS(M+H)$^+$=520.3

Step 3: Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(2-(2-(2-((2-(2,6-dioxopiperidin-3-yl)-1,3-dioxo isoindolin-4-yl)amino)ethoxy)ethoxy)ethyl)azetidin-3-yl)-2-fluoro-5-methoxybenzamide (Compound 123)

To the solution of N-(azetidin-3-yl)-4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzamide (150 mg, 288.73 umol) and 2-(2-(2-((2-(2,6-dioxopiperidin-3-yl)-1,3-dioxoisoindolin-4-yl)amino)ethoxy)ethoxy)ethyl 4-methylbenzenesulfonate (161.57 mg, 288.73 umol) in dioxane (3 mL) were added NaI (4.33 mg, 28.87 umol) and DIPEA (111.95 mg, 866.19 umol, 150.87 uL) and the resulting mixture was stirred at 60° C. for 12 hr. TLC (Petroleum ether:Ethyl acetate=10:1) showed that most of reactant was consumed and new spots were formed. The mixture was poured into water (20 mL) and extracted with EtOAc (20 mL×3). The combined organic layer was washed with brine (50 mL), dried over Na$_2$SO$_4$, filtered. The filtrate was concentrated. The residue was purified by pre-HPLC (column: Waters Xbridge C18 150*50 mm*10 um; mobile phase: [water (10 mM NH$_4$HCO$_3$)-ACN]; B %: 35%-65%, min) to afford the titled compound (7.8 mg, 7.81 umol, 3.54% yield, 90.8% purity) as a yellow solid. MS (M+H)$^+$=907.2

$^1$H NMR (400 MHz, DMSO-d$_6$) δ=11.23-10.96 (m, 1H), 8.41-8.36 (m, 1H), 8.32-8.23 (m, 2H), 8.13-7.95 (m, 1H), 7.60-7.55 (m, 1H), 7.21-7.13 (m, 2H), 7.03 (d, J=7.0 Hz, 1H), 6.66-6.56 (m, 1H), 5.08-5.02 (m, 1H), 4.87-4.79 (m, 1H), 4.45-4.38 (m, 1H), 4.11-4.04 (m, 2H), 3.91 (s, 3H), 3.66-3.59 (m, 3H), 3.57-3.46 (m, 10H), 3.38-3.37 (m, 2H), 3.34-3.33 (m, 3H), 3.02-2.95 (m, 2H), 2.92-2.83 (m, 1H), 2.09-1.83 (m, 4H), 1.74-1.57 (m, 6H).

Example 124. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-((1-(2-(2-((2-(2,6-dioxopiperidin-3-yl)-1,3-dioxoisoindolin-4-yl)amino)ethoxy)ethyl)pyrrolidin-2-yl)methyl)-2-fluoro-5-methoxybenzamide

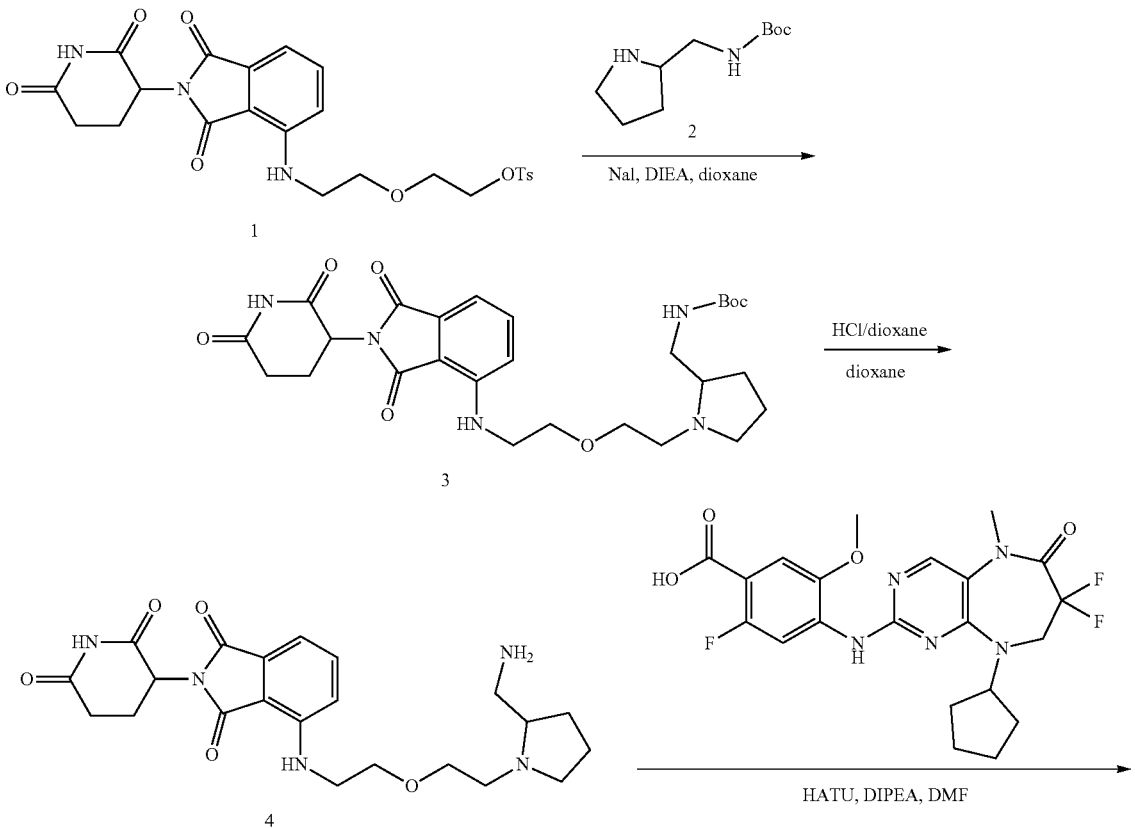

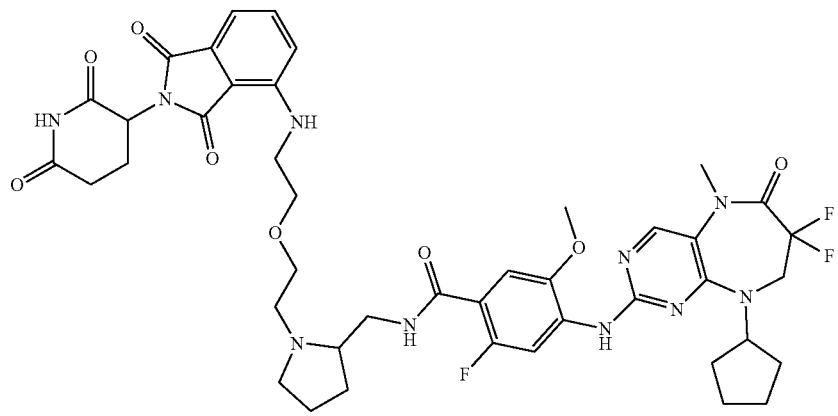

Compound 124

Step 1: Synthesis of tert-butyl N-[[1-[2-[2-[[2-(2,6-dioxo-3-piperidyl)-1,3-dioxo-isoindolin-4-yl]amino]ethoxy]ethyl]pyrrolidin-2-yl]methyl]carbamate (3)

To a solution of 2-(2-((2-((2-(2,6-dioxopiperidin-3-yl)-1,3-dioxoisoindolin-4-yl)amino)ethoxy)ethyl 4-methylbenzenesulfonate (400 mg, 775.89 μmol) and tert-butyl (pyrrolidin-2-ylmethyl) carbamate (155.39 mg, 775.89 μmol) in dioxane (5 mL) were added NaI (11.63 mg, 77.59 μmol) and DIEA (200.56 mg, 1.55 mmol, 270.29 μL), the mixture was heated at 80° C. for 12 h. LCMS showed the desired mass was detected. The mixture was concentrated in vacuo. The residue was purified by flash silica gel chromatography (Biotage, 12 g SepaFlash® Silica Flash Column, Eluent of 30-100% Ethyl acetate/Petroleum ether gradient @ 60 mL/min) to afford the titled compound (337 mg, 607.53 μmol, 78.30% yield, 98% purity) as yellow solid. MS (M+H)$^+$=544.2

Step 2: Synthesis of 4-((2-(2-(2-(aminomethyl)pyrrolidin-1-yl)ethoxy)ethyl)amino)-2-(2,6-dioxopiperidin-3-yl)isoindoline-1,3-dione (4)

To a solution of tert-butyl ((1-(2-(2-((2-(2,6-dioxopiperidin-3-yl)-1,3-dioxoisoindolin-4-yl)amino) ethoxy)ethyl) pyrrolidin-2-yl)methyl)carbamate (337 mg, 619.93 μmol) in dioxane (4 mL) was added HCl/dioxane (4 M, 2 mL) and the mixture was stirred at 25° C. for 30 min. LCMS showed the desired mass detected. The mixture was concentrated in vacuo to afford the titled compound (450 mg, crude, HCl salt) as a yellow solid. Ms(M+H)$^+$=444.1

Step 3: Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-((1-(2-(2-((2-(2,6-dioxopiperidin-3-yl)-1,3-dioxoisoindolin-4-yl) amino)ethoxy)ethyl)pyrrolidin-2-yl)methyl)-2-fluoro-5-methoxybenzamide (Compound 124)

To a solution of 4-((2-(2-(2-(aminomethyl)pyrrolidin-1-yl)ethoxy)ethyl)amino)-2-(2,6-dioxopiperidin-3-yl)isoindoline-1,3-dione (150 mg, 312.53 μmol, HCl salt) and 4-((9-cyclopentyl-7,7-difluoro-5-methyl-6-oxo-6,7,8,9-tetrahydro-5H-pyrimido[4,5-b][1,4]diazepin-2-yl) amino)-2-fluoro-5-methoxybenzoic acid (121.22 mg, 260.44 μmol) in DMF (5 mL) were added HATU (198.05 mg, 520.88 μmol) and DIEA (100.98 mg, 781.32 μmol, 136.09 μL), the mixture was stirred at 25° C. for 12 h. LCMS showed the desired mass was detected. The reaction mixture was concentrated in vacuo. The residue was purified by prep-HPLC (column: Phenomenex luna C$_{18}$ 150*40 mm*15 um; mobile phase: [water (0.225% FA)-ACN]; B %: 20%-50%, 10 min) to afford the titled compound (128.4 mg, 138.93 μmol, 53.35% yield, 96.4% purity) as a yellow solid. MS (M+H)$^+$=891.3

$^1$H NMR (400 MHz, DMSO-d$_6$) δ=11.09 (s, 1H), 8.29 (s, 1H), 8.25 (d, J=13.9 Hz, 1H), 8.16-8.03 (m, 2H), 7.54 (t, J=7.8 Hz, 1H), 7.29 (d, J=6.8 Hz, 1H), 7.15-7.10 (m, 1H), 7.02-6.98 (m, 1H), 6.64-6.56 (m, 1H), 5.06-5.00 (m, 1H), 4.84-4.76 (m, 1H), 4.08 (t, J=13.8 Hz, 2H), 3.89 (d, J=1.3 Hz, 3H), 3.81-3.61 (m, 6H), 3.58-3.47 (m, 6H), 3.34 (s, 3H), 2.95-2.81 (m, 2H), 2.57 (d, J=18.7 Hz, 2H), 2.06-1.92 (m, 5H), 1.74-1.72 (m, 4H), 1.67-1.59 (m, 4H).

Example 125. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-((1-(2-(2-((2-(2,6-dioxopiperidin-3-yl)-1,3-dioxoisoindolin-4-yl)amino)ethoxy)ethyl)piperidin-3-yl)methyl)-2-fluoro-5-methoxybenzamide

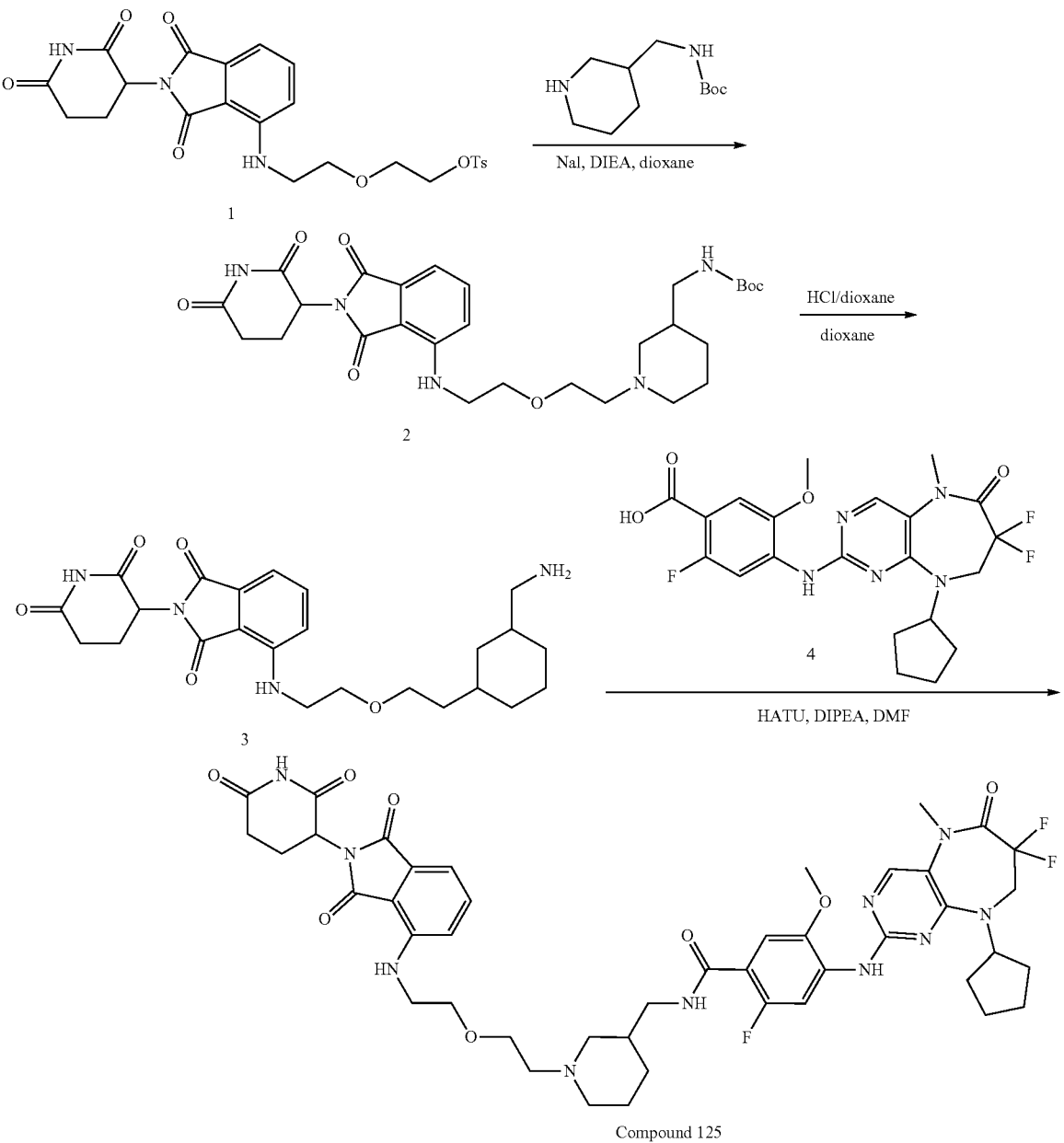

Step 1: Synthesis of tert-butyl ((1-(2-(2-((2-(2,6-dioxopiperidin-3-yl)-1,3-dioxoisoindolin-4-yl)amino) ethoxyl)ethyl)piperidin-3-yl)methyl)carbamate (2)

To a solution of 2-(2-((2-(2,6-dioxopiperidin-3-yl)-1,3-dioxoisoindolin-4-yl)amino)ethoxy)ethyl 4-methylbenzenesulfonate (400 mg, 775.89 µmol) and tert-butyl (piperidin-3-ylmethyl)carbamate (332.55 mg, 1.55 mmol) in dioxane (5 mL) were added NaI (11.63 mg, 77.59 µmol) and DIPEA (200.56 mg, 1.55 mmol, 270.29 µL), the mixture was heated at 80° C. for 12 h. LCMS showed the desired mass was detected. The mixture was concentrated in vacuo. The residue was purified by flash silica gel chromatography (Biotage, 12 g SepaFlash® Silica Flash Column, Eluent of 10~20% EtOAc/MeOH gradient @ 60 mL/min) to afford the titled compound (613 mg, crude) as a yellow solid. MS(M+H)$^+$=558.2

Step 2: Synthesis of 4-((2-(2-(3-(aminomethyl)piperidin-1-yl)ethoxy)ethyl)amino)-2-(2,6-dioxopiperidin-3-yl)isoindoline-1,3-dione (3)

A solution of tert-butyl ((1-(2-(2-((2-(2,6-dioxopiperidin-3-yl)-1,3-dioxoisoindolin-4-yl)amino) ethoxy)ethyl)piperidin-3-yl)methyl)carbamate (613 mg, 1.10 mmol) and HCl/dioxane (4 M, 4 mL) in dioxane (2 mL) was stirred at 25° C. for 12 h. LCMS showed the desired mass was detected. The mixture was concentrated in vacuo to afford the titled compound (540 mg, crude, HCl salt) as a yellow solid. MS(M+H)$^+$=458.1

Step 3: Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-((1-(2-(2-((2-(2,6-dioxopiperidin-3-yl)-1,3-dioxoisoindolin-4-yl)amino)ethoxy)ethyl)piperidin-3-yl)methyl)-2-fluoro-5-methoxybenzamide (Compound 125) (4)

To a solution of 4-((2-(2-(3-(aminomethyl) piperidin-1-yl)ethoxy)ethyl)amino)-2-(2,6-dioxopiperidin-3-yl) isoindoline-1,3-dione (150 mg, 303.65 μmol, HCl salt) and 4-((9-cyclopentyl-7,7-difluoro-5-methyl-6-oxo-6,7,8,9-tetrahydro-5H-pyrimido[4,5-b][1,4]diazepin-2-yl) amino)-2-fluoro-5-methoxybenzoic acid (117.77 mg, 253.05 μmol) in DMF (3 mL) were added HATU (192.43 mg, 506.09 μmol) and DIEA (98.11 mg, 759.14 μmol, 132.22 μL), the mixture was stirred at 25° C. for 12 h. LCMS showed the desired mass was detected. The mixture was concentrated in vacuo. The residue was purified by prep-HPLC (column: Shim-pack C$_{18}$ 150*25*10 um; mobile phase: [water (0.225% FA)-ACN]; B %: 27%-51%, 12 min). Compound 4-((9-cyclopentyl-7,7-difluoro-5-methyl-6-oxo-6,7,8,9-tetrahydro-5H-pyrimido[4,5-b][1,4]diazepin-2-yl)amino)-N-((1-(2-(2-((2-(2,6-dioxopiperidin-3-yl)-1,3-dioxoisoindolin-4-yl)amino)ethoxy)ethyl)piperidin-3-yl)methyl)-2-fluoro-5-methoxybenzamide (82.6 mg, 88.54 μmol, 34.99% yield, 97% purity) was obtained as a yellow solid. MS(M+H)$^+$=905.3

$^1$H NMR (400 MHz, DMSO-d$_6$) δ=11.09 (s, 1H), 8.29 (s, 1H), 8.23 (d, J=13.6 Hz, 1H), 8.17-8.09 (m, 1H), 8.03 (s, 1H), 7.55 (t, J=7.6 Hz, 1H), 7.24 (d, J=6.8 Hz, 1H), 7.10 (d, J=8.5 Hz, 1H), 7.01 (d, J=6.9 Hz, 1H), 6.58 (t, J=6.0 Hz, 1H), 5.12-4.98 (m, 1H), 4.86-4.75 (m, 1H), 4.13-4.03 (m, 2H), 3.90 (s, 3H), 3.80-3.69 (m, 2H), 3.63 (t, J=4.5 Hz, 2H), 3.50-3.35 (m, 12H), 2.98-2.81 (m, 2H), 2.63-2.54 (m, 3H), 2.08-1.87 (m, 4H), 1.85-1.48 (m, 9H).

Example 126. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-((1-(2-(2-((2-(2,6-dioxopiperidin-3-yl)-1,3-dioxoisoindolin-4-yl)amino)ethoxy)ethyl)piperidin-2-yl)methyl)-2-fluoro-5-methoxybenzamide

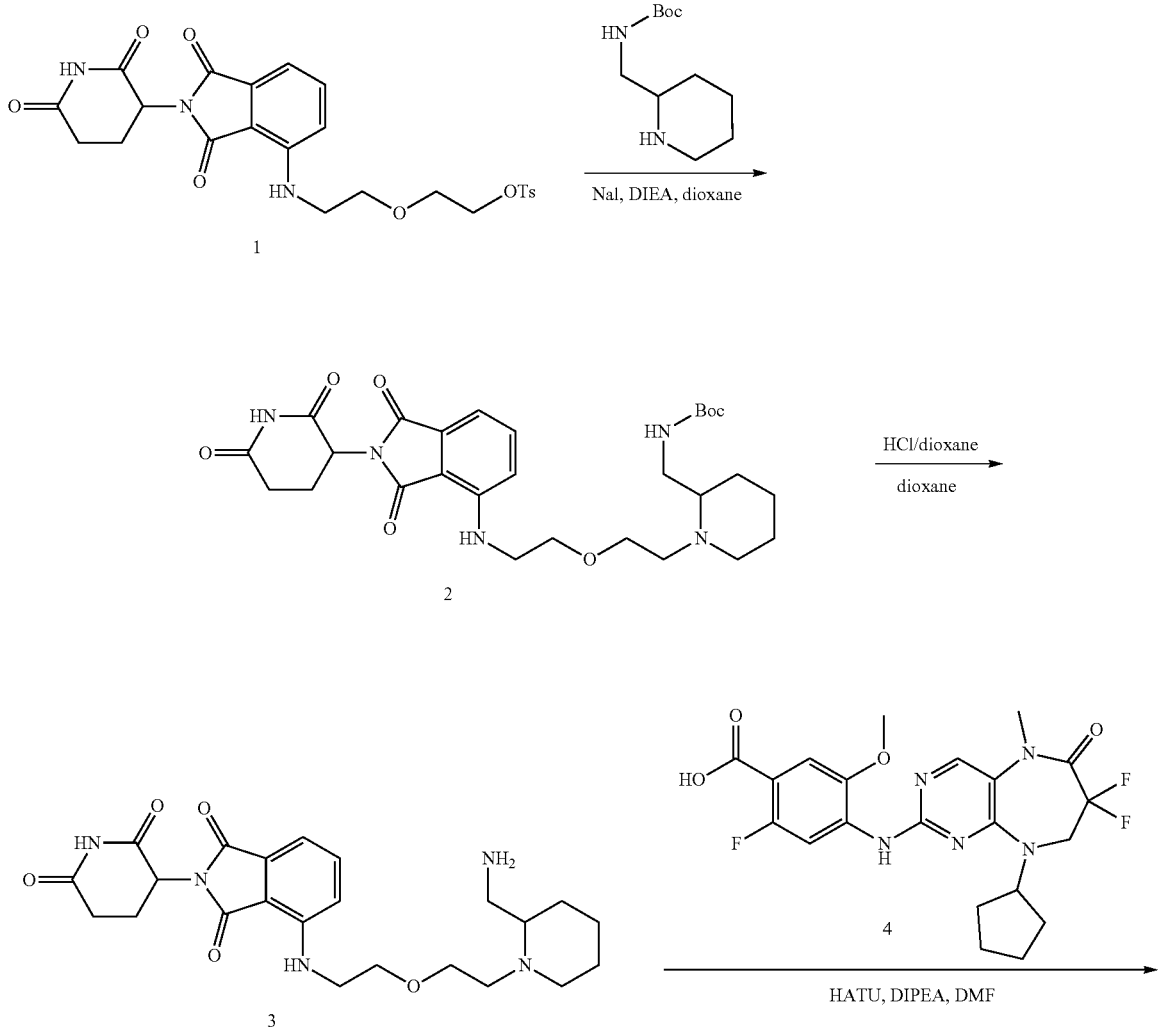

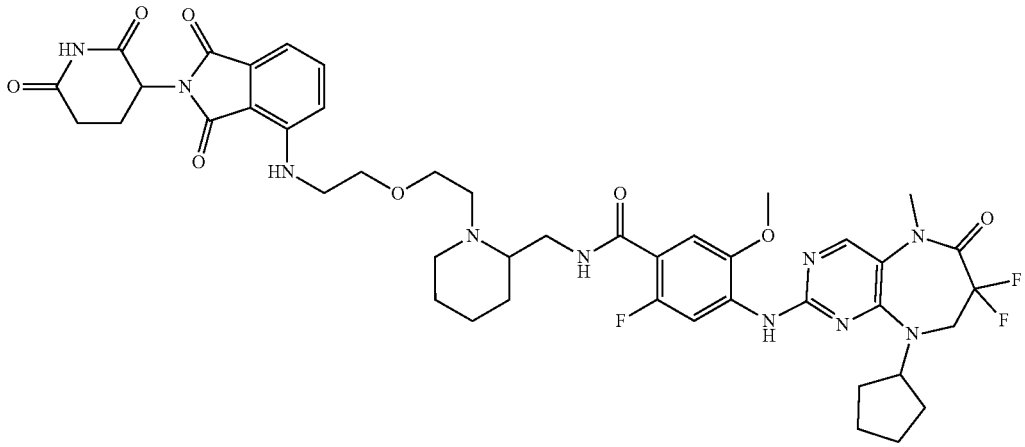

Compound 126

Step 1: Synthesis of tert-butyl ((1-(2-(2-((2-(2,6-dioxopiperidin-3-yl)-1,3-dioxoisoindolin-4-yl) amino) ethoxy) ethyl)piperidin-2-yl)methyl)carbamate (2)

To a solution of 2-(2-((2-(2,6-dioxopiperidin-3-yl)-1,3-dioxoisoindolin-4-yl)amino)ethoxy)ethyl 4-methylbenzenesulfonate (400 mg, 775.89 µmol), tert-butyl (piperidin-2-ylmethyl)carbamate (166.28 mg, 775.89 µmol) in dioxane (5 mL) were added NaI (11.63 mg, 77.59 µmol) and DIPEA (200.56 mg, 1.55 mmol, 270.29 µL), the mixture was heated at 80° C. for 12 h. LCMS showed reactant remained, additional tert-butyl (piperidin-2-ylmethyl)carbamate (332.56 mg, 1.55 mmol) was added and the resulting mixture was heated at 80° C. for another 12 h. LCMS showed the desired mass was detected. The mixture was concentrated in vacuo. The residue was purified by flash silica gel chromatography (Biotage, 12 g SepaFlash® Silica Flash Column, Eluent of EtOAc/MeOH=10:1 gradient @ 60 mL/min) to afford the titled compound (268 mg, 478.68 µmol, 61.69% yield, 99.6% purity) as a yellow solid. MS(M+H)$^+$=558.1

Step 2: Synthesis of 4-((2-(2-(2-(aminomethyl)piperidin-1-yl)ethoxy)ethyl)amino)-2-(2,6-dioxopiperidin-3-yl)isoindoline-1,3-dione (3)

A solution of tert-butyl ((1-(2-(2-((2-(2,6-dioxopiperidin-3-yl)-1,3-dioxoisoindolin-4-yl)amino) ethoxy) ethyl)piperidin-2-yl)methyl)carbamate (268 mg, 480.60 µmol) and HCl/dioxane (4 M, 2 mL) in dioxane (2 mL) was stirred at 25° C. for 12 h. LCMS showed the desired mass was detected. The mixture was concentrated in vacuo to afford the titled compound (235 mg, crude, HCl salt) as a yellow solid. MS (M+H)$^+$=458.2

Step 3: Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-((1-(2-(2-((2-(2,6-dioxopiperidin-3-yl)-1,3-dioxoisoindolin-4-yl) amino)ethoxy)ethyl)piperidin-2-yl)methyl)-2-fluoro-5-methoxybenzamide (Compound 126) (4)

To a solution of 4-((2-(2-(2-(aminomethyl)piperidin-1-yl) ethoxy)ethyl)amino)-2-(2,6-dioxopiperidin-3-yl)isoindoline-1,3-dione (150 mg, 303.65 µmol, HCl salt) and 4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzoic acid (117.77 mg, 253.05 µmol) in DMF (3 mL) were added HATU (192.43 mg, 506.09 µmol) and DIEA (98.11 mg, 759.14 µmol, 132.23 µL), the mixture was stirred at 25° C. for 12 h. LCMS showed the desired mass was detected. The mixture was concentrated in vacuo. The residue was purified by prep-HPLC (column: Unisil 3-100 C$_{1-8}$ µLtra 150*50 mm*3 um; mobile phase: [water (0.225% FA)-ACN]; B %: 30%-50%, 10 min) and the eluent was freeze dried. The residue was diluted with H$_2$O (3 mL), then basified with NaHCO$_3$ (2 mL), then extracted with EtOAc (15 mL×2). The combined organic layer was dried over Na$_2$SO$_4$, filtered. The filtrate was concentrated under reduced pressure to afford the titled compound (90.9 mg, 98.34 µmol, 90.81% yield, 97.9% purity) as a yellow solid. Ms (M+H)$^+$=905.4

$^1$H NMR (400 MHz, DMSO-d$_6$) δ=11.21-11.01 (m, 1H), 8.29 (s, 1H), 8.24-8.13 (m, 1H), 8.01 (s, 1H), 7.73 (s, 1H), 7.52-7.42 (m, 1H), 7.25 (d, J=7.0 Hz, 1H), 7.08-7.02 (m, 1H), 7.01-6.89 (m, 1H), 6.63-6.48 (m, 1H), 5.07-4.99 (m, 1H), 4.84-4.75 (m, 1H), 4.12-4.03 (m, 2H), 3.88 (s, 3H), 3.61-3.56 (m, 3H), 3.54-3.48 (m, 2H), 3.30-3.50 (m, 4H), 2.96-2.80 (m, 4H), 2.31-2.25 (m, 1H), 2.05-1.89 (m, 4H), 1.75-1.43 (m, 11H), 1.40-1.18 (m, 5H).

Example 127. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(2-(2-(2-((2-(2,6-dioxopiperidin-3-yl)-1,3-dioxoisoindolin-4-yl)oxy)acetamido)ethoxy)ethyl)pyrrolidin-3-yl)-2-fluoro-5-methoxybenzamide
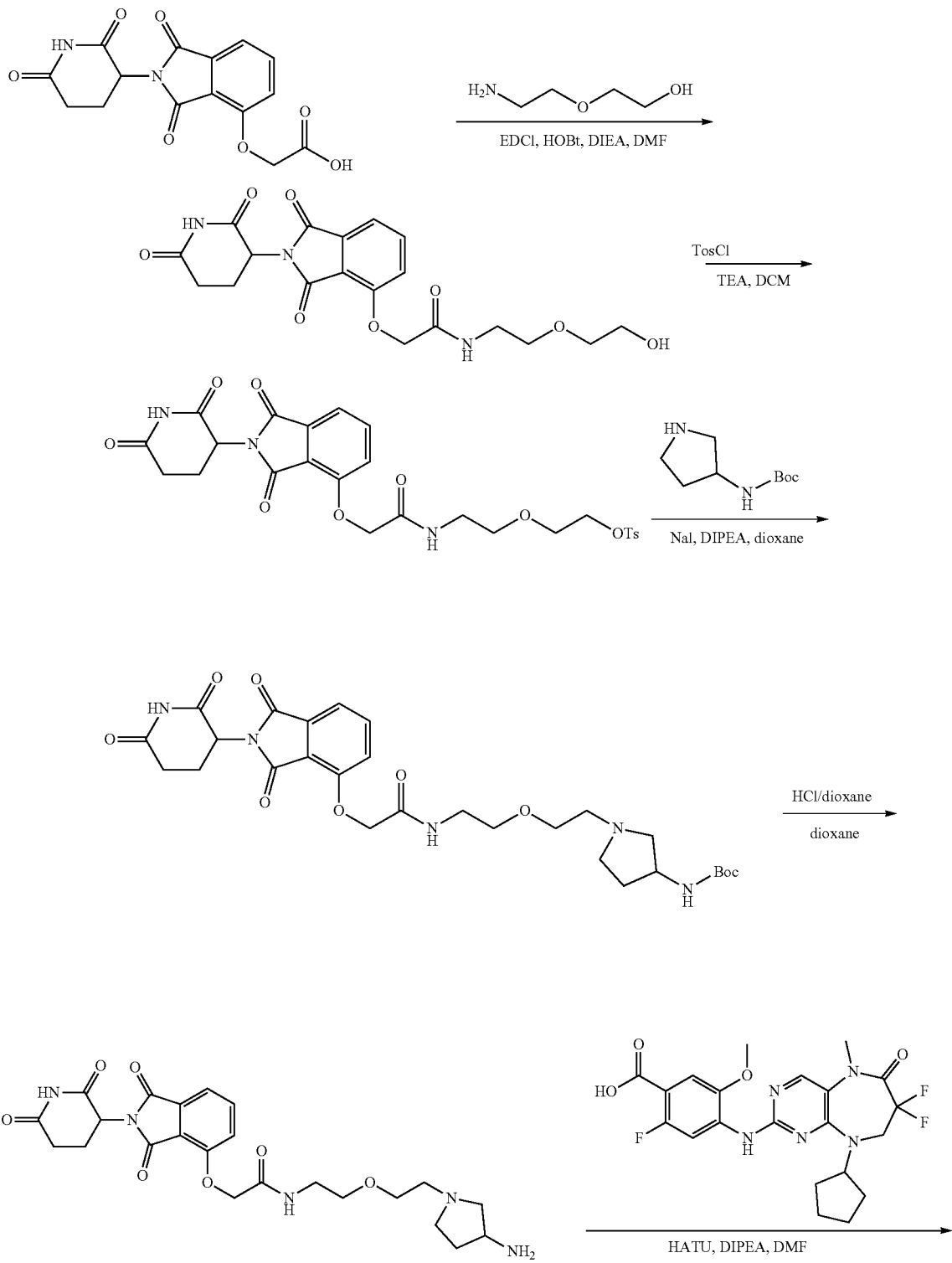

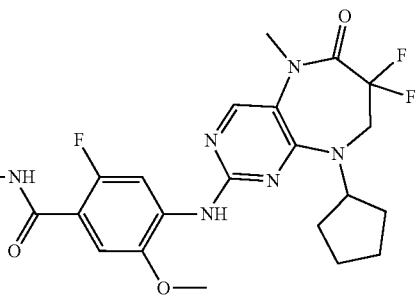

Compound 127

According to the above reaction scheme, in a manner similar to the other examples, obtained the titled compound (10.1 mg, 10.06 umol, 6.54% yield, 93.1% purity) as a white solid. MS(M+H)$^+$=935.3

$^1$H NMR (400 MHz, DMSO-d$_6$) δ=11.13 (s, 1H), 9.74-9.45 (m, 1H), 8.32-8.25 (m, 2H), 8.08 (s, 1H), 8.00 (s, 1H), 7.79 (s, 1H), 7.53-7.46 (m, 1H), 7.43-7.36 (m, 1H), 7.25 (d, J=2.4 Hz, 1H), 5.15-5.09 (m, 1H), 4.88-4.76 (m, 3H), 4.67-4.54 (m, 1H), 4.09 (t, J=13.9 Hz, 2H), 3.91 (s, 3H), 3.72 (s, 2H), 3.56 (d, J=5.4 Hz, 2H), 3.50-3.30 (m, 3H), 2.95-2.86 (m, 1H), 2.65-2.53 (m, 10H), 2.14-1.89 (m, 5H), 1.77-1.70 (m, 2H), 1.68-1.58 (m, 4H).

Example 128. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(3-(4-(2-(2,6-dioxopiperidin-3-yl)-1,3-dioxoisoindolin-4-yl)piperazin-1-yl)propanoyl)piperidin-4-yl)-3-methoxybenzamide

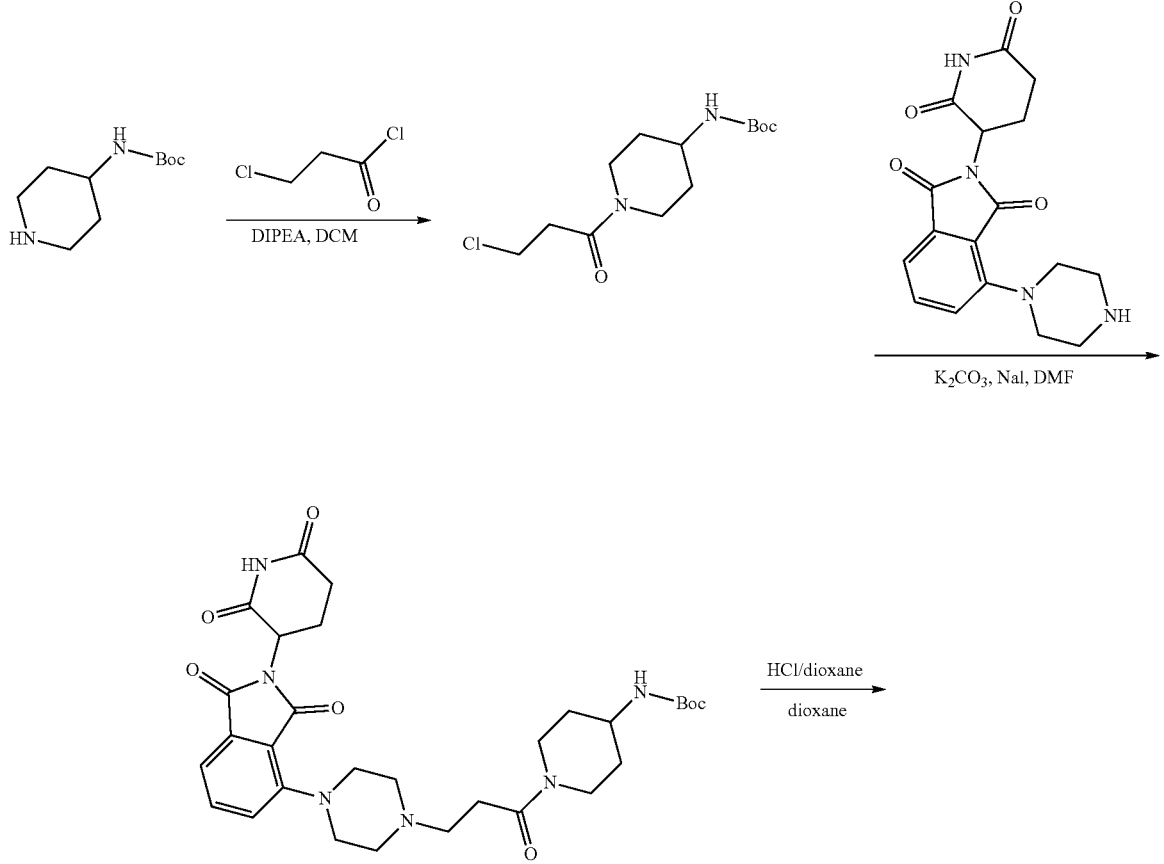

-continued

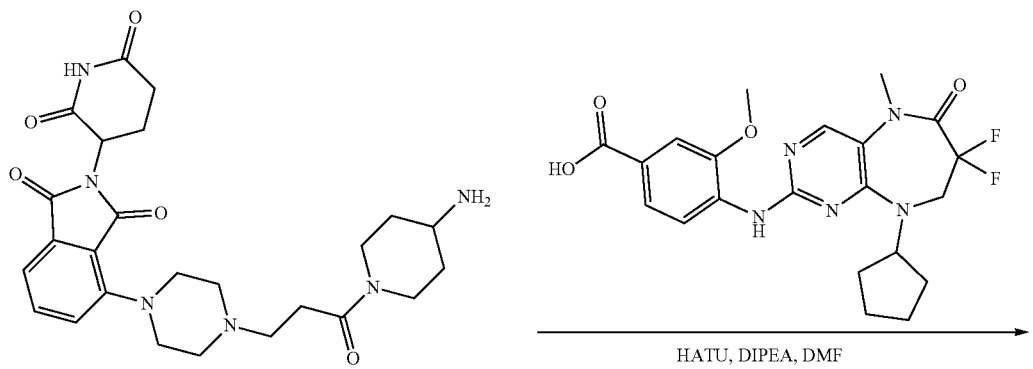

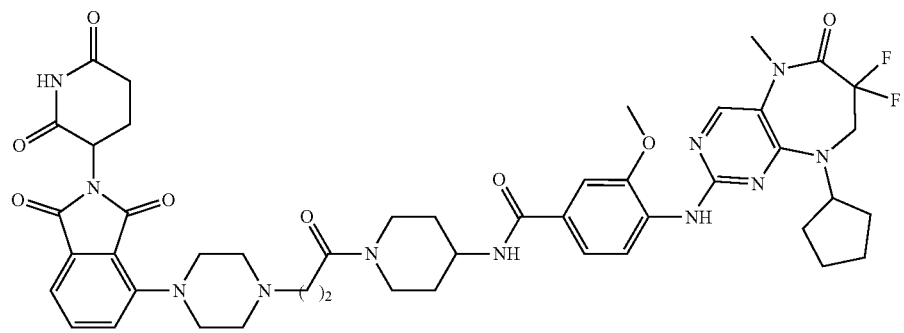

Compound 128

According to the above reaction scheme, in a manner similar to the other examples, obtained the titled compound (13.2 mg, 13.69 μmol, 9.42% yield, 96% purity) as a yellow solid. MS(M+H)$^+$=926.4

$^1$H NMR (400 MHz, CDCl$_3$) δ=8.48 (d, J=8.5 Hz, 1H), 8.37 (br d, J=10.4 Hz, 1H), 8.06 (s, 1H), 7.77 (s, 1H), 7.64 (dd, J=7.4, 8.3 Hz, 1H), 7.50-7.41 (m, 2H), 7.29 (br d, J=1.8 Hz, 1H), 7.18 (d, J=8.3 Hz, 1H), 6.14 (br d, J=8.0 Hz, 1H), 4.97 (dd, J=5.3, 12.2 Hz, 1H), 4.82 (quin, J=8.4 Hz, 1H), 4.62 (br d, J=13.8 Hz, 1H), 4.33-4.15 (m, 1H), 3.99 (s, 3H), 3.94-3.86 (m, 3H), 3.55 (br s, 4H), 3.41 (s, 3H), 3.26-3.18 (m, 2H), 3.14 (br s, 3H), 2.97-2.86 (m, 2H), 2.84-2.77 (m, 3H), 2.26-1.97 (m, 6H), 1.87-1.30 (m, 10H).

Example 129. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(3-(4-(2-(2,6-dioxopiperidin-3-yl)-1,3-dioxoisoindolin-4-yl)piperazin-1-yl)propanoyl)piperidin-4-yl) benzamide

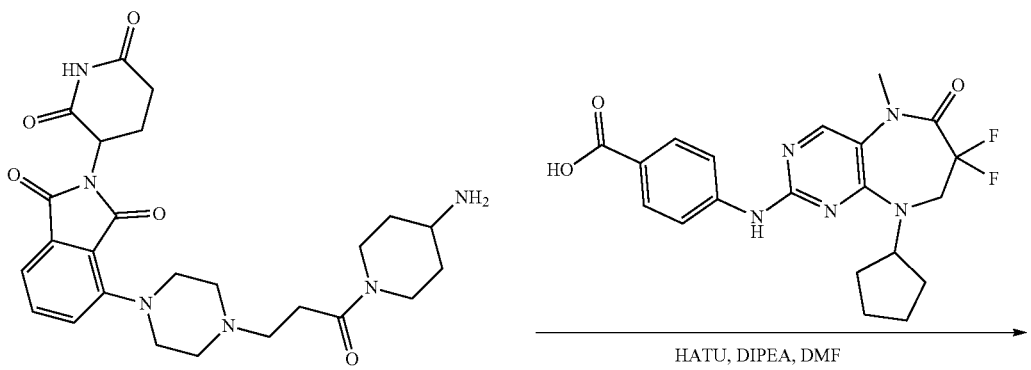

-continued

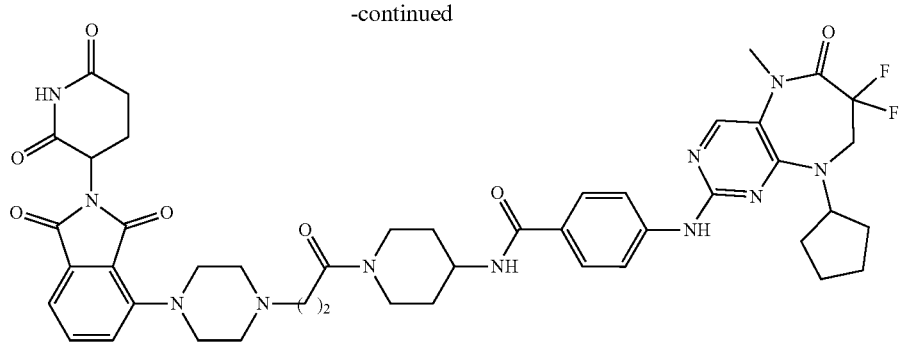

Compound 129

According to the above reaction scheme, in a manner similar to the other examples, obtained the titled compound (16.8 mg, 17.06 μmol, 11.87% yield, 97% purity) as a yellow solid. MS(M+H)+=896.1

¹H NMR (400 MHz, CDCl₃) δ=9.45 (br d, J=7.0 Hz, 1H), 8.06 (s, 1H), 7.77-7.71 (m, 2H), 7.70-7.64 (m, 3H), 7.60 (dd, J=7.3, 8.3 Hz, 1H), 7.41 (d, J=7.0 Hz, 1H), 7.17 (d, J=8.4 Hz, 1H), 6.14 (br dd, J=7.8, 16.3 Hz, 1H), 4.97 (dd, J=5.4, 12.3 Hz, 1H), 4.83 (quin, J=8.3 Hz, 1H), 4.63 (br d, J=13.0 Hz, 1H), 4.29-4.15 (m, 1H), 3.89 (br t, J=13.3 Hz, 3H), 3.40 (s, 3H), 3.37 (br d, J=4.6 Hz, 3H), 3.21 (br t, J=12.4 Hz, 1H), 2.93-2.80 (m, 4H), 2.72 (br s, 4H), 2.64-2.55 (m, 2H), 2.27-1.95 (m, 6H), 1.80-1.39 (m, 10H).

Example 130. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-((3S)-1-(2-(4-(2-(2,6-dioxopiperidin-3-yl)-1,3-dioxo isoindolin-4-yl)piperazin-1-yl)acetyl)pyrrolidin-3-yl)-2-fluoro-5-methoxybenzamide

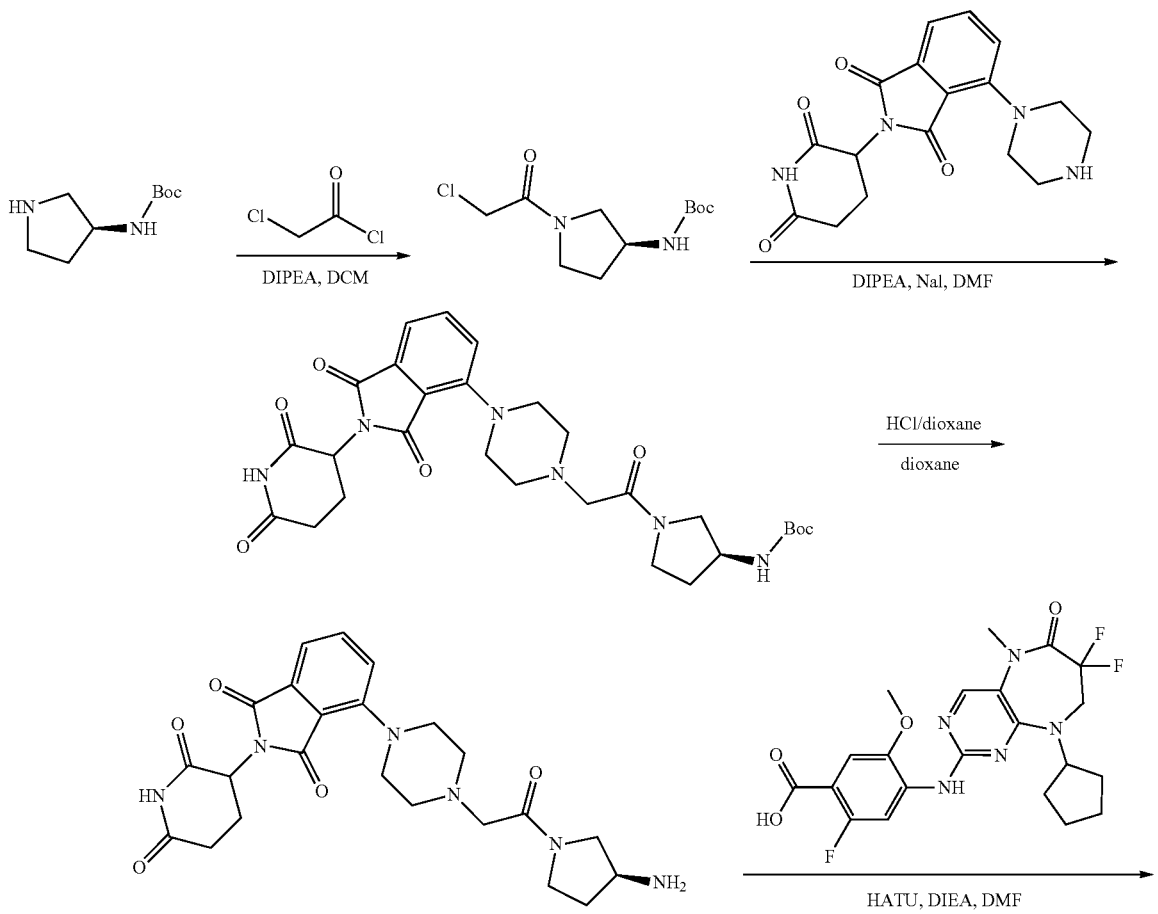

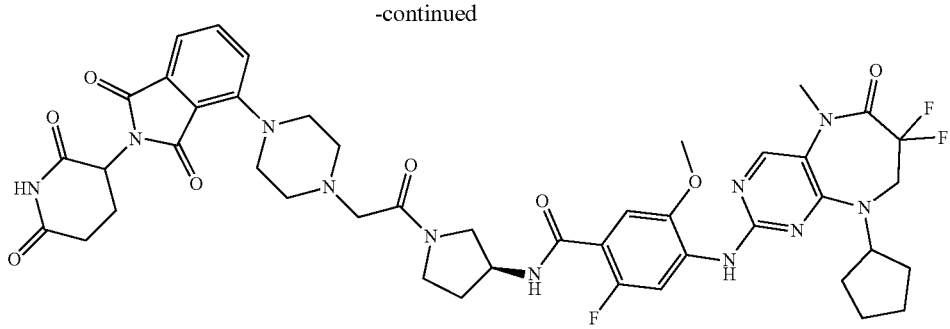

Compound 130

According to the above reaction scheme, in a manner similar to the other examples, obtained the titled compound (22.8 mg, 23.90 μmol, 11.12% yield, 96% purity) as a light yellow solid. MS(M+H)$^+$=916.6

$^1$H NMR (400 MHz, DMSO-d$_6$) δ 11.08 (br s, 1H), 8.32-8.23 (m, 3H), 8.05 (s, 1H), 7.72-7.64 (m, 1H), 7.37-7.27 (m, 2H), 7.21 (d, J=6.7 Hz, 1H), 5.11-5.08 (m, 1H), 4.86-4.78 (mz, 1H), 4.53-4.39 (m, 1H), 4.08 (t, J=13.9 Hz, 2H), 3.91 (d, J=7.3 Hz, 3H), 3.85-3.60 (m, 2H), 3.57-3.43 (m, 2H), 3.32 (s, 3H), 3.28-3.26 (m, 2H), 3.21-3.15 (m, 2H), 2.93-2.82 (m, 1H), 2.70-2.59 (m, 6H), 2.23-2.03 (m, 2H), 2.02-1.82 (m, 4H), 1.79-1.54 (m, 7H).

Example 131. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-((3S)-1-(3-(4-(2-(2,6-dioxopiperidin-3-yl)-1,3-dioxo isoindolin-4-yl)piperazin-1-yl)propanoyl)pyrrolidin-3-yl)-2-fluoro-5-methoxybenzamide

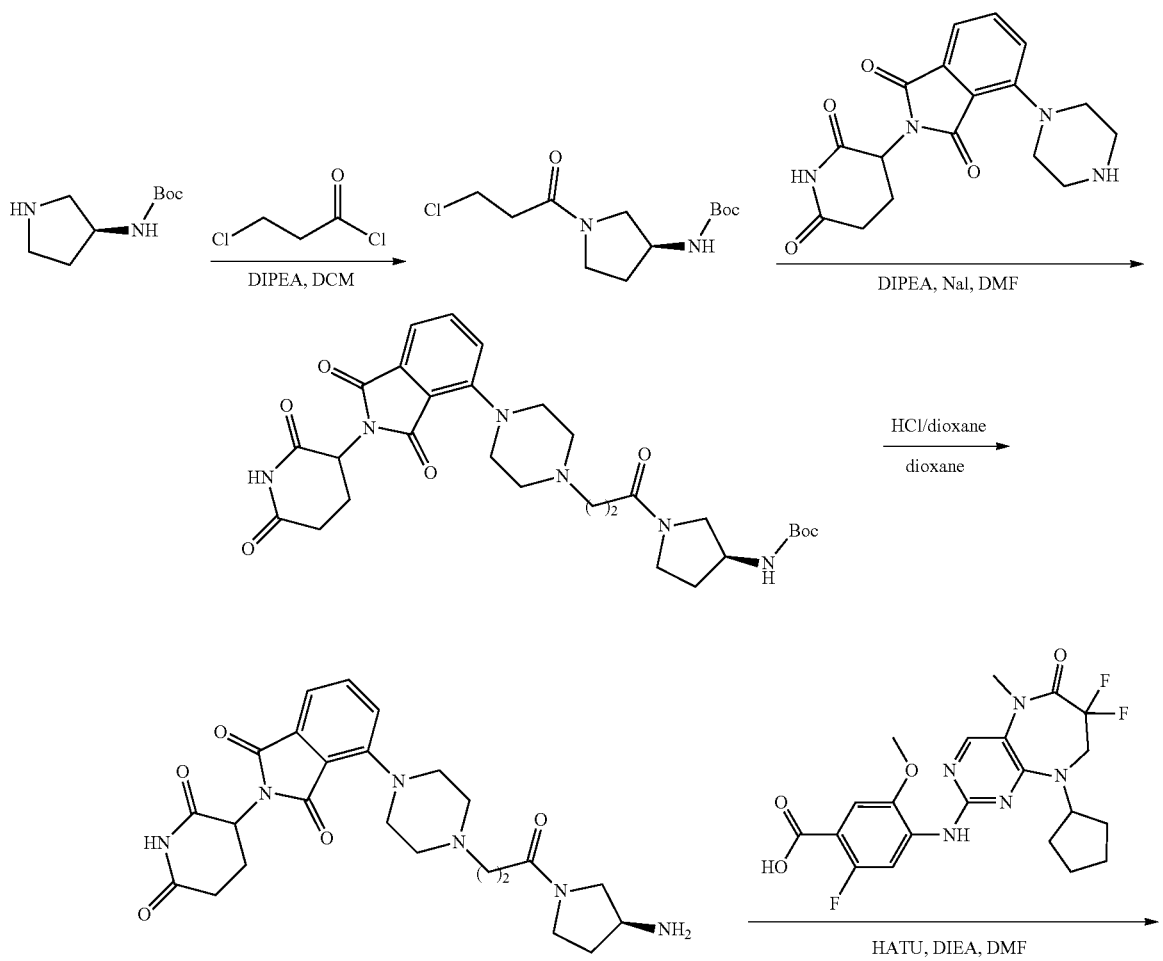

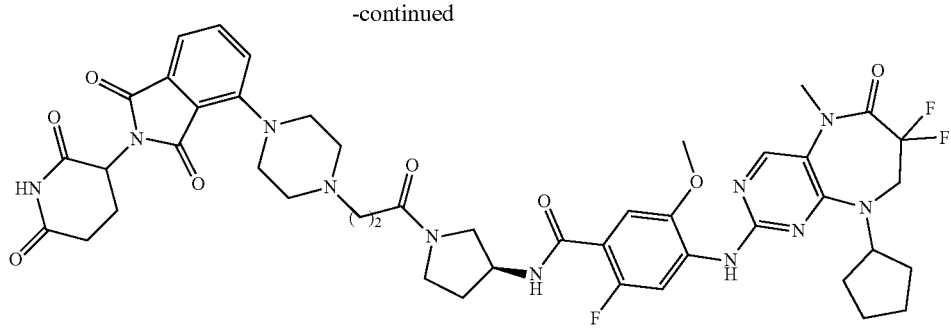

Compound 131

According to the above reaction scheme, in a manner similar to the other examples, obtained the titled compound (70.4 mg, 69.65 μmol, 21.61% yield, 92% purity) as a light yellow solid. MS(M+H)$^+$=930.6

$^1$H NMR (400 MHz, DMSO-d$_6$) δ 11.08 (br s, 1H), 8.32-8.22 (m, 3H), 8.04 (s, 1H), 7.72-7.64 (m, 1H), 7.37-7.27 (m, 2H), 7.21 (d, J=6.7 Hz, 1H), 5.16-5.05 (m, 1H), 4.87-4.78 (m, 1H), 4.54-4.40 (m, 1H), 4.08 (t, J=13.9 Hz, 2H), 3.92 (d, J=2.9 Hz, 3H), 3.83-3.56 (m, 2H), 3.55-3.4 (m, 2H), 3.34 (s, 3H), 3.29-3.27 (m, 4H), 2.94-2.82 (m, 1H), 2.64-2.56 (m, 8H), 2.25-2.03 (m, 2H), 2.03-1.84 (m, 4H), 1.78-1.41 (m, 7H).

Example 132. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-((3R)-1-(3-(4-(2-(2,6-dioxopiperidin-3-yl)-1,3-dioxoisoindolin-4-yl)piperazin-1-yl)propanoyl)pyrrolidin-3-yl)-2-fluoro-5-methoxybenzamide

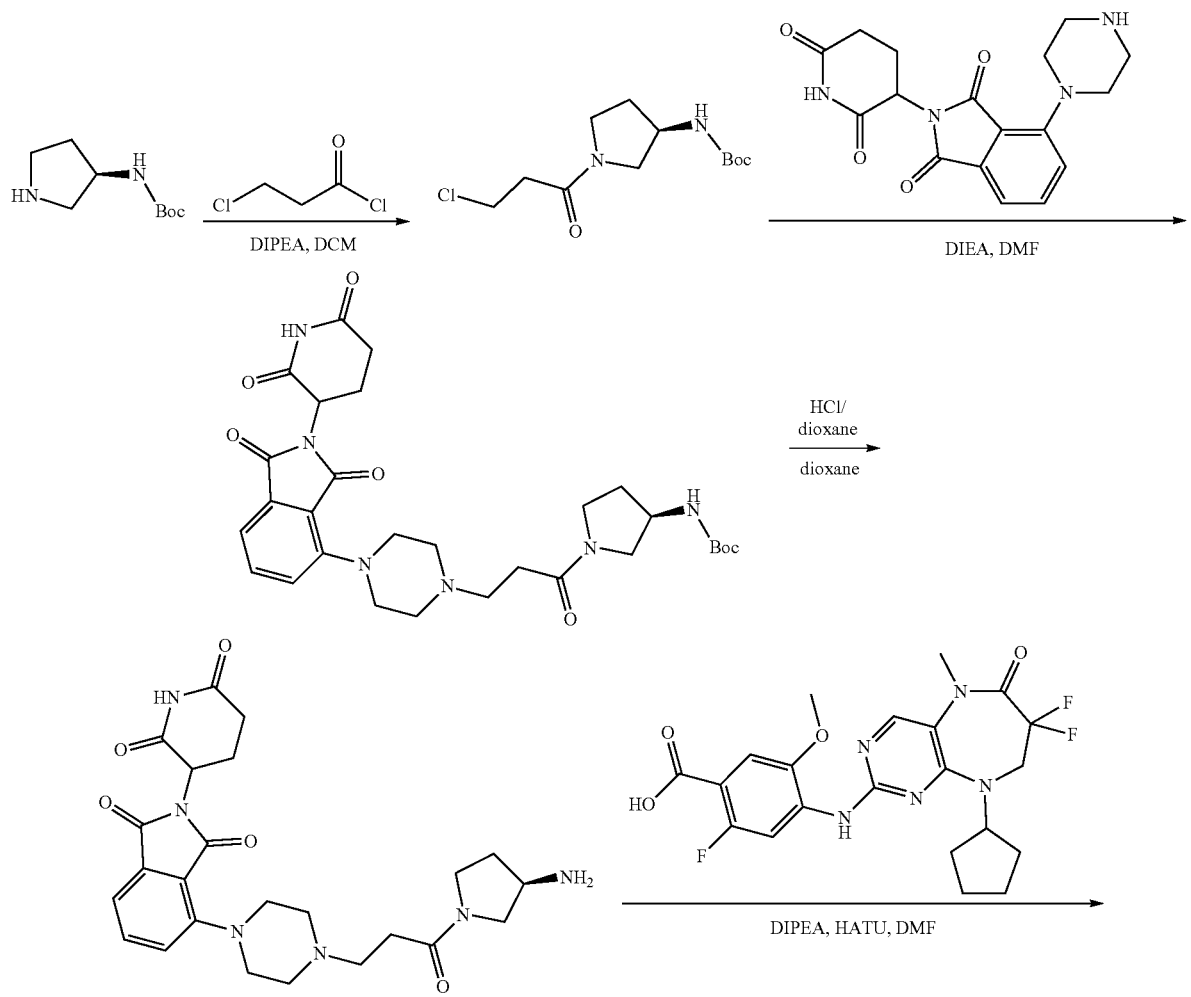

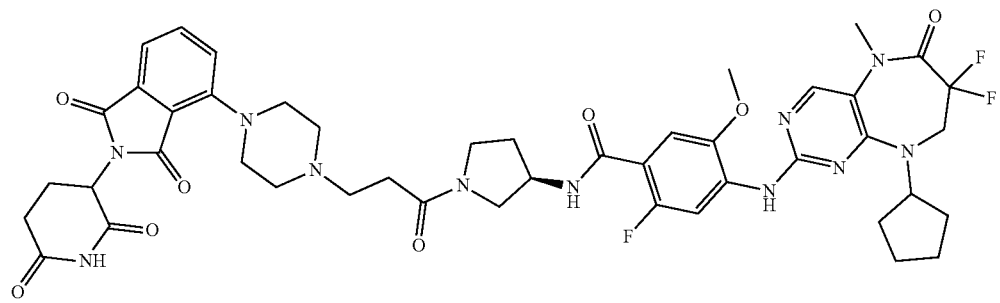

Compound 132

According to the above reaction scheme, in a manner similar to the other examples, obtained the titled compound (94.1 mg, 95.42 μmol, 33.02% yield, 94.3% purity) as yellow solid. MS(M+H)$^+$=930.2

$^1$H NMR (400 MHz, DMSO-d$_6$) δ=11.08 (s, 1H), 8.31-8.22 (m, 3H), 8.04 (s, 1H), 7.72-7.64 (m, 1H), 7.37-7.26 (m, 2H), 7.20 (d, J=6.6 Hz, 1H), 5.13-5.05 (m, 1H), 4.86-4.75 (m, 1H), 4.55-4.37 (m, 1H), 4.07 (t, J=14.0 Hz, 2H), 3.91 (d, J=2.8 Hz, 3H), 3.53-3.35 (m, 2H), 3.33 (s, 3H), 3.28 (d, J=5.1 Hz, 2H), 2.94-2.81 (m, 1H), 2.65-2.55 (m, 8H), 2.69-2.52 (m, 4H), 2.50-2.32 (m, 2H), 2.25-2.14 (m, 1H), 2.04-1.92 (m, 4H), 1.76-1.69 (m, 2H), 1.66-1.57 (m, 4H).

Example 133. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-((3R)-1-(4-(4-(2-(2,6-dioxopiperidin-3-yl)-1,3-dioxo isoindolin-4-yl)piperazin-1-yl)butanoyl)pyrrolidin-3-yl)-2-fluoro-5-methoxybenzamide

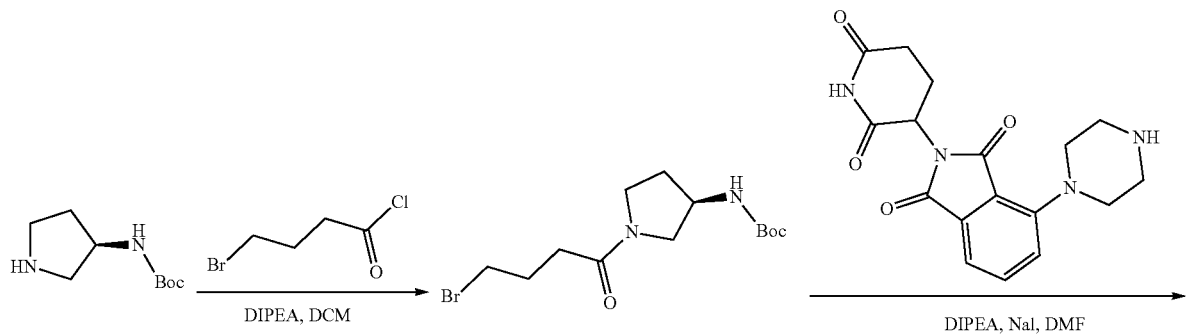

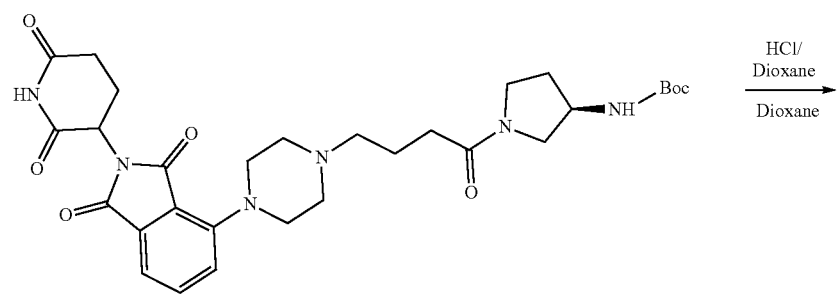

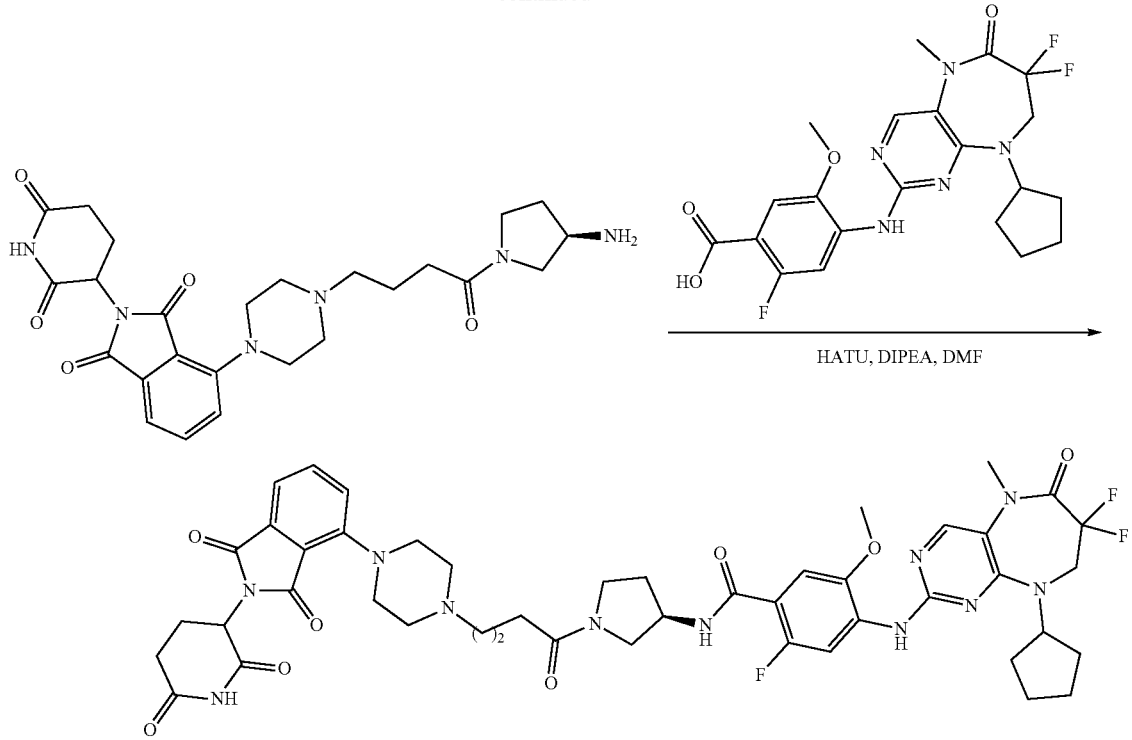

Compound 133

According to the above reaction scheme, in a manner similar to the other examples, obtained the titled compound (37.2 mg, 37.44 μmol, 11.62% yield, 95% purity) as a light yellow solid. MS(M+H)+=944.8

$^1$H NMR (400 MHz, DMSO-d$_6$) δ 11.08 (br s, 1H), 8.34-8.23 (m, 3H), 8.04 (s, 1H), 7.74-7.65 (m, 1H), 7.38-7.29 (m, 2H), 7.20 (d, J=6.5 Hz, 1H), 5.07 (dd, J=5.5, 12.6 Hz, 1H), 4.89-4.76 (m, 1H), 4.52-4.36 (m, 1H), 4.08 (t, J=13.9 Hz, 2H), 3.92 (s, 3H), 3.83-3.53 (m, 2H), 3.52-3.38 (m, 2H), 3.34 (s, 3H), 3.29 (s, 3H), 2.92-2.81 (m, 1H), 2.65-2.55 (m, 4H), 2.40-2.25 (m, 5H), 2.21-2.09 (m, 1H), 2.08-1.82 (m, 5H), 1.81-1.54 (m, 9H).

Example 134. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-((3R)-1-(5-(4-(2-(2,6-dioxopiperidin-3-yl)-1,3-dioxo isoindolin-4-yl)piperazin-1-yl)pentanoyl)pyrrolidin-3-yl)-2-fluoro-5-methoxybenzamide

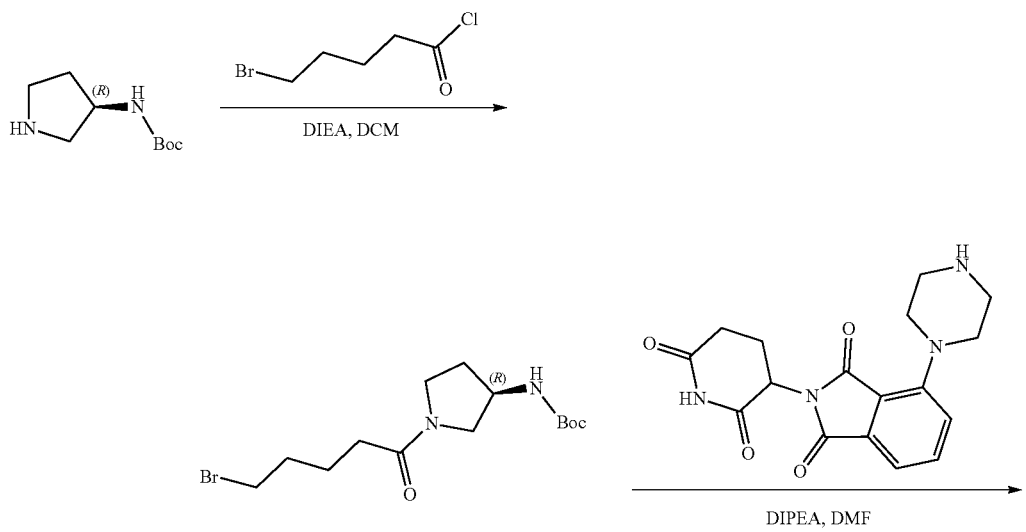

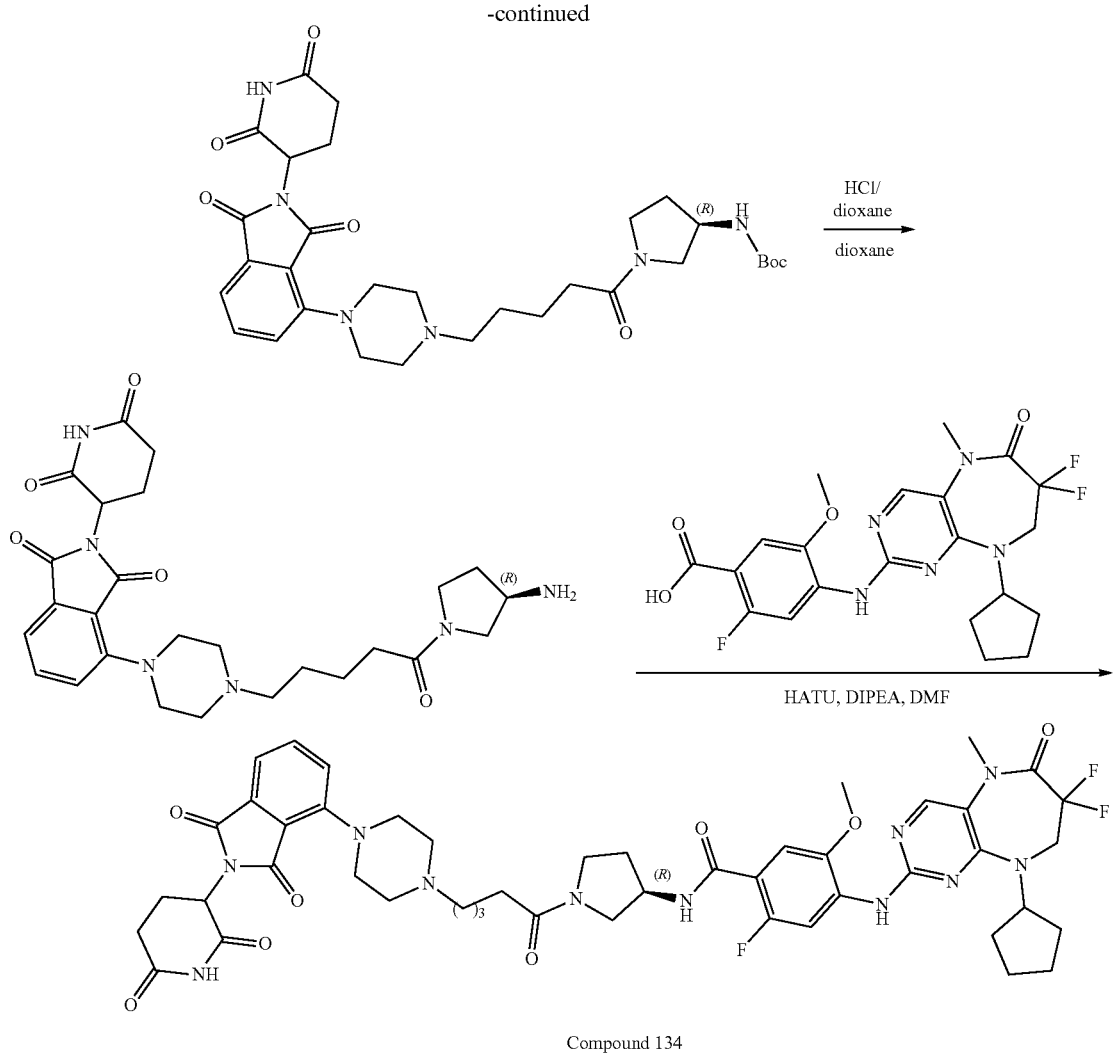

Compound 134

According to the above reaction scheme, in a manner similar to the other examples, obtained the titled compound (13.2 mg, 13.50 umol, 5.91% yield, 98% purity) as yellow solid. MS (M+H)$^+$=958.4

1H NMR (400 MHz, DMSO-d$_6$) δ=11.07 (s, 1H), 8.30-8.21 (m, 3H), 8.05 (s, 1H), 7.81-7.72 (m, 1H), 7.48-7.38 (m, 2H), 7.22-7.17 (m, 1H), 5.01-5.11 (m, 1H), 4.87-4.7 (m, 1H), 4.36 4.51 m, 1H), 4.07 (br t, J=13.8 Hz, 2H), 3.91 (s, 3H), 3.8-3.7 (m, 1H), 3.67-3.52 (m, 2H), 3.55-3.41 (m, 2H), 3.45-3.33 (m, 12H), 2.95-2.81 (m, 1H), 2.68-2.50 (m, 2H), 2.37-2.28 (m, 2H), 2.13-1.88 (m, 5H), 1.74-1.48 (m, 10H).

Example 135. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-((3S)-1-(2-(4-(2-(2,6-dioxopiperidin-3-yl)-1,3-dioxo isoindolin-5-yl)piperazin-1-yl)acetyl)pyrrolidin-3-yl)-2-fluoro-5-methoxybenzamide

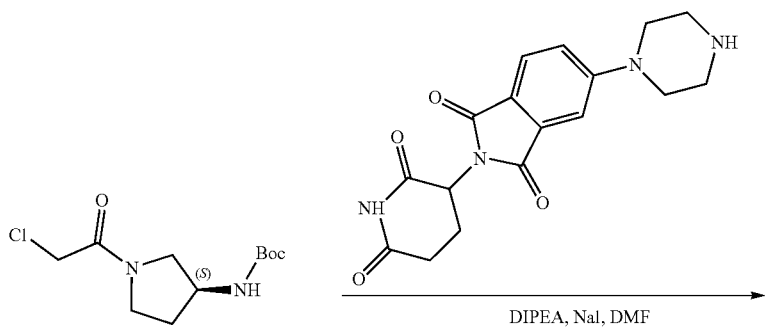

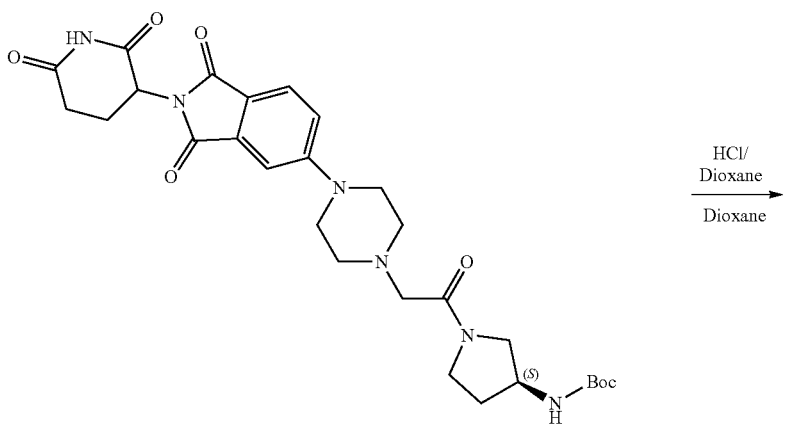
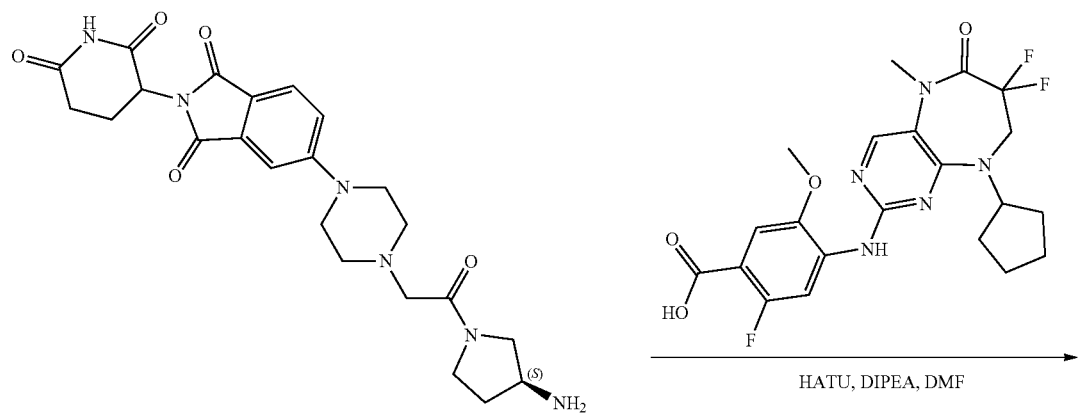
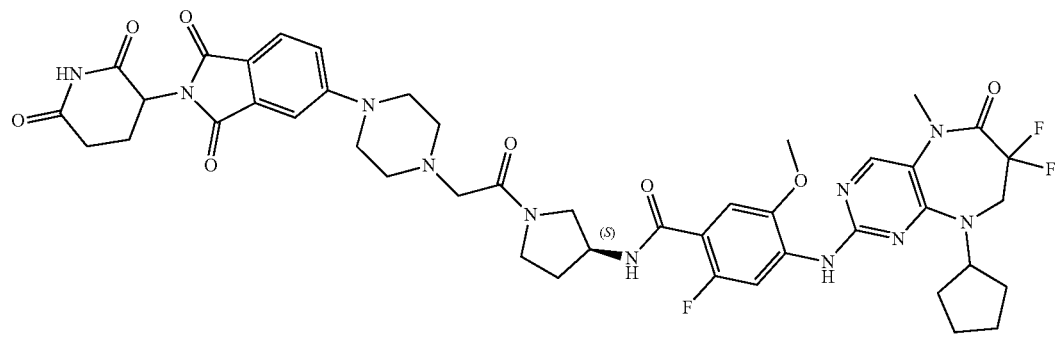
Compound 136
According to the above reaction scheme, in a manner similar to the other examples, obtained the titled compound (58.0 mg, 61.42 μmol, 19.06% yield, 97% purity) as a light yellow solid. MS(M+H)$^+$=916.6
$^1$H NMR (400 MHz, DMSO-d$_6$) δ 11.07 (br s, 1H), 8.32-8.19 (m, 3H), 8.04 (d, J=11.7 Hz, 1H), 7.76-7.61 (m, 1H), 7.38-7.29 (m, 1H), 7.28-7.13 (m, 2H), 5.09-5.05 (m, 1H), 4.87-4.74 (m, 1H), 4.54-4.39 (m, 1H), 4.08 (t, J=13.9 Hz, 2H), 3.95-3.87 (m, 3H), 3.85-3.60 (m, 2H), 3.60-3.43 (m, 4H), 3.41 (s, 3H), 3.24-3.13 (m, 2H), 2.94-2.83 (m, 1H), 2.66-2.54 (m, 7H), 2.23-1.75 (m, 6H), 1.74-1.54 (m, 6H).

Example 136. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-((3S)-1-(3-(4-(2-(2,6-dioxopiperidin-3-yl)-1,3-dioxo isoindolin-5-yl)piperazin-1-yl)propanoyl)pyrrolidin-3-yl)-2-fluoro-5-methoxybenzamide
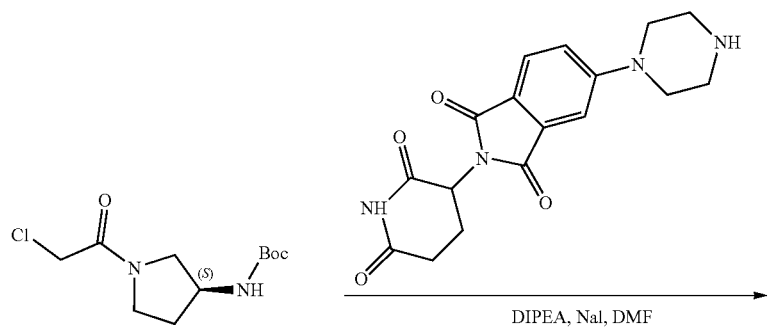
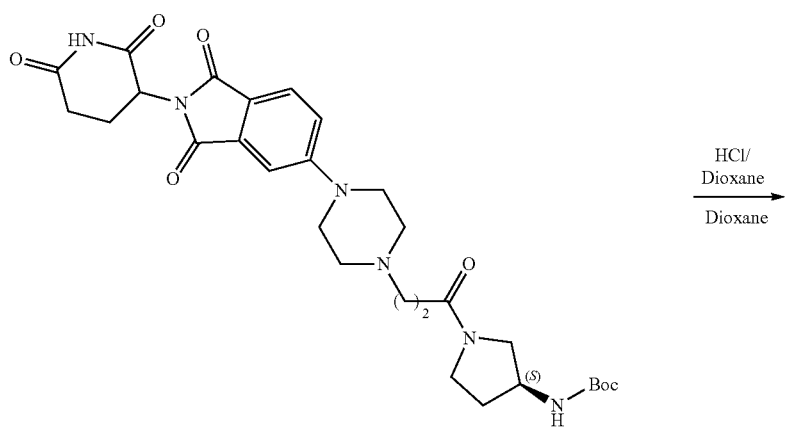
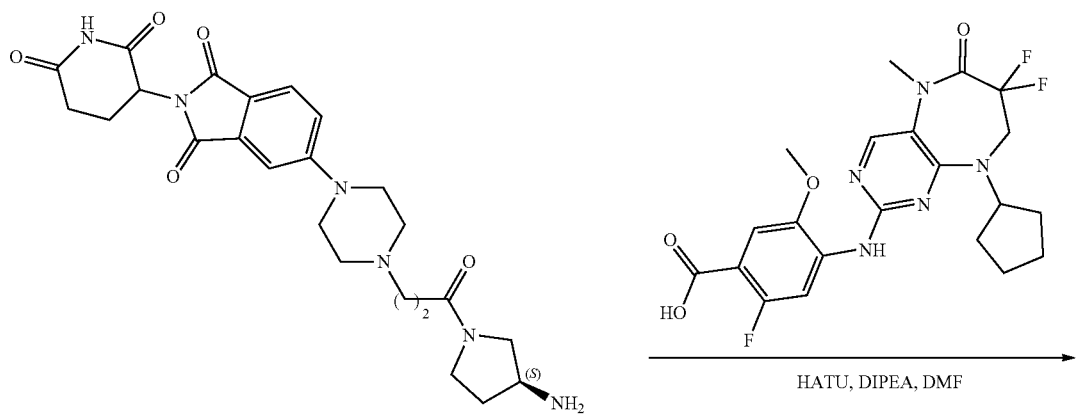

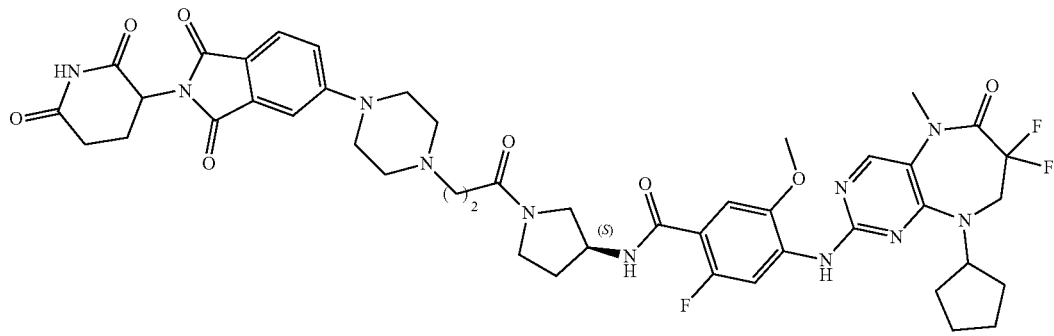

Compound 136

According to the above reaction scheme, in a manner similar to the other examples, obtained the titled compound (77.2 mg, 82.19 μmol, 25.45% yield, 99% purity) as a light yellow solid. MS (M+H)⁺=930.7

¹H NMR (400 MHz, DMSO-d₆) δ 11.08 (s, 1H), 8.32-8.20 (m, 3H), 8.05-8.00 (m, 1H), 7.65 (dd, J=8.5, 14.8 Hz, 1H), 7.35-7.19 (m, 3H), 5.11-5.03 (m, 1H), 4.86-4.76 (m, 1H), 4.51-4.38 (m, 1H), 4.08 (t, J=13.8 Hz, 2H), 3.91 (d, J=5.9 Hz, 3H), 3.82-3.57 (m, 2H), 3.54-3.44 (m, 2H), 3.41-3.37 (m, 3H), 2.94-2.85 (m, 1H), 2.65-2.52 (m, 8H), 2.49-2.39 (m, 4H), 2.22-2.03 (m, 2H), 2.02-1.87 (m, 4H), 1.81-1.53 (m, 7H)

Example 137. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-((3R)-1-(3-(4-(2-(2,6-dioxopiperidin-3-yl)-1,3-dioxoisoindolin-5-yl)piperazin-1-yl)propanoyl)pyrrolidin-3-yl)-2-fluoro-5-methoxybenzamide

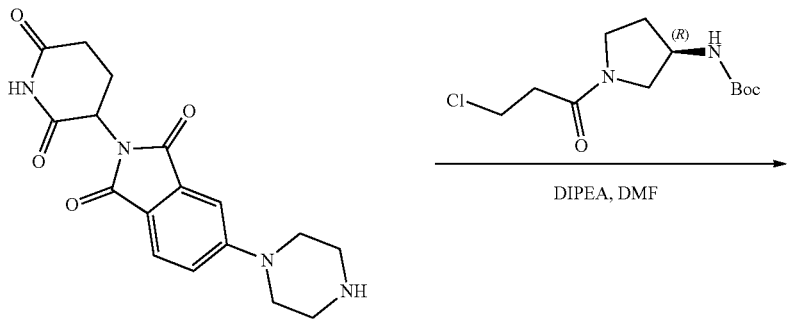

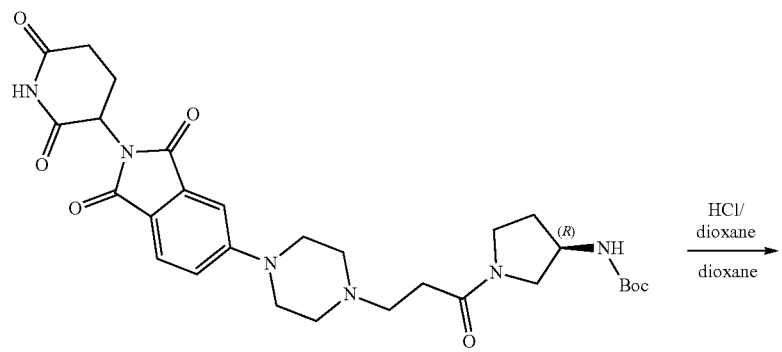

-continued

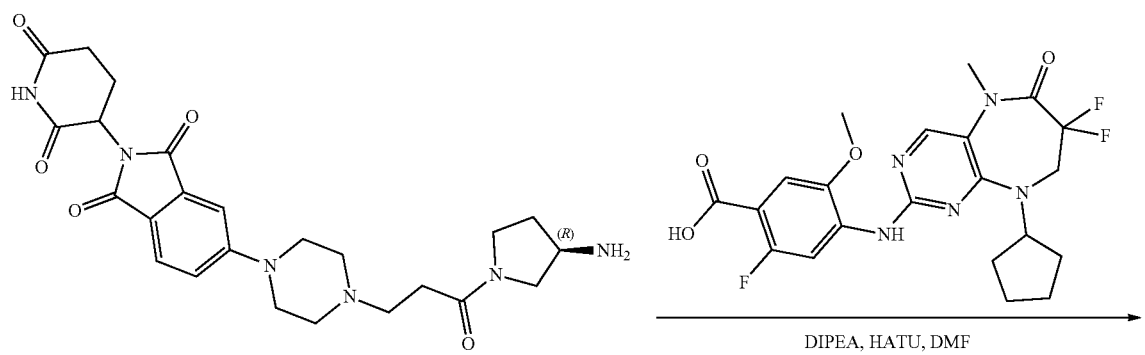

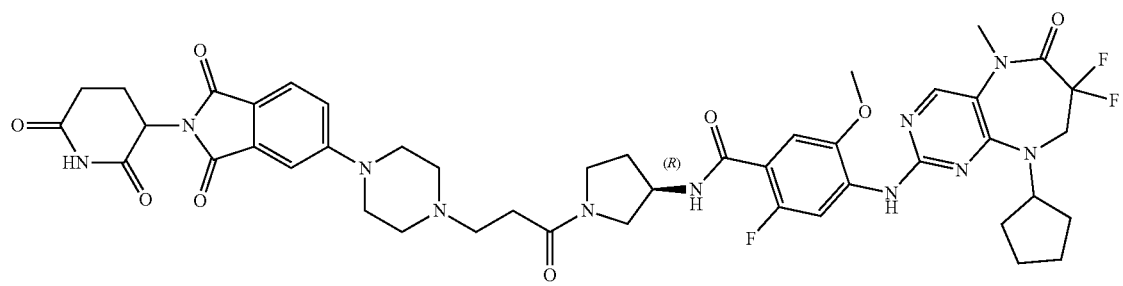

Compound 137

According to the above reaction scheme, in a manner similar to the other examples, obtained the titled compound (21.5 mg, 20.86 μmol, 29.53% yield, 90.24% purity) as yellow solid. MS(M+H)+=930.4

$^1$H NMR (400 MHz, DMSO-d$_6$) δ=11.07 (s, 1H), 8.32-8.18 (m, 3H), 8.11-7.95 (m, 1H), 7.73-7.58 (m, 1H), 7.37-7.15 (m, 3H), 5.11-5.02 (m, 1H), 4.89-4.72 (m, 1H), 4.52-4.37 (m, 1H), 4.14-4.01 (m, 2H), 3.94-3.86 (m, 3H), 3.83-3.70 (m, 1H), 3.67-3.48 (m, 3H), 3.46-3.35 (m, 3H), 3.33 (s, 3H), 2.93-2.83 (m, 1H), 2.64-2.53 (m, 11H), 2.24-1.92 (m, 5H), 1.76-1.68 (m, 2H), 1.66-1.52 (m, 4H).

Example 138. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-((3R)-1-(4-(4-(2-(2,6-dioxopiperidin-3-yl)-1,3-dioxoisoindolin-5-yl)piperazin-1-yl)butanoyl)pyrrolidin-3-yl)-2-fluoro-5-methoxybenzamide

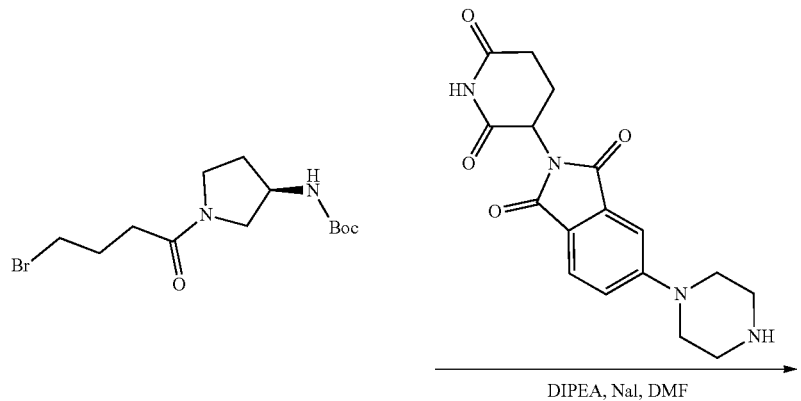

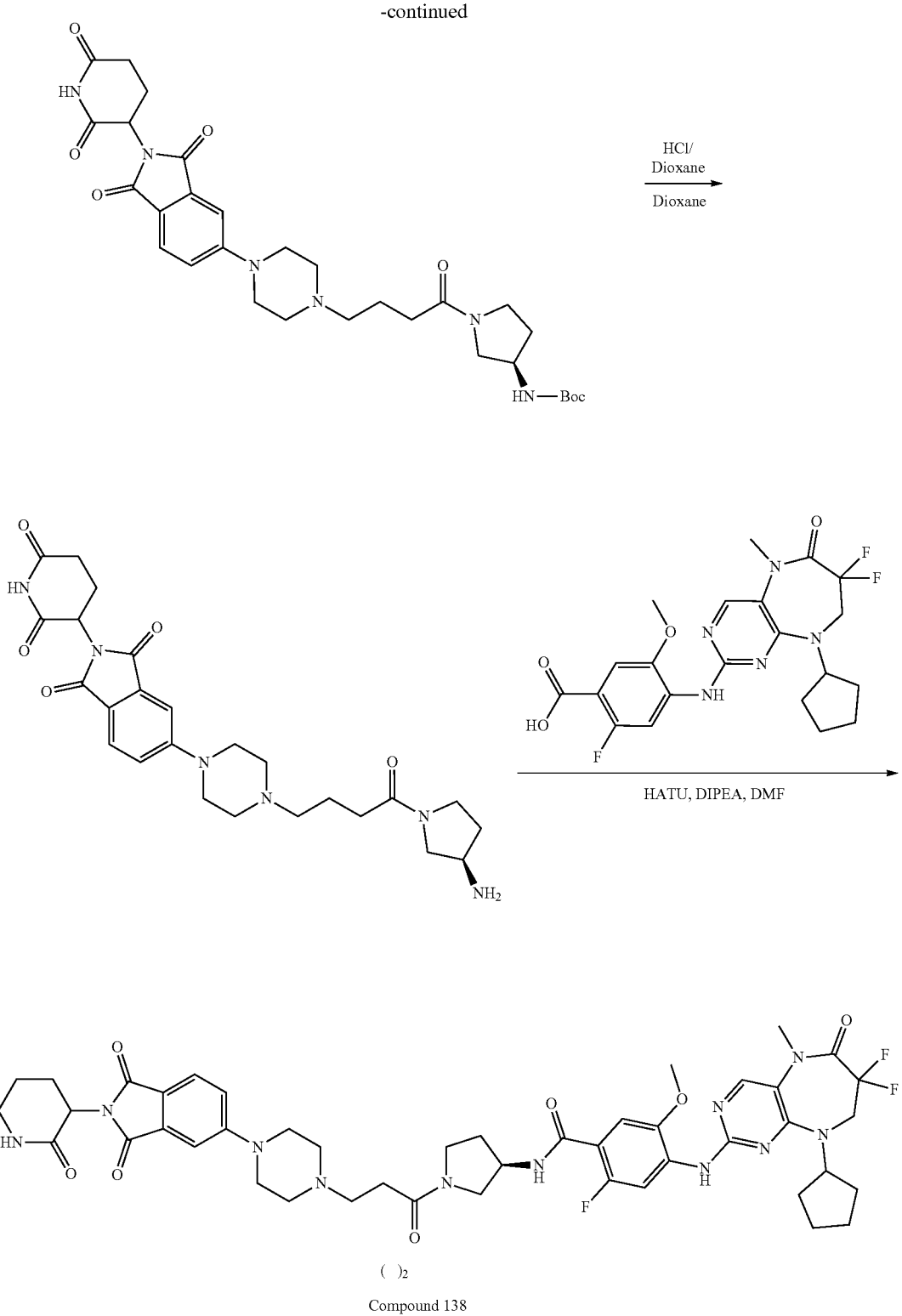
Compound 138
According to the above reaction scheme, in a manner similar to the other examples, obtained the titled compound (51.0 mg, 52.95 mol, 16.43% yield, 98% purity) as a light yellow solid. MS(M+H)$^+$=944.7
$^1$H NMR (400 MHz, DMSO-d$_6$) δ 11.08 (s, 1H), 8.33-8.23 (m, 3H), 8.04 (s, 1H), 7.66 (dd, J=4.3, 8.5 Hz, 1H), 7.36-7.30 (m, 1H), 7.26-7.18 (m, 2H), 5.07 (dd, J=5.4, 13.0 Hz, 1H), 4.82 (t, J=7.7 Hz, 1H), 4.53-4.39 (m, 1H), 4.08 (t, J=13.9 Hz, 2H), 3.93-3.91 (m, 3H), 3.82-3.57 (m, 2H), 3.52-3.45 (m, 5H), 3.34 (s, 3H), 2.94-2.83 (m, 1H), 2.71-2.57 (m, 4H), 2.39-2.23 (m, 5H), 2.21-1.89 (m, 6H), 1.79-1.58 (m, 9H).

Example 139. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-((3R)-1-(5-(4-(2-(2,6-dioxopiperidin-3-yl)-1,3-dioxo isoindolin-5-yl)piperazin-1-yl)pentanoyl)pyrrolidin-3-yl)-2-fluoro-5-methoxybenzamide
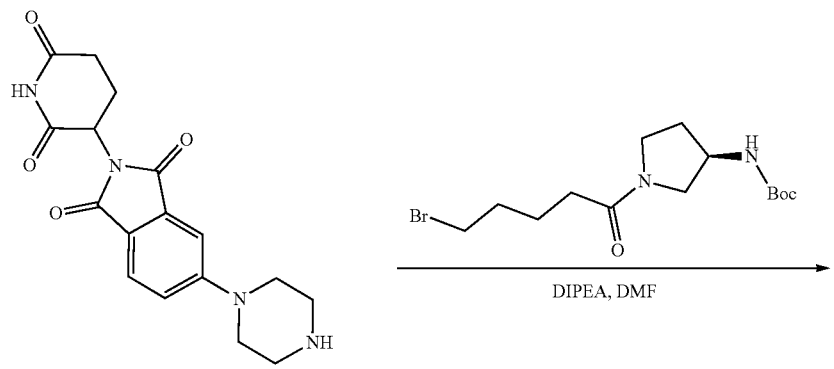
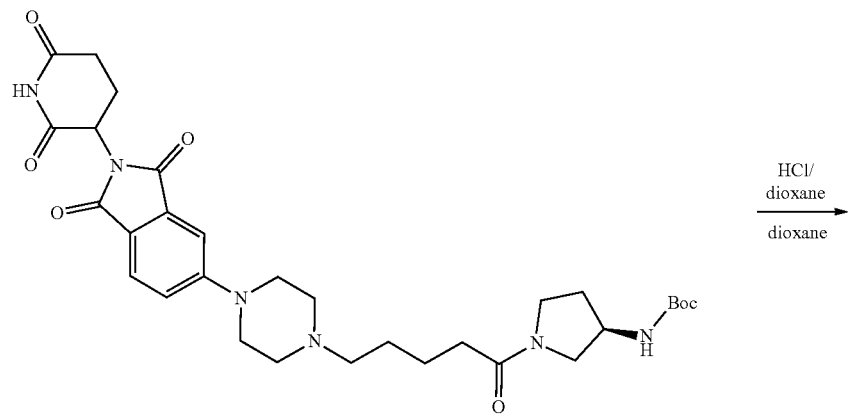
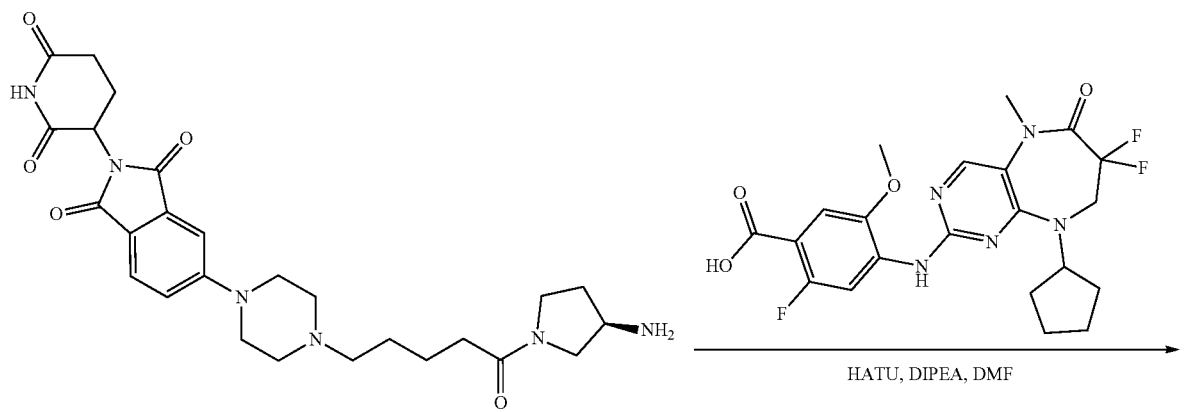

-continued

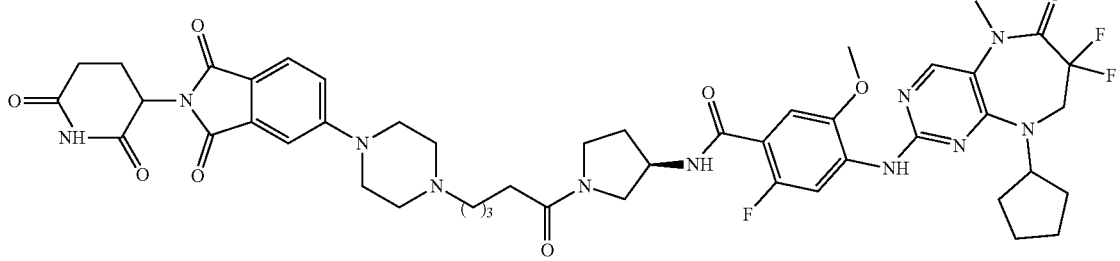

Compound 139

According to the above reaction scheme, in a manner similar to the other examples, obtained the titled compound (13.2 mg, 13.50 umol, 5.91% yield, 98% purity) as a yellow solid. MS(M+H)⁺=958.4

¹H NMR (400 MHz, DMSO-d6) δ 11.07 (s, 1H), 8.36-8.19 (m, 3H), 8.03 (d, J=7.3 Hz, 1H), 7.70-7.60 (m, 1H), 7.38-7.14 (m, 3H), 5.06 (d, J=12.7 Hz, 1H), 4.87-4.76 (m, 1H), 4.44 (dd, J=33.7, 7.1 Hz, 1H), 4.07 (t, J=13.9 Hz, 2H), 3.91 (d, J=5.2 Hz, 3H), 3.82-3.45 (m, 3H), 3.46-3.35 (m, 6H), 2.95-2.80 (m, 1H), 2.69-2.53 (m, 4H), 2.47-2.41 (m, 3H), 2.38-2.21 (m, 5H), 2.20-1.86 (m, 5H), 1.79-1.69 (m, 2H), 1.67-1.57 (m, 4H), 1.57-1.42 (m, 4H).

Example 140. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-((3S)-1-(4-(4-(2-(2,6-dioxopiperidin-3-yl)-1,3-dioxo isoindolin-4-yl)piperazin-1-yl)-4-oxobutanoyl)pyrrolidin-3-yl)-2-fluoro-5-methoxybenzamide

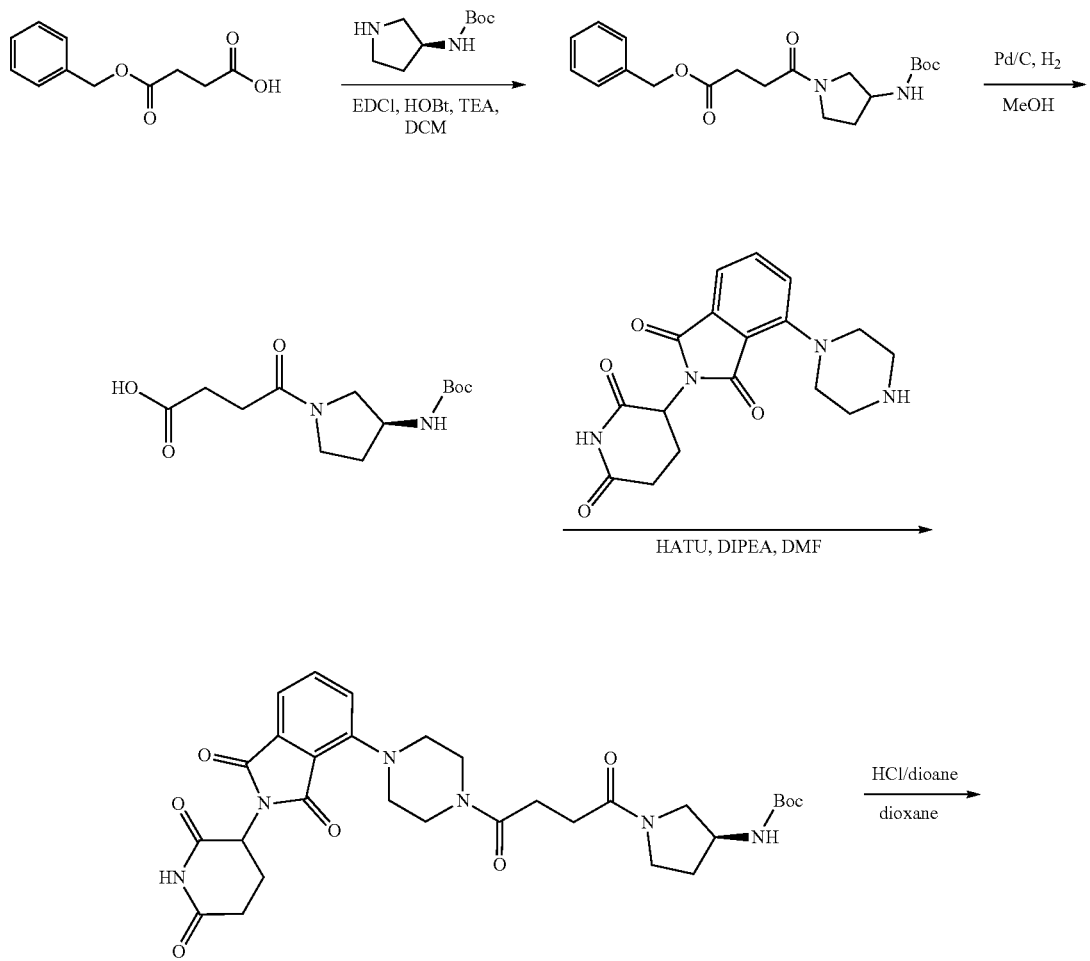

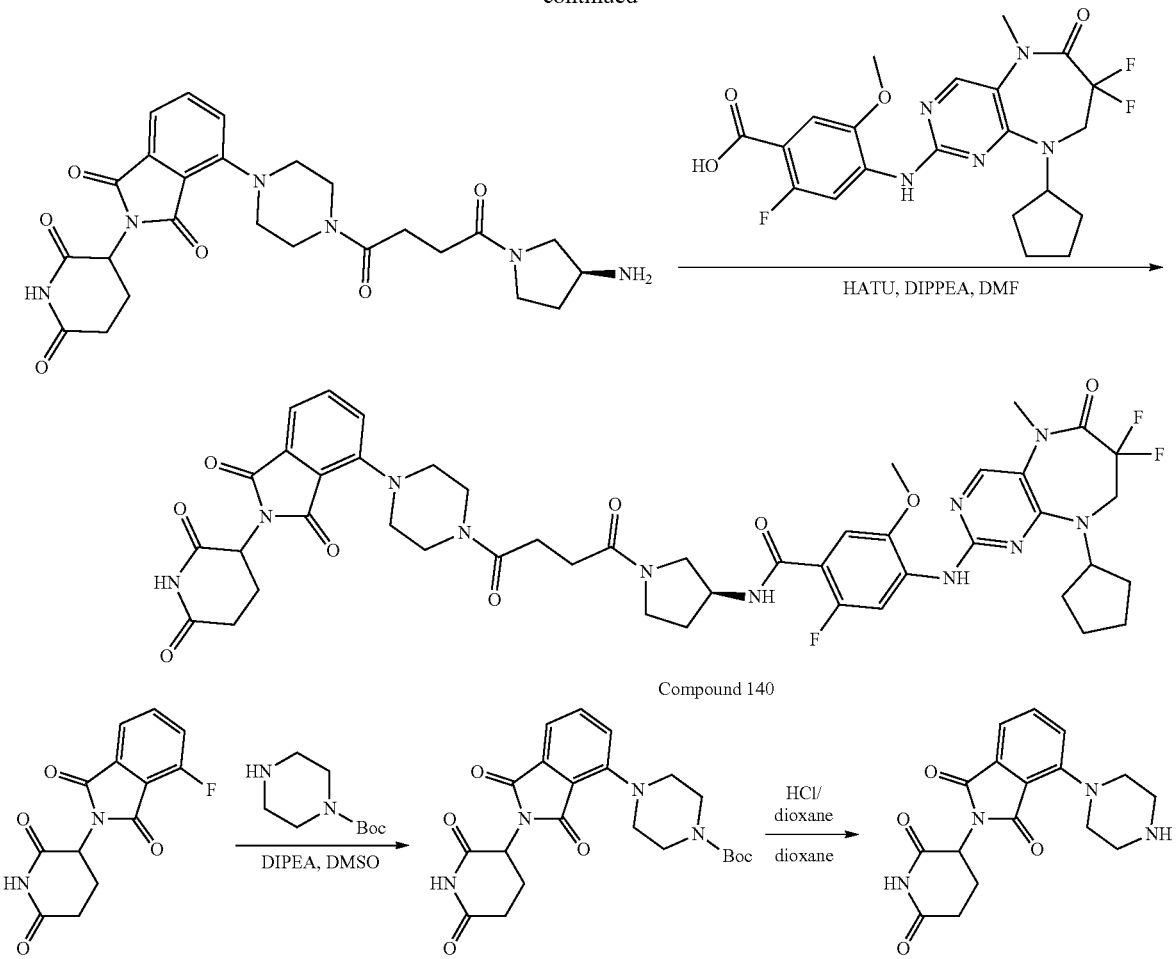

According to the above reaction scheme, in a manner similar to the other examples, obtained the titled compound (94.1 mg, 95.28 μmol, 36.96% yield, 97% purity) as a yellow solid. MS(M+H)+=958.0

$^1$H NMR (400 MHz, DMSO-$d_6$) δ=11.09 (s, 1H), 8.34-8.23 (m, 3H), 8.05 (s, 1H), 7.76-7.68 (m, 1H), 7.42-7.33 (m, 2H), 7.21 (dd, J=3.2, 6.6 Hz, 1H), 5.11 (dd, J=5.4, 12.8 Hz, 1H), 4.87-4.77 (m, 1H), 4.54-4.37 (m, 1H), 4.07 (t, J=13.8 Hz, 2H), 3.92 (s, 3H), 3.89-3.77 (m, 1H), 3.71-3.51 (m, 6H), 3.51-3.40 (m, 3H), 3.33 (br s, 3H), 3.27-3.24 (m, 3H), 2.93-2.83 (m, 1H), 2.63-2.59 (m, 2H), 2.59-2.53 (m, 2H), 2.52-2.50 (m, 1H), 2.14-1.87 (m, 5H), 1.77-1.68 (m, 2H), 1.68-1.57 (m, 4H)

Example 141. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-((3S)-1-(4-(4-(2-(2,6-dioxopiperidin-3-yl)-1,3-dioxo isoindolin-4-yl)piperazin-1-yl)-4-oxobutanoyl)pyrrolidin-3-yl)-3-methoxybenzamide

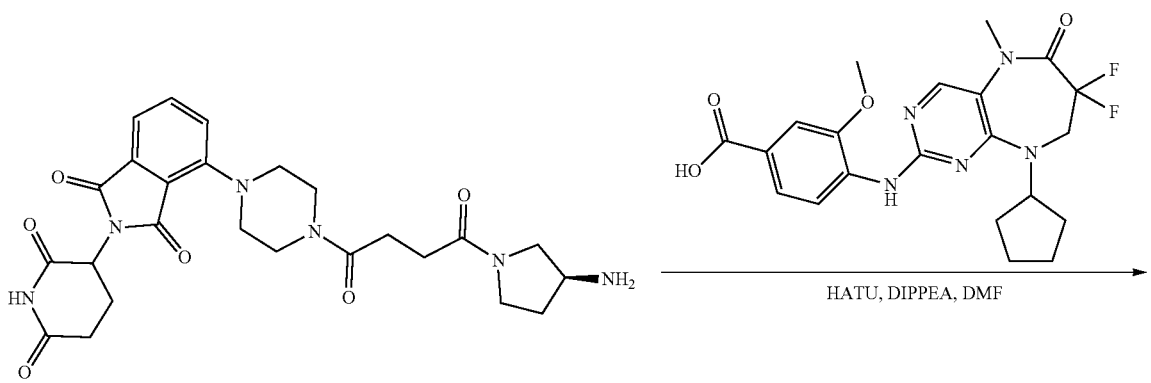

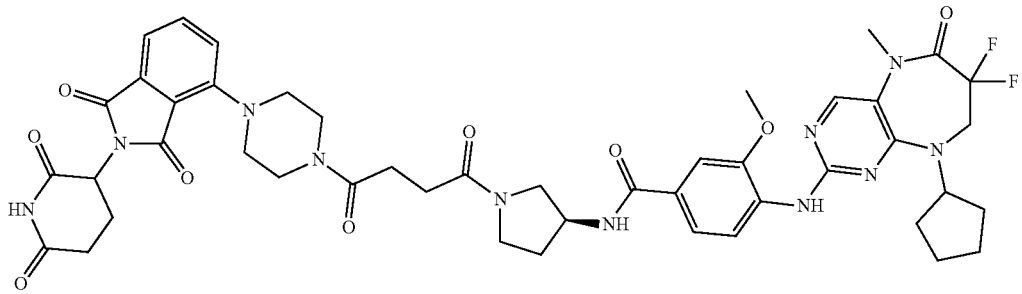

Compound 141

According to the above reaction scheme, in a manner similar to the other examples, obtained the titled compound (20.9 mg, 21.12 µmol, 13.59% yield, 95% purity) as a yellow solid. MS(M+H)$^+$=940.1.

$^1$H NMR (400 MHz, DMSO-d$_6$) δ=11.02 (br s, 1H), 8.48-8.35 (m, 1H), 8.33-8.23 (m, 2H), 7.98 (d, J=2.4 Hz, 1H), 7.72 (t, J=7.6 Hz, 1H), 7.56-7.46 (m, 2H), 7.37 (dd, J=7.8, 16.4 Hz, 2H), 5.11 (dd, J=5.5, 12.8 Hz, 1H), 4.77 (quin, J=7.9 Hz, 1H), 4.58-4.38 (m, 1H), 4.04 (br t, J=14.0 Hz, 2H), 3.94 (s, 3H), 3.84 (br dd, J=6.9, 10.3 Hz, 1H), 3.77-3.58 (m, 5H), 3.58-3.48 (m, 1H), 3.37-3.46 (m, 1H), 3.34-3.37 (m, 5H), 3.22-3.28 (m, 2H), 2.95-2.82 (m, 1H), 2.65-2.52 (m, 6H), 2.27-2.08 (m, 1H), 2.07-1.87 (m, 4H), 1.78-1.66 (m, 2H), 1.66-1.52 (m, 4H).

Example 142. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-((3S)-1-(4-(4-(2-(2,6-dioxopiperidin-3-yl)-1,3-dioxoisoindolin-4-yl)piperazin-1-yl)-4-oxobutanoyl)pyrrolidin-3-yl)benzamide

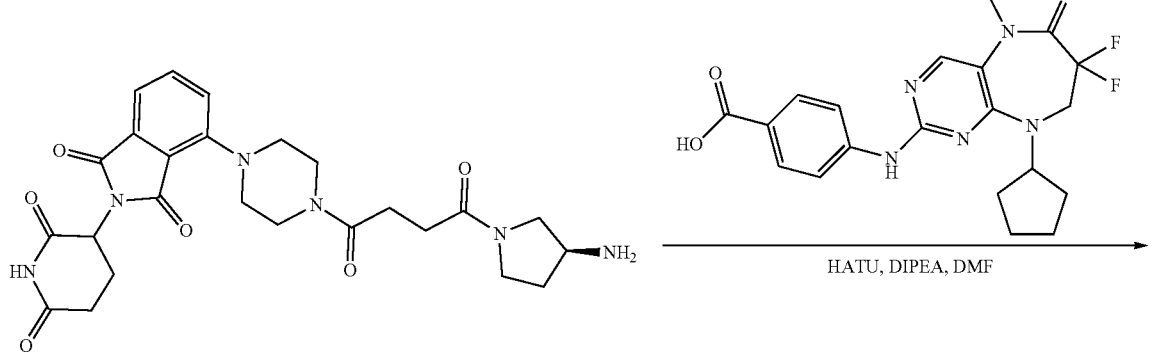

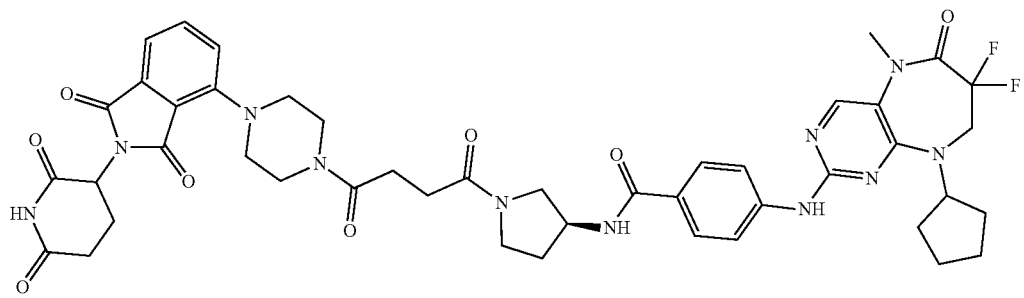

Compound 142

According to the above reaction scheme, in a manner similar to the other examples, obtained the titled compound (32.2 mg, 32.38 μmol, 65.47% yield, 91.5% purity) as a yellow solid. MS(M+H)+=910.0

$^1$H NMR (400 MHz, DMSO-d$_6$) δ=11.08 (s, 1H), 9.68 (d, J=1.5 Hz, 1H), 8.38-8.28 (m, 1H), 8.27 (s, 1H), 7.79 (d, J=3.5 Hz, 4H), 7.72 (t, J=7.9 Hz, 1H), 7.42-7.33 (m, 2H), 5.13-5.09 (m, 1H), 4.84-4.74 (m, 1H), 4.53-4.38 (m, 1H), 4.04 (br t, J=14.1 Hz, 2H), 3.88-3.75 (m, 1H), 3.73-3.39 (m, 8H), 3.33 (br s, 3H), 3.29 (s, 1H), 3.26 (br d, J=4.8 Hz, 1H), 2.93-2.83 (m, 1H), 2.79-2.70 (m, 1H), 2.61 (br d, J=5.0 Hz, 3H), 2.56 (br d, J=7.3 Hz, 1H), 2.27-2.14 (m, 1H), 2.13-1.86 (m, 6H), 1.76-1.68 (m, 2H), 1.65-1.56 (m, 4H).

Example 143. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-((3S)-1-(5-(4-(2-(2,6-dioxopiperidin-3-yl)-1,3-dioxo isoindolin-4-yl)piperazin-1-yl)-5-oxopentanoyl)pyrrolidin-3-yl)-2-fluoro-5-methoxybenzamide

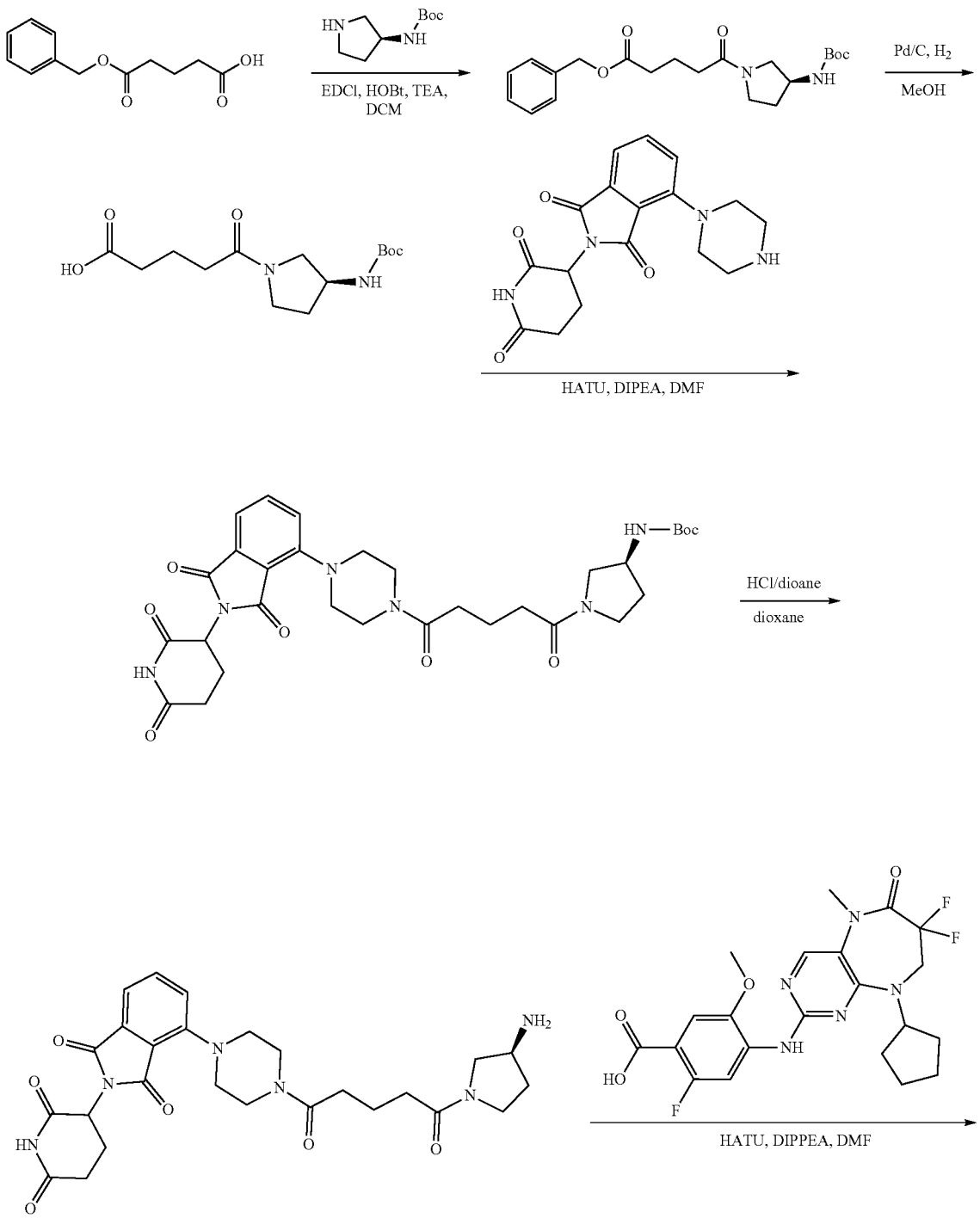

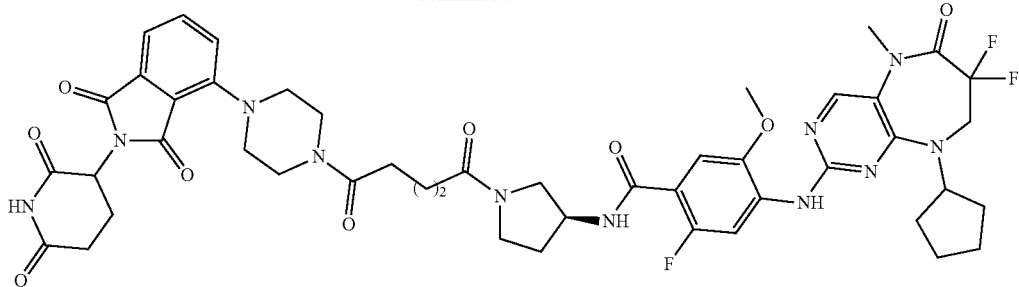

Compound 143

According to the above reaction scheme, in a manner similar to the other examples, obtained the titled compound (63.3 mg, 63.82 μmol, 24.75% yield, 98% purity) as a yellow solid. MS(M+H)$^+$=972.0

$^1$H NMR (400 MHz, DMSO-d$_6$) δ=11.10 (br s, 1H), 8.35-8.23 (m, 3H), 8.04 (s, 1H), 7.75-7.68 (m, 1H), 7.41-7.32 (m, 2H), 7.19 (d, J=6.4 Hz, 1H), 5.11 (dd, J=5.4, 12.8 Hz, 1H), 4.86-4.77 (m, 1H), 4.53-4.36 (m, 1H), 4.12-4.03 (m, 2H), 3.91 (s, 3H), 3.69-3.60 (m, 4H), 3.59-3.42 (m, 4H), 3.33 (s, 3H), 3.25-3.17 (m, 3H), 2.92-2.83 (m, 1H), 2.62-2.54 (m, 2H), 2.42-2.37 (m, 2H), 2.29 (q, J=7.6 Hz, 2H), 2.22-1.87 (m, 6H), 1.79-1.68 (m, 4H), 1.66-1.54 (m, 4H)

Example 144. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-((3S)-1-(4-(4-(2-(2,6-dioxopiperidin-3-yl)-1,3-dioxo isoindolin-5-yl)piperazin-1-yl)-4-oxobutanoyl)pyrrolidin-3-yl)-2-fluoro-5-methoxybenzamide

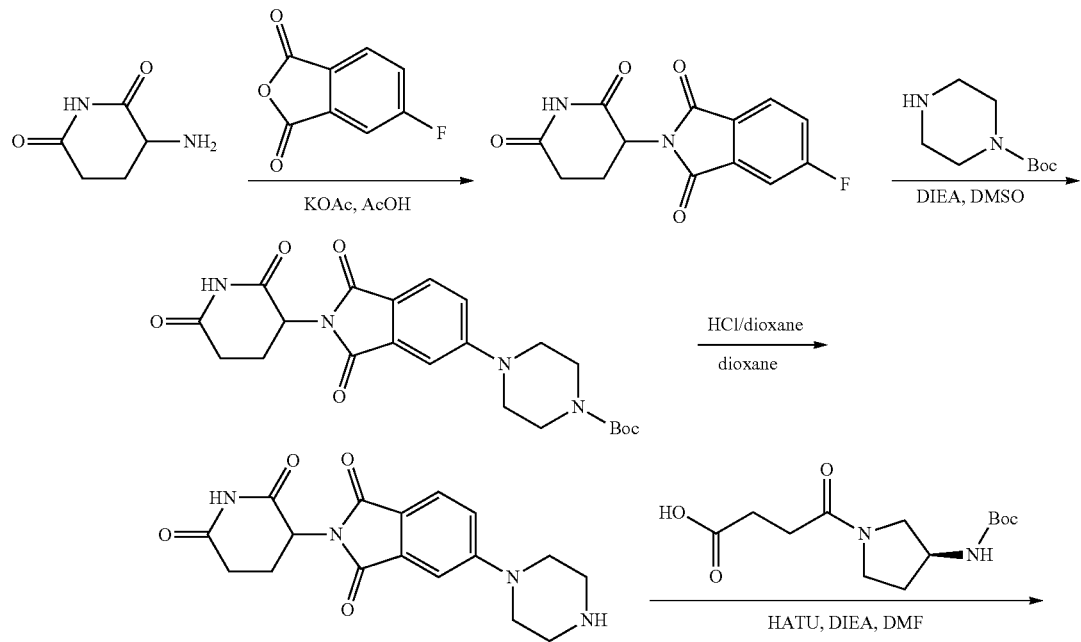

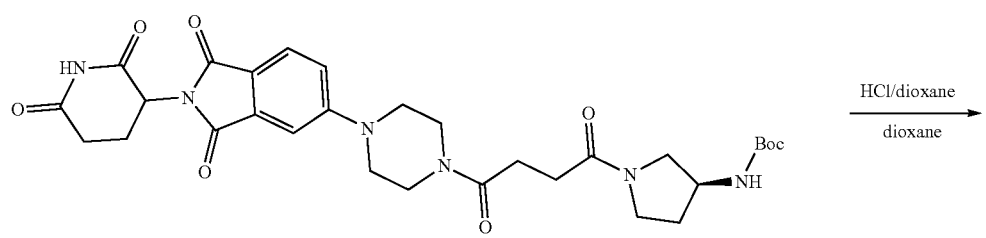

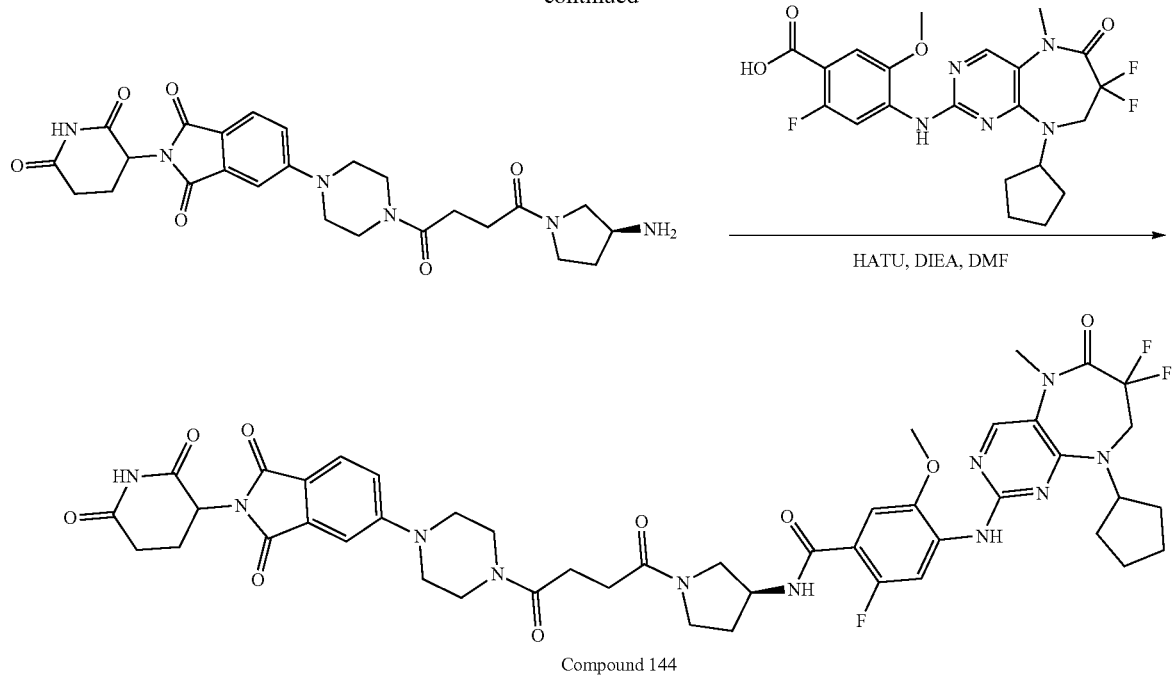

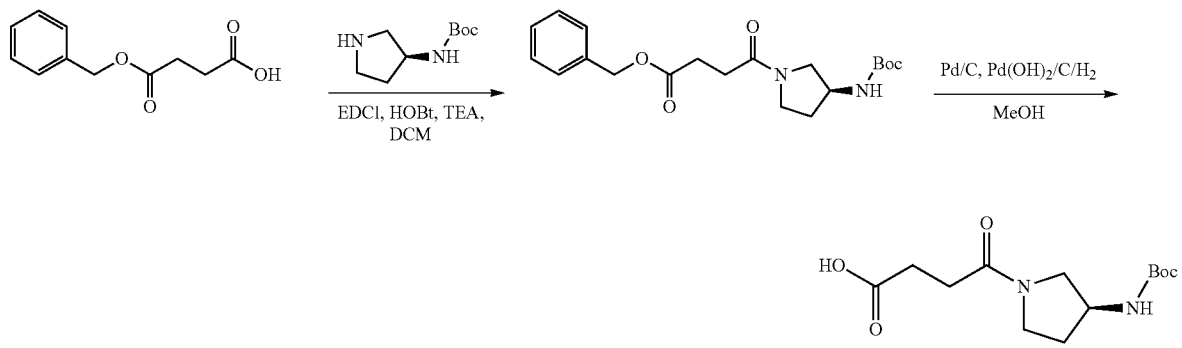

Compound 144

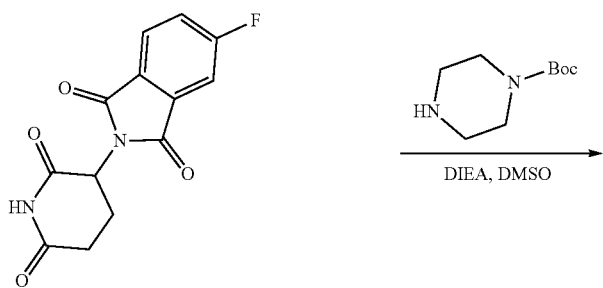

According to the above reaction scheme, in a manner similar to the other examples, obtained the titled compound (31.9 mg, 30.64 μmol, 12.96% yield, 92% purity) as a yellow solid. MS(M+H)⁺=958.3.

¹H NMR (400 MHz, DMSO-d6) δ 11.03 (s, 1H), 8.37-8.19 (m, 3H), 8.04 (s, 1H), 7.70 (d, J=8.5 Hz, 1H), 7.34 (d, J=2.3 Hz, 1H), 7.30-7.15 (m, 2H), 5.06 (dd, J=12.8, 5.4 Hz, 1H), 4.92-4.75 (m, 1H), 4.45 (dd, J=37.6, 6.3 Hz, 1H), 4.07 (t, J=13.8 Hz, 2H), 3.92 (s, 3H), 3.85-3.50 (m, 8H), 3.50-3.35 (m, 5H), 3.29-3.17 (m, 2H), 2.94-2.80 (m, 1H), 2.70-2.53 (m, 6H), 2.26-2.06 (m, 1H), 2.05-1.87 (m, J=7.0, 6.2 Hz, 4H), 1.80-1.68 (m, 2H), 1.68-1.53 (m, 4H).

Example 145. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-((3S)-1-(4-(4-(2-(2,6-dioxopiperidin-3-yl)-1,3-dioxoisoindolin-5-yl)piperazin-1-yl)-4-oxobutanoyl)pyrrolidin-3-yl)-3-methoxybenzamide 571 572
-continued
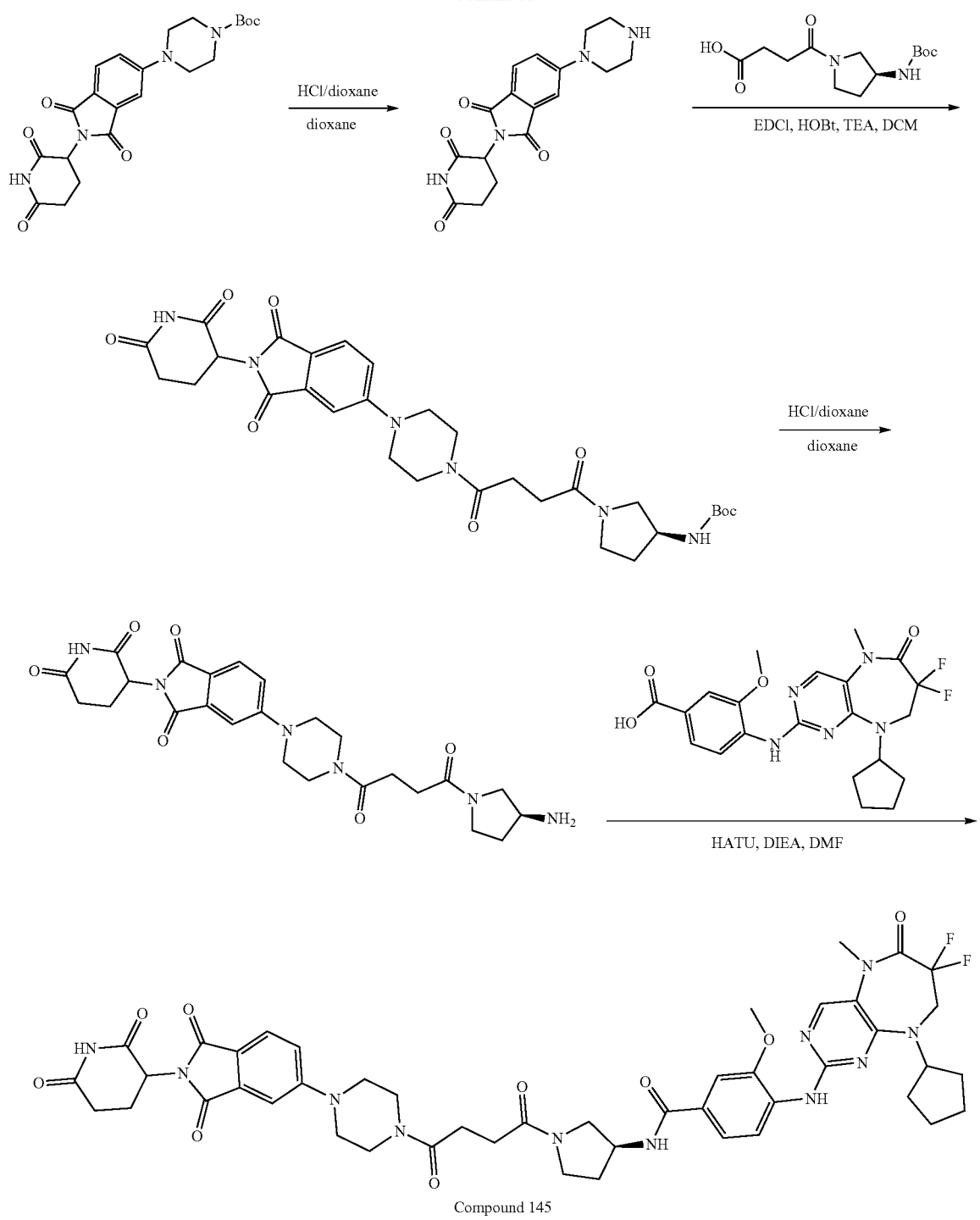
Compound 145
According to the above reaction scheme, in a manner similar to the other examples, obtained the titled compound (24.9 mg, 25.17 µmol, 14.08% yield, 97% purity) as a yellow solid. MS(M+H)⁺=940.1.
¹H NMR (400 MHz, DMSO-d₆) δ=11.35-10.65 (m, 1H), 8.50-8.35 (m, 1H), 8.34-8.23 (m, 2H), 7.98 (d, J=2.9 Hz, 1H), 7.70 (d, J=8.5 Hz, 1H), 7.59-7.45 (m, 2H), 7.34 (d, J=1.8 Hz, 1H), 7.29-7.19 (m, 1H), 5.07 (dd, J=5.4, 12.9 Hz, 1H), 4.84-4.70 (m, 1H), 4.57-4.38 (m, 1H), 4.04 (t, J=14.1 Hz, 2H), 3.94 (s, 3H), 3.88-3.80 (m, 1H), 3.71-3.58 (m, 5H), 3.58-3.49 (m, 3H), 3.48-3.44 (m, 2H), 3.43-3.37 (m, 1H), 3.36-3.32 (m, 3H), 2.93-2.81 (m, 1H), 2.65-2.53 (m, 6H), 2.27-2.08 (m, 1H), 2.06-1.87 (m, 4H), 1.77-1.67 (m, 2H), 1.66-1.53 (m, 4H).

Example 146. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-((3S)-1-(4-(4-(2-(2,6-dioxopiperidin-3-yl)-1,3-dioxo isoindolin-5-yl)piperazin-1-yl)-4-oxobutanoyl)pyrrolidin-3-yl)benzamide

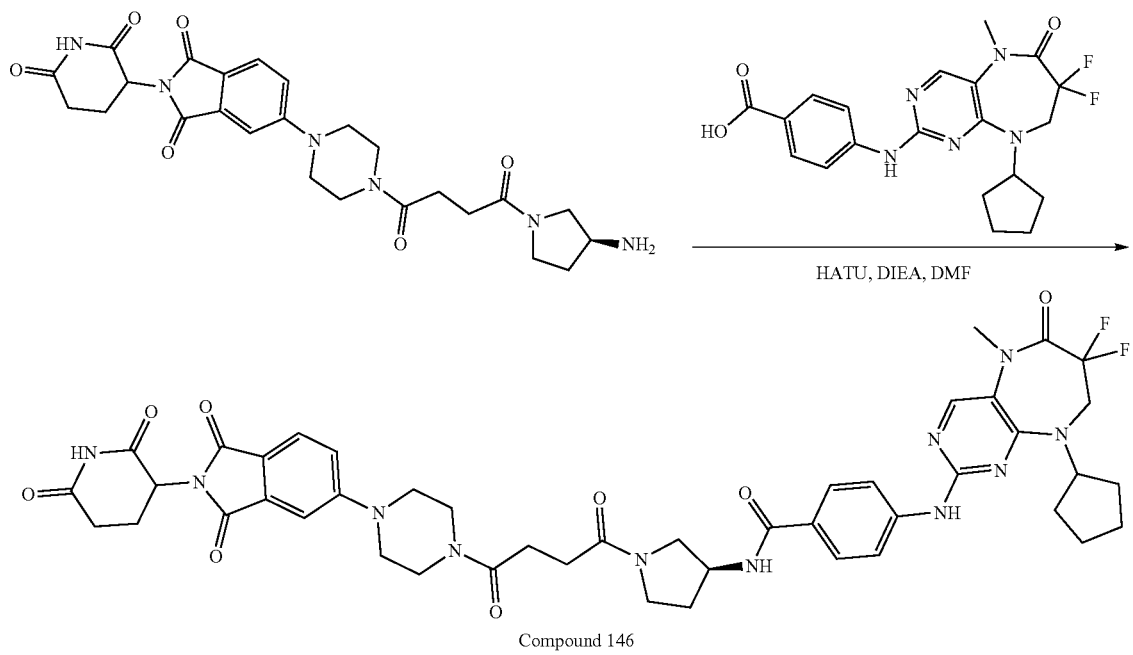

Compound 146

According to the above reaction scheme, in a manner similar to the other examples, obtained the titled compound (15.4 mg, 16.42 μmol, 8.57% yield, 94% purity) as a yellow solid. MS(M+H)$^+$=911.0.

$^1$H NMR (400 MHz, DMSO-d$_6$) δ=11.08 (br s, 1H), 9.70 (d, J=2.5 Hz, 1H), 8.40-8.29 (m, 1H), 8.27 (s, 1H), 7.79 (d, J=3.6 Hz, 4H), 7.70 (d, J=8.5 Hz, 1H), 7.35 (d, J=1.9 Hz, 1H), 7.24 (dd, J=1.8, 8.6 Hz, 1H), 5.08 (dd, J=5.3, 12.9 Hz, 1H), 4.85-4.73 (m, 1H), 4.54-4.35 (m, 1H), 4.04 (t, J=14.1 Hz, 2H), 3.85-3.64 (m, 3H), 3.63-3.52 (m, 5H), 3.51-3.41 (m, 3H), 3.41-3.33 (m, 3H), 3.30-3.22 (m, 1H), 2.95-2.83 (m, 1H), 2.64-2.56 (m, 3H), 2.56-2.52 (m, 3H), 2.24-2.08 (m, 1H), 2.04-1.91 (m, 4H), 1.76-1.68 (m, 2H), 1.65-1.54 (m, 4H).

Example 147. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-((3S)-1-(5-(4-(2-(2,6-dioxopiperidin-3-yl)-1,3-dioxo isoindolin-5-yl)piperazin-1-yl)-5-oxopentanoyl)pyrrolidin-3-yl)-2-fluoro-5-methoxybenzamide

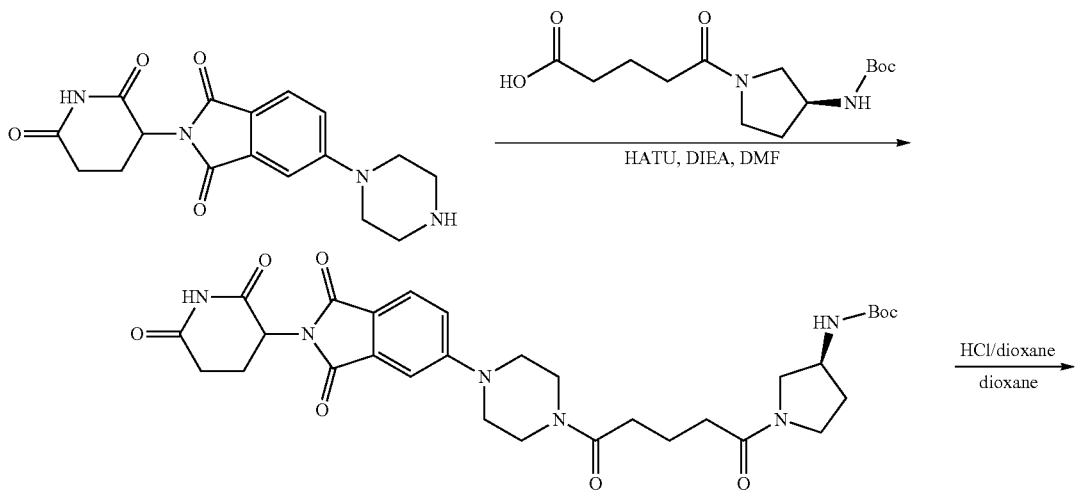

-continued
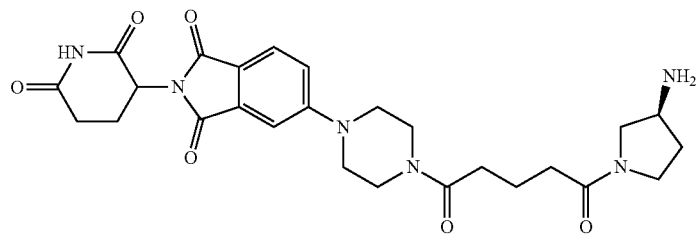 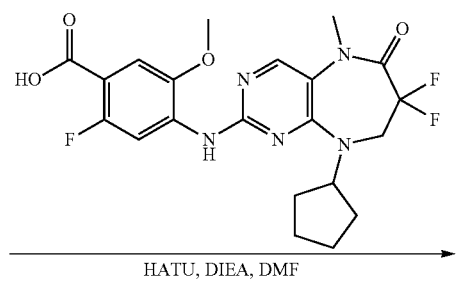
HATU, DIEA, DMF
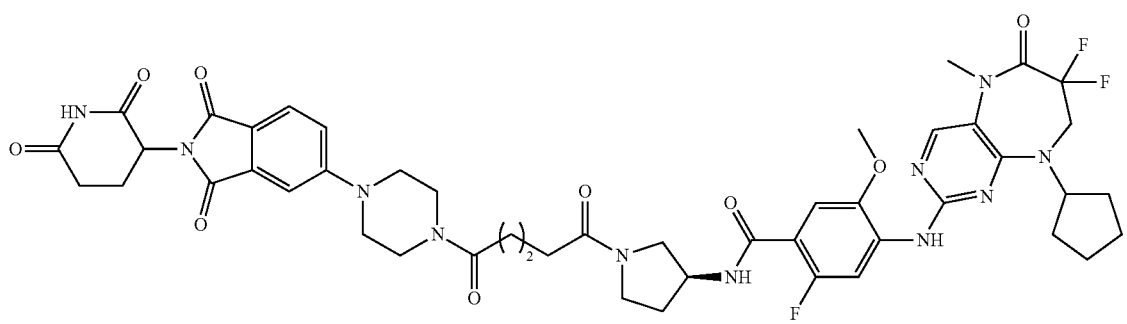
Compound 147
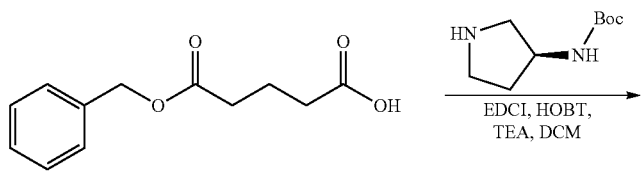
EDCI, HOBT, TEA, DCM
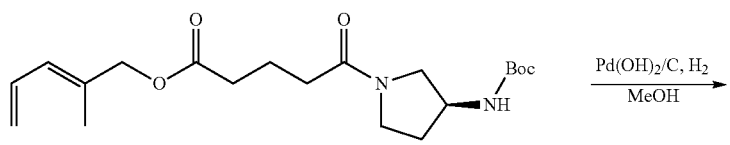
Pd(OH)$_2$/C, H$_2$
MeOH
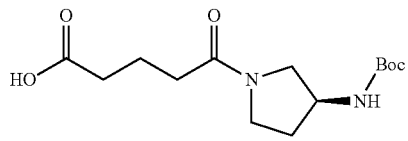
According to the above reaction scheme, in a manner similar to the other examples, obtained the titled compound (45.3 mg, 45.67 μmol, 21.26% yield, 98% purity) as a yellow solid. MS(M+H)$^+$=972.8.
$^1$H NMR (400 MHz, DMSO-d$_6$) δ=11.07 (br s, 1H), 8.36-8.20 (m, 3H), 8.03 (s, 1H), 7.68 (dd, J$_1$=3.2, J$_2$=8.5 Hz, 1H), 7.33 (br s, 1H), 7.28-7.21 (m, 1H), 7.19 (dd, J$_1$=1.6, J$_2$=6.6 Hz, 1H), 5.07 (dd, J$_1$=5.4, J$_2$=13.1 Hz, 1H), 4.90-4.72 (m, 1H), 4.54-4.35 (m, 1H), 4.07 (br t, J=13.9 Hz, 2H), 3.91 (s, 3H), 3.76-3.55 (m, 6H), 3.54-3.38 (m, 9H), 2.94-2.82 (m, 1H), 2.70-2.56 (m, 2H), 2.44-2.37 (m, 2H), 2.34-2.26 (m, 2H), 2.19-2.05 (m, 1H), 2.05-1.89 (m, 4H), 1.80-1.68 (m, 4H), 1.68-1.54 (m, 4H).

Example 148. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-((3S)-1-(4-(6-(2-(2,6-dioxopiperidin-3-yl)-1,3-dioxoisoindolin-4-yl)-2,6-diazaspiro[3.3]heptan-2-yl)-4-oxobutanoyl)pyrrolidin-3-yl)-2-fluoro-5-methoxybenzamide
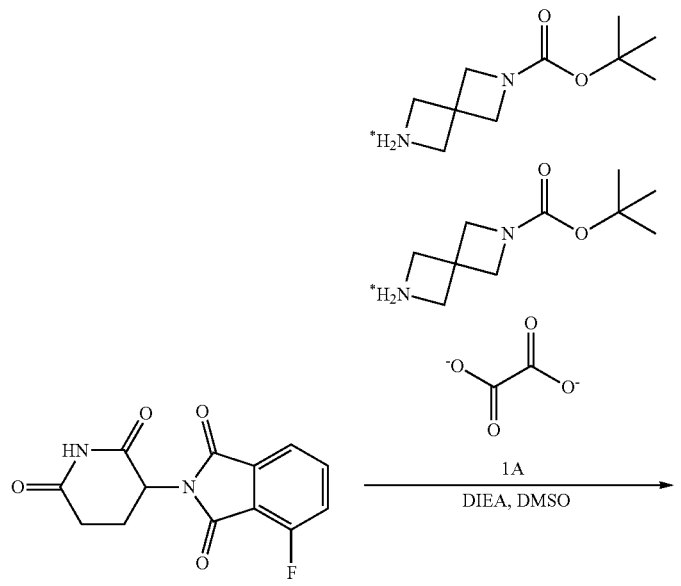
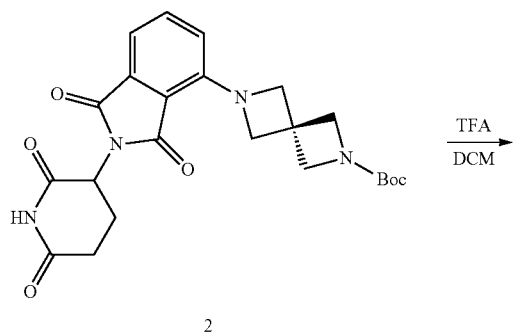
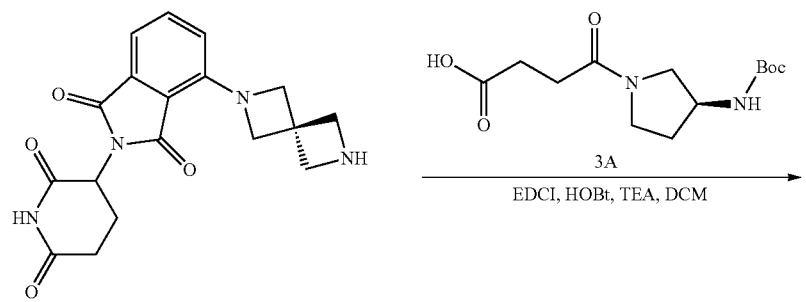

-continued

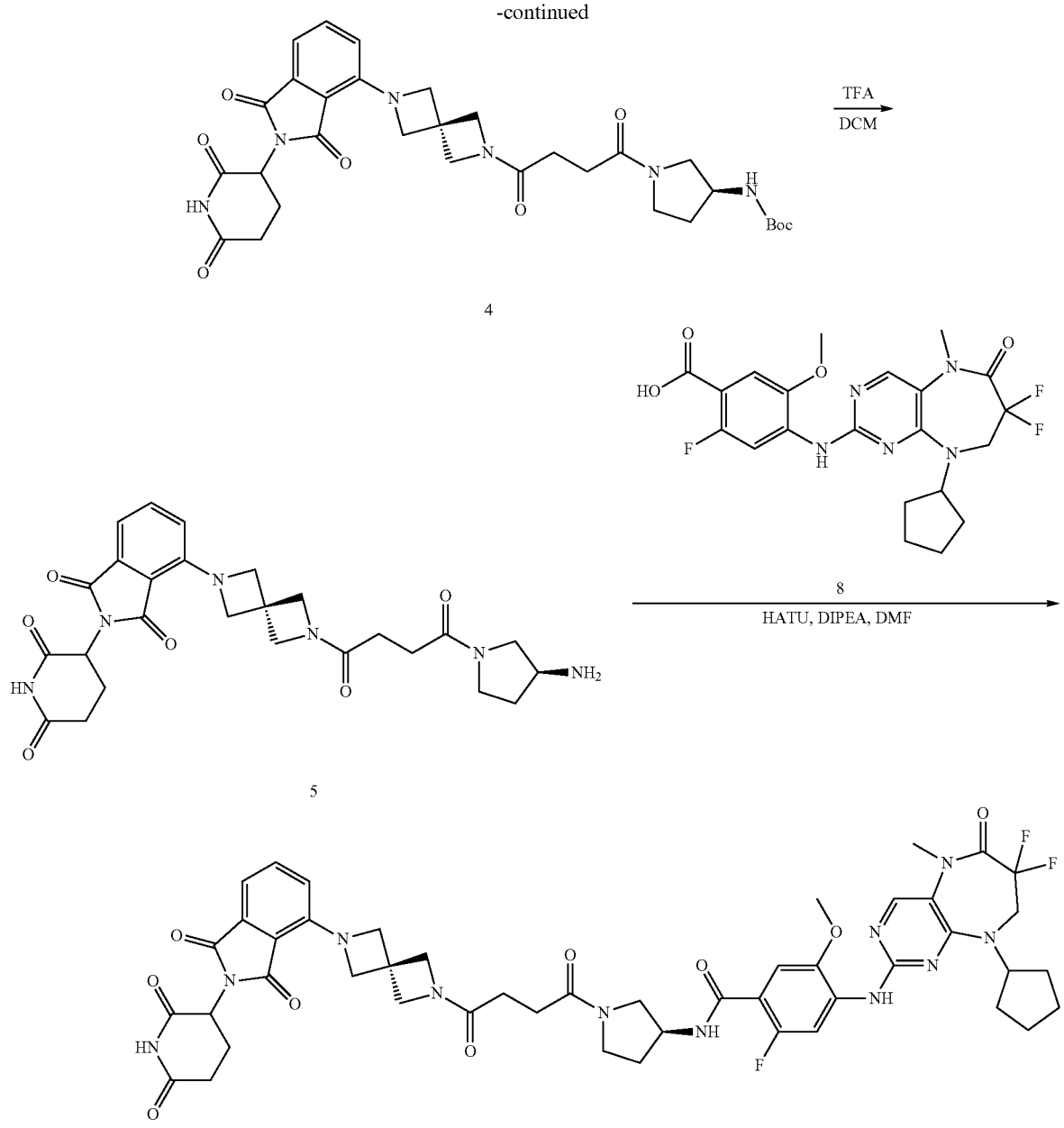

4

5

Compound 148

Step 1: Synthesis of tert-butyl 6-(2-(2,6-dioxopiperidin-3-yl)-1,3-dioxoisoindolin-4-yl)-2,6-diazaspiro[3.3]heptane-2-carboxylate (2)

A mixture of 2-(2,6-dioxopiperidin-3-yl)-4-fluoroisoindoline-1,3-dione (1.6 g, 5.79 mmol), 6-(tert-butoxycarbonyl)-6-aza-2-azoniaspiro[3.3]heptane oxalate (3.10 g, 6.37 mmol) and DIEA (2.25 g, 17.38 mmol, 3.03 mL) in DMSO (15 mL) was stirred at 80° C. for 40 hours. LCMS showed 30% of reactant remained and 51% of desired mass was detected. The reaction mixture was diluted with H$_2$O (100 mL) and extracted with EtOAc (80 mL×3). The combined organic layers were washed with brine (100 mL×5), dried over Na$_2$SO$_4$, filtered. The filtrate was concentrated in vacuo. The residue was purified by flash silica gel chromatography (12 g SepaFlash® Silica Flash Column, Eluent of 33~45% Ethyl acetate/Petroleum ether gradient @ 60 mL/min) to afford the titled compound (1.36 g, 2.99 mmol, 51.66% yield) as a yellow solid. MS(M+H)$^+$=455.1.

Step 2: Synthesis of 2-(2,6-dioxopiperidin-3-yl)-4-(2,6-diazaspiro[3.3]heptan-2-yl)isoindoline-1,3-dione (3)

To a solution of tert-butyl 6-(2-(2,6-dioxopiperidin-3-yl)-1,3-dioxoisoindolin-4-yl)-2,6-diazaspiro[3.3]heptane-2-carboxylate (300 mg, 660.10 μmol) in DCM (3 mL) was added TFA (3.31 g, 29.04 mmol, 2.15 mL) at 0° C., the mixture was stirred at 15° C. for 0.5 hours. LCMS showed the starting material was consumed completely. To the mixture was added TEA at 0° C. to adjust pH>7, the resulting mixture was used for the next step directly. MS(M+H)$^+$=355.1.

Step 3: Synthesis of tert-butyl ((3S)-1-(4-(6-(2-(2,6-dioxopiperidin-3-yl)-1,3-dioxoisoindolin-4-yl)-2,6-diazaspiro[3.3]heptan-2-yl)-4-oxobutanoyl)pyrrolidin-3-yl)carbamate (4)

To a solution of 2-(2,6-dioxopiperidin-3-yl)-4-(2,6-diazaspiro[3.3]heptan-2-yl)isoindoline-1,3-dione (230 mg, 649.06 µmol), (S)-4-(3-((tert-butoxycarbonyl)amino)pyrrolidin-1-yl)-4-oxobutanoic acid (223.01 mg, 778.87 µmol), EDCI (248.85 mg, 1.30 mmol) and HOBt (175.41 mg, 1.30 mmol) in DCM (4 mL) was added TEA (262.71 mg, 2.60 mmol, 361.36 µL) and the resulting mixture was stirred at 15° C. for 16 hours. LCMS showed reactant was consumed completely and 75% of desired mass was detected. To the mixture was added $CH_3COOH$ at 0° C. to adjust pH<7, most of the solvent was blown away with $N_2$, the residue was diluted with DMF and purified by prep-HPLC (column: Phenomenex Synergi $C_{18}$ 150*25 mm*10 um; mobile phase: [water(0.225% FA)-ACN]; B %: 25%-55%, 10 min) and the eluent was freeze-dried to afford the titled compound (200 mg, 321.20 µmol, 49.49% yield) as a yellow solid. MS(M+H)$^+$=623.2.

Step 4: Synthesis of 4-(6-(4-((S)-3-aminopyrrolidin-1-yl)-4-oxobutanoyl)-2,6-diazaspiro[3.3]heptan-2-yl)-2-(2,6-dioxopiperidin-3-yl)isoindoline-1,3-dione (5)

To a solution of tert-butyl ((3S)-1-(4-(6-(2-(2,6-dioxopiperidin-3-yl)-1,3-dioxoisoindolin-4-yl)-2,6-diazaspiro[3.3]heptan-2-yl)-4-oxobutanoyl)pyrrolidin-3-yl)carbamate (200 mg, 321.20 µmol) in DCM (2 mL) was added TFA (1.61 g, 14.13 mmol, 1.05 mL) at 0° C., the mixture was stirred at 15° C. for 0.5 hours. LCMS showed the starting material was consumed completely and 89% of desired mass was detected. To the mixture was added TEA at 0° C. to adjust pH>7, most of the solvent was blown away with $N_2$, the residue was diluted with DMF and purified by prep-HPLC (column: Waters Xbridge 150*25 mm*5 um; mobile phase: [water(10 mM $NH_4HCO_3$)-ACN]; B %: 11%-41%, 10 min), the eluent was freeze-dried to afford the titled compound (110 mg, 210.51 mol, 65.54% yield) as a yellow solid. MS(M+H)$^+$=523.0.

Step 5: Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-((3S)-1-(4-(6-(2-(2,6-dioxopiperidin-3-yl)-1,3-dioxoisoindolin-4-yl)-2,6-diazaspiro[3.3]heptan-2-yl)-4-oxobutanoyl)pyrrolidin-3-yl)-2-fluoro-5-methoxybenzamide (Compound 148)

To a solution of 4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzoic acid (85 mg, 182.63 mol) in DMF (1 mL) were added HATU (83.33 mg, 219.15 µmol) and DIEA (59.01 mg, 456.57 µmol, 79.53 µL), the mixture was stirred at 15° C. for 15 minutes, then to the mixture was added 4-(6-(4-((S)-3-aminopyrrolidin-1-yl)-4-oxobutanoyl)-2,6-diazaspiro[3.3]heptan-2-yl)-2-(2,6-dioxopiperidin-3-yl)isoindoline-1,3-dione (104.98 mg, 200.89 µmol) and the resulting mixture was stirred at 15° C. for 1 hour. LCMS showed reactant was consumed completely and 78% of desired mass was detected. The reaction mixture was purified by prep-HPLC (column: Waters Xbridge 150*25 mm*5 um; mobile phase: [water(10 mM $NH_4HCO_3$)-ACN]; B %: 35%-65%, 10 min), the eluent was freeze-dried to afford the titled compound (71.8 mg, 72.54 µmol, 39.72% yield, 98% purity) as a yellow solid. MS(M+H)$^+$=970.4.

$^1$H NMR (400 MHz, DMSO-$d_6$) δ=11.21-10.75 (m, 1H), 8.32-8.24 (m, 3H), 8.04 (s, 1H), 7.57 (t, J=7.8 Hz, 1H), 7.20 (dd, J=2.5, 6.3 Hz, 1H), 7.13 (d, J=7.0 Hz, 1H), 6.79 (d, J=8.5 Hz, 1H), 5.05 (dd, J=5.3, 12.6 Hz, 1H), 4.91-4.72 (m, 1H), 4.54-4.40 (m, 1H), 4.34 (m, 5H), 4.14-3.98 (m, 4H), 3.92 (s, 3H), 3.76 (m, 1H), 3.54 (m, 1H), 3.47-3.37 (m, 1H), 3.31 (m, 3H), 3.31-3.22 (m, 1H), 2.96-2.79 (m, 1H), 2.64-2.51 (m, 3H), 2.48-2.40 (m, 2H), 2.30-2.21 (m, 2H), 2.21-2.08 (m, 1H), 2.06-1.87 (m, 4H), 1.73 (m, 2H), 1.68-1.52 (m, 4H).

Example 149. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-((3S)-1-(5-(6-(2-(2,6-dioxopiperidin-3-yl)-1,3-dioxoisoindolin-4-yl)-2,6-diazaspiro[3.3]heptan-2-yl)-5-oxopentanoyl)pyrrolidin-3-yl)-2-fluoro-5-methoxybenzamide

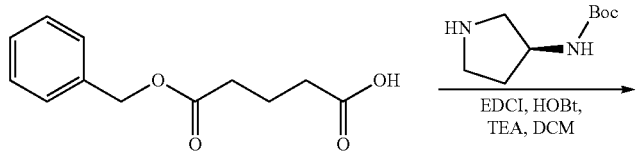

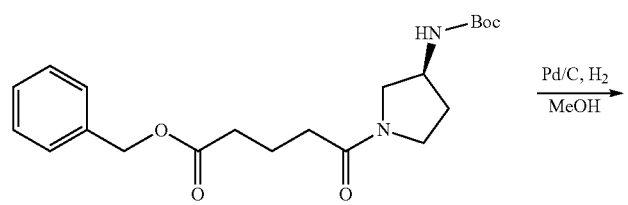

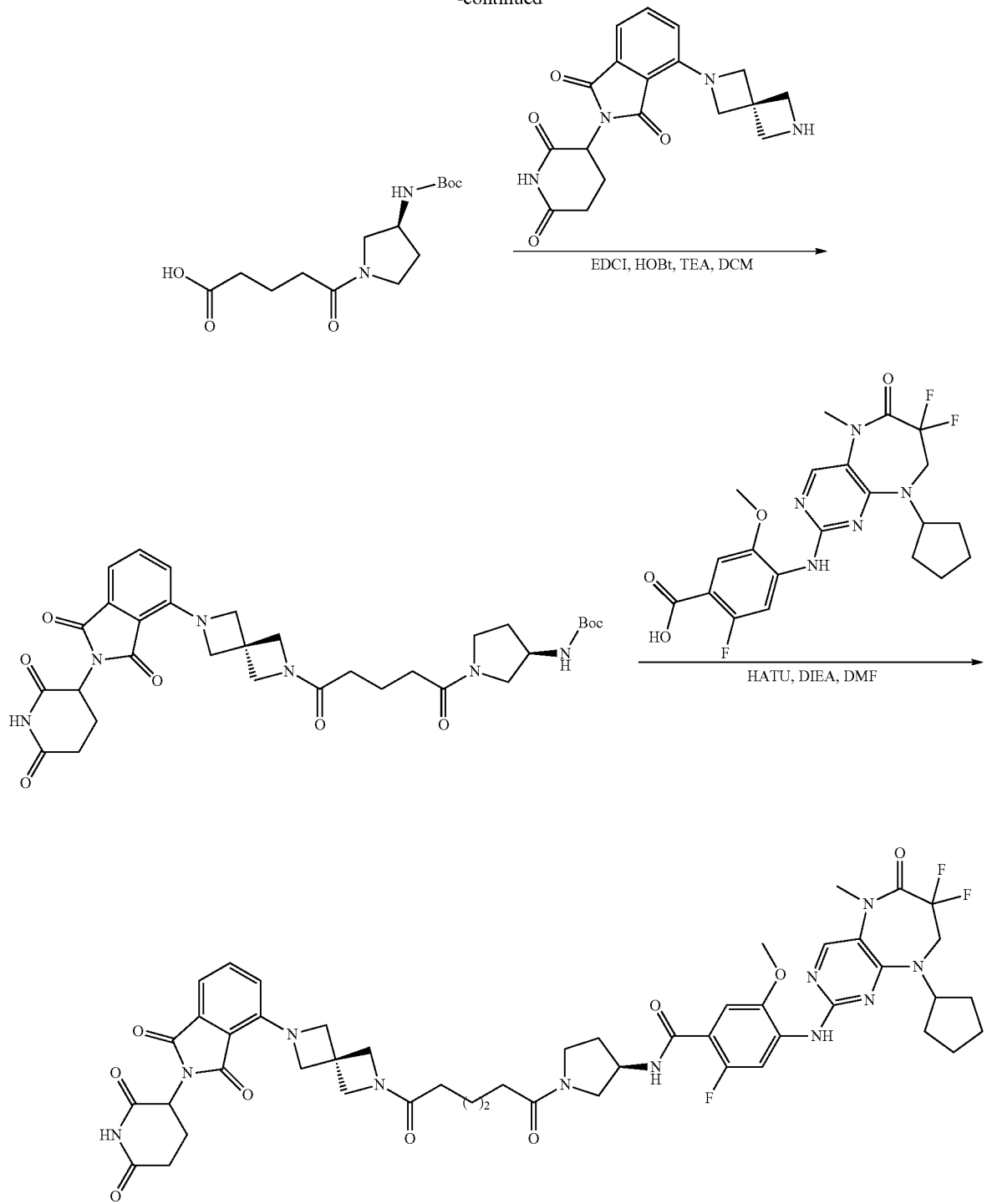
Compound 149
According to the above reaction scheme, in a manner similar to the other examples, obtained the titled compound (47.1 mg, 47.39 μmol, 36.76% yield, 99% purity) as a yellow solid. MS(M+H)$^+$=984.0.
$^1$H NMR (400 MHz, DMSO-d$_6$) δ=11.02 (br s, 1H), 8.38-8.14 (m, 3H), 8.03 (s, 1H), 7.56 (ddd, J=2.6, 7.0, 8.5 Hz, 1H), 7.20 (dd, J=1.0, 6.6 Hz, 1H), 7.13 (dd, J=1.3, 6.9 Hz, 1H), 6.77 (dd, J=4.3, 8.4 Hz, 1H), 5.05 (dd, J=5.4, 12.7 Hz, 1H), 4.81 (quin, J=7.9 Hz, 1H), 4.52-4.38 (m, 1H), 4.26-4.37 (m, 4H), 4.27 (br d, J=3.4 Hz, 2H), 4.14-3.98 (m, 4H), 3.91 (s, 3H), 3.72 (dd, J=6.6, 10.3 Hz, 1H), 3.64-3.52 (m, 1H), 3.51-3.42 (m, 1H), 3.34-3.40 (m, 2H), 3.26-3.32 (m, 2H), 2.93-2.80 (m, 1H), 2.63-2.51 (m, 2H), 2.21-2.29 (m, 2H), 2.20-2.04 (m, 3H), 2.03-1.87 (m, 4H), 1.67-1.78 (m, 4H), 1.66-1.53 (m, 4H).

Example 150. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(2-(2-(2-((2-(2,6-dioxopiperidin-3-yl)-1-oxoisoindolin-4-yl)amino)ethoxy)ethoxy)acetyl)pyrrolidin-3-yl)-2-fluoro-5-methoxybenzamide
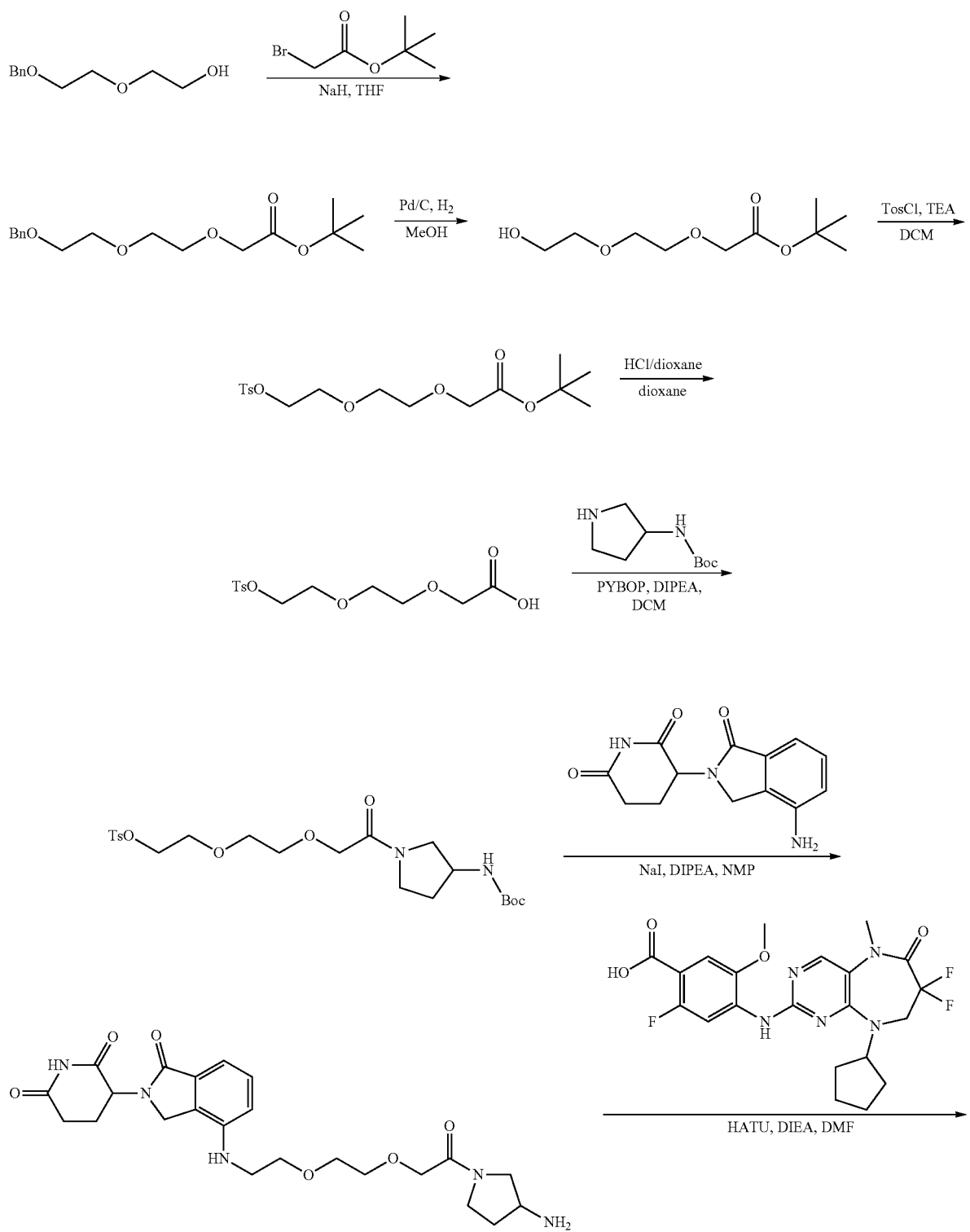

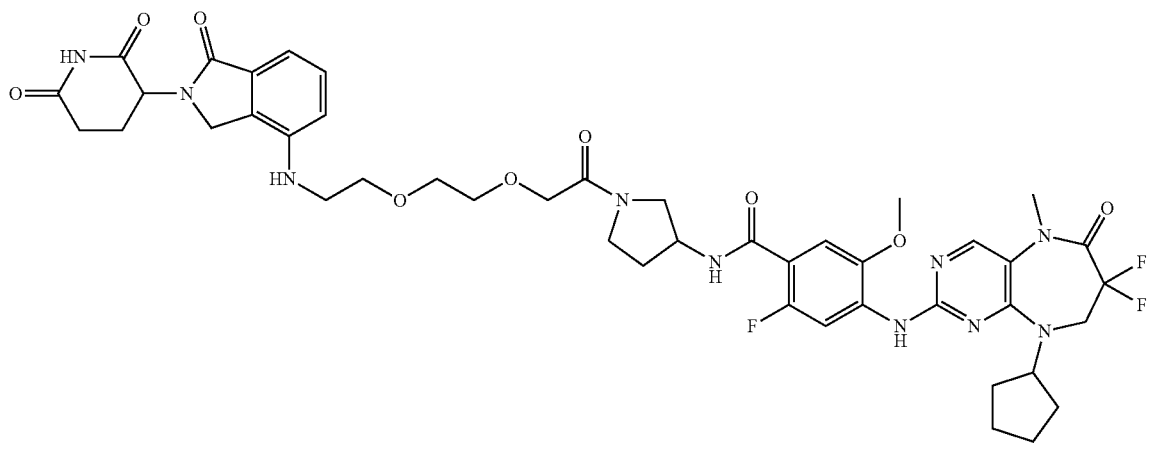

Compound 150

According to the above reaction scheme, in a manner similar to the other examples, obtained the titled compound (40.6 mg, 42.76 μmol, 24.23% yield, 97% purity) as yellow solid. MS(M+H)$^+$=921.5

$^1$H NMR (400 MHz, DMSO-d$_6$) δ=11.01 (br s, 1H), 8.32-8.24 (m, 4H), 8.05 (s, 1H), 7.31-7.25 (m, 1H), 7.22-7.17 (m, 1H), 6.97-6.91 (m, 1H), 6.83-6.77 (m, 1H), 5.64-5.57 (m, 1H), 5.16-5.05 (m, 1H), 4.86-4.76 (m, 1H), 4.51-4.36 (m, 1H), 4.27-4.20 (m, 1H), 4.17-4.11 (m, 1H), 4.11-4.03 (m, 4H), 3.91 (d, J=3.8 Hz, 3H), 3.75-3.68 (m, 1H), 3.65-3.54 (m, 6H), 3.53-3.41 (m, 4H), 3.33-3.27 (m, 2H), 2.99-2.86 (m, 1H), 2.61 (br d, J=17.4 Hz, 1H), 2.31-2.24 (m, 1H), 2.19-2.10 (m, 1H), 2.08-1.85 (m, 5H), 1.78-1.54 (m, 6H).

Example 151. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(2-(2-((2-(2,6-dioxopiperidin-3-yl)-1,3-dioxoisoindolin-4-yl)amino)ethoxy)ethyl)-2-fluoro-5-methoxybenzamide

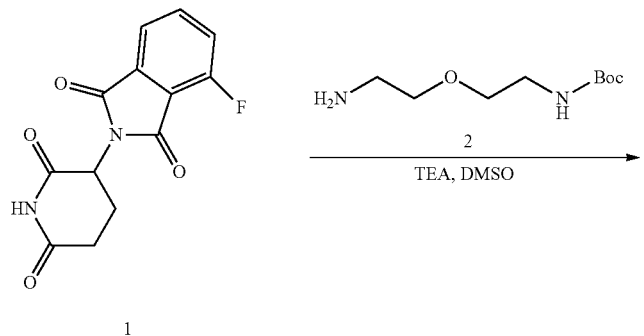

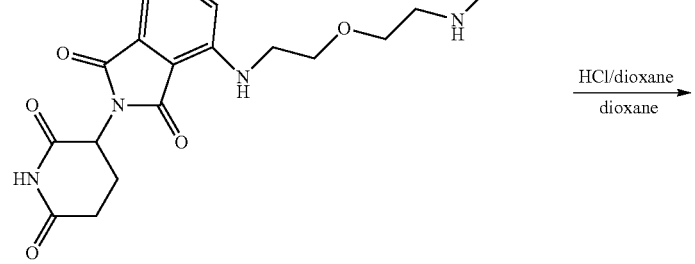

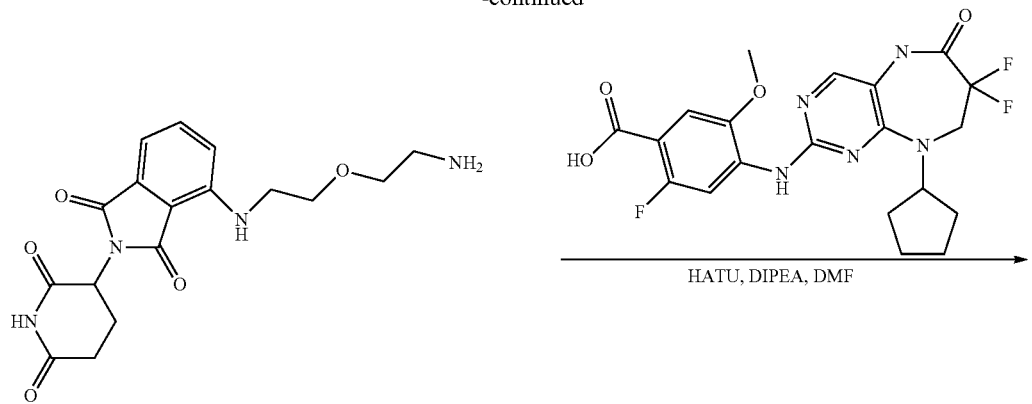

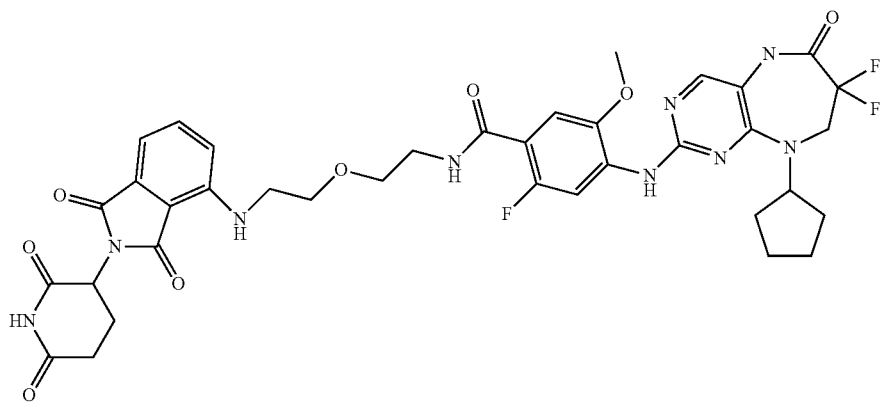

Compound 151

Step 1: Synthesis of tert-butyl (2-(2-((2-(2,6-dioxopiperidin-3-yl)-1,3-dioxoisoindolin-4-yl)amino)ethoxy)ethyl)carbamate (3)

To a mixture of 2-(2,6-dioxopiperidin-3-yl)-4-fluoroisoindoline-1,3-dione (1 g, 3.62 mmol) in DMSO (5 mL) were added TEA (1.10 g, 10.86 mmol, 1.51 mL) and tert-butyl (2-(2-aminoethoxy)ethyl)carbamate (887.41 mg, 4.34 mmol) in one portion at 20° C. and the resulting mixture was stirred at 80° C. for 16 h. LCMS showed starting material was consumed completely and desired mass was detected. The reaction mixture was diluted with H$_2$O (20 mL) and extracted with EtOAC (20 mL×3). The organic layer was washed with brine (20 mL×3), dried over Na$_2$SO$_4$, filtered and concentrated. The residue was purified by column chromatography (SiO$_2$, Petroleum ether/Ethyl acetate=5/1 to 1/1) to afford the titled compound (687 mg, 1.46 mmol, 40.39% yield, 98% purity) as a green oil. MS(M−100+H)$^+$=361.3

Step 2: Synthesis of 4-((2-(2-aminoethoxy)ethyl)amino)-2-(2,6-dioxopiperidin-3-yl)isoindoline-1,3-dione To a mixture of tert-butyl (2-(2-((2-(2,6-dioxopiperidin-3-yl)-1,3-dioxoisoindolin-4-yl)amino)ethoxy)ethyl)carbamate (680 mg, 1.48 mmol) in dioxane (5 mL) was added HCl/dioxane (4 M, 10 mL) in one portion at 20° C. and the resulting mixture was stirred at 20° C. for 1 h. LCMS showed starting material was consumed completely and desired mass was detected. The reaction mixture was concentrated in vacuum to afford the titled compound (590 mg, crude, HCl) as a yellow solid. MS(M+H)$^+$=361.3

Step 3: Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(2-(2-((2-(2,6-dioxopiperidin-3-yl)-1,3-dioxoisoindolin-4-yl)amino)ethoxy)ethyl)-2-fluoro-5-methoxybenzamide (Compound 151)

To a solution of 4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzoic acid (150 mg, 322.29 µmol) in DMF (2 mL) was added HATU (134.80 mg, 354.51 µmol) and DIPEA (83.31 mg, 644.57 µmol, 112.27 µL). The mixture was stirred at 20° C. for 10 min and a solution of 4-((2-(2-aminoethoxy)ethyl)amino)-2-(2,6-dioxopiperidin-3-yl)isoindoline-1,3-dione (166.26 mg, 418.97 µmol, HCl) in DMF (2 mL) and DIPEA (83.31 mg, 644.57 µmol, 112.27 µL) was added drop-wise and the resulting mixture was stirred at 20° C. for 1 h. LCMS showed starting material was consumed completely and desired mass was detected. The reaction mixture was diluted with H$_2$O (10 mL) and extracted with EtOAc (10 mL×3). The organic layer was dried over Na$_2$SO$_4$, filtered and concentrated. The residue was purified by prep-HPLC (column: 3_Phenomenex Luna C$_{18}$ 75*30 mm*3 um; mobile phase: [water (0.1% TFA)-ACN]; B %: 46%-66%, 7 min) and then lyophilized to afford the titled compound (95.9 mg, 101.96 μmol, 31.64% yield, 98% purity, TFA) as a yellow solid. MS(M+H)$^+$=808.1

$^1$H NMR (400 MHz, CD$_3$OD) δ=8.22-8.17 (m, 2H), 7.51 (dd, J=7.2, 8.6 Hz, 1H), 7.42 (d, J=6.7 Hz, 1H), 7.09 (d, J=8.6 Hz, 1H), 7.00 (d, J=7.2 Hz, 1H), 5.06-4.98 (m, 1H), 4.98-4.92 (m, 1H), 4.13 (t, J=12.8 Hz, 2H), 3.98 (s, 3H), 3.79-3.75 (m, 2H), 3.74-3.70 (m, 2H), 3.65-3.59 (m, 2H), 3.54-3.49 (m, 2H), 3.42 (s, 3H), 2.78-2.50 (m, 3H), 2.08-1.93 (m, 3H), 1.85-1.66 (m, 6H)

Example 152. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(2-(2-(2-((2-(2,6-dioxopiperidin-3-yl)-1,3-dioxoisoindolin-4-yl)amino)ethoxy)ethoxy)ethyl)-2-fluoro-5-methoxybenzamide

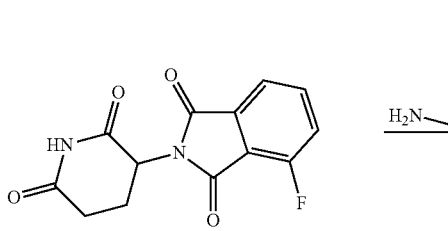
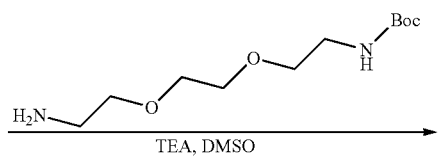

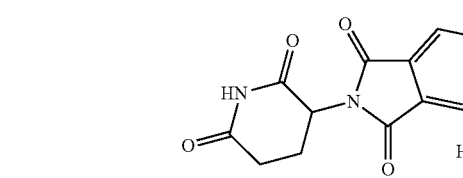
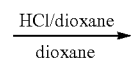

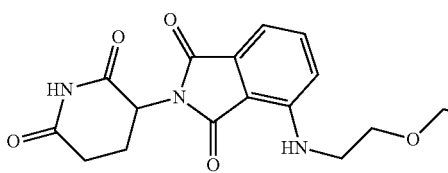
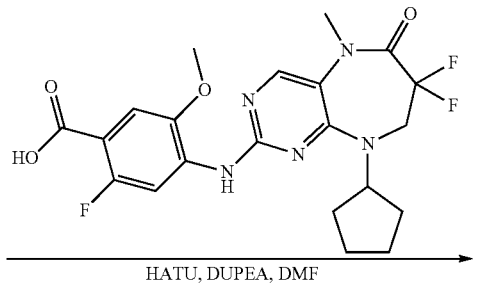

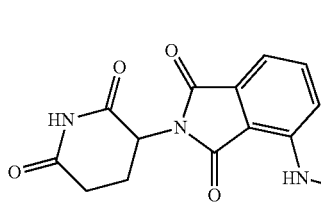
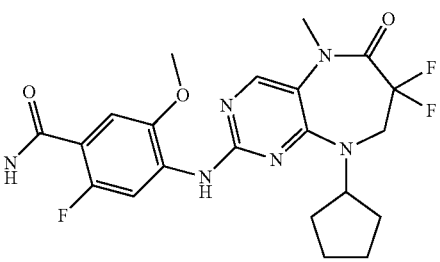

Compound 152

According to the above reaction scheme, in a manner similar to the other examples, obtained the titled compound (167.6 mg, 190.85 μmol, 44.41% yield, 97% purity) as a yellow solid. MS(M+H)⁺=852.6

¹H NMR (400 MHz, MeOD) δ=8.23 (d, J=14.6 Hz, 1H), 8.19 (s, 1H), 7.39-7.33 (m, 2H), 6.90 (dd, J=7.8, 11.8 Hz, 2H), 4.98 (dd, J=5.5, 12.7 Hz, 1H), 4.84-4.79 (m, 1H), 4.04 (t, J=13.4 Hz, 2H), 3.95 (s, 3H), 3.77-3.70 (m, 8H), 3.64-3.60 (m, 2H), 3.42-3.39 (m, 5H), 2.89-2.78 (m, 1H), 2.75-2.60 (m, 2H), 2.13-2.03 (m, 3H), 1.86-1.76 (m, 2H), 1.74-1.61 (m, 4H)

Example 153. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(2-(2-(2-(2-((2-(2,6-dioxopiperidin-3-yl)-1,3-dioxoisoindolin-4-yl)amino)ethoxy)ethoxy)ethoxy)ethyl)-2-fluoro-5-methoxybenzamide

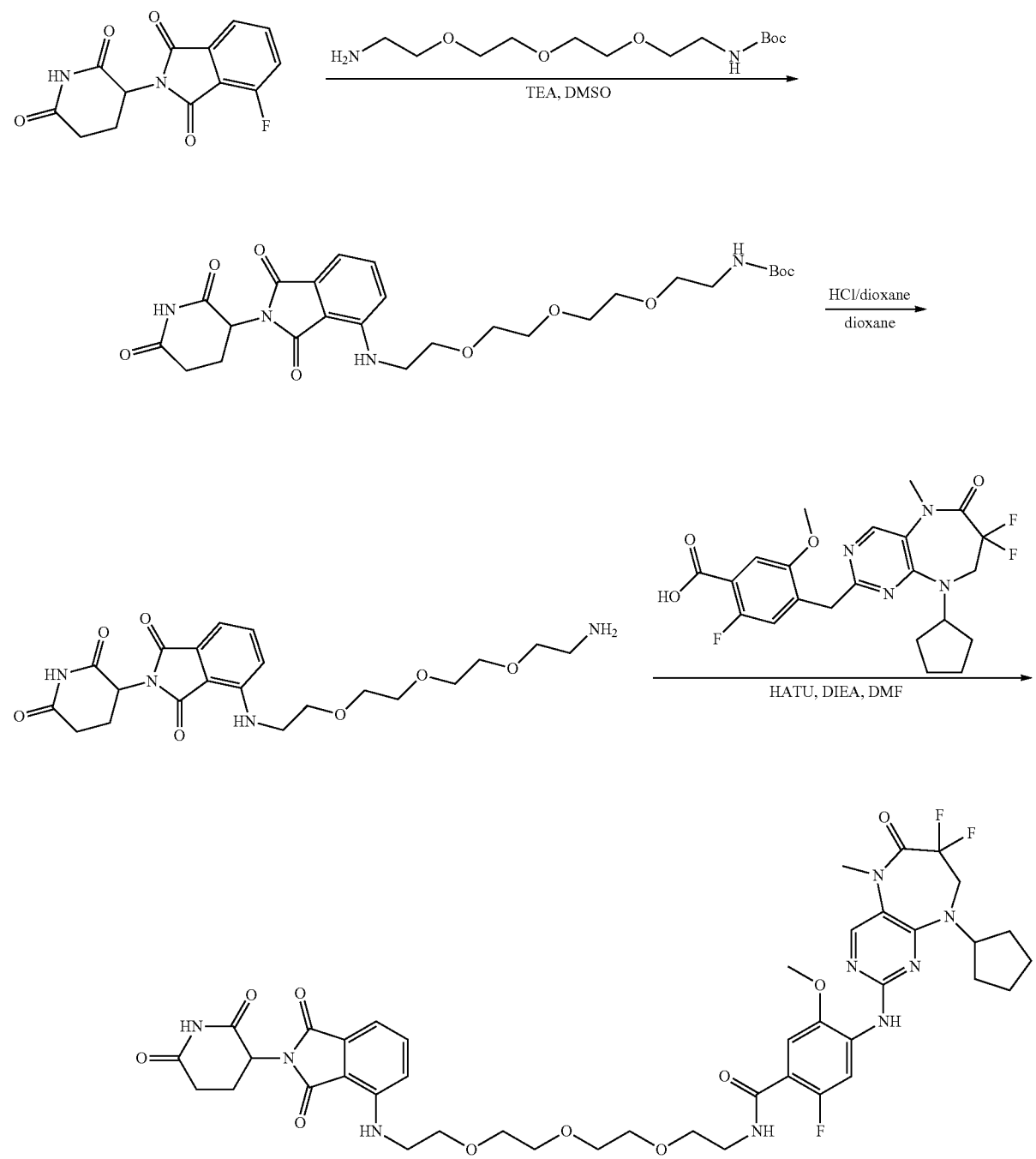

Compound 153

According to the above reaction scheme, in a manner similar to the other examples, obtained the titled compound (80.8 mg, 88.39 μmol, 21.43% yield, 98% purity) was obtained as a yellow solid. MS(M+H)⁺=896.7.

¹H NMR (400 MHz, DMSO-d₆) δ=11.10 (s, 1H), 8.29 (s, 1H), 8.25 (d, J=13.8 Hz, 1H), 8.04 (s, 1H), 7.88-7.99 (m, 1H), 7.55 (dd, J₁=8.3 Hz, J₂=7.3 Hz, 1H), 7.28 (d, J=6.8 Hz, 1H), 7.10 (d, J=8.7 Hz, 1H), 7.01 (d, J=7.0 Hz, 1H), 6.58 (t, J=5.7 Hz, 1H), 5.05 (dd, J₁=12.9 Hz, J₂=5.4 Hz, 1H), 4.88-4.73 (m, 1H), 4.07 (t, J=13.9 Hz, 2H), 3.90 (s, 3H), 3.65-3.48 (m, 12H), 3.48-3.39 (m, 7H), 2.93-2.79 (m, 1H), 2.62-2.52 (m, 2H), 2.06-1.86 (m, 3H), 1.78-1.51 (m, 6H).

Example 154. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(8-((2-(2,6-dioxopiperidin-3-yl)-1,3-dioxoisoindolin-4-yl)amino)octyl)-2-fluoro-5-methoxybenzamide

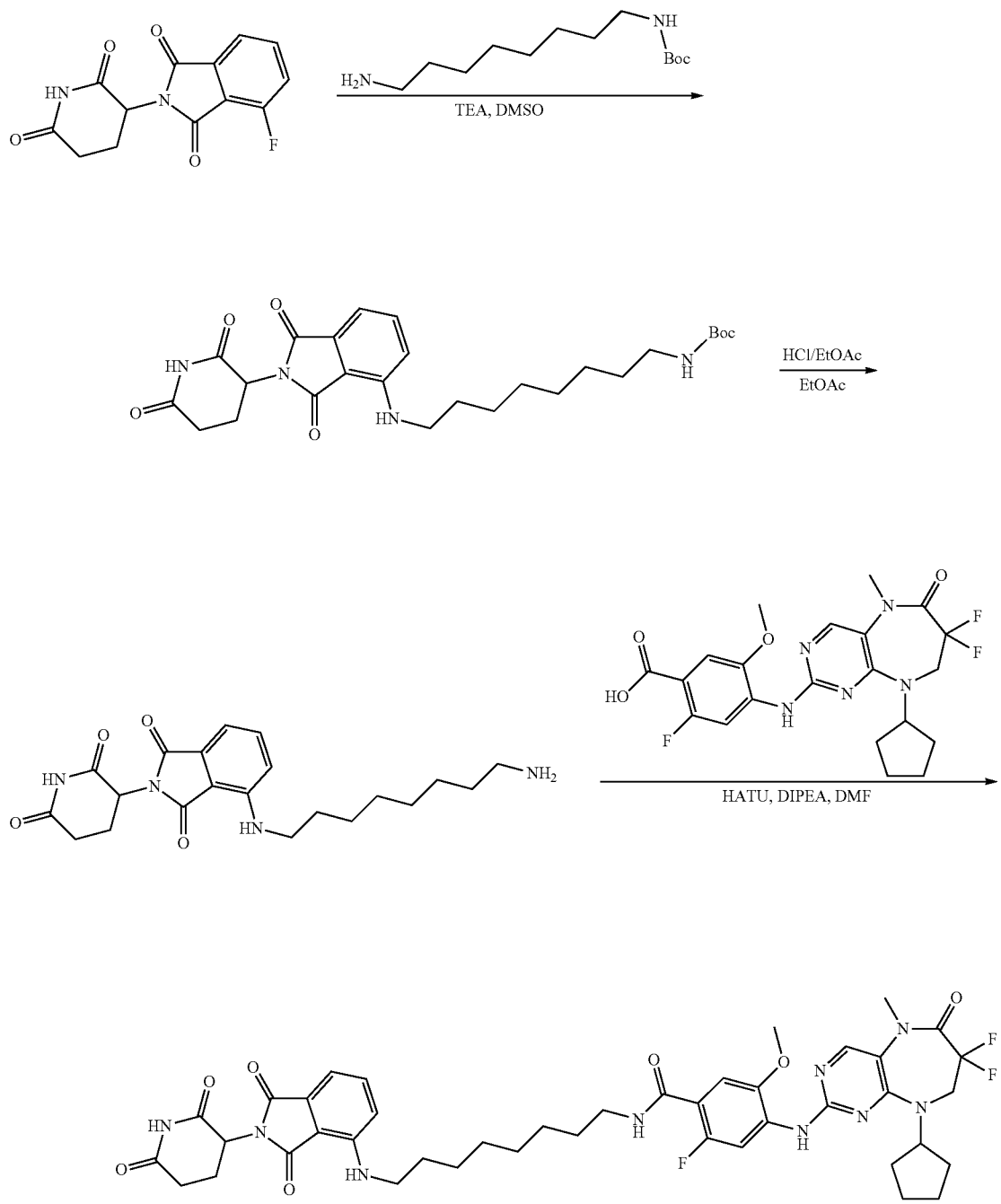

Compound 154

According to the above reaction scheme, in a manner similar to the other examples, obtained the titled compound (122.3 mg, 141.36 μmol, 61.76% yield, 98% purity) as yellow solid. MS(M+H)$^+$=848.6.

$^1$H NMR (400 MHz, DMSO-d6) δ 11.08 (s, 1H), 8.34-8.18 (m, 2H), 8.07-7.95 (m, 2H), 7.57 (dd, J=8.6, 7.0 Hz, 1H), 7.23 (d, J=6.7 Hz, 1H), 7.08 (d, J=8.6 Hz, 1H), 7.01 (d, J=7.0 Hz, 1H), 6.52 (t, J=5.9 Hz, 1H), 5.04 (dd, J=12.9, 5.4 Hz, 1H), 4.81 (t, J=8.0 Hz, 1H), 4.07 (t, J=13.9 Hz, 2H), 3.90 (s, 3H), 3.29-3.16 (m, 6H), 2.95-2.81 (m, 1H), 2.62-2.52 (m, 3H), 2.08-1.90 (m, 3H), 1.77-1.46 (m, 10H), 1.41-1.26 (m, 8H).

Example 155. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(2-(3-((2-(2,6-dioxopiperidin-3-yl)-1,3-dioxoisoindolin-4-yl)amino)propoxy)ethyl)-2-fluoro-5-methoxybenzamide According to the above reaction scheme, in a manner similar to the other examples, obtained the titled compound (50.4 mg, 57.65 μmol, 26.83% yield, 94% purity) as a yellow solid. MS(M+H)$^+$=822.6.

$^1$H NMR (400 MHz, DMSO-d$_6$) δ=11.08 (s, 1H), 8.29 (s, 1H), 8.22 (d, J=13.8 Hz, 1H), 8.04 (s, 1H), 7.96 (q, J=5.4 Hz, 1H), 7.54 (dd, J$_1$=7.2, J$_2$=8.4 Hz, 1H), 7.28 (d, J=6.9 Hz, 1H), 7.07 (d, J=8.6 Hz, 1H), 6.98 (d, J=7.0 Hz, 1H), 6.69 (t, J=5.9 Hz, 1H), 5.03 (dd, J$_1$=5.4, J$_2$=12.9 Hz, 1H), 4.88-4.70 (m, 1H), 4.07 (t, J=13.9 Hz, 2H), 3.89 (s, 3H), 3.59-3.51 (m, 4H), 3.50-3.47 (m, 2H), 3.42-3.33 (m, 5H), 2.93-2.80 (m, 1H), 2.60-2.52 (m, 2H), 2.05-1.88 (m, 3H), 1.82 (br t, J=6.1 Hz, 2H), 1.75-1.50 (m, 6H).

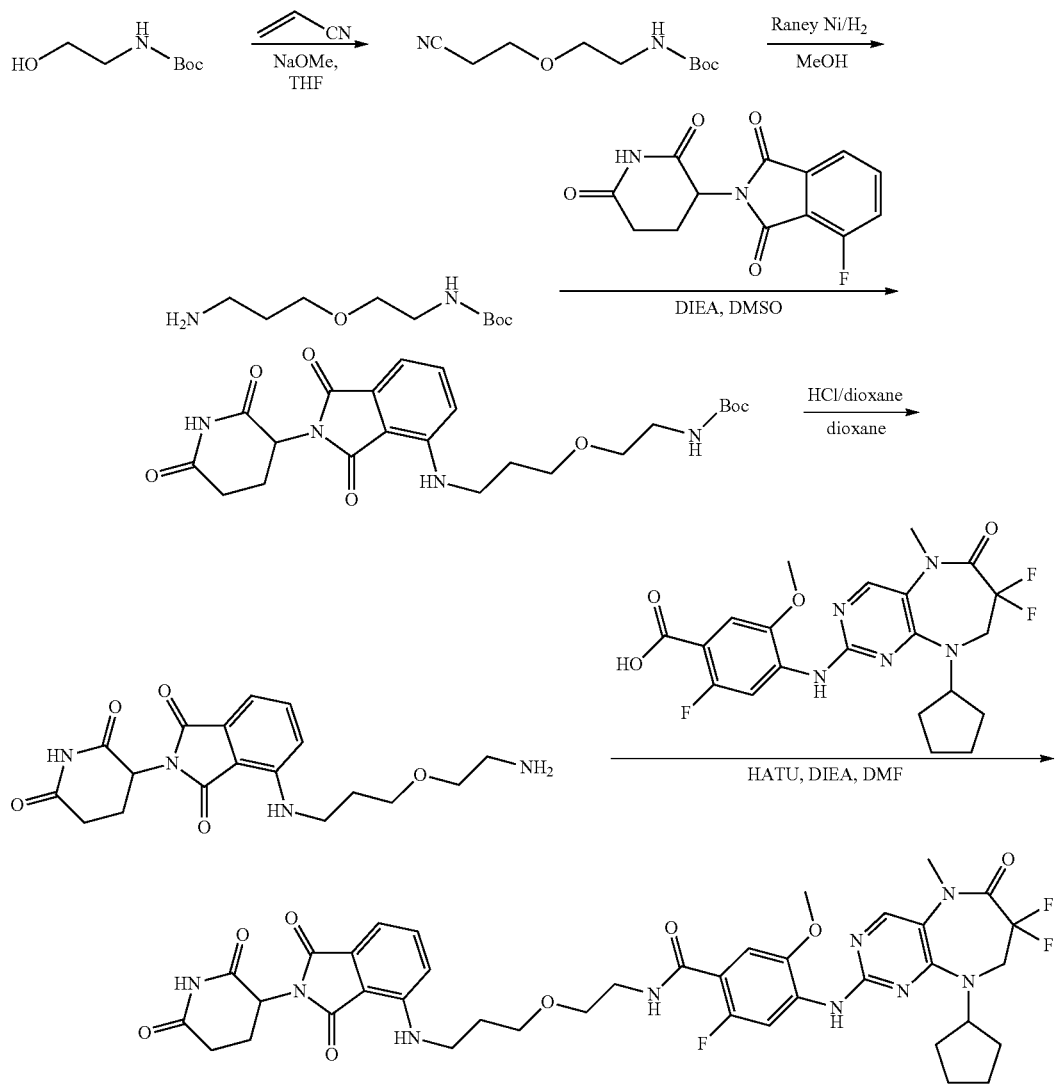

Compound 155

Example 156. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(2-(3-(2-((2-(2,6-dioxopiperidin-3-yl)-1,3-dioxoisoindolin-4-yl)amino)ethoxy)propoxy)ethyl)-2-fluoro-5-methoxybenzamide
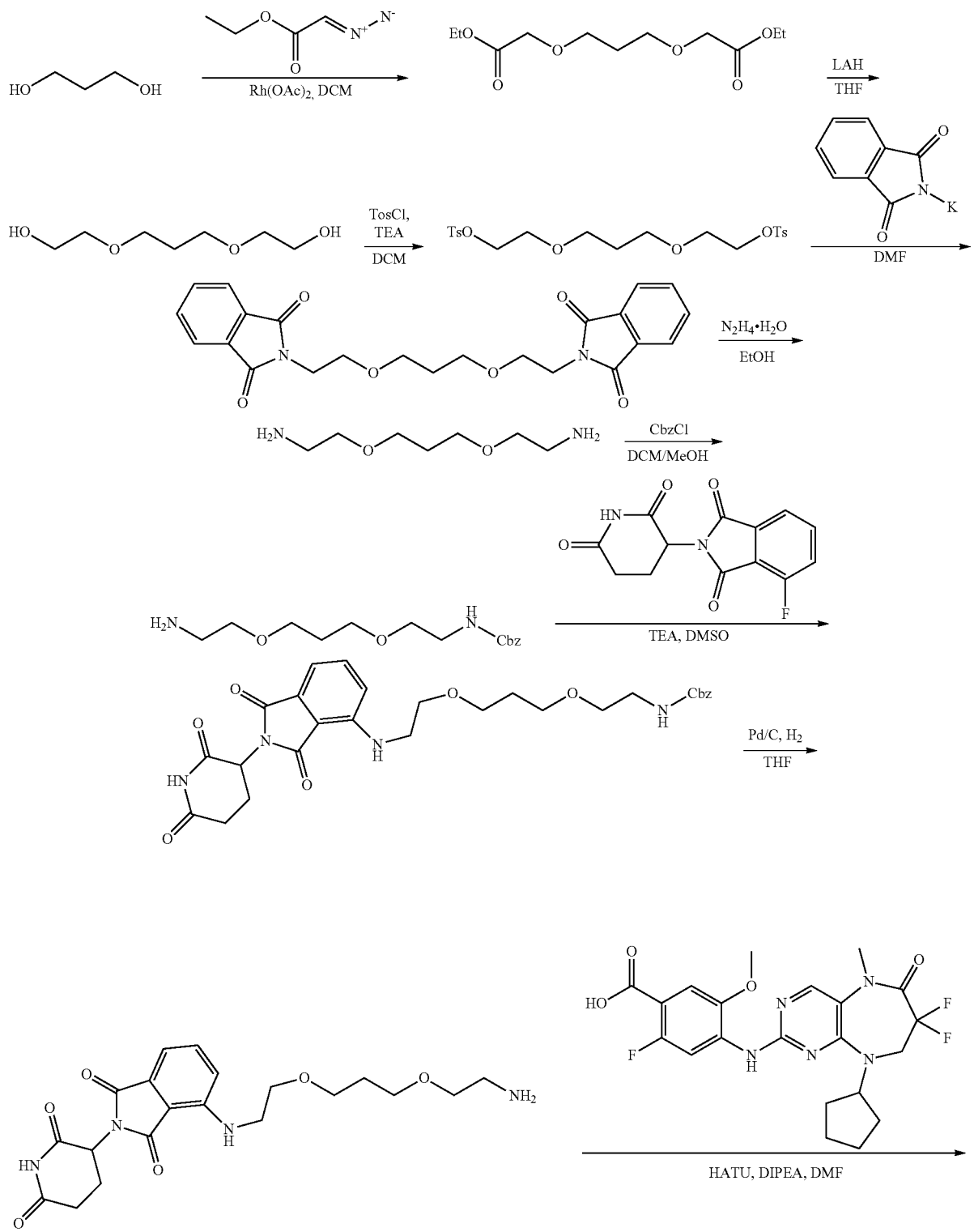

601

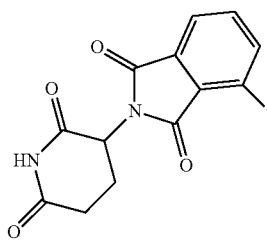

-continued

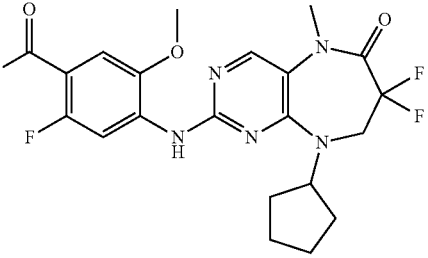

Compound 156

According to the above reaction scheme, in a manner similar to the other examples, obtained the titled compound (27.6 mg, 27.89 μmol, 12.98% yield, 99% purity, TFA) as a yellow solid. MS(M+H)+=866.3

$^1$H NMR (400 MHz, CD$_3$OD) δ=8.20 (s, 1H), 8.11 (d, J=13.8 Hz, 1H), 7.45-7.39 (m, 2H), 6.95 (t, J=7.4 Hz, 2H), 5.01 (dd, J=5.4, 12.8 Hz, 1H), 4.98-4.90 (m, 1H), 4.15 (t, J=12.6 Hz, 2H), 3.97 (s, 3H), 3.65-3.59 (m, 10H), 3.45-3.42 (m, 2H), 3.41 (s, 3H), 2.89-2.80 (m, 1H), 2.76-2.62 (m, 2H), 2.15-2.02 (m, 3H), 1.90-1.81 (m, 4H), 1.77-1.68 (m, 4H)

Example 157. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(3-(3-(2-((2-(2,6-dioxopiperidin-3-yl)-1,3-dioxoisoindolin-4-yl)amino)ethoxy)propoxy)propyl)-2-fluoro-5-methoxybenzamide

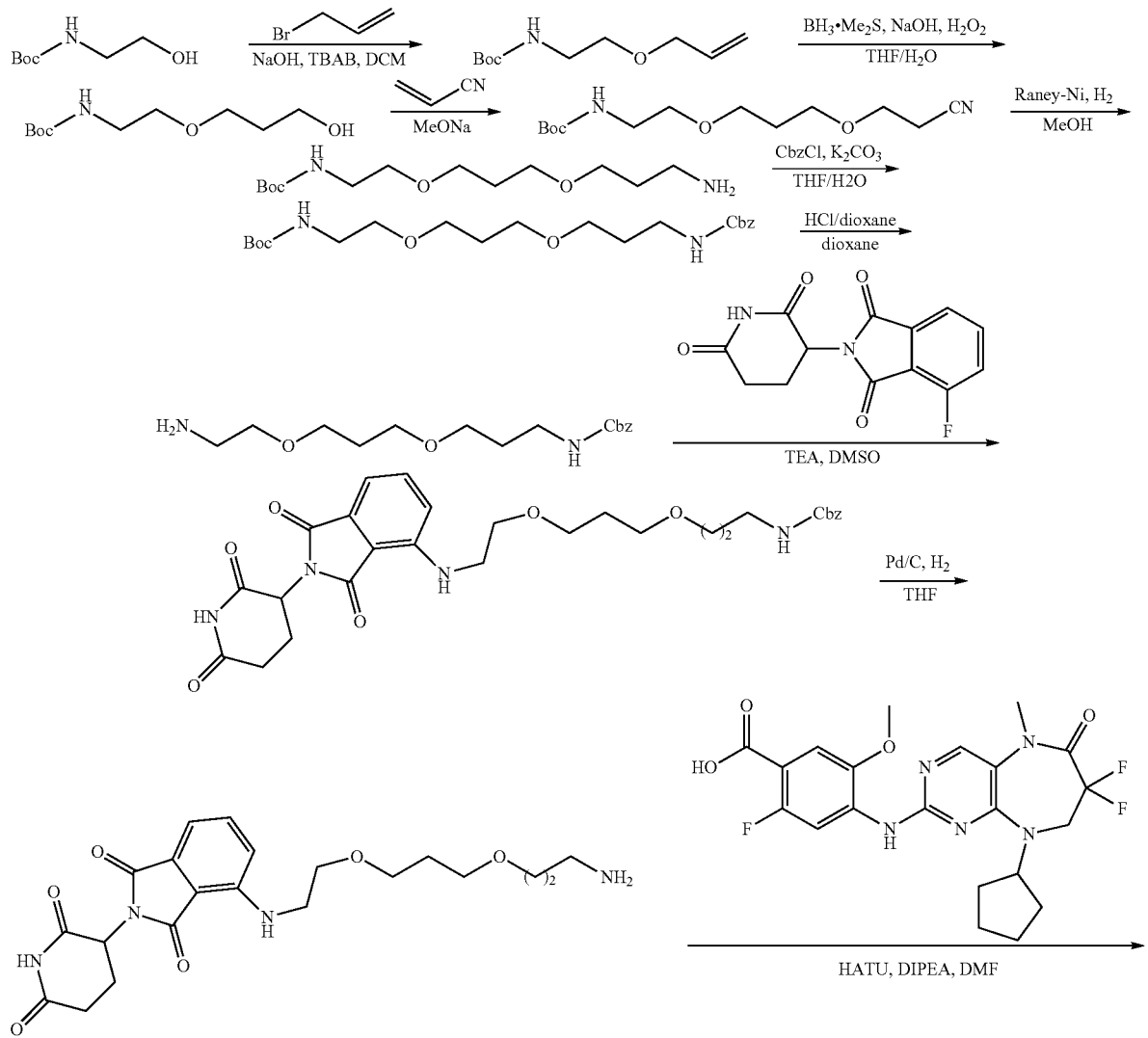

603

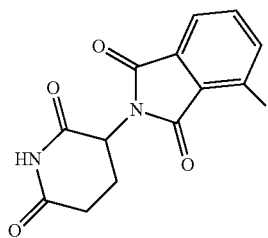

-continued

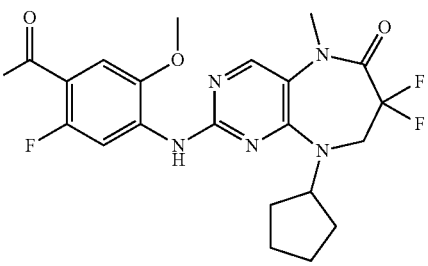

Compound 167

According to the above reaction scheme, in a manner similar to the other examples, obtained the titled compound (74.7 mg, 72.15 μmol, 16.79% yield, 96% purity, TFA) as a yellow solid. MS(M+H)$^+$=880.0

$^1$H NMR (400 MHz, CD 30D) δ=8.21-8.14 (m, 2H), 7.52-7.40 (m, 2H), 7.04-6.96 (m, 2H), 5.02 (br dd, J=5.6, 12.4 Hz, 1H), 4.99-4.95 (m, 1H), 4.13 (t, J=12.6 Hz, 2H), 3.98 (s, 3H), 3.65-3.61 (m, 2H), 3.61-3.55 (m, 6H), 3.51 (t, J=6.6 Hz, 2H), 3.44-3.41 (m, 2H), 3.40 (s, 3H), 2.89-2.63 (m, 3H), 2.13-2.02 (m, 3H), 1.89-1.66 (m, 10H)

Example 158. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(8-((2-(2,6-dioxopiperidin-3-yl)-1,3-dioxoisoindolin-4-yl)amino)-8-oxooctyl)-2-fluoro-5-methoxybenzamide

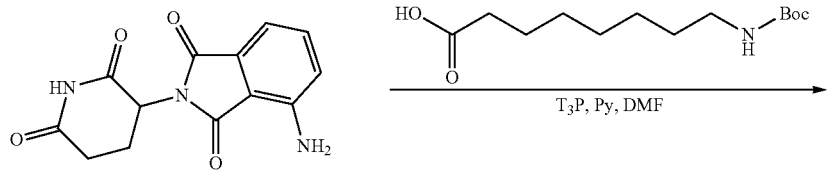

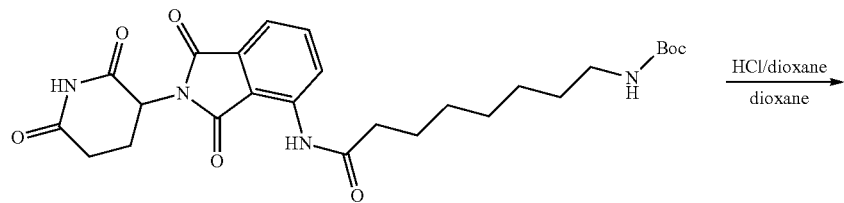

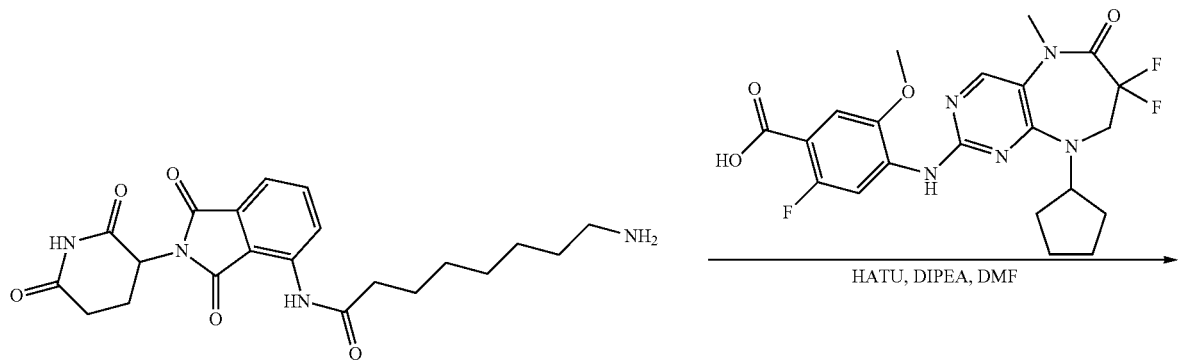

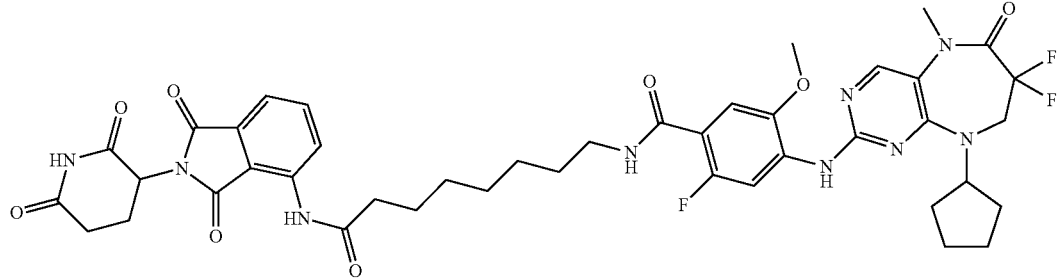

Compound 158

According to the above reaction scheme, in a manner similar to the other examples, obtained the titled compound (66.7 mg, 64.93 μmol, 15.11% yield, 95% purity) as a light yellow solid. MS(M+H)=862.6.

$^1$H NMR (400 MHz, CD$_3$OD) δ 8.63 (d, J=8.4 Hz, 1H), 8.25-8.14 (m, 2H), 7.79-7.69 (m, 1H), 7.54 (d, J=7.3 Hz, 1H), 7.38 (d, J=6.7 Hz, 1H), 5.17-5.09 (m, 1H), 5.05-4.98 (m, 1H), 4.13 (t, J=12.7 Hz, 2H), 3.98 (s, 3H), 3.43-3.40 (m, 2H), 2.91-2.81 (m, 1H), 2.78-2.66 (m, 2H), 2.50 (t, J=7.4 Hz, 2H), 2.15-2.03 (m, 3H), 1.84-1.60 (m, 10H), 1.52-1.38 (m, 6H)

Example 159. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(2-(3-((2-(2,6-dioxopiperidin-3-yl)-1,3-dioxoisoindolin-4-yl)amino)propanoyl)-2-azaspiro[3.3]heptan-6-yl)-2-fluoro-5-methoxybenzamide

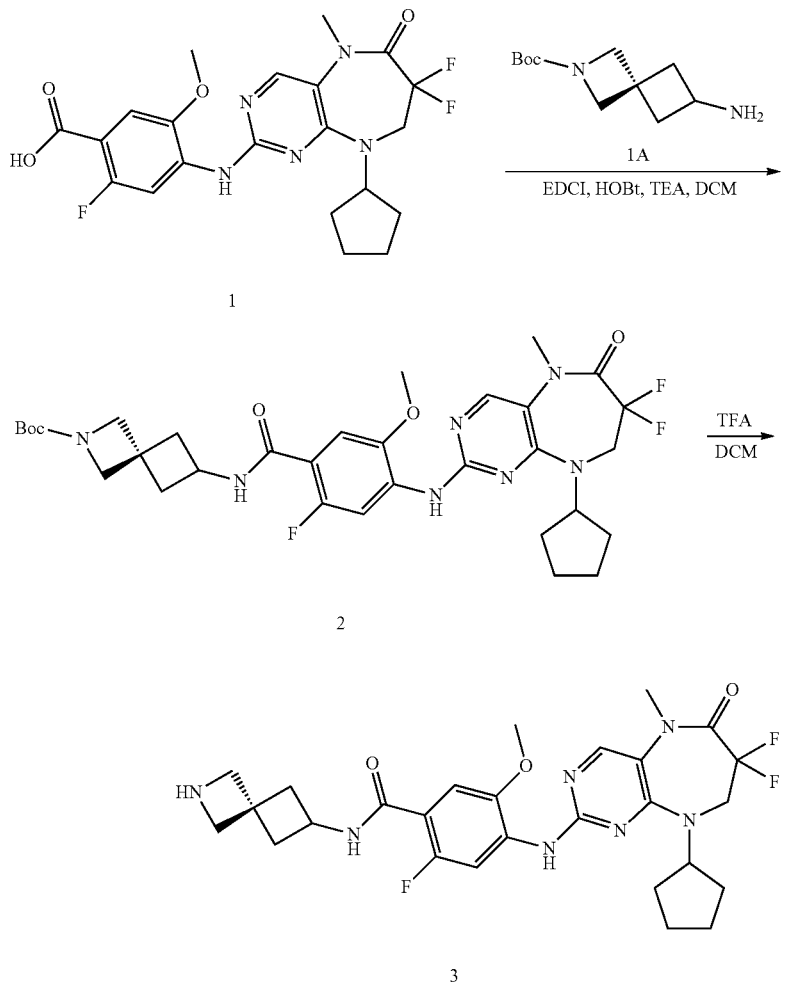

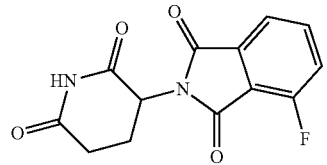
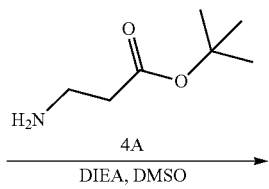
4
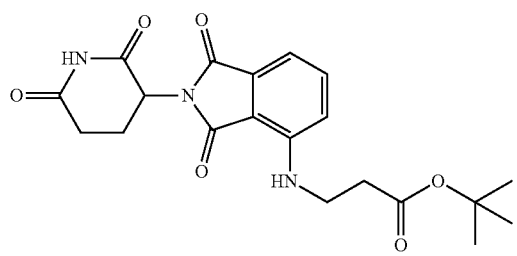
5
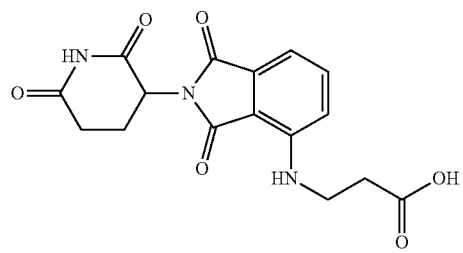
6
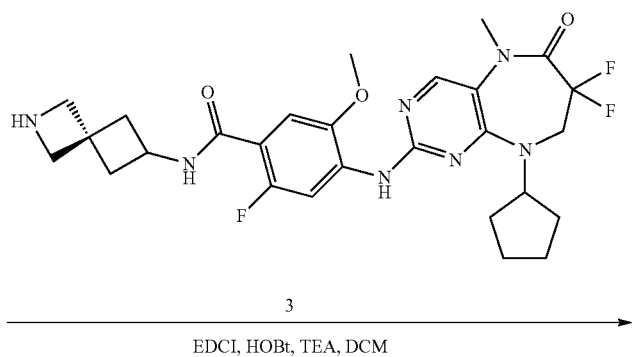
3
EDCI, HOBt, TEA, DCM
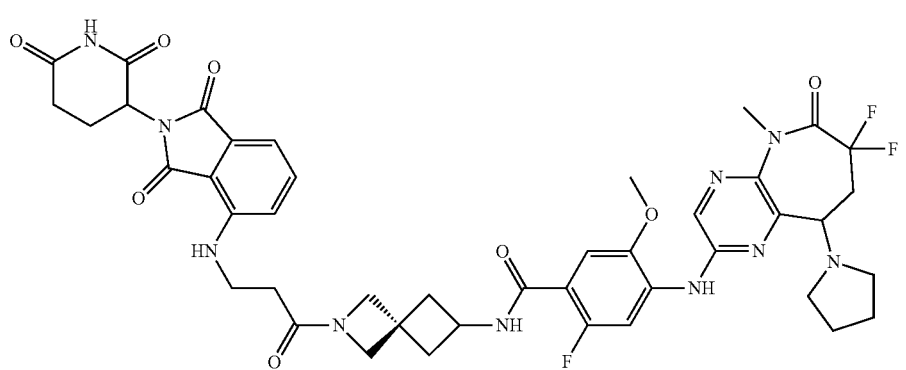
Compound 159

Step 1: Synthesis of tert-butyl 6-(4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzamido)-2-azaspiro[3.3]heptane-2-carboxylate (2)

A mixture of 4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzoic acid (100 mg, 214.86 μmol), tert-butyl 6-amino-2-azaspiro[3.3]heptane-2-carboxylate (54.73 mg, 257.83 μmol), EDCI (61.78 mg, 322.29 umol), HOBt (43.55 mg, 322.29 umol) and TEA (65.22 mg, 644.57 mol, 89.72 μL) in DCM (2 mL) was stirred at 15° C. for 12 hours. LCMS showed reactant was consumed completely and 87% of desired mass was detected. The reaction mixture was combined with another batch (30 mg scale) and concentrated in vacuo. The residue was purified by flash silica gel chromatography (4 g SepaFlash® Silica Flash Column, Eluent of 25~41% Ethyl acetate/Petroleum ether gradient @ 60 mL/min) to afford the titled compound (190 mg, 288.01 μmol, 134.05% yield) as a brown solid. MS(M+H)$^+$=660.6.

Step 2: Synthesis of 4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxy-N-(2-azaspiro [3.3] heptan-6-yl)benzamide (3)

To a solution of tert-butyl 6-(4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzamido)-2-azaspiro [3.3]heptane-2-carboxylate (160 mg, 242.54 μmol) in DCM (2 mL) was added TFA (1.23 g, 10.80 mmol, 800 μL) at 0° C. and the mixture was stirred at 15° C. for 0.5 hours. LCMS showed the starting material was consumed completely and 93% of desired mass was detected. To the reaction mixture was added TEA to adjust pH>7, the resulting mixture was used for the next step directly. MS(M+H)$^+$=560.5.

Step 3: Synthesis of tert-butyl 3-((2-(2,6-dioxopiperidin-3-yl)-1,3-dioxoisoindolin-4-yl)amino)propanoate (5)

A mixture of 2-(2,6-dioxopiperidin-3-yl)-4-fluoroisoindoline-1,3-dione (300 mg, 1.09 mmol), tert-butyl 3-aminopropanoate (205.01 mg, 1.41 mmol) and DIEA (421.11 mg, 3.26 mmol, 567.53 μL) in DMSO (6 mL) was stirred at 80° C. for 12 hours. LCMS showed trace of the starting material remained and 50% of desired mass was detected. The reaction mixture was combined with another batch (30 mg scale), the combined mixture was diluted with H$_2$O (100 mL) and extracted with EtOAc (50 mL×5). The combined organic layers were washed with brine (80 mL×5), dried over Na$_2$SO$_4$, filtered. The filtrate was concentrated in vacuo. The residue was purified by flash silica gel chromatography (12 g SepaFlash® Silica Flash Column, Eluent of 18~45% Ethyl acetate/Petroleum ether gradient @ 100 mL/min) to afford the titled compound (240 mg, 597.89 μmol, 55.05% yield) as a yellow oil. MS(M+H)$^+$=402.4.

Step 4: Synthesis of 3-((2-(2,6-dioxopiperidin-3-yl)-1,3-dioxoisoindolin-4-yl)amino)propanoic acid (6)

To a solution of tert-butyl 3-((2-(2,6-dioxopiperidin-3-yl)-1,3-dioxoisoindolin-4-yl)amino)propanoate (240 mg, 597.89 mol) in dioxane (5 mL) was added HCl/dioxane (4 M, 10 mL), the mixture was stirred at 15° C. for 12 hours. LCMS showed trace starting material remained and 84% of desired mass was detected. The reaction mixture was concentrated in vacuo to afford the titled compound (170 mg, crude) as a yellow solid, which was used for the next step directly. MS(M+H)$^+$=345.9.

Step 5: Synthesis of 4-((9-cyclopentyl-7,7-difluoro-5-methyl-6-oxo-6,7,8,9-tetrahydro-5H-pyrimido[4,5-b][1, 4]diazepin-2-yl)amino)-N-(2-(3-((2-(2,6-dioxopiperidin-3-yl)-1,3-dioxoisoindolin-4-yl)amino)propanoyl)-2-azaspiro[3.3]heptan-6-yl)-2-fluoro-5-methoxybenzamide (Compound 159)

To the above mixture from step 2 in DCM (2 mL) were added 3-((2-(2,6-dioxopiperidin-3-yl)-1,3-dioxoisoindolin-4-yl)amino)propanoic acid (100 mg, 289.60 μmol), EDCI (83.27 mg, 434.40 μmol), HOBt (58.70 mg, 434.40 μmol) and TEA (146.52 mg, 1.45 mmol, 201.54 μL) and the resulting mixture was stirred at 15° C. for 16 hours. LCMS showed 44% of desired mass was detected. The reaction mixture was concentrated in vacuo to remove most of the solvent, to the residue was added CH$_3$COOH to adjust pH<7. The resulting mixture was diluted with DMF, the mixture was purified by prep-HPLC (column: Waters Xbridge 150*25 mm*5 um; mobile phase: [water(10 mM NH$_4$HCO$_3$)-ACN]; B %: 41%-71%, 10 min) followed by prep-HPLC (column: Phenomenex Synergi C$_{18}$ 150*25 mm*10 um; mobile phase: [water (0.225% FA)-ACN]; B %: 43%-73%, 10 min), the eluent was freeze-dried to afford the titled compound (28.9 mg, 30.96 μmol, 10.69% yield, 95% purity) as a yellow solid. MS(M+H)$^+$=887.7.

$^1$H NMR (400 MHz, DMSO-d$_6$) δ=11.11-11.03 (m, 1H), 8.30 (s, 1H), 8.25 (br d, J=13.3 Hz, 2H), 8.04 (s, 1H), 7.63-7.55 (m, 1H), 7.20 (d, J=6.4 Hz, 1H), 7.14 (dd, J=3.1, 8.8 Hz, 1H), 7.04 (dd, J=1.9, 7.0 Hz, 1H), 6.79-6.68 (m, 1H), 5.05 (dd, J=5.0, 12.7 Hz, 1H), 4.88-4.76 (m, 1H), 4.32-4.23 (m, 1H), 4.17 (s, 1H), 4.13-4.02 (m, 3H), 3.91 (s, 4H), 3.79 (s, 1H), 3.51 (q, J=6.0 Hz, 2H), 3.34-3.33 (m, 3H), 2.94-2.82 (m, 1H), 2.63-2.55 (m, 2H), 2.48-2.42 (m, 2H), 2.36 (q, J=6.8 Hz, 2H), 2.28-2.19 (m, 2H), 2.06-1.91 (m, 3H), 1.73 (m, 2H), 1.68-1.55 (m, 4H).

Example 160. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(2-(4-((2-(2,6-dioxopiperidin-3-yl)-1,3-dioxoisoindolin-4-yl)amino)butanoyl)-2-azaspiro[3.3]heptan-6-yl)-2-fluoro-5-methoxybenzamide

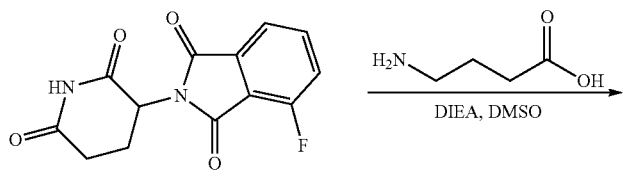

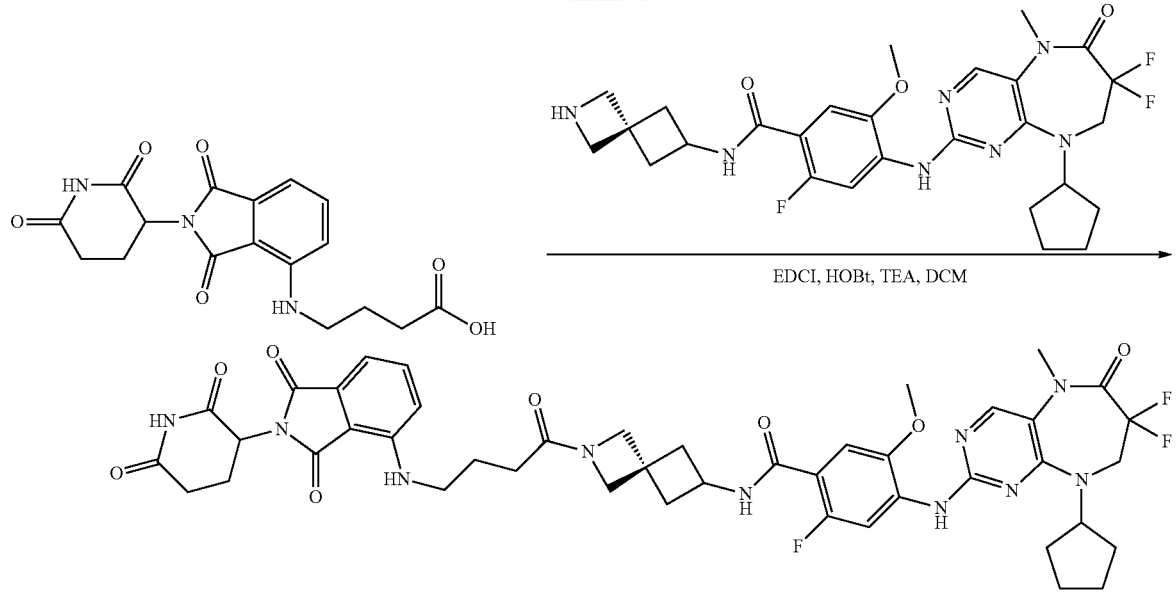

Compound 160

According to the above reaction scheme, in a manner similar to the other examples, obtained the titled compound (75.4 mg, 82.02 umol, 22.67% yield, 98% purity) as a yellow solid. MS(M+H)$^+$=901.0.

$^1$H NMR (400 MHz, DMSO-d$_6$) δ=11.04-11.00 (m, 1H), 8.30 (s, 1H), 8.27-8.23 (m, 2H), 8.04 (s, 1H), 7.58 (t, J=7.8 Hz, 1H), 7.20 (d, J=6.5 Hz, 1H), 7.15 (dd, J=2.1, 8.6 Hz, 1H), 7.02 (dd, J=1.6, 7.0 Hz, 1H), 6.69-6.56 (m, 1H), 5.05 (ddd, J=2.9, 5.3, 12.8 Hz, 1H), 4.82 (quin, J=8.0 Hz, 1H), 4.28 (m, 1H), 4.20-3.98 (m, 4H), 3.91 (s, 4H), 3.78 (s, 1H), 3.33 (s, 3H), 3.30 (m, 2H), 2.95-2.80 (m, 1H), 2.63-2.52 (m, 2H), 2.47 (m, 2H), 2.30-2.18 (m, 2H), 2.11 (q, J=6.7 Hz, 2H), 2.06-2.00 (m, 1H), 1.96 (m, 2H), 1.82-1.69 (m, 4H), 1.68-1.55 (m, 4H).

Example 161. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(2-(5-((2-(2,6-dioxopiperidin-3-yl)-1,3-dioxoisoindolin-4-yl)amino)pentanoyl)-2-azaspiro[3.3]heptan-6-yl)-2-fluoro-5-methoxybenzamide

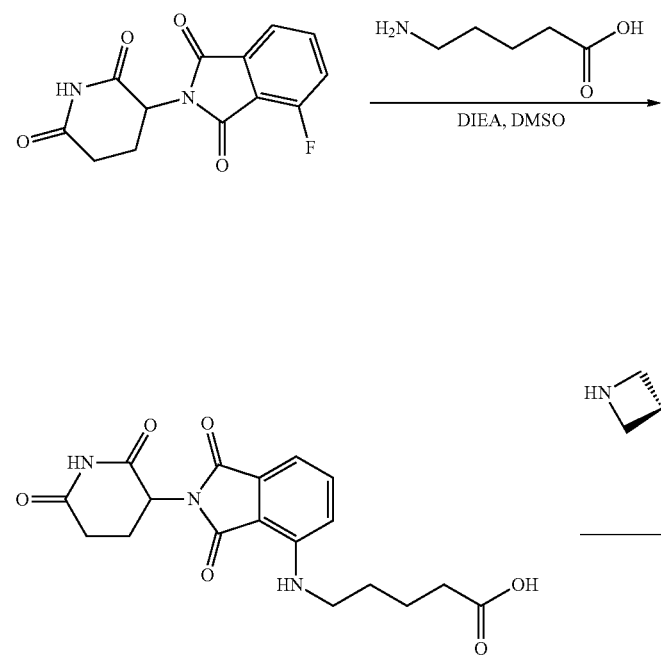

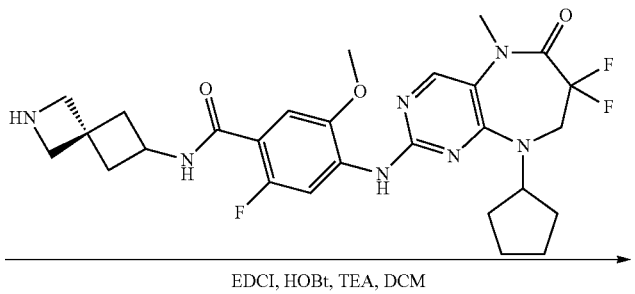

-continued

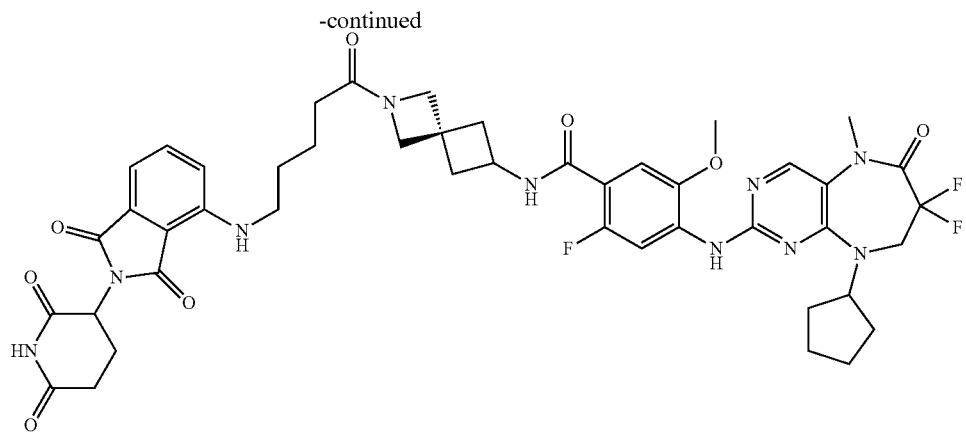

Compound 161

According to the above reaction scheme, in a manner similar to the other examples, obtained the titled compound (38.3 mg, 41.02 μmol, 30.63% yield, 98% purity) as a yellow solid. MS(M+H)+=915.1.

$^1$H NMR (400 MHz, DMSO-$d_6$) δ=11.11-11.00 (m, 1H), 8.30 (s, 1H), 8.25 (br d, J=13.4 Hz, 2H), 8.04 (s, 1H), 7.62-7.51 (m, 1H), 7.20 (d, J=6.6 Hz, 1H), 7.10 (dd, J=3.1, 8.6 Hz, 1H), 7.02 (dd, J=1.6, 6.9 Hz, 1H), 6.57 (q, J=5.1 Hz, 1H), 5.10-5.00 (m, 1H), 4.82 (quin, J=8.0 Hz, 1H), 4.28 (m, 1H), 4.17 (s, 1H), 4.13-3.99 (m, 3H), 3.94-3.82 (m, 4H), 3.77 (s, 1H), 3.33 (br s, 3H), 3.30 (m, 2H), 2.96-2.81 (m, 1H), 2.63-2.51 (m, 4H), 2.25 (br t, J=9.6 Hz, 2H), 2.10-1.91 (m, 5H), 1.79-1.68 (m, 2H), 1.68-1.50 (m, 8H).

Example 162. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(5-(2-((2-(2,6-dioxopiperidin-3-yl)-1,3-dioxoisoindolin-4-yl)oxy)acetamido)pentyl)-2-fluoro-5-methoxybenzamide

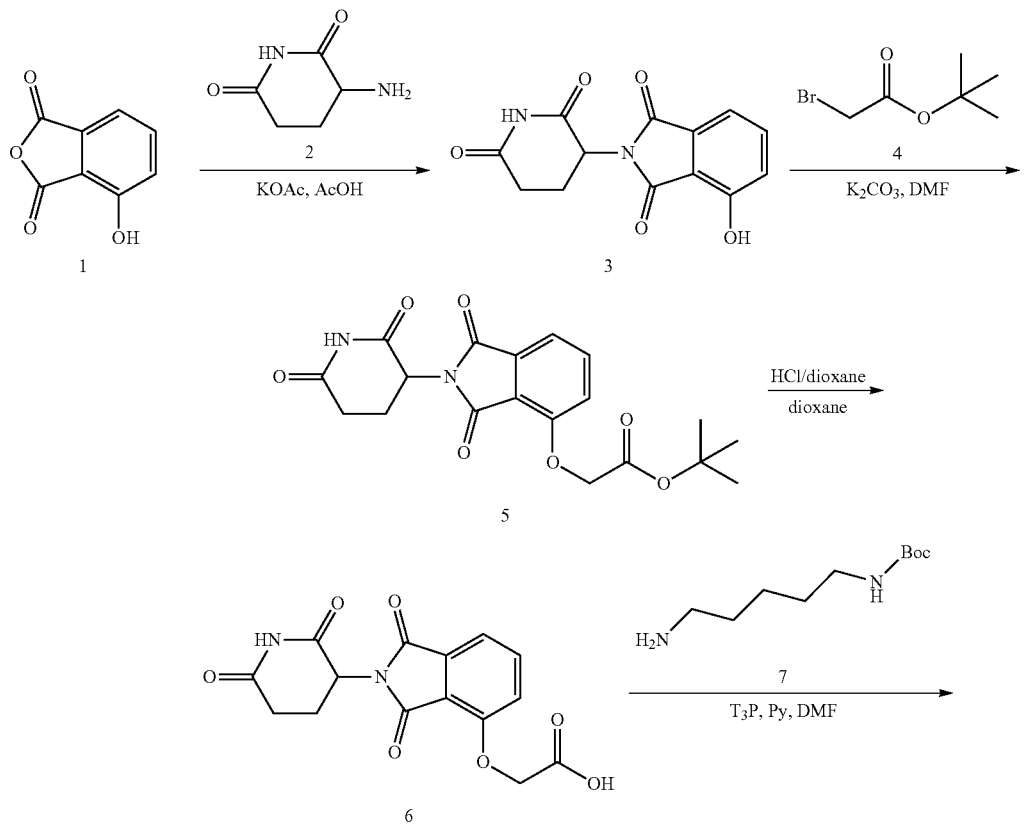

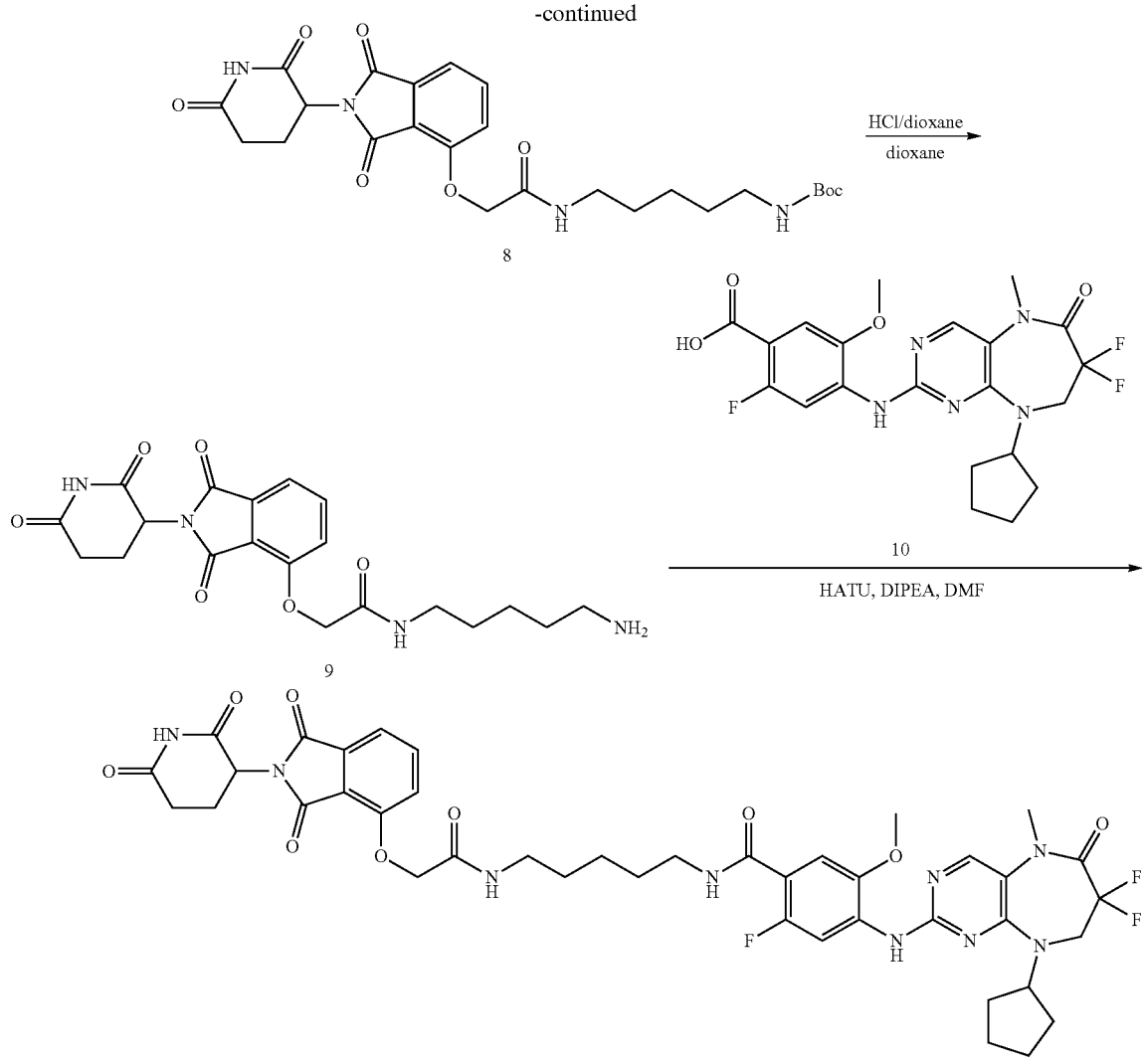

Compound 162

Step 1: Synthesis of 2-(2,6-dioxopiperidin-3-yl)-4-hydroxyisoindoline-1,3-dione (3)

To the solution of 3-aminopiperidine-2,6-dione (16.55 g, 100.54 mmol, HCl) and 4-hydroxyisobenzofuran-1,3-dione (15 g, 91.40 mmol) in AcOH (300 mL) was added KOAc (27.81 g, 283.34 mmol) and the resulting mixture was stirred at 120° C. for 24 h. LCMS showed that the reaction was completed. The mixture was combined with the pilot (10 g scale) and filtered, the cake was washed with H$_2$O (300 mL) and dried in vacuum to afford the titled compound (36.59 g, crude) as a black solid. MS(M+H)$^+$=275.1

Step 2: Synthesis of tert-butyl 2-((2-(2,6-dioxopiperidin-3-yl)-1,3-dioxoisoindolin-4-yl)oxy)acetate (5)

To a solution of 2-(2,6-dioxopiperidin-3-yl)-4-hydroxyisoindoline-1,3-dione (10 g, 36.47 mmol) in DMF (200 mL) were added K$_2$CO$_3$ (7.56 g, 54.70 mmol) and tert-butyl 2-bromoacetate (7.11 g, 36.47 mmol, 5.39 mL) and the mixture was stirred at 20° C. for 2 h. LCMS showed that the reaction was completed. The mixture poured into H$_2$O (450 mL) and extracted with EtOAc (450 mL×3), the combined organic layer was washed with brine (1000 mL), dried over Na$_2$SO$_4$, filtered and concentrated. The residue was purified by column chromatography (SiO$_2$, Petroleum ether/Ethyl acetate=1/0 to 0/1) to afford the titled compound (12 g, 30.90 mmol, 84.73% yield) as white solid. MS(M+H)$^+$=389.1

Step 3: Synthesis of 2-((2-(2,6-dioxopiperidin-3-yl)-1,3-dioxoisoindolin-4-yl)oxy)acetic acid (6)

To a solution of tert-butyl 2-((2-(2,6-dioxopiperidin-3-yl)-1,3-dioxoisoindolin-4-yl)oxy)acetate (12 g, 30.90 mmol) in dioxane (50 mL) was added HCl/dioxane (4 M, 50 mL) and the mixture was stirred at 20° C. for 6 h. LCMS showed that the reaction was completed. The reaction mixture was concentrated in vacuum to afford the titled compound (10.27 g, crude) as white solid. MS (M+H)$^+$=333.1

Step 4: Synthesis of tert-butyl (5-(2-((2-(2,6-dioxopiperidin-3-yl)-1,3-dioxoisoindolin-4-yl)oxy)acetamido)pentyl)carbamate (8)

To a solution of 2-((2-(2,6-dioxopiperidin-3-yl)-1,3-dioxoisoindolin-4-yl)oxy)acetic acid (1 g, 3.01 mmol) and tert-butyl N-(5-aminopentyl) carbamate (608.83 mg, 3.01 mmol, 626.37 μL) in DMF (10 mL) were added T₃P (11.49 g, 18.06 mmol, 10.74 mL, 50% purity) and Py (2.38 g, 30.10 mmol, 2.43 mL) at 20° C. and the mixture was stirred at 80° C. for 16 h. LCMS showed that the reaction was completed. The reaction mixture was poured into H₂O (80 mL) and extracted with EtOAc (30 mL×3), the organic phase was washed with brine (30 mL×3), dried over Na₂SO₄, filtered and concentrated under reduced pressure. The residue was purified by column chromatography (SiO₂, Petroleum ether/ Ethyl acetate=1/0 to 0/1) to afford the titled compound (1.33 g, 2.50 mmol, 82.99% yield, 97% purity) as a yellow oil. MS(M+H)⁺=517.2

Step 5: Synthesis of N-(5-aminopentyl)-2-((2-(2,6-dioxopiperidin-3-yl)-1,3-dioxoisoindolin-4-yl) oxy) acetamide (9)

To a solution of tert-butyl (5-(2-((2-(2,6-dioxopiperidin-3-yl)-1,3-dioxoisoindolin-4-yl)oxy)acetamido)pentyl)carbamate (1.33 g, 2.57 mmol) in dioxane (20 mL) was added HCl/dioxane (4 M, 20 mL) and the mixture was stirred at 20° C. for 16 h. LCMS showed that the reaction was completed. The reaction mixture was concentrated in vacuum to afford the titled compound (1.29 g, HCl) as white solid. MS(M+H)⁺=417.1

Step 6: Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(5-(2-((2-(2,6-dioxopiperidin-3-yl)-1,3-dioxoisoindolin-4-yl)oxy)acetamido)pentyl)-2-fluoro-5-methoxybenzamide (Compound 162)

To the solution of N-(5-aminopentyl)-2-((2-(2,6-dioxopiperidin-3-yl)-1,3-dioxoisoindolin-4-yl)oxy)acetamide (0.2 g, 441.61 μmol, HCl) and 4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzoic acid (205.54 mg, 441.61 μmol) in DMF (4 mL) were added HATU (335.83 mg, 883.22 μmol) and DIPEA (171.23 mg, 1.32 mmol, 230.76 μL) and the resulting mixture was stirred at 20° C. for 1 h. LCMS showed that the reaction was completed. The mixture was poured into water (20 mL) and extracted with EtOAc (20 mL×3), the combined organic layer was washed with brine (50 mL), dried over Na₂SO₄, filtered and concentrated. The residue was purified by prep-HPLC (column: Phenomenex luna C₁₈ 150*25 mm*10 um; mobile phase: [water (0.225% FA)-ACN]; B %: 41%-71%, 10 min) and the eluant was lyophilized, the solid was re-purified by prep-HPLC (column: 3_Phenomenex Luna C₁₈ 75*30 mm*3 um; mobile phase: [water (0.1% TFA)-ACN]; B %: 40%-60%, 7 min) and the eluant was lyophilized to afford the titled compound (94.8 mg, 94.04 μmol, 21.29% yield, 97% purity, TFA) as white solid. MS(M+H)⁺=864.2.

¹H NMR (400 MHz, DMSO-d₆) δ=11.13 (s, 1H), 8.34-8.26 (m, 2H), 8.19 (d, J=13.3 Hz, 1H), 8.06 (d, J=4.5 Hz, 1H), 7.96 (t, J=5.6 Hz, 1H), 7.86-7.77 (m, 1H), 7.49 (d, J=7.3 Hz, 1H), 7.40 (d, J=8.4 Hz, 1H), 7.25 (d, J=6.7 Hz, 1H), 5.18-5.09 (m, 1H), 4.84 (t, J=8.2 Hz, 1H), 4.77 (s, 2H), 4.12 (t, J=13.6 Hz, 2H), 3.94-3.90 (m, 3H), 3.34 (s, 3H), 3.28-3.22 (m, 2H), 3.20-3.13 (m, 2H), 2.97-2.85 (m, 1H), 2.66-2.55 (m, 2H), 2.09-1.93 (m, 3H), 1.75-1.46 (m, 10H), 1.38-1.25 (m, 2H).

Example 163. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(2-(2-(2-((2-(2,6-dioxopiperidin-3-yl)-1,3-dioxoisoindolin-5-yl)amino)ethoxy)ethoxy)ethyl)-2-fluoro-5-methoxybenzamide

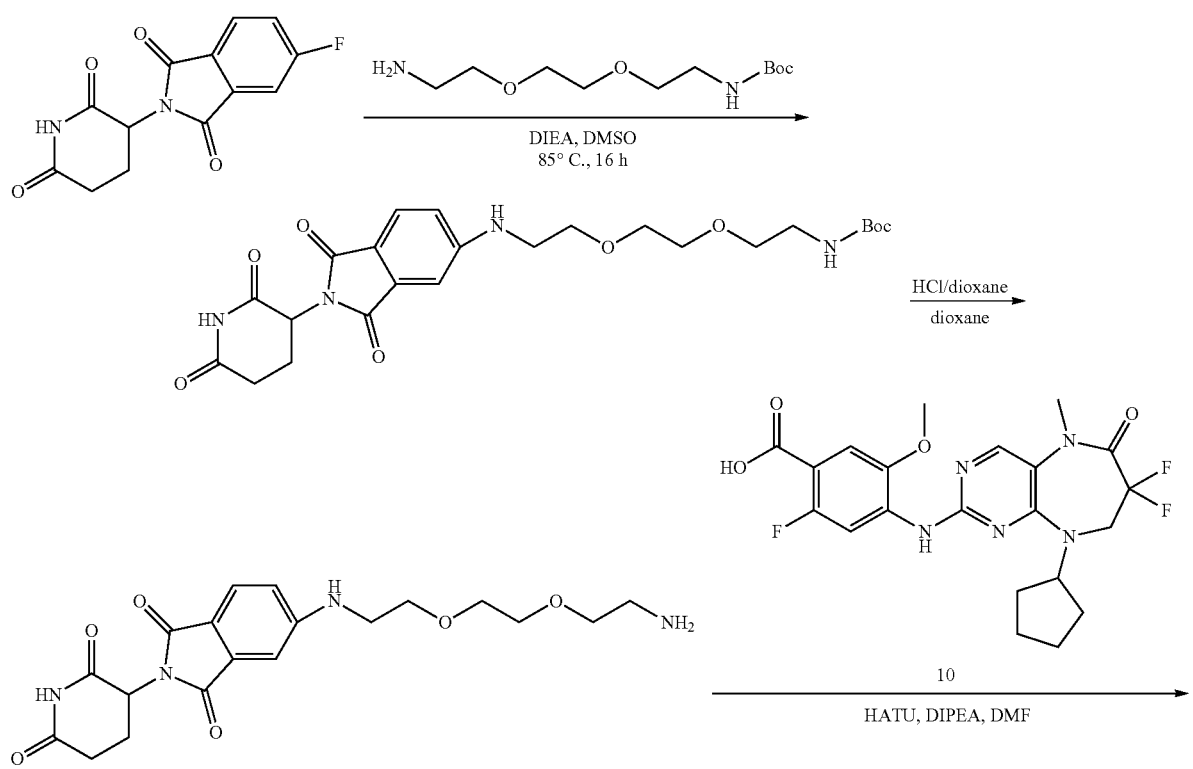

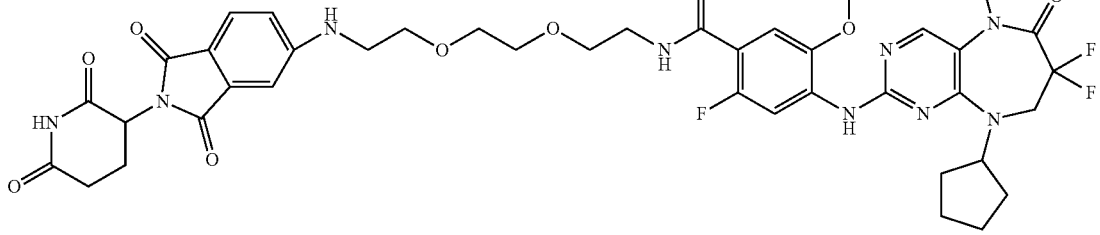

Compound 163

According to the above reaction scheme, in a manner similar to the other examples, obtained the titled compound (31.1 mg, 35.05 μmol, 4.05% yield, 96% purity) as a yellow solid. MS(M+H)$^+$=852.3.

$^1$H NMR (400 MHz, DMSO-d$_6$) δ=11.31-10.73 (m, 1H), 8.33-8.14 (m, 2H), 8.04 (s, 1H), 7.96 (q, J=5.6 Hz, 1H), 7.52 (d, J=8.4 Hz, 1H), 7.28 (d, J=6.9 Hz, 1H), 7.13 (t, J=5.4 Hz, 1H), 6.98 (d, J=1.8 Hz, 1H), 6.86 (dd, J$_1$=8.4 Hz, J$_2$=2.0 Hz, 1H), 5.02 (dd, J$_1$=12.9 Hz, J$_2$=5.4 Hz, 1H), 4.90-4.70 (m, 1H), 4.07 (t, J=13.8 Hz, 2H), 3.90 (s, 3H), 3.67-3.48 (m, 8H), 3.47-3.32 (m, 7H), 2.94-2.80 (m, 1H), 2.61-2.53 (m, 1H), 2.49-2.40 (m, 1H), 2.04-1.86 (m, 3H), 1.79-1.68 (m, 2H), 1.66-1.54 (m, 4H).

Example 164. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(6-(2-(2,6-dioxopiperidin-3-yl)-1-oxoisoindolin-4-yl)hexyl)-2-fluoro-5-methoxybenzamide

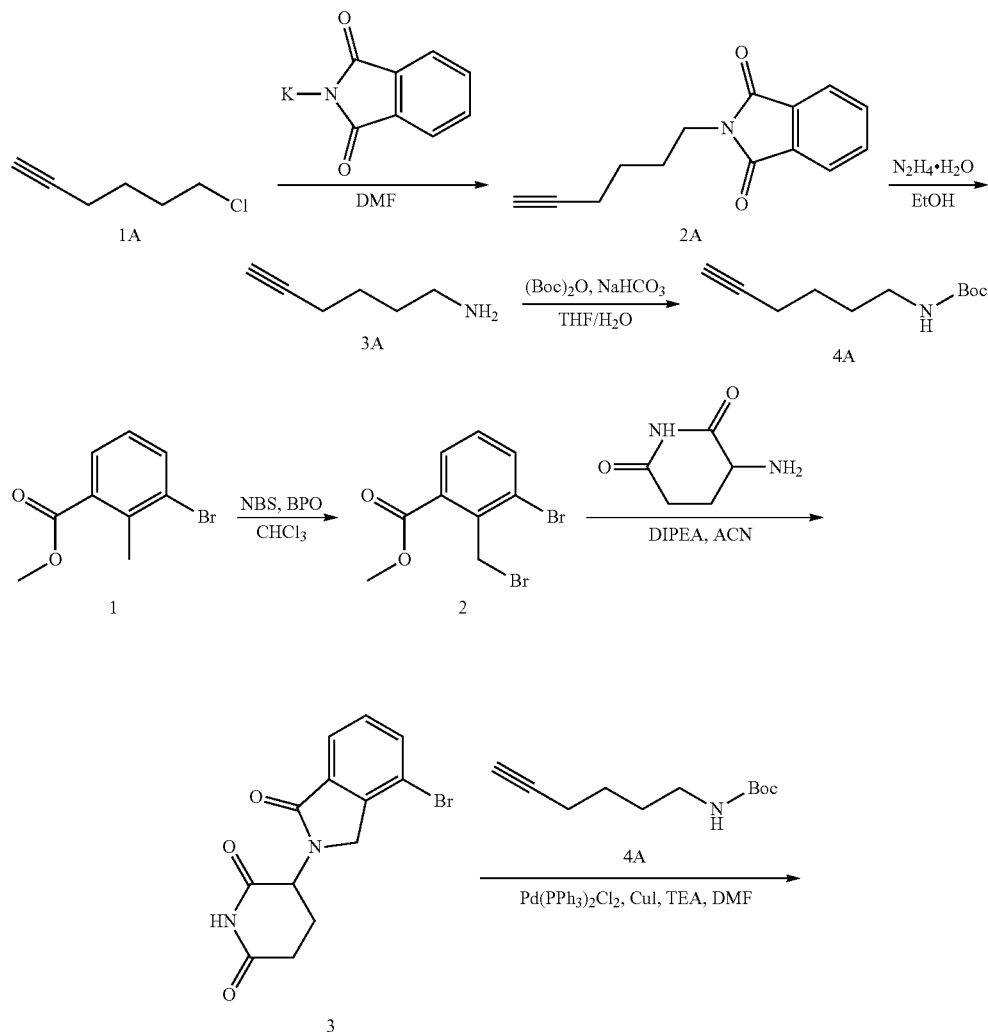

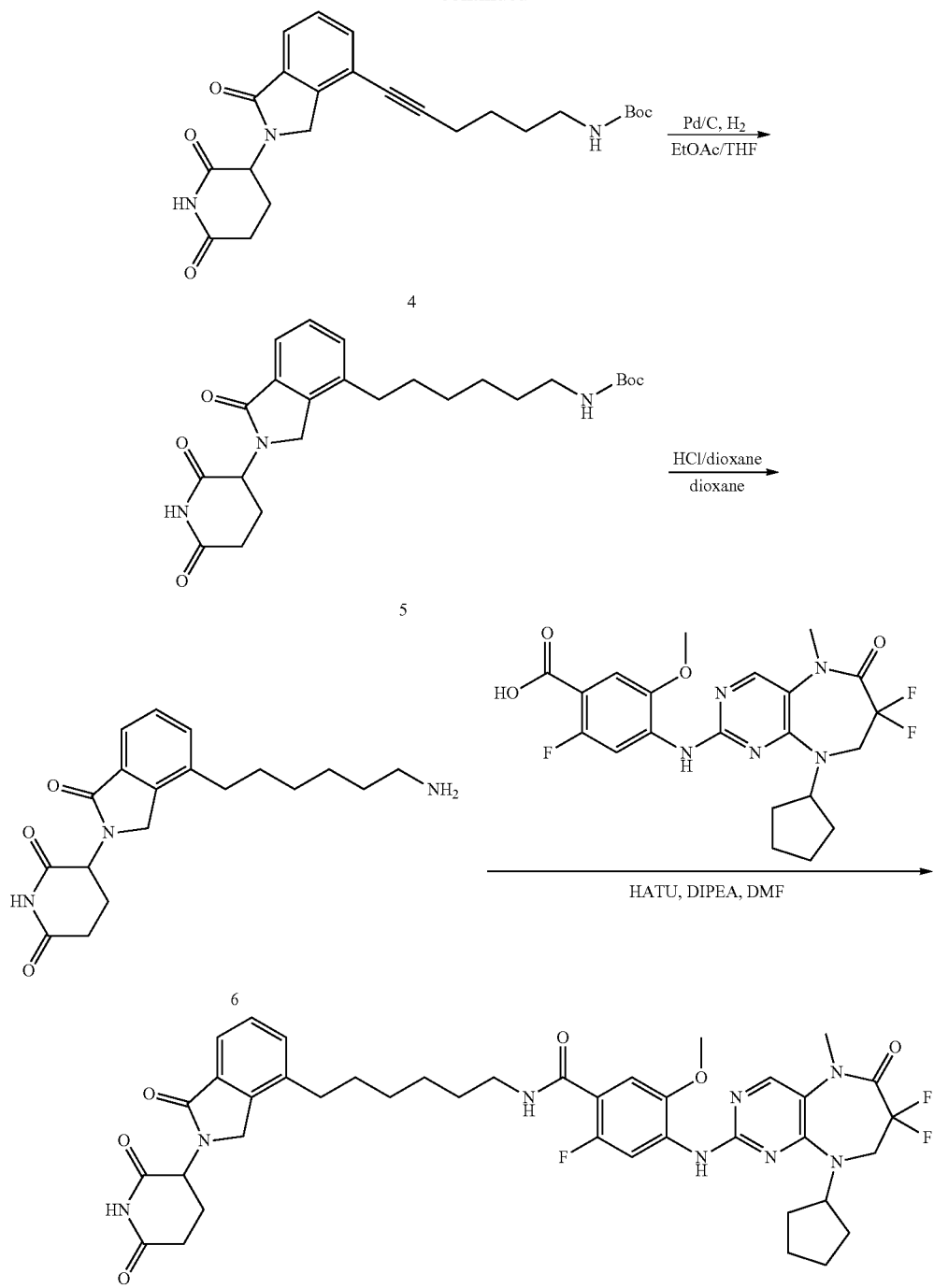

Compound 164

Step 1: Synthesis of 2-(hex-5-yn-1-yl)isoindoline-1,3-dione (2A)

To a mixture of 6-chlorohex-1-yne (5 g, 42.89 mmol, 5.20 mL) was added potassium 1,3-dioxoisoindolin-2-ide (15.89 g, 85.77 mmol) in DMF (50 mL) at 20° C. and the resulting mixture was stirred at 85° C. for 16 h. LCMS showed all starting material was consumed completely and one peak with desired mass was detected. TLC (SiO$_2$, Petroleum ether:Ethyl acetate=2:1) indicated 6-chlorohex-1-yne was consumed completely and two new spots were detected. The reaction mixture was diluted with H$_2$O (100 mL) and extracted with EtOAc (100 mL×3). The organic layer was washed with brine (100 mL×3), dried over Na$_2$SO$_4$, filtered and concentrated. The residue was purified by column chromatography (SiO$_2$, Petroleum ether/Ethyl acetate=8/1 to 2/1) to afford the titled compound (8.3 g, 35.43 mmol, 82.61% yield, 97% purity) as a white solid. MS(M+H)$^+$=228.4

$^1$H NMR (400 MHz, CDCl$_3$) δ=7.87-7.81 (m, 2H), 7.75-7.67 (m, 2H), 3.71 (t, J=7.1 Hz, 2H), 2.29-2.21 (m, 2H), 1.94 (t, J=2.7 Hz, 1H), 1.87-1.76 (m, 2H), 1.63-1.52 (m, 2H)

Step 2: Synthesis of hex-5-yn-1-amine (3A)

To a mixture of 2-(hex-5-yn-1-yl)isoindoline-1,3-dione (8.3 g, 36.52 mmol) in EtOH (90 mL) was added N$_2$H$_4$·H$_2$O (21.51 g, 365.20 mmol, 20.88 mL, 85% purity) in one portion at 20° C. and the resulting mixture was stirred at 80° C. for 4 h. TLC (SiO$_2$, Petroleum ether:Ethyl acetate=2:1) indicated starting material was consumed completely and one new spot was detected. The reaction mixture was diluted with EtOH (200 mL) and filtered. The filtrate was concentrated in vacuum. The residue was diluted with DCM (150 mL) and filtered. The filtrate was concentrated in vacuum to afford the titled compound (4.7 g, crude) as colorless oil.

Step 3: Synthesis of tert-butyl hex-5-yn-1-ylcarbamate (4A)

To a mixture of hex-5-yn-1-amine (4.7 g, 48.37 mmol) in THF (50 mL) and H$_2$O (50 mL) was added NaHCO$_3$ (8.13 g, 96.75 mmol, 3.76 mL) followed by (Boc)$_2$O (13.72 g, 62.89 mmol, 14.45 mL) drop-wise at 0° C. and the resulting mixture was stirred at 20° C. for 16 h. TLC (SiO$_2$, Petroleum ether:Ethyl acetate=3:1) indicated hex-5-yn-1-amine was consumed completely and two new spots were detected. The reaction mixture was diluted with H$_2$O (100 mL) and extracted with EtOAc (100 mL×3). The organic layer was dried over Na$_2$SO$_4$, filtered and concentrated. The residue was purified by column chromatography (SiO$_2$, Petroleum ether/Ethyl acetate=10/1 to 3/1) to afford the titled compound (1.8 g, 9.12 mmol, 18.86% yield) as a colorless oil.

Step 4: Synthesis of methyl 3-bromo-2-(bromomethyl)benzoate (2)

To a mixture of methyl 3-bromo-2-methyl-benzoate (10 g, 43.65 mmol) in CHCl$_3$ (100 mL) were added NBS (8.55 g, 48.02 mmol) and BPO (528.72 mg, 2.18 mmol) in one portion at 20° C. and the resulting mixture was stirred at 85° C. for 16 h. LCMS showed no peak with desired mass was detected. TLC (SiO$_2$, Petroleum ether:Ethyl acetate=5:1) indicated a little of 3-bromo-2-methyl-benzoate remained and one new spot was detected. The reaction mixture was quenched with saturated Na$_2$SO$_3$ (100 mL) and extracted with DCM (100 mL×3). The organic layer was dried over Na$_2$SO$_4$ filtered and concentrated. The residue was purified by column chromatography (SiO$_2$, Petroleum ether/Ethyl acetate=1/1 to 200/1) to afford the titled compound (9.4 g, 30.52 mmol, 69.92% yield) as an orange oil.

$^1$H NMR (400 MHz, CDCl$_3$) δ=7.86 (d, J=7.7 Hz, 1H), 7.74 (d, J=7.5 Hz, 1H), 7.21 (t, J=7.9 Hz, 1H), 5.12 (s, 2H), 3.94 (s, 3H)

Step 5: Synthesis of 3-(4-bromo-1-oxoisoindolin-2-yl))piperidine-2,6-dione (3)

To a mixture of methyl 3-bromo-2-(bromomethyl) benzoate (9.4 g, 30.52 mmol) and 3-aminopiperidine-2,6-dione; hydrochloride (6.03 g, 36.63 mmol) in ACN (100 mL) was added DIPEA (19.72 g, 152.61 mmol, 26.58 mL) in one portion at 20° C. and the resulting mixture was stirred at 90° C. for 16 h. TLC (SiO$_2$, Petroleum ether:Ethyl acetate=5:1) indicated methyl 3-bromo-2-(bromomethyl) benzoate was consumed completely and one new spot was detected. The reaction mixture was diluted with ACN (200 mL) and filtrated. The filter cake was washed with methyl tert-butyl ether (20 mL×4). The filter cake was dried in vacuum to afford the titled compound (7.6 g, 23.52 mmol, 77.05% yield) as a purple solid.

$^1$H NMR (400 MHz, DMSO-d$_6$) δ=11.02 (s, 1H), 7.87 (dd, J=0.6, 7.9 Hz, 1H), 7.79-7.75 (m, 1H), 7.54-7.48 (m, 1H), 5.15 (dd, J=5.0, 13.3 Hz, 1H), 4.46-4.38 (m, 1H), 4.30-4.22 (m, 1H), 2.98-2.85 (m, 1H), 2.65-2.54 (m, 1H), 2.49-2.38 (m, 1H), 2.06-1.97 (m, 1H)

Step 6: Synthesis of tert-butyl (6-(2-(2,6-dioxopiperidin-3-yl)-1-oxoisoindolin-4-yl)hex-5-yn-1-yl) carbamate (4)

To a mixture of 3-(4-bromo-1-oxoisoindolin-2-yl)piperidine-2,6-dione (2 g, 6.19 mmol) and tert-butyl hex-5-yn-1-ylcarbamate (1.47 g, 7.43 mmol) in DMF (20 mL) were added CuI (235.75 mg, 1.24 mmol), TEA (6.26 g, 61.89 mmol, 8.61 mL), Pd(PPh$_3$)$_2$Cl$_2$ (217.21 mg, 309.46 µmol) in one portion at 20° C. under N$_2$ and the resulting mixture was stirred at 80° C. for 16 h. LCMS showed 15% of 3-(4-bromo-1-oxoisoindolin-2-yl)piperidine-2,6-dione remained and 80% peak with desired mass was detected. TLC (SiO$_2$, Petroleum ether:Ethyl acetate=1:2) indicated 3-(4-bromo-1-oxoisoindolin-2-yl)piperidine-2,6-dione remained and three new spots were detected. The reaction mixture was diluted with H$_2$O (60 mL) and extracted with EtOAc (60 mL×3). The organic layer was washed with brine (60 mL×3), dried over Na$_2$SO$_4$, filtered and concentrated. The residue was purified by column chromatography (SiO$_2$, Petroleum ether/Ethyl acetate=5/1 to 1/2) and re-purified by reversed-phase HPLC (method: FA, MeCN/water) and then lyophilized to afford the titled compound (819 mg, 1.66 mmol, 26.80% yield, 89% purity) as a white solid. MS(M−100+H)$^+$=340.4

Step 7: Synthesis of tert-butyl (6-(2-(2,6-dioxopiperidin-3-yl)-1-oxoisoindolin-4-yl)hexyl)carbamate (5)

To a solution of tert-butyl (6-(2-(2,6-dioxopiperidin-3-yl)-1-oxoisoindolin-4-yl)hex-5-yn-1-yl)carbamate (810 mg, 1.64 mmol, 89% purity) in EtOAc (8 mL) and THF (2 mL) was added Pd/C (0.4 mg, 164.03 µmol, 10% purity) under N$_2$. The suspension was degassed under vacuum and purged with H$_2$ several times. The mixture was stirred under H$_2$ (15 psi) at 20° C. for 16 h. LCMS showed starting material was consumed completely and one peak with desired mass was detected. The reaction mixture was diluted with THF (20 mL) and filtered. The filtrate was concentrated in vacuum to afford the titled compound (449 mg, 1.01 mmol, 61.72% yield) as a white solid. MS (M−100+H)$^+$=344.3

Step 8: Synthesis of 3-(4-(6-aminohexyl)-1-oxoisoindolin-2-yl)piperidine-2,6-dione (6)

To a mixture of tert-butyl (6-(2-(2,6-dioxopiperidin-3-yl)-1-oxoisoindolin-4-yl)hexyl)carbamate (449 mg, 1.01 mmol) in dioxane (5 mL) was added HCl/dioxane (4 M, 5 mL) in one portion at 20° C. and the resulting mixture was stirred at 20° C. for 1 h. TLC (SiO$_2$, Petroleum ether:Ethyl acetate=1:2) indicated starting material was consumed completely and one new spot was detected. The reaction mixture was concentrated in vacuum to afford the titled compound (398 mg, crude, HCl) as a white solid.

Step 9: Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(6-(2-(2,6-dioxopiperidin-3-yl)-1-oxoisoindolin-4-yl)hexyl)-2-fluoro-5-methoxybenzamide (Compound 164)

To a solution of 4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzoic acid (150 mg, 322.29 μmol) in DMF (2 mL) were added HATU (122.54 mg, 322.29 μmol) and DIPEA (83.31 mg, 644.57 μmol, 112.27 μL). The mixture was stirred at 20° C. for 20 min and a solution of 3-(4-(6-aminohexyl)-1-oxoisoindolin-2-yl)piperidine-2,6-dione (183.65 mg, 483.43 mol, HCl) in DMF (2 mL) and DIPEA (83.31 mg, 644.57 μmol, 112.27 μL) were added and the resulting mixture was stirred at 20° C. for 2 h. LCMS showed all starting material was consumed completely and one peak with desired mass was detected. The reaction mixture was diluted with H$_2$O (15 mL) and extracted with EtOAc (15 mL×3). The organic layer was washed with brine (15 mL×3), dried over Na$_2$SO$_4$, filtered and concentrated. The residue was purified by prep-HPLC (column: Phenomenex luna C$_{18}$ 150*25 mm*10 um; mobile phase: [water (0.225% FA)-ACN]; B %: 45%-75%, 11 min) and then lyophilized to afford the titled compound (104 mg, 130.19 μmol, 40.40% yield, 99% purity) as a white solid. MS(M+H)$^+$=791.6

$^1$H NMR (400 MHz, DMSO-d$_6$) δ=10.98 (br s, 1H), 8.32-8.27 (m, 1H), 8.24 (d, J=13.4 Hz, 1H), 8.07-7.98 (m, 2H), 7.59-7.53 (m, 1H), 7.48-7.41 (m, 2H), 7.23 (d, J=6.8 Hz, 1H), 5.12 (dd, J=5.1, 13.2 Hz, 1H), 4.87-4.76 (m, 1H), 4.50-4.42 (m, 1H), 4.35-4.26 (m, 1H), 4.07 (t, J=13.9 Hz, 2H), 3.90 (s, 3H), 3.33 (s, 3H), 3.27-3.21 (m, 2H), 2.97-2.86 (m, 1H), 2.67-2.56 (m, 3H), 2.46-2.36 (m, 1H), 2.05-1.90 (m, 3H), 1.74-1.48 (m, 10H), 1.42-1.32 (m, 4H)

Example 165. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(5-(2-(2,6-dioxopiperidin-3-yl)-1-oxoisoindolin-4-yl)pentyl)-2-fluoro-5-methoxybenzamide

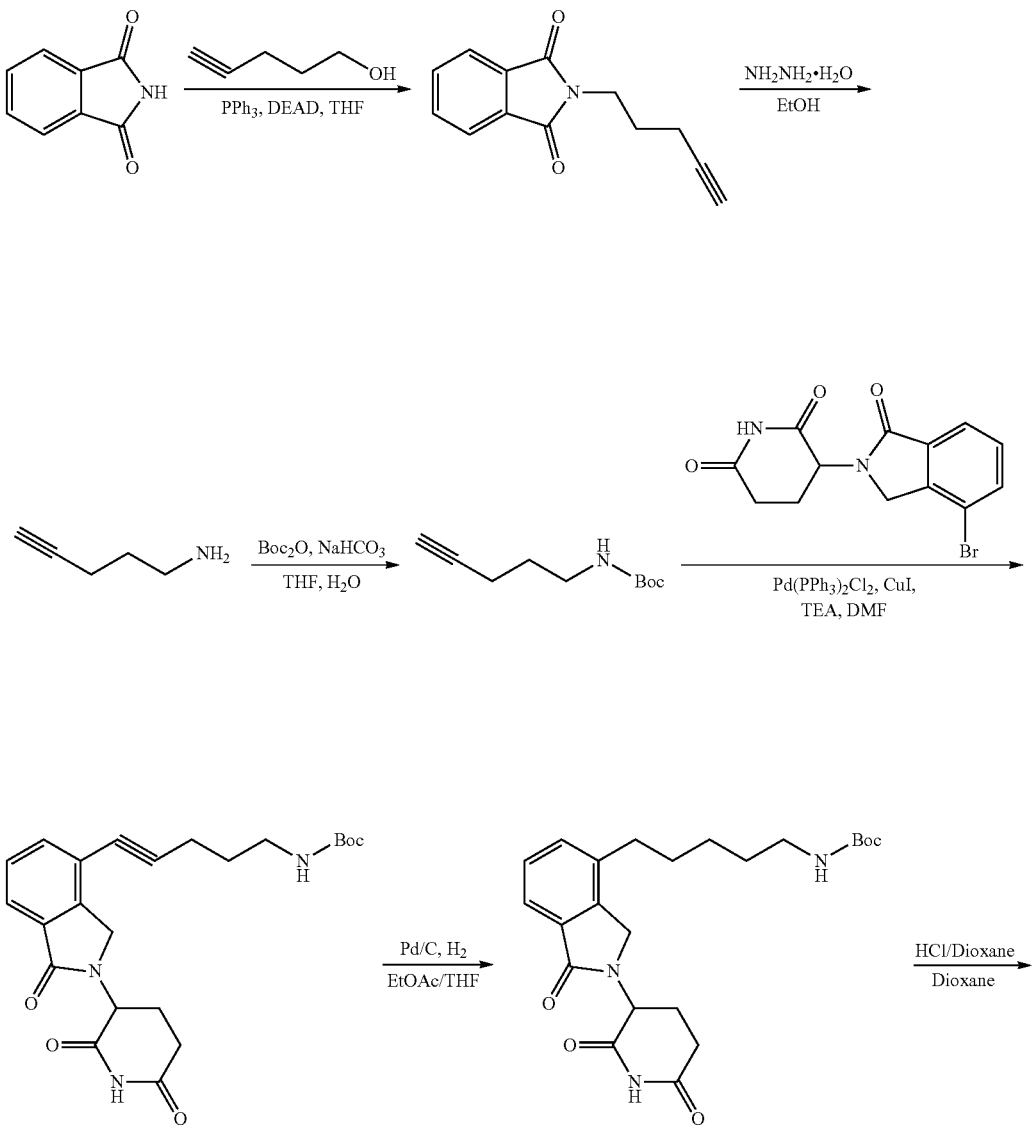

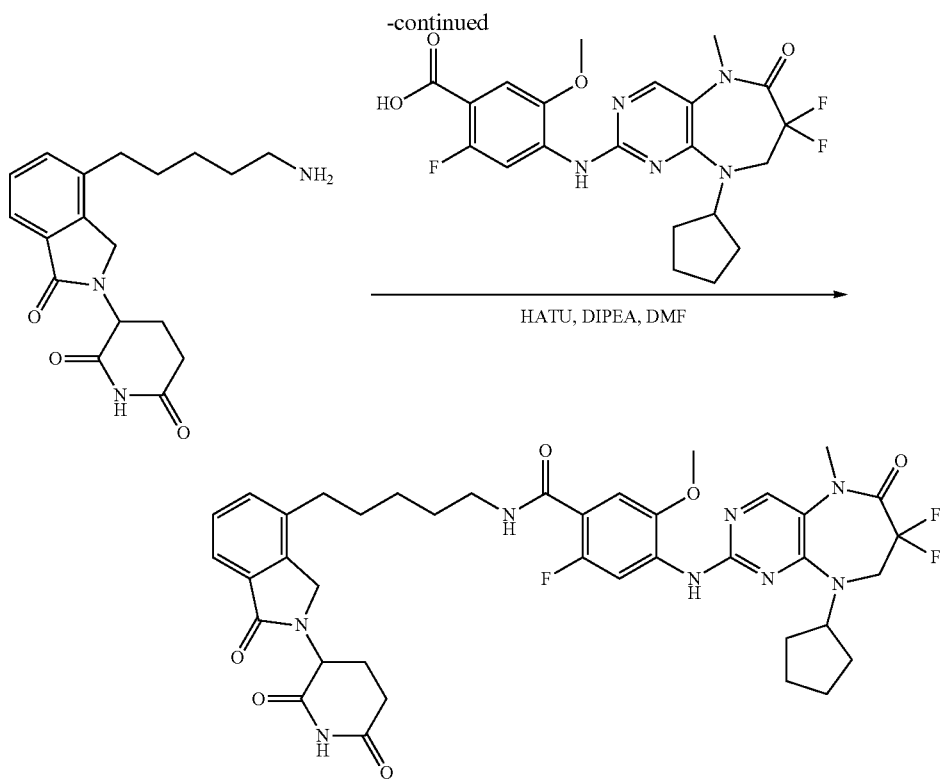

Compound 165

According to the above reaction scheme, in a manner similar to the other examples, obtained the titled compound (37.1 mg, 46.80 μmol, 55.59% yield, 98% purity) as a light yellow solid. MS(M+H)$^+$=777.6

$^1$H NMR (400 MHz, CD$_3$OD) δ 8.42 (d, J=14.3 Hz, 1H), 8.23 (s, 1H), 7.67-7.61 (m, 1H), 7.51-7.44 (m, 2H), 7.36 (d, J=6.8 Hz, 1H), 5.19 (d, J=5.4 Hz, 1H), 5.16 (d, J=5.3 Hz, 1H), 4.62-4.45 (m, 2H), 4.06 (t, J=13.6 Hz, 2H), 4.01-3.98 (m, 3H), 3.43 (s, 3H), 3.42-3.36 (m, 2H), 3.09-2.83 (m, 2H), 2.78-2.74 (m, 2H), 2.55-2.37 (m, 1H), 2.26-2.07 (m, 3H), 1.87-1.67 (m, 10H), 1.55-1.46 (m, 2H)

Example 166. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(7-(2-(2, 6-dioxopiperidin-3-yl)-1-oxoisoindolin-4-yl)heptyl)-2-fluoro-5-methoxybenzamide

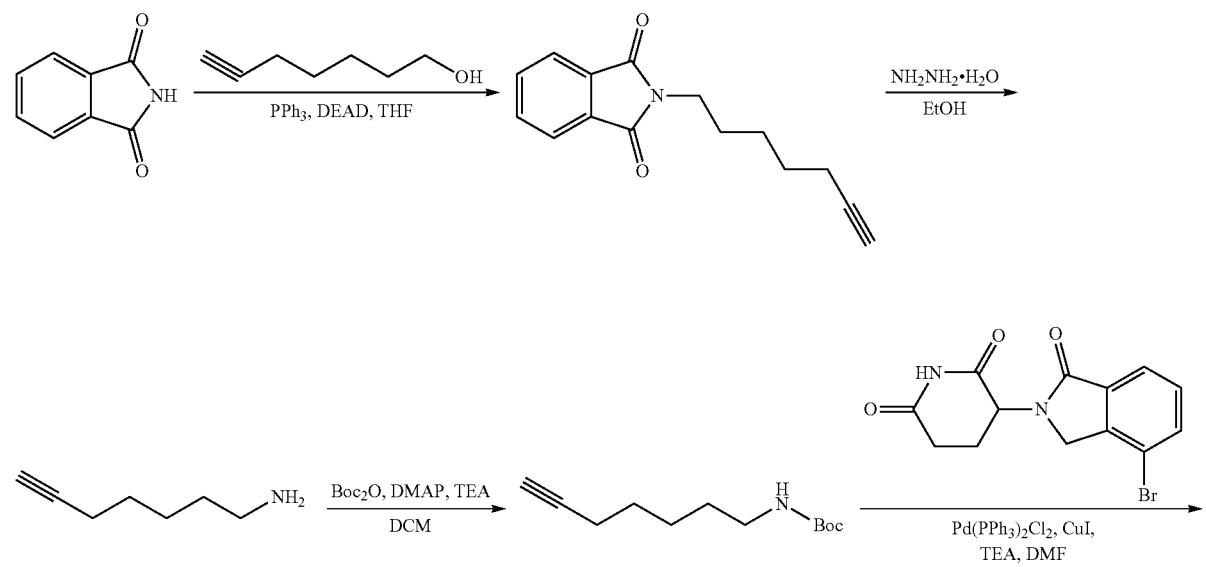

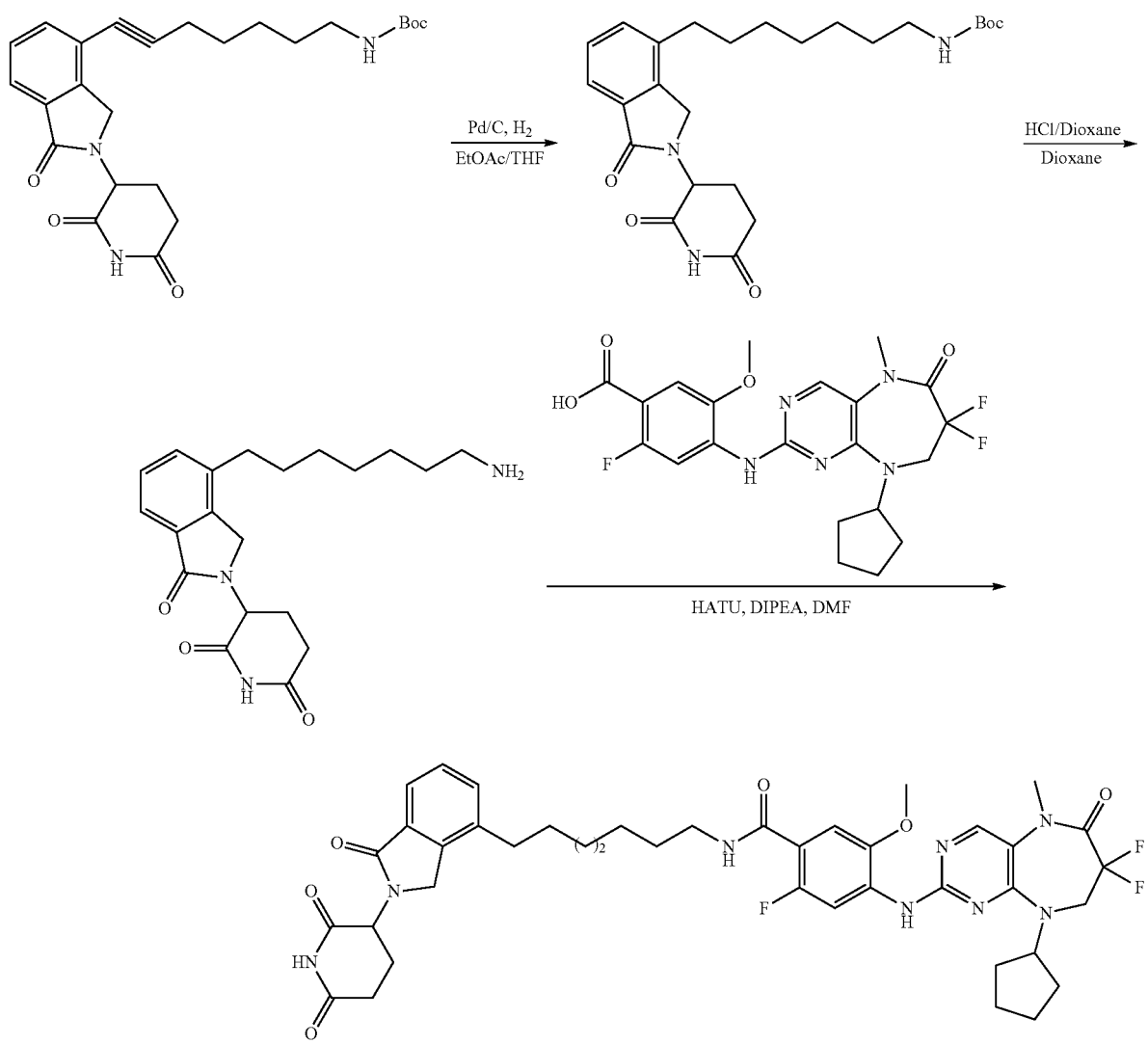

According to the above reaction scheme, in a manner similar to the other examples, obtained the titled compound (67.9 mg, 77.61 μmol, 59.43% yield, 92% purity) as a light yellow solid.

MS(M+H)$^+$=805.6

$^1$H NMR (400 MHz, DMSO-d$_6$) δ 10.98 (br s, 1H), 8.30 (s, 1H), 8.24 (d, J=13.4 Hz, 1H), 8.07-8.00 (m, 2H), 7.59-7.54 (m, 1H), 7.47-7.43 (m, 2H), 7.24 (d, J=6.8 Hz, 1H), 5.13 (dd, J=5.1, 13.3 Hz, 1H), 4.86-4.77 (m, 1H), 4.49-4.43 (m, 1H), 4.34-4.28 (m, 1H), 4.08 (t, J=13.9 Hz, 2H), 3.91 (s, 3H), 3.37-3.36 (m, 3H), 3.26-3.21 (m, 2H), 2.97-2.87 (m, 1H), 2.67-2.63 (m, 2H), 2.48-2.38 (m, 2H), 2.05-1.93 (m, 3H), 1.73-1.50 (m, 10H), 1.37-1.29 (m, 6H).

Example 167. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(2-(2-(2-((2-(2,6-dioxopiperidin-3-yl)-1,3-dioxoisoindolin-4-yl)amino)ethoxy)ethoxy)ethyl)-2-fluoro-5-methoxybenzamide

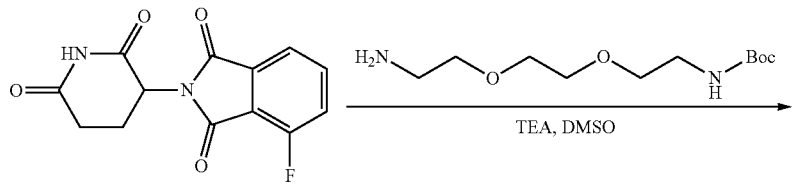

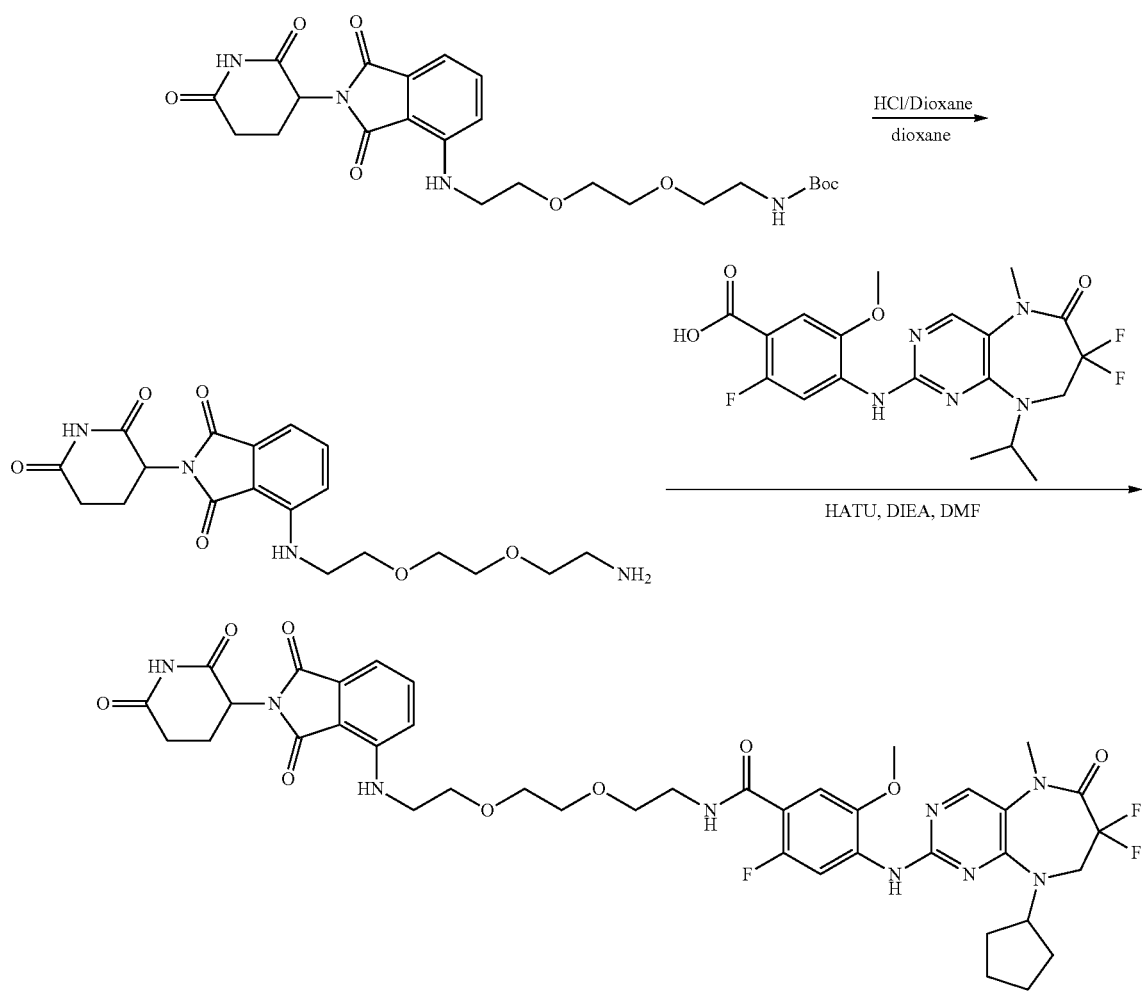

Compound 167

According to the above reaction scheme, in a manner similar to the other examples, obtained the titled compound (65.0 mg, 77.93 μmol, 17.18% yield, 99% purity) as a yellow solid. MS(M+H)+=826.6.

$^1$H NMR (400 MHz, DMSO-d$_6$) δ=11.09 (s, 1H), 8.36-8.13 (m, 2H), 8.08-7.74 (m, 2H), 7.53 (dd, J$_1$=8.4 Hz, J$_2$=7.3 Hz, 1H), 7.26 (d, J=6.8 Hz, 1H), 7.10 (d, J=8.7 Hz, 1H), 6.99 (d, J=7.1 Hz, 1H), 6.59 (t, J=5.6 Hz, 1H), 5.04 (dd, J$_1$=12.9, J$_2$=5.3 Hz, 1H), 4.94-4.81 (m, 1H), 4.05 (t, J=13.4 Hz, 2H), 3.90 (s, 3H), 3.66-3.60 (m, 2H), 3.60-3.51 (m, 6H), 3.49-3.38 (m, 7H), 2.94-2.81 (m, 1H), 2.63-2.52 (m, 2H), 2.07-1.95 (m, 1H), 1.24 (d, J=6.7 Hz, 6H).

Example 168. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(2-(2-(2-((2-(2,6-dioxopiperidin-3-yl)-1,3-dioxoisoindolin-4-yl)amino)ethoxy)ethoxy)ethyl)-3-methoxybenzamide

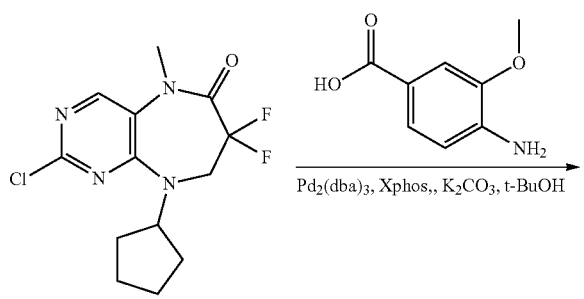

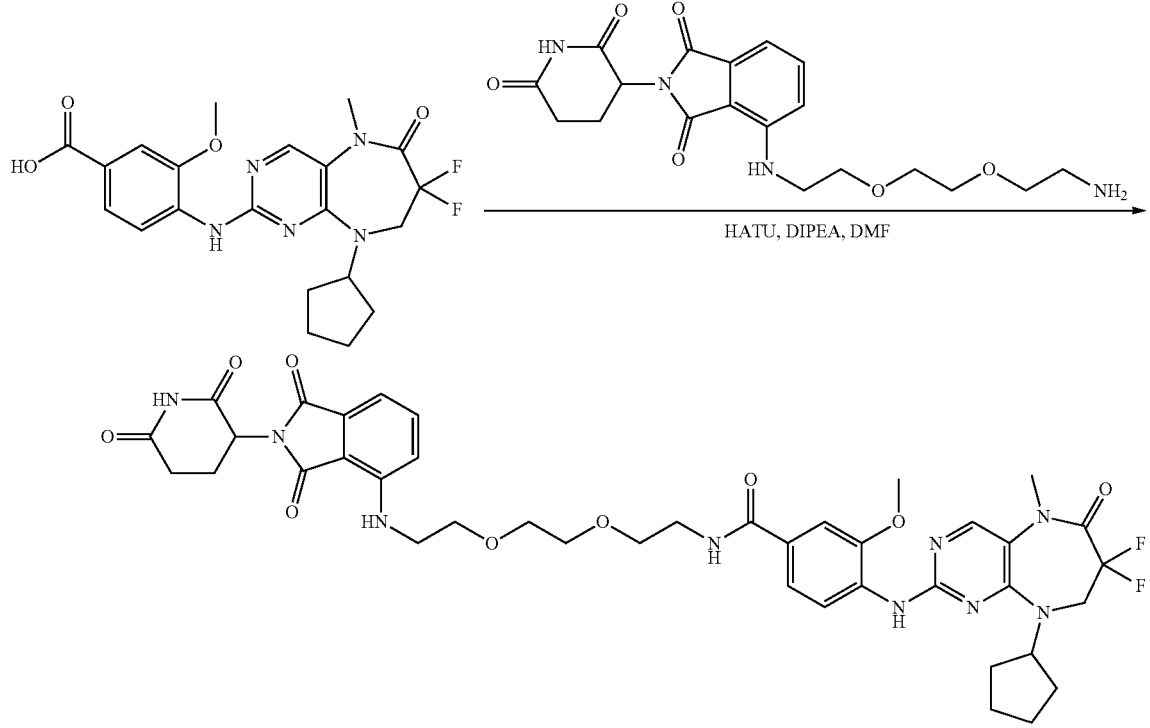

Compound 168

According to the above reaction scheme, in a manner similar to the other examples, obtained the titled compound (38.6 mg, 45.37 μmol, 12.69% yield, 98% purity) as a yellow solid. MS(M+H)$^+$=834.6.

$^1$H NMR (400 MHz, DMSO-d$_6$) δ=11.06 (s, 1H), 8.43 (t, J=5.4 Hz, 1H), 8.35-8.21 (m, 2H), 7.95 (s, 1H), 7.62-7.42 (m, 3H), 7.10 (d, J=8.7 Hz, 1H), 7.01 (d, J=7.1 Hz, 1H), 6.59 (t, J=5.7 Hz, 1H), 5.05 (dd, J$_1$=12.8 Hz, J$_2$=5.4 Hz, 1H), 4.85-4.68 (m, 1H), 4.04 (t, J=14.1 Hz, 2H), 3.92 (s, 3H), 3.64-3.50 (m, 8H), 3.45-3.39 (m, 4H), 3.33 (s, 3H), 2.94-2.81 (m, 1H), 2.63-2.54 (m, 2H), 2.06-1.85 (m, 3H), 1.78-1.66 (m, 2H), 1.65-1.49 (m, 4H).

Example 169. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(3-(3-(2-((2-(2,6-dioxopiperidin-3-yl)-1,3-dioxoisoindolin-4-yl)amino)ethoxy)propoxy)propyl)-3-methoxybenzamide

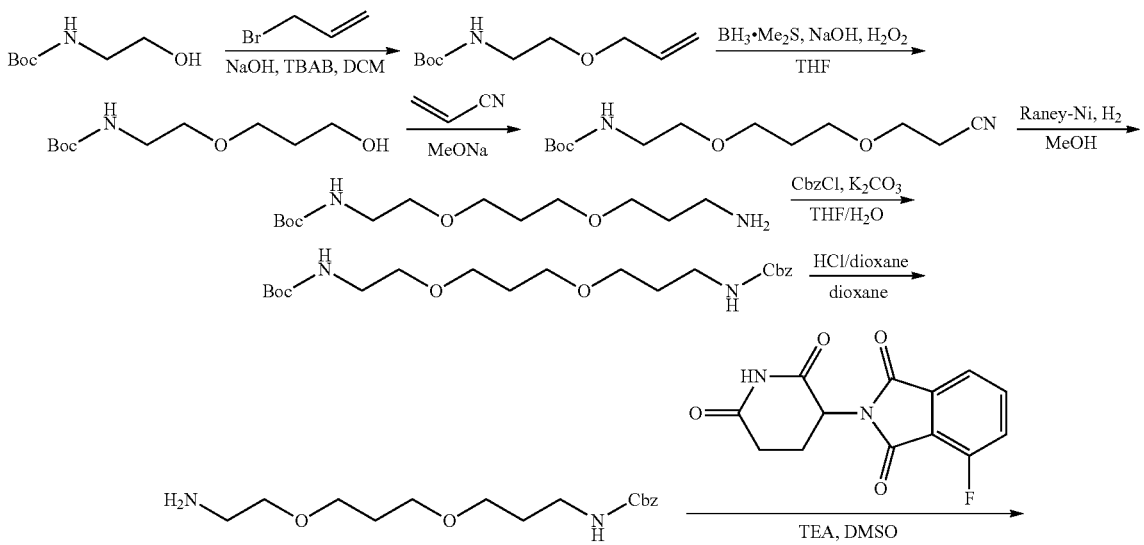

-continued

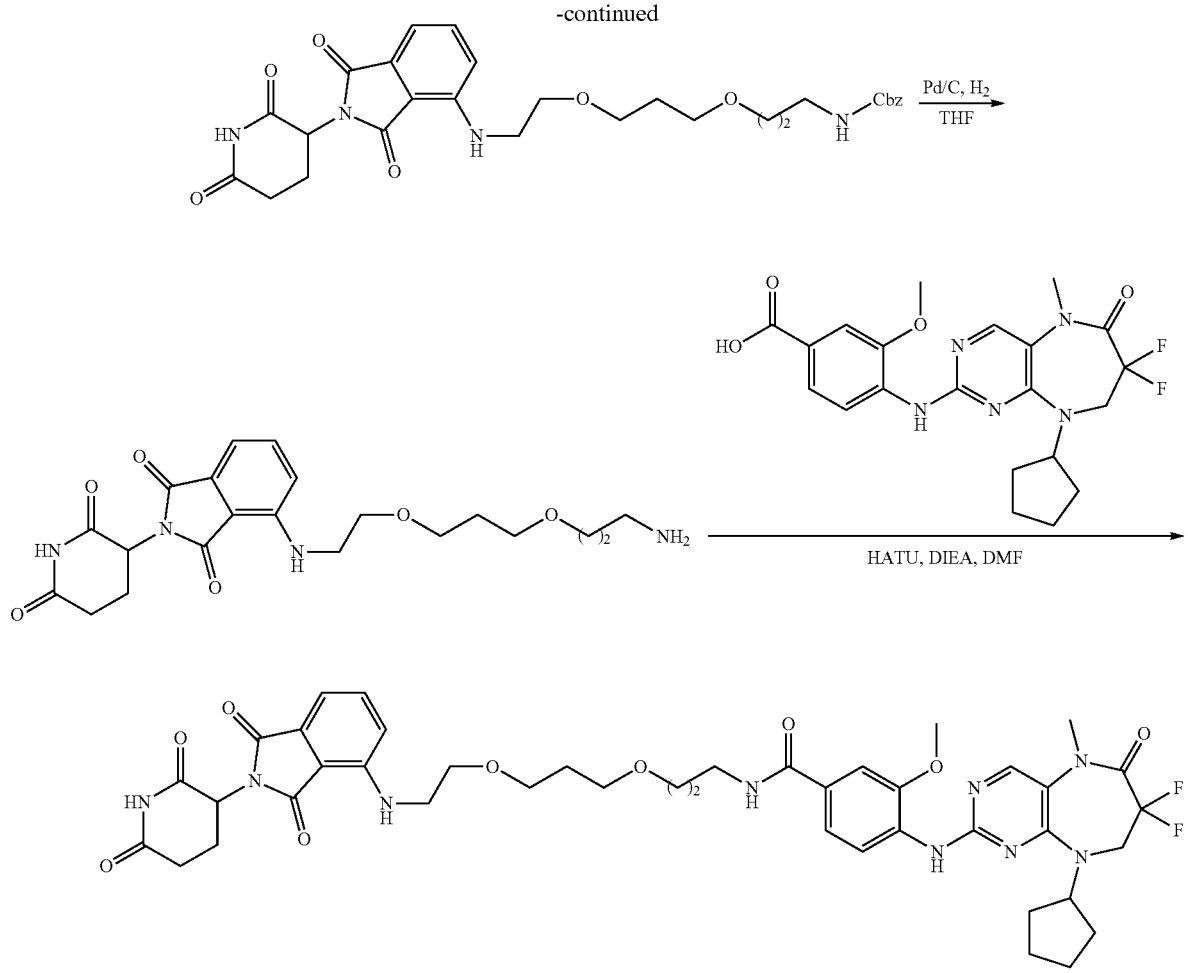

Compound 169

According to the above reaction scheme, in a manner similar to the other examples, obtained the titled compound (29.7 mg, 33.43 μmol, 18.69% yield, 97% purity) as a yellow solid. MS(M+H)$^+$=862.1

$^1$H NMR (400 MHz, DMSO-d$_6$) δ=11.07 (br s, 1H), 8.33 (t, J=5.6 Hz, 1H), 8.29-8.23 (m, 2H), 7.95 (s, 1H), 7.60-7.54 (m, 1H), 7.51-7.43 (m, 2H), 7.13 (d, J=8.5 Hz, 1H), 7.03 (d, J=7.0 Hz, 1H), 6.60 (t, J=5.6 Hz, 1H), 5.06 (dd, J=5.4, 12.9 Hz, 1H), 4.82-4.70 (m, 1H), 4.04 (t, J=14.0 Hz, 2H), 3.92 (s, 3H), 3.60-3.54 (m, 2H), 3.49 (t, J=6.4 Hz, 2H), 3.45-3.38 (m, 6H), 3.33 (s, 3H), 3.30-3.27 (m, 2H), 2.94-2.82 (m, 1H), 2.62-2.58 (m, 1H), 2.57-2.54 (m, 1H), 2.06-1.98 (m, 1H), 1.98-1.89 (m, 2H), 1.79-1.68 (m, 6H), 1.65-1.55 (m, 4H)

Example 170. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(3-(3-(2-((2-(2,6-dioxopiperidin-3-yl)-1,3-dioxoisoindolin-4-yl)amino)ethoxy)propoxy)propyl)benzamide

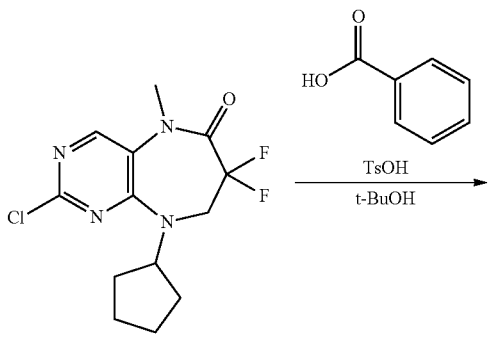

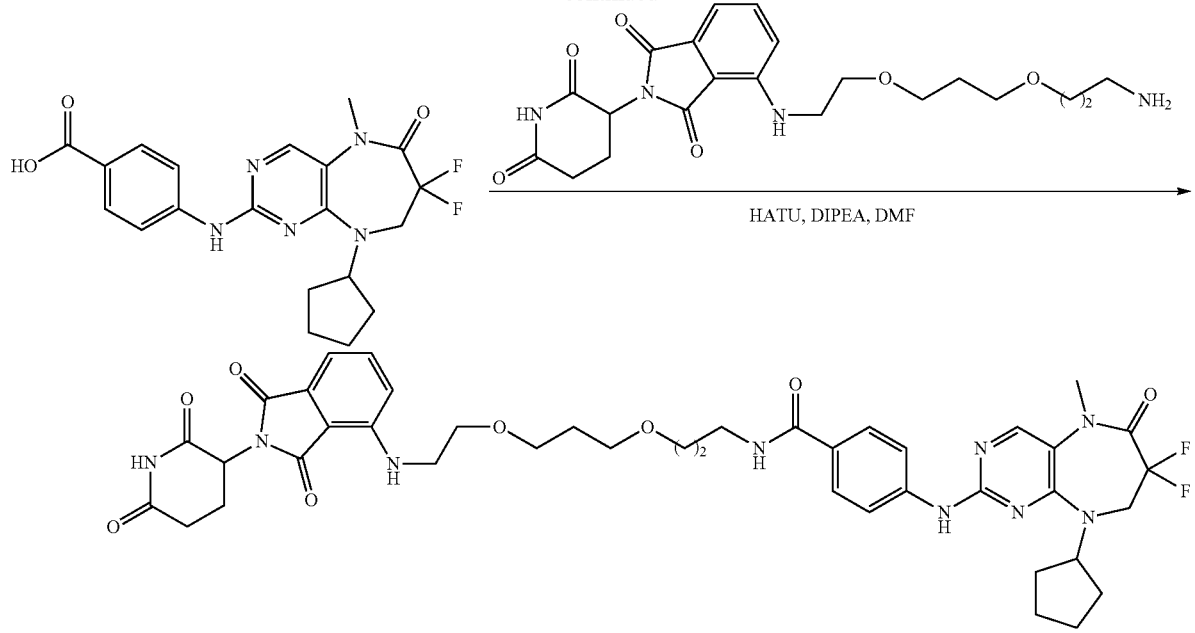

Compound 170

According to the above reaction scheme, in a manner similar to the other examples, obtained the titled compound (20.7 mg, 23.64 μmol, 12.33% yield, 95% purity) as a yellow solid. MS(M+H)⁺=832.1

$^1$H NMR (400 MHz, DMSO-d$_6$) δ=11.07 (s, 1H), 9.66 (s, 1H), 8.26 (s, 1H), 8.23 (t, J=5.6 Hz, 1H), 7.80-7.73 (m, 4H), 7.60-7.54 (m, 1H), 7.13 (d, J=8.6 Hz, 1H), 7.03 (d, J=7.0 Hz, 1H), 6.60 (t, J=5.6 Hz, 1H), 5.06 (dd, J=5.4, 12.9 Hz, 1H), 4.78 (t, J=8.1 Hz, 1H), 4.08-4.00 (m, 2H), 3.59-3.55 (m, 2H), 3.50-3.47 (m, 2H), 3.46-3.43 (m, 2H), 3.43-3.38 (m, 4H), 3.33 (s, 3H), 3.29-3.25 (m, 2H), 2.90-2.81 (m, 1H), 2.64-2.55 (m, 1H), 2.56-2.54 (m, 1H), 2.08-1.99 (m, 2H), 1.96-1.92 (m, 1H), 1.78-1.68 (m, 6H), 1.68-1.50 (m, 4H)

Example 171. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(3-(3-(2-((2-(2,6-dioxopiperidin-3-yl)-1-oxoisoindolin-4-yl)amino)ethoxy)propoxy)propyl)-3-methoxybenzamide

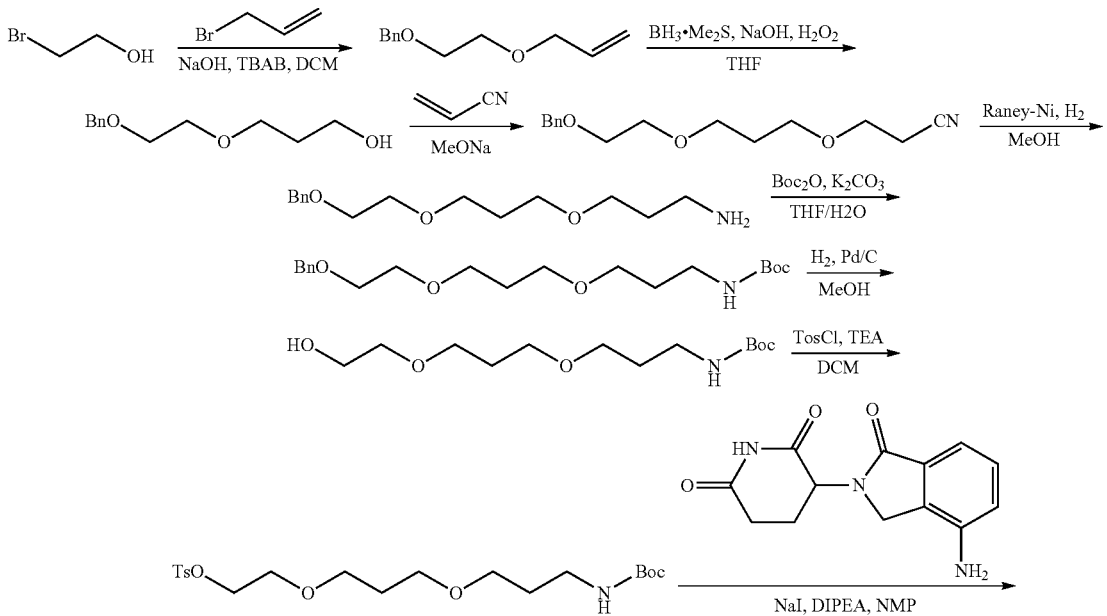

-continued

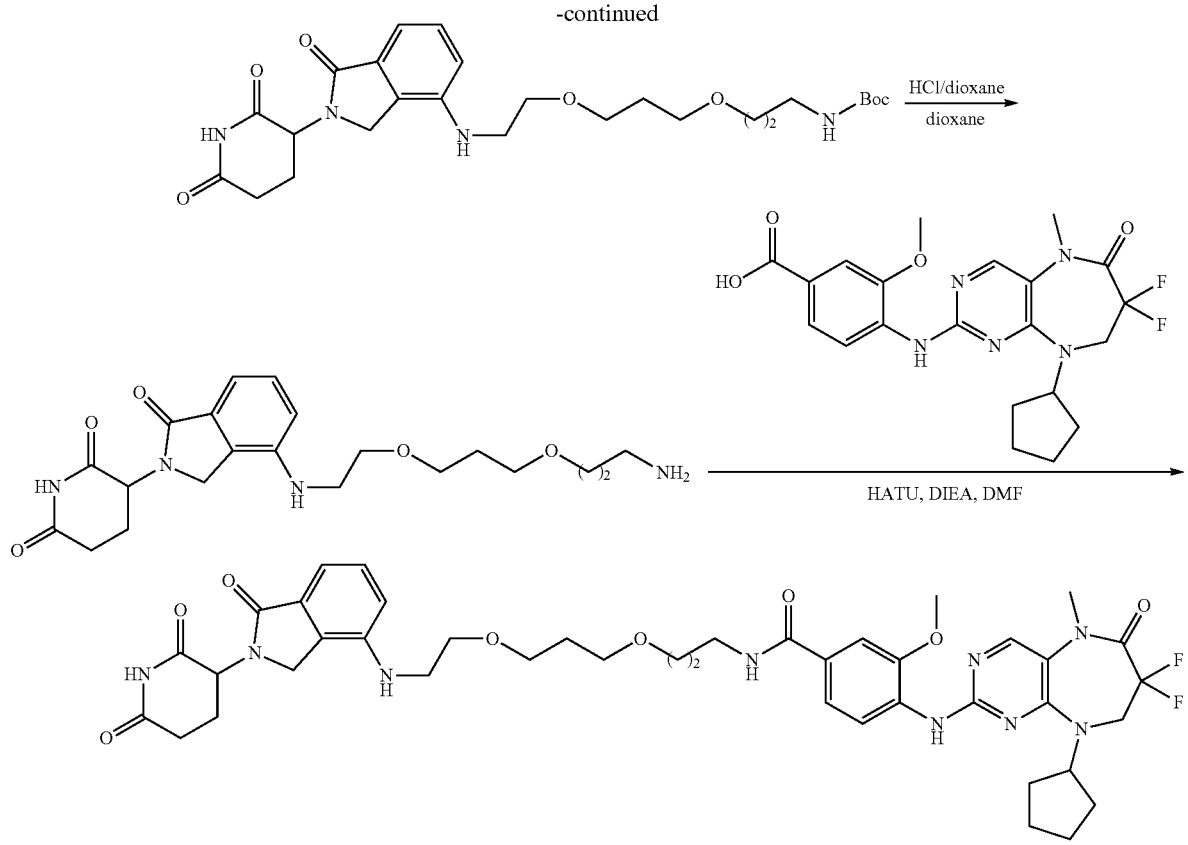

Compound 171

According to the above reaction scheme, in a manner similar to the other examples, obtained the titled compound (26 mg, 29.74 μmol, 16.64% yield, 97% purity) as a white solid. MS(M+H)$^+$=848.1

$^1$H NMR (400 MHz, CDCl$_3$) δ=8.94 (br s, 1H), 8.46 (d, J=8.3 Hz, 1H), 8.07 (s, 1H), 7.84 (s, 1H), 7.43 (d, J=1.7 Hz, 1H), 7.37-7.32 (m, 1H), 7.30 (dd, J=1.7, 8.4 Hz, 1H), 7.28-7.26 (m, 2H), 6.83 (t, J=5.0 Hz, 1H), 6.78 (d, J=7.8 Hz, 1H), 5.22 (dd, J=5.3, 13.1 Hz, 1H), 4.87-4.77 (m, 1H), 4.33 (d, J=15.5 Hz, 1H), 4.12 (d, J=15.5 Hz, 1H), 3.95 (s, 3H), 3.89 (t, J=13.4 Hz, 2H), 3.64 (t, J=5.0 Hz, 2H), 3.61-3.51 (m, 8H), 3.43-3.31 (m, 5H), 2.92-2.75 (m, 2H), 2.34-2.21 (m, 1H), 2.21-2.13 (m, 1H), 2.10-2.02 (m, 2H), 1.89 (m, 4H), 1.78-1.73 (m, 2H), 1.72-1.66 (m, 2H), 1.62-1.55 (m, 2H)

Example 172. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(23-((2-(2,6-dioxopiperidin-3-yl)-1,3-dioxoisoindolin-4-yl)amino)-3,6,9,12,15,18,21-heptaoxatricosyl)piperidin-4-yl)-2-fluoro-5-methoxybenzamide

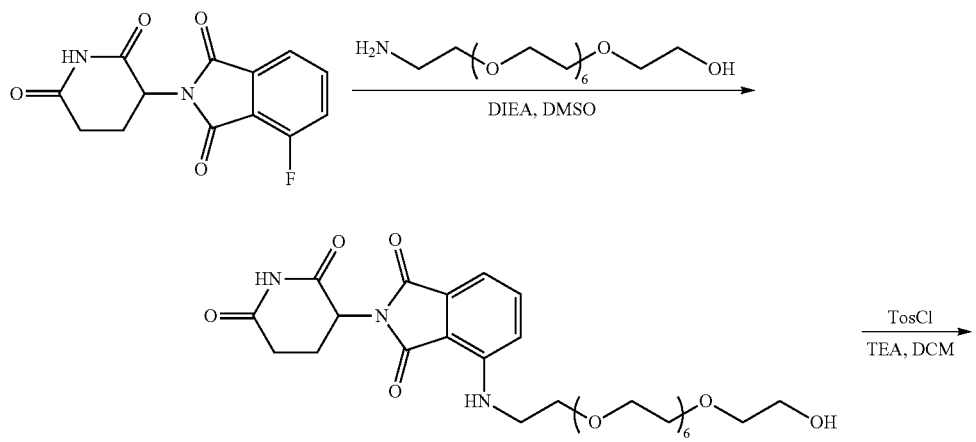

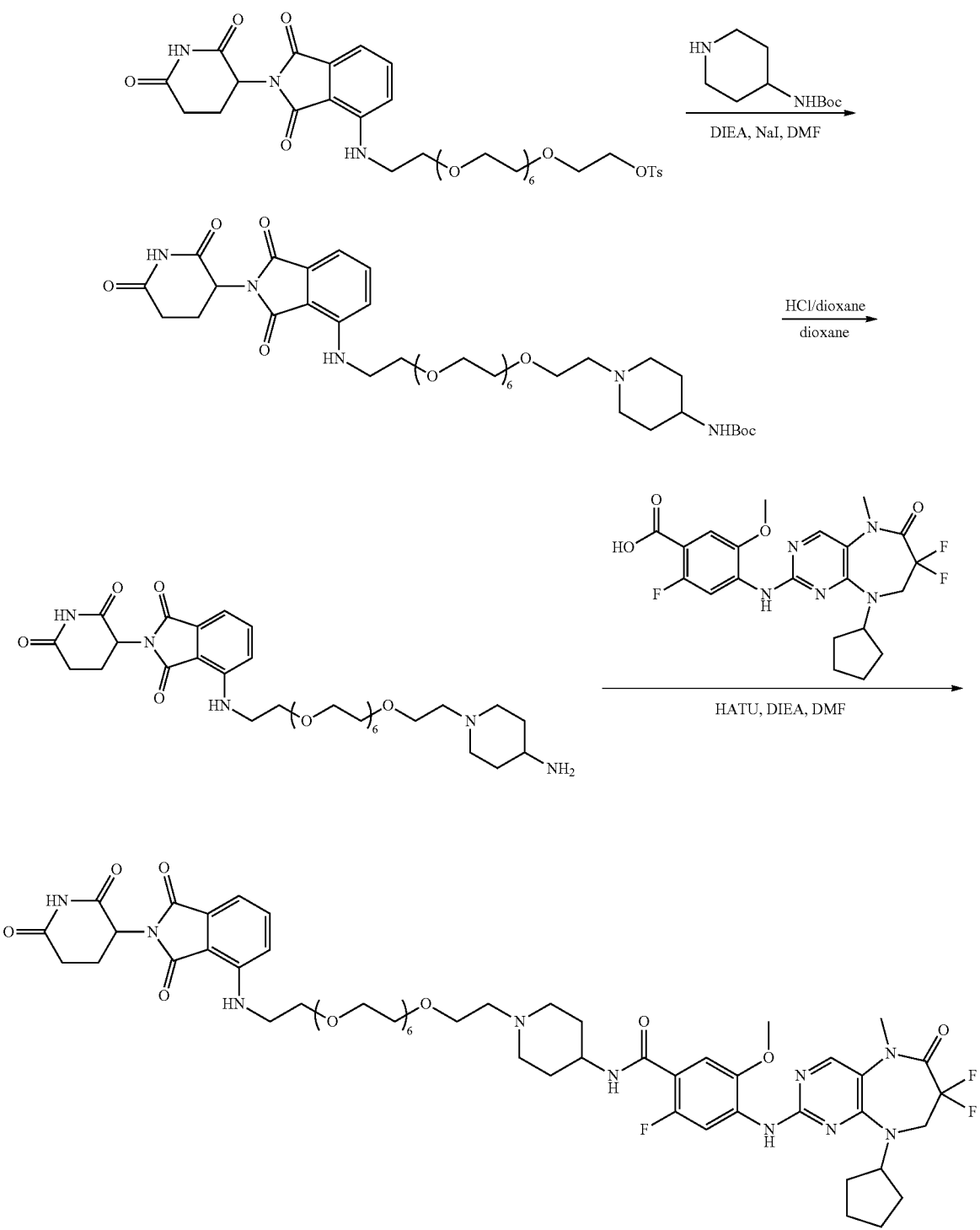
Compound 172
According to the above reaction scheme, in a manner similar to the other examples, obtained the titled compound (26.4 mg, 21.02 umol, 12.23% yield, 92% purity) as a yellow solid. MS(M+H)$^+$=1155.4.
$^1$H NMR (400 MHz, DMSO-d$_6$) δ=11.35-10.83 (m, 1H), 8.30 (s, 1H), 8.24 (d, J=13.3 Hz, 1H), 8.03 (s, 1H), 7.87 (dd, J=3.5, 7.6 Hz, 1H), 7.58 (dd, J=7.3, 8.4 Hz, 1H), 7.18 (d, J=6.7 Hz, 1H), 7.14 (d, J=8.7 Hz, 1H), 7.03 (d, J=7.1 Hz, 1H), 6.60 (t, J=5.6 Hz, 1H), 5.05 (dd, J=5.4, 13.0 Hz, 1H), 4.88-4.76 (m, 1H), 4.07 (br t, J=13.9 Hz, 2H), 3.91 (s, 3H), 3.75-3.69 (m, 1H), 3.63-3.60 (m, 2H), 3.58-3.51 (m, 6H), 3.51-3.48 (m, 19H), 3.48-3.44 (m, 4H), 2.90-2.81 (m, 3H), 2.63-2.52 (m, 4H), 2.47-2.43 (m, 2H), 2.09-2.00 (m, 3H), 1.99-1.92 (m, 2H), 1.81-1.69 (m, 4H), 1.66-1.50 (m, 6H).

Example 173. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-((3S)-1-(5-(4-(2-(2,6-dioxopiperidin-3-yl)-1,3-dioxoisoindolin-4-yl)piperazin-1-yl)pentanoyl)pyrrolidin-3-yl)-2-fluoro-5-methoxybenzamide
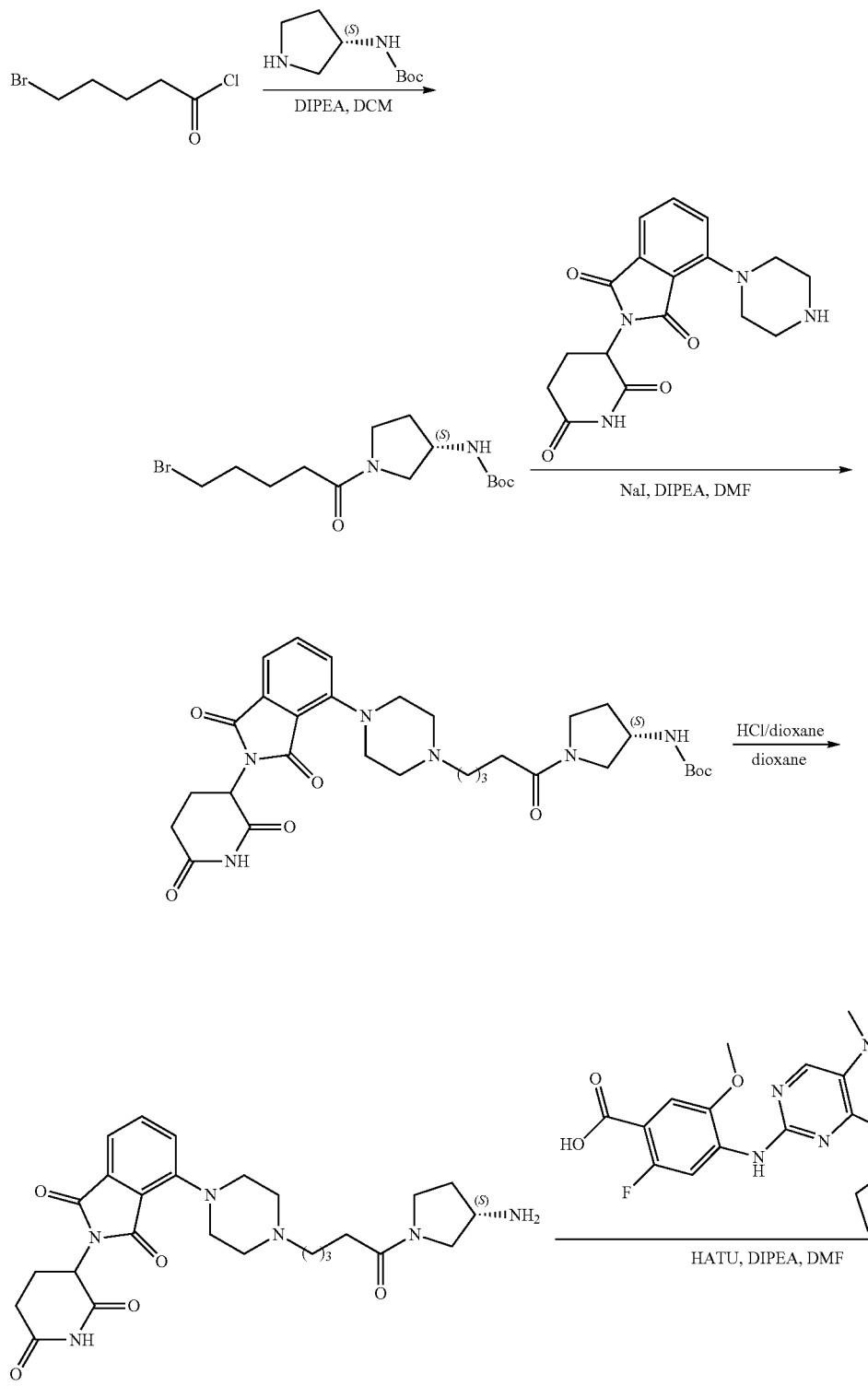

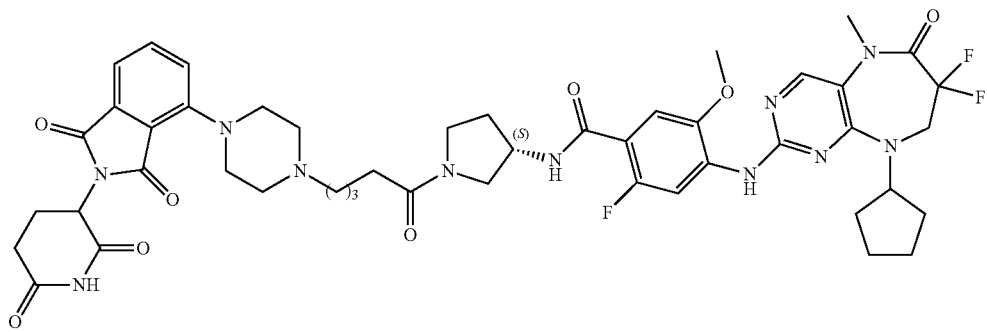

Compound 173

According to the above reaction scheme, in a manner similar to the other examples, obtained the titled compound (119.3 mg, 119.80 mol, 33.29% yield, 96.2% purity) as a yellow solid. MS(M+H)$^+$=958.3.

$^1$H NMR (400 MHz, CD$_3$CN) δ=8.92-8.91 (m, 1H), 8.41-8.34 (m, 1H), 8.11 (s, 1H), 7.80-7.74 (m, 1H), 7.64-7.54 (m, 1H), 7.37 (t, J=7.5 Hz, 1H), 7.32-7.16 (m, 2H), 7.03-6.91 (m, 1H), 5.00-4.93 (m, 1H), 4.91-4.84 (m, 1H), 4.64-4.49 (m, 1H), 4.02-3.89 (m, 6H), 3.84-3.76 (m, 1H), 3.67-3.36 (m, 4H), 3.35-3.20 (m, 8H), 2.74-2.66 (m, 2H), 2.60-2.49 (m, 3H), 2.41-2.34 (m, 2H), 2.31-2.22 (m, 2H), 2.07-2.00 (m, 4H), 1.81-1.73 (m, 2H), 1.69-1.57 (m, 6H), 1.56-1.49 (m, 2H).

Example 174. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-((3S)-1-(3-(4-(2-(2,6-dioxopiperidin-3-yl)-1,3-dioxoisoindolin-5-yl)piperazin-1-yl)propanoyl)pyrrolidin-3-yl)-3-methoxybenzamide

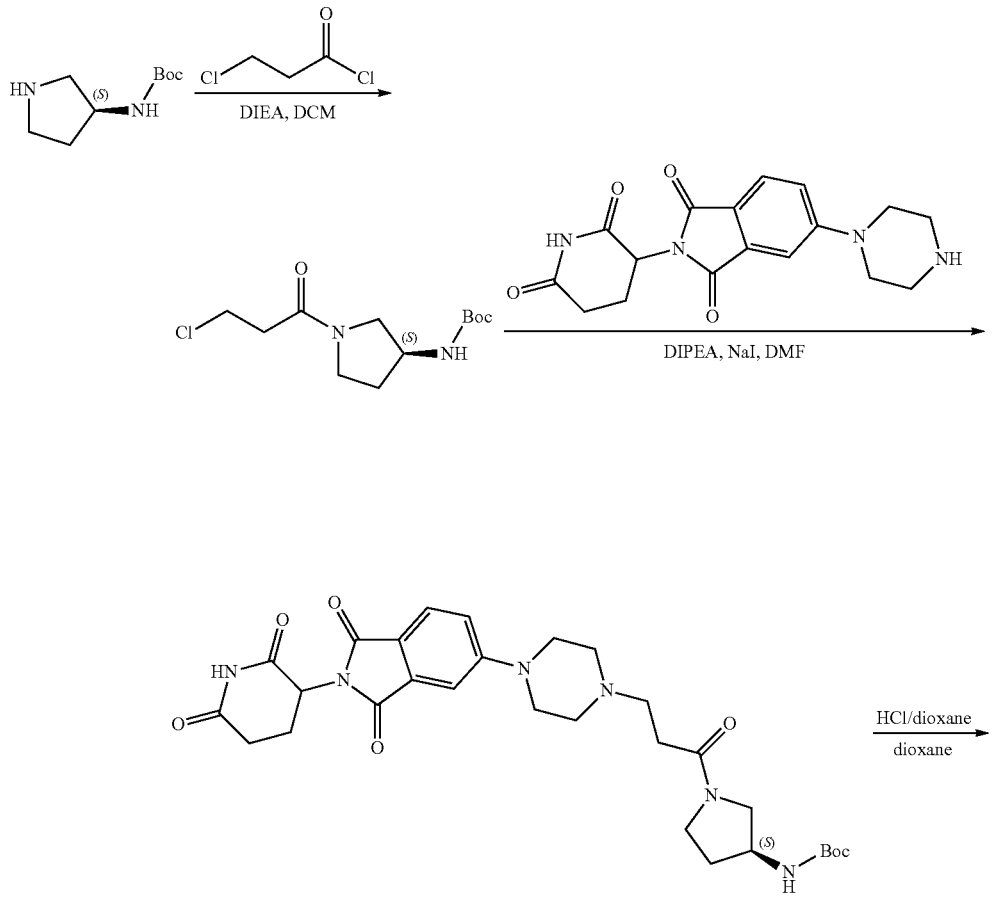

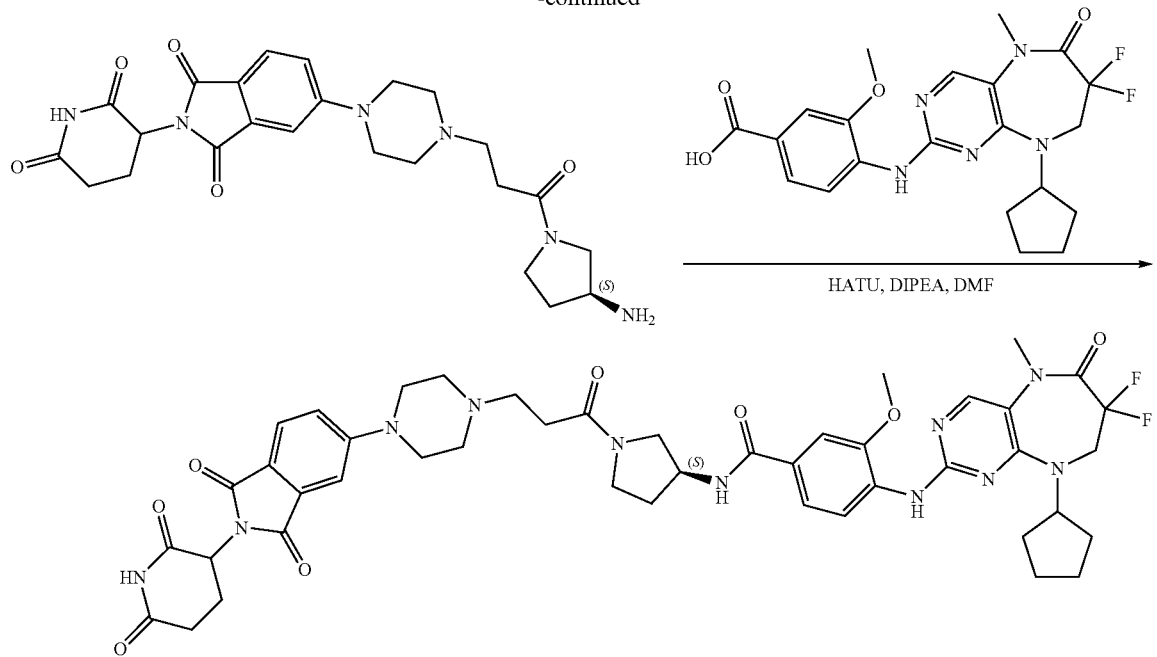

Compound 174

According to the above reaction scheme, in a manner similar to the other examples, obtained the titled compound (44.2 mg, 47.98 μmol, 21.47% yield, 99% purity) as a yellow solid. MS(M+H)⁺=912.3

¹H NMR (400 MHz, DMSO-d₆) δ=11.11-11.03 (m, 1H), 8.41 (dd, J=6.5, 19.3 Hz, 1H), 8.31-8.21 (m, 2H), 7.97 (d, J=7.7 Hz, 1H), 7.66 (dd, J=8.6, 11.9 Hz, 1H), 7.49 (dd, J=1.8, 5.6 Hz, 2H), 7.32 (dd, J=1.9, 16.2 Hz, 1H), 7.28-7.18 (m, 1H), 5.06 (ddd, J=2.9, 5.3, 13.0 Hz, 1H), 4.82-4.68 (m, 1H), 4.56-4.35 (m, 1H), 4.04 (br t, J=14.1 Hz, 2H), 3.93 (d, J=5.0 Hz, 3H), 3.82 (dd, J=6.6, 10.2 Hz, 1H), 3.69-3.61 (m, 1H), 3.61-3.49 (m, 2H), 3.44-3.33 (m, 7H), 2.93-2.82 (m, 1H), 2.60 (br t, J=6.3 Hz, 8H), 2.47-2.42 (m, 2H), 2.24-2.08 (m, 1H), 2.05-1.88 (m, 4H), 1.81-1.65 (m, 2H), 1.65-1.53 (m, 4H).

Example 175. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-((3S)-1-(4-(6-(2-(2,6-dioxopiperidin-3-yl)-1,3-dioxoisoindolin-4-yl)-2,6-diazaspiro[3.3]heptan-2-yl)butanoyl)pyrrolidin-3-yl)-2-fluoro-5-methoxybenzamide

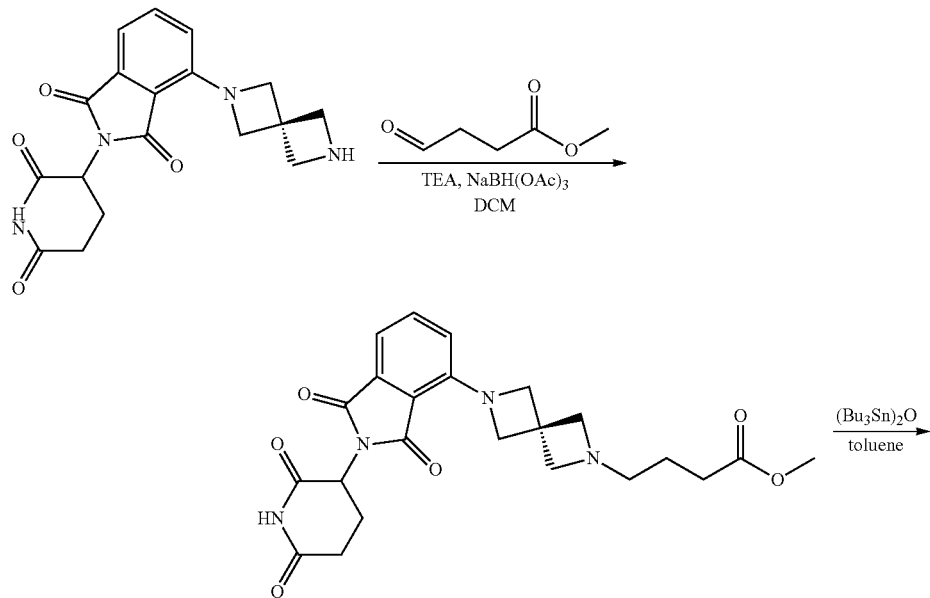

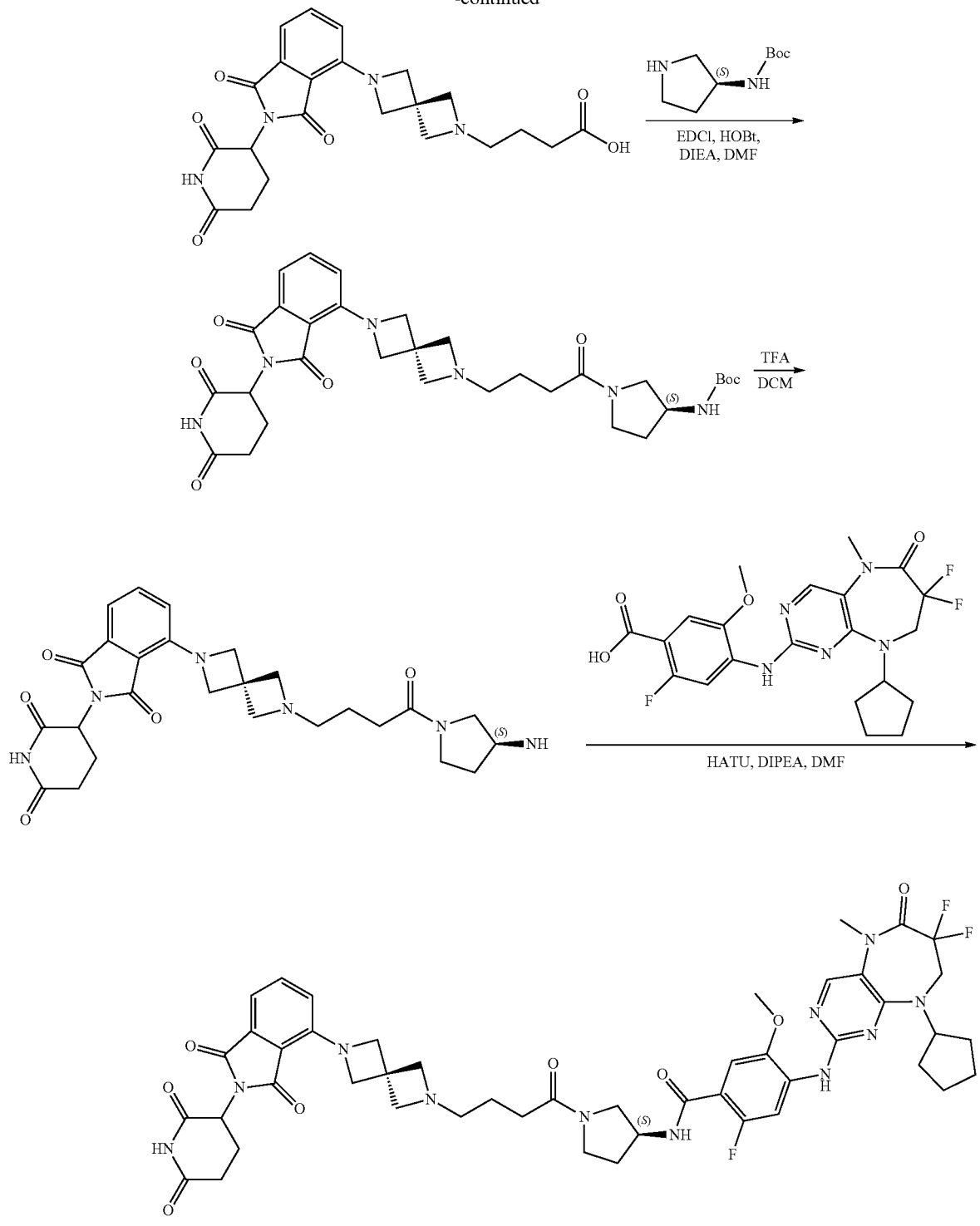
Compound 175
According to the above reaction scheme, in a manner similar to the other examples, obtained the titled compound (17.5 mg, 17.39 μmol, 16.19% yield, 95% purity) as a yellow solid. MS(M+H)$^+$=956.3
$^1$H NMR (400 MHz, DMSO-d$_6$) δ=11.05-11.03 (m, 1H), 8.30-8.23 (m, 3H), 8.03 (s, 1H), 7.58-7.51 (m, 1H), 7.20 (d, J=6.4 Hz, 1H), 7.13-7.08 (m, 1H), 6.76 (t, J=8.4 Hz, 1H), 5.08-4.99 (m, 1H), 4.87-4.76 (m, 1H), 4.51-4.37 (m, 1H), 4.26-4.21 (m, 3H), 4.07 (br t, J=14.0 Hz, 2H), 3.92-3.90 (m, 2H), 3.79-3.70 (m, 1H), 3.62-3.53 (m, 1H), 3.52-3.42 (m, 2H), 3.38-3.34 (m, 2H), 3.33-3.32 (m, 3H), 3.27-3.20 (m, 4H), 2.92-2.81 (m, 1H), 2.61-2.54 (m, 2H), 2.47-2.42 (m, 1H), 2.36-2.29 (m, 2H), 2.26-2.17 (m, 2H), 2.03-1.86 (m, 4H), 1.76-1.56 (m, 6H), 1.53-1.43 (m, 2H).

Comparative Example 1. Exemplary Compound Disclosed in CN 106543185 A
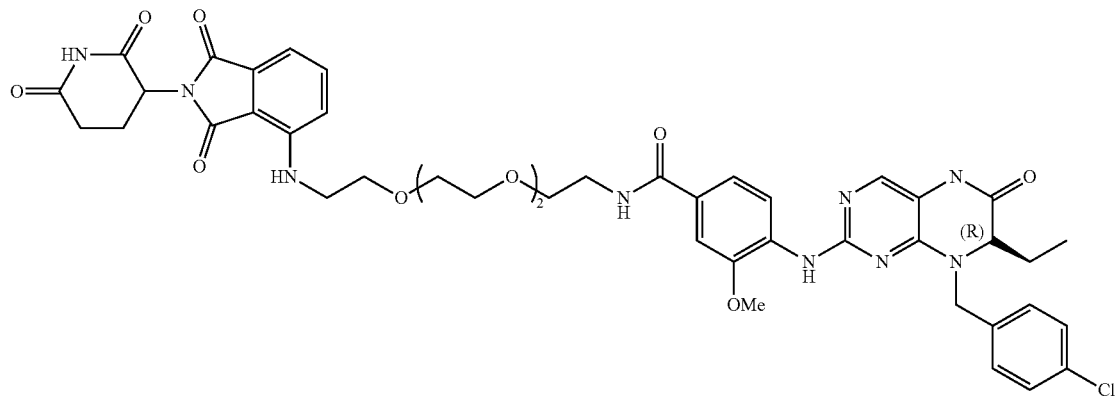
Comparative Example 2. Exemplary Compound Disclosed in CN 106543185 A
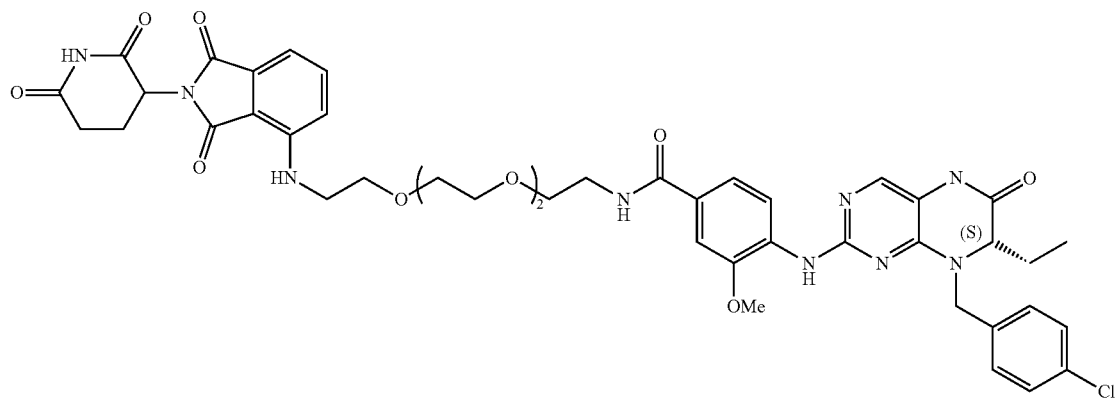
Comparative Example 3. 4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxy-N-(1-(2-(2-(2-(phenylamino)ethoxy)ethoxy)ethyl)piperidin-4-yl)benzamide
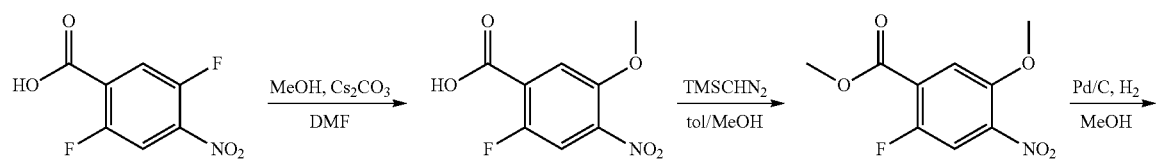
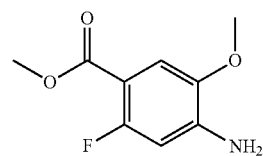

-continued
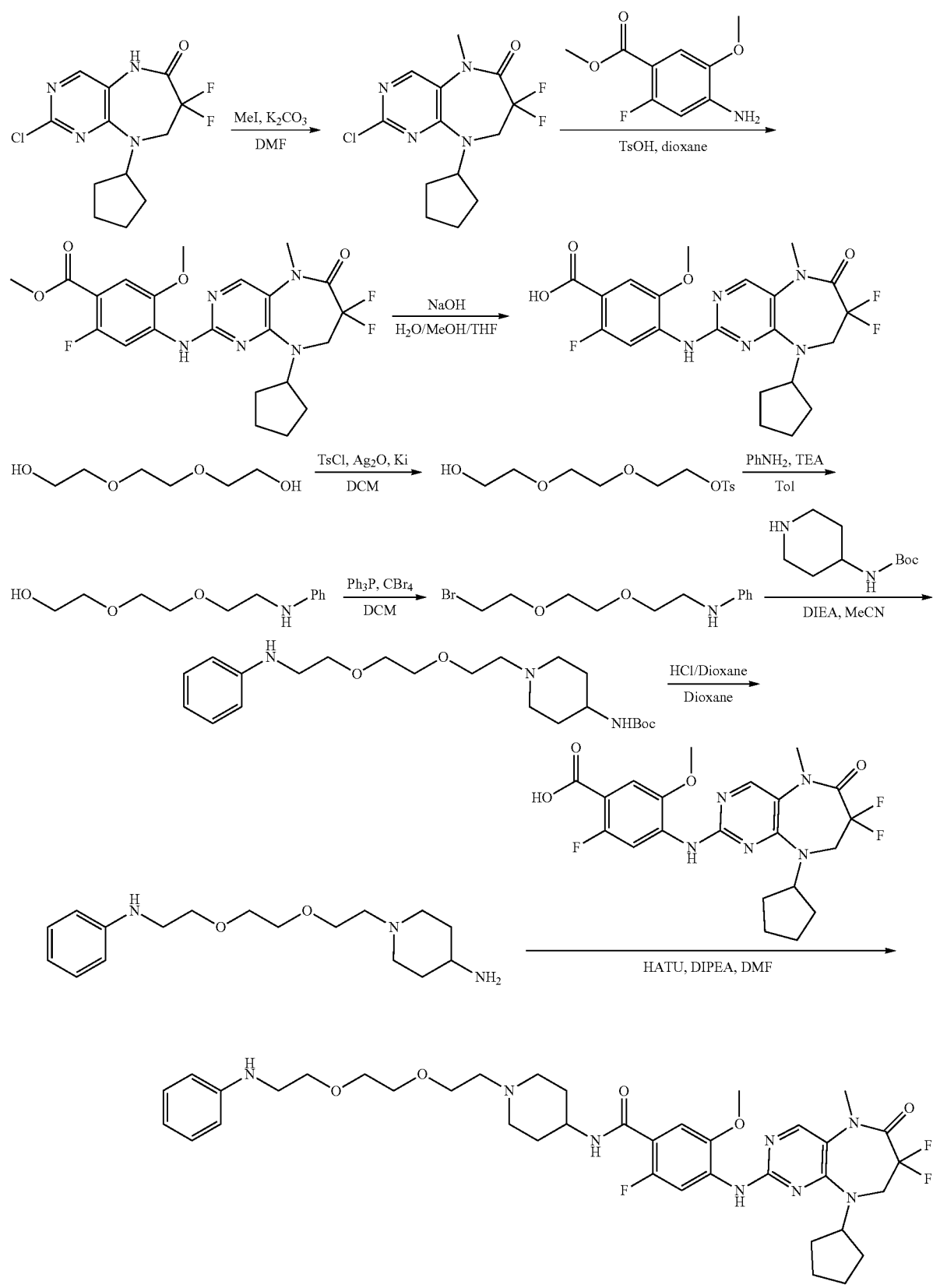
Comparative Compound 3

Step 1-11 are Described in the Above Reaction Scheme

Step 12: Synthesis of 4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxy-N-(1-(2-(2-(2-(phenylamino)ethoxy)ethoxy)ethyl)piperidin-4-yl)benzamide (Comparative Compound 1)

To the solution of 4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzoic acid (200 mg, 429.71 umol) and HATU (326.78 mg, 859.43 umol) in DMF (5 mL) was added DIPEA (166.61 mg, 1.29 mmol, 224.55 uL), the mixture was stirred at 25° C. for 10 min, 1-(2-(2-(2-(phenylamino)ethoxy)ethoxy)ethyl)piperidin-4-amine (184.00 mg, 483.76 umol, 2HCl salt) was added and the resulting mixture was stirred at 25° C. for 1 h. LCMS showed that the reaction was completed. The mixture was poured into water (20 mL) and extracted with EtOAc (20 mL×3). The combined organic layer was washed with brine (50 mL), dried over $Na_2SO_4$, filtered and concentrated. The residue was purified by prep-HPLC (column: Waters Xbridge C18 150*50 mm*10 um; mobile phase: [water(10 mM $NH_4HCO_3$)-ACN]; B %: 45%-75%, 11.5 min) to 4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxy-N-(1-(2-(2-(2-(phenylamino)ethoxy)ethoxy)ethyl)piperidin-4-yl)benzamide (106.2 mg, 139.29 umol, 32.41% yield, 99% purity) as off-white solid.

MS $(M+H)^+$=755.5

$^1$H NMR (400 MHz, CDCl3) δ=8.37 (d, J=15.0 Hz, 1H), 8.07 (s, 1H), 7.82 (s, 1H), 7.57 (d, J=7.2 Hz, 1H), 7.22-7.14 (m, 2H), 6.75-6.56 (m, 5H), 4.86 (q, J=8.5 Hz, 1H), 4.04 (br s, 1H), 3.97 (s, 3H), 3.92 (t, J=13.2 Hz, 2H), 3.72 (t, J=5.2 Hz, 2H), 3.68-3.58 (m, 6H), 3.42 (s, 3H), 3.31 (t, J=5.2 Hz, 2H), 2.91 (br s, 2H), 2.64 (br s, 2H), 2.29 (br s, 2H), 2.17-2.02 (m, 4H), 1.84-1.68 (m, 4H), 1.65-1.52 (br s, 4H).

Experimental Examples

1. Culture of HeLa Cell Line

The HeLa cell line was purchased from Korea Cell Line Bank (KCLB), Seoul, Korea. The passage in cell culture was maintained at P115 to P125.

For cell counting, cell counter (Thermo Fisher Scientific Inc., Catalog #AMQAX1000) and 0.4% trypan blue solution were used.

For cell culture, DMEM (Gibco, Cat. No. 1195-65; Lot. No. 2085318), FBS (Gibco, Cat. No. 16000-044; Lot. No. 2097593), Penicillin/Streptomycin (PS) (Gibco, Cat. No. 15140-122; Lot. No. 2058855), 100 mm² cell culture dish (SPL, Cat. No. 20100), 150 mm² cell culture dish (SPL, Cat. No. 20150), 12-well culture plate (SPL, Cat. No. 30012), PBS pH 7.4 (Gibco, Cat. No. 10010-023; Lot. No. 2085080), TrypLE™ Express (Gibco, Cat. No. 12605-010; Lot No. 2070638), Counting Chamber (Hematocytometer) (Hirschmann, Cat. No. 8100204), and 0.4% Trypan Blue Solution (DYNEBIO, Cat. No. CBT3710; Lot. No. 20190723) were used.

2. Treatment of Compounds of the Present Invention $2\times10^5$ cells were seeded for each well of a 12-well plate (SPL), and the cells were cultured in the culture medium in a total volume of 2 ml.

The compounds of Examples were completely dissolved in DMSO and used in the experiment, and thymidine was completely dissolved in DW and used in the experiment. For thymidine block, the products were treated with 2 mM of thymidine (Sigma-Aldrich Cat. No. T9250-5G) and then incubated for 24 hours.

For release and chemical treatment, the medium was suctioned and washed 3 times with 1×PBS. Complete media was added, followed by incubation for 4 hours in a $CO_2$ incubator. Each compound was diluted three folds from the highest concentration of 3 μM to the lowest concentration in 10 points and then incubated for 6 hours again.

3. Western Blotting

For SDS-PAGE and Western blotting, 1×RIPA lysis buffer (Rockland, Cat. No. MB-030-0050; Lot no. 39751), 100× Protease Inhibitor Cocktail (Quartett, Cat. No. PPI1015; Lot no. PCO50038424), Pierce™ BCA protein assay kit (ThermoScientific, Cat. No. 23225; Lot no. UC276876), albumin standard (ThermoScientific, Cat. No. 23209; Lot no. UB269561), 4-15% Mini-PROTEAN TGX stain-free gel (Bio-rad, Cat. No. 4568085; Lot no. L007041B), 10× Tris/Glycine/SDS buffer (Bio-rad, Cat. No. 1610732; Lot no. 10000044375B); 10×TBS (Bio-rad, Cat. No. 1706435; Lot no. 1000045140B), 10% Tween 20 (Cat. No. 1610781; Lot no. L004152B), Color protein standard broad range (NEB, Cat. No. P7719S; Lot no. 10040349), 4× Laemmli sample buffer (Bio-rad, Cat. No. 1610747; Lot no. L004133B), β-mercaptoethanol (Sigma-Aldrich, Cat. No. M3148; Lot no. 60-24-2), SuperBlock™ T20 (TBS) blocking buffer (ThermoScientific, Cat. No. 37536; Lot no. UC282578), 1M sodium azide solution (Sigma-Aldrich, Cat. No. 08591-1 mL-F; Lot no. BCBV4989), α-Rabbit pAb to Ms IgG (abcam, Cat. No. ab97046; Lot no. GR3252115-1), α-Goat pAb to Rb IgG (CST, Cat. No. 7074S; Lot no. 28), α-GAPDH (abeam, Cat. No. ab8245; Lot no. GR3275542-2), α-Plk1 (CST, Cat. No. 208G4), α-BRD4 (CST, Cat. No. 13440S), ECL™ Prime western blotting reagents (GE Healthcare, Cat. No. RPN2232; Lot no. 17001655), Ponceau S solution (Sigma-Aldrich, Cat. No. P7170; Lot no. SLBV4112), Difco™ Skim milk (BD, Cat. No. 232100; Lot no. 8346795), and iBlot® 2 NC Regular stacks (Invitrogen, Cat. No. IB23001; Lot no. 2NR110619-02) were used.

For cell harvesting, the cells were first separated from the plate using trypsin and then washed with the medium and PBS. Specifically, the medium was suctioned off and washed with 1 mL of PBS, and PBS was suctioned off. The cells were treated with 0.5 mL TrypLE™ Express at 37° C. for 7 minutes to separate the cells, and then 0.5 mL of complete medium was added to collect 1 mL of cell culture solution. 1 mL of the cell collection solution was centrifuged at 8,000 rpm for 120 seconds, and the supernatant was removed. After washing with 0.2 mL of PBS, the PBS was removed.

For cell lysis, a lysis buffer was added and cell debris was removed to obtain a cell lysate. Specifically, the cells were treated with 70 μL of 1×RIPA buffer containing a protease inhibitor and incubated for 30 minutes on ice. Then, the cells were centrifuged at 4° C. and 15,000 rpm for 10 minutes to obtain a cell lysate.

Then, a standard curve was obtained using the BCA assay, and the protein mass in the lysate was quantified by substituting the curve equation. The mixture was incubated at 37° C. for 30 minutes using 20 μL of standard or sample solution, and 200 μL of BCA or Bradford solution, and measured at 562 nm absorbance. Samples were prepared by adding 4× sample buffer so that the quantity of protein added to each well was 15 μg.

Sodium dodecyl sulfate polyacrylamide gel electrophoresis (SDS-PAGE) was performed by setting a running time of 100 minutes at 120 V on a 4-15% Mini-PROTEAN TGX stain-free gel (15 well). Transferring was performed on iBlot® 2 NC Mini stacks at P0 mode of the dry blotting system. After staining using Ponceau S solution, blocking was performed for 1 hour with a blocking buffer (Thermo). After washing with 1×TBS containing 0.05% Tween 20, the product was reacted at 4° C. for 16 hours with anti-Plk1 (CST) antibody (1:500), anti-BRD4 (Cell signaling) antibody (1:1000) or anti-GAPDH (abcam) antibody (1:10,000) in 1 TBS-T as a primary antibody, washing three times for 10 minutes with 1×TBS containing 0.05% Tween20, the product was reacted at room temperature for 1 hour with anti-mouse antibody (abcam) (1:10000) or anti-rabbit antibody (CST) (1:5000) in 1×TBS-T as a secondary antibody. Then, after washing three times for 10 minutes with 1×TBS containing 0.05% Tween 20, the product was detected with an ECL working solution (1:1).

To analyze the results, an image analyzer (GE) was used to obtain final blot data. The ratio of PLK1 to GAPDH for each sample was calculated using the ImageQuant TL (ver. 8.2.0) program. Each calculated value was entered into each cell of the Graphpad Prism 9 program, and the graph was automatically calculated to confirm the Dmax value corresponding to the protein degradation ability (A: Dmax is 80% or more; B: Dmax is 80% or less and 60% or more; C: less than 60%). If the grade of Dmax is A or B, $DC_{50}$ value was also measured (Grade A: $DC_{50}$ is 50 nM or less; B: 500 nM or less; C: more than 500 nM).

4. PLK1 Degradability of the Compounds of the Present Invention

As a result of the experiment, Dmax and DC50 values for the compounds of the compounds of the present invention were measured as shown in the following table.

TABLE 2

| No. | $D_{max}$ | $DC_{50}$ | No. | $D_{max}$ | $DC_{50}$ |
|---|---|---|---|---|---|
| 1 | A | A | 2 | A | A |
| 3 | A | A | 4 | A | A |
| 5 | A | A | 6 | C | — |
| 7 | C | — | 8 | C | |
| 9 | B | B | 10 | B | B |
| 11 | B | B | 12 | B | C |
| 13 | B | B | 14 | C | |
| 15 | B | C | 16 | C | |
| 17 | C | | 18 | B | B |
| 19 | B | B | 20 | C | |
| 21 | A | A | 22 | B | B |
| 23 | A | A | 24 | A | A |
| 25 | A | A | 26 | C | |
| 27 | B | B | 28 | B | B |
| 29 | A | A | 30 | A | A |
| 31 | C | | 32 | A | A |
| 33 | A | A | 34 | A | A |
| 35 | A | A | 36 | A | A |
| 37 | B | B | 38 | B | B |
| 39 | A | A | 40 | B | B |
| 41 | A | A | 42 | B | C |
| 43 | A | A | 44 | A | A |
| 45 | A | A | 46 | C | |
| 47 | C | | 48 | B | B |
| 49 | B | B | 50 | A | A |
| 51 | A | A | 52 | A | A |
| 53 | A | A | 54 | B | B |
| 55 | B | B | 56 | B | B |
| 57 | B | B | 58 | C | |
| 59 | C | | 60 | A | A |
| 61 | B | A | 62 | B | A |
| 63 | A | A | 64 | A | A |
| 65 | A | A | 66 | B | B |
| 67 | B | B | 68 | B | B |
| 69 | A | A | 70 | B | B |
| 71 | A | A | 72 | B | B |
| 73 | A | A | 74 | A | A |
| 75 | A | A | 76 | B | B |
| 77 | B | B | 78 | A | A |
| 79 | A | A | 80 | C | |
| 81 | C | | 82 | C | |
| 83 | C | | 84 | B | B |
| 85 | C | | 86 | C | |
| 87 | C | | 88 | C | |
| 89 | B | B | 90 | B | B |
| 91 | B | B | 92 | A | A |
| 93 | A | A | 94 | B | C |
| 95 | B | C | 96 | A | A |
| 97 | C | | 98 | B | B |
| 99 | B | B | 100 | B | B |
| 101 | A | A | 102 | A | A |
| 103 | A | A | 104 | A | A |
| 105 | B | B | 106 | B | B |
| 107 | A | A | 108 | A | A |
| 109 | B | B | 110 | A | A |
| 111 | A | A | 112 | B | B |
| 113 | C | | 114 | A | A |
| 115 | A | A | 116 | A | A |
| 117 | A | A | 118 | A | A |
| 119 | A | A | 120 | A | A |
| 121 | A | A | 122 | A | A |
| 123 | A | A | 124 | B | B |
| 125 | A | A | 126 | B | B |
| 127 | B | B | 128 | A | A |
| 129 | A | A | 130 | A | A |
| 131 | A | A | 132 | A | A |
| 133 | A | A | 134 | A | A |
| 135 | A | A | 136 | A | A |
| 137 | A | A | 138 | A | A |
| 139 | A | A | 140 | A | A |
| 141 | A | A | 142 | B | B |
| 143 | B | B | 144 | A | A |
| 145 | B | C | 146 | C | |
| 147 | B | B | 148 | A | A |
| 149 | B | B | 150 | A | A |
| 151 | B | B | 152 | A | A |
| 153 | A | A | 154 | C | |
| 155 | B | B | 156 | A | A |
| 157 | A | A | 158 | B | B |
| 159 | A | A | 160 | A | A |
| 161 | A | A | 162 | A | A |
| 163 | B | B | 164 | B | B |
| 165 | C | | 166 | B | B |
| 167 | B | B | 168 | A | A |
| 169 | A | A | 170 | A | A |
| 171 | A | A | 172 | A | A |
| 173 | A | A | 174 | A | A |
| 175 | A | A | | | |

In particular, it was confirmed that Compounds 1 and 2 of the present invention exhibited excellent PLK1 protein degradability in comparison with the PLK PROTAC (Comparative Compounds 1 and 2) of CN106543185A as well as Comparative Compound 3 in which an aniline group was connected by a linker (FIG. 1).

5. Selective PLK1 Degradability of the Compounds of the Present Invention

In addition to excellent PLK1 degradability compared to Comparative Compounds 1 and 2 (whose protein target moieties are PLK1 inhibitor molecules from BI), it was also confirmed that Compounds 2 to 4 of the present invention did not exhibit protein degradability of Brd4, a target protein other than PLK1 (FIG. 2). This demonstrates that the compounds of the present invention have excellent selective PLK1 degradability.

The contents of all references, patents, pending patent applications and published patents, cited throughout this application are hereby expressly incorporated by reference.

Those skilled in the art will recognize, or be able to ascertain using no more than routine experimentation, many equivalents to the specific embodiments of the disclosure described herein. Such equivalents are intended to be encompassed by the following claims. It is understood that the detailed examples and embodiments described herein are given by way of example for illustrative purposes only, and are in no way considered to be limiting to the disclosure. Various modifications or changes in light thereof will be suggested to persons skilled in the art and are included within the spirit and purview of this application and are considered within the scope of the appended claims. For example, the relative quantities of the ingredients may be varied to optimize the desired effects, additional ingredients may be added, and/or similar ingredients may be substituted for one or more of the ingredients described. Additional advantageous features and functionalities associated with the systems, methods, and processes of the present disclosure will be apparent from the appended claims. Moreover, those skilled in the art will recognize, or be able to ascertain using no more than routine experimentation, many equivalents to the specific embodiments of the disclosure described herein. Such equivalents are intended to be encompassed by the following claims.

The invention claimed is:

1. A compound represented by Formula I, a stereoisomer thereof, or a pharmaceutically acceptable salt thereof:

ULM-Linker-PTM       [Formula I]

in the Formula I above,

ULM is a CRBN or a VHL E3 ubiquitin ligase binding moiety;

the CRBN E3 ubiquitin ligase binding moiety is represented by Formula A-1:

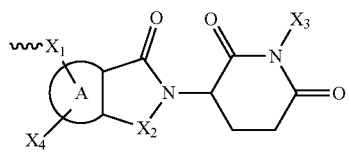

wherein:

is a ring selected from the group consisting of

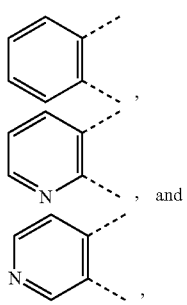

$X_1$ is a single bond, —$CH_2$—, —NH—, —O—, —$CH_2CH_2$—, —C≡C—, —CO—, —COO—, —NHCO—, or —CONH;

$X_2$ is —$CH_2$—, —CO—, —$CH_2$—$CH_2$—, or —N=N—;

$X_3$ is hydrogen or $C_{1-4}$ alkyl; and $X_4$ is hydrogen, halogen, $C_{1-6}$ alkyl, CN, $NH_2$, $NO_2$, OH, COH, COOH, or $CF_3$;

the VHL E3 ubiquitin ligase binding moiety is represented by Formula B-1:

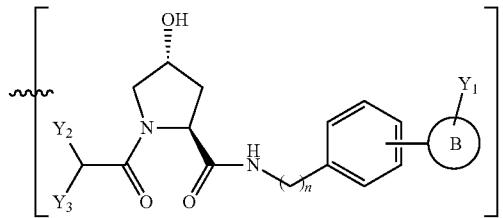

wherein:

n is an integer from 1 to 3;

is 5- to 6-membered heteroaryl, wherein the heteroaryl contains one to two N or S atoms;

$Y_1$ is hydrogen or $C_{1-4}$ alkyl;

$Y_2$ is $C_{1-4}$ alkyl;

$Y_3$

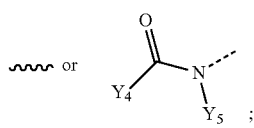

$Y_4$ is $C_{1-4}$ alkyl, or $C_{3-6}$ cycloalkyl, optionally substituted by halogen, —OH, or —CN; and $Y_5$ is hydrogen or $C_{1-4}$ alkyl;

the PTM is a PLK1 binding moiety represented by Formula II:

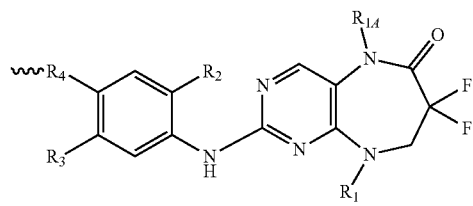

wherein $R_1$ is $C_{1-3}$ alkyl or $C_{3-6}$ cycloalkyl;

$R_{1A}$ is hydrogen or $C_{1-3}$ alkyl;

$R_2$ is hydrogen, halogen, or —$OR_{2A}$;

$R_{2A}$ is $C_{1-4}$ alkyl or $C_{3-6}$ cycloalkyl, optionally substituted by one or more halogen or hydroxy;

$R_3$ is hydrogen or halogen; and
$R_4$ is

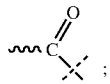

and
⁓⁓⁓ indicates a covalent bond that links the PTM or the ULM into the Linker, and
the Linker is a chemical group that links the ULM and the PTM, and is represented by Formula L:

[Formula L]

wherein:
⁓⁓⁓ and – – – – – are each independently a bond;
$L_{ULM}$ is covalently bonded to the ULM moiety through ⁓⁓⁓ that is linked thereto,
$L_{PTM}$ is covalently bonded to the PTM moiety through ⁓⁓⁓ that is linked thereto,
wherein $L_{ULM}$ is

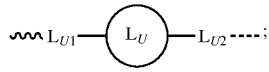

$L_{U1}$ is selected from a single bond, —$CH_2$—, —$CH_2CH_2$—, —CH=CH—, —C≡C—, —NH—, —$NCH_3$—, —CO—, —NHCO—, or —O—;
$L_{U2}$ is selected from single bond, —$CH_2$—, —NH—, —O—, —CO—, or —CONH—; and

is a single bond or a ring selected from 3 to 10-membered cycloalkyl, 4- to 10-membered heterocycloalkyl, 6- to 10-membered aryl, or 5- to 10-membered heteroaryl;
wherein $L_{PTM}$ is

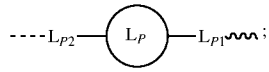

$L_{P1}$ is selected from single bond, —O—, —S—, —NH—, —N($C_{1-4}$ alkyl)-, —$CH_2$—, —CH($C_{1-4}$ alkyl)-, —$CH_2NH$—, or —$CH_2CH_2$—;
$L_{P2}$ is selected from a single bond, —CO—, —$COCH_2$—, —NHCO—, —$NHCOCH_2$—, -HET, or -HET-$CH_2$—, wherein HET is a 5- to 6-membered heterocyclyl or heteroaryl containing one or more N, S, or O atoms; and

is a single bond, amino substituted with $C_{1-8}$ alkyl, or a ring selected from 3- to 10-membered cycloalkyl, 4- to 10-membered heterocycloalkyl, 6- to 10-membered aryl, or 5- to 10-membered heteroaryl;
wherein

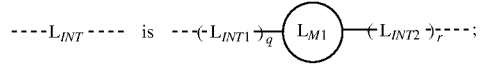

is a single bond or a ring selected from 3- to 10-membered cycloalkyl, 4- to 10-membered heterocycloalkyl, 6- to 10-membered aryl, or 5- to 10-membered heteroaryl;

$L_{INT1}$ and $L_{INT2}$ are each independently selected from —$CH_2$—, —NH—, —$NCH_3$—, —O—, —S—, —SO—, —$SO_2$—, —CO—, —$CH_2CH_2O$—, —$OCH_2CH_2$—, —$CH_2CH_2S$—, —$SCH_2CH_2$—, —COO—, —CONH—, or —NHCO—; and q and r are each independently an integer from 1 to 10.

2. The compound of claim 1, wherein ULM is a CRBN E3 ubiquitin ligase moiety represented by Formula A-2:

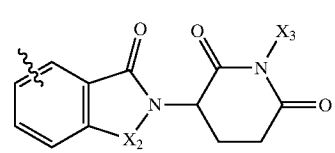

[Formula A-2]

wherein:
$X_2$ is —$CH_2$—, —CO—, or —N=N—; and
$X_3$ is hydrogen or $C_{1-3}$ alkyl.

3. The compound of claim 2, wherein Formula A-2 is selected from:

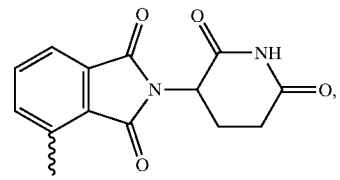

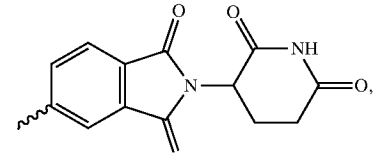

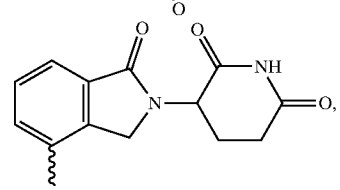

-continued

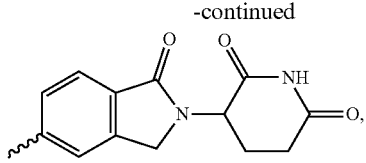

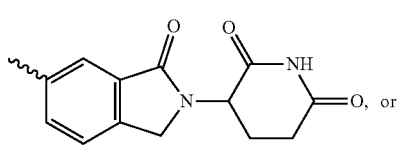

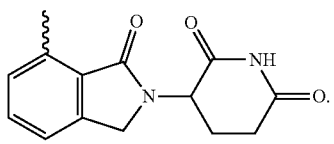

4. The compound of claim 1, wherein ULM is a VHL E3 ubiquitin ligase ligand selected from B-2-1 or Formula B-2-2:

[Formula B-2-1]

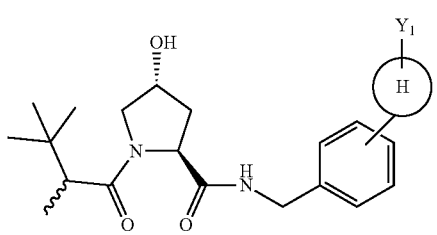

[Formula B-2-2]

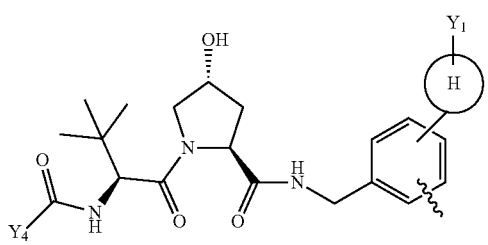

wherein:

is a 5-membered heteroaryl ring selected from thiazole or isothiazole;

$Y_1$ is hydrogen or $C_{1-3}$ alkyl; and $Y_4$ is $C_{1-4}$ alkyl or $C_{3-5}$ cycloalkyl, optionally substituted by halogen.

5. The compound of claim 4, wherein Formula B-2-1 is selected from

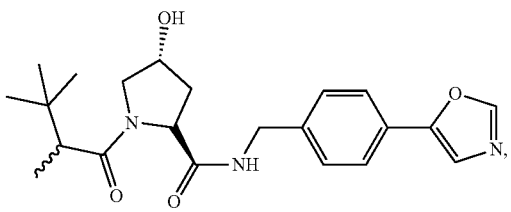

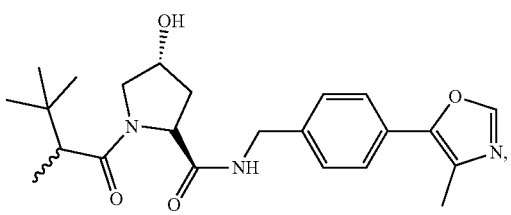

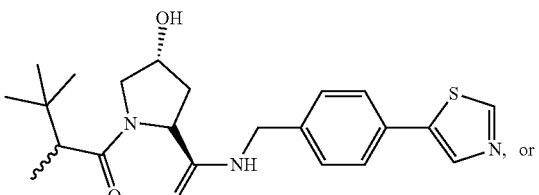

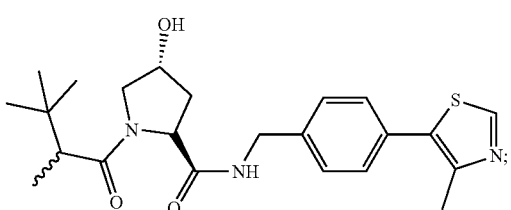

and wherein Formula B-2-2 is selected from

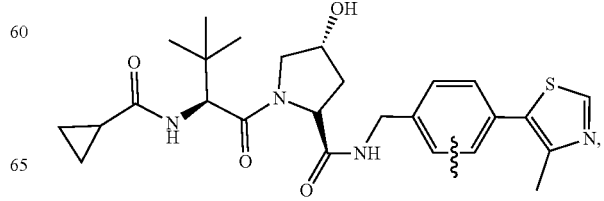

-continued
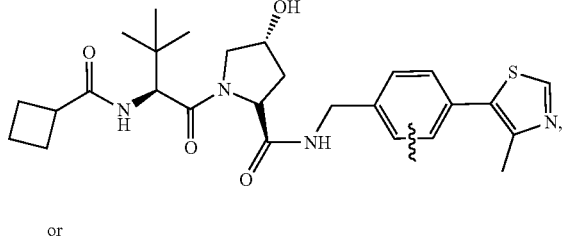
or
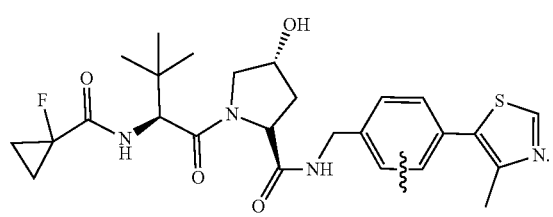
6. The compound of claim 1, wherein Formula II is represented by Formula III:
[Formula III]
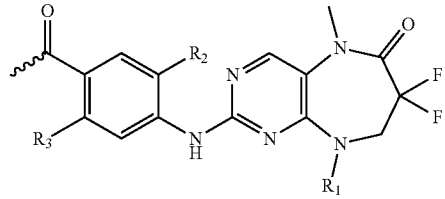
wherein:
$R_1$ is $C_{1-3}$ alkyl or $C_{3-6}$ cycloalkyl;
$R_2$ is hydrogen or —$OR_{2A}$;
$R_{2A}$ is $C_{1-4}$ alkyl, $C_{3-6}$ cycloalkyl, $CF_3$, or —($C_{1-3}$ alkylene)-OH; and
$R_3$ is hydrogen or halogen.
7. The compound of claim 1, wherein the compound is a compound selected from:
TABLE 1
| Compound | Structure |
| --- | --- |
| 1 | 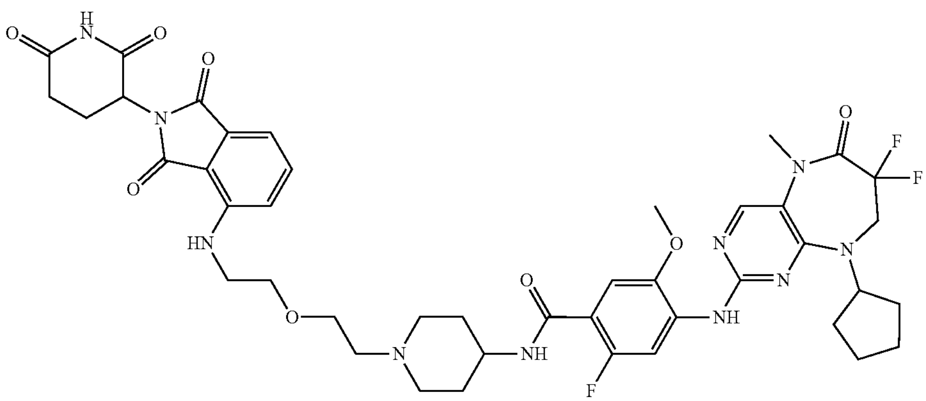 [SMILES: COc1cc(C(=O)NC2CCN(CCOCCNc3cccc4c3C(=O)N(C3CCC(=O)NC3=O)C4=O)CC2)c(F)cc1Nc1ncc2c(n1)N(C1CCCC1)CC(F)(F)C(=O)N2C] |
| 2 | 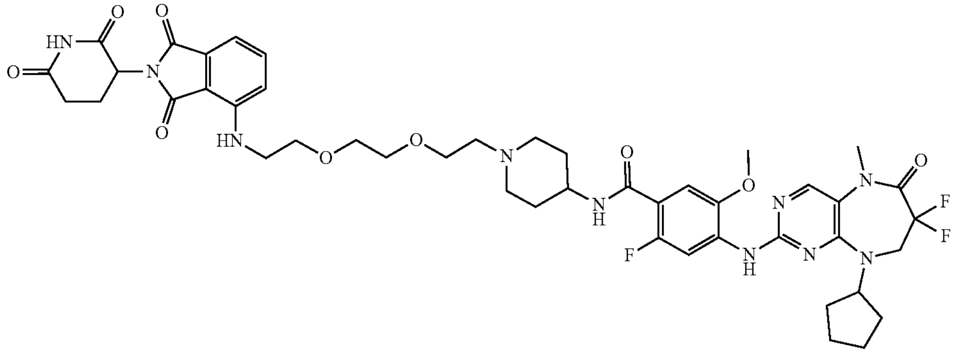 [SMILES: COc1cc(C(=O)NC2CCN(CCOCCOCCNc3cccc4c3C(=O)N(C3CCC(=O)NC3=O)C4=O)CC2)c(F)cc1Nc1ncc2c(n1)N(C1CCCC1)CC(F)(F)C(=O)N2C] |

TABLE 1-continued
| Compound | Structure |
|---|---|
| 3 | 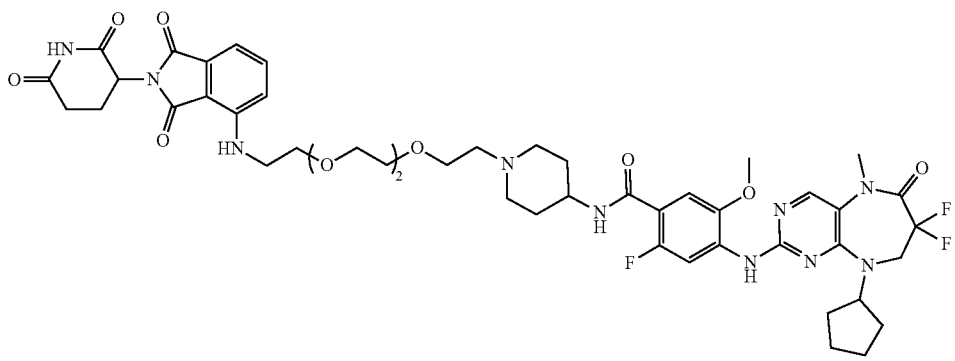 |
| 4 | 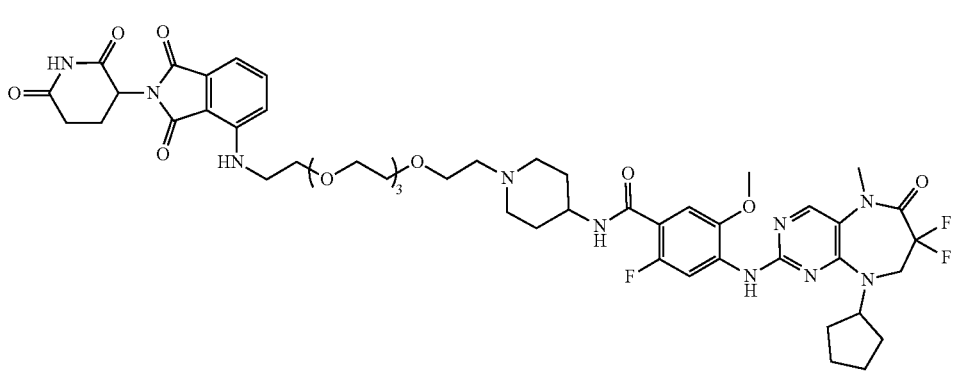 |
| 5 | 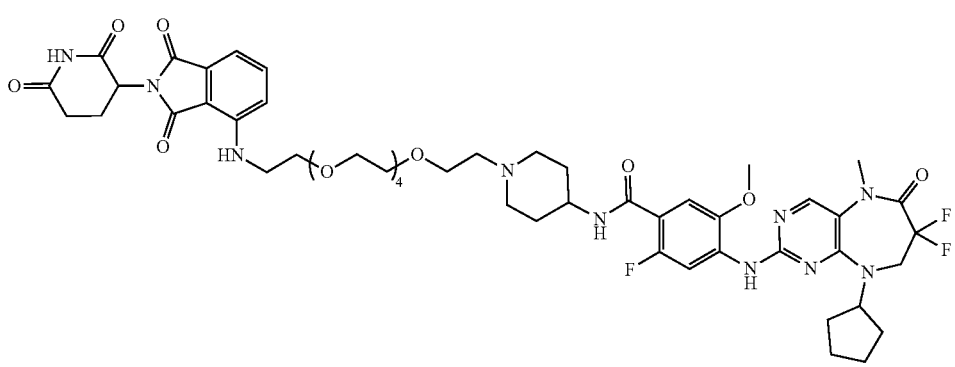 |
| 6 | 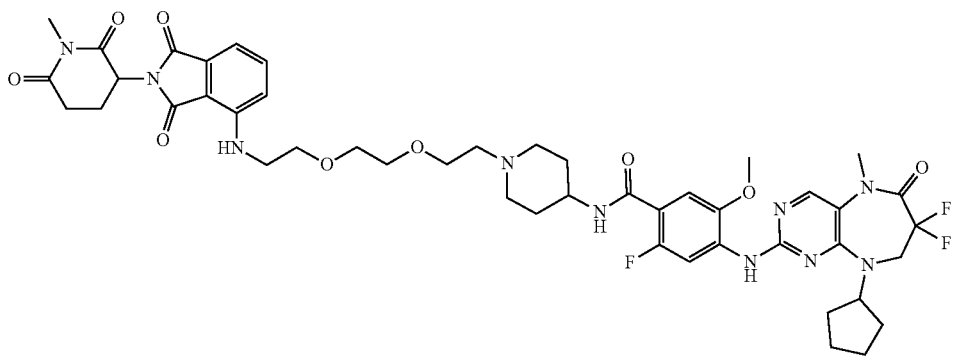 [SMILES: COc1cc(C(=O)NC2CCN(CCOCCOCCNc3cccc4c3C(=O)N(C3CCC(=O)N(C)C3=O)C4=O)CC2)c(F)cc1Nc1ncc2c(n1)N(C1CCCC1)CC(F)(F)C(=O)N2C] |

TABLE 1-continued
| Compound | Structure |
|---|---|
| 7 | 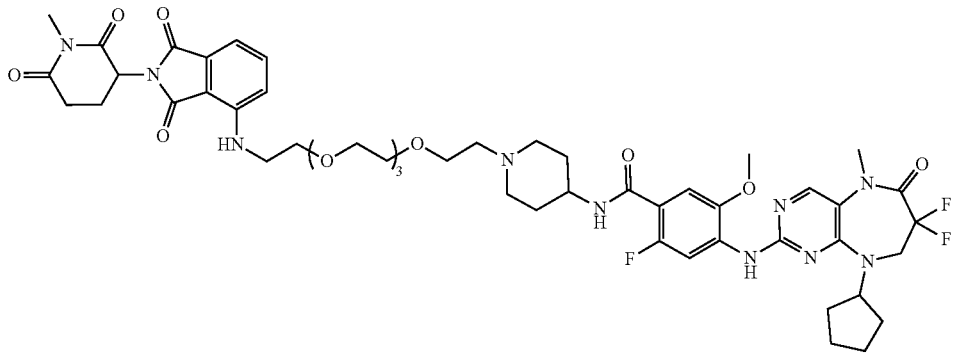 |
| 8 | 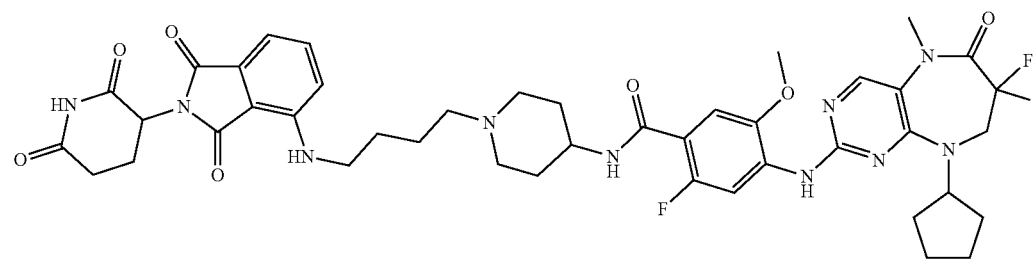 |
| 9 | 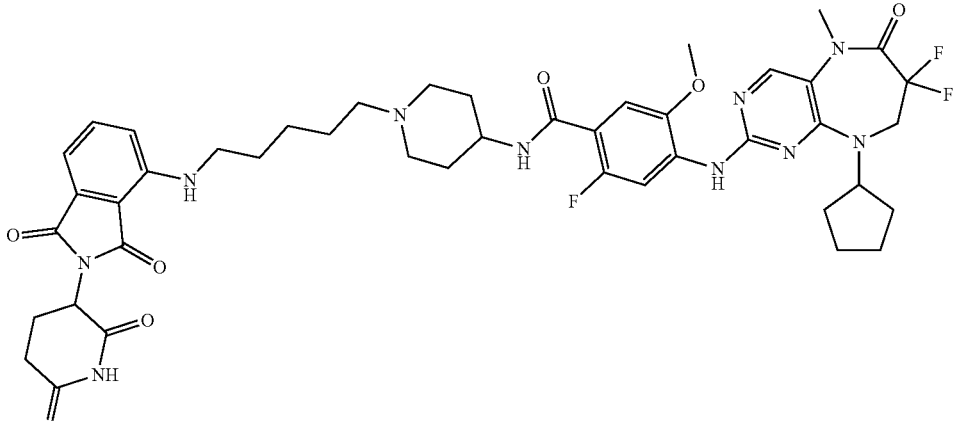 |
| 10 | 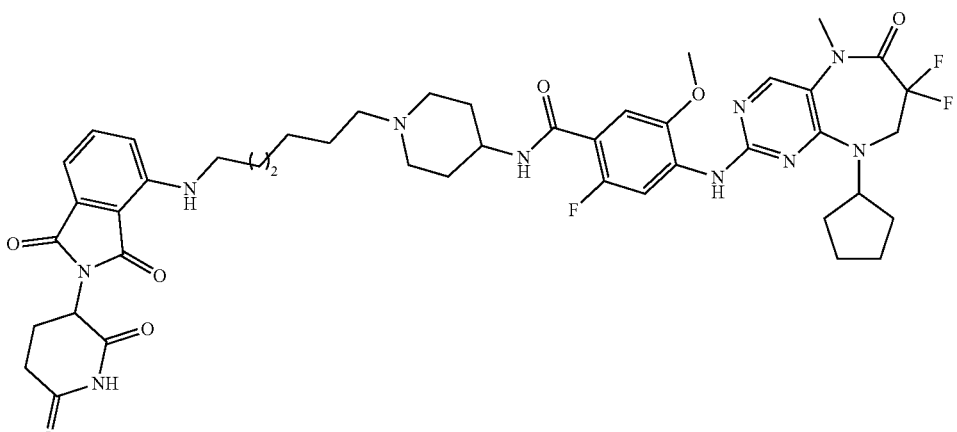 |

TABLE 1-continued

| Compound | Structure |
| --- | --- |
| 11 | (structure with linker (CH₂)₃) |
| 12 | (structure with linker (CH₂)₄) |
| 13 | (structure with linker (CH₂)₅) |

TABLE 1-continued
| Compound | Structure |
|---|---|
| 14 | 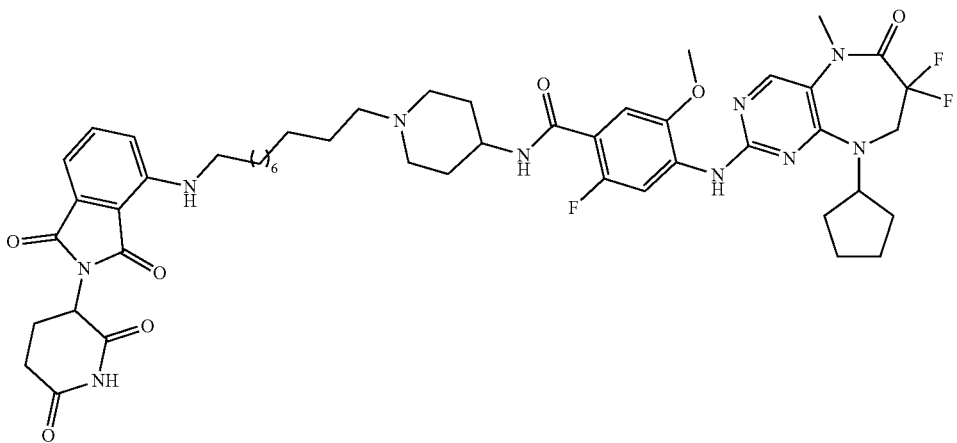 |
| 15 | 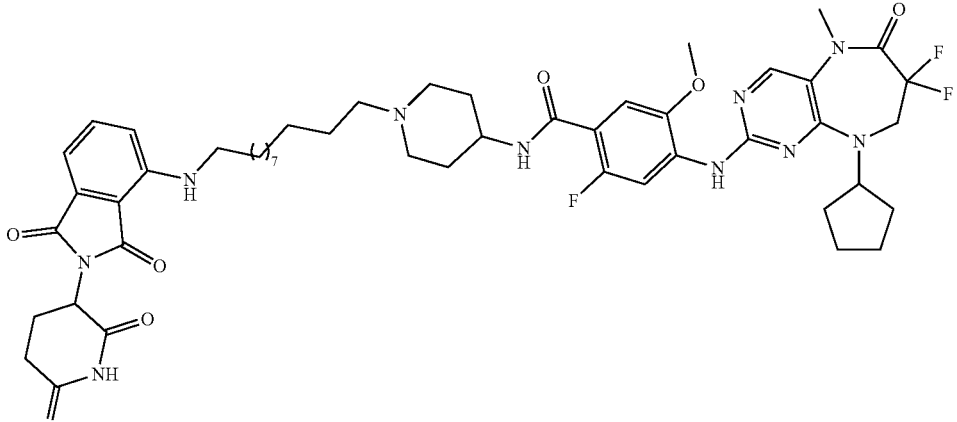 |
| 16 | 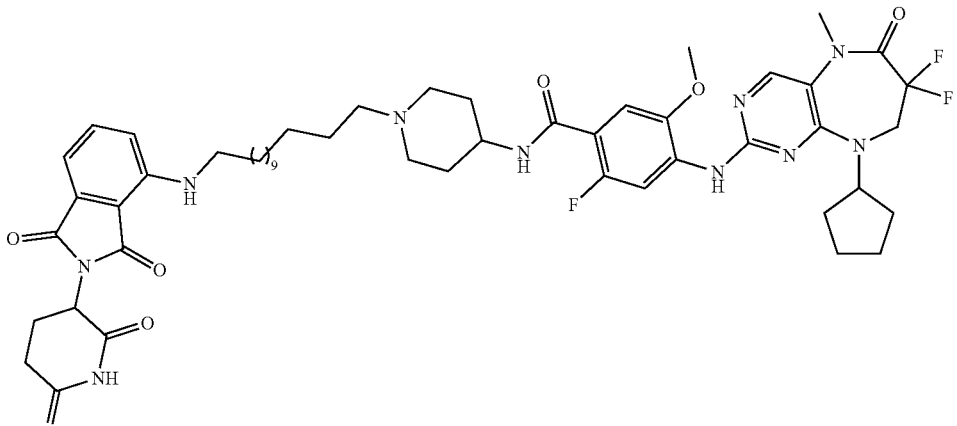 |

TABLE 1-continued
| Compound | Structure |
|---|---|
| 17 | 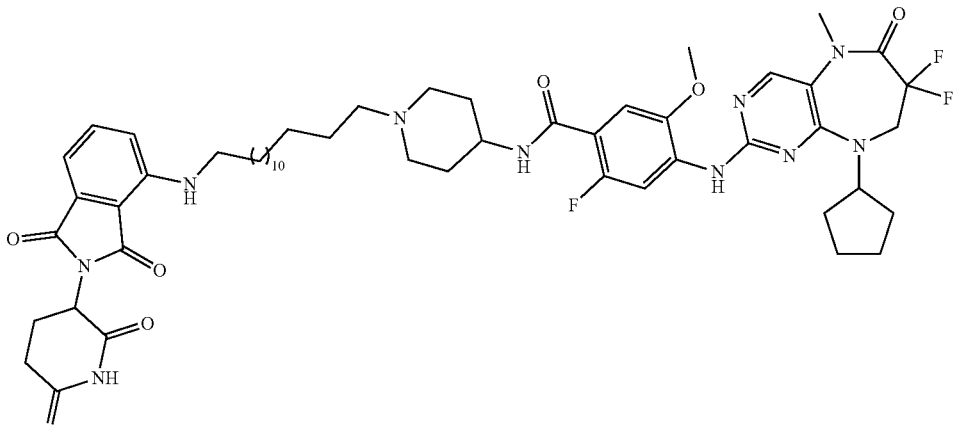 |
| 18 | 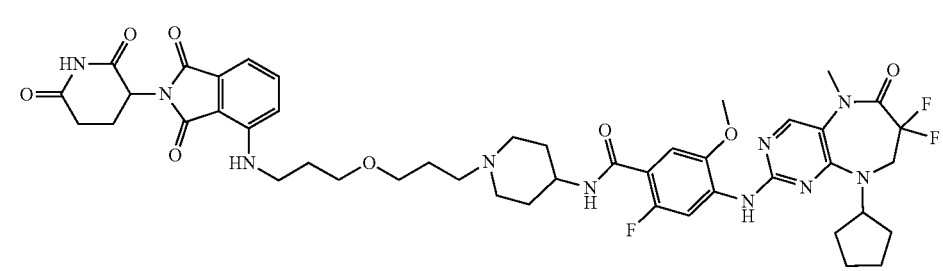 [SMILES: COc1cc(C(=O)NC2CCN(CCCOCCCNc3cccc4c3C(=O)N(C3CCC(=O)NC3=O)C4=O)CC2)c(F)cc1Nc1ncc2c(n1)N(C1CCCC1)CC(F)(F)C(=O)N2C] |
| 19 | 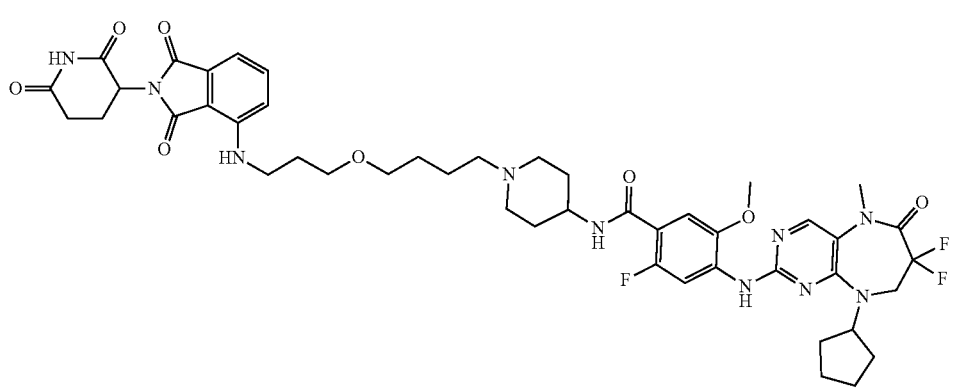 [SMILES: COc1cc(C(=O)NC2CCN(CCCCOCCCNc3cccc4c3C(=O)N(C3CCC(=O)NC3=O)C4=O)CC2)c(F)cc1Nc1ncc2c(n1)N(C1CCCC1)CC(F)(F)C(=O)N2C] |
| 20 | 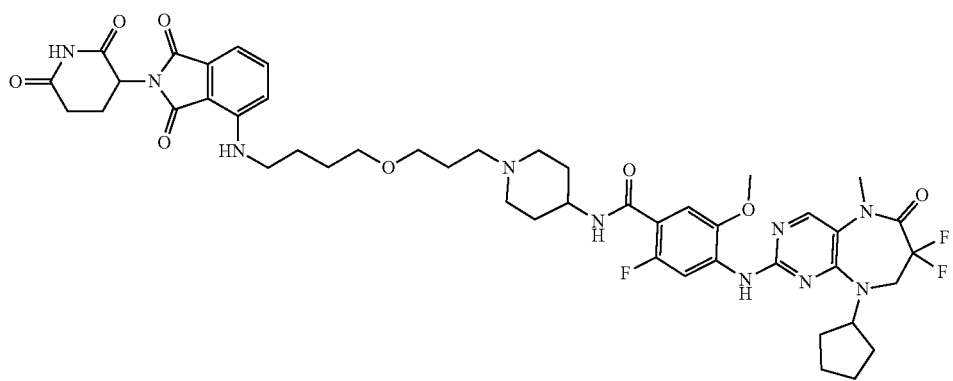 [SMILES: COc1cc(C(=O)NC2CCN(CCCOCCCCNc3cccc4c3C(=O)N(C3CCC(=O)NC3=O)C4=O)CC2)c(F)cc1Nc1ncc2c(n1)N(C1CCCC1)CC(F)(F)C(=O)N2C] |

TABLE 1-continued

| Compound | Structure |
|---|---|
| 21 | (structure) |
| 22 | (structure) |
| 23 | (structure) |
| 24 | (structure) |
| 25 | (structure) |
| 26 | (structure) |

TABLE 1-continued

| Compound | Structure |
|---|---|
| 27 | 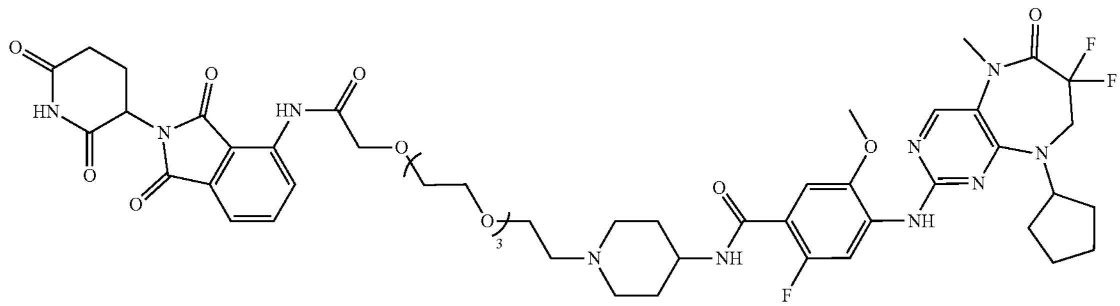 |
| 28 | 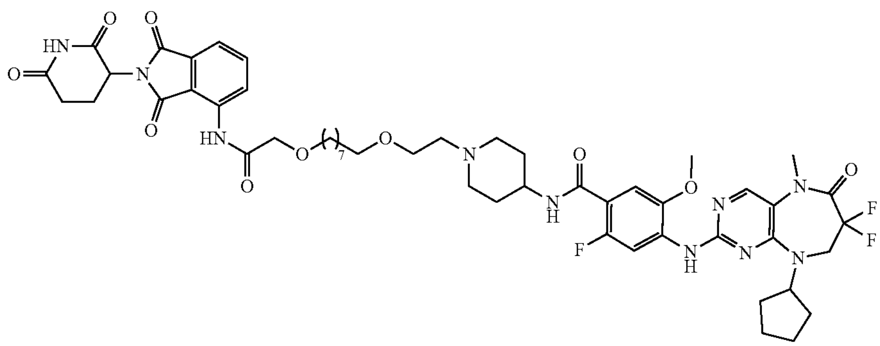 |
| 29 | 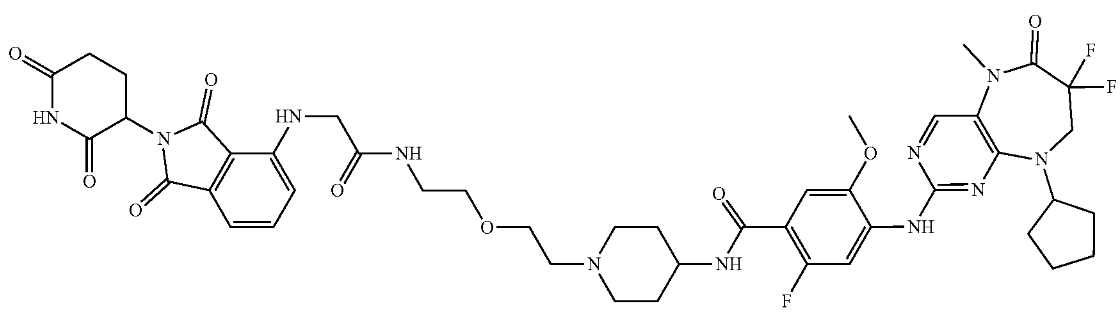 [SMILES: COc1cc(C(=O)NC2CCN(CCOCCNC(=O)CNc3cccc4c3C(=O)N(C3CCC(=O)NC3=O)C4=O)CC2)c(F)cc1Nc1ncc2c(n1)N(C1CCCC1)CC(F)(F)C(=O)N2C] |
| 30 | 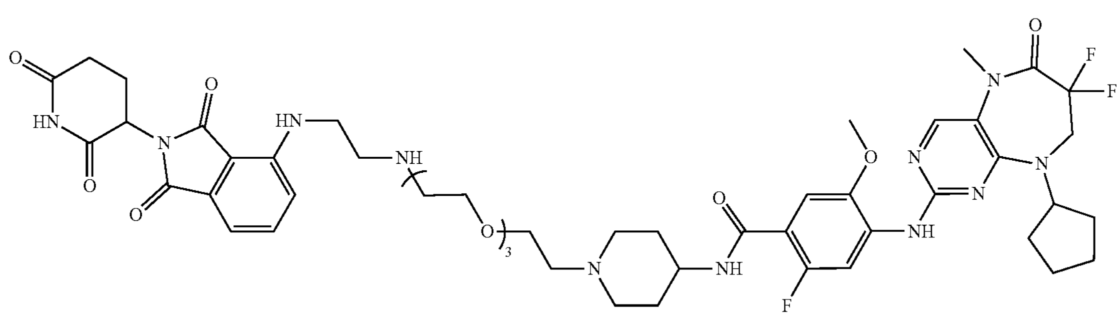 |

TABLE 1-continued
| Compound | Structure |
|---|---|
| 31 | 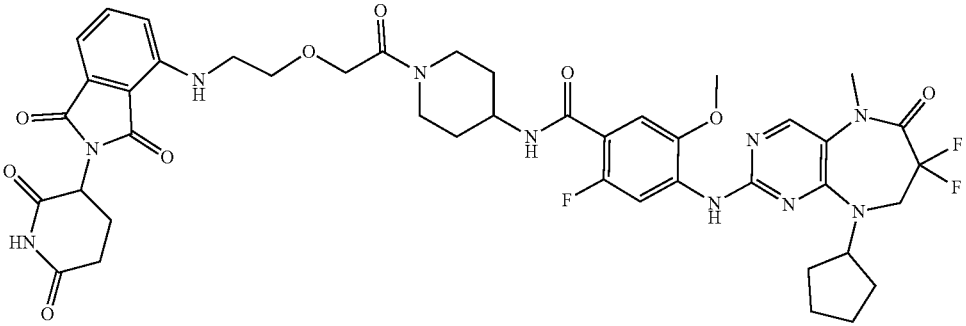 [SMILES: COc1cc(C(=O)NC2CCN(C(=O)COCCNc3cccc4c3C(=O)N(C3CCC(=O)NC3=O)C4=O)CC2)c(F)cc1Nc1ncc2c(n1)N(C1CCCC1)CC(F)(F)C(=O)N2C] |
| 32 | 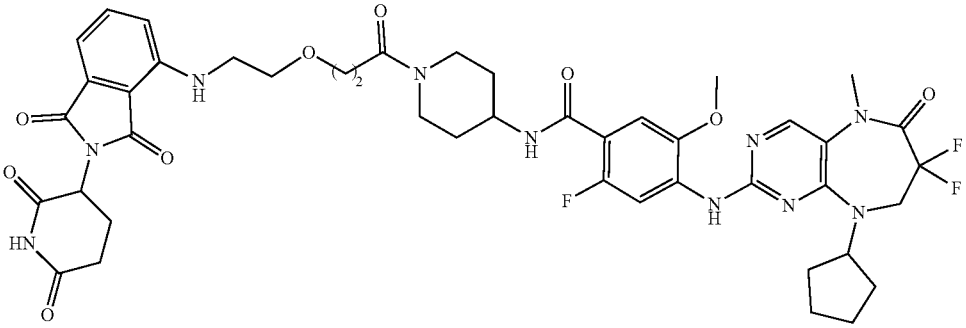 |
| 33 | 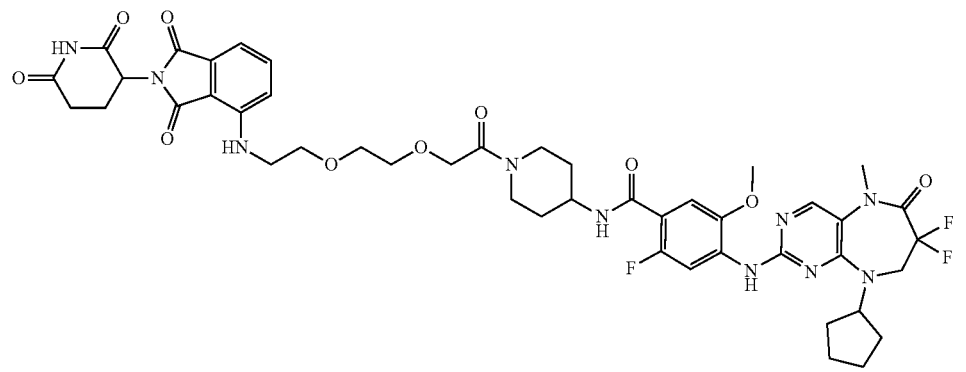 [SMILES: COc1cc(C(=O)NC2CCN(C(=O)COCCOCCNc3cccc4c3C(=O)N(C3CCC(=O)NC3=O)C4=O)CC2)c(F)cc1Nc1ncc2c(n1)N(C1CCCC1)CC(F)(F)C(=O)N2C] |
| 34 | 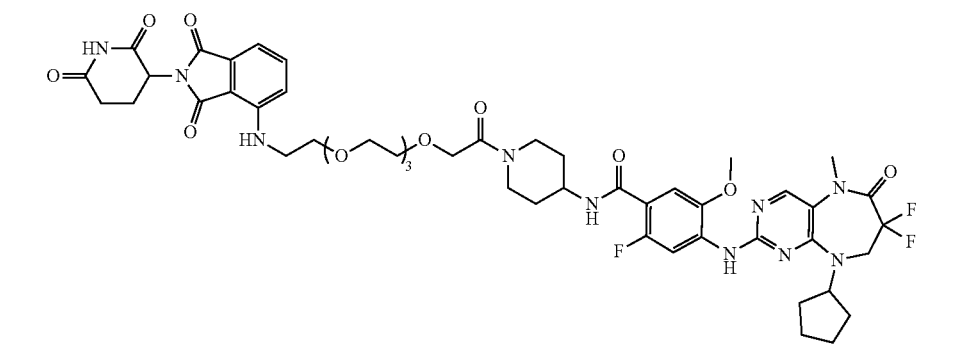 |

TABLE 1-continued
| Compound | Structure |
|---|---|
| 35 | 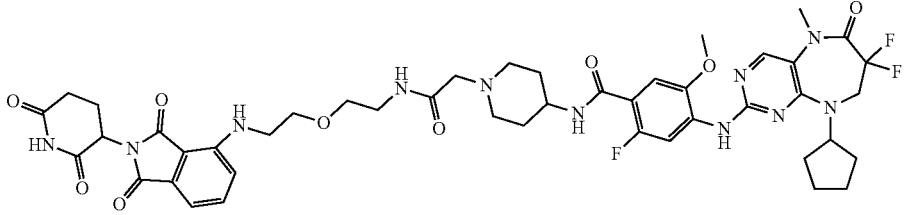 [SMILES: COc1cc(C(=O)NC2CCN(CC(=O)NCCOCCNc3cccc4c3C(=O)N(C3CCC(=O)NC3=O)C4=O)CC2)c(F)cc1Nc1ncc2c(n1)N(C1CCCC1)CC(F)(F)C(=O)N2C] |
| 36 | 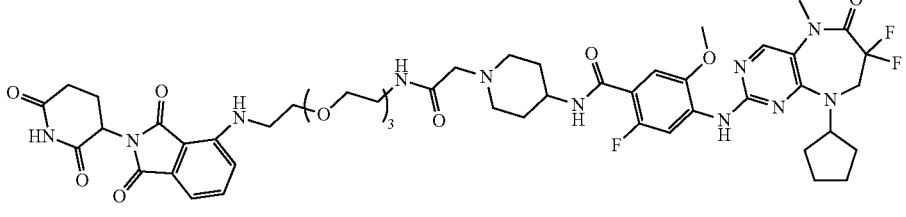 |
| 37 | 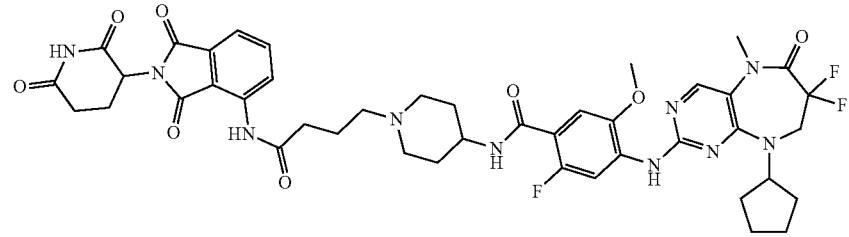 [SMILES: COc1cc(C(=O)NC2CCN(CCCC(=O)Nc3cccc4c3C(=O)N(C3CCC(=O)NC3=O)C4=O)CC2)c(F)cc1Nc1ncc2c(n1)N(C1CCCC1)CC(F)(F)C(=O)N2C] |
| 38 | 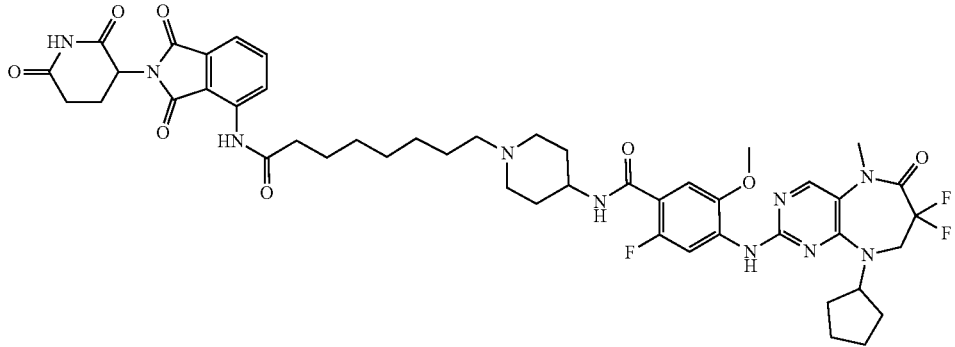 [SMILES: COc1cc(C(=O)NC2CCN(CCCCCCCC(=O)Nc3cccc4c3C(=O)N(C3CCC(=O)NC3=O)C4=O)CC2)c(F)cc1Nc1ncc2c(n1)N(C1CCCC1)CC(F)(F)C(=O)N2C] |
| 39 | 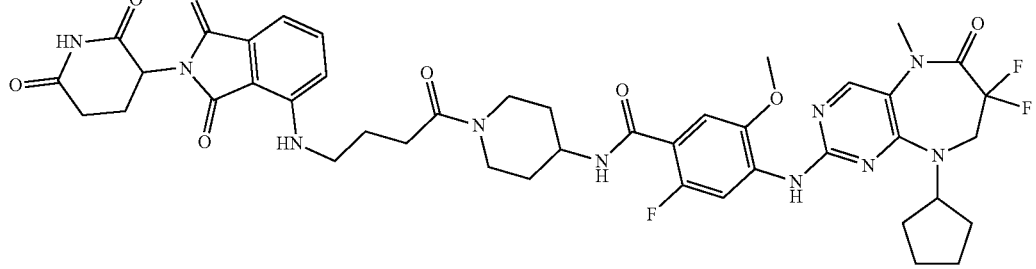 |

TABLE 1-continued
| Compound | Structure |
|---|---|
| 40 | 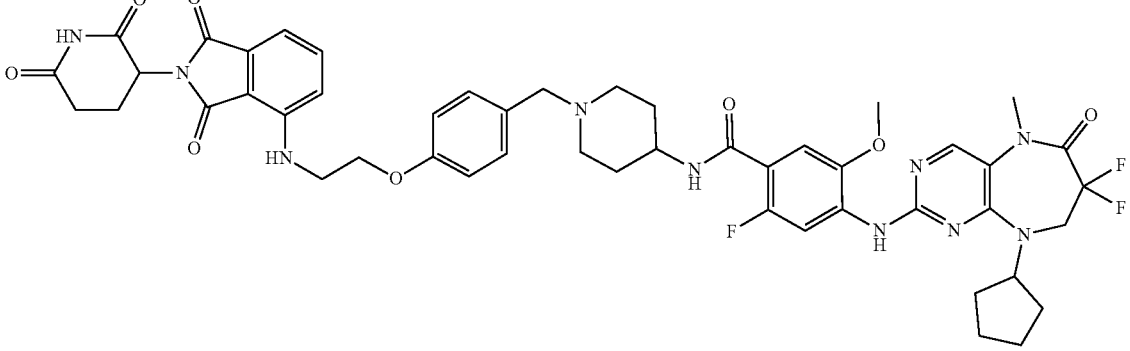 |
| 41 | 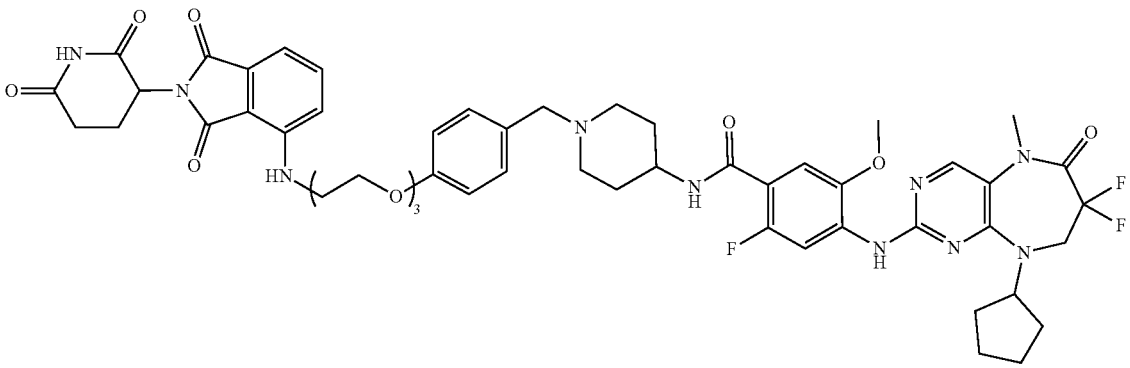 |
| 42 | 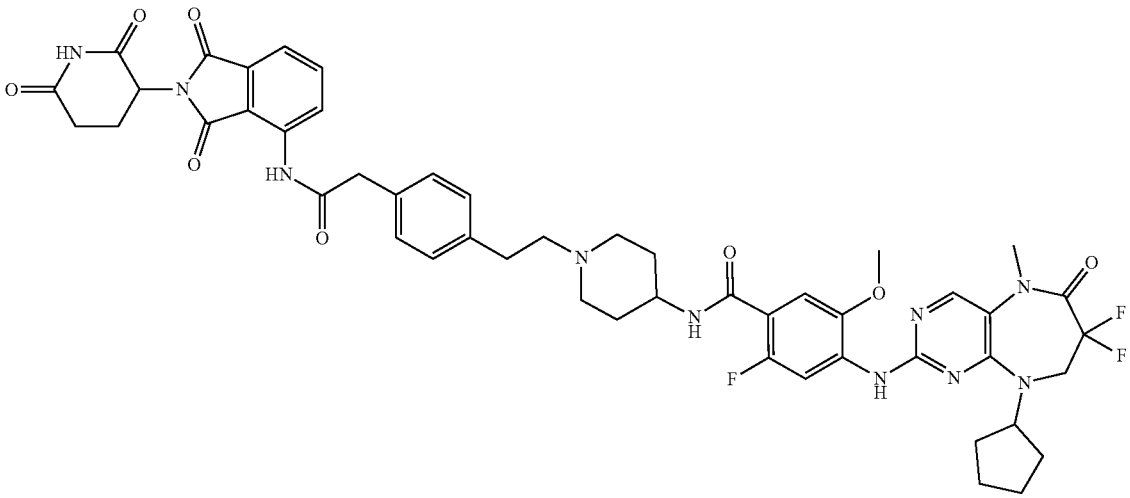 [SMILES: COc1cc(C(=O)NC2CCN(CCc3ccc(CC(=O)Nc4cccc5c4C(=O)N(C4CCC(=O)NC4=O)C5=O)cc3)CC2)c(F)cc1Nc1ncc2c(n1)N(C1CCCC1)CC(F)(F)C(=O)N2C] |
| 43 | 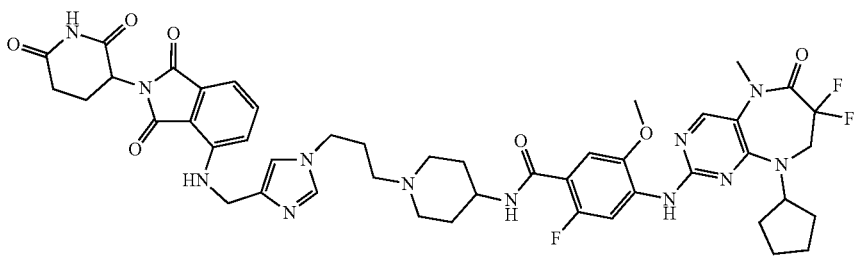 [SMILES: COc1cc(C(=O)NC2CCN(CCCn3cnc(CNc4cccc5c4C(=O)N(C4CCC(=O)NC4=O)C5=O)c3)CC2)c(F)cc1Nc1ncc2c(n1)N(C1CCCC1)CC(F)(F)C(=O)N2C] |

TABLE 1-continued

| Compound | Structure |
|---|---|
| 44 | 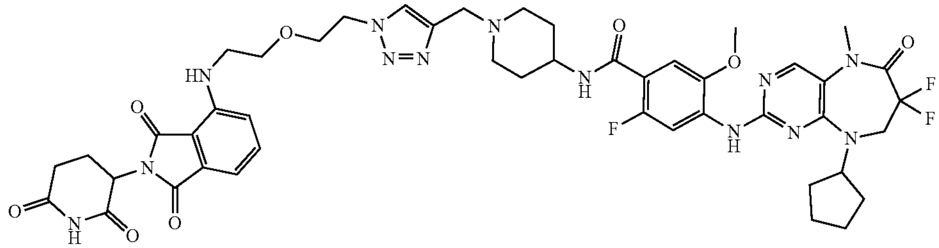 [SMILES: COc1cc(C(=O)NC2CCN(Cc3cn(CCOCCNc4cccc5c4C(=O)N(C4CCC(=O)NC4=O)C5=O)nn3)CC2)c(F)cc1Nc1ncc2c(n1)N(C1CCCC1)CC(F)(F)C(=O)N2C] |
| 45 | 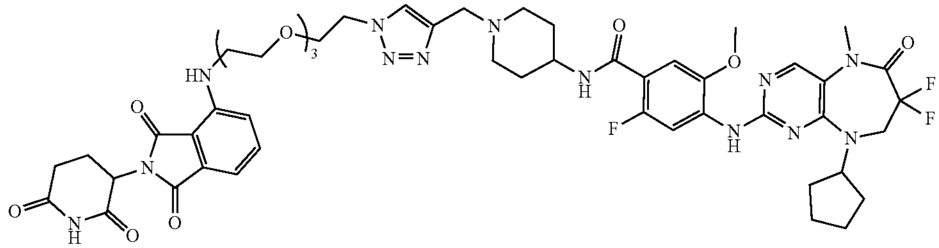 |
| 46 | 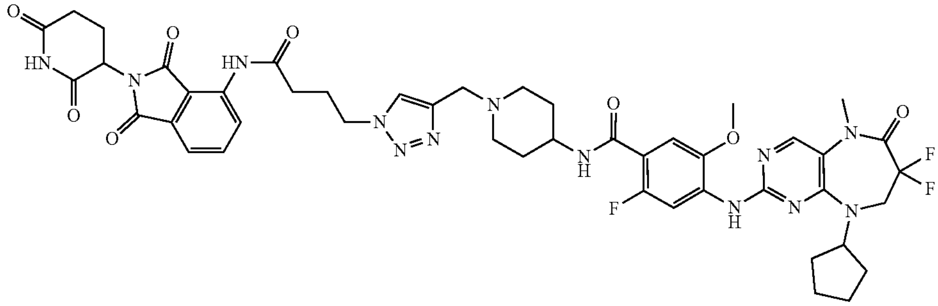 [SMILES: COc1cc(C(=O)NC2CCN(Cc3cn(CCCC(=O)Nc4cccc5c4C(=O)N(C4CCC(=O)NC4=O)C5=O)nn3)CC2)c(F)cc1Nc1ncc2c(n1)N(C1CCCC1)CC(F)(F)C(=O)N2C] |
| 47 | 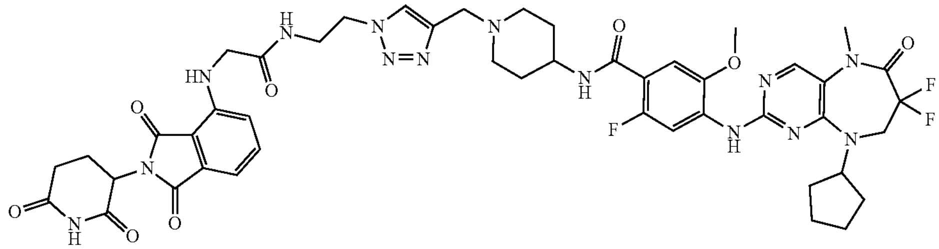 [SMILES: COc1cc(C(=O)NC2CCN(Cc3cn(CCNC(=O)CNc4cccc5c4C(=O)N(C4CCC(=O)NC4=O)C5=O)nn3)CC2)c(F)cc1Nc1ncc2c(n1)N(C1CCCC1)CC(F)(F)C(=O)N2C] |
| 48 | 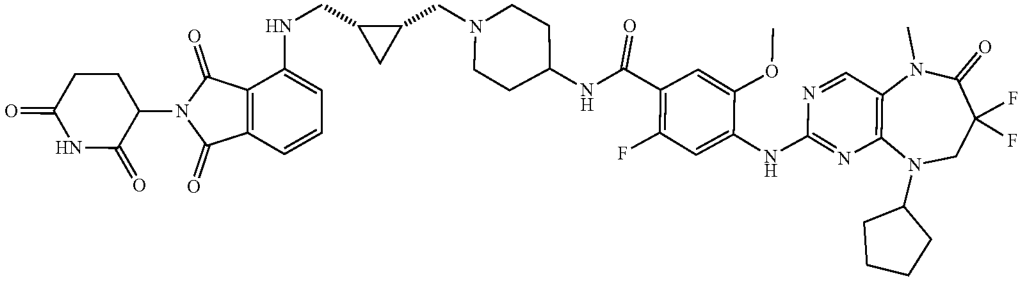 |
| 49 | 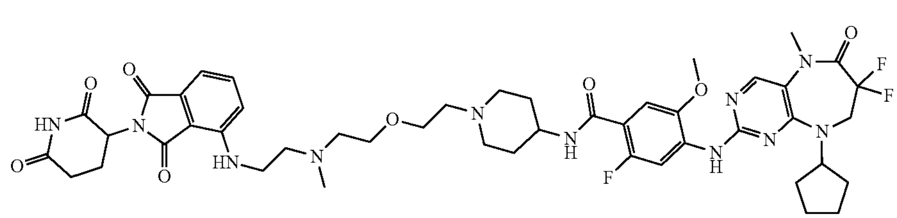 [SMILES: COc1cc(C(=O)NC2CCN(CCOCCN(C)CCNc3cccc4c3C(=O)N(C3CCC(=O)NC3=O)C4=O)CC2)c(F)cc1Nc1ncc2c(n1)N(C1CCCC1)CC(F)(F)C(=O)N2C] |

TABLE 1-continued

| Compound | Structure |
|---|---|
| 50 | 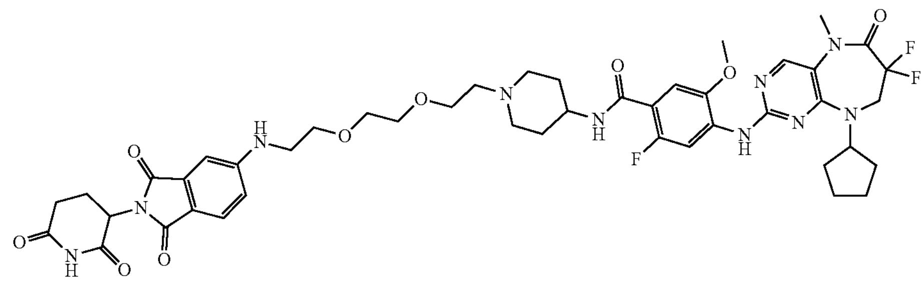 [SMILES: COc1cc(C(=O)NC2CCN(CCOCCOCCNc3ccc4c(c3)C(=O)N(C3CCC(=O)NC3=O)C4=O)CC2)c(F)cc1Nc1ncc2c(n1)N(C1CCCC1)CC(F)(F)C(=O)N2C] |
| 51 | 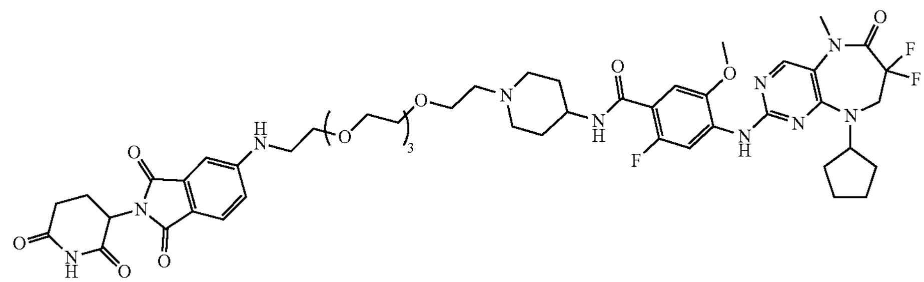 |
| 52 | 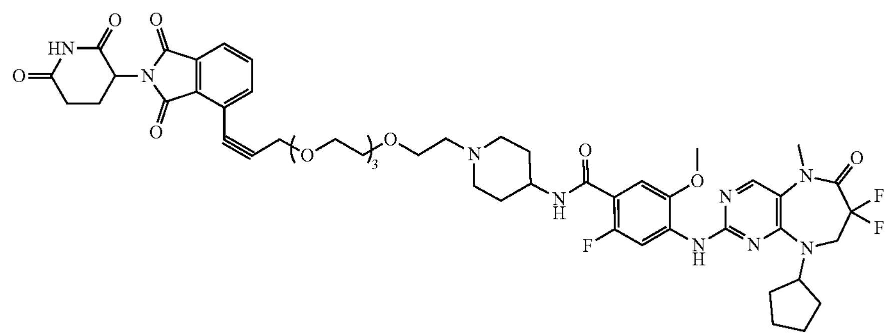 |
| 53 | 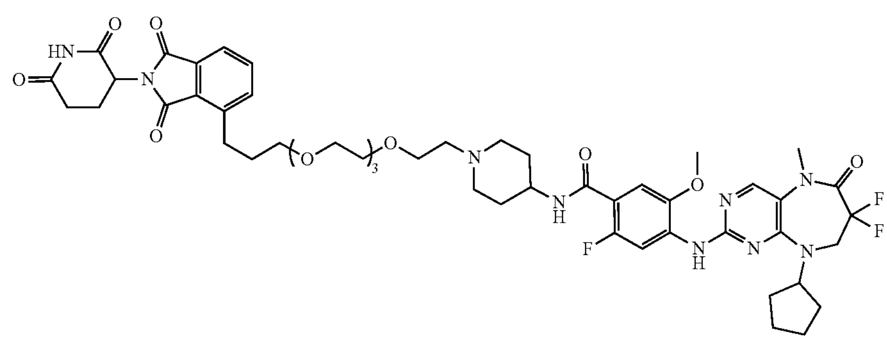 |
| 54 | 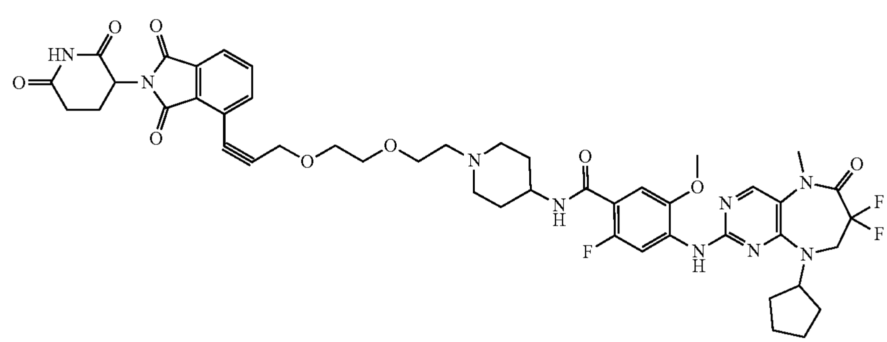 [SMILES: COc1cc(C(=O)NC2CCN(CCOCCOCC#Cc3cccc4c3C(=O)N(C3CCC(=O)NC3=O)C4=O)CC2)c(F)cc1Nc1ncc2c(n1)N(C1CCCC1)CC(F)(F)C(=O)N2C] |

TABLE 1-continued

| Compound | Structure |
|---|---|
| 55 | 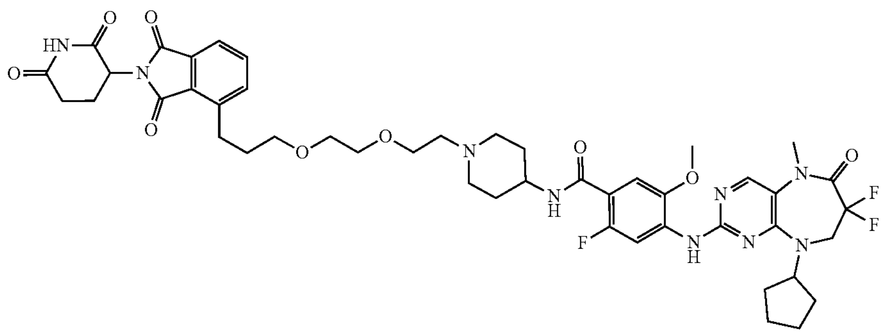 [SMILES: COc1cc(C(=O)NC2CCN(CCOCCOCCCc3cccc4c3C(=O)N(C3CCC(=O)NC3=O)C4=O)CC2)c(F)cc1Nc1ncc2c(n1)N(C1CCCC1)CC(F)(F)C(=O)N2C] |
| 56 | 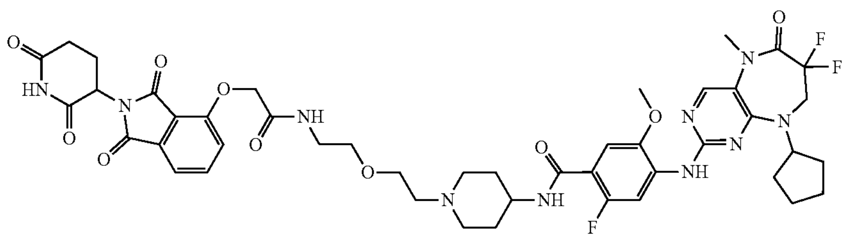 [SMILES: COc1cc(C(=O)NC2CCN(CCOCCNC(=O)COc3cccc4c3C(=O)N(C3CCC(=O)NC3=O)C4=O)CC2)c(F)cc1Nc1ncc2c(n1)N(C1CCCC1)CC(F)(F)C(=O)N2C] |
| 57 | 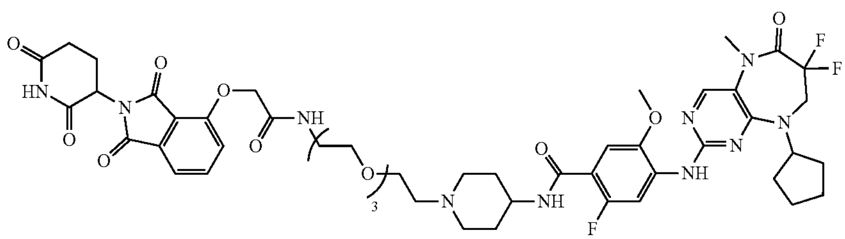 |
| 58 | 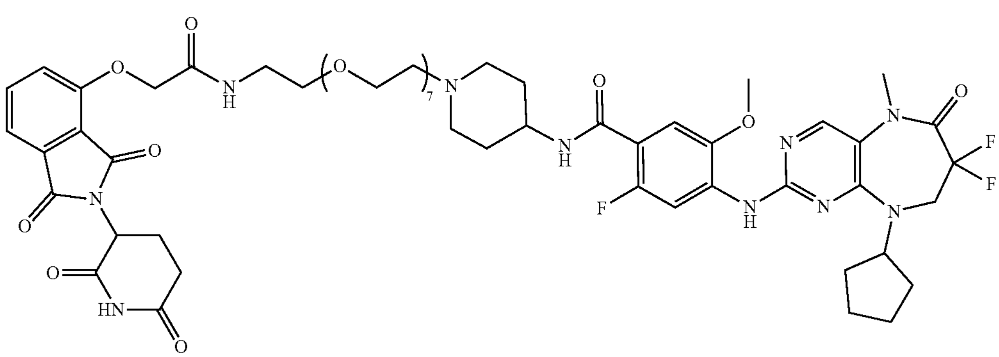 |
| 59 | 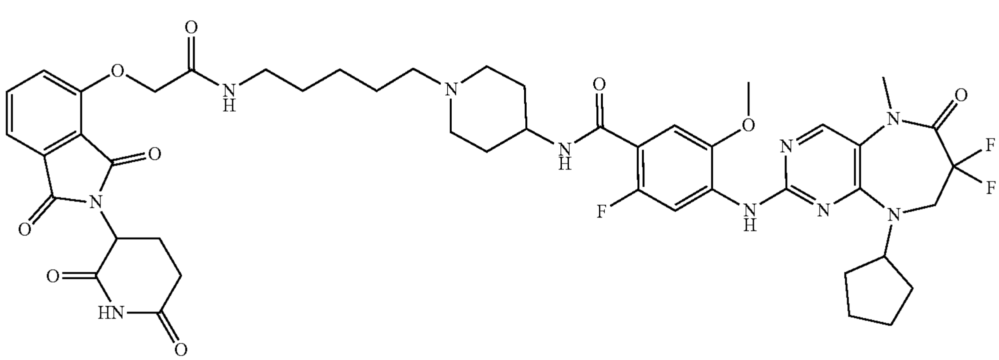 [SMILES: COc1cc(C(=O)NC2CCN(CCCCCNC(=O)COc3cccc4c3C(=O)N(C3CCC(=O)NC3=O)C4=O)CC2)c(F)cc1Nc1ncc2c(n1)N(C1CCCC1)CC(F)(F)C(=O)N2C] |

TABLE 1-continued

| Compound | Structure |
|---|---|
| 60 | 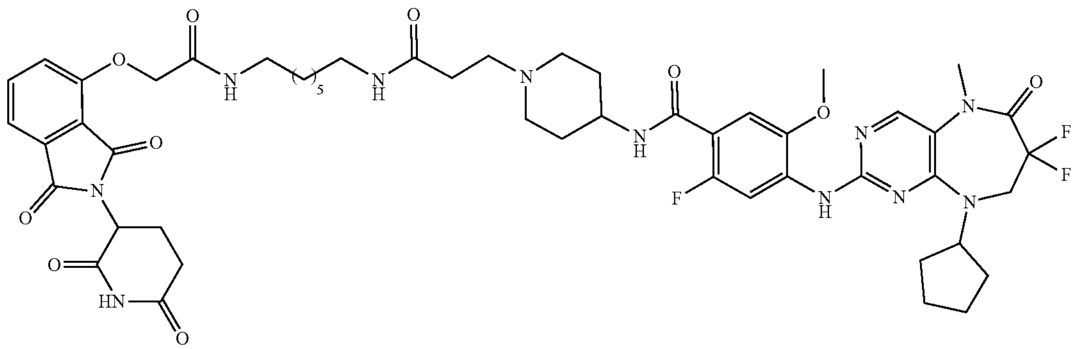 |
| 61 | 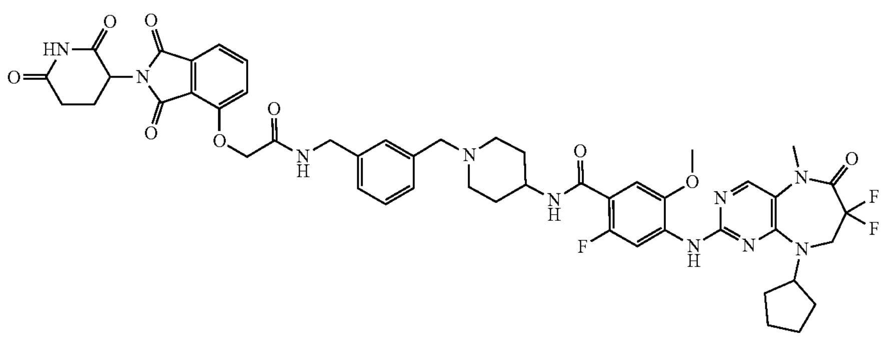 [SMILES: COc1cc(C(=O)NC2CCN(Cc3cccc(CNC(=O)COc4cccc5c4C(=O)N(C4CCC(=O)NC4=O)C5=O)c3)CC2)c(F)cc1Nc1ncc2c(n1)N(C1CCCC1)CC(F)(F)C(=O)N2C] |
| 62 | 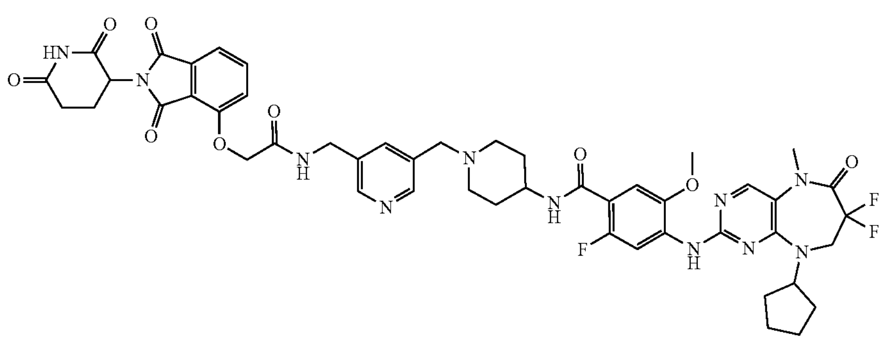 [SMILES: COc1cc(C(=O)NC2CCN(Cc3cncc(CNC(=O)COc4cccc5c4C(=O)N(C4CCC(=O)NC4=O)C5=O)c3)CC2)c(F)cc1Nc1ncc2c(n1)N(C1CCCC1)CC(F)(F)C(=O)N2C] |
| 63 | 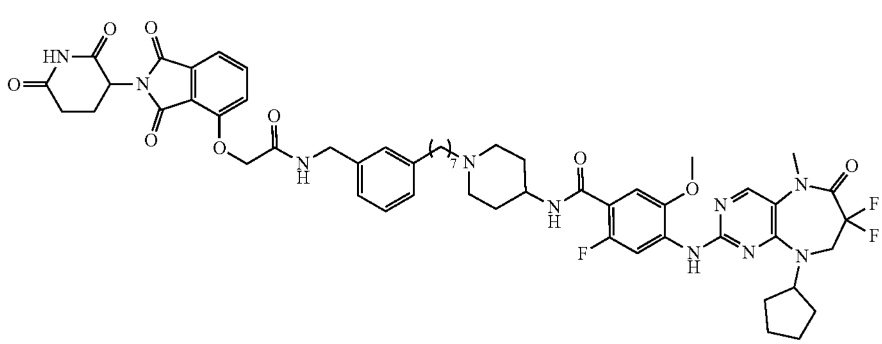 |

TABLE 1-continued
| Compound | Structure |
|---|---|
| 64 | 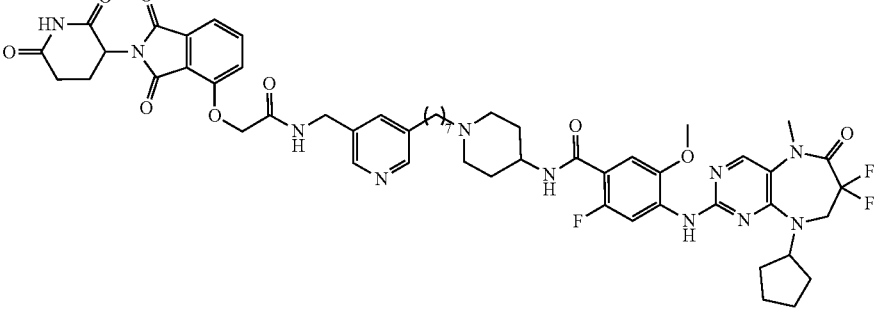 |
| 65 | 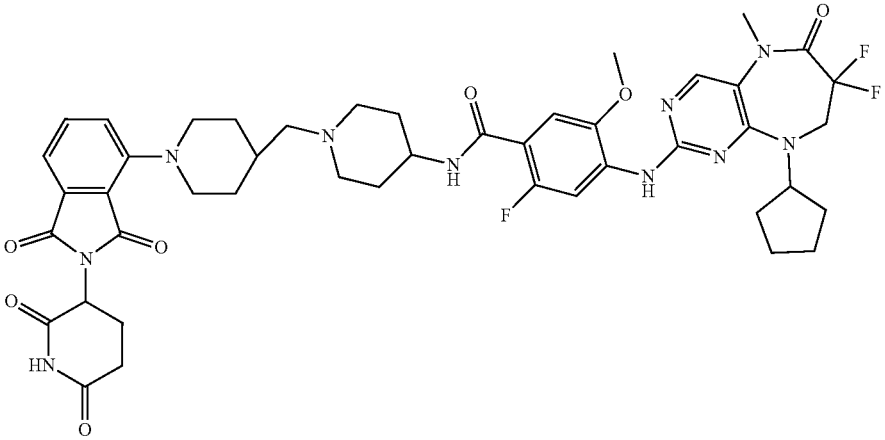 [SMILES: COc1cc(C(=O)NC2CCN(CC3CCN(c4cccc5c4C(=O)N(C4CCC(=O)NC4=O)C5=O)CC3)CC2)c(F)cc1Nc1ncc2c(n1)N(C1CCCC1)CC(F)(F)C(=O)N2C] |
| 66 | 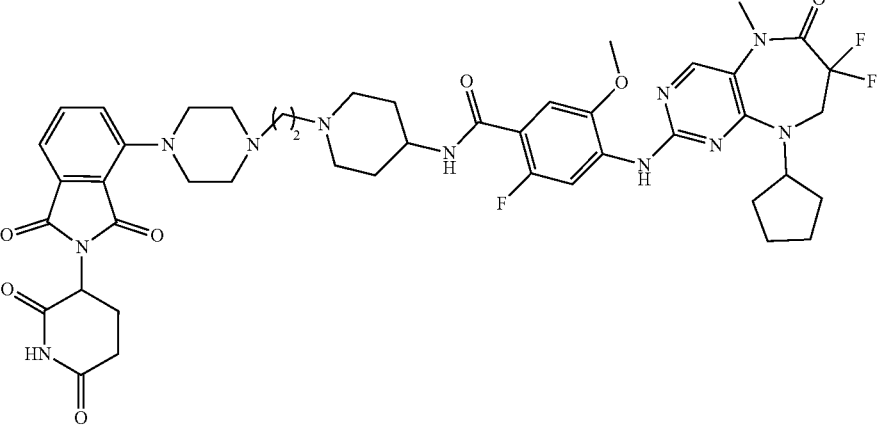 |
| 67 | 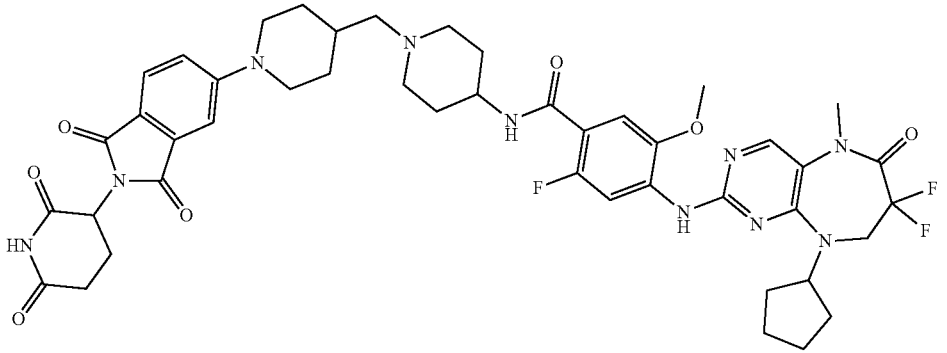 [SMILES: COc1cc(C(=O)NC2CCN(CC3CCN(c4ccc5c(c4)C(=O)N(C4CCC(=O)NC4=O)C5=O)CC3)CC2)c(F)cc1Nc1ncc2c(n1)N(C1CCCC1)CC(F)(F)C(=O)N2C] |

TABLE 1-continued

| Compound | Structure |
|---|---|
| 68 | 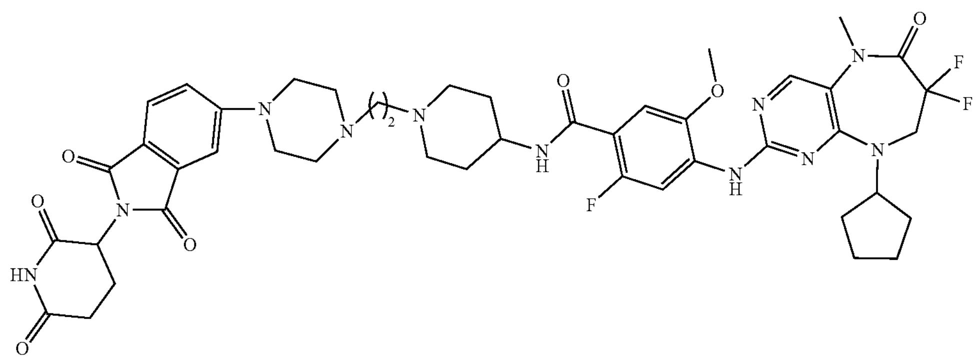 |
| 69 | 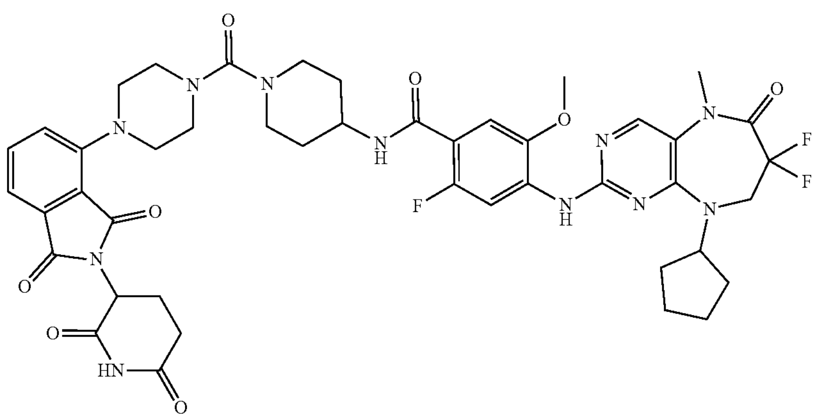 [SMILES: COc1cc(C(=O)NC2CCN(C(=O)N3CCN(c4cccc5c4C(=O)N(C4CCC(=O)NC4=O)C5=O)CC3)CC2)c(F)cc1Nc1ncc2c(n1)N(C1CCCC1)CC(F)(F)C(=O)N2C] |
| 70 | 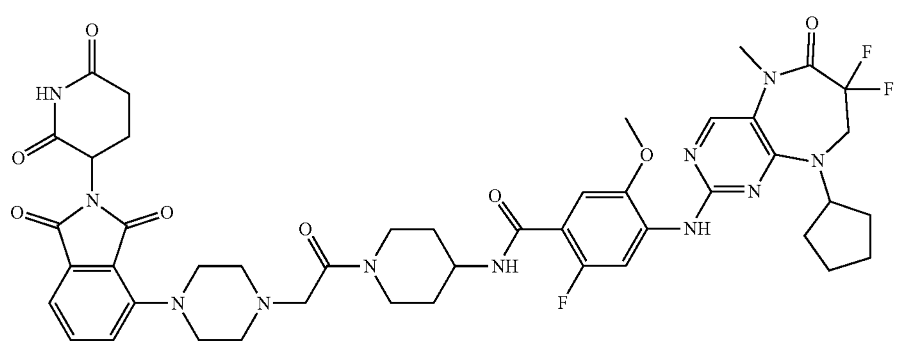 [SMILES: COc1cc(C(=O)NC2CCN(C(=O)CN3CCN(c4cccc5c4C(=O)N(C4CCC(=O)NC4=O)C5=O)CC3)CC2)c(F)cc1Nc1ncc2c(n1)N(C1CCCC1)CC(F)(F)C(=O)N2C] |
| 71 | 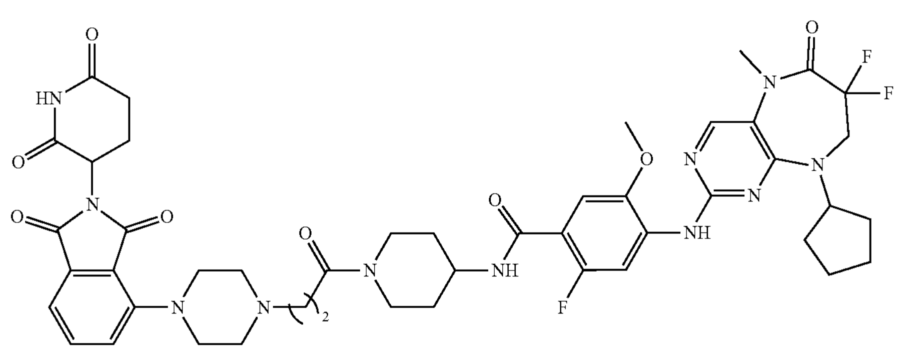 |

TABLE 1-continued

| Compound | Structure |
|---|---|
| 72 | 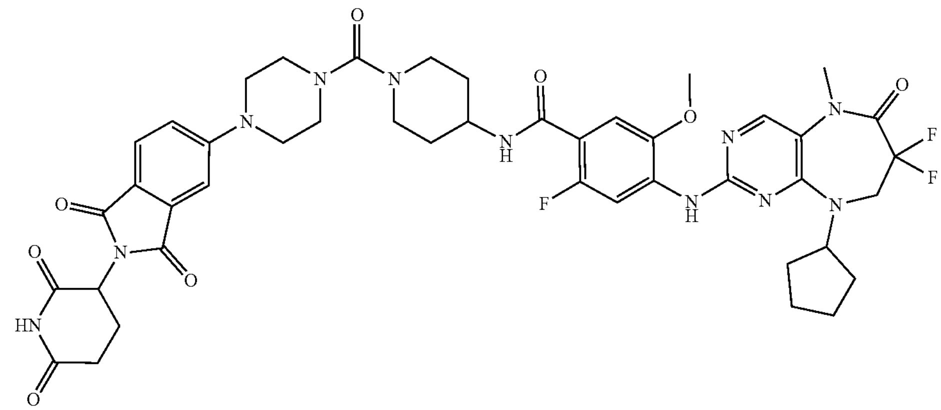 [SMILES: COc1cc(C(=O)NC2CCN(C(=O)N3CCN(c4ccc5c(c4)C(=O)N(C4CCC(=O)NC4=O)C5=O)CC3)CC2)c(F)cc1Nc1ncc2c(n1)N(C1CCCC1)CC(F)(F)C(=O)N2C] |
| 73 | 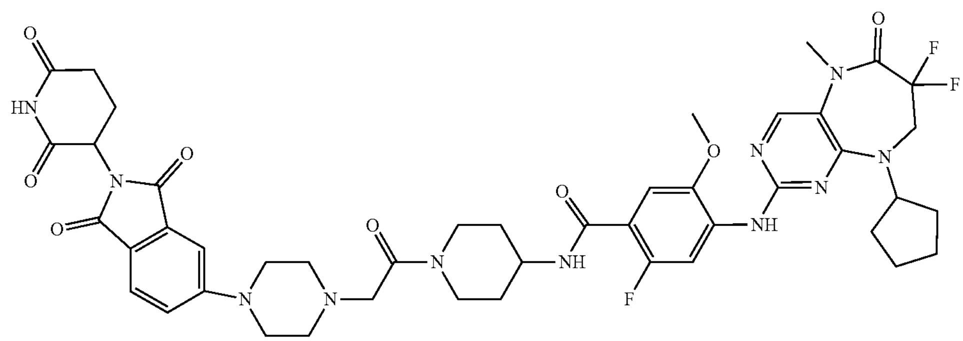 [SMILES: COc1cc(C(=O)NC2CCN(C(=O)CN3CCN(c4ccc5c(c4)C(=O)N(C4CCC(=O)NC4=O)C5=O)CC3)CC2)c(F)cc1Nc1ncc2c(n1)N(C1CCCC1)CC(F)(F)C(=O)N2C] |
| 74 | 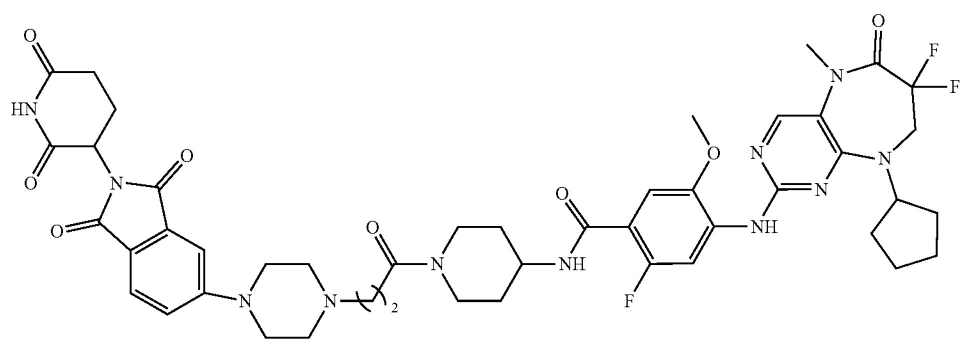 |
| 75 | 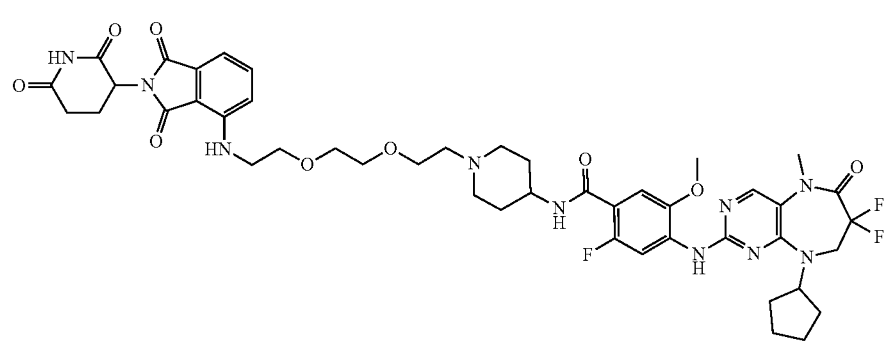 [SMILES: COc1cc(C(=O)NC2CCN(CCOCCOCCNc3cccc4c3C(=O)N(C3CCC(=O)NC3=O)C4=O)CC2)c(F)cc1Nc1ncc2c(n1)N(C1CCCC1)CC(F)(F)C(=O)N2C] |

TABLE 1-continued
| Compound | Structure |
|---|---|
| 76 | 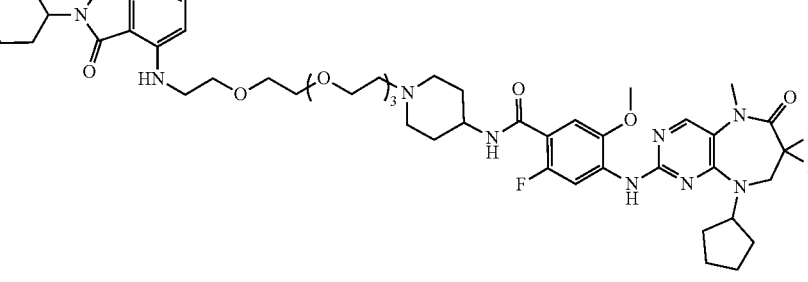 |
| 77 | 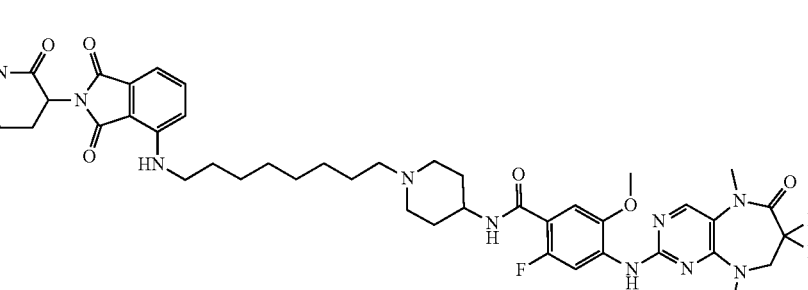 |
| 78 | 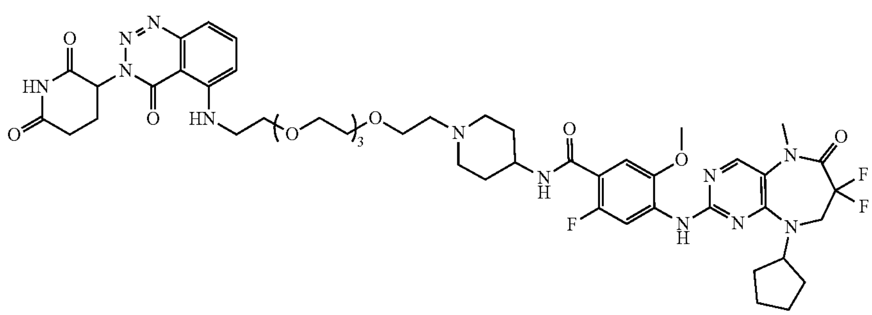 |
| 79 | 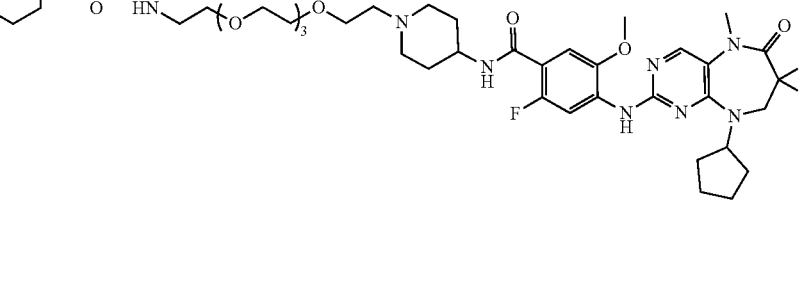 |

TABLE 1-continued

| Compound | Structure |
|---|---|
| 80 | 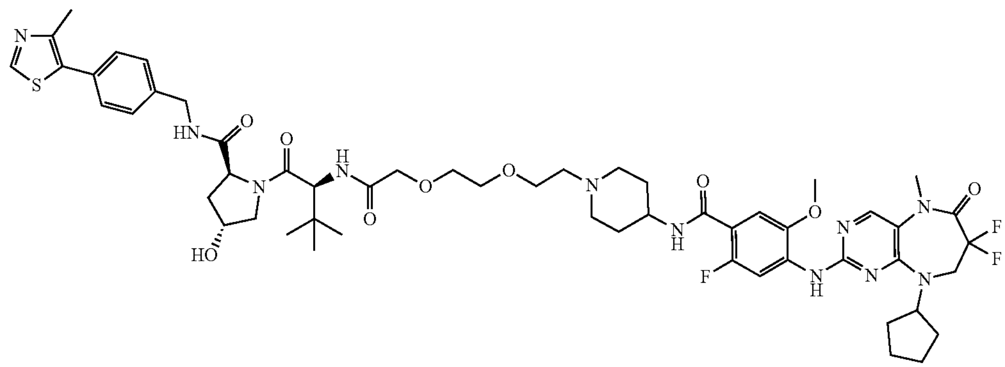 [SMILES: COc1cc(C(=O)NC2CCN(CCOCCOCC(=O)N[C@H](C(=O)N3C[C@H](O)C[C@H]3C(=O)NCc3ccc(-c4scnc4C)cc3)C(C)(C)C)CC2)c(F)cc1Nc1ncc2c(n1)N(C1CCCC1)CC(F)(F)C(=O)N2C] |
| 81 | 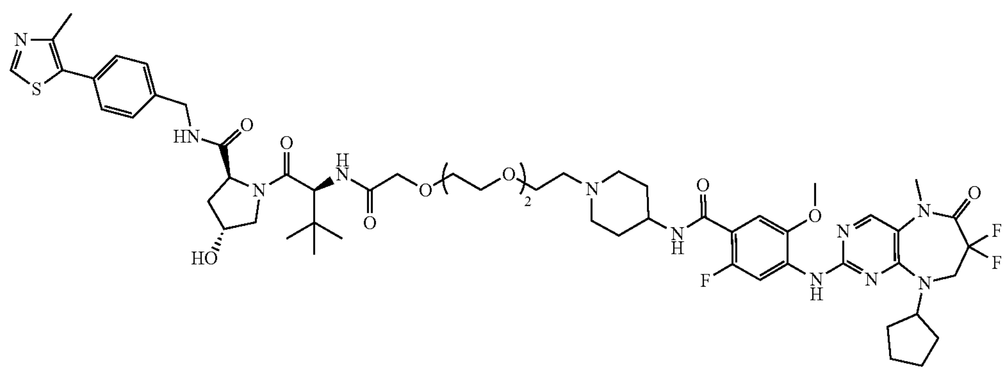 |
| 82 | 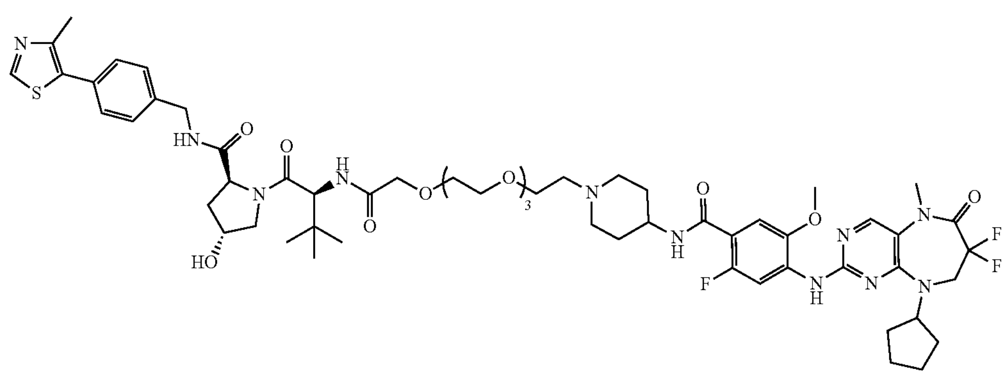 |
| 83 | 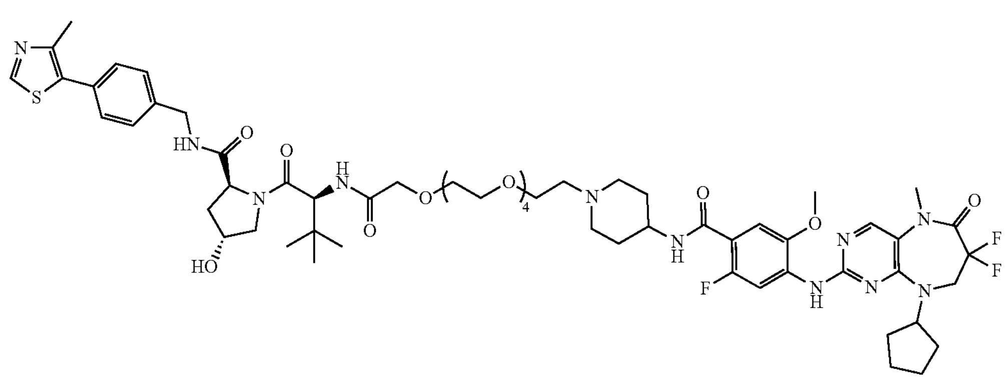 |

TABLE 1-continued
| Compound | Structure |
|---|---|
| 84 | 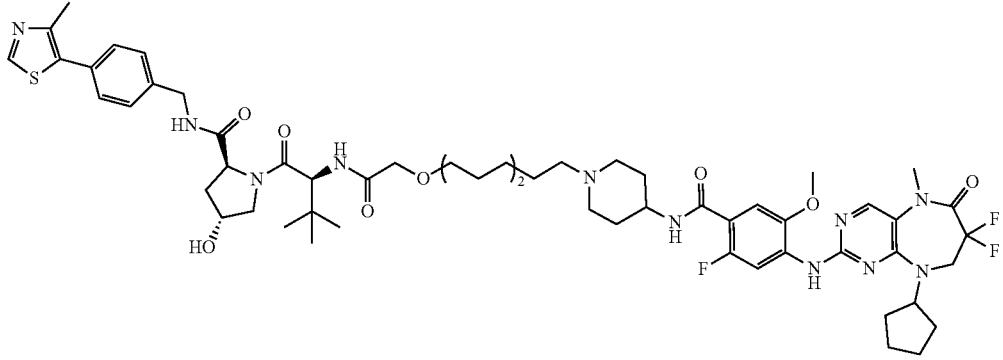 |
| 85 | 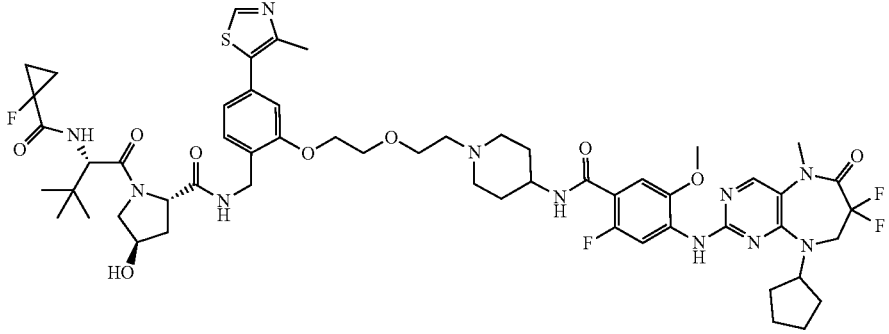 [SMILES: COc1cc(C(=O)NC2CCN(CCOCCOc3cc(-c4scnc4C)ccc3CNC(=O)[C@@H]3C[C@@H](O)CN3C(=O)[C@@H](NC(=O)C3(F)CC3)C(C)(C)C)CC2)c(F)cc1Nc1ncc2c(n1)N(C1CCCC1)CC(F)(F)C(=O)N2C] |
| 86 | 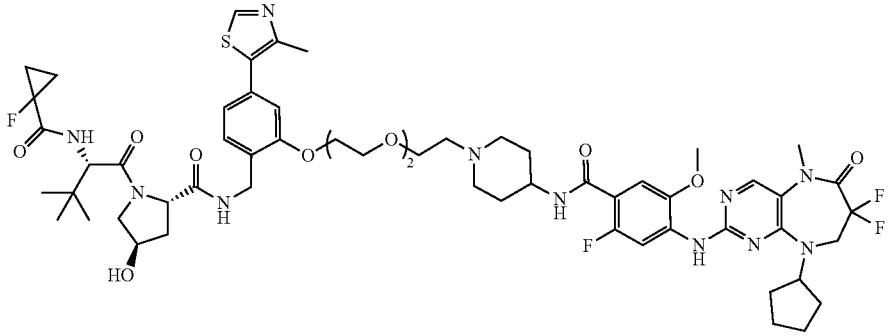 |
| 87 | 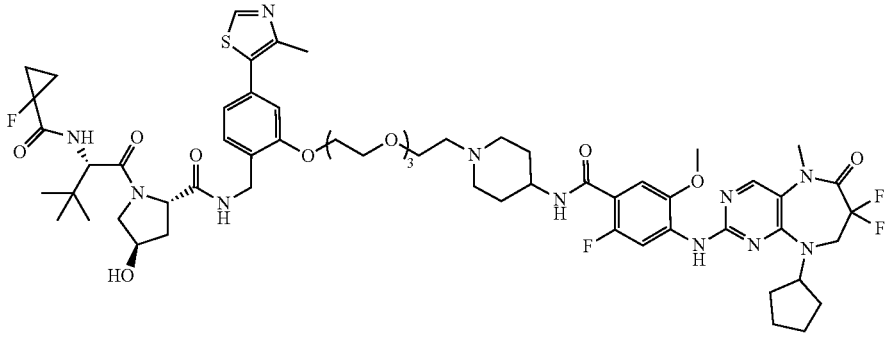 |

TABLE 1-continued
| Compound | Structure |
|---|---|
| 88 | 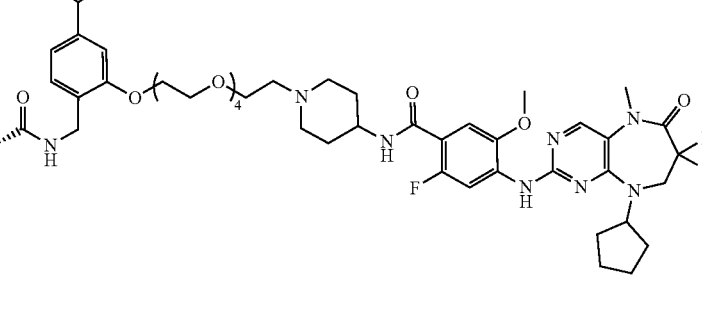 |
| 89 | 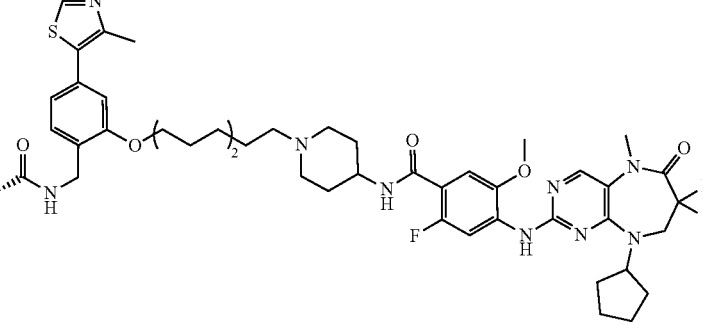 |
| 90 | 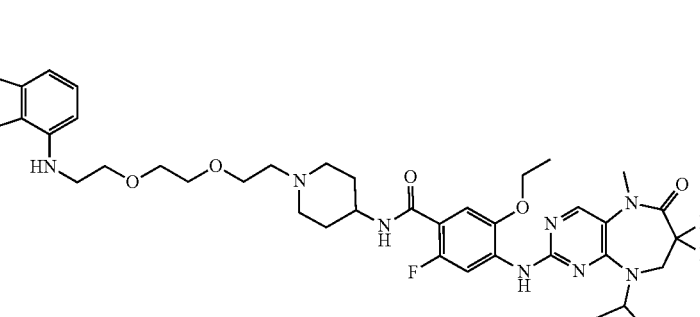 |
| 91 | 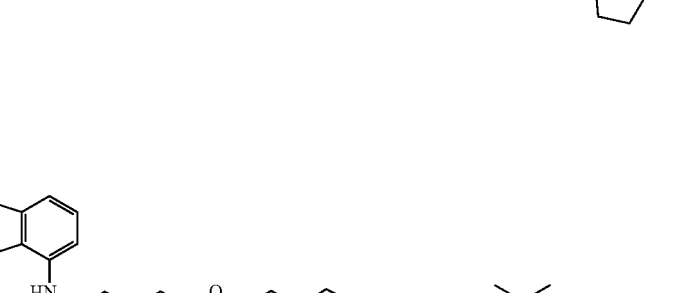 |

TABLE 1-continued
| Compound | Structure |
|---|---|
| 92 | 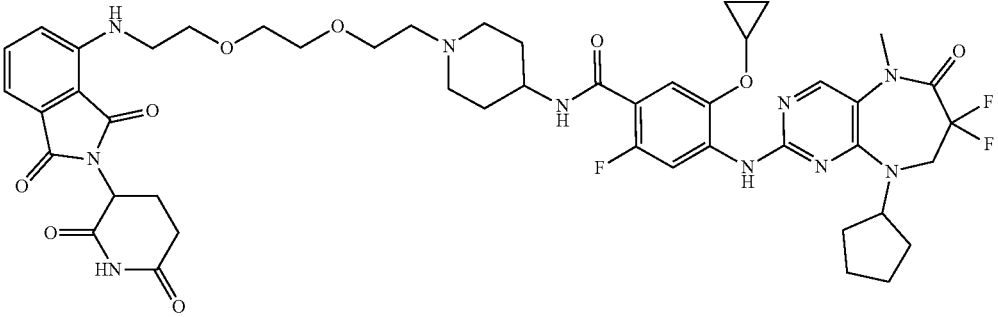 [SMILES: CN1C(=O)C(F)(F)CN(C2CCCC2)c2nc(Nc3cc(F)c(C(=O)NC4CCN(CCOCCOCCNc5cccc6c5C(=O)N(C5CCC(=O)NC5=O)C6=O)CC4)cc3OC3CC3)ncc21] |
| 93 | 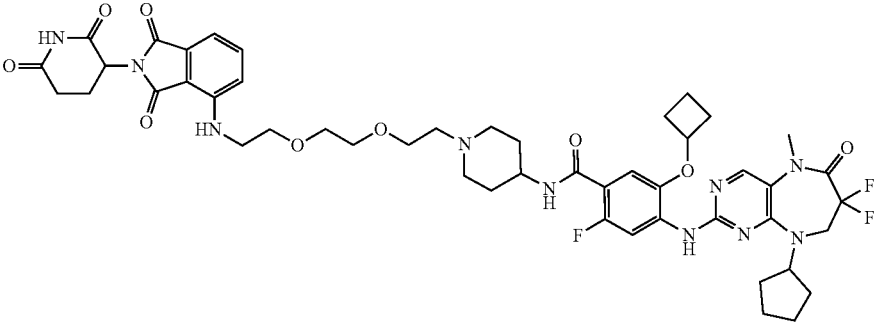 [SMILES: CN1C(=O)C(F)(F)CN(C2CCCC2)c2nc(Nc3cc(F)c(C(=O)NC4CCN(CCOCCOCCNc5cccc6c5C(=O)N(C5CCC(=O)NC5=O)C6=O)CC4)cc3OC3CCC3)ncc21] |
| 94 | 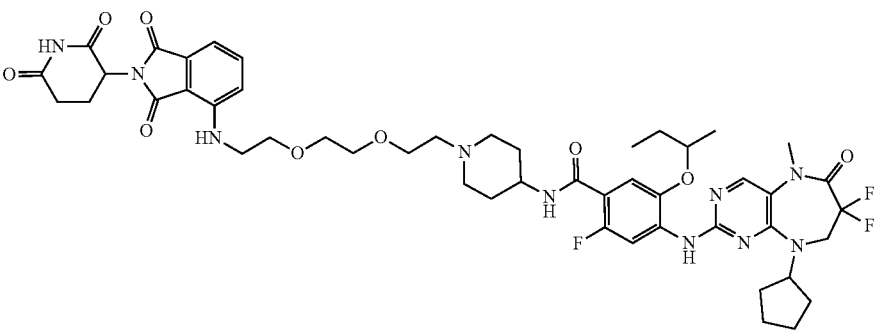 [SMILES: CCC(C)Oc1cc(C(=O)NC2CCN(CCOCCOCCNc3cccc4c3C(=O)N(C3CCC(=O)NC3=O)C4=O)CC2)c(F)cc1Nc1ncc2c(n1)N(C1CCCC1)CC(F)(F)C(=O)N2C] |
| 95 | 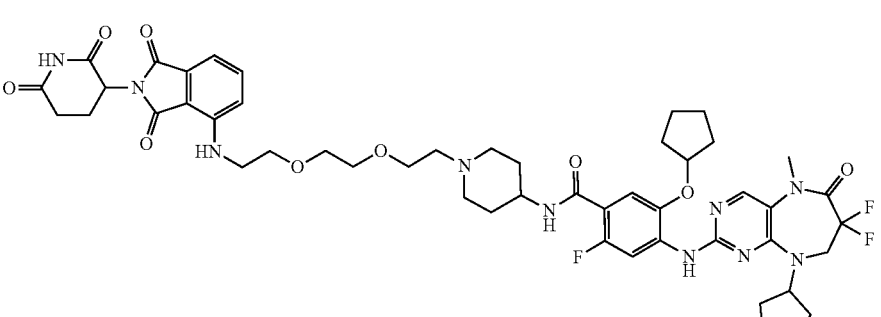 |

TABLE 1-continued

| Compound | Structure |
|---|---|
| 96 | 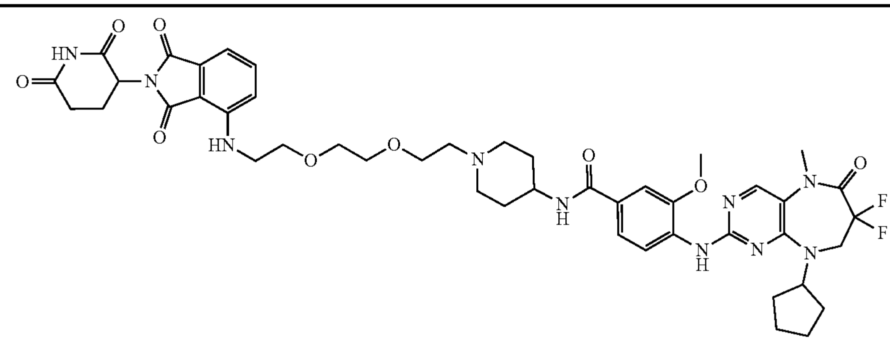 |
| 97 | 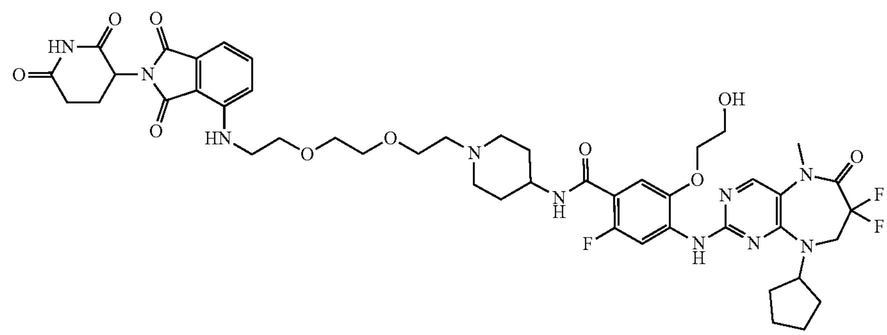 [SMILES: CN1C(=O)C(F)(F)CN(C2CCCC2)c2nc(Nc3cc(F)c(C(=O)NC4CCN(CCOCCOCCNc5cccc6c5C(=O)N(C5CCC(=O)NC5=O)C6=O)CC4)cc3OCCO)ncc21] |
| 98 | 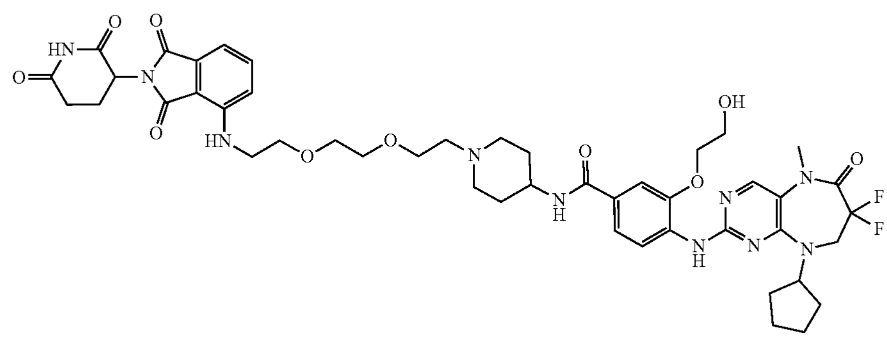 [SMILES: CN1C(=O)C(F)(F)CN(C2CCCC2)c2nc(Nc3ccc(C(=O)NC4CCN(CCOCCOCCNc5cccc6c5C(=O)N(C5CCC(=O)NC5=O)C6=O)CC4)cc3OCCO)ncc21] |
| 99 | 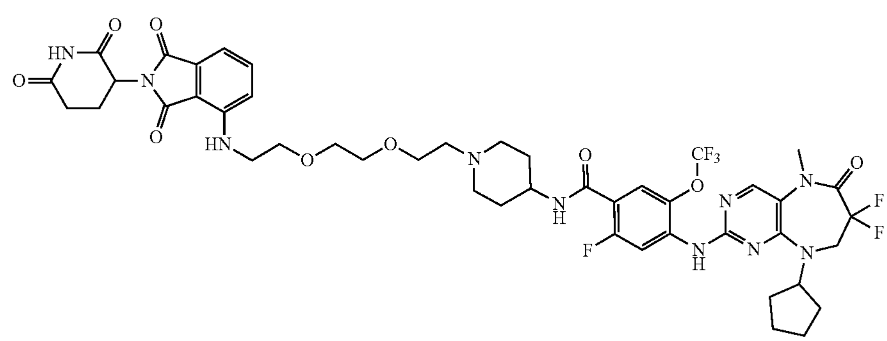 [SMILES: CN1C(=O)C(F)(F)CN(C2CCCC2)c2nc(Nc3cc(F)c(C(=O)NC4CCN(CCOCCOCCNc5cccc6c5C(=O)N(C5CCC(=O)NC5=O)C6=O)CC4)cc3OC(F)(F)F)ncc21] |
| 100 | 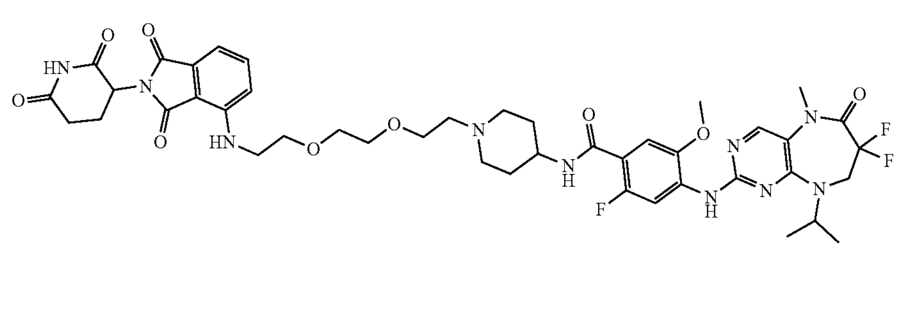 [SMILES: COc1cc(C(=O)NC2CCN(CCOCCOCCNc3cccc4c3C(=O)N(C3CCC(=O)NC3=O)C4=O)CC2)c(F)cc1Nc1ncc2c(n1)N(C(C)C)CC(F)(F)C(=O)N2C] |

TABLE 1-continued

| Compound | Structure |
|---|---|
| 101 | (structure) |
| 102 | (structure) |
| 103 | (structure) |
| 104 | (structure) |
| 105 | (structure) |

TABLE 1-continued
| Compound | Structure |
|---|---|
| 106 | 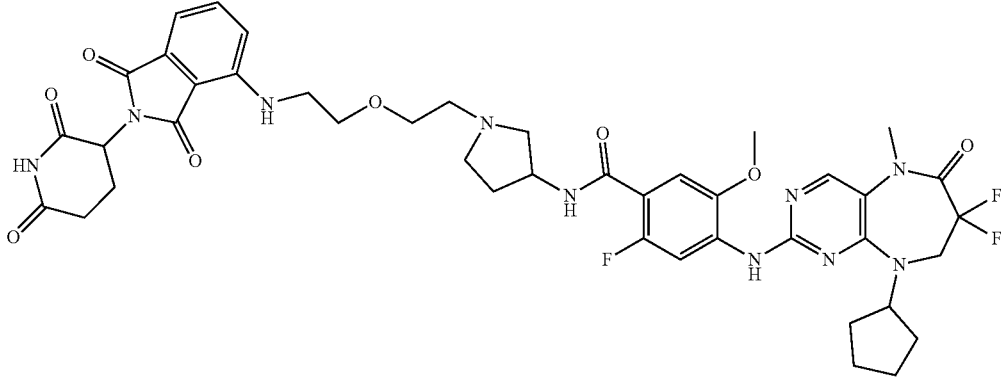 [SMILES: COc1cc(C(=O)NC2CCN(CCOCCNc3cccc4c3C(=O)N(C3CCC(=O)NC3=O)C4=O)C2)c(F)cc1Nc1ncc2c(n1)N(C1CCCC1)CC(F)(F)C(=O)N2C] |
| 107 | 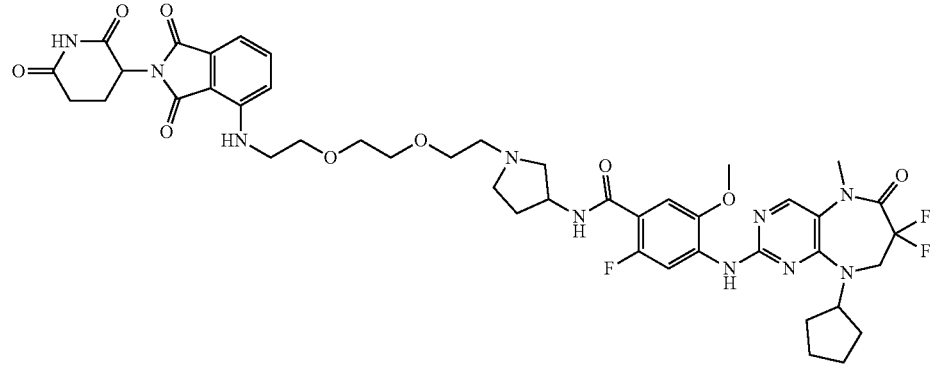 [SMILES: COc1cc(C(=O)NC2CCN(CCOCCOCCNc3cccc4c3C(=O)N(C3CCC(=O)NC3=O)C4=O)C2)c(F)cc1Nc1ncc2c(n1)N(C1CCCC1)CC(F)(F)C(=O)N2C] |
| 108 | 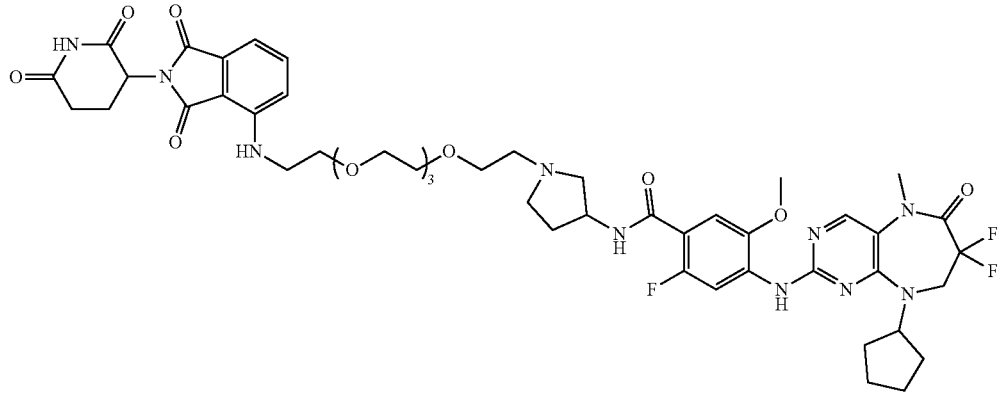 |
| 109 | 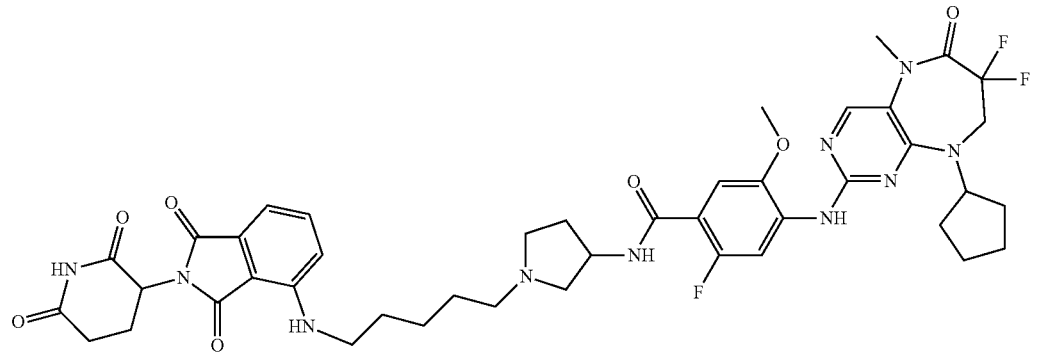 [SMILES: COc1cc(C(=O)NC2CCN(CCCCCNc3cccc4c3C(=O)N(C3CCC(=O)NC3=O)C4=O)C2)c(F)cc1Nc1ncc2c(n1)N(C1CCCC1)CC(F)(F)C(=O)N2C] |

TABLE 1-continued

| Compound | Structure |
|---|---|
| 110 | 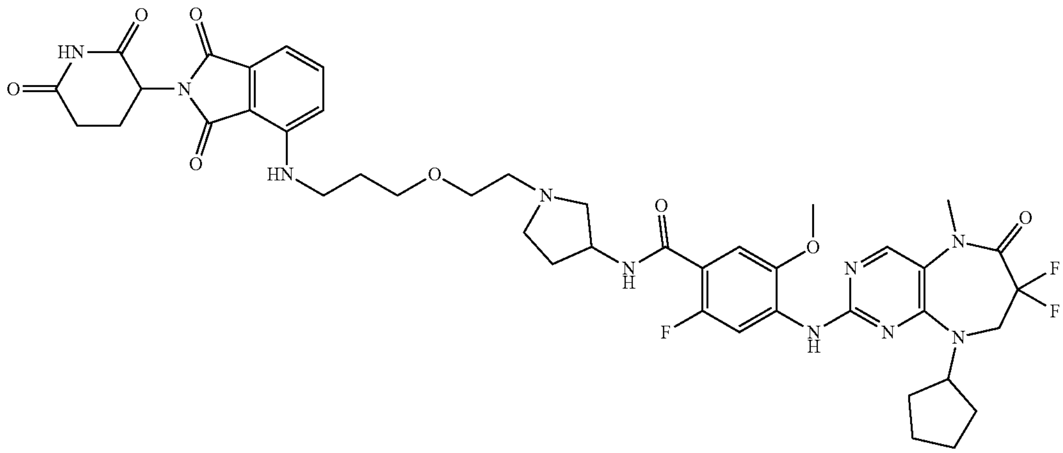 [SMILES: COc1cc(C(=O)NC2CCN(CCOCCCNc3cccc4c3C(=O)N(C3CCC(=O)NC3=O)C4=O)C2)c(F)cc1Nc1ncc2c(n1)N(C1CCCC1)CC(F)(F)C(=O)N2C] |
| 111 | 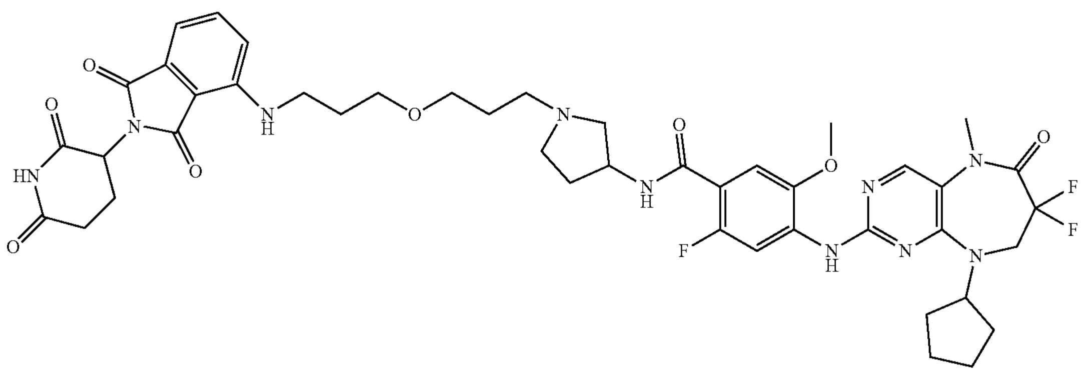 [SMILES: COc1cc(C(=O)NC2CCN(CCCOCCCNc3cccc4c3C(=O)N(C3CCC(=O)NC3=O)C4=O)C2)c(F)cc1Nc1ncc2c(n1)N(C1CCCC1)CC(F)(F)C(=O)N2C] |
| 112 | 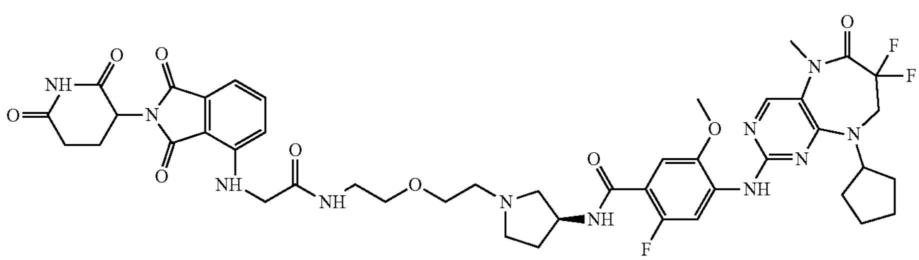 [SMILES: COc1cc(C(=O)N[C@H]2CCN(CCOCCNC(=O)CNc3cccc4c3C(=O)N(C3CCC(=O)NC3=O)C4=O)C2)c(F)cc1Nc1ncc2c(n1)N(C1CCCC1)CC(F)(F)C(=O)N2C] |
| 113 | 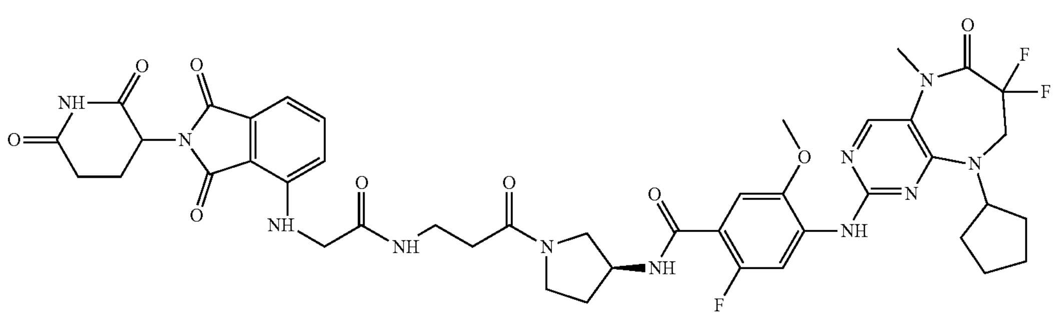 [SMILES: COc1cc(C(=O)N[C@H]2CCN(C(=O)CCNC(=O)CNc3cccc4c3C(=O)N(C3CCC(=O)NC3=O)C4=O)C2)c(F)cc1Nc1ncc2c(n1)N(C1CCCC1)CC(F)(F)C(=O)N2C] |

TABLE 1-continued
| Compound | Structure |
|---|---|
| 114 | 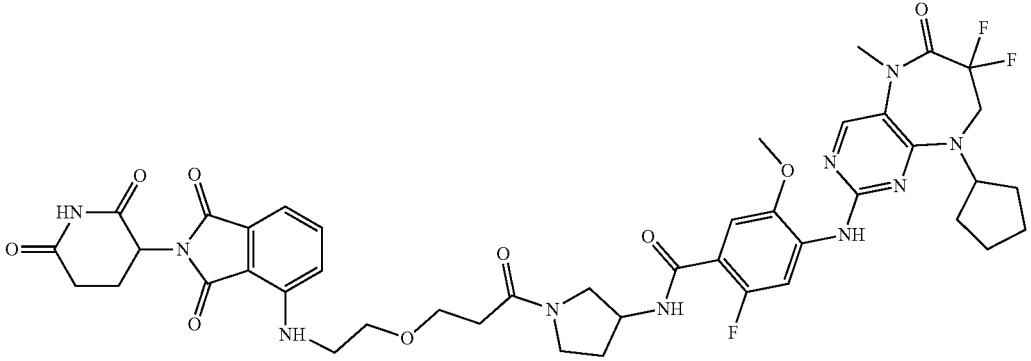 [SMILES: COc1cc(C(=O)NC2CCN(C(=O)CCOCCNc3cccc4c3C(=O)N(C3CCC(=O)NC3=O)C4=O)C2)c(F)cc1Nc1ncc2c(n1)N(C1CCCC1)CC(F)(F)C(=O)N2C] |
| 115 | 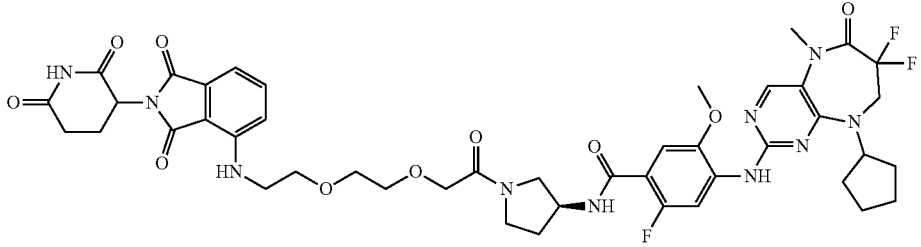 [SMILES: COc1cc(C(=O)N[C@H]2CCN(C(=O)COCCOCCNc3cccc4c3C(=O)N(C3CCC(=O)NC3=O)C4=O)C2)c(F)cc1Nc1ncc2c(n1)N(C1CCCC1)CC(F)(F)C(=O)N2C] |
| 116 | 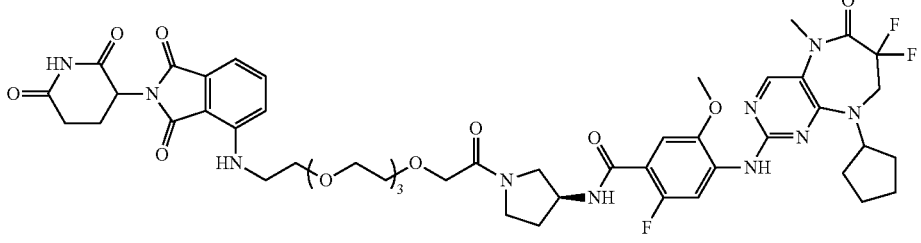 |
| 117 | 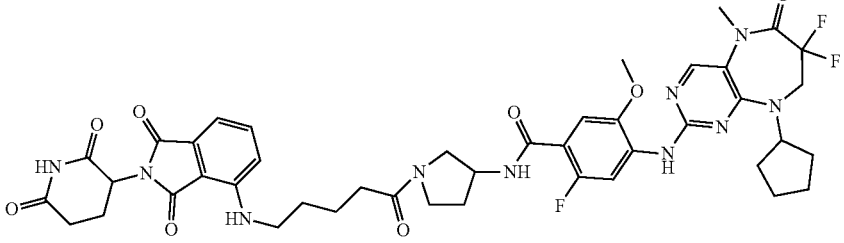 |
| 118 | 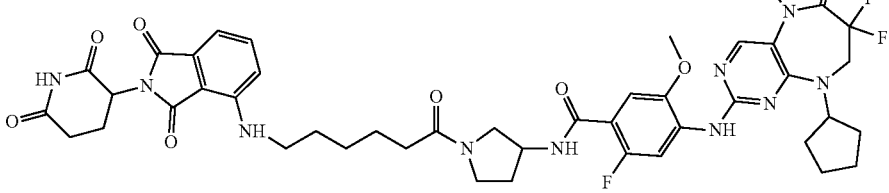 |

TABLE 1-continued

| Compound | Structure |
|---|---|
| 119 | 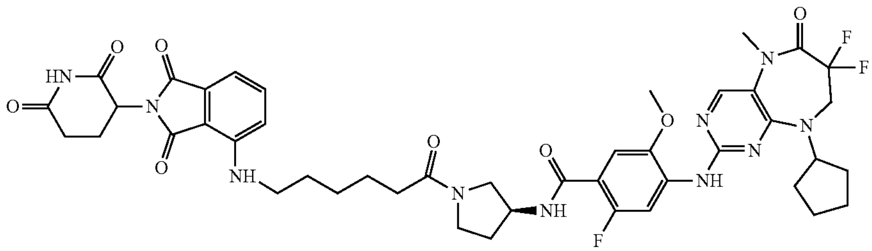 [SMILES: COc1cc(C(=O)N[C@H]2CCN(C(=O)CCCCCNc3cccc4c3C(=O)N(C3CCC(=O)NC3=O)C4=O)C2)c(F)cc1Nc1ncc2c(n1)N(C1CCCC1)CC(F)(F)C(=O)N2C] |
| 120 | 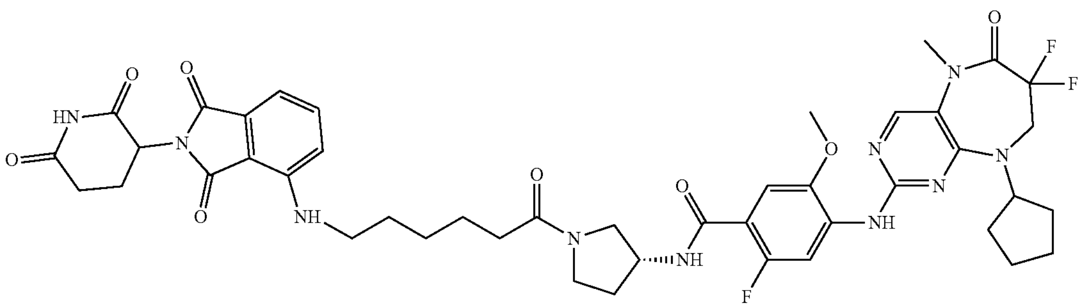 [SMILES: COc1cc(C(=O)N[C@@H]2CCN(C(=O)CCCCCNc3cccc4c3C(=O)N(C3CCC(=O)NC3=O)C4=O)C2)c(F)cc1Nc1ncc2c(n1)N(C1CCCC1)CC(F)(F)C(=O)N2C] |
| 121 | 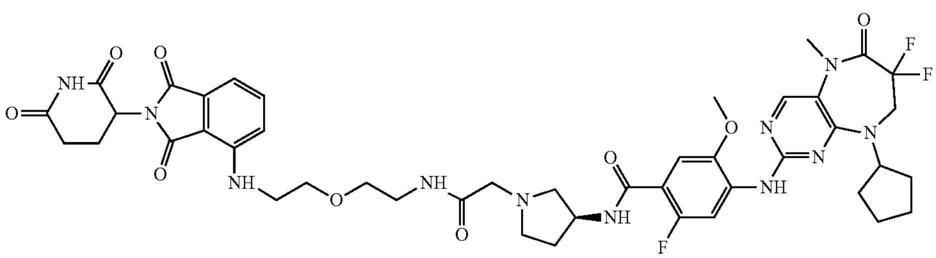 [SMILES: COc1cc(C(=O)N[C@H]2CCN(CC(=O)NCCOCCNc3cccc4c3C(=O)N(C3CCC(=O)NC3=O)C4=O)C2)c(F)cc1Nc1ncc2c(n1)N(C1CCCC1)CC(F)(F)C(=O)N2C] |
| 122 | 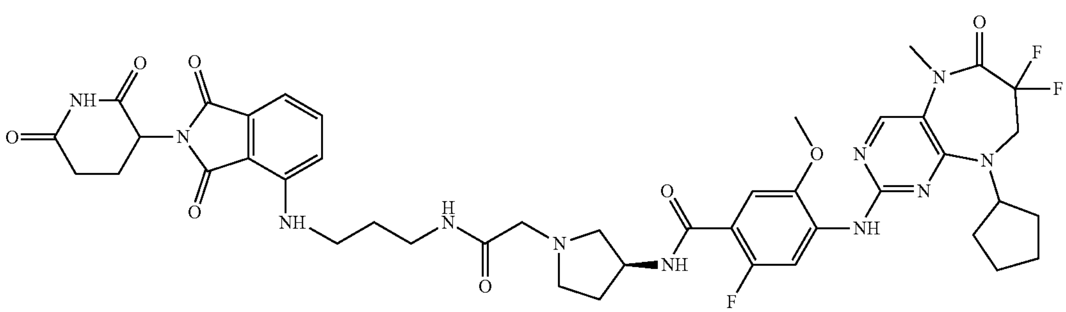 [SMILES: COc1cc(C(=O)N[C@H]2CCN(CC(=O)NCCCNc3cccc4c3C(=O)N(C3CCC(=O)NC3=O)C4=O)C2)c(F)cc1Nc1ncc2c(n1)N(C1CCCC1)CC(F)(F)C(=O)N2C] |
| 123 | 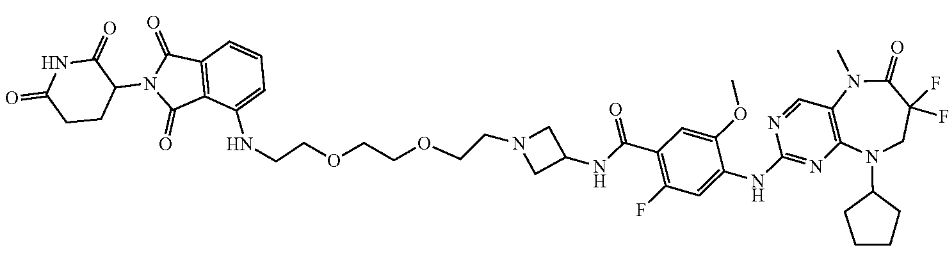 [SMILES: COc1cc(C(=O)NC2CN(CCOCCOCCNc3cccc4c3C(=O)N(C3CCC(=O)NC3=O)C4=O)C2)c(F)cc1Nc1ncc2c(n1)N(C1CCCC1)CC(F)(F)C(=O)N2C] |

TABLE 1-continued
| Compound | Structure |
|---|---|
| 124 | 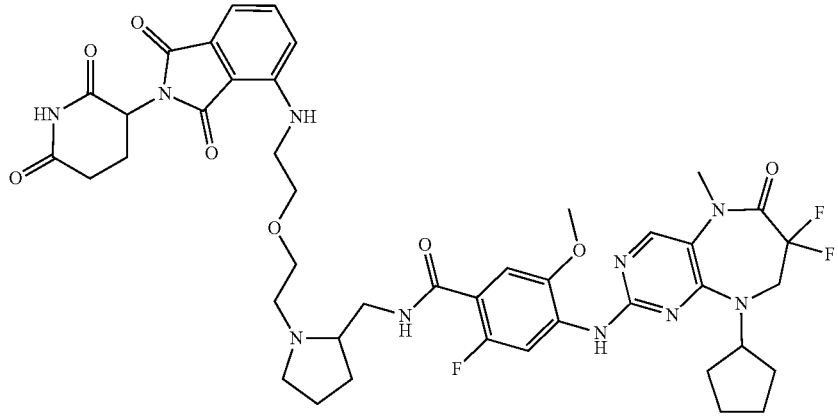 [SMILES: COc1cc(C(=O)NCC2CCCN2CCOCCNc2cccc3c2C(=O)N(C2CCC(=O)NC2=O)C3=O)c(F)cc1Nc1ncc2c(n1)N(C1CCCC1)CC(F)(F)C(=O)N2C] |
| 125 | 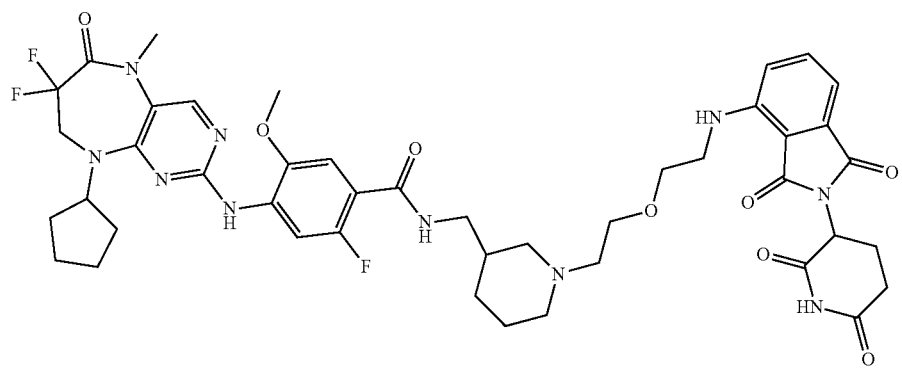 [SMILES: COc1cc(C(=O)NCC2CCCN(CCOCCNc3cccc4c3C(=O)N(C3CCC(=O)NC3=O)C4=O)C2)c(F)cc1Nc1ncc2c(n1)N(C1CCCC1)CC(F)(F)C(=O)N2C] |
| 126 | 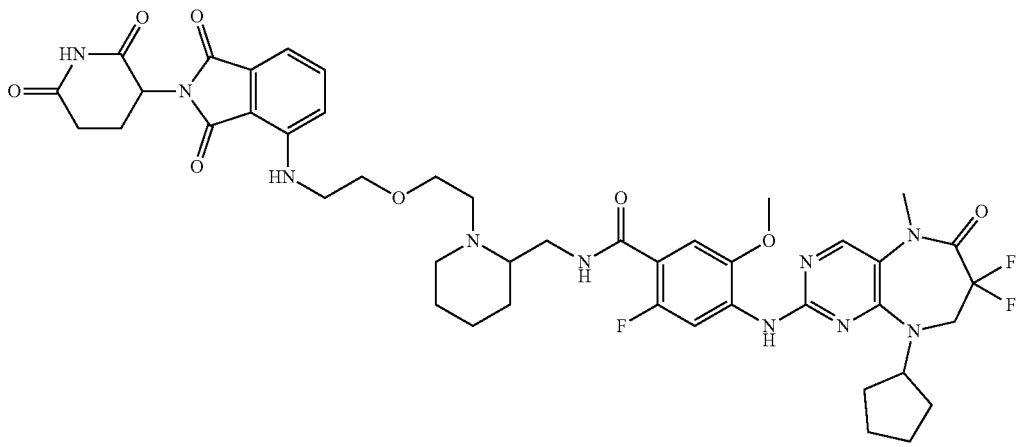 [SMILES: COc1cc(C(=O)NCC2CCCCN2CCOCCNc2cccc3c2C(=O)N(C2CCC(=O)NC2=O)C3=O)c(F)cc1Nc1ncc2c(n1)N(C1CCCC1)CC(F)(F)C(=O)N2C] |

TABLE 1-continued

| Compound | Structure |
| --- | --- |
| 127 | 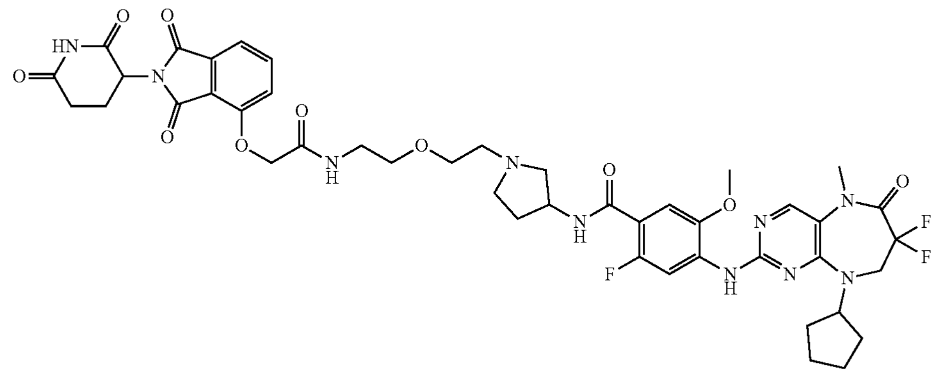 [SMILES: COc1cc(C(=O)NC2CCN(CCOCCNC(=O)COc3cccc4c3C(=O)N(C3CCC(=O)NC3=O)C4=O)C2)c(F)cc1Nc1ncc2c(n1)N(C1CCCC1)CC(F)(F)C(=O)N2C] |
| 128 | 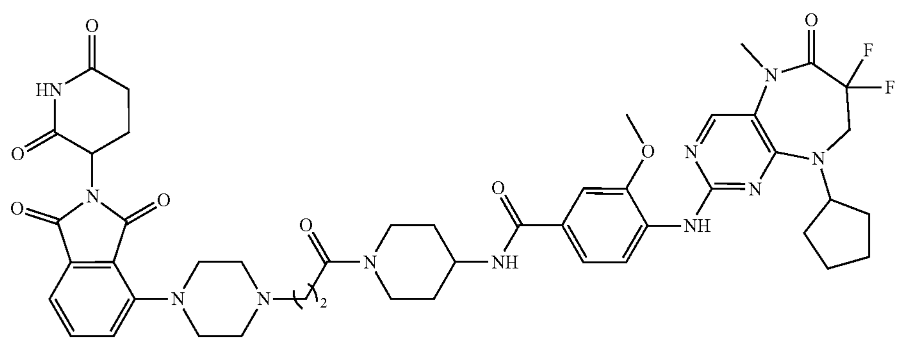 |
| 129 | 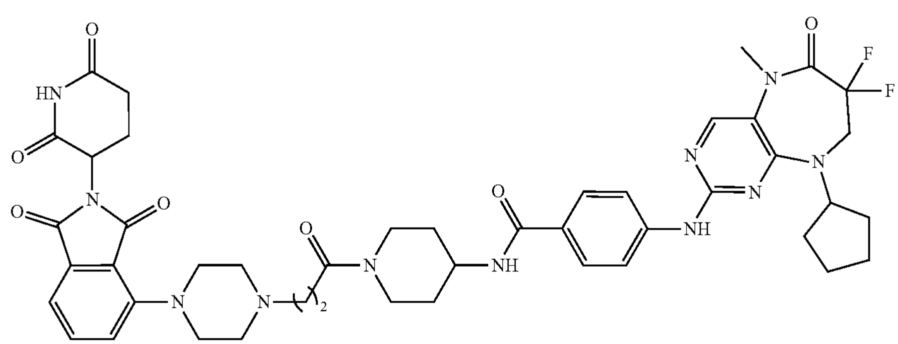 |
| 130 | 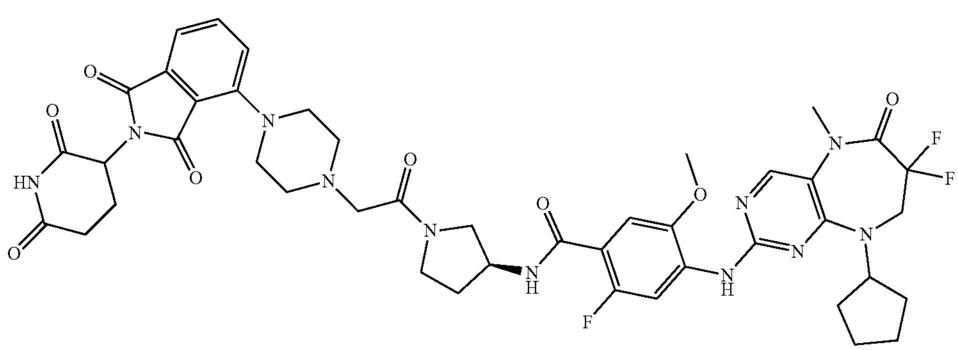 [SMILES: COc1cc(C(=O)N[C@H]2CCN(C(=O)CN3CCN(c4cccc5c4C(=O)N(C4CCC(=O)NC4=O)C5=O)CC3)C2)c(F)cc1Nc1ncc2c(n1)N(C1CCCC1)CC(F)(F)C(=O)N2C] |

TABLE 1-continued

| Compound | Structure |
|---|---|
| 131 | 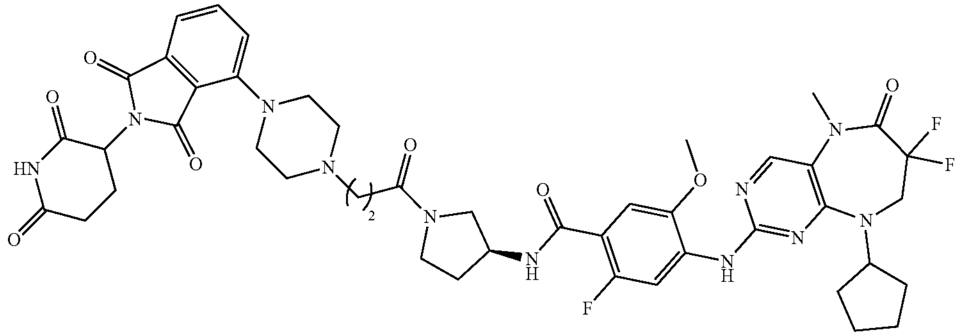 |
| 132 | 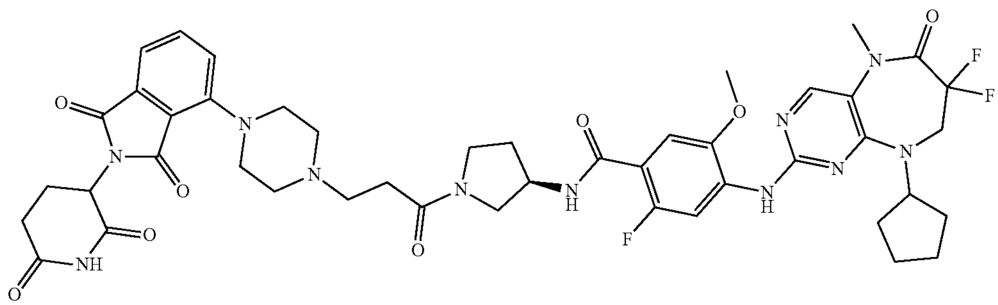 [SMILES: COc1cc(C(=O)N[C@@H]2CCN(C(=O)CCN3CCN(c4cccc5c4C(=O)N(C4CCC(=O)NC4=O)C5=O)CC3)C2)c(F)cc1Nc1ncc2c(n1)N(C1CCCC1)CC(F)(F)C(=O)N2C] |
| 133 | 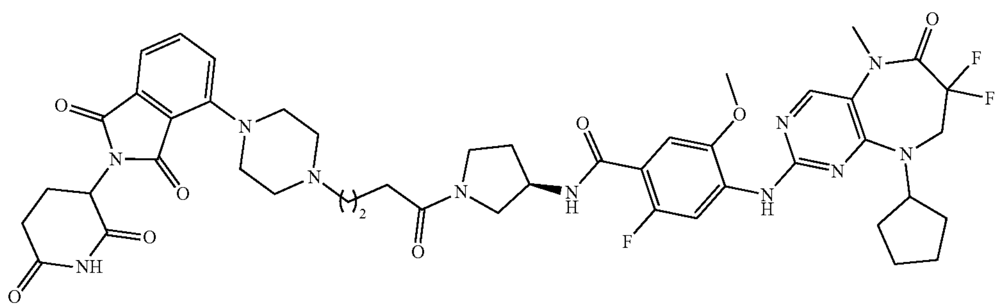 |
| 134 | 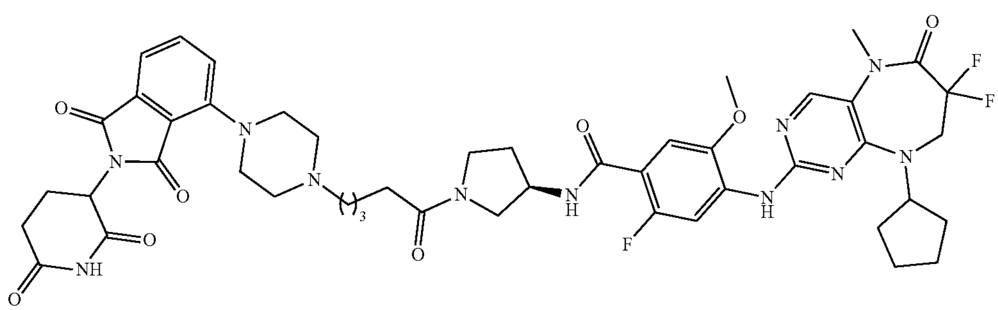 |
| 135 | 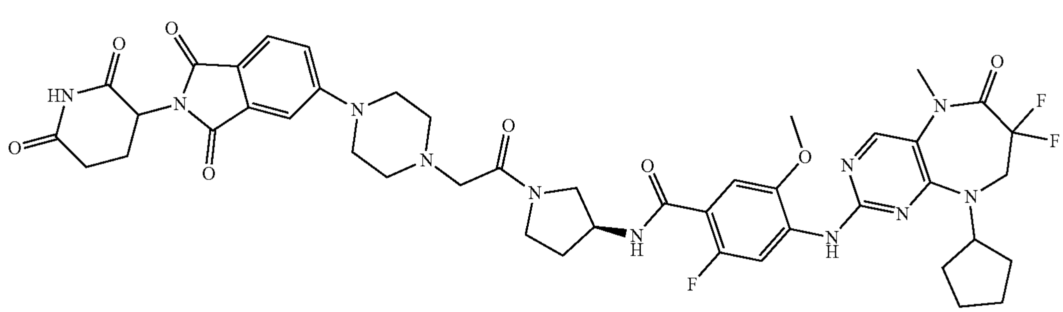 [SMILES: COc1cc(C(=O)N[C@H]2CCN(C(=O)CN3CCN(c4ccc5c(c4)C(=O)N(C4CCC(=O)NC4=O)C5=O)CC3)C2)c(F)cc1Nc1ncc2c(n1)N(C1CCCC1)CC(F)(F)C(=O)N2C] |

TABLE 1-continued

| Compound | Structure |
|---|---|
| 136 | 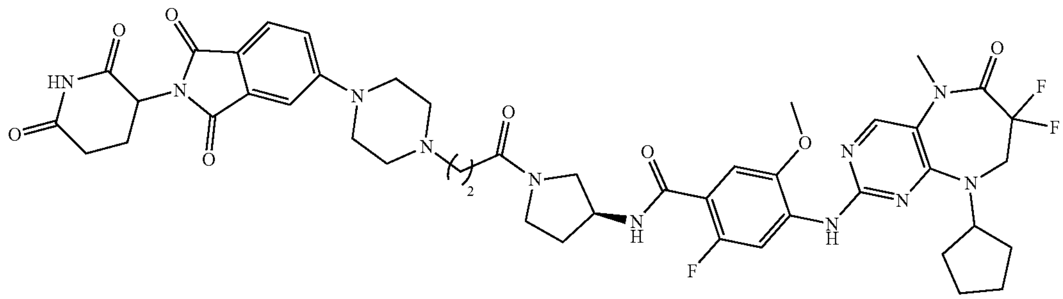 |
| 137 | 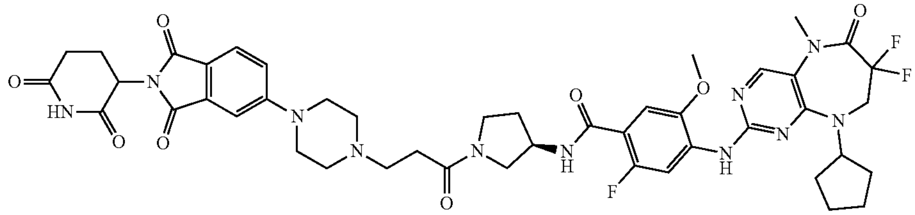 [SMILES: COc1cc(C(=O)N[C@@H]2CCN(C(=O)CCN3CCN(c4ccc5c(c4)C(=O)N(C4CCC(=O)NC4=O)C5=O)CC3)C2)c(F)cc1Nc1ncc2c(n1)N(C1CCCC1)CC(F)(F)C(=O)N2C] |
| 138 | 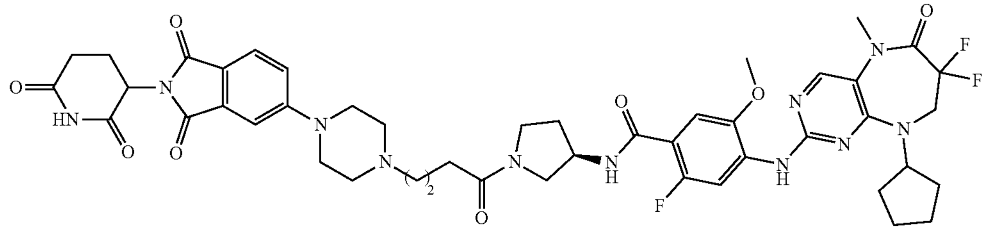 |
| 139 | 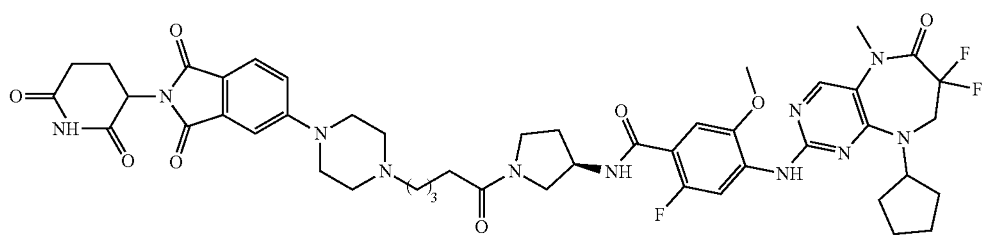 |
| 140 | 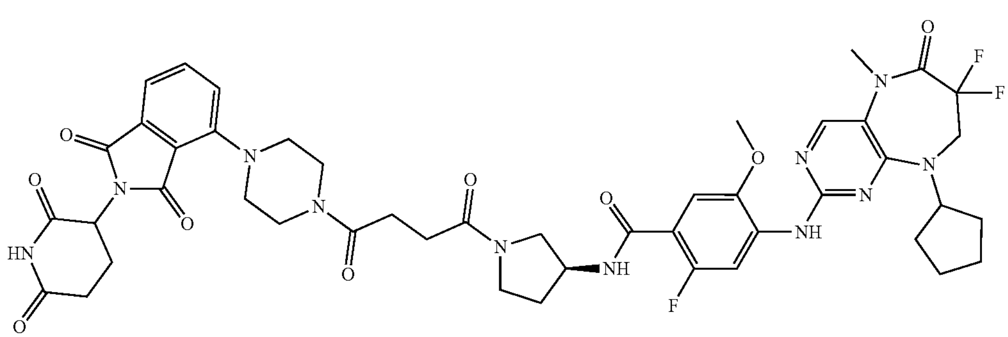 [SMILES: COc1cc(C(=O)N[C@H]2CCN(C(=O)CCC(=O)N3CCN(c4cccc5c4C(=O)N(C4CCC(=O)NC4=O)C5=O)CC3)C2)c(F)cc1Nc1ncc2c(n1)N(C1CCCC1)CC(F)(F)C(=O)N2C] |

TABLE 1-continued

| Compound | Structure |
|---|---|
| 141 | 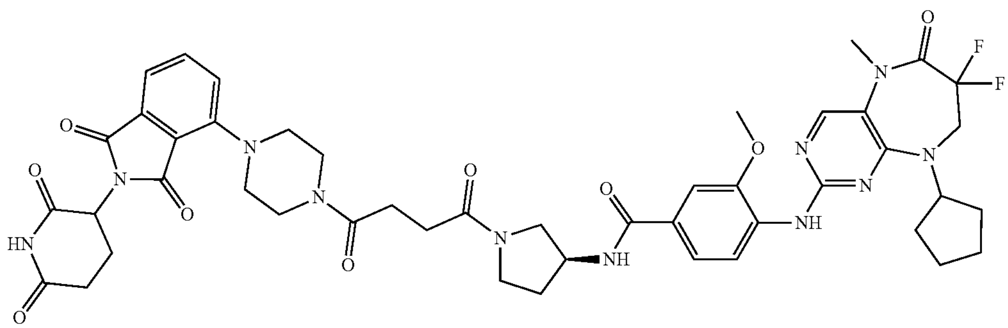 [SMILES: COc1cc(C(=O)N[C@H]2CCN(C(=O)CCC(=O)N3CCN(c4cccc5c4C(=O)N(C4CCC(=O)NC4=O)C5=O)CC3)C2)ccc1Nc1ncc2c(n1)N(C1CCCC1)CC(F)(F)C(=O)N2C] |
| 142 | 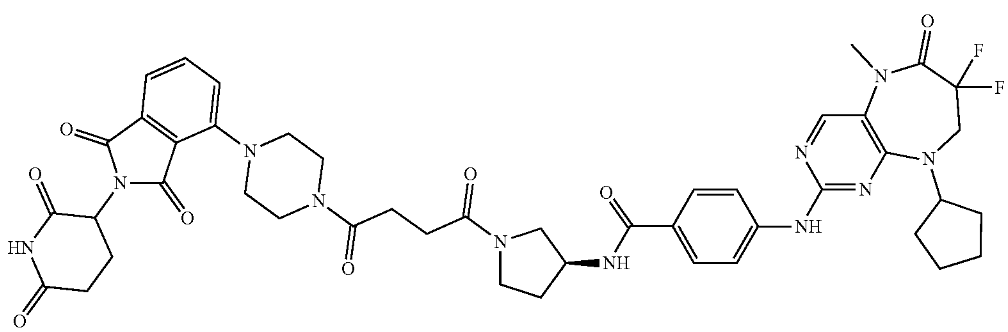 [SMILES: CN1C(=O)C(F)(F)CN(C2CCCC2)c2nc(Nc3ccc(C(=O)N[C@H]4CCN(C(=O)CCC(=O)N5CCN(c6cccc7c6C(=O)N(C6CCC(=O)NC6=O)C7=O)CC5)C4)cc3)ncc21] |
| 143 | 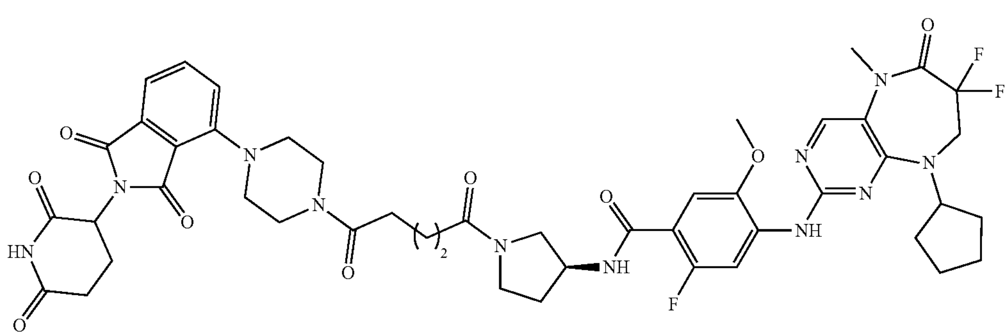 |
| 144 | 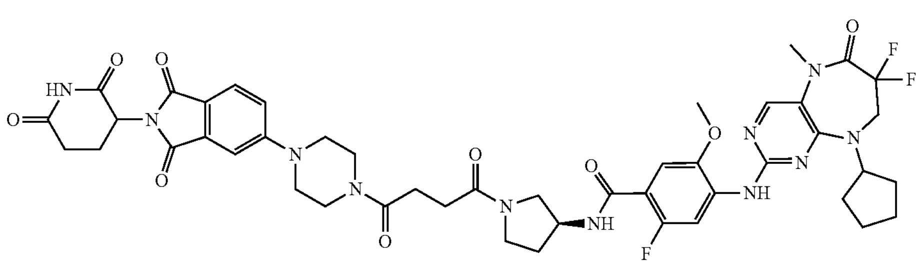 [SMILES: COc1cc(C(=O)N[C@H]2CCN(C(=O)CCC(=O)N3CCN(c4ccc5c(c4)C(=O)N(C4CCC(=O)NC4=O)C5=O)CC3)C2)c(F)cc1Nc1ncc2c(n1)N(C1CCCC1)CC(F)(F)C(=O)N2C] |
| 145 | 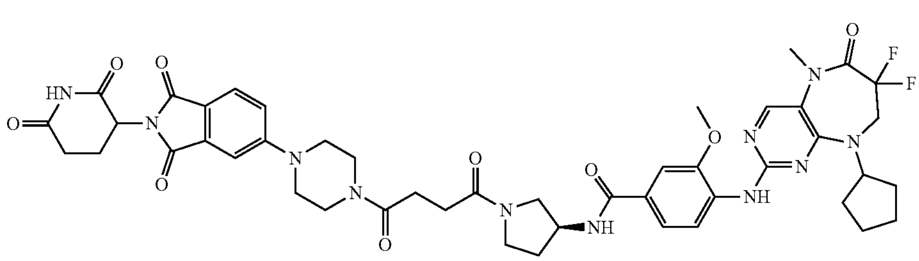 [SMILES: COc1cc(C(=O)N[C@H]2CCN(C(=O)CCC(=O)N3CCN(c4ccc5c(c4)C(=O)N(C4CCC(=O)NC4=O)C5=O)CC3)C2)ccc1Nc1ncc2c(n1)N(C1CCCC1)CC(F)(F)C(=O)N2C] |

TABLE 1-continued

| Compound | Structure |
|---|---|
| 146 | 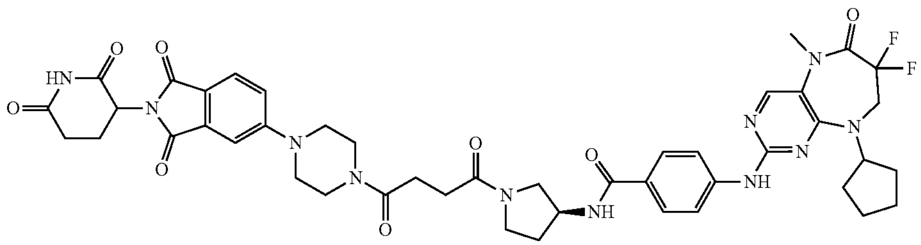 [SMILES: CN1C(=O)C(F)(F)CN(C2CCCC2)c2nc(Nc3ccc(C(=O)N[C@H]4CCN(C(=O)CCC(=O)N5CCN(c6ccc7c(c6)C(=O)N(C6CCC(=O)NC6=O)C7=O)CC5)C4)cc3)ncc21] |
| 147 | 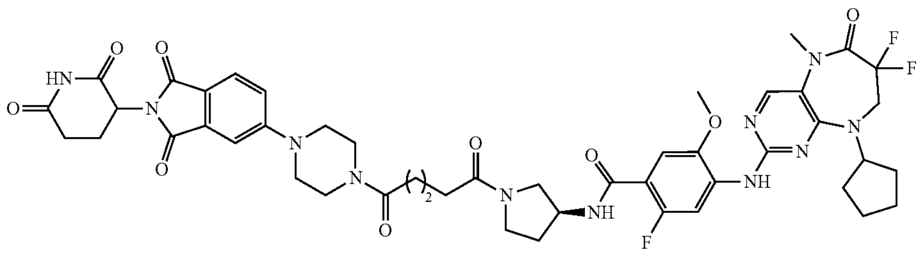 |
| 148 | 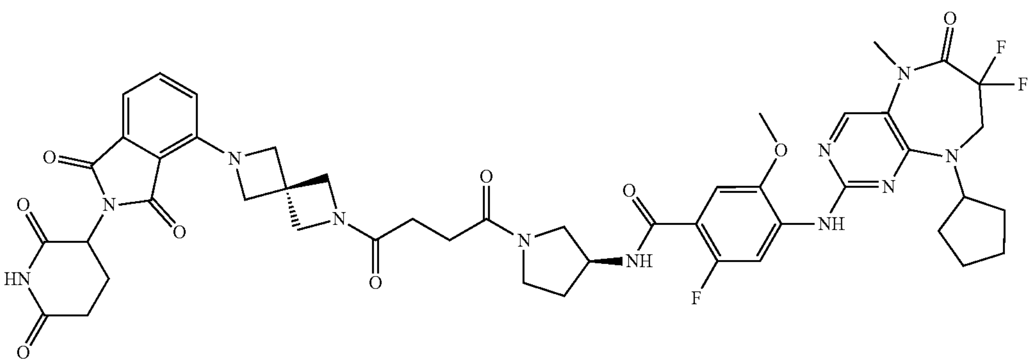 |
| 149 | 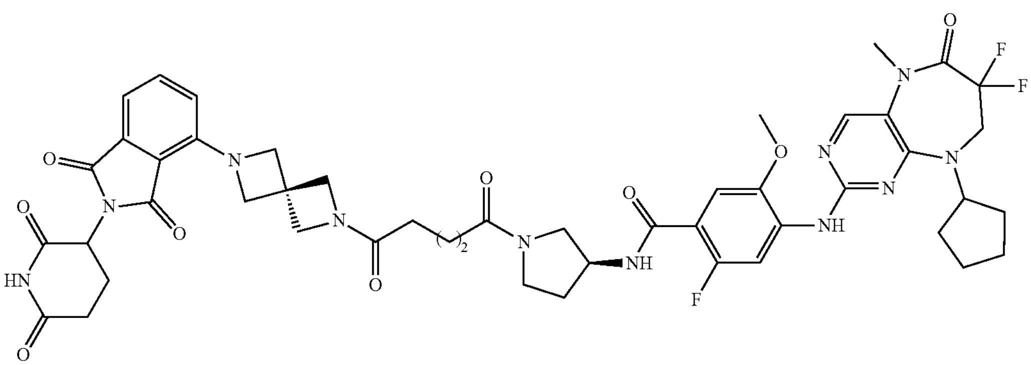 |
| 150 | 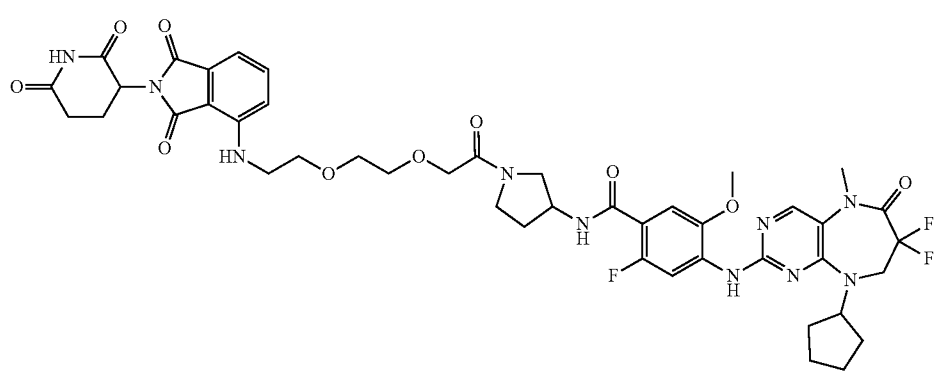 [SMILES: COc1cc(C(=O)NC2CCN(C(=O)COCCOCCNc3cccc4c3C(=O)N(C3CCC(=O)NC3=O)C4=O)C2)c(F)cc1Nc1ncc2c(n1)N(C1CCCC1)CC(F)(F)C(=O)N2C] |

TABLE 1-continued

| Compound | Structure |
|---|---|
| 151 | 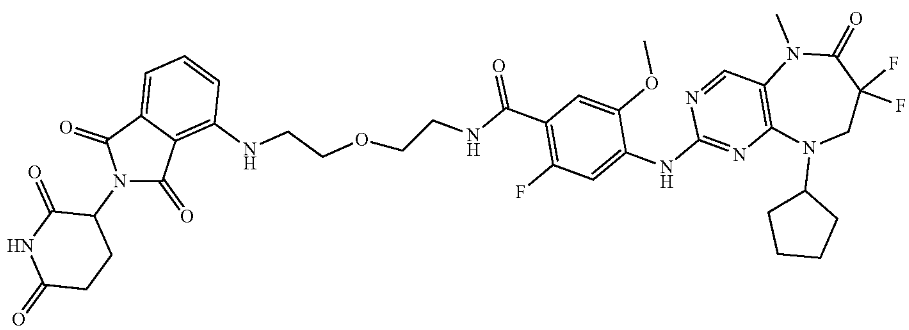 [SMILES: COc1cc(C(=O)NCCOCCNc2cccc3c2C(=O)N(C2CCC(=O)NC2=O)C3=O)c(F)cc1Nc1ncc2c(n1)N(C1CCCC1)CC(F)(F)C(=O)N2C] |
| 152 | 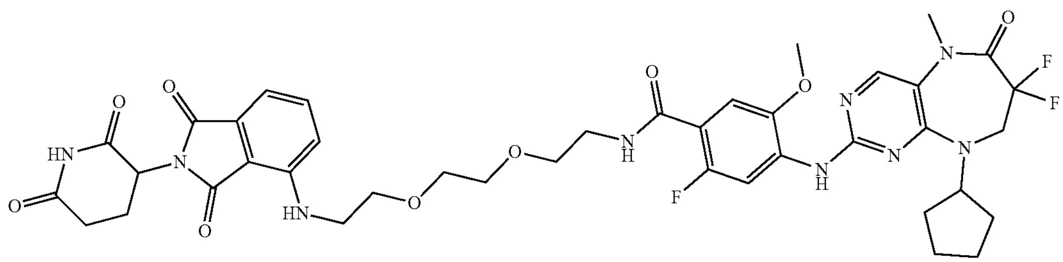 [SMILES: COc1cc(C(=O)NCCOCCOCCNc2cccc3c2C(=O)N(C2CCC(=O)NC2=O)C3=O)c(F)cc1Nc1ncc2c(n1)N(C1CCCC1)CC(F)(F)C(=O)N2C] |
| 153 | 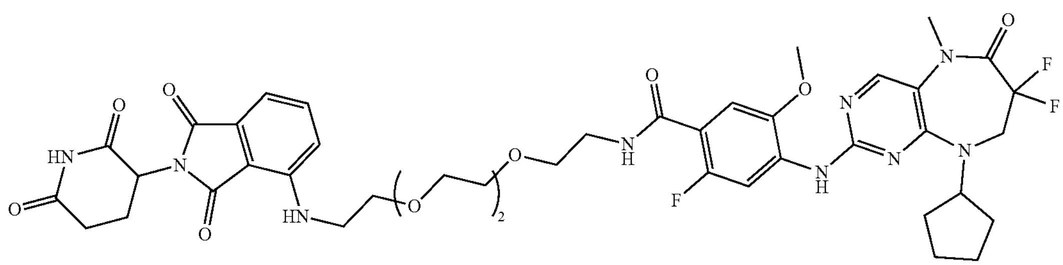 |
| 154 | 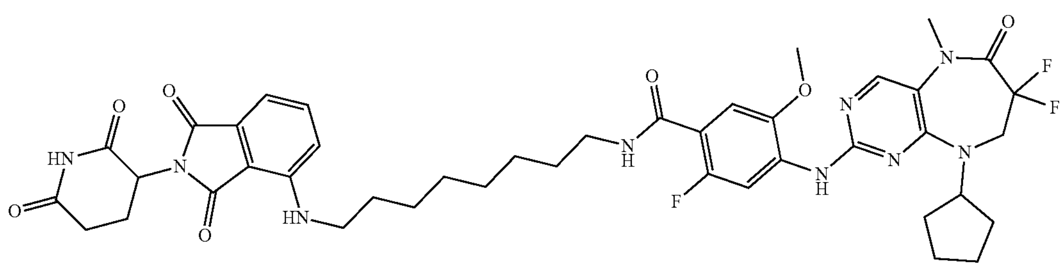 [SMILES: COc1cc(C(=O)NCCCCCCCCNc2cccc3c2C(=O)N(C2CCC(=O)NC2=O)C3=O)c(F)cc1Nc1ncc2c(n1)N(C1CCCC1)CC(F)(F)C(=O)N2C] |
| 155 | 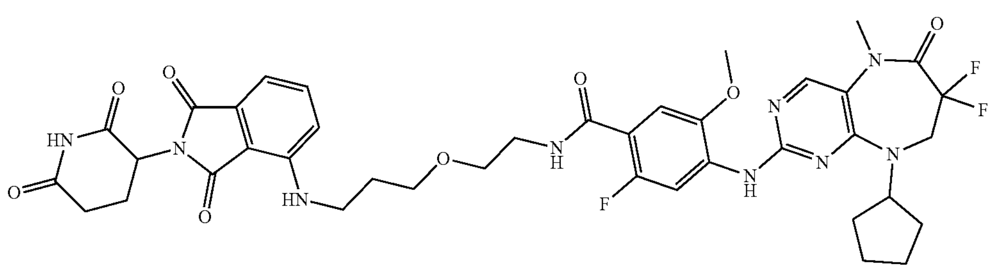 [SMILES: COc1cc(C(=O)NCCOCCCNc2cccc3c2C(=O)N(C2CCC(=O)NC2=O)C3=O)c(F)cc1Nc1ncc2c(n1)N(C1CCCC1)CC(F)(F)C(=O)N2C] |

TABLE 1-continued

| Compound | Structure |
|---|---|
| 156 | 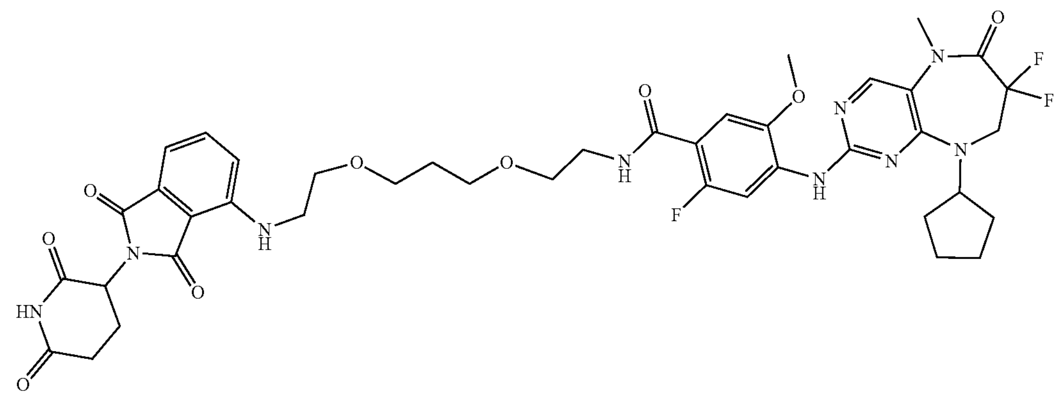 [SMILES: COc1cc(C(=O)NCCOCCCOCCNc2cccc3c2C(=O)N(C2CCC(=O)NC2=O)C3=O)c(F)cc1Nc1ncc2c(n1)N(C1CCCC1)CC(F)(F)C(=O)N2C] |
| 157 | 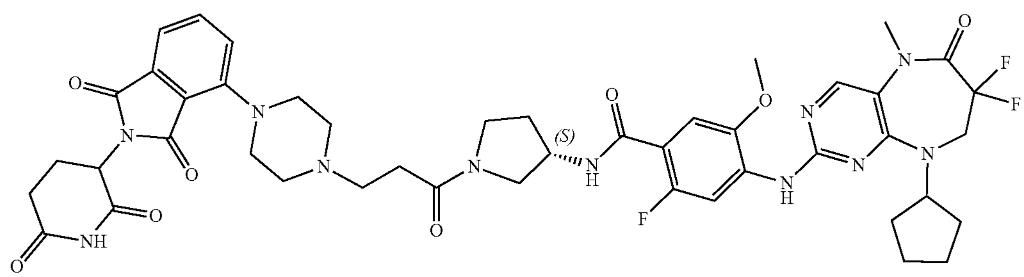 |
| 158 | 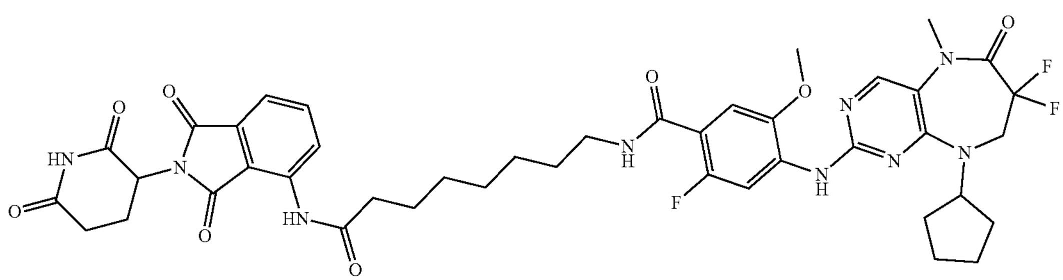 [SMILES: COc1cc(C(=O)NCCCCCCCC(=O)Nc2cccc3c2C(=O)N(C2CCC(=O)NC2=O)C3=O)c(F)cc1Nc1ncc2c(n1)N(C1CCCC1)CC(F)(F)C(=O)N2C] |
| 159 | 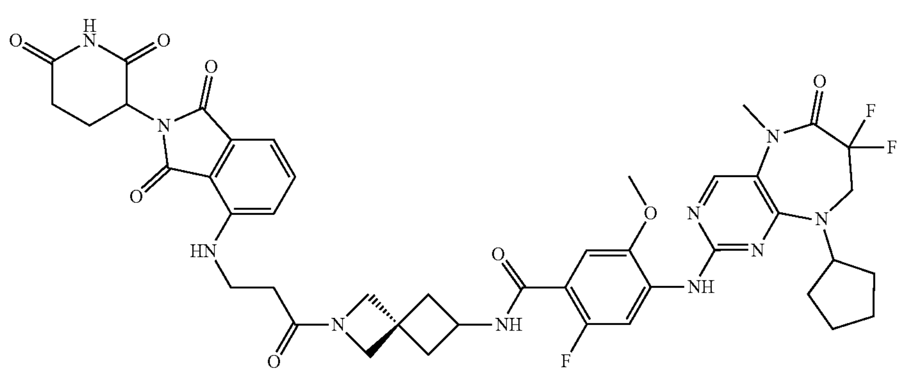 |

TABLE 1-continued

| Compound | Structure |
|---|---|
| 160 | 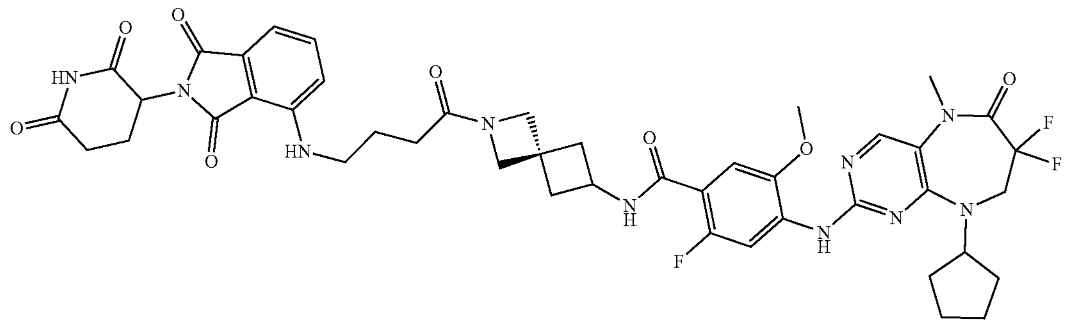 |
| 161 | 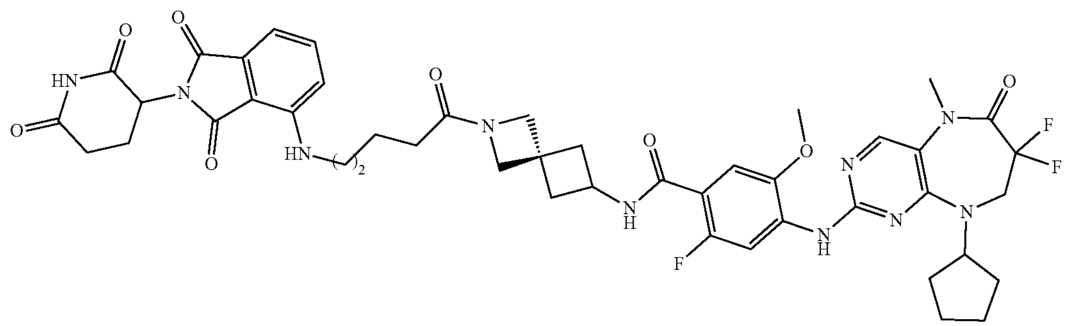 |
| 162 | 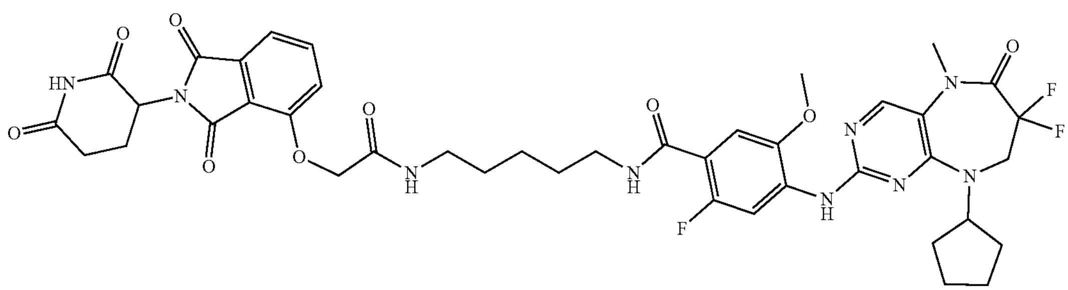 [SMILES: COc1cc(C(=O)NCCCCCNC(=O)COc2cccc3c2C(=O)N(C2CCC(=O)NC2=O)C3=O)c(F)cc1Nc1ncc2c(n1)N(C1CCCC1)CC(F)(F)C(=O)N2C] |
| 163 | 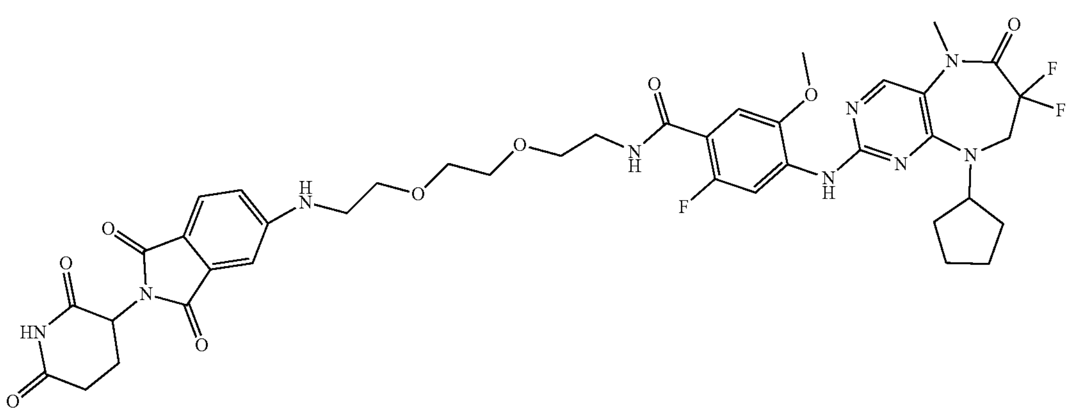 [SMILES: COc1cc(C(=O)NCCOCCOCCNc2ccc3c(c2)C(=O)N(C2CCC(=O)NC2=O)C3=O)c(F)cc1Nc1ncc2c(n1)N(C1CCCC1)CC(F)(F)C(=O)N2C] |

TABLE 1-continued

| Compound | Structure |
|---|---|
| 164 | 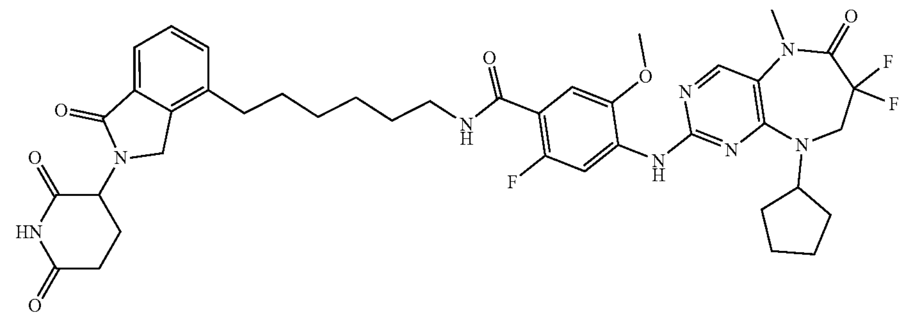 |
| 165 | 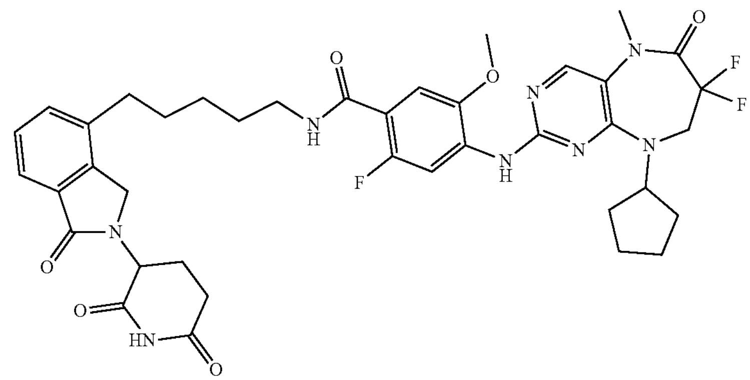 [SMILES: COc1cc(C(=O)NCCCCCc2cccc3c2CN(C2CCC(=O)NC2=O)C3=O)c(F)cc1Nc1ncc2c(n1)N(C1CCCC1)CC(F)(F)C(=O)N2C] |
| 166 | 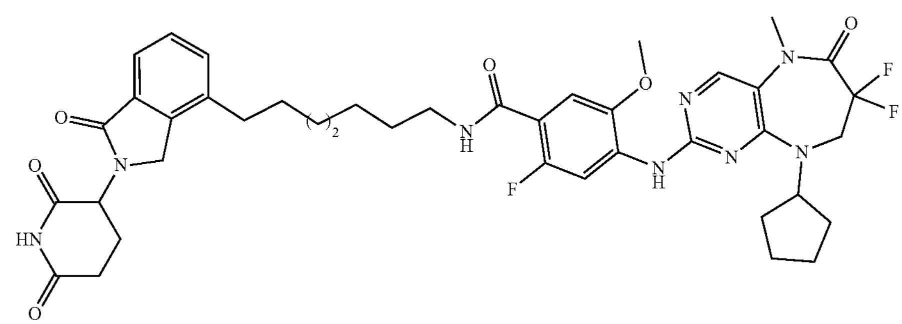 |
| 167 | 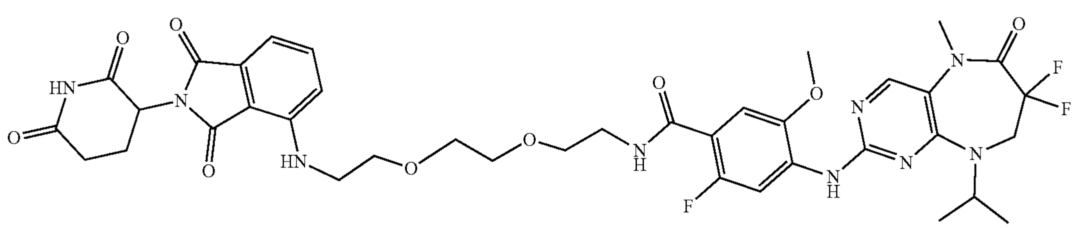 [SMILES: COc1cc(C(=O)NCCOCCOCCNc2cccc3c2C(=O)N(C2CCC(=O)NC2=O)C3=O)c(F)cc1Nc1ncc2c(n1)N(C(C)C)CC(F)(F)C(=O)N2C] |
| 168 | 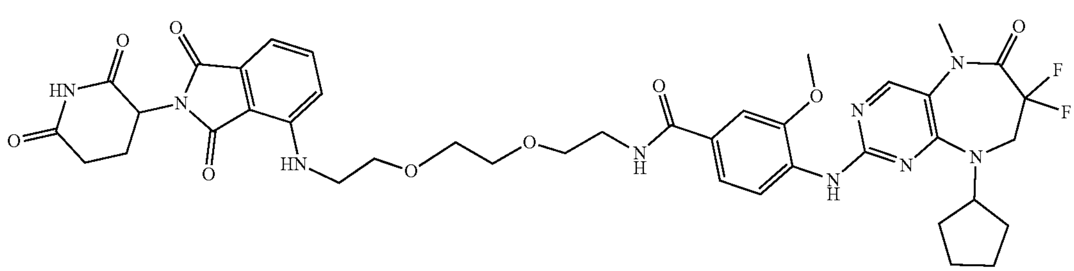 [SMILES: COc1cc(C(=O)NCCOCCOCCNc2cccc3c2C(=O)N(C2CCC(=O)NC2=O)C3=O)ccc1Nc1ncc2c(n1)N(C1CCCC1)CC(F)(F)C(=O)N2C] |

TABLE 1-continued

| Compound | Structure |
| --- | --- |
| 169 | 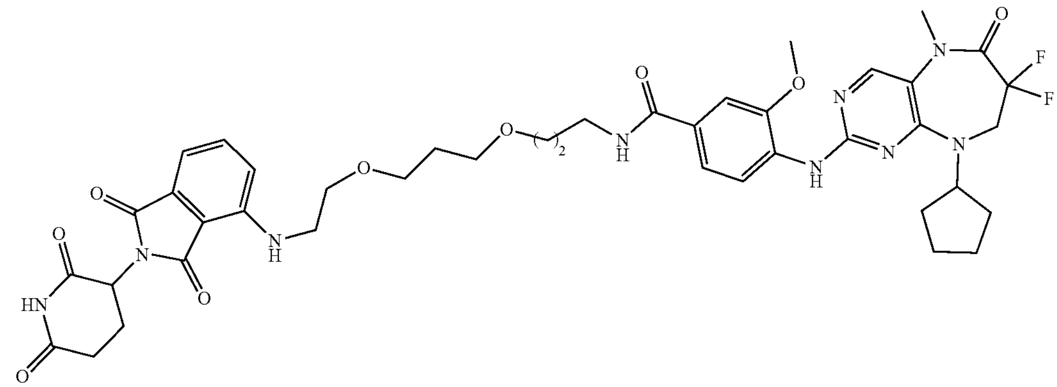 |
| 170 | 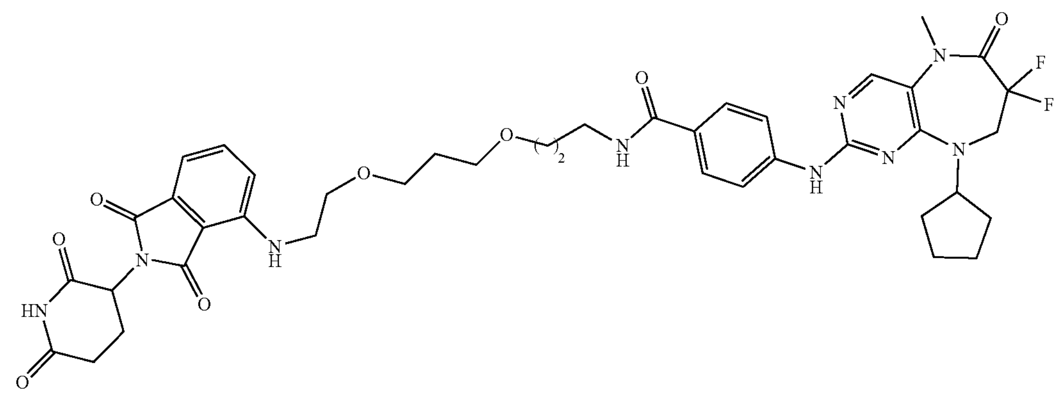 |
| 171 | 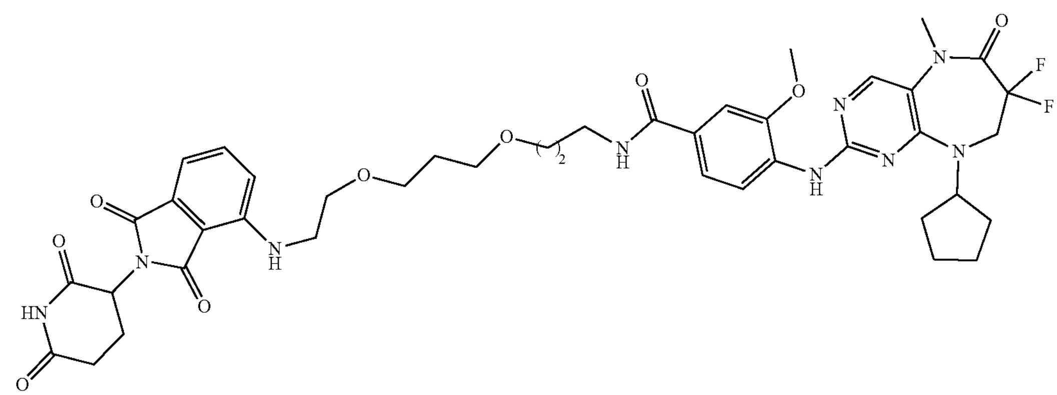 |
| 172 | 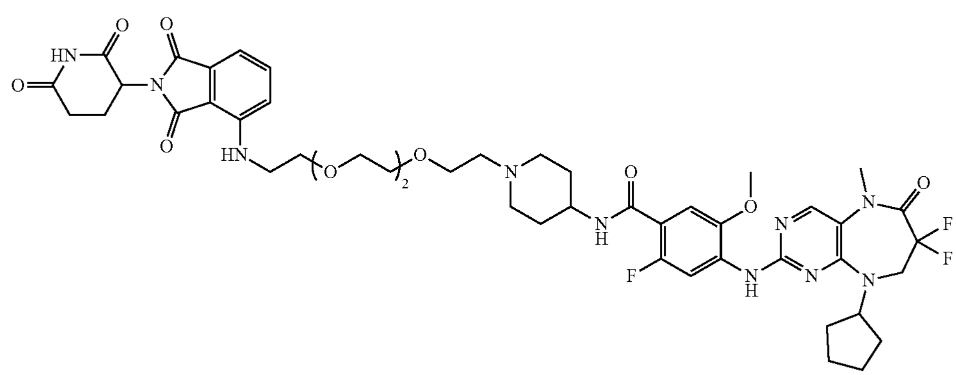 |

TABLE 1-continued

| Compound | Structure |
|---|---|
| 173 | 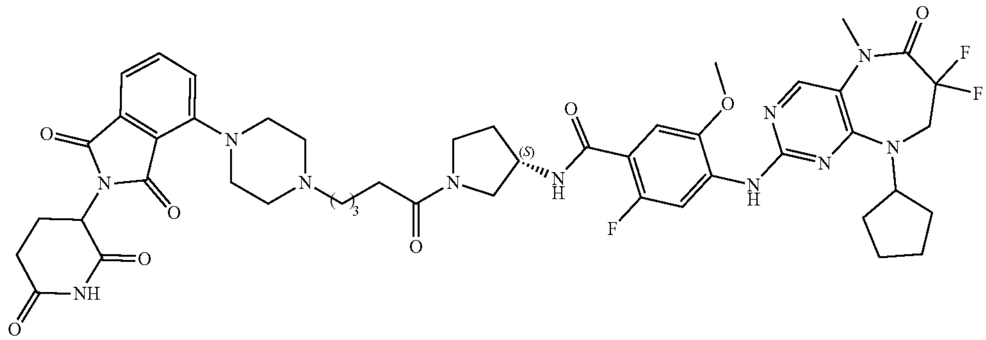 |
| 174 | (structure) or |
| 175 | 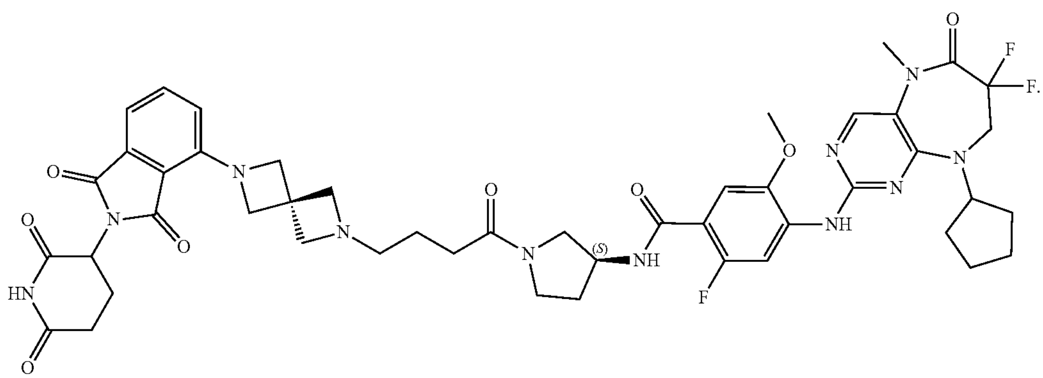 |

8. The compound of claim 1, wherein the compound induces selective PLK1 protein degradation.

* * * * *